US012543494B2

(12) United States Patent
Mitani et al.

(10) Patent No.: US 12,543,494 B2
(45) Date of Patent: Feb. 3, 2026

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicants: IDEMITSU KOSAN CO.,LTD., Tokyo (JP); National University Corporation Tokai National Higher Education and Research System, Nagoya (JP)

(72) Inventors: Masato Mitani, Chiyoda-ku (JP); Keita Seda, Chiyoda-ku (JP); Taro Yamaki, Chiyoda-ku (JP); Shota Tanaka, Chiyoda-ku (JP); Tsukasa Sawato, Chiyoda-ku (JP); Masatoshi Saito, Chiyoda-ku (JP); Hiroaki Itoi, Chiyoda-ku (JP); Tasuku Haketa, Chiyoda-ku (JP); Kei Yoshida, Chiyoda-ku (JP); Sayaka Mizutani, Chiyoda-ku (JP); Kenichiro Itami, Nagoya (JP); Kei Murakami, Nagoya (JP); Satoshi Matsubara, Nagoya (JP); Yoshito Koga, Nagoya (JP)

(73) Assignees: IDEMITSU KOSAN CO., LTD., Tokyo (JP); National University Corporation Tokai National Higher Education and Research System, Nagoya (JP)

( * ) Notice: Subject to any disclaimer, the term of this patent is extended or adjusted under 35 U.S.C. 154(b) by 881 days.

(21) Appl. No.: 17/859,480

(22) Filed: Jul. 7, 2022

(65) Prior Publication Data

US 2023/0085328 A1 Mar. 16, 2023

(30) Foreign Application Priority Data

Jul. 12, 2021 (JP) ................................ 2021-115244

(51) Int. Cl.
*H10K 85/60* (2023.01)
*C07C 13/62* (2006.01)
(Continued)

(52) U.S. Cl.
CPC ........... *H10K 85/624* (2023.02); *C07C 13/62* (2013.01); *C07C 211/54* (2013.01); *C07D 251/24* (2013.01); *C09K 11/06* (2013.01); *H10K 85/622* (2023.02); *H10K 85/626* (2023.02); *H10K 85/633* (2023.02); *H10K 85/654* (2023.02); *C07C 2603/50* (2017.05); *C07C 2603/54* (2017.05); *C09K 2211/1007* (2013.01); *C09K 2211/1011* (2013.01);
(Continued)

(58) Field of Classification Search
None
See application file for complete search history.

(56) References Cited

U.S. PATENT DOCUMENTS 5,077,142 A * 12/1991 Sakon .................... C09K 11/06 428/917
2016/0343951 A1* 11/2016 Kwong ................ C07D 333/54
(Continued)

FOREIGN PATENT DOCUMENTS

JP 2019-91748 A 6/2019
WO WO 2006/130598 A2 12/2006

OTHER PUBLICATIONS

Satoshi Matsubara et al., "Creation of negatively curved polyaromatics enabled by annulative coupling that forms an eight-membered ring", Nature Catalysis, vol. 3, 2020, pp. 710-718.

*Primary Examiner* — Robert S Loewe
(74) *Attorney, Agent, or Firm* — Oblon, McClelland, Maier & Neustadt, L.L.P.

(57) ABSTRACT

A compound represented by the following formula (1A) or (1B):

(1A)

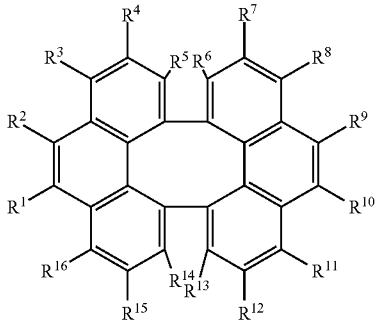

(1B)

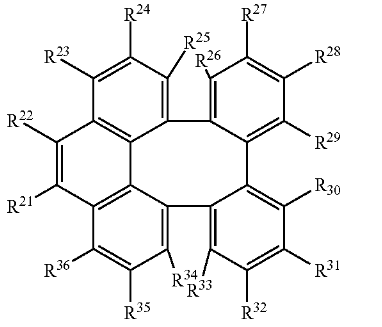

(the symbols in the formulae (1A) and (1B) have the same meaning as defined in the specification), an organic electroluminescent device containing the compound, and an electronic device including the organic electroluminescent device.

26 Claims, 1 Drawing Sheet

(51) Int. Cl.

| | |
|---|---|
| ***C07C 211/54*** | (2006.01) |
| ***C07D 251/24*** | (2006.01) |
| ***C09K 11/06*** | (2006.01) |
| *H10K 50/15* | (2023.01) |
| *H10K 50/16* | (2023.01) |

(52) U.S. Cl.
CPC ................. *C09K 2211/1014* (2013.01); *C09K 2211/1018* (2013.01); *H10K 50/156* (2023.02); *H10K 50/166* (2023.02)

(56) References Cited

U.S. PATENT DOCUMENTS

| | | | | |
|---|---|---|---|---|
| 2018/0108844 | A1* | 4/2018 | Lee ...................... | C07D 493/04 |
| 2018/0287087 | A1* | 10/2018 | Thompson ......... | H10K 85/6572 |
| 2019/0115541 | A1* | 4/2019 | Xia ...................... | C07D 491/04 |
| 2019/0185412 | A1* | 6/2019 | Xia ...................... | C07D 209/86 |

* cited by examiner

COMPOUND, MATERIAL FOR ORGANIC ELECTROLUMINESCENT ELEMENTS, ORGANIC ELECTROLUMINESCENT ELEMENT, AND ELECTRONIC DEVICE

CROSS-REFERENCE TO RELATED APPLICATION

This application is based upon and claims the benefit of priority from the prior Japanese Patent Application No. 2021-115244, filed on Jul. 12, 2021; the entire contents of which are incorporated herein by reference.

TECHNICAL FIELD

The present invention relates to a compound, a material for organic electroluminescent devices, an organic electroluminescent device, and an electronic device comprising the organic electroluminescent device.

BACKGROUND ART

An organic electroluminescent device (which may be hereinafter referred to as an "organic EL device") is generally composed of an anode, a cathode, and organic layers sandwiched between the anode and the cathode. Upon application of a voltage between the electrodes, electrons from the cathode and holes from the anode are injected into a light emitting region. The injected electrons and holes recombine in the light emitting region to produce an excited state, which then returns to the ground state while emitting light. Accordingly, in order to obtain a high-performance organic EL device, it is important to develop a material that efficiently transports electrons or holes to the light emitting region, thereby facilitating recombination of the electrons and holes.

Patent Literatures 1 and 2 and Non Patent Literature 1 each disclose a compound for use as a material for organic electroluminescent devices.

CITATION LIST

Patent Literatures

Patent Literature 1: WO 2006/130598 A2
Patent Literature 2: JP 2019-91748 A

Non Patent Literature

Non Patent Literature [3] 1: Nature Catalysis, (Germany), 2020, Vol. 3, pp. 710-718

SUMMARY OF INVENTION

While various compounds for organic EL devices have been reported, a demand still exists for a compound which further enhances the performance of an organic EL device.

The present invention has been made to solve the above problem. It is therefore an object of the present invention to provide a compound which further improves the performance of an organic EL device, an organic EL device having a further improved performance, and an electronic device comprising the organic EL device.

The present inventors, through their intensive studies on the performances of organic EL devices containing novel compounds, have found that an organic EL device containing a compound represented by the following formula (1A) or (1B) has a further improved performance.

In one embodiment, the present invention provides a compound represented by the following formula (1A) or (1B):

(1A)

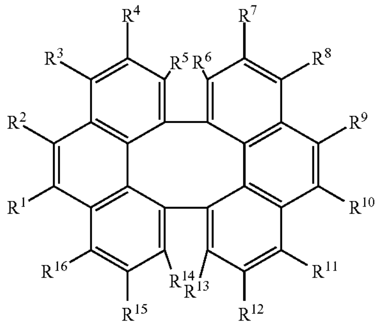

(1B)

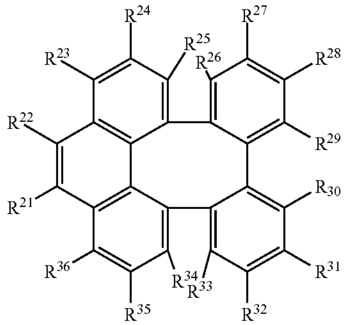

where at least one selected from $R^1$ to $R^{16}$ and at least one selected from $R^{21}$ to $R^{36}$ are represented by the following formula (2A), (2B), (2C) or (2D):

$$*-(L^1)_a-HET \quad (2A)$$

(2B)

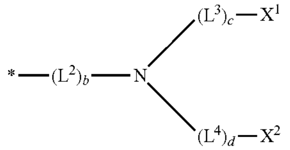

$$*-(L^5)_e-Ar \quad (2C)$$

$$*-(L^6)_f-Y \quad (2D)$$

where * represents a bonding position to a carbon atom in the formula (1A) at which $R^1$ to $R^{16}$ are bonded or a bonding position to a carbon atom in the formula (1B) at which $R^{21}$ to $R^{36}$ are bonded, $L^1$ to $L^6$ each independently represent a substituted or unsubstituted arylene group having 6 to 50 ring carbon atoms, or a substituted or unsubstituted divalent heterocyclic group having 5 to 50 ring atoms, a, b, c, d, e and f each independently represent 0, 1, 2 or 3, and $(L^1)_0$, $(L^2)_0$, $(L^3)_0$, $(L^4)_0$, $(L^5)_0$ and $(L^6)_0$ each independently represent a single bond, when two or more $L^1$s are present, they may be the same or different, when two or more $L^2$s are present, they may be the same or different, when two or more $L^3$s are present, they may be the same or different, when two or more $L^4$s are present, they may be the same or different, when two or more $L^5$s are present, they may be the same or different, and when two or more $L^6$s are present, they may be the same or different, HET represents a substituted or unsubstituted heterocyclic group having 5 to 50 ring atoms, $X^1$ and $X^2$ each independently represent a substituted or unsubstituted aryl group having 6 to 50 ring carbon atoms, or a substituted or unsubstituted heterocyclic group having 5 to 50 ring atoms, Ar represents a substituted or unsubstituted aryl group having 10 to 50 ring carbon atoms, Y represents a group selected from the following formulae (i) to (viii):

(i)

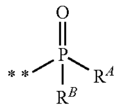

(ii)

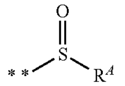

(iii)

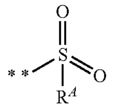

(iv)

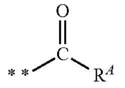

(v)

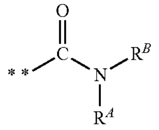

(vi)

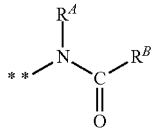

(vii)

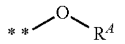

(viii)

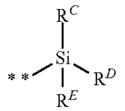

where ** represents a bonding position at which Y is bonded to $L^6$ in the formula (2D), $R^A$ and $R^B$ each independently represent a hydrogen atom or a substituent $Z^1$, $R^C$, $R^D$ and $R^E$ each independently represent a substituted or unsubstituted aryl group having 6 to 50 ring carbon atoms, the substituent $Z^1$ is a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted aralkyl group having 7 to 50 carbon atoms, a substituted or unsubstituted heterocyclic group having 5 to 50 ring atoms, a substituted or unsubstituted haloalkyl group having 1 to 50 carbon atoms, a substituted or unsubstituted haloalkoxy group having 1 to 50 carbon atoms, a group represented by $—Si(R_{901})(R_{902})(R_{903})$, a group represented by $—O—(R_{904})$, a group represented by $—S—(R_{905})$, or a group represented by $—N(R_{906})(R_{907})$, where $R_{901}$ to $R_{907}$ each independently represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, when two or more $R_{901}$'s are present, the $R_{901}$'s may be the same or different, when two or more $R_{902}$'s are present, the $R_{902}$'s may be the same or different, when two or more $R_{903}$'s are present, the $R_{903}$'s may be the same or different, when two or more $R_{904}$'s are present, the $R_{904}$'s may be the same or different, when two or more $R_{905}$'s are present, the $R_{905}$'s may be the same or different, when two or more $R_{906}$'s are present, the $R_{906}$'s may be the same or different, when two or more $R_{907}$'s are present, the $R_{907}$'s may be the same or different, when $R^1$, $R^2$, $R^9$ and $R^{10}$ in the formula (1A) are all represented by the formula (2A), at least one selected from $R^1$, $R^2$, $R^9$ and $R^{10}$ is the formula (2A) in which HET contains a nitrogen atom, when two or more selected from $R^1$ to $R^{16}$ in the formula (1A) are represented by the formula (2A), they may be the same or different, when two or more selected from $R^1$ to $R^{16}$ are represented by the formula (2B), they may be the same or different, when two or more selected from $R^1$ to $R^{16}$ are represented by the formula (2C), they may be the same or different, and when two or more selected from $R^1$ to $R^{16}$ are represented by the formula (2D), they may be the same or different, and $R^1$ to $R^{16}$ are not bonded to each other, when two or more selected from $R^{21}$ to $R^{36}$ in the formula (1B) are represented by the formula (2A), they may be the same or different, when two or more selected from $R^{21}$ to $R^{36}$ are represented by the formula (2B), they may be the same or different, when two or more selected from $R^{21}$ to $R^{36}$ are represented by the formula (2C), they may be the same or different, and when two or more selected from $R^{21}$ to $R^{36}$ are represented by the formula (2D), they may be the same or different, and $R^{21}$ to $R^{36}$ are not bonded to each other, in the formulae (1A) and (1B), $R^1$ to $R^{16}$ and $R^{21}$ to $R^{36}$ which are not represented by the formula (2A), (2B), (2C) or (2D) each independently represent a hydrogen atom or a substituent $Z^2$, the substituent $Z^2$ is a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted phenyl group, a substituted or unsubstituted aralkyl group having 7 to 50 carbon atoms, a substituted or unsubstituted haloalkyl group having 1 to 50 carbon atoms, a substituted or unsubstituted haloalkoxy group having 1 to 50 carbon atoms, a group represented by —Si($R_{901}$)($R_{902}$)($R_{903}$), a group represented by —S—($R_{905}$), or a group represented by —N($R_{906}$)($R_{907}$), $R_{901}$ to $R_{907}$ each independently represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, when two or more $R_{901}$'s are present, the $R_{901}$'s may be the same or different, when two or more $R_{902}$'s are present, the $R_{902}$'s may be the same or different, when two or more $R_{903}$'s are present, the $R_{903}$'s may be the same or different, when two or more $R_{905}$'s are present, the $R_{905}$'s may be the same or different, when two or more $R_{906}$'s are present, the $R_{906}$'s may be the same or different, when two or more $R_{907}$'s are present, the $R_{907}$'s may be the same or different, at least one of $R_{901}$ to $R_{903}$ is not a substituted or unsubstituted aryl group having 6 to 50 ring carbon atoms, and at least one of $R_{906}$ and $R_{907}$ is a hydrogen atom, a substituted or unsubstituted alkyl group having 1 to 50 carbon atoms, or a substituted or unsubstituted cycloalkyl group having 3 to 50 ring carbon atoms, and $R_{901}$ to $R_{903}$ are not bonded to each other, and $R_{906}$ and $R_{907}$ are not bonded to each other.

In another embodiment, the present invention provides a material for organic electroluminescent devices, comprising the compound represented by the formula (1A) or (1B).

In yet another embodiment, the present invention provides an organic electroluminescent device comprising a cathode, an anode, and organic layers disposed between the cathode and the anode, wherein the organic layers include a light emitting layer, and at least one layer of the organic layers comprises the compound represented by the formula (1A) or (1B).

In yet another embodiment, the present invention provides an electronic device comprising the organic electroluminescent device.

The organic EL device containing the compound represented by the formula (1A) or (1B) exhibits an improved performance.

DESCRIPTION OF EMBODIMENTS

Definitions

Figure 1:
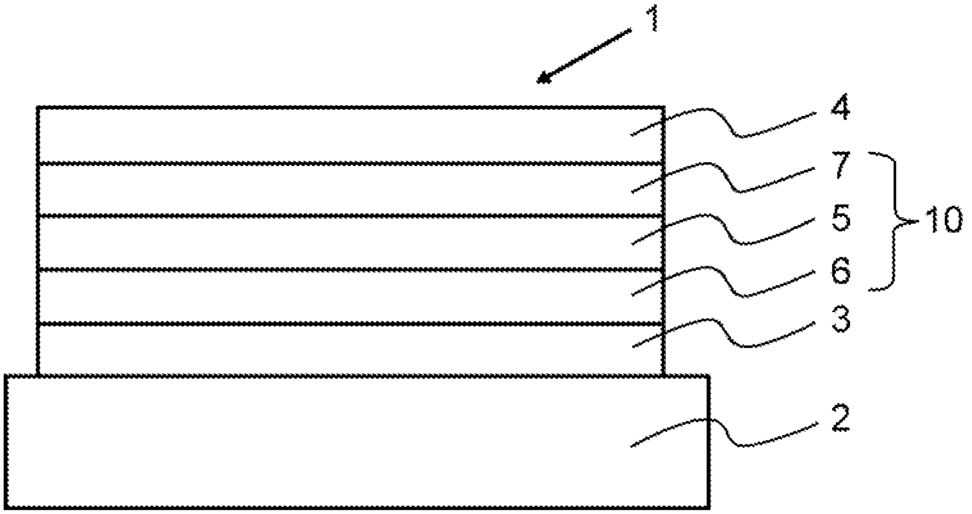
FIG. 1 is a schematic illustration showing an example of the layer configuration of the organic EL device according to one embodiment of the present invention.

In the description herein, the hydrogen atom encompasses isotopes thereof having different numbers of neutrons, i.e., a light hydrogen atom (protium), a heavy hydrogen atom (deuterium), and a tritium.

In the description herein, the bonding site where the symbol, such as "R", or "D" representing a deuterium atom is not shown is assumed to have a hydrogen atom, i.e., a protium atom, a deuterium atom, or a tritium atom, bonded thereto.

In the description herein, the number of ring carbon atoms shows the number of carbon atoms among the atoms constituting the ring itself of a compound having a structure including atoms bonded to form a ring (such as a monocyclic compound, a condensed ring compound, a bridged compound, a carbocyclic compound, and a heterocyclic compound). In the case where the ring is substituted by a substituent, the carbon atom contained in the substituent is not included in the number of ring carbon atoms. The same definition is applied to the "number of ring carbon atoms" described hereinafter unless otherwise indicated. For example, a benzene ring has 6 ring carbon atoms, a naphthalene ring has 10 ring carbon atoms, a pyridine ring has 5 ring carbon atoms, and a furan ring has 4 ring carbon atoms. For example, 9,9-diphenylfluorenyl group has 13 ring carbon atoms, and 9,9'-spirobifluorenyl group has 25 ring carbon atoms.

In the case where a benzene ring has, for example, an alkyl group substituted thereon as a substituent, the number of carbon atoms of the alkyl group is not included in the number of ring carbon atoms of the benzene ring. Accordingly, a benzene ring having an alkyl group substituted thereon has 6 ring carbon atoms. In the case where a naphthalene ring has, for example, an alkyl group substituted thereon as a substituent, the number of carbon atoms of the alkyl group is not included in the number of ring carbon atoms of the naphthalene ring. Accordingly, a naphthalene ring having an alkyl group substituted thereon has 10 ring carbon atoms.

In the description herein, the number of ring atoms shows the number of atoms constituting the ring itself of a compound having a structure including atoms bonded to form a ring (such as a monocyclic ring, a condensed ring, and a set of rings) (such as a monocyclic compound, a condensed ring compound, a bridged compound, a carbocyclic compound, and a heterocyclic compound). The atom that does not constitute the ring (such as a hydrogen atom terminating the bond of the atom constituting the ring) and, in the case where the ring is substituted by a substituent, the atom contained in the substituent are not included in the number of ring atoms. The same definition is applied to the "number of ring atoms"

described hereinafter unless otherwise indicated. For example, a pyridine ring has 6 ring atoms, a quinazoline ring has 10 ring atoms, and a furan ring has 5 ring atoms. For example, the number of hydrogen atoms bonded to a pyridine ring or atoms constituting a substituent is not included in the number of ring atoms of the pyridine ring. Accordingly, a pyridine ring having a hydrogen atom or a substituent bonded thereto has 6 ring atoms. For example, the number of hydrogen atoms bonded to carbon atoms of a quinazoline ring or atoms constituting a substituent is not included in the number of ring atoms of the quinazoline ring. Accordingly, a quinazoline ring having a hydrogen atom or a substituent bonded thereto has 10 ring atoms.

In the description herein, the expression "having XX to YY carbon atoms" in the expression "substituted or unsubstituted ZZ group having XX to YY carbon atoms" means the number of carbon atoms of the unsubstituted ZZ group, and, in the case where the ZZ group is substituted, the number of carbon atoms of the substituent is not included. Herein, "YY" is larger than "XX", "XX" represents an integer of 1 or more, and "YY" represents an integer of 2 or more.

In the description herein, the expression "having XX to YY atoms" in the expression "substituted or unsubstituted ZZ group having XX to YY atoms" means the number of atoms of the unsubstituted ZZ group, and, in the case where the ZZ group is substituted, the number of atoms of the substituent is not included. Herein, "YY" is larger than "XX", "XX" represents an integer of 1 or more, and "YY" represents an integer of 2 or more.

In the description herein, an unsubstituted ZZ group means the case where the "substituted or unsubstituted ZZ group" is an "unsubstituted ZZ group", and a substituted ZZ group means the case where the "substituted or unsubstituted ZZ group" is a "substituted ZZ group".

In the description herein, the expression "unsubstituted" in the expression "substituted or unsubstituted ZZ group" means that hydrogen atoms in the ZZ group are not substituted by a substituent. The hydrogen atoms in the "unsubstituted ZZ group" each are a protium atom, a deuterium atom, or a tritium atom.

In the description herein, the expression "substituted" in the expression "substituted or unsubstituted ZZ group" means that one or more hydrogen atom in the ZZ group is substituted by a substituent. The expression "substituted" in the expression "BB group substituted by an AA group" similarly means that one or more hydrogen atom in the BB group is substituted by the AA group.

Substituents in Description

The substituents described in the description herein will be explained.

In the description herein, the number of ring carbon atoms of the "unsubstituted aryl group" is 6 to 50, preferably 6 to 30, and more preferably 6 to 18, unless otherwise indicated in the description.

In the description herein, the number of ring atoms of the "unsubstituted heterocyclic group" is 5 to 50, preferably 5 to 30, and more preferably 5 to 18, unless otherwise indicated in the description.

In the description herein, the number of carbon atoms of the "unsubstituted alkyl group" is 1 to 50, preferably 1 to 20, and more preferably 1 to 6, unless otherwise indicated in the description.

In the description herein, the number of carbon atoms of the "unsubstituted alkenyl group" is 2 to 50, preferably 2 to 20, and more preferably 2 to 6, unless otherwise indicated in the description.

In the description herein, the number of carbon atoms of the "unsubstituted alkynyl group" is 2 to 50, preferably 2 to 20, and more preferably 2 to 6, unless otherwise indicated in the description.

In the description herein, the number of ring carbon atoms of the "unsubstituted cycloalkyl group" is 3 to 50, preferably 3 to 20, and more preferably 3 to 6, unless otherwise indicated in the description.

In the description herein, the number of ring carbon atoms of the "unsubstituted arylene group" is 6 to 50, preferably 6 to 30, and more preferably 6 to 18, unless otherwise indicated in the description.

In the description herein, the number of ring atoms of the "unsubstituted divalent heterocyclic group" is 5 to 50, preferably 5 to 30, and more preferably 5 to 18, unless otherwise indicated in the description.

In the description herein, the number of carbon atoms of the "unsubstituted alkylene group" is 1 to 50, preferably 1 to 20, and more preferably 1 to 6, unless otherwise indicated in the description.

Substituted or Unsubstituted Aryl Group

In the description herein, specific examples (set of specific examples G1) of the "substituted or unsubstituted aryl group" include the unsubstituted aryl groups (set of specific examples G1A) and the substituted aryl groups (set of specific examples G1B) shown below. (Herein, the unsubstituted aryl group means the case where the "substituted or unsubstituted aryl group" is an "unsubstituted aryl group", and the substituted aryl group means the case where the "substituted or unsubstituted aryl group" is a "substituted aryl group".) In the description herein, the simple expression "aryl group" encompasses both the "unsubstituted aryl group" and the "substituted aryl group".

The "substituted aryl group" means a group formed by substituting one or more hydrogen atom of the "unsubstituted aryl group" by a substituent. Examples of the "substituted aryl group" include groups formed by one or more hydrogen atom of each of the "unsubstituted aryl groups" in the set of specific examples G1A by a substituent, and the examples of the substituted aryl groups in the set of specific examples G1B. The examples of the "unsubstituted aryl group" and the examples of the "substituted aryl group" enumerated herein are mere examples, and the "substituted aryl group" in the description herein encompasses groups formed by substituting a hydrogen atom bonded to the carbon atom of the aryl group itself of each of the "substituted aryl groups" in the set of specific examples G1B by a substituent, and groups formed by substituting a hydrogen atom of the substituent of each of the "substituted aryl groups" in the set of specific examples G1B by a substituent.

Unsubstituted Aryl Group (Set of Specific Examples G1A):

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group, a benzanthryl group, a phenanthryl group, a benzophenanthryl group, a phenarenyl group, a pyrenyl group, a chrysenyl group, a benzochrysenyl group, a triphenylenyl group, a benzotriphenylenyl group, a tetracenyl group, a pentacenyl group, a fluorenyl group, a 9,9'-spirobifluorenyl group, a benzofluorenyl group, a dibenzofluorenyl group, a fluoranthenyl group, a benzofluoranthenyl group, a perylenyl group, and monovalent aryl groups derived by removing one hydrogen atom from each of the ring structures represented by the following general formulae (TEMP-1) to (TEMP-15):

(TEMP-1)

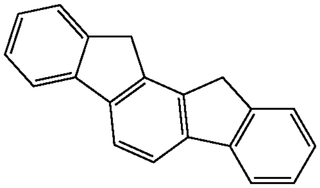

(TEMP-2)

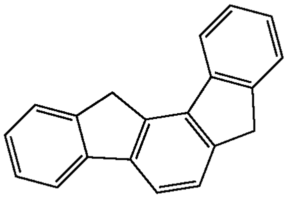

(TEMP-3)

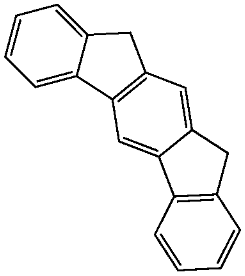

(TEMP-4)

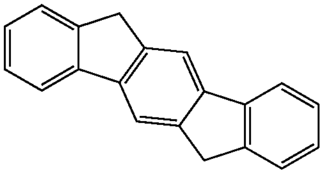

-continued (TEMP-5)

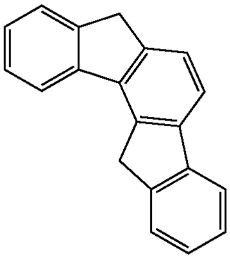

(TEMP-6)

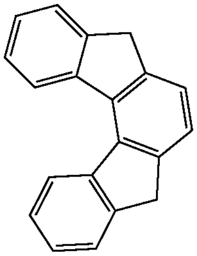

(TEMP-7)

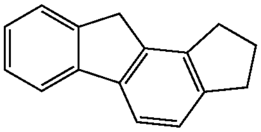

(TEMP-8)

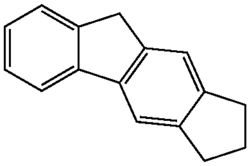

(TEMP-9)

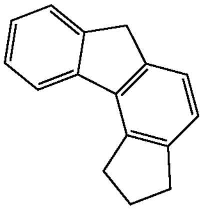

(TEMP-10)

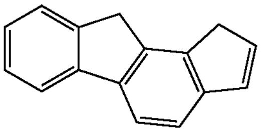

(TEMP-11)

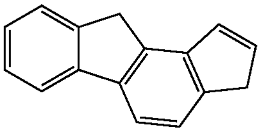

(TEMP-12)

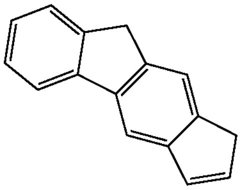

-continued (TEMP-13)

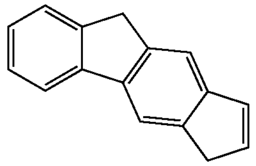

(TEMP-14)

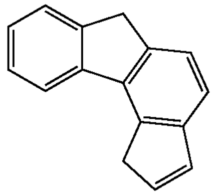

(TEMP-15)

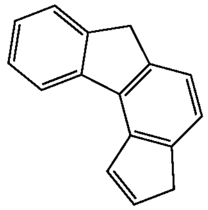

Substituted Aryl Group (Set of Specific Examples G1B):

- an o-tolyl group,
- a m-tolyl group,
- a p-tolyl group,
- a p-xylyl group,
- a m-xylyl group,
- an o-xylyl group,
- a p-isopropylphenyl group,
- a m-isopropylphenyl group,
- an o-isopropylphenyl group,
- a p-t-butylphenyl group,
- a m-t-butylphenyl group,
- a o-t-butylphenyl group,
- a 3,4,5-trimethylphenyl group,
- a 9,9-dimethylfluorenyl group,
- a 9,9-diphenylfluorenyl group,
- a 9,9-bis(4-methylphenyl)fluorenyl group,
- a 9,9-bis(4-isopropylphenyl)fluorenyl group,
- a 9,9-bis(4-t-butylphenyl)fluorenyl group,
- a cyanophenyl group,
- a triphenylsilylphenyl group,
- a trimethylsilylphenyl group,
- a phenylnaphthyl group,
- a naphthylphenyl group, and
- groups formed by substituting one or more hydrogen atom of each of monovalent aryl groups derived from the ring structures represented by the general formulae (TEMP-1) to (TEMP-15) by a substituent.

Substituted or Unsubstituted Heterocyclic Group

In the description herein, the “heterocyclic group” means a cyclic group containing at least one hetero atom in the ring atoms. Specific examples of the hetero atom include a nitrogen atom, an oxygen atom, a sulfur atom, a silicon atom, a phosphorus atom, and a boron atom.

In the description herein, the “heterocyclic group” is a monocyclic group or a condensed ring group.

In the description herein, the “heterocyclic group” is an aromatic heterocyclic group or a non-aromatic heterocyclic group.

In the description herein, specific examples (set of specific examples G2) of the “substituted or unsubstituted heterocyclic group” include the unsubstituted heterocyclic groups (set of specific examples G2A) and the substituted heterocyclic groups (set of specific examples G2B) shown below. (Herein, the unsubstituted heterocyclic group means the case where the “substituted or unsubstituted heterocyclic group” is an “unsubstituted heterocyclic group”, and the substituted heterocyclic group means the case where the “substituted or unsubstituted heterocyclic group” is a “substituted heterocyclic group”.) In the description herein, the simple expression “heterocyclic group” encompasses both the “unsubstituted heterocyclic group” and the “substituted heterocyclic group”.

The “substituted heterocyclic group” means a group formed by substituting one or more hydrogen atom of the “unsubstituted heterocyclic group” by a substituent. Specific examples of the “substituted heterocyclic group” include groups formed by substituting a hydrogen atom of each of the “unsubstituted heterocyclic groups” in the set of specific examples G2A by a substituent, and the examples of the substituted heterocyclic groups in the set of specific examples G2B. The examples of the “unsubstituted heterocyclic group” and the examples of the “substituted heterocyclic group” enumerated herein are mere examples, and the “substituted heterocyclic group” in the description herein encompasses groups formed by substituting a hydrogen atom bonded to the ring atom of the heterocyclic group itself of each of the “substituted heterocyclic groups” in the set of specific examples G2B by a substituent, and groups formed by substituting a hydrogen atom of the substituent of each of the “substituted heterocyclic groups” in the set of specific examples G2B by a substituent.

The set of specific examples G2A includes, for example, the unsubstituted heterocyclic group containing a nitrogen atom (set of specific examples G2A1), the unsubstituted heterocyclic group containing an oxygen atom (set of specific examples G2A2), the unsubstituted heterocyclic group containing a sulfur atom (set of specific examples G2A3), and monovalent heterocyclic groups derived by removing one hydrogen atom from each of the ring structures represented by the following general formulae (TEMP-16) to (TEMP-33) (set of specific examples G2A4).

The set of specific examples G2B includes, for example, the substituted heterocyclic groups containing a nitrogen atom (set of specific examples G2B1), the substituted heterocyclic groups containing an oxygen atom (set of specific examples G2B2), the substituted heterocyclic groups containing a sulfur atom (set of specific examples G2B3), and groups formed by substituting one or more hydrogen atom of each of monovalent heterocyclic groups derived from the ring structures represented by the following general formulae (TEMP-16) to (TEMP-33) by a substituent (set of specific examples G2B4).

Unsubstituted Heterocyclic Group containing Nitrogen Atom (Set of Specific Examples G2A1):

- a pyrrolyl group,
- an imidazolyl group,
- a pyrazolyl group,
- a triazolyl group,
- a tetrazolyl group,
- an oxazolyl group,
- an isoxazolyl group,
- an oxadiazolyl group,
- a thiazolyl group,
- an isothiazolyl group,
- a thiadiazolyl group, a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolinyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group containing Oxygen Atom (Set of Specific Examples G2A2)

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group containing Sulfur Atom (Set of Specific Examples G2A3)

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group),
an azadibenzothiophenyl group (azadibenzothienyl group),
a diazadibenzothiophenyl group (diazadibenzothienyl group),
an azanaphthobenzothiophenyl group (azanaphthobenzothienyl group), and
a diazanaphthobenzothiophenyl group (diazanaphthobenzothienyl group).

Monovalent Heterocyclic Group derived by removing One Hydrogen Atom from Ring Structures represented by General Formulae (TEMP-16) to (TEMP-33) (Set of Specific Examples G2A4)

(TEMP-16)

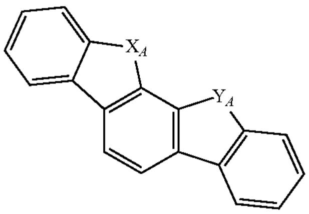

(TEMP-17)

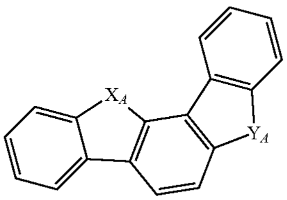

(TEMP-18)

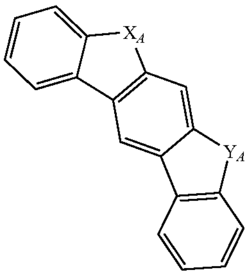

(TEMP-19)

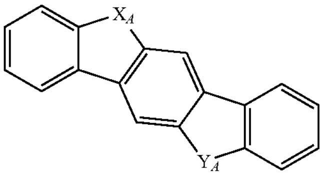

(TEMP-20)

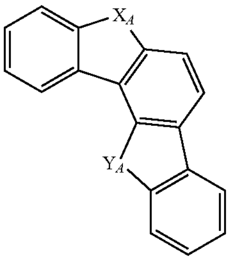

(TEMP-21)

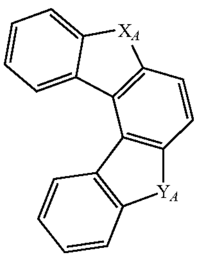

-continued (TEMP-22)

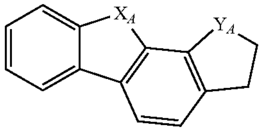

(TEMP-23)

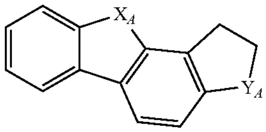

(TEMP-24)

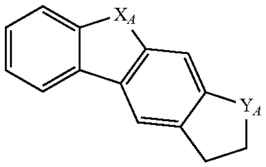

(TEMP-25)

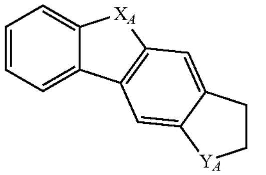

(TEMP-26)

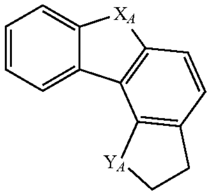

(TEMP-27)

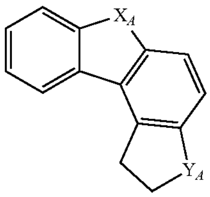

(TEMP-28)

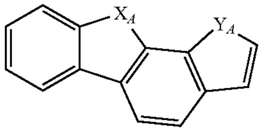

(TEMP-29)

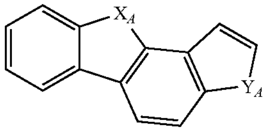

(TEMP-30)

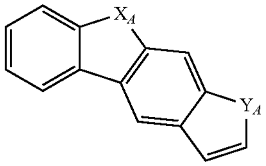

-continued (TEMP-31)

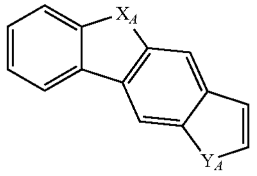

(TEMP-32)

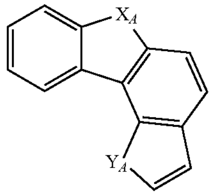

(TEMP-33)

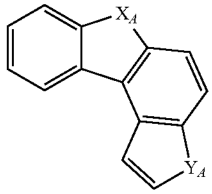

In the general formulae (TEMP-16) to (TEMP-33), $X_A$ and $Y_A$ each independently represent an oxygen atom, a sulfur atom, NH, or $CH_2$, provided that at least one of $X_A$ and $Y_A$ represents an oxygen atom, a sulfur atom, or NH.

In the general formulae (TEMP-16) to (TEMP-33), in the case where at least one of $X_A$ and $Y_A$ represents NH or $CH_2$, the monovalent heterocyclic groups derived from the ring structures represented by the general formulae (TEMP-16) to (TEMP-33) include monovalent groups formed by removing one hydrogen atom from the NH or $CH_2$.

Substituted Heterocyclic Group containing Nitrogen Atom (Set of Specific Examples G2B1):

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenyltriazinyl group,
a diphenyltriazinyl group,
a phenylquinazolinyl group, and
a biphenylquinazolinyl group.

Substituted Heterocyclic Group containing Oxygen Atom (Set of Specific Examples G2B2):

a phenyldibenzofuranyl group,
a methyldibenzofuranyl group,
a t-butyldibenzofuranyl group, and
a monovalent residual group of spiro[9H-xanthene-9,9'-[9H]fluorene].

Substituted Heterocyclic Group containing Sulfur Atom (Set of Specific Examples G2B3):

a phenyldibenzothiophenyl group,
a methyldibenzothiophenyl group,
a t-butyldibenzothiophenyl group, and
a monovalent residual group of spiro[9H-thioxanthene-9,9'-[9H]fluorene].

Group formed by substituting one or more Hydrogen Atom of Monovalent Heterocyclic Group derived from Ring Structures represented by General Formulae (TEMP-16) to (TEMP-33) by Substituent (Set of Specific Examples G2B4)

The "one or more hydrogen atom of the monovalent heterocyclic group" means one or more hydrogen atom selected from the hydrogen atom bonded to the ring carbon atom of the monovalent heterocyclic group, the hydrogen atom bonded to the nitrogen atom in the case where at least one of $X_A$ and $Y_A$ represents NH, and the hydrogen atom of the methylene group in the case where one of $X_A$ and $Y_A$represents $CH_2$.

Substituted or Unsubstituted Alkyl Group

In the description herein, specific examples (set of specific examples G3) of the "substituted or unsubstituted alkyl group" include the unsubstituted alkyl groups (set of specific examples G3A) and the substituted alkyl groups (set of specific examples G3B) shown below. (Herein, the unsubstituted alkyl group means the case where the "substituted or unsubstituted alkyl group" is an "unsubstituted alkyl group", and the substituted alkyl group means the case where the "substituted or unsubstituted alkyl group" is a "substituted alkyl group".) In the description herein, the simple expression "alkyl group" encompasses both the "unsubstituted alkyl group" and the "substituted alkyl group".

The "substituted alkyl group" means a group formed by substituting one or more hydrogen atom of the "unsubstituted alkyl group" by a substituent. Specific examples of the "substituted alkyl group" include groups formed by substituting one or more hydrogen atom of each of the "unsubstituted alkyl groups" (set of specific examples G3A) by a substituent, and the examples of the substituted alkyl groups (set of specific examples G3B). In the description herein, the alkyl group in the "unsubstituted alkyl group" means a chain-like alkyl group. Accordingly, the "unsubstituted alkyl group" encompasses an "unsubstituted linear alkyl group" and an "unsubstituted branched alkyl group". The examples of the "unsubstituted alkyl group" and the examples of the "substituted alkyl group" enumerated herein are mere examples, and the "substituted alkyl group" in the description herein encompasses groups formed by substituting a hydrogen atom of the alkyl group itself of each of the "substituted alkyl groups" in the set of specific examples G3B by a substituent, and groups formed by substituting a hydrogen atom of the substituent of each of the "substituted alkyl groups" in the set of specific examples G3B by a substituent.

Unsubstituted Alkyl Group (Set of Specific Examples G3A):

a methyl group,
an ethyl group,
a n-propyl group,
an isopropyl group,
a n-butyl group,
an isobutyl group,
a s-butyl group, and
a t-butyl group.

Substituted Alkyl Group (Set of Specific Examples G3B):

a heptafluoropropyl group (including isomers),
a pentafluoroethyl group,
a 2,2,2-trifluoroethyl group, and
a trifluoromethyl group.

Substituted or Unsubstituted Alkenyl Group

In the description herein, specific examples (set of specific examples G4) of the "substituted or unsubstituted alkenyl group" include the unsubstituted alkenyl groups (set of specific examples G4A) and the substituted alkenyl groups (set of specific examples G4B) shown below. (Herein, the unsubstituted alkenyl group means the case where the "substituted or unsubstituted alkenyl group" is an "unsubstituted alkenyl group", and the substituted alkenyl group means the case where the "substituted or unsubstituted alkenyl group" is a "substituted alkenyl group".) In the description herein, the simple expression "alkenyl group" encompasses both the "unsubstituted alkenyl group" and the "substituted alkenyl group".

The "substituted alkenyl group" means a group formed by substituting one or more hydrogen atom of the "unsubstituted alkenyl group" by a substituent. Specific examples of the "substituted alkenyl group" include the "unsubstituted alkenyl groups" (set of specific examples G4A) that each have a substituent, and the examples of the substituted alkenyl groups (set of specific examples G4B). The examples of the "unsubstituted alkenyl group" and the examples of the "substituted alkenyl group" enumerated herein are mere examples, and the "substituted alkenyl group" in the description herein encompasses groups formed by substituting a hydrogen atom of the alkenyl group itself of each of the "substituted alkenyl groups" in the set of specific examples G4B by a substituent, and groups formed by substituting a hydrogen atom of the substituent of each of the "substituted alkenyl groups" in the set of specific examples G4B by a substituent.

Unsubstituted Alkenyl Group (Set of Specific Examples G4A):

a vinyl group,
an allyl group,
a 1-butenyl group,
a 2-butenyl group, and
a 3-butenyl group.

Substituted Alkenyl Group (Set of Specific Examples G4B):

a 1,3-butanedienyl group,
a 1-methylvinyl group,
a 1-methylallyl group,
a 1,1-dimethylallyl group,
a 2-methylallyl group, and
a 1,2-dimethylallyl group.

Substituted or Unsubstituted Alkynyl Group

In the description herein, specific examples (set of specific examples G5) of the "substituted or unsubstituted alkynyl group" include the unsubstituted alkynyl group (set of specific examples G5A) shown below. (Herein, the unsubstituted alkynyl group means the case where the "substituted or unsubstituted alkynyl group" is an "unsubstituted alkynyl group".) In the description herein, the simple expression "alkynyl group" encompasses both the "unsubstituted alkynyl group" and the "substituted alkynyl group".

The "substituted alkynyl group" means a group formed by substituting one or more hydrogen atom of the "unsubstituted alkynyl group" by a substituent. Specific examples of the "substituted alkenyl group" include groups formed by substituting one or more hydrogen atom of the "unsubstituted alkynyl group" (set of specific examples G5A) by a substituent.

Unsubstituted Alkynyl Group (Set of Specific Examples G5A):

an ethynyl group.

Substituted or Unsubstituted Cycloalkyl Group

In the description herein, specific examples (set of specific examples G6) of the "substituted or unsubstituted cycloalkyl group" include the unsubstituted cycloalkyl groups (set of specific examples G6A) and the substituted cycloalkyl group (set of specific examples G6B) shown below. (Herein, the unsubstituted cycloalkyl group means the case where the "substituted or unsubstituted cycloalkyl group" is an "unsubstituted cycloalkyl group", and the substituted cycloalkyl group means the case where the "substituted or unsubstituted cycloalkyl group" is a "substituted cycloalkyl group".) In the description herein, the simple expression "cycloalkyl group" encompasses both the "unsubstituted cycloalkyl group" and the "substituted cycloalkyl group".

The "substituted cycloalkyl group" means a group formed by substituting one or more hydrogen atom of the "unsubstituted cycloalkyl group" by a substituent. Specific examples of the "substituted cycloalkyl group" include groups formed by substituting one or more hydrogen atom of each of the "unsubstituted cycloalkyl groups" (set of specific examples G6A) by a substituent, and the example of the substituted cycloalkyl group (set of specific examples G6B). The examples of the "unsubstituted cycloalkyl group" and the examples of the "substituted cycloalkyl group" enumerated herein are mere examples, and the "substituted cycloalkyl group" in the description herein encompasses groups formed by substituting one or more hydrogen atom bonded to the carbon atoms of the cycloalkyl group itself of the "substituted cycloalkyl group" in the set of specific examples G6B by a substituent, and groups formed by substituting a hydrogen atom of the substituent of the "substituted cycloalkyl group" in the set of specific examples G6B by a substituent.

Unsubstituted Cycloalkyl Group (Set of Specific Examples G6A):

a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted Cycloalkyl Group (Set of Specific Examples G6B):

a 4-methylcyclohexyl group.

Group represented by —Si($R_{901}$)($R_{902}$)($R_{903}$)

In the description herein, specific examples (set of specific examples G7) of the group represented by —Si($R_{901}$)($R_{902}$)($R_{903}$) include:

—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

Herein,

G1 represents the "substituted or unsubstituted aryl group" described in the set of specific examples G1,
G2 represents the "substituted or unsubstituted heterocyclic group" described in the set of specific examples G2,
G3 represents the "substituted or unsubstituted alkyl group" described in the set of specific examples G3, and
G6 represents the "substituted or unsubstituted cycloalkyl group" described in the set of specific examples G6.

Plural groups represented by G1 in —Si(G1)(G1)(G1) are the same as or different from each other.

Plural groups represented by G2 in —Si(G1)(G2)(G2) are the same as or different from each other.

Plural groups represented by G1 in —Si(G1)(G1)(G2) are the same as or different from each other.

Plural groups represented by G2 in —Si(G2)(G2)(G2) are the same as or different from each other.

Plural groups represented by G3 in —Si(G3)(G3)(G3) are the same as or different from each other.

Plural groups represented by G6 in —Si(G6)(G6)(G6) are the same as or different from each other.

Group Represented by —O—($R_{904}$)

In the description herein, specific examples (set of specific examples G8) of the group represented by —O—($R_{904}$) include:

—O(G1),
—O(G2),
—O(G3), and
—O(G6).

Herein,

G1 represents the "substituted or unsubstituted aryl group" described in the set of specific examples G1,
G2 represents the "substituted or unsubstituted heterocyclic group" described in the set of specific examples G2,
G3 represents the "substituted or unsubstituted alkyl group" described in the set of specific examples G3, and
G6 represents the "substituted or unsubstituted cycloalkyl group" described in the set of specific examples G6.

Group Represented by —S—($R_{905}$)

In the description herein, specific examples (set of specific examples G9) of the group represented by —S—($R_{905}$) include:

—S(G1),
—S(G2),
—S(G3), and
—S(G6).

Herein,

G1 represents the "substituted or unsubstituted aryl group" described in the set of specific examples G1,
G2 represents the "substituted or unsubstituted heterocyclic group" described in the set of specific examples G2,
G3 represents the "substituted or unsubstituted alkyl group" described in the set of specific examples G3, and
G6 represents the "substituted or unsubstituted cycloalkyl group" described in the set of specific examples G6.

Group Represented by —N($R_{906}$)($R_{907}$)

In the description herein, specific examples (set of specific examples G10) of the group represented by —N($R_{906}$)($R_{907}$) include:

—N(G1)(G1),
—N(G2)(G2),
—N(G1)(G2),
—N(G3)(G3), and
—N(G6)(G6).

G1 represents the "substituted or unsubstituted aryl group" described in the set of specific examples G1,
G2 represents the "substituted or unsubstituted heterocyclic group" described in the set of specific examples G2,
G3 represents the "substituted or unsubstituted alkyl group" described in the set of specific examples G3, and
G6 represents the "substituted or unsubstituted cycloalkyl group" described in the set of specific examples G6.

Plural groups represented by G1 in —N(G1)(G1) are the same as or different from each other.

Plural groups represented by G2 in —N(G2)(G2) are the same as or different from each other.

Plural groups represented by G3 in —N(G3)(G3) are the same as or different from each other.

Plural groups represented by G6 in —N(G6)(G6) are the same as or different from each other.

Halogen Atom

In the description herein, specific examples (set of specific examples G11) of the "halogen atom" include a fluorine atom, a chlorine atom, a bromine atom, and an iodine atom.

Substituted or Unsubstituted Fluoroalkyl Group

In the description herein, the "substituted or unsubstituted fluoroalkyl group" means a group formed by substituting at least one hydrogen atom bonded to the carbon atom constituting the alkyl group in the "substituted or unsubstituted alkyl group" by a fluorine atom, and encompasses a group formed by substituting all the hydrogen atoms bonded to the carbon atoms constituting the alkyl group in the "substituted or unsubstituted alkyl group" by fluorine atoms (i.e., a perfluoroalkyl group). The number of carbon atoms of the "unsubstituted fluoroalkyl group" is 1 to 50, preferably 1 to 30, and more preferably 1 to 18, unless otherwise indicated in the description. The "substituted fluoroalkyl group" means a group formed by substituting one or more hydrogen atom of the "fluoroalkyl group" by a substituent. In the description herein, the "substituted fluoroalkyl group" encompasses a group formed by substituting one or more hydrogen atom bonded to the carbon atom of the alkyl chain in the "substituted fluoroalkyl group" by a substituent, and a group formed by substituting one or more hydrogen atom of the substituent in the "substituted fluoroalkyl group" by a substituent. Specific examples of the "unsubstituted fluoroalkyl group" include examples of groups formed by substituting one or more hydrogen atom in each of the "alkyl group" (set of specific examples G3) by a fluorine atom.

Substituted or Unsubstituted Haloalkyl Group

In the description herein, the "substituted or unsubstituted haloalkyl group" means a group formed by substituting at least one hydrogen atom bonded to the carbon atom constituting the alkyl group in the "substituted or unsubstituted alkyl group" by a halogen atom, and encompasses a group formed by substituting all the hydrogen atoms bonded to the carbon atoms constituting the alkyl group in the "substituted or unsubstituted alkyl group" by halogen atoms. The number of carbon atoms of the "unsubstituted haloalkyl group" is 1 to 50, preferably 1 to 30, and more preferably 1 to 18, unless otherwise indicated in the description. The "substituted haloalkyl group" means a group formed by substituting one or more hydrogen atom of the "haloalkyl group" by a substituent. In the description herein, the "substituted haloalkyl group" encompasses a group formed by substituting one or more hydrogen atom bonded to the carbon atom of the alkyl chain in the "substituted haloalkyl group" by a substituent, and a group formed by substituting one or more hydrogen atom of the substituent in the "substituted haloalkyl group" by a substituent. Specific examples of the "unsubstituted haloalkyl group" include examples of groups formed by substituting one or more hydrogen atom in each of the "alkyl group" (set of specific examples G3) by a halogen atom. A haloalkyl group may be referred to as a halogenated alkyl group in some cases.

Substituted or Unsubstituted Alkoxy Group

In the description herein, specific examples of the "substituted or unsubstituted alkoxy group" include a group represented by —O(G3), wherein G3 represents the "substituted or unsubstituted alkyl group" described in the set of specific examples G3. The number of carbon atoms of the "unsubstituted alkoxy group" is 1 to 50, preferably 1 to 30, and more preferably 1 to 18, unless otherwise indicated in the description.

Substituted or Unsubstituted Alkylthio Group

In the description herein, specific examples of the "substituted or unsubstituted alkylthio group" include a group represented by —S(G3), wherein G3 represents the "substituted or unsubstituted alkyl group" described in the set of specific examples G3. The number of carbon atoms of the "unsubstituted alkylthio group" is 1 to 50, preferably 1 to 30, and more preferably 1 to 18, unless otherwise indicated in the description.

Substituted or Unsubstituted Aryloxy Group

In the description herein, specific examples of the "substituted or unsubstituted aryloxy group" include a group represented by —O(G1), wherein G1 represents the "substituted or unsubstituted aryl group" described in the set of specific examples G1. The number of ring carbon atoms of the "unsubstituted aryloxy group" is 6 to 50, preferably 6 to 30, and more preferably 6 to 18, unless otherwise indicated in the description.

Substituted or Unsubstituted Arylthio Group

In the description herein, specific examples of the "substituted or unsubstituted arylthio group" include a group represented by —S(G1), wherein G1 represents the "substituted or unsubstituted aryl group" described in the set of specific examples G1. The number of ring carbon atoms of the "unsubstituted arylthio group" is 6 to 50, preferably 6 to 30, and more preferably 6 to 18, unless otherwise indicated in the description.

Substituted or Unsubstituted Trialkylsilyl Group

In the description herein, specific examples of the "trialkylsilyl group" include a group represented by —Si(G3)(G3)(G3), wherein G3 represents the "substituted or unsubstituted alkyl group" described in the set of specific examples G3. Plural groups represented by G3 in —Si(G3)(G3)(G3) are the same as or different from each other. The number of carbon atoms of each of alkyl groups of the "substituted or unsubstituted trialkylsilyl group" is 1 to 50, preferably 1 to 20, and more preferably 1 to 6, unless otherwise indicated in the description.

Substituted or Unsubstituted Aralkyl Group

In the description herein, specific examples of the "substituted or unsubstituted aralkyl group" include a group represented by -(G3)-(G1), wherein G3 represents the "substituted or unsubstituted alkyl group" described in the set of specific examples G3, and G1 represents the "substituted or unsubstituted aryl group" described in the set of specific examples G1. Accordingly, the "aralkyl group" is a group formed by substituting a hydrogen atom of an "alkyl group" by an "aryl group" as a substituent, and is one embodiment of the "substituted alkyl group". The "unsubstituted aralkyl group" is an "unsubstituted alkyl group" that is substituted by an "unsubstituted aryl group", and the number of carbon atoms of the "unsubstituted aralkyl group" is 7 to 50, preferably 7 to 30, and more preferably 7 to 18, unless otherwise indicated in the description.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

In the description herein, the substituted or unsubstituted aryl group is preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-dimethylfluorenyl group, a 9,9-diphenylfluorenyl group, and the like, unless otherwise indicated in the description.

In the description herein, the substituted or unsubstituted heterocyclic group is preferably a pyridyl group, a pyrimidinyl group, a triazinyl group, a quinolyl group, an isoquinolyl group, a quinazolinyl group, a benzimidazolyl group, a phenanthrolinyl group, a carbazolyl group (e.g., a 1-carbazolyl, group, a 2-carbazolyl, group, a 3-carbazolyl, group, a 4-carbazolyl, group, or a 9-carbazolyl, group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (e.g., a (9-phenyl)carbazol-1-yl group, a (9-phenyl)carbazol-2-yl group, a (9-phenyl)carbazol-3-yl group, or a (9-phenyl) carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like, unless otherwise indicated in the description.

In the description herein, the carbazolyl group is specifically any one of the following groups unless otherwise indicated in the description.

(TEMP-Cz1)

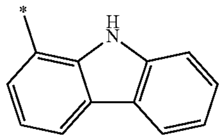

(TEMP-Cz2)

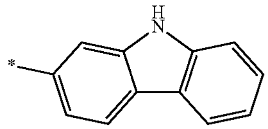

(TEMP-Cz3)

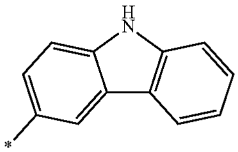

(TEMP-Cz4)

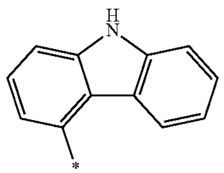

(TEMP-Cz5)

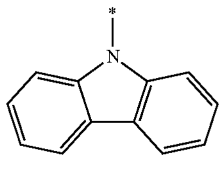

In the description herein, the (9-phenyl)carbazolyl group is specifically any one of the following groups unless otherwise indicated in the description.

(TEMP-Cz6)

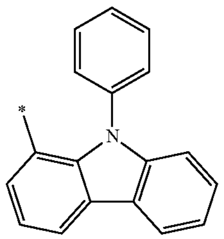

(TEMP-Cz7)

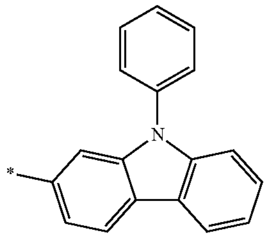

(TEMP-Cz8)

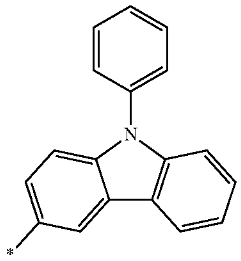

(TEMP-Cz9)

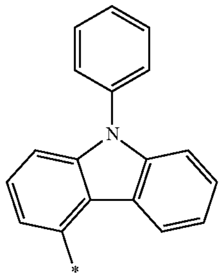

In the general formulae (TEMP-Cz1) to (TEMP-Cz9), * represents a bonding site.

In the description herein, the dibenzofuranyl group and the dibenzothiophenyl group are specifically any one of the following groups unless otherwise indicated in the description.

(TEMP-34)

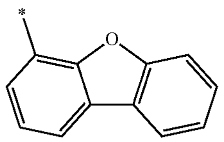

(TEMP-35)

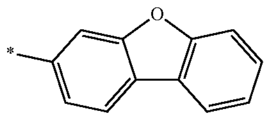

-continued (TEMP-36)

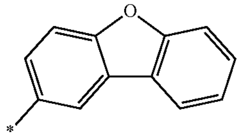

(TEMP-37)

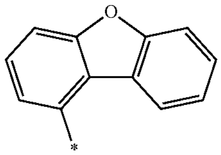

(TEMP-38)

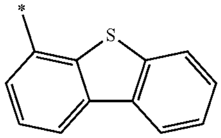

(TEMP-39)

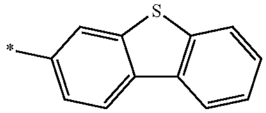

(TEMP-40)

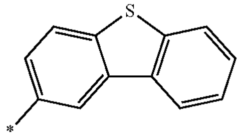

TEMP-41)

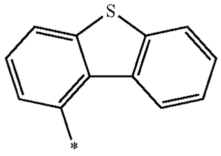

In the general formulae (TEMP-34) to (TEMP-41), *represents a bonding site.

In the description herein, the substituted or unsubstituted alkyl group is preferably a methyl group, an ethyl group, a propyl group, an isopropyl group, a n-butyl group, an isobutyl group, a t-butyl group, or the like unless otherwise indicated in the description.

Substituted or Unsubstituted Arylene Group

In the description herein, the "substituted or unsubstituted arylene group" is a divalent group derived by removing one hydrogen atom on the aryl ring from the "substituted or unsubstituted aryl group" described above unless otherwise indicated in the description. Specific examples (set of specific examples G12) of the "substituted or unsubstituted arylene group" include divalent groups derived by removing one hydrogen atom on the aryl ring from the "substituted or unsubstituted aryl groups" described in the set of specific examples G1.

Substituted or Unsubstituted Divalent Heterocyclic Group

In the description herein, the "substituted or unsubstituted divalent heterocyclic group" is a divalent group derived by removing one hydrogen atom on the heterocyclic ring from the "substituted or unsubstituted heterocyclic group" described above unless otherwise indicated in the description. Specific examples (set of specific examples G13) of the "substituted or unsubstituted divalent heterocyclic group" include divalent groups derived by removing one hydrogen atom on the heterocyclic ring from the "substituted or unsubstituted heterocyclic groups" described in the set of specific examples G2.

Substituted or Unsubstituted Alkylene Group

In the description herein, the "substituted or unsubstituted alkylene group" is a divalent group derived by removing one hydrogen atom on the alkyl chain from the "substituted or unsubstituted alkyl group" described above unless otherwise indicated in the description. Specific examples (set of specific examples G14) of the "substituted or unsubstituted alkylene group" include divalent groups derived by removing one hydrogen atom on the alkyl chain from the "substituted or unsubstituted alkyl groups" described in the set of specific examples G3.

In the description herein, the substituted or unsubstituted arylene group is preferably any one of the groups represented by the following general formulae (TEMP-42) to (TEMP-68) unless otherwise indicated in the description.

(TEMP-42)

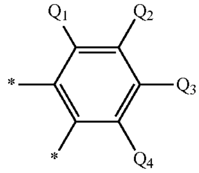

(TEMP-43)

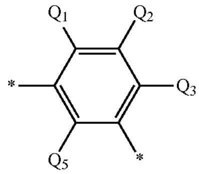

(TEMP-44)

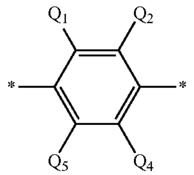

(TEMP-45)

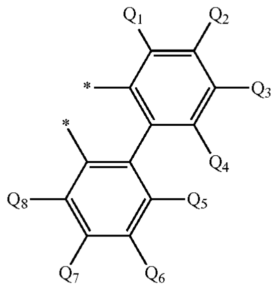

(TEMP-46)

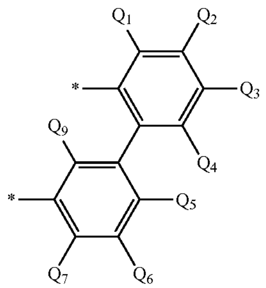

-continued
(TEMP-47)
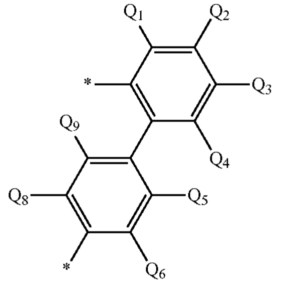
(TEMP-48)
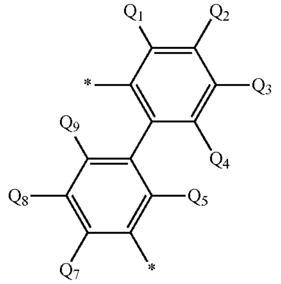
(TEMP-49)
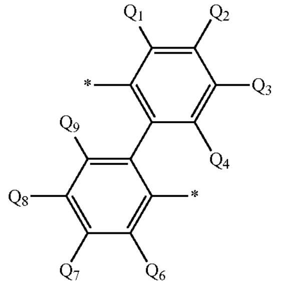
(TEMP-50)
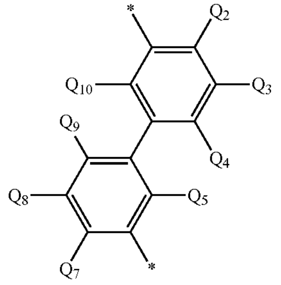
(TEMP-51)
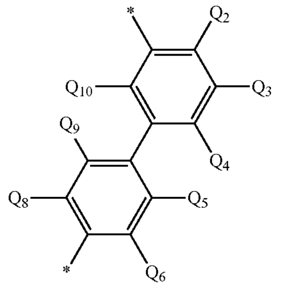
-continued
(TEMP-52)
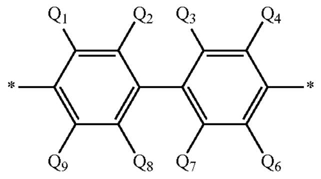
In the general formulae (TEMP-42) to (TEMP-52), $Q_1$ to $Q_{10}$ each independently represent a hydrogen atom or a substituent.
In the general formulae (TEMP-42) to (TEMP-52), * represents a bonding site.
(TEMP-53)
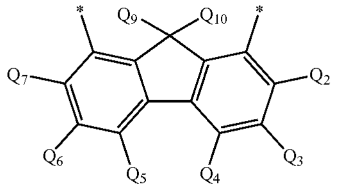
(TEMP-54)
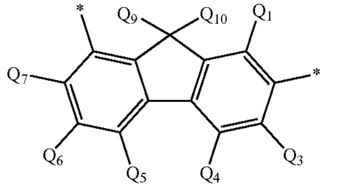
(TEMP-55)
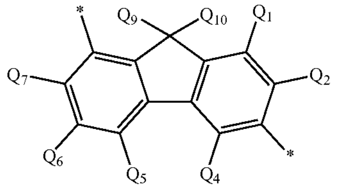
(TEMP-56)
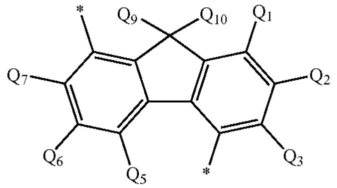
(TEMP-57)
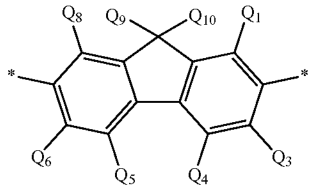
(TEMP-58)
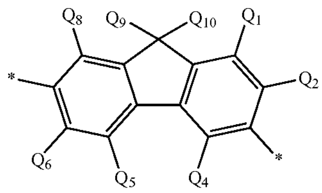

-continued (TEMP-59)

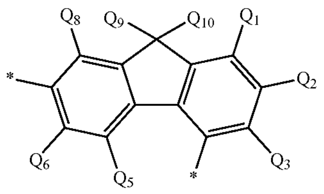

(TEMP-60)

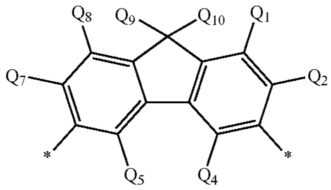

(TEMP-61)

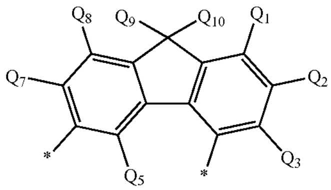

(TEMP-62)

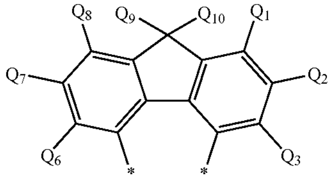

In the general formulae (TEMP-53) to (TEMP-62), $Q_1$ to $Q_{10}$ each independently represent a hydrogen atom or a substituent.

The formulae $Q_9$ and $Q_{10}$ may be bonded to each other to form a ring via a single bond.

In the general formulae (TEMP-53) to (TEMP-62), * represents a bonding site.

(TEMP-63)

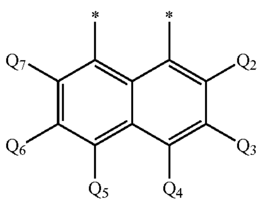

(TEMP-64)

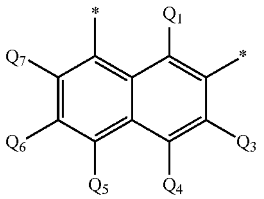

-continued (TEMP-65)

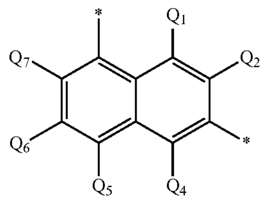

(TEMP-66)

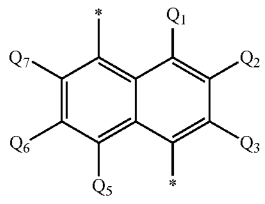

(TEMP-67)

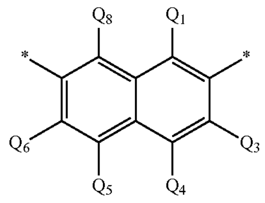

(TEMP-68)

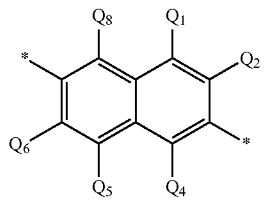

In the general formulae (TEMP-63) to (TEMP-68), $Q_1$ to $Q_8$ each independently represent a hydrogen atom or a substituent.

In the general formulae (TEMP-63) to (TEMP-68), * represents a bonding site.

In the description herein, the substituted or unsubstituted divalent heterocyclic group is preferably the groups represented by the following general formulae (TEMP-69) to (TEMP-102) unless otherwise indicated in the description.

(TEMP-69)

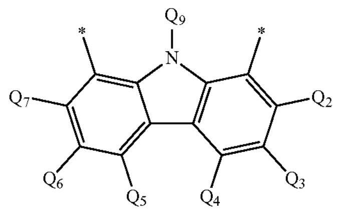

(TEMP-70)

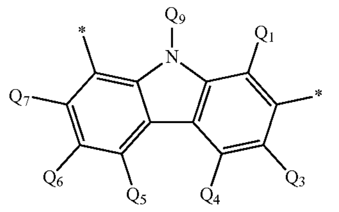

-continued
(TEMP-71)
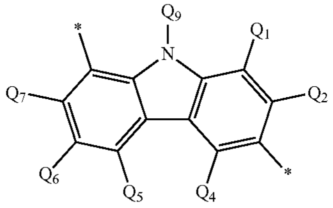
(TEMP-72)
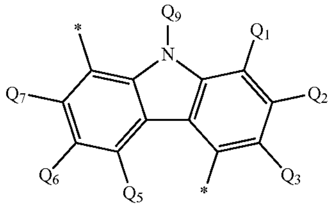
(TEMP-73)
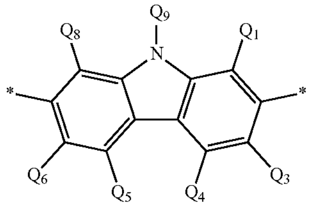
(TEMP-74)
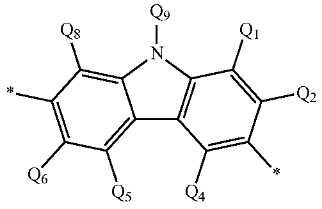
(TEMP-75)
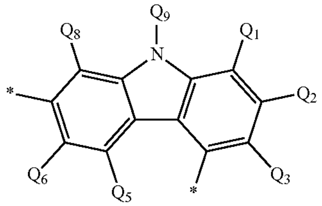
(TEMP-76)
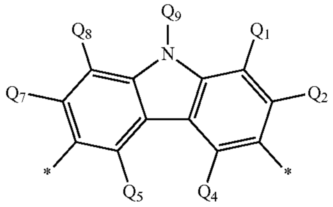
(TEMP-77)
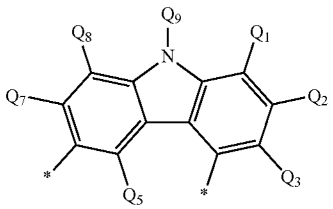
-continued
(TEMP-78)
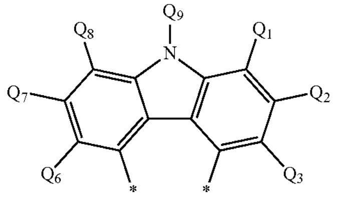
(TEMP-79)
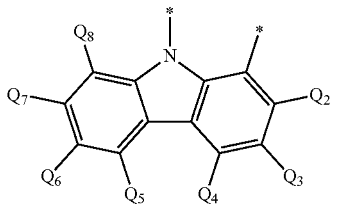
(TEMP-80)
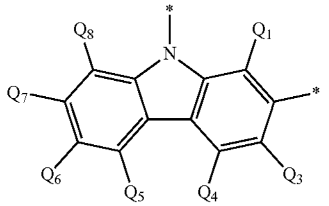
(TEMP-81)
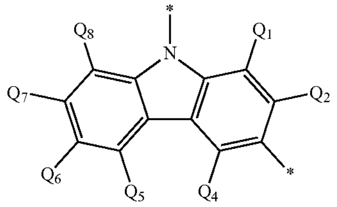
(TEMP-82)
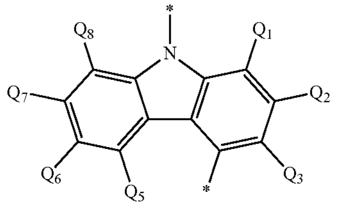
In the general formulae (TEMP-69) to (TEMP-82), $Q_1$ to $Q_9$ each independently represent a hydrogen atom or a substituent.
(TEMP-83)
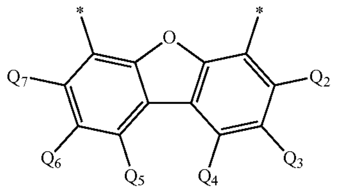
(TEMP-84)
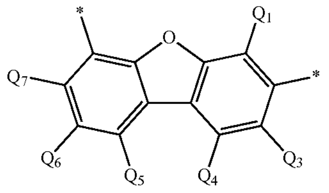

-continued
(TEMP-85)
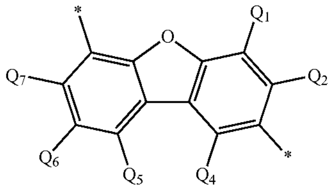
(TEMP-86)
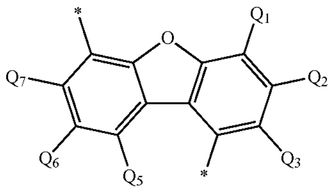
(TEMP-87)
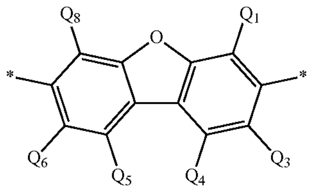
(TEMP-88)
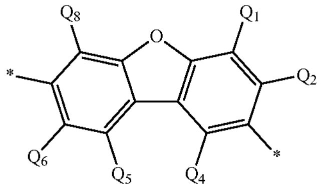
(TEMP-89)
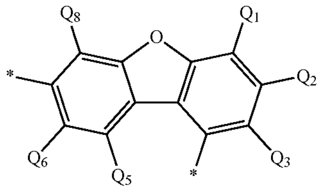
(TEMP-90)
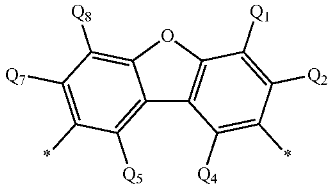
(TEMP-91)
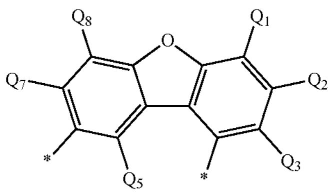
(TEMP-92)
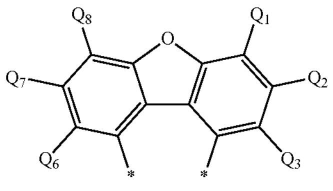
-continued
(TEMP-93)
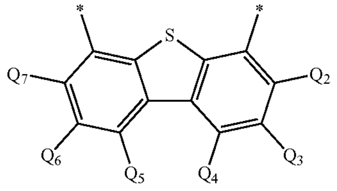
(TEMP-94)
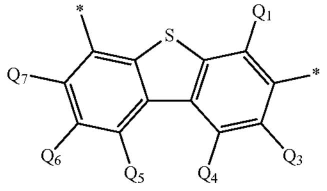
(TEMP-95)
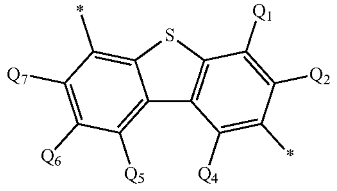
(TEMP-96)
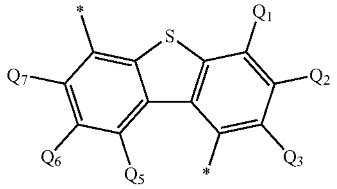
(TEMP-97)
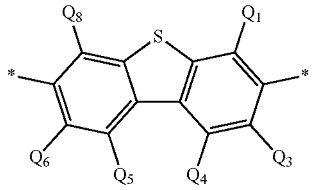
(TEMP-98)
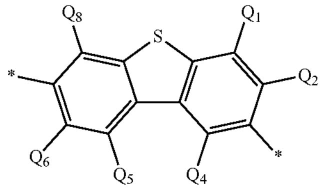
(TEMP-99)
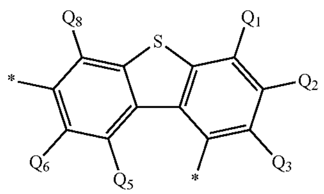
(TEMP-100)
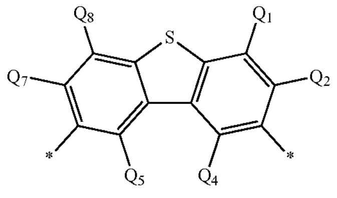

-continued (TEMP-101)

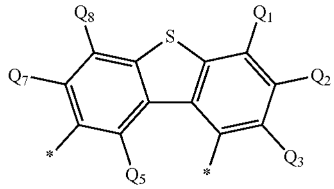

(TEMP-102)

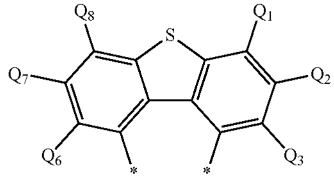

In the general formulae (TEMP-83) to (TEMP-102), $Q_1$ to $Q_8$ each independently represent a hydrogen atom or a substituent.

The above are the explanation of the "substituents in the description herein".

Case Forming Ring by Bonding

In the description herein, the case where "one or more combinations of combinations each including adjacent two or more each are bonded to each other to form a substituted or unsubstituted monocyclic ring, or each are bonded to each other to form a substituted or unsubstituted condensed ring, or each are not bonded to each other" means a case where "one or more combinations of combinations each including adjacent two or more each are bonded to each other to form a substituted or unsubstituted monocyclic ring", a case where "one or more combinations of combinations each including adjacent two or more each are bonded to each other to form a substituted or unsubstituted condensed ring", and a case where "one or more combinations of combinations each including adjacent two or more each are not bonded to each other".

In the description herein, the case where "one or more combinations of combinations each including adjacent two or more each are bonded to each other to form a substituted or unsubstituted monocyclic ring" and the case where "one or more combinations of combinations each including adjacent two or more each are bonded to each other to form a substituted or unsubstituted condensed ring" (which may be hereinafter collectively referred to as a "case forming a ring by bonding") will be explained below. The cases will be explained for the anthracene compound represented by the following general formula (TEMP-103) having an anthracene core skeleton as an example.

(TEMP-103)

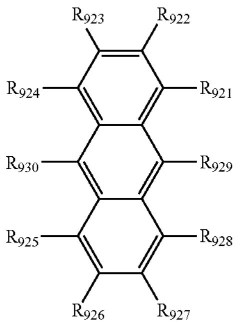

For example, in the case where "one or more combinations of combinations each including adjacent two or more each are bonded to each other to form a ring" among $R_{921}$ to $R_{930}$, the combinations each including adjacent two as one combination include a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, and a combination of $R_{929}$ and $R_{921}$.

The "one or more combinations" mean that two or more combinations each including adjacent two or more may form rings simultaneously. For example, in the case where $R_{921}$ and $R_{922}$ are bonded to each other to form a ring $Q_A$, and simultaneously $R_{925}$ and $R_{926}$ are bonded to each other to form a ring $Q_B$, the anthracene compound represented by the general formula (TEMP-103) is represented by the following general formula (TEMP-104).

(TEMP-104)

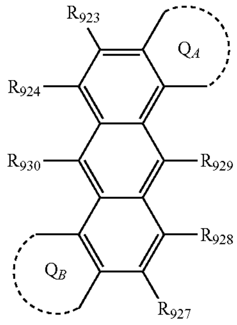

The case where the "combination including adjacent two or more forms rings" encompasses not only the case where adjacent two included in the combination are bonded as in the aforementioned example, but also the case where adjacent three or more included in the combination are bonded. For example, this case means that $R_{921}$ and $R_{922}$ are bonded to each other to form a ring $Q_A$, $R_{922}$ and $R_{923}$ are bonded to each other to form a ring $Q_C$, and adjacent three ($R_{921}$, $R_{922}$, and $R_{923}$) included in the combination are bonded to each other to form rings, which are condensed to the anthracene core skeleton, and in this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

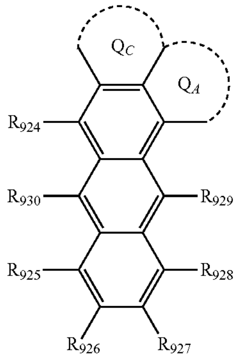

The formed "monocyclic ring" or "condensed ring" may be a saturated ring or an unsaturated ring in terms of structure of the formed ring itself. In the case where the "one combination including adjacent two" forms a "monocyclic ring" or a "condensed ring", the "monocyclic ring" or the "condensed ring" may form a saturated ring or an unsaturated ring. For example, the ring $Q_A$ and the ring $Q_B$ formed in the general formula (TEMP-104) each are a "monocyclic ring" or a "condensed ring". The ring $Q_A$ and the ring $Q_C$ formed in the general formula (TEMP-105) each are a "condensed ring". The ring $Q_A$ and the ring $Q_C$ in the general formula (TEMP-105) form a condensed ring through condensation of the ring $Q_A$ and the ring $Q_C$. In the case where the ring $Q_A$ in the general formula (TMEP-104) is a benzene ring, the ring $Q_A$ is a monocyclic ring. In the case where the ring $Q_A$ in the general formula (TMEP-104) is a naphthalene ring, the ring $Q_A$ is a condensed ring.

The "unsaturated ring" means an aromatic hydrocarbon ring or an aromatic heterocyclic ring. The "saturated ring" means an aliphatic hydrocarbon ring or a non-aromatic heterocyclic ring.

Specific examples of the aromatic hydrocarbon ring include the structures formed by terminating the groups exemplified as the specific examples in the set of specific examples G1 with a hydrogen atom.

Specific examples of the aromatic heterocyclic ring include the structures formed by terminating the aromatic heterocyclic groups exemplified as the specific examples in the set of specific examples G2 with a hydrogen atom.

Specific examples of the aliphatic hydrocarbon ring include the structures formed by terminating the groups exemplified as the specific examples in the set of specific examples G6 with a hydrogen atom.

The expression "to form a ring" means that the ring is formed only with the plural atoms of the core structure or with the plural atoms of the core structure and one or more arbitrary element. For example, the ring $Q_A$ formed by bonding $R_{921}$ and $R_{922}$ each other shown in the general formula (TEMP-104) means a ring formed with the carbon atom of the anthracene skeleton bonded to $R_{921}$, the carbon atom of the anthracene skeleton bonded to $R_{922}$, and one or more arbitrary element. As a specific example, in the case where the ring $Q_A$ is formed with $R_{921}$ and $R_{922}$, and in the case where a monocyclic unsaturated ring is formed with the carbon atom of the anthracene skeleton bonded to $R_{921}$, the carbon atom of the anthracene skeleton bonded to $R_{922}$, and four carbon atoms, the ring formed with $R_{921}$ and $R_{922}$ is a benzene ring.

Herein, the "arbitrary element" is preferably at least one kind of an element selected from the group consisting of a carbon element, a nitrogen element, an oxygen element, and a sulfur element, unless otherwise indicated in the description. For the arbitrary element (for example, for a carbon element or a nitrogen element), a bond that does not form a ring may be terminated with a hydrogen atom or the like, and may be substituted by an "arbitrary substituent" described later. In the case where an arbitrary element other than a carbon element is contained, the formed ring is a heterocyclic ring.

The number of the "one or more arbitrary element" constituting the monocyclic ring or the condensed ring is preferably 2 or more and 15 or less, more preferably 3 or more and 12 or less, and further preferably 3 or more and 5 or less, unless otherwise indicated in the description.

What is preferred between the "monocyclic ring" and the "condensed ring" is the "monocyclic ring" unless otherwise indicated in the description.

What is preferred between the "saturated ring" and the "unsaturated ring" is the "unsaturated ring" unless otherwise indicated in the description.

The "monocyclic ring" is preferably a benzene ring unless otherwise indicated in the description.

The "unsaturated ring" is preferably a benzene ring unless otherwise indicated in the description.

In the case where the "one or more combinations of combinations each including adjacent two or more" each are "bonded to each other to form a substituted or unsubstituted monocyclic ring", or each are "bonded to each other to form a substituted or unsubstituted condensed ring", it is preferred that the one or more combinations of combinations each including adjacent two or more each are bonded to each other to form a substituted or unsubstituted "unsaturated ring" containing the plural atoms of the core skeleton and 1 or more and 15 or less at least one kind of an element selected from the group consisting of a carbon element, a nitrogen element, an oxygen element, and a sulfur element, unless otherwise indicated in the description.

In the case where the "monocyclic ring" or the "condensed ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

In the case where the "saturated ring" or the "unsaturated ring" has a substituent, the substituent is, for example, an "arbitrary substituent" described later. In the case where the "monocyclic ring" or the "condensed ring" has a substituent, specific examples of the substituent include the substituents explained in the section "Substituents in Description" described above.

The above are the explanation of the case where "one or more combinations of combinations each including adjacent two or more" each are "bonded to each other to form a substituted or unsubstituted monocyclic ring", and the case where "one or more combinations of combinations each including adjacent two or more" each are "bonded to each other to form a substituted or unsubstituted condensed ring" (i.e., the "case forming a ring by bonding").

Substituent for "Substituted or Unsubstituted"

In one embodiment in the description herein, the substituent for the case of "substituted or unsubstituted" (which may be hereinafter referred to as an "arbitrary substituent") is, for example, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$) ($R_{902}$)($R_{903}$),

—O—($R_{904}$),

—S—($R_{905}$),

—N($R_{906}$)($R_{907}$), a halogen atom, a cyano group, a nitro group, an unsubstituted aryl group having 6 to 50 ring carbon atoms, and an unsubstituted heterocyclic group having 5 to 50 ring atoms, wherein $R_{901}$ to $R_{907}$ each independently represent a hydrogen atom, a substituted or unsubstituted alkyl group having 1 to 50 carbon atoms a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the case where two or more groups each represented by $R_{901}$ exist, the two or more groups each represented by $R_{901}$ are the same as or different from each other, in the case where two or more groups each represented by $R_{902}$ exist, the two or more groups each represented by $R_{902}$ are the same as or different from each other, in the case where two or more groups each represented by $R_{903}$ exist, the two or more groups each represented by $R_{903}$ are the same as or different from each other, in the case where two or more groups each represented by $R_{904}$ exist, the two or more groups each represented by $R_{904}$ are the same as or different from each other, in the case where two or more groups each represented by $R_{905}$ exist, the two or more groups each represented by $R_{905}$ are the same as or different from each other, in the case where two or more groups each represented by $R_{906}$ exist, the two or more groups each represented by $R_{906}$ are the same as or different from each other, and in the case where two or more groups each represented by $R_{907}$ exist, the two or more groups each represented by $R_{907}$ are the same as or different from each other.

In one embodiment, the substituent for the case of "substituted or unsubstituted" may be a group selected from the group consisting of an alkyl group having 1 to 50 carbon atoms, an aryl group having 6 to 50 ring carbon atoms, and a heterocyclic group having 5 to 50 ring atoms.

In one embodiment, the substituent for the case of "substituted or unsubstituted" may be a group selected from the group consisting of an alkyl group having 1 to 18 carbon atoms, an aryl group having 6 to 18 ring carbon atoms, and a heterocyclic group having 5 to 18 ring atoms.

The specific examples of the groups for the arbitrary substituent described above are the specific examples of the substituent described in the section "Substituents in Description" described above.

In the description herein, the arbitrary adjacent substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, and more preferably form a benzene ring, unless otherwise indicated.

In the description herein, the arbitrary substituent may further have a substituent unless otherwise indicated in the description. The definition of the substituent that the arbitrary substituent further has may be the same as the arbitrary substituent.

In the description herein, a numerical range shown by "AA to BB" means a range including the numerical value AA as the former of "AA to BB" as the lower limit value and the numerical value BB as the latter of "AA to BB" as the upper limit value.

The compound of the present invention will now be described.

The compound according to an embodiment of the present invention is represented by the following formula (1A) or (1B).

The compound of the present invention, represented by the formula (1A) or (1B) or by any of the below-described formulae included in the formula (1A) or (1B), may be hereinafter simply referred to as an "inventive compound".

(1A)

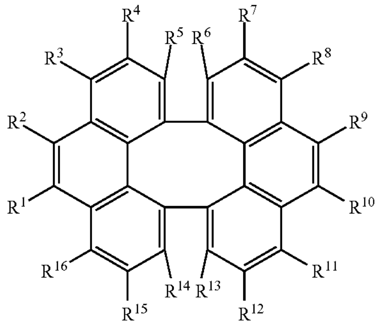

(1B)

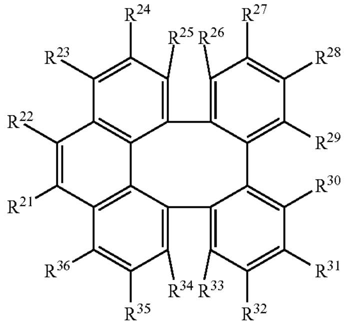

Symbols in the formula (1A) or (1B) or in the below-described formulae included in the formula (1A) or (1B) will now be described. The same symbols have the same meaning.

In the formulae (1A) and (1B), at least one selected from $R^1$ to $R^{16}$ and at least one selected from $R^{21}$ to $R^{36}$ are represented by the following formula (2A), (2B), (2C) or (2D).

$$*-(L^1)_a-HET \quad (2A)$$

(2B)

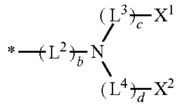

$$*-(L^5)_e-Ar \quad (2C)$$

$$*-(L^6)_f-Y \quad (2D)$$

In the formulae (2A), (2B), (2C) and (2D), * represents a bonding position to a carbon atom in the formula (1A) at which $R^1$ to $R^{16}$ are bonded or a bonding position to a carbon atom in the formula (1B) at which $R^{21}$ to $R^{36}$ are bonded.

In the formulae (2A), (2B), (2C) and (2D), $L^1$ to $L^6$ each independently represent a substituted or unsubstituted arylene group having 6 to 50 ring carbon atoms, or a substituted or unsubstituted divalent heterocyclic group having 5 to 50 ring atoms.

In the formulae (2A), (2B), (2C) and (2D), a, b, c, d, e and f each independently represent 0, 1, 2 or 3, and $(L^1)_0$, $(L^2)_0$, $(L^3)_0$, $(L^4)_0$, $(L^5)_0$ and $(L^6)_0$ each independently represent a single bond.

When two or more $L^1$s are present, they may be the same or different, when two or more $L^2$s are present, they may be the same or different, when two or more $L^3$s are present, they may be the same or different, when two or more $L^4$s are present, they may be the same or different, when two or more $L^5$s are present, they may be the same or different, and when two or more $L^6$s are present, they may be the same or different.

In the formula (2A), HET represents a substituted or unsubstituted heterocyclic group having 5 to 50 ring atoms.

In the formula (2B), $X^1$ and $X^2$ each independently represent a substituted or unsubstituted aryl group having 6 to 50 ring carbon atoms, or a substituted or unsubstituted heterocyclic group having 5 to 50 ring atoms.

In the formula (2C), Ar represents a substituted or unsubstituted aryl group having 10 to 50 ring carbon atoms.

In the formula (2D), Y represents a group selected from the following formulae (i) to (viii).

(i)

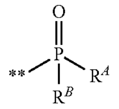

(ii)

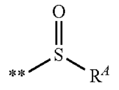

(iii)

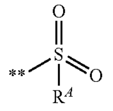

(iv)

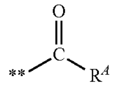

(v)

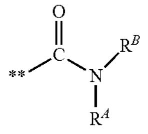

(vi)

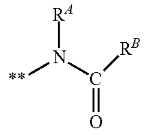

(vii)

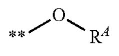

(viii)

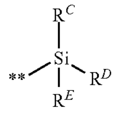

In the formulae (i) to (viii), ** represents a bonding position at which Y is bonded to $L^6$ in the formula (2D).

In the formulae (i) to (vii), $R^A$ and $R^B$ each independently represent a hydrogen atom or a substituent $Z^1$.

In the formula (viii), $R^C$, $R^D$ and $R^E$ each independently represent a substituted or unsubstituted aryl group having 6 to 50 ring carbon atoms.

The substituent $Z^1$ is a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted aralkyl group having 7 to 50 carbon atoms, a substituted or unsubstituted heterocyclic group having 5 to 50 ring atoms, a substituted or unsubstituted haloalkyl group having 1 to 50 carbon atoms, a substituted or unsubstituted haloalkoxy group having 1 to 50 carbon atoms, a group represented by $-Si(R_{901})(R_{902})(R_{903})$, a group represented by $-O-(R_{904})$, a group represented by $-S-(R_{905})$, or a group represented by $-N(R_{906})(R_{907})$, where $R_{901}$ to $R_{907}$ each independently represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, when two or more Rsol's are present, the $R_{901}$'s may be the same or different, when two or more $R_{902}$'s are present, the $R_{902}$'s may be the same or different, when two or more $R_{903}$'s are present, the $R_{903}$'s may be the same or different, when two or more $R_{904}$'s are present, the $R_{904}$'s may be the same or different, when two or more $R_{905}$'s are present, the $R_{905}$'s may be the same or different, when two or more $R_{906}$'s are present, the $R_{906}$'s may be the same or different, when two or more $R_{907}$'s are present, the $R_{907}$'s may be the same or different.

When $R^1$, $R^2$, $R^9$ and $R^{10}$ in the formula (1A) are all represented by the formula (2A), at least one selected from $R^1$, $R^2$, $R^9$ and $R^{10}$ is the formula (2A) in which HET contains a nitrogen atom.

When two or more selected from $R^1$ to $R^{16}$ in the formula (1A) are represented by the formula (2A), they may be the same or different, when two or more selected from $R^1$ to $R^{16}$ are represented by the formula (2B), they may be the same or different, when two or more selected from $R^1$ to $R^{16}$ are represented by the formula (2C), they may be the same or different, and when two or more selected from $R^1$ to $R^{16}$ are represented by the formula (2D), they may be the same or different, and $R^1$ to $R^{16}$ are not bonded to each other.

When two or more selected from $R^{21}$ to $R^{36}$ in the formula (1B) are represented by the formula (2A), they may be the same or different, when two or more selected from $R^{21}$ to $R^{36}$ are represented by the formula (2B), they may be the same or different, when two or more selected from $R^{21}$ to $R^{36}$ are represented by the formula (2C), they may be the same or different, and when two or more selected from $R^{21}$ to $R^{36}$ are represented by the formula (2D), they may be the same or different, and $R^{21}$ to $R^{36}$ are not bonded to each other.

In the formulae (1A) and (1B), $R^1$ to $R^{16}$ and $R^{21}$ to $R^{36}$ which are not represented by the formula (2A), (2B), (2C) or (2D) each independently represent a hydrogen atom or a substituent $Z^2$.

The substituent $Z^2$ is a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted phenyl group, a substituted or unsubstituted aralkyl group having 7 to 50 carbon atoms, a substituted or unsubstituted haloalkyl group having 1 to 50 carbon atoms, a substituted or unsubstituted haloalkoxy group having 1 to 50 carbon atoms, a group represented by $-Si(R_{901})(R_{902})(R_{903})$, a group represented by $-S-(R_{905})$, or a group represented by $-N(R_{906})(R_{907})$, $R_{901}$ to $R_{907}$ each independently represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, when two or more $R_{901}$'s are present, the $R_{901}$'s may be the same or different, when two or more $R_{902}$'s are present, the $R_{902}$'s may be the same or different, when two or more $R_{903}$'s are present, the $R_{903}$'s may be the same or different, when two or more $R_{905}$'s are present, the $R_{905}$'s may be the same or different, when two or more $R_{906}$'s are present, the $R_{906}$'s may be the same or different, when two or more $R_{907}$'s are present, the $R_{907}$'s may be the same or different.

At least one of $R_{901}$ to $R_{903}$ is not a substituted or unsubstituted aryl group having 6 to 50 ring carbon atoms, and at least one of $R_{906}$ and $R_{907}$ is a hydrogen atom, a substituted or unsubstituted alkyl group having 1 to 50 carbon atoms, or a substituted or unsubstituted cycloalkyl group having 3 to 50 ring carbon atoms.

$R_{901}$ to $R_{903}$ are not bonded to each other, and $R_{906}$ and $R_{907}$ are not bonded to each other.

In one embodiment of the inventive compound, $L^1$ to $L^6$ are preferably each independently a substituted or unsubstituted arylene group having 6 to 50 ring carbon atoms.

In one embodiment of the inventive compound, the arylene groups having 6 to 50 ring carbon atoms in the substituted or unsubstituted arylene groups having 6 to 50 ring carbon atoms, represented by $L^1$ to $L^6$, are preferably each independently a phenylene group, a biphenylene group, a naphthylene group, or an anthracenediyl group. Thus, in one embodiment of the inventive compound, the unsubstituted arylene groups having 6 to 50 ring carbon atoms, represented by $L^1$ to $L^6$, are preferably each independently one selected from the group consisting of the above-listed arylene groups. The substituted arylene groups having 6 to 50 ring carbon atoms, represented by $L^1$ to $L^6$, are preferably each independently one selected from the group consisting of the above-listed arylene groups and having a substituent.

In one embodiment of the inventive compound, the arylene groups having 6 to 50 ring carbon atoms in the substituted or unsubstituted arylene groups having 6 to 50 ring carbon atoms, represented by $L^1$ to $L^6$, may each independently be represented by one of the below-described structural formulae. In the below-described structural formulae, * represents a bonding position. Thus, in one embodiment of the inventive compound, the unsubstituted arylene groups having 6 to 50 ring carbon atoms, represented by $L^1$ to $L^6$, may each independently be one selected from the group consisting of the below-described structural formulae. The substituted arylene groups having 6 to 50 ring carbon atoms, represented by $L^1$ to $L^6$, may each independently be one selected from the group consisting of the below-described structural formulae and having a substituent bonded to a carbon atom other than the carbon atom positioned at the bonding position *.

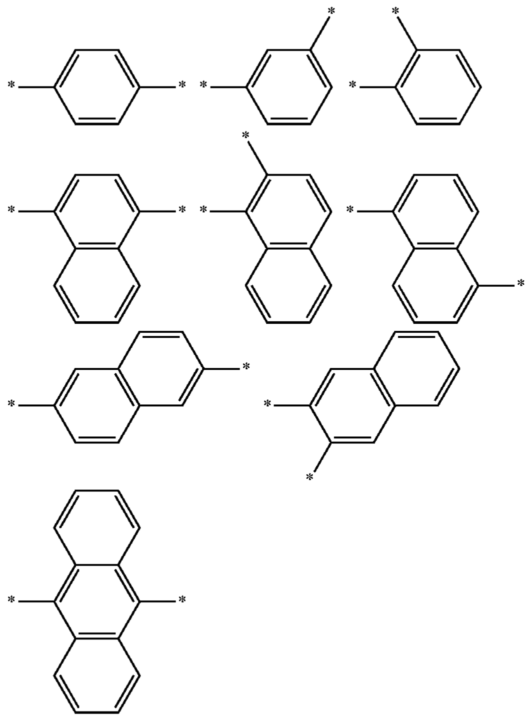

In one embodiment of the inventive compound, the divalent heterocyclic groups having 5 to 50 ring atoms in the substituted or unsubstituted divalent heterocyclic groups having 5 to 50 ring atoms, represented by $L^1$ to $L^6$, are preferably each independently a divalent group derived by removing a hydrogen atom on a hetero ring from a pyridyl group, a pyridazinyl group, a pyrimidinyl group, a pyrazinyl group, a triazinyl group, a quinoxalinyl group, a quinazolinyl group, a carbazolyl group, a dibenzofuranyl group or a dibenzothiophenyl group. Thus, in one embodiment of the inventive compound, the unsubstituted divalent heterocyclic groups having 5 to 50 ring atoms, represented by $L^1$ to $L^6$, are preferably each independently a divalent group derived by removing a hydrogen atom on a hetero ring from a heterocyclic group selected from the group consisting of the above-listed heterocyclic groups. The substituted divalent heterocyclic groups having 5 to 50 ring atoms, represented by $L^1$ to $L^6$, are preferably each independently a divalent group derived by removing a hydrogen atom on a hetero ring from a heterocyclic group selected from the group consisting of the above-listed heterocyclic groups, and having a substituent.

In one embodiment of the inventive compound, the divalent heterocyclic group having 5 to 50 ring atoms in the substituted or unsubstituted divalent heterocyclic group having 5 to 50 ring atoms, represented by $L^5$, is more preferably a divalent group derived by removing a hydrogen atom on a hetero ring from a carbazolyl group, a dibenzofuranyl group or a dibenzothiophenyl group. Thus, in one embodiment of the inventive compound, it is more preferred that the unsubstituted divalent heterocyclic groups having 5 to 50 ring atoms, represented by $L^5$, be each independently a divalent group derived by removing a hydrogen atom on a hetero ring from a heterocyclic group selected from the group consisting of the above-listed heterocyclic groups, and that the substituted divalent heterocyclic groups having 5 to 50 ring atoms, represented by $L^5$, be each independently a divalent group derived by removing a hydrogen atom on a hetero ring from a heterocyclic group selected from the group consisting of the above-listed heterocyclic groups, and having a substituent.

In one embodiment of the inventive compound, the divalent heterocyclic groups having 5 to 50 ring atoms in the substituted or unsubstituted divalent heterocyclic groups having 5 to 50 ring atoms, represented by $L^1$ to $L^6$, may each independently be represented by one of the below-described structural formulae. In the below-described structural formulae, * represents a bonding position. Thus, in one embodiment of the inventive compound, the unsubstituted divalent heterocyclic groups having 5 to 50 ring atoms, represented by $L^1$ to $L^6$, may each independently be one selected from the group consisting of the below-described structural formulae. The substituted divalent heterocyclic groups having 5 to 50 ring atoms, represented by $L^1$ to $L^6$, may each independently be one selected from the group consisting of the below-described structural formulae and having a substituent bonded to a carbon atom other than the carbon atom positioned at the bonding position *.

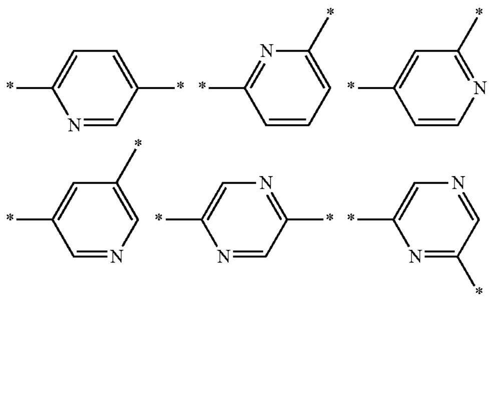

-continued

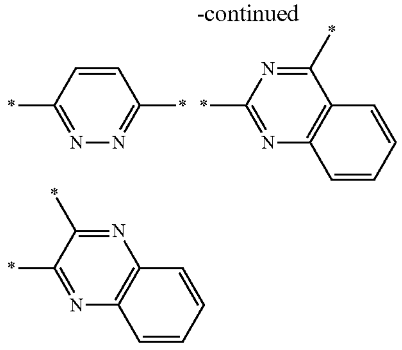

In one embodiment of the inventive compound, the heterocyclic group having 5 to 50 ring atoms in the substituted or unsubstituted heterocyclic group having 5 to 50 ring atoms, represented by HET, preferably contains a nitrogen atom as a ring atom. Thus, in one embodiment of the inventive compound, the unsubstituted heterocyclic group having 5 to 50 ring atoms, represented by HET, preferably contains a nitrogen atom as a ring atom. The substituted heterocyclic group having 5 to 50 ring atoms, represented by HET, preferably contains a nitrogen atom as a ring atom and has a substituent.

In one embodiment of the inventive compound, the heterocyclic group having 5 to 50 ring atoms in the substituted or unsubstituted heterocyclic group having 5 to 50 ring atoms, represented by HET, is preferably a pyridyl group, a pyridazinyl group, a pyrimidinyl group, a pyrazinyl group, a bipyridinyl group, a triazinyl group, a quinolizinyl group, a quinolyl group, an isoquinolyl group, a cinnonyl group, a phthalazinyl group, a quinazolinyl group, a quinoxalinyl group, benzoimidazolyl group, an indazolyl group, an imidazopyridyl group, an imidazopyrimidyl group, a phenanthrolinyl group, a phenanthridinyl group, a carbazolyl group, an azacarbazolyl group or a diazacarbazolyl group. Thus, in one embodiment of the inventive compound, it is preferred that the unsubstituted heterocyclic groups having 5 to 50 ring atoms, represented by HET, be each independently one selected from the group consisting of the above-listed heterocyclic groups, and that the substituted heterocyclic groups having 5 to 50 ring atoms, represented by HET, be each independently one selected from the group consisting of the above-listed heterocyclic groups and having a substituent.

In one embodiment of the inventive compound, HET may be represented, for example, by one of the following structural formulae.

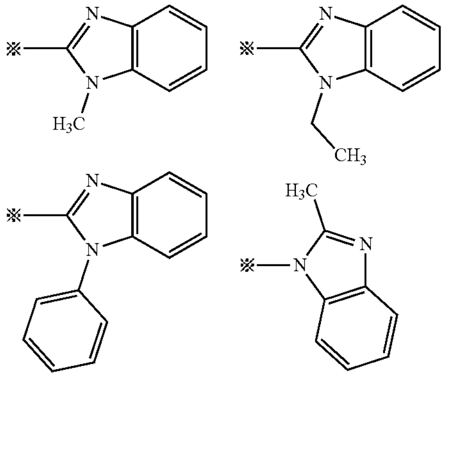

-continued
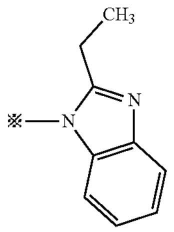
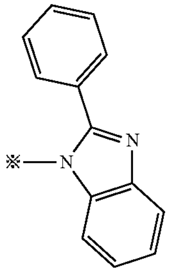
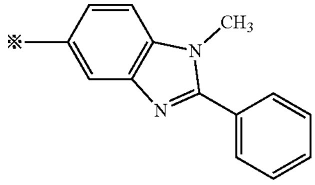
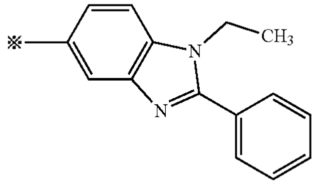
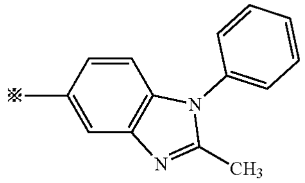
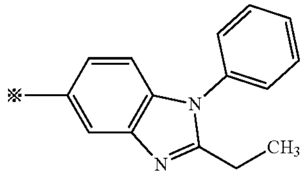
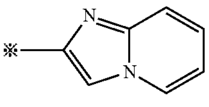
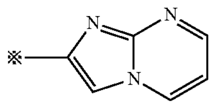
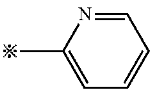
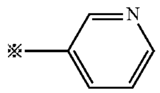
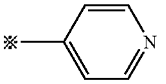
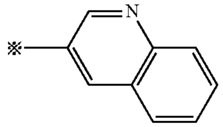
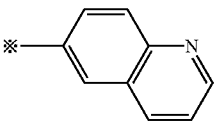
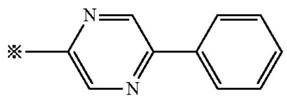
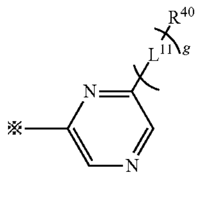
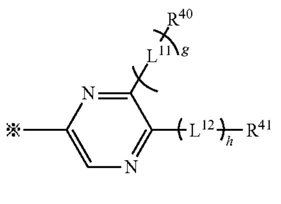
-continued
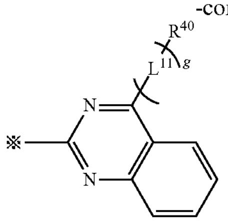
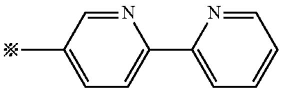
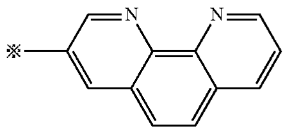
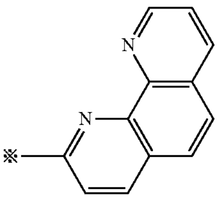
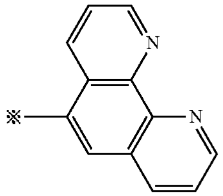
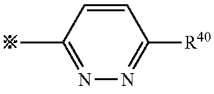
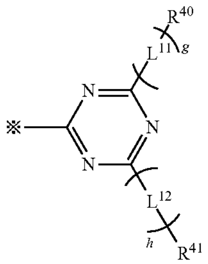
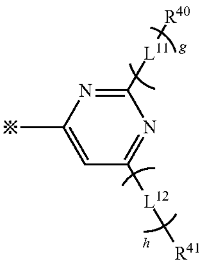
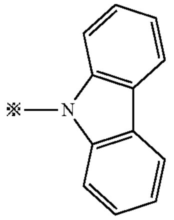
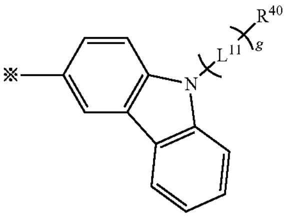
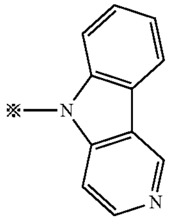
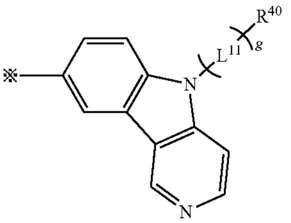
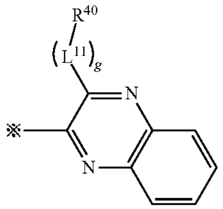
In the above exemplary structural formulae of HET, * represents a bonding position.
In the above exemplary structural formulae of HET, $L^{11}$ and $L^{12}$ are each independently the same as each of $L^1$ to $L^6$, i.e., a substituted or unsubstituted arylene group having 6 to 50 ring carbon atoms, or a substituted or unsubstituted divalent heterocyclic group having 5 to 50 ring atoms. Preferred embodiments of $L^{11}$ and $L^{12}$ are also the same as those of $L^1$ to $L^6$.

In the above exemplary structural formulae of HET, g and h each independently represent 0, 1, 2 or 3, and $(L^{11})_0$ and $(L^{12})_0$ each independently represent a single bond.

In the above exemplary structural formulae of HET, $R^{40}$ and $R^{41}$ may each independently be represented by, for example, a hydrogen atom or one of the following structural formulae. In the following structural formulae, * represents a bonding position.

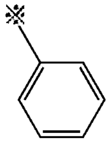
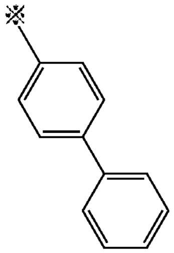
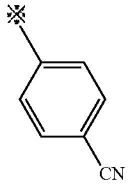
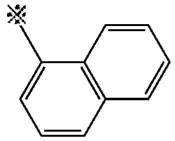
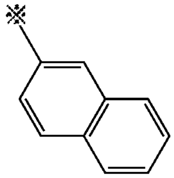
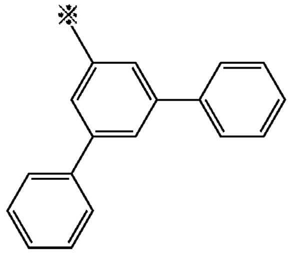
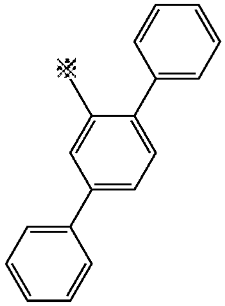
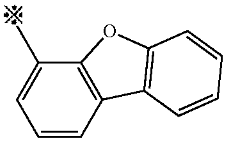
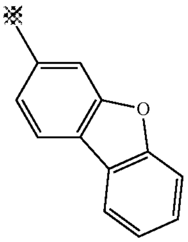
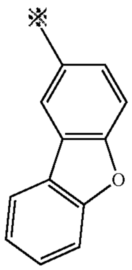
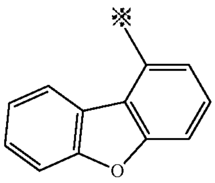

-continued

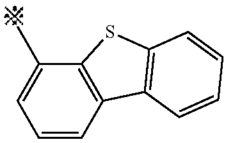
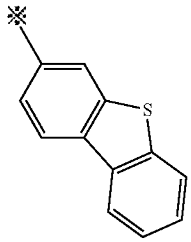
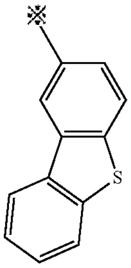
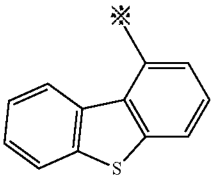
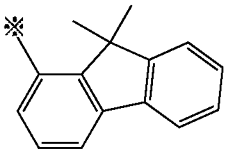
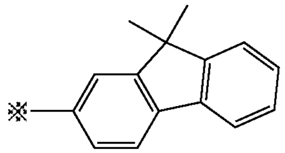
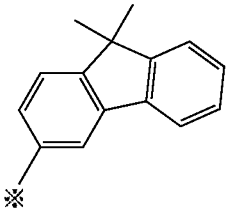
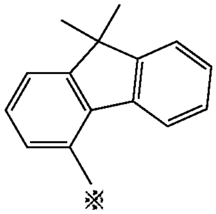
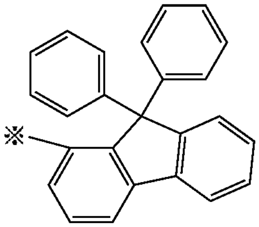
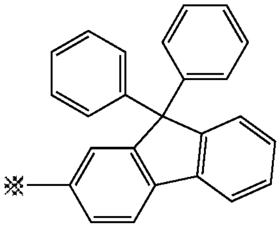
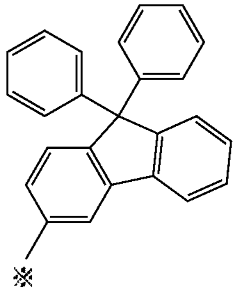
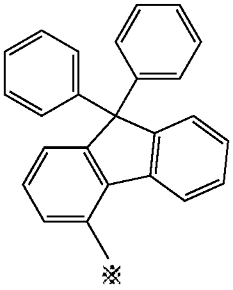
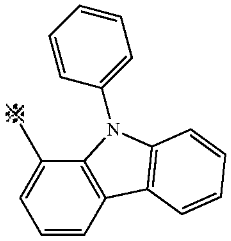

-continued

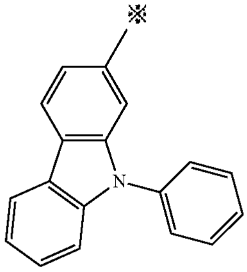

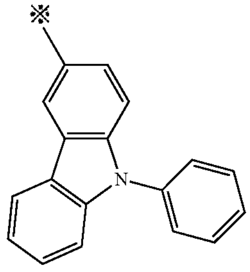

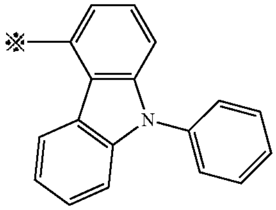

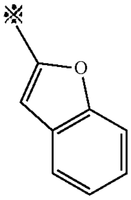

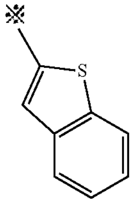

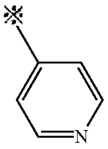

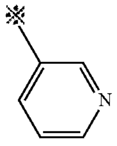

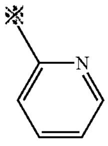

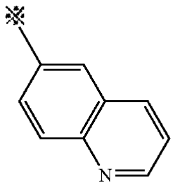

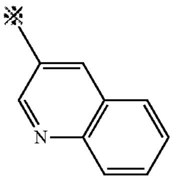

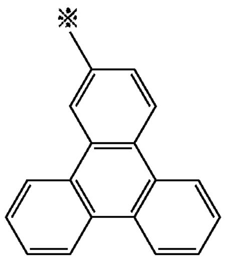

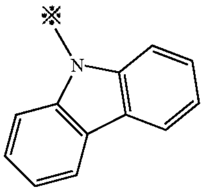

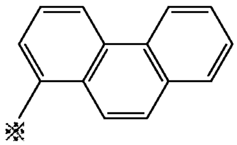

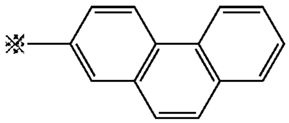

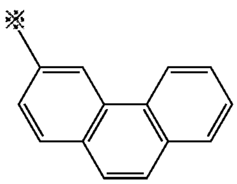

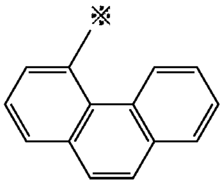

-continued

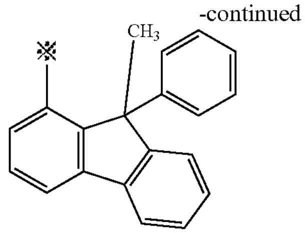

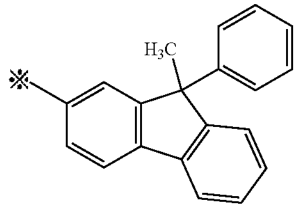

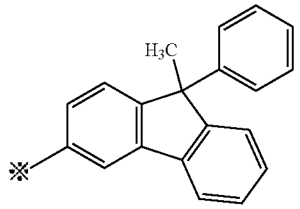

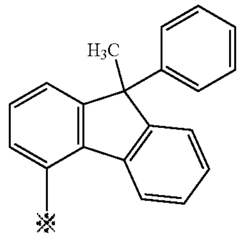

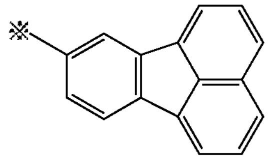

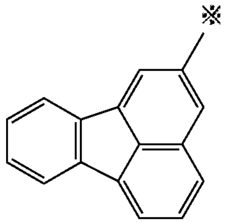

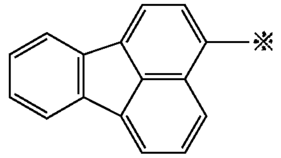

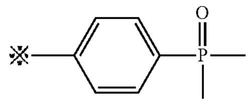

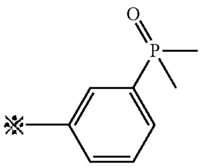

In one embodiment of the inventive compound, details of the substituent in the substituted or unsubstituted arylene group having 6 to 50 ring carbon atoms or the substituted or unsubstituted divalent heterocyclic group having 5 to 50 ring atoms, represented by $L^1$ to $L^6$, are the same as described above in the paragraph headed [Substituent for "Substituted or Unsubstituted"]. The substituent may preferably be a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms, more preferably a substituted or unsubstituted aryl group having 6 to 50 ring carbon atoms, or a substituted or unsubstituted heterocyclic group having 5 to 50 ring atoms, and even more preferably a substituted or unsubstituted aryl group having 6 to 18 ring carbon atoms, or a substituted or unsubstituted heterocyclic group having 5 to 18 ring atoms.

As described above in the paragraph headed "Substituents in Description", the substituted or unsubstituted divalent heterocyclic group having 5 to 50 ring atoms, represented by $L^1$ to $L^6$, is divalent when $L^1$ to $L^6$ are unsubstituted. For example, when "a" is 1 in the formula (2A), the bond of $L^1$ with * and the bond with HET correspond to the "divalent". When $L^1$ has a substituent, the valence of the bonding moiety between $L^1$ and the substituent is not included in the "divalent". Thus, as described above, when $L^1$ to $L^6$ have a substituent(s), they can have a structure having a valence of (2+p) according to p which represents the number of the substituents.

In one embodiment of the inventive compound, the heterocyclic groups having 5 to 50 ring atoms in the substituted or unsubstituted heterocyclic groups having 5 to 50 ring atoms, represented by $X^1$ and $X^2$, are preferably each independently a carbazolyl group, a benzocarbazolyl group, a dibenzofuranyl group, a naphthobenzofuranyl group, a dibenzothiophenyl group, or a naphthobenzothiophenyl group. Thus, in one embodiment of the inventive compound, the unsubstituted heterocyclic groups having 5 to 50 ring atoms, represented by $X^1$ and $X^2$, are preferably each independently one selected from the group consisting of the above-listed heterocyclic groups, and the substituted heterocyclic groups having 5 to 50 ring atoms, represented by $X^1$ and $X^2$, are preferably each independently one selected from the group consisting of the above-listed heterocyclic groups and having a substituent.

In one embodiment of the inventive compound, the aryl groups having 6 to 50 ring carbon atoms in the substituted or unsubstituted aryl groups having 6 to 50 ring carbon atoms, represented by $X^1$ and $X^2$, are preferably each independently a phenyl group, a biphenyl group, a terphenyl group, a naphthyl group, an anthryl group, a benzoantryl group, a phenanthryl group, a benzophenanthril group, a pyrenyl group, a triphenylenyl group, a benzotriphenylenyl group, a fluorenyl group, a fluoranthenyl group, or a benzofluoranthenyl group. Thus, in one embodiment of the inventive compound, the unsubstituted aryl groups having 6 to 50 ring carbon atoms, represented by $X^1$ and $X^2$, are preferably each independently one selected from the group consisting of the above-listed aryl groups, and the substituted aryl groups having 6 to 50 ring carbon atoms, represented by $X^1$ and $X^2$, are preferably each independently one selected from the group consisting of the above-listed aryl groups and having a substituent.

In one embodiment of the inventive compound, the aryl group having 10 to 50 ring carbon atoms in the substituted or unsubstituted aryl group having 10 to 50 ring carbon atoms, represented by Ar, is preferably a biphenyl group, a terphenyl group, a naphthyl group, an anthryl group, a benzoantryl group, a phenanthryl group, a benzophenanthril group, a pyrenyl group, a triphenylenyl group, a benzotriphenylenyl group, a fluorenyl group, a fluoranthenyl group, or a benzofluoranthenyl group. Thus, in one embodiment of the inventive compound, the unsubstituted aryl group having 10 to 50 ring carbon atoms, represented by Ar, is preferably one selected from the group consisting of the above-listed aryl groups, and the substituted aryl group having 10 to 50 ring carbon atoms, represented by Ar, is preferably one selected from the group consisting of the above-listed aryl groups and having a substituent.

In one embodiment of the inventive compound, details of the substituent in the substituted or unsubstituted aryl group having 10 to 50 ring carbon atoms, represented by Ar, are the same as described above in the paragraph headed [Substituent for "Substituted or Unsubstituted" ]. When the substituent in Ar is a heterocyclic group having 5 to 50 ring atoms, the heterocyclic group preferably contains no nitrogen atom as a ring atom and preferably contains an oxygen atom. The heterocyclic group is more preferably a substituted or unsubstituted dibenzofuranyl group, or a substituted or unsubstituted naphthobenzofuranyl group.

In one embodiment of the inventive compound, Y is preferably represented by the above formula (i).

In one embodiment of the inventive compound, details of the substituents represented by the substituent $Z^1$ are the same as described above in the paragraph headed "Substituents in Description".

The substituted or unsubstituted haloalkoxy group having 1 to 50 carbon atoms, which can be represented by the substituent $Z^1$, is a group represented by —O(G15), where G15 is the above-described substituted or unsubstituted haloalkyl group.

The substituted or unsubstituted haloalkoxy group having 1 to 50 carbon atoms is preferably a substituted or unsubstituted fluoroalkoxy group having 1 to 50 carbon atoms.

The fluoroalkoxy group having 1 to 50 carbon atoms in the substituted or unsubstituted fluoroalkoxy group having 1 to 50 carbon atoms is preferably a trifluoromethoxy group, a 2,2,2-trifluoroethoxy group, a pentafluoroethoxy group, or a heptafluoropropoxy group, more preferably a trifluoromethoxy group, a 2,2,2-trifluoroethoxy group, or a pentafluoroethoxy group, and even more preferably a trifluoromethoxy group. Thus, in one embodiment of the inventive compound, preferred embodiments and their preference order of the unsubstituted fluoroalkoxy group having 1 to 50 carbon atoms, which can be represented by the substituent $Z^1$, are the same as those of the fluoroalkoxy groups described herein, and preferred embodiments and their preference order of the substituted fluoroalkoxy group having 1 to 50 carbon atoms are the same as those of one selected from the group consisting of the fluoroalkoxy groups described herein and having a substituent.

In one embodiment of the inventive compound, $R^A$ and $R^B$ are preferably each independently a hydrogen atom, a substituted or unsubstituted alkyl group having 1 to 50 carbon atoms, or a substituted or unsubstituted aryl group having 6 to 50 carbon atoms, more preferably a hydrogen atom, a substituted or unsubstituted alkyl group having 1 to 6 carbon atoms, or a substituted or unsubstituted aryl group having 6 to 18 carbon atoms, and even more preferably a hydrogen atom, a methyl group, a substituted or unsubstituted phenyl group, or a substituted or unsubstituted naphthyl group.

$R^A$ and $R^B$ may or may not be bonded together by a single bond to form a ring or not.

In one embodiment of the inventive compound, $R^C$, $R^D$ and $R^B$ are preferably each independently a substituted or unsubstituted aryl group having 6 to 18 carbon atoms, more preferably a substituted or unsubstituted phenyl group, or a substituted or unsubstituted naphthyl group.

In one embodiment of the inventive compound, details of the substituents represented by the substituent $Z^2$ are the same as described above in the paragraph headed "Substituents in Description".

The substituted or unsubstituted haloalkoxy group having 1 to 50 carbon atoms, which can be represented by the substituent $Z^2$, is a group represented by —O(G15), where G15 is the above-described substituted or unsubstituted haloalkyl group. Thus, the haloalkoxy group having 1 to 50 carbon atoms and its preferred embodiments are the same as those described above with reference to the substituent $Z^1$.

In one embodiment of the inventive compound, in the formula (1A), at least one selected from $R^1$, $R^2$, $R^4$, $R^7$, $R^9$, $R^{10}$, $R^{12}$, and $R^{15}$ is preferably represented by the formula (2A), (2B), (2C) or (2D) and, in the formula (1B), at least one selected from $R^{21}$, $R^{22}$, $R^{24}$, $R^{27}$, $R^{28}$, $R^{29}$, $R^{30}$, $R^{31}$, $R^{32}$, and $R^{35}$ is preferably represented by the formula (2A), (2B), (2C) or (2D).

In one embodiment of the inventive compound, the formula (1A) is more preferably represented by the following formula (1A2A-1), (1A2A-2), (1A2B-1), (1A2B-2), (1A2C-1), (1A2C-2), (1A2D-1) or (1A2D-2), and the formula (1B) is more preferably represented by the following formula (1B2A-1), (1B2A-2), (1B2A-3), (1B2A-4), (1B2A-5), (1B2B-1), (1B2B-2), (1B2B-3), (1B2B-4), (1B2B-5), (1B2C-1), (1B2C-2), (1B2C-3), (1B2C-4), (1B2C-5), (1B2D-1), (1B2D-2), (1B2D-3), (1B2D-4) or (1B2D-5).

(1A2A-1)

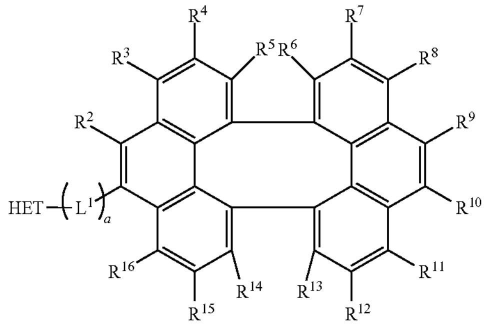

(1A2A-2)

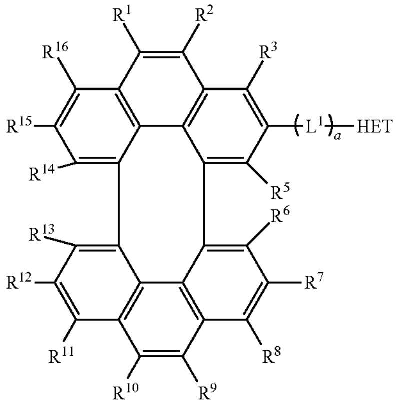

(1A2B-1)

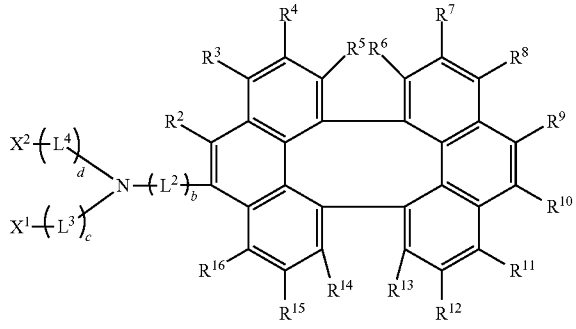

-continued (1A2B-2)

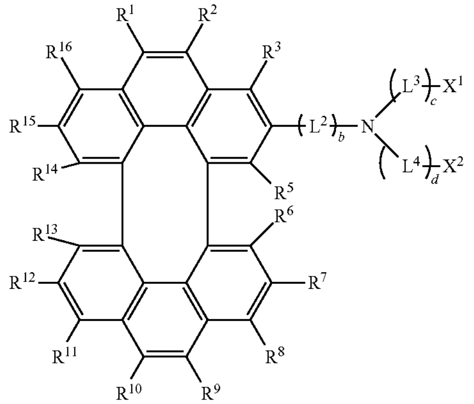

(1A2C-1)

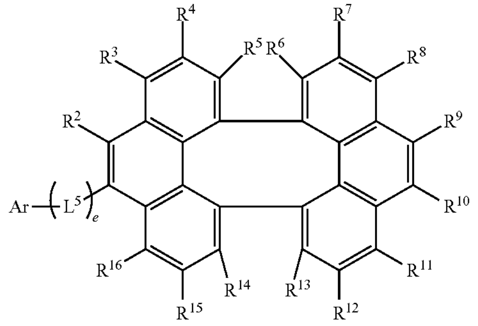

(1A2C-2)

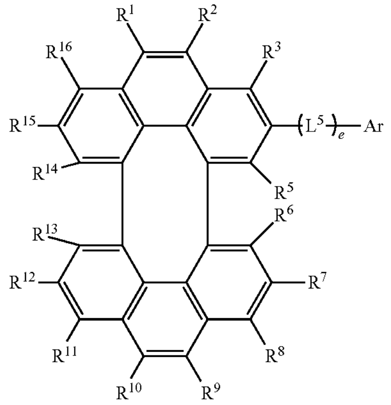

(1A2D-1)

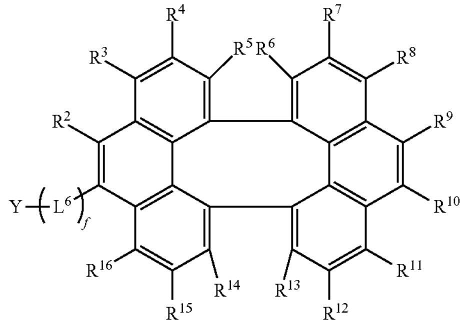

-continued
(1A2D-2)
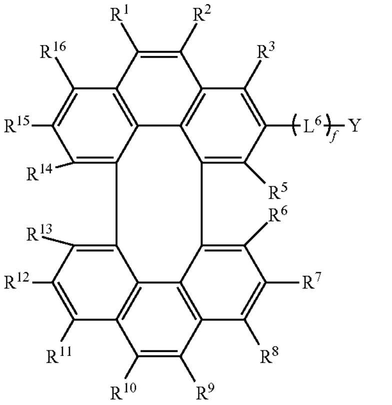
(1B2A-1)
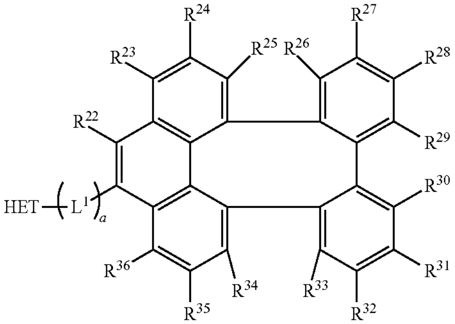
(1B2A-2)
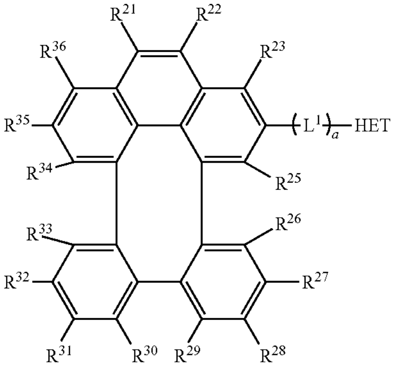
(1B2A-3)
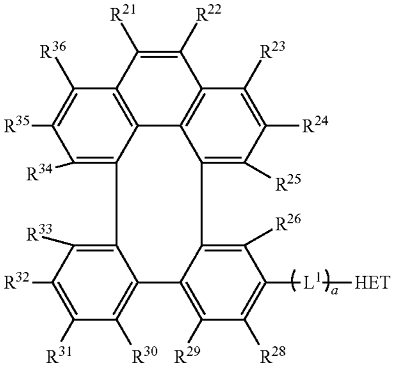
-continued
(1B2A-4)
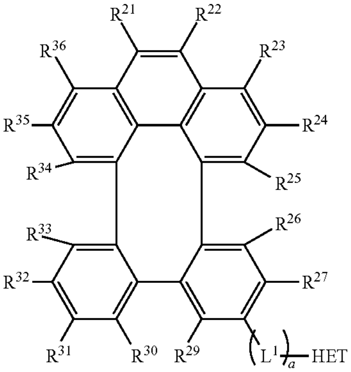
(1B2A-5)
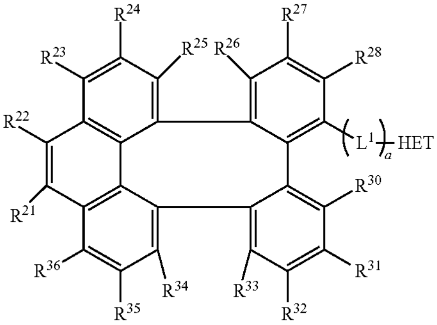
(1B2B-1)
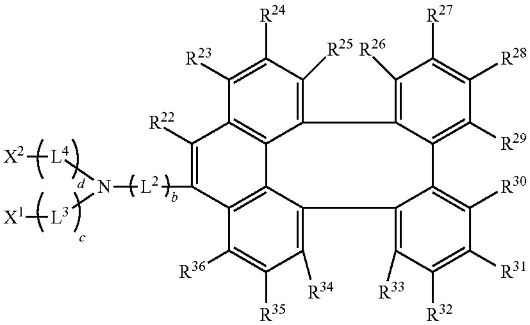
(1B2B-2)
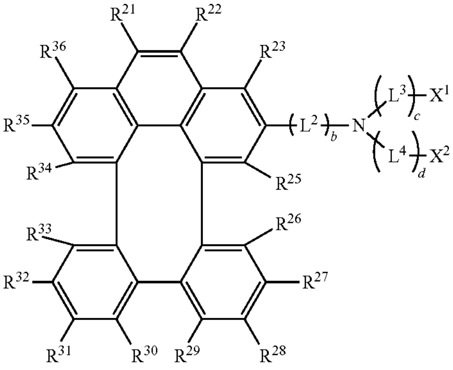

-continued
(1B2B-3)
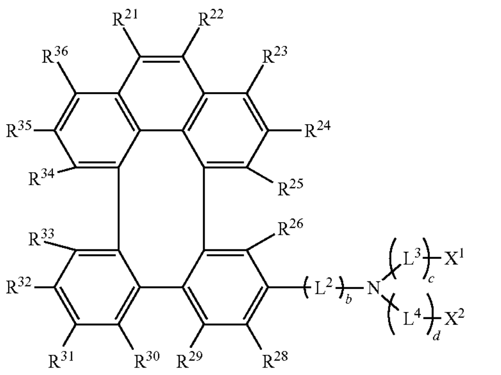
(1B2B-4)
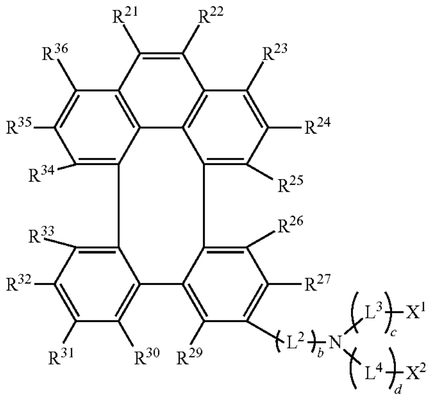
(1B2B-4)
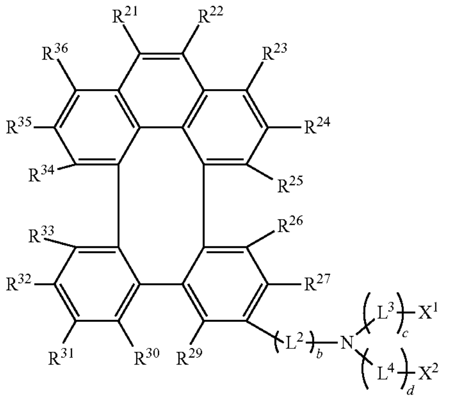
(1B2B-5)
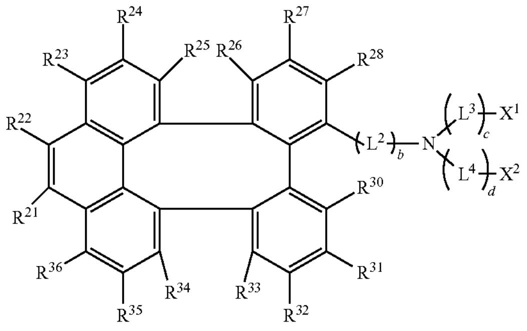
-continued
(1B2C-1)
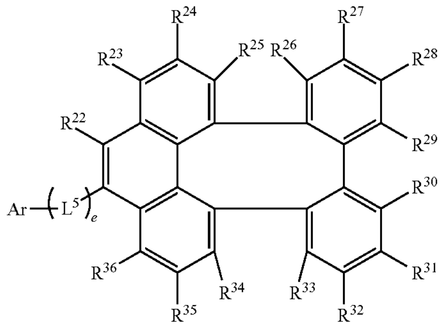
(1B2C-2)
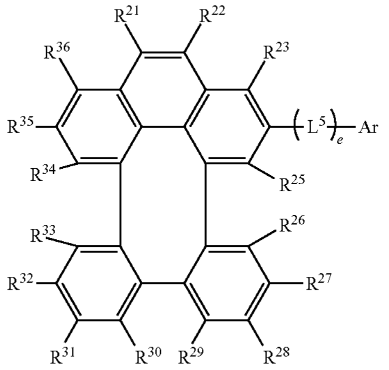
(1B2C-3)
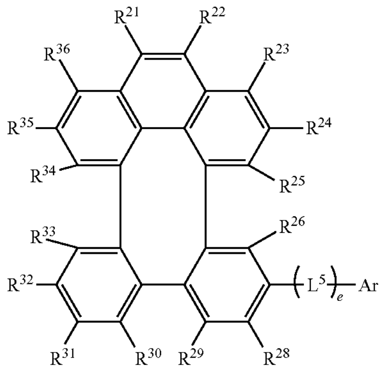
(1B2C-4)
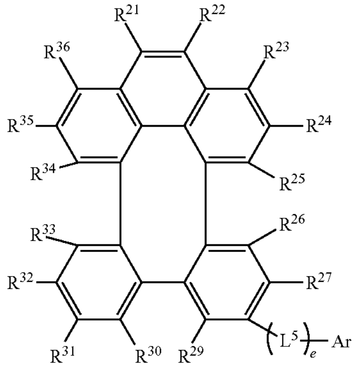

-continued (1B2C-5)

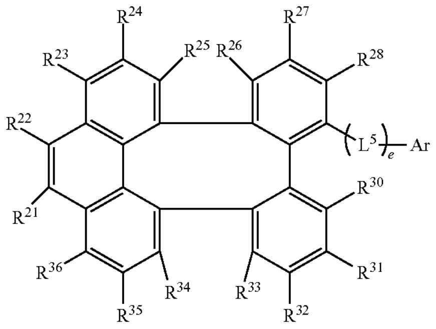

(1B2D-1)

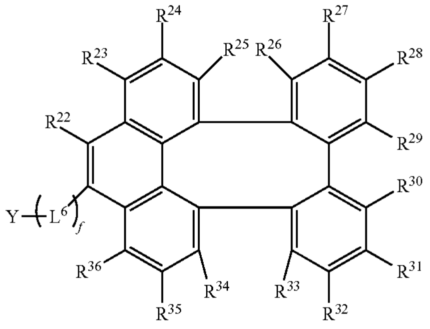

(1B2D-2)

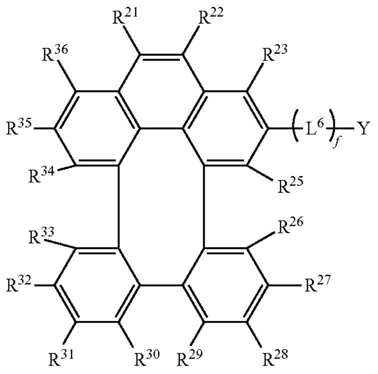

(1B2D-3)

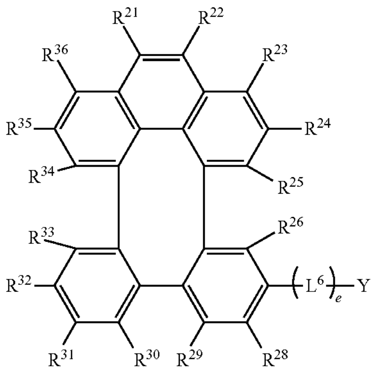

-continued (1B2D-4)

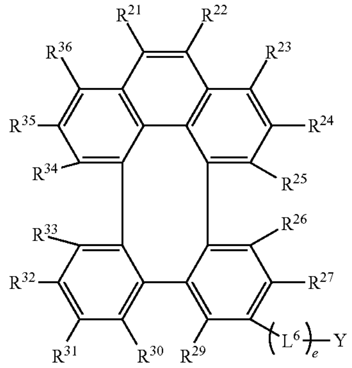

(1B2D-5)

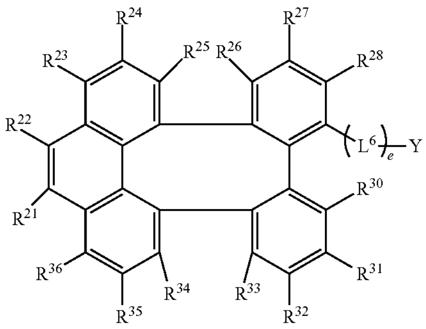

In the formulae (1A2A-1), (1A2A-2), (1A2B-1), (1A2B-2), (1A2C-1), (1A2C-2), (1A2D-1), (1A2D-2), (1B2A-1), (1B2A-2), (1B2A-3), (1B2A-4), (1B2A-5), (1B2B-1), (1B2B-2), (1B2B-3), (1B2B-4), (1B2B-5), (1B2C-1), (1B2C-2), (1B2C-3), (1B2C-4), (1B2C-5), (1B2D-1), (1B2D-2), (1B2D-3), (1B2D-4) and (1B2D-5), $R^1$ to $R^{16}$, $R^{21}$ to $R^{36}$, $L^1$ to $L^6$, a, b, c, d, e, f, HET, $X^1$, $X^2$, Y and Ar have the same meaning as defined in the formulae (1A) and (1B) above.

In one embodiment of the inventive compound, the formula (1A) is even more preferably represented by the following formula (1A2A-11), (1A2A-12), (1A2A-13), (1A2A-14), (1A2A-15), (1A2B-11), (1A2B-12), (1A2B-13), (1A2B-14), (1A2B-15), (1A2C-11), (1A2C-12), (1A2C-13), (1A2C-14), (1A2C-15), (1A2D-11), (1A2D-12), (1A2D-13), (1A2D-14) or (1A2D-15), and the formula (1B) is even more preferably represented by the following formula (1B2A-11), (1B2A-12), (1B2A-13), (1B2A-14), (1B2A-15), (1B2A-16), (1B2B-11), (1B2B-12), (1B2B-13), (1B2B-14), (1B2B-15), (1B2B-16), (1B2C-11), (1B2C-12), (1B2C-13), (1B2C-14), (1B2C-15), (1B2C-16), (1B2D-11), (1B2D-12), (1B2D-13), (1B2D-14), (1B2D-15) or (1B2D-16).

(1A2A-11)
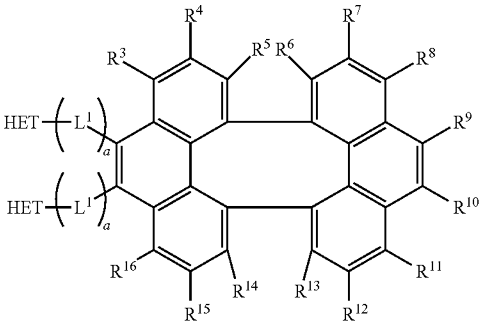
(1A2A-12)
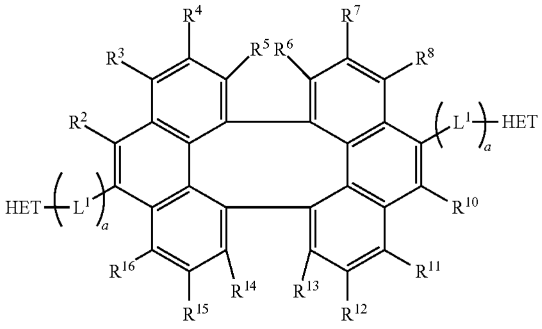
(1A2A-13)
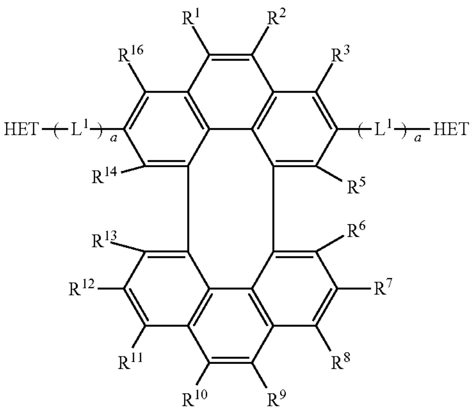
(1A2A-14)
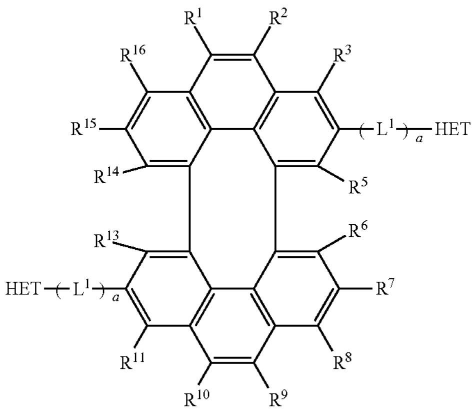
(1A2A-15)
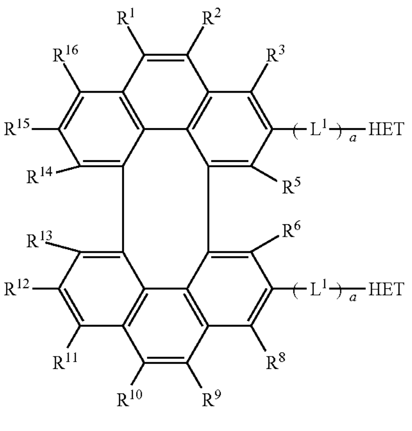
(1A2B-11)
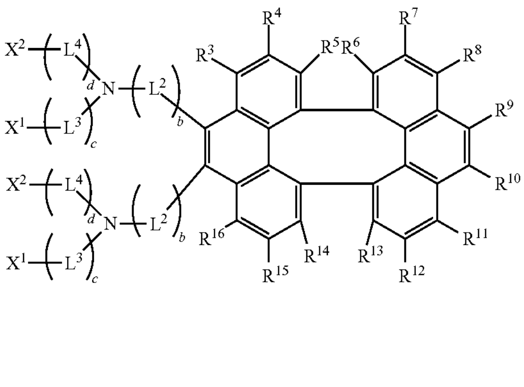
(1A2B-12)
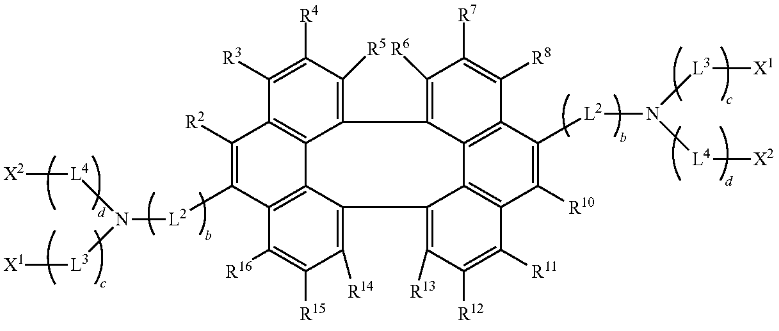

-continued
(1A2B-13)
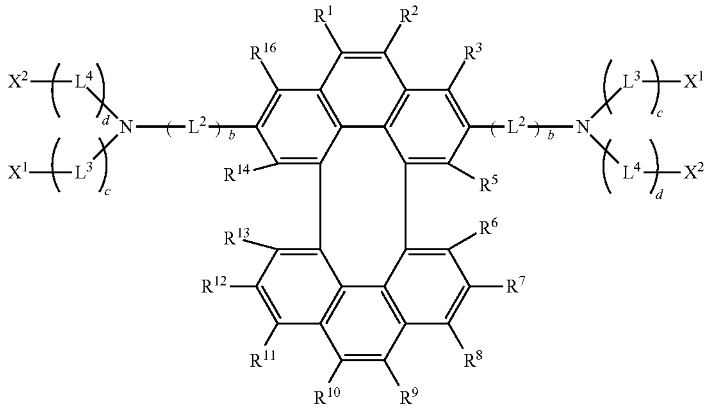
(1A2B-14)
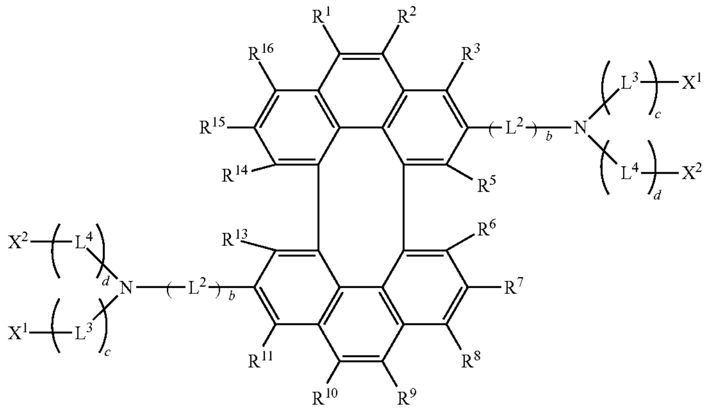
(1A2B-15)
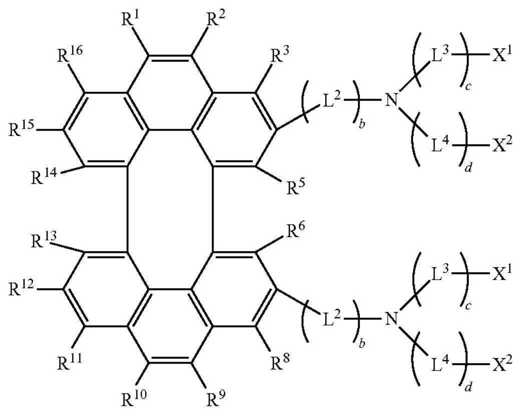
(1A2C-11)
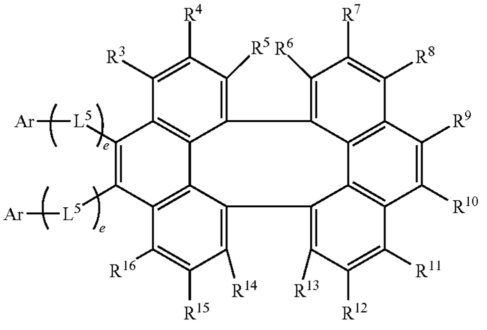

-continued
(1A2C-12)
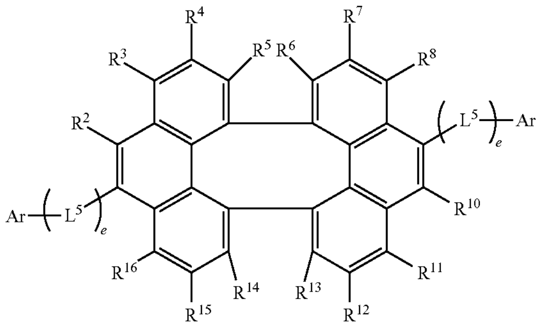
(1A2C-13)
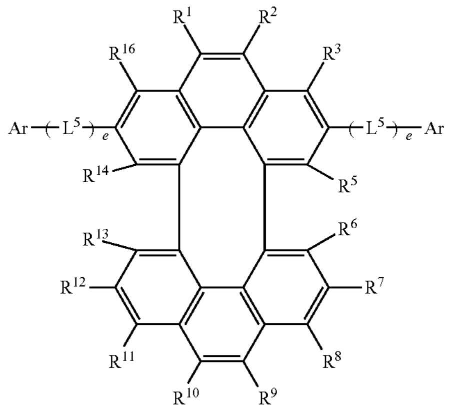
(1A2C-14)
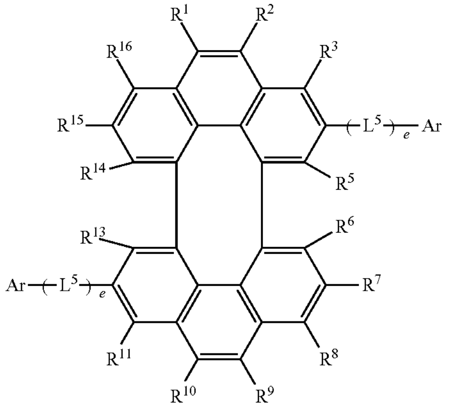
(1A2C-15)
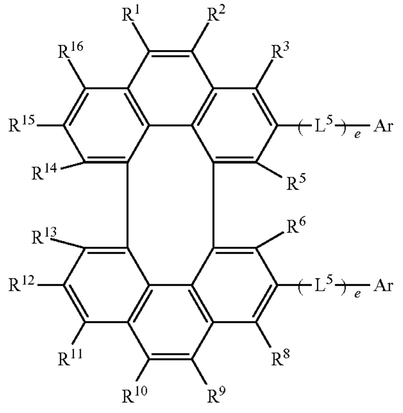
(1A2D-11)
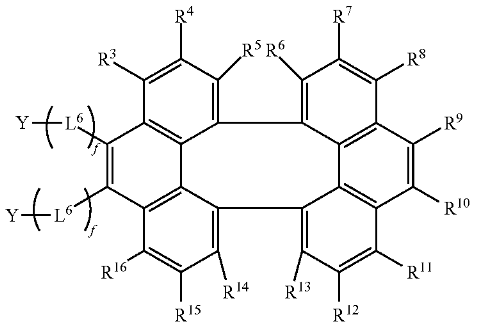
(1A2D-12)
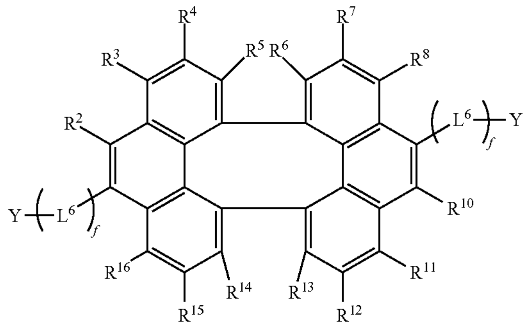
(1A2D-13)
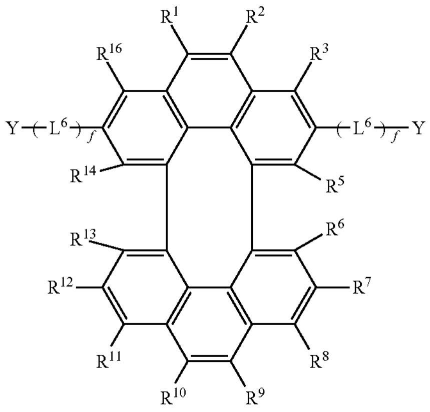
(1A2D-14)
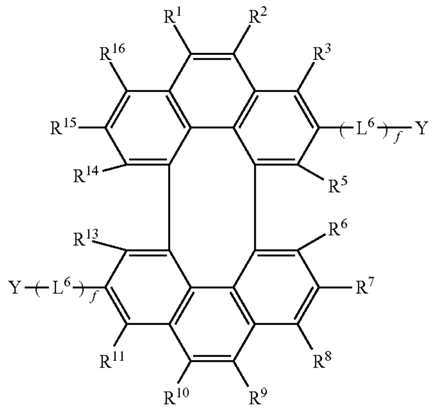

-continued
(1A2D-15)
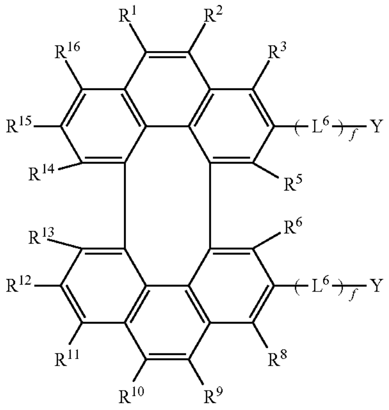
(1B2A-11)
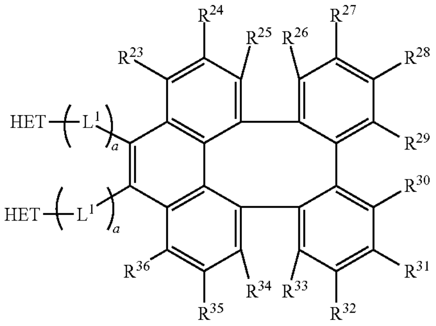
(1B2A-12)
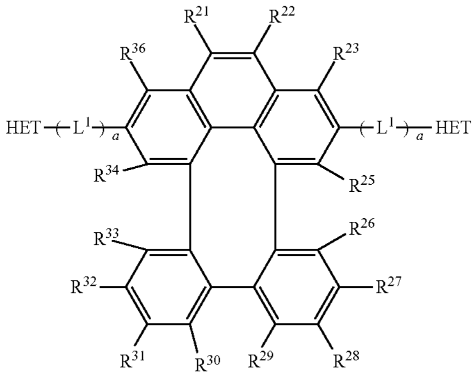
(1B2A-13)
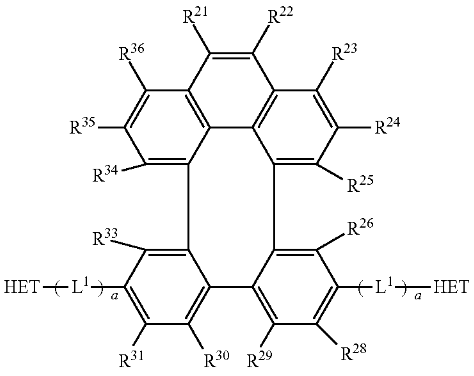
(1B2A-14)
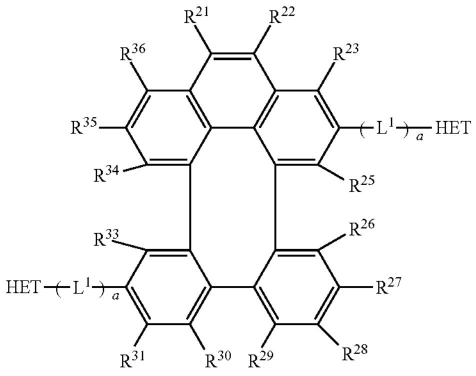
(1B2A-15)
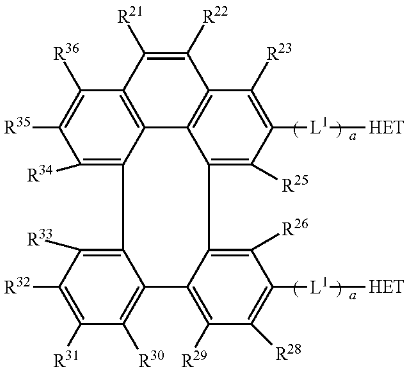
(1B2A-16)
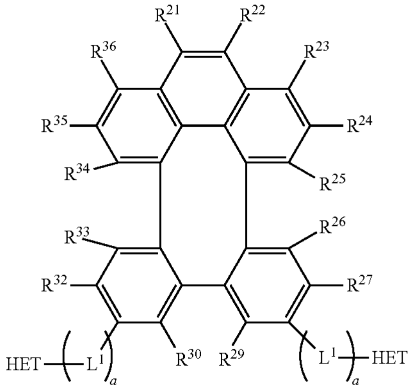
(1B2B-11)
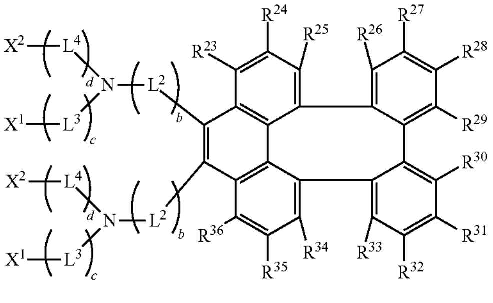

-continued
(1B2B-12)
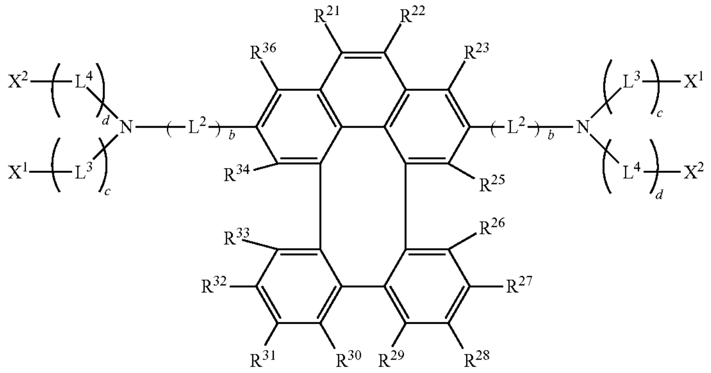
(1B2B-13)
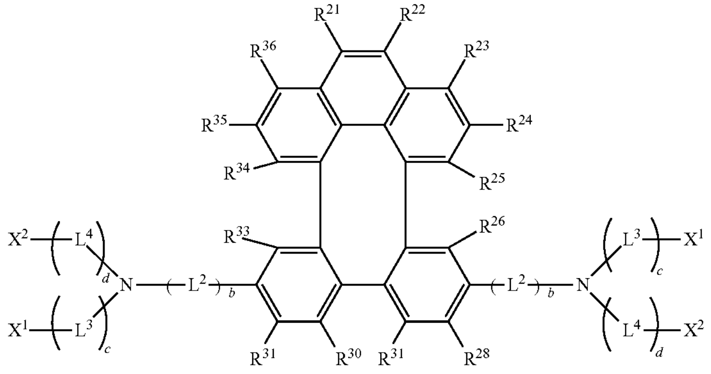
(1B2B-14)
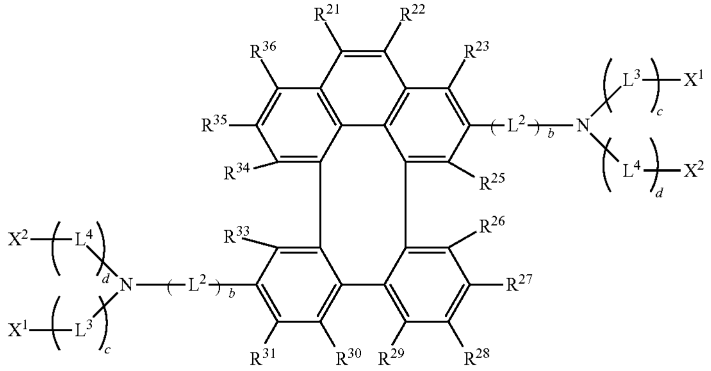
(1B2B-15)
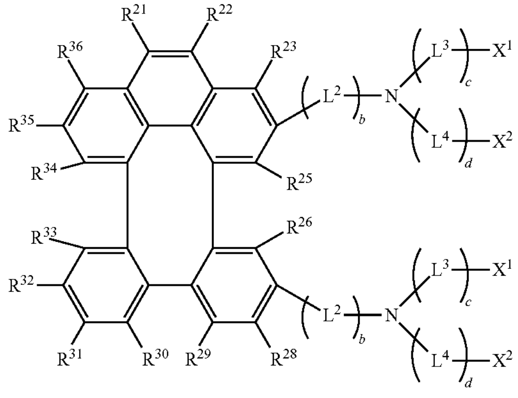
(1B2B-16)
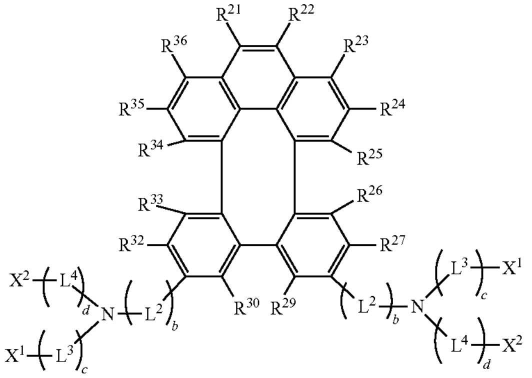

-continued
(1B2C-11)
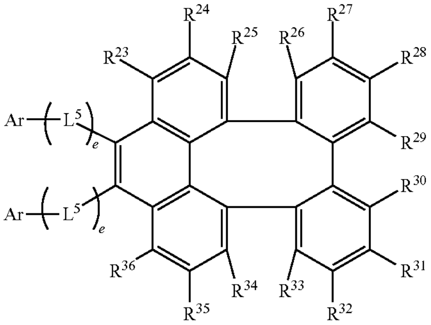
(1B2C-12)
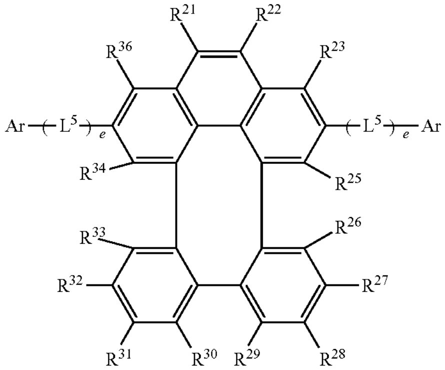
(1B2C-13)
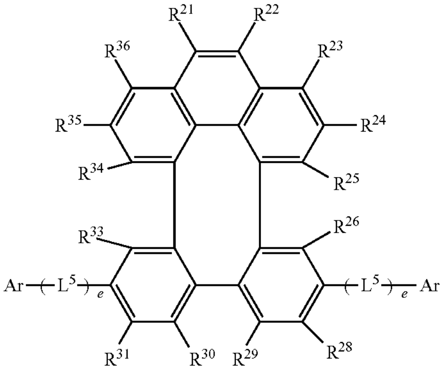
(1B2C-14)
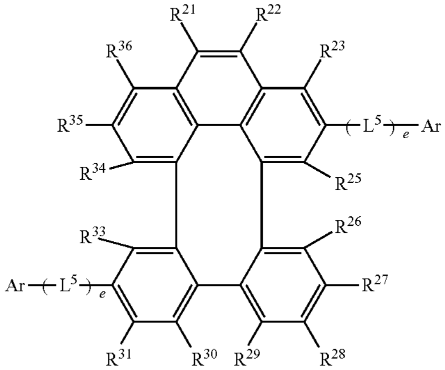
(1B2C-15)
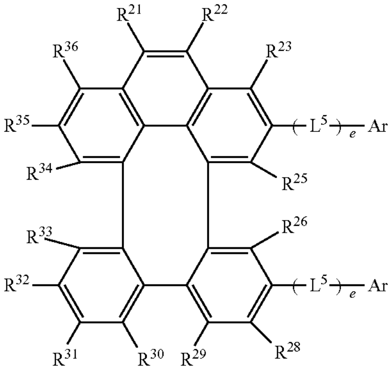
(1B2C-16)
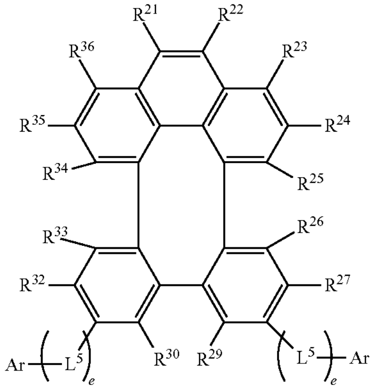
(1B2D-11)
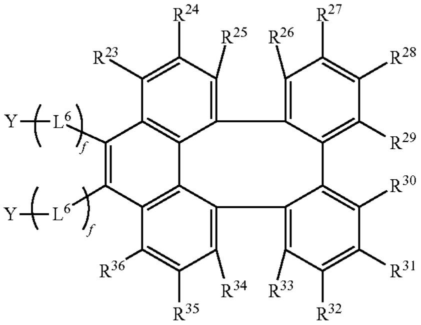
(1B2D-12)
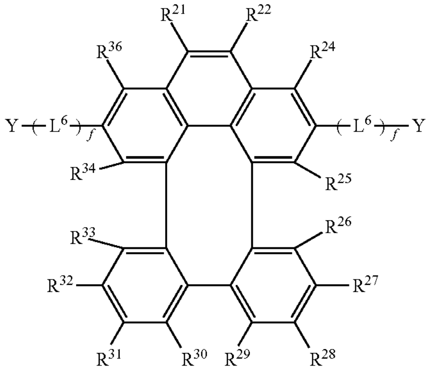

-continued (1B2D-13)

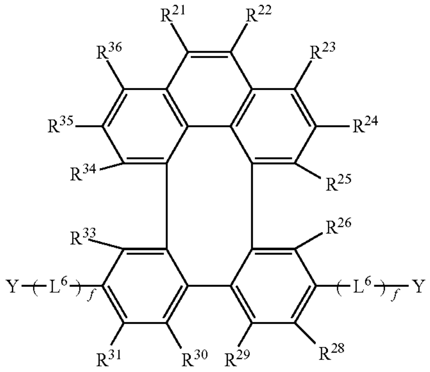

(1B2D-14)

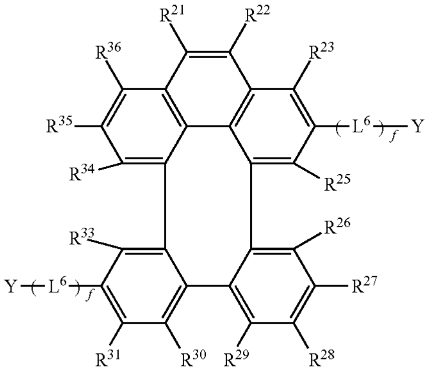

(1B2D-15)

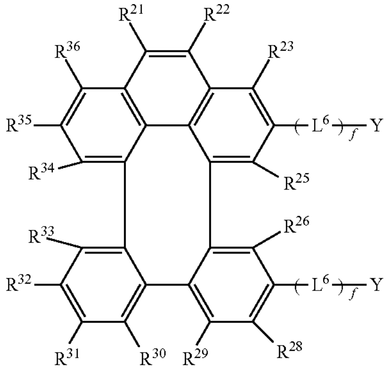

(1B2C-16)

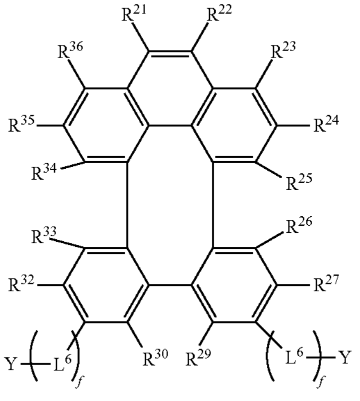

In the formulae (1A2A-11), (1A2A-12), (1A2A-13), (1A2A-14), (1A2A-15), (1A2B-11), (1A2B-12), (1A2B-13), (1A2B-14), (1A2B-15), (1A2C-11), (1A2C-12), (1A2C-13), (1A2C-14), (1A2C-15), (1A2D-11), (1A2D-12), (1A2D-13), (1A2D-14), (1A2D-15), (1B2A-11), (1B2A-12), (1B2A-13), (1B2A-14), (1B2A-15), (1B2A-16), (1B2B-11), (1B2B-12), (1B2B-13), (1B2B-14), (1B2B-15), (1B2B-16), (1B2C-11), (1B2C-12), (1B2C-13), (1B2C-14), (1B2C-15), (1B2C-16), (1B2D-11), (1B2D-12), (1B2D-13), (1B2D-14), (1B2D-15) and (1B2D-16), $R^1$ to $R^{16}$, $R^{21}$ to $R^{36}$, $L^1$ to $L^6$, a, b, c, d, e, f, HET, $X^1$, $X^2$, Y and Ar have the same meaning as defined in the formulae (1A) and (1B) above. When there is a plurality of $L^1$ to $L^6$, a, b, c, d, e, f, HET, $X^1$, $X^2$, Y or Ar in each formula, they may be the same or different.

In one embodiment of the inventive compound, the compound can be exemplified by compounds having the following structural formulae. $L^1$, a, and HET in the structural formulae have the same meaning as defined in the formulae (1A) and (1B) above.

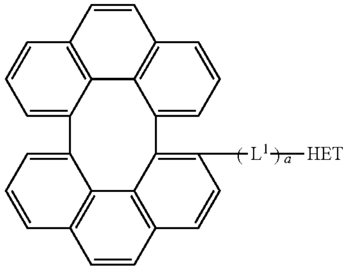

-continued

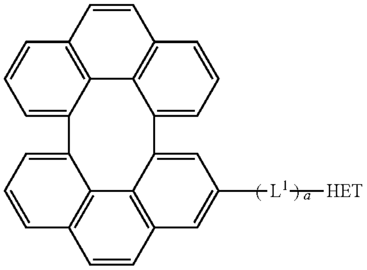

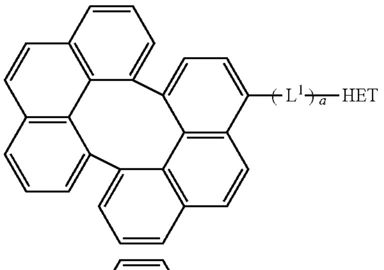

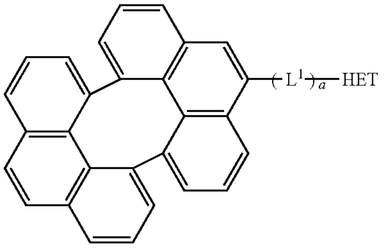

-continued

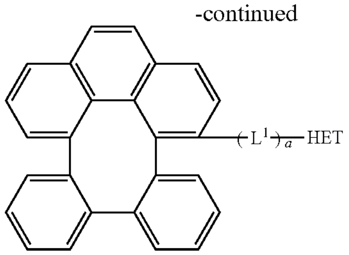

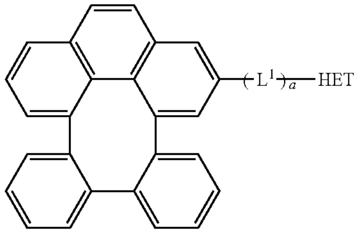

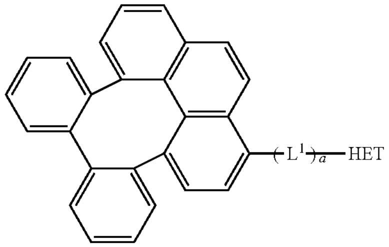

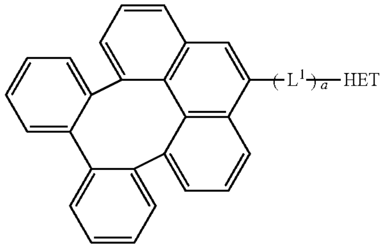

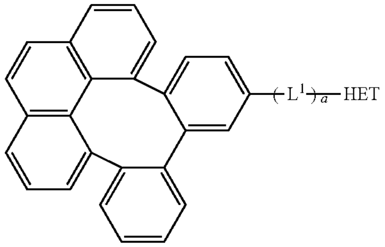

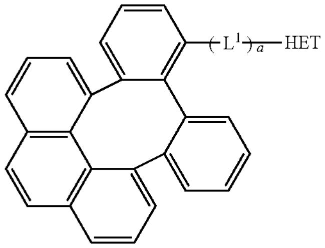

In one embodiment of the inventive compound, in the formulae (1A) and (1B), $R^1$ to $R^{16}$ and $R^{21}$ to $R^{36}$ which are not represented by the formulae (2A), (2B), (2C) or (2D) may all be hydrogen atoms.

As described above, the term "hydrogen atom" as used herein includes a light hydrogen atom, a deuterium atom, and a tritium atom. The inventive compound may contain a naturally-derived deuterium atom.

A deuterium atom may be intentionally introduced into the inventive compound by using a deuterated compound in part or all of the raw compound. Therefore, in one embodiment of the present invention, the invention compound contains at least one deuterium atom. Thus, the inventive compound may be a compound represented by the formula (1A) or (1B), in which at least one of the hydrogen atoms contained is a deuterium atom.

In the compound represented by the formula (1A) or (1B), at least one hydrogen atom, selected from the following hydrogen atoms, may be a deuterium atom:

a hydrogen atom represented by $R^1$ to $R^{16}$ and $R^{21}$ to $R^{36}$ which are not represented by the formula (2A), (2B), (2C) or (2D); a hydrogen atom in a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted phenyl group, a substituted or unsubstituted aralkyl group having 7 to 50 carbon atoms, a substituted or unsubstituted haloalkyl group having 1 to 50 carbon atoms, or a substituted or unsubstituted haloalkoxy group having 1 to 50 carbon atoms, represented by $R^1$ to $R^{16}$ and $R^{21}$ to $R^{36}$ which are not represented by the formula (2A), (2B), (2C) or (2D);

a hydrogen atom in a substituted or unsubstituted arylene group having 6 to 50 ring carbon atoms, or a substituted or unsubstituted divalent heterocyclic group having 5 to 50 ring atoms, represented by $L^1$ to $L^6$;

a hydrogen atom in a substituted or unsubstituted heterocyclic group having 5 to 50 ring atoms, represented by HET;

a hydrogen atom in a substituted or unsubstituted arylene group having 6 to 50 ring carbon atoms, or a substituted or unsubstituted divalent heterocyclic group having 5 to 50 ring atoms, represented by $L^{11}$ and $L^{12}$;

a hydrogen atom represented by $R^{40}$ and $R^{41}$; a hydrogen atom in the above-described structural formulae of $R^{40}$ and $R^{41}$;

a hydrogen atom in a substituted or unsubstituted aryl group having 6 to 50 ring carbon atoms, or a substituted or unsubstituted heterocyclic group having 5 to 50 ring atoms, represented by $X^1$ and $X^2$;

a hydrogen atom in a hydrogen atom in a substituted or unsubstituted aryl group having 10 to 50 ring carbon atoms, represented by Ar;

a hydrogen atom represented by $R^A$ and $R^B$; a hydrogen atom in a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted aralkyl group having 7 to 50 carbon atoms, a substituted or unsubstituted heterocyclic group having 5 to 50 ring atoms, a substituted or unsubstituted haloalkyl group having 1 to 50 carbon atoms, or a substituted or unsubstituted haloalkoxy group having 1 to 50 carbon atoms, represented by $R^A$ and $R^B$;

a hydrogen atom in a substituted or unsubstituted aryl group having 6 to 50 ring carbon atoms, represented by $R^C$, $R^D$ and $R^E$;

a hydrogen atom represented by $R_{901}$ to $R_{907}$; and a hydrogen atom in a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, represented by $R_{901}$ to $R_{907}$.

The deuteration rate of the inventive compound depends on the deuteration rate of the raw material compound used. Even if a raw material having a predetermined deuteration rate is used, a naturally derived light hydrogen isotope can be contained at a certain ratio. Accordingly, the embodiment of the deuteration rate of the inventive compound shown below includes a ratio obtained by simply counting the number of deuterium atoms represented by the chemical formula in consideration of a trace amount of naturally derived isotope.

The deuteration rate of the inventive compound is preferably 1% or more, more preferably 3% or more, even more preferably 5% or more, still more preferably 10% or more, and yet more preferably 50% or more.

The invention compound may be a deuterium compound in which all the hydrogen atoms are deuterium atoms (i.e. the deuteration rate of the inventive compound is 100%).

The inventive compound may be a mixture comprising a deuterated compound and a non-deuterated compound, or a mixture of two or more compounds having different deuteration rates. The deuteration rate of such a mixture is preferably 1% or more, more preferably 3% or more, even more preferably 5% or more, still more preferably 10% or more, and yet more preferably 50% or more, and is less than 100%.

The ratio of the number of deuterium atoms to the total number of hydrogen atoms in the inventive compound is preferably 1% or more, more preferably 3% or more, even more preferably 5% or more, and still more preferably 10% or more, and is 100% or less.

Details of the substituent (arbitrary substituent) associated with the phrase "substituted or unsubstituted" included in the definition of each of the above formulae are the same as those described above in the paragraph headed [Substituent for "Substituted or Unsubstituted"] unless otherwise indicated in the description.

One skilled in the art can easily produce the inventive compound by reference to the below-described synthetic examples and a known synthetic method.

The following are specific examples of the inventive compound. It is to be noted that the present invention is not limited to the following exemplary compounds.

In the specific examples, D represents a deuterium atom.

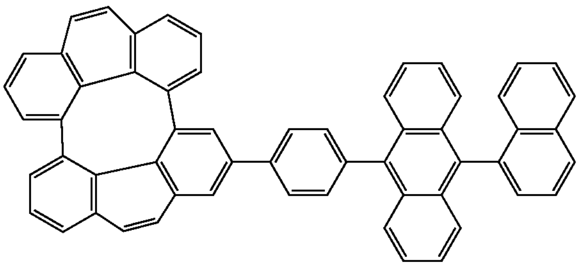

-continued

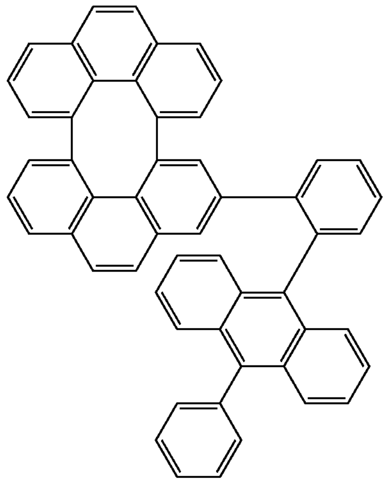

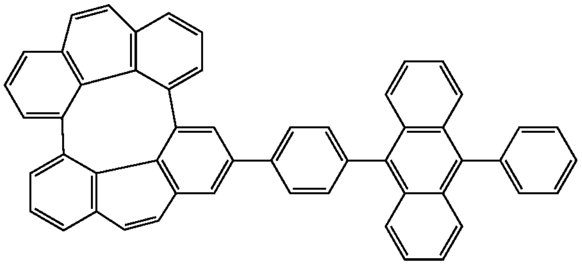

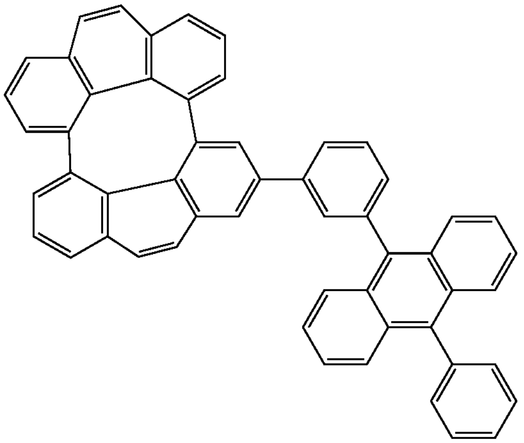

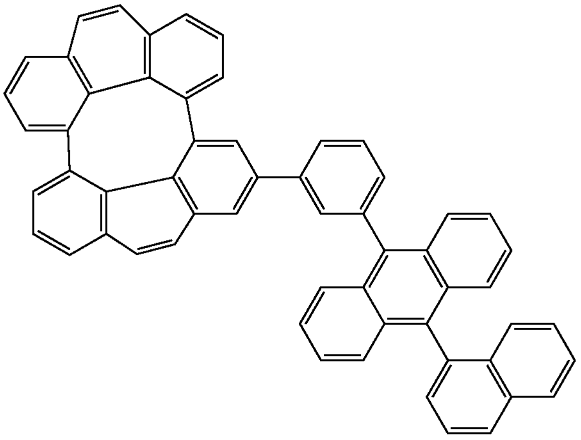

-continued
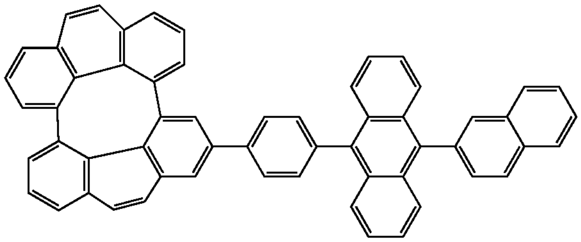
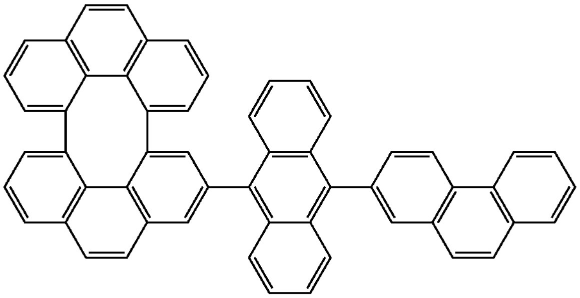
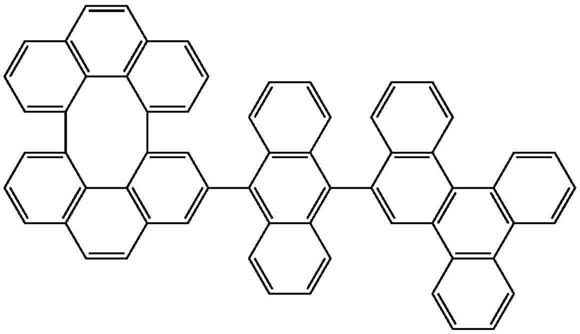
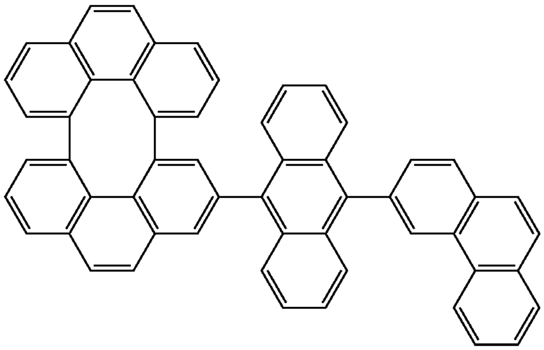
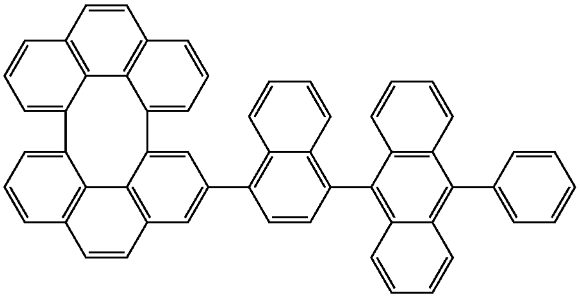
-continued
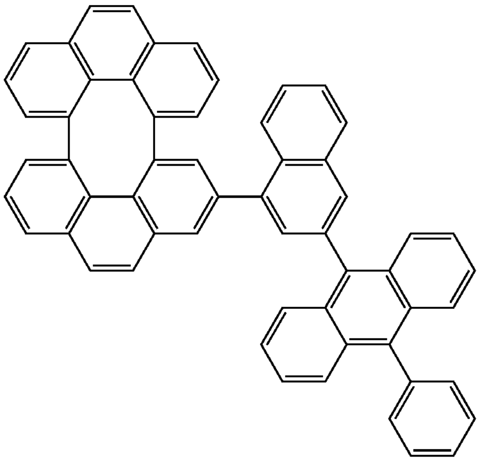
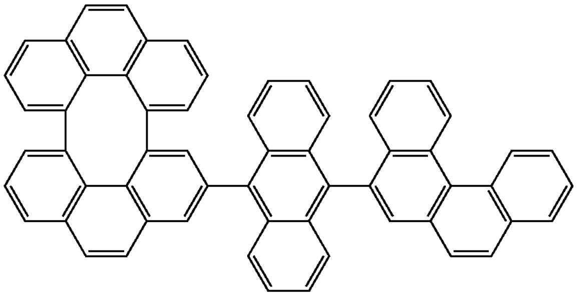
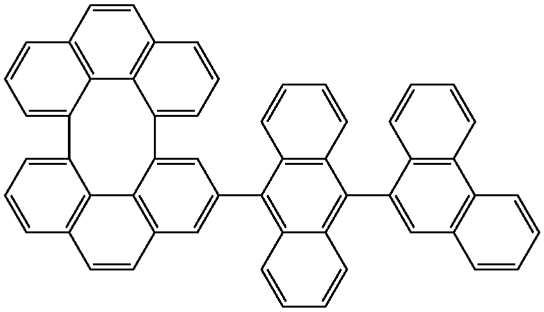
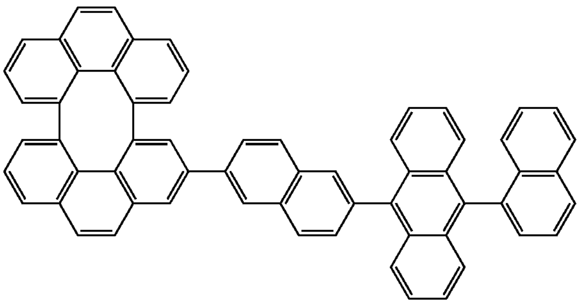
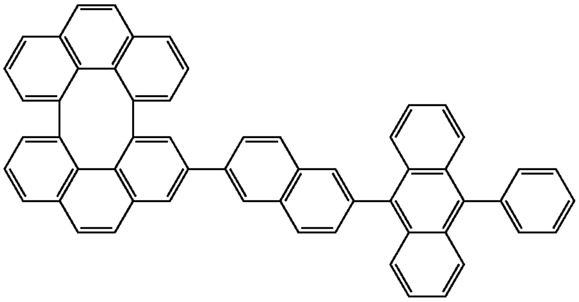

-continued
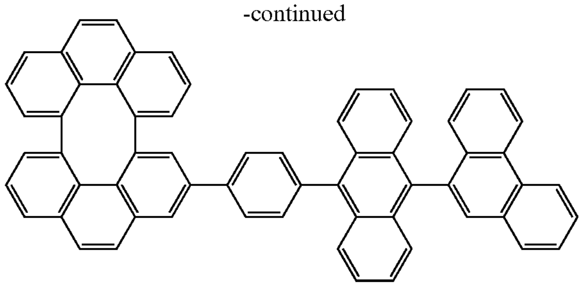
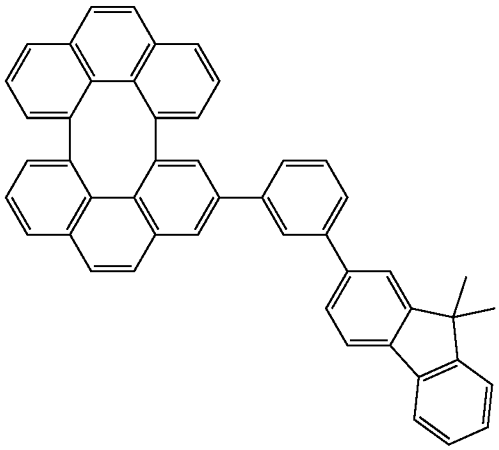
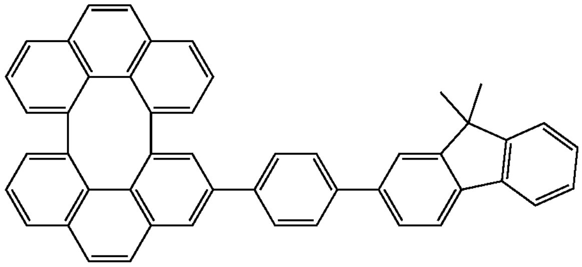
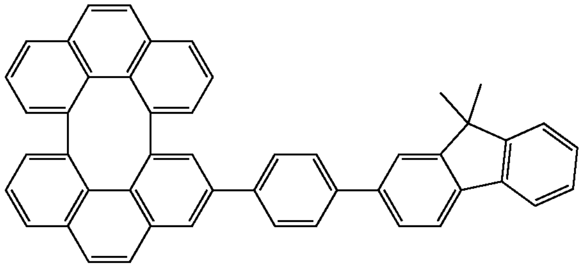
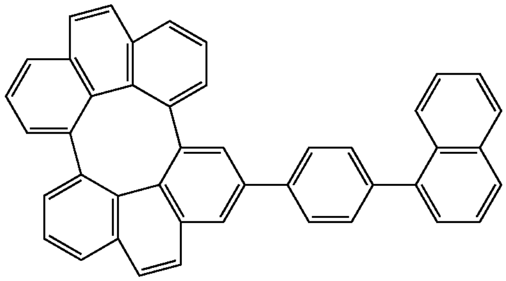
-continued
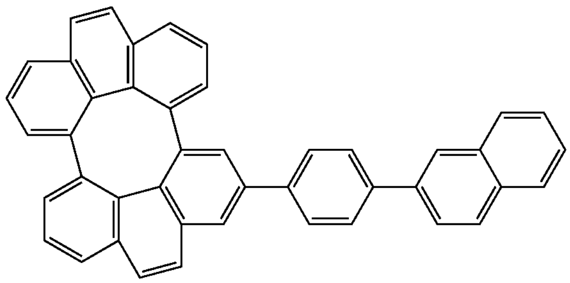
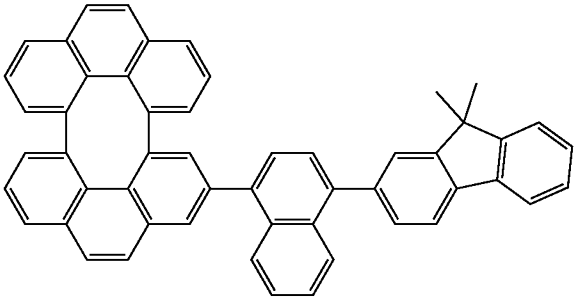
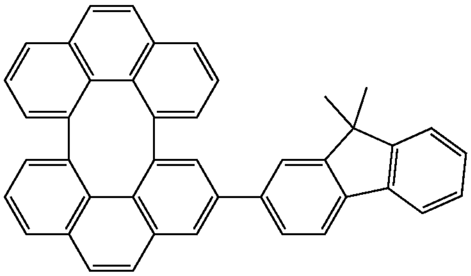
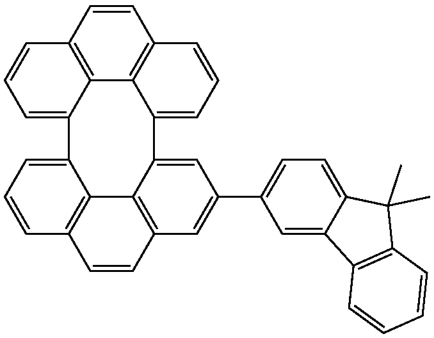
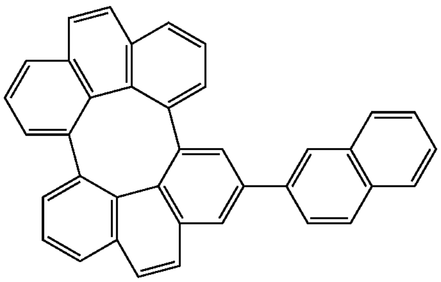

-continued
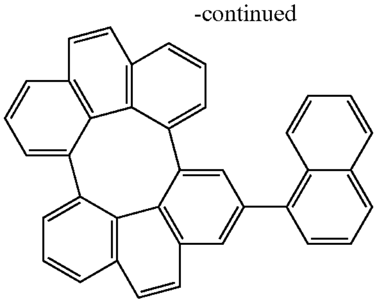
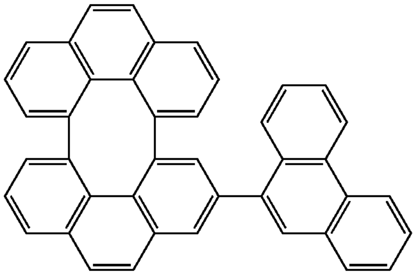
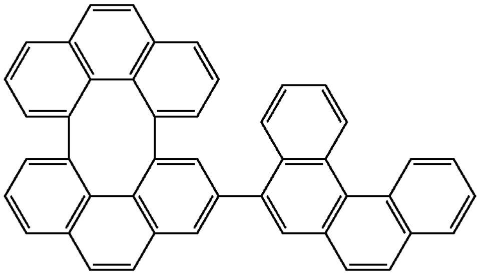
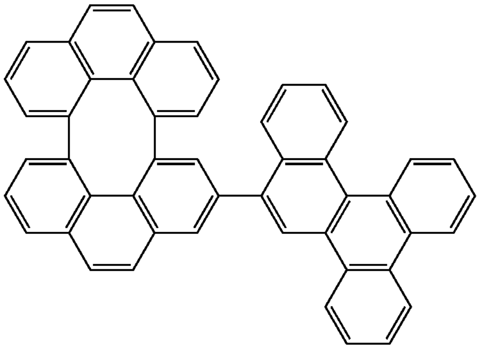
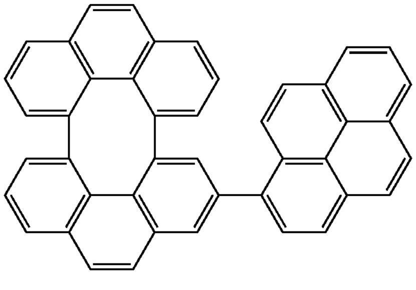
-continued
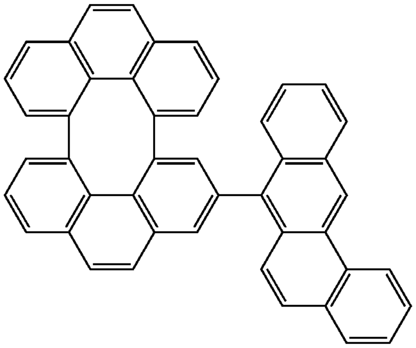
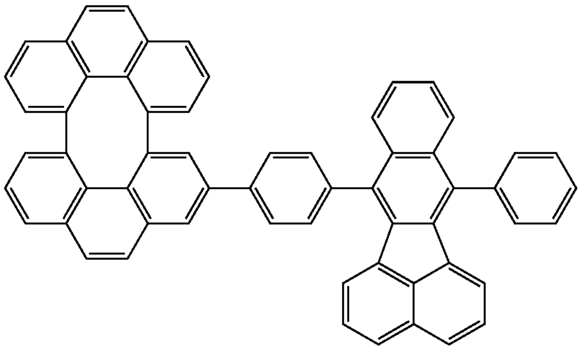
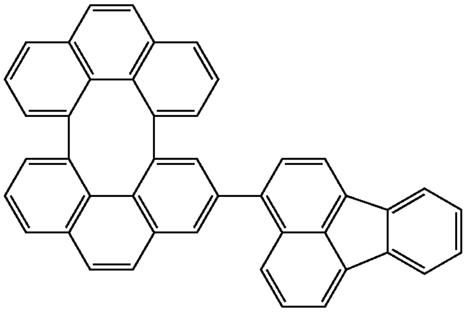
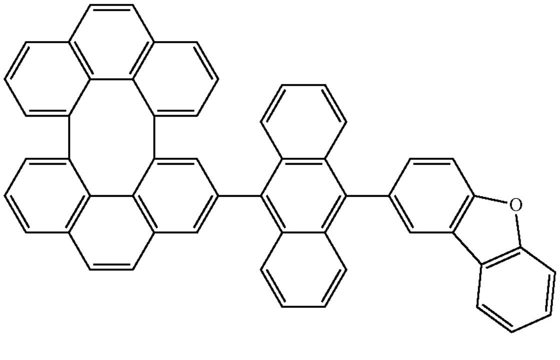

-continued
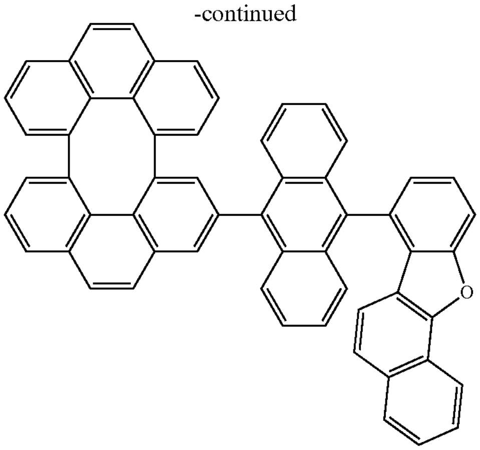
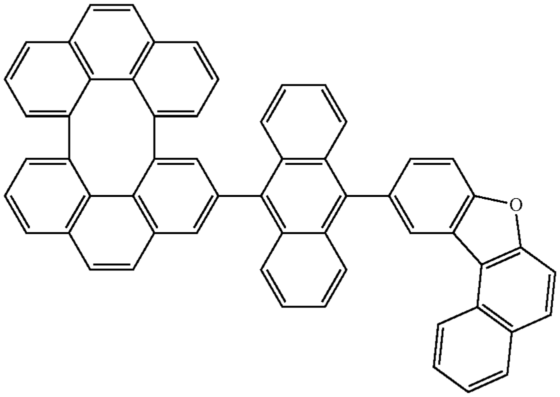
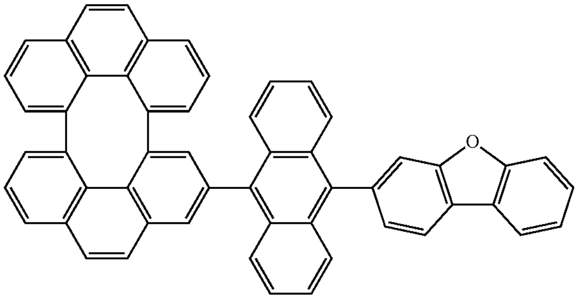
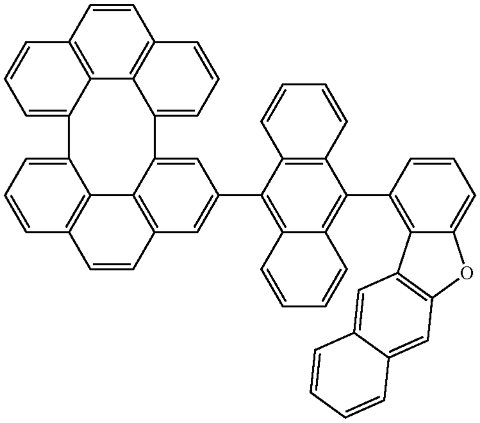
-continued
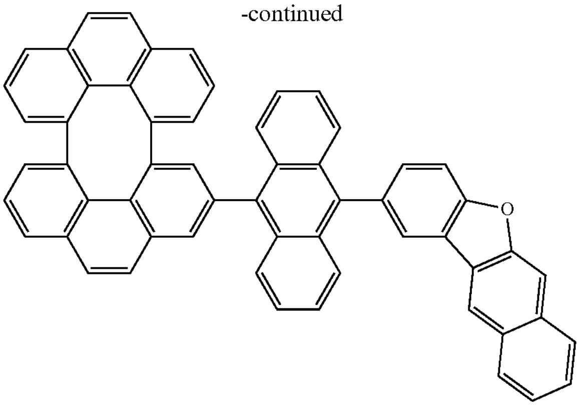
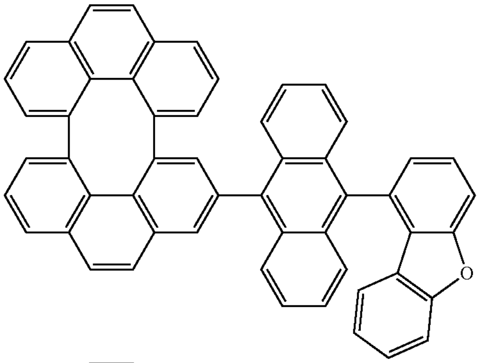
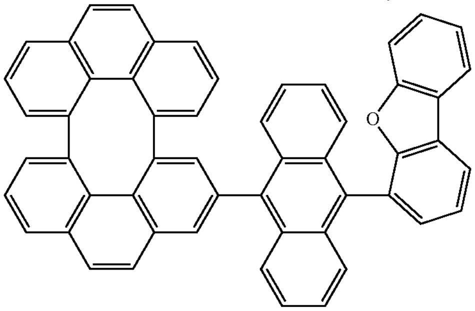
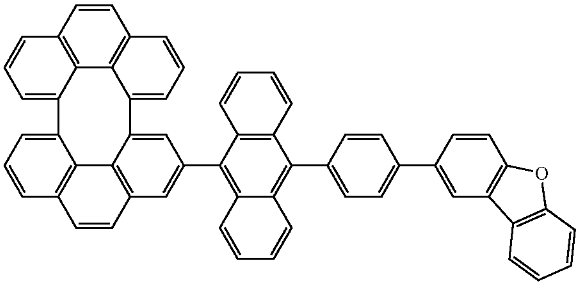
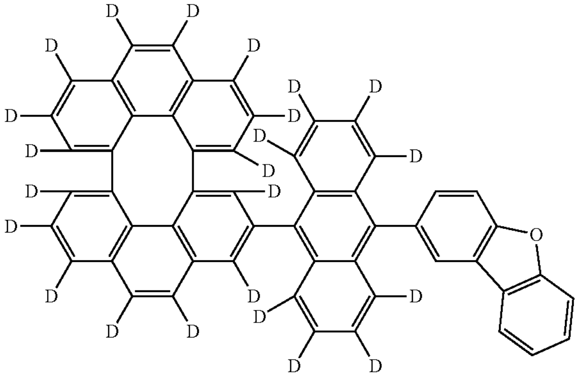

-continued
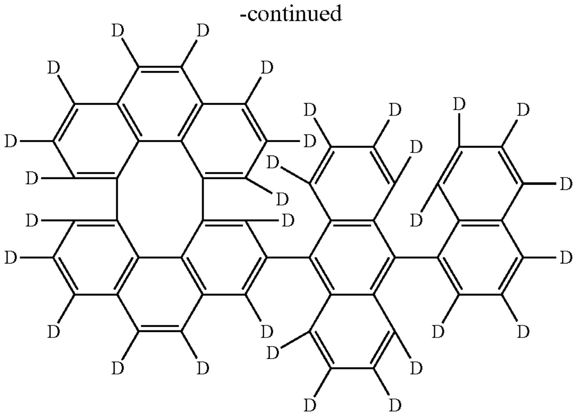
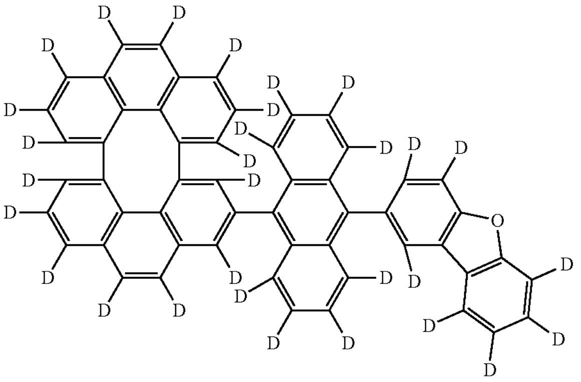
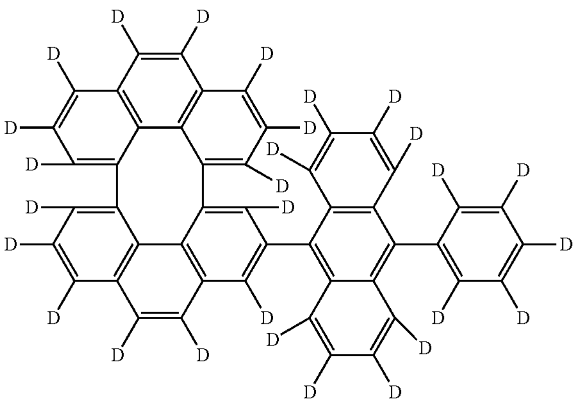
-continued
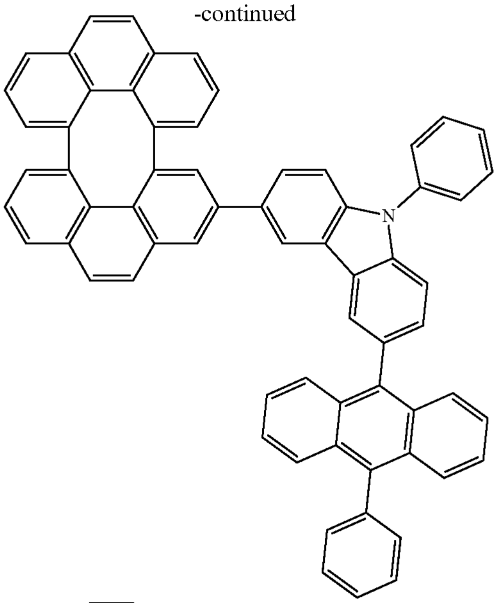
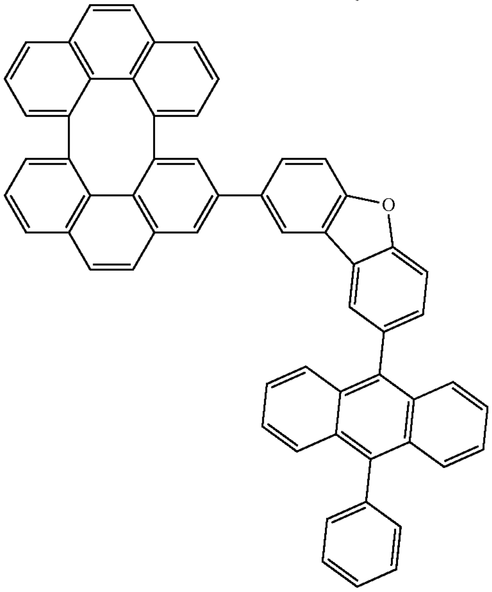
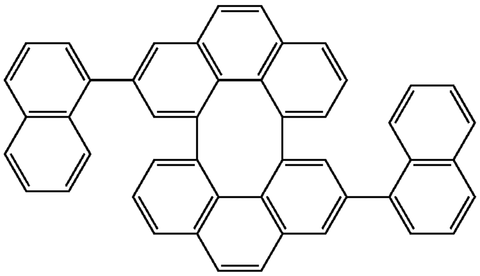
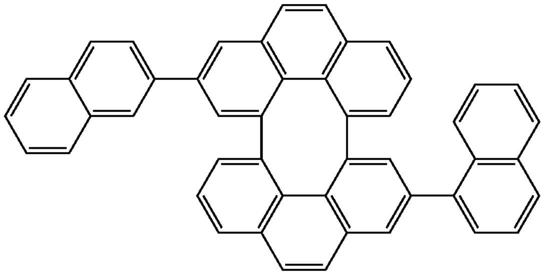

-continued
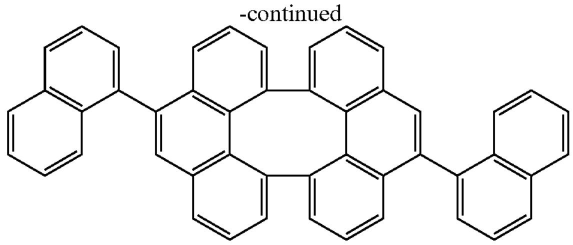
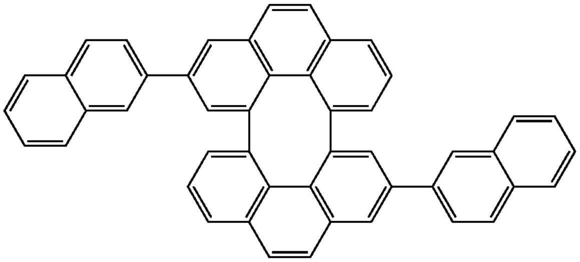
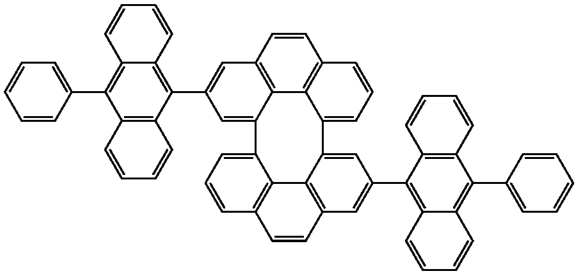
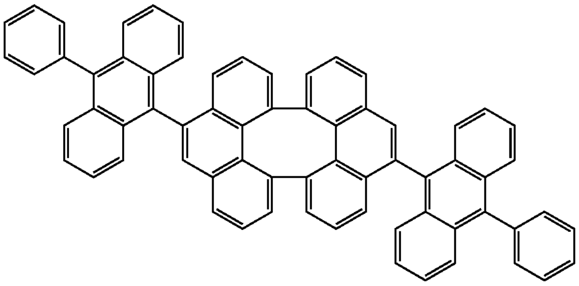
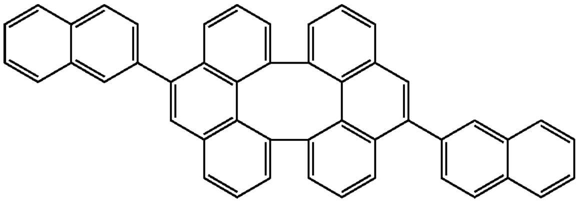
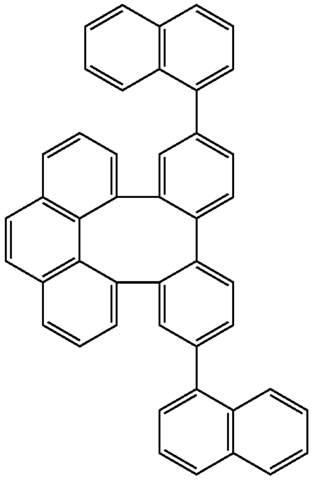
-continued
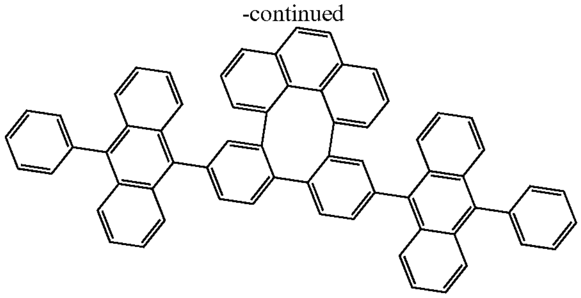
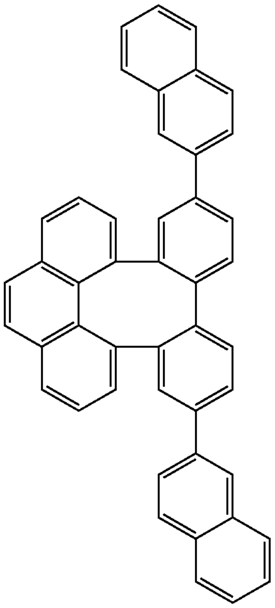
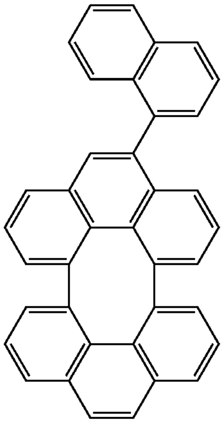

-continued
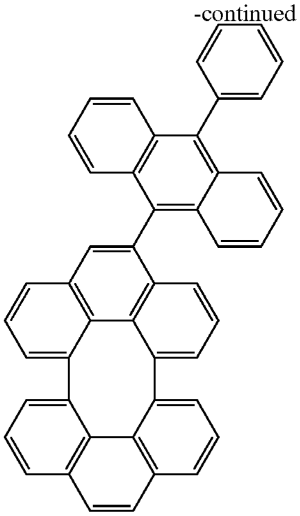
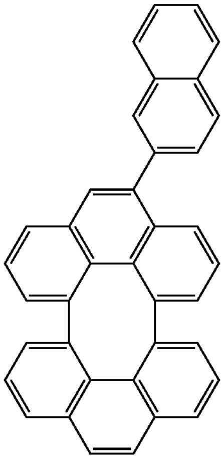
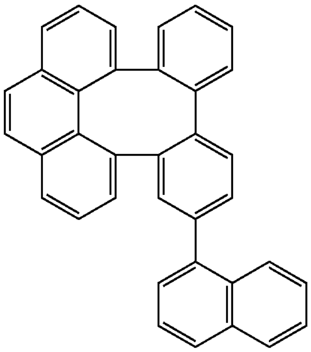
-continued
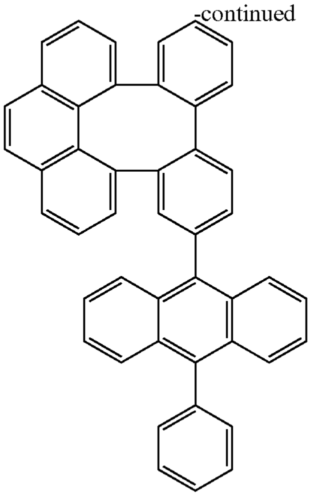
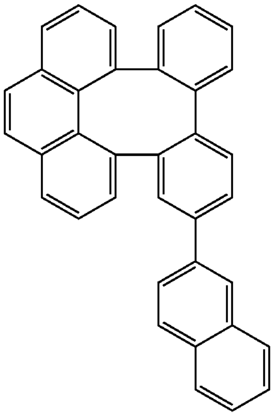
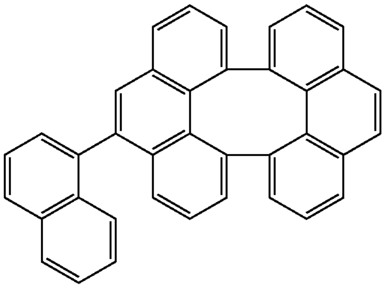
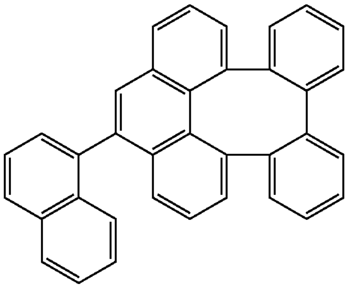

-continued
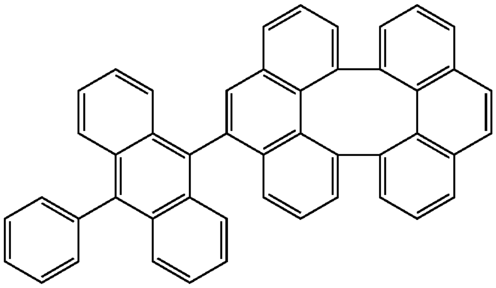
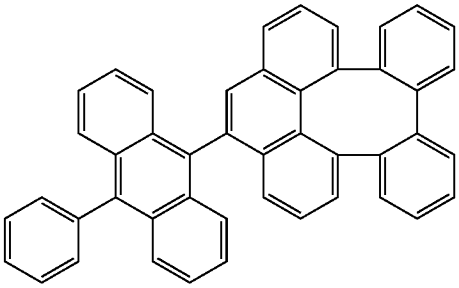
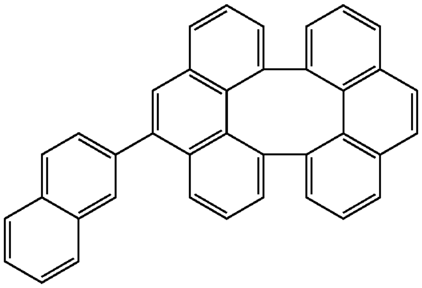
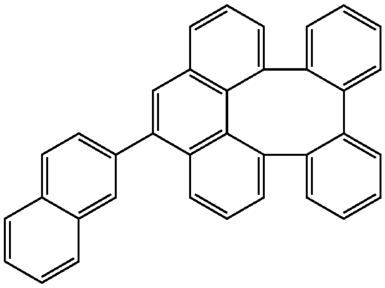
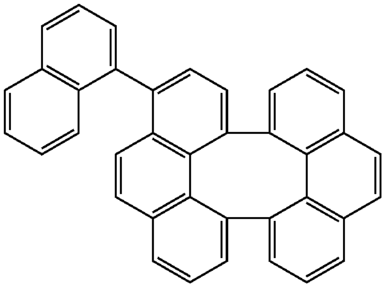
-continued
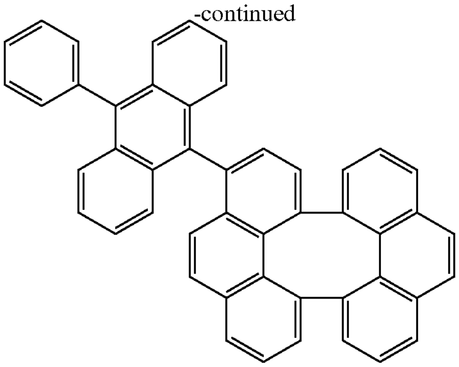
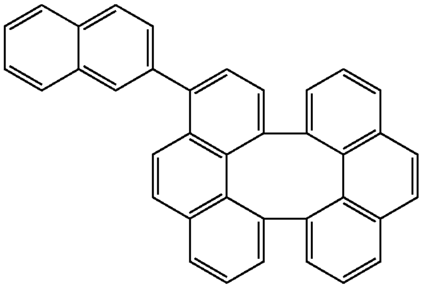
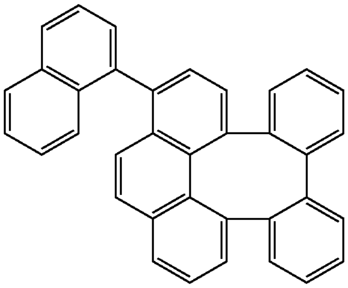
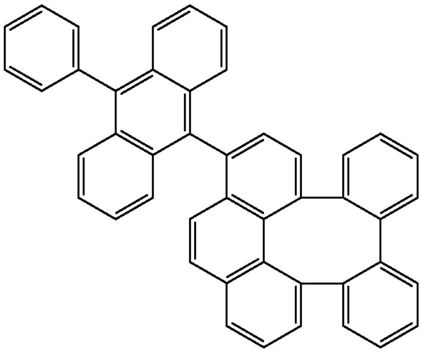
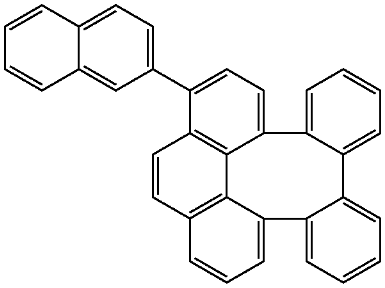

-continued
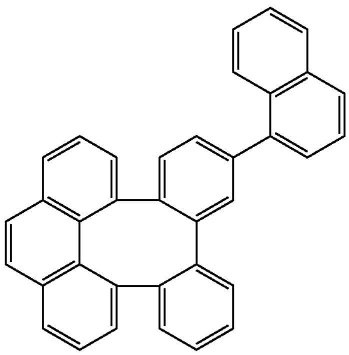
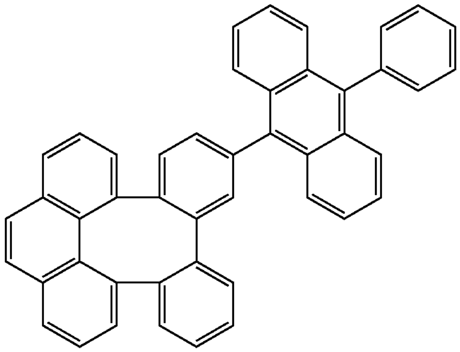
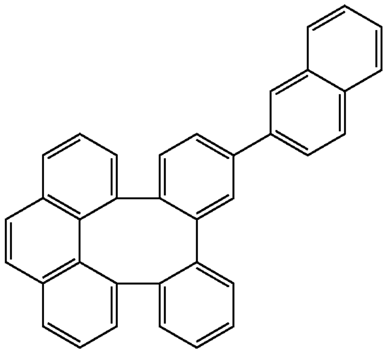
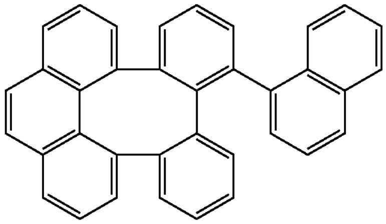
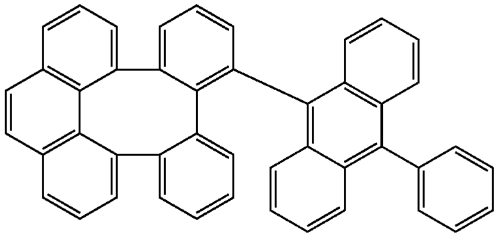
-continued
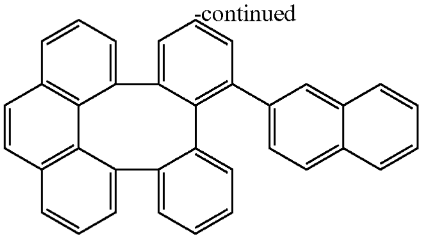
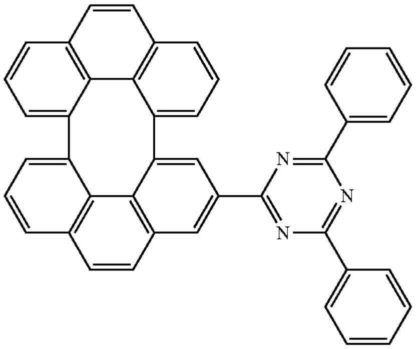
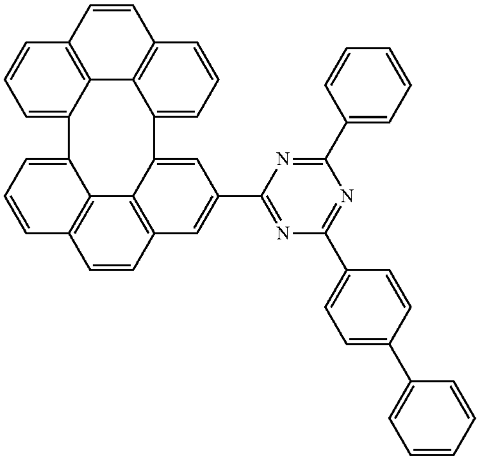
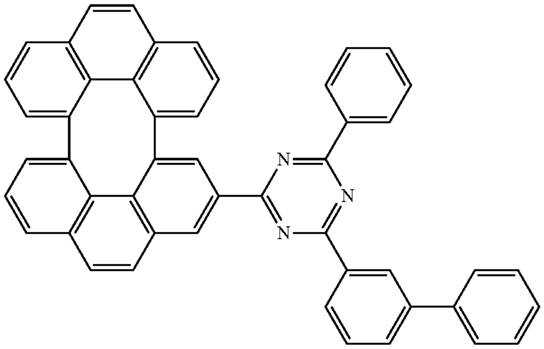
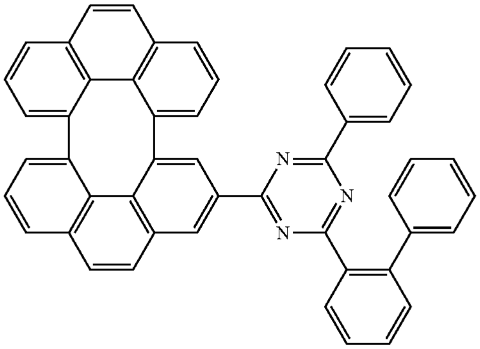

-continued
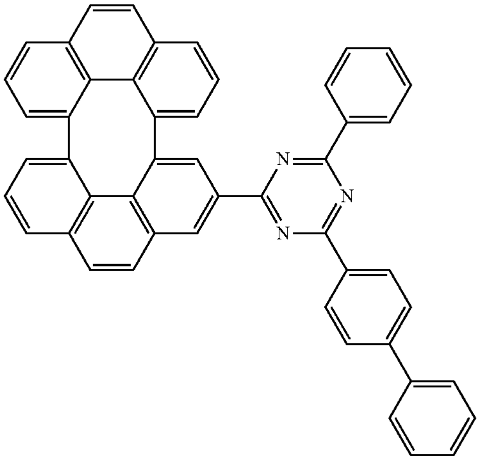
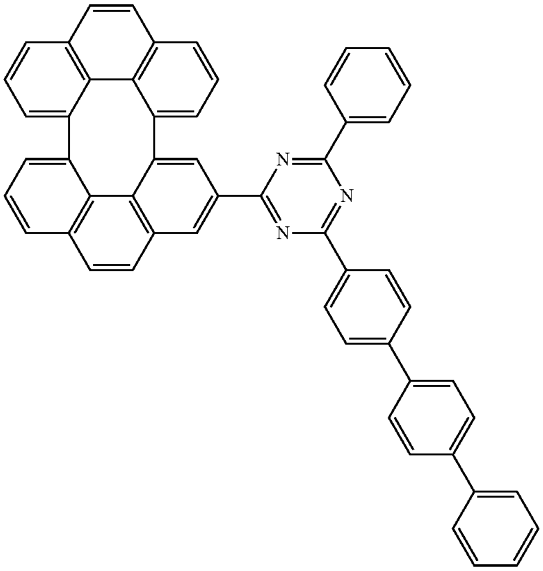
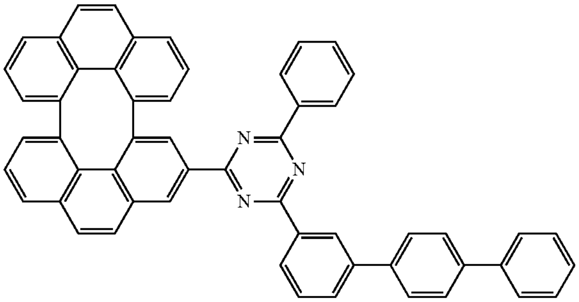
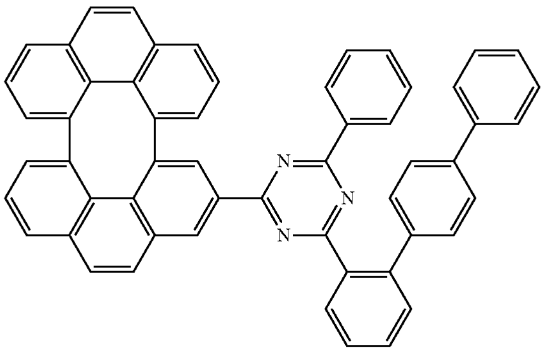
-continued
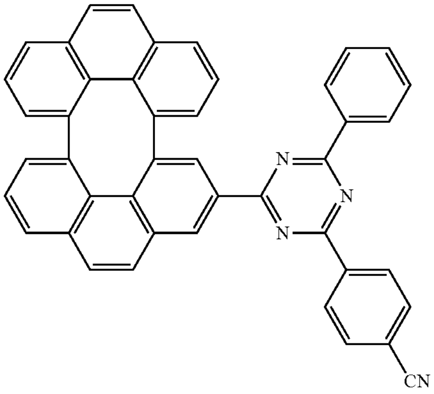
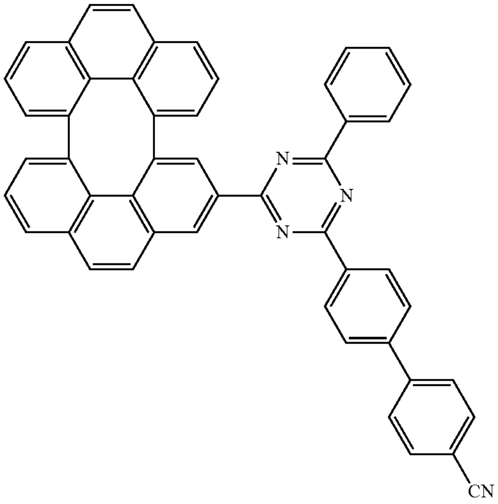
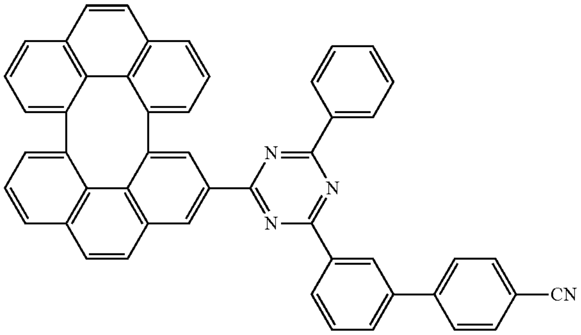
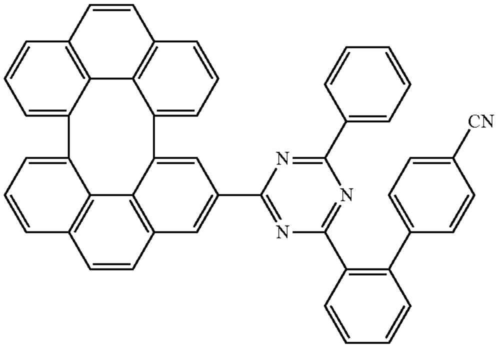

-continued
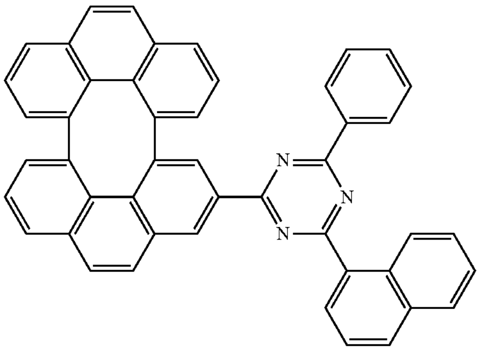
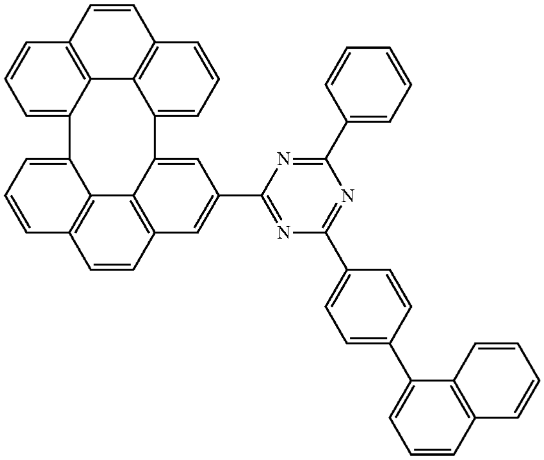
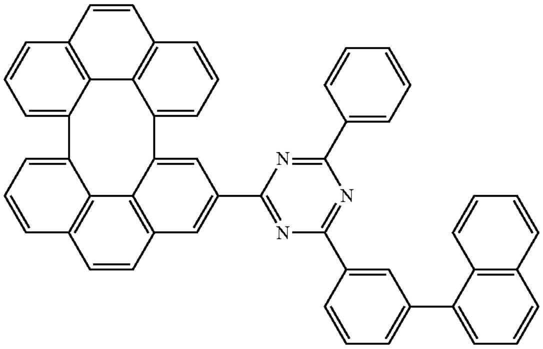
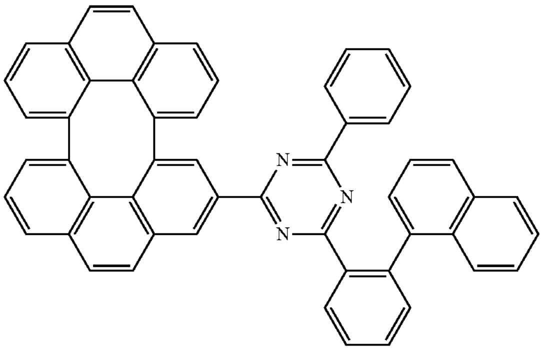
-continued
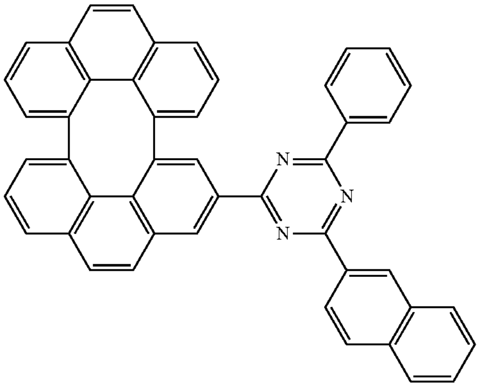
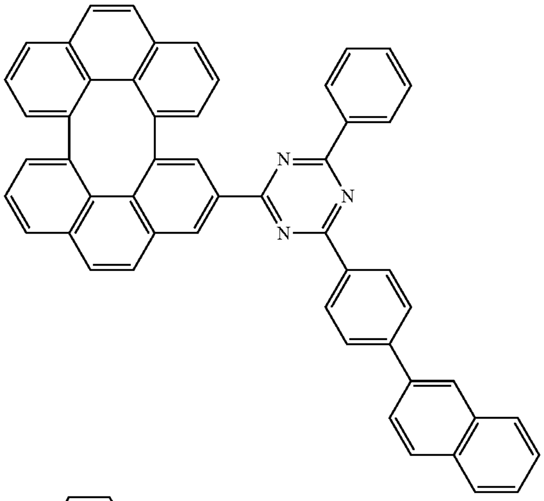
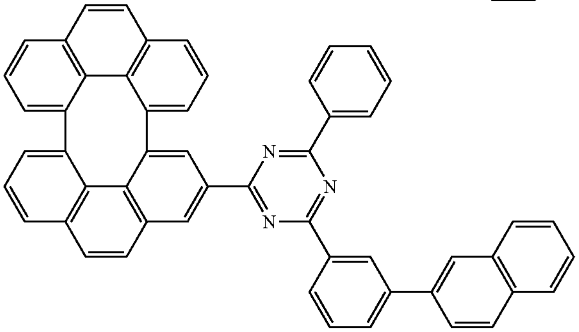
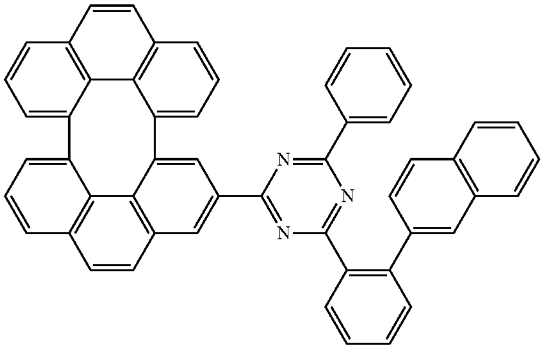

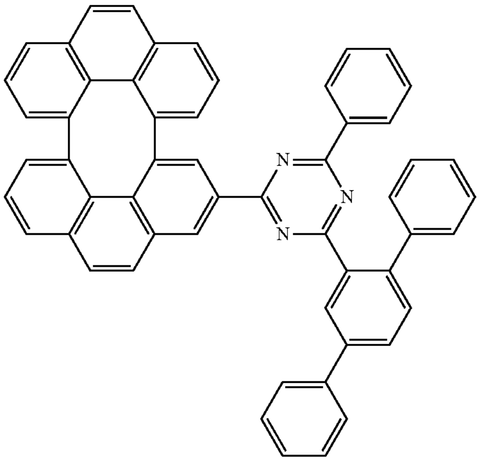
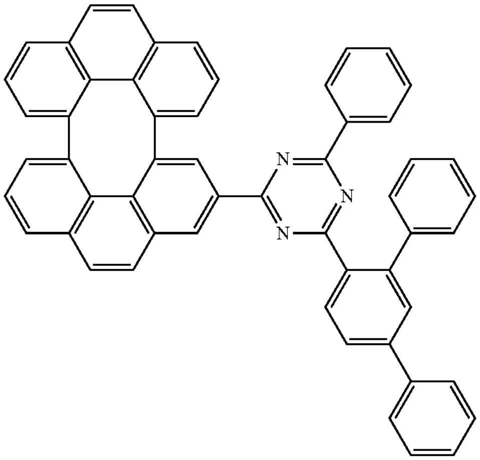
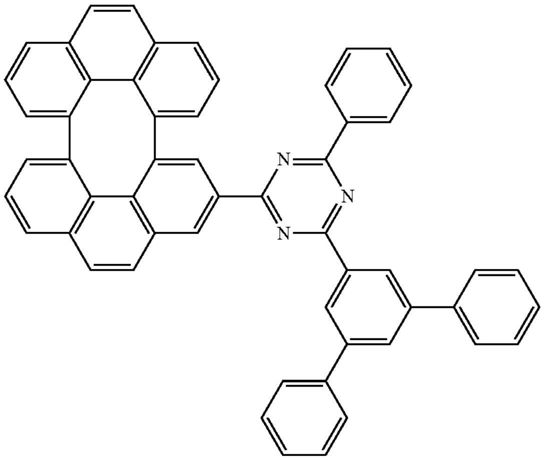
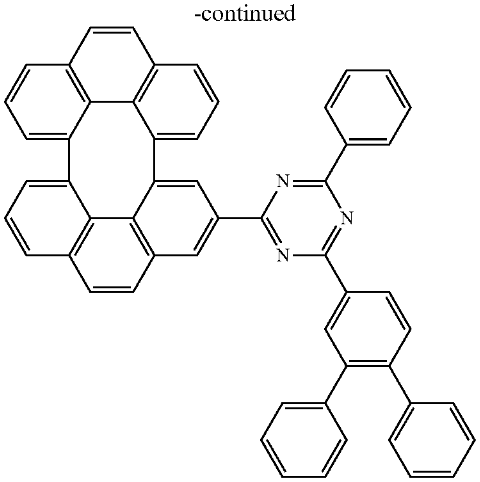
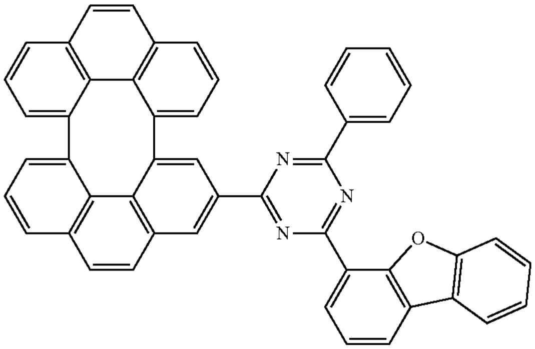
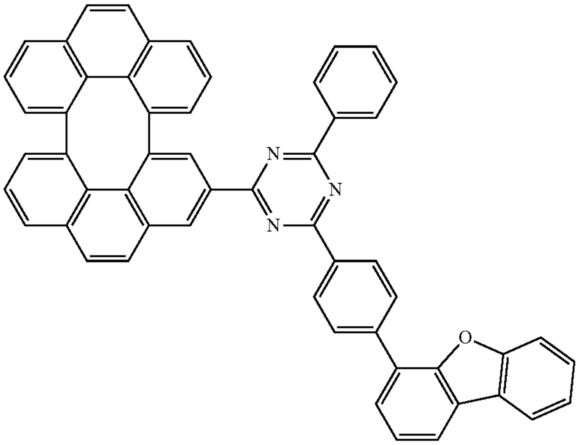
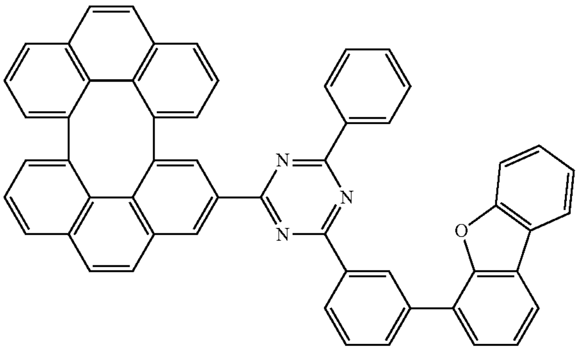

-continued
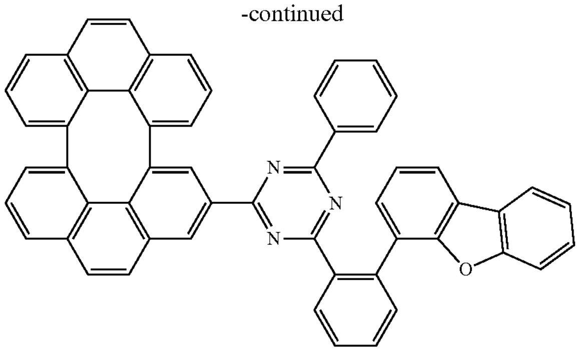
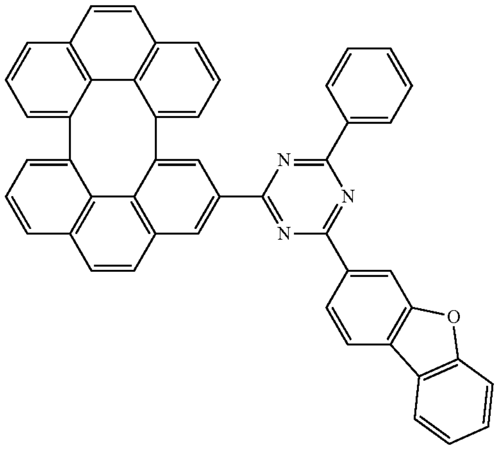
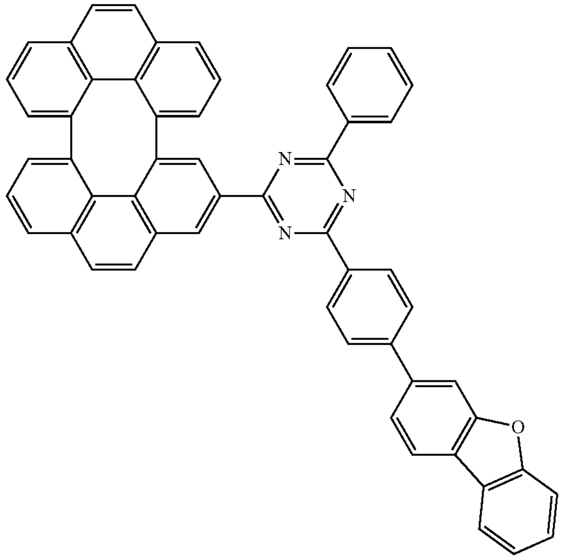
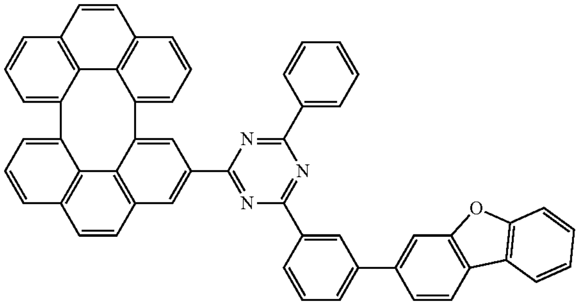
-continued
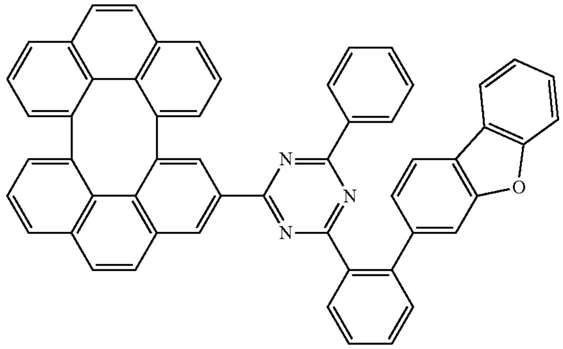
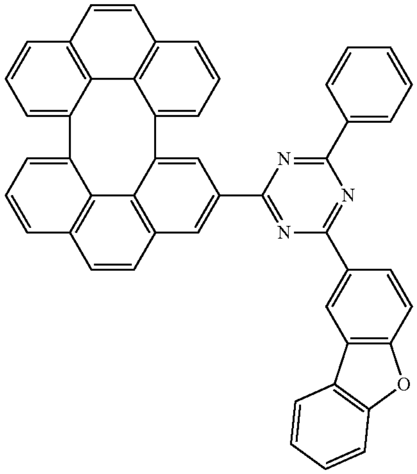
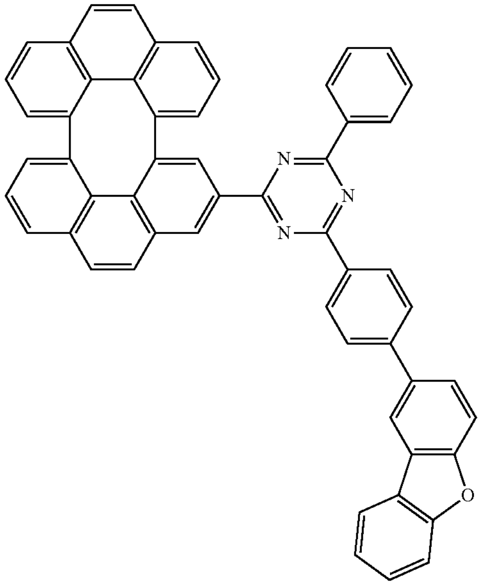

-continued
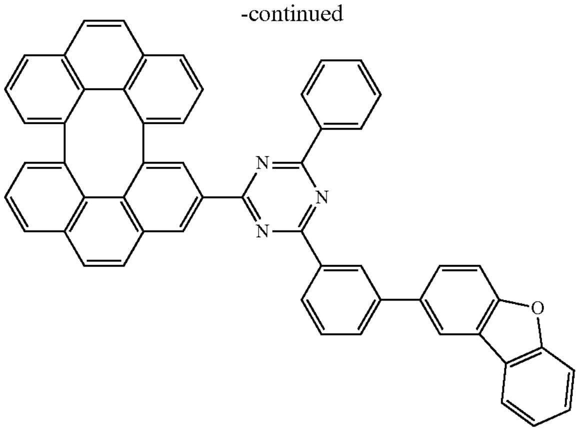
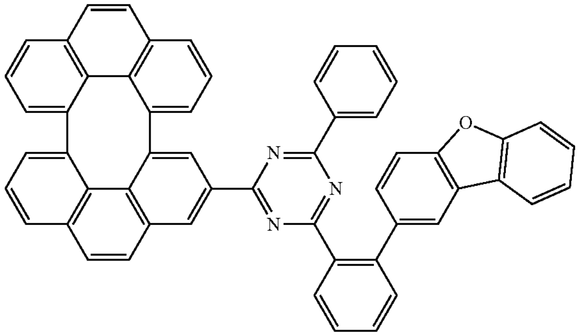
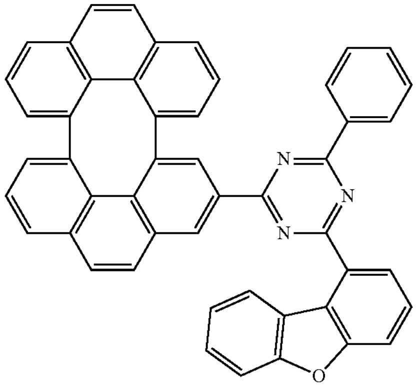
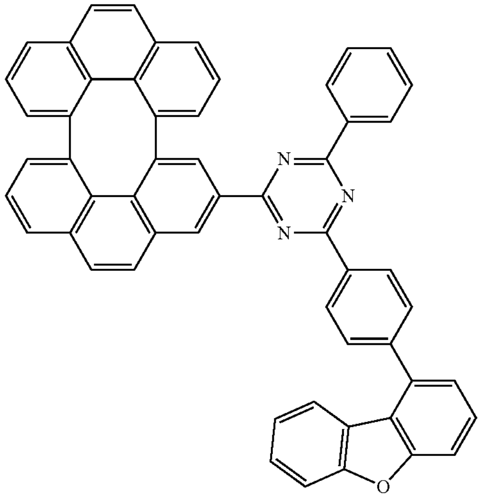
-continued
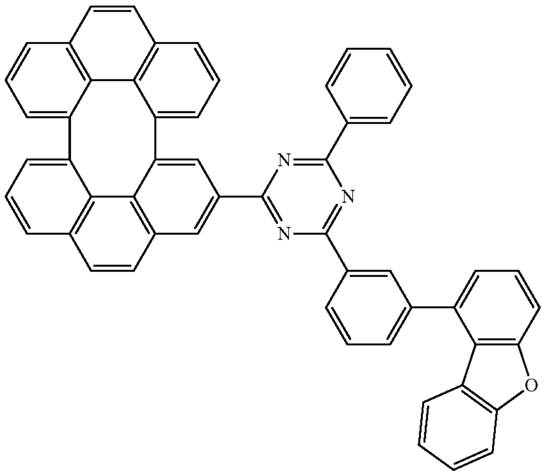
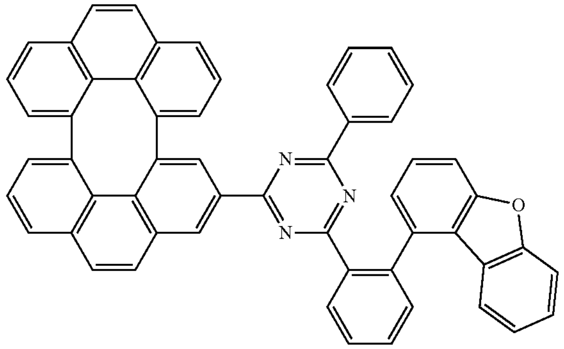
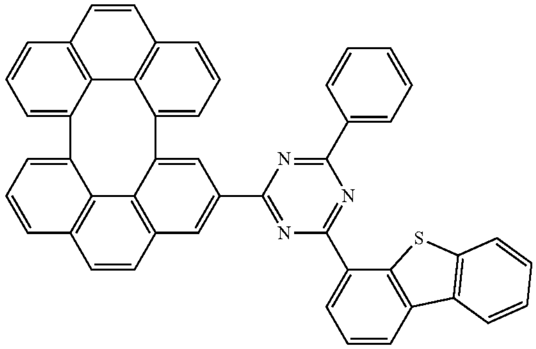
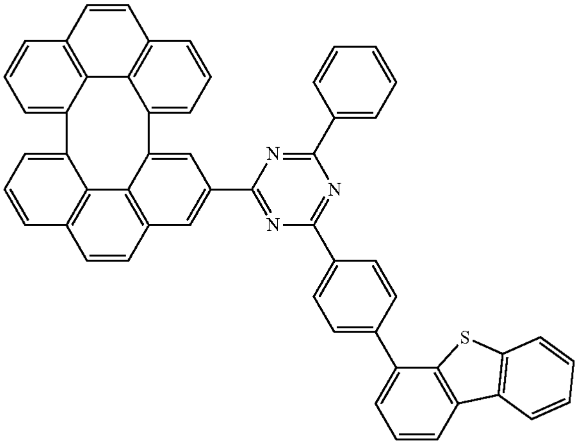

-continued
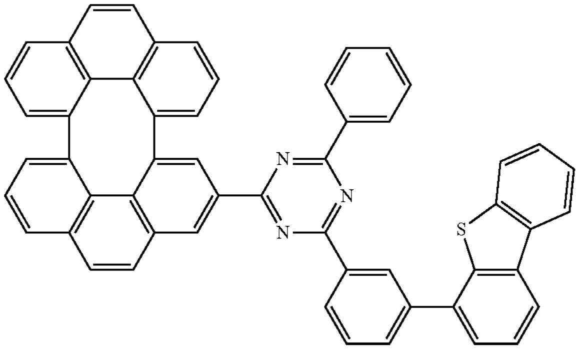
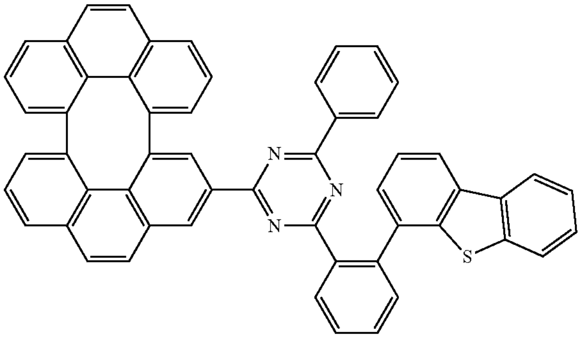
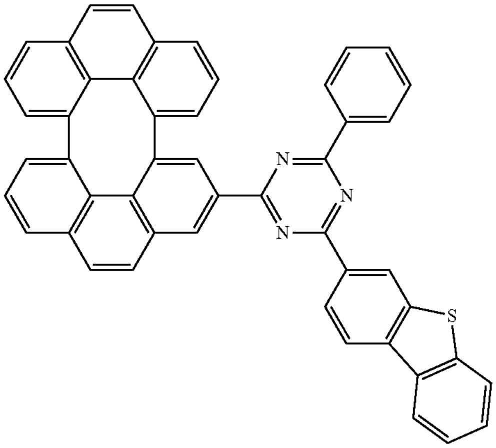
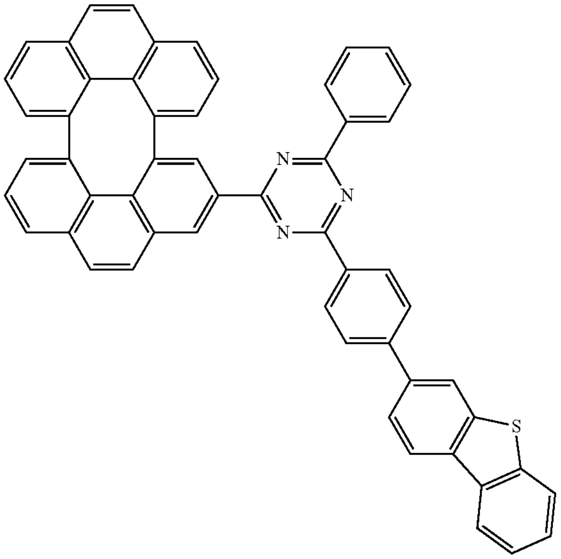
-continued
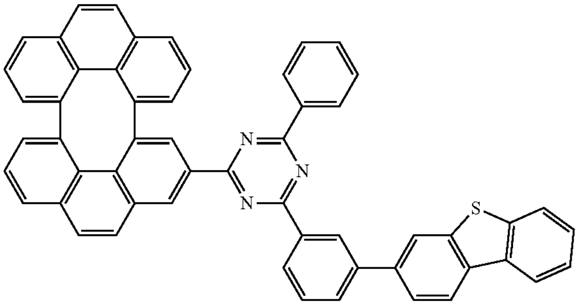
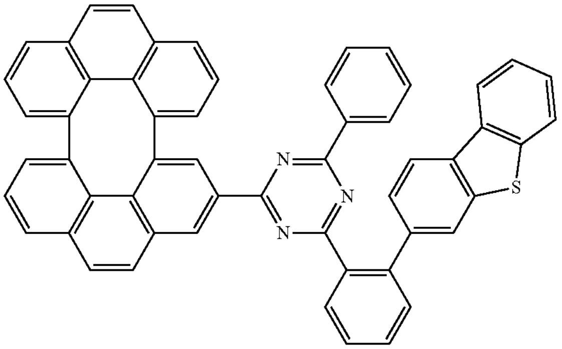
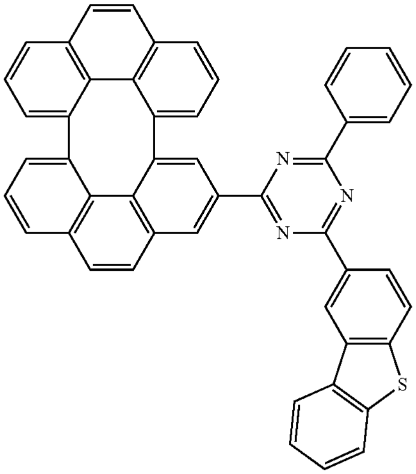
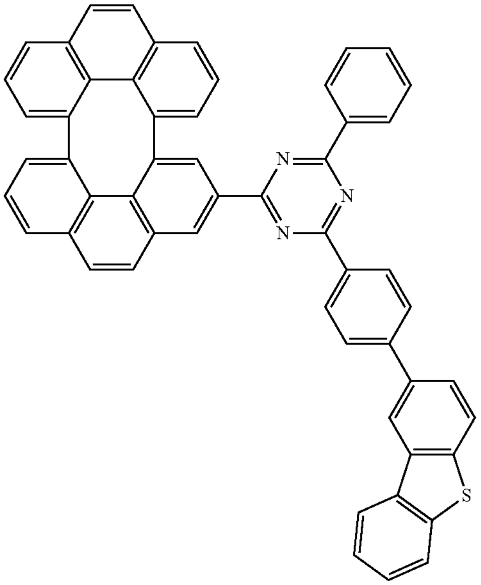

-continued
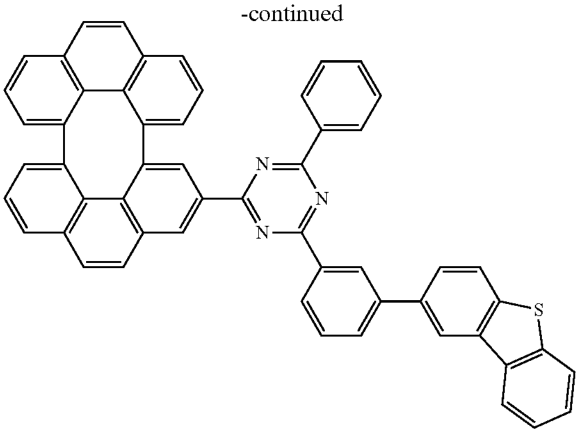
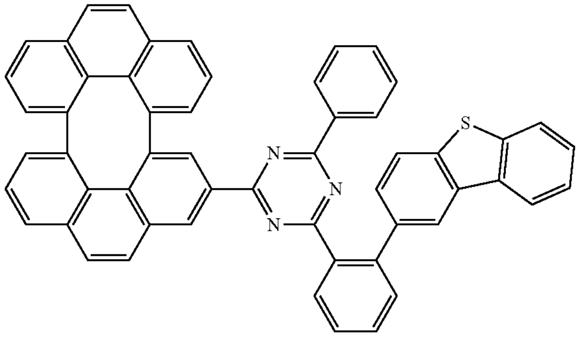
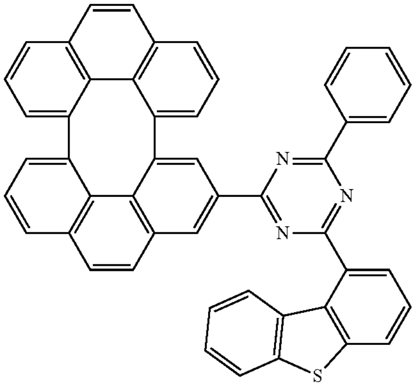
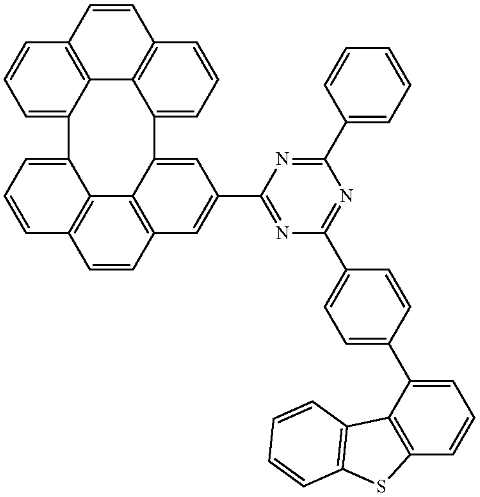
-continued
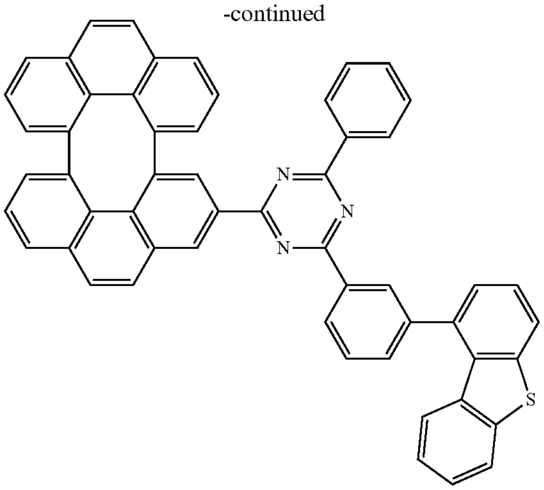
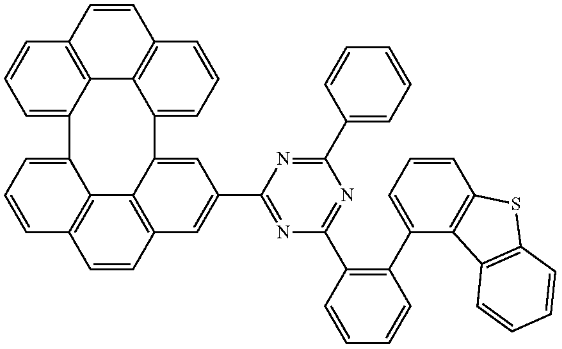
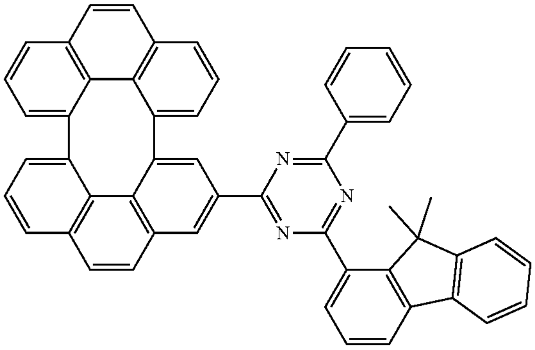
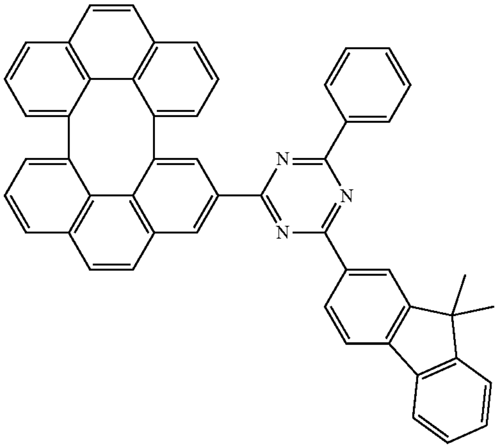

-continued
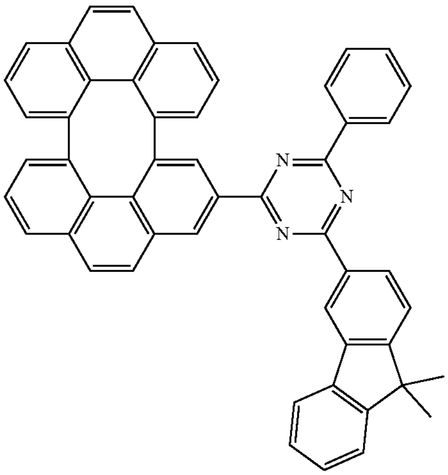
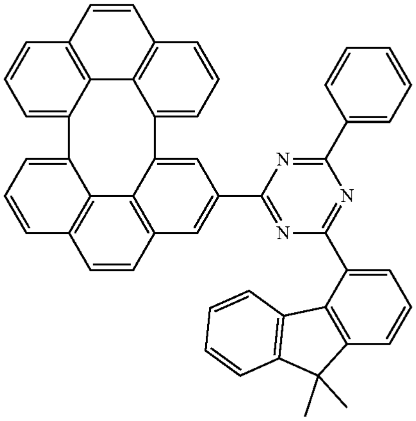
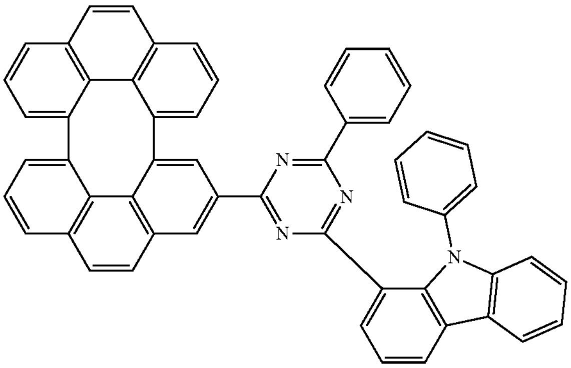
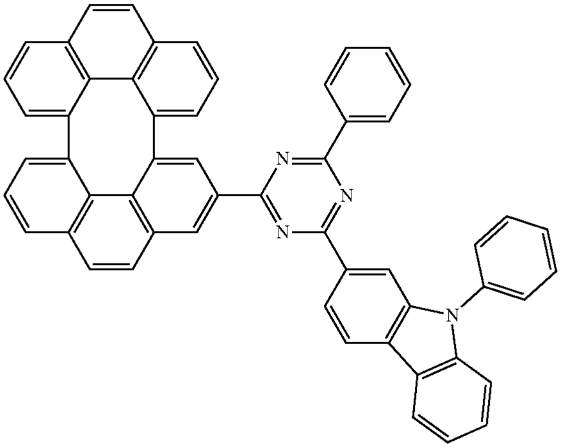
-continued
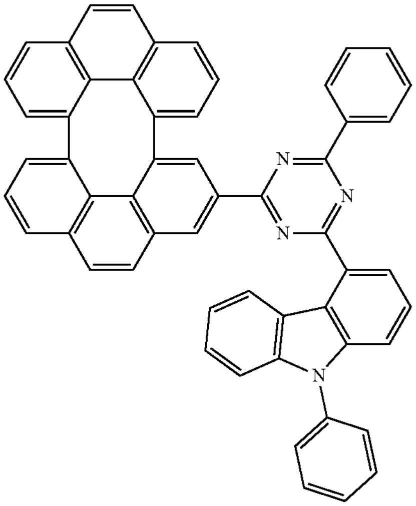
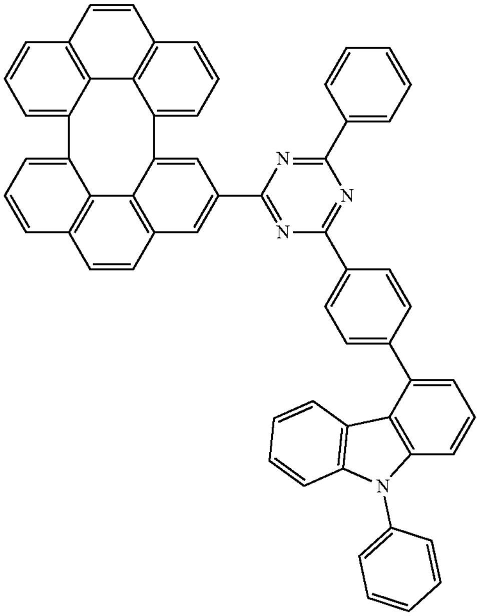
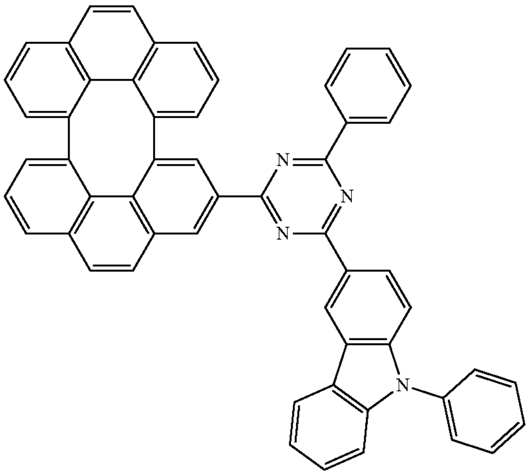

-continued
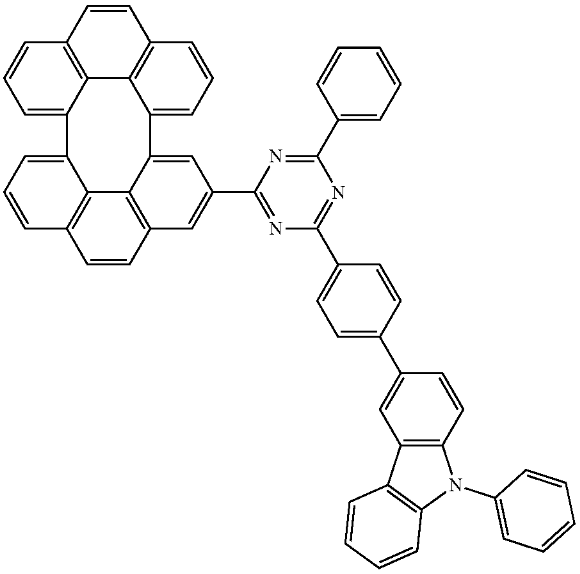
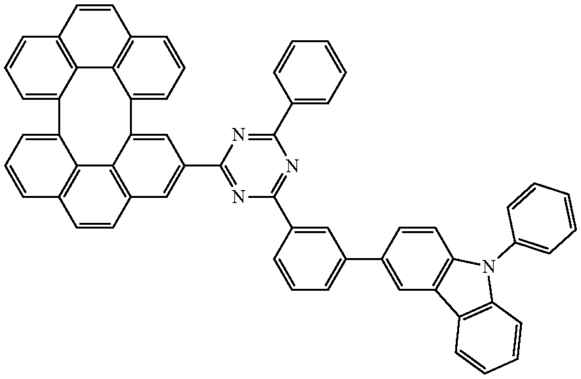
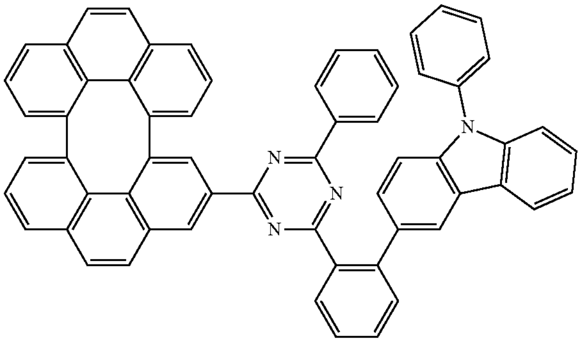
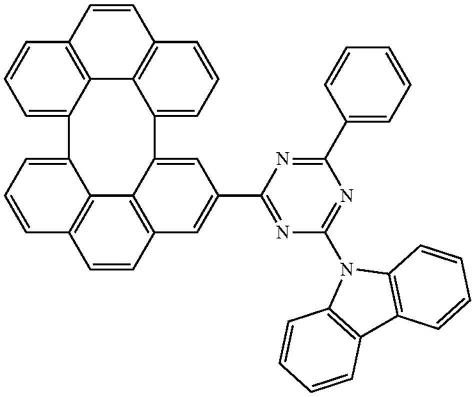
-continued
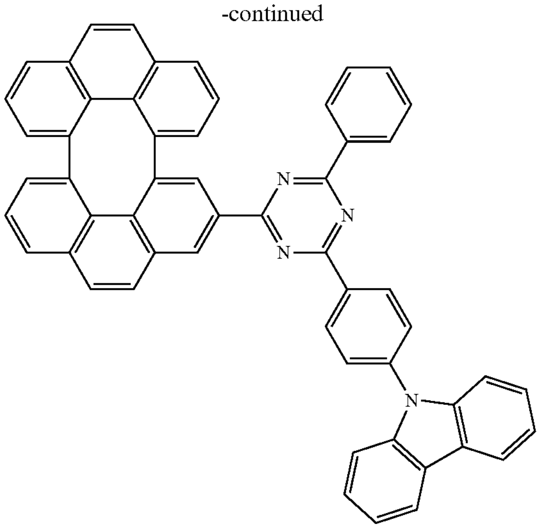
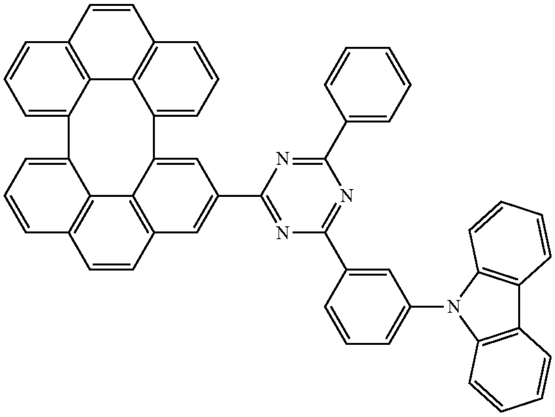
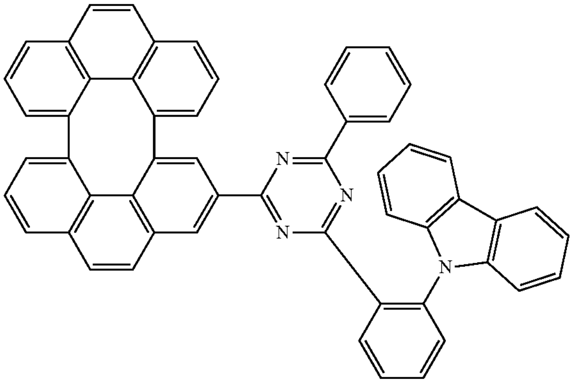
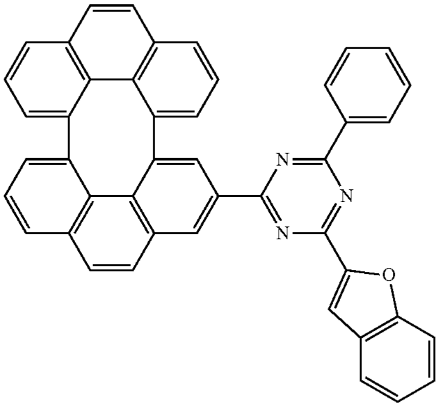

-continued
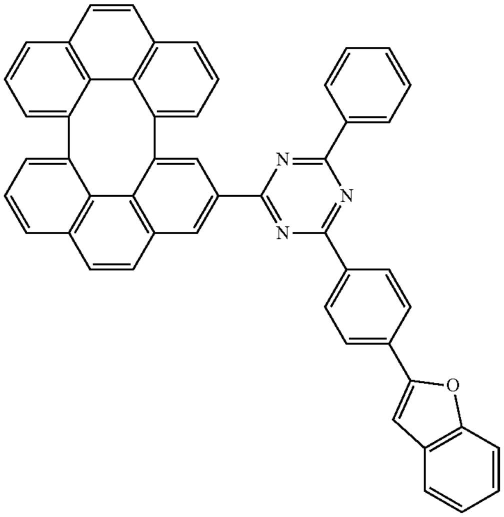
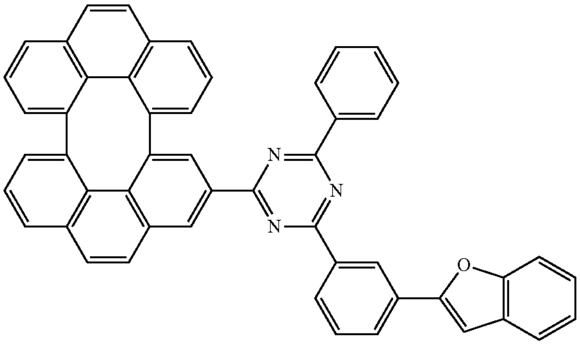
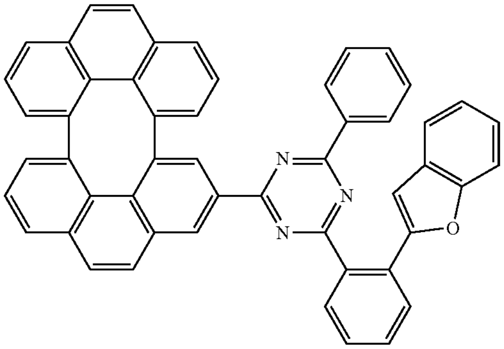
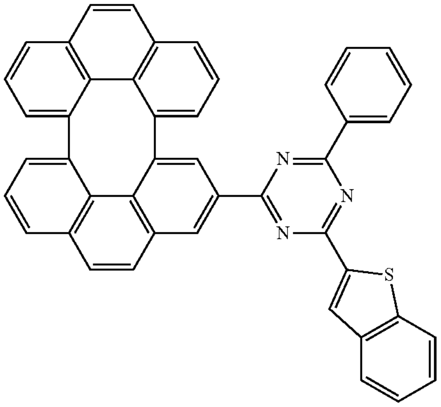
-continued
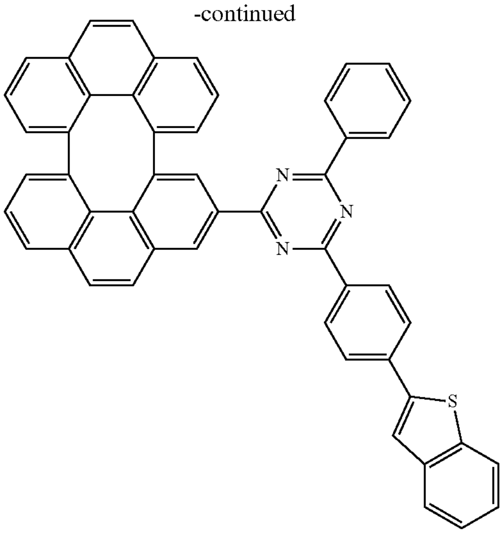
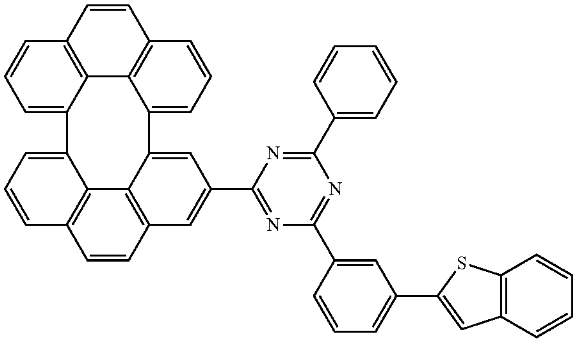
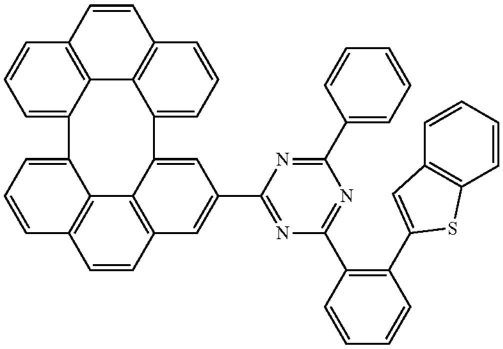
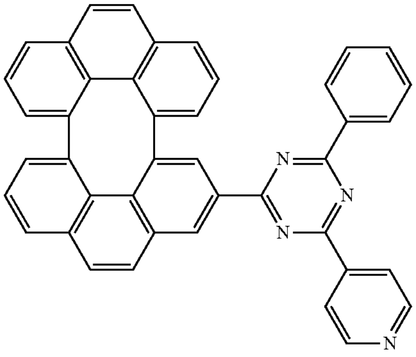

-continued
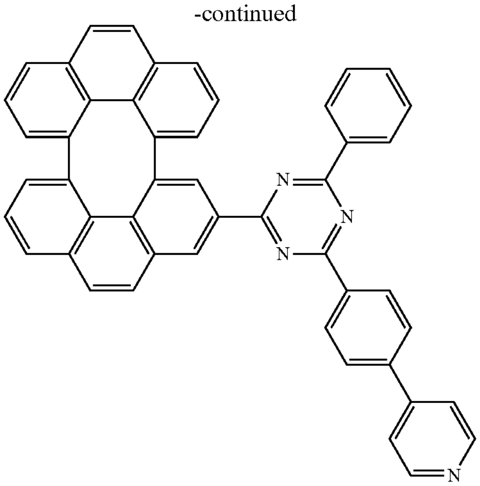
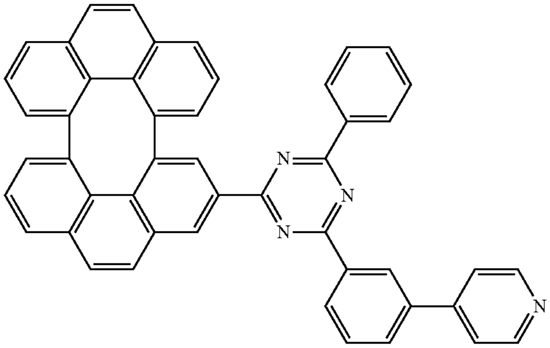
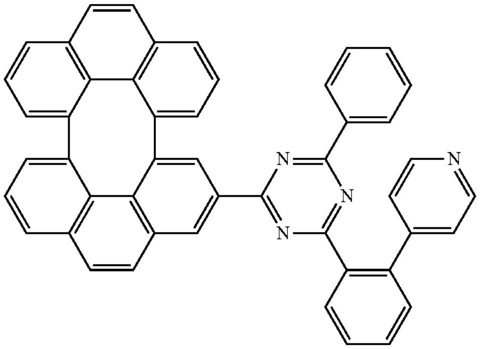
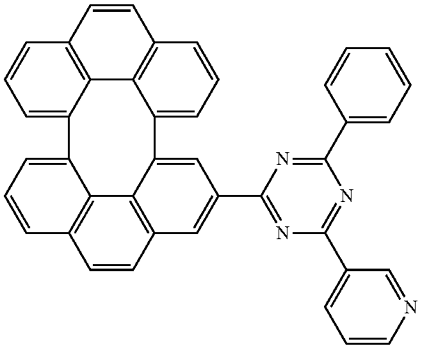
-continued
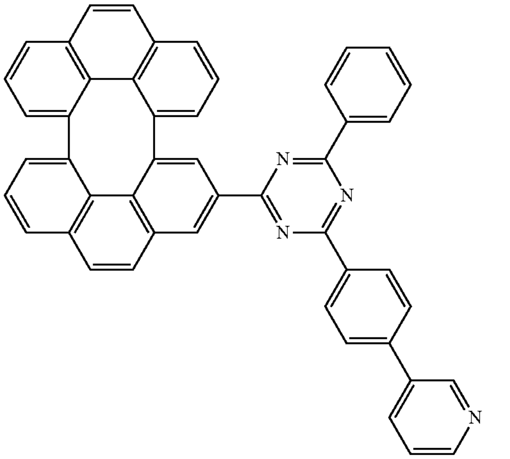
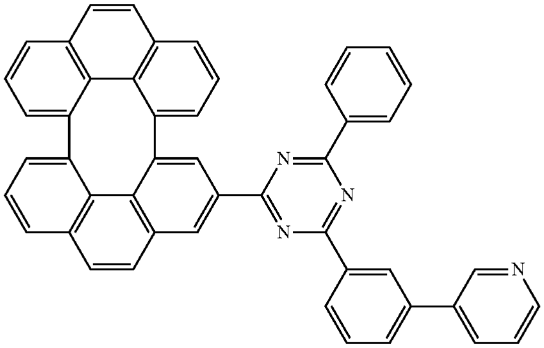
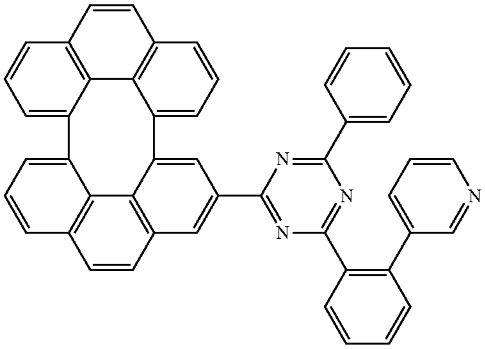
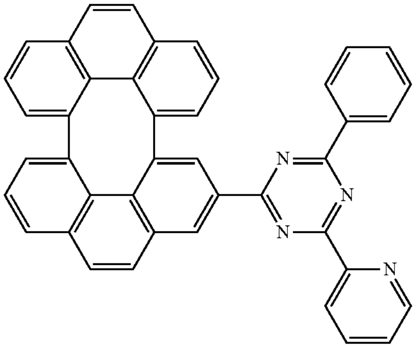

-continued
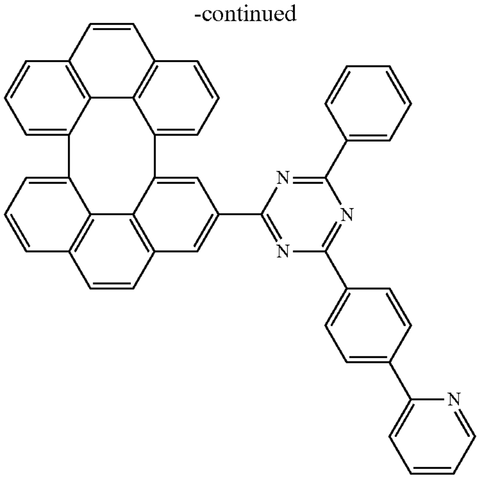
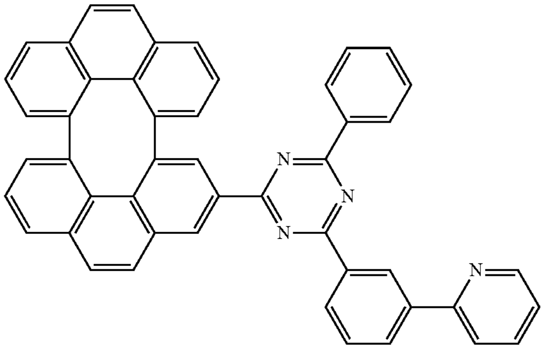
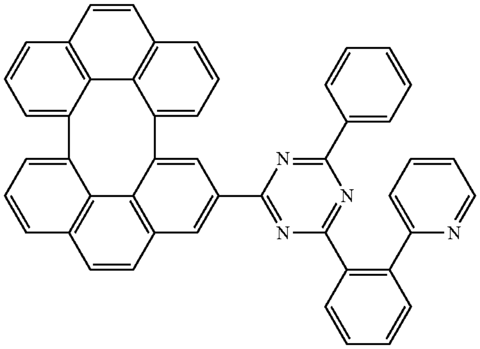
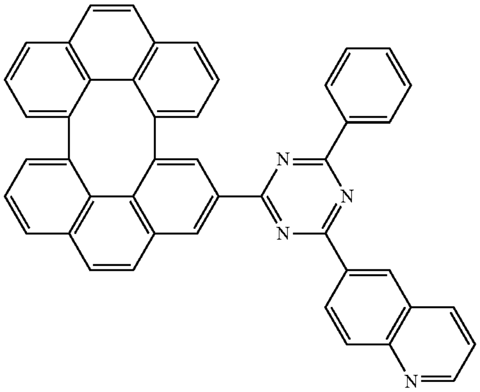
-continued
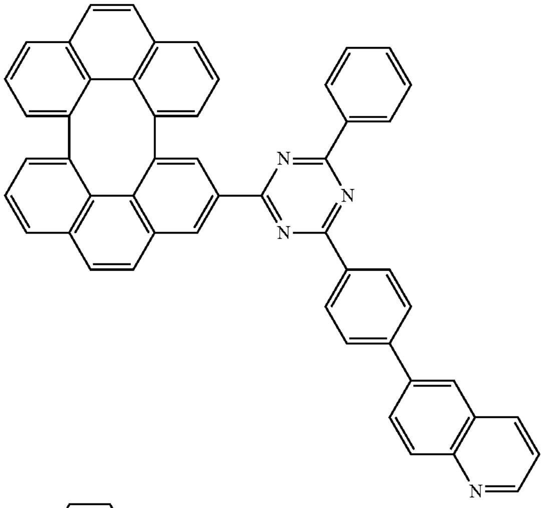
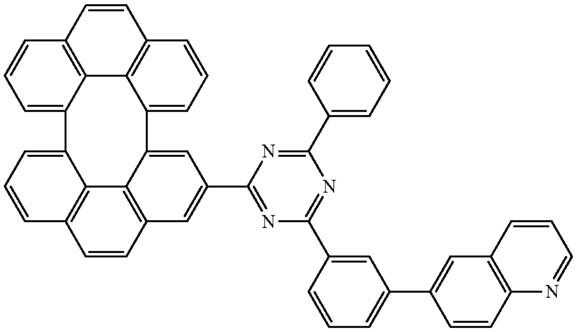
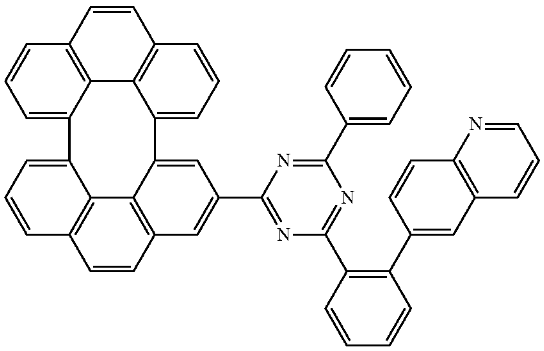
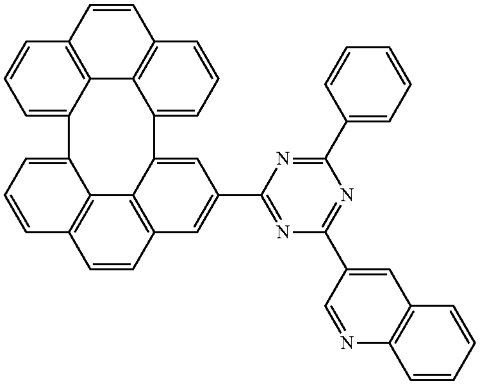

-continued
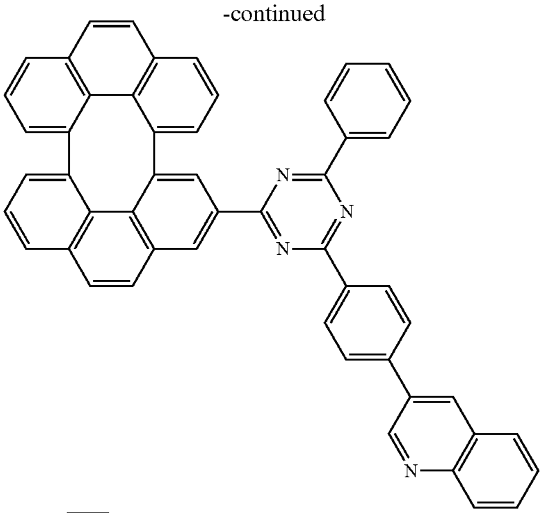
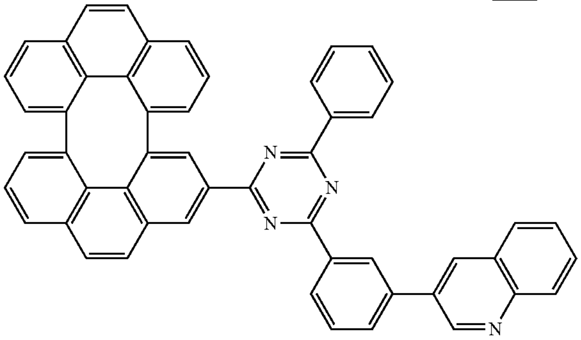
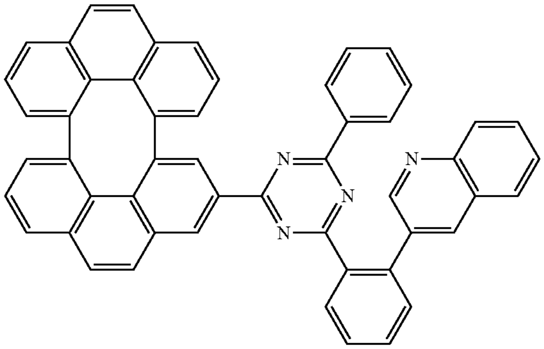
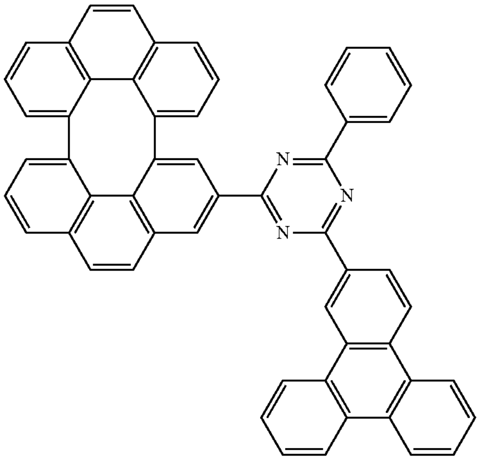
-continued
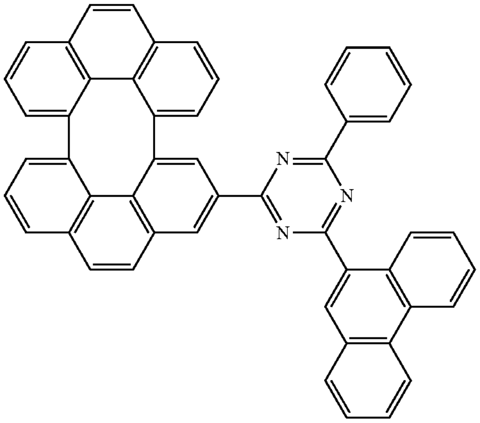
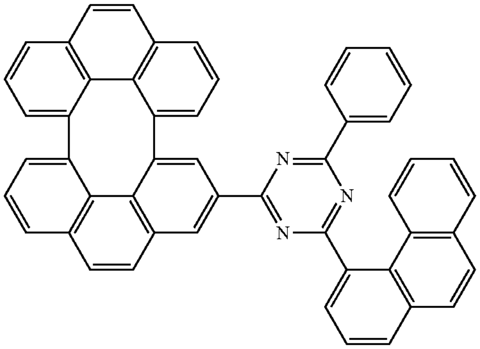
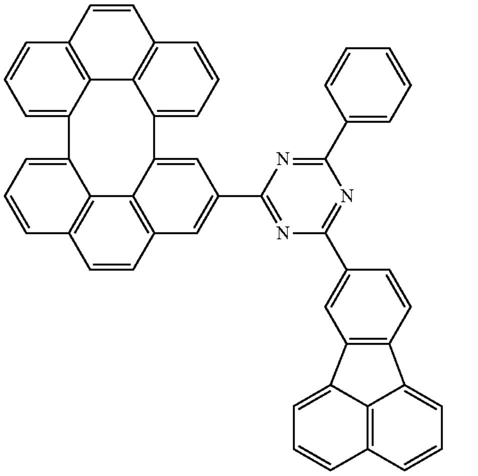
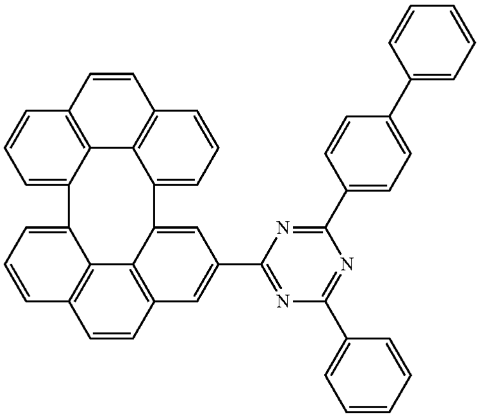

-continued
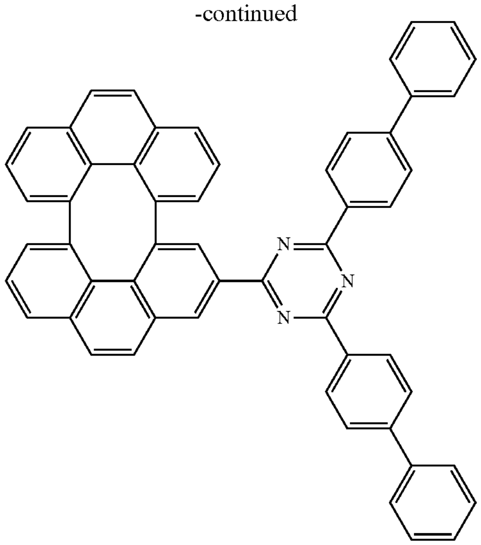
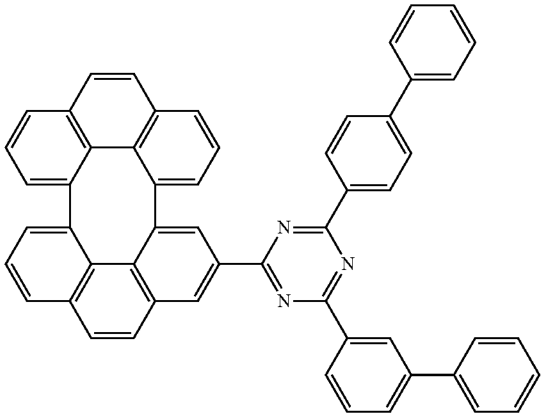
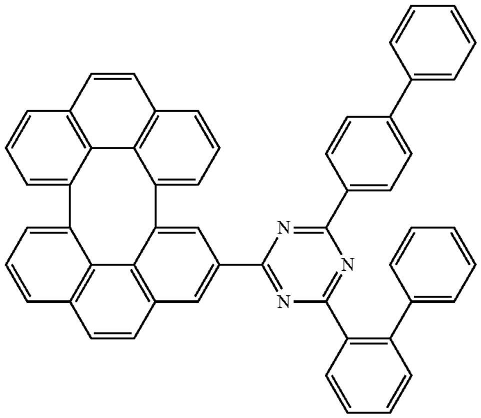
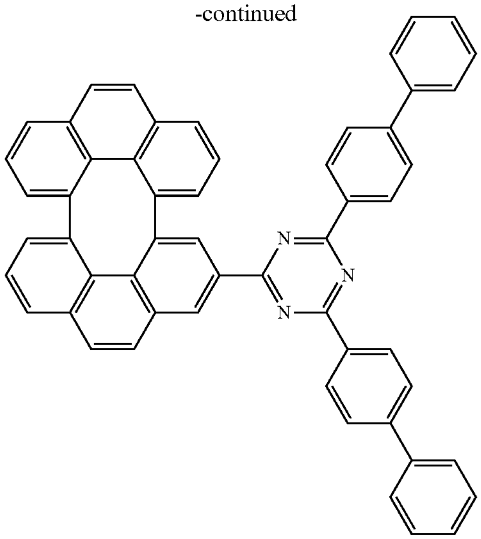
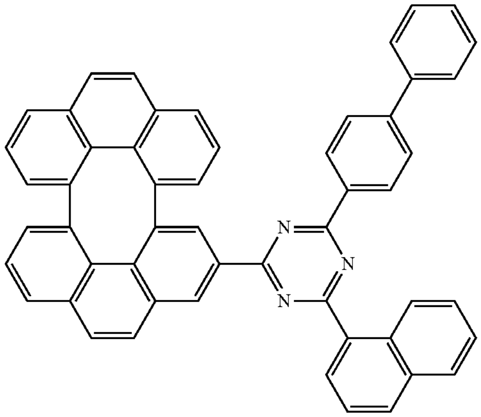
-continued
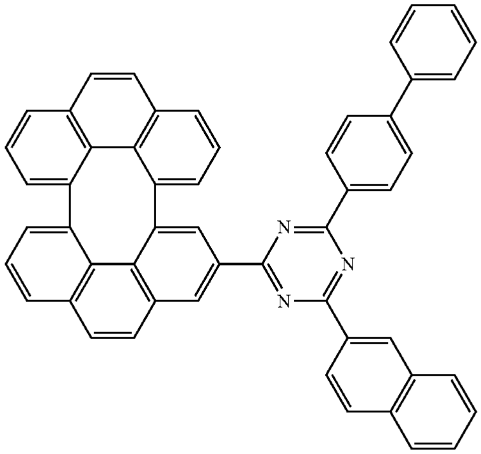

-continued
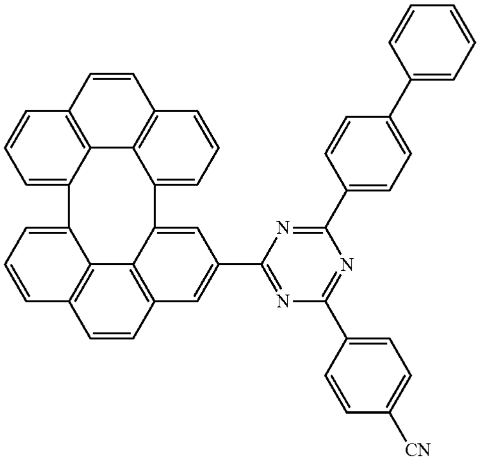
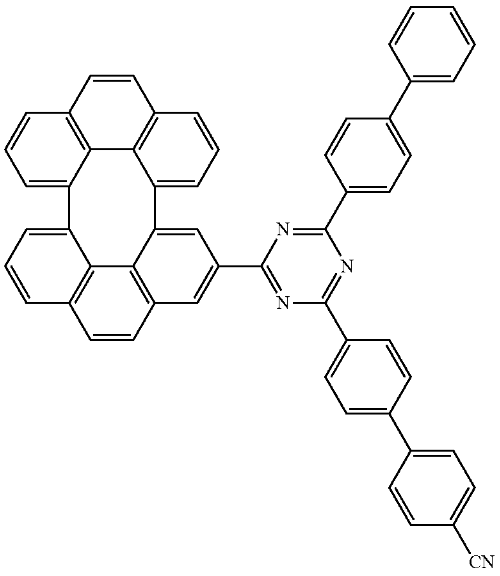
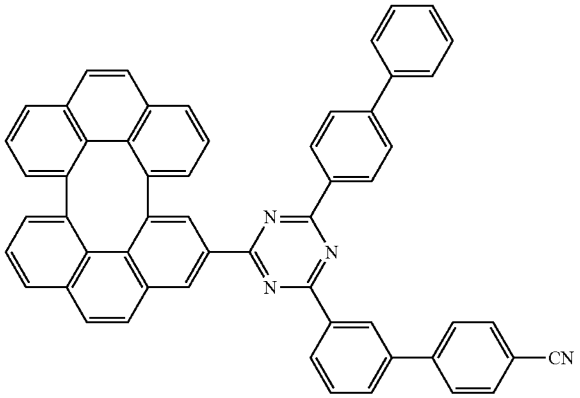
-continued
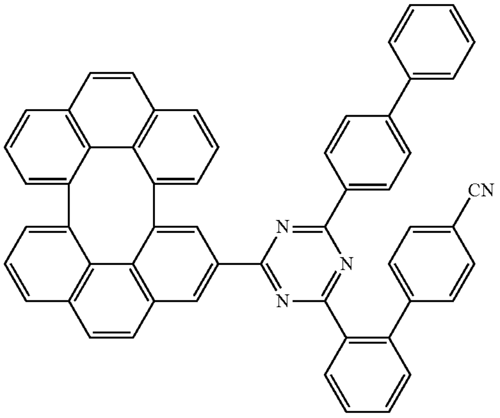
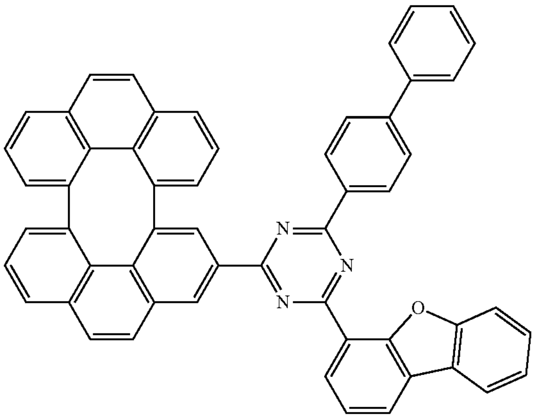
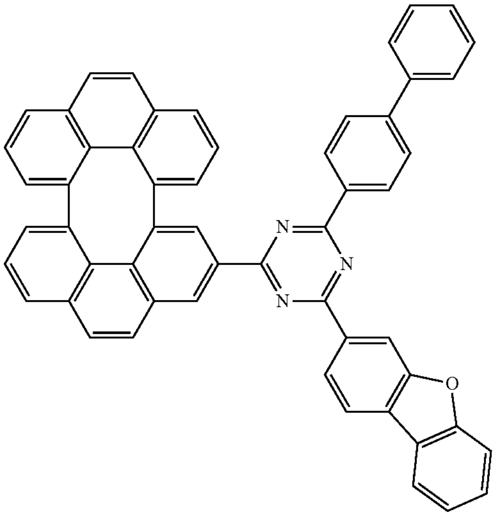

-continued
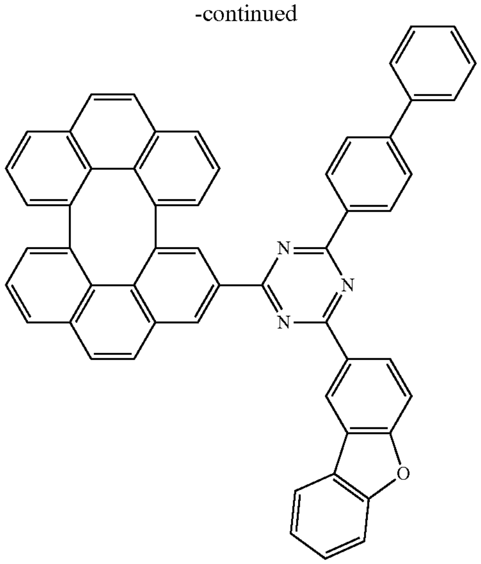
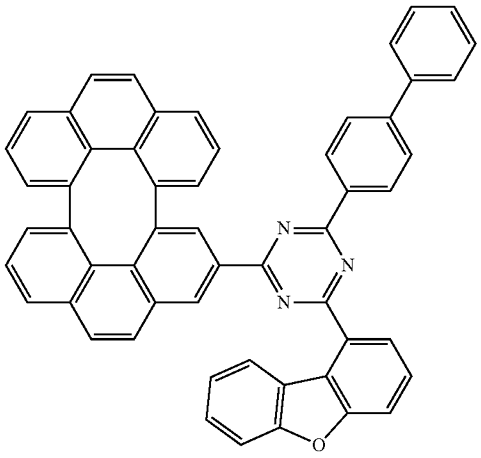
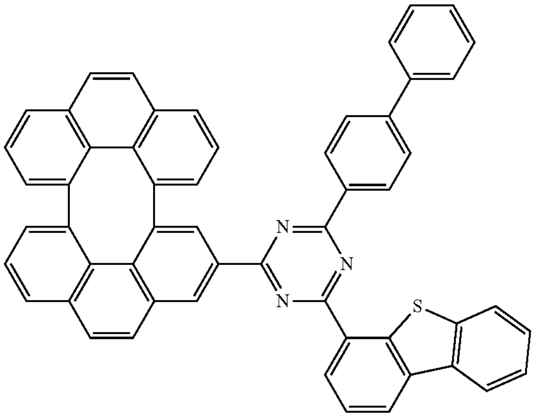
-continued
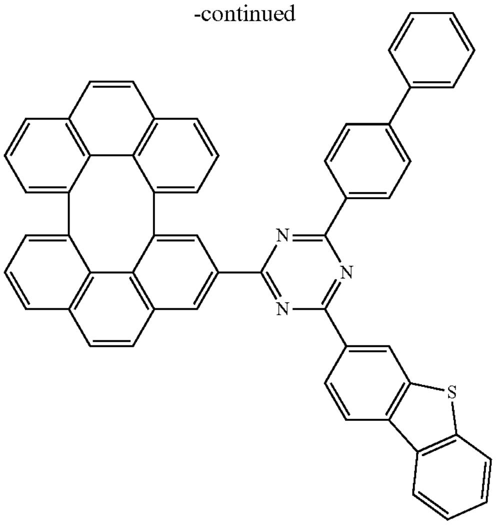
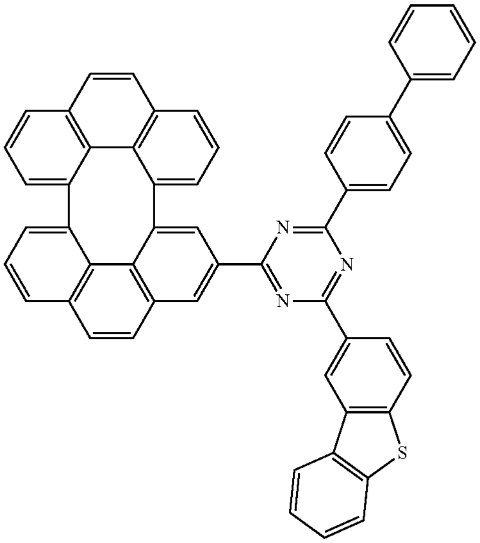
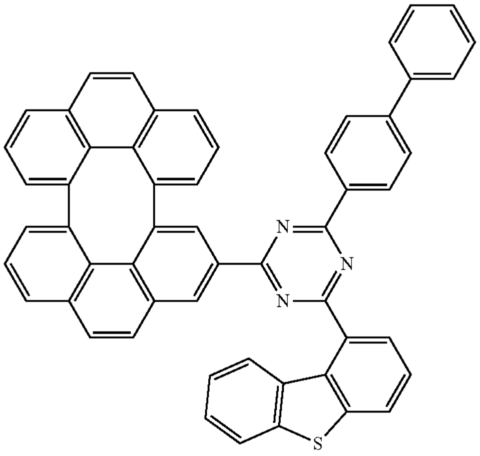

-continued
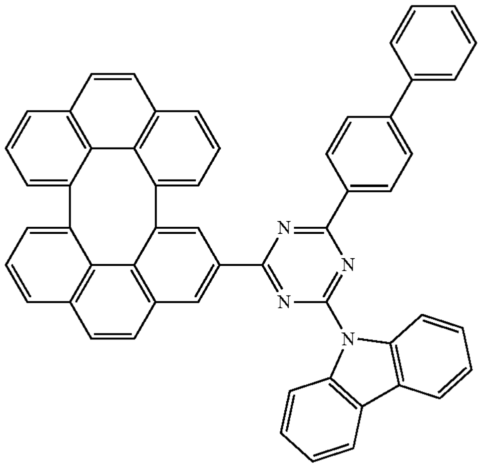
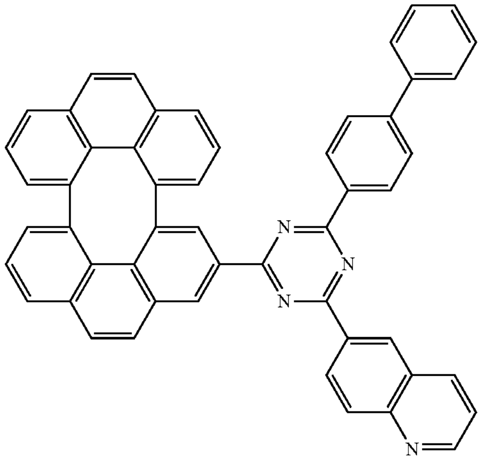
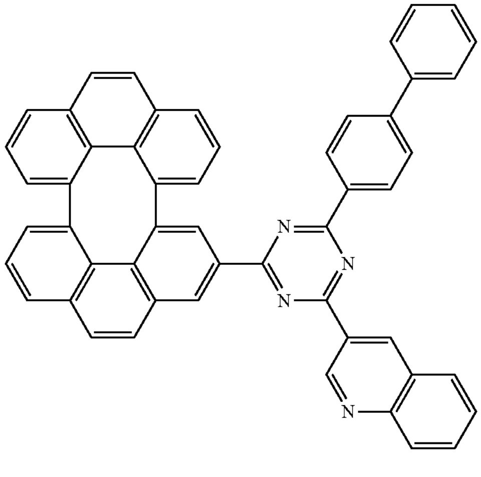
-continued
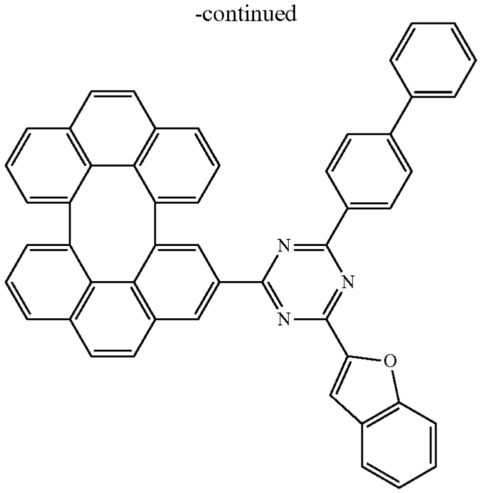
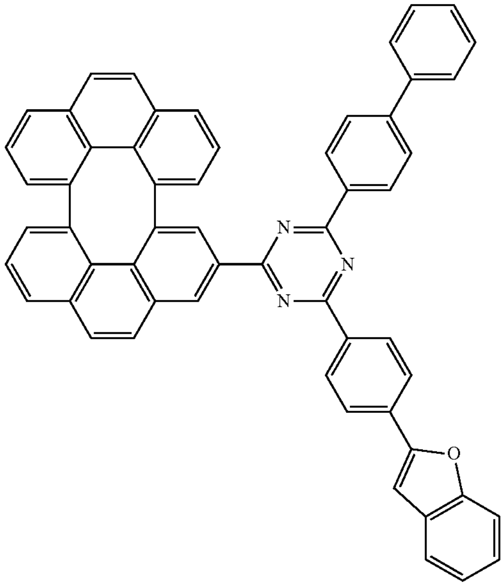
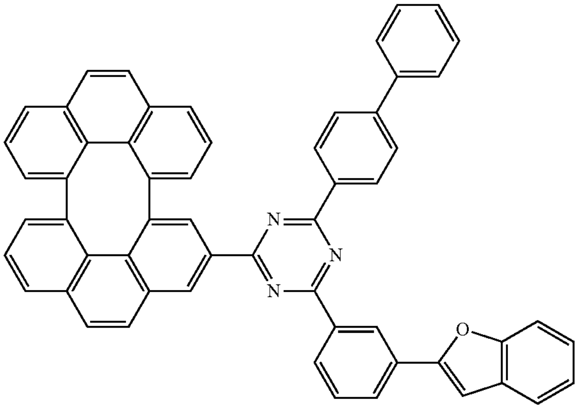

-continued
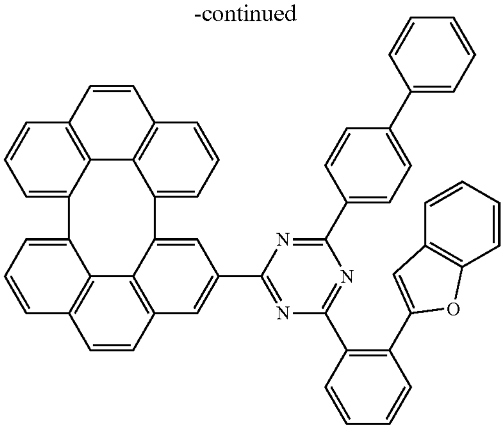
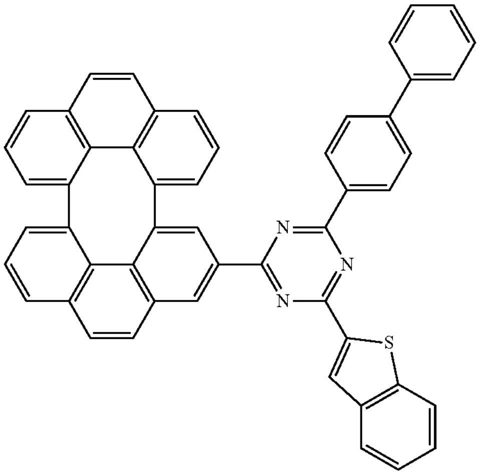
-continued
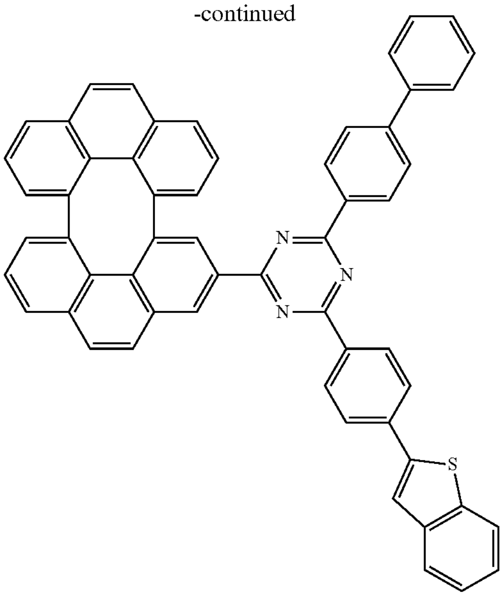
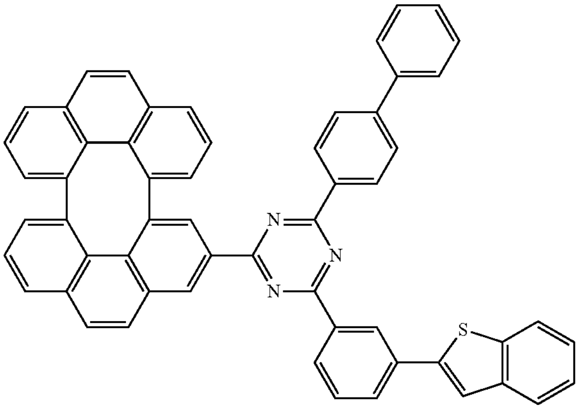
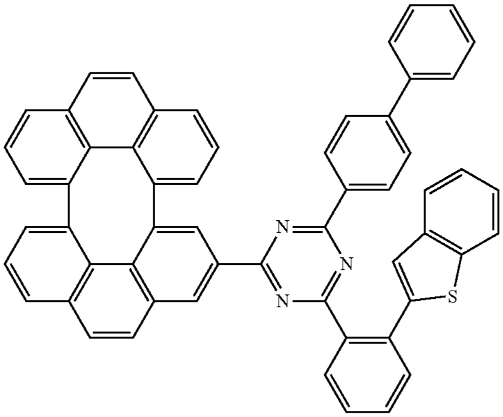

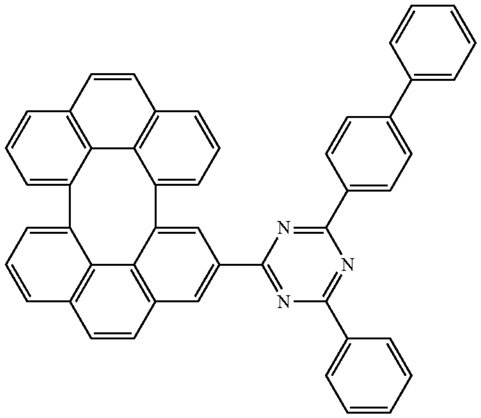
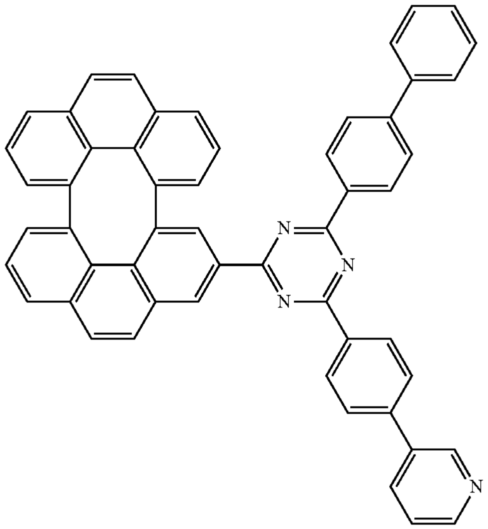
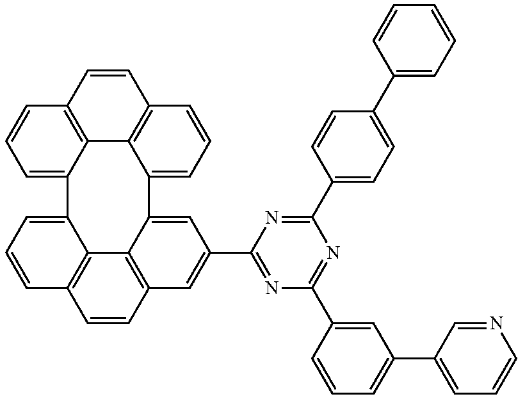

-continued
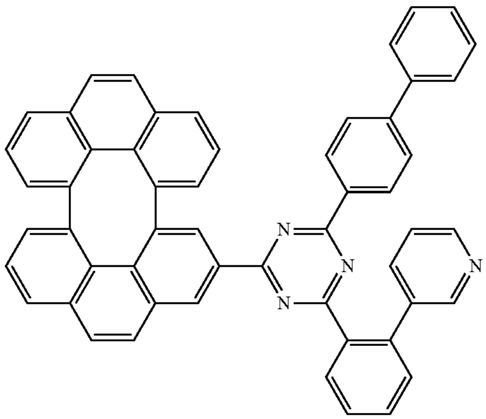
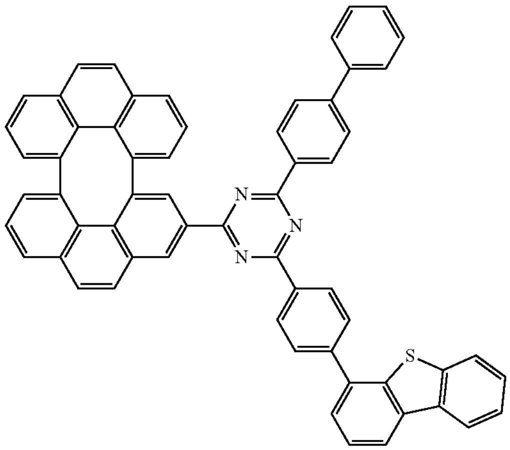
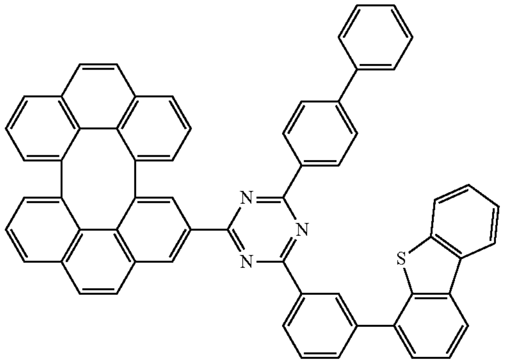

-continued
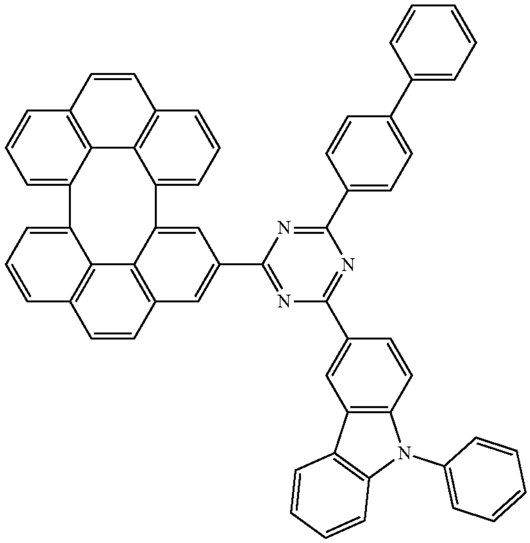
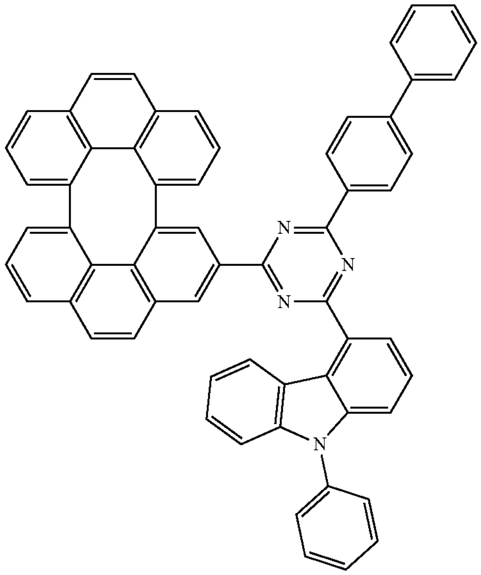
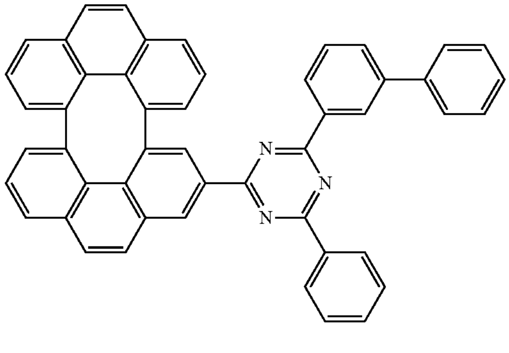

-continued
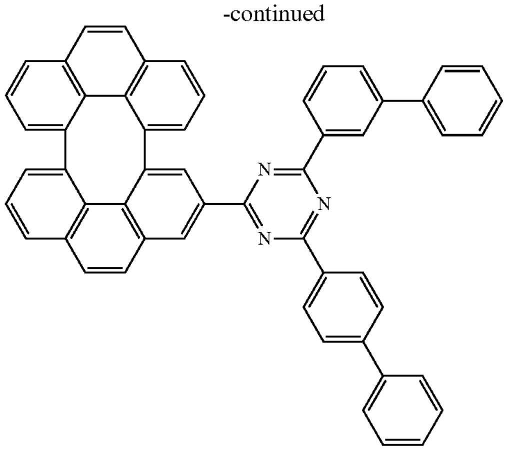
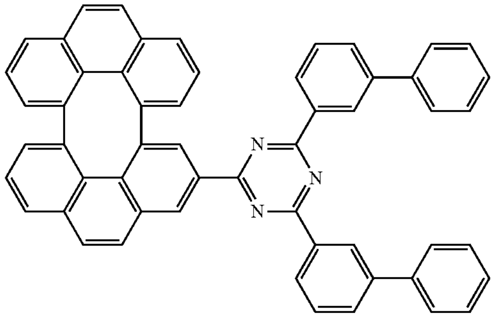
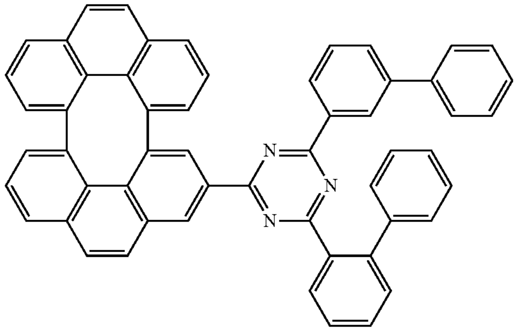
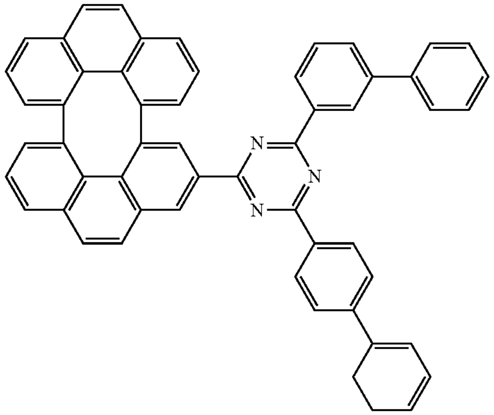

-continued
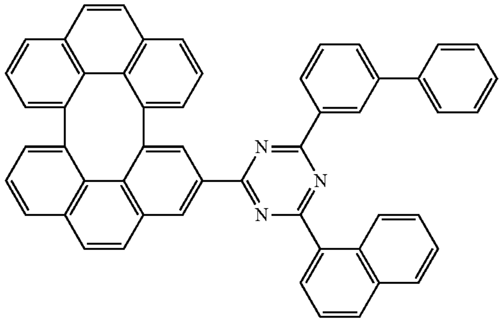
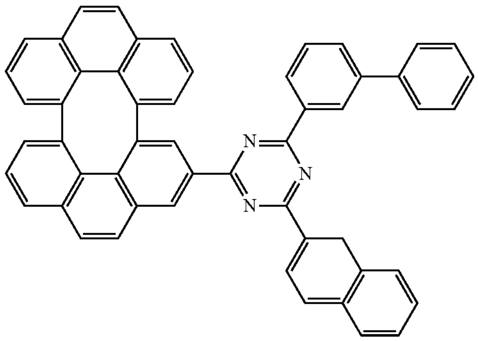
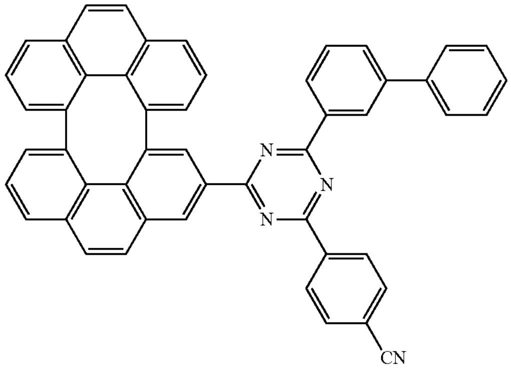
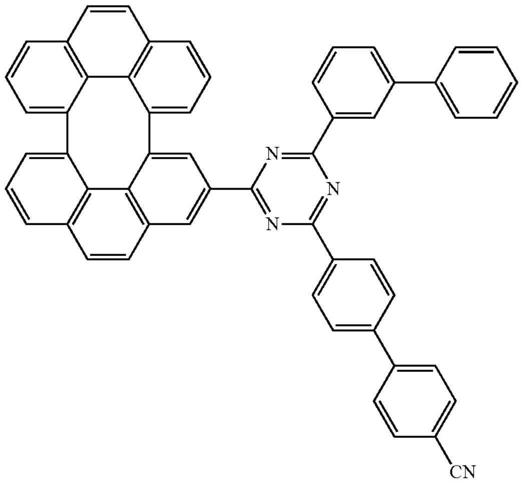

-continued
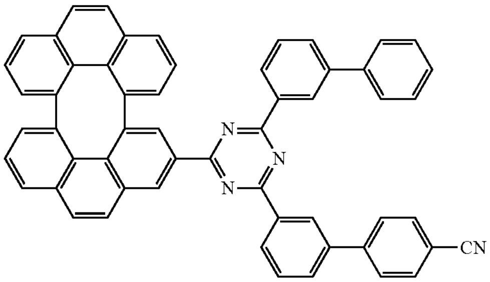
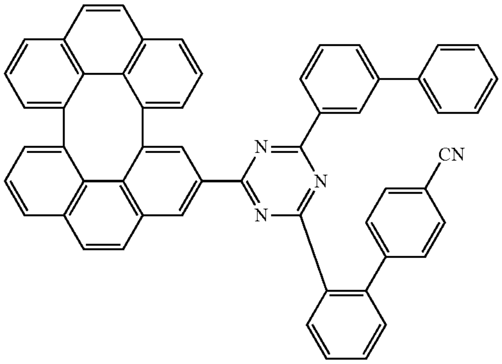
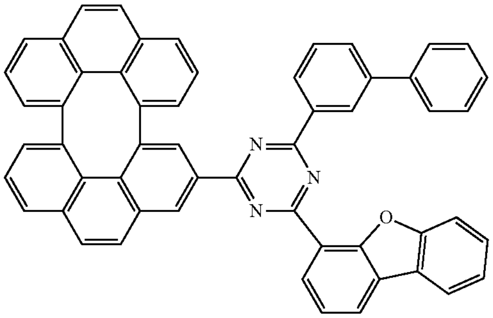
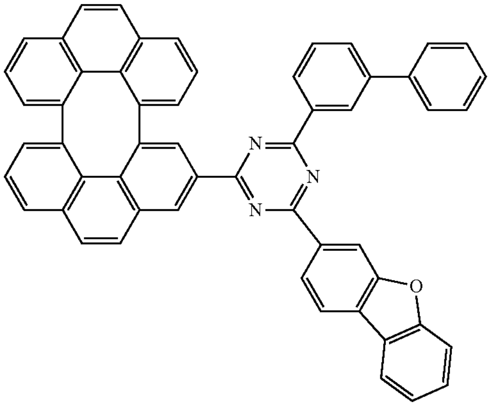

-continued
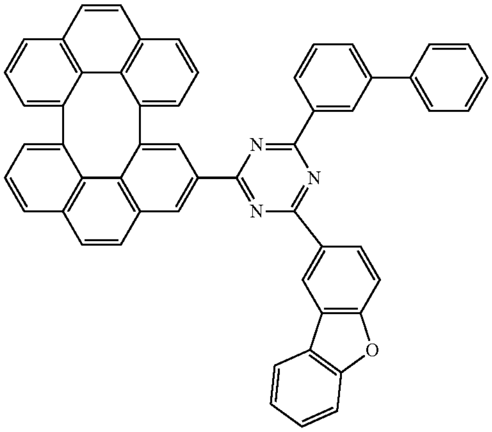
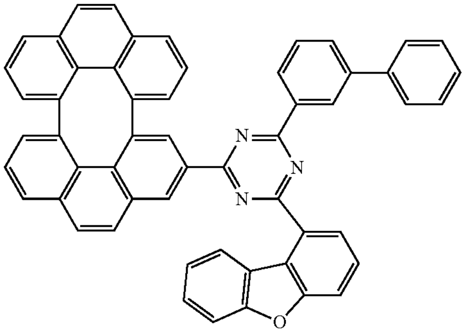
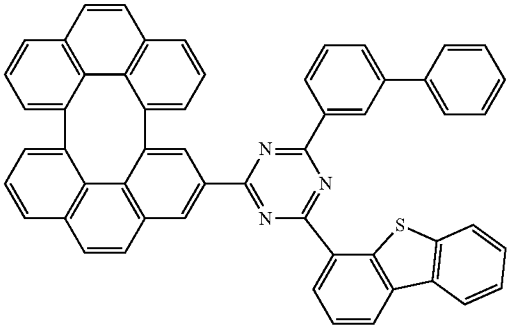
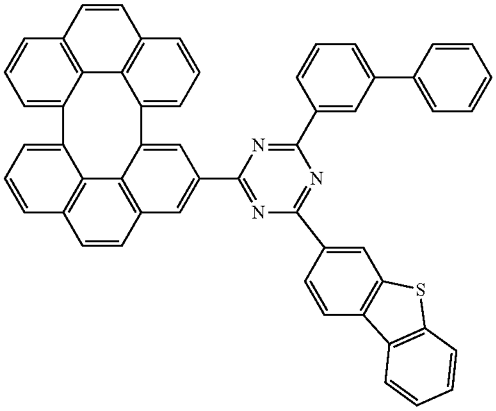

-continued
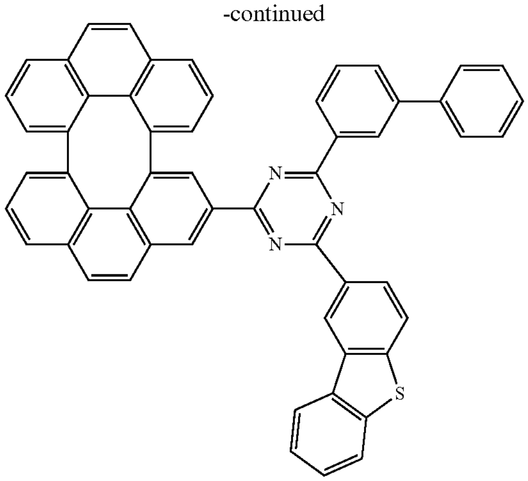
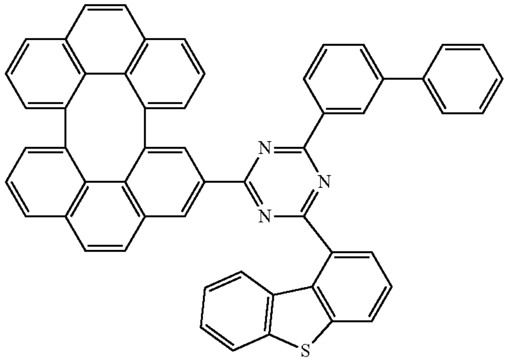
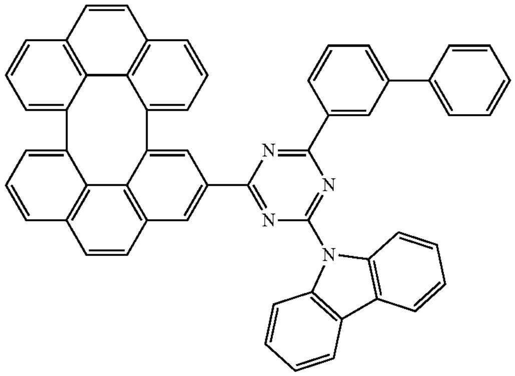
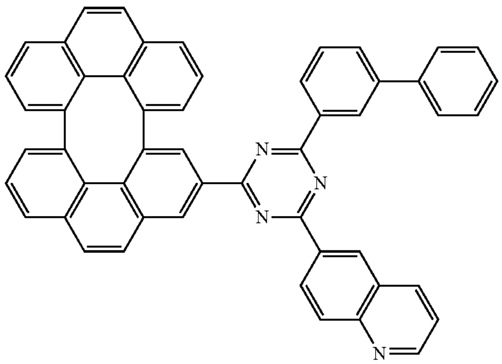

-continued
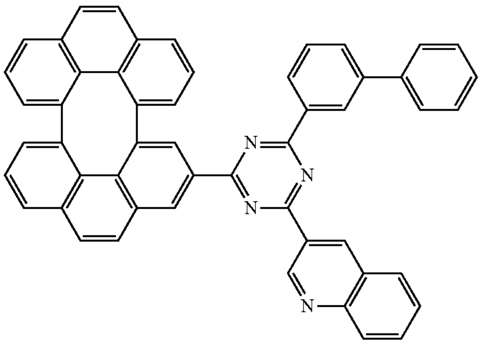
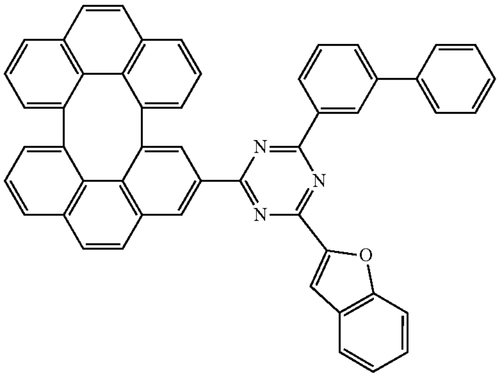
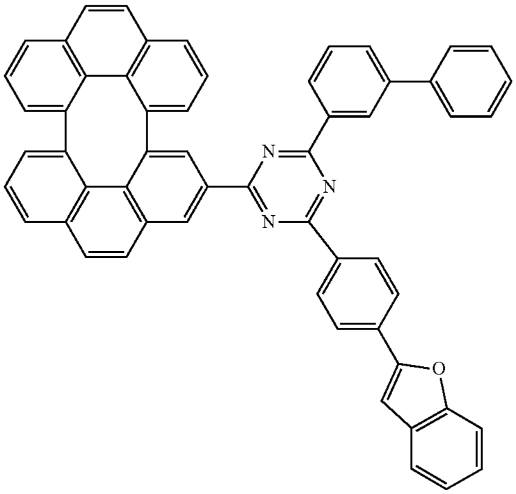
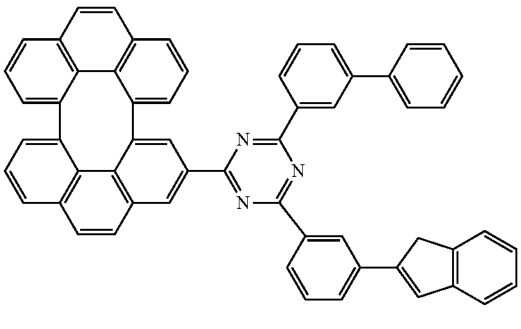

-continued
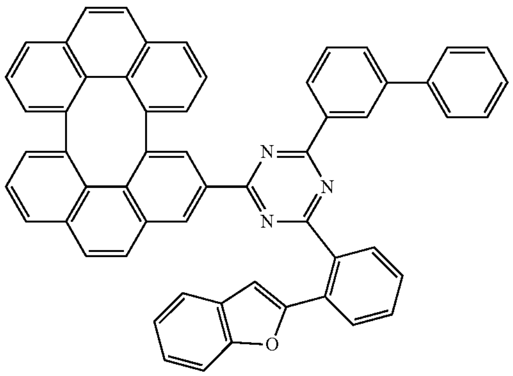
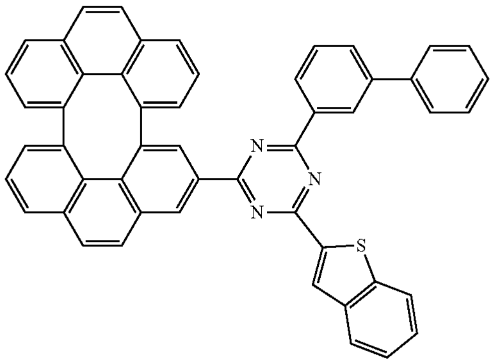
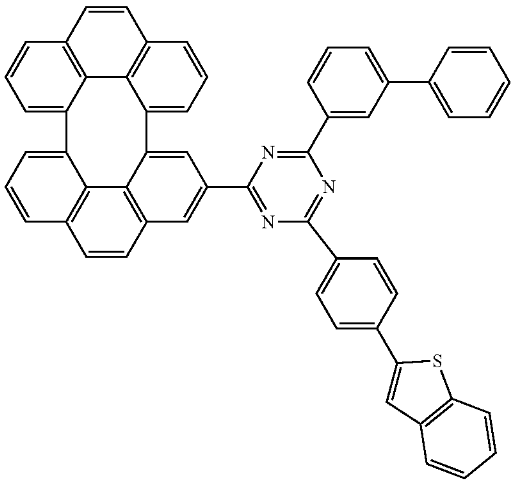
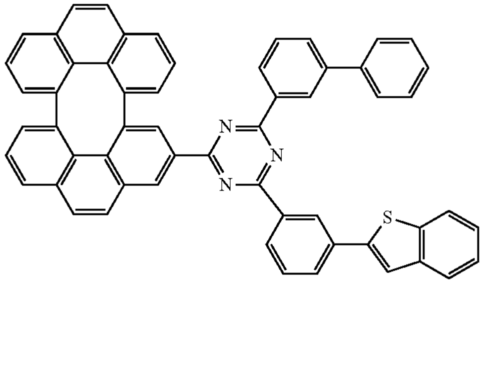

-continued
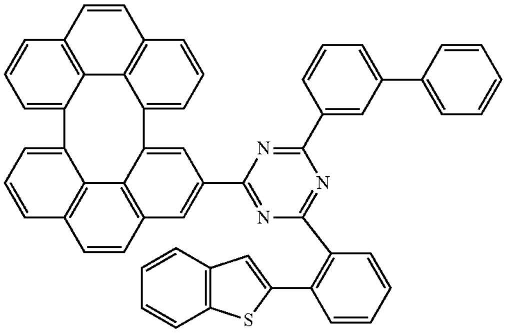
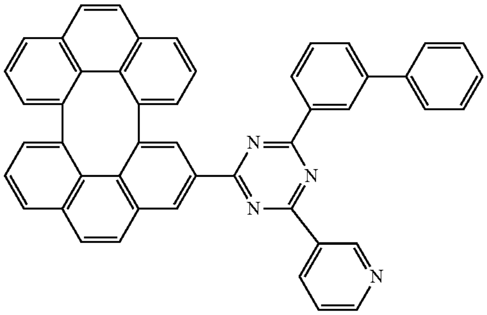
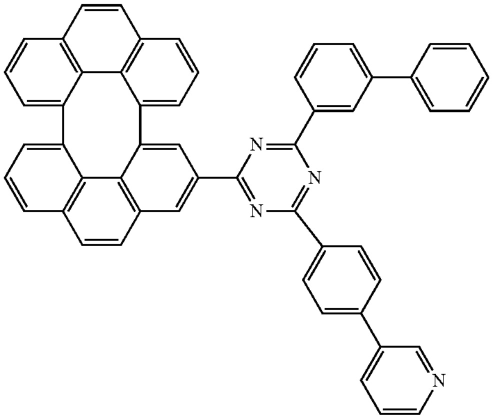
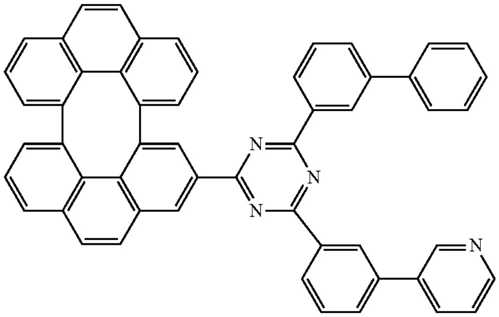
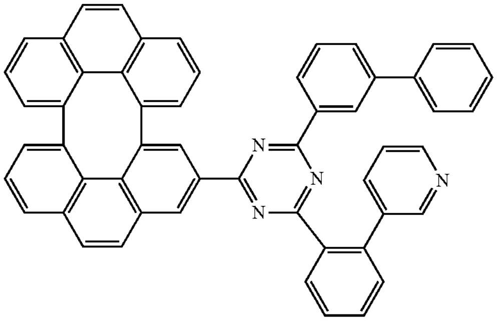

-continued
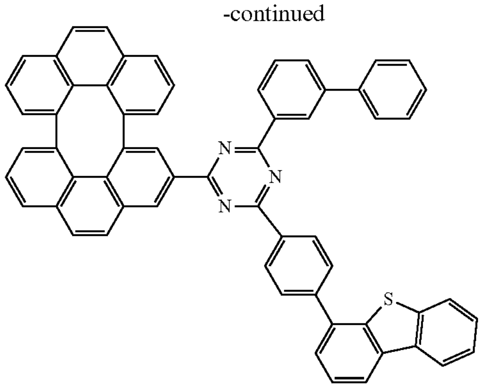
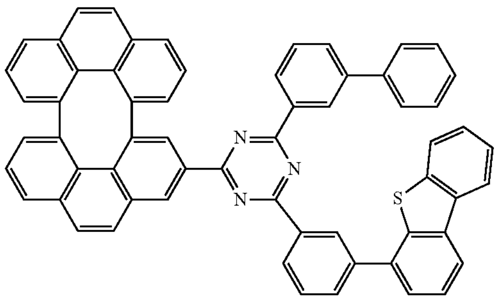
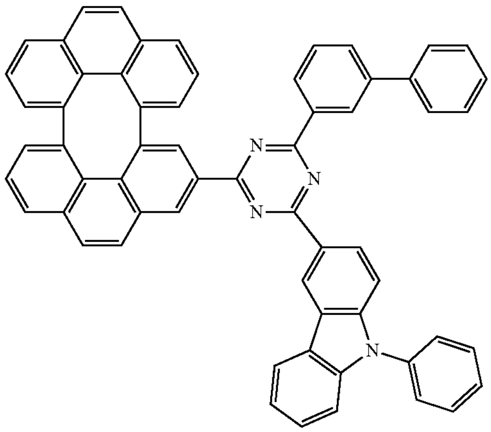
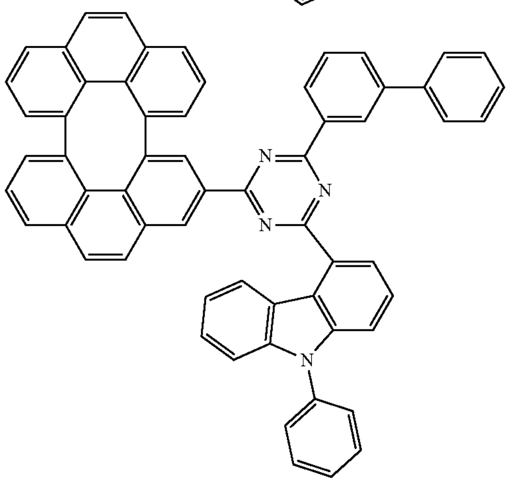

-continued
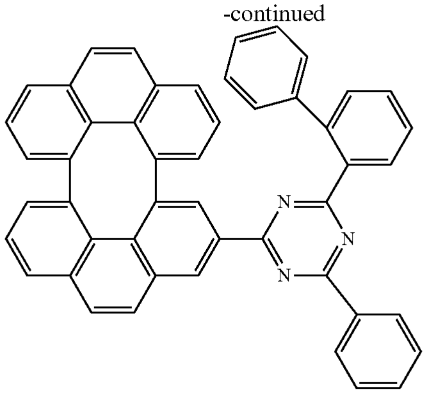
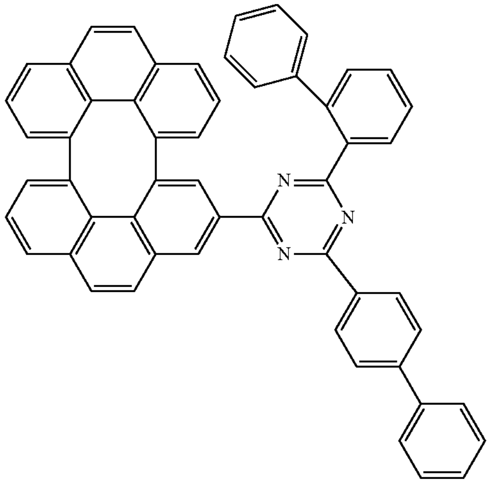
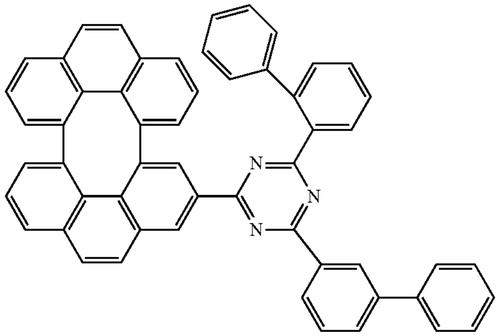
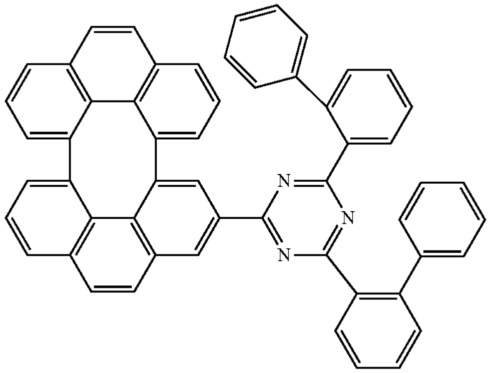

-continued
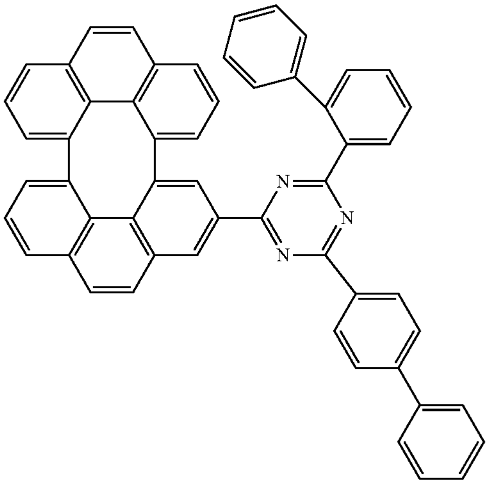
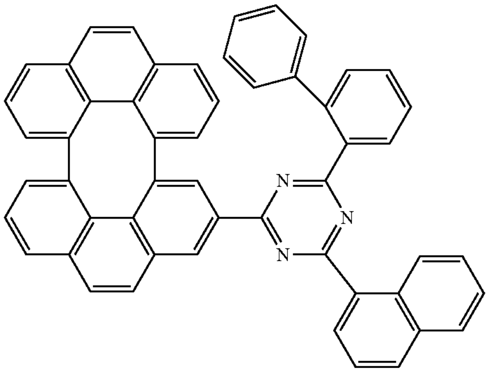
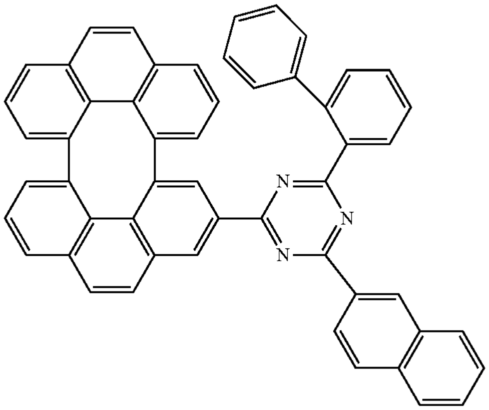
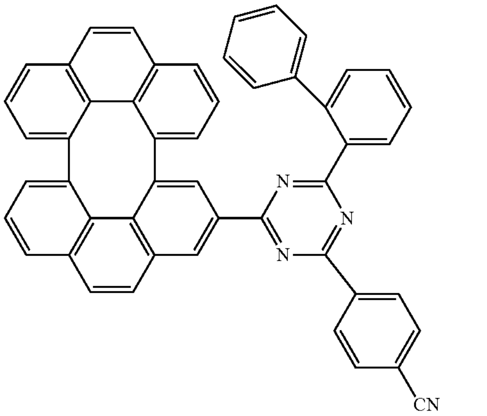

-continued
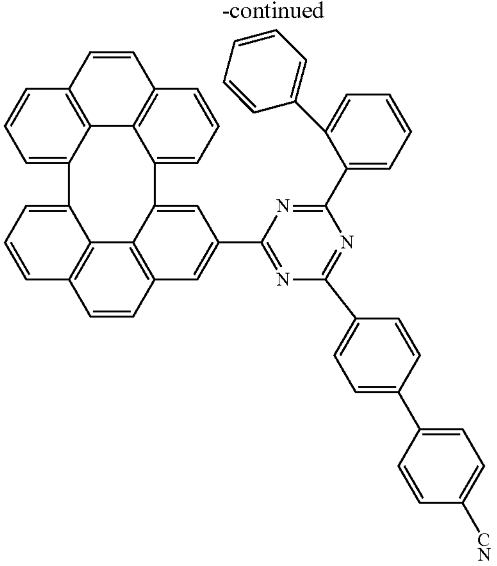
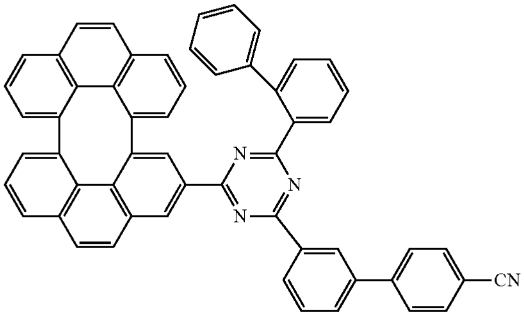
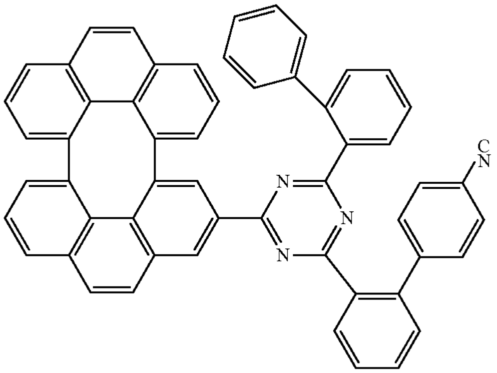
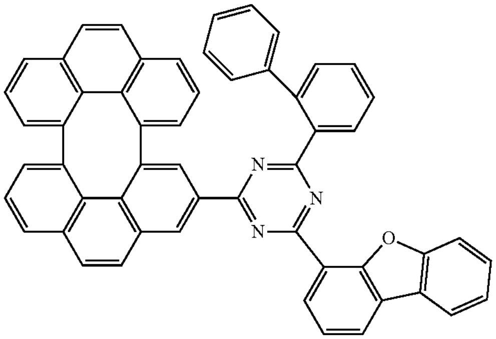

-continued
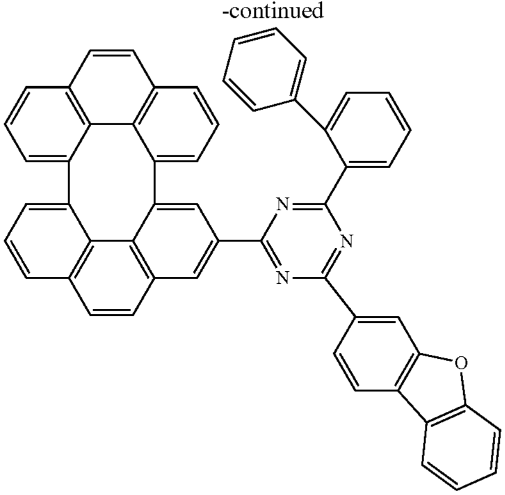
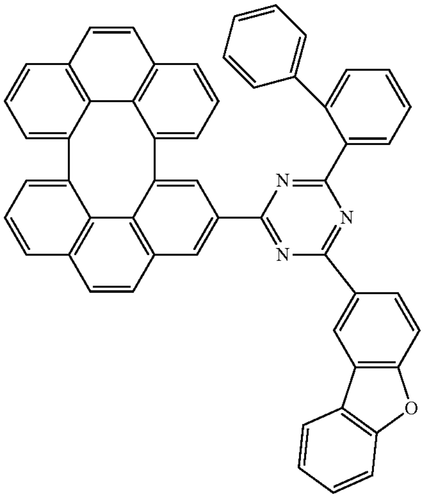
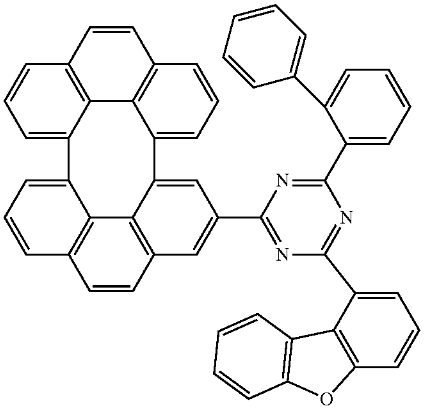
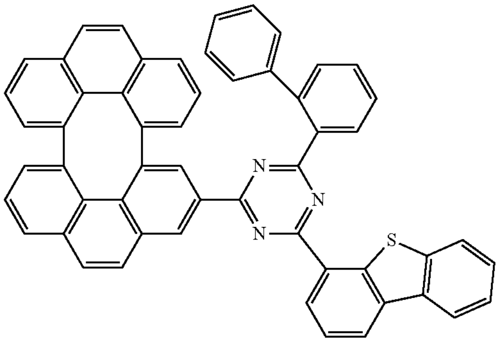

-continued
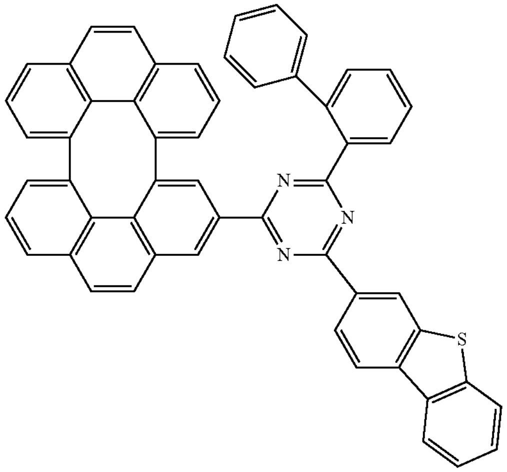
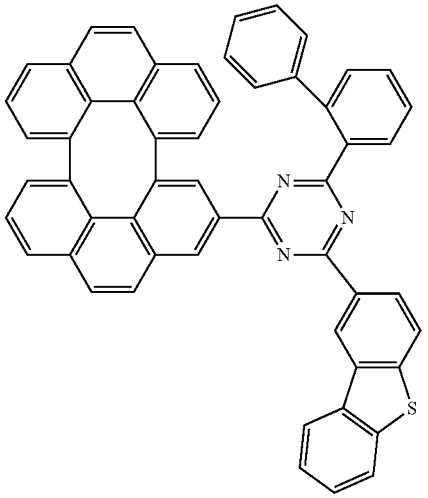
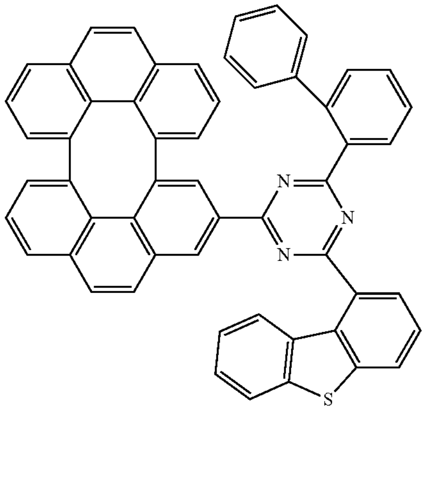

-continued
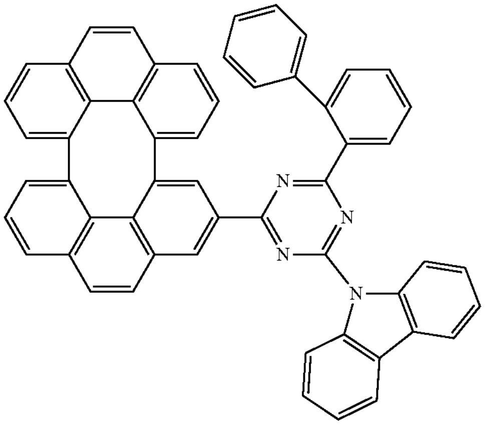
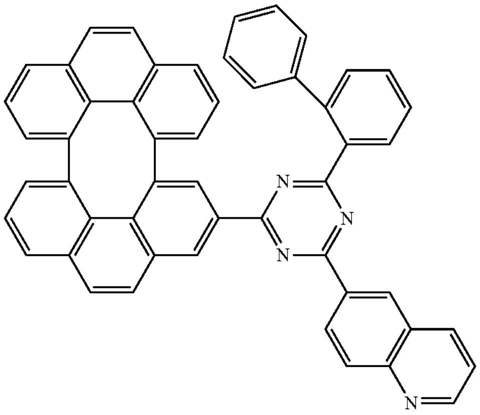
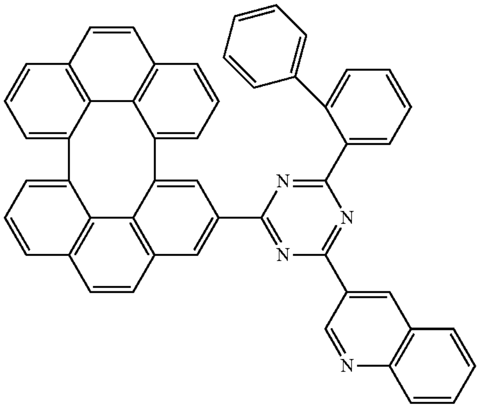
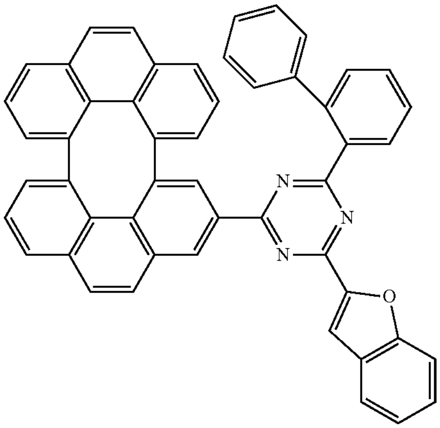

-continued
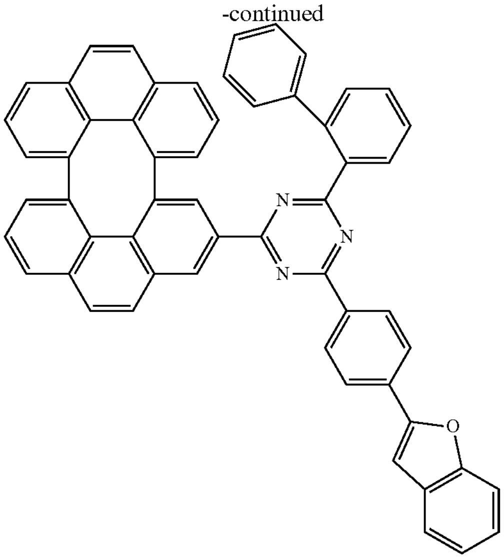
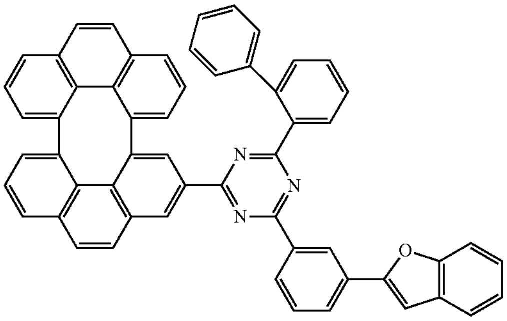
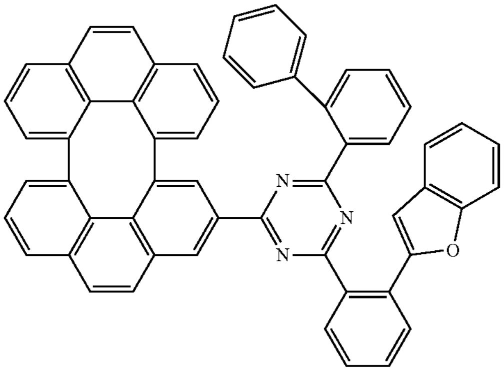
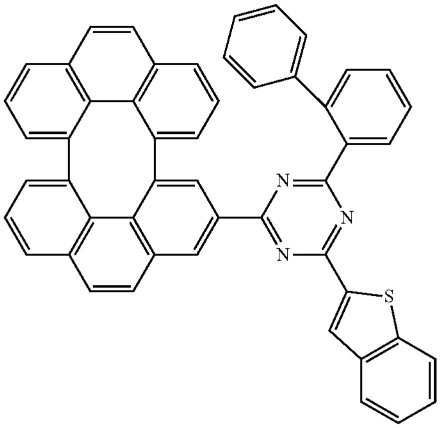

-continued
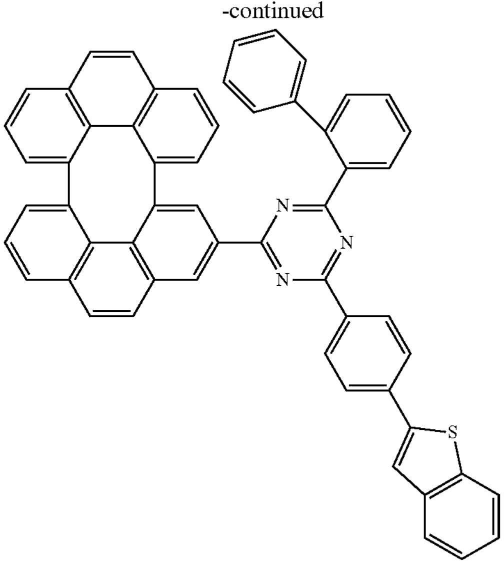
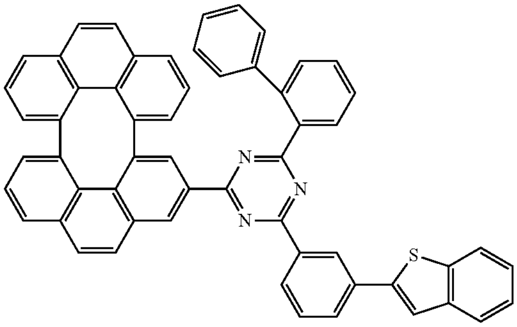
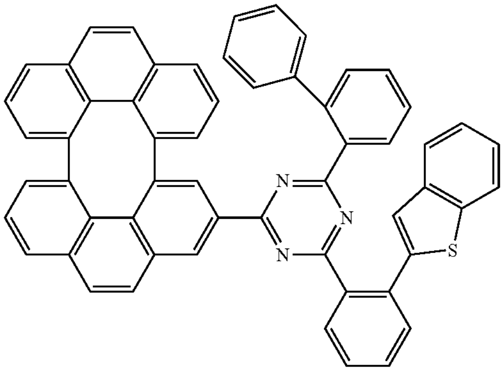
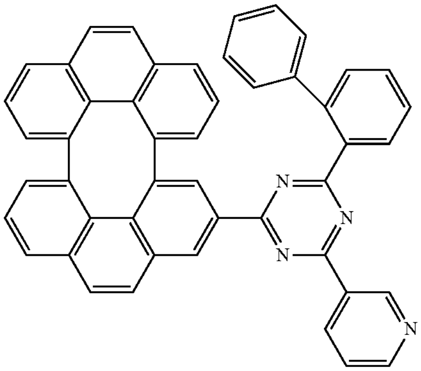

-continued
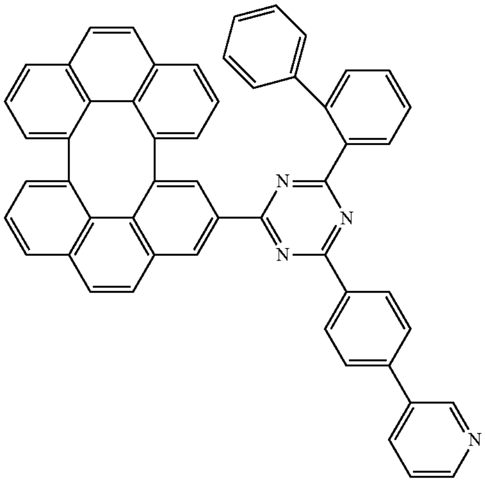
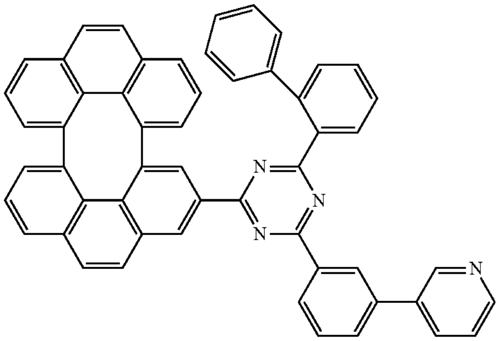
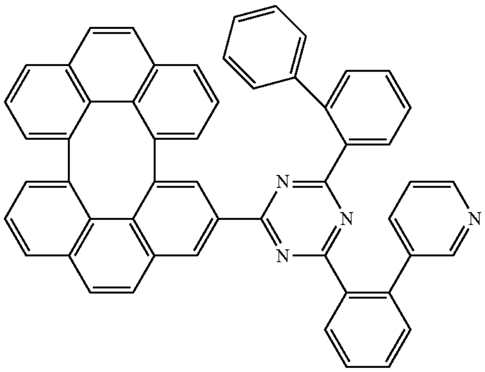
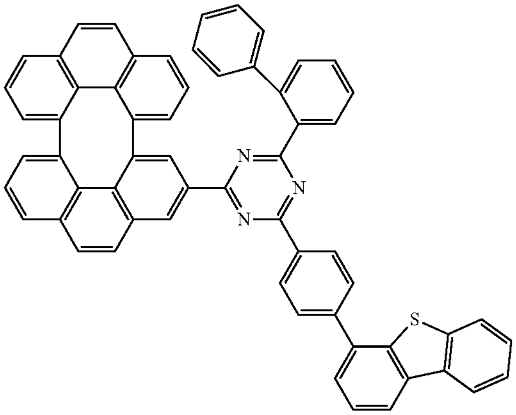

-continued
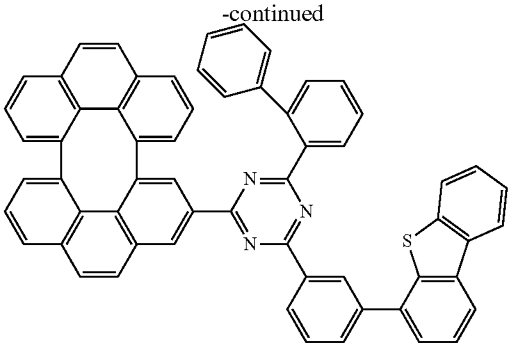
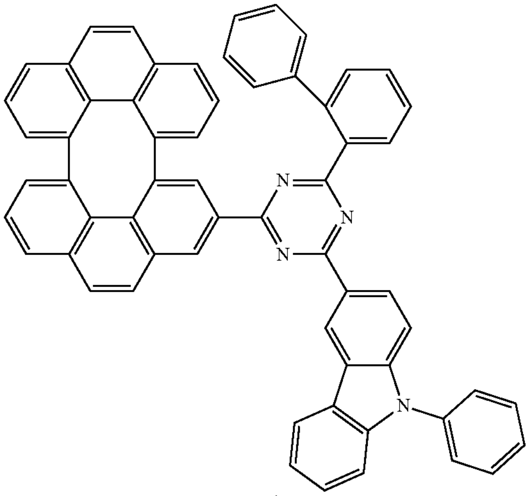
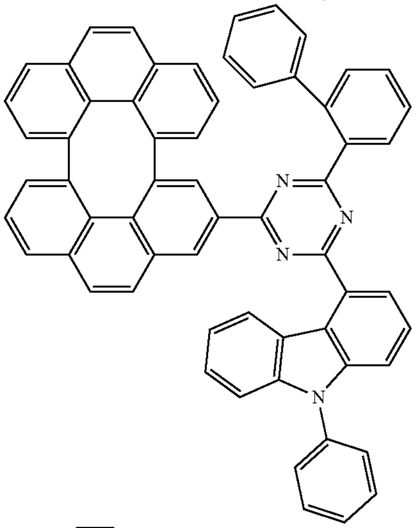
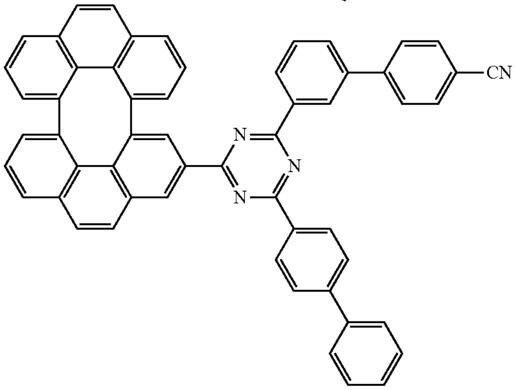

-continued
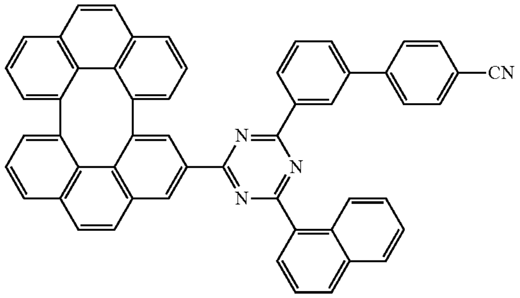
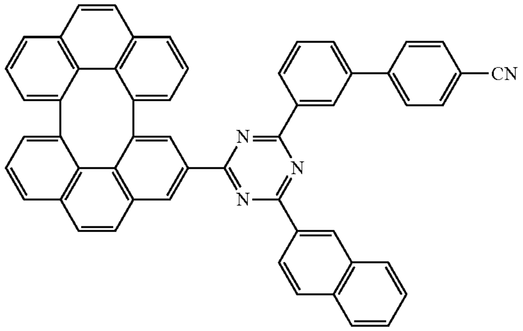
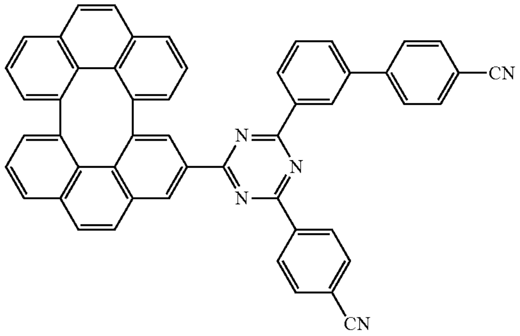
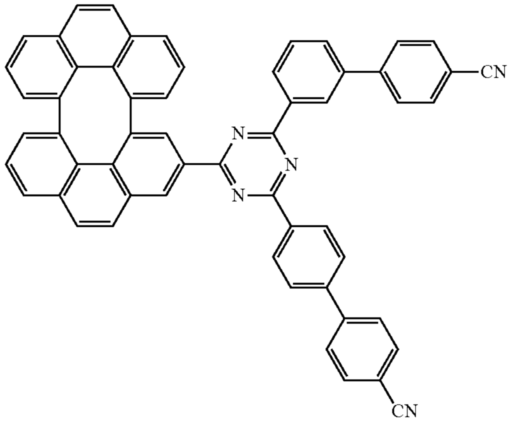
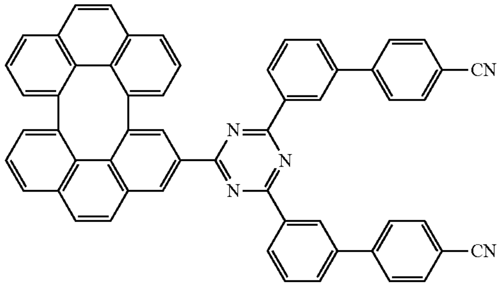

-continued
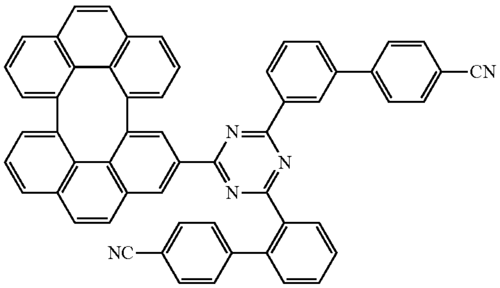
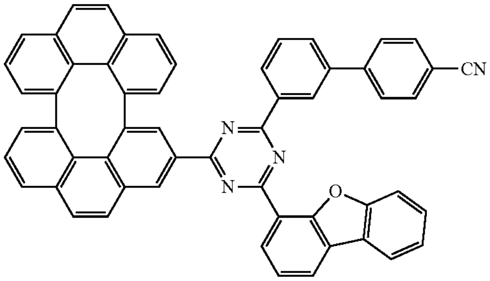
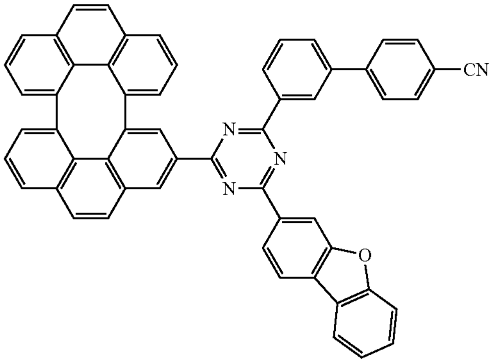
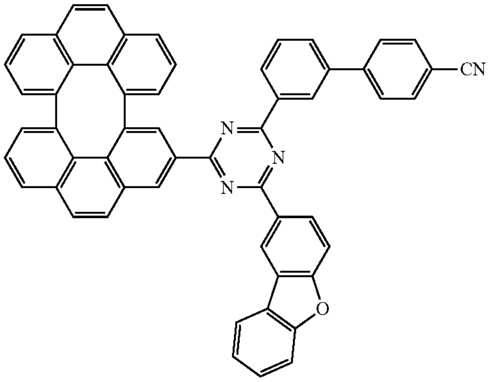
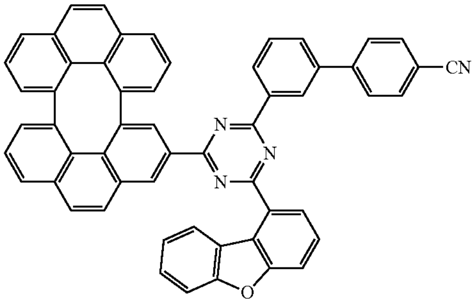

-continued
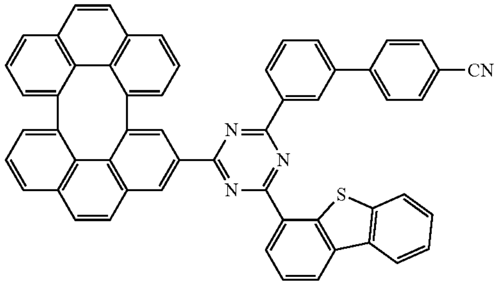
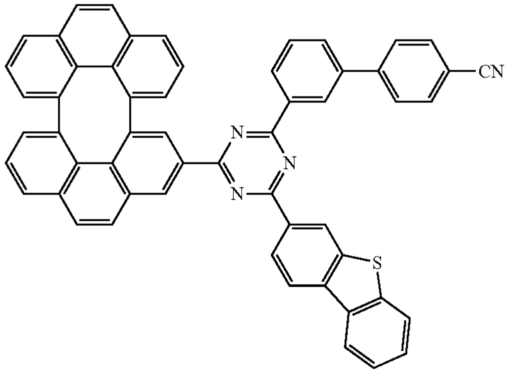
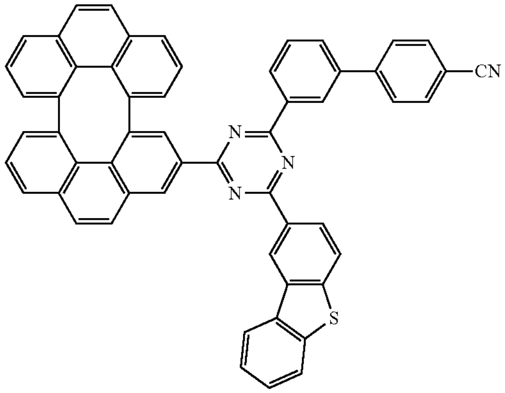
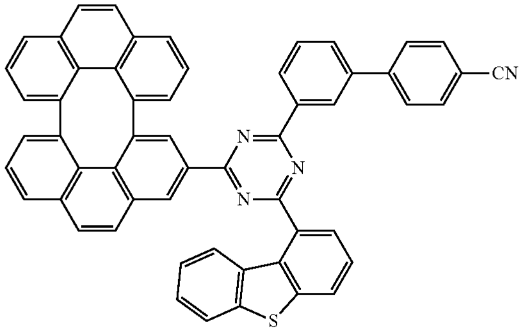
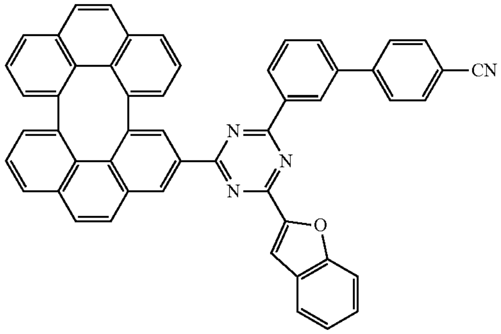

-continued
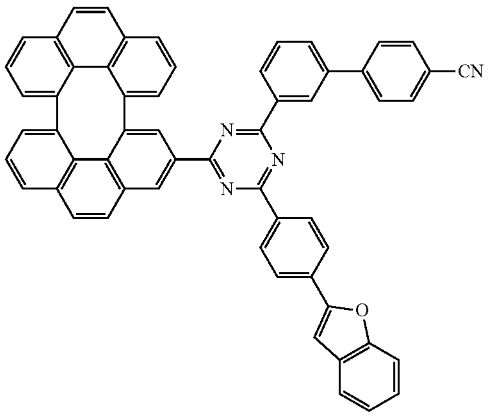
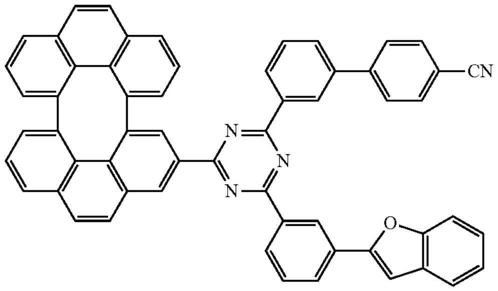
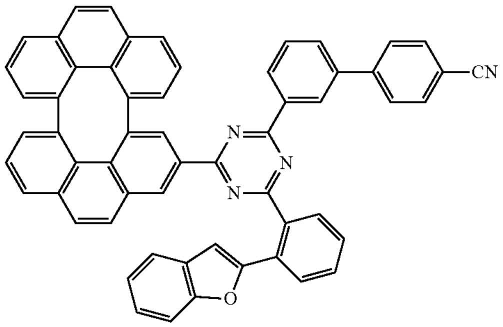
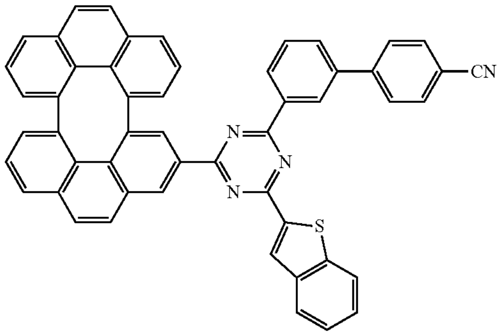

-continued
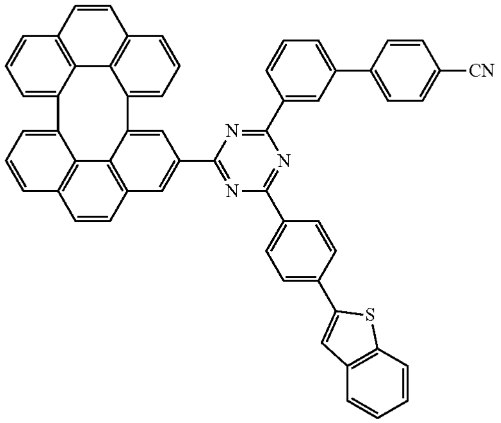
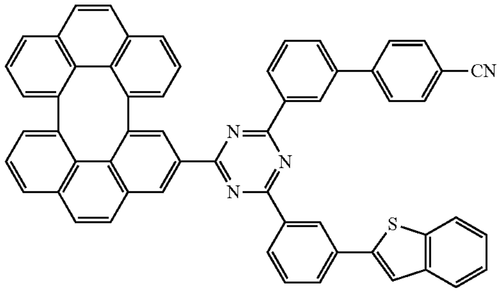
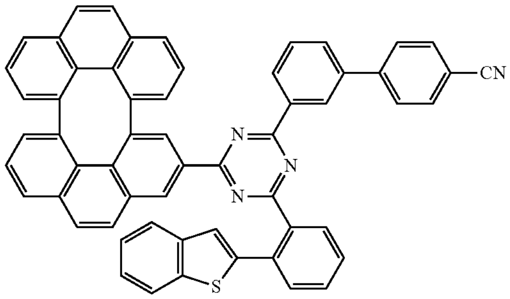
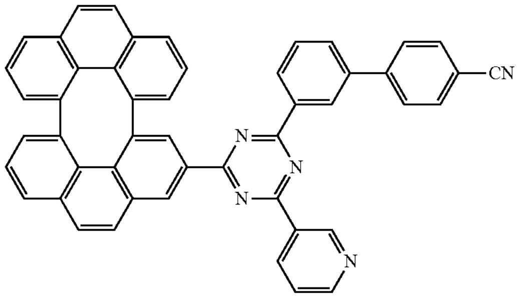
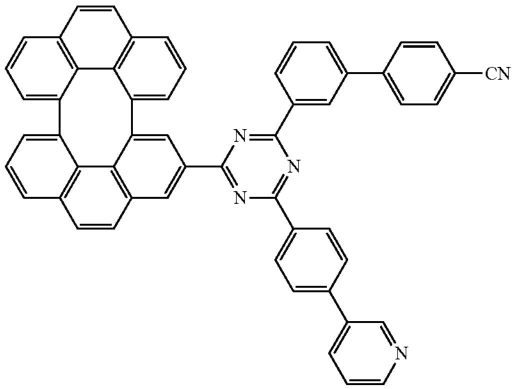

-continued
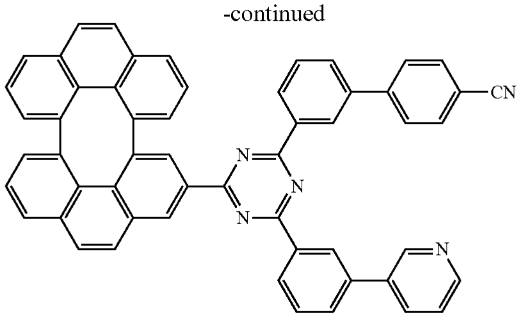
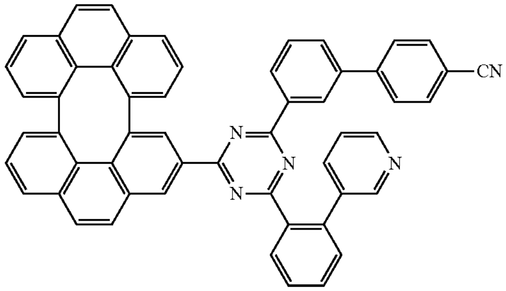
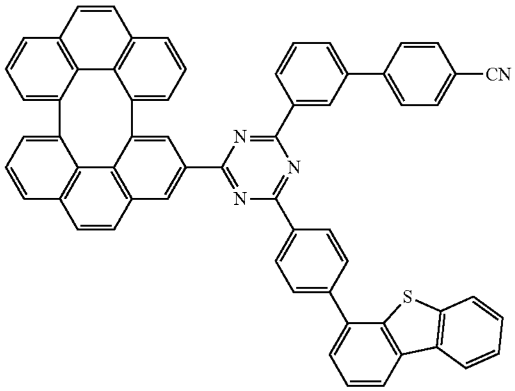
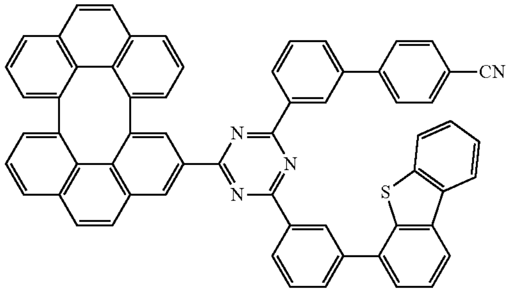
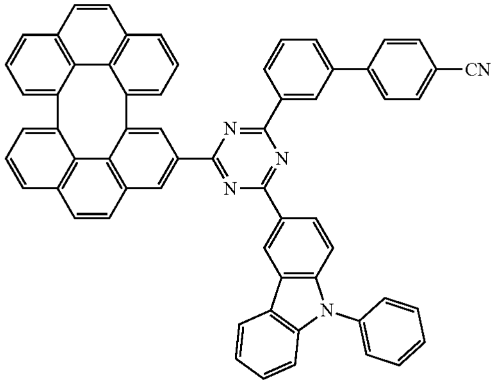

-continued
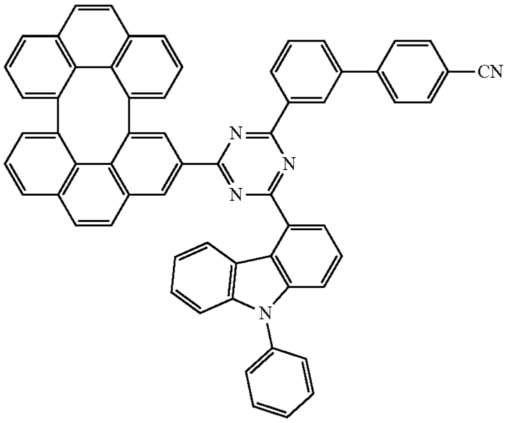
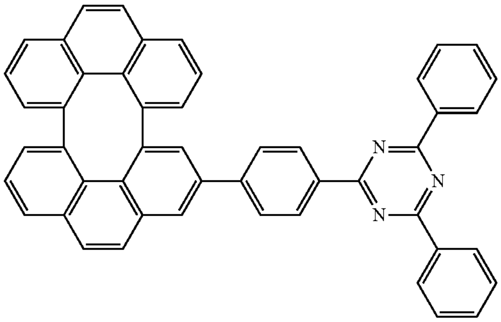
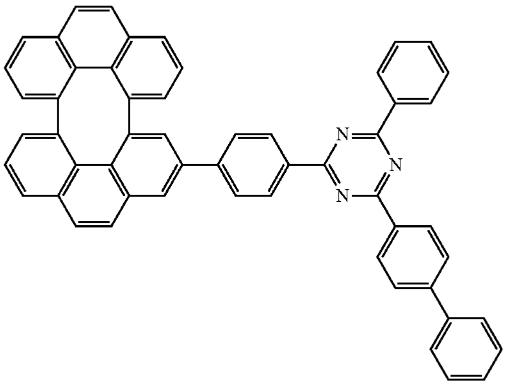
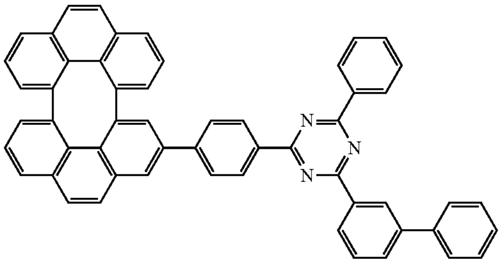
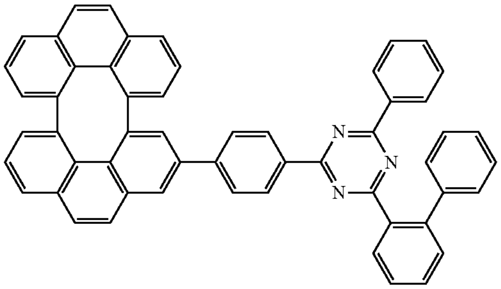

-continued
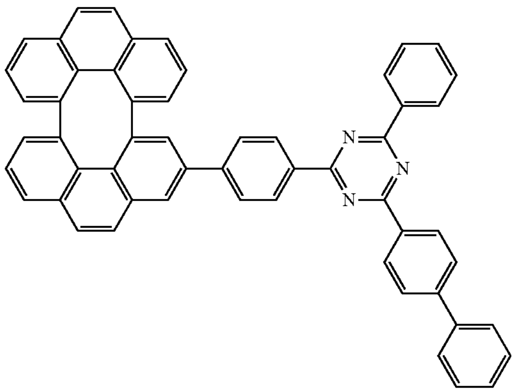
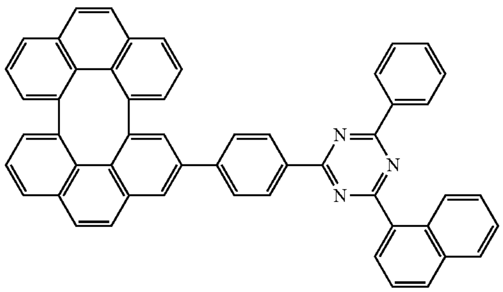
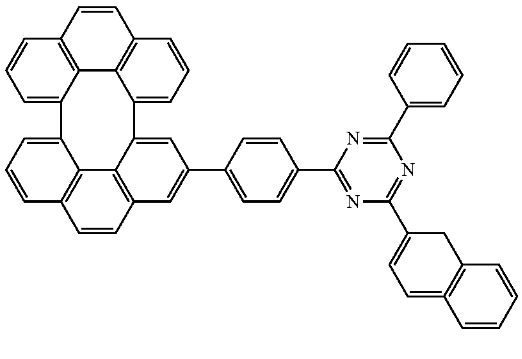
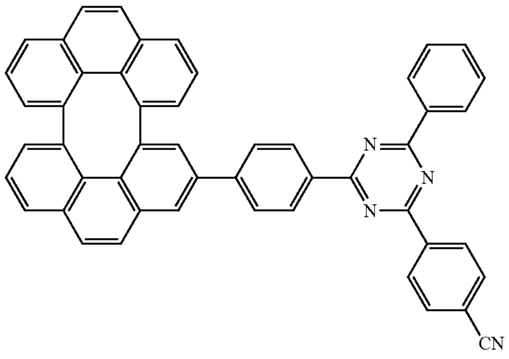

-continued
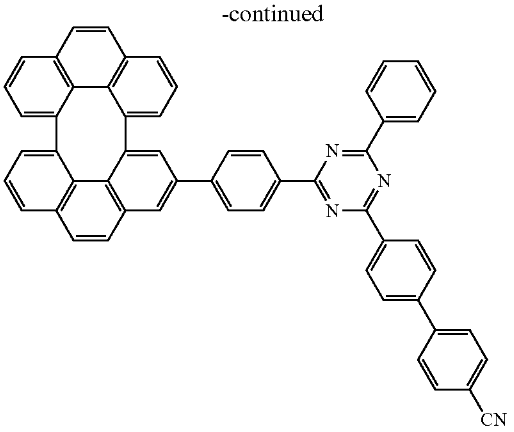
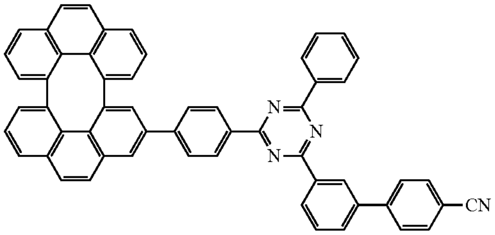
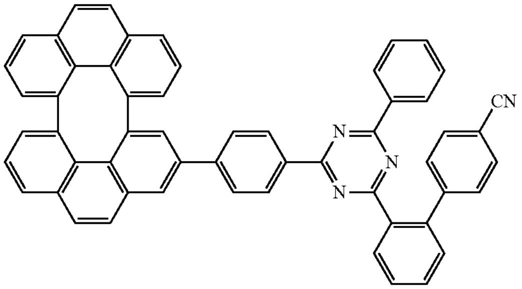
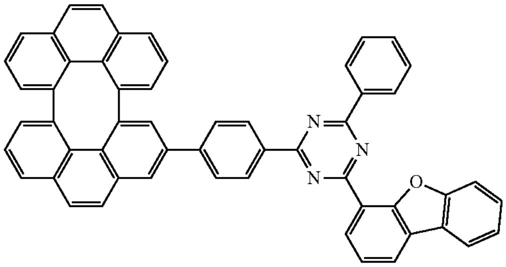
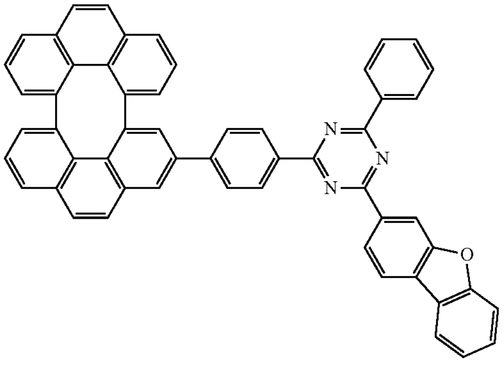

-continued
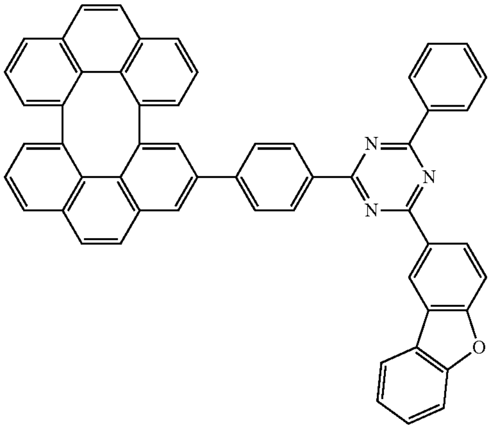
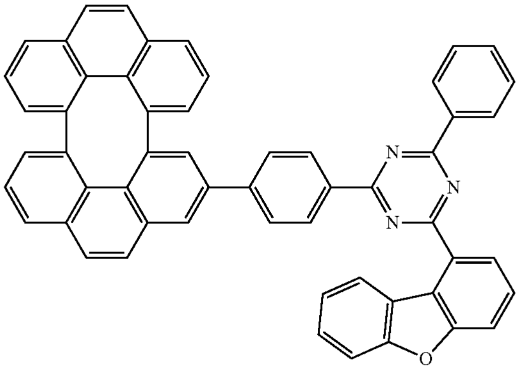
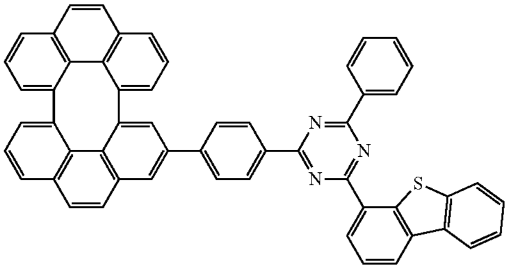
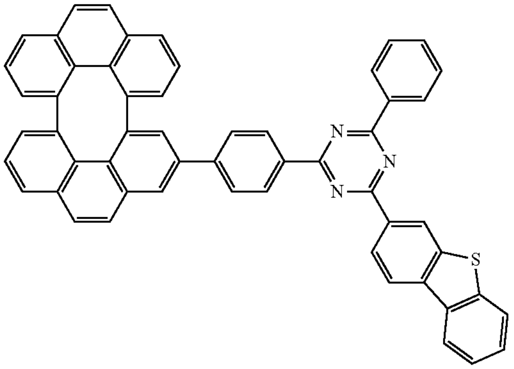

-continued
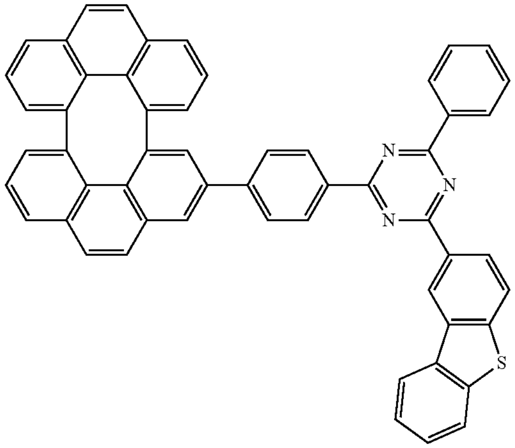
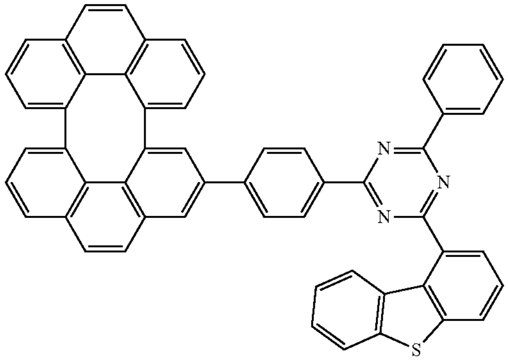
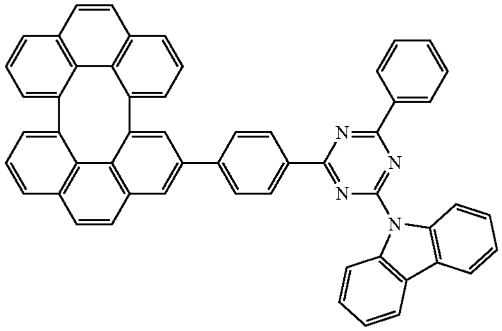
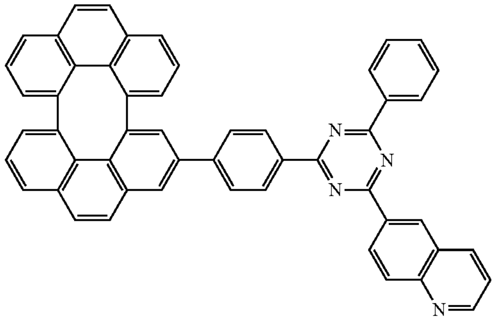

-continued
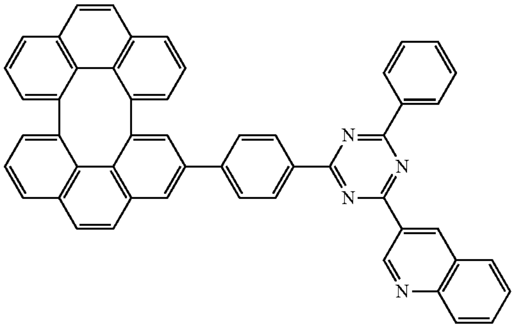
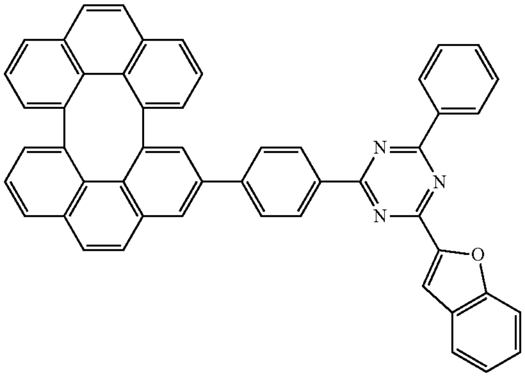
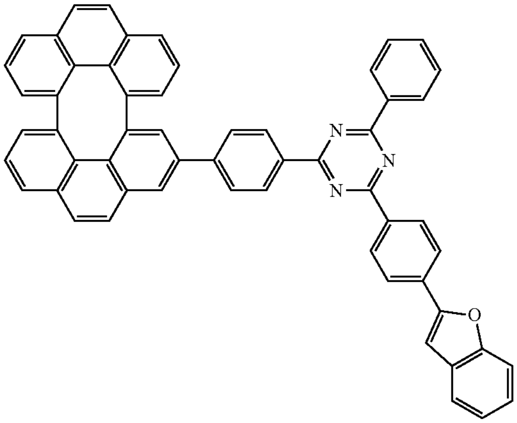
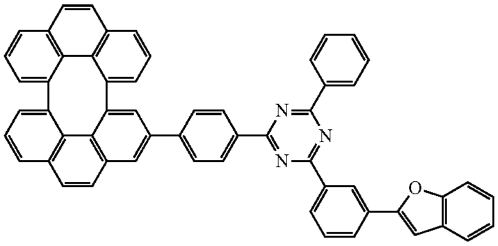
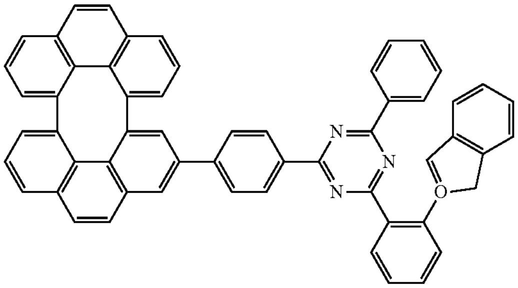

-continued
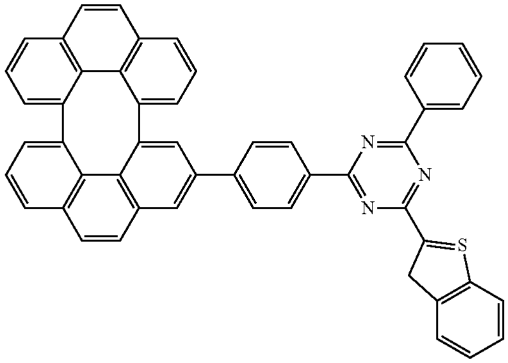
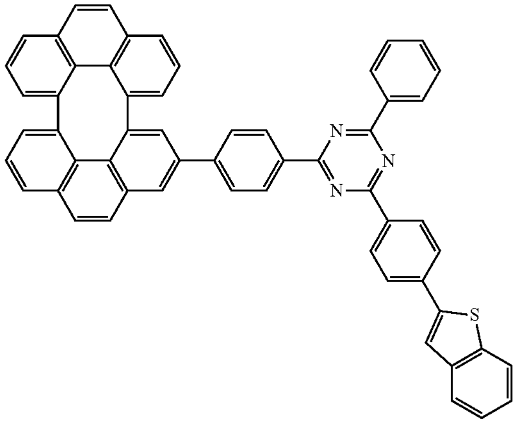
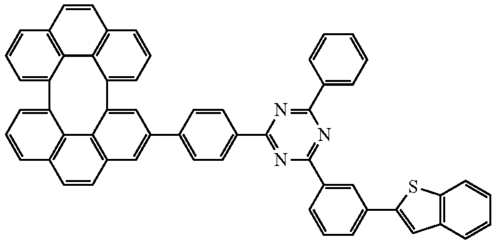
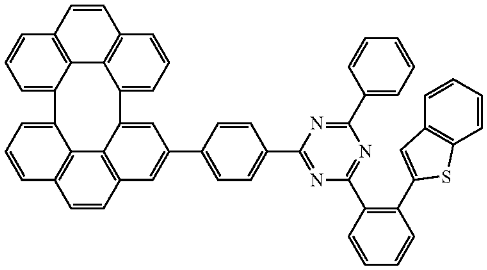
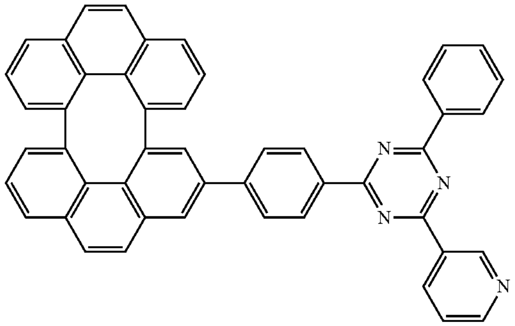

-continued
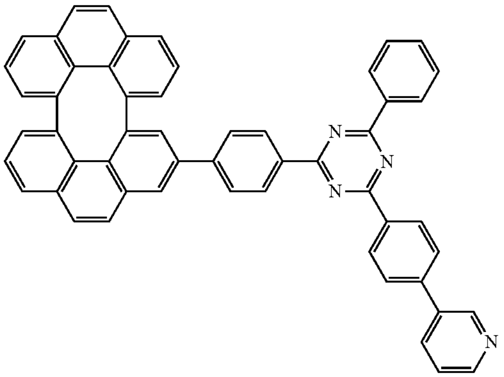
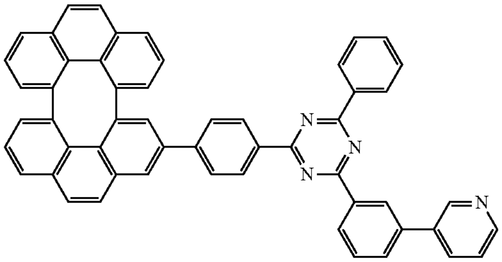
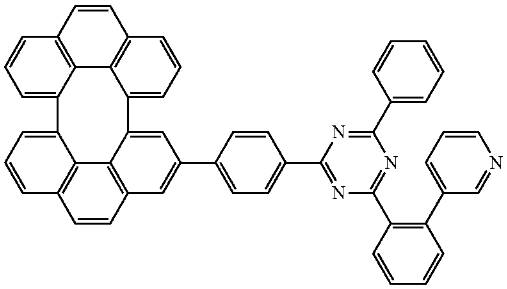
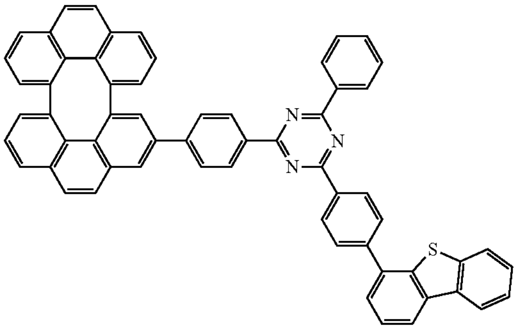
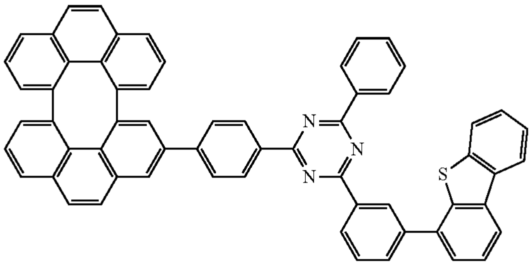

-continued
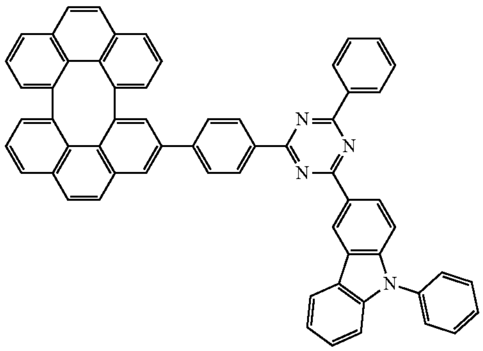
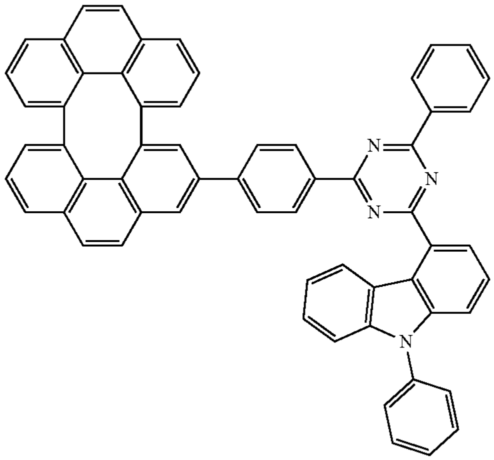
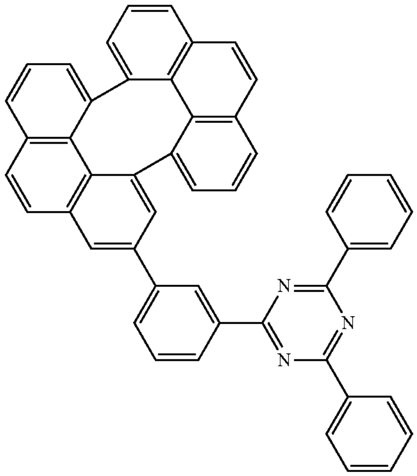

-continued
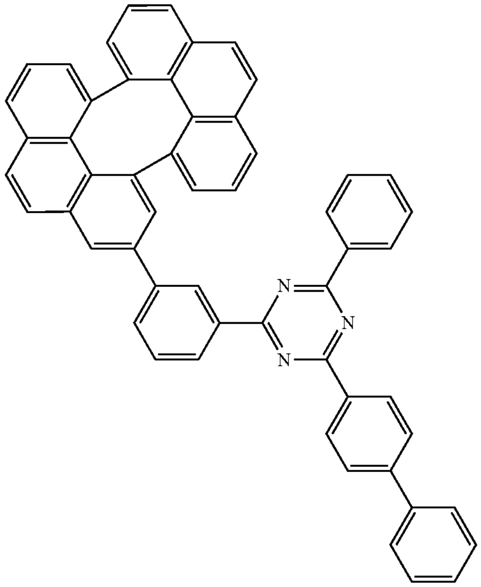
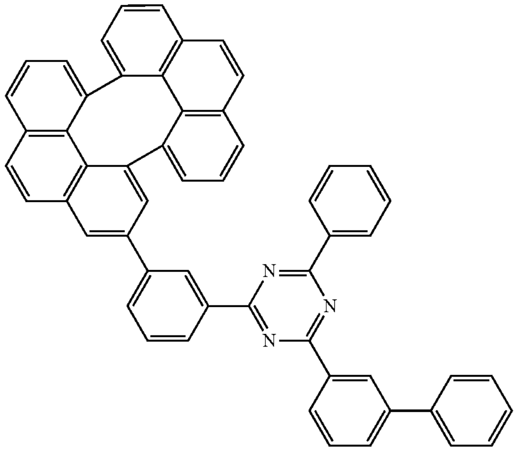
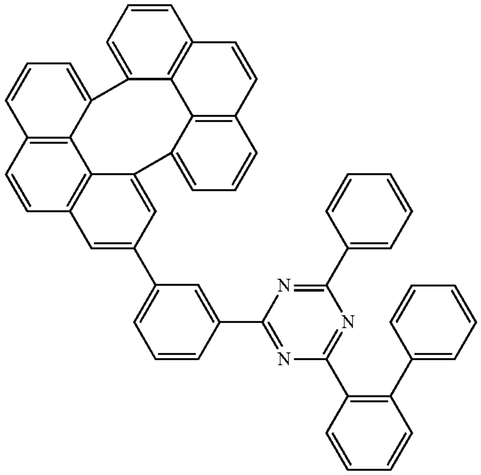

-continued
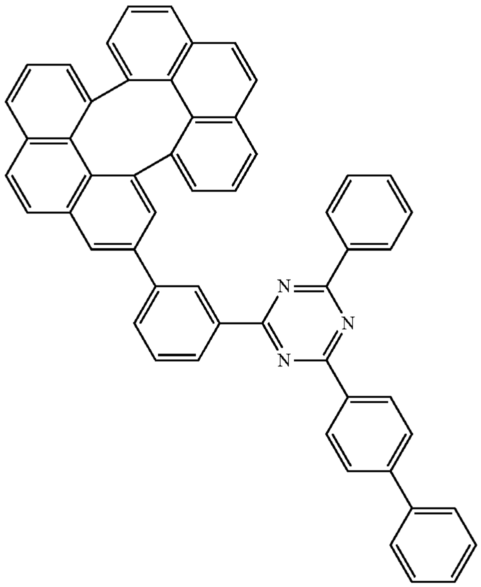
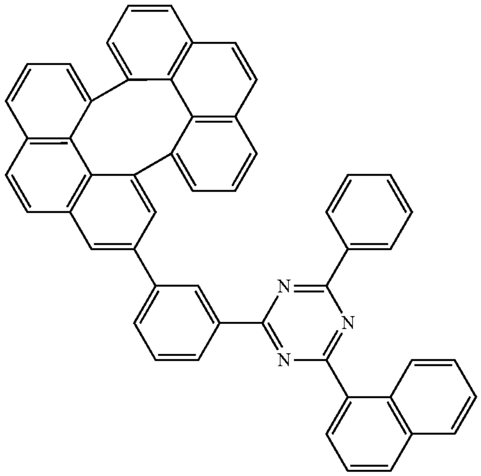
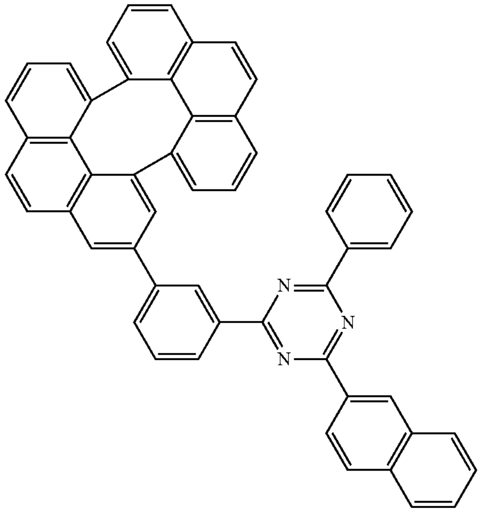

-continued
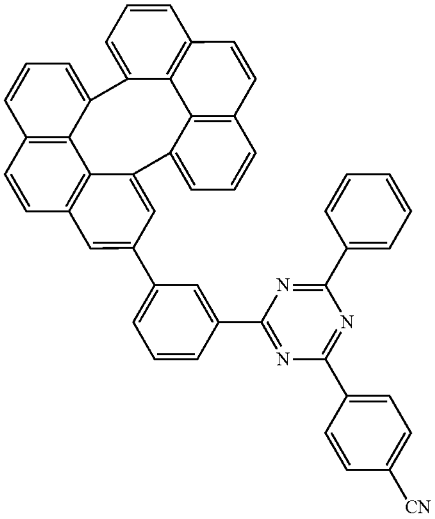
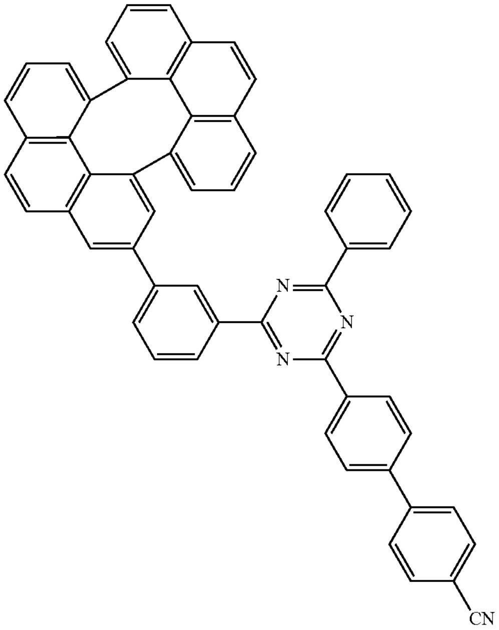
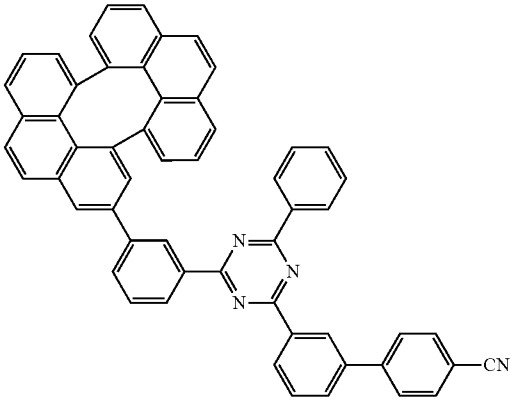

-continued
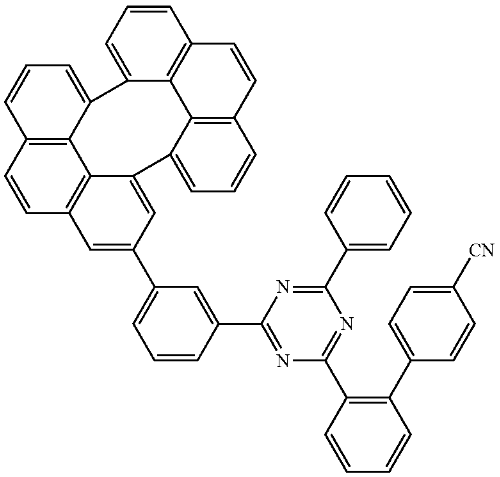
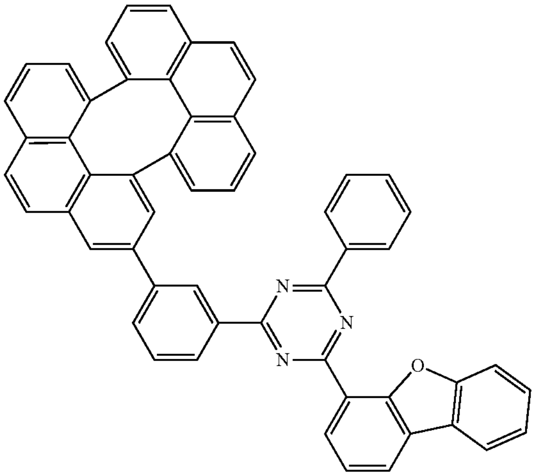
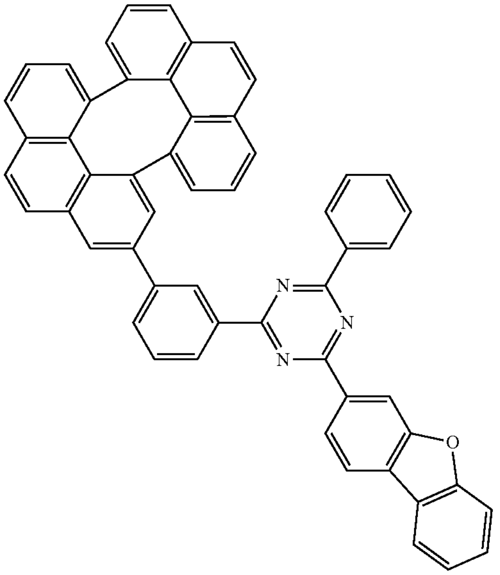

-continued
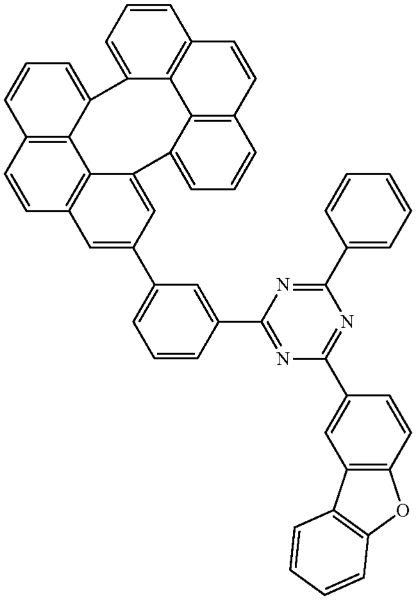
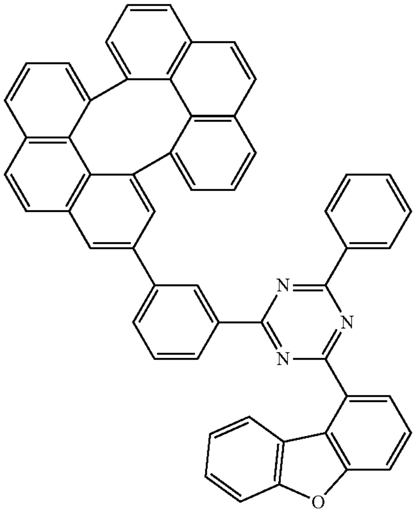
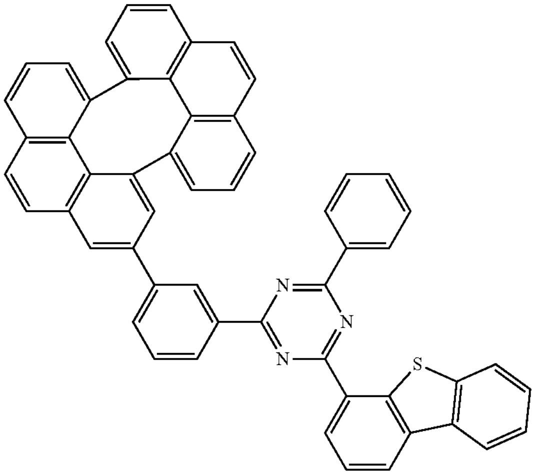

-continued
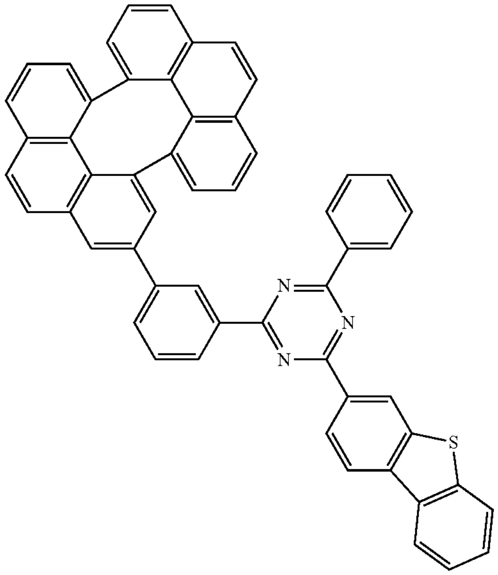
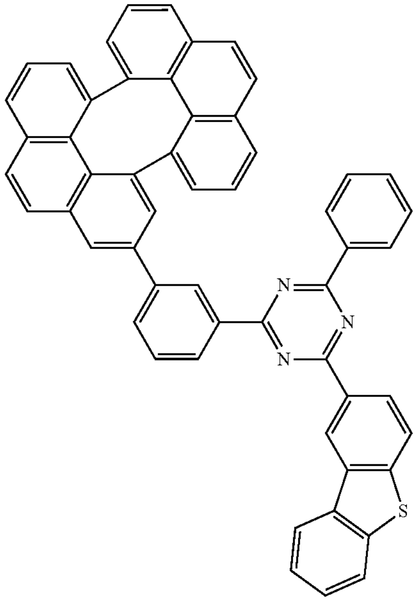
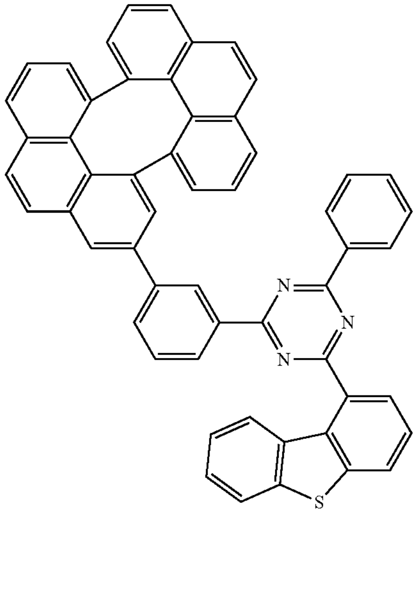

-continued
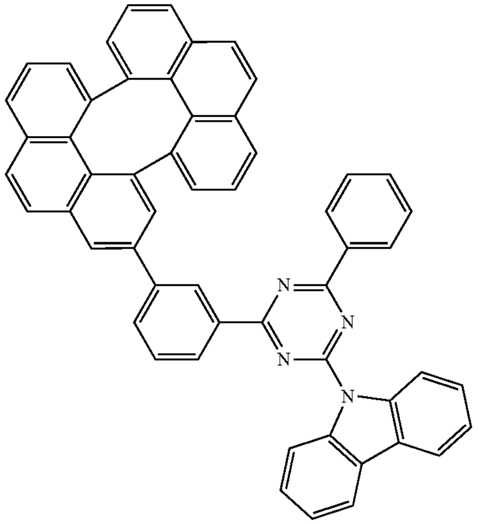
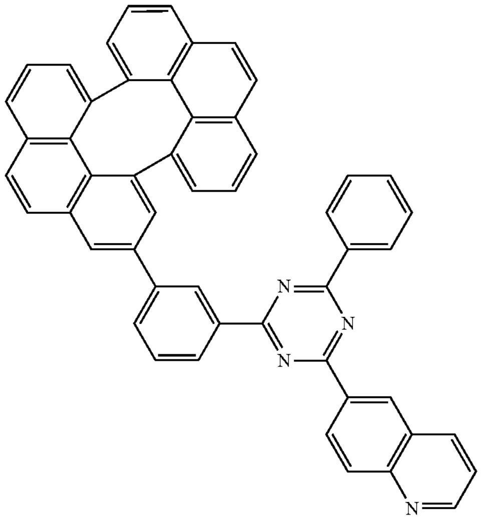
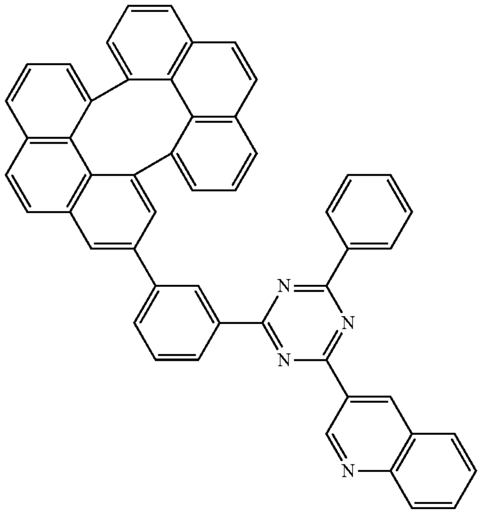

-continued
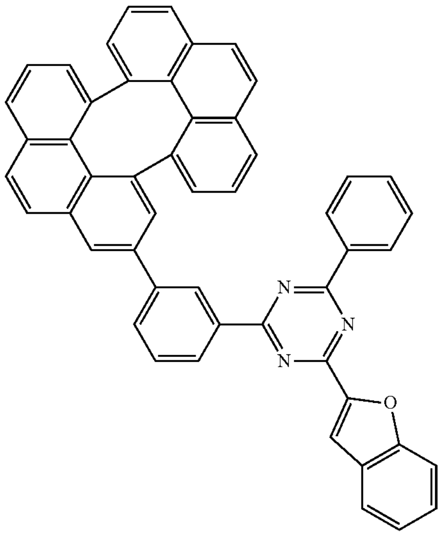
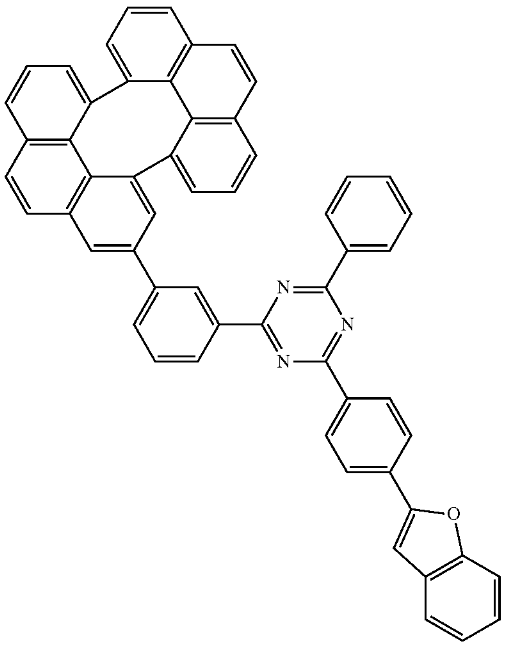
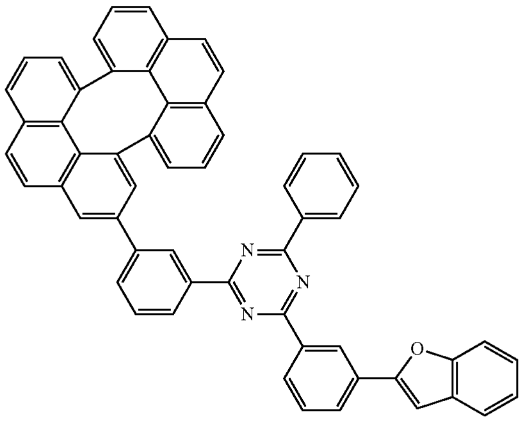

-continued
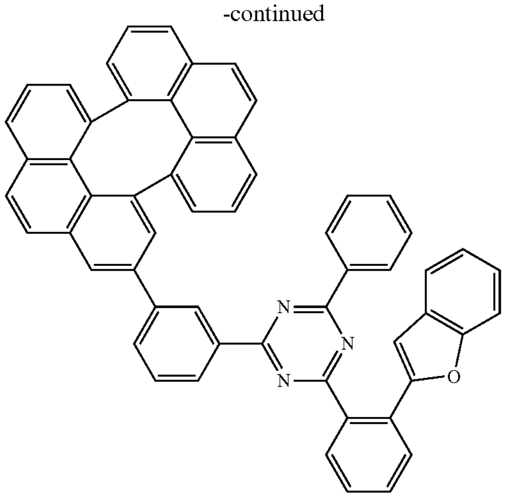
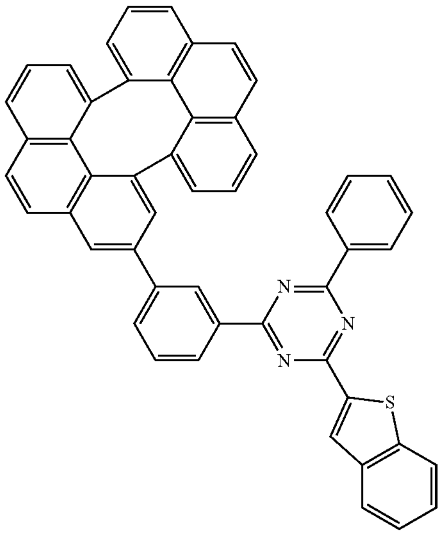
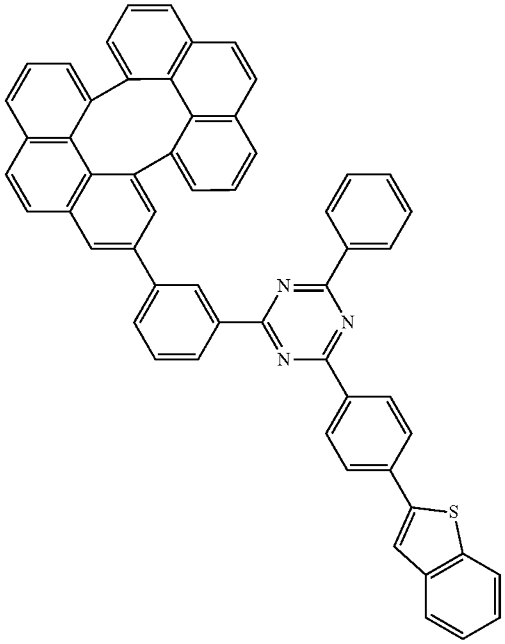

-continued
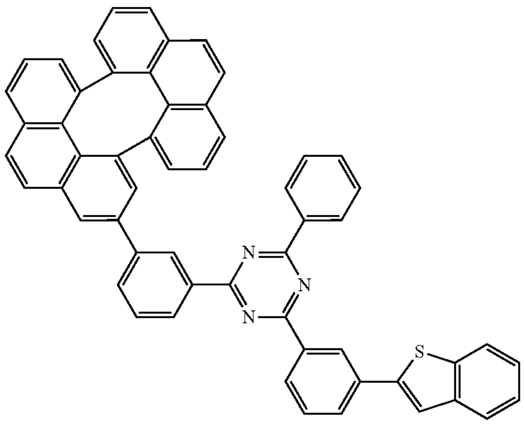
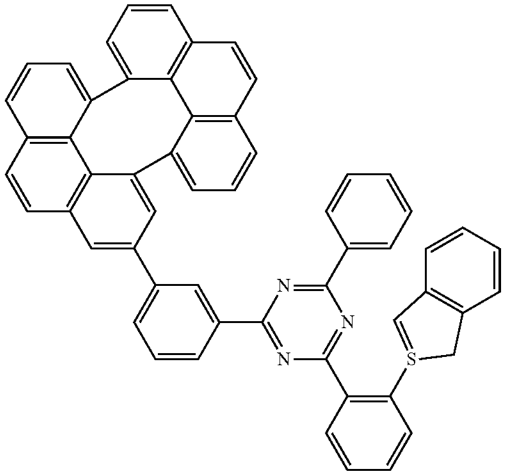
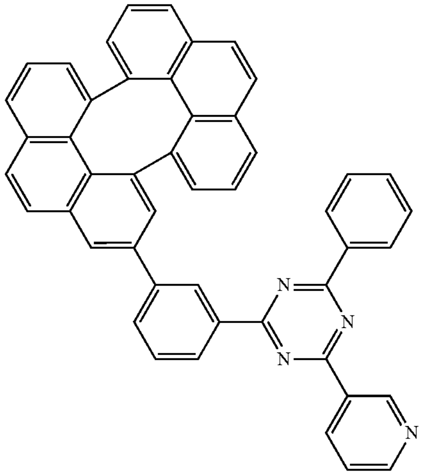

-continued
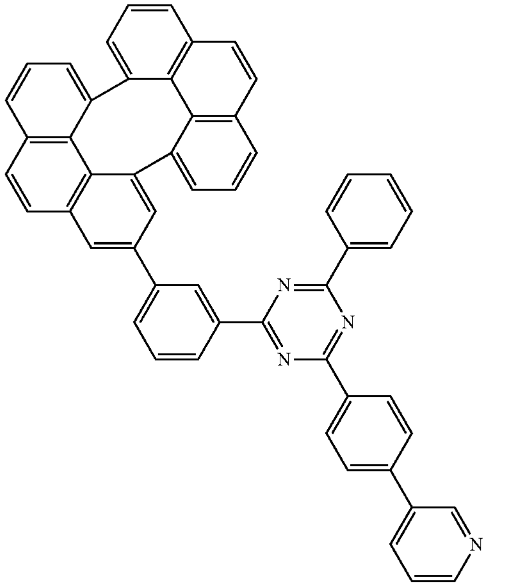
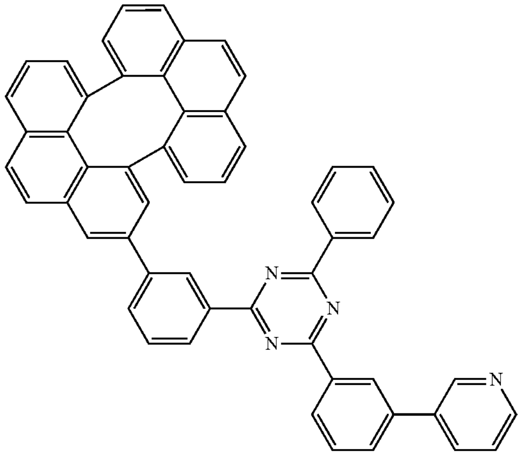
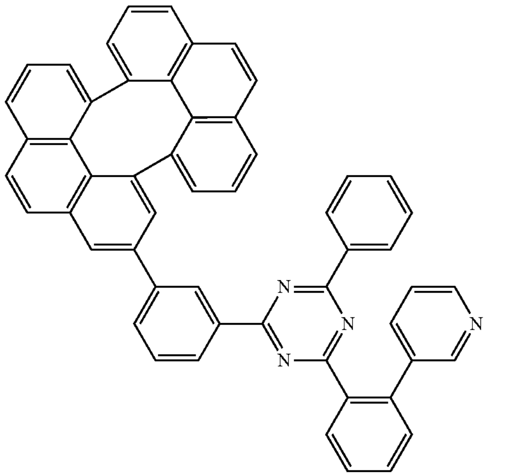

-continued
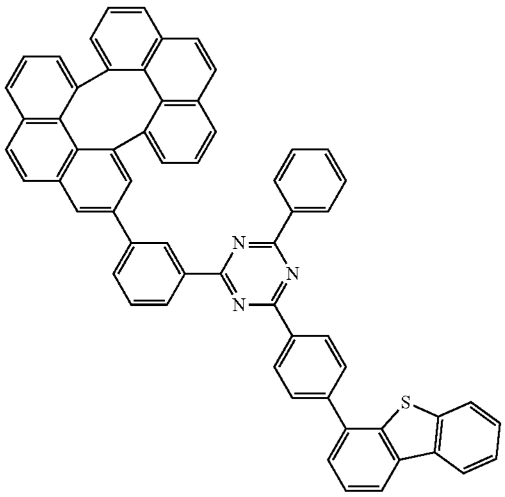
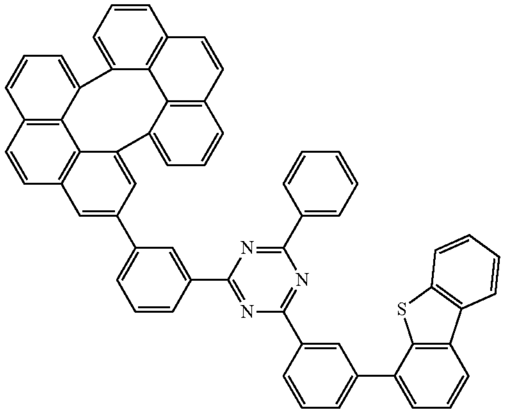
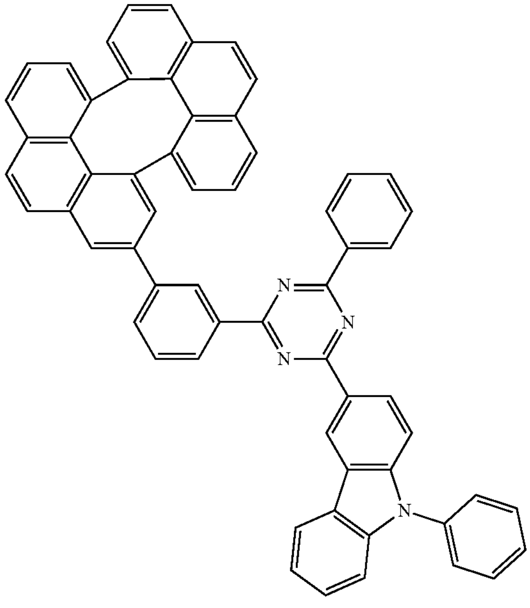

-continued
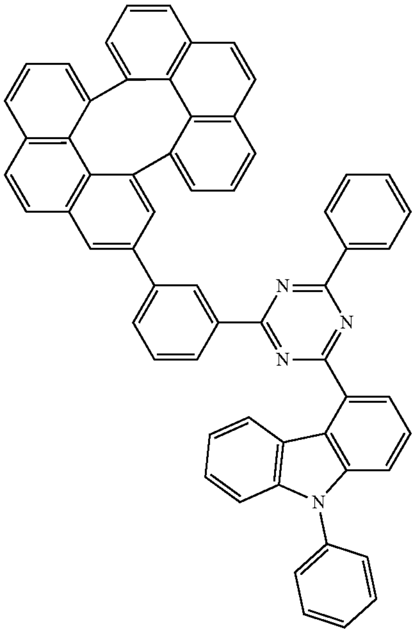
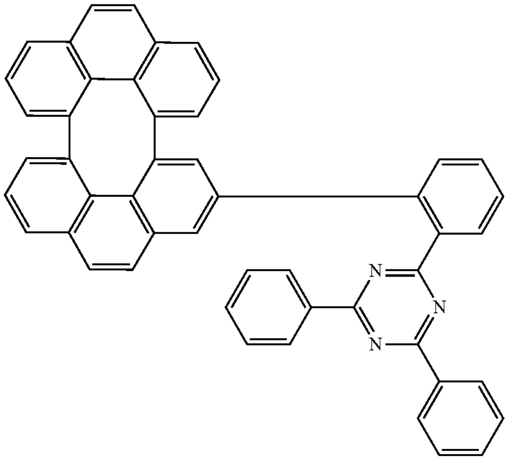
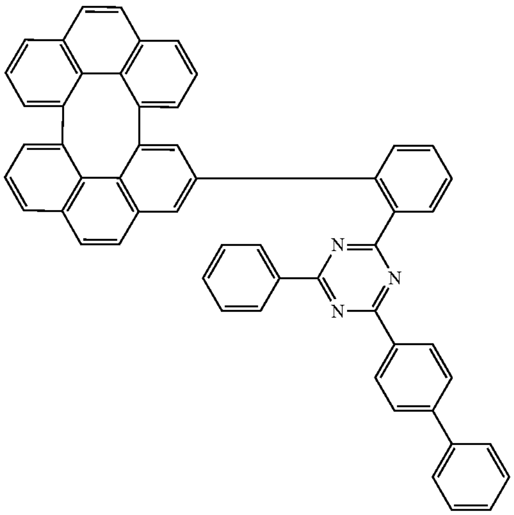

-continued
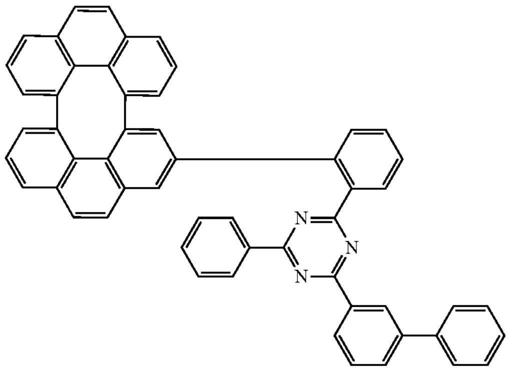
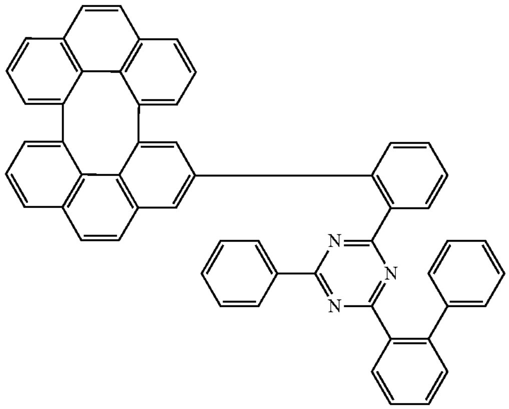
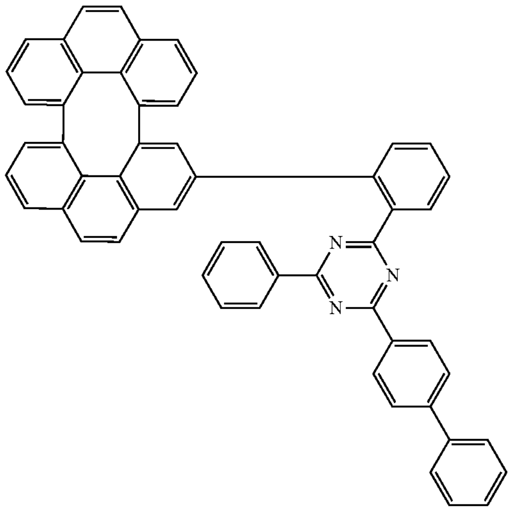
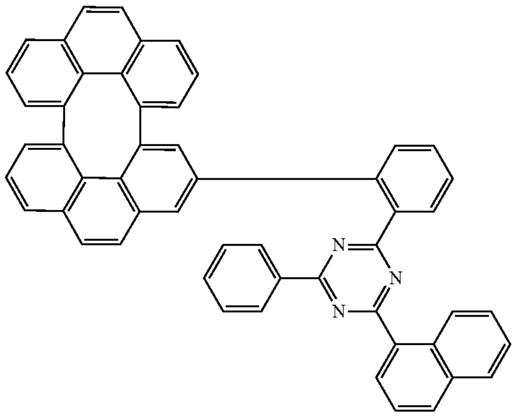

-continued
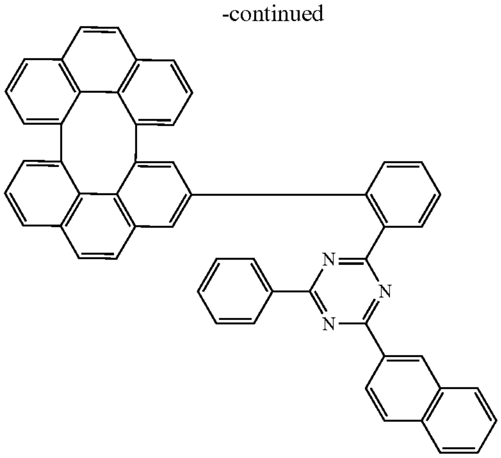
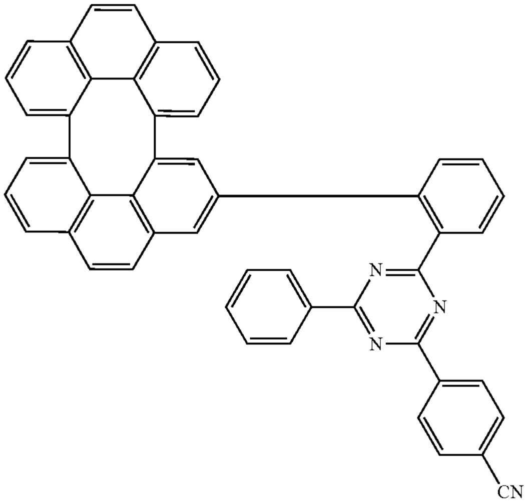
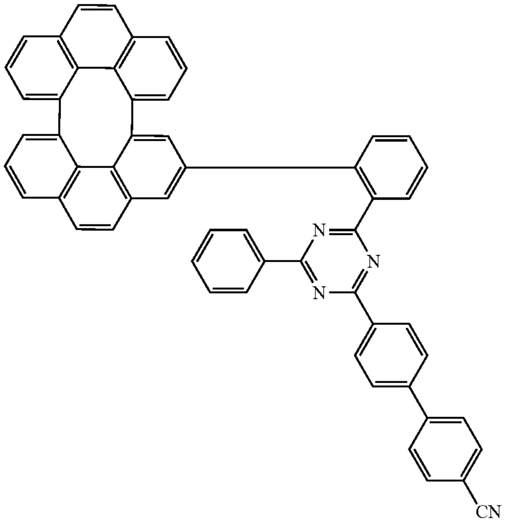

-continued
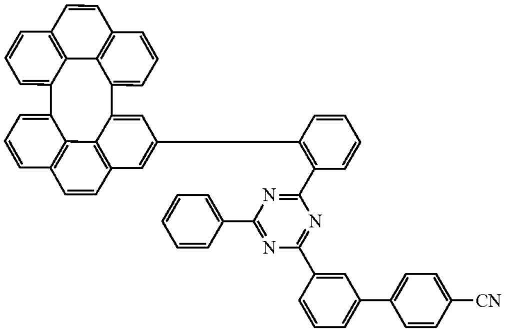
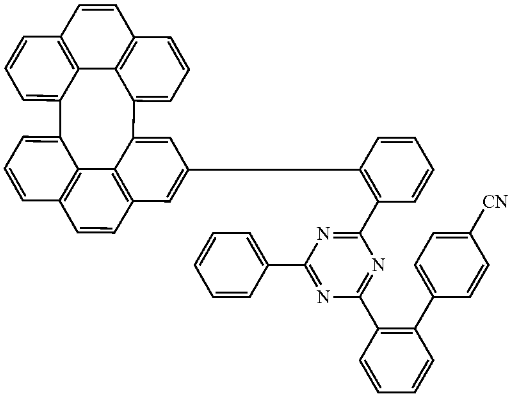
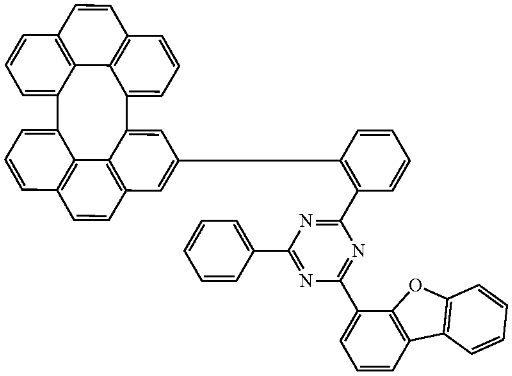
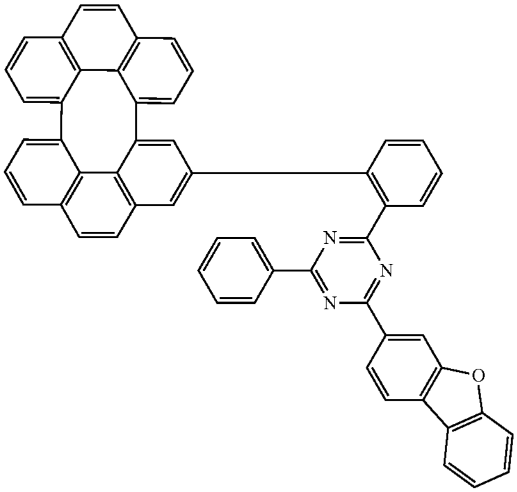

-continued
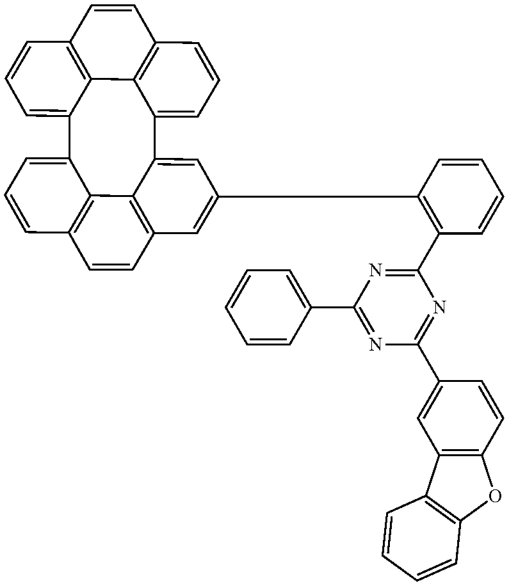
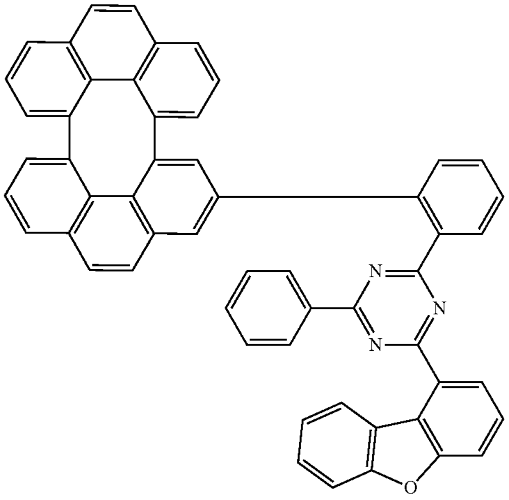
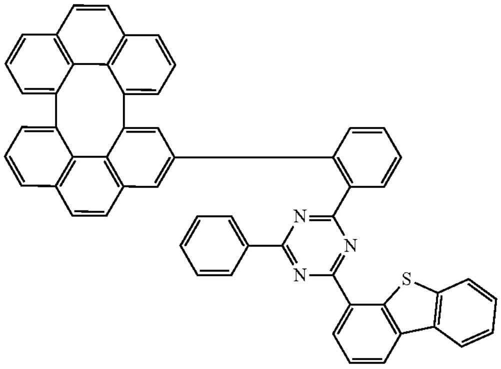

-continued
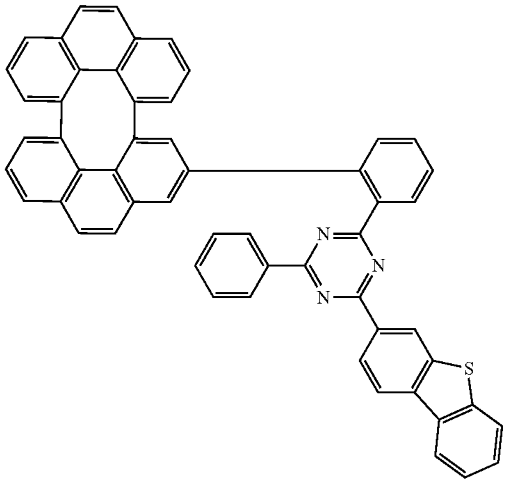
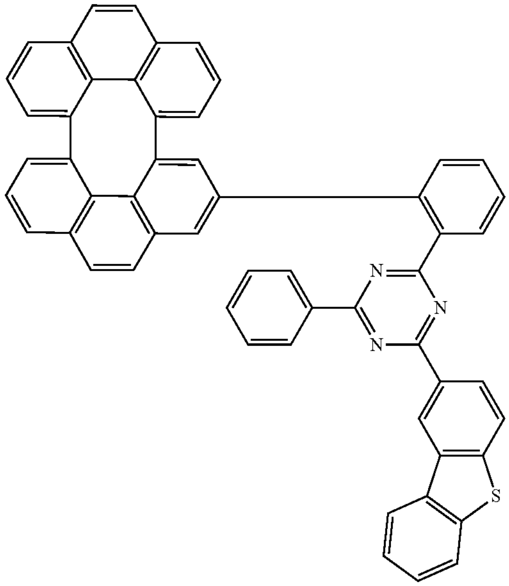
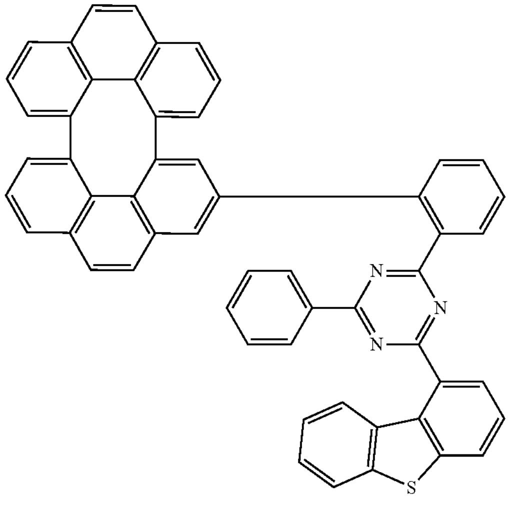

-continued
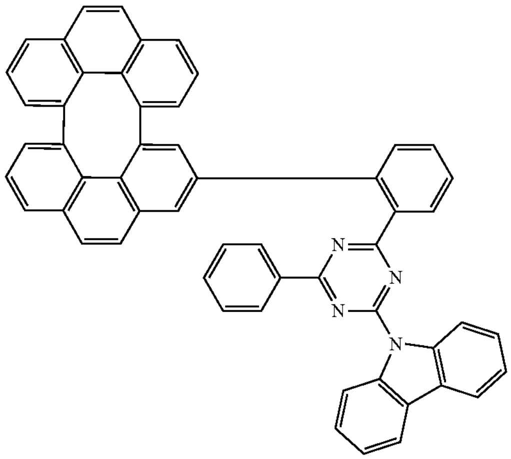
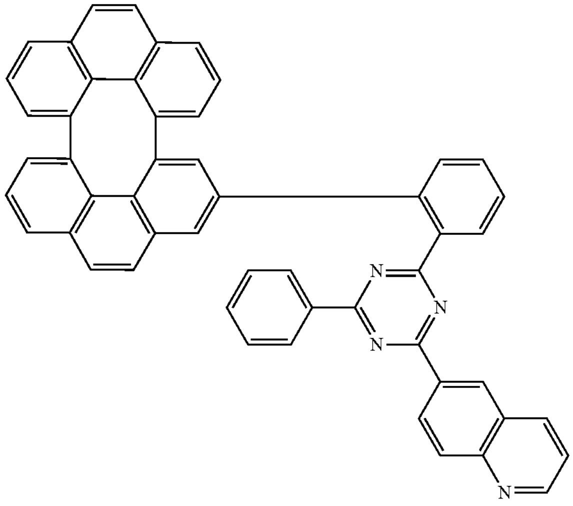
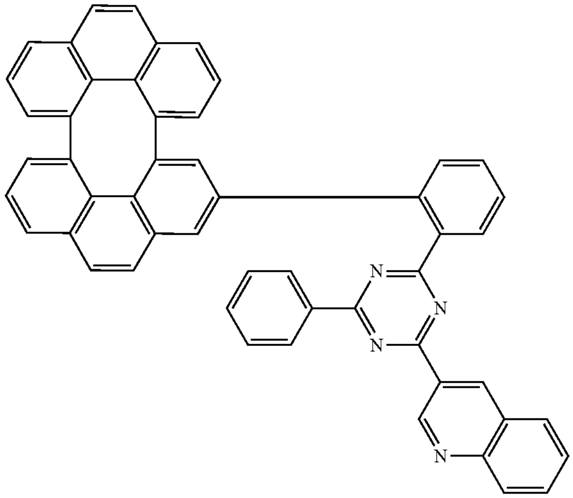

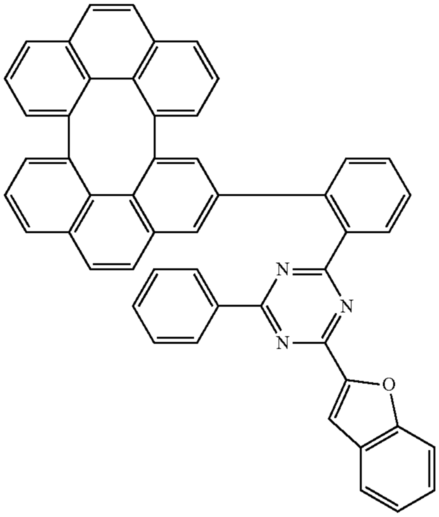
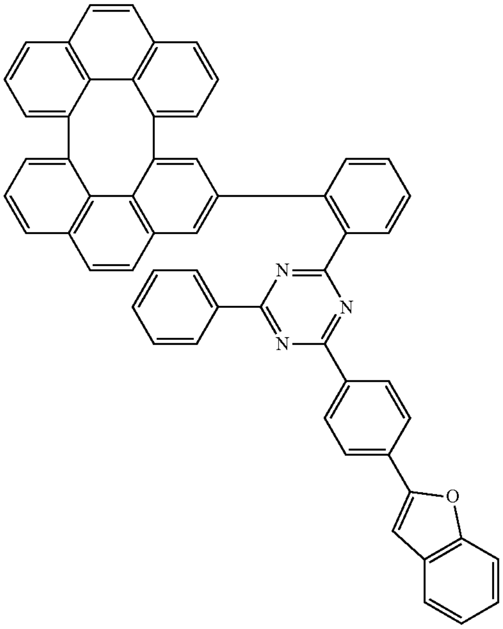
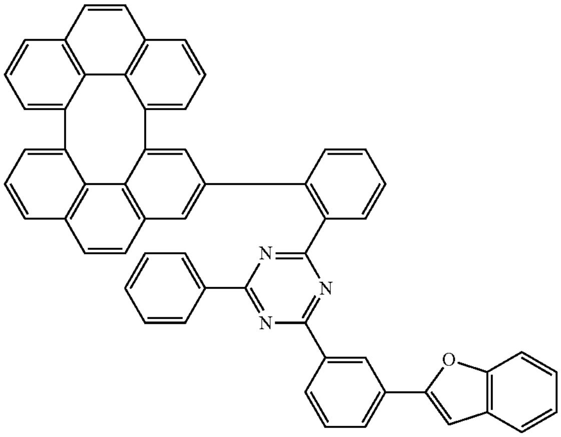
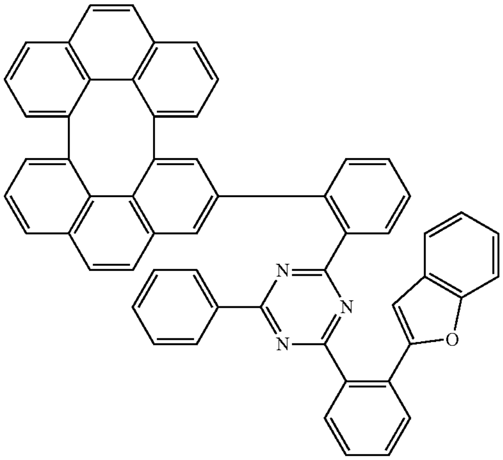
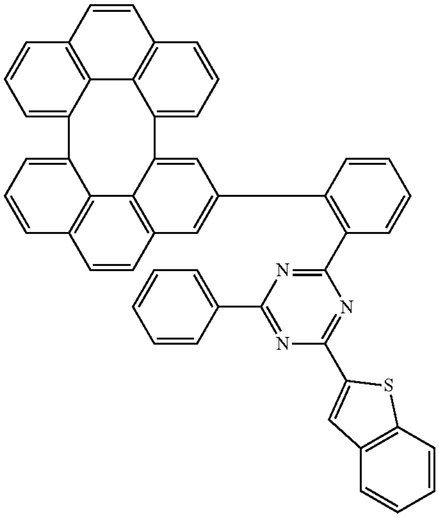
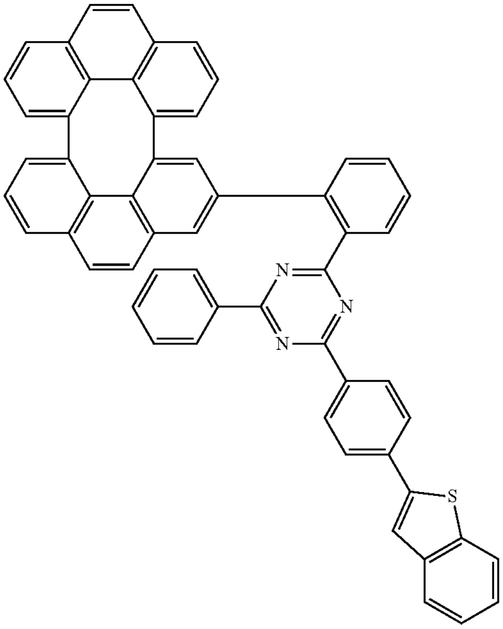

-continued
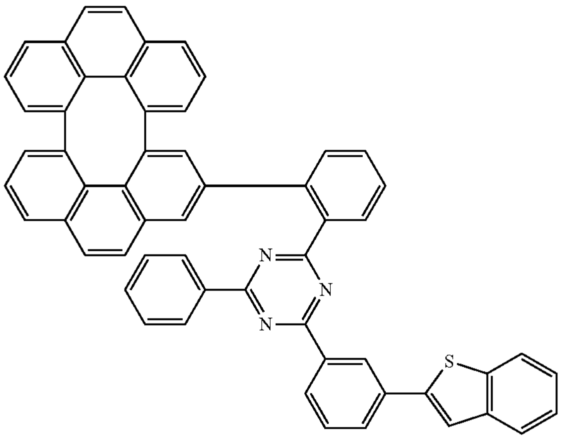
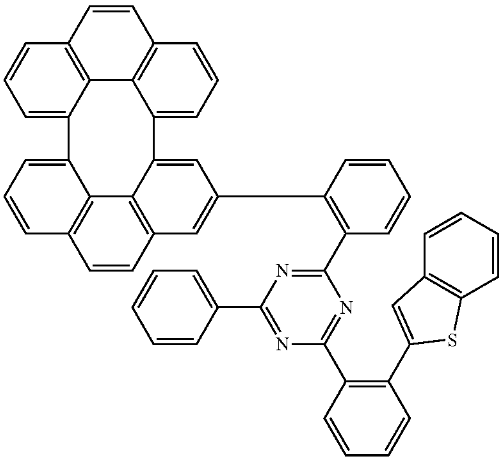
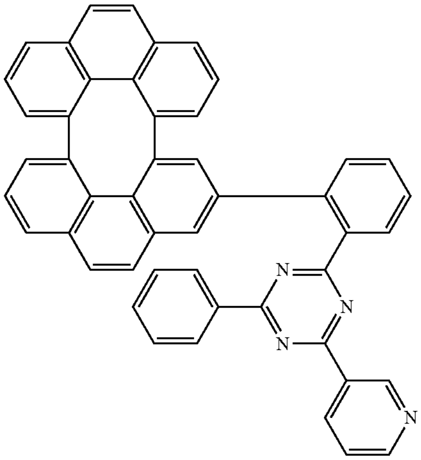
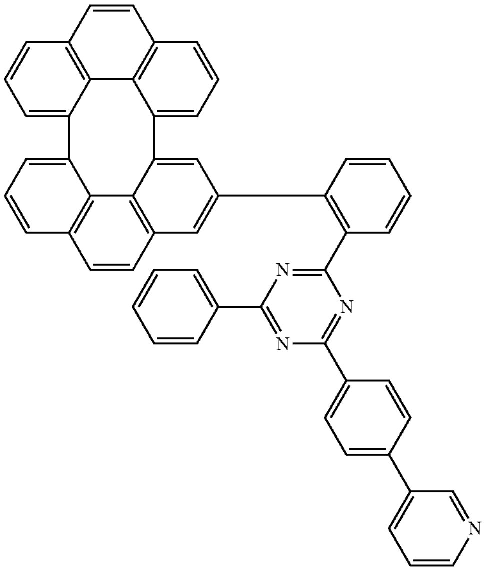
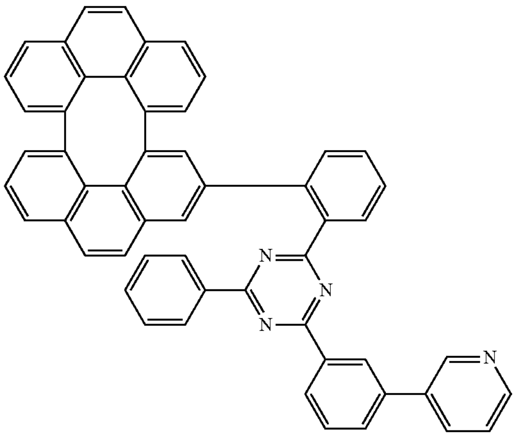
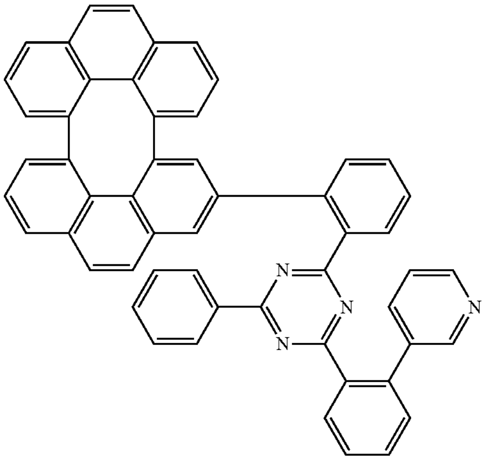

-continued
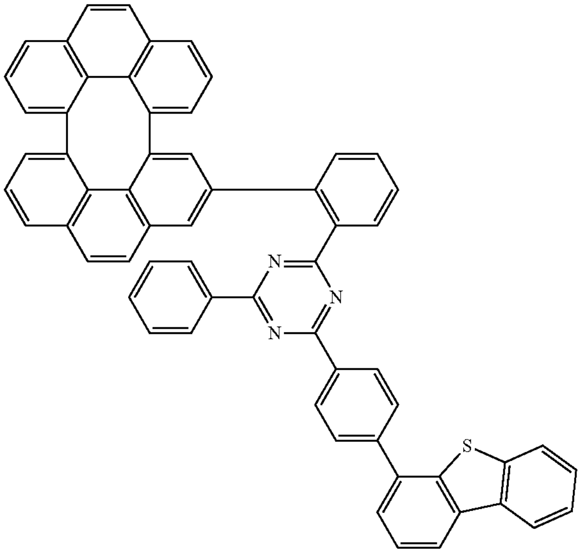
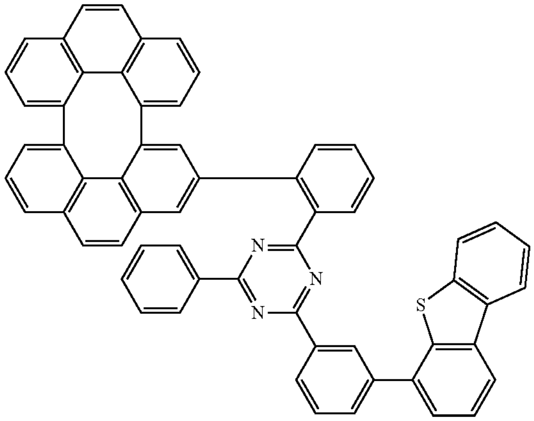
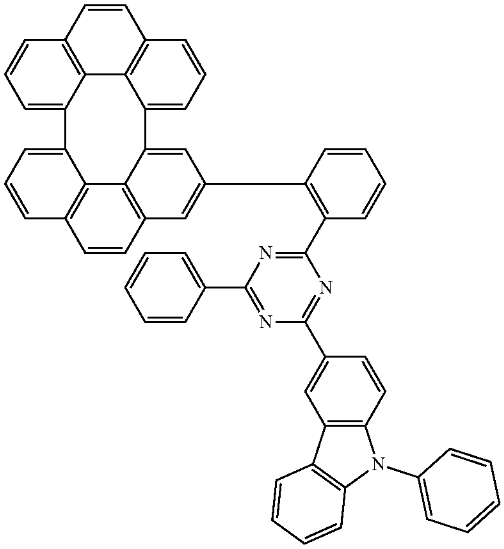
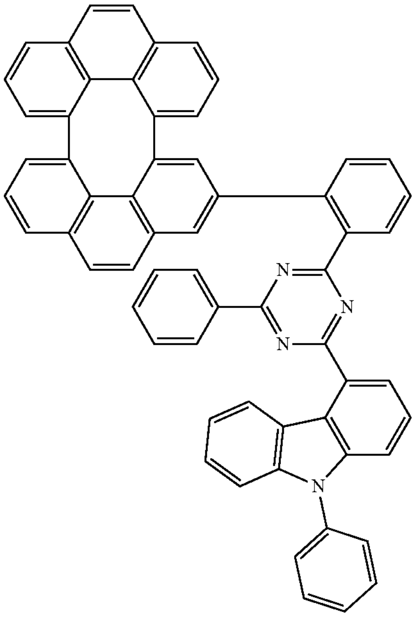
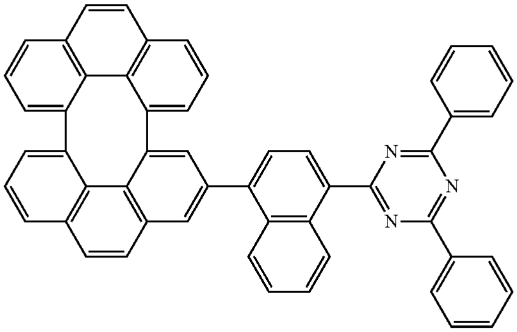
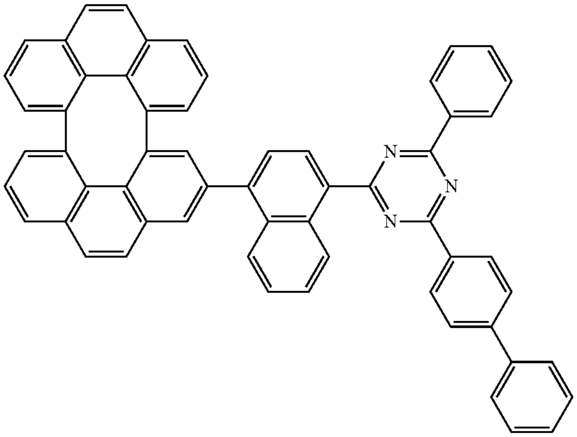

-continued
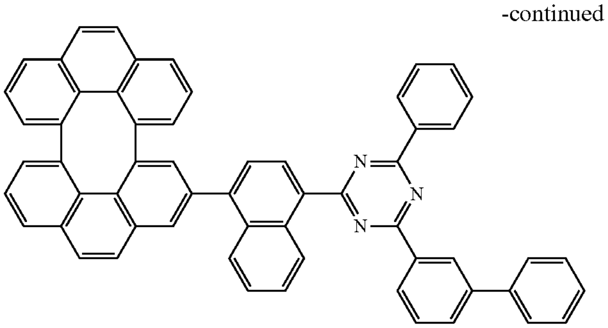
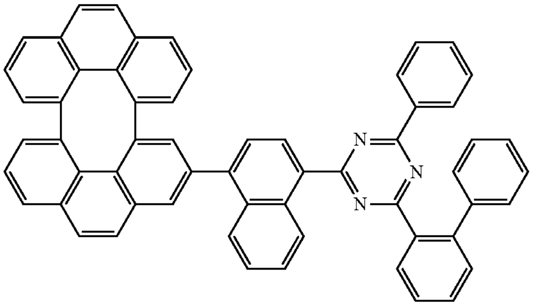
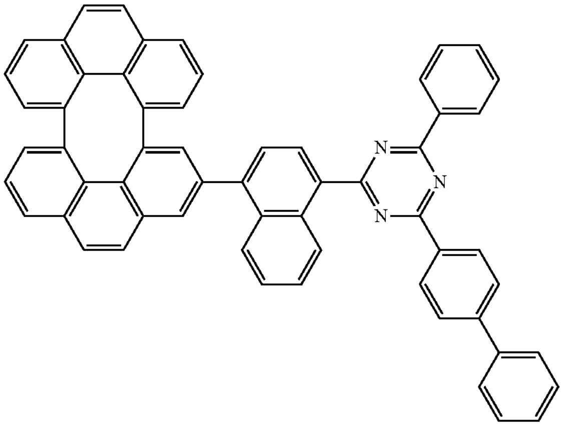
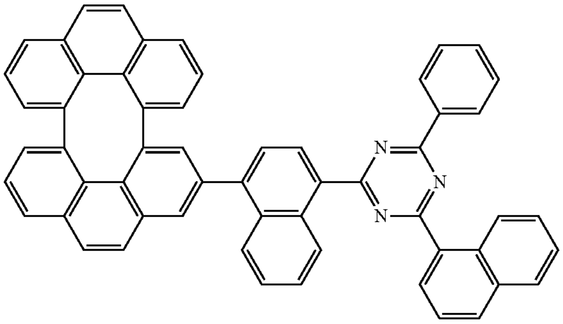
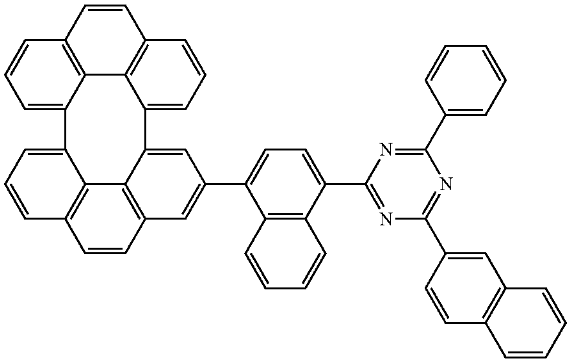
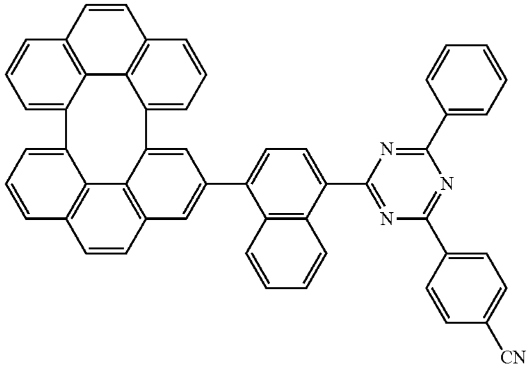
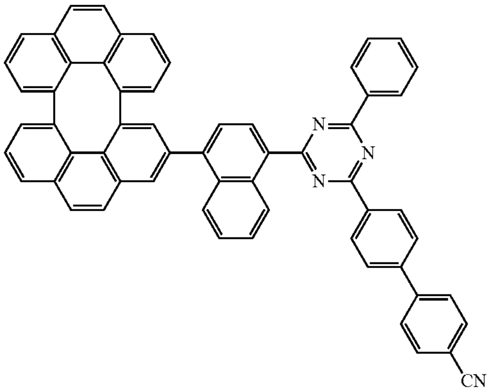
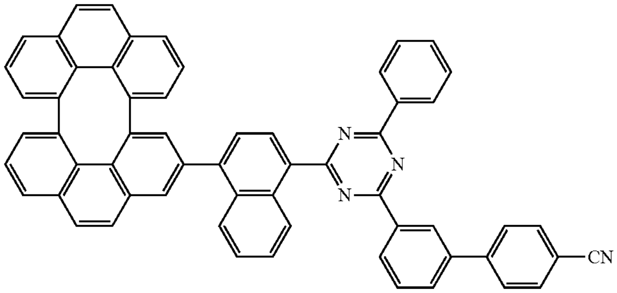

-continued
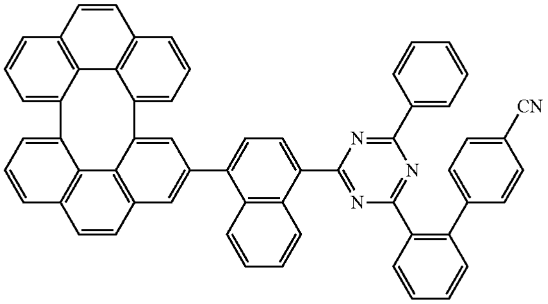
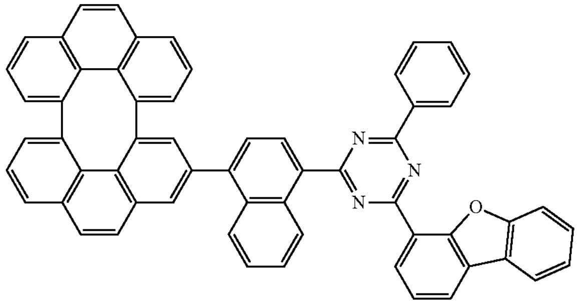
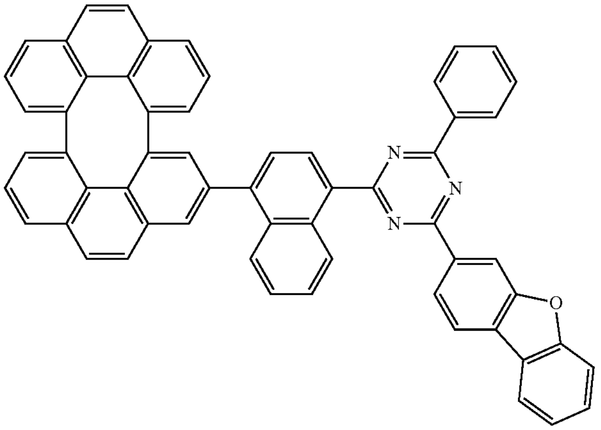
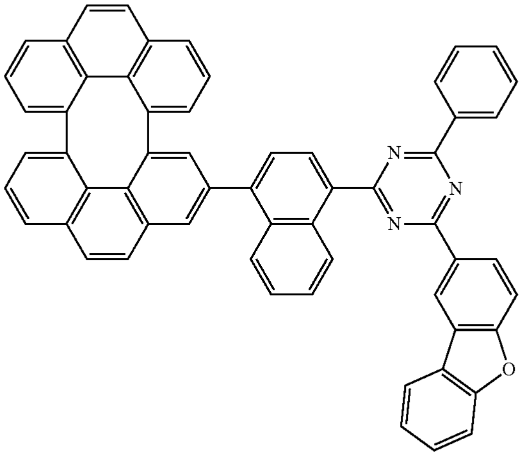
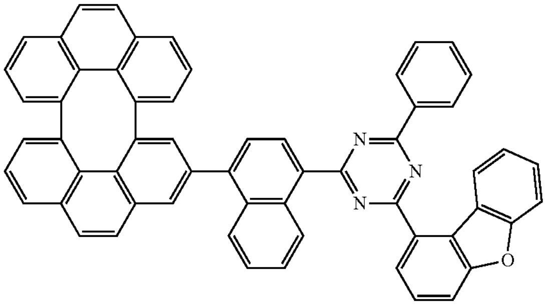
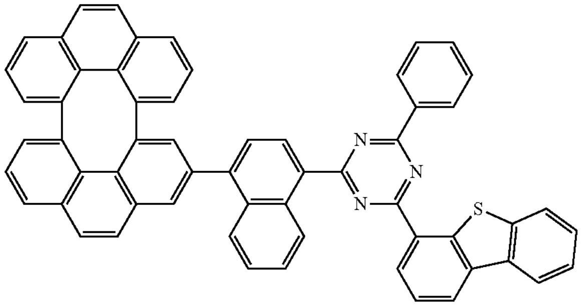
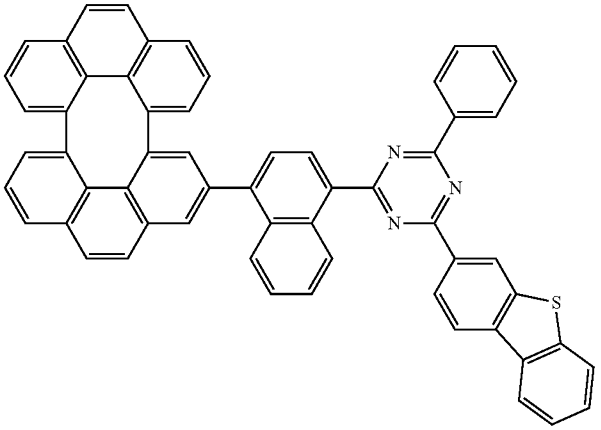
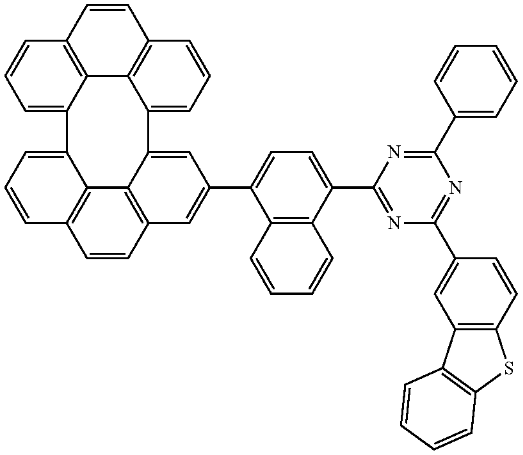

-continued
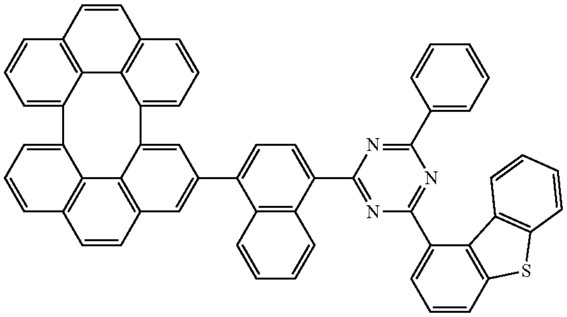
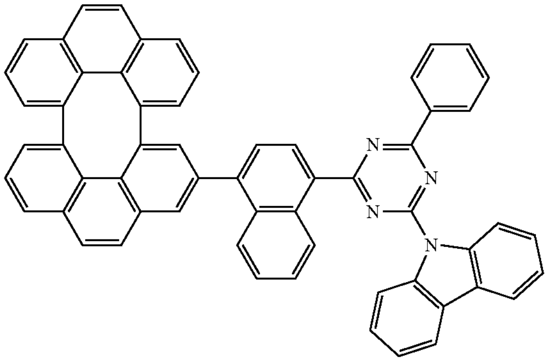
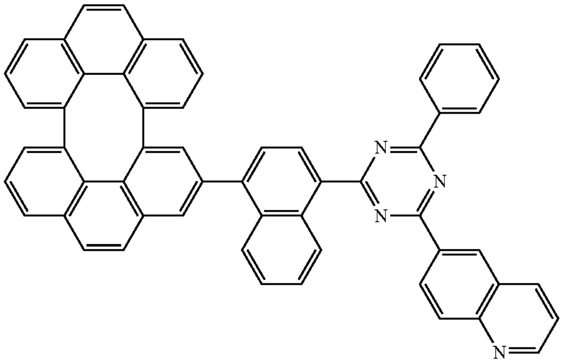
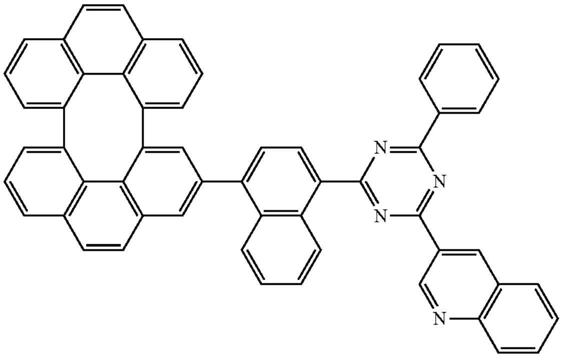
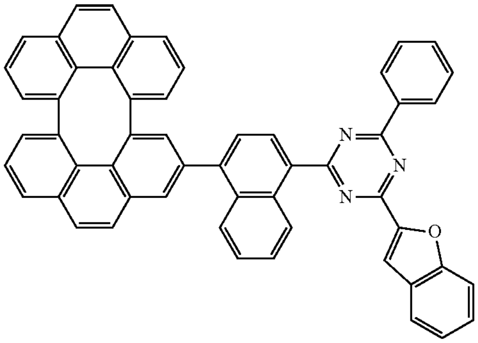
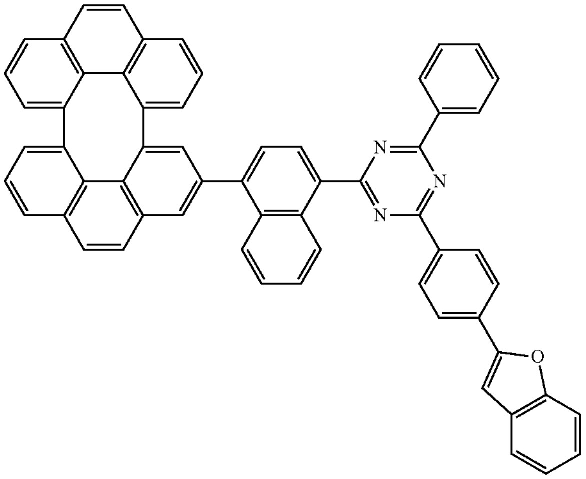
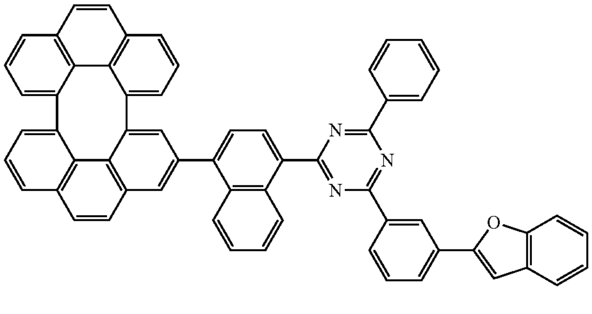
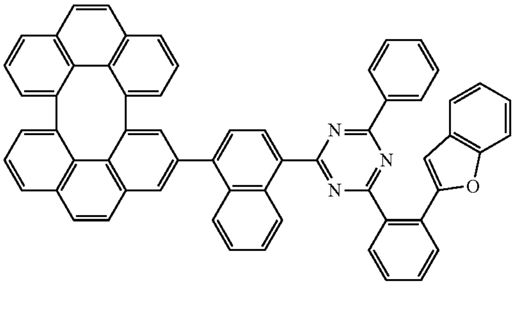

-continued
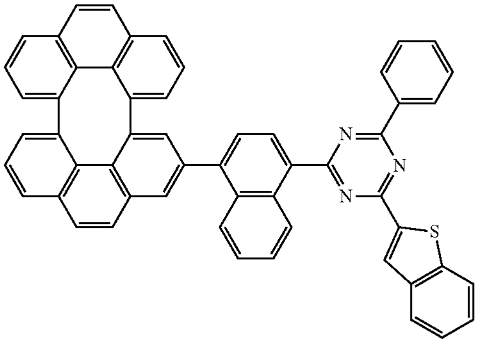
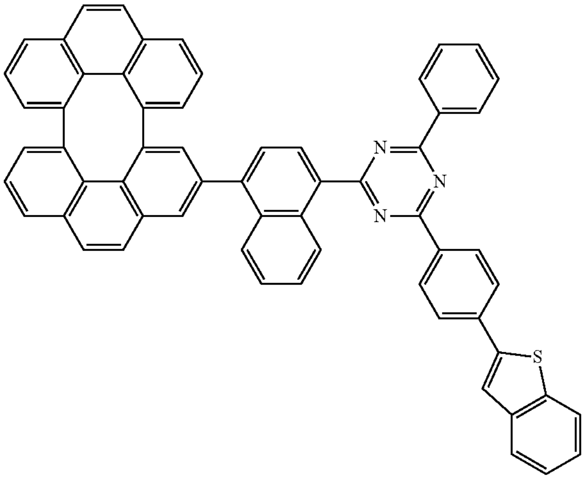
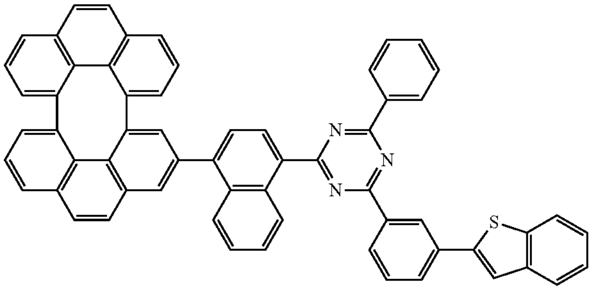
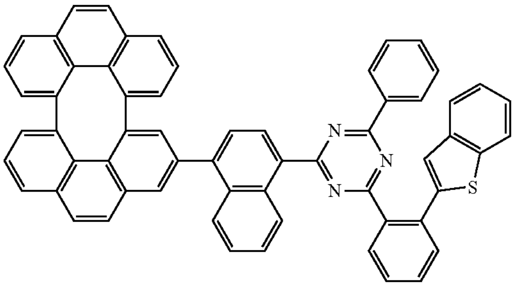
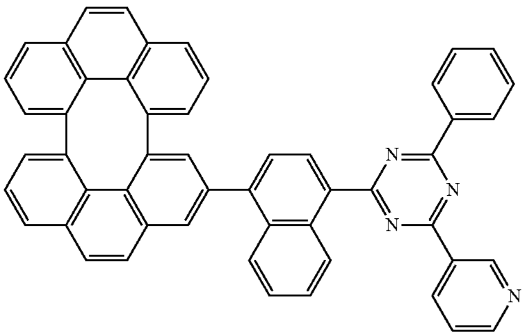
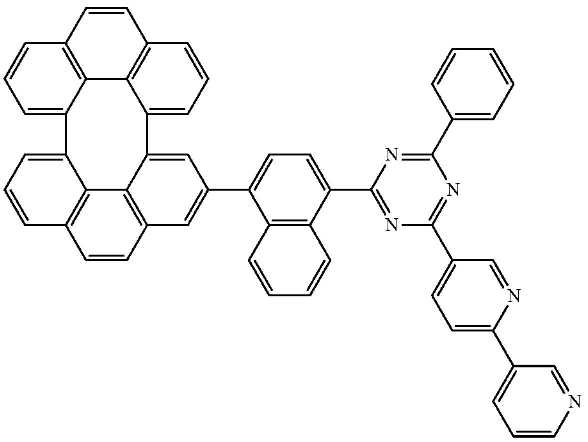
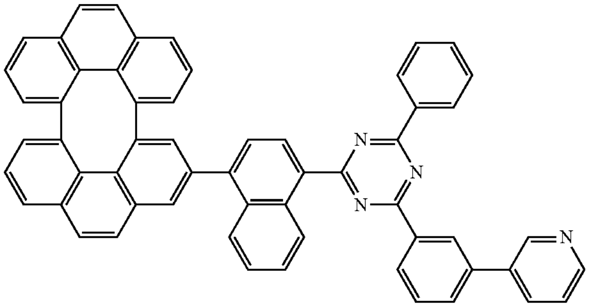
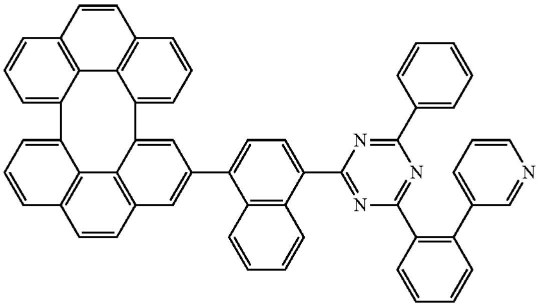

-continued
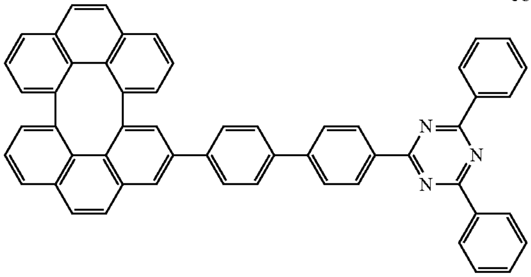
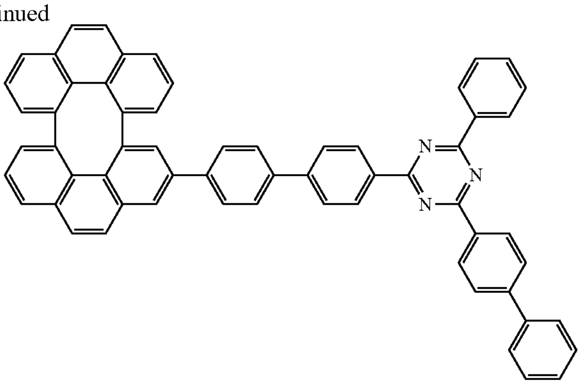
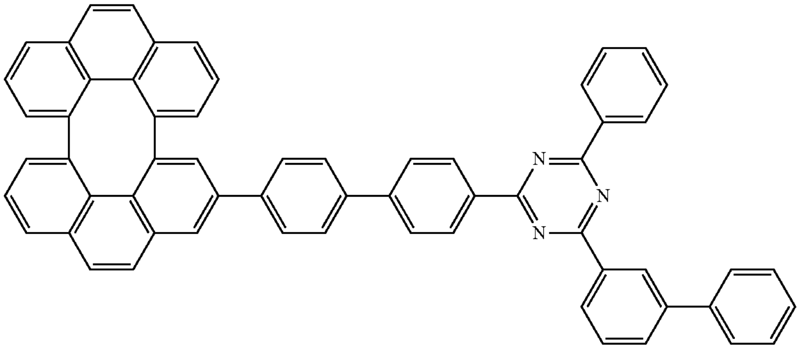
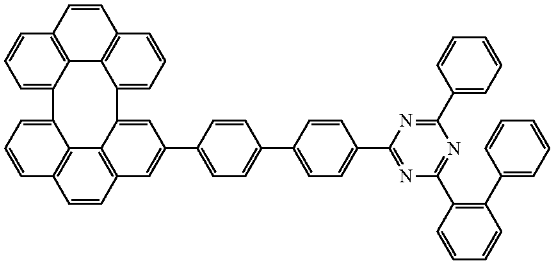
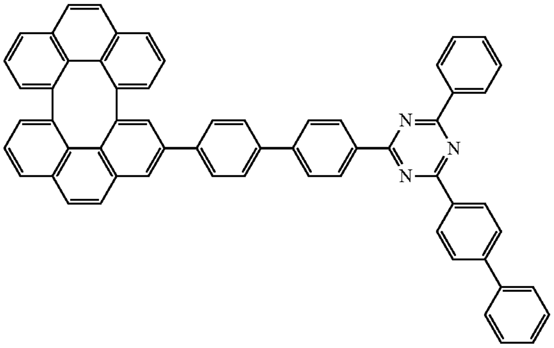
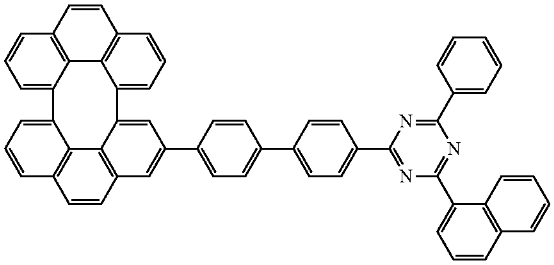
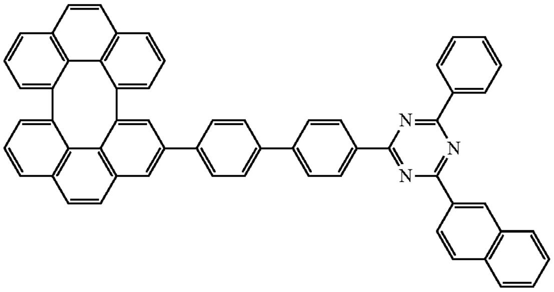
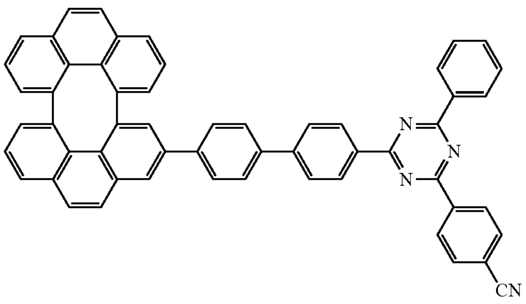
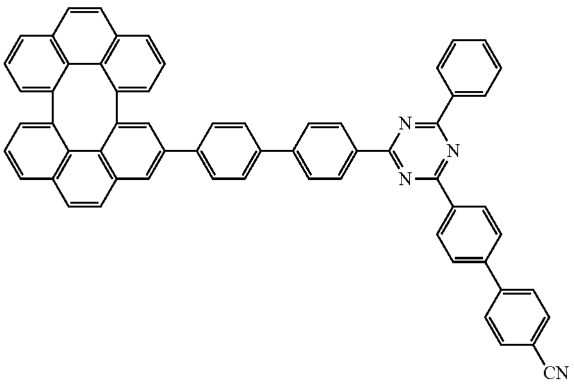

-continued
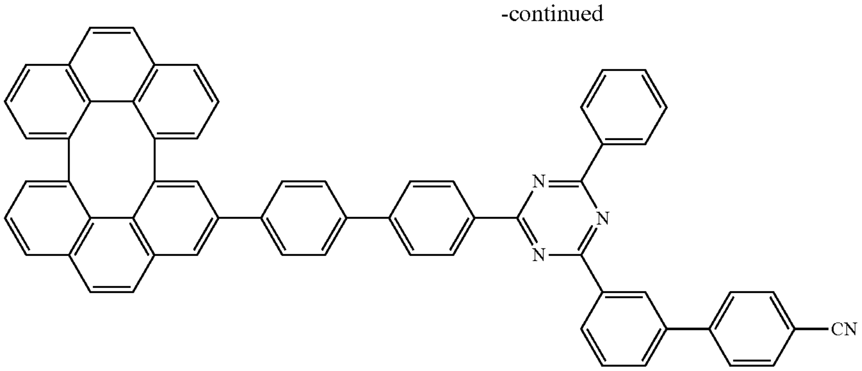
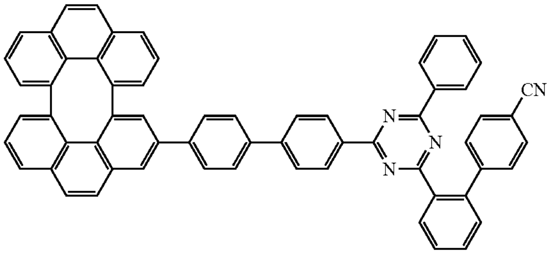
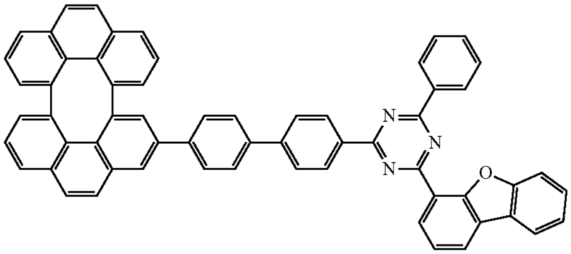
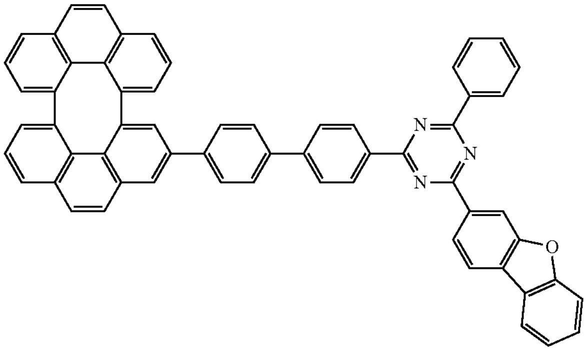
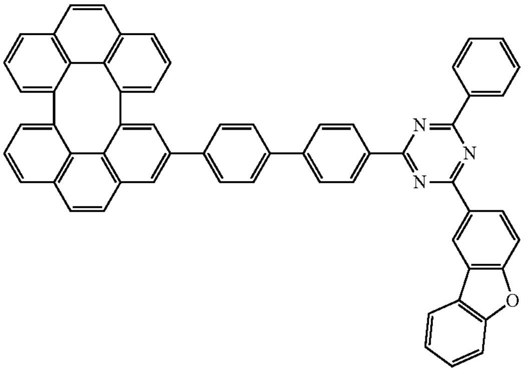
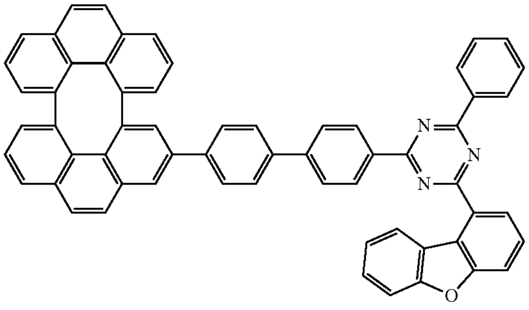
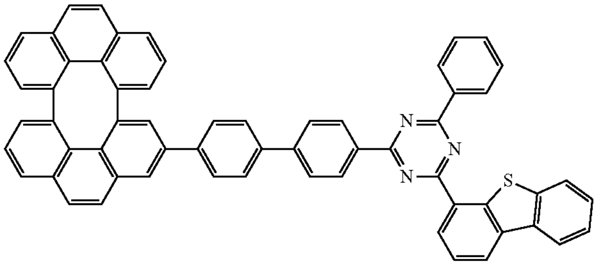
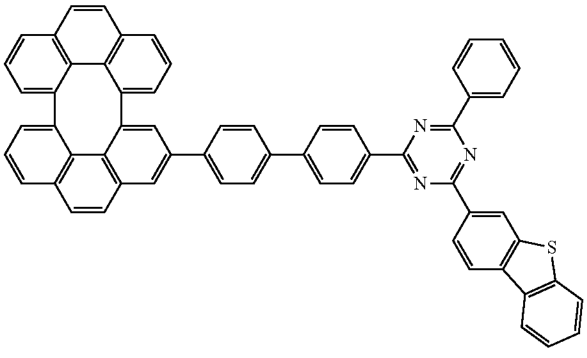
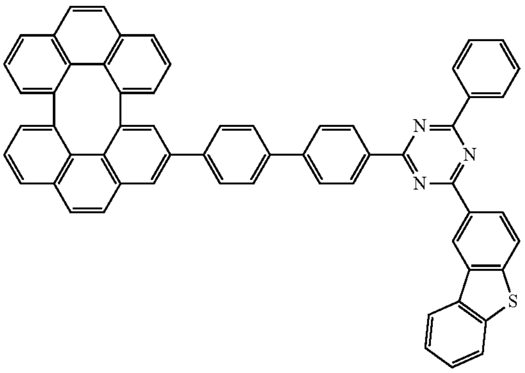

-continued
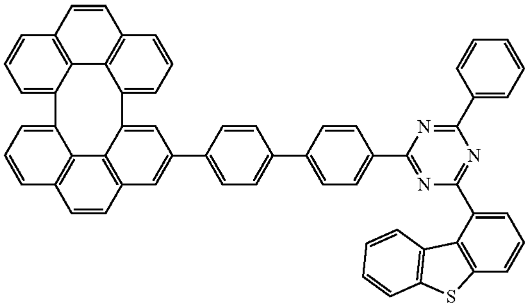
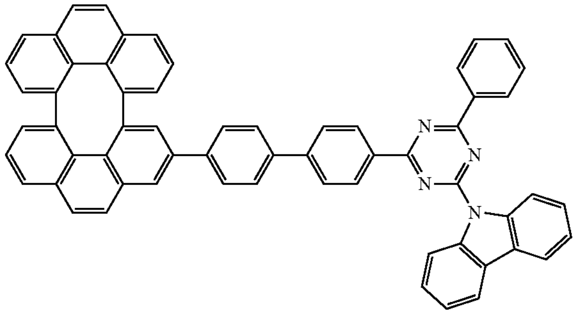
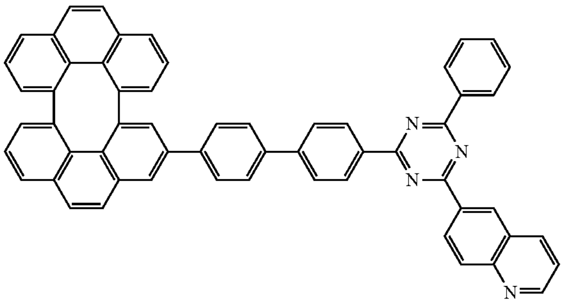
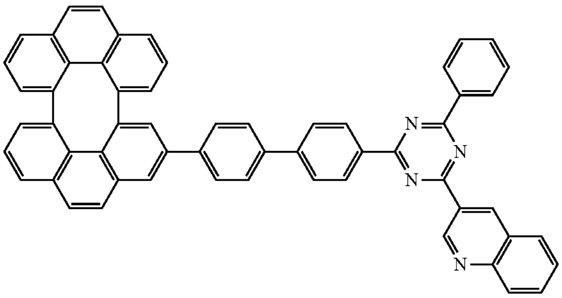
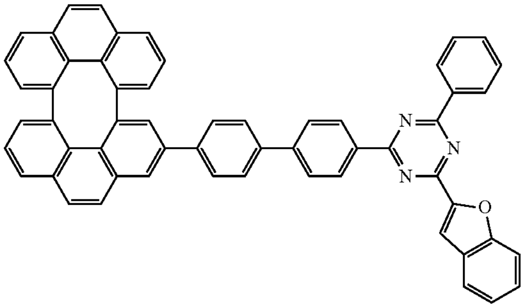
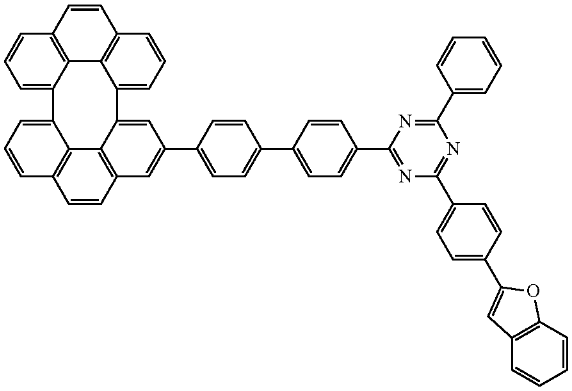
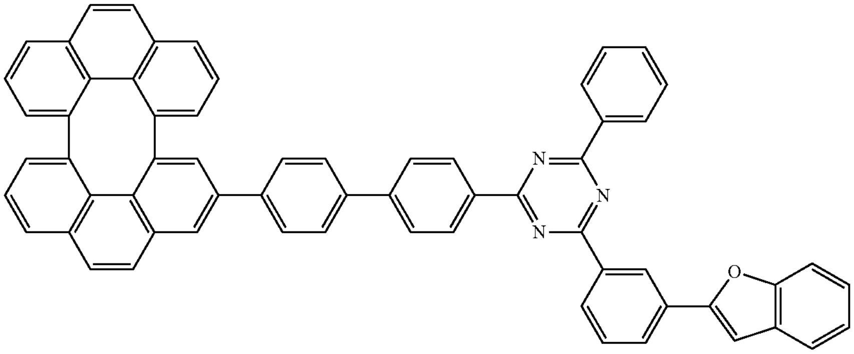
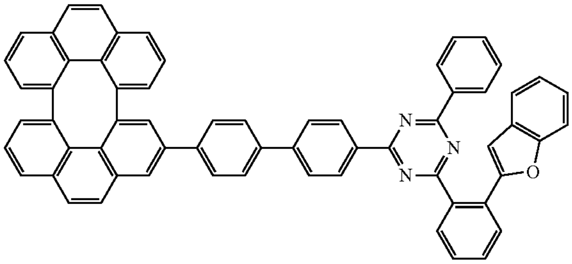
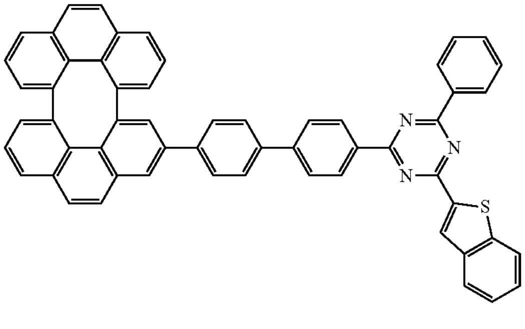

-continued
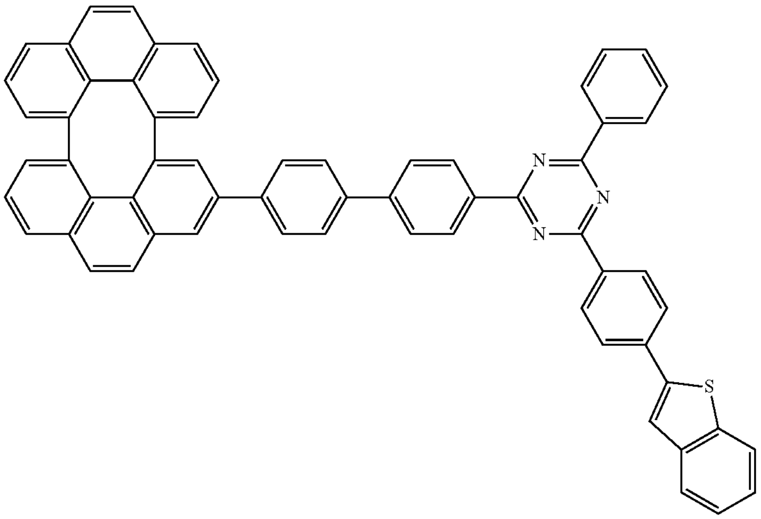
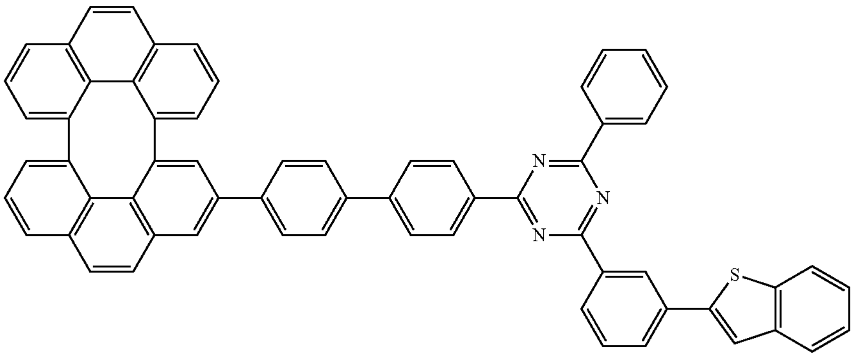
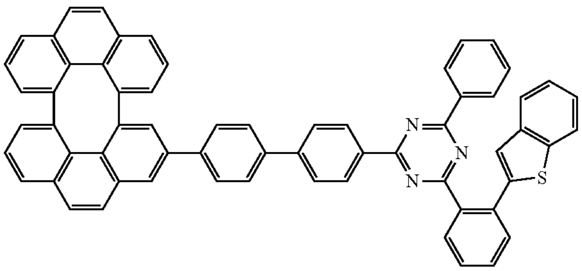
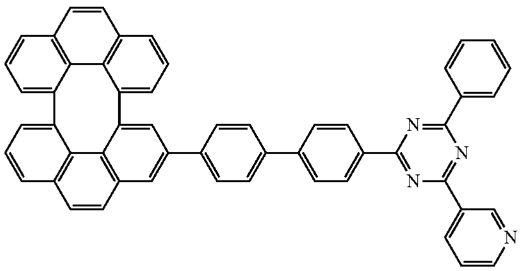
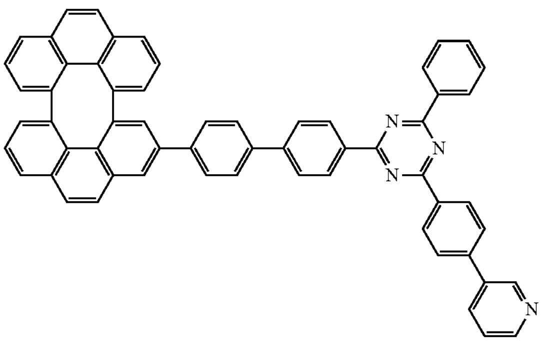
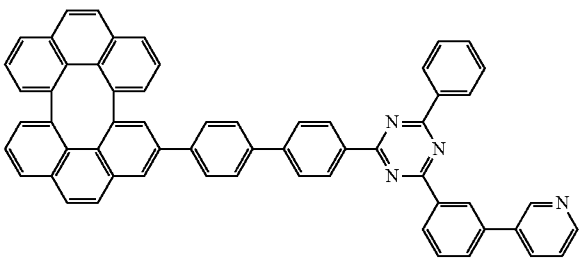

-continued
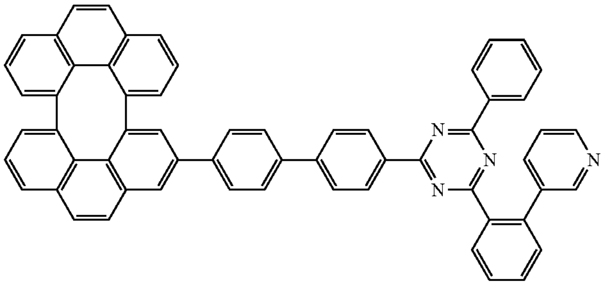
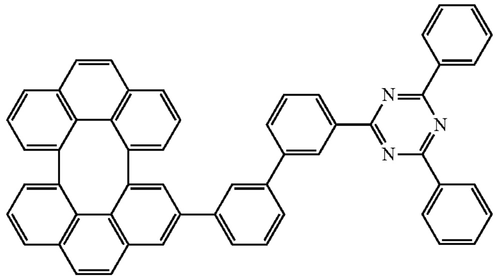
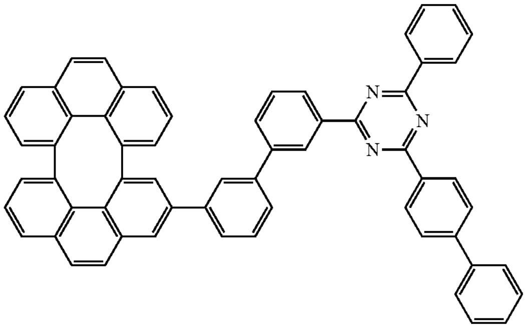
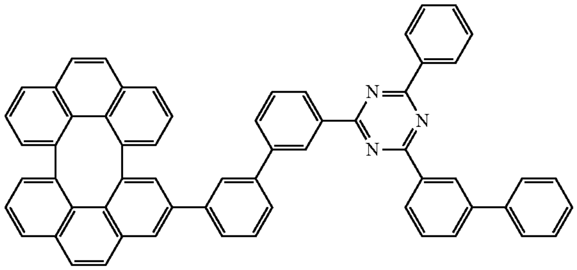
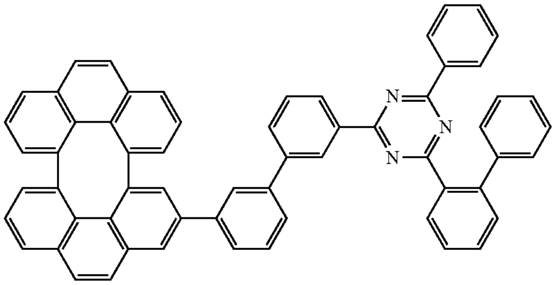
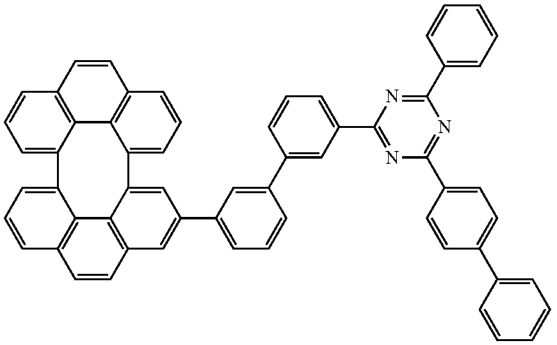
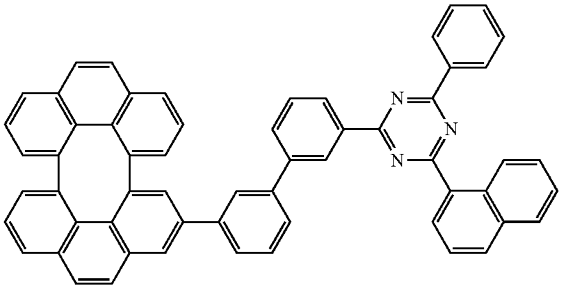
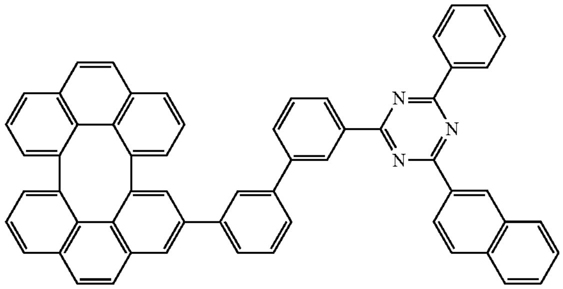
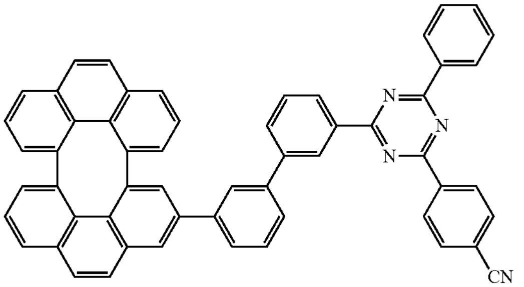
CN
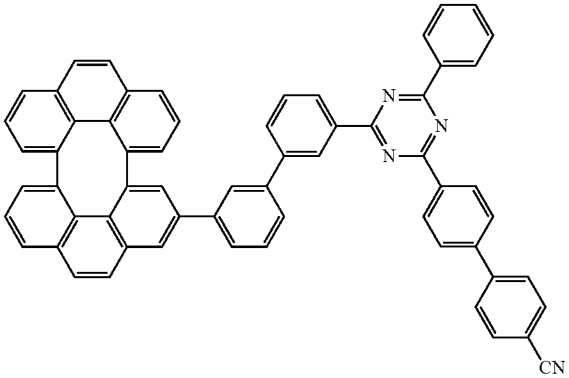
CN -continued
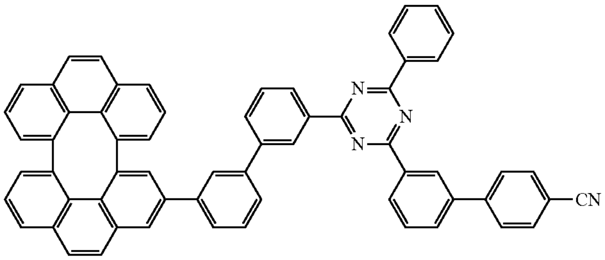
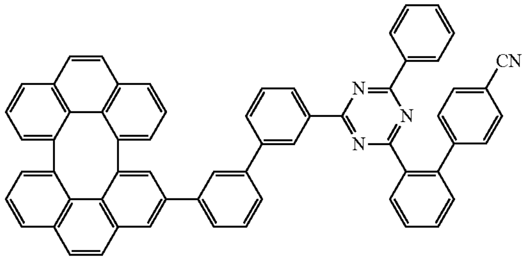
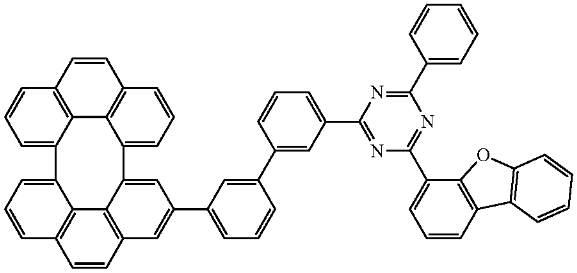
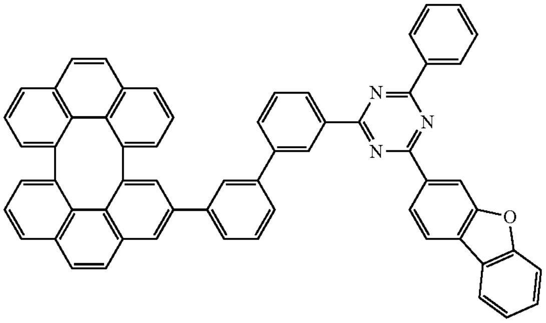
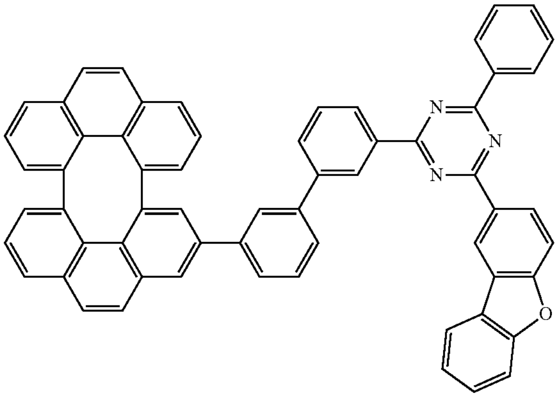
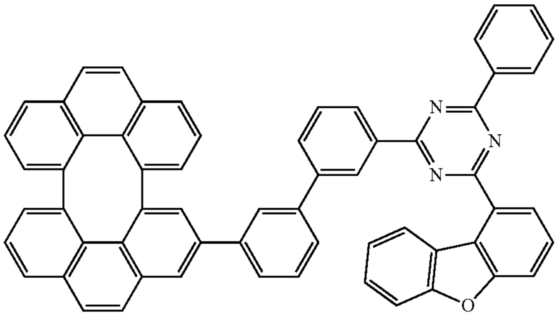
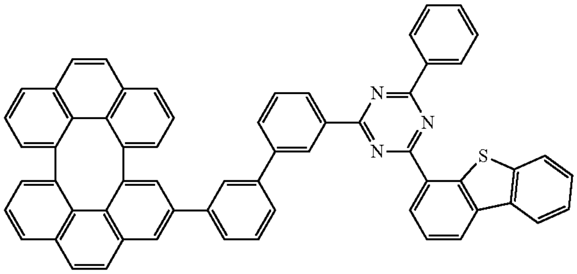
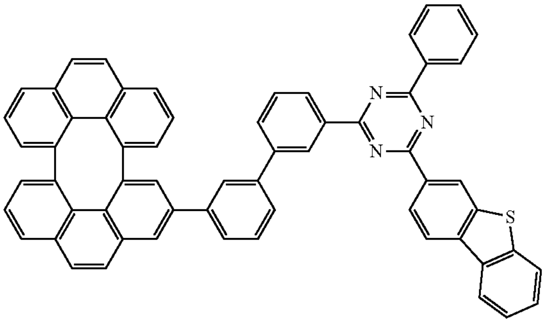
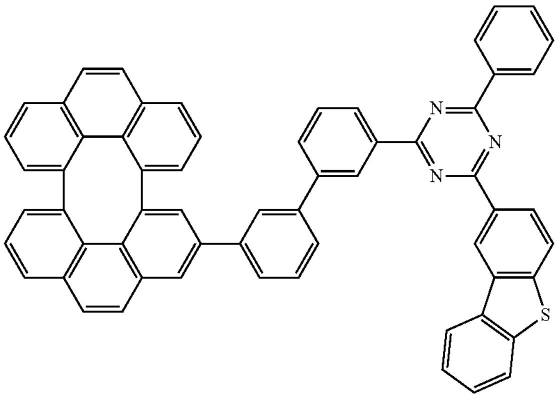
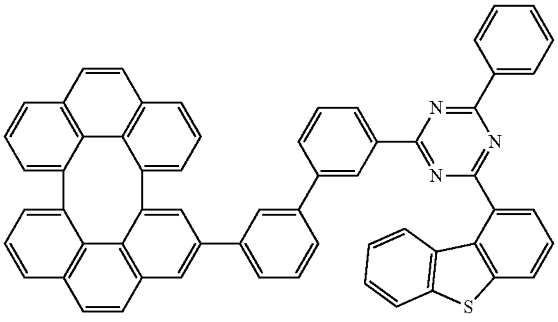

-continued
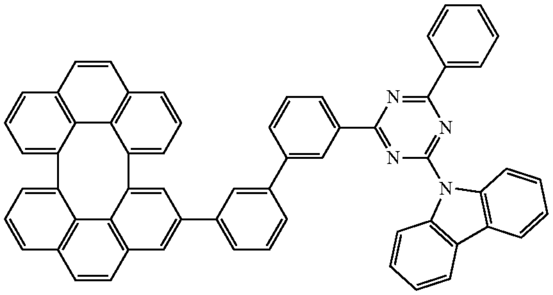
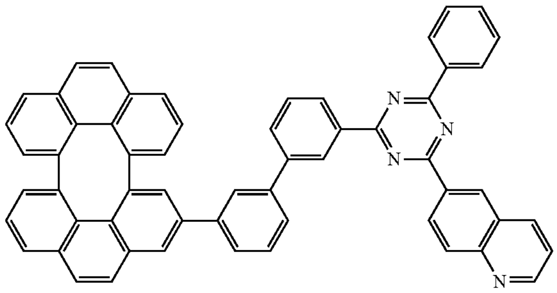
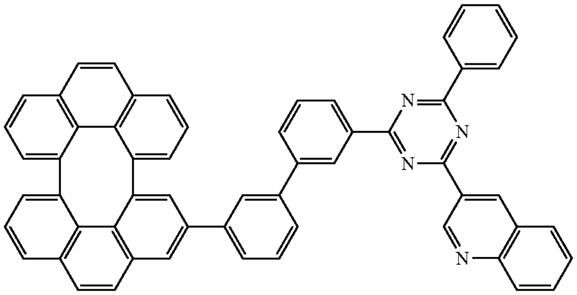
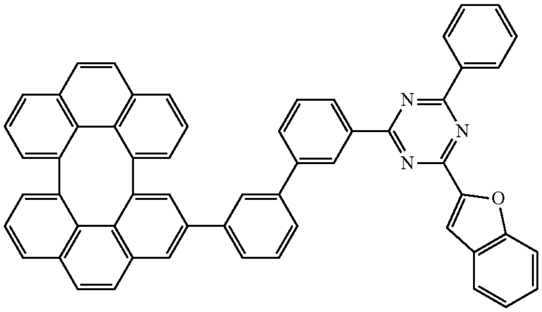
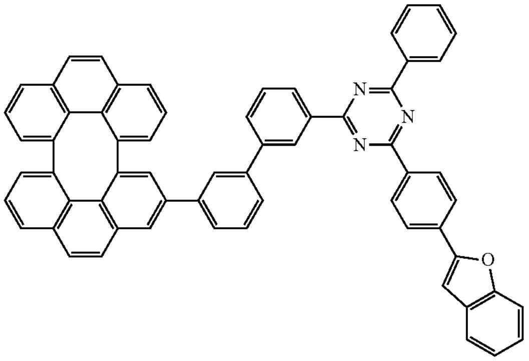
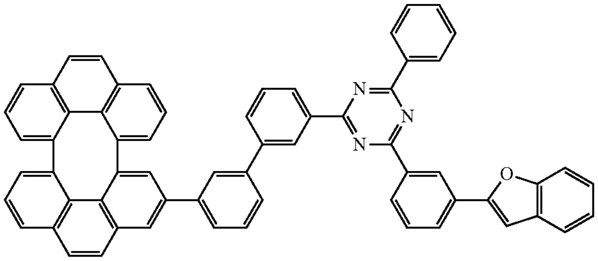
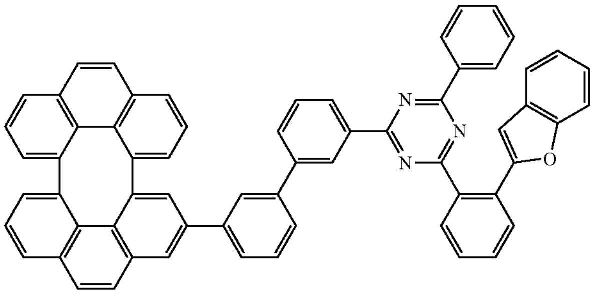
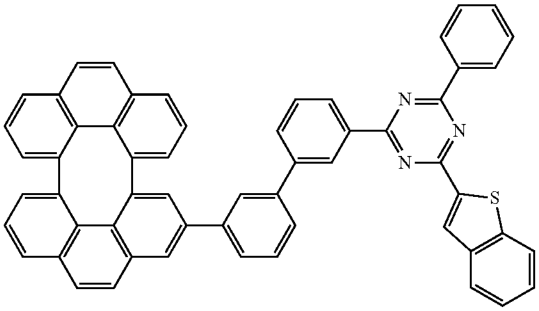
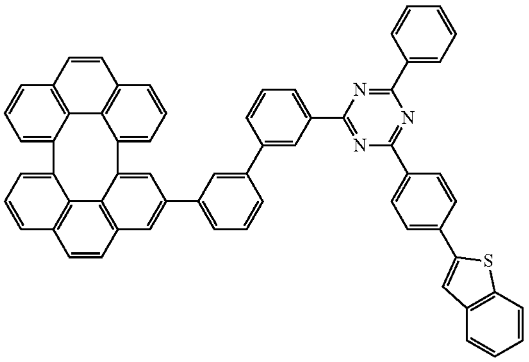
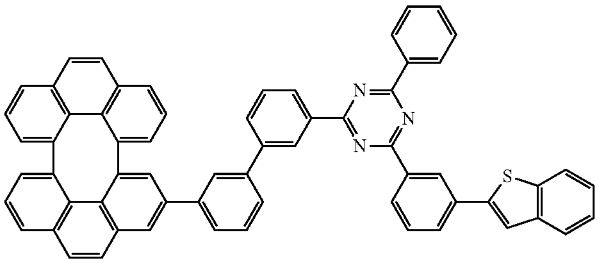

-continued
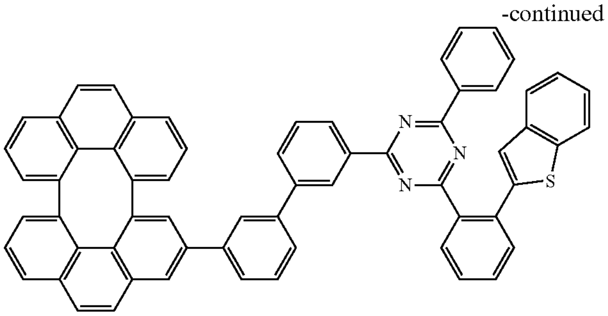
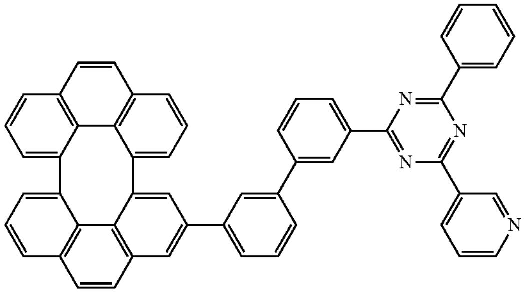
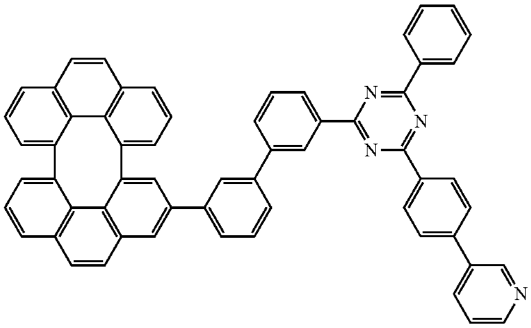
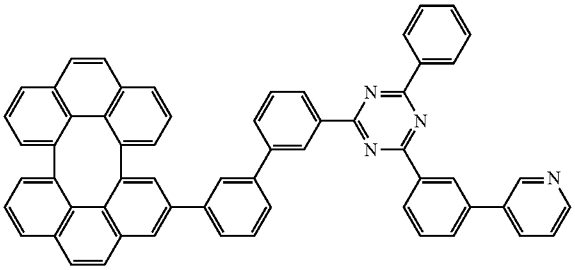
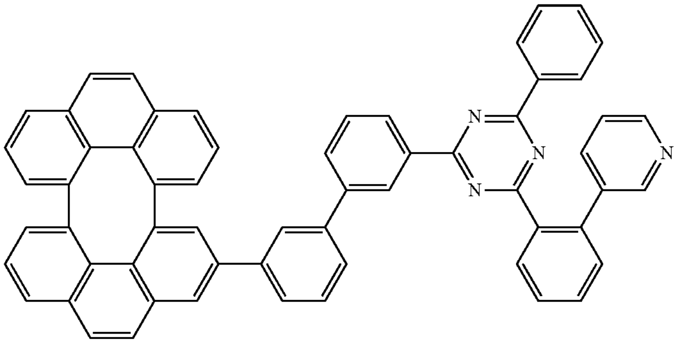
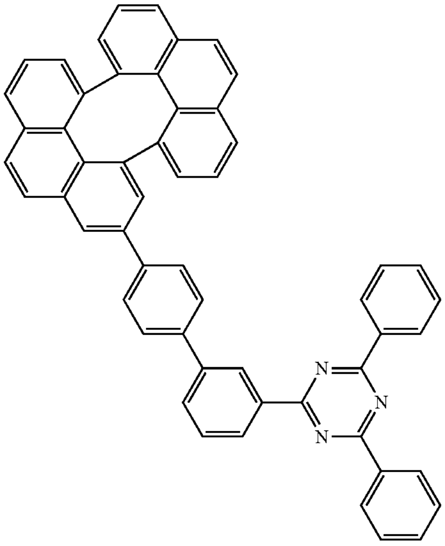
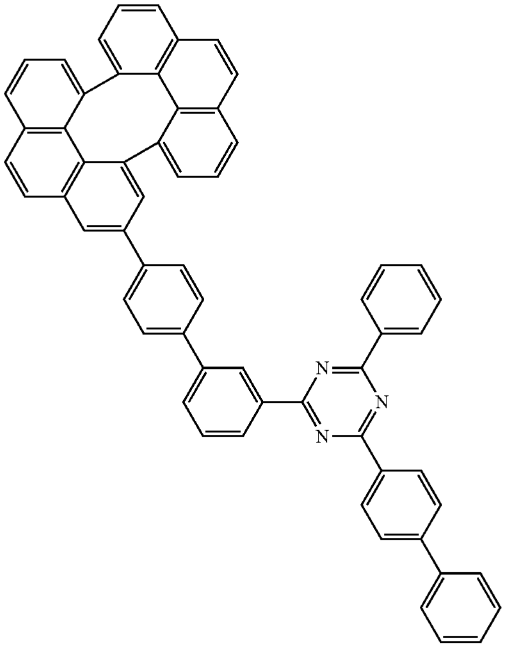

-continued
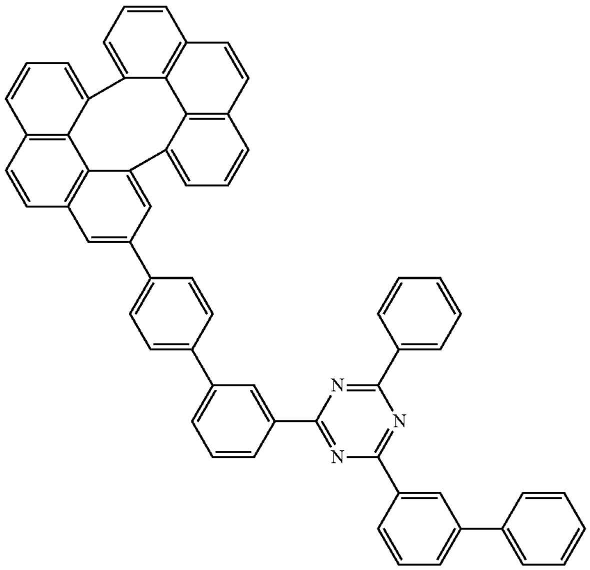
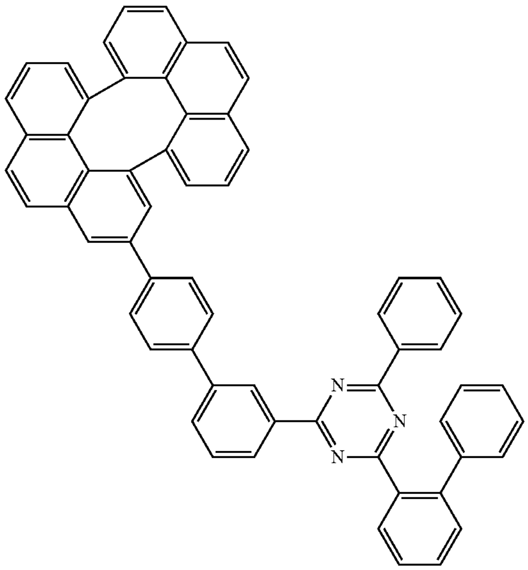
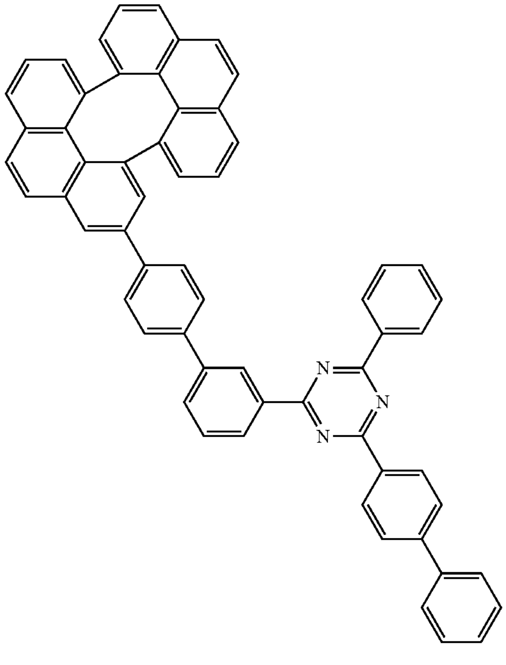
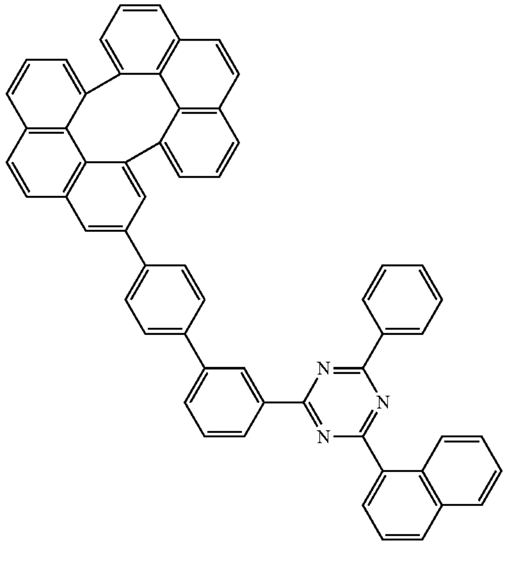

-continued
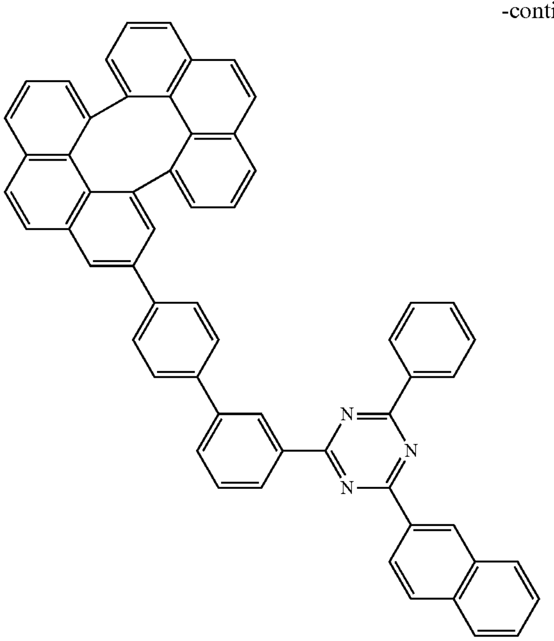
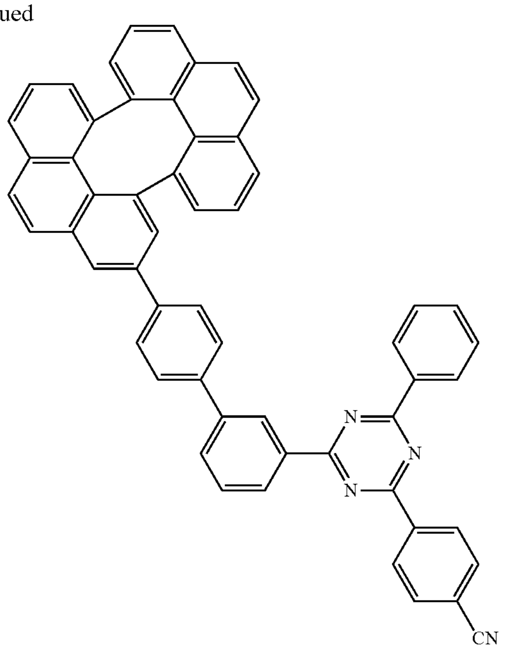
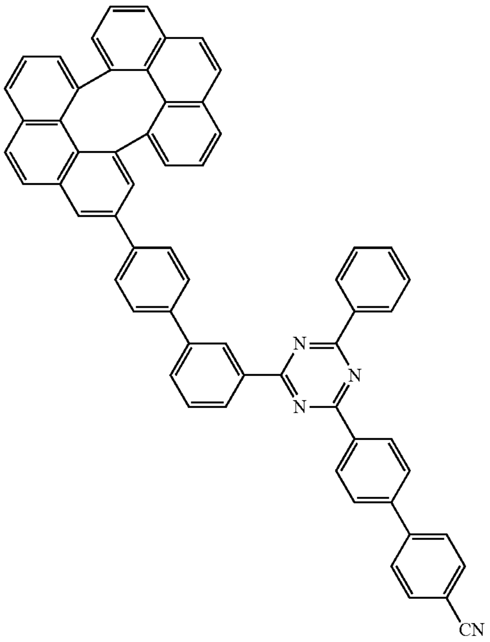
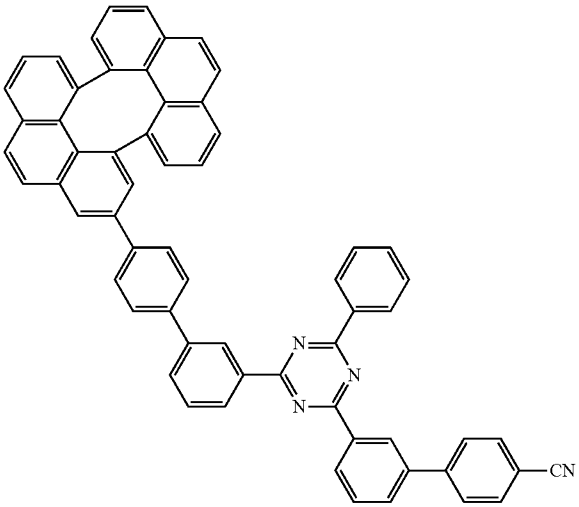

-continued
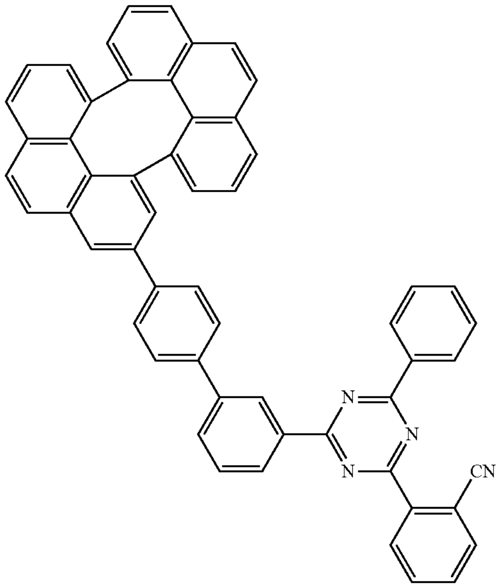
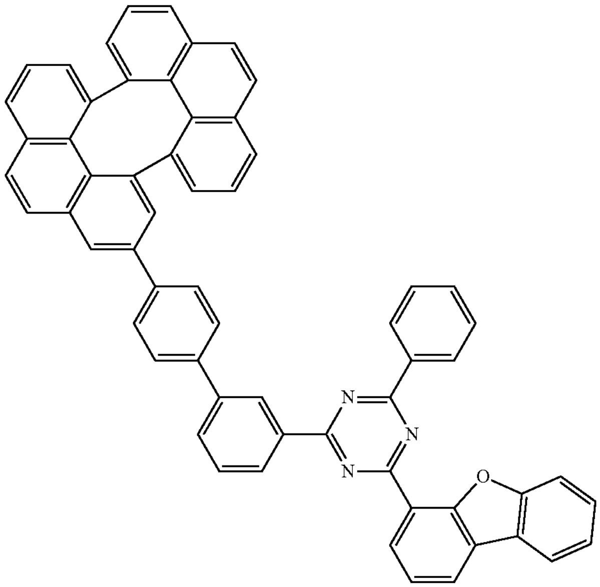
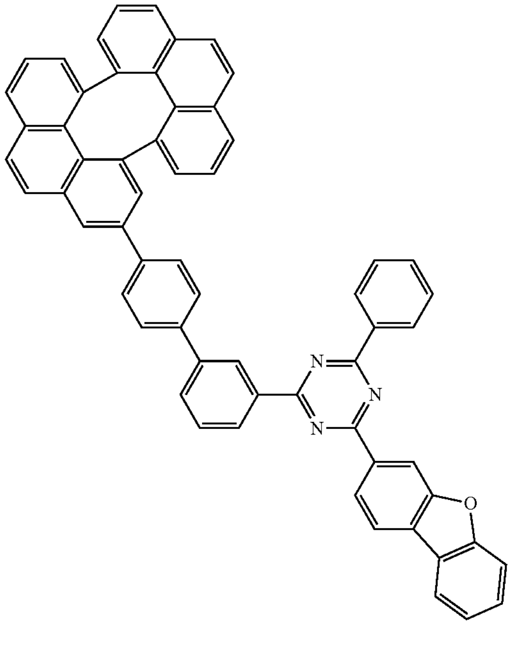
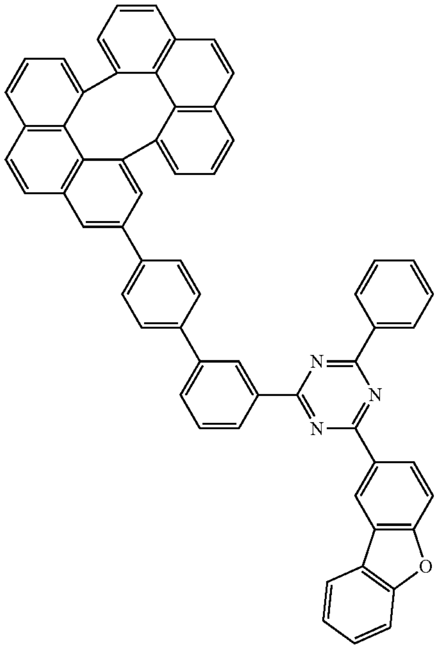

-continued
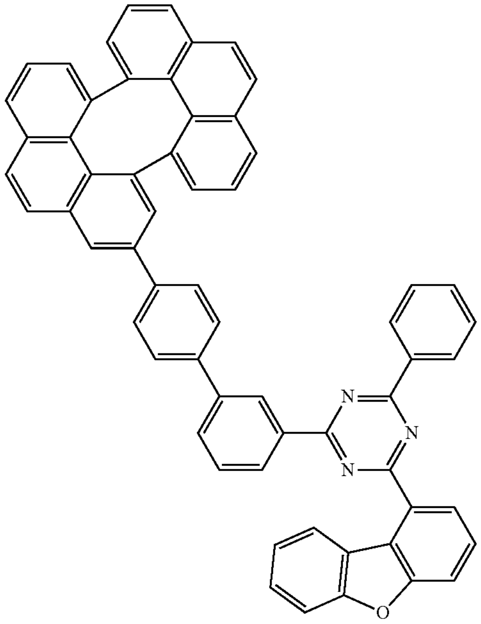
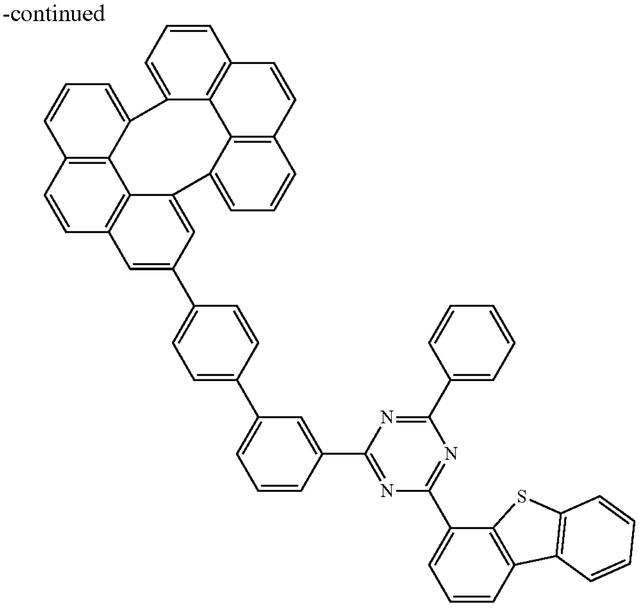
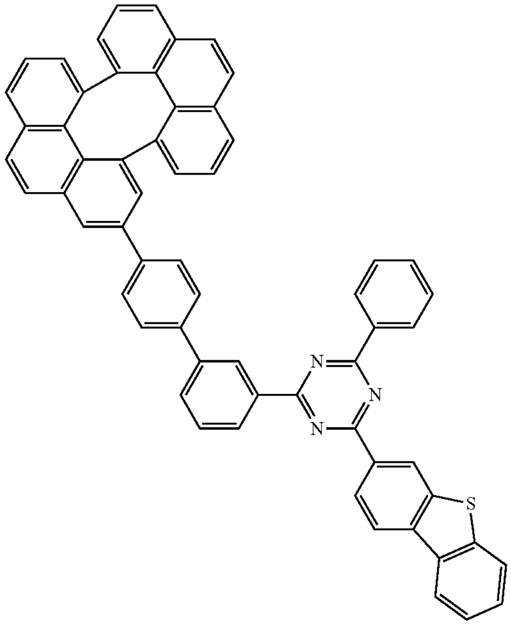
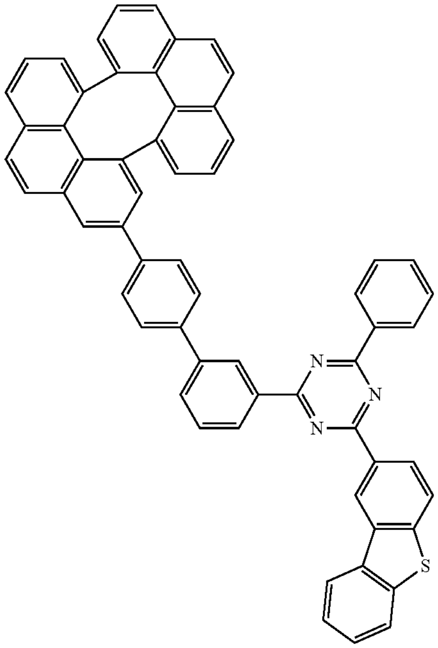

-continued
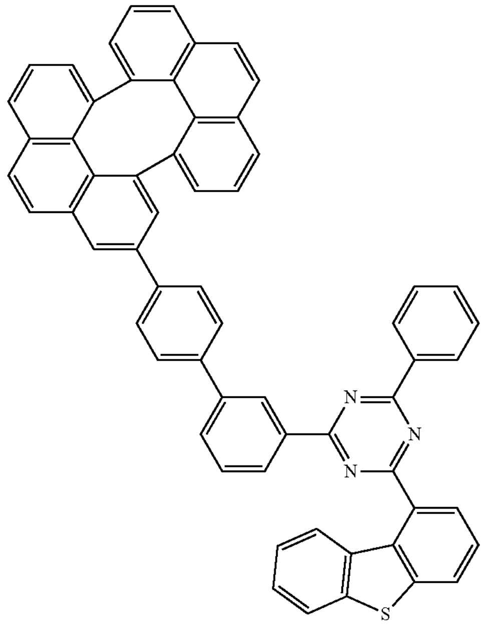
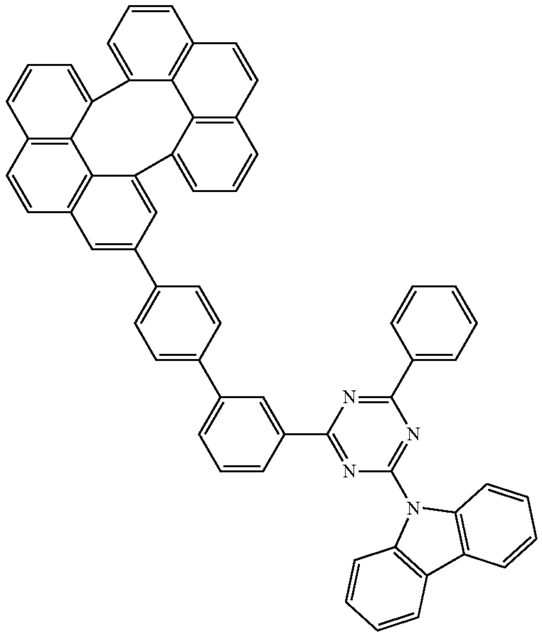
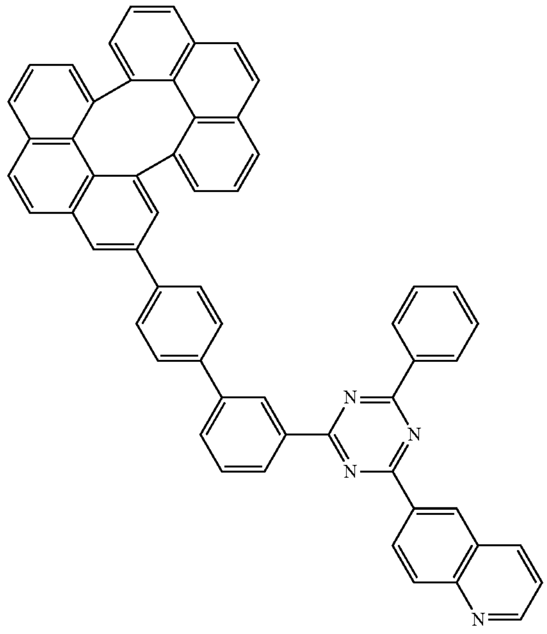
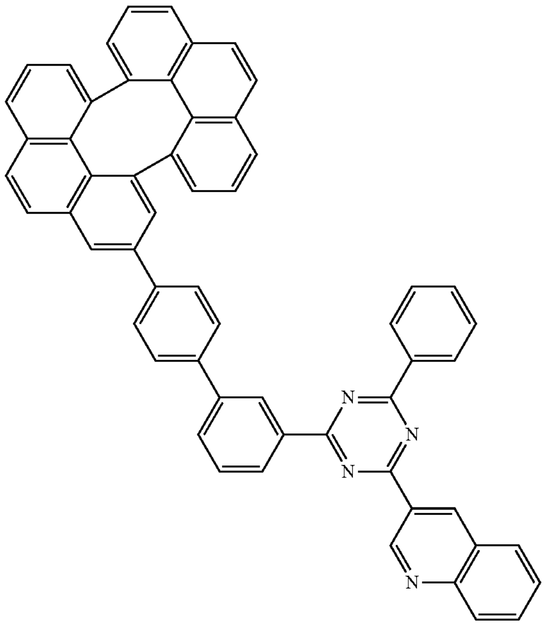

-continued
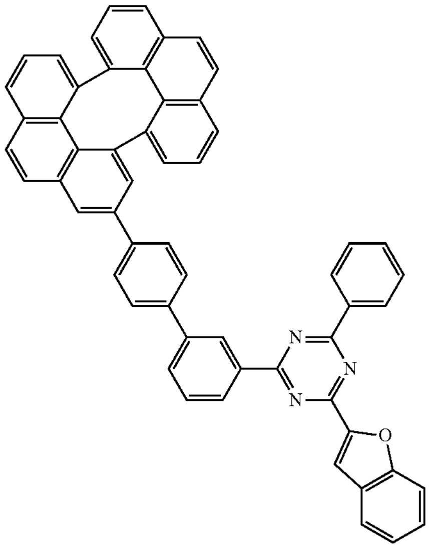
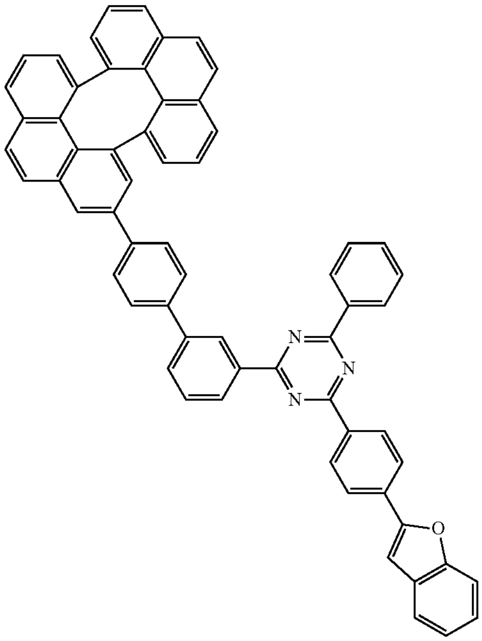
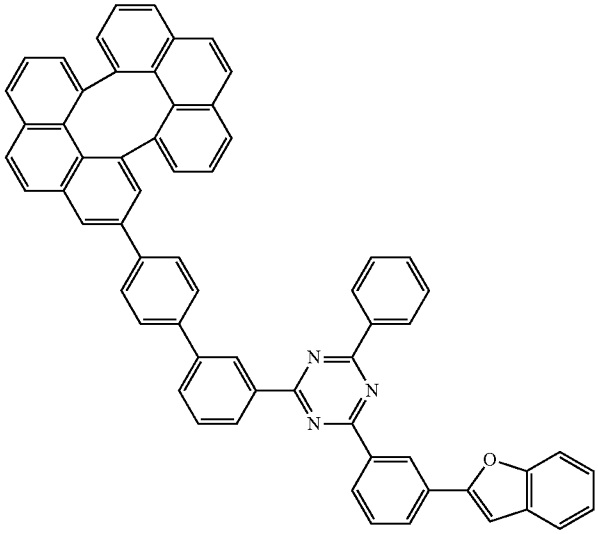
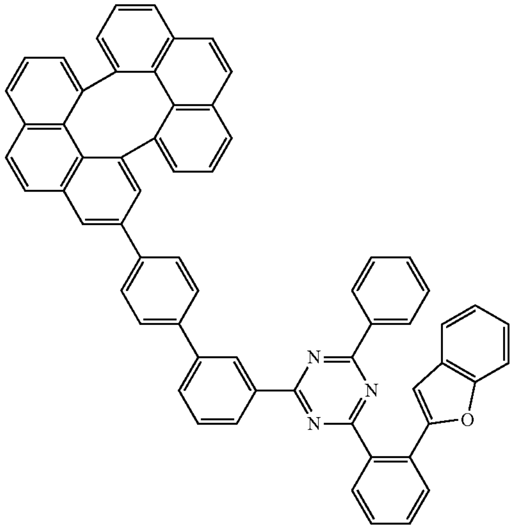

-continued
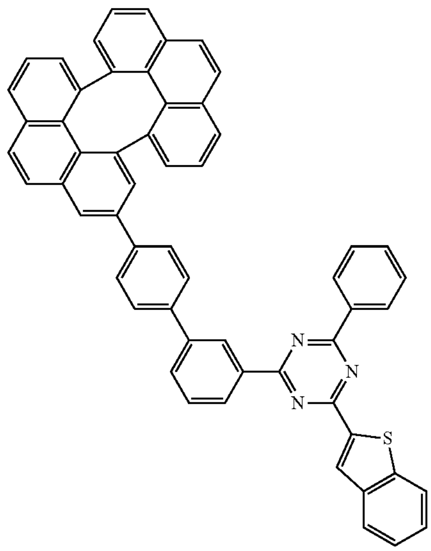
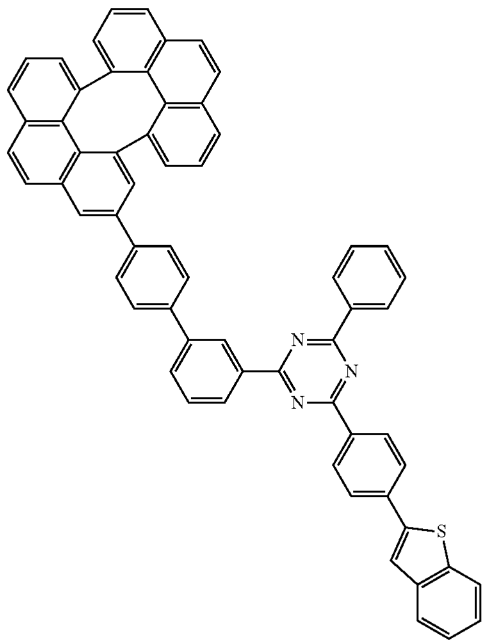
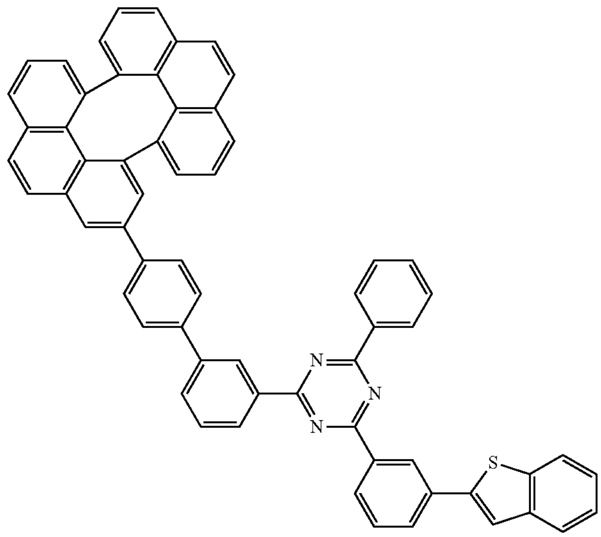
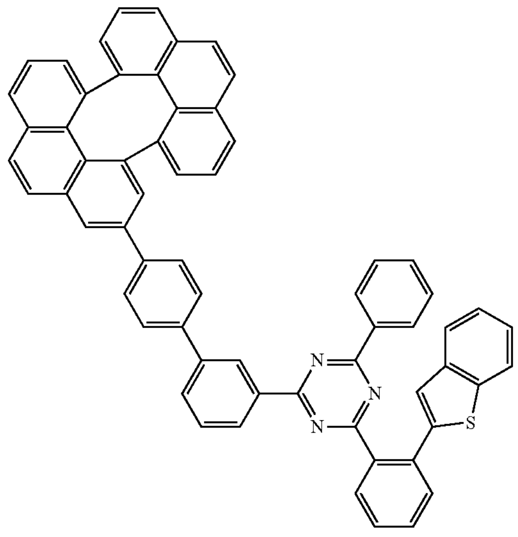

-continued
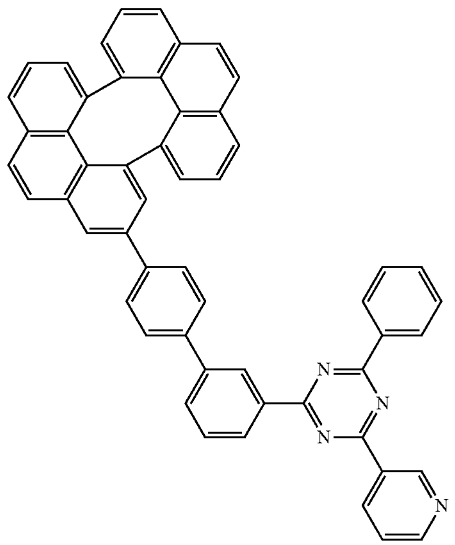
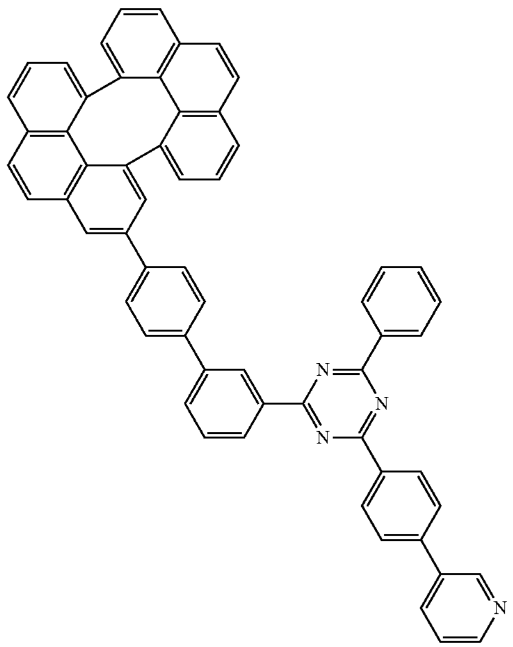
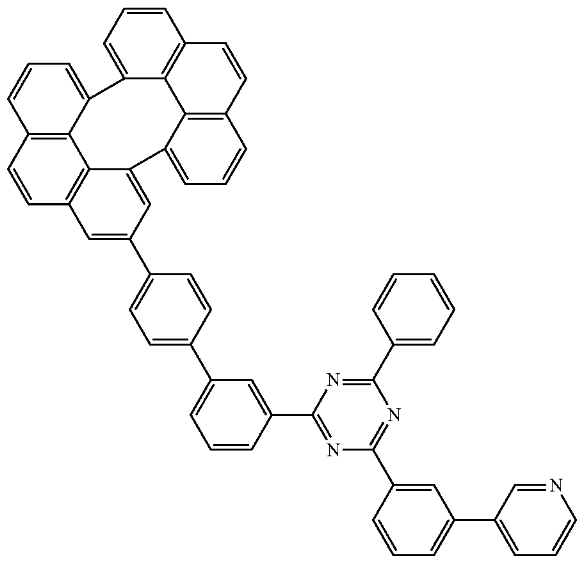
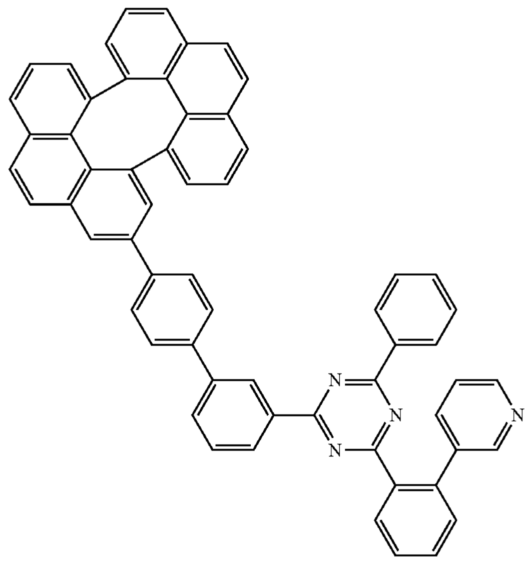

-continued
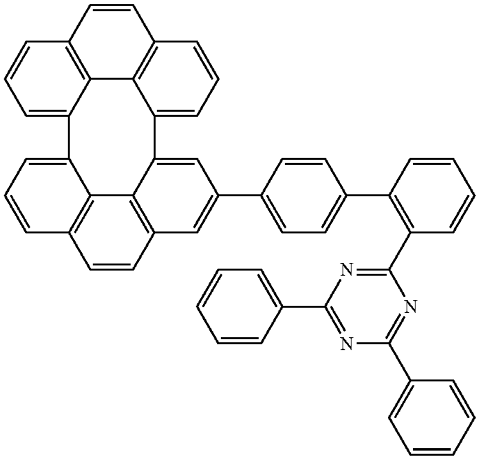
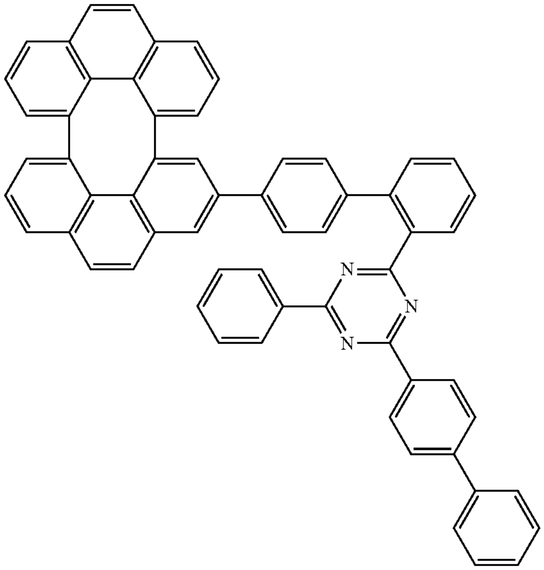
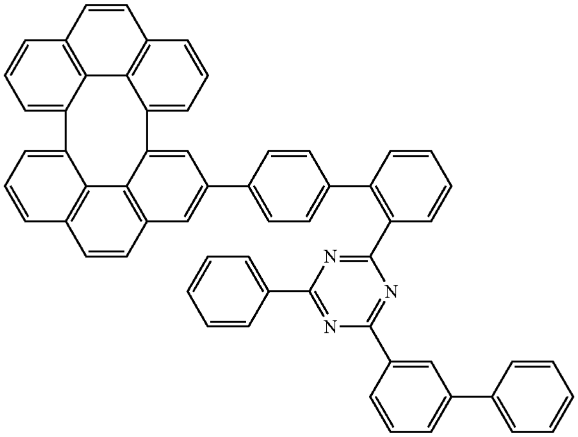
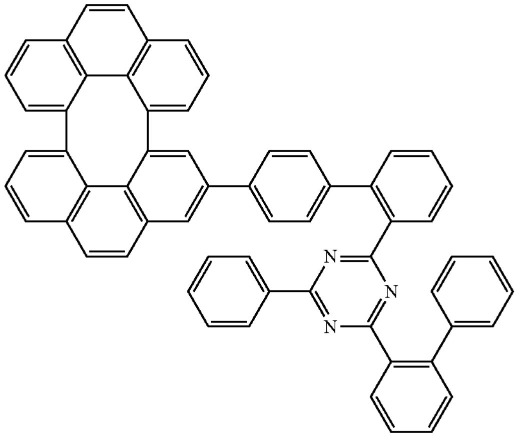
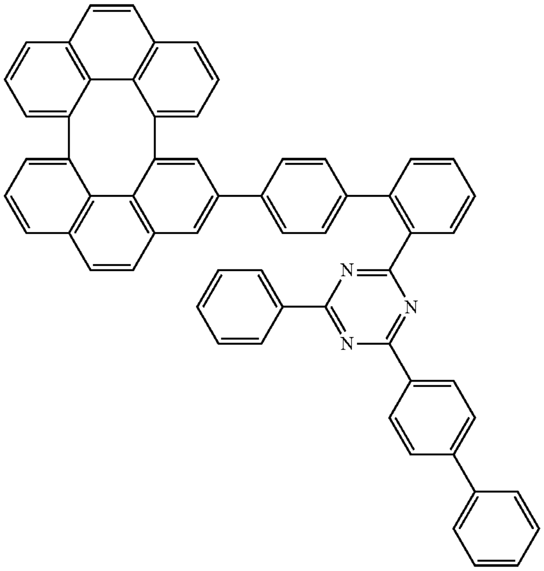
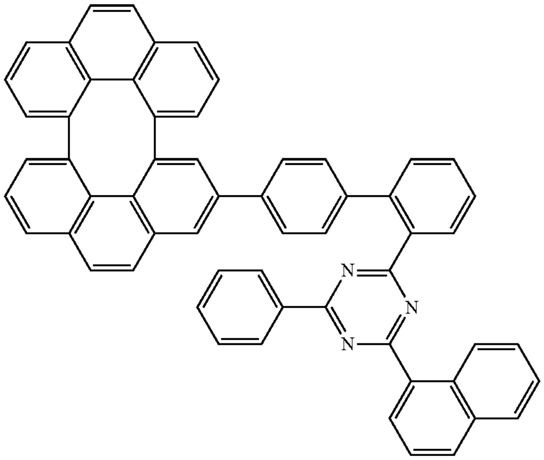

-continued
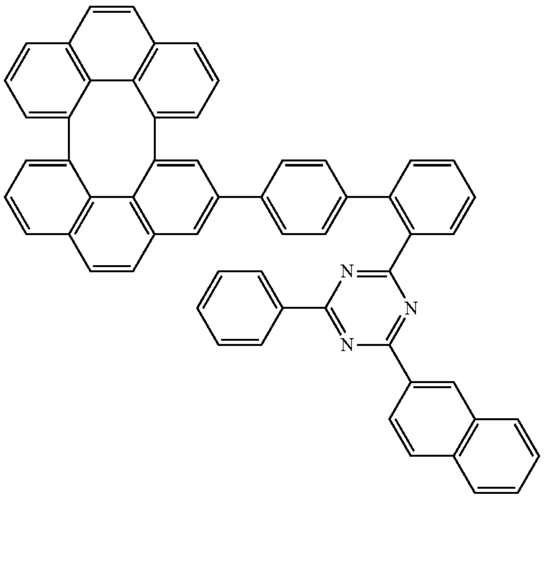
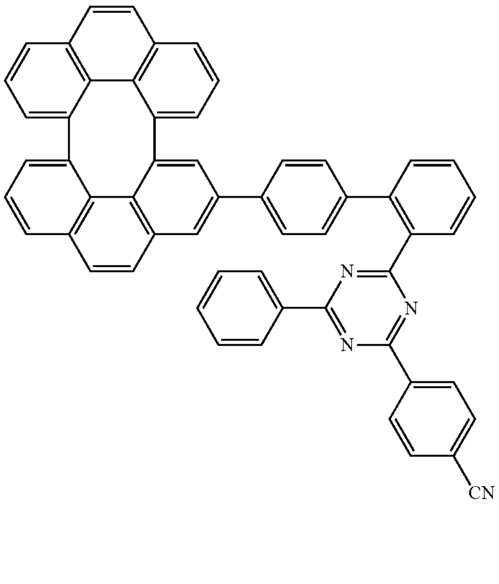
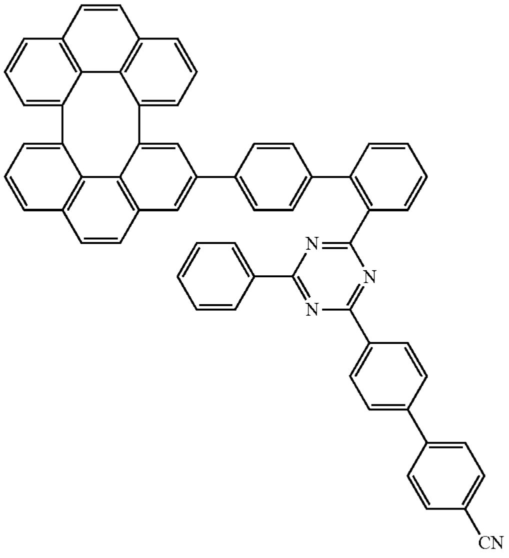
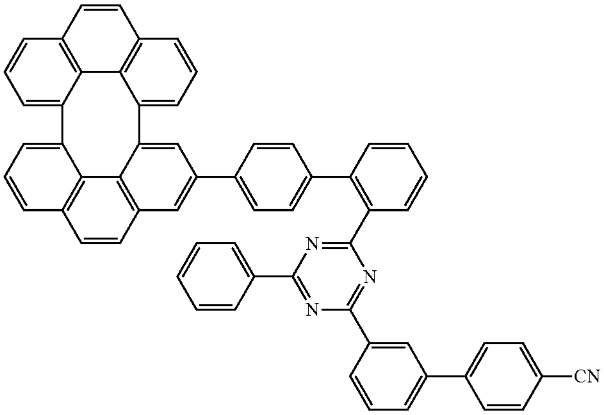
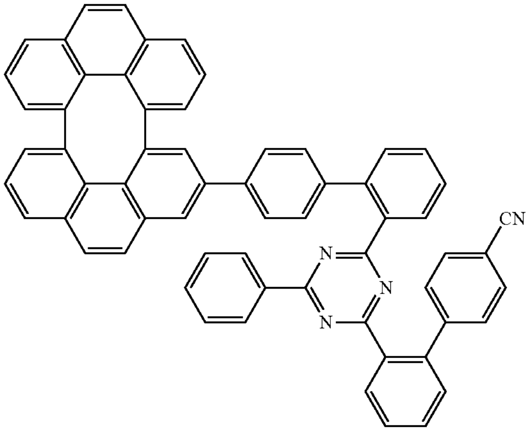
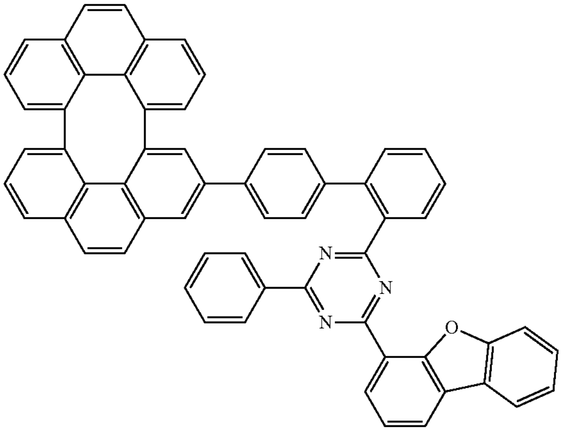

-continued
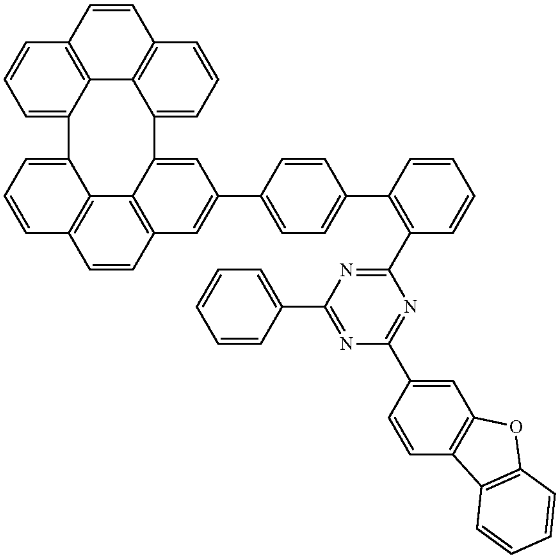
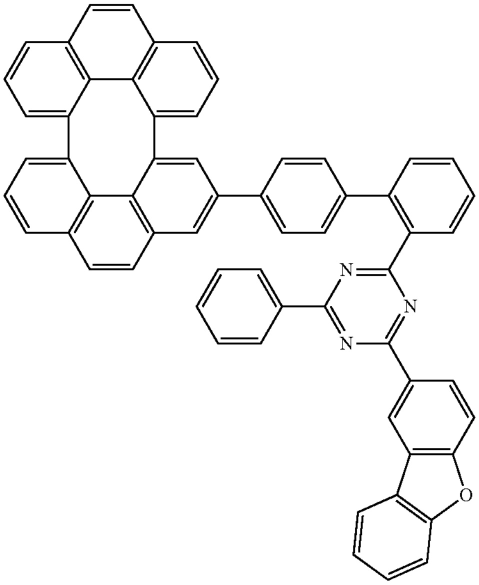
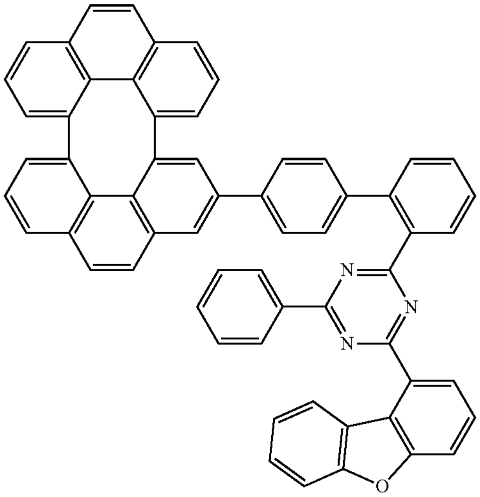
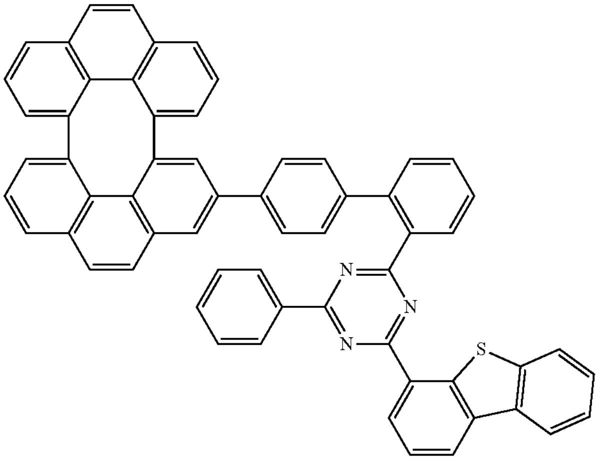
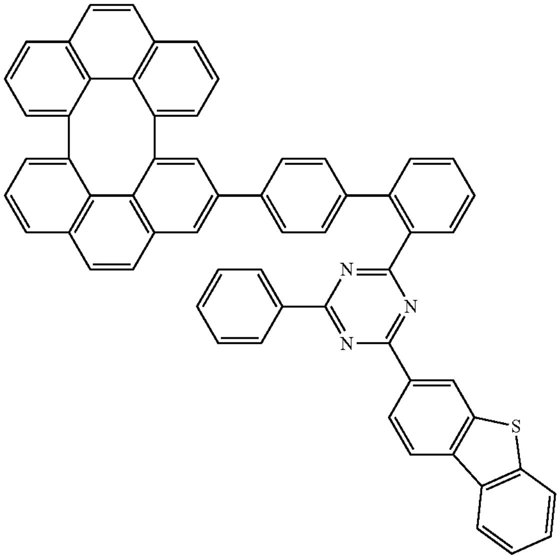
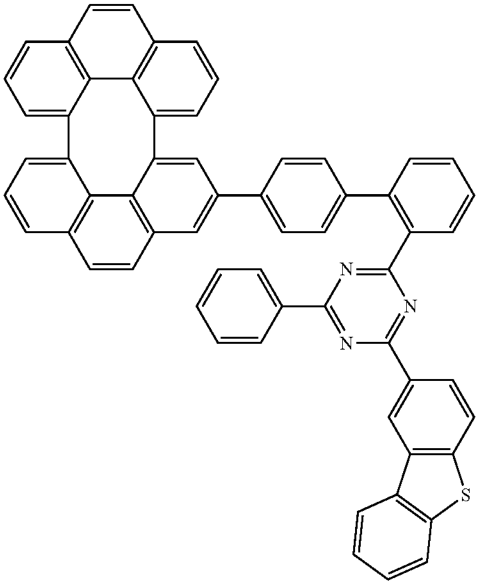

-continued
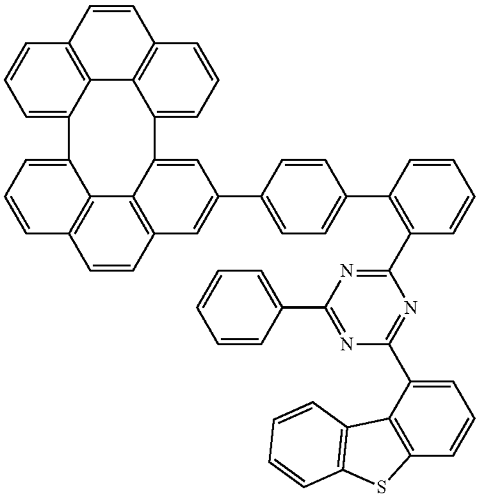
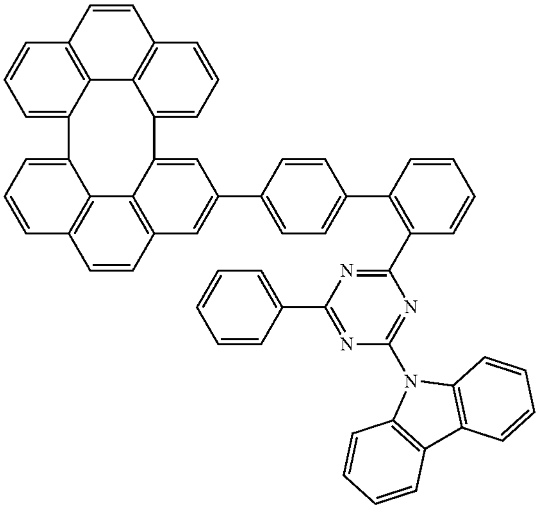
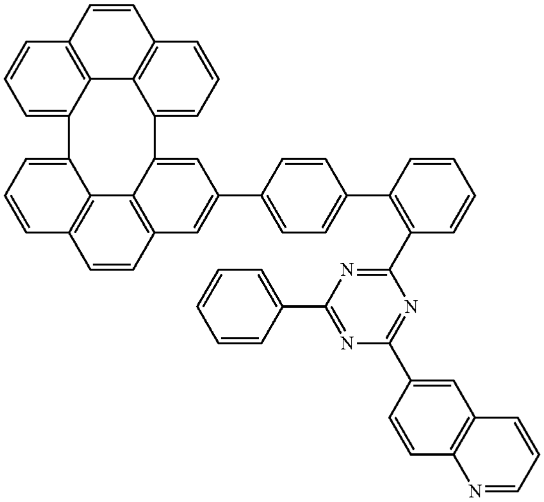
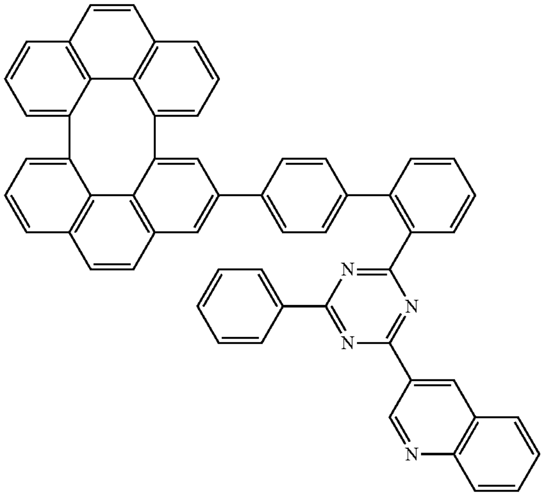
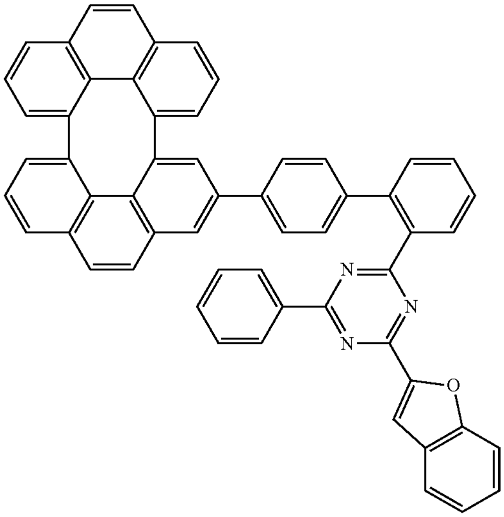
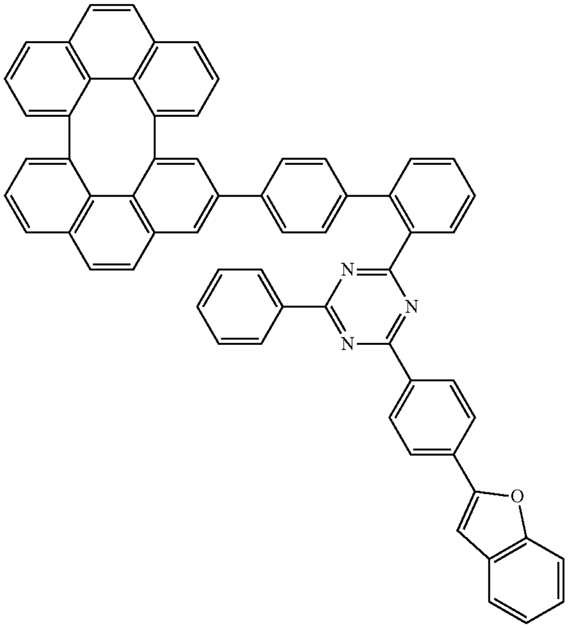

-continued
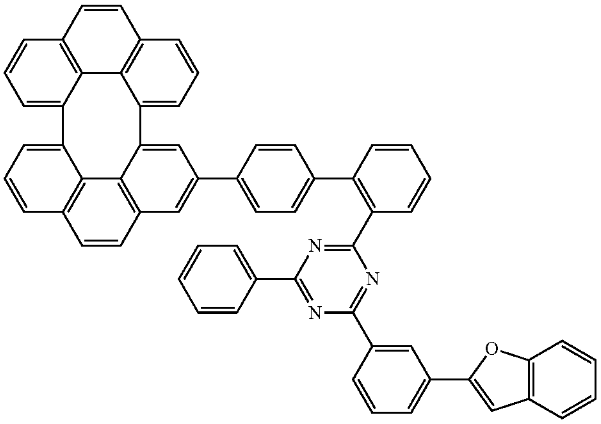
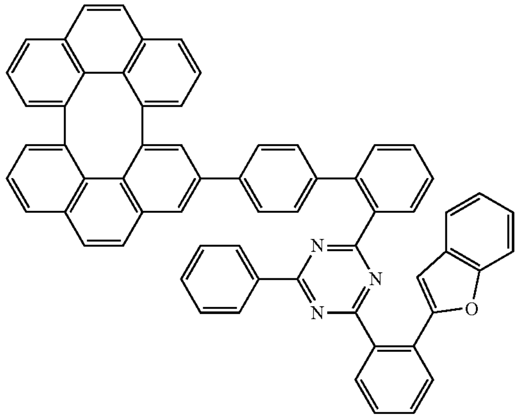
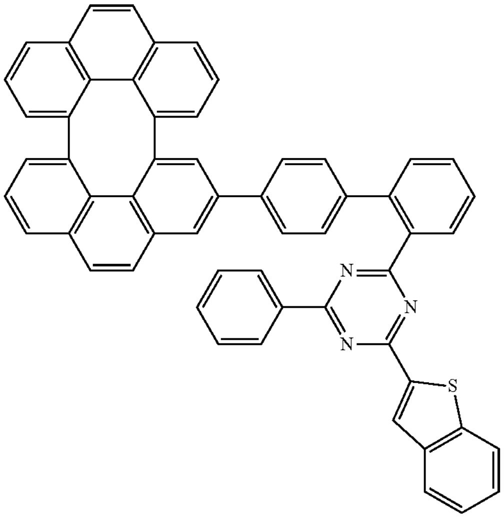
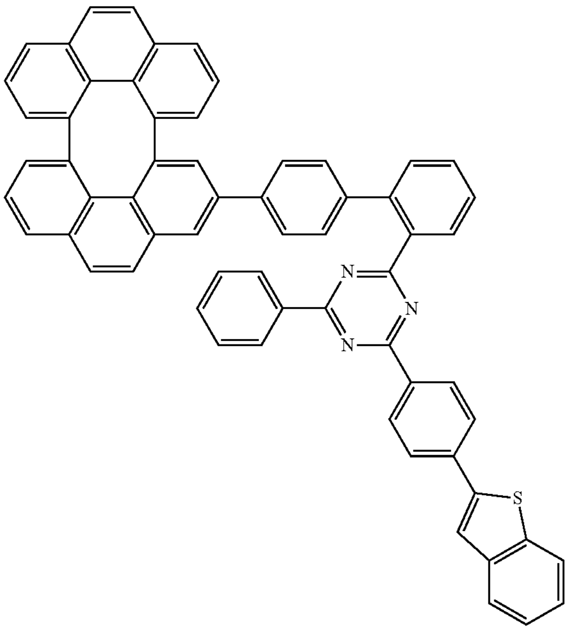
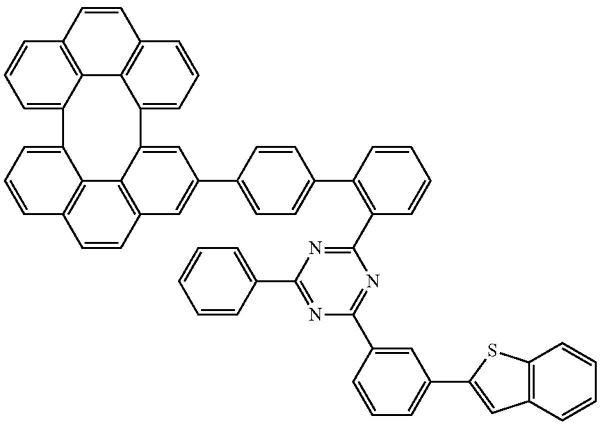
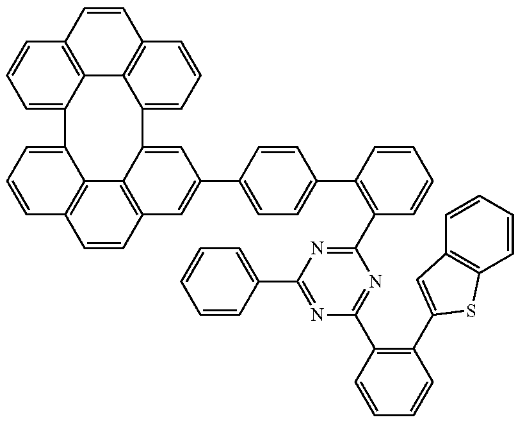

-continued
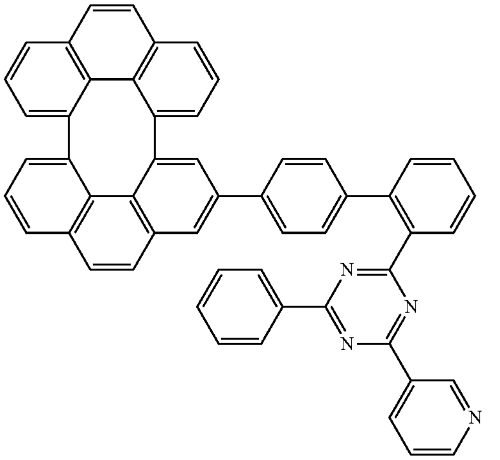
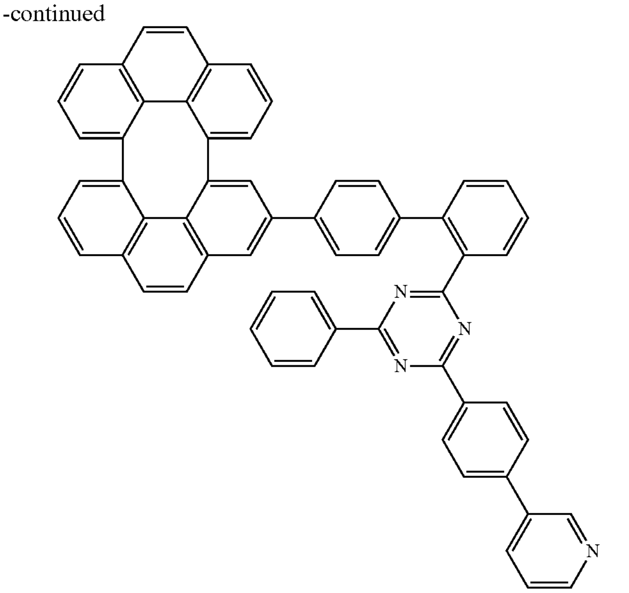
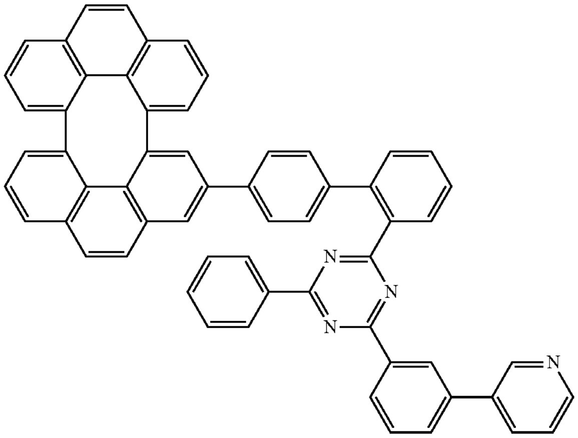
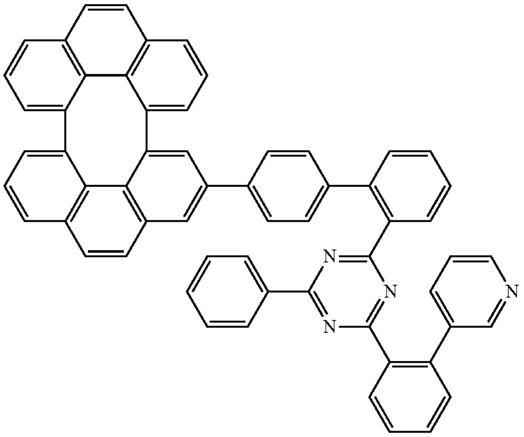
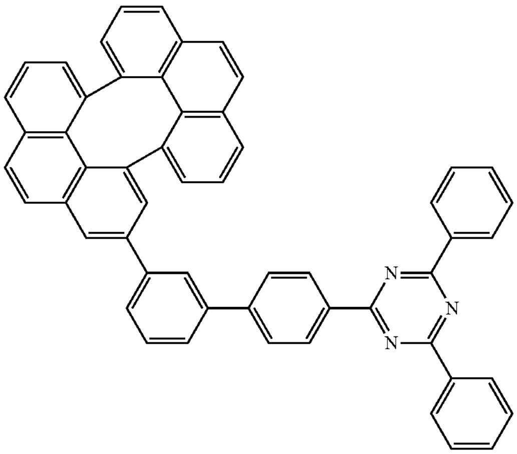
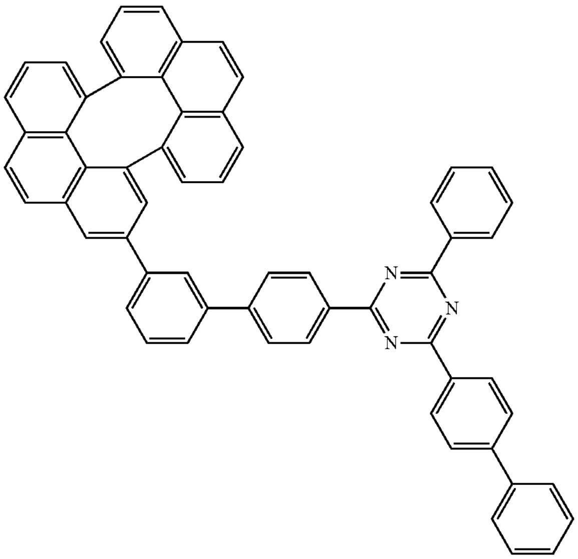

-continued
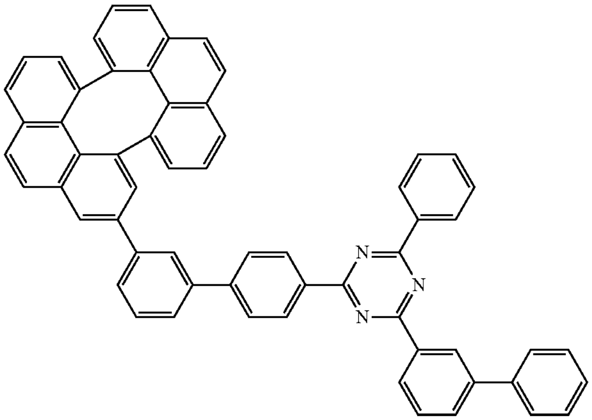
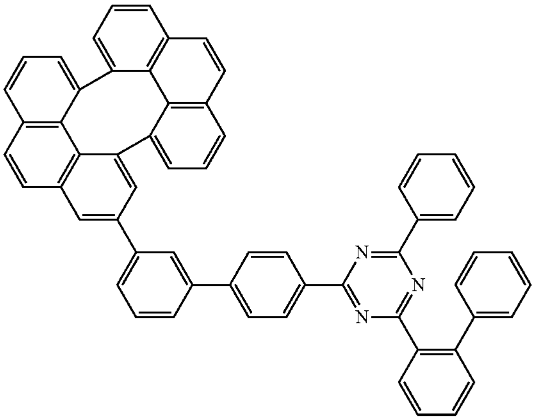
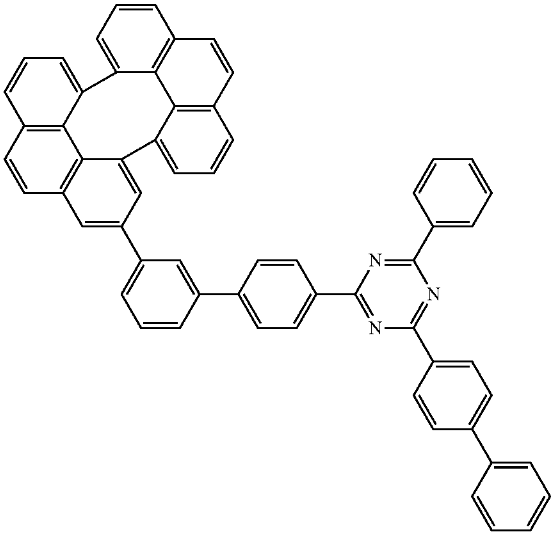
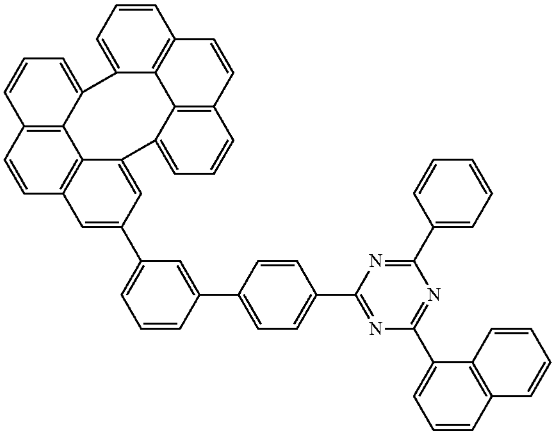
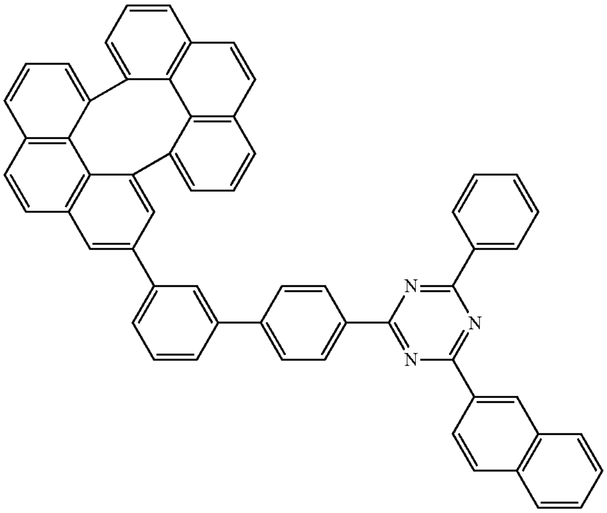
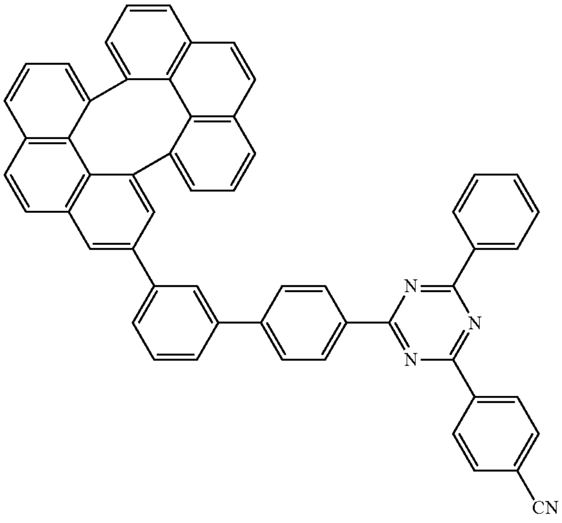

-continued
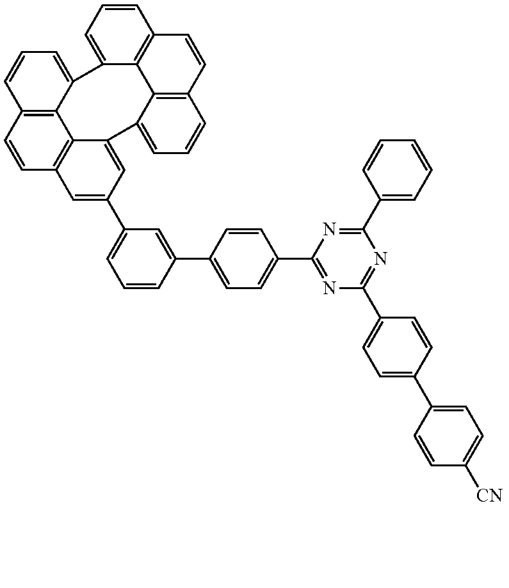
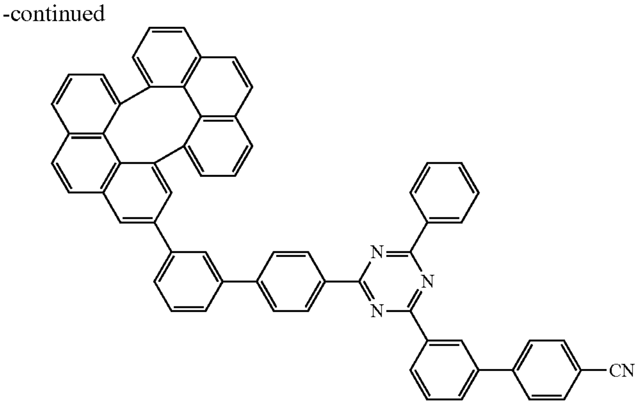
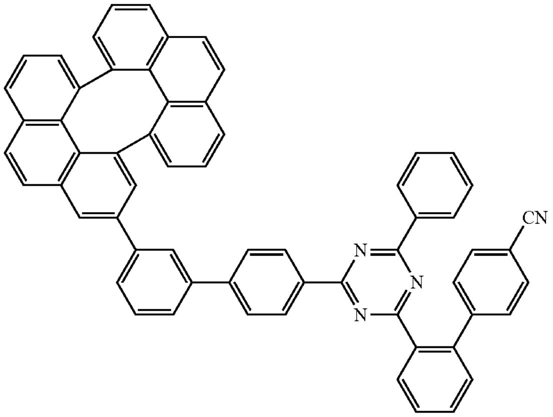
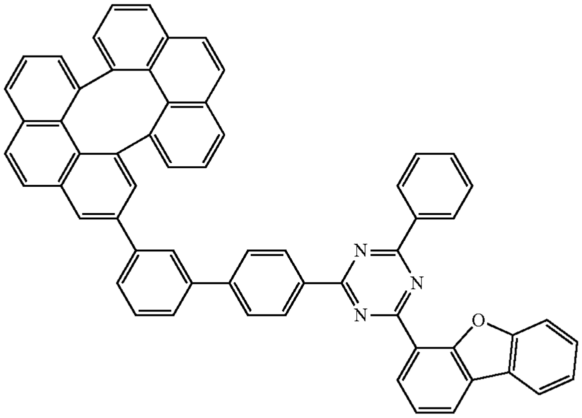
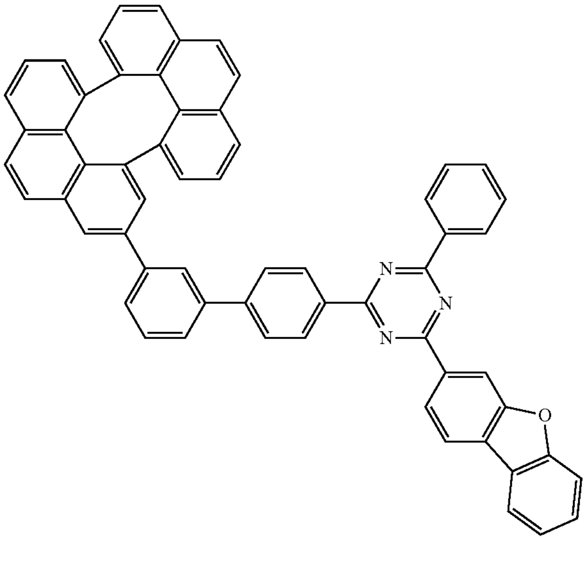
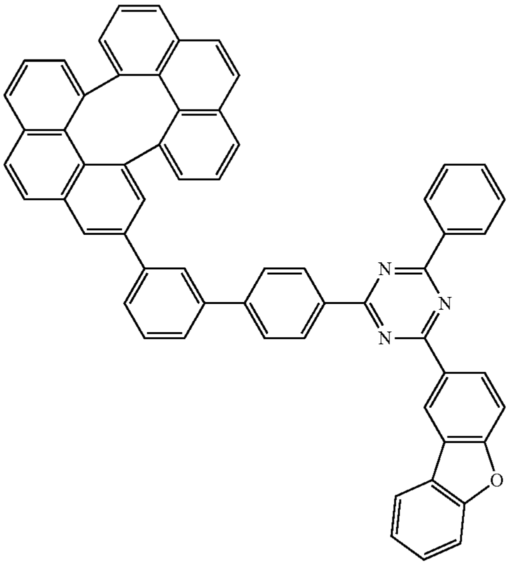

-continued
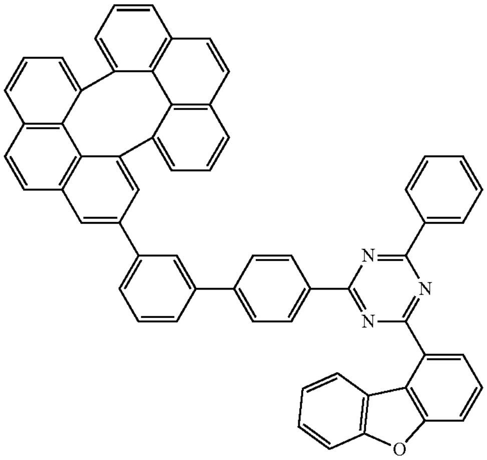
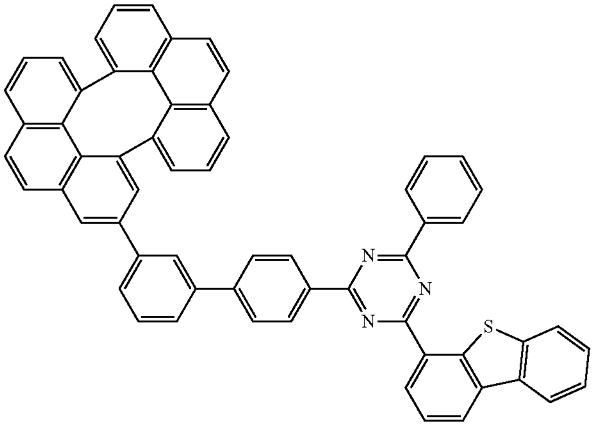
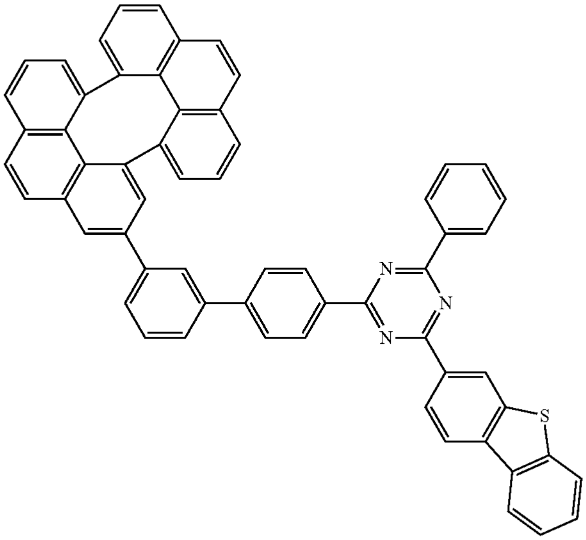
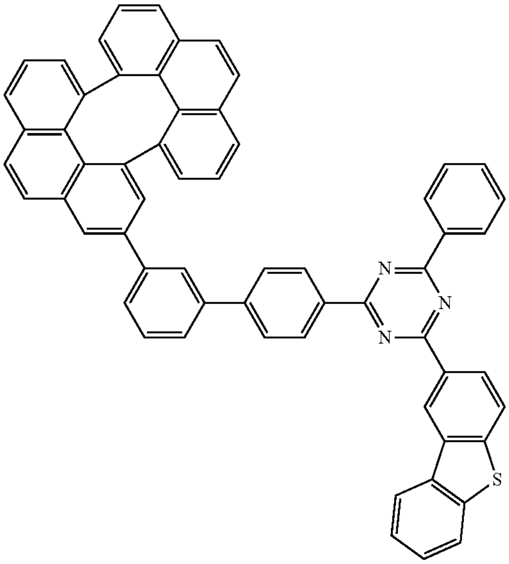
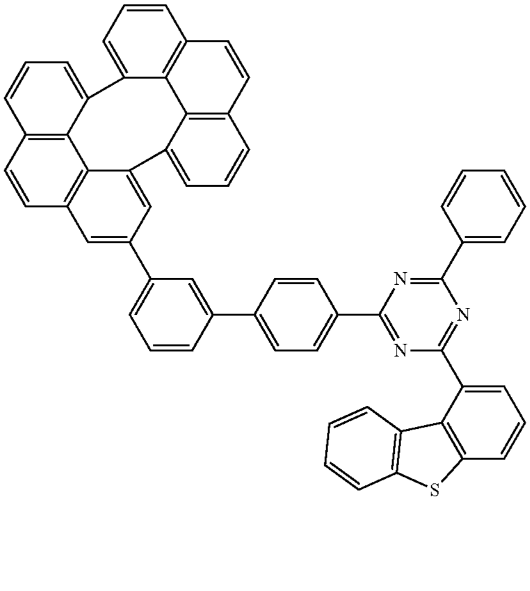
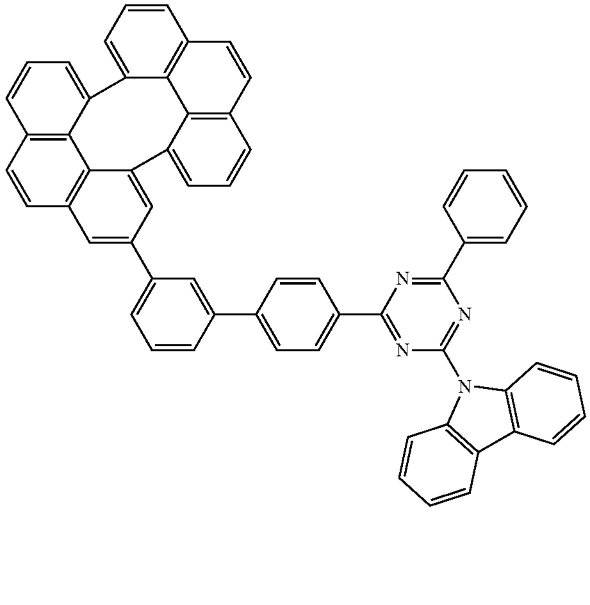

-continued
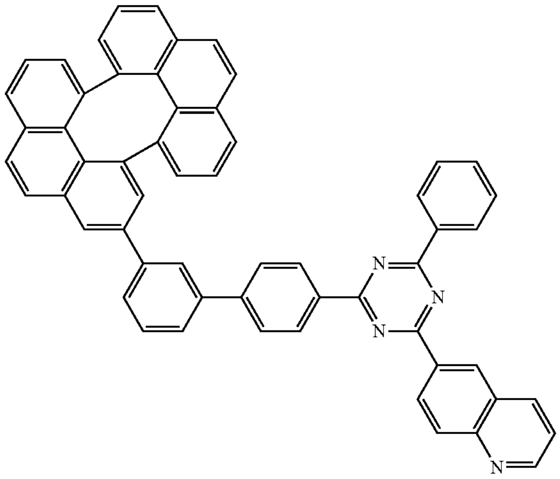
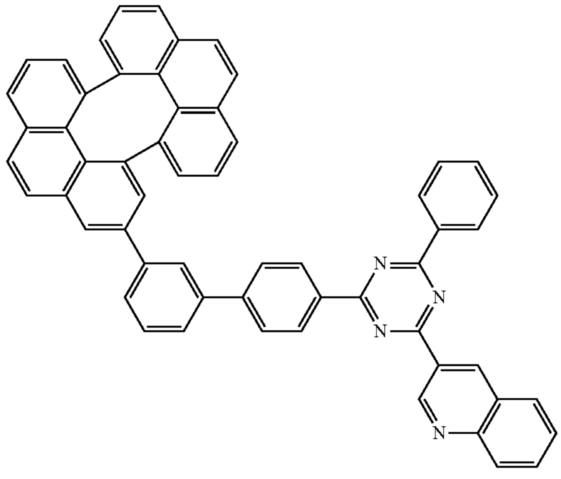
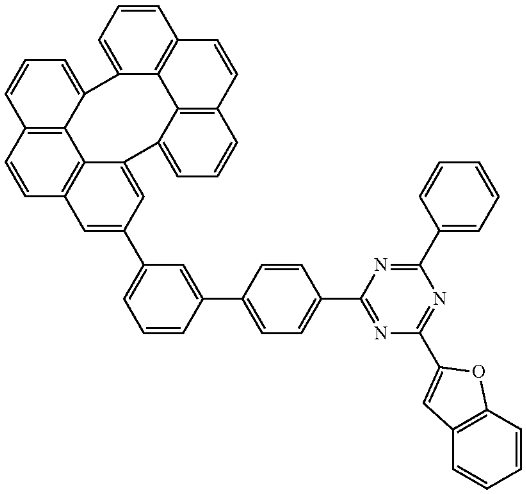
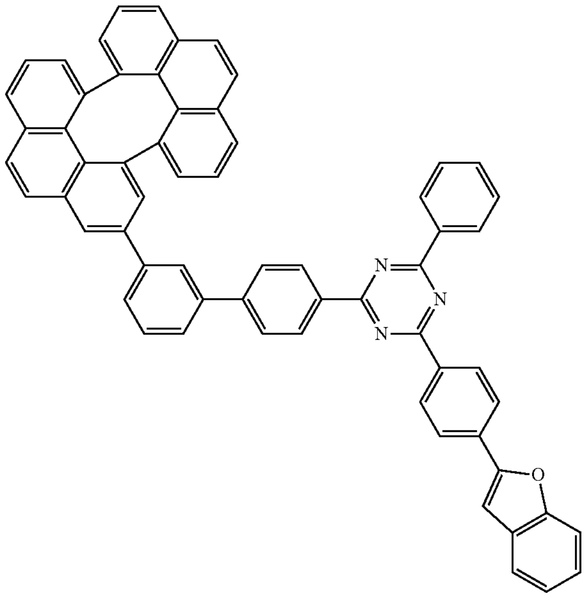
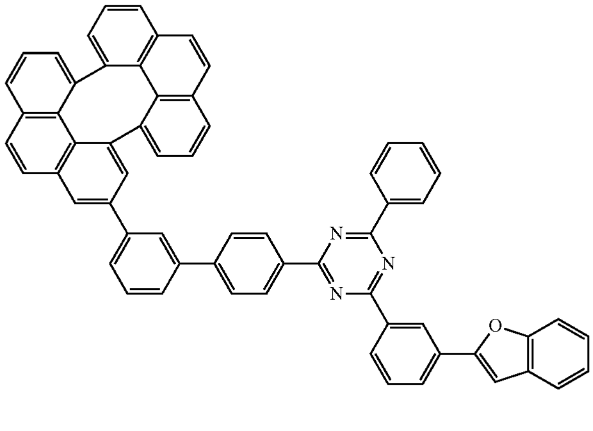
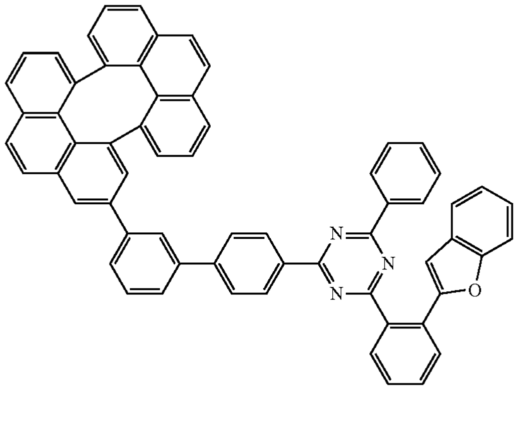

-continued
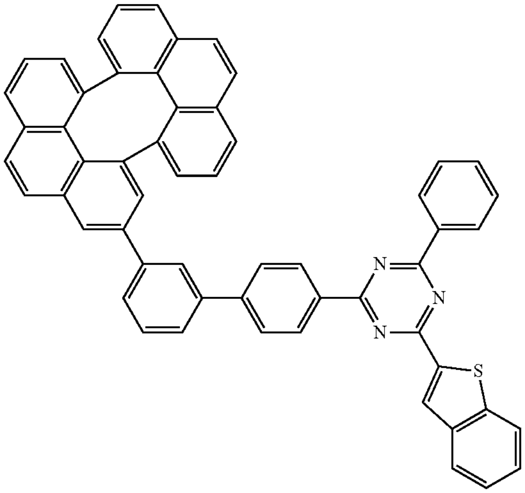
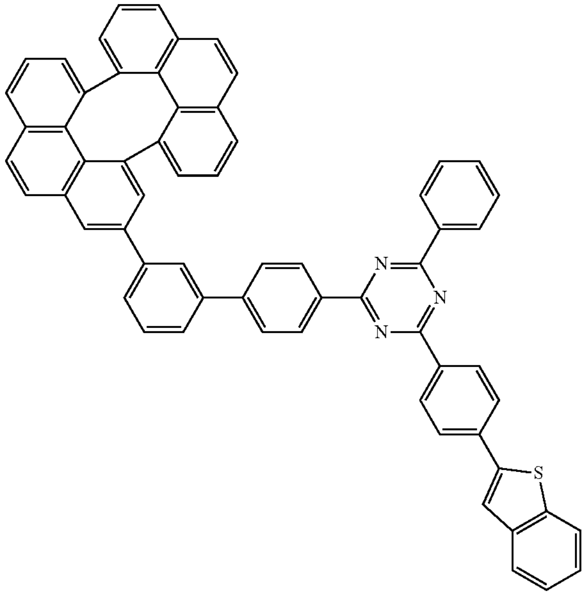
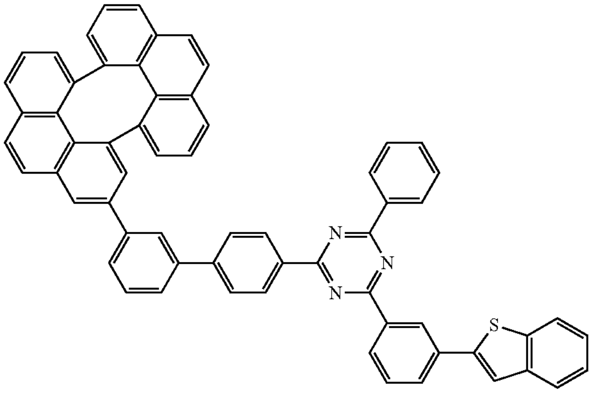
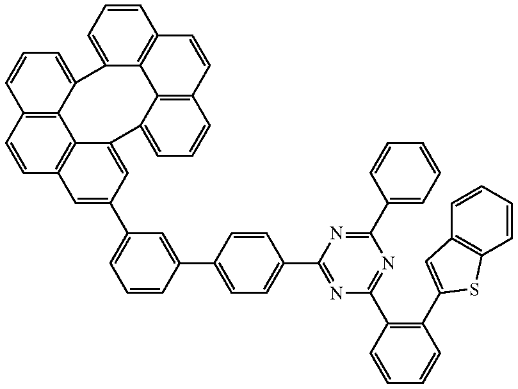
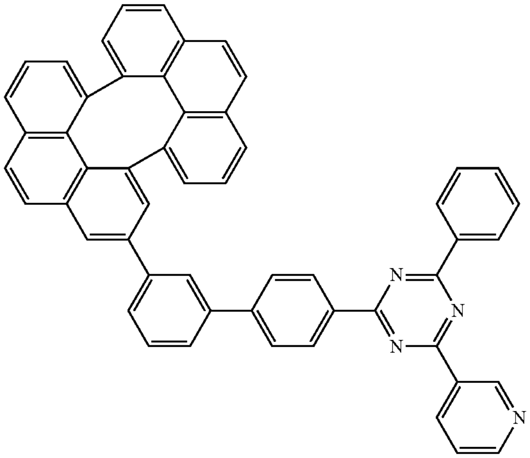
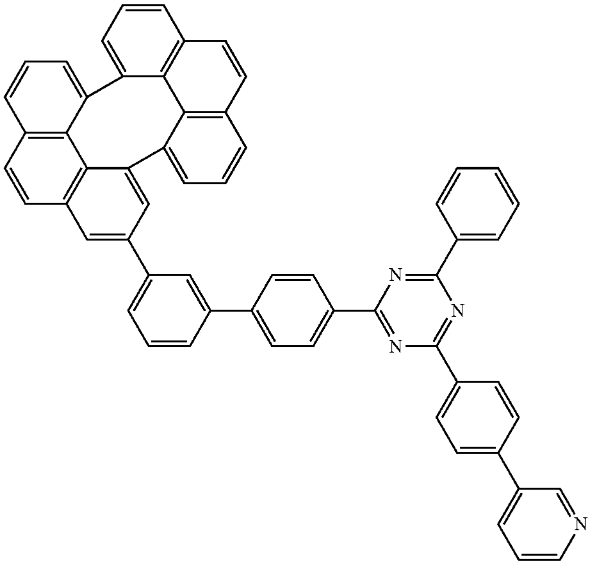

-continued
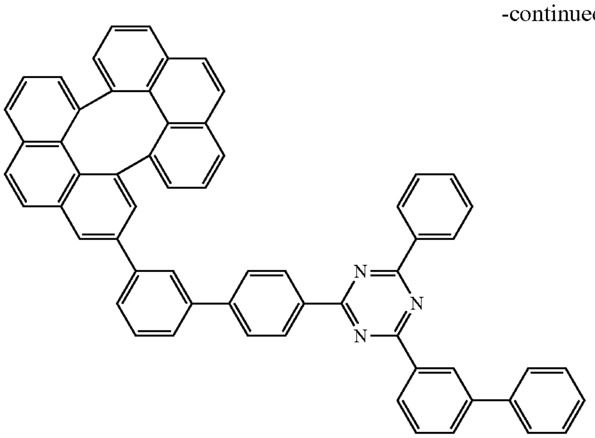
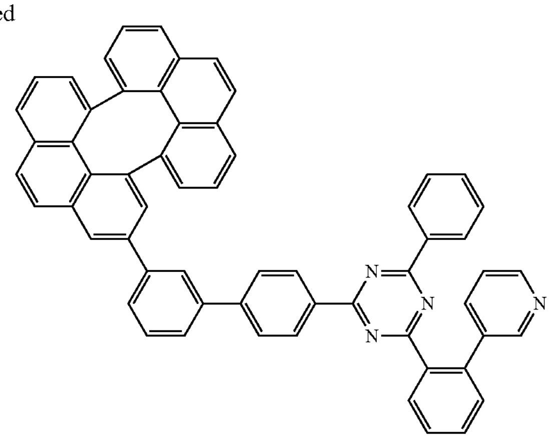
-continued
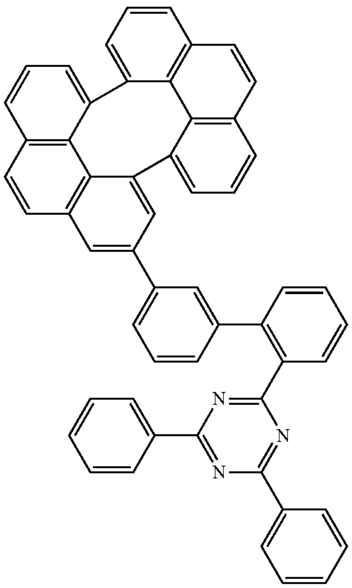
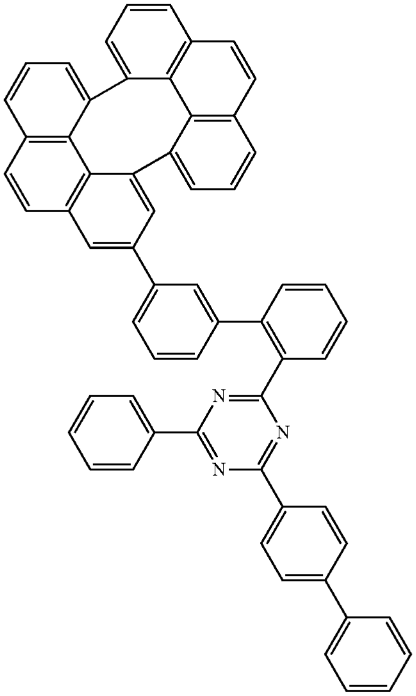

-continued
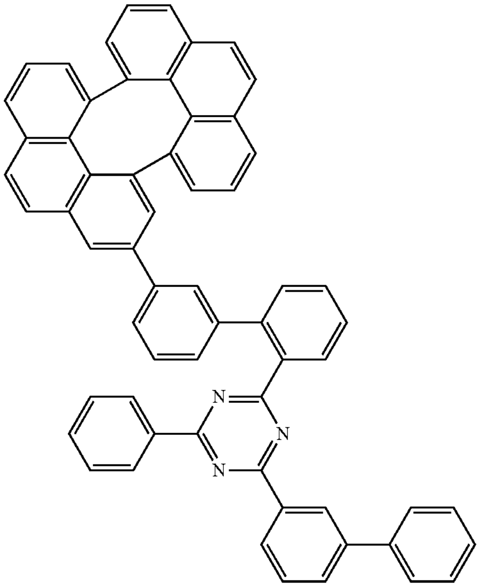
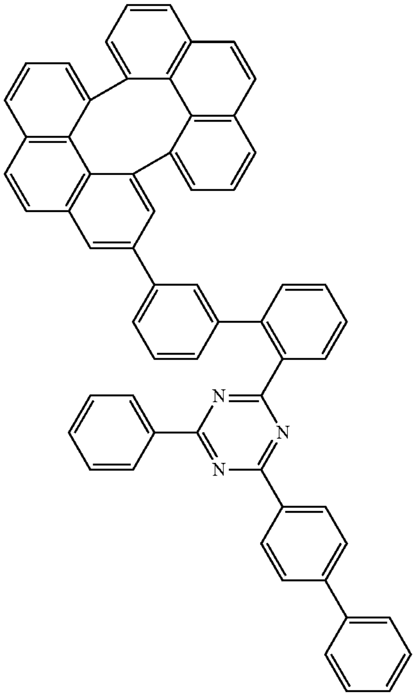
-continued
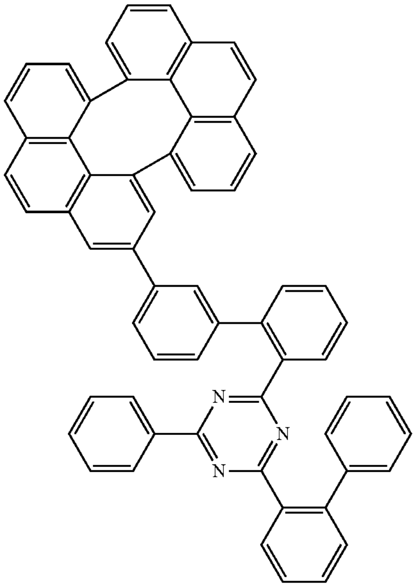
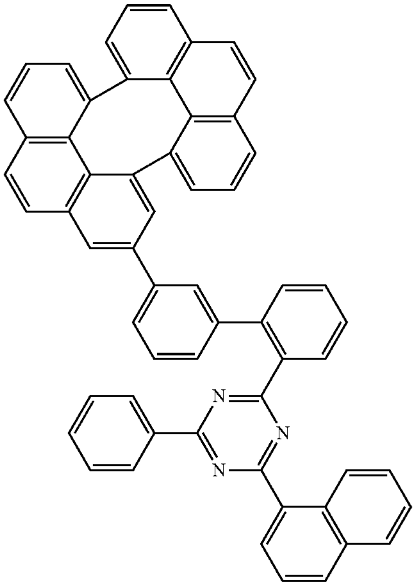

-continued
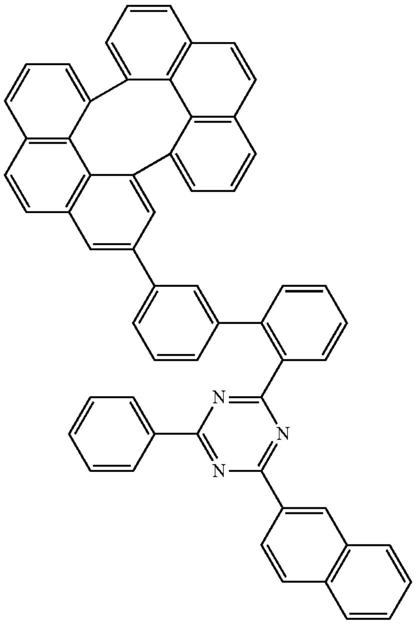
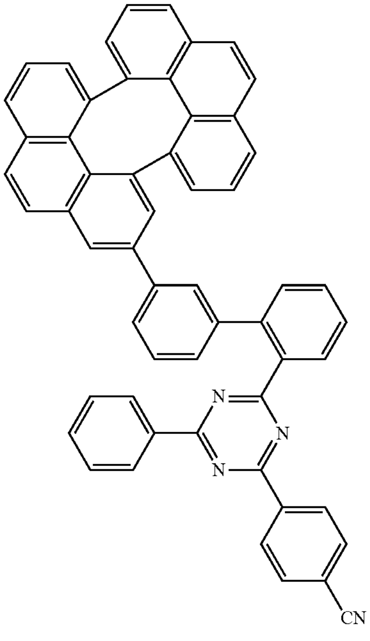
-continued
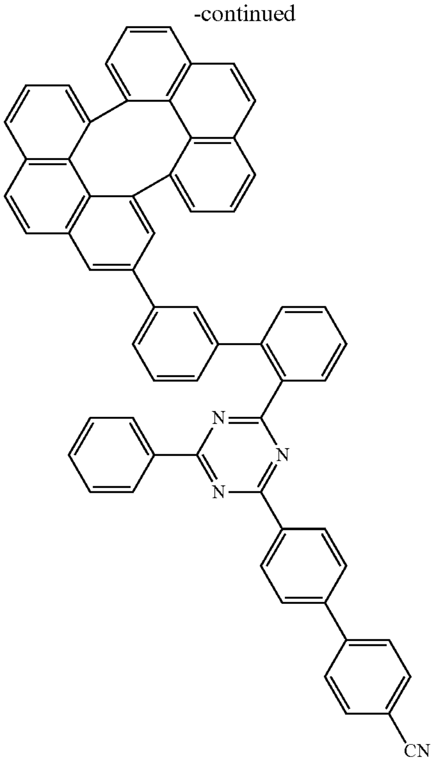
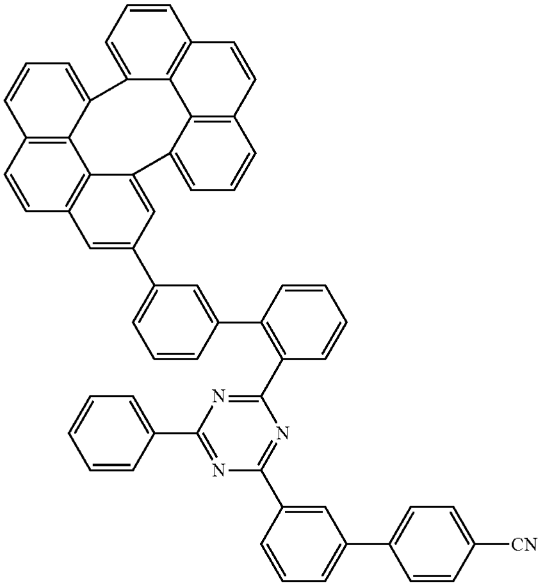

-continued
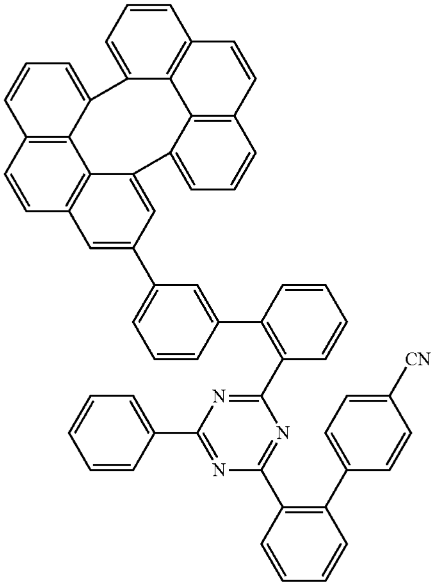
-continued
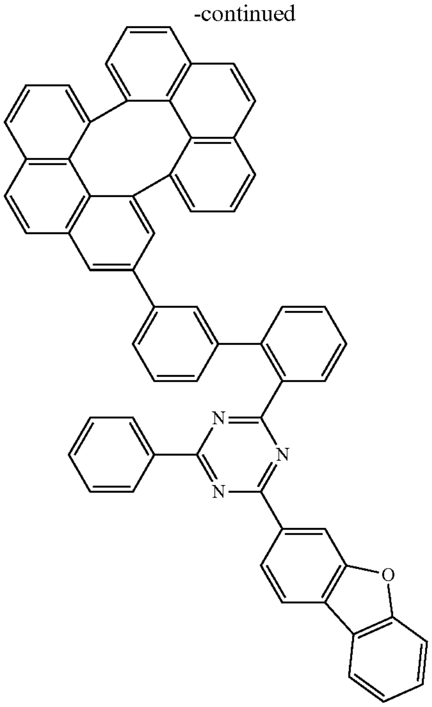
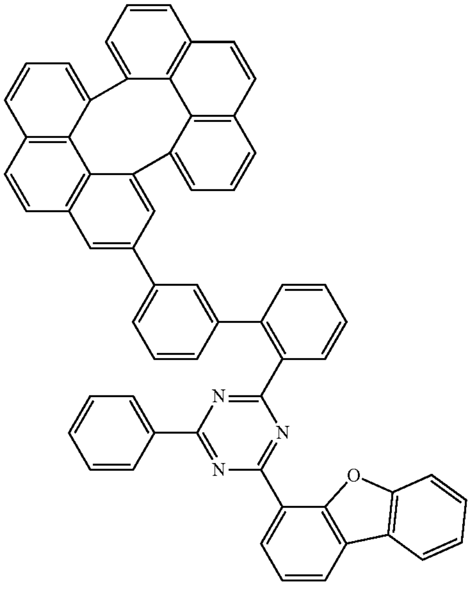
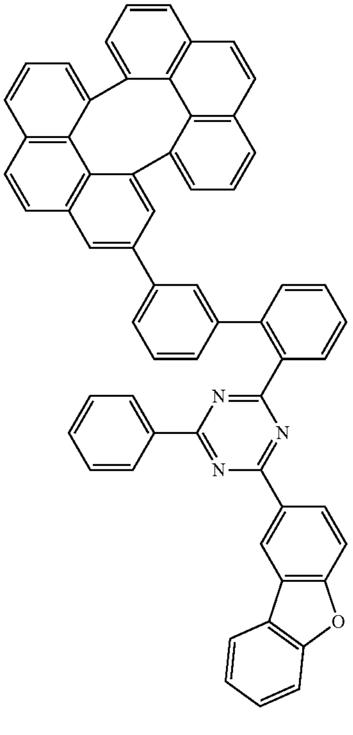

-continued
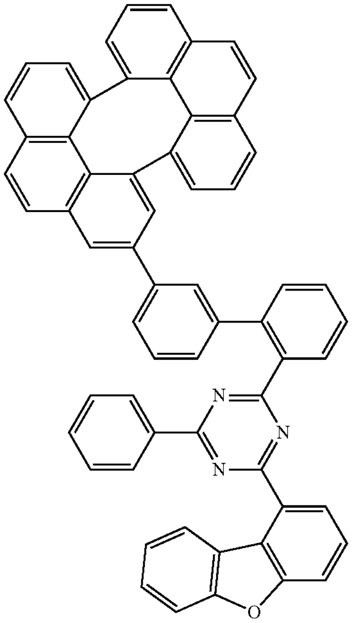
-continued
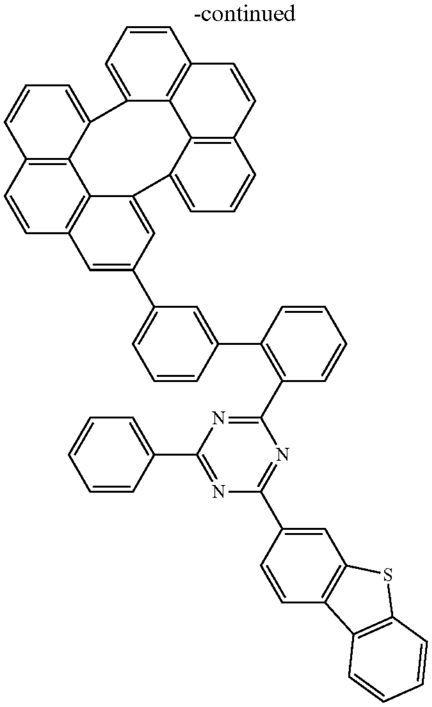
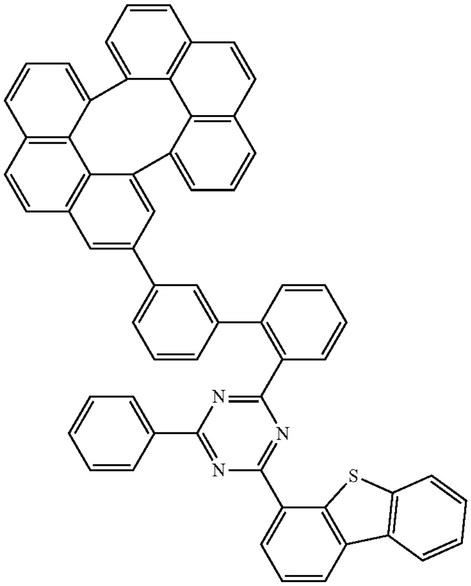
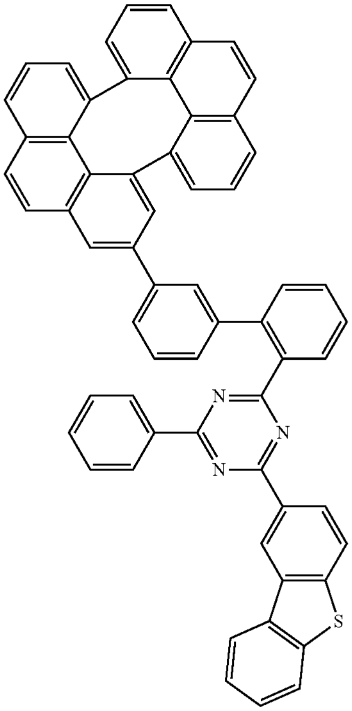

-continued
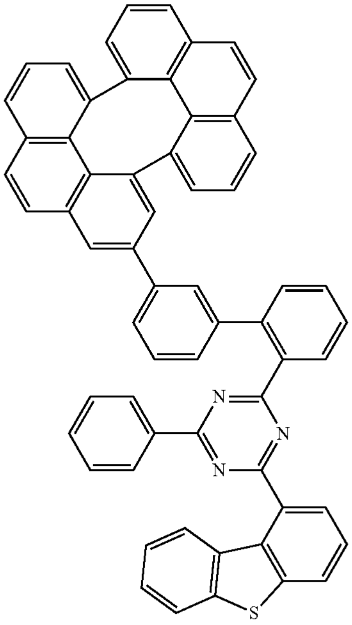
-continued
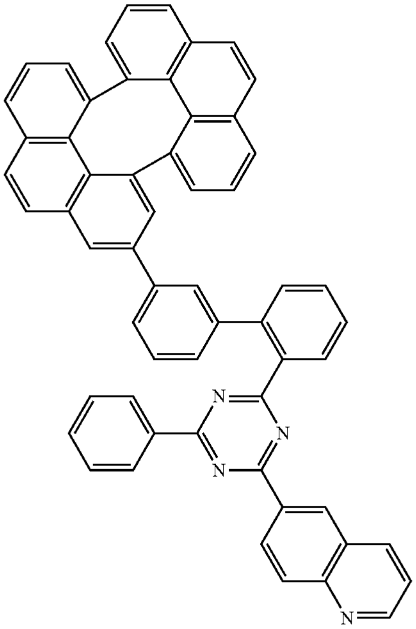
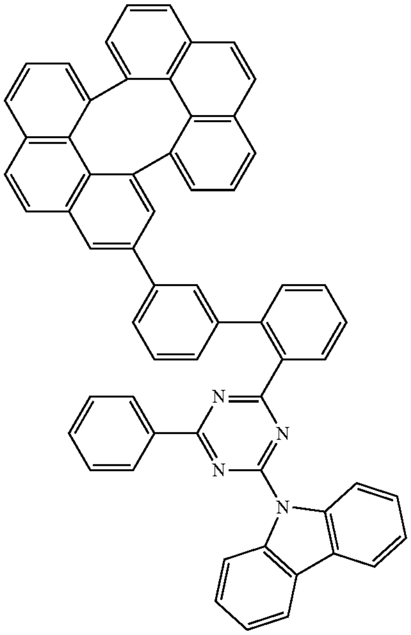
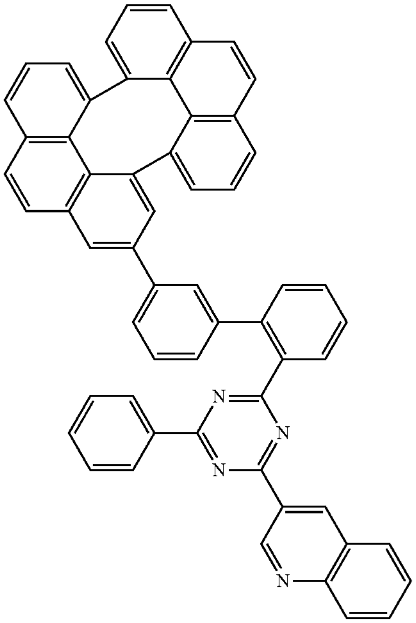

-continued
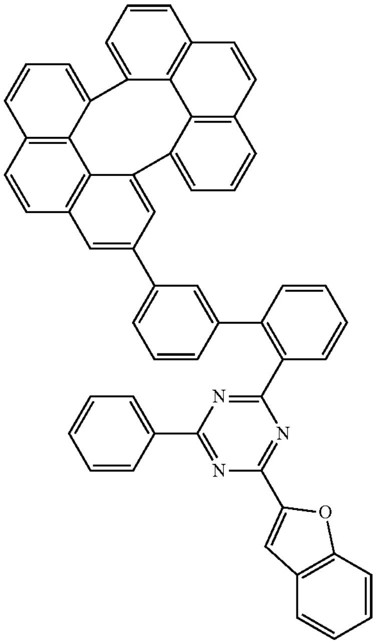
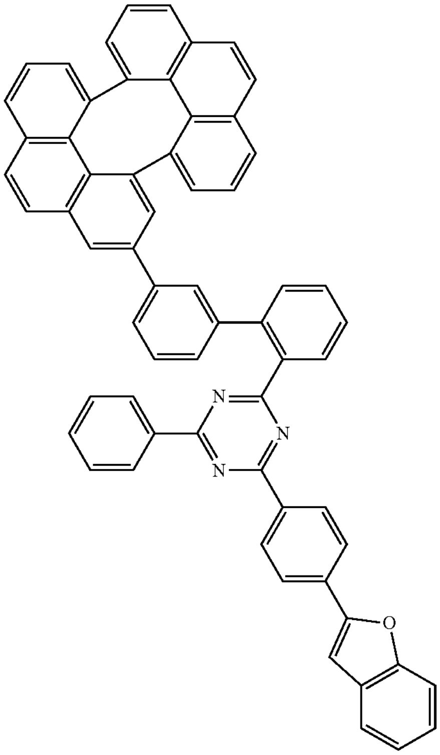
-continued
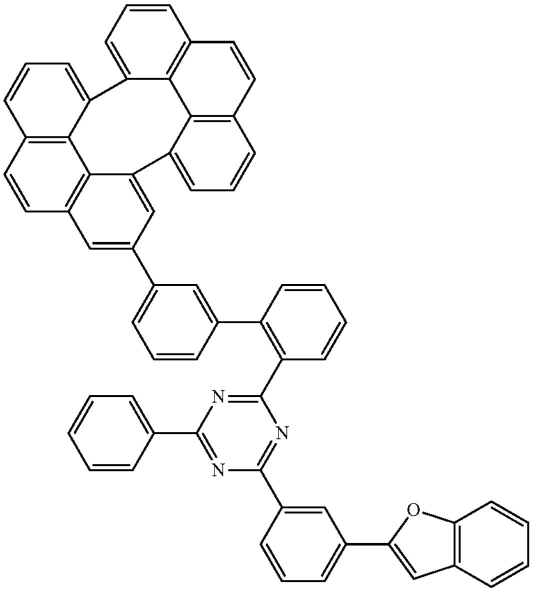
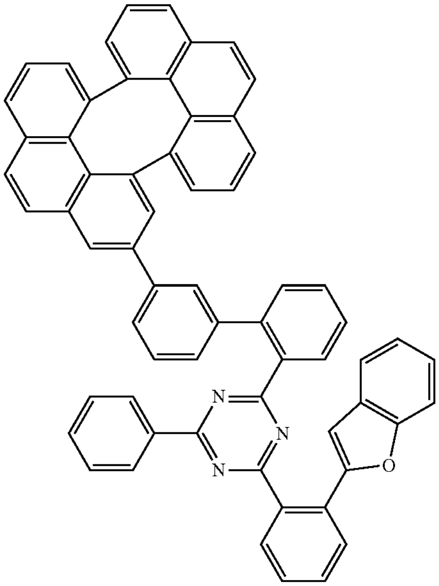

-continued
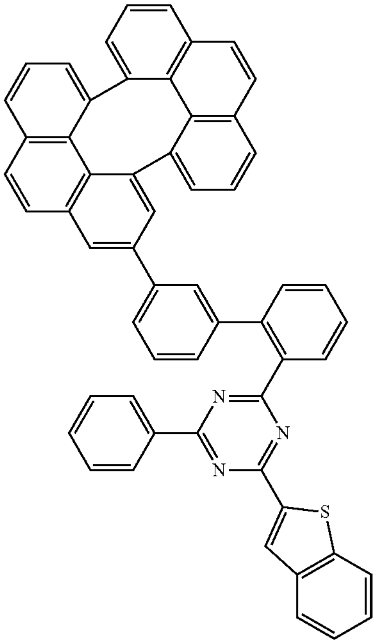
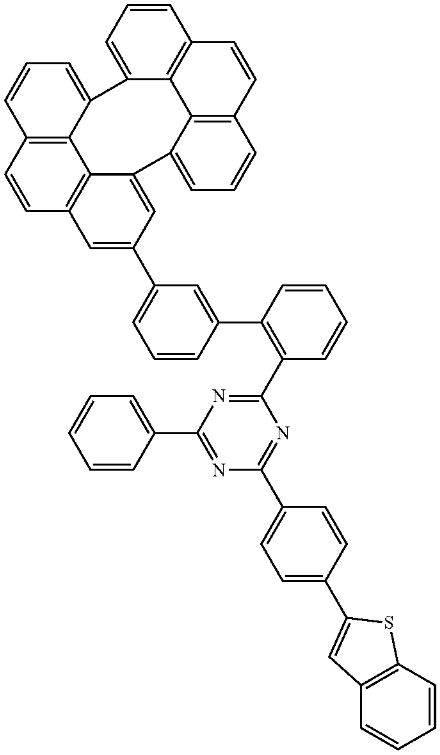
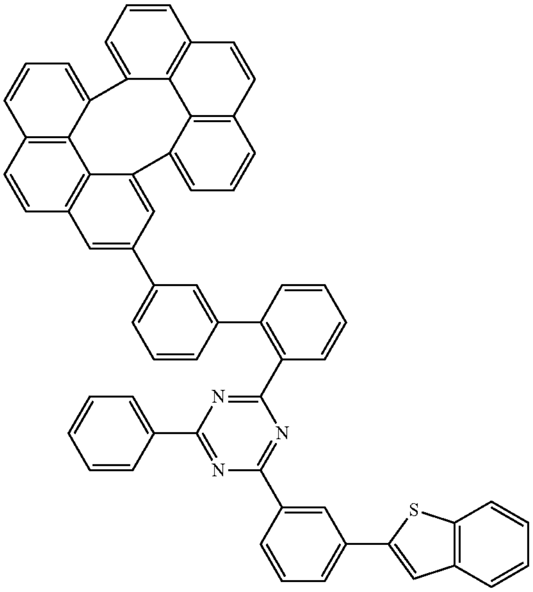
-continued
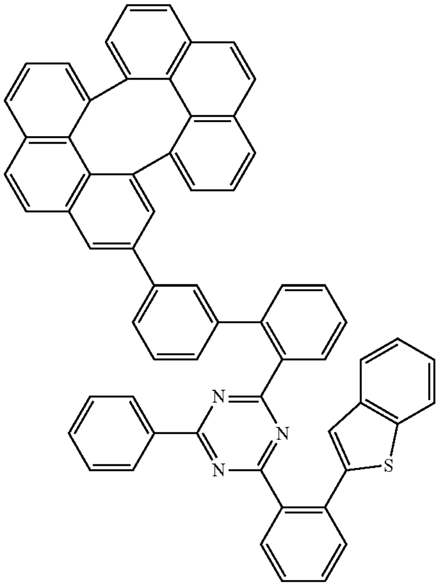

-continued
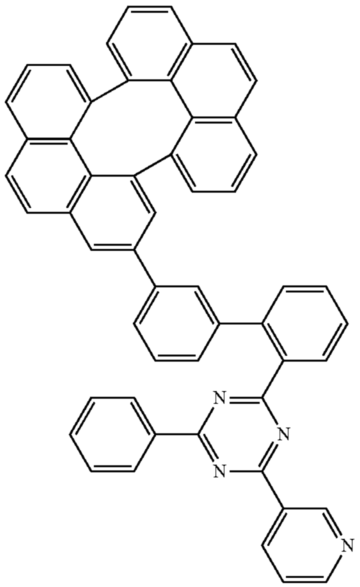
-continued
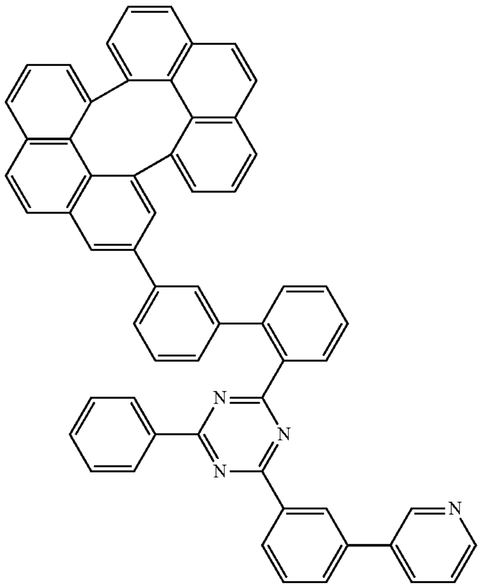
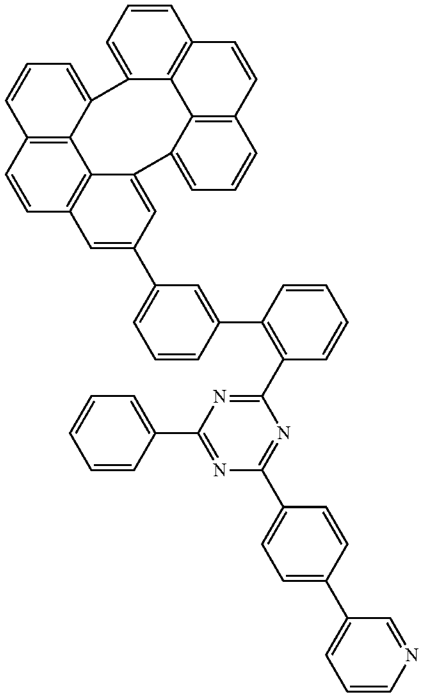
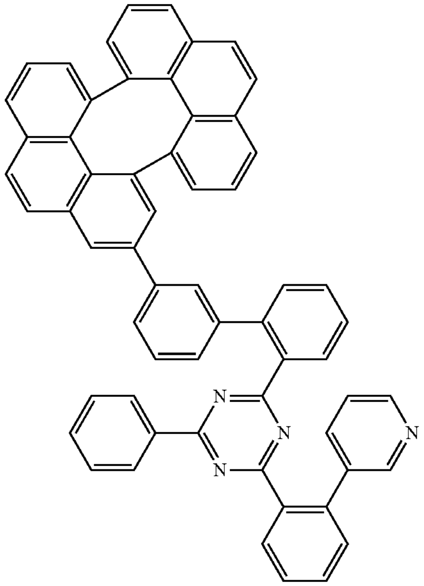

-continued
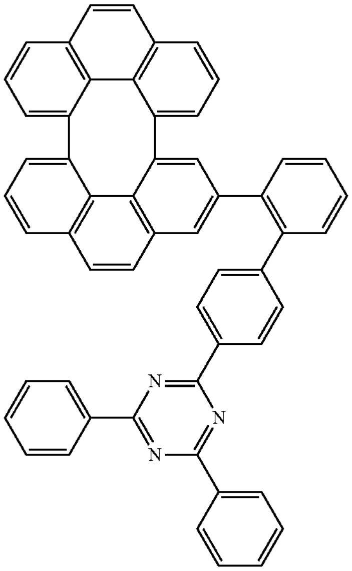
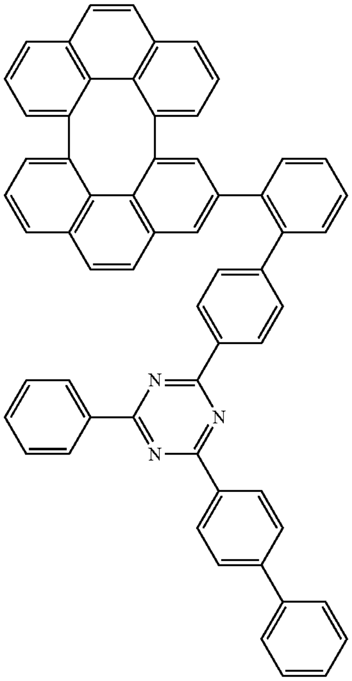
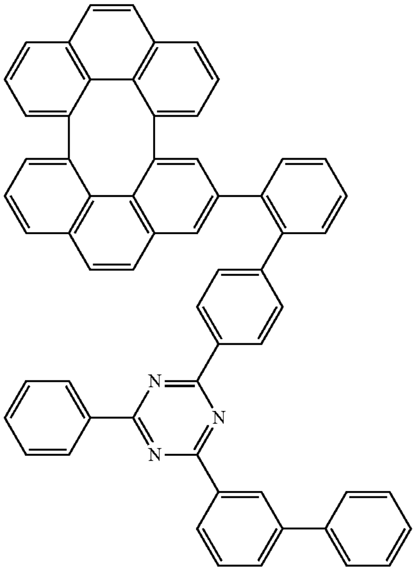
-continued
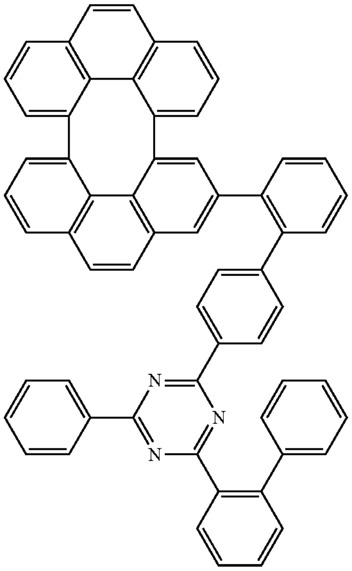

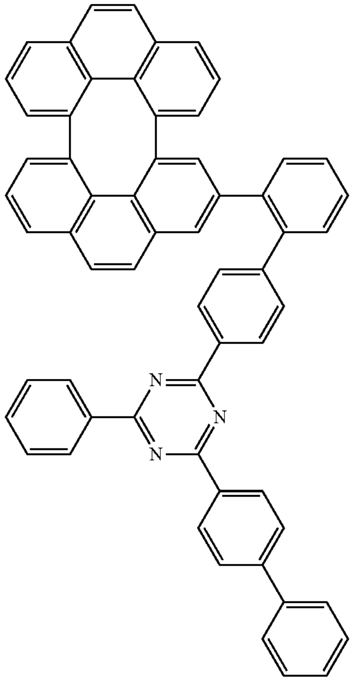
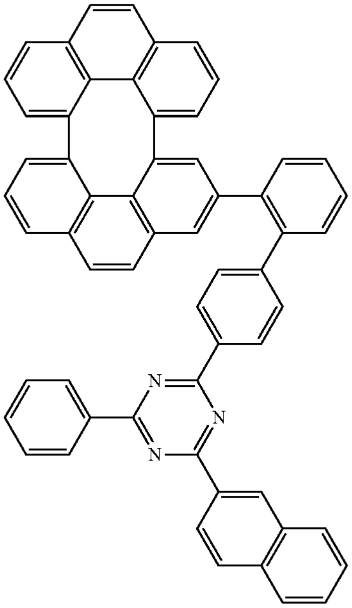
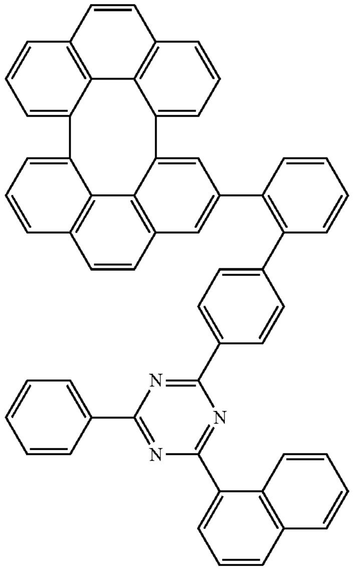
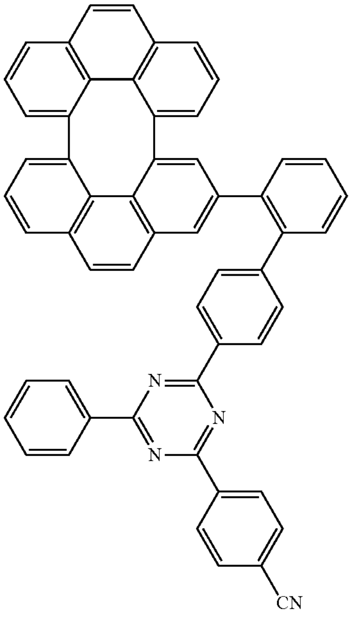

-continued
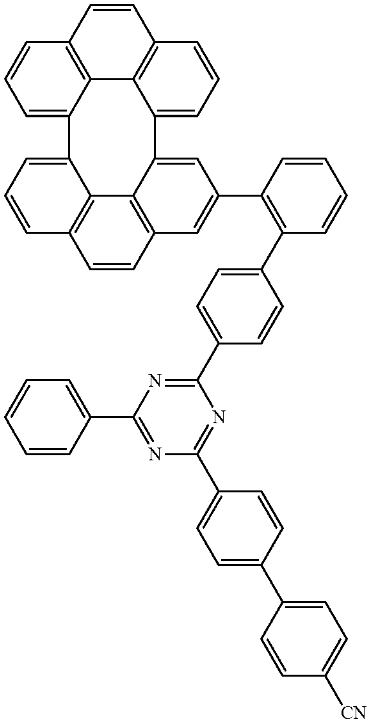
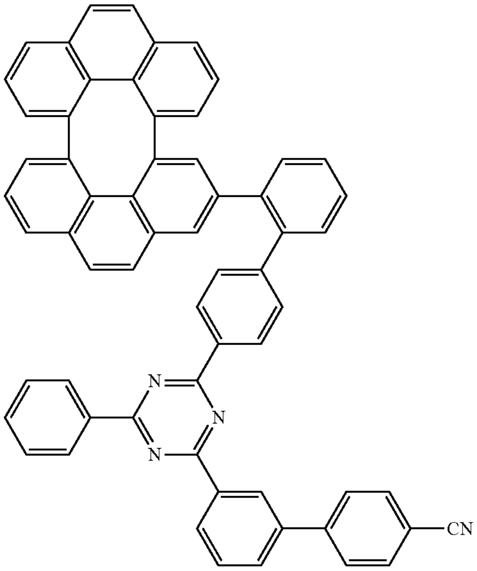
-continued
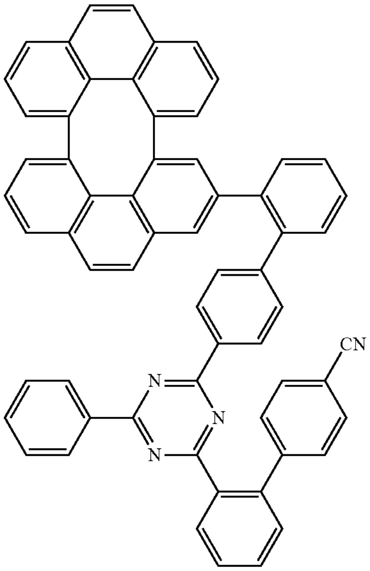
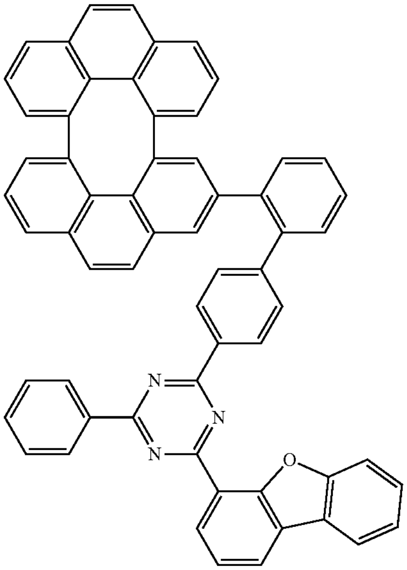

-continued
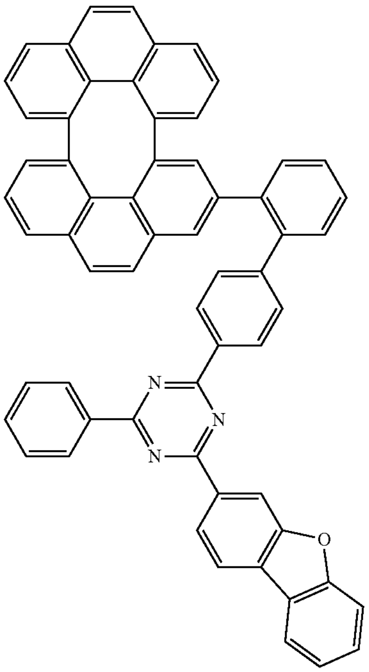
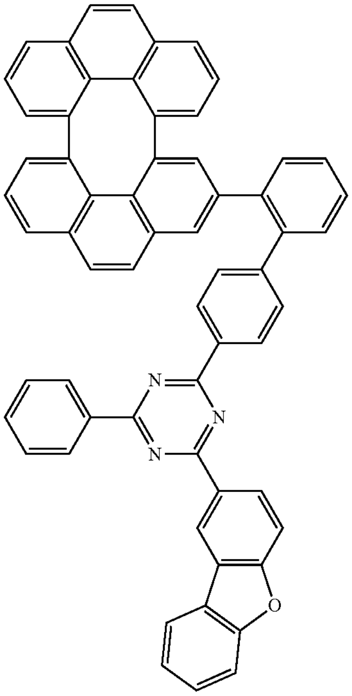
-continued
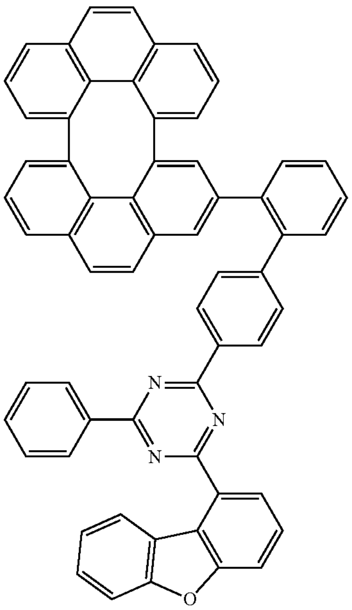
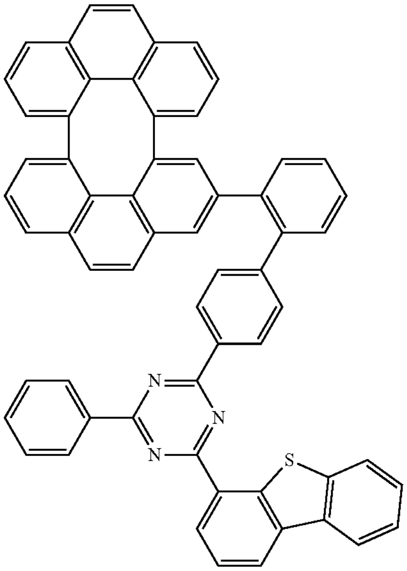

-continued
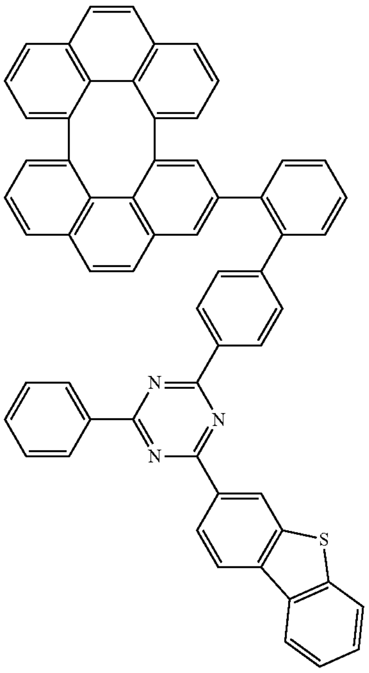
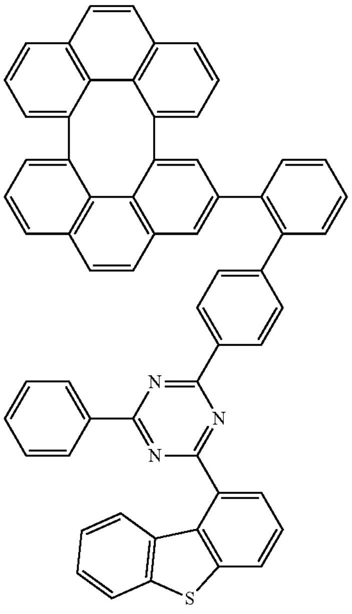
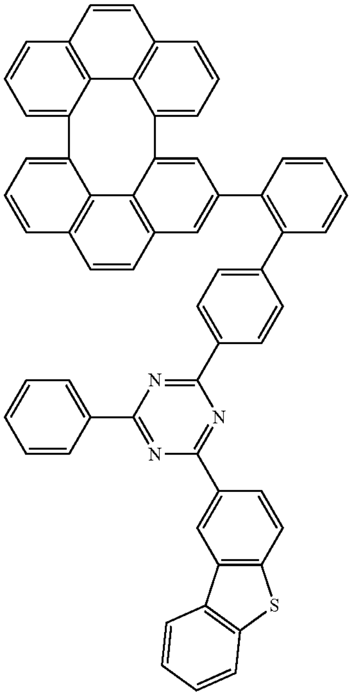
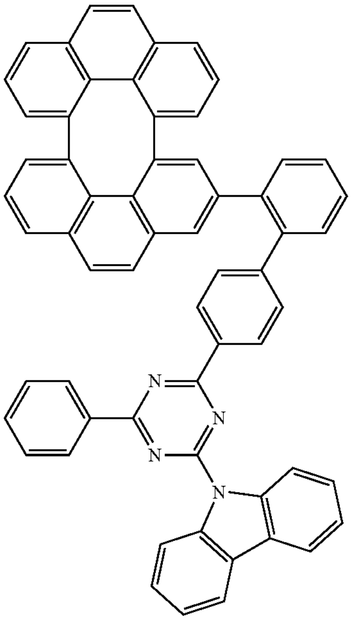

-continued
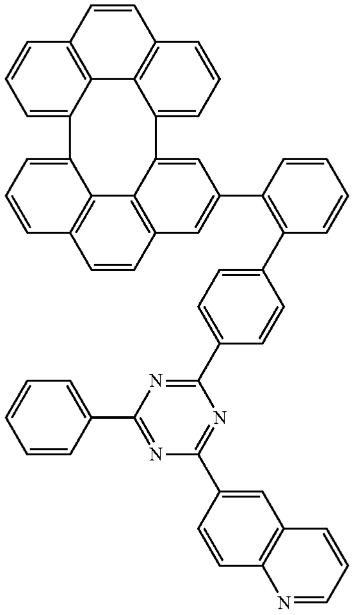
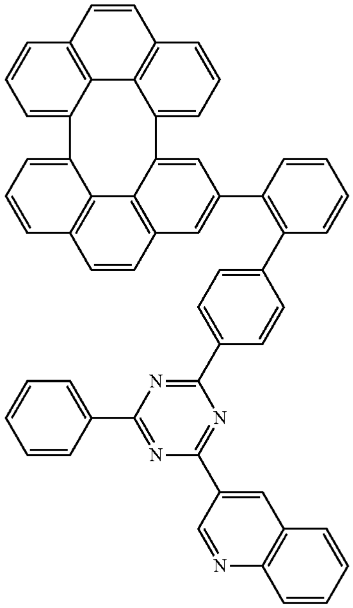
-continued
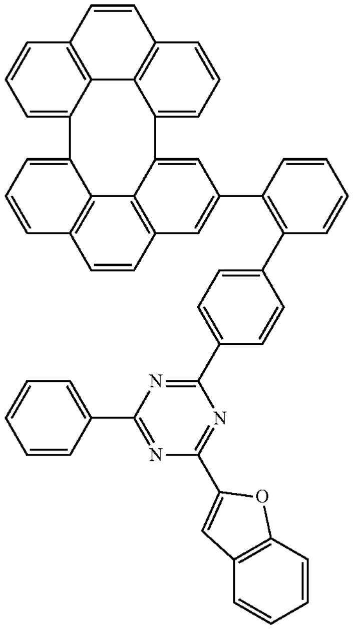
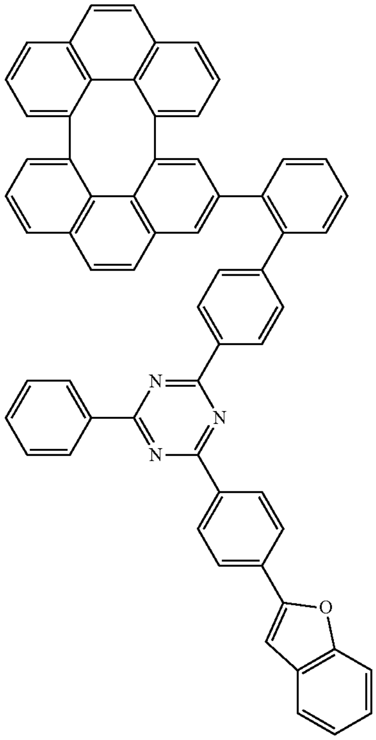

-continued
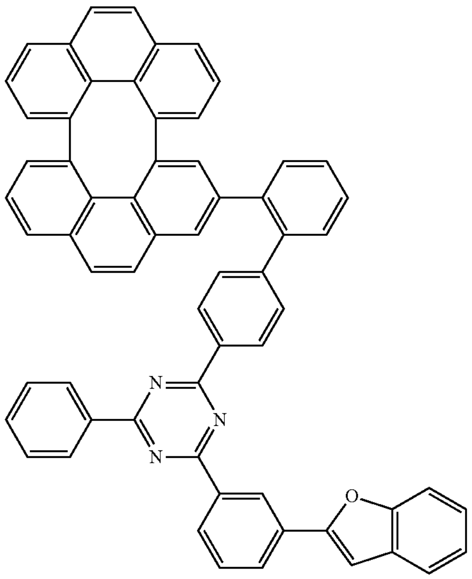
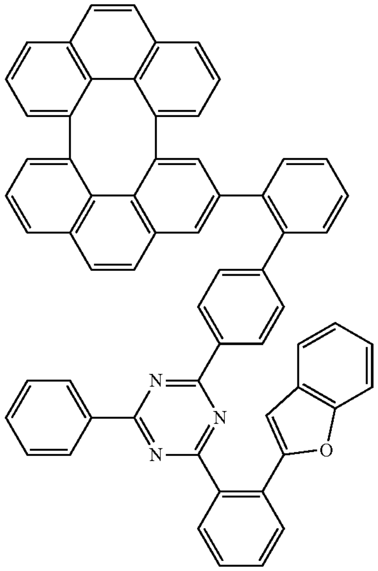
-continued
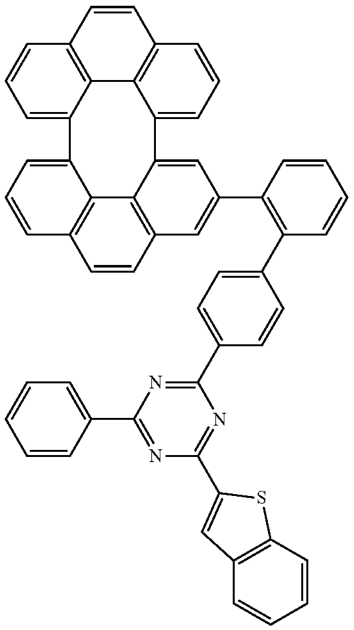
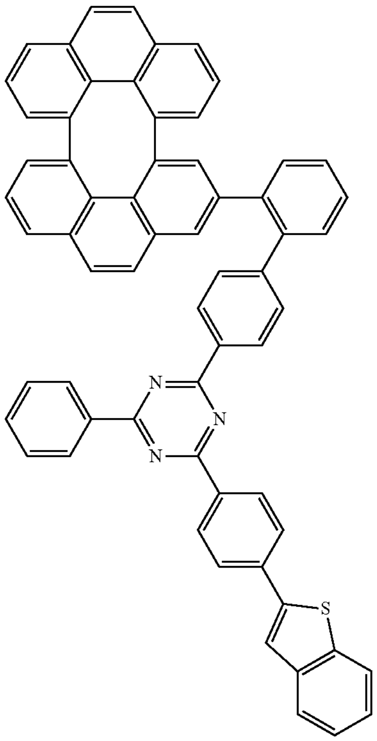

-continued
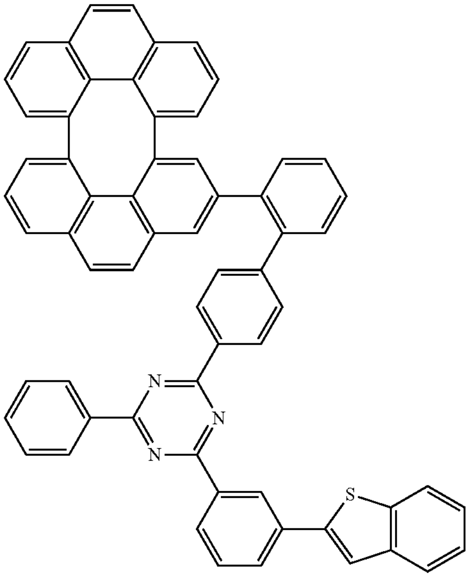
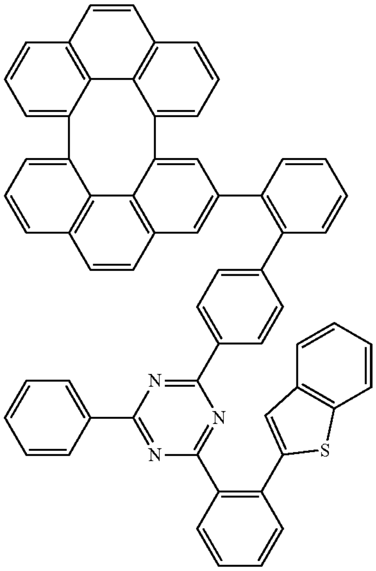
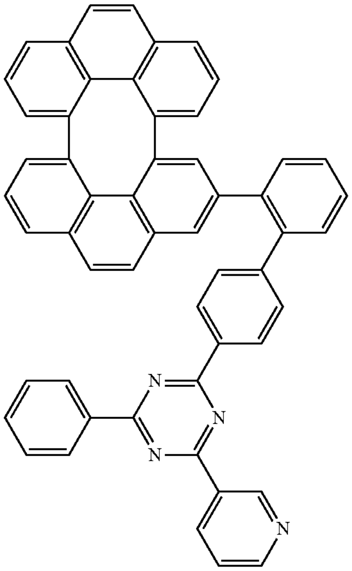
-continued
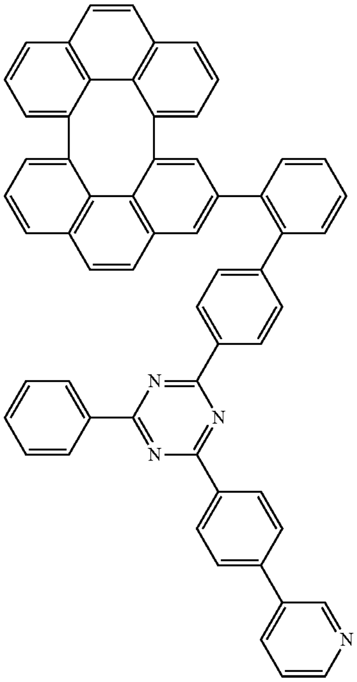
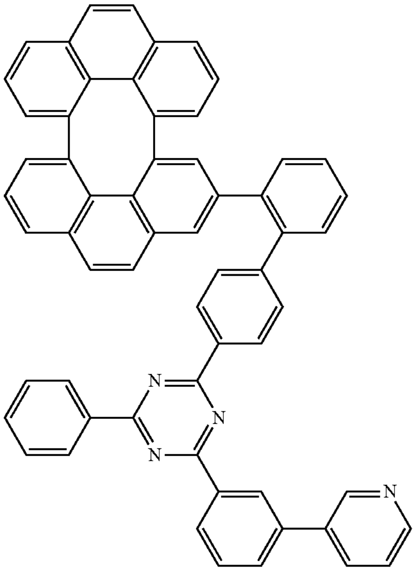

-continued
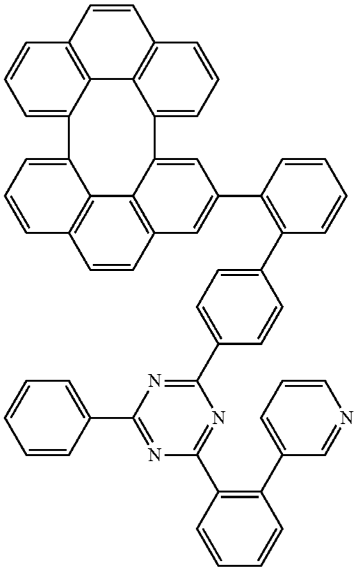
-continued
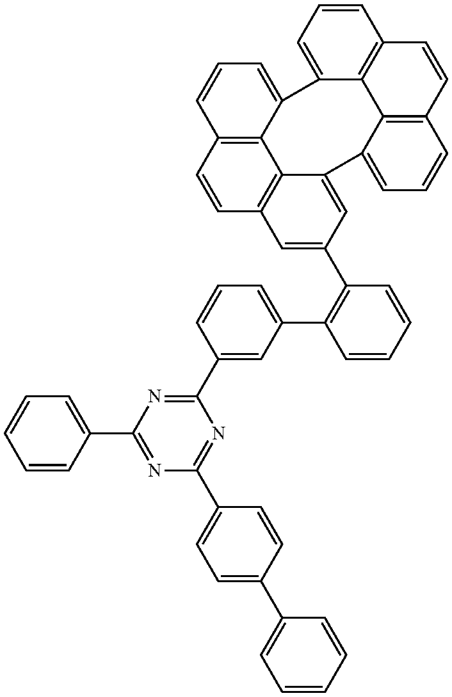
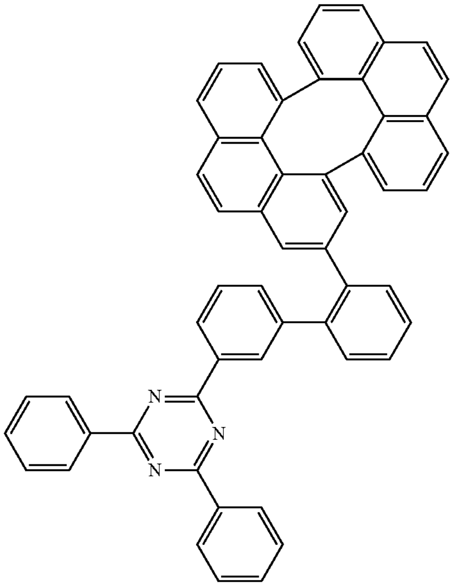
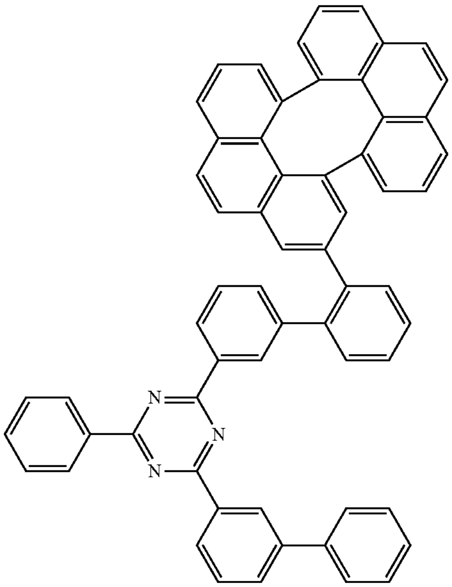

-continued
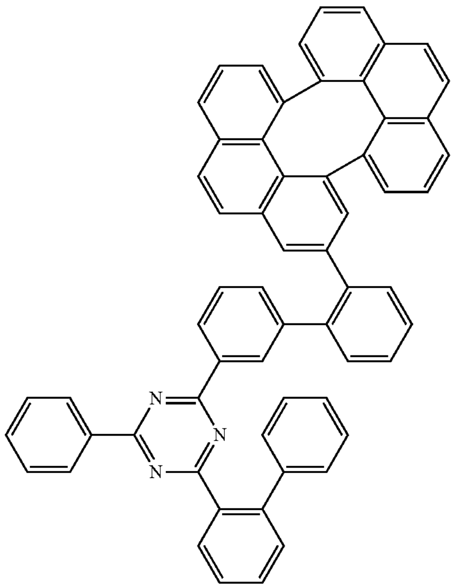
-continued
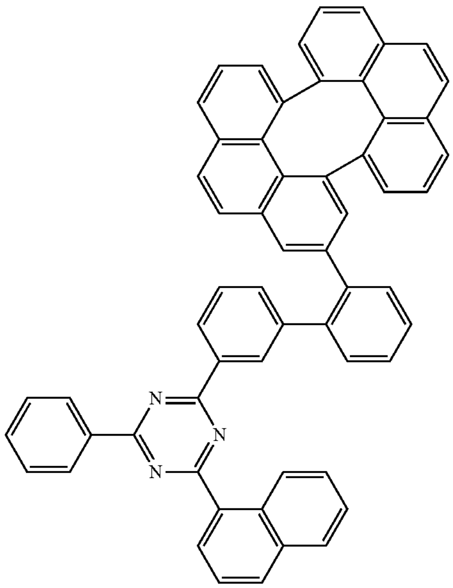
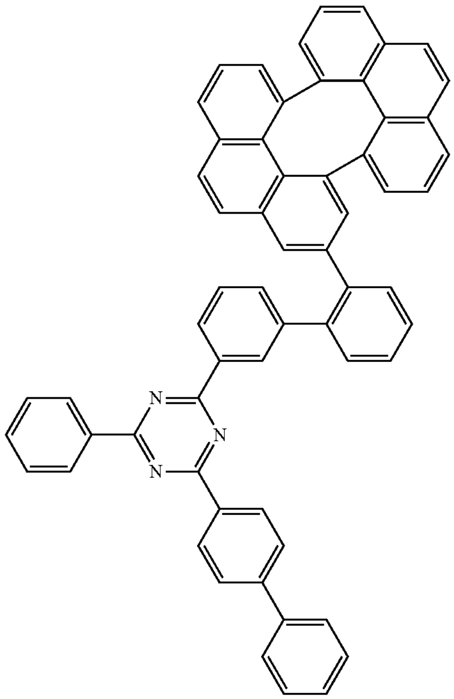
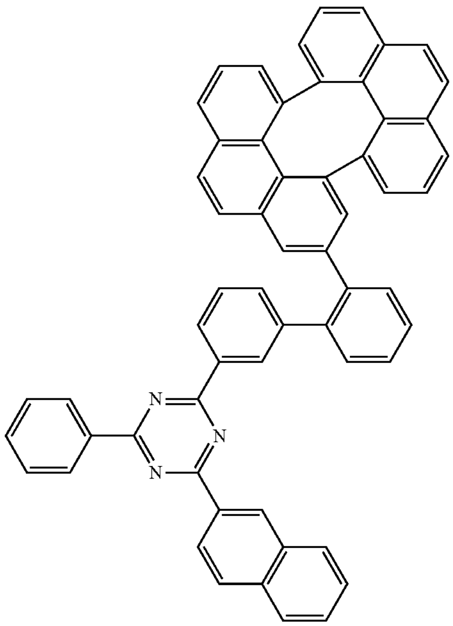

-continued
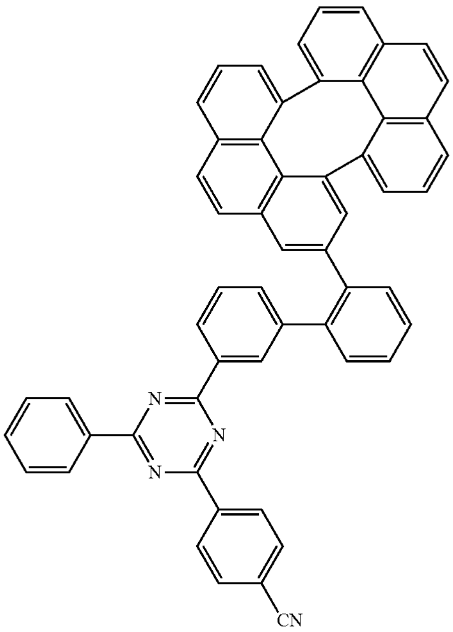
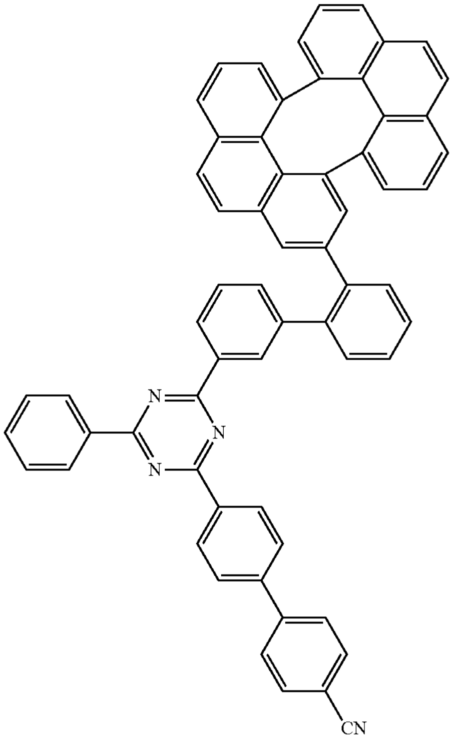
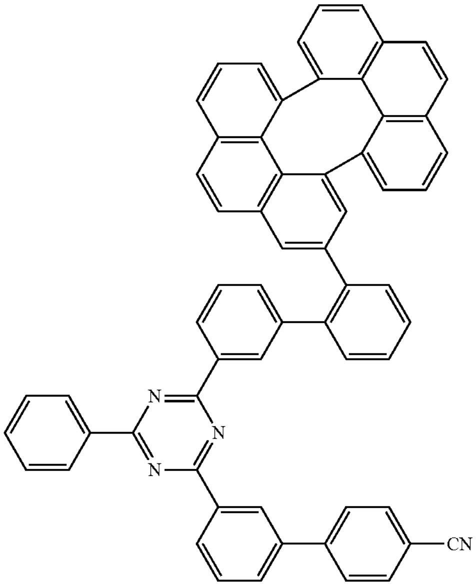
-continued
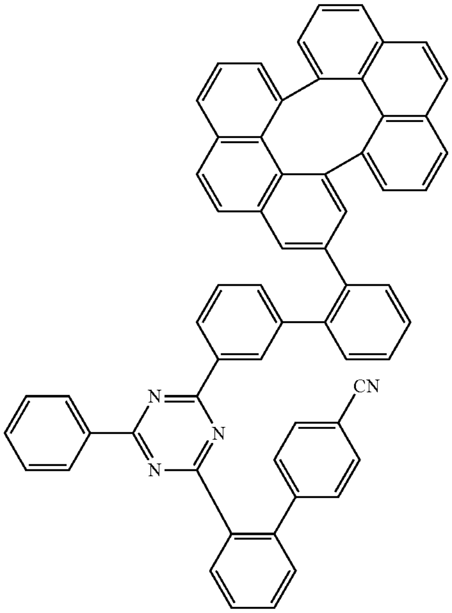

-continued
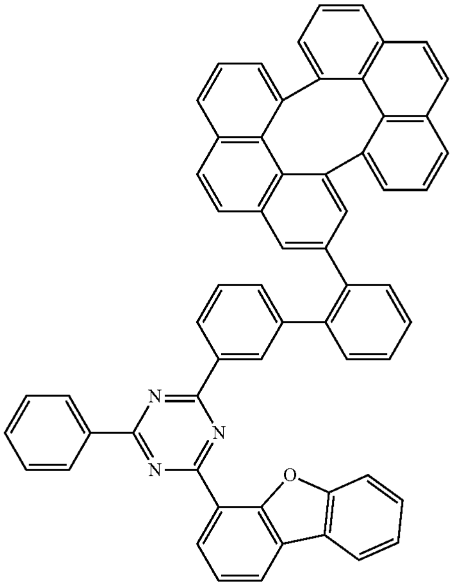
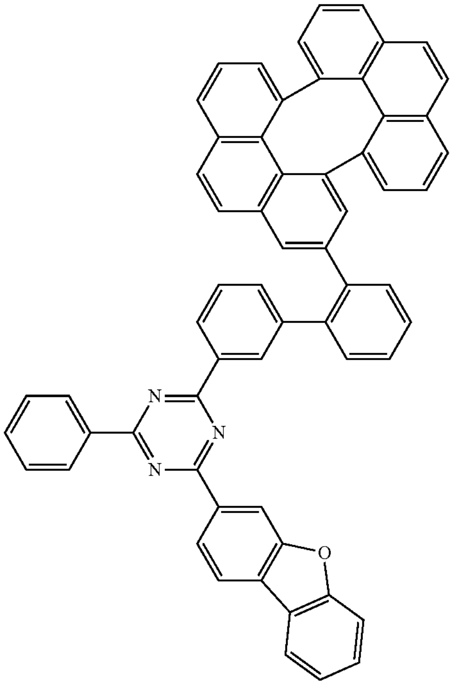
-continued
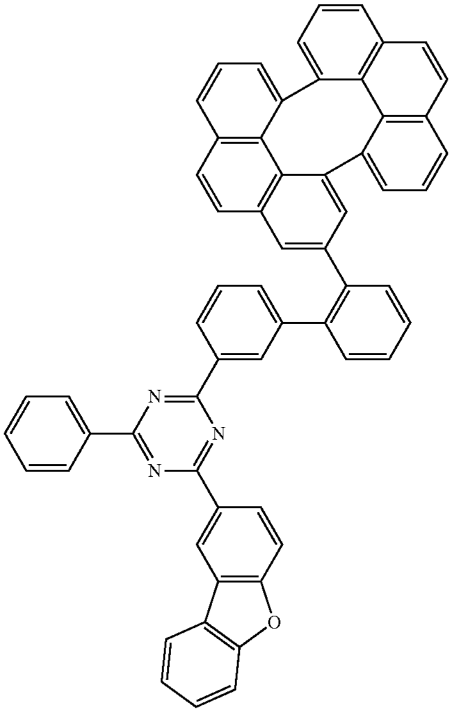
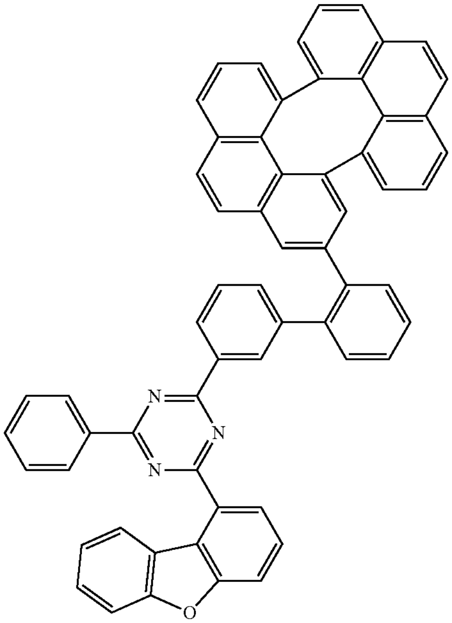

-continued
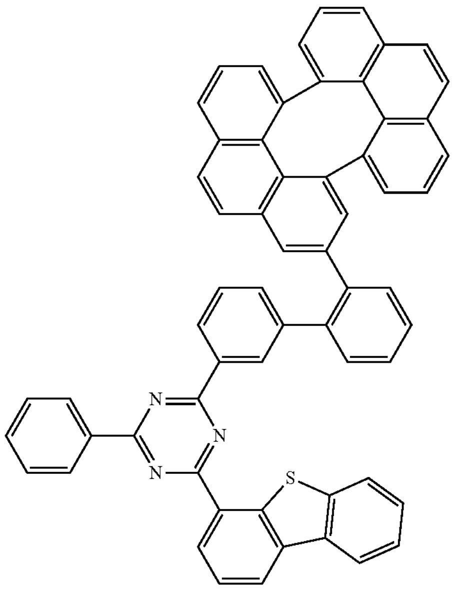
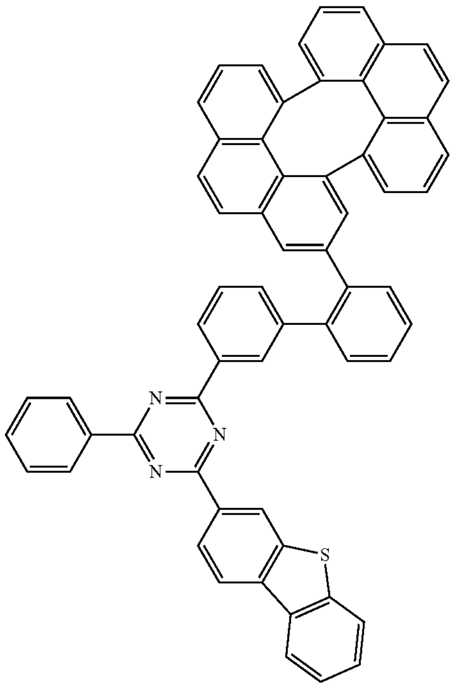
-continued
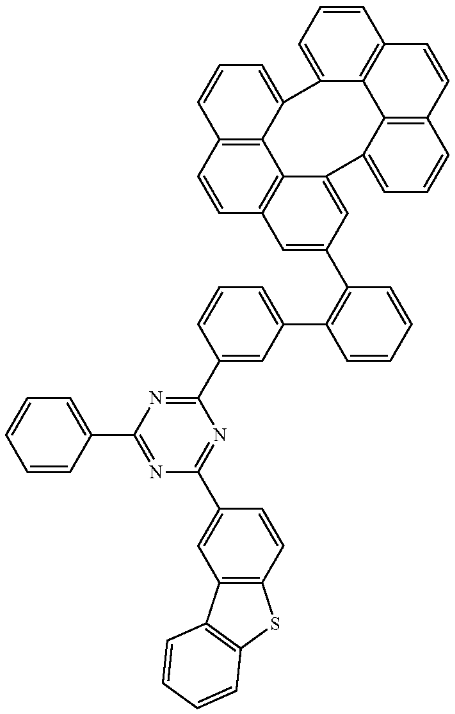
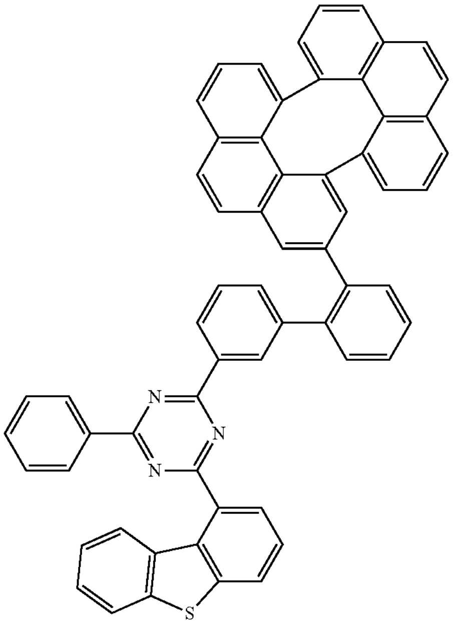

-continued
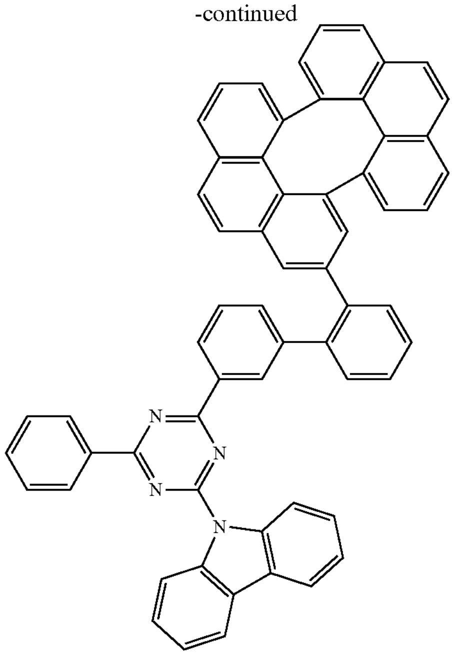
-continued
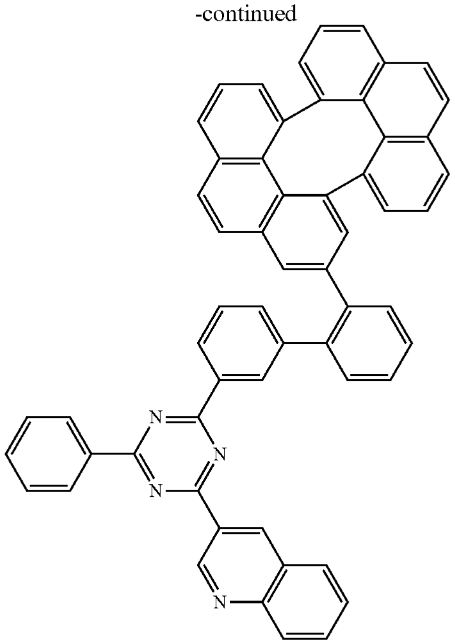
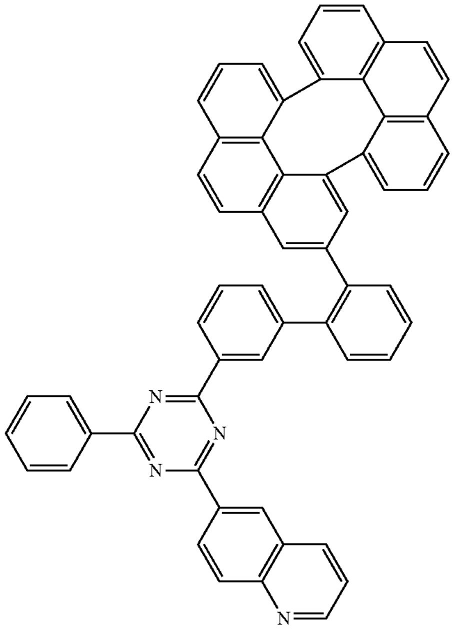
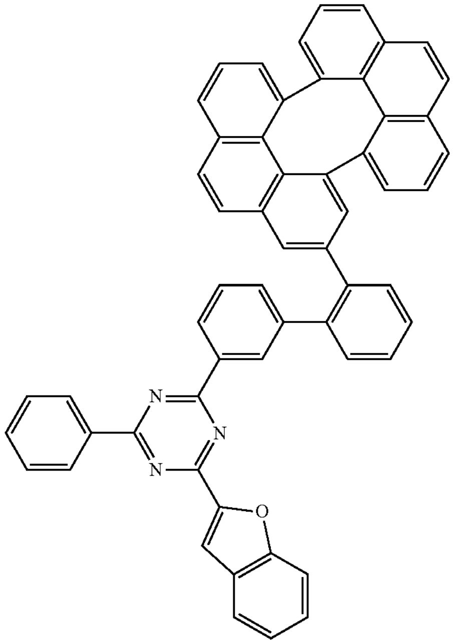

-continued
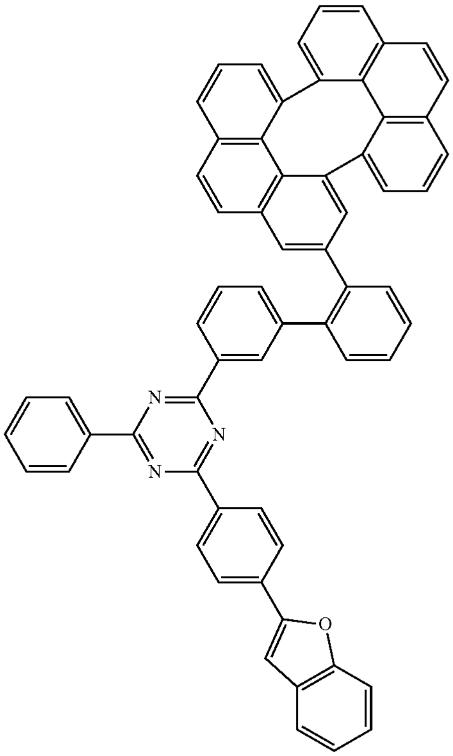
-continued
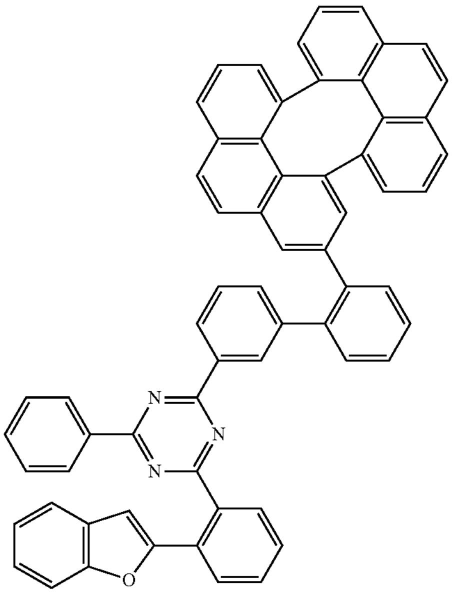
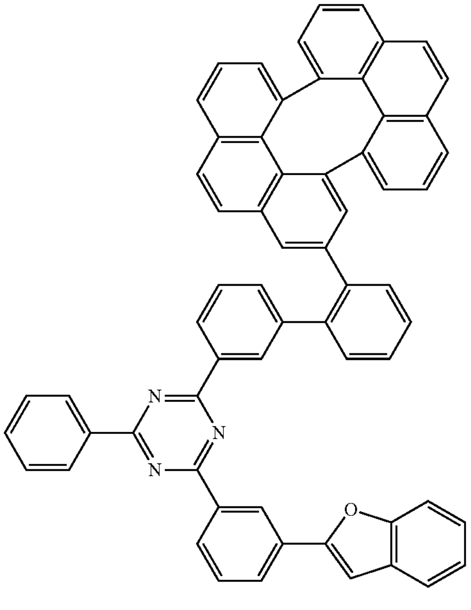
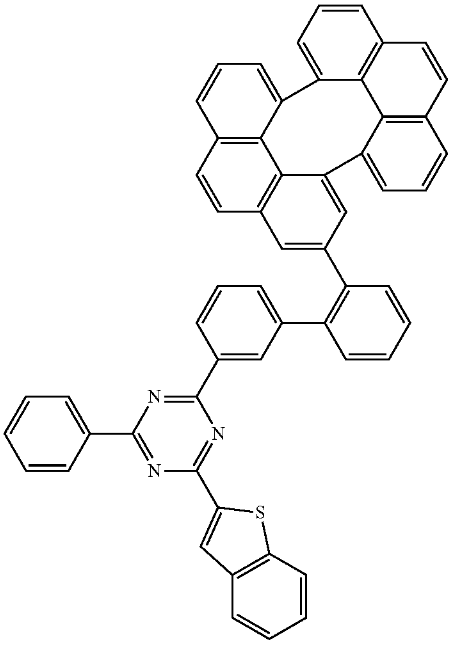

-continued
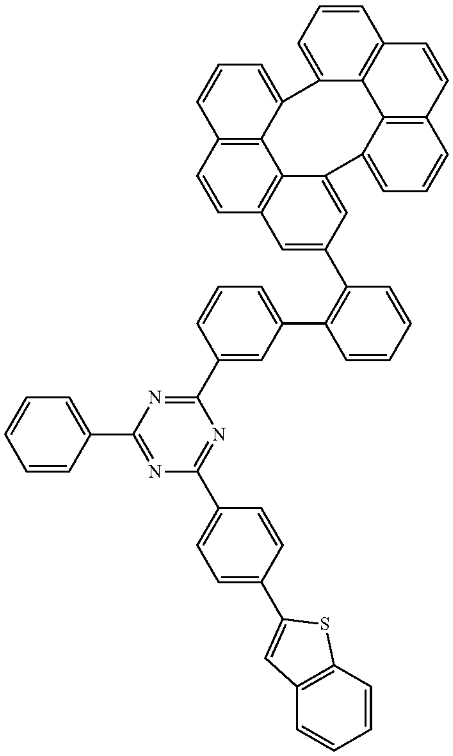
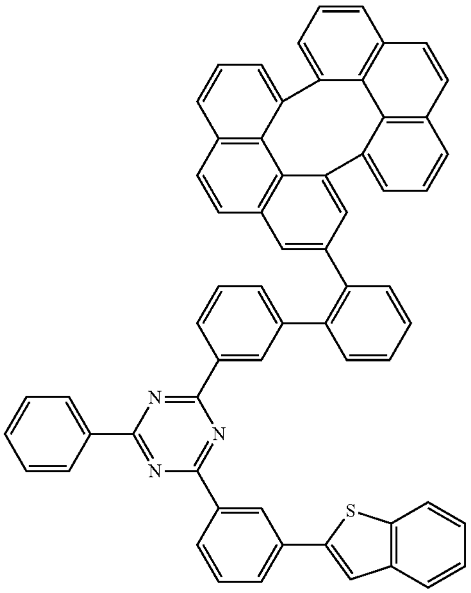
-continued
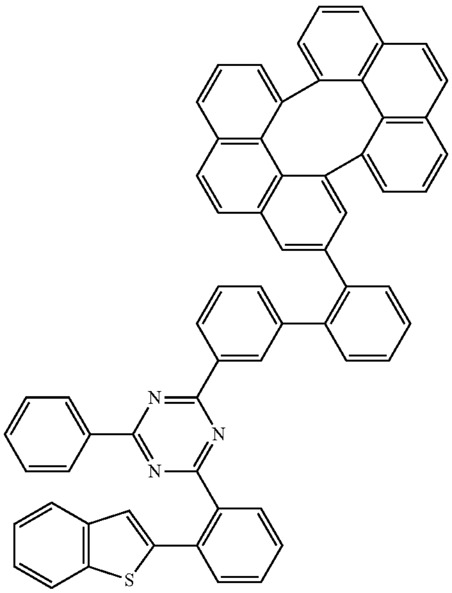
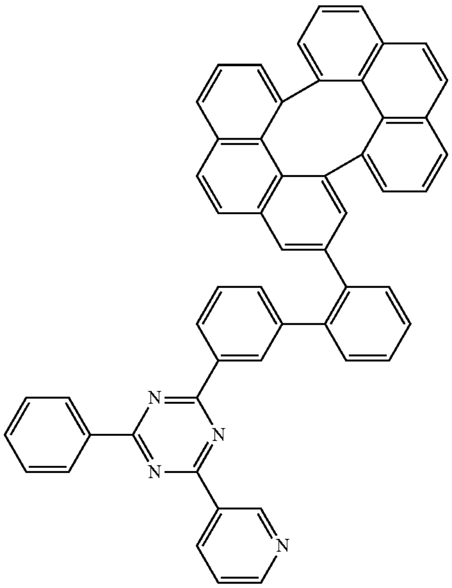

-continued
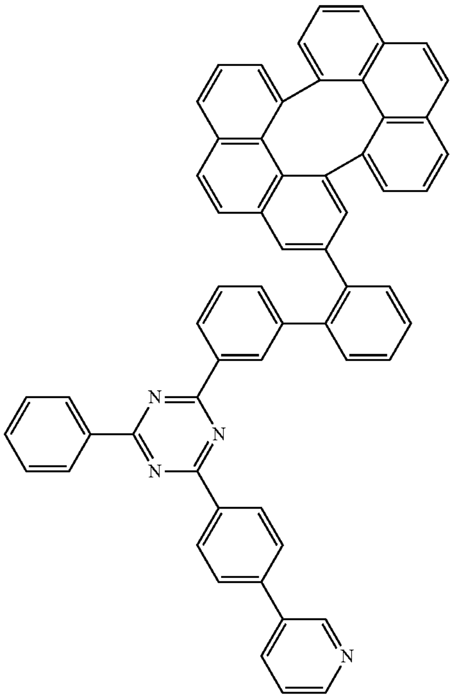
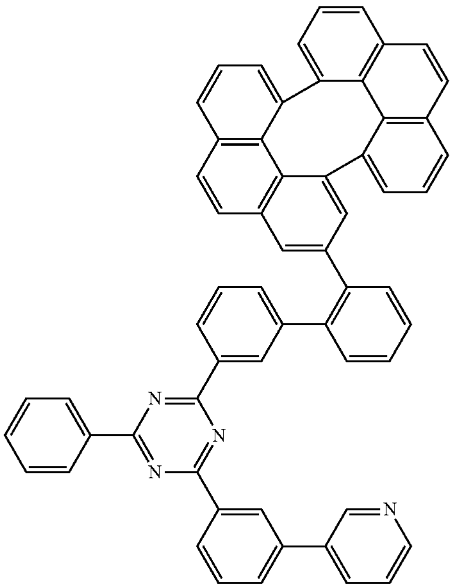
-continued
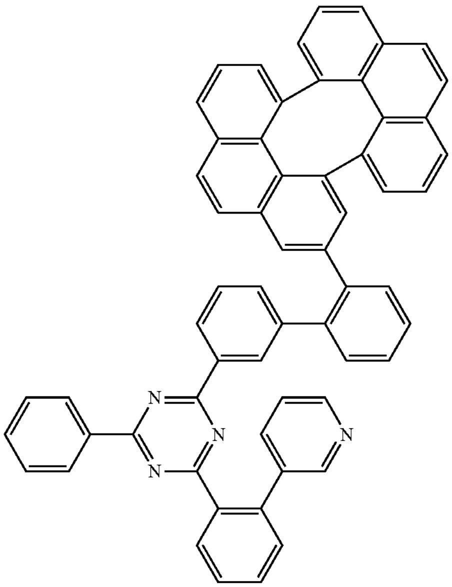
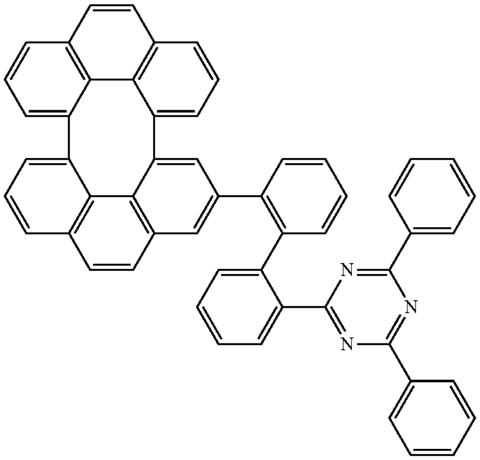
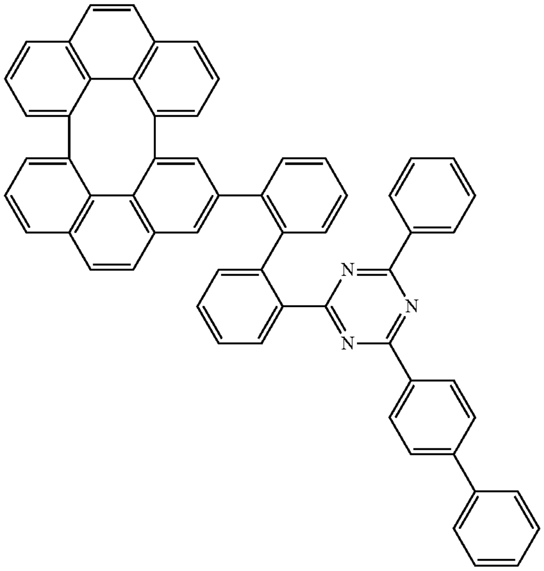

-continued
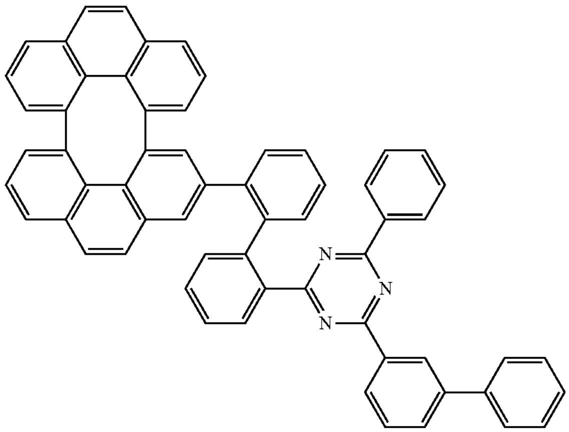
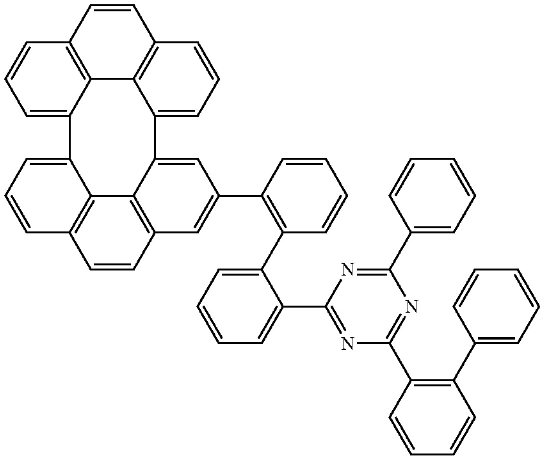
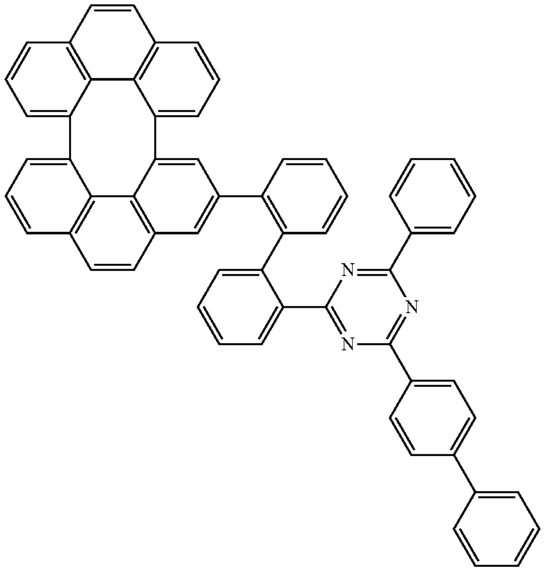
-continued
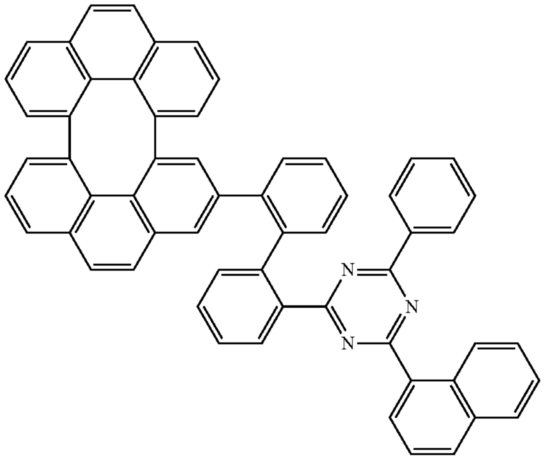
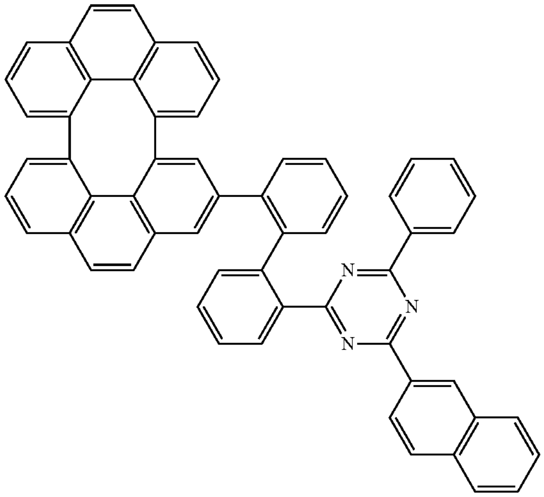
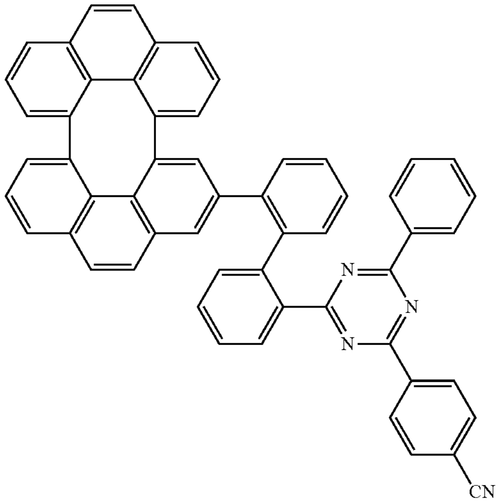

-continued
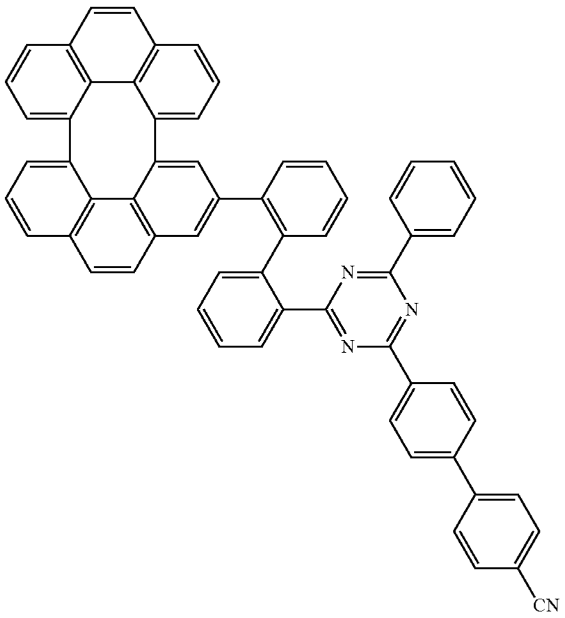
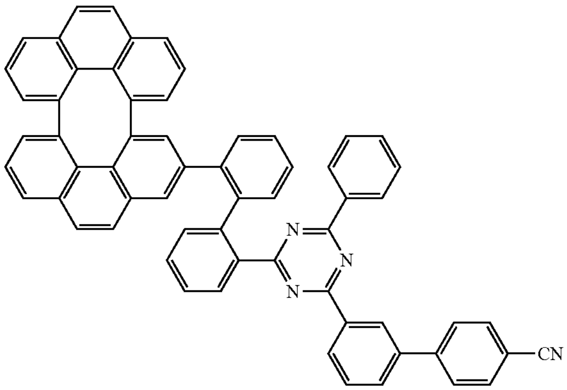
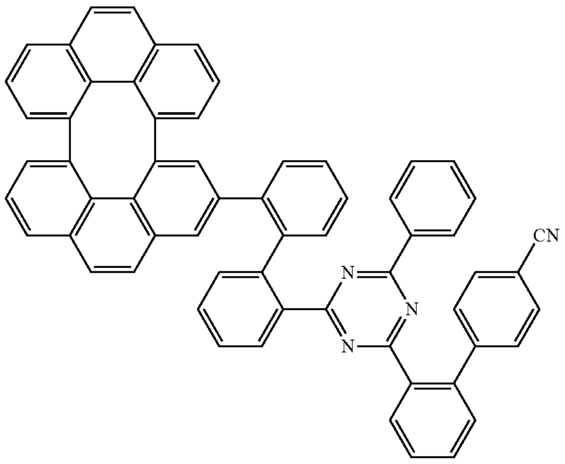
-continued
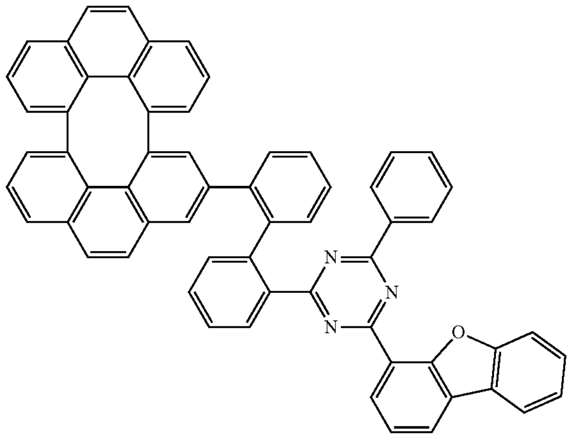
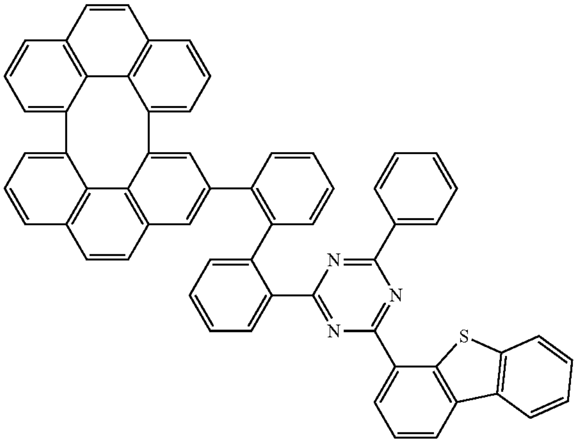
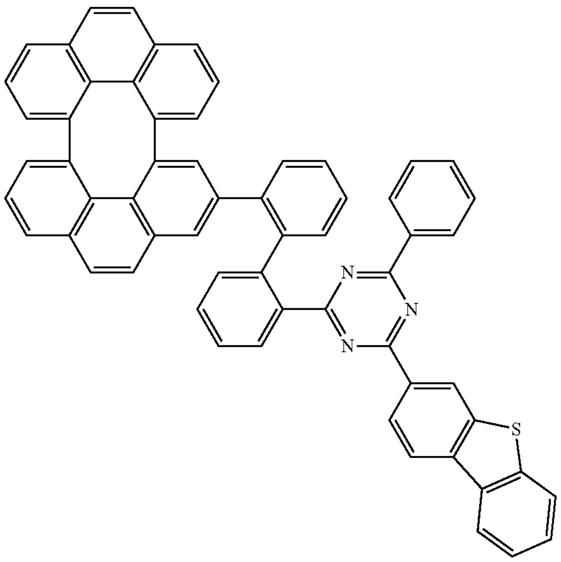

-continued
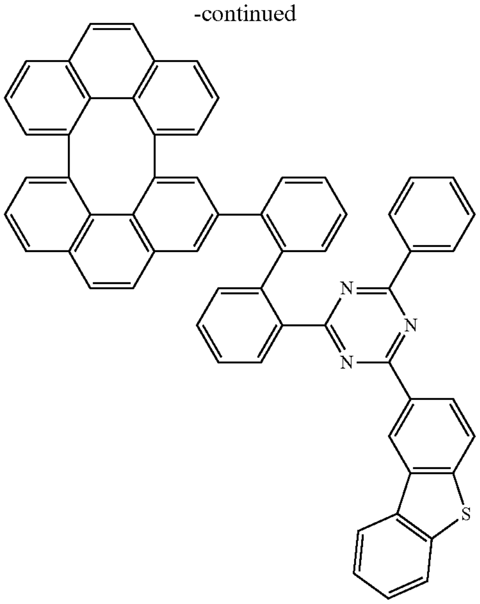
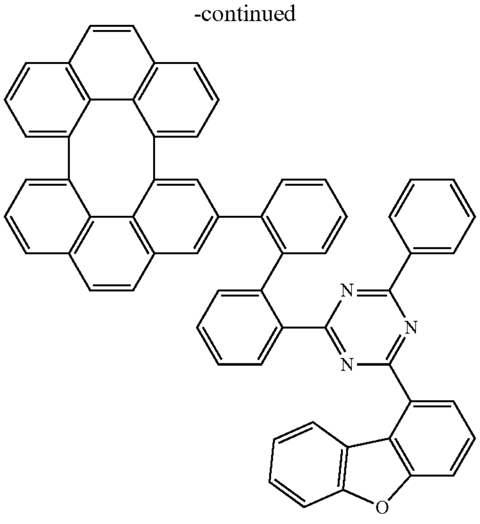
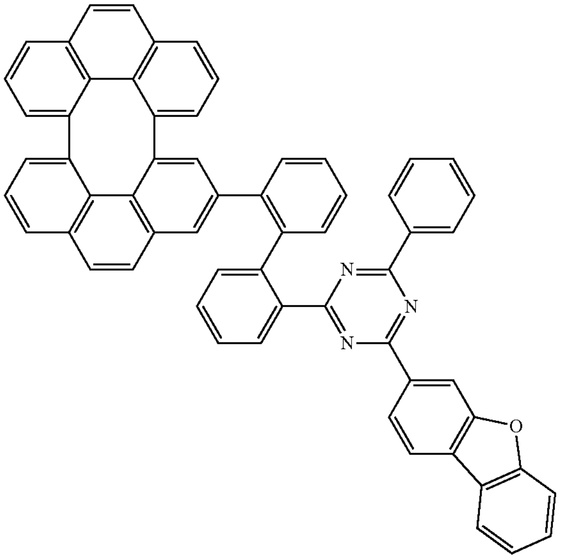
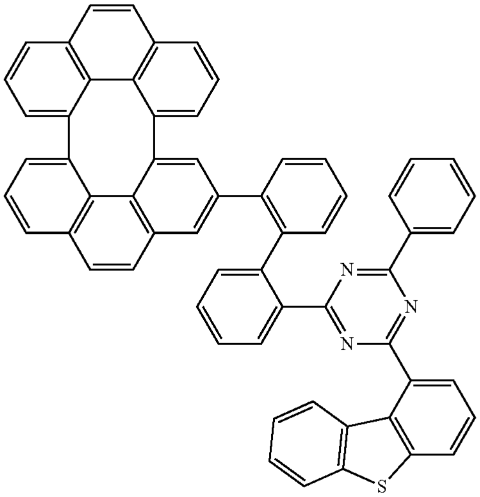
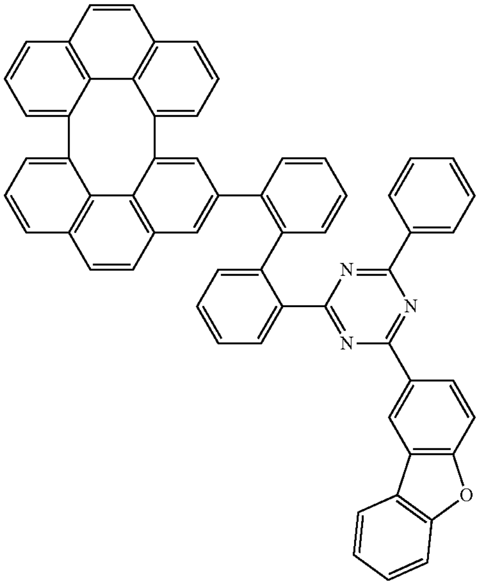
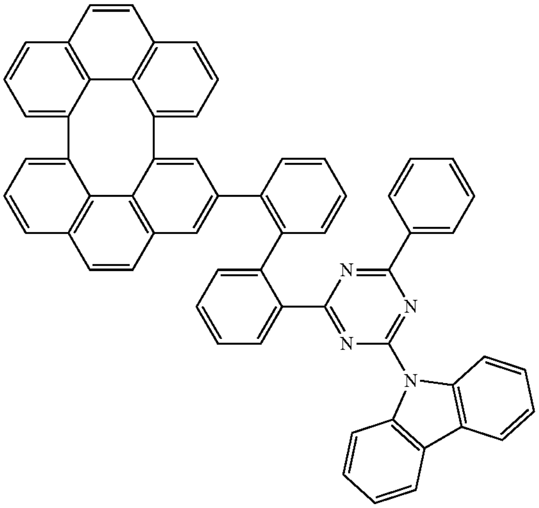
-continued -continued
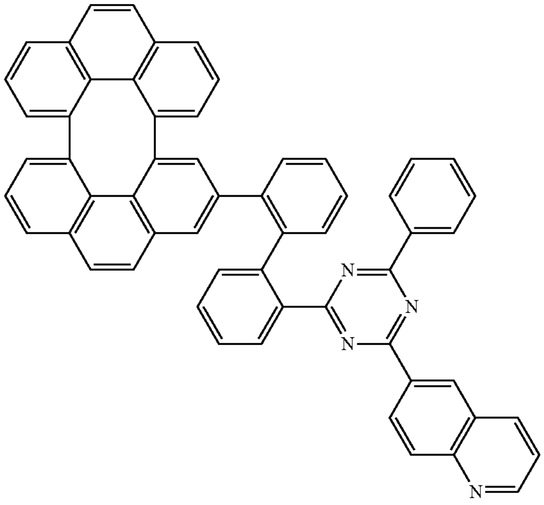
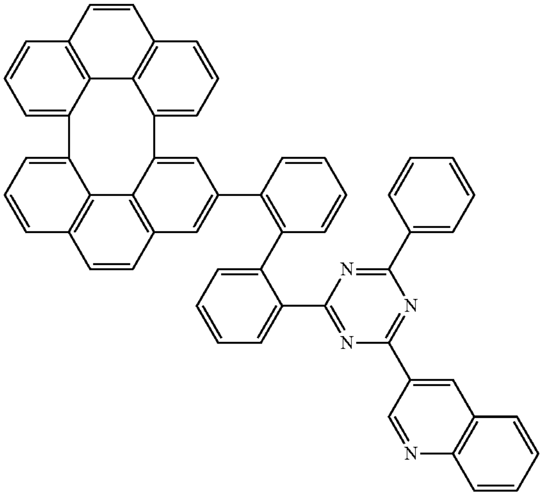
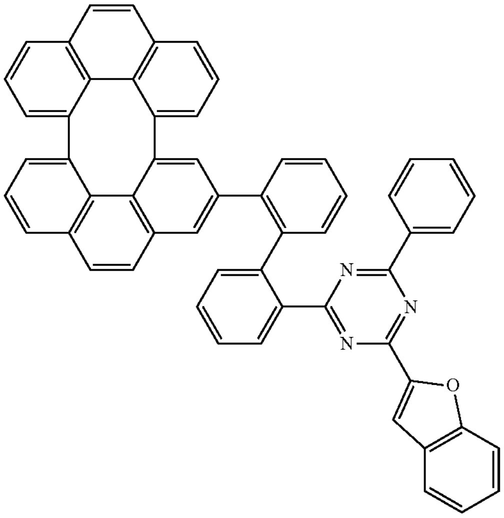
-continued
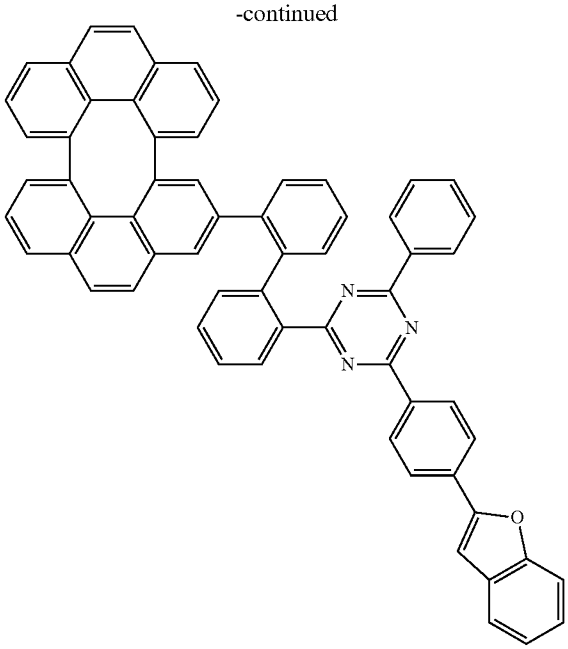
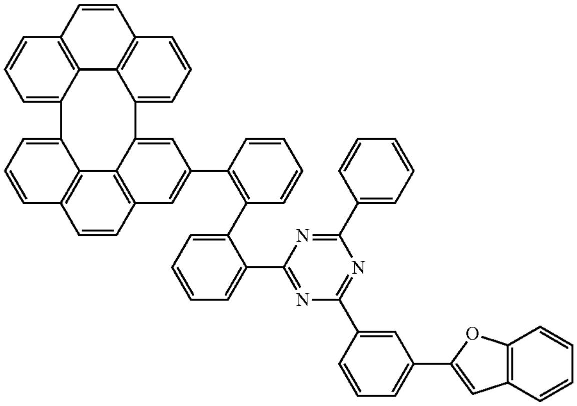
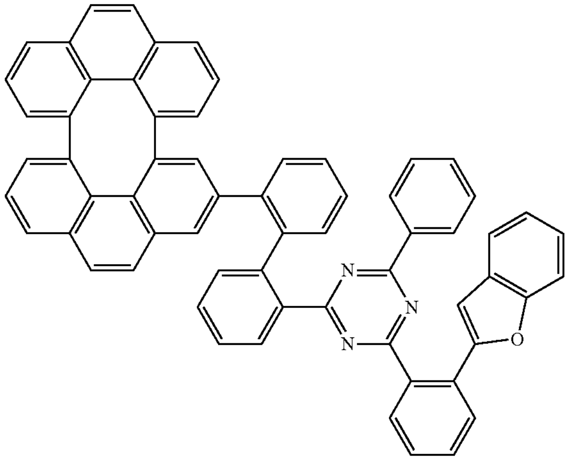

-continued
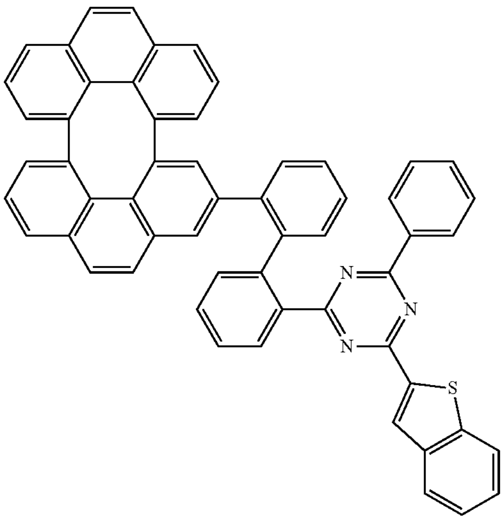
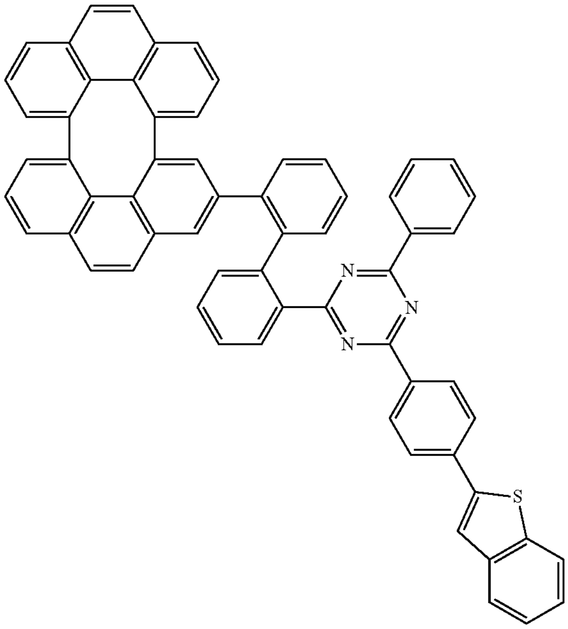
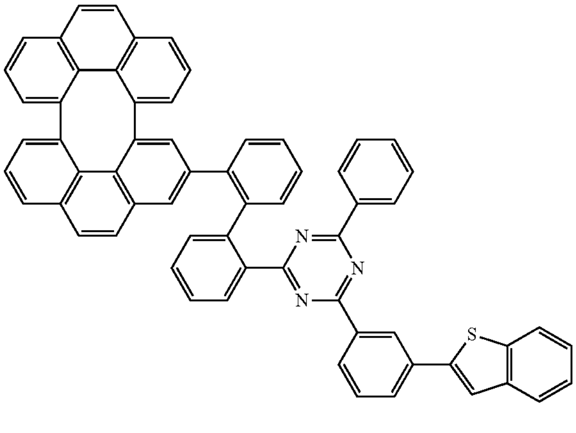
-continued
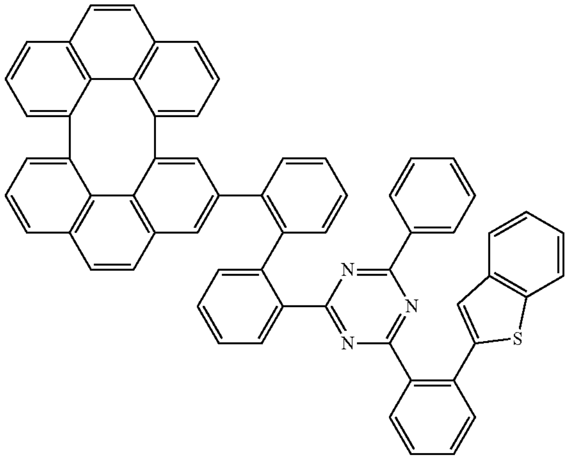
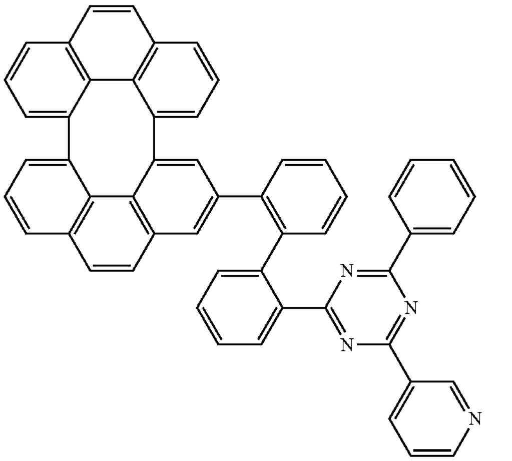
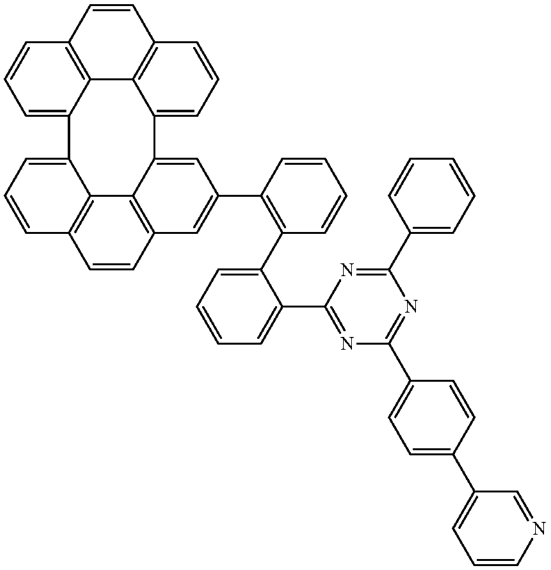

-continued
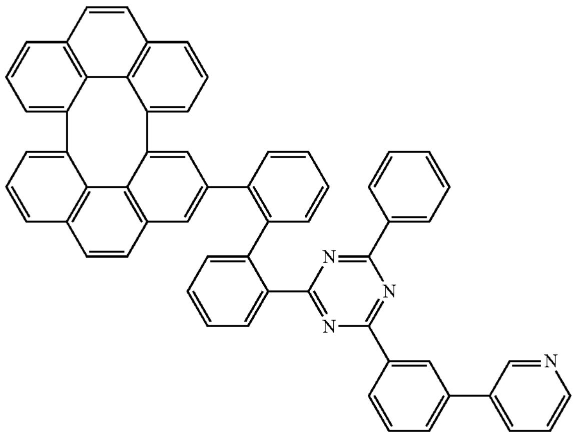
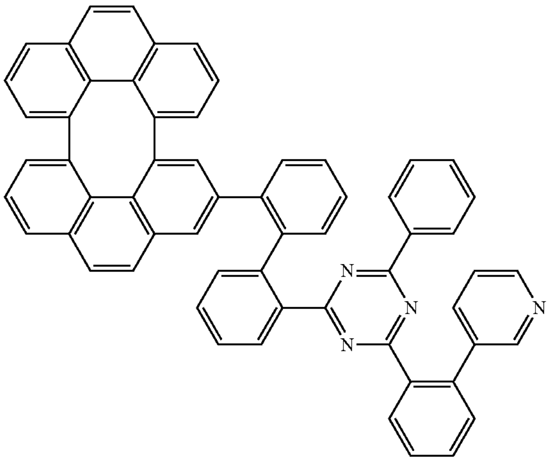
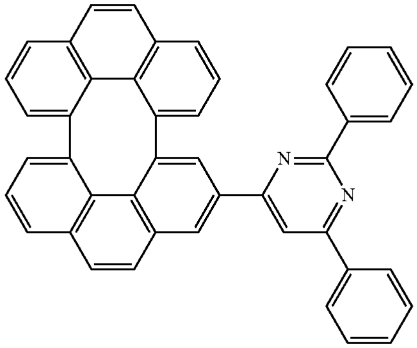
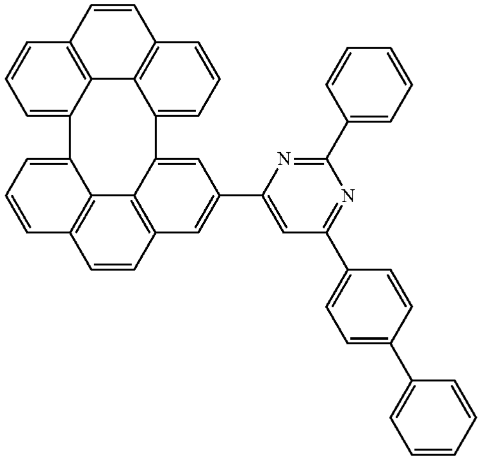
-continued
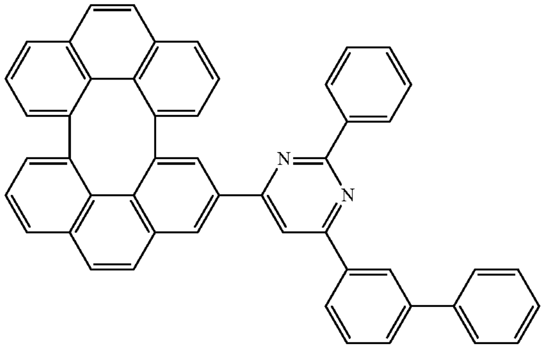
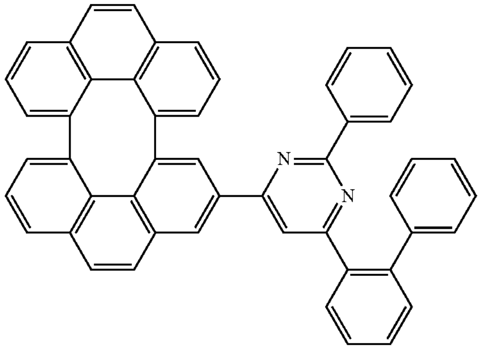
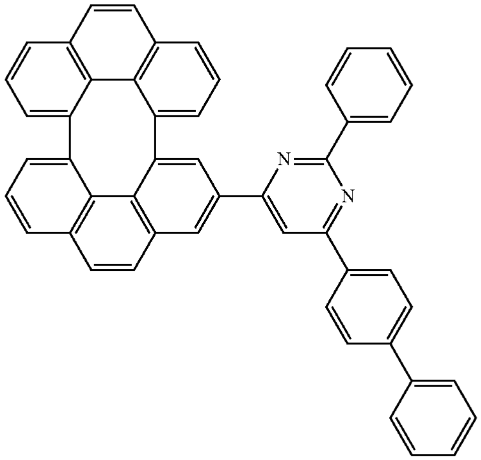
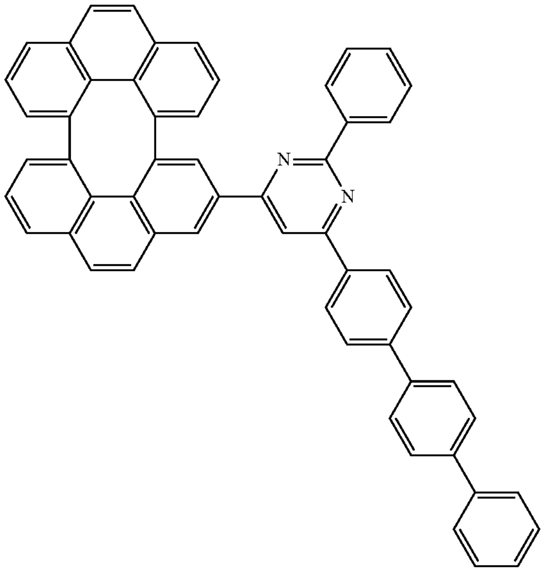

-continued
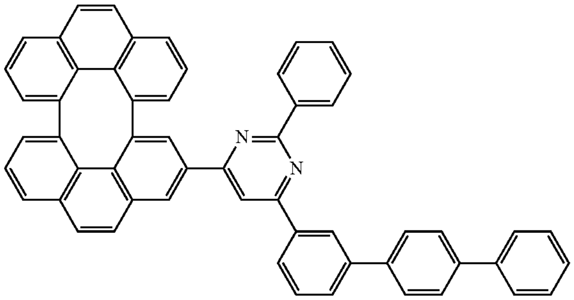
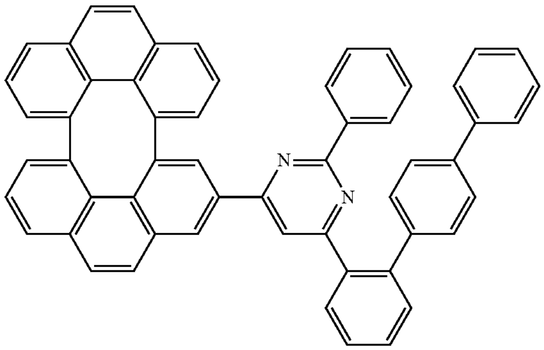
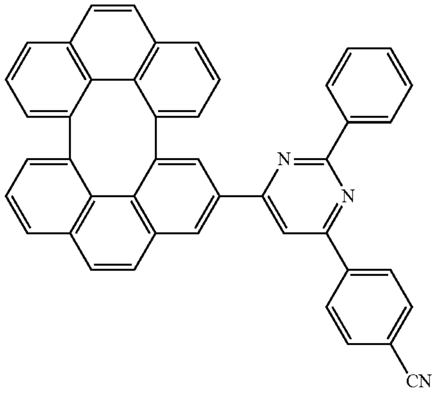
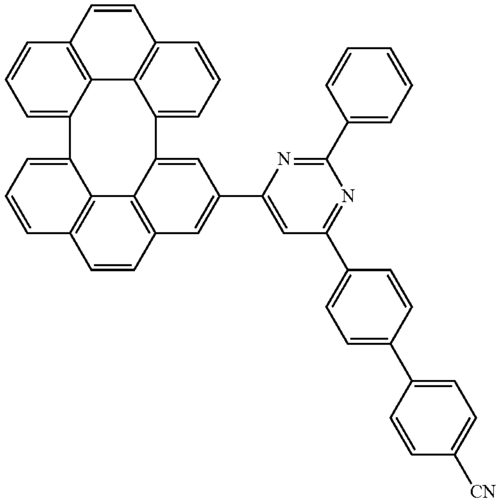
-continued
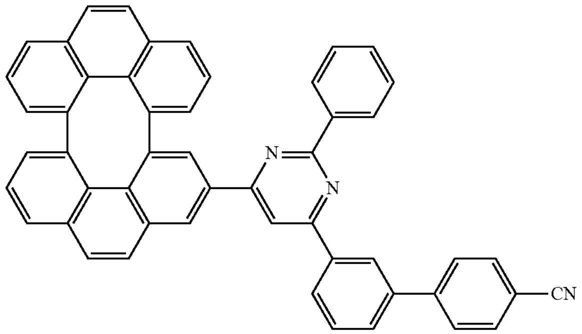
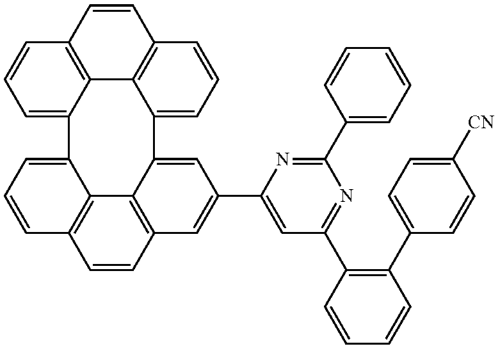
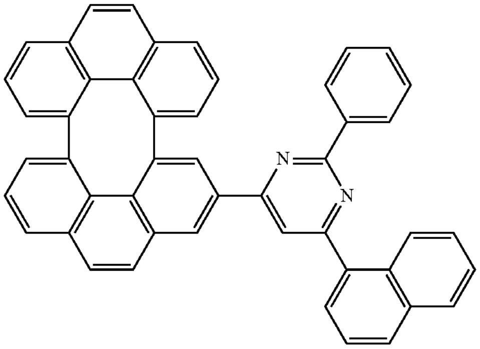
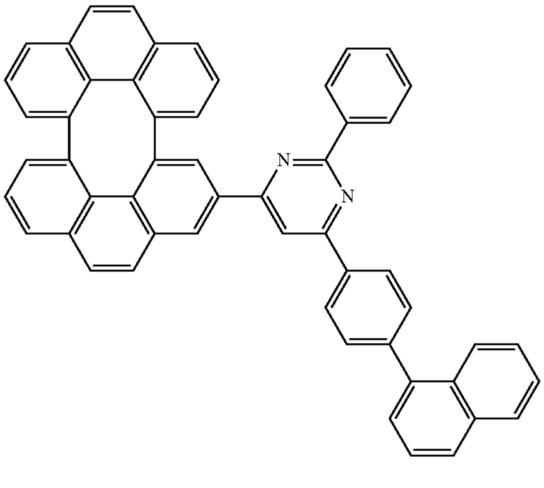

-continued
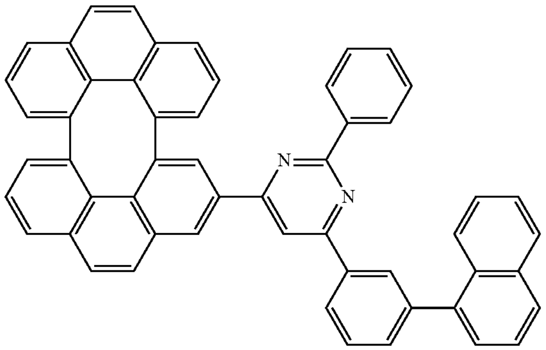
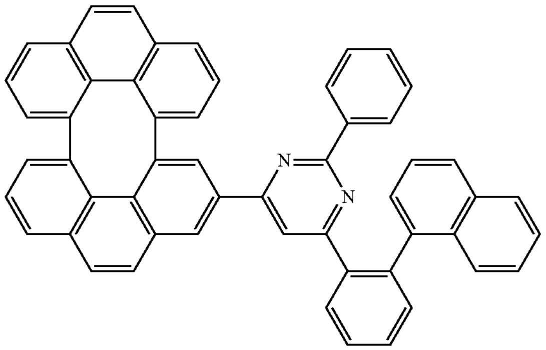
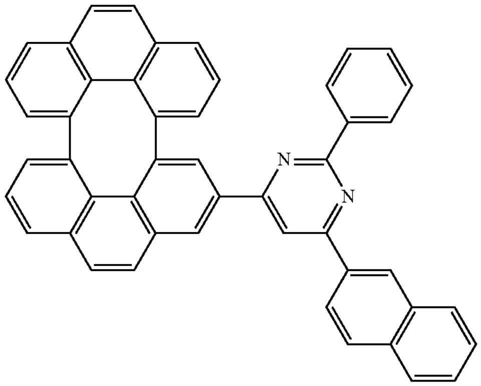
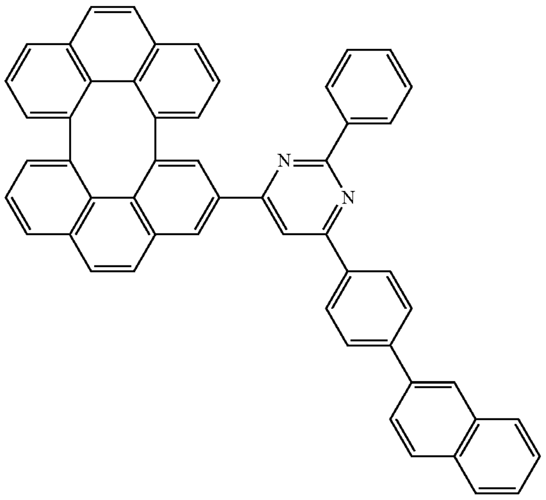
-continued
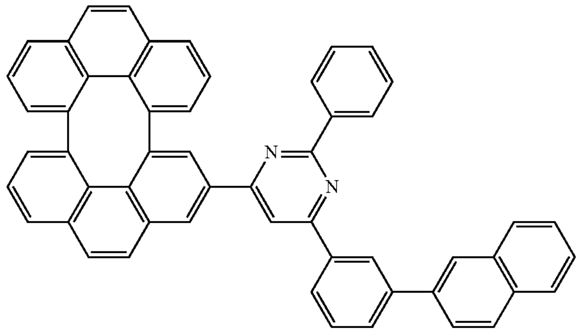
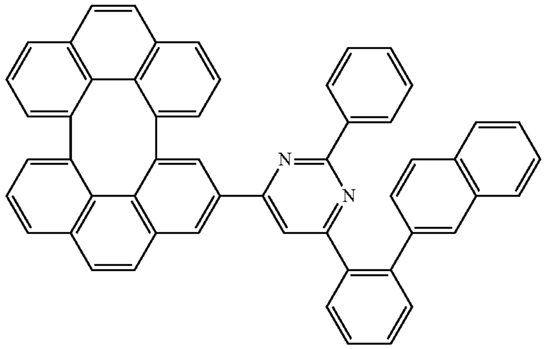
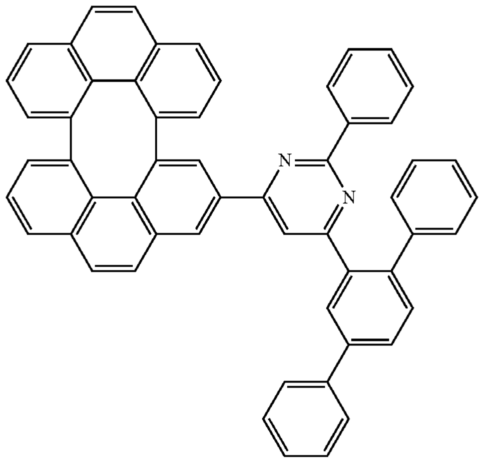
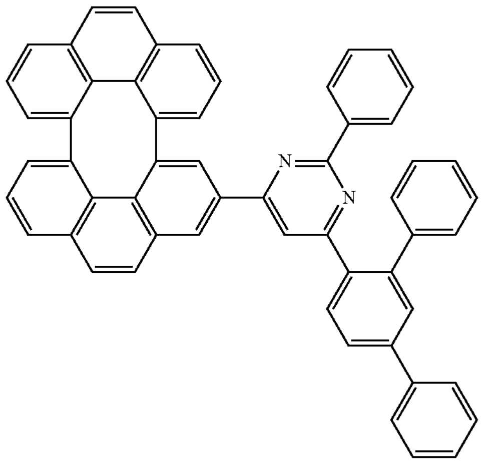

-continued
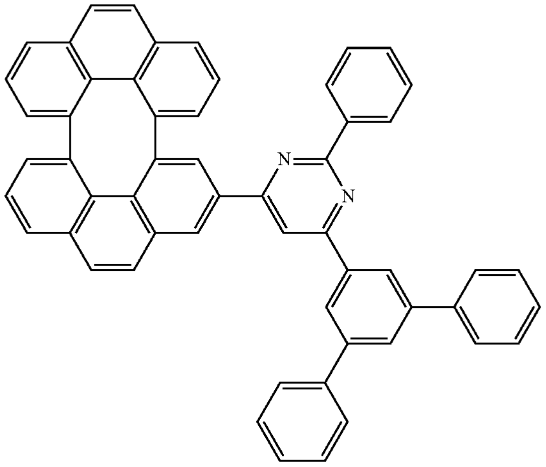
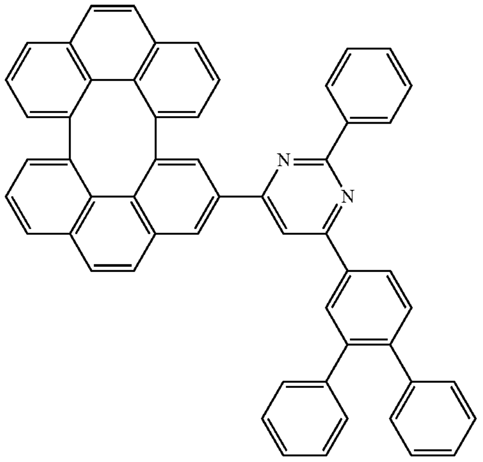
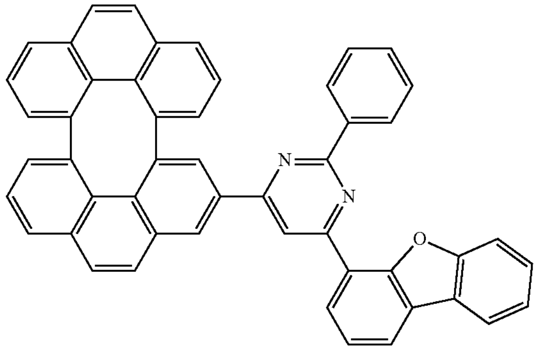
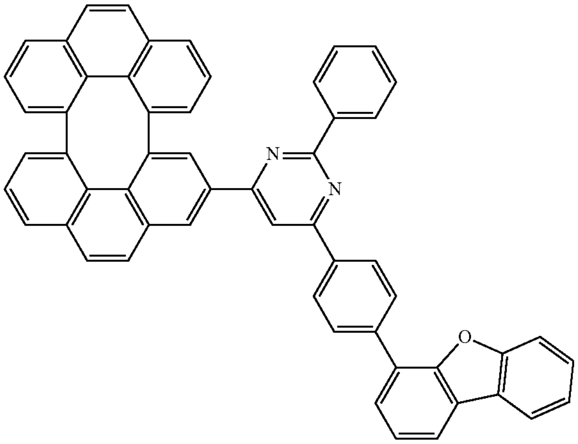
-continued
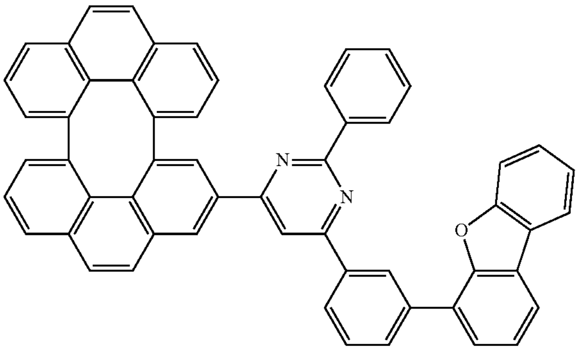
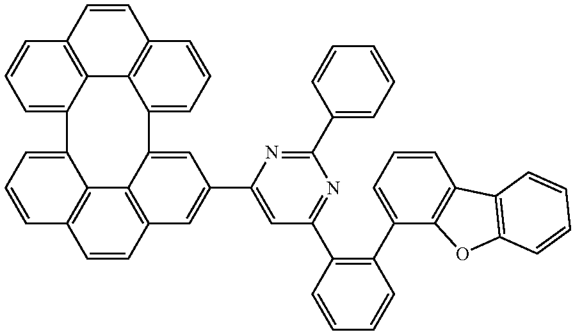
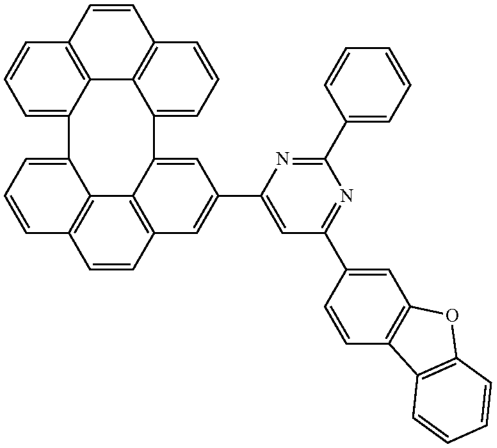
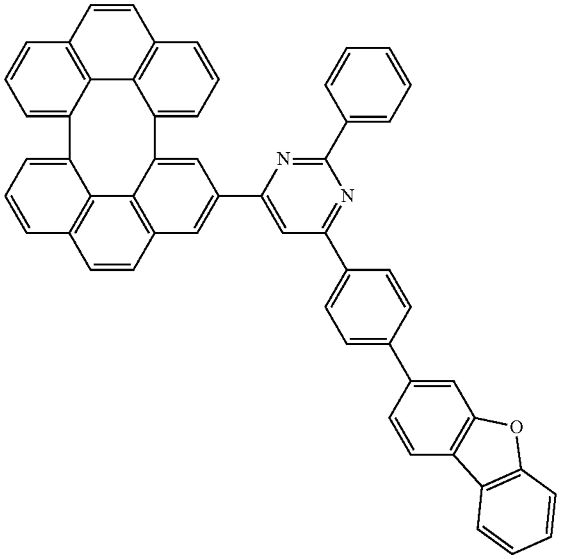

-continued
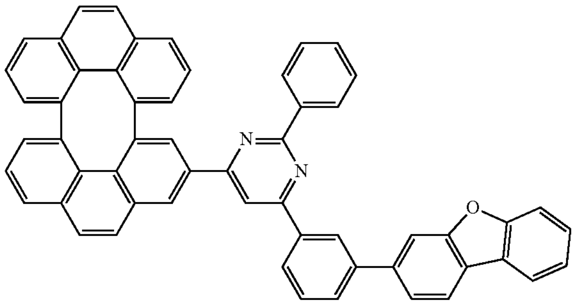
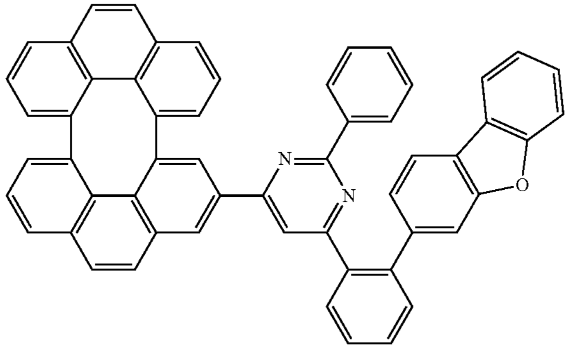
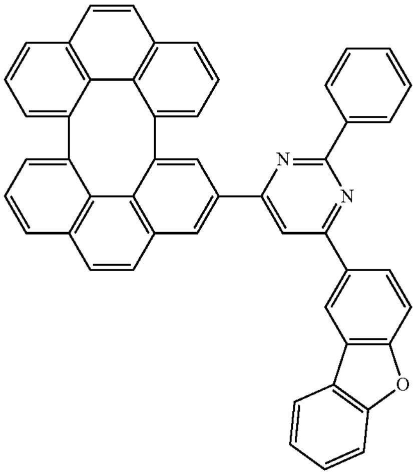
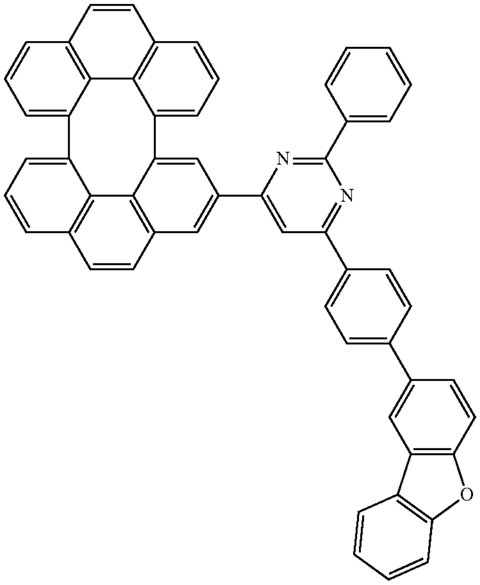
-continued
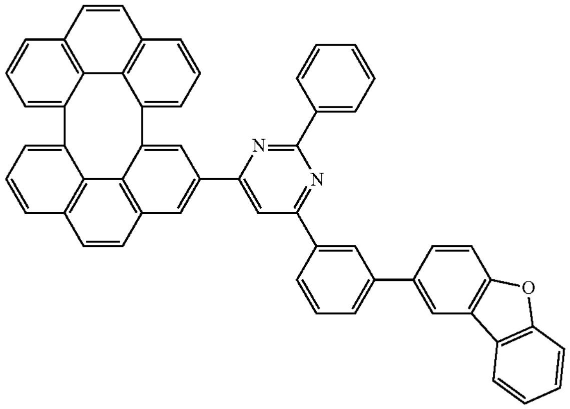
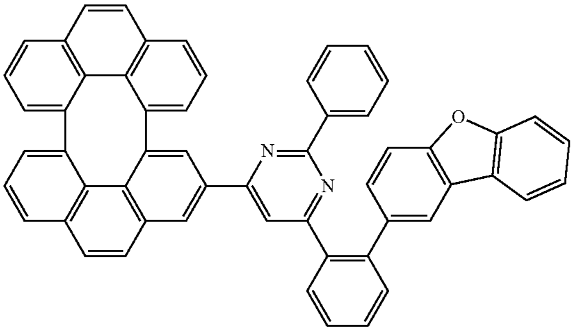
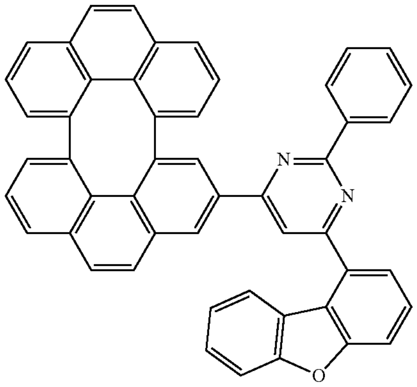
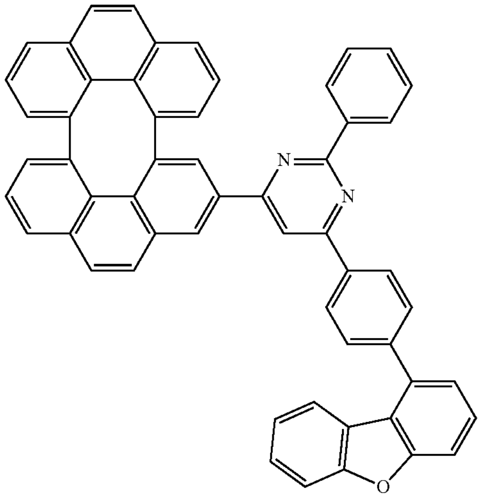

-continued
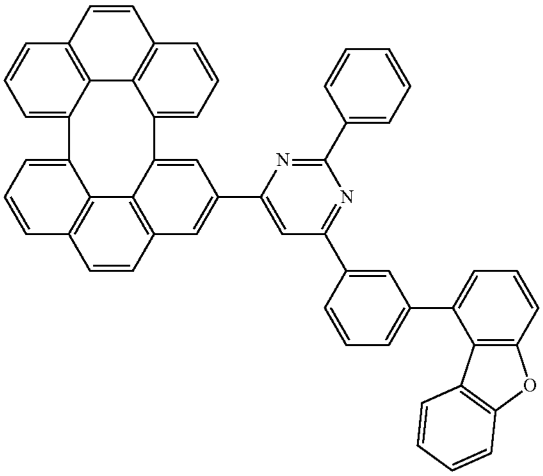
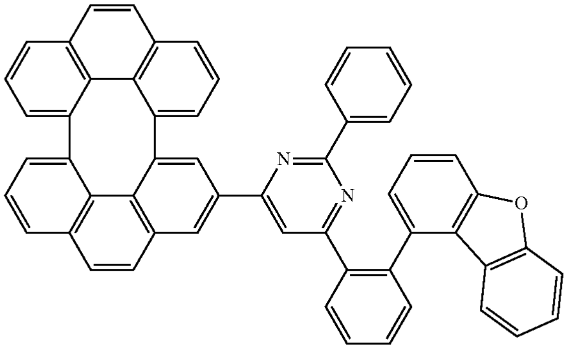
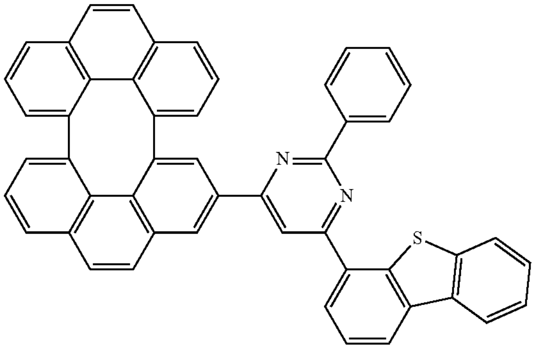
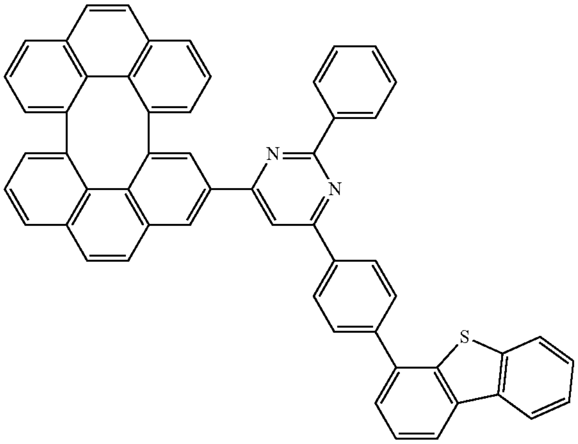
-continued
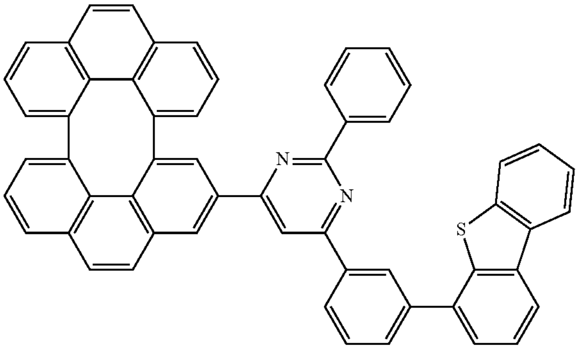
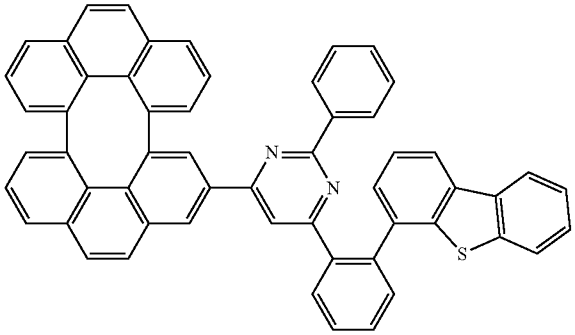
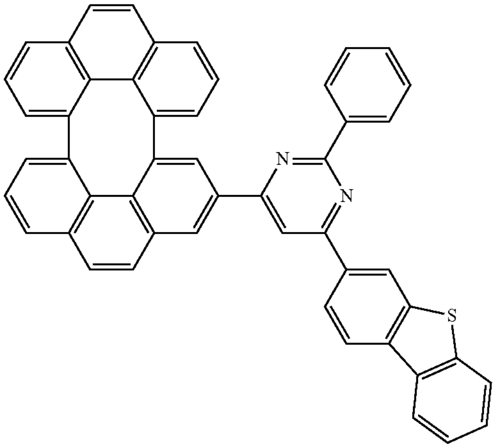
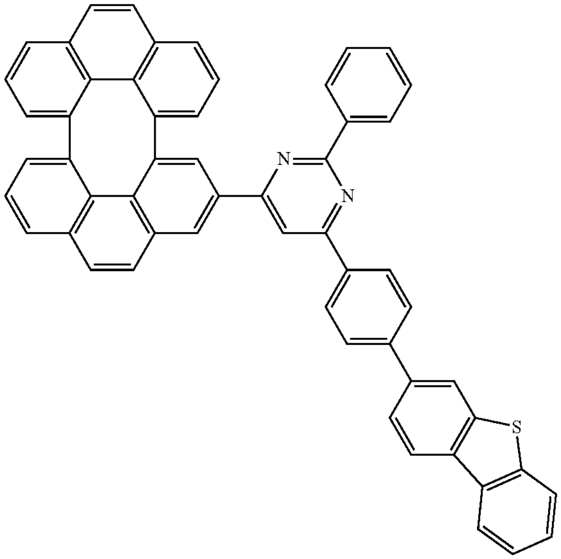

-continued
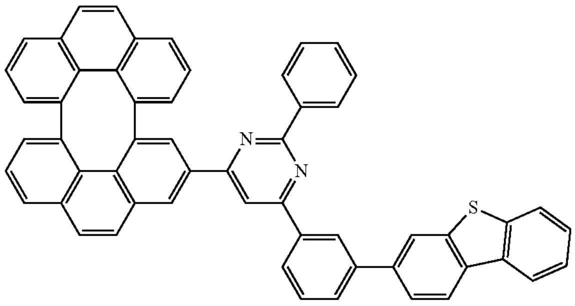
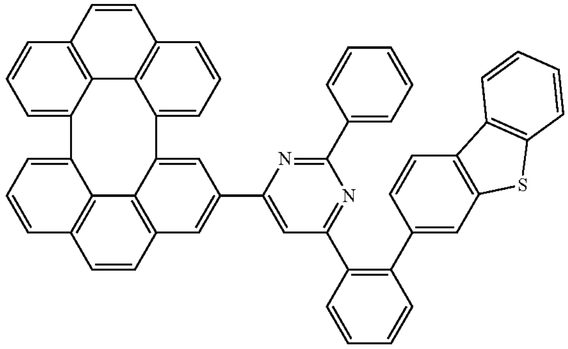
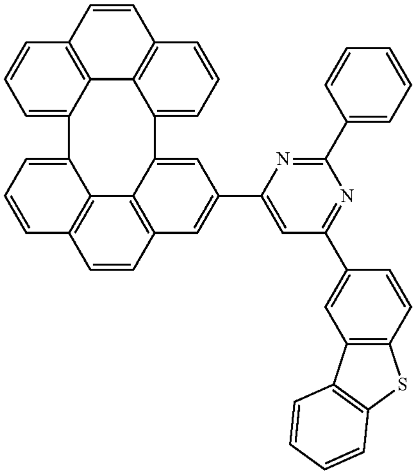
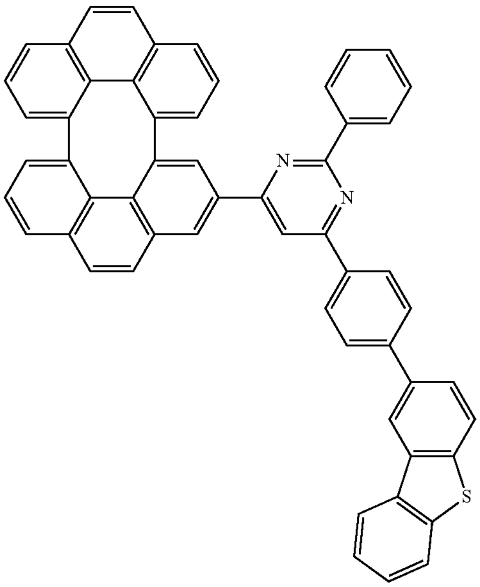
-continued
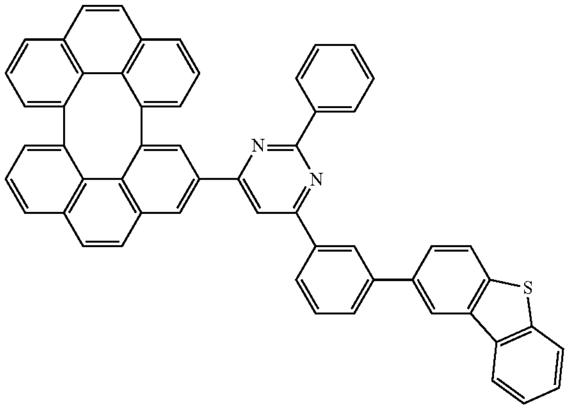
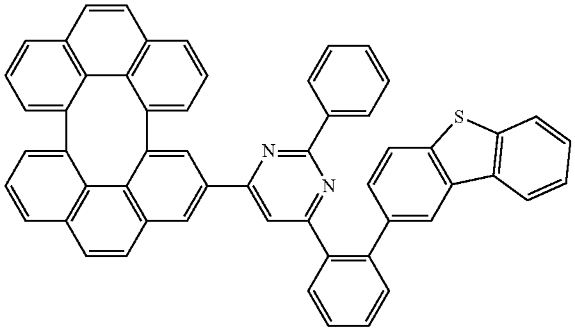
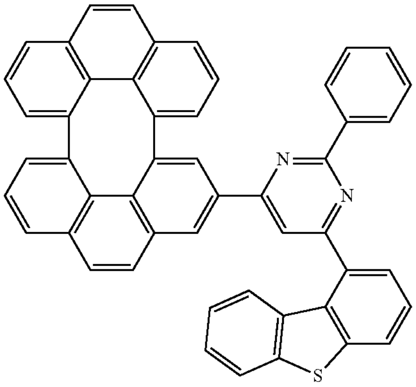
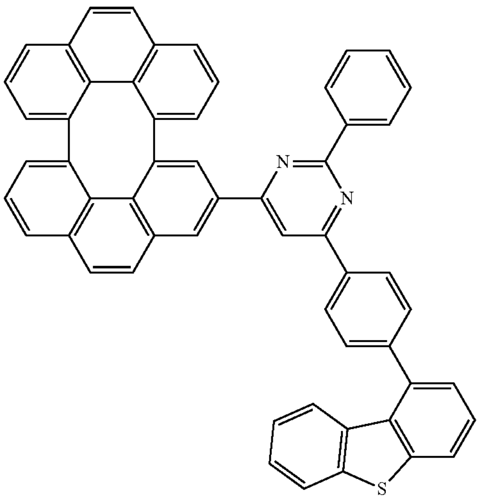

-continued
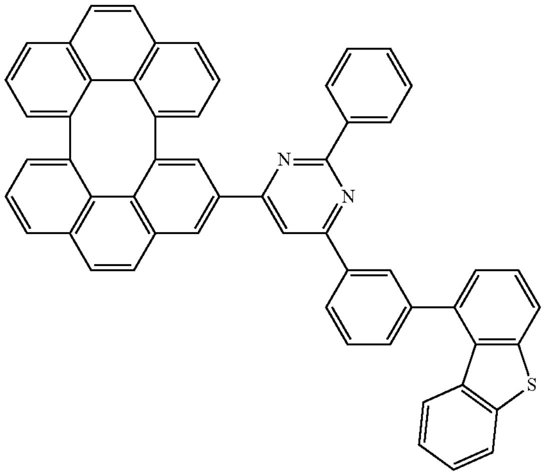
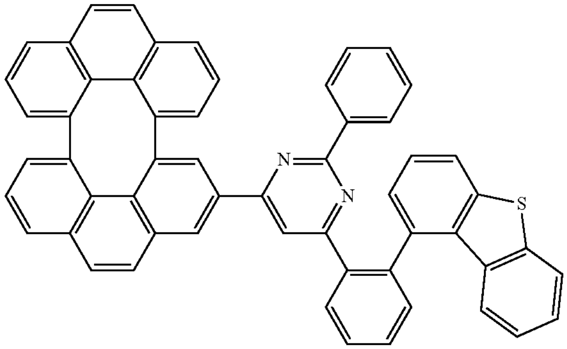
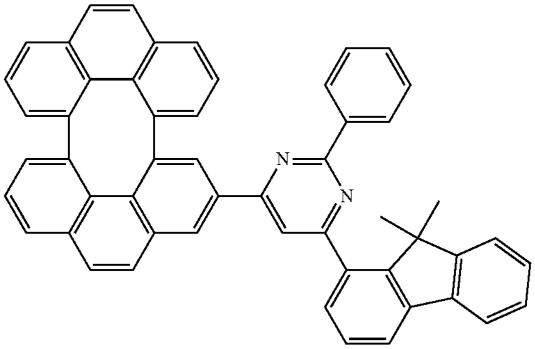
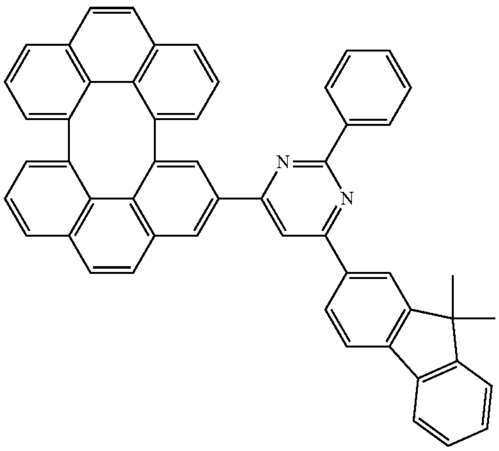
-continued
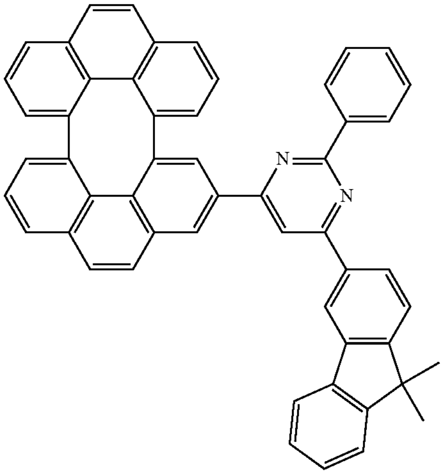
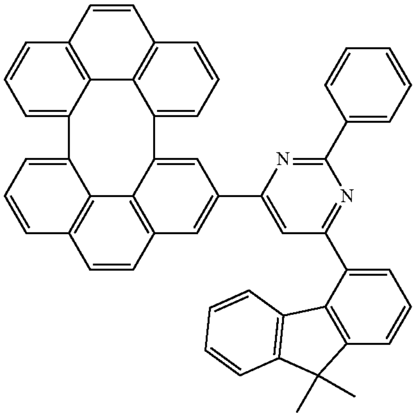
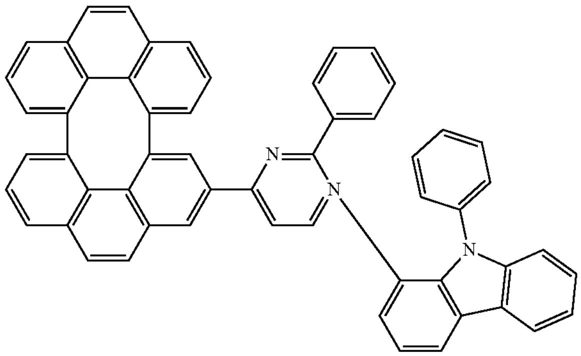

-continued
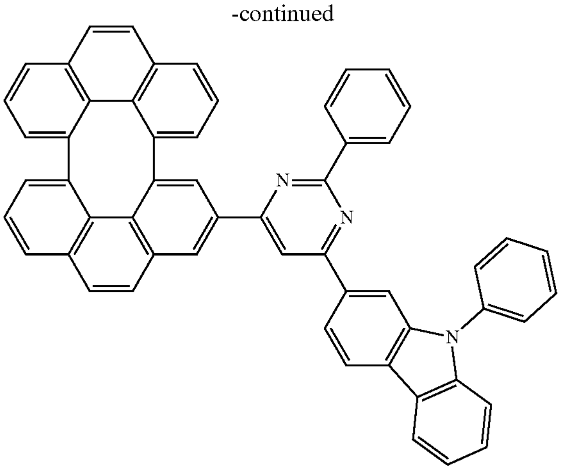
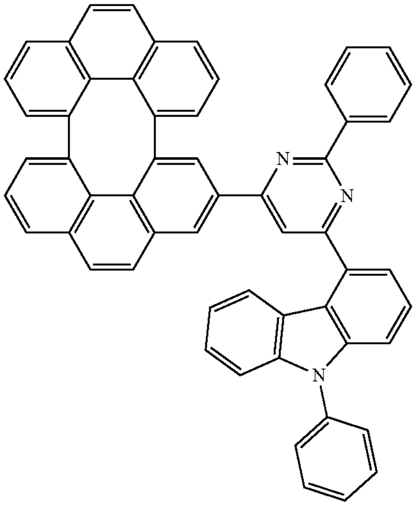
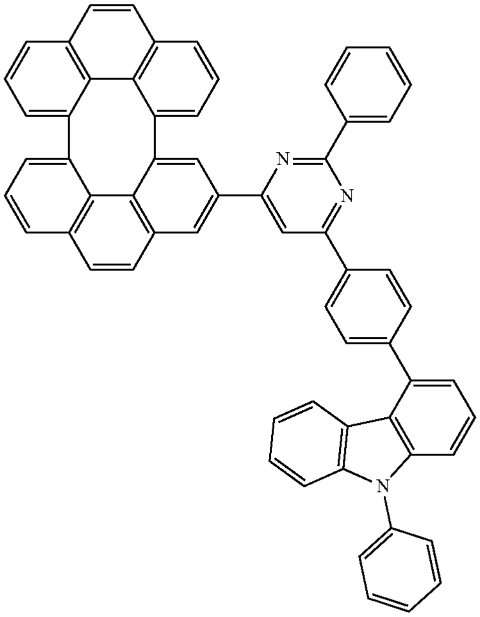
-continued
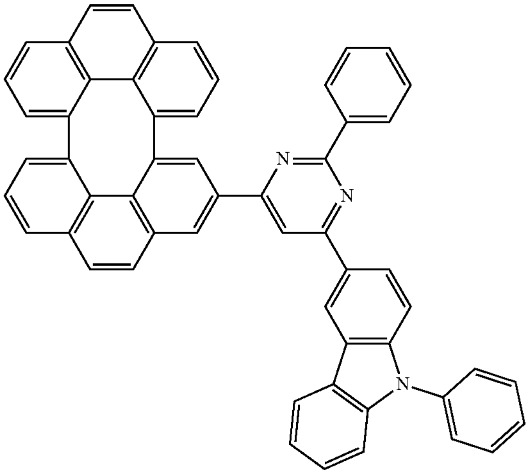
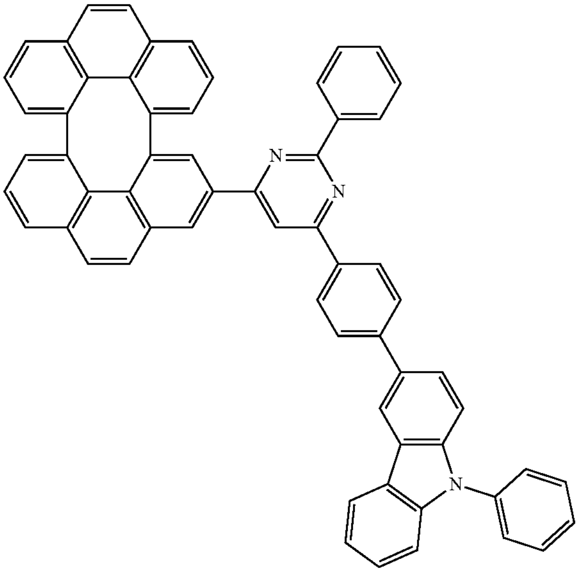
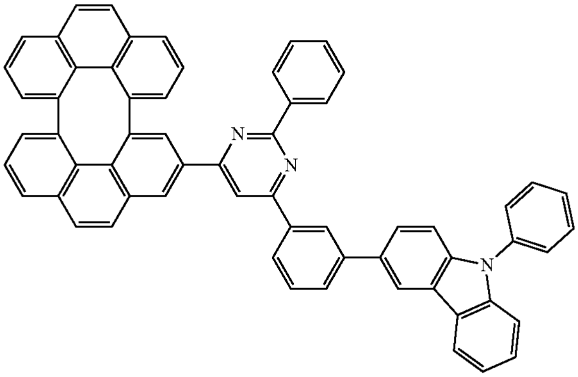

-continued
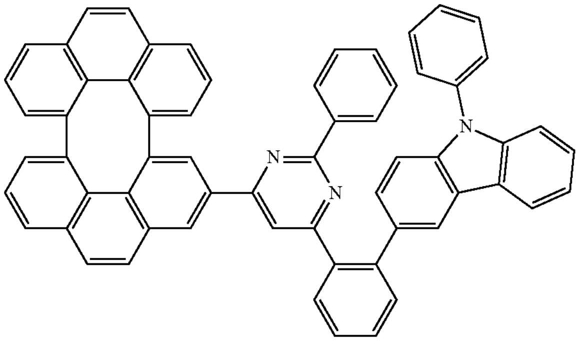
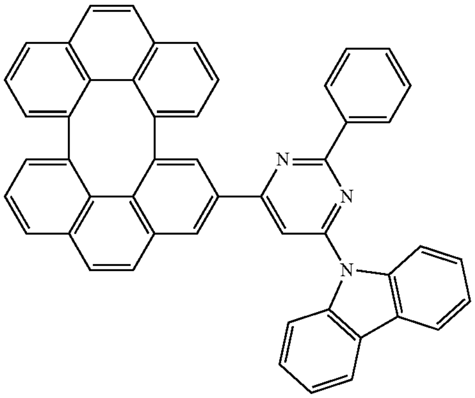
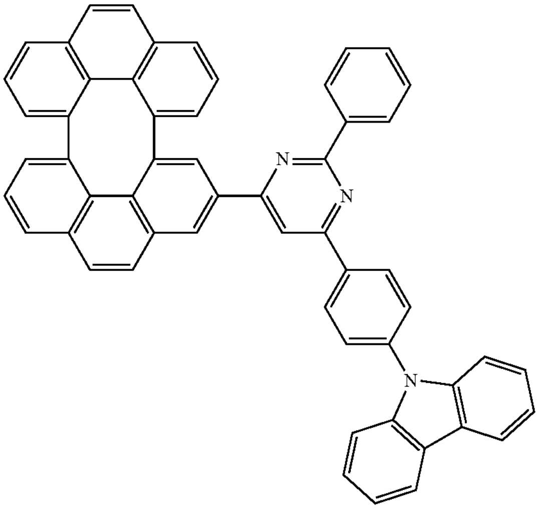
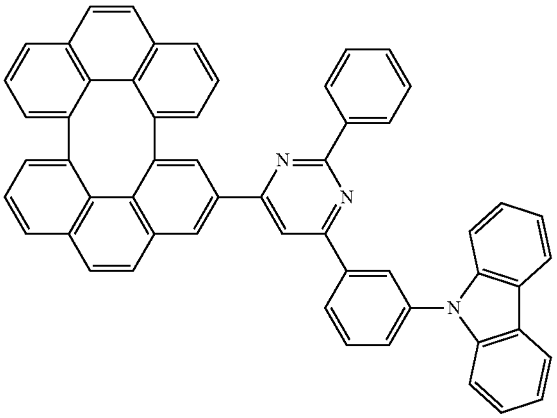
-continued
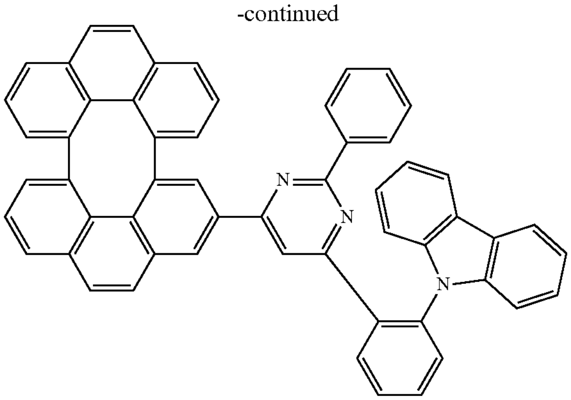
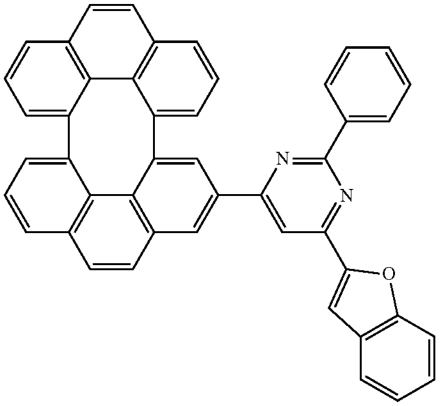
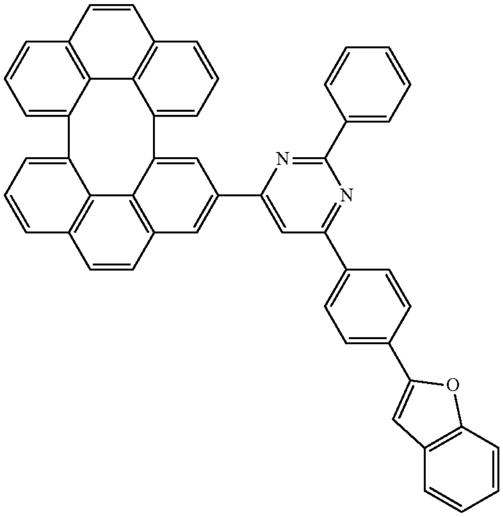
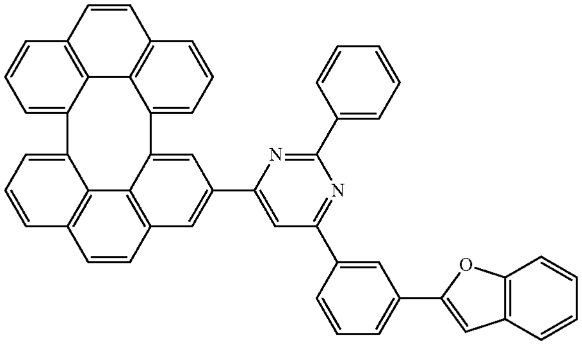

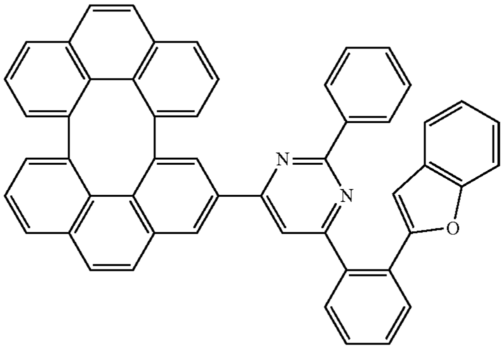
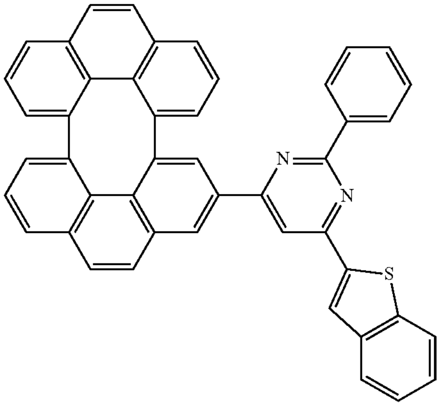
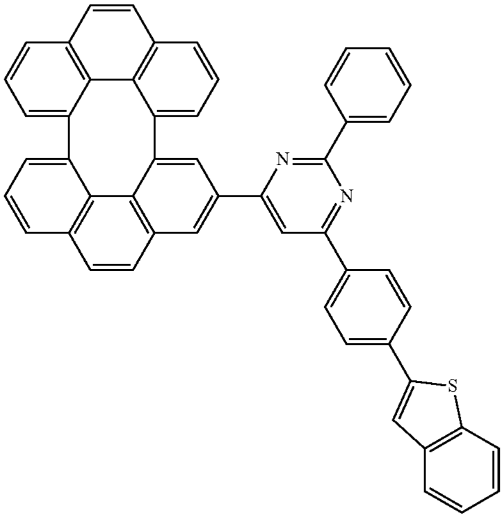
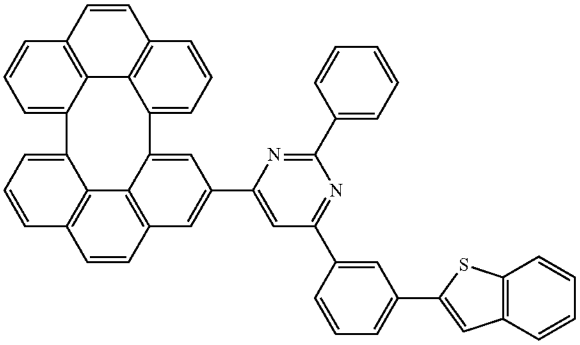
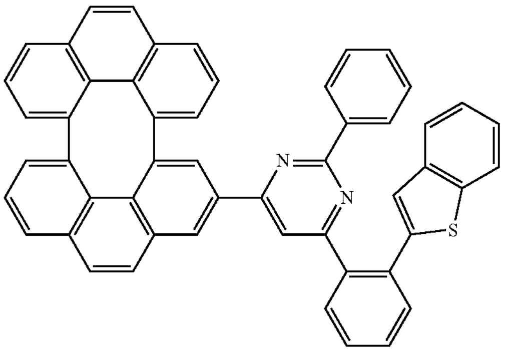
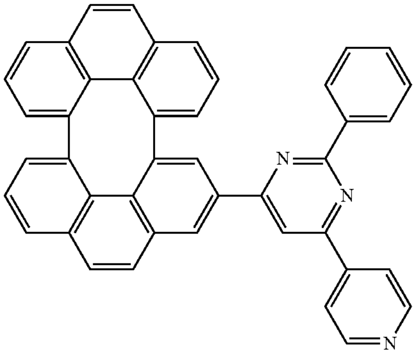
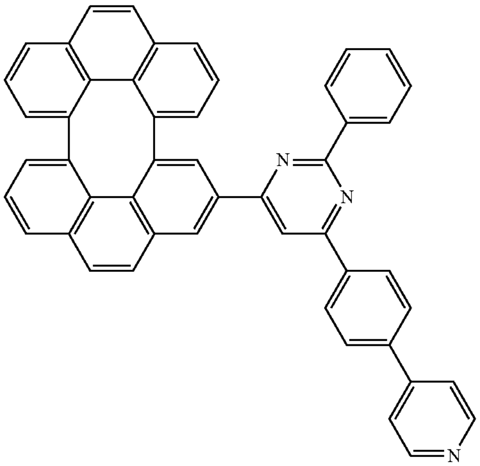
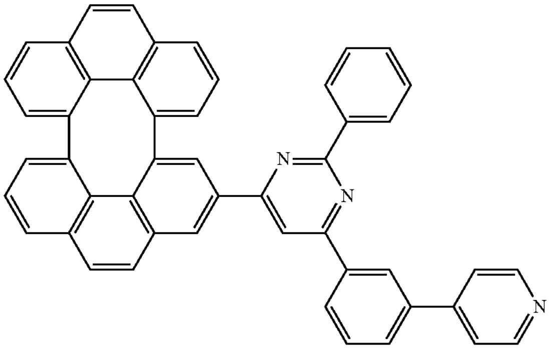

-continued
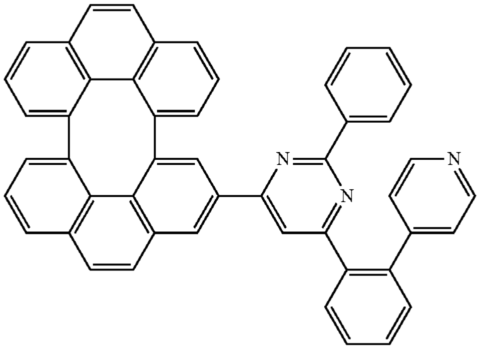
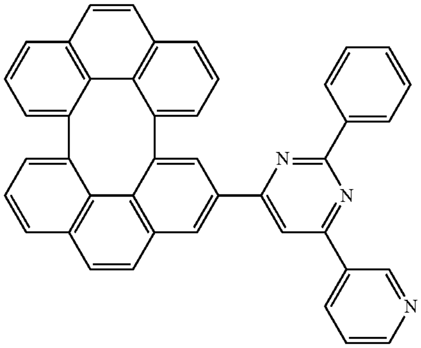
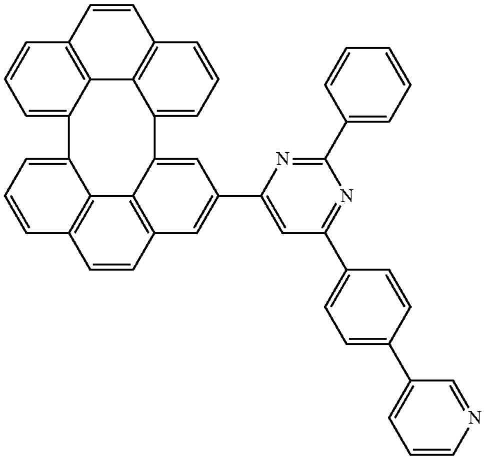
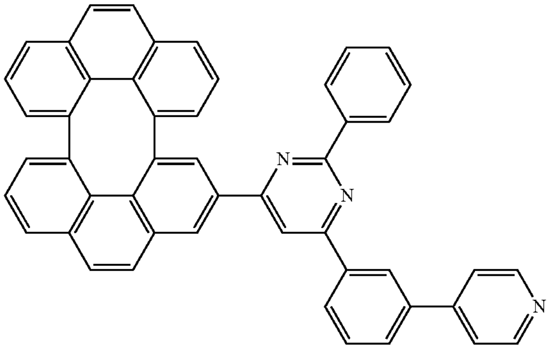
-continued
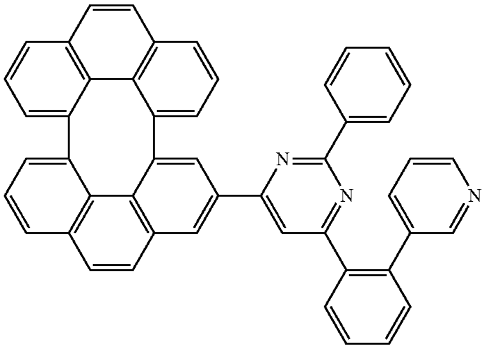
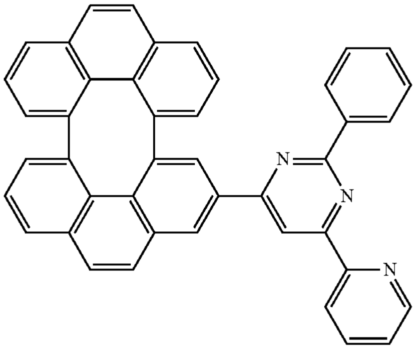
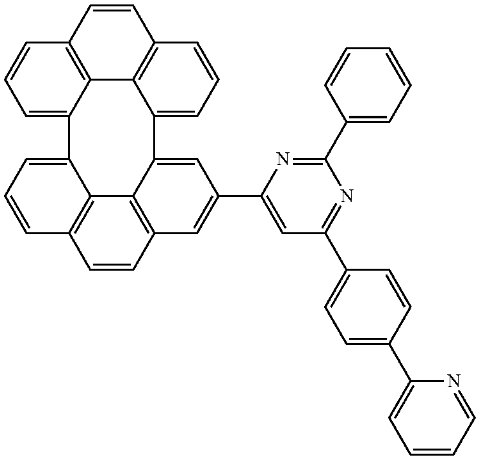
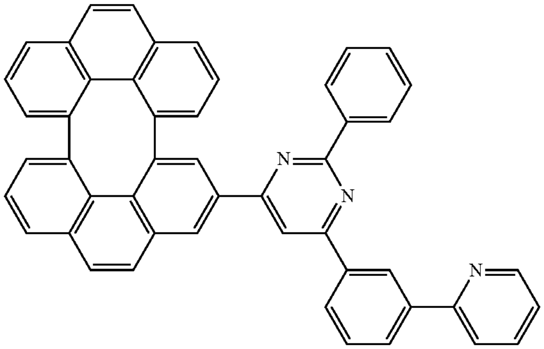

-continued
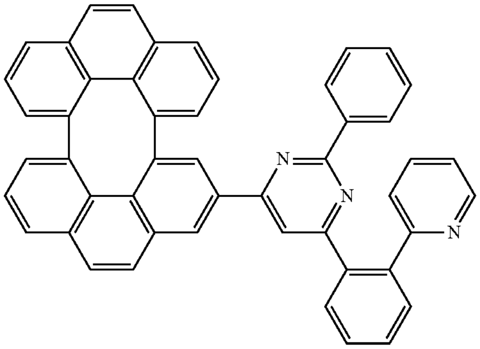
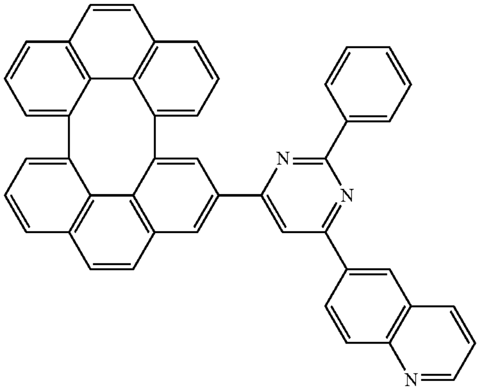
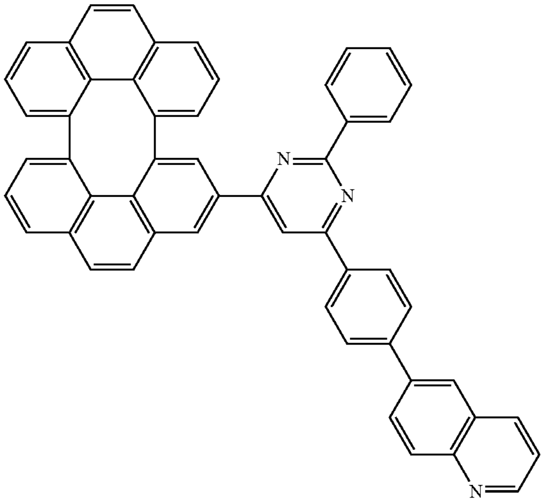
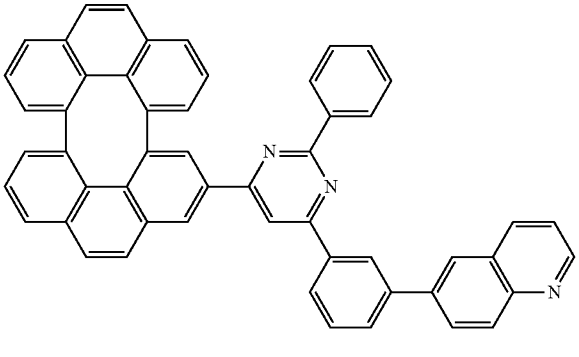
-continued
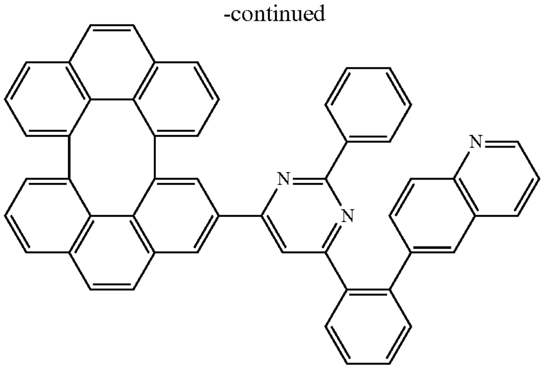
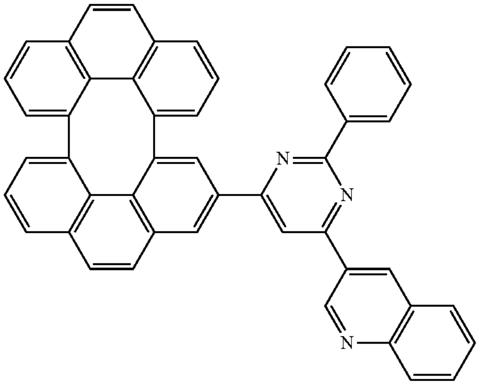
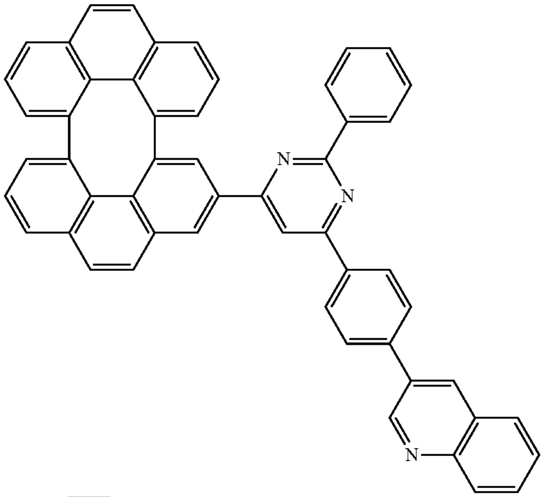
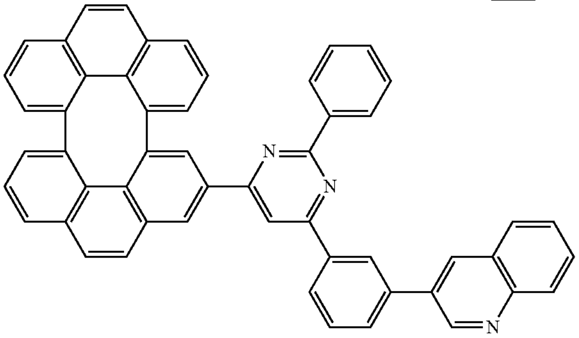

-continued
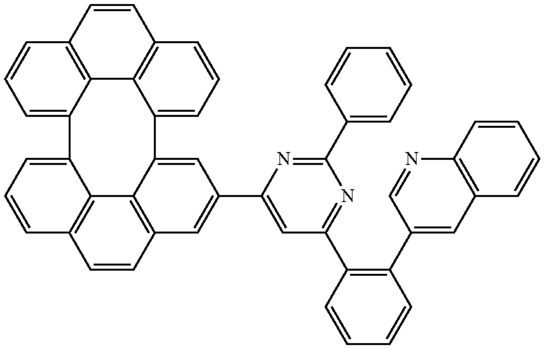
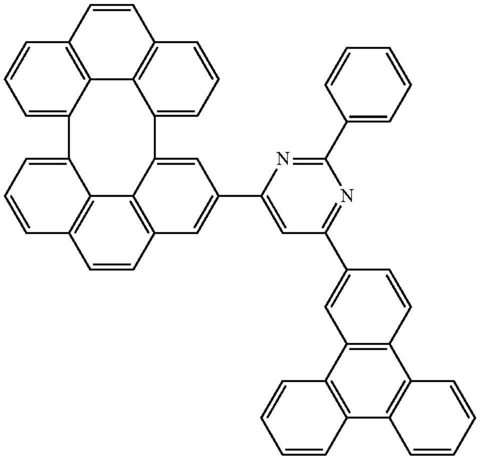
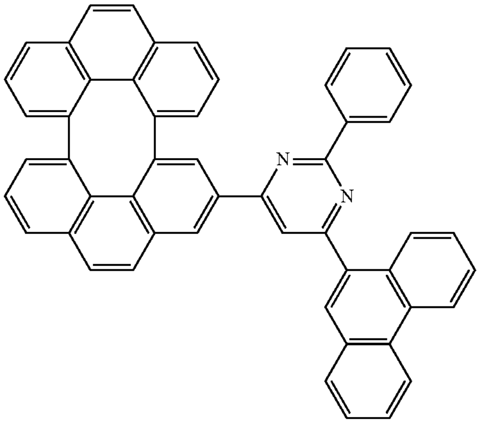
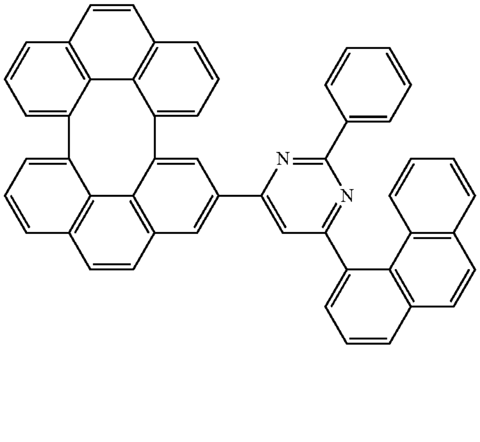
-continued
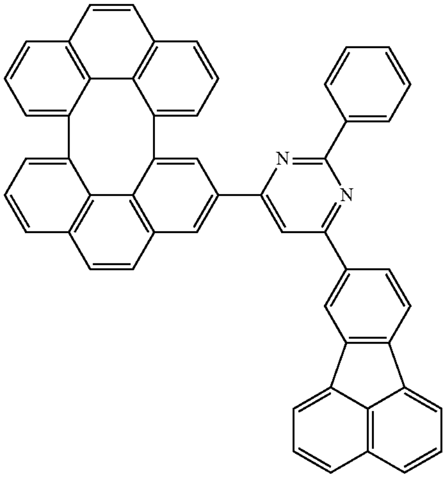
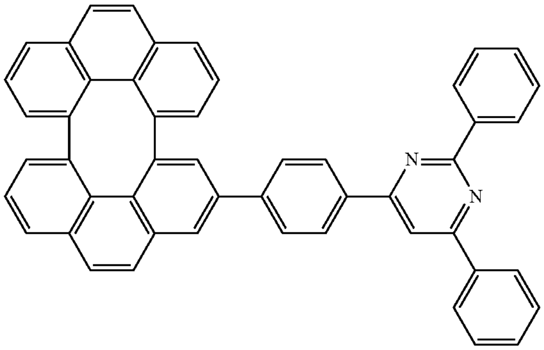
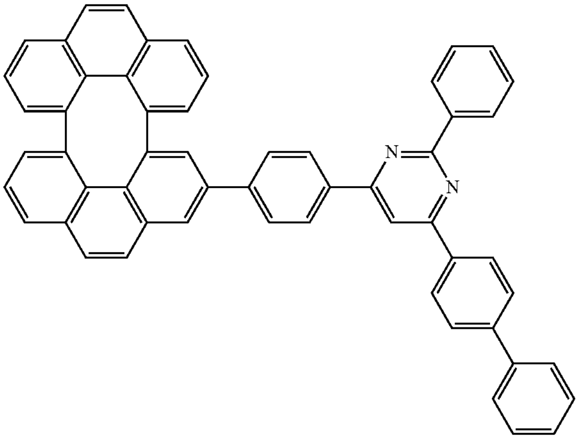
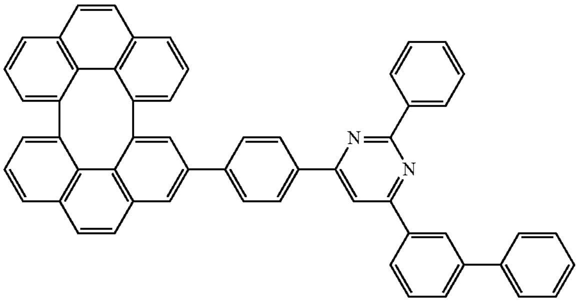

-continued
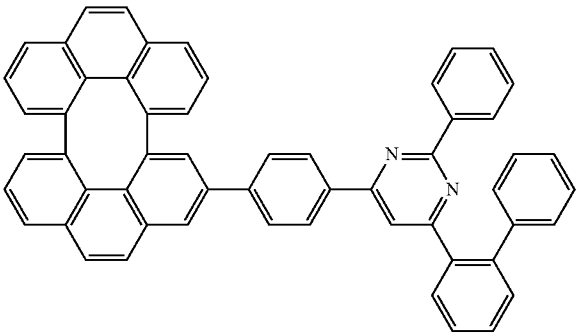
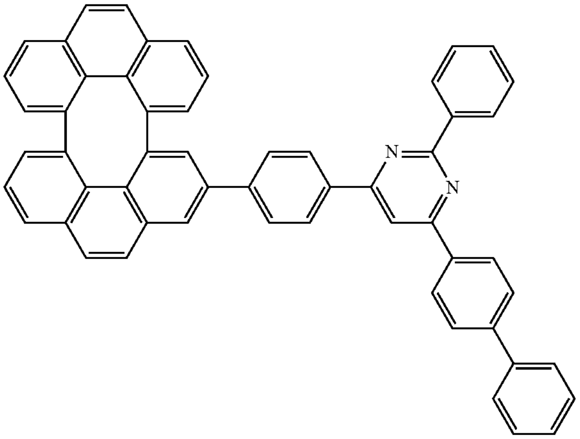
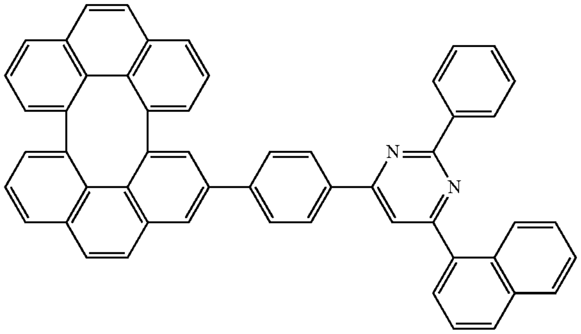
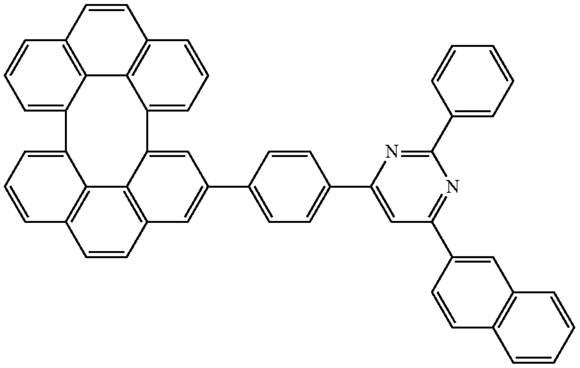
-continued
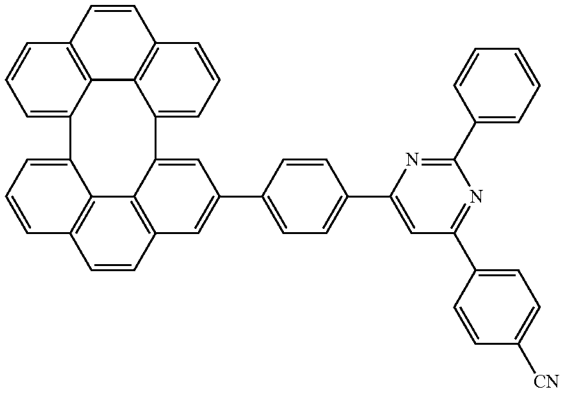
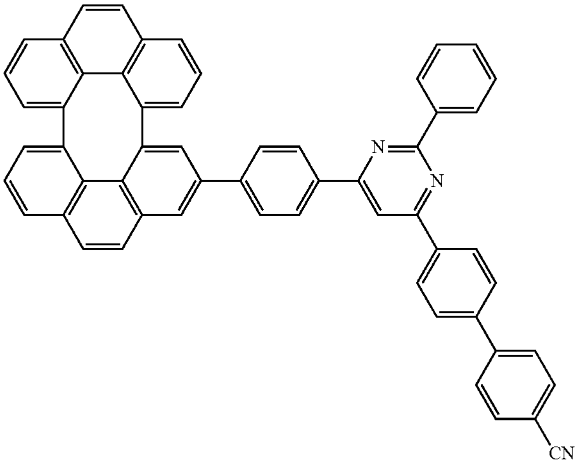
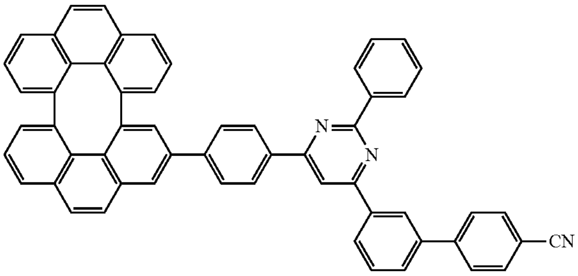
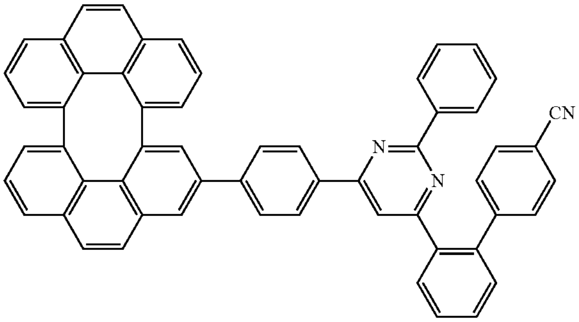

-continued
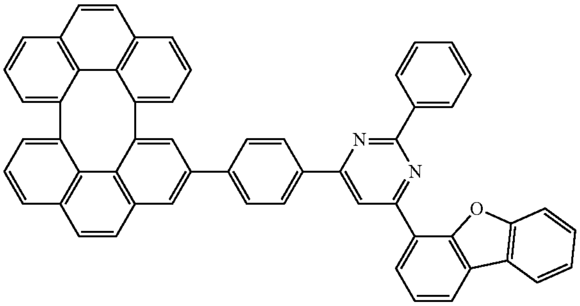
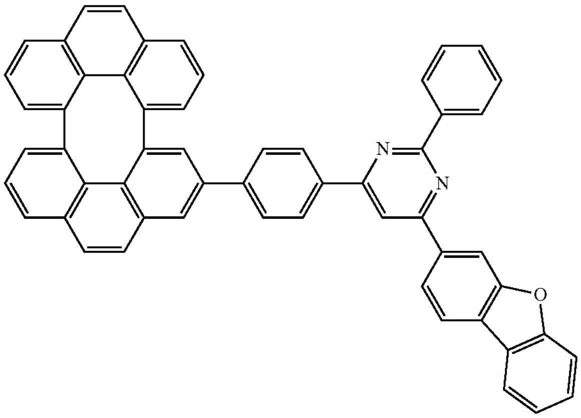
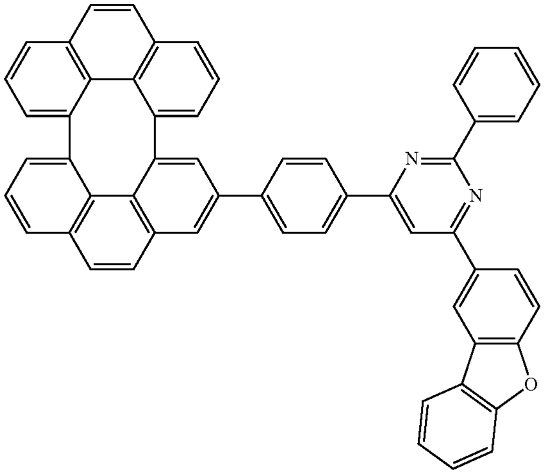
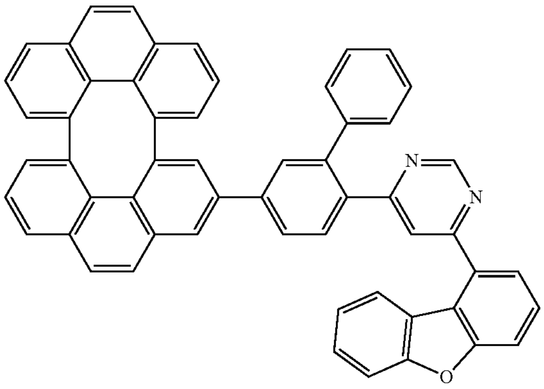
-continued
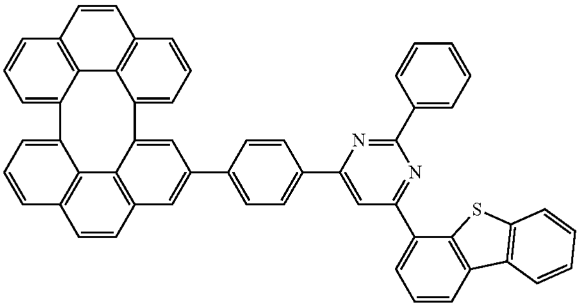
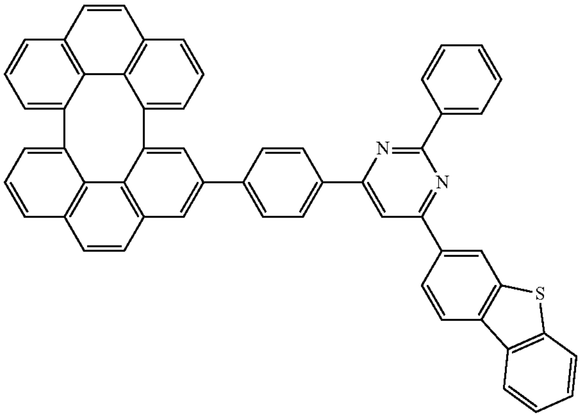
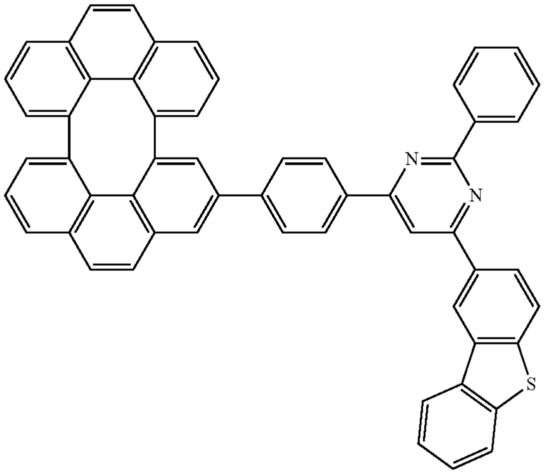
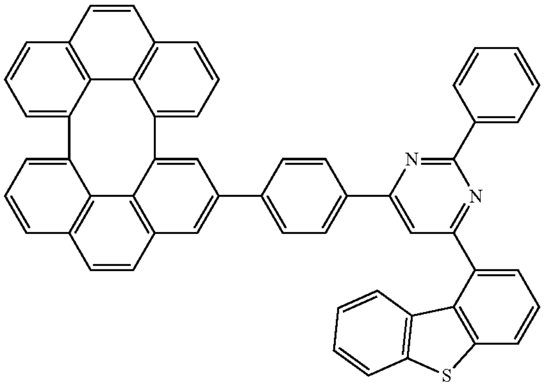

-continued
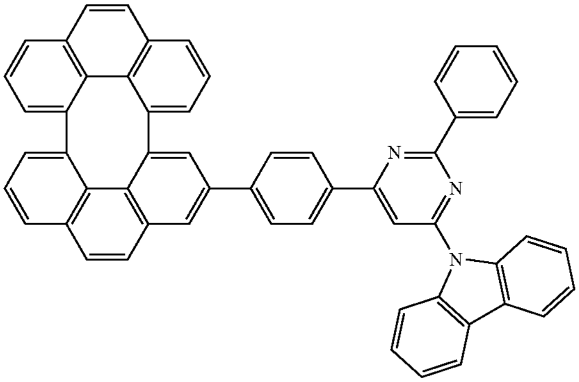
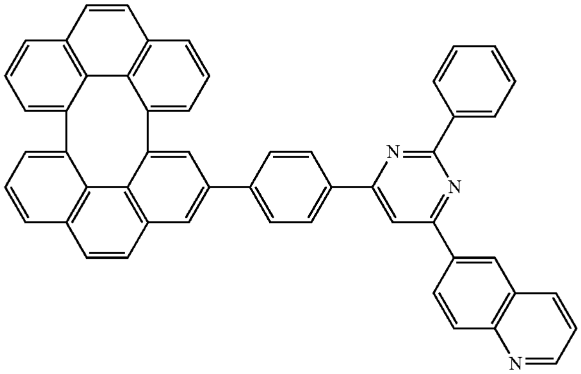
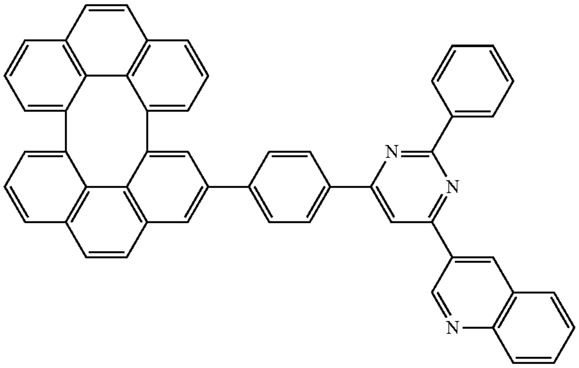
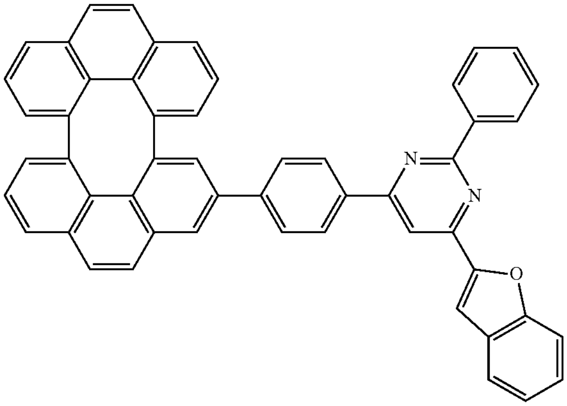
-continued
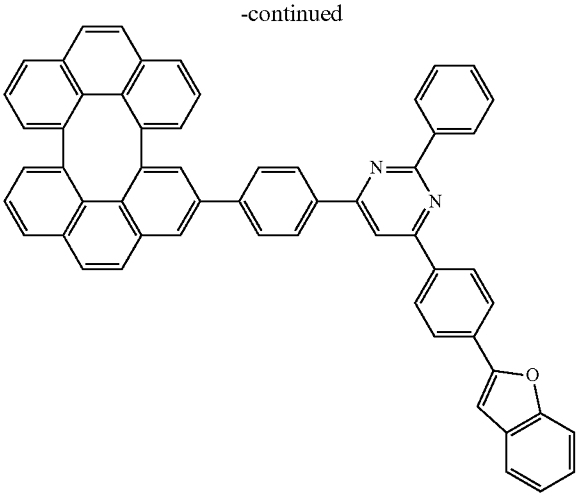
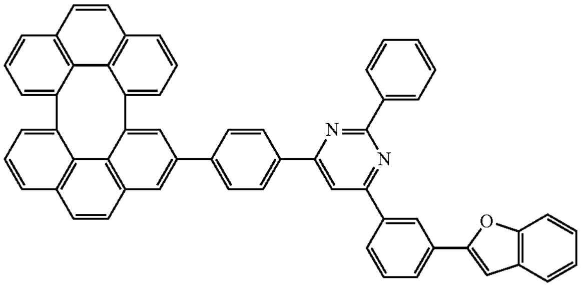
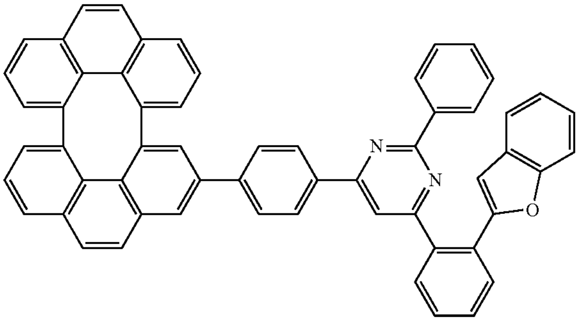
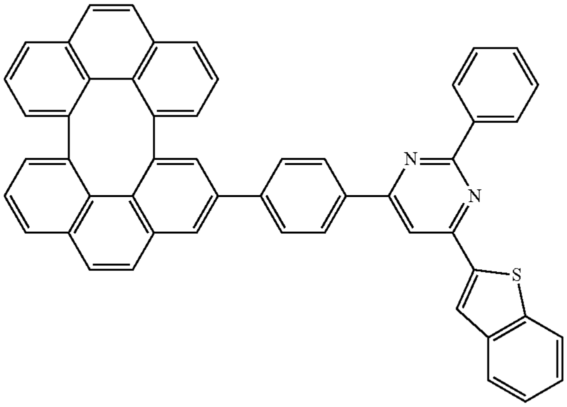

-continued
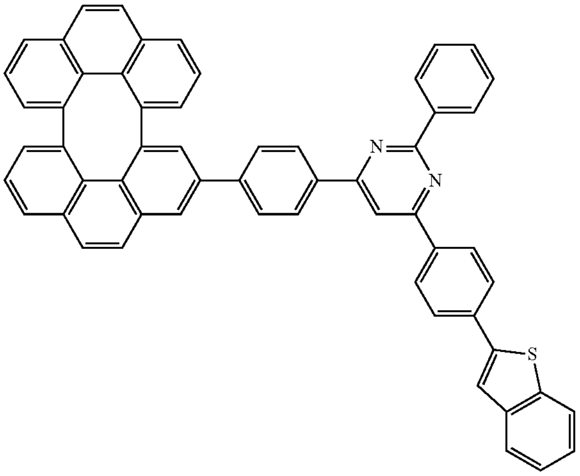
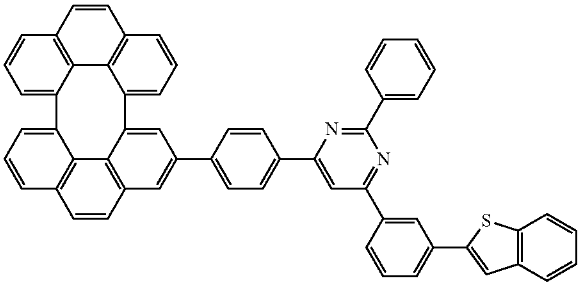
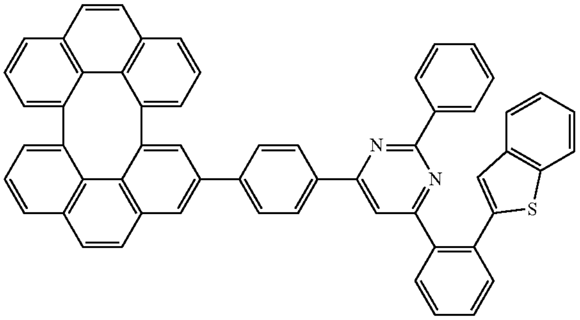
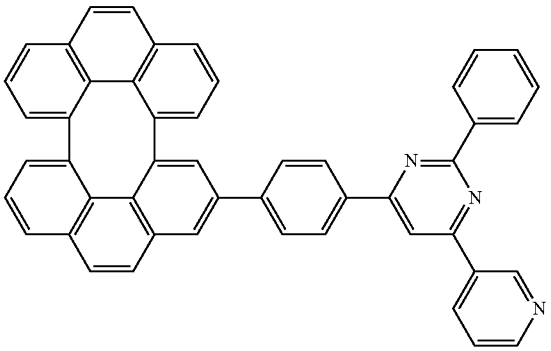
-continued
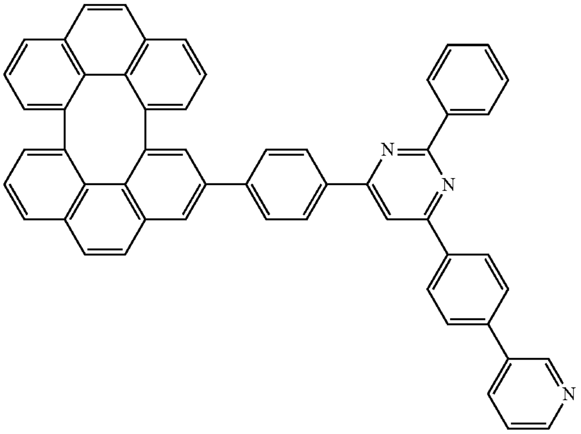
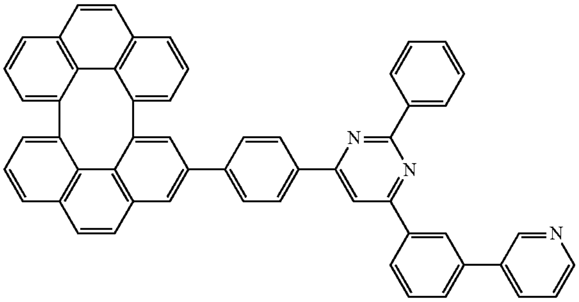
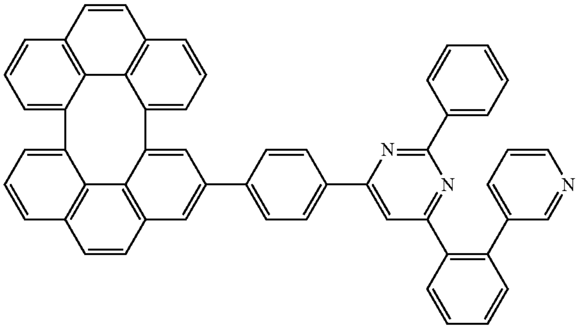
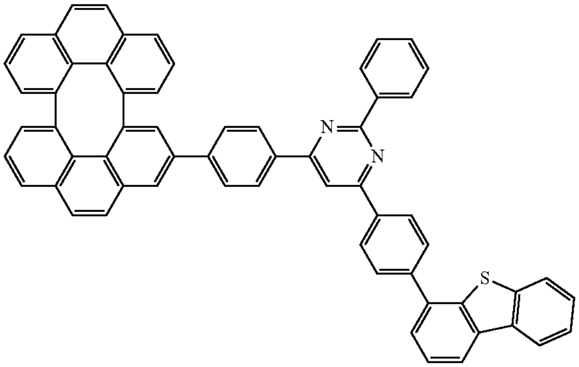
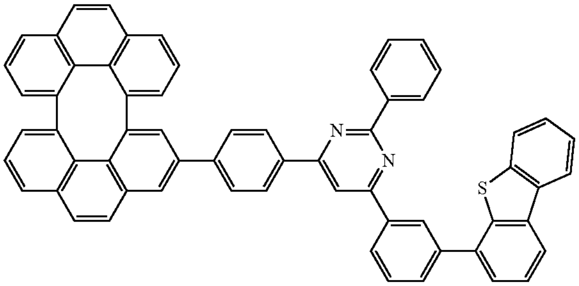

-continued
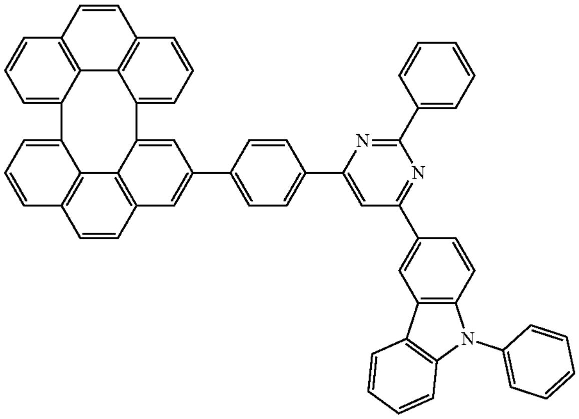
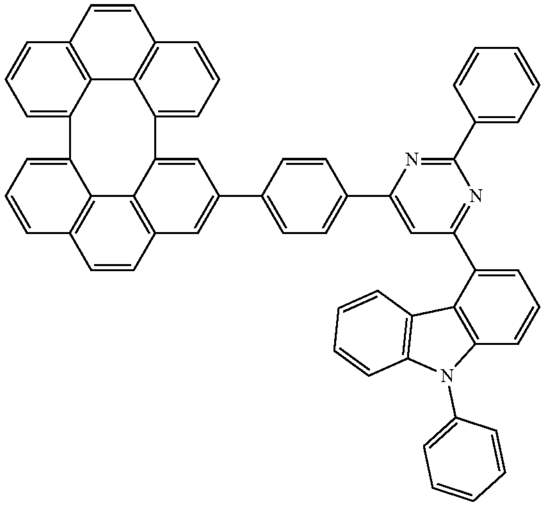
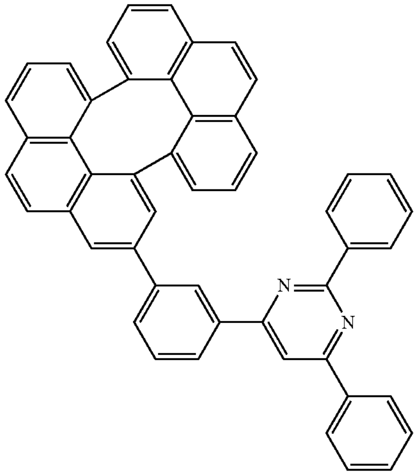
-continued
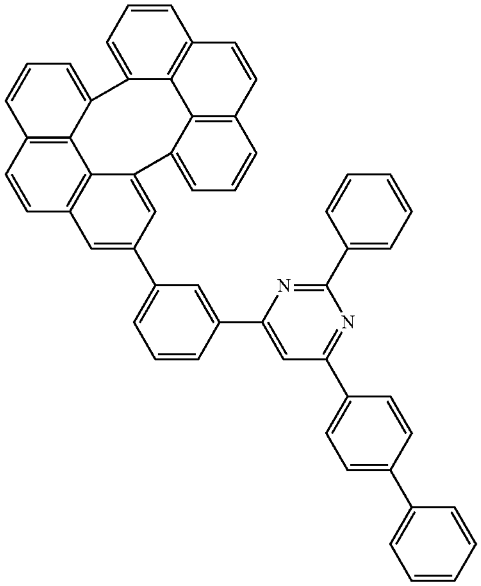
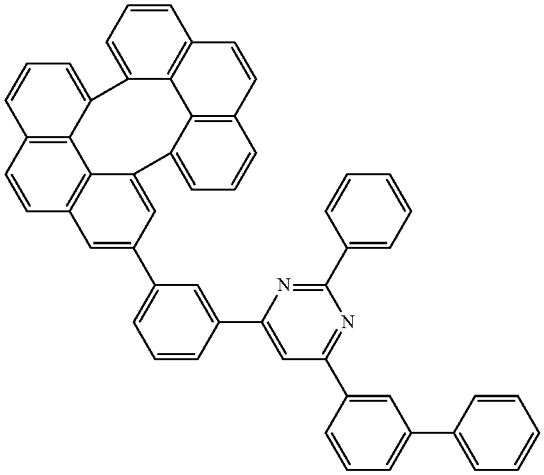
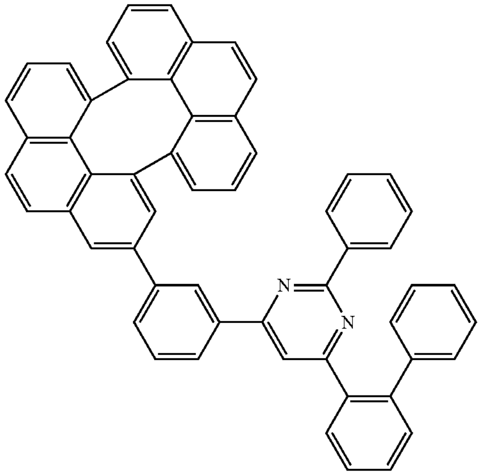

-continued
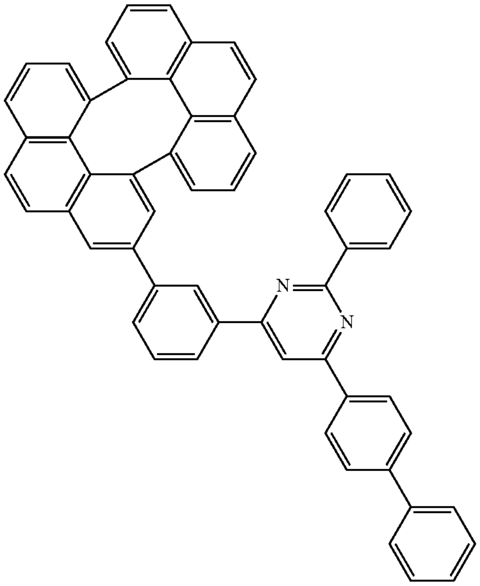
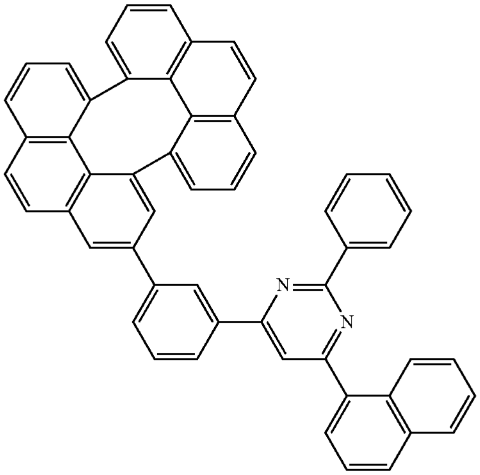
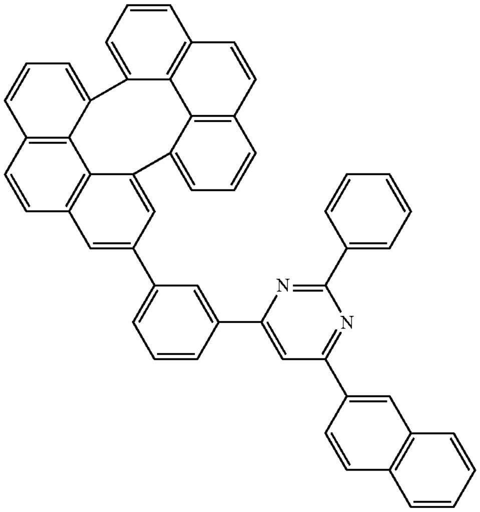
-continued
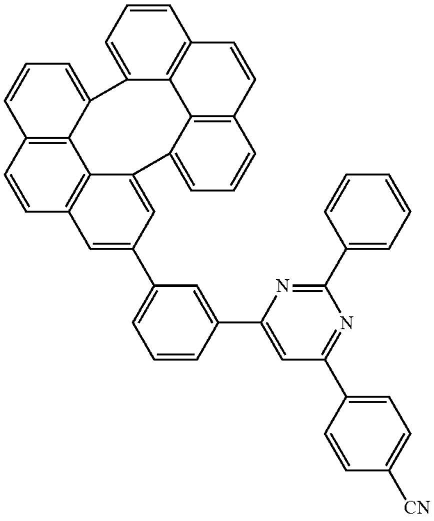
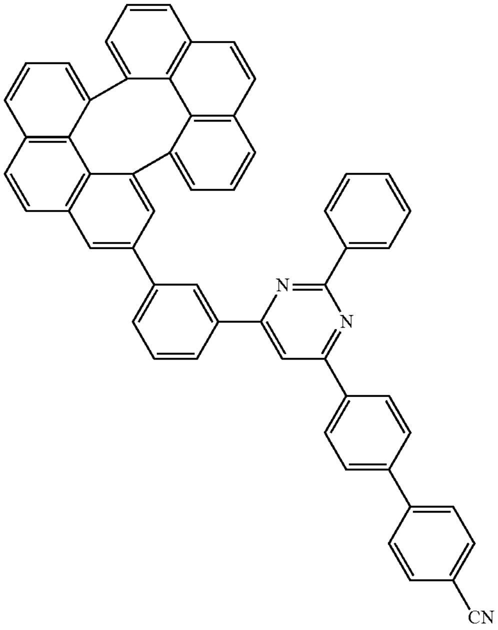
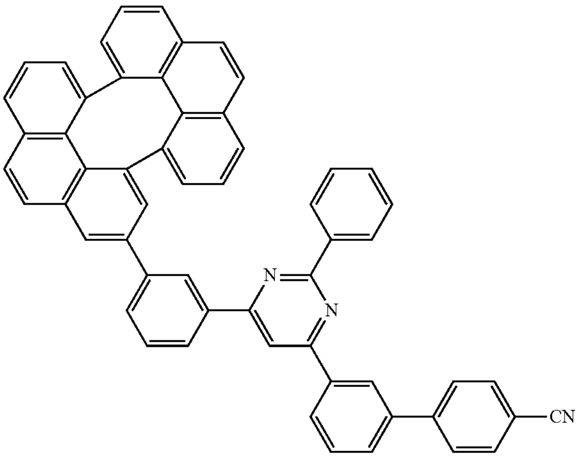

-continued
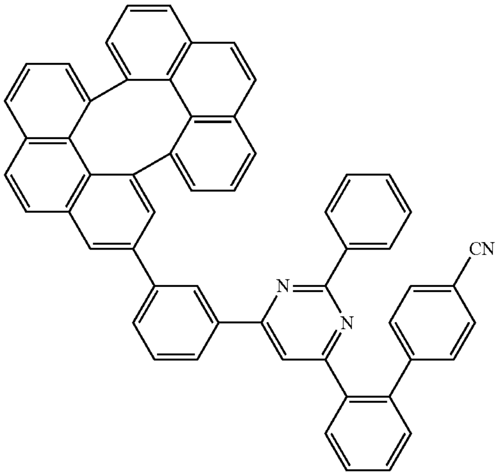
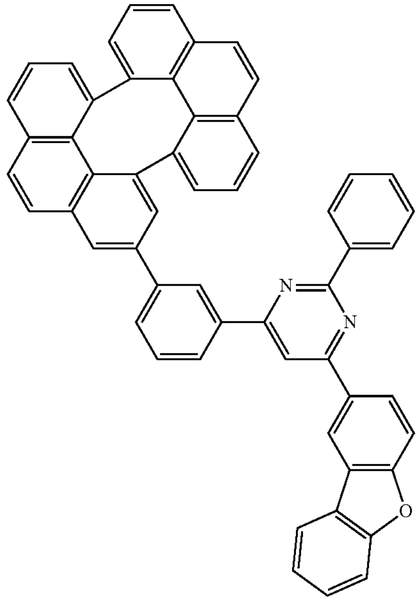
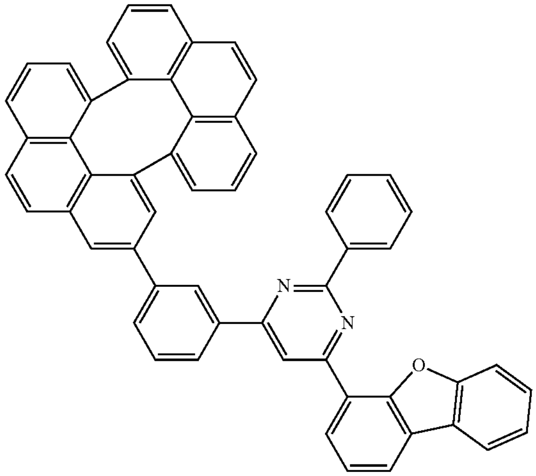
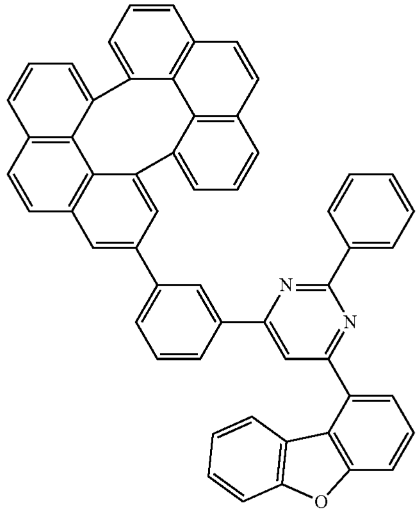
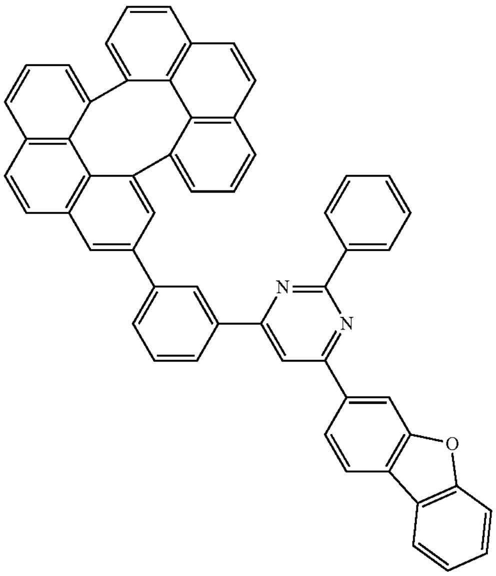
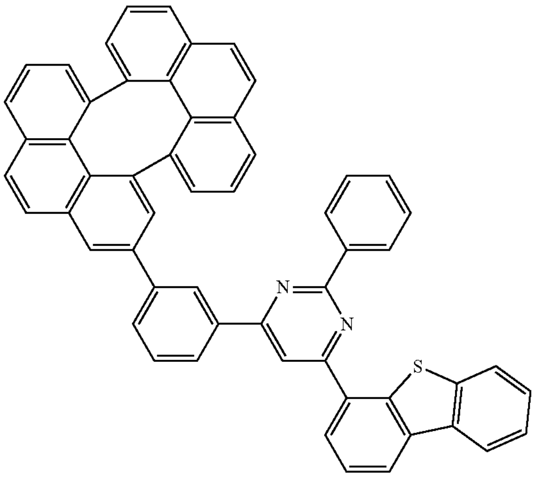
-continued -continued
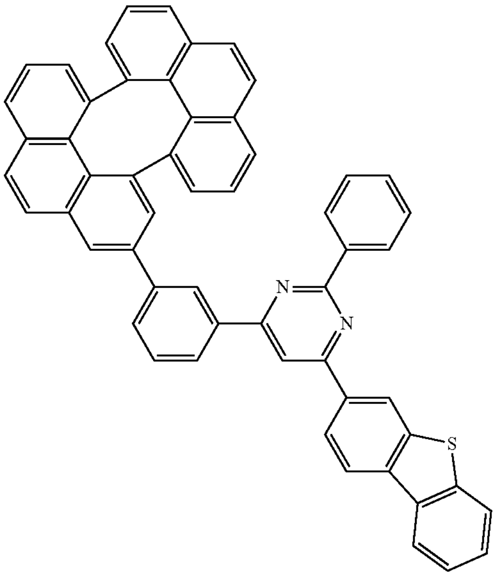
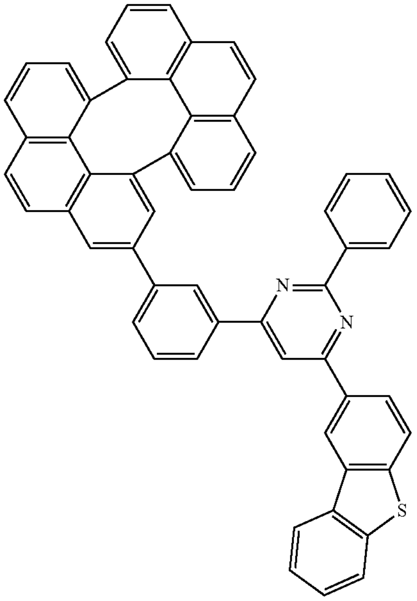
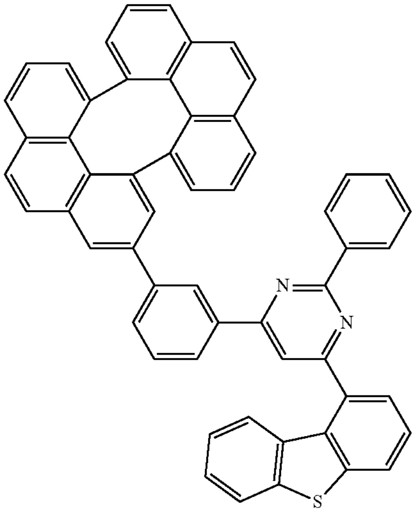
-continued
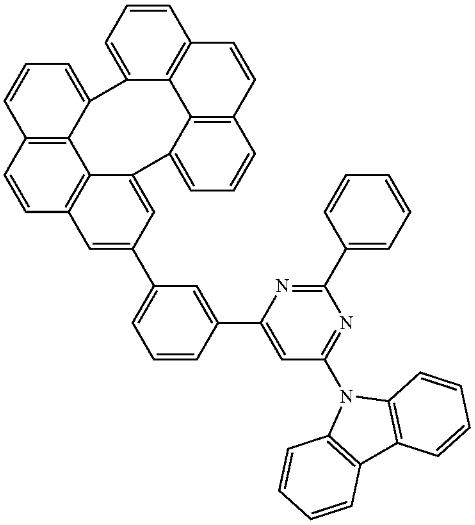
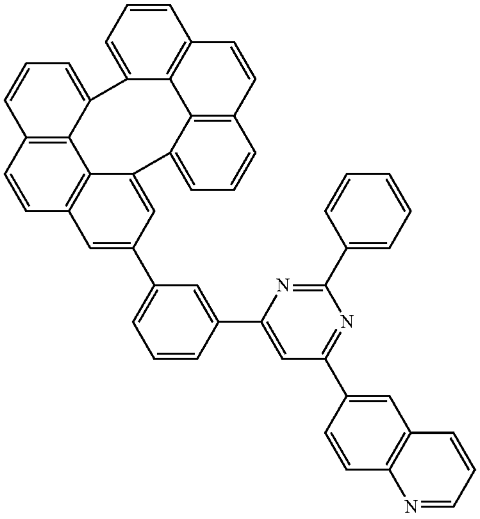
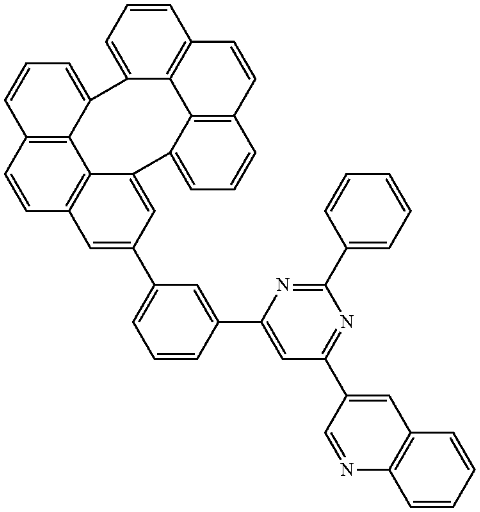

-continued
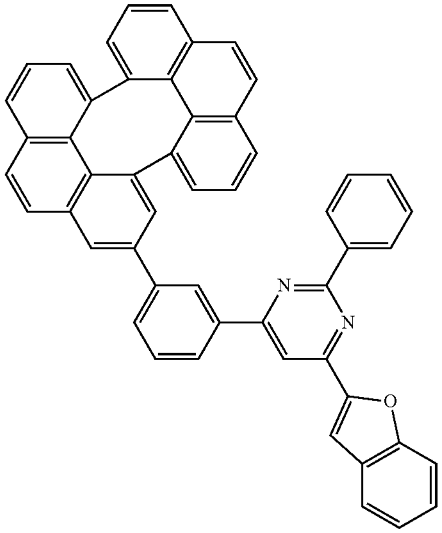
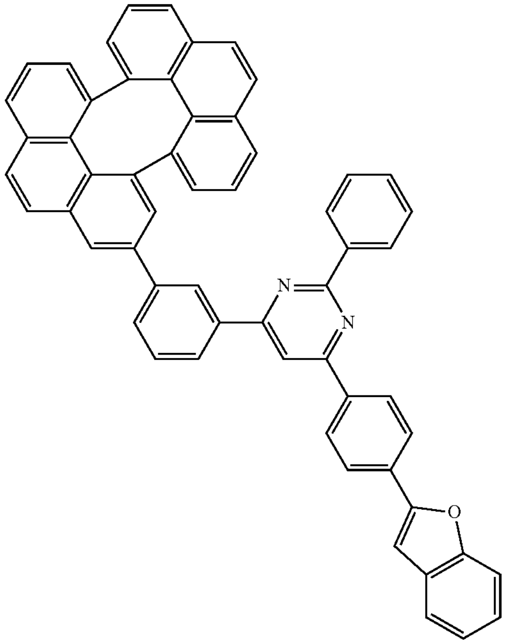
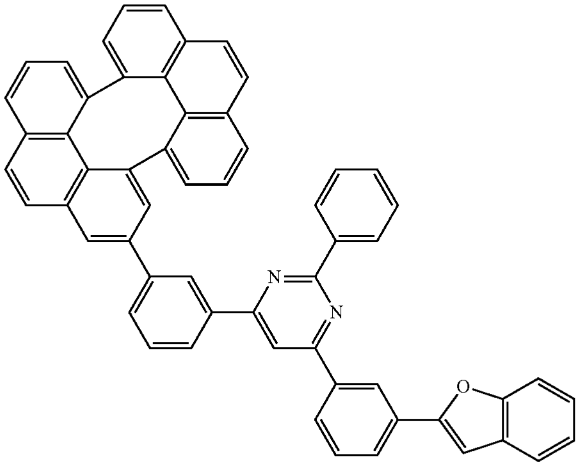
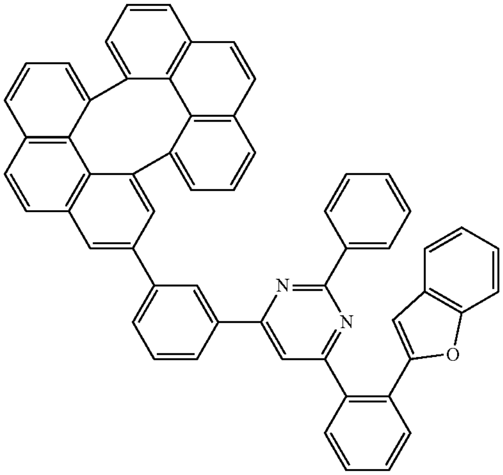
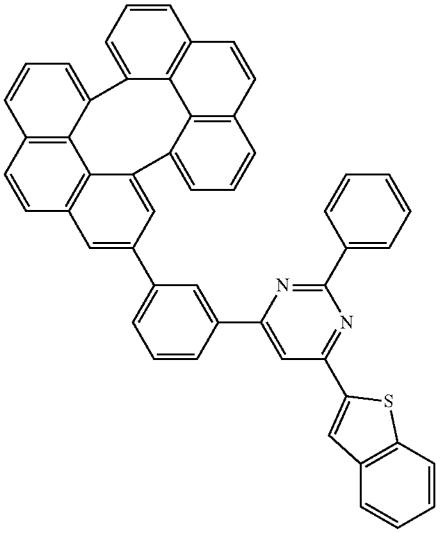
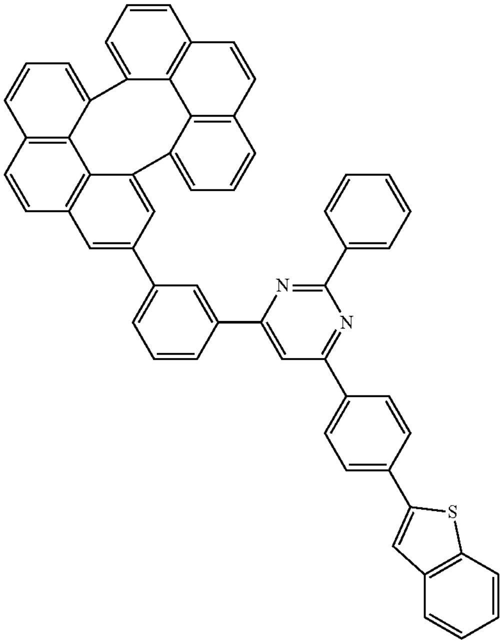

-continued
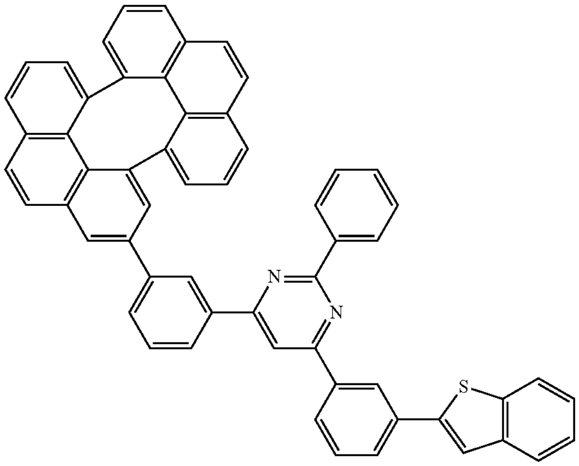
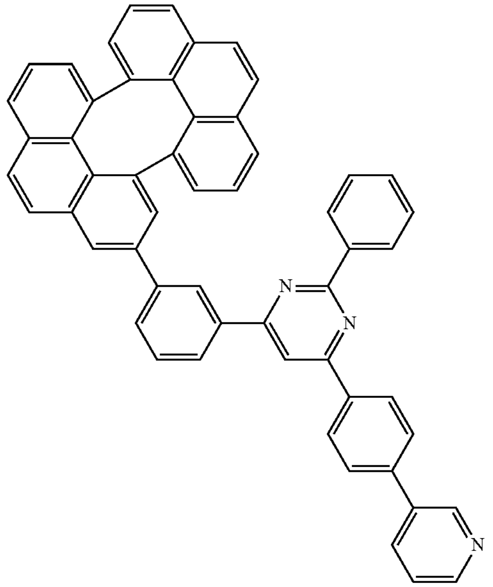
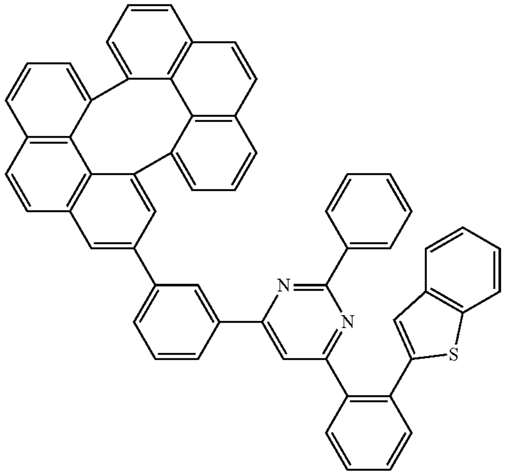
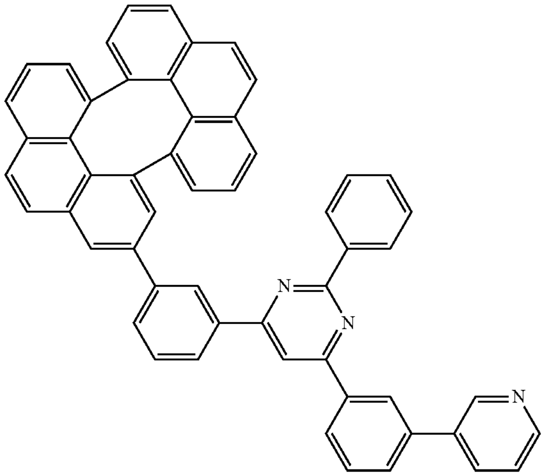
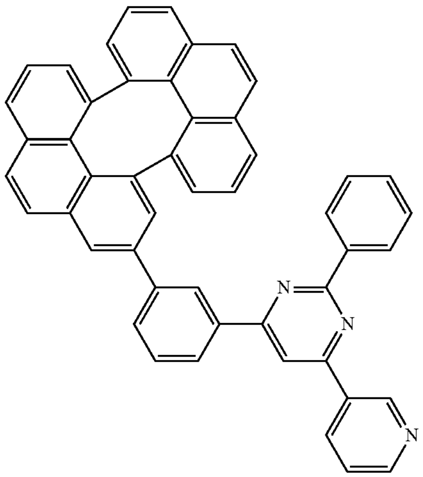
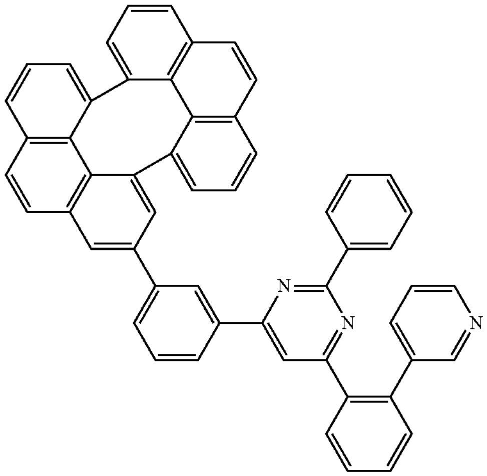
-continued -continued
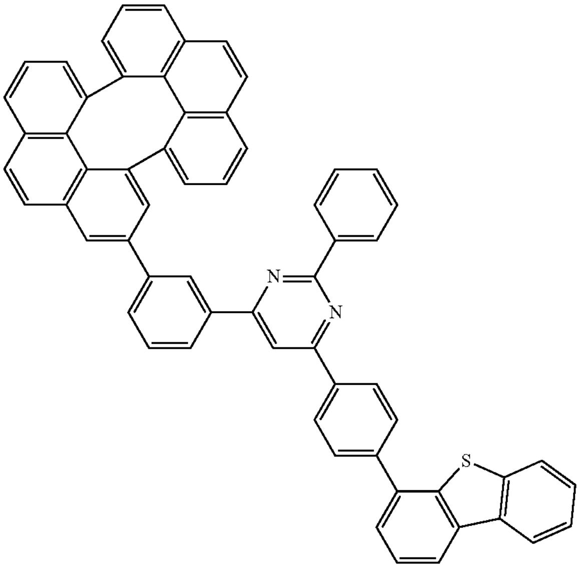
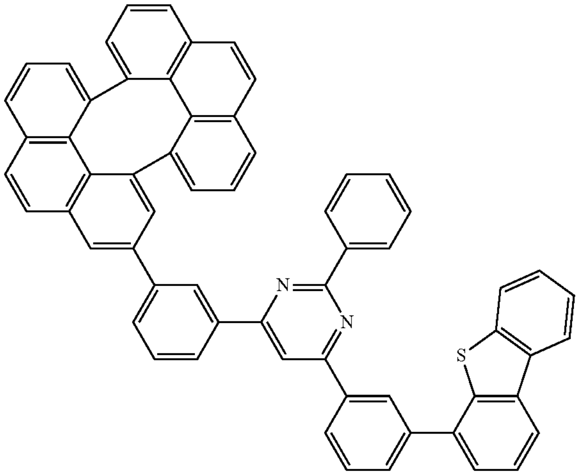
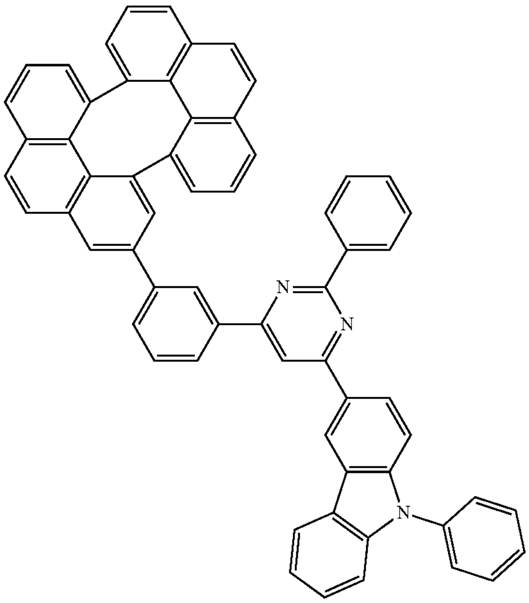
-continued
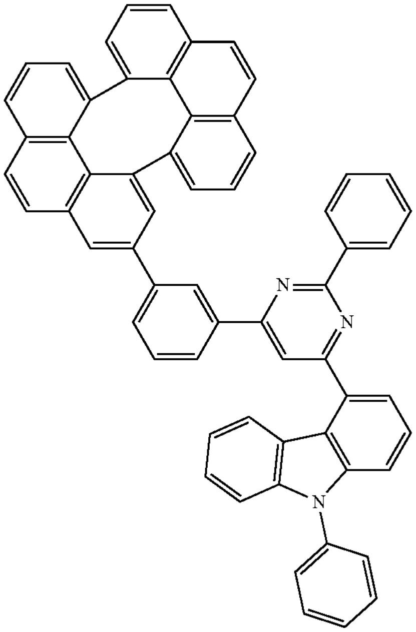
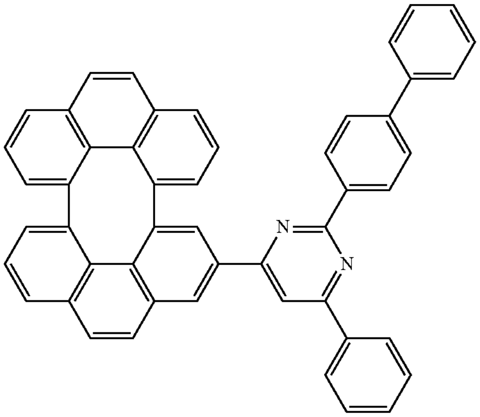
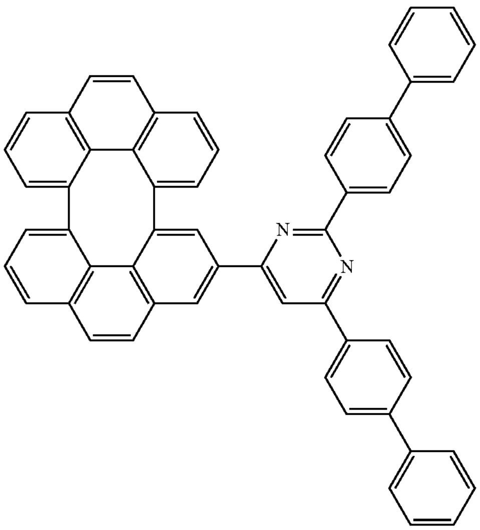

-continued
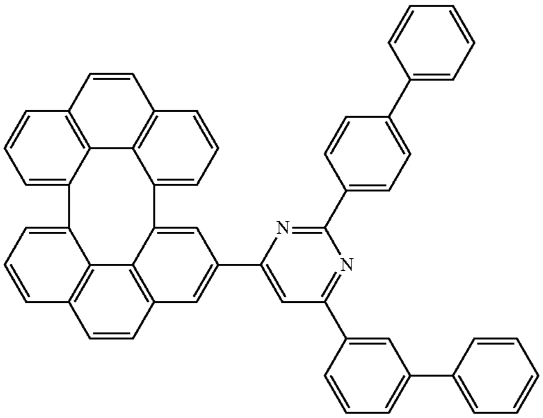
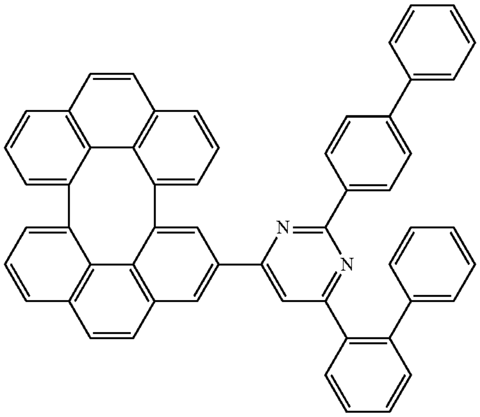
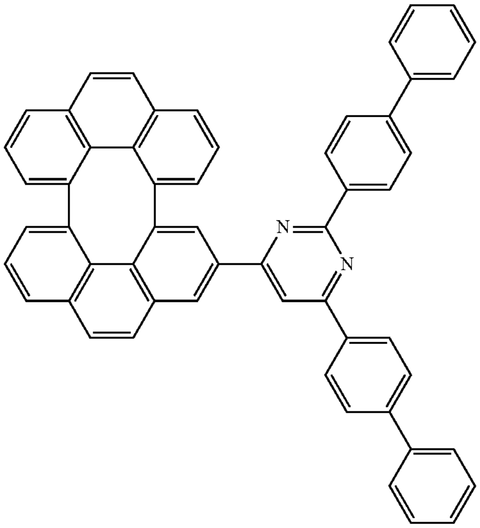
-continued
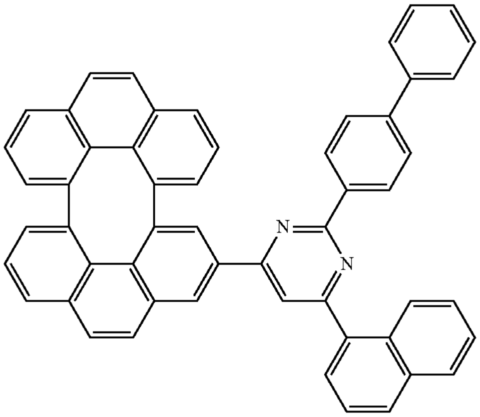
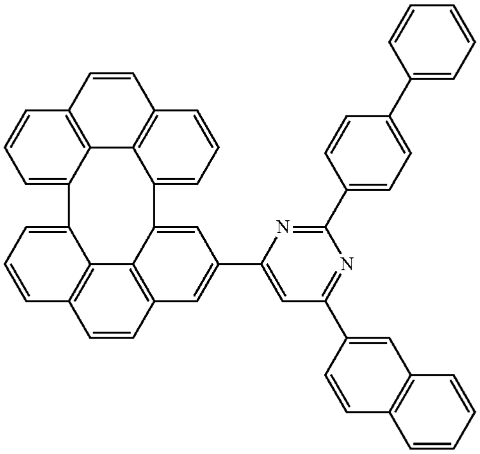
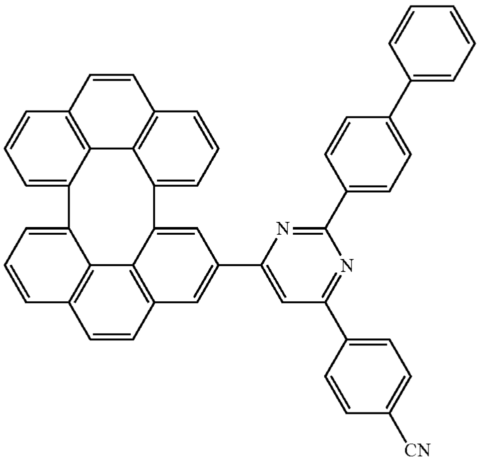

-continued
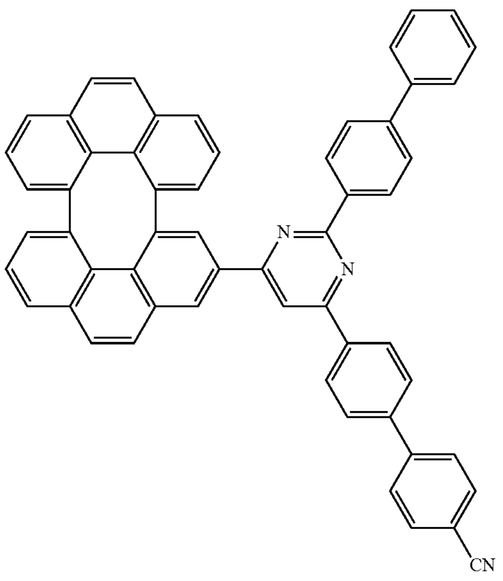
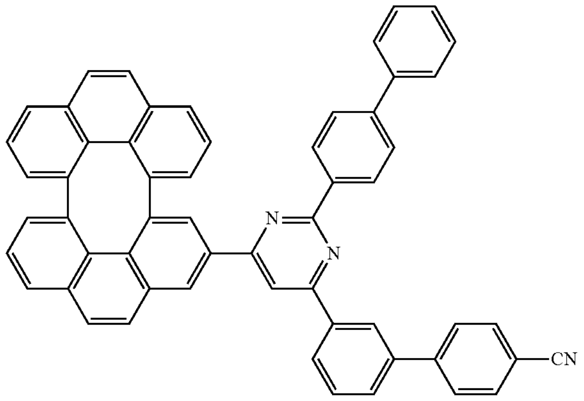
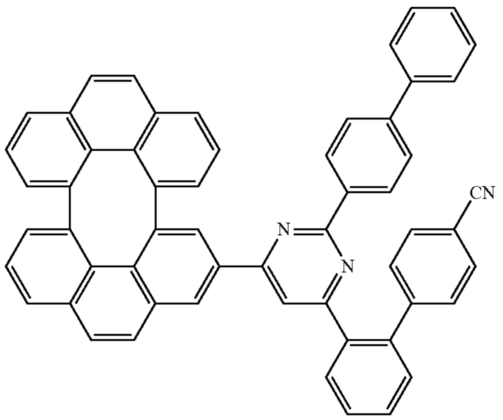
-continued
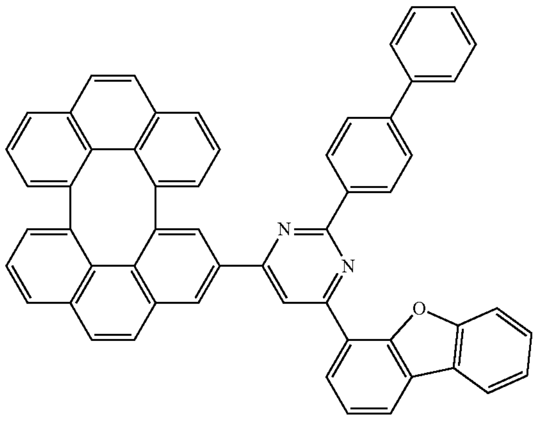
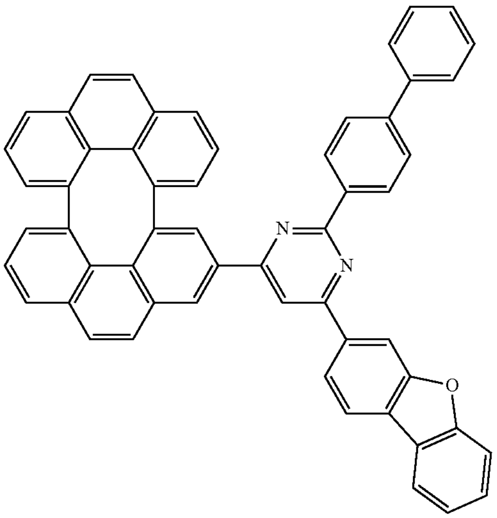
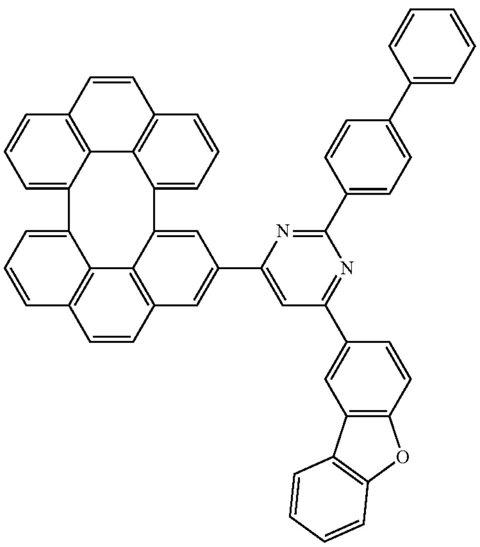

-continued
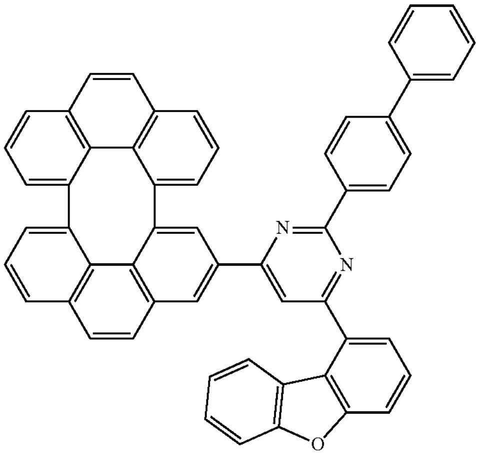
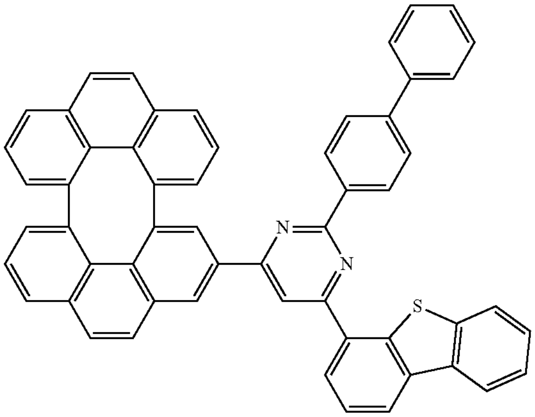
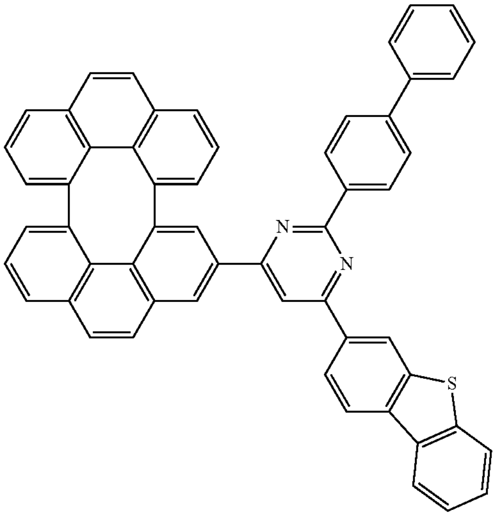
-continued
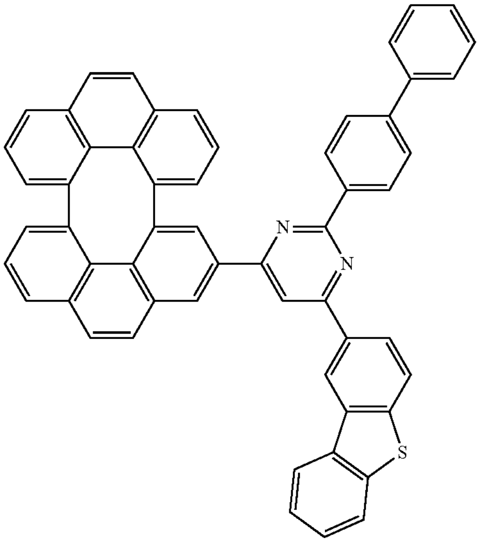
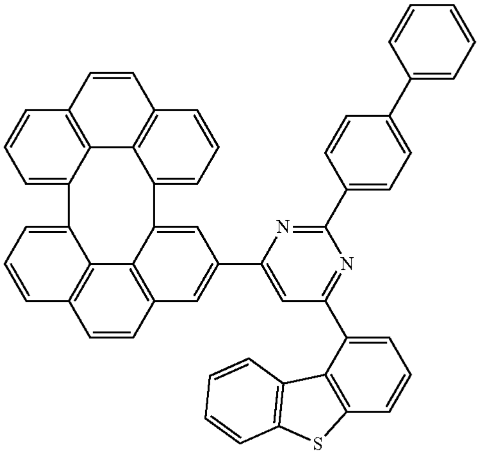
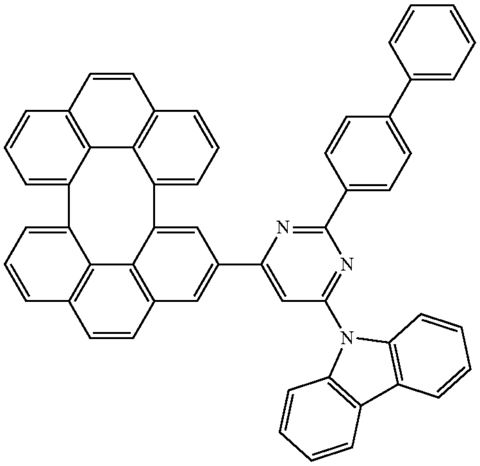

-continued
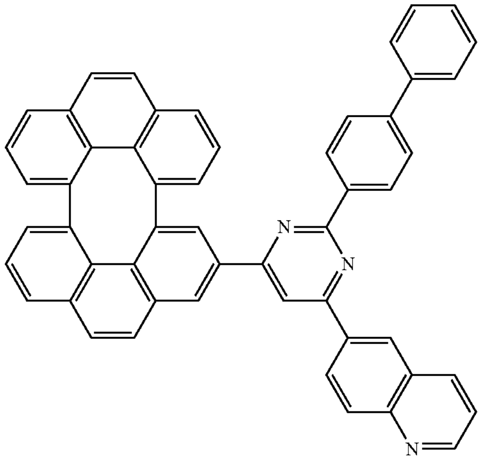
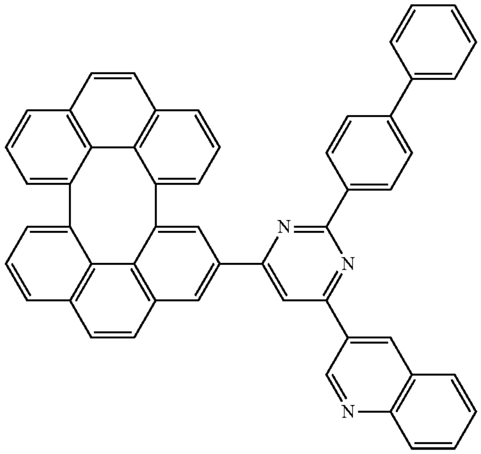
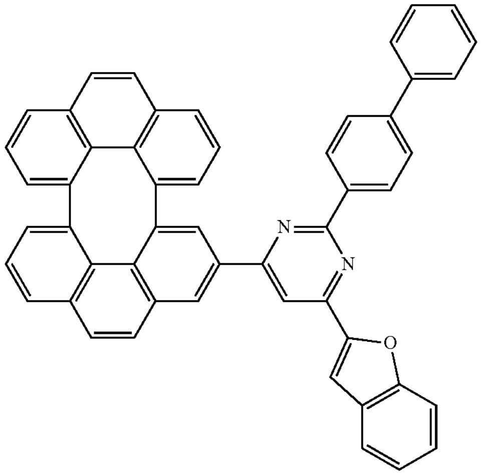
-continued
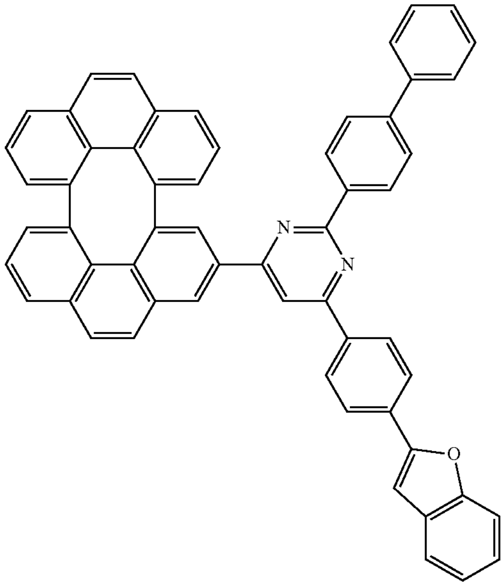
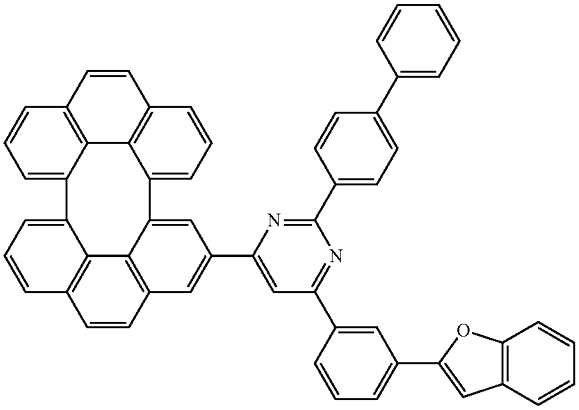
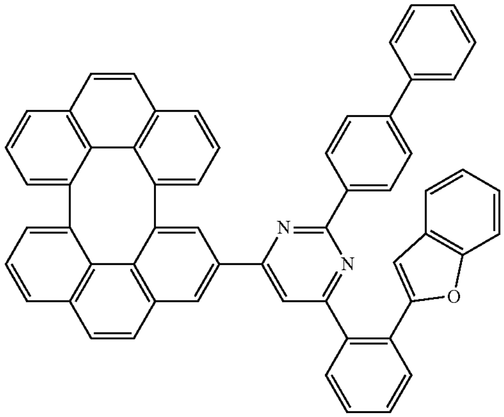

-continued
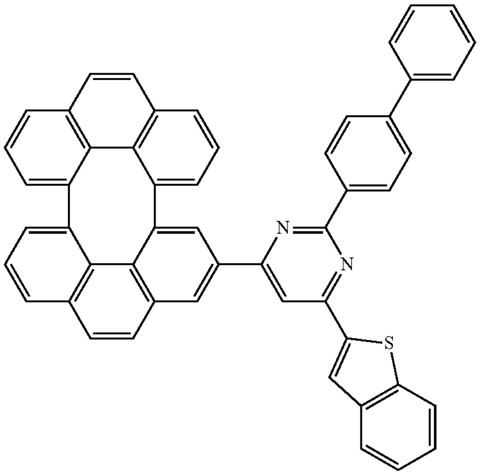
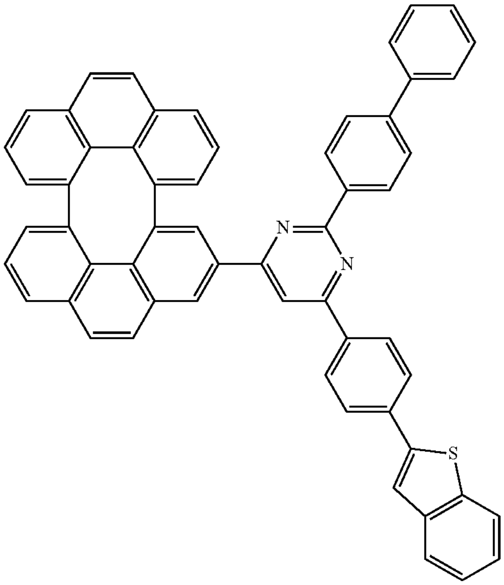
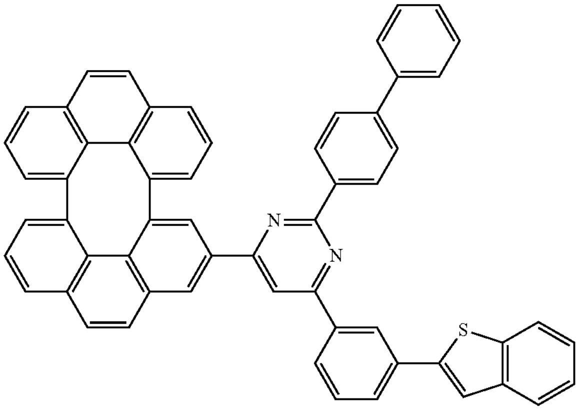
-continued
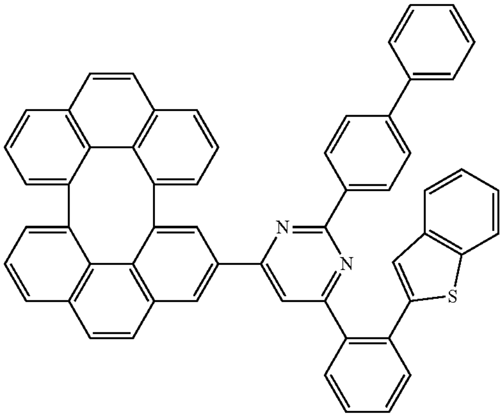
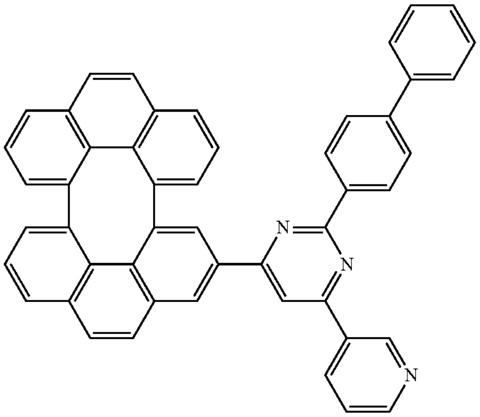
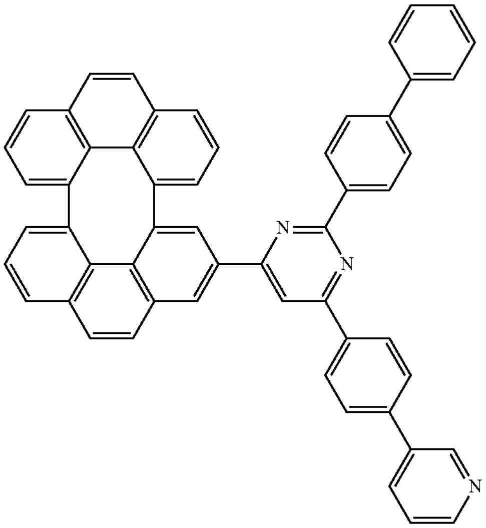

-continued
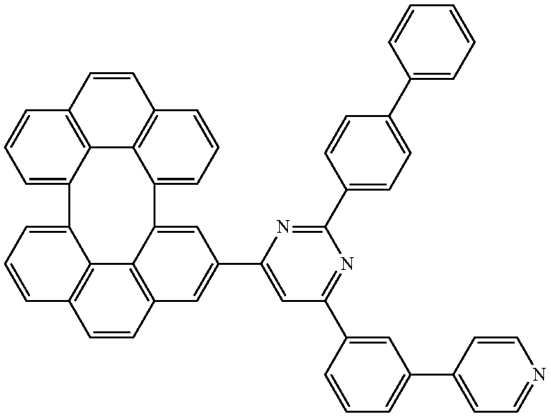
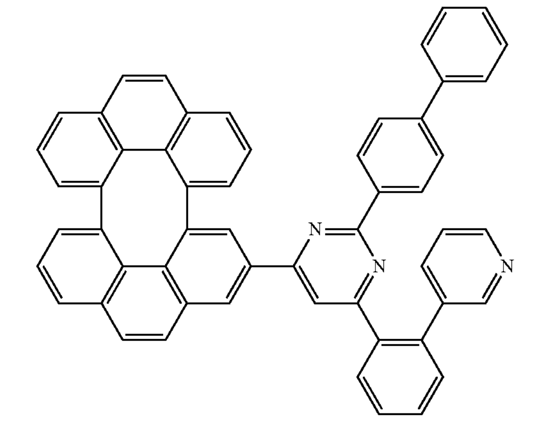
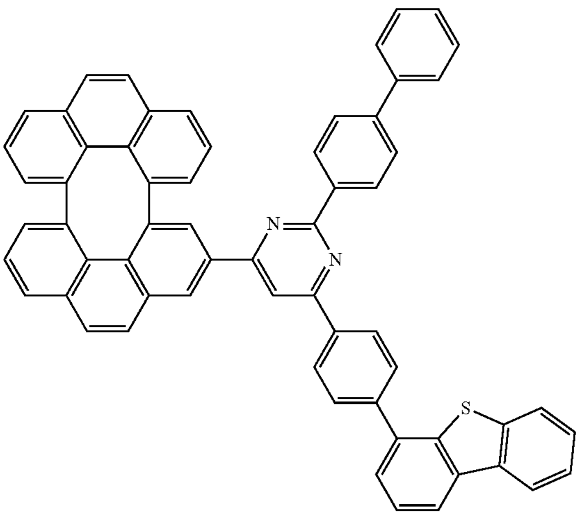
-continued
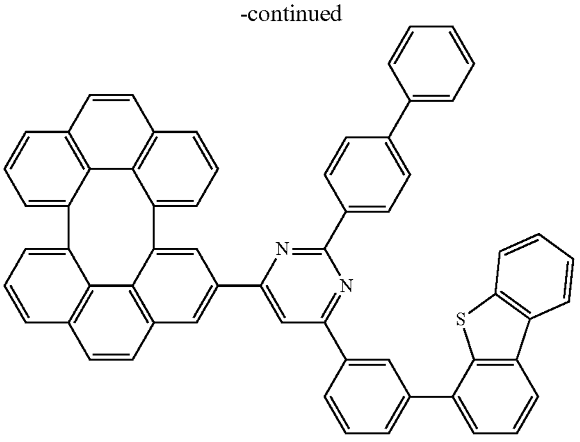
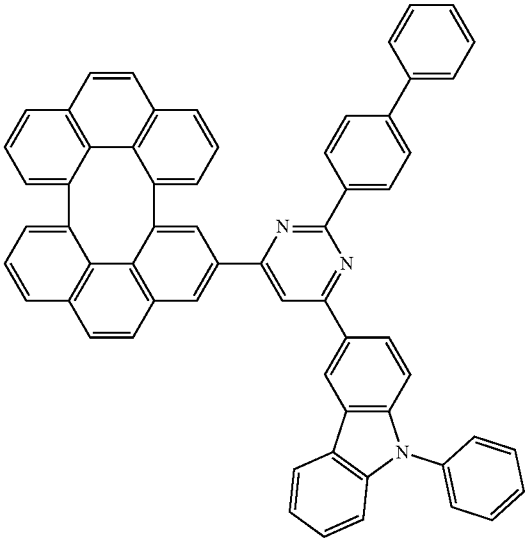
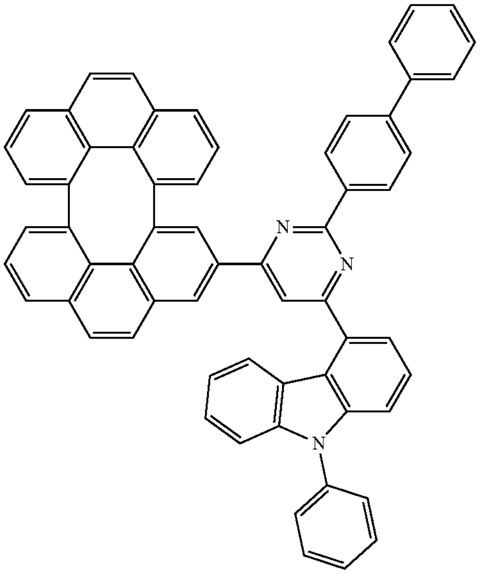

-continued
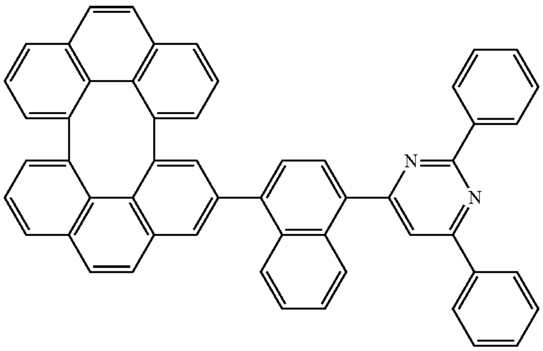
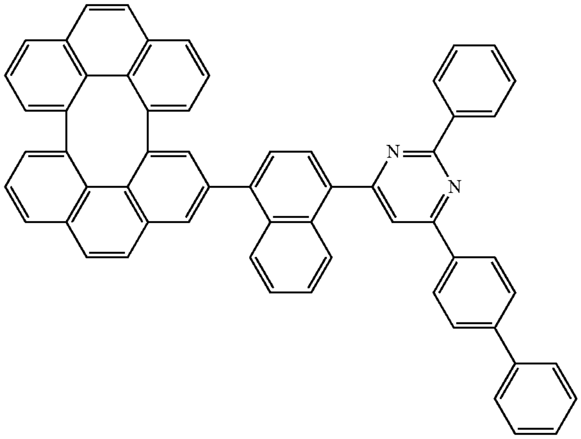
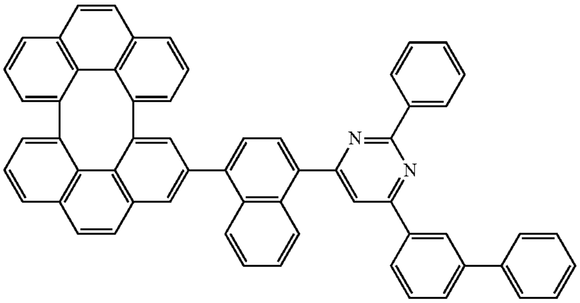
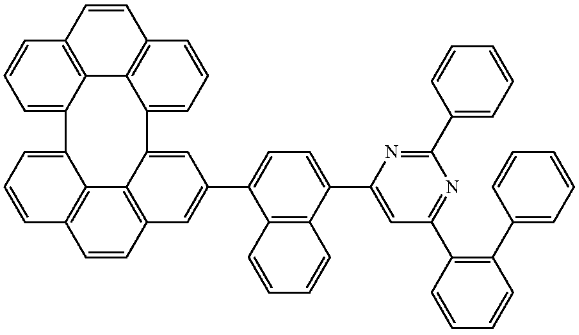
-continued
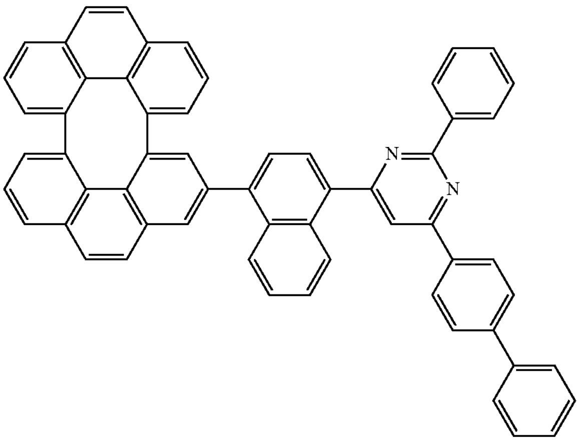
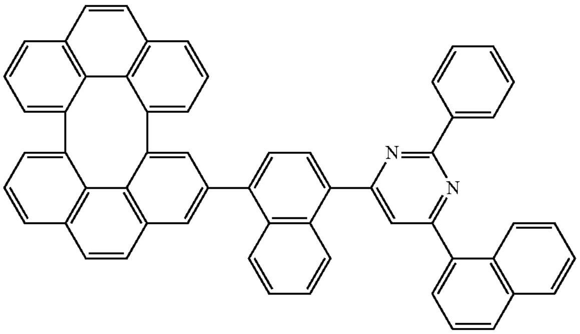
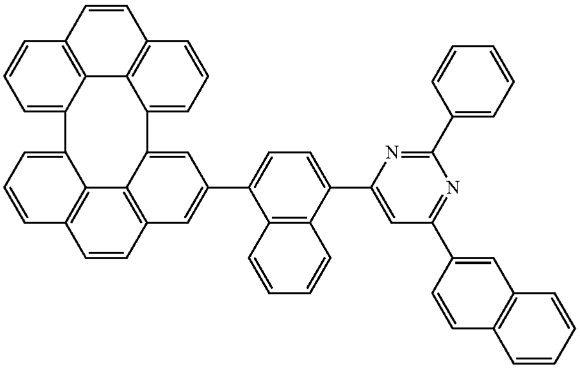
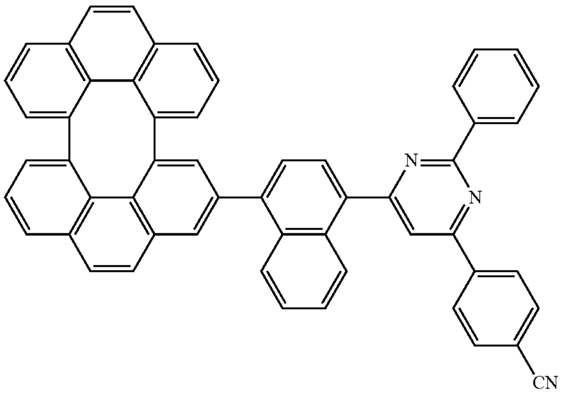

-continued
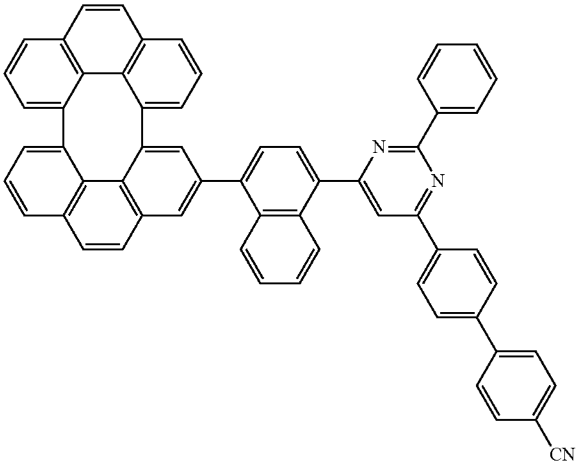
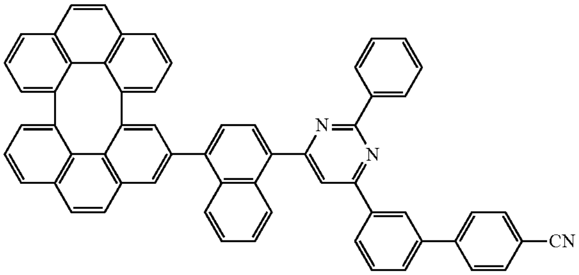
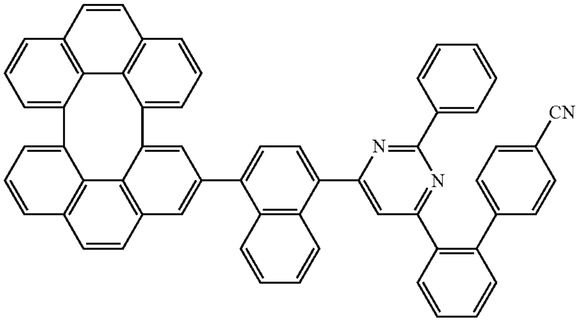
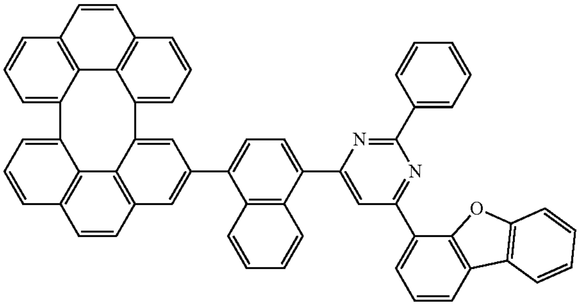
-continued
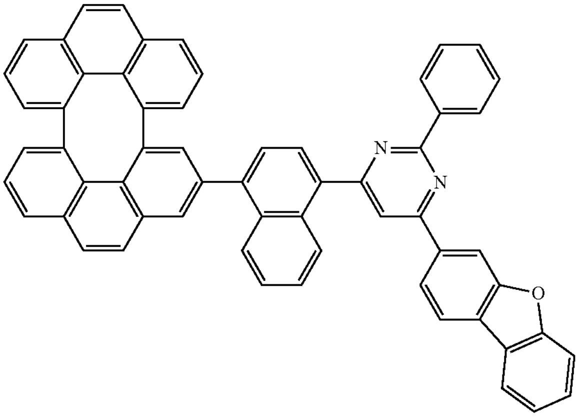
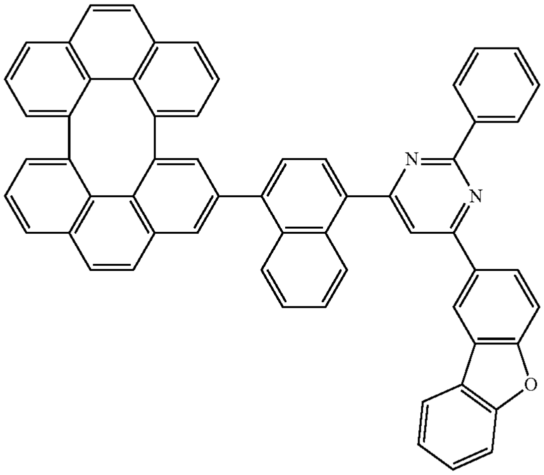
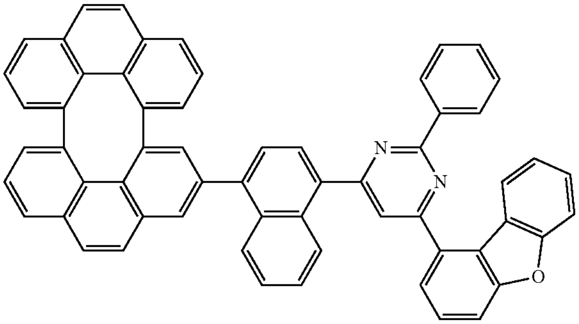
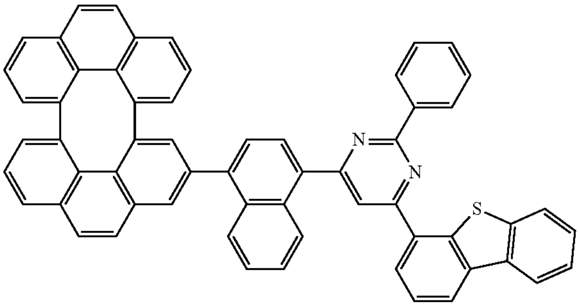

-continued
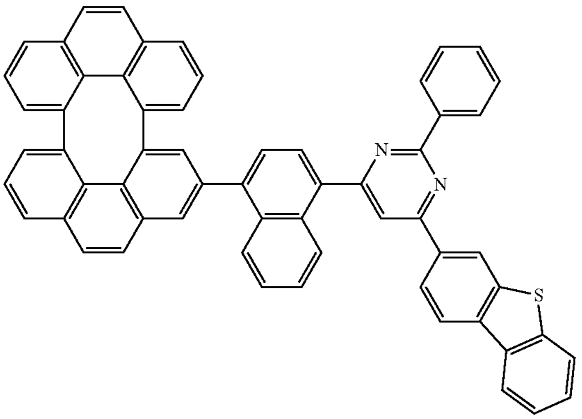
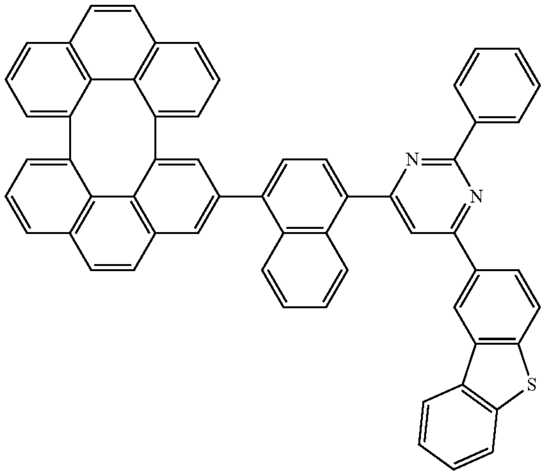
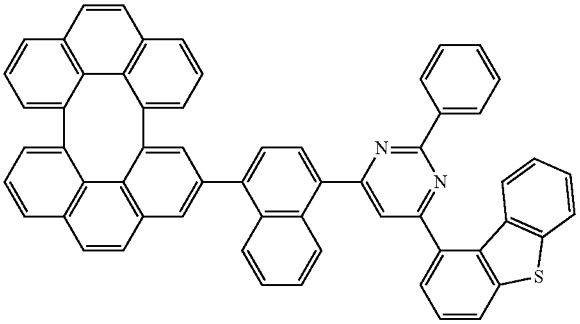
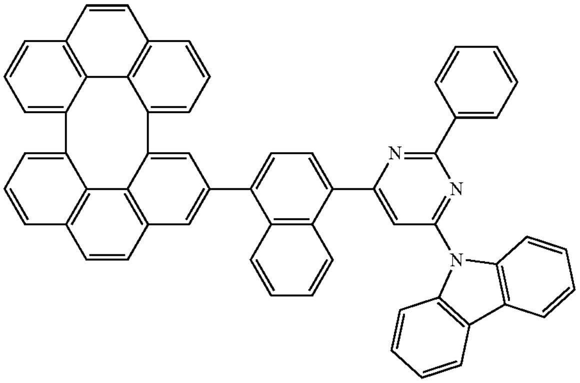
-continued
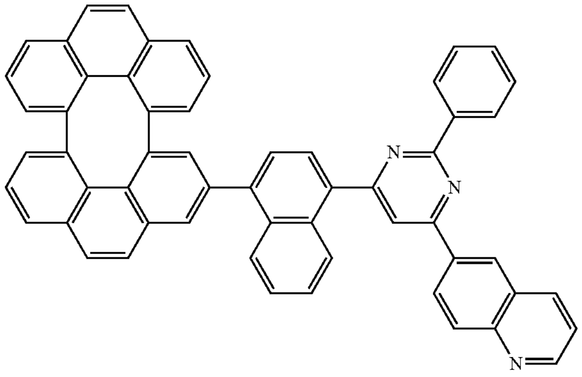
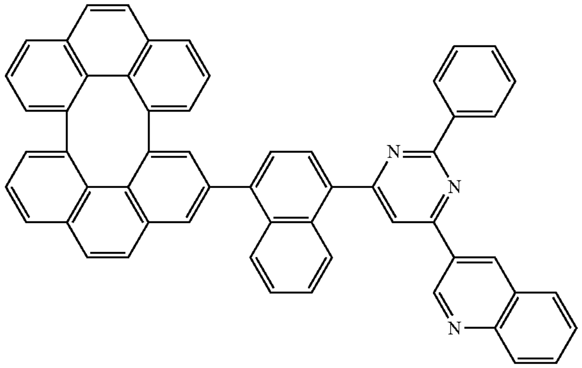
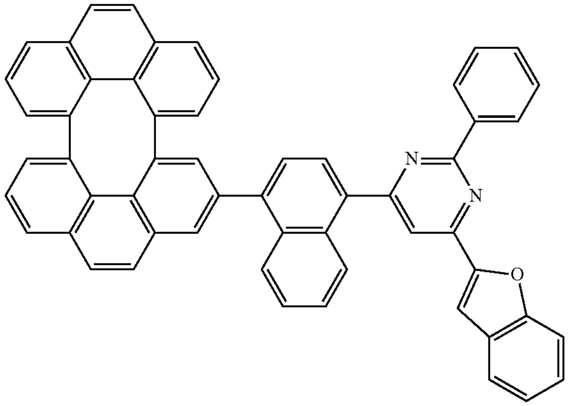
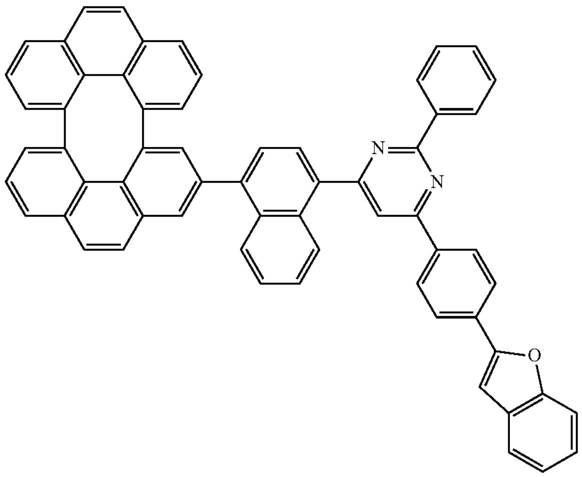

-continued
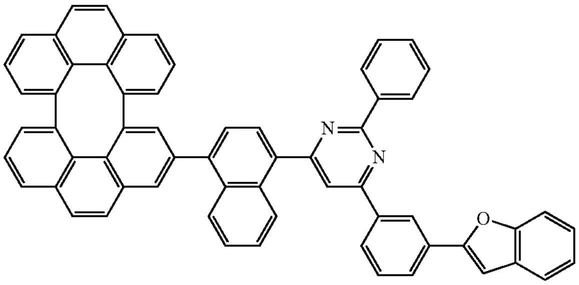
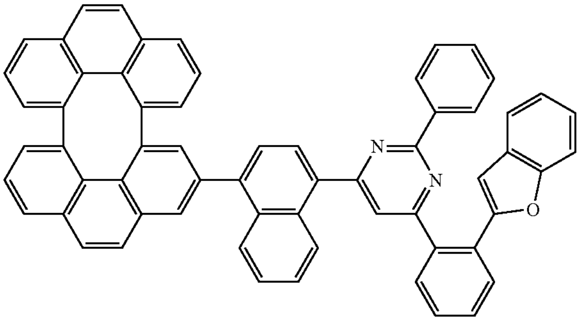
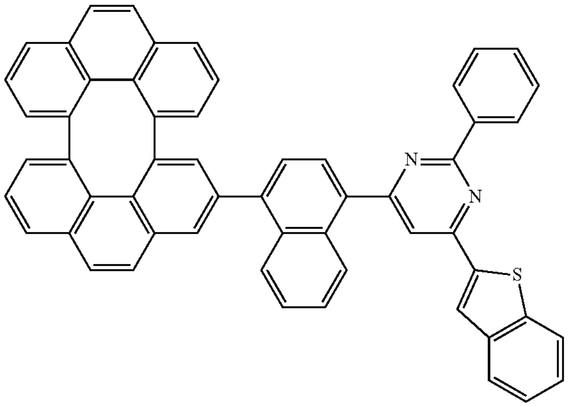
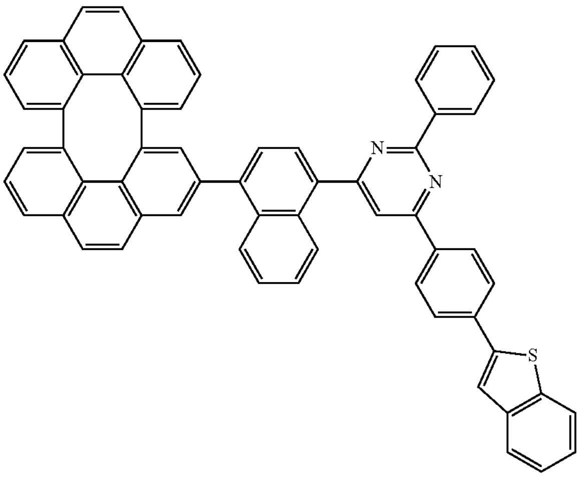
-continued
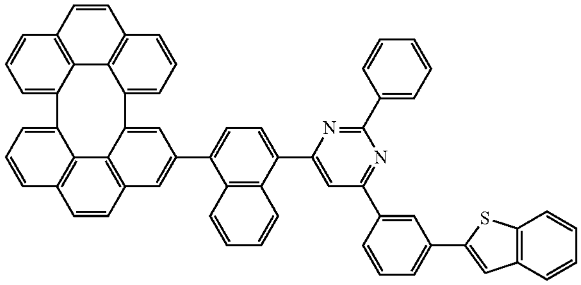
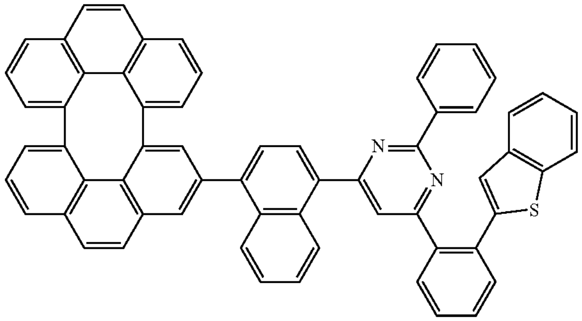
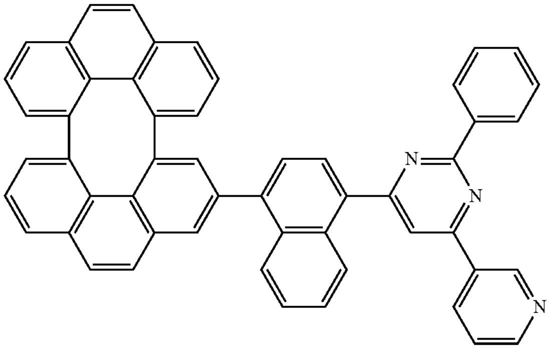
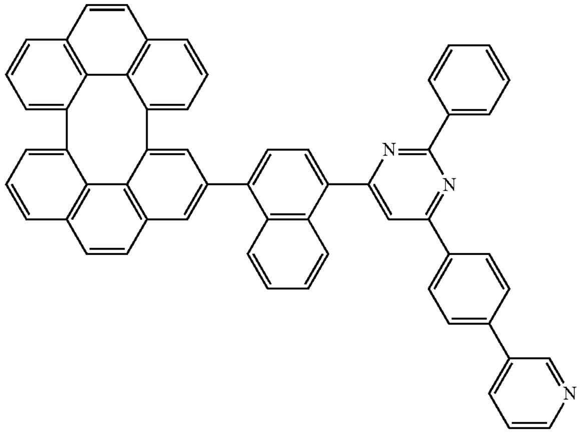
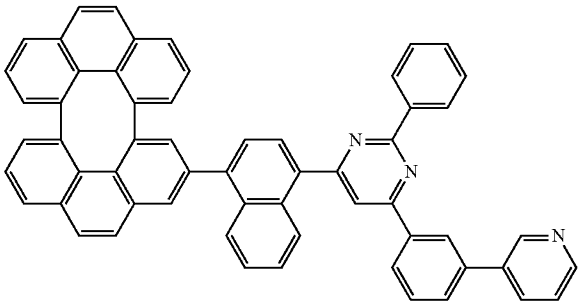

-continued
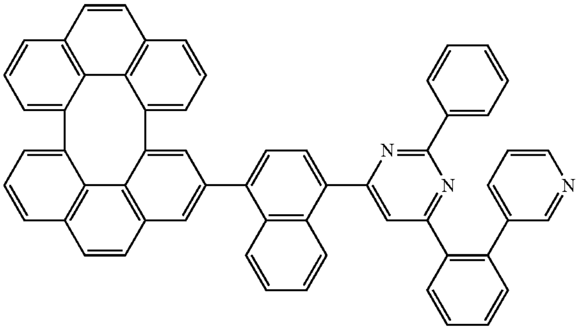
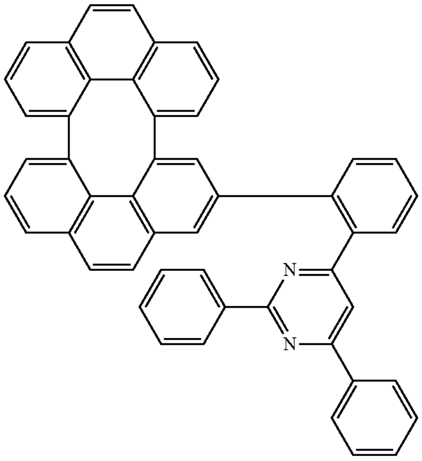
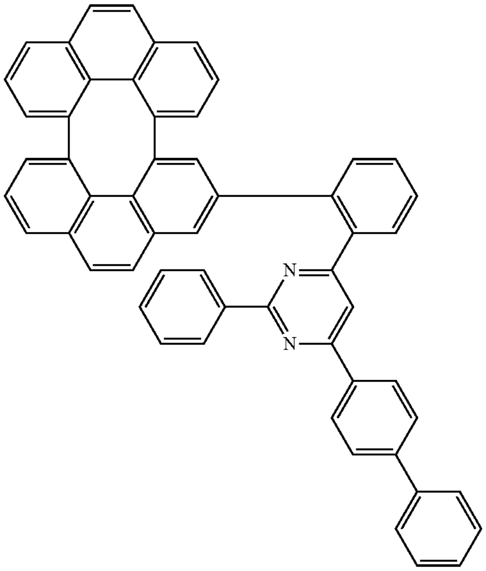
-continued
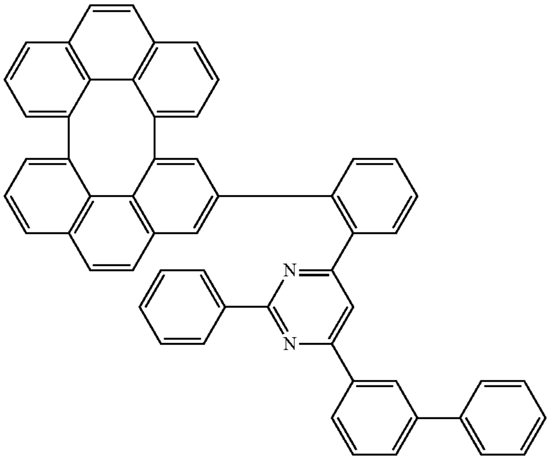
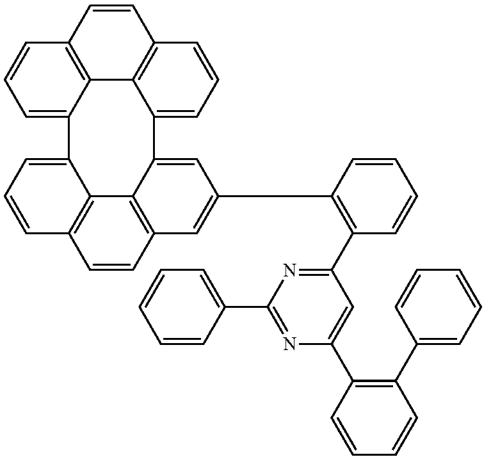
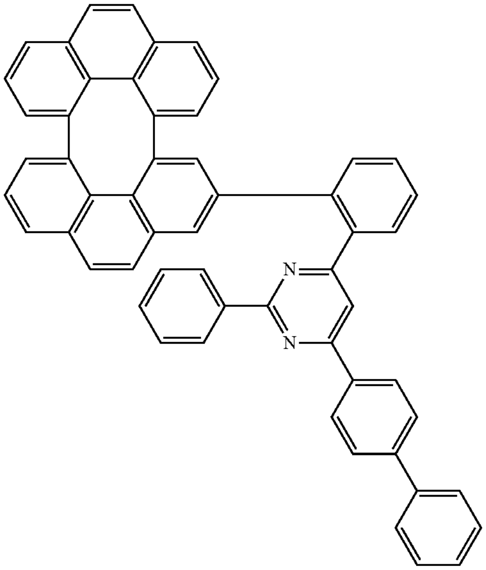

-continued
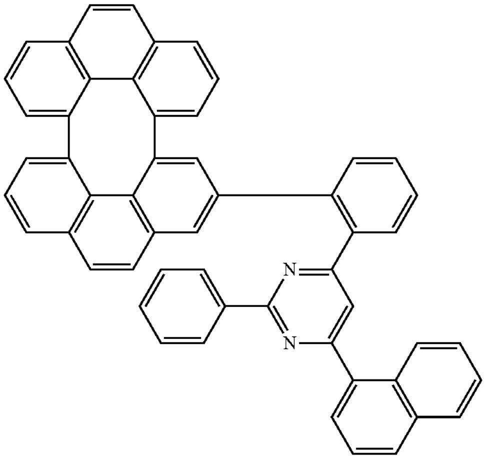
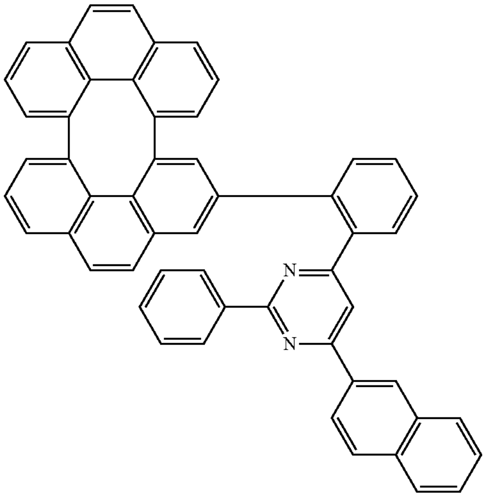
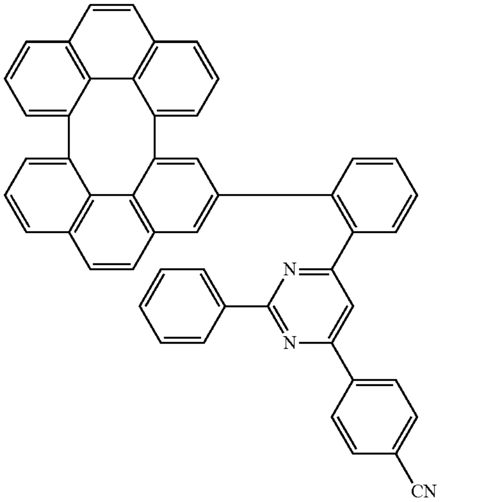
-continued
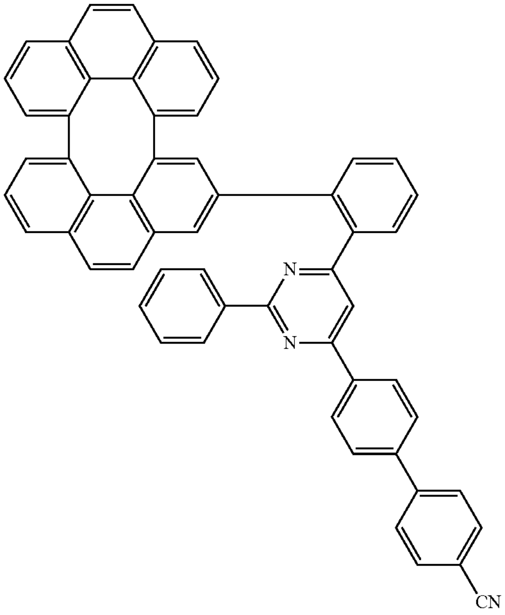
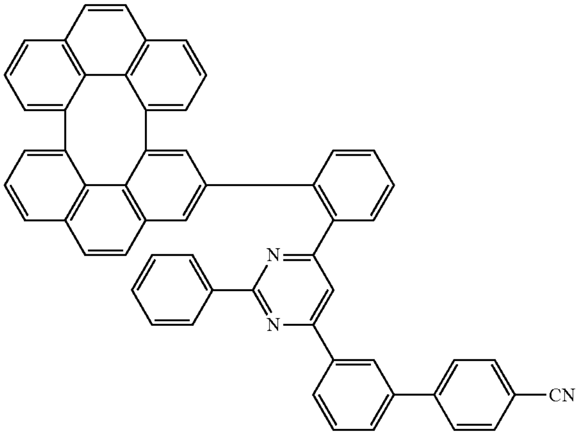
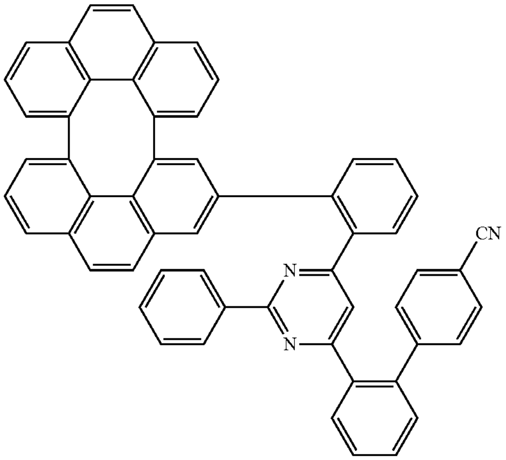

-continued
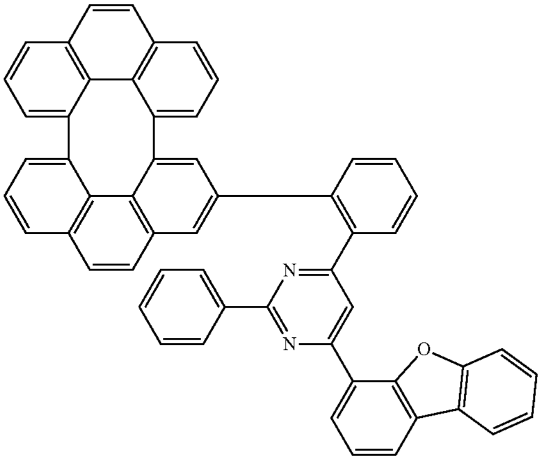
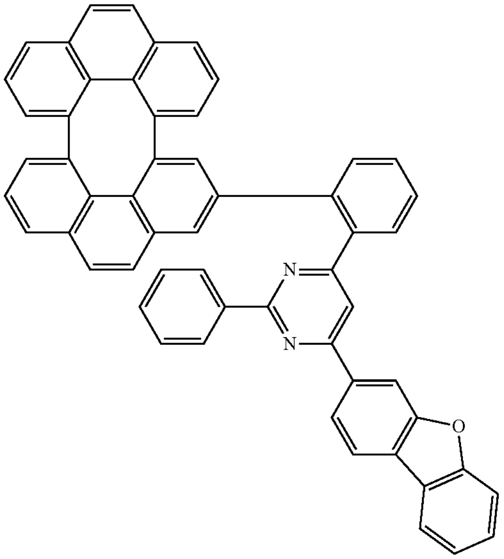
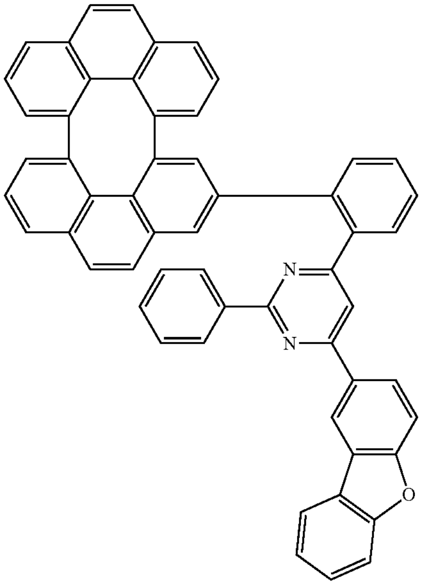
-continued
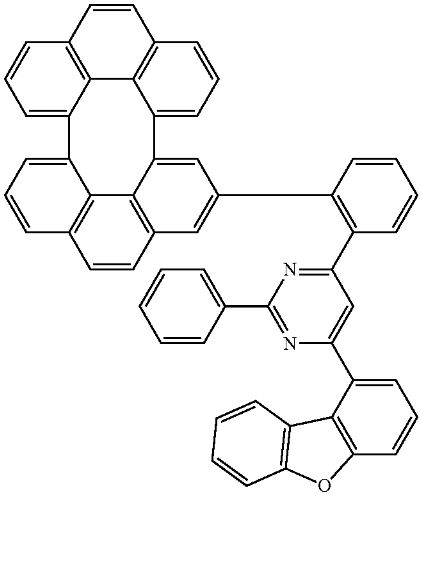
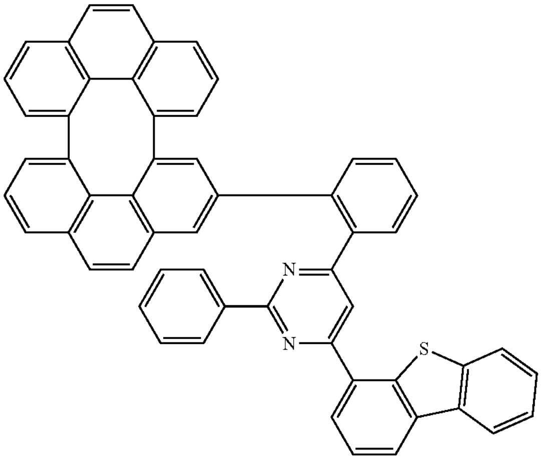
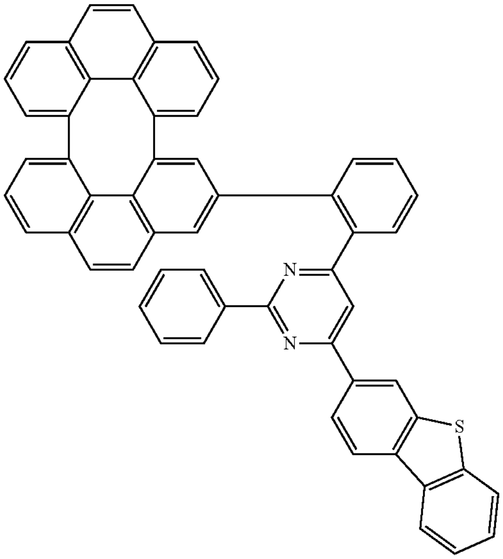

-continued
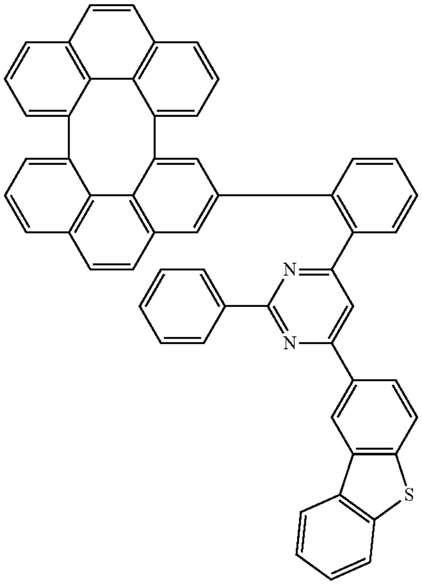
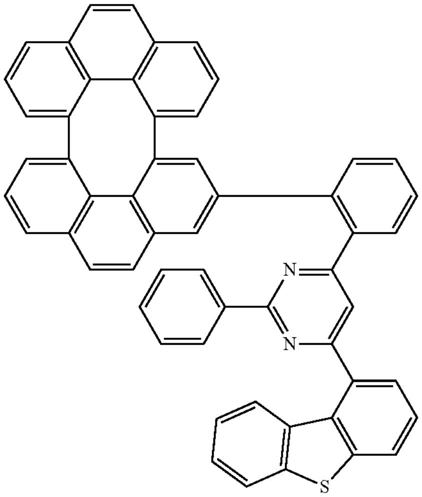
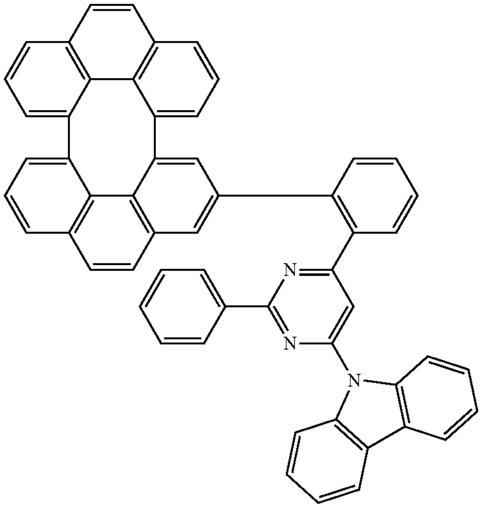
-continued
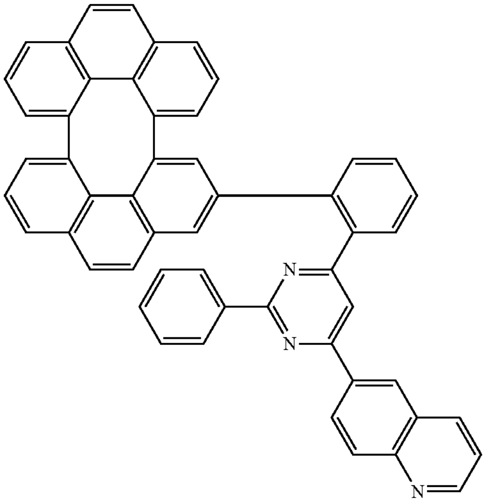
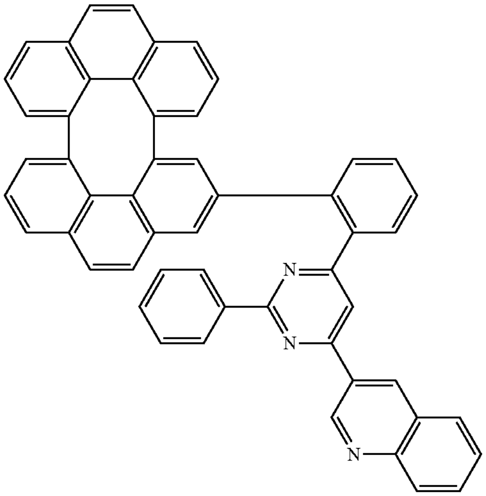

-continued
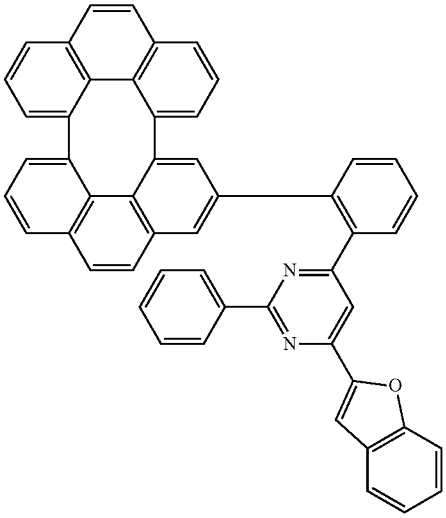
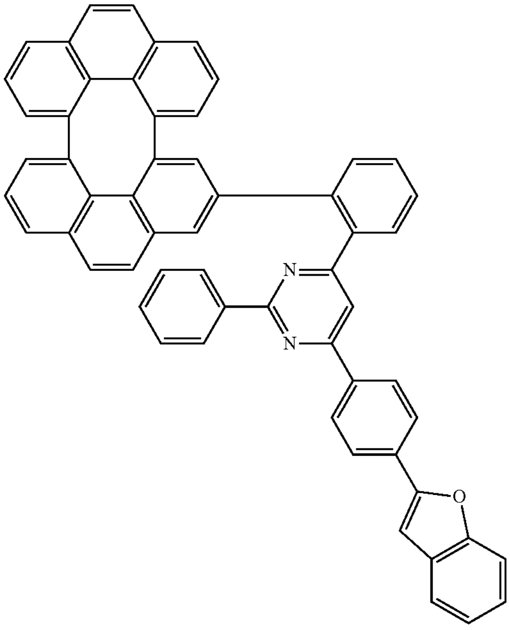
-continued
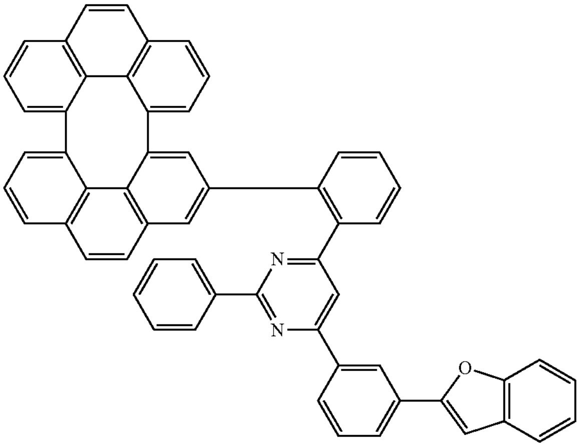
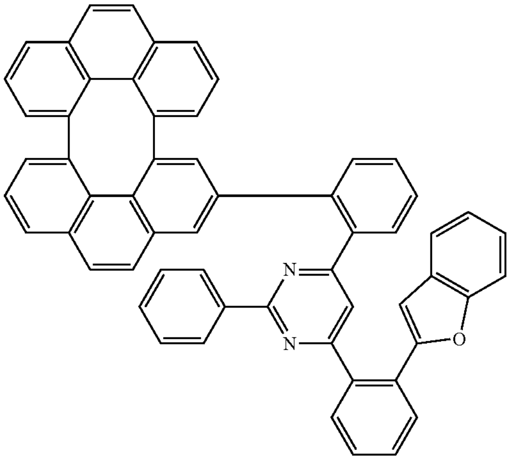

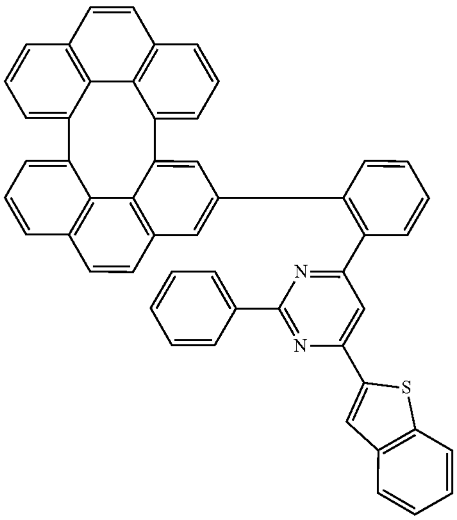
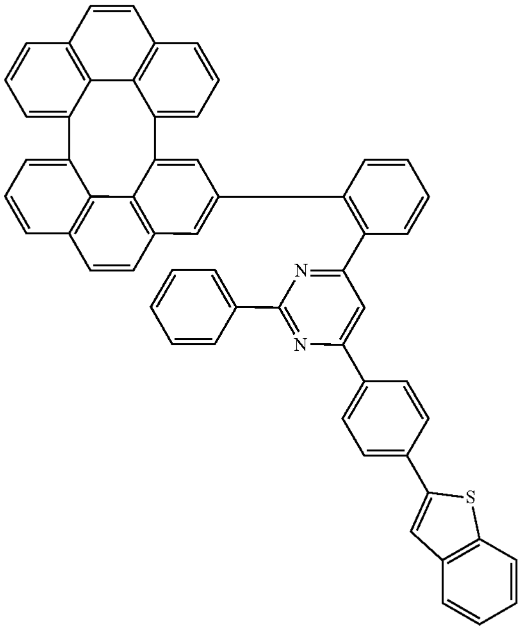
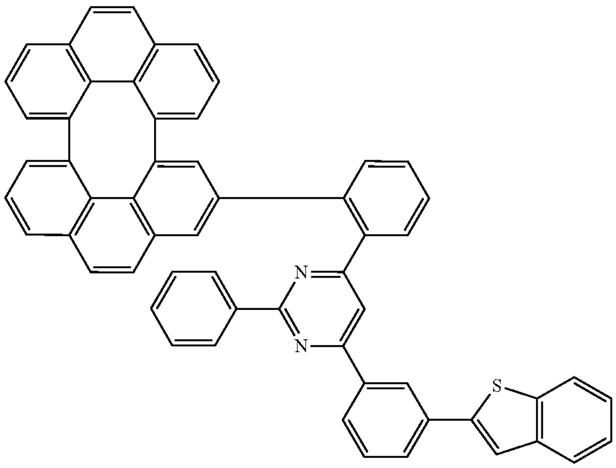
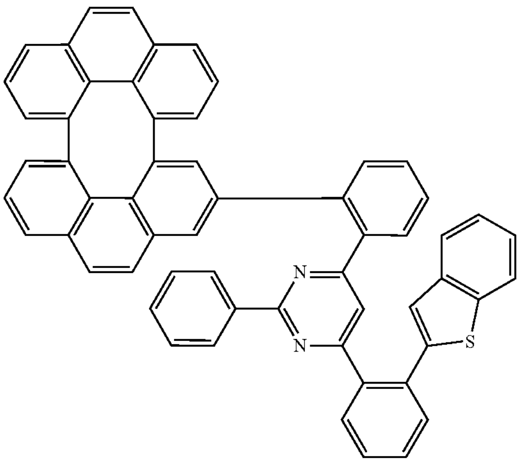
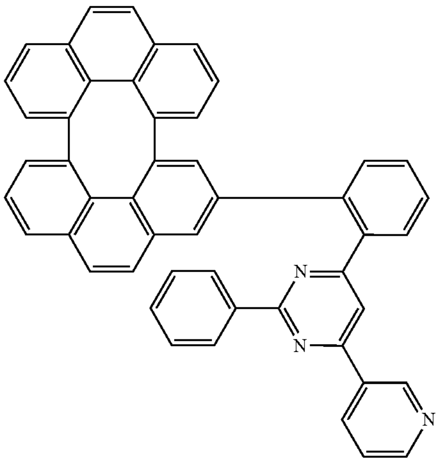
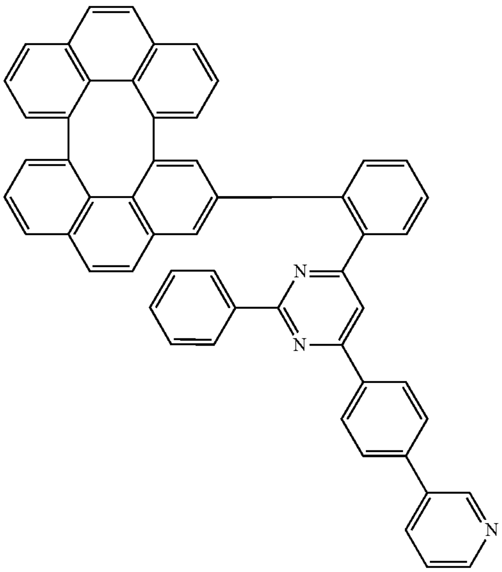

-continued
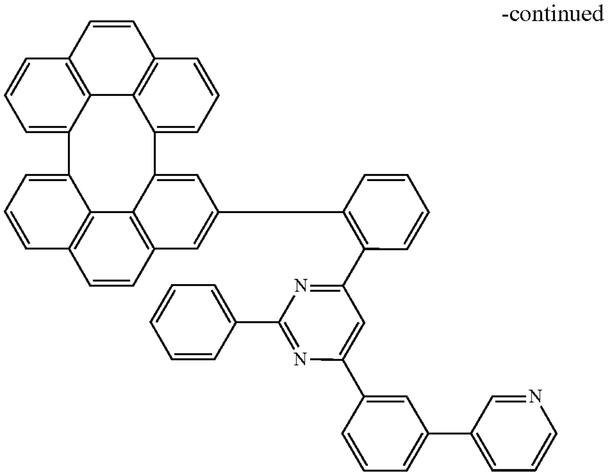
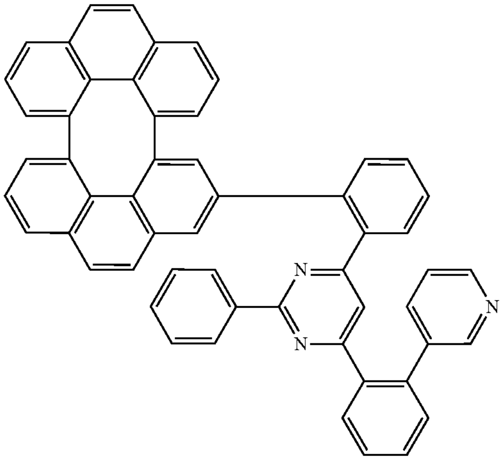
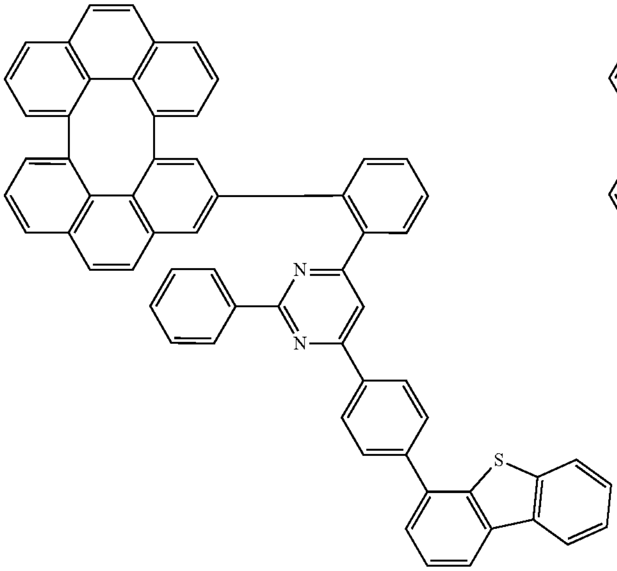
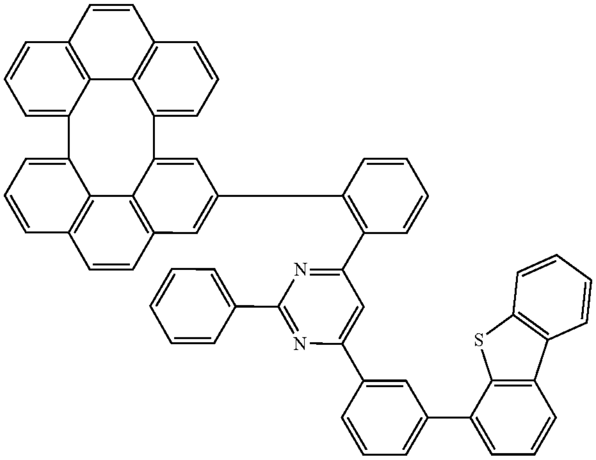
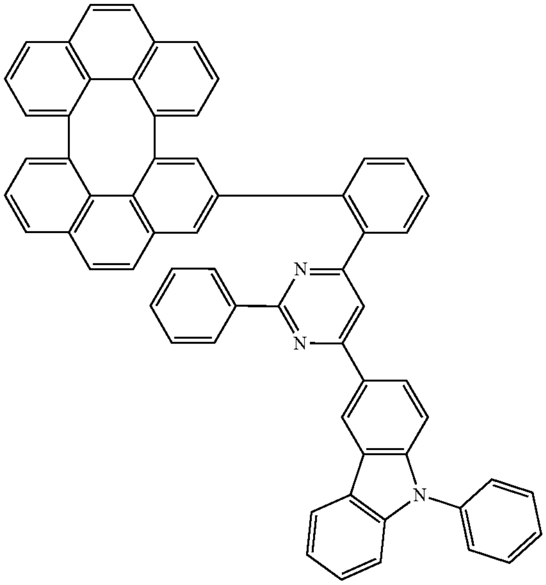
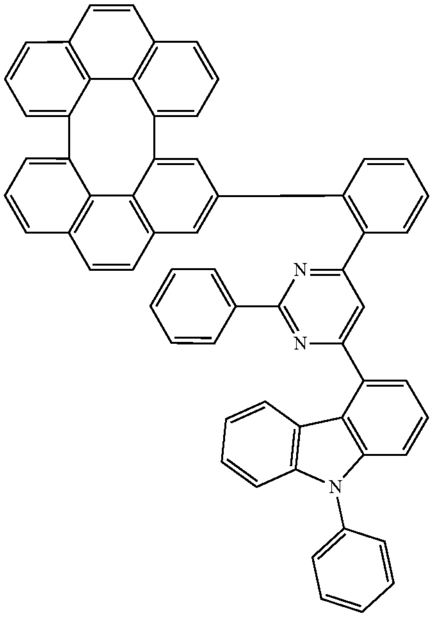

-continued
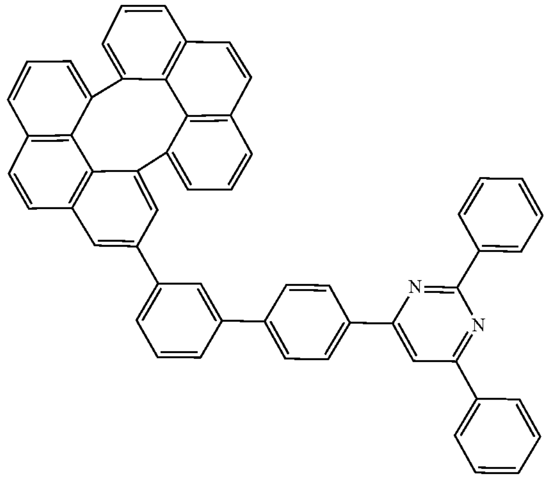
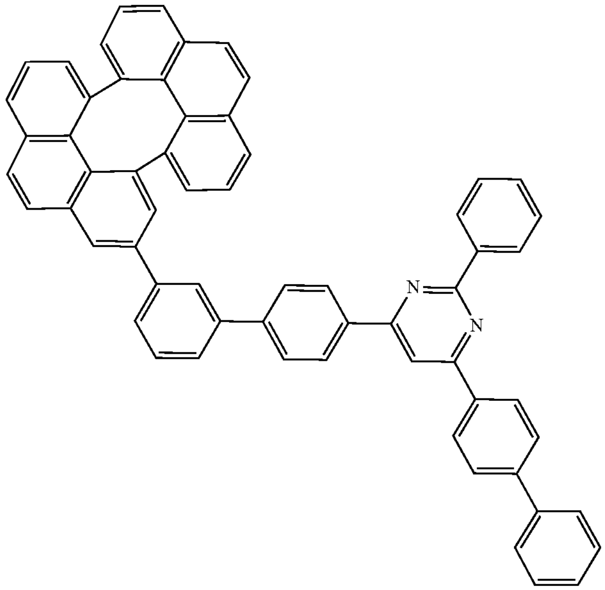
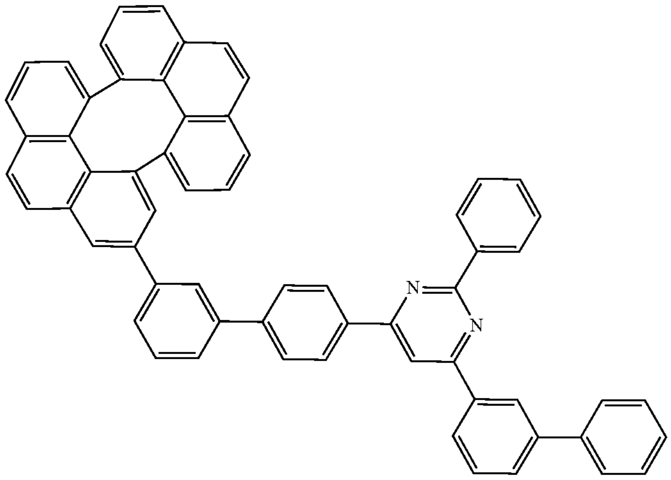
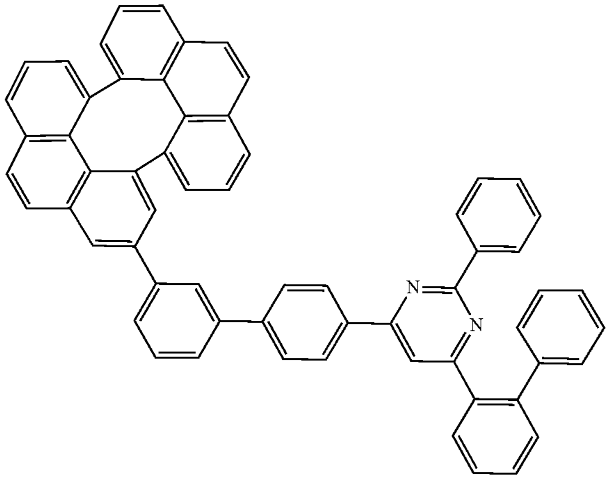

-continued
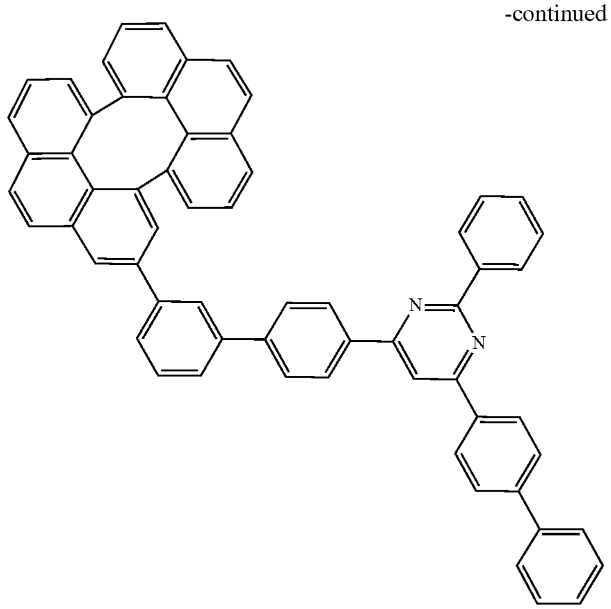
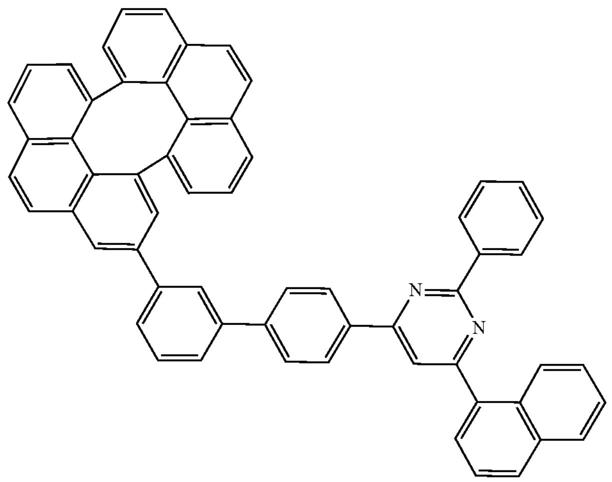
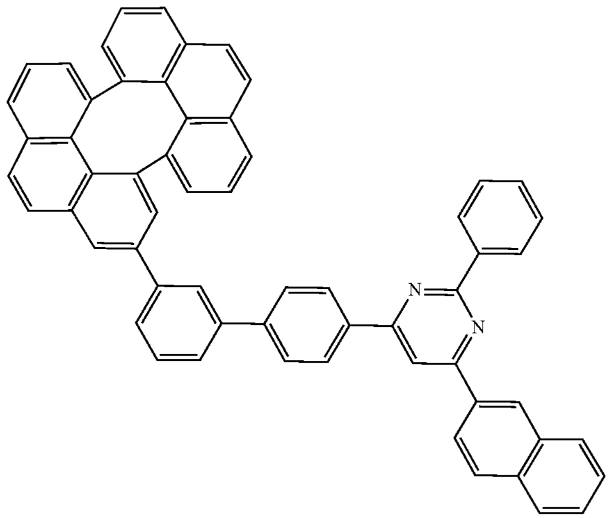
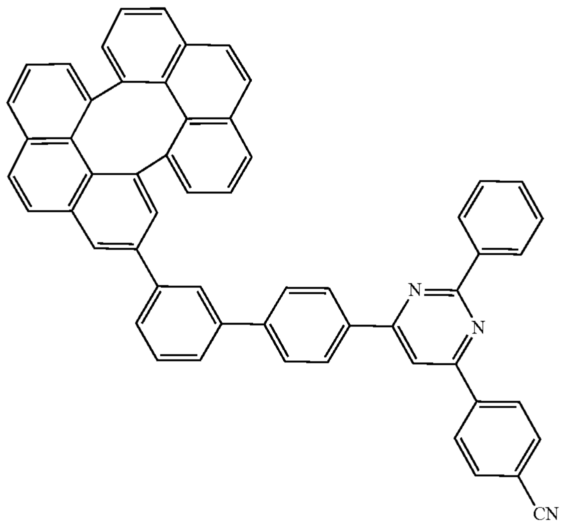

-continued
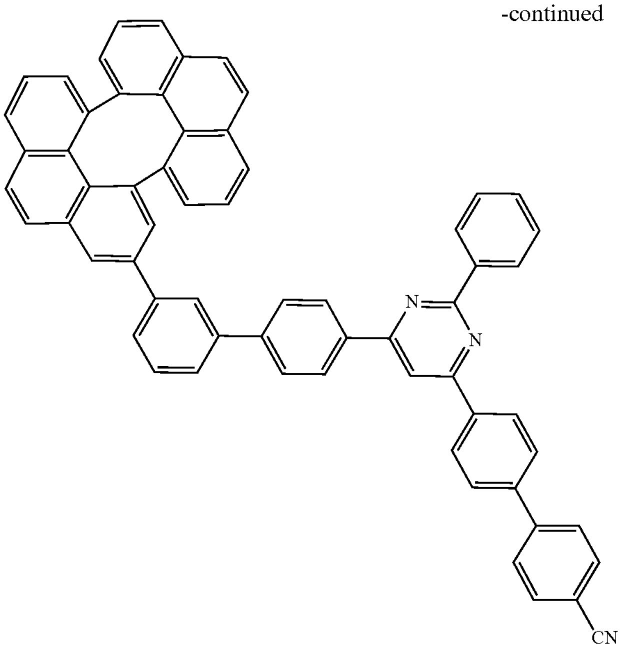
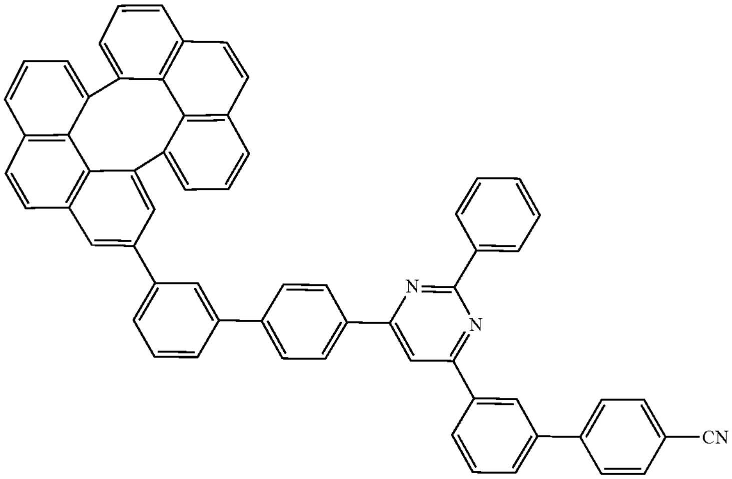
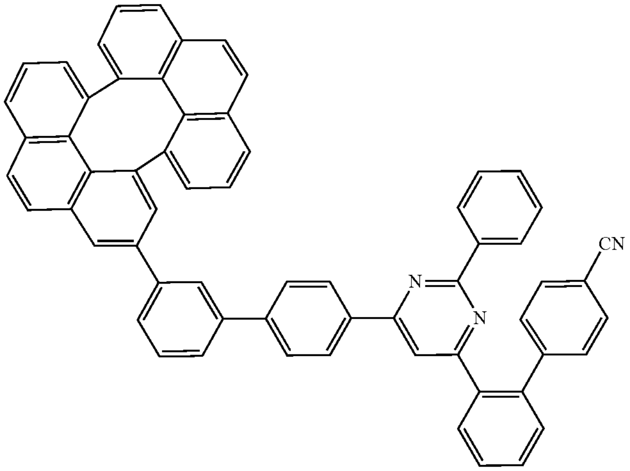

-continued
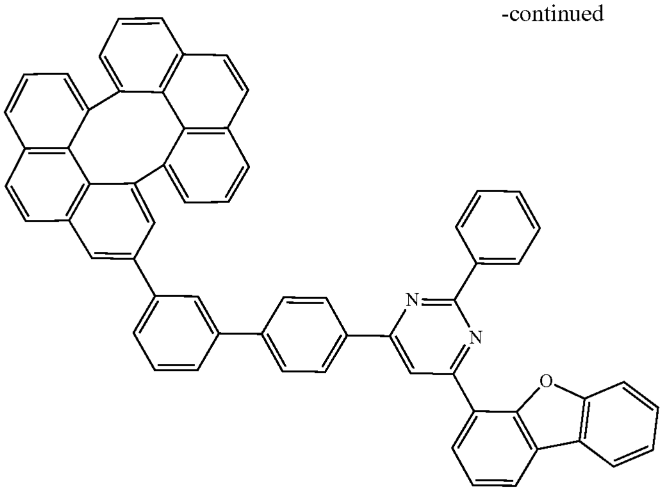
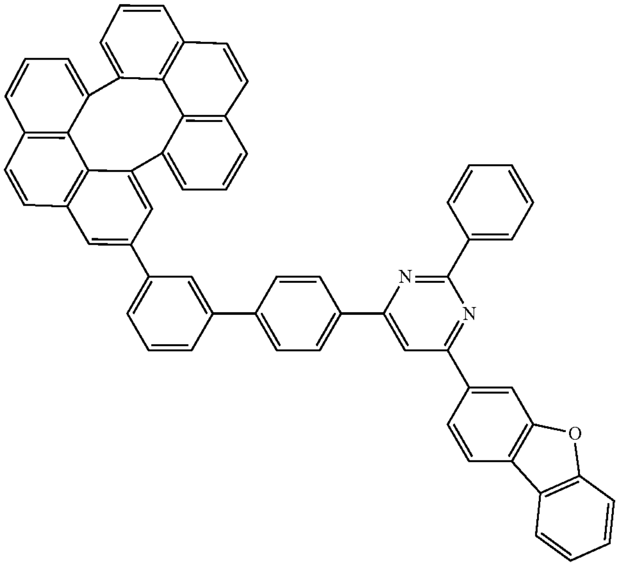
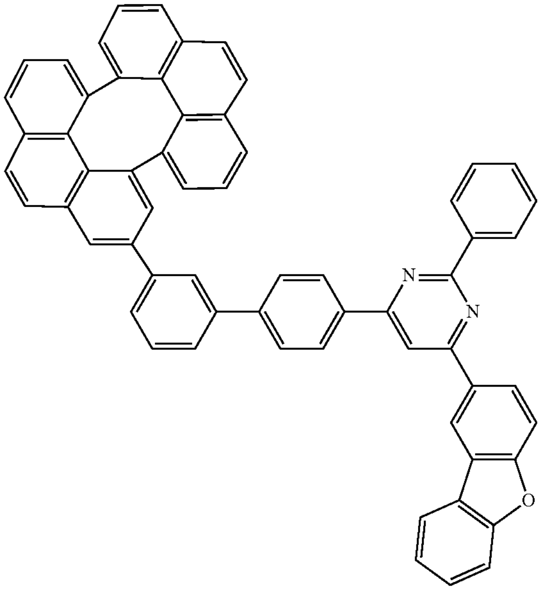
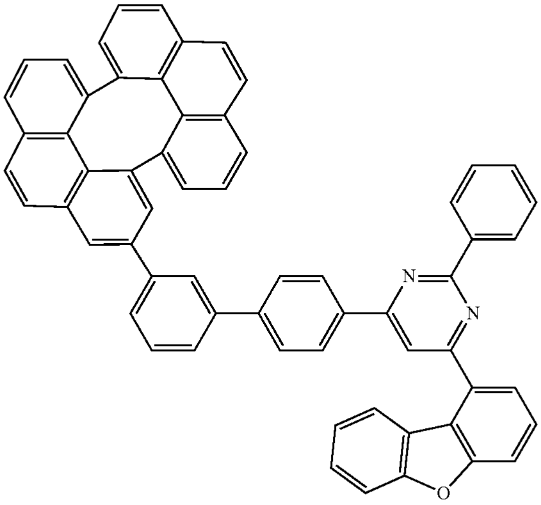

-continued
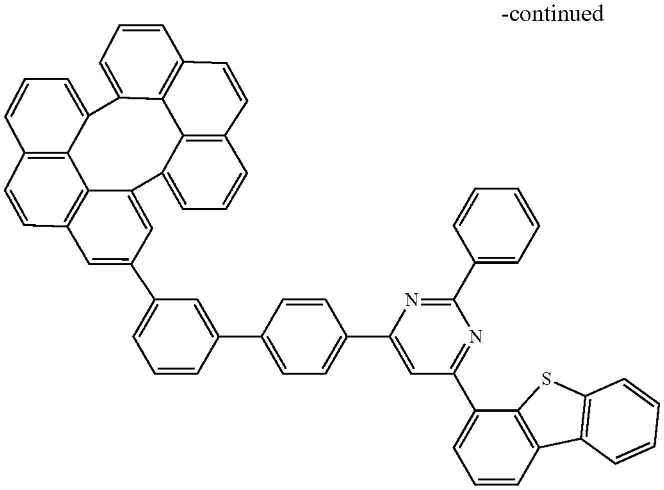
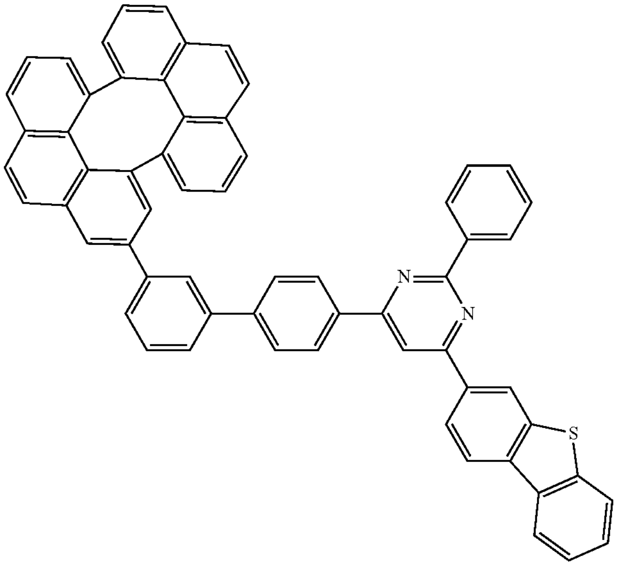
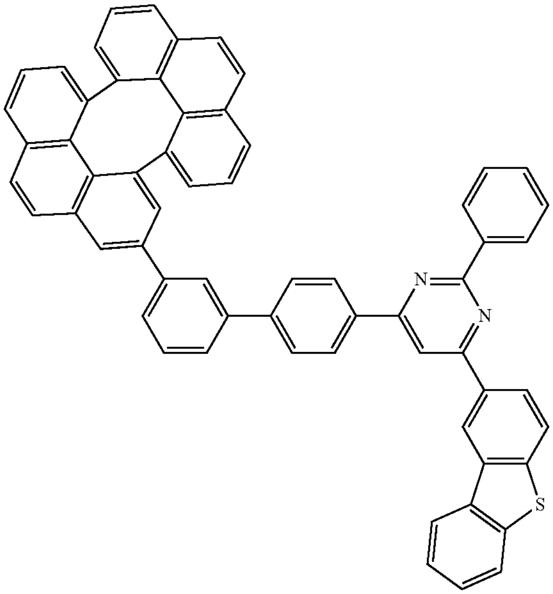
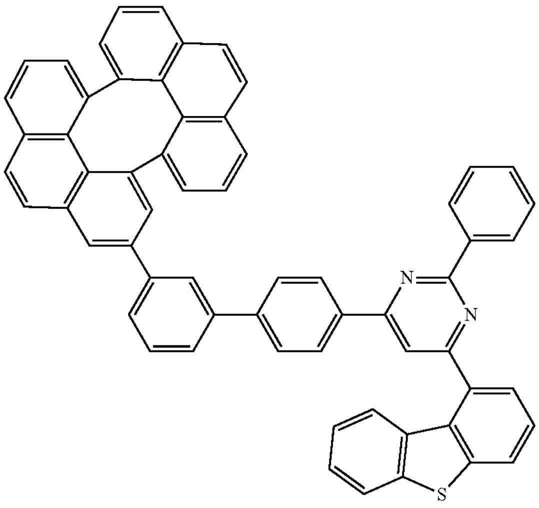

-continued
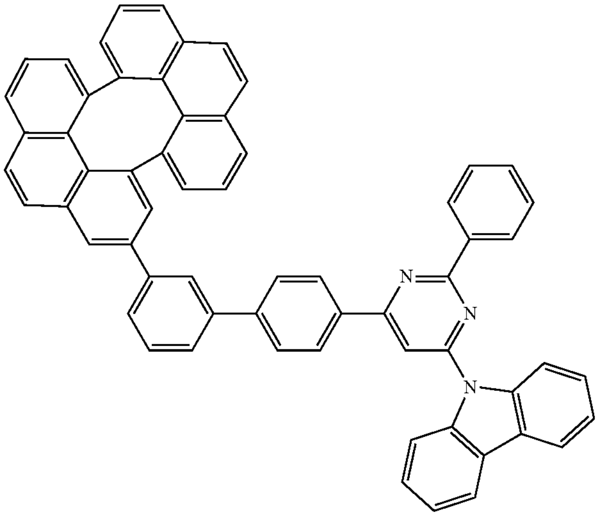
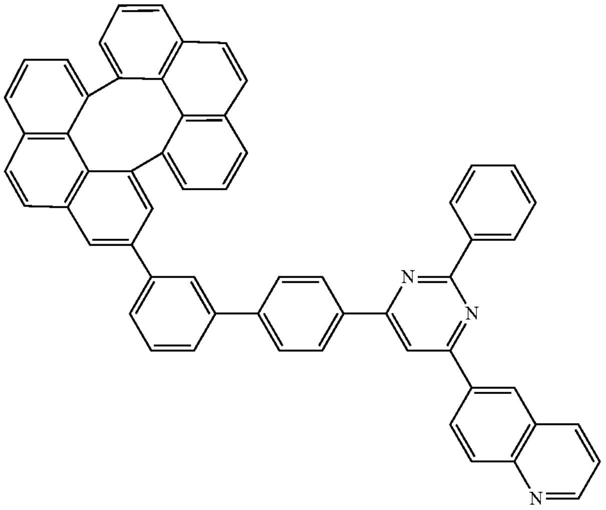
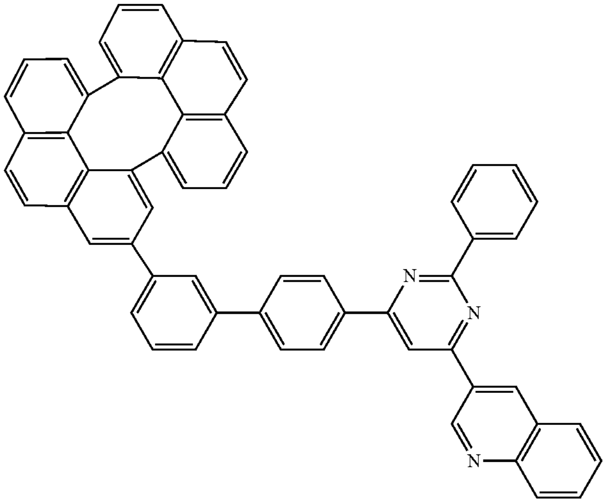

-continued
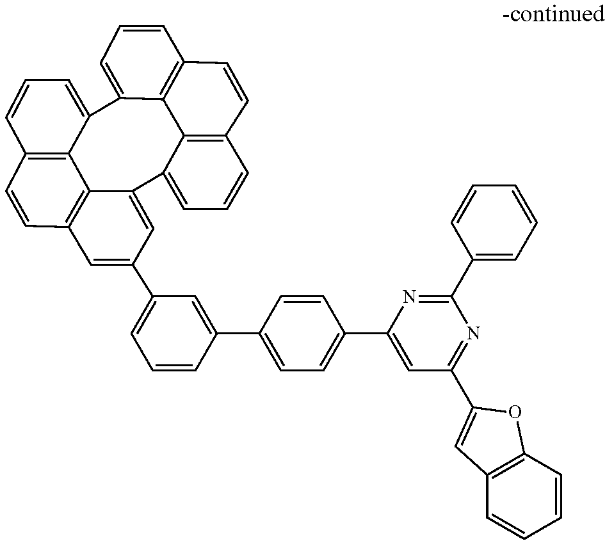
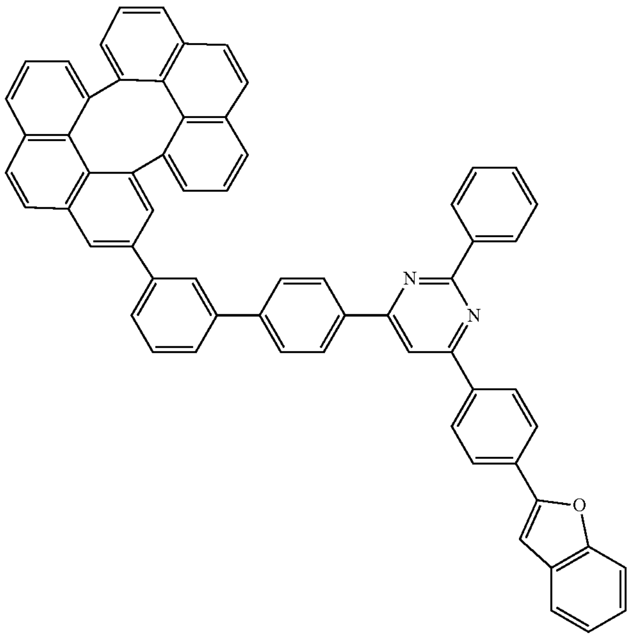
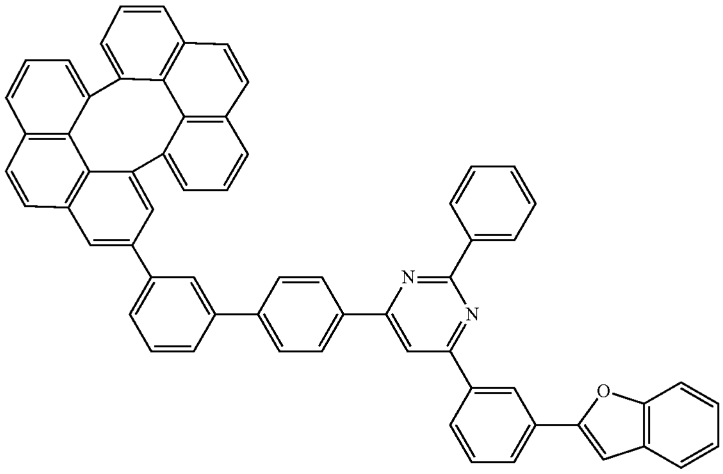

-continued
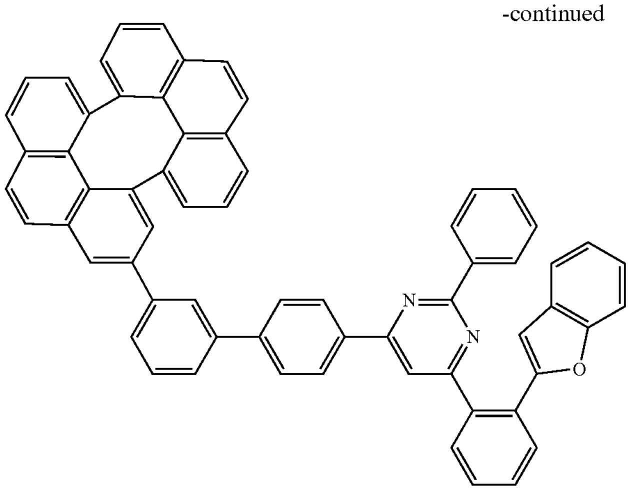
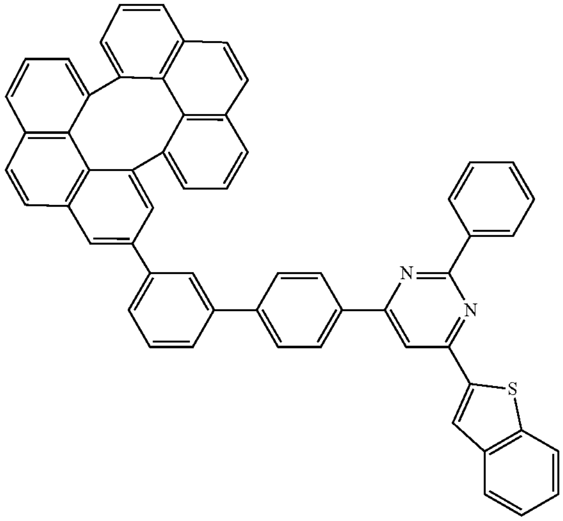
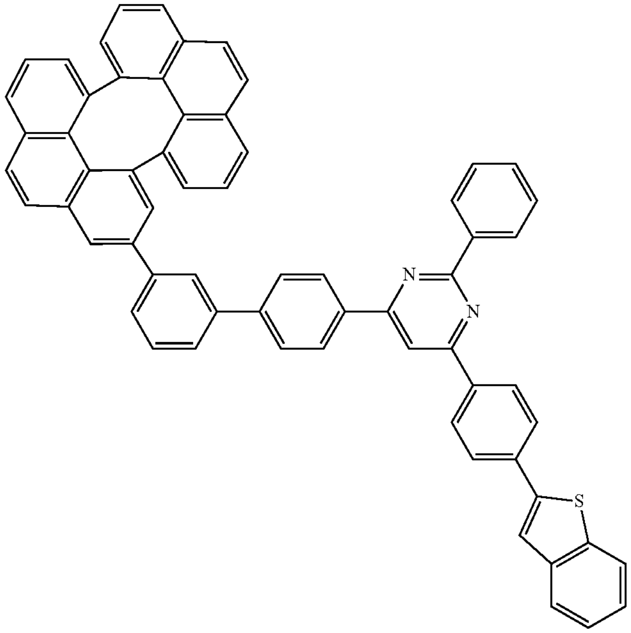

-continued
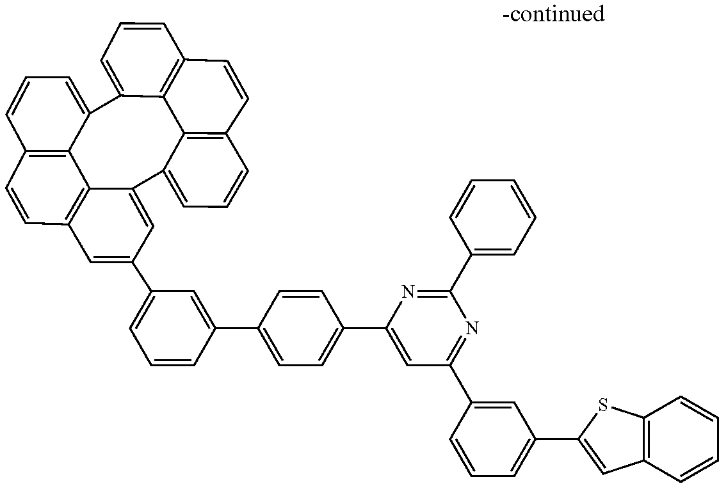
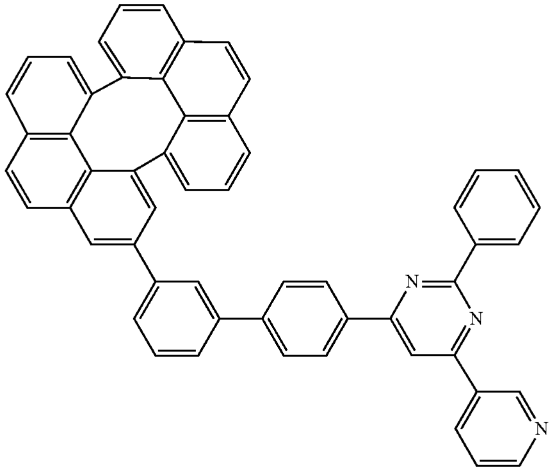
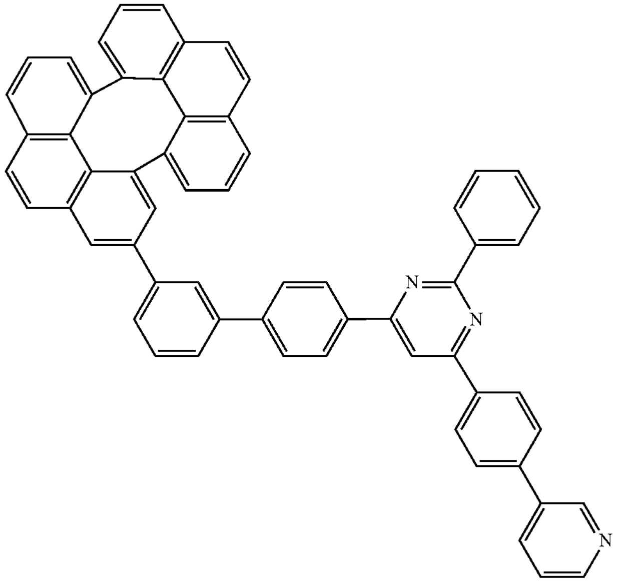

-continued
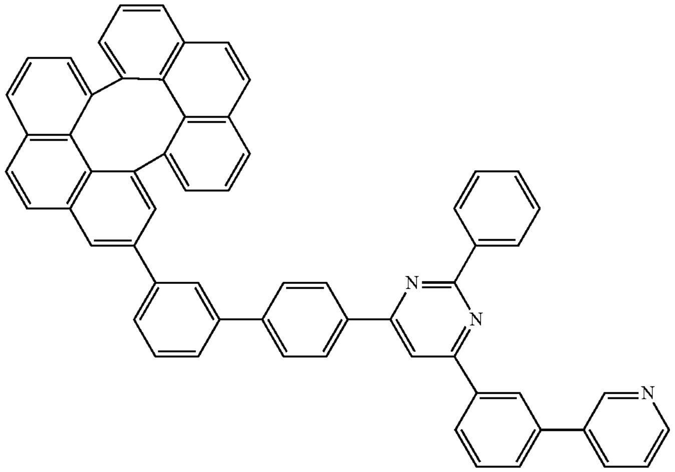
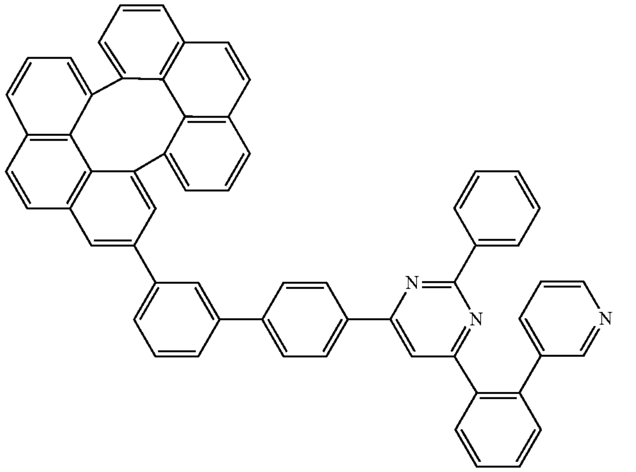
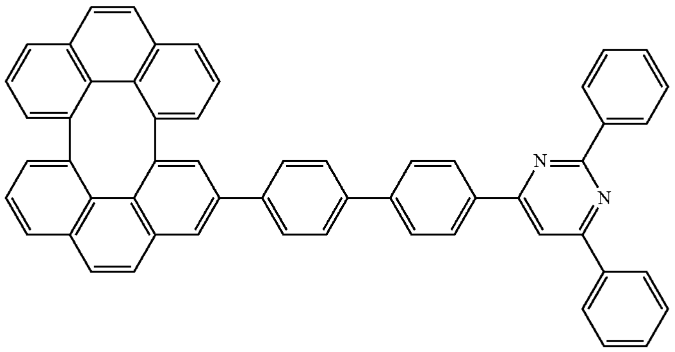

-continued
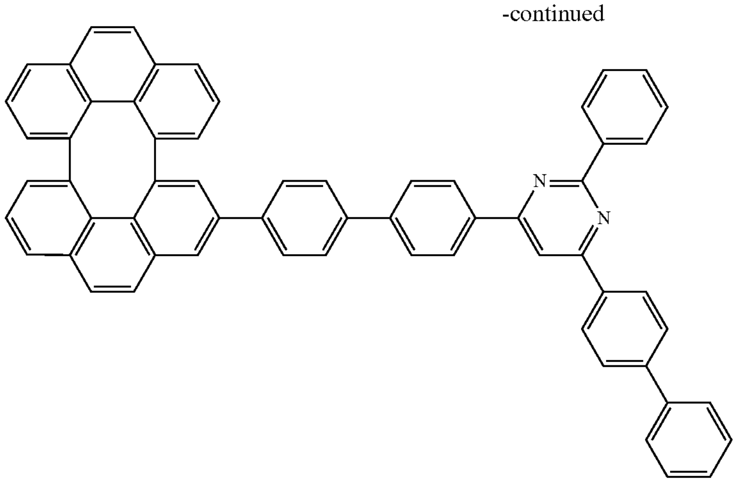
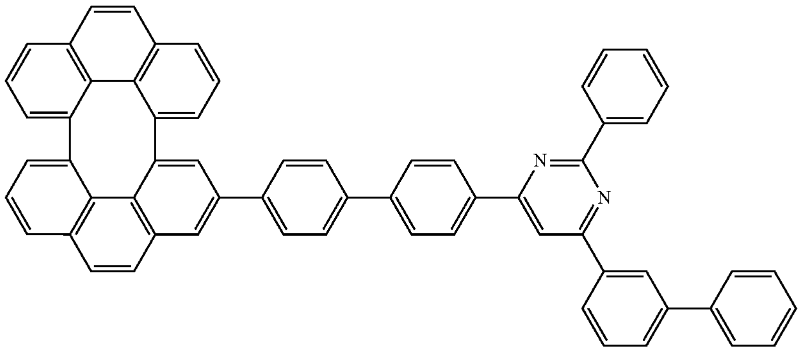
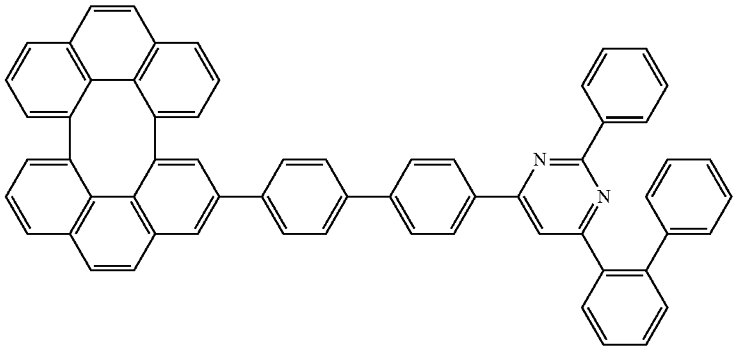
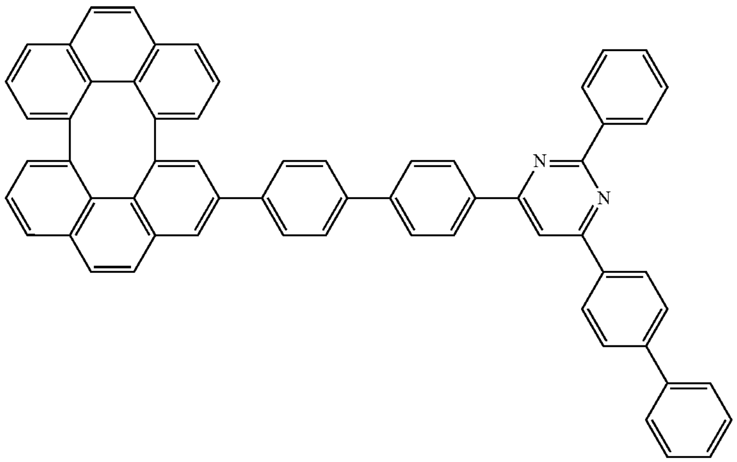

-continued
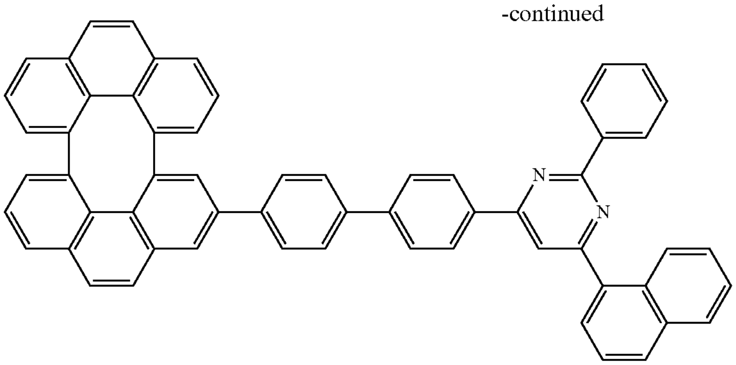
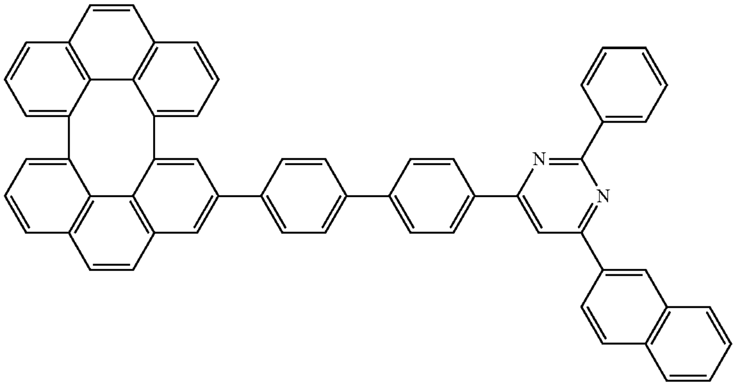
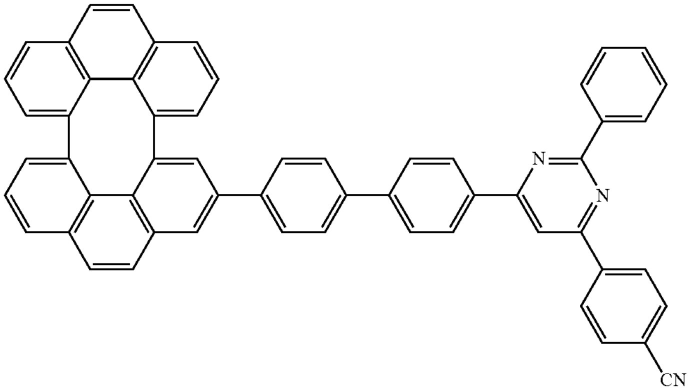
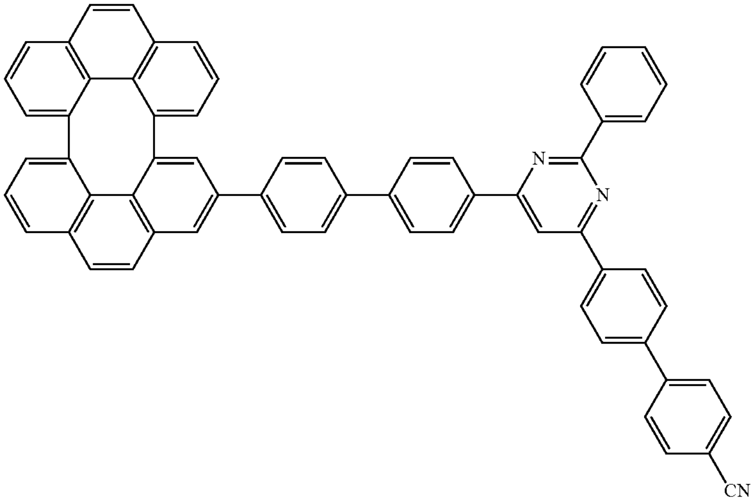

-continued
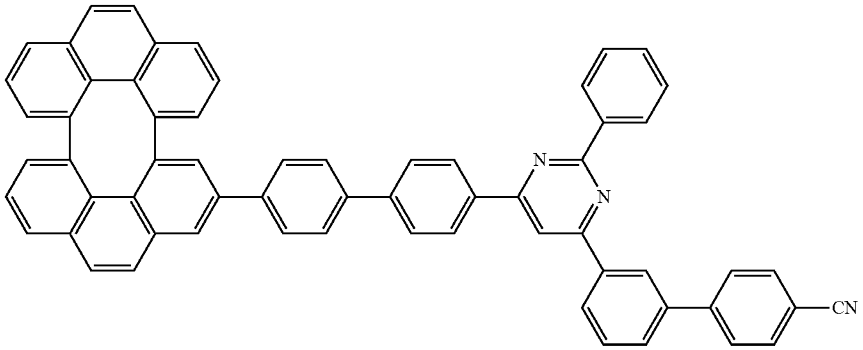
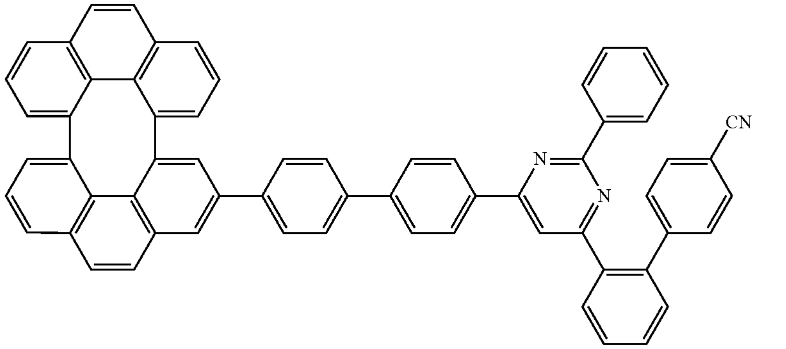
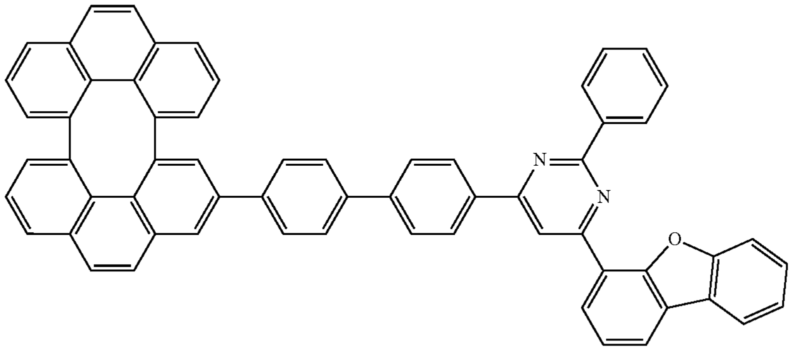
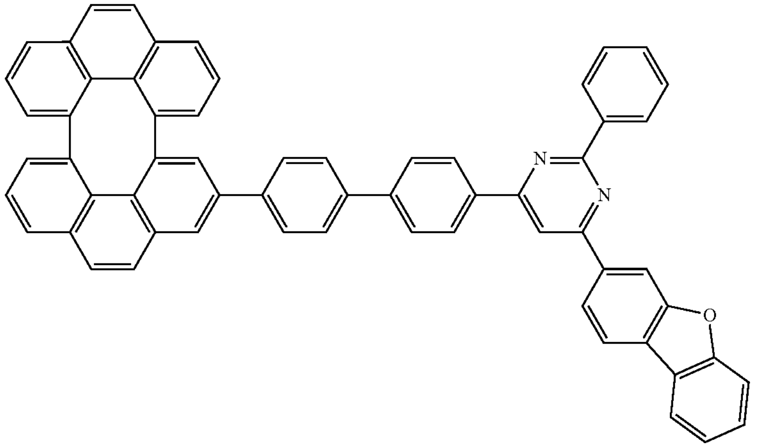

-continued
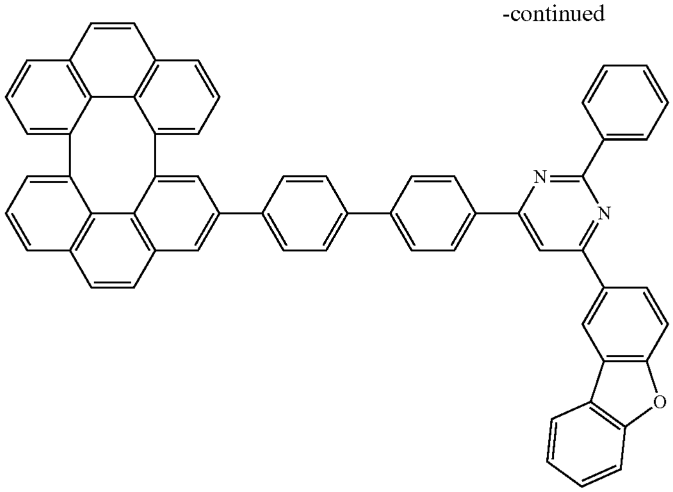
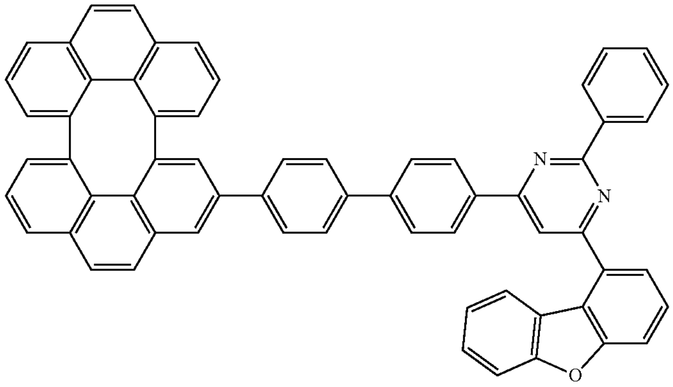
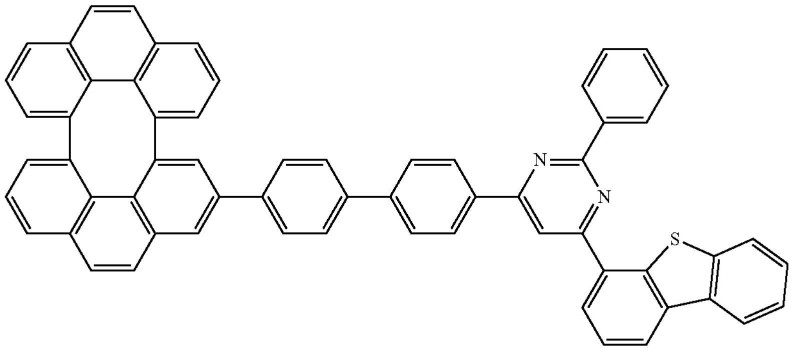
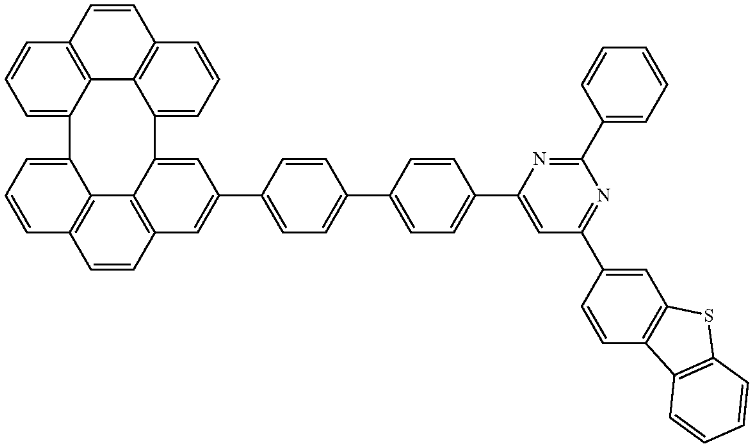

-continued
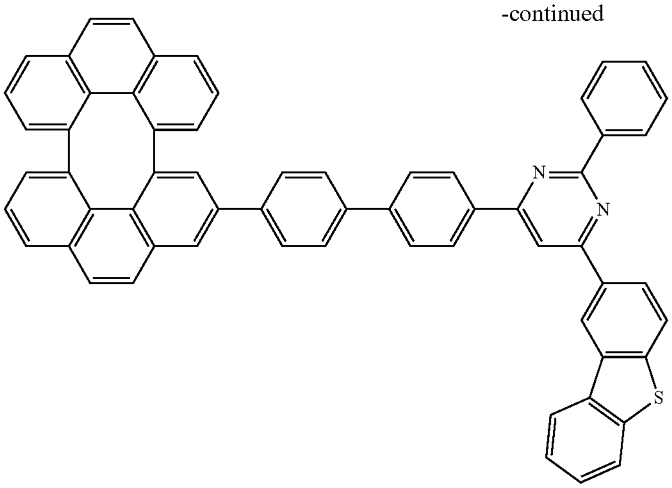
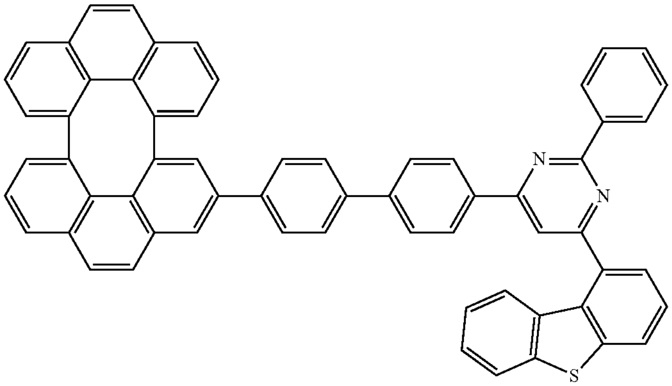
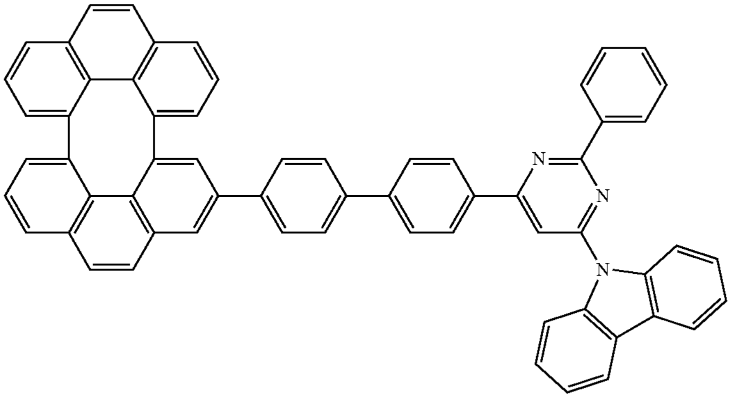
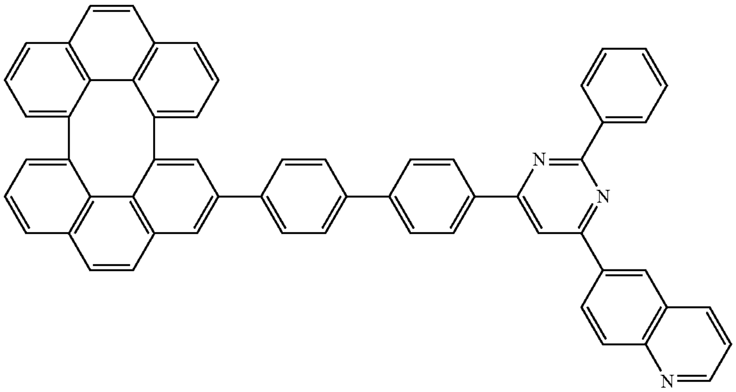

-continued
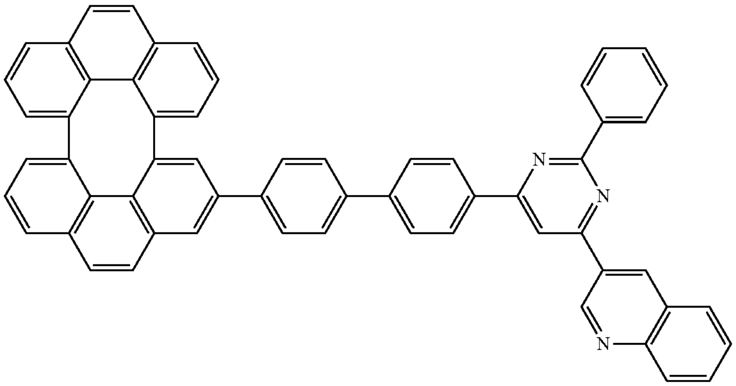
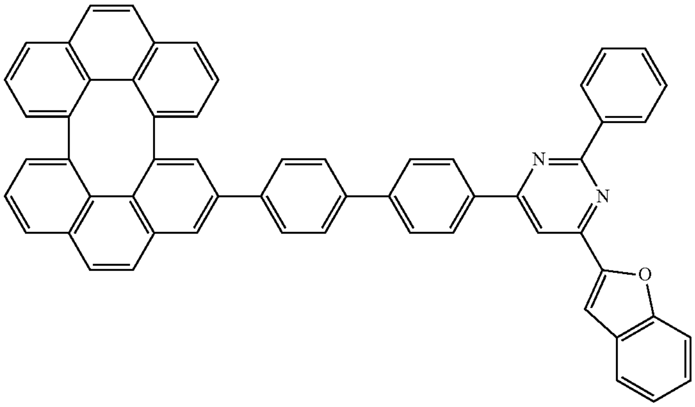
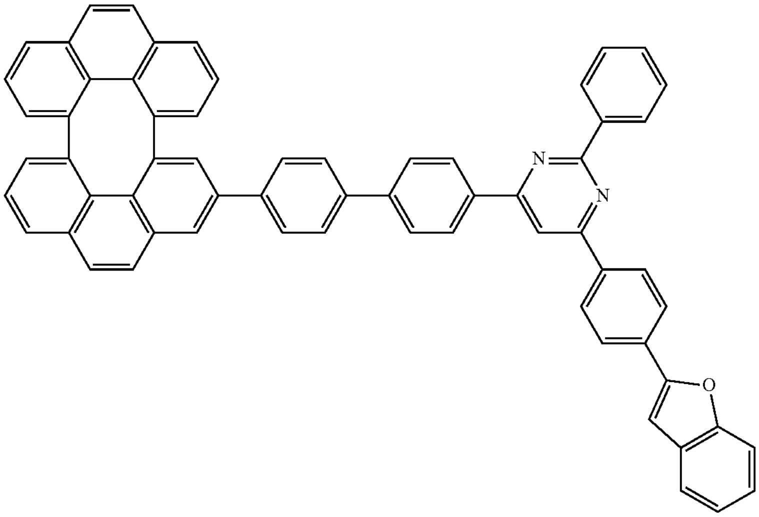
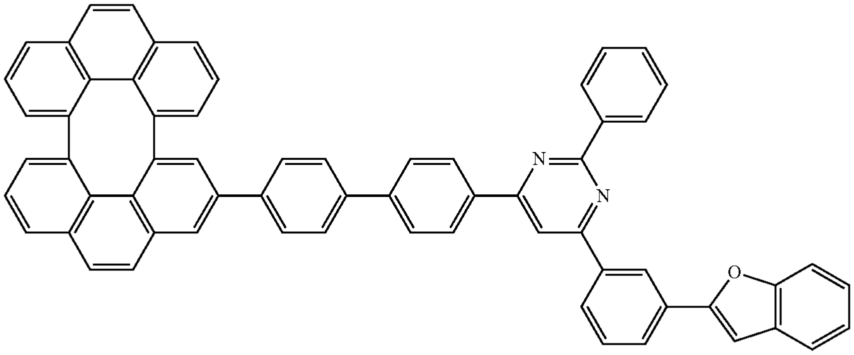

-continued
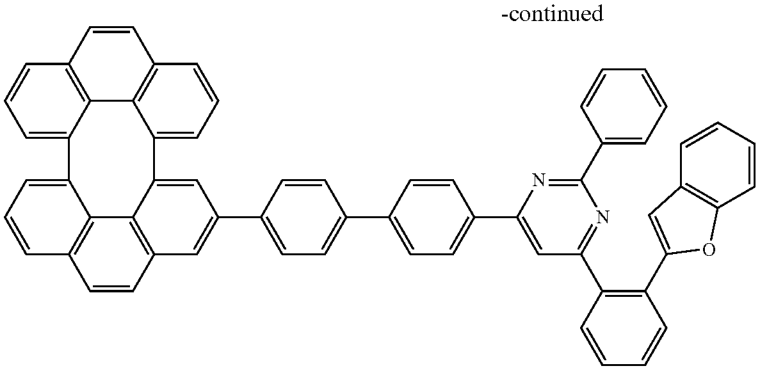
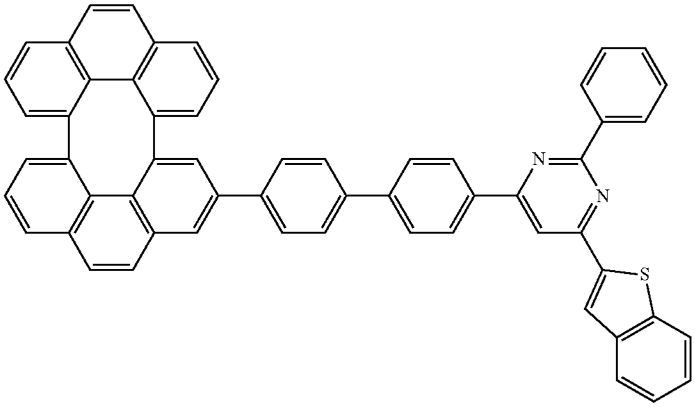
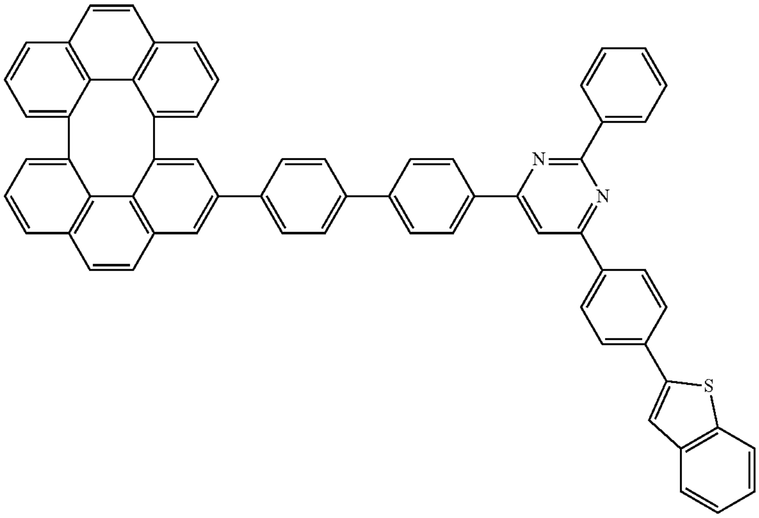
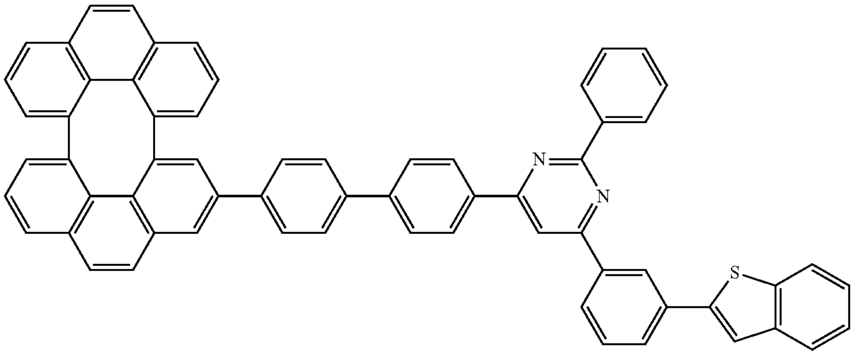

-continued
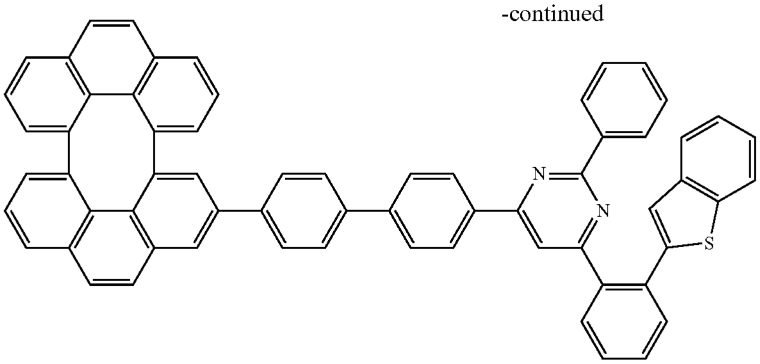
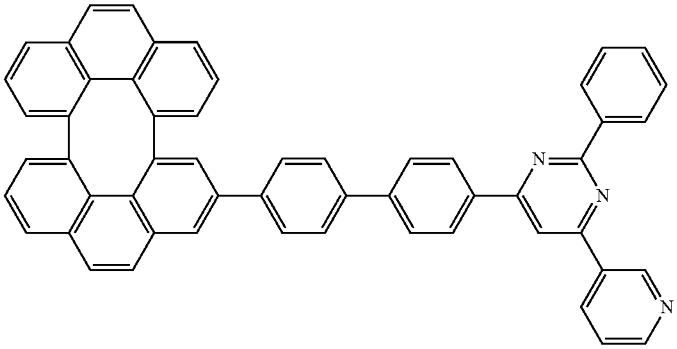
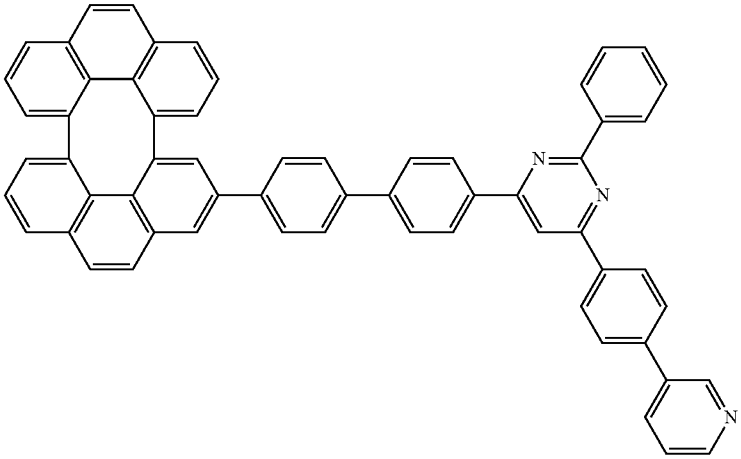
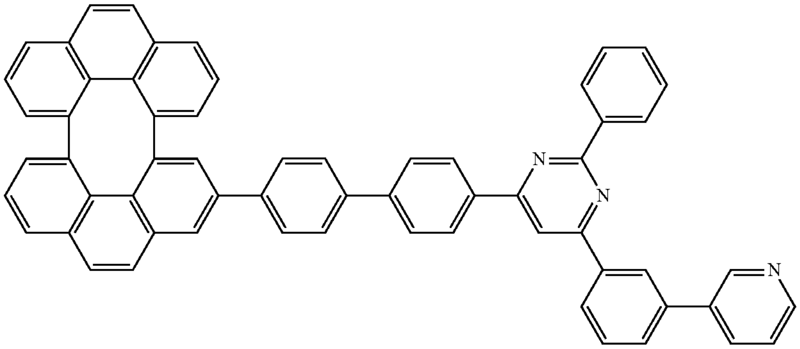

-continued
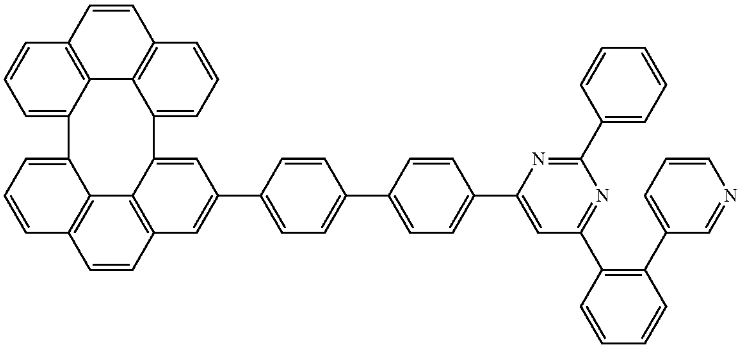
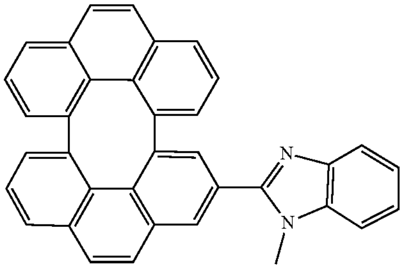
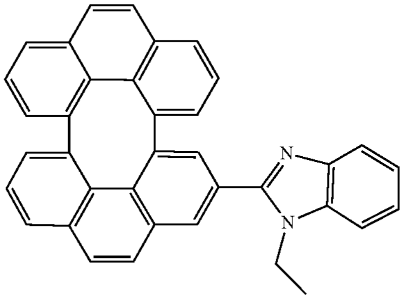
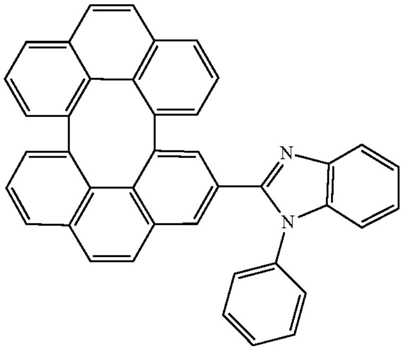
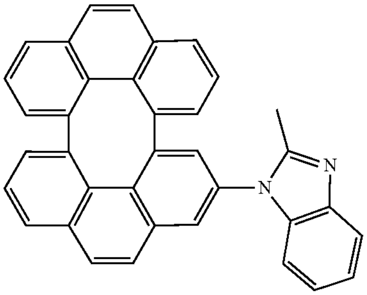
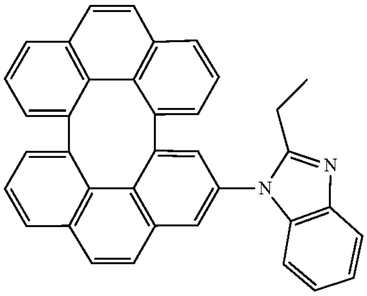
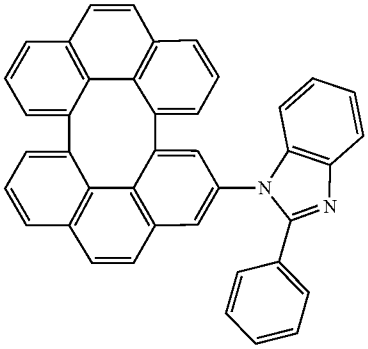
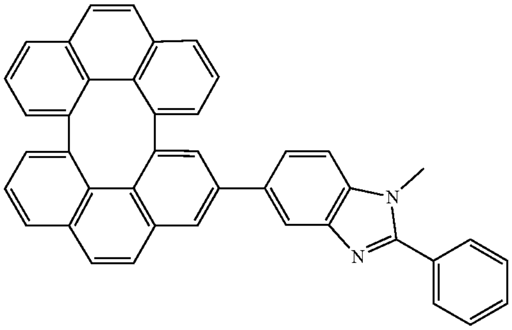
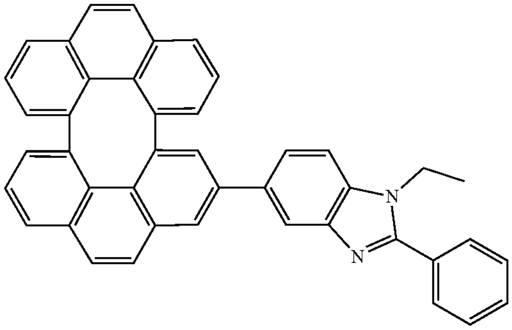

-continued
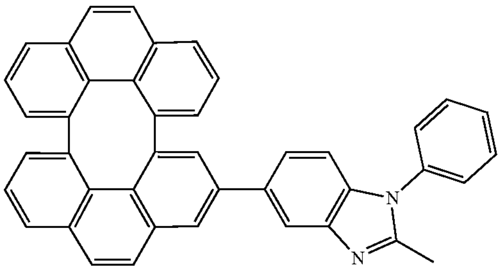
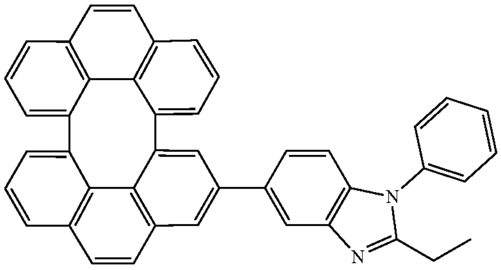
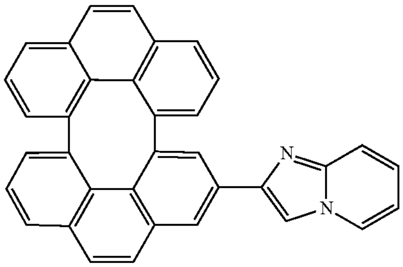
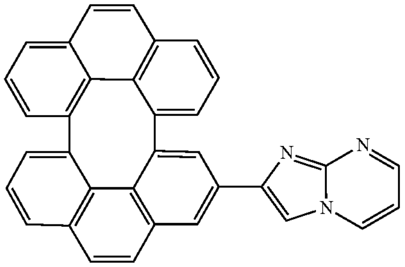
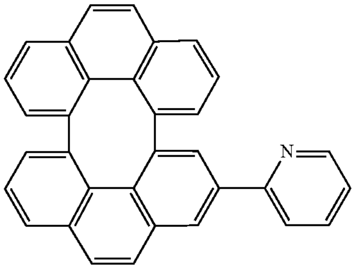
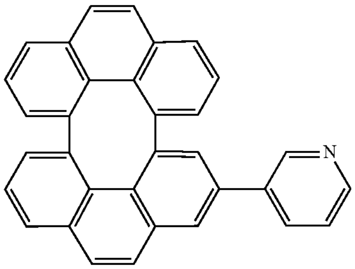
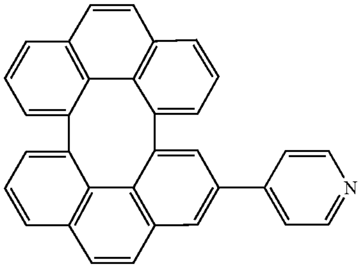
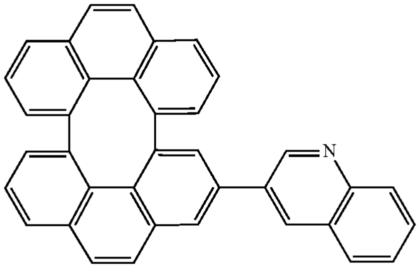
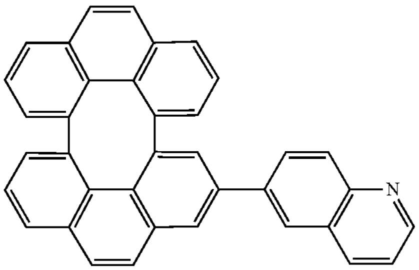
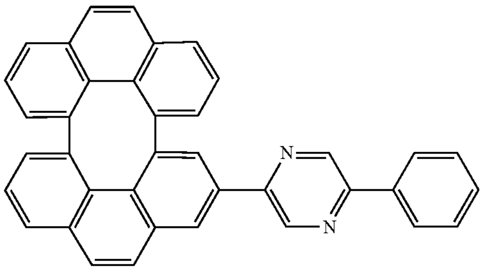
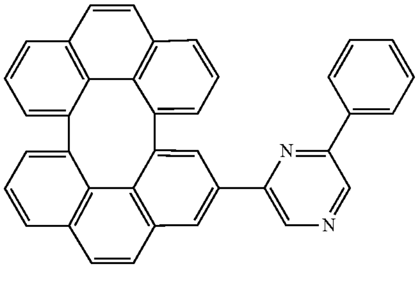
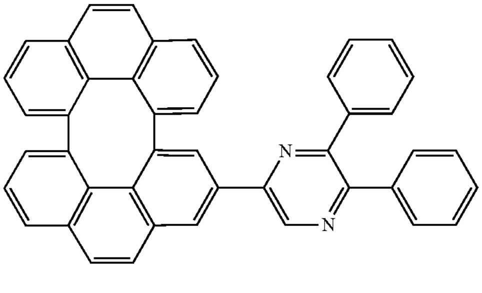

-continued
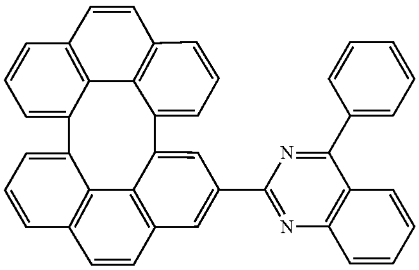
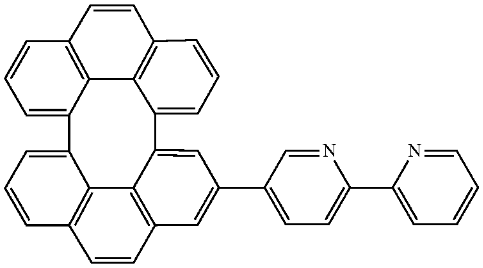
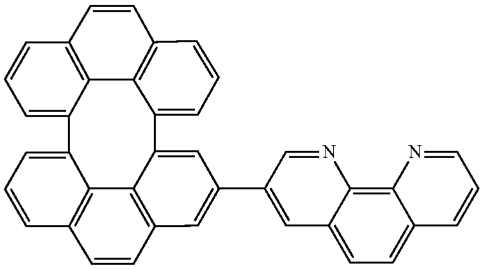
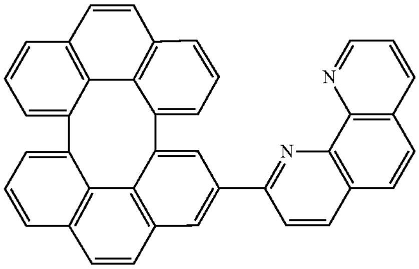
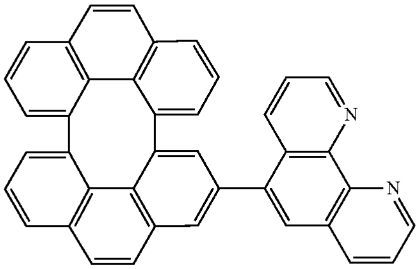
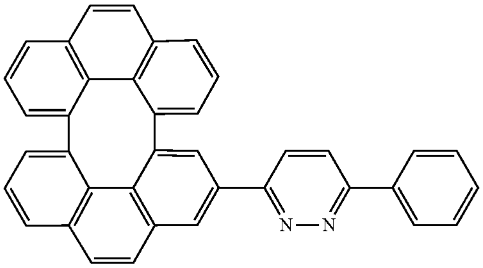
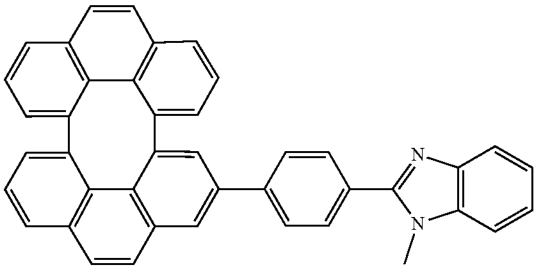
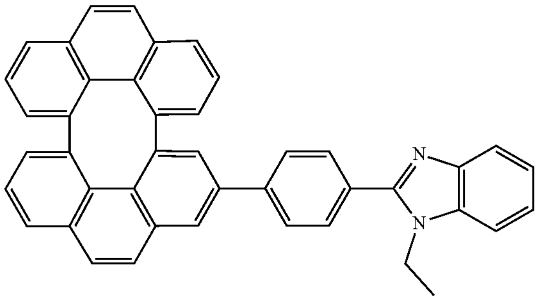
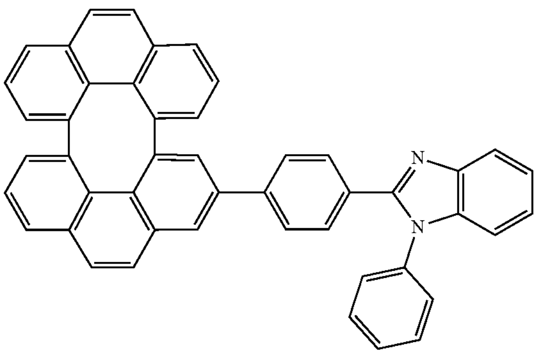
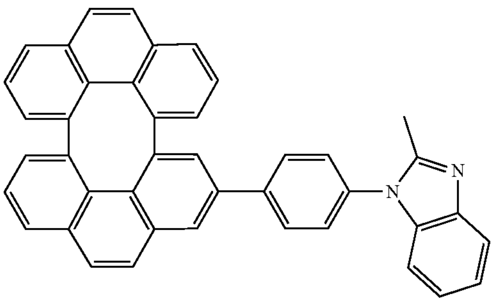

-continued
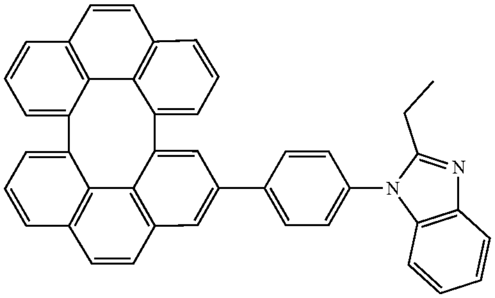
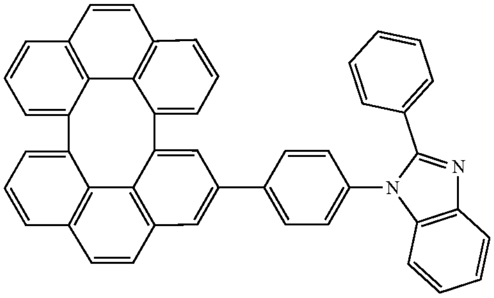
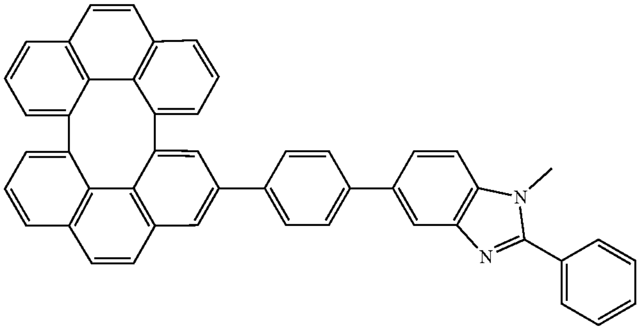
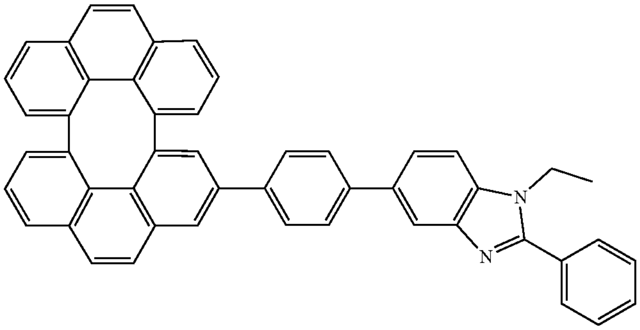
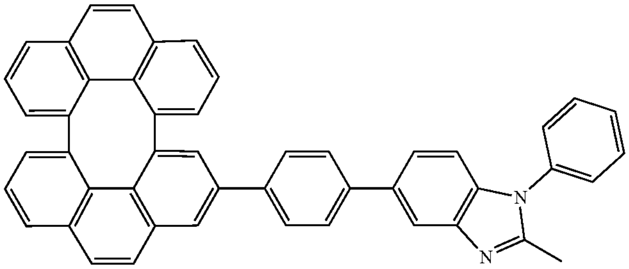
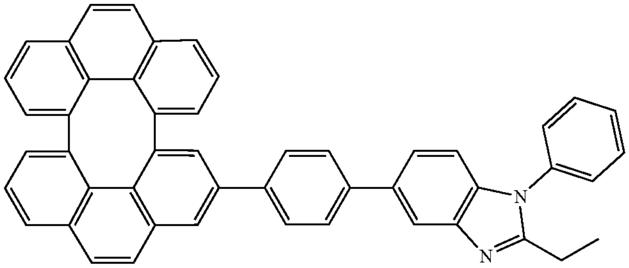

-continued
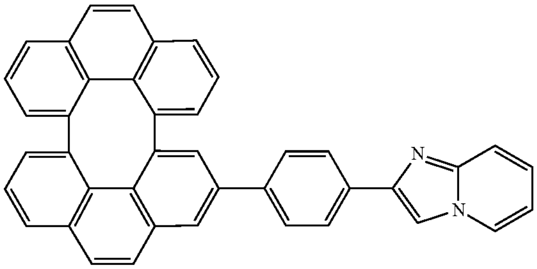
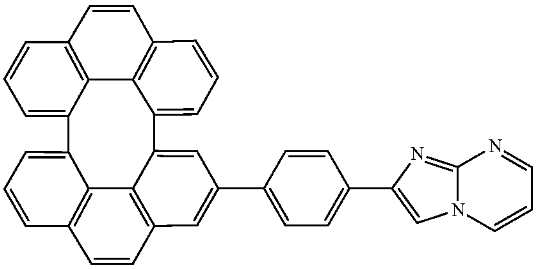
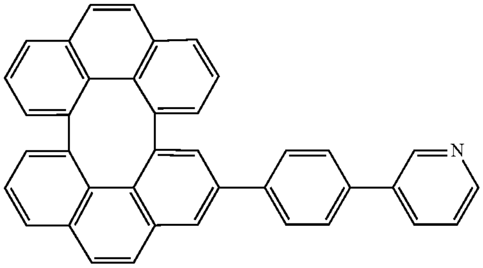
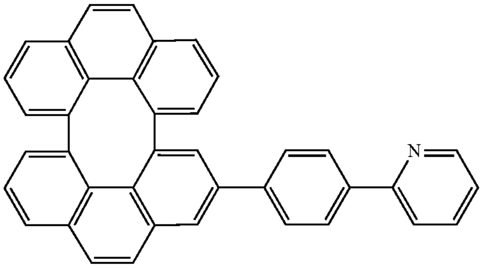
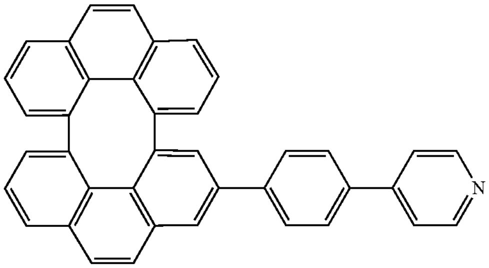
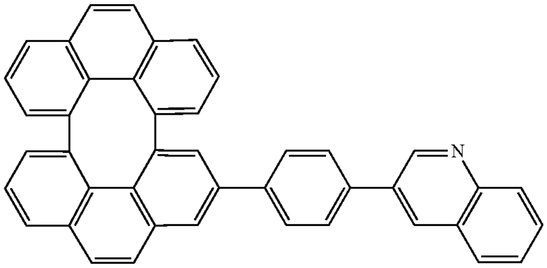
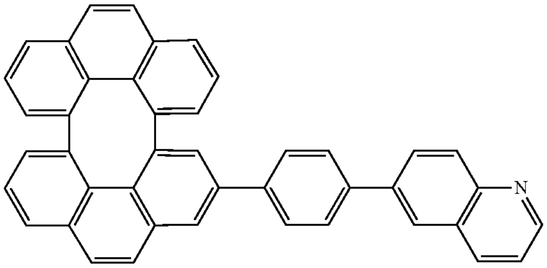
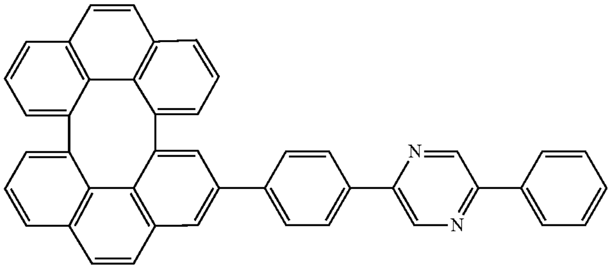
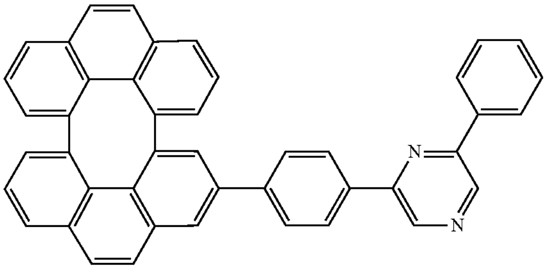
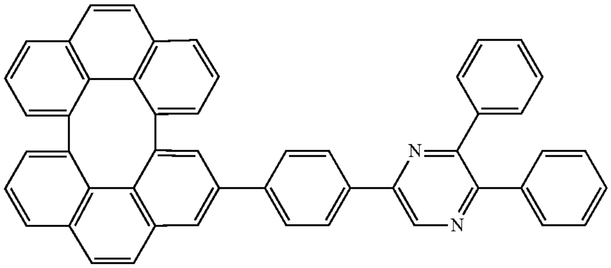
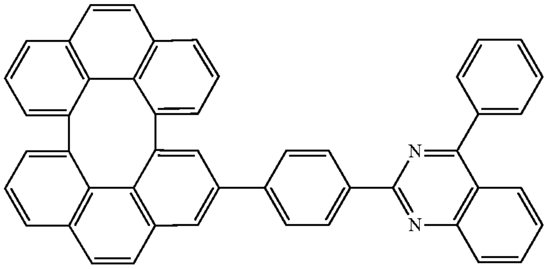
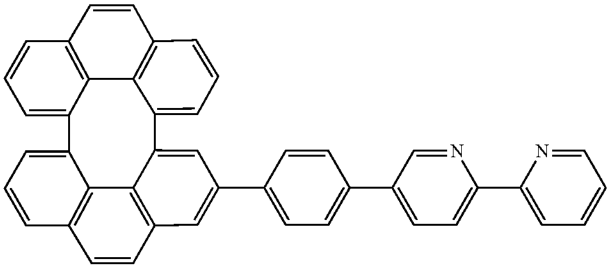

-continued
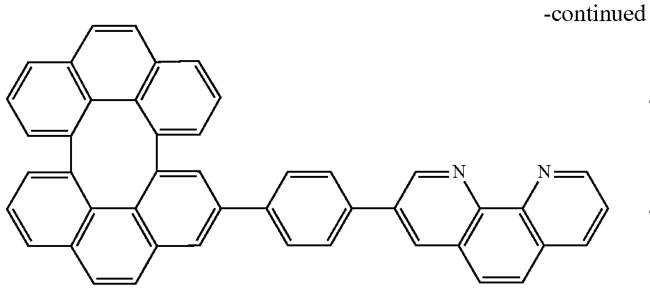
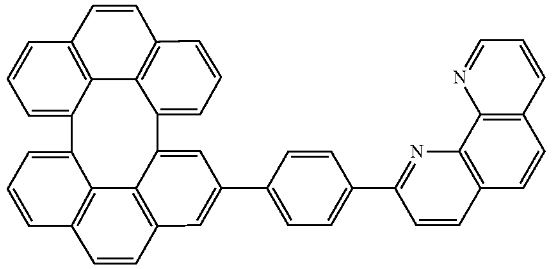
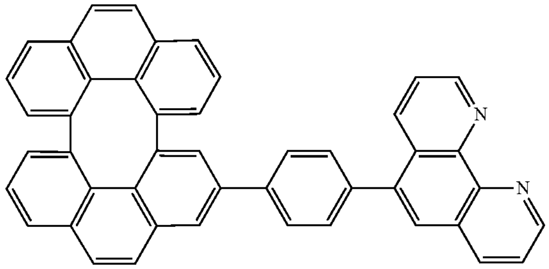
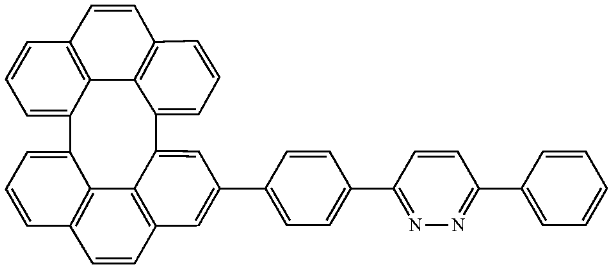
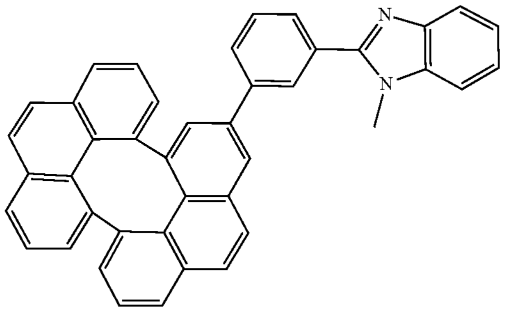
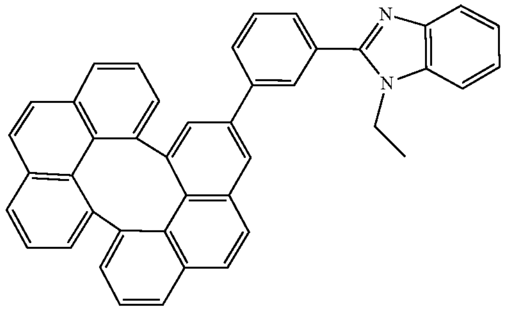
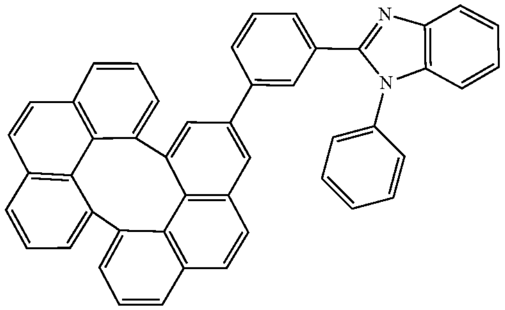
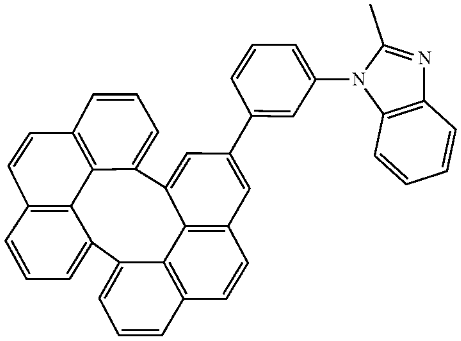
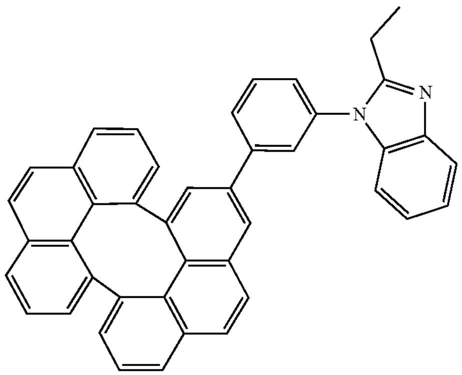
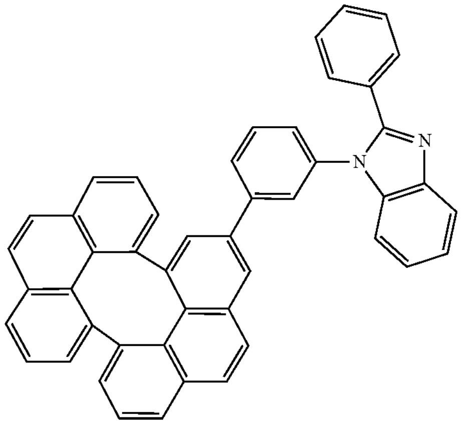

-continued
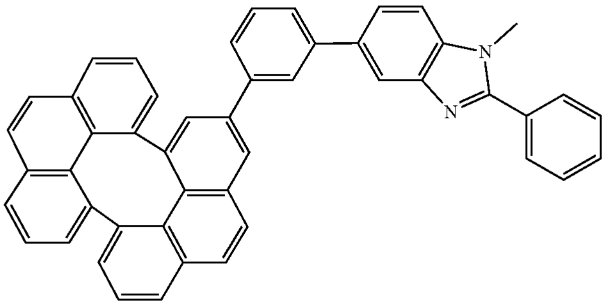
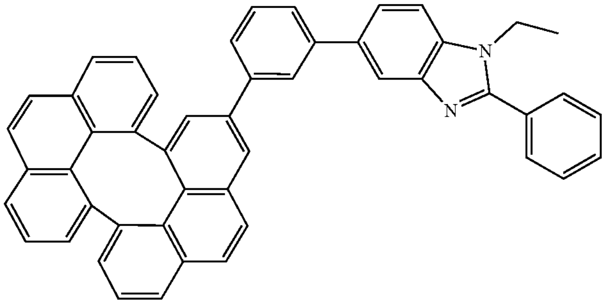
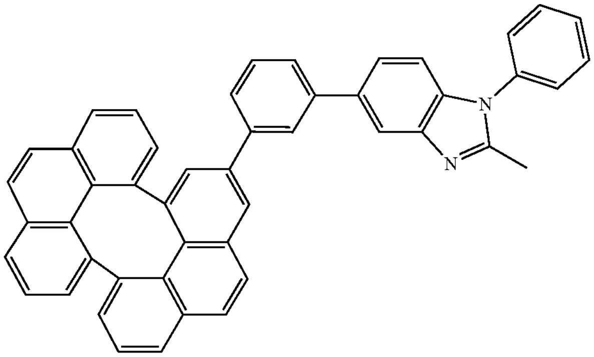
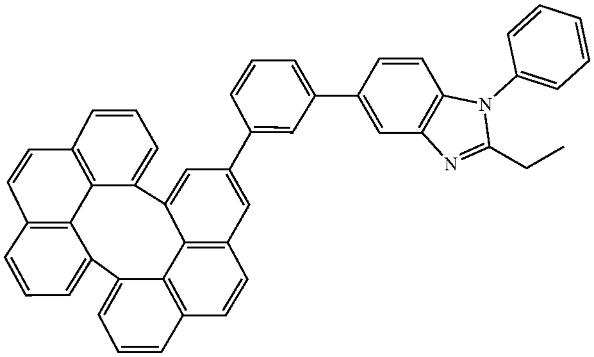
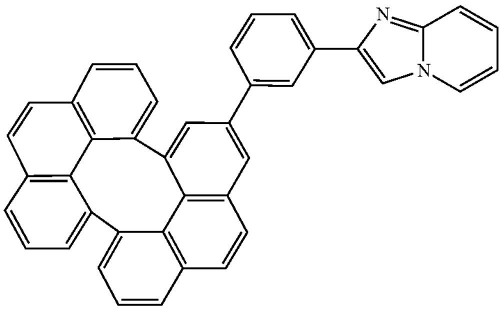
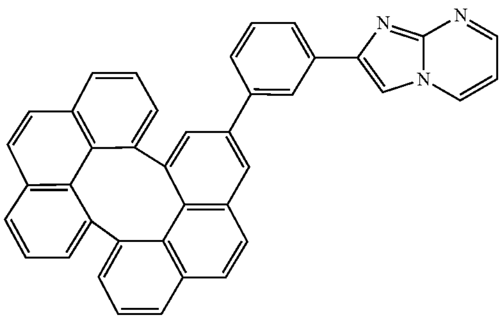
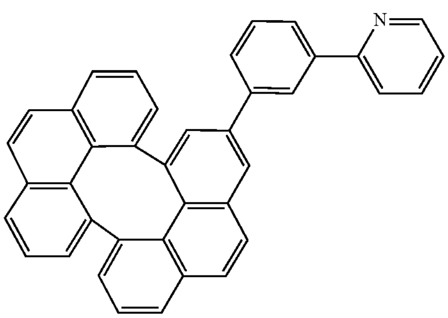

-continued
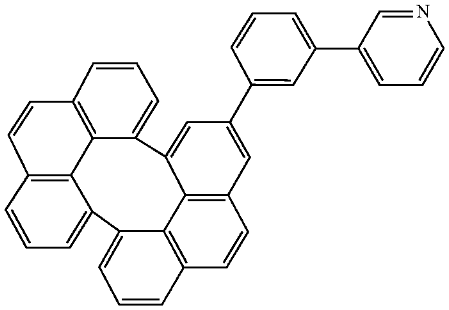
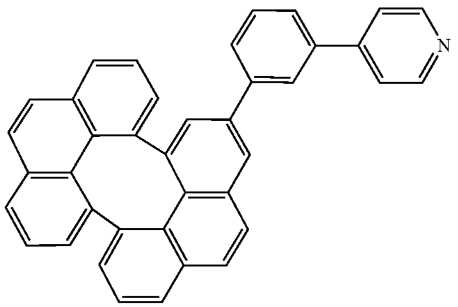
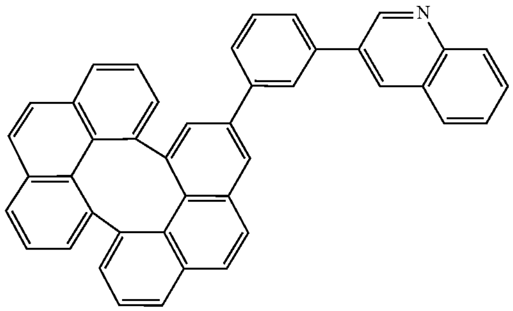
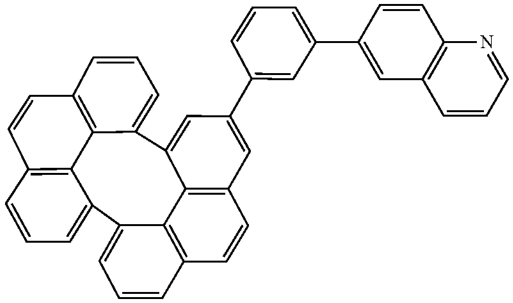
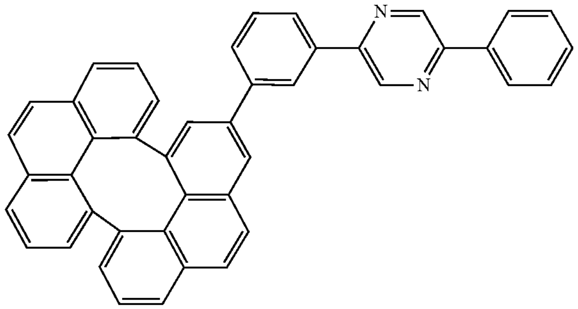
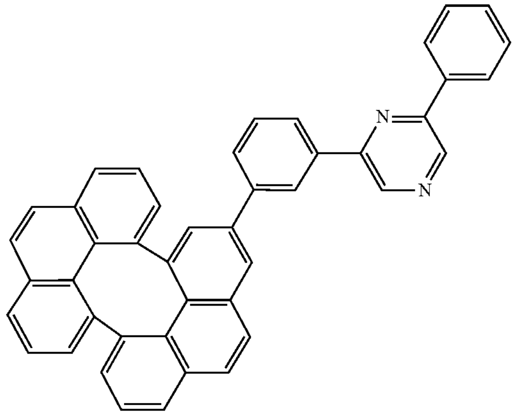
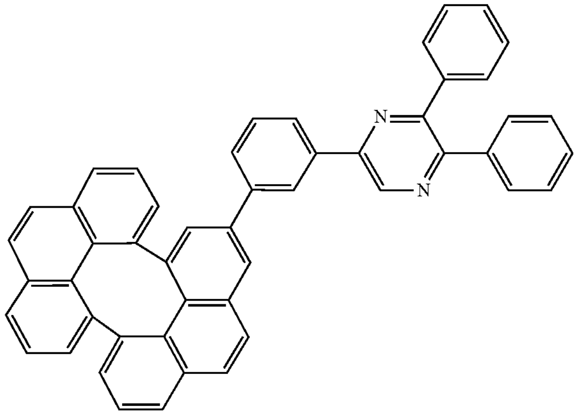
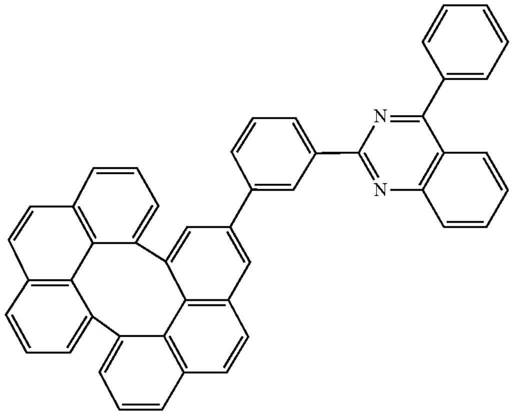

-continued
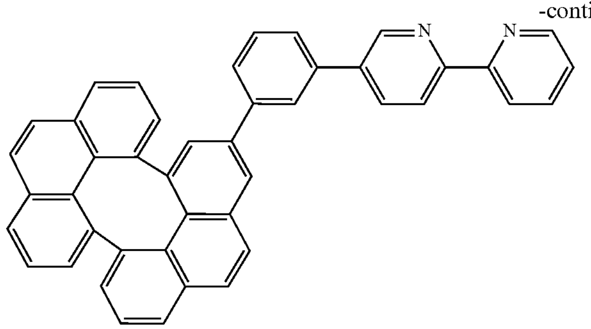
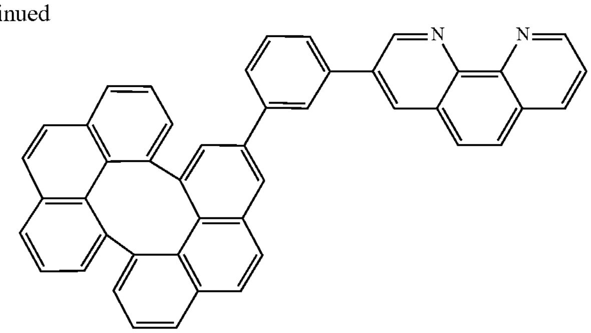
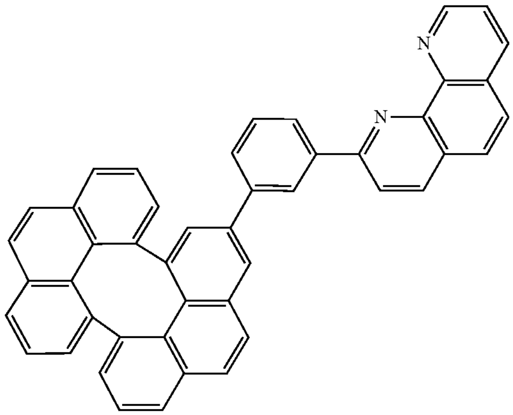
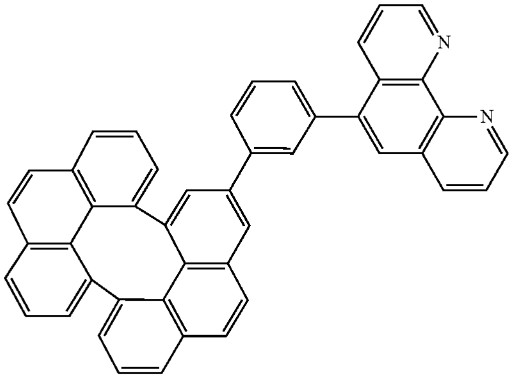
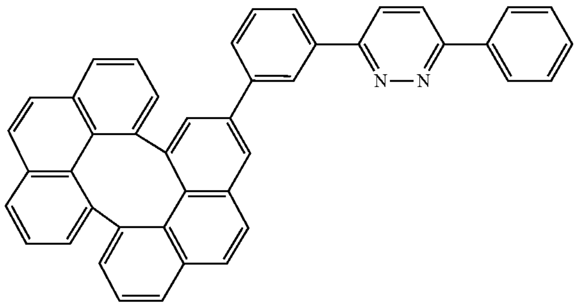
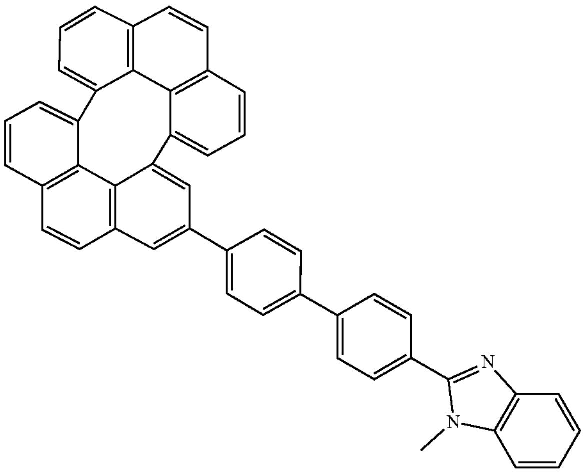

-continued
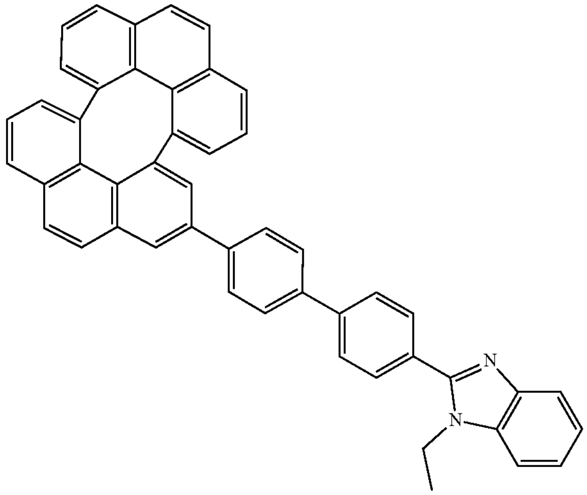
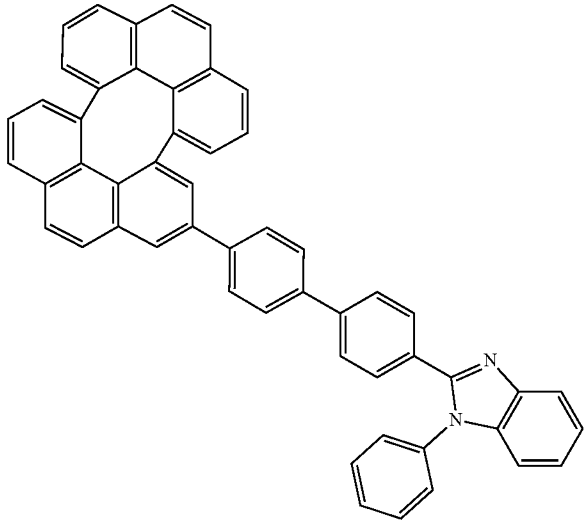
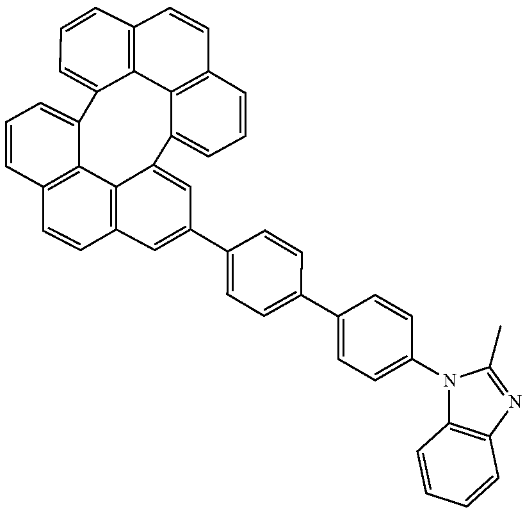
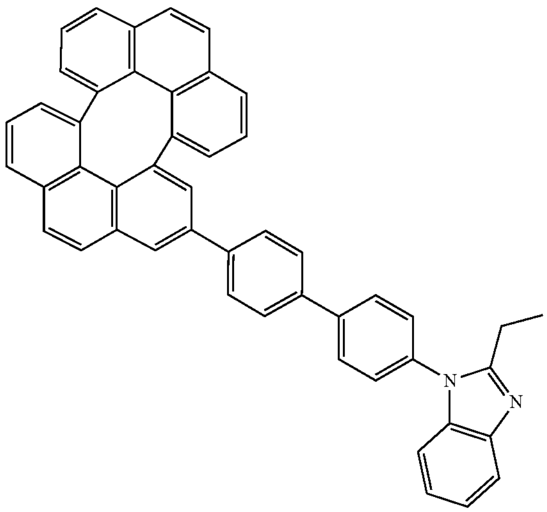
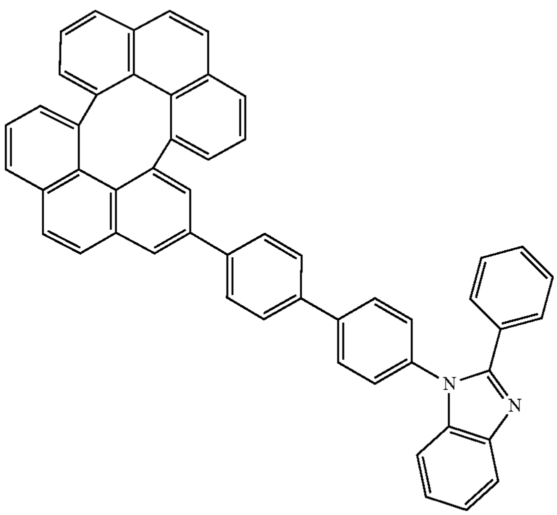

-continued
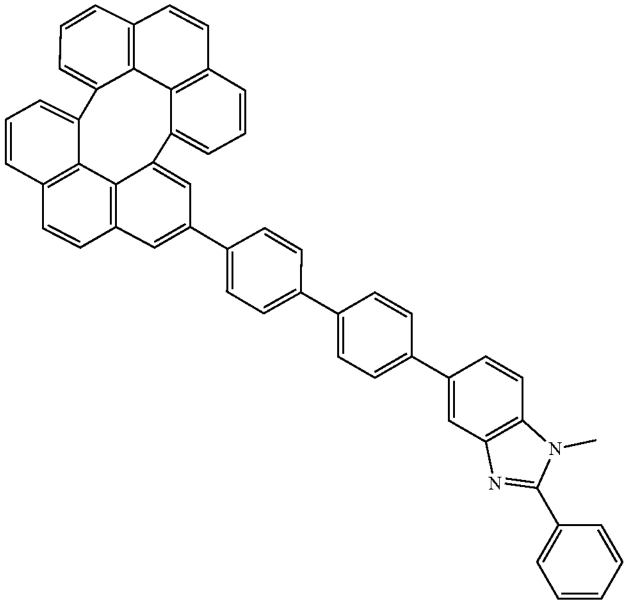
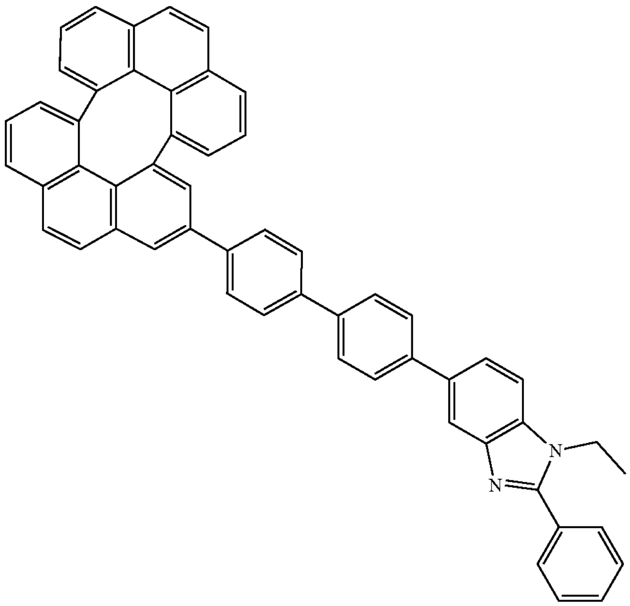

-continued
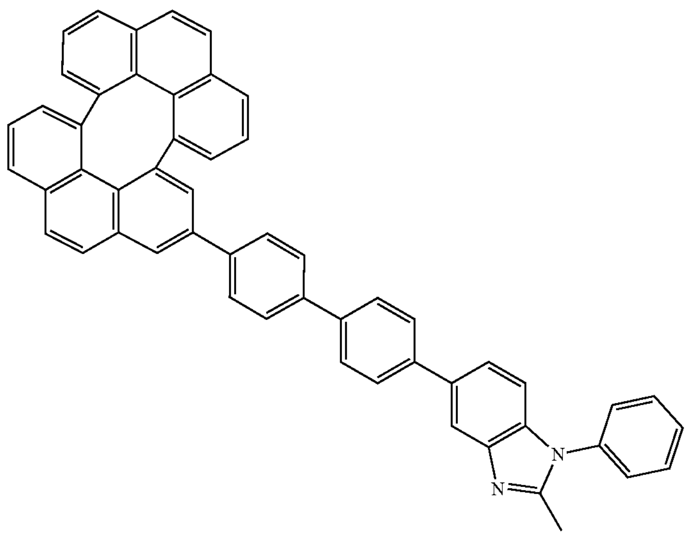
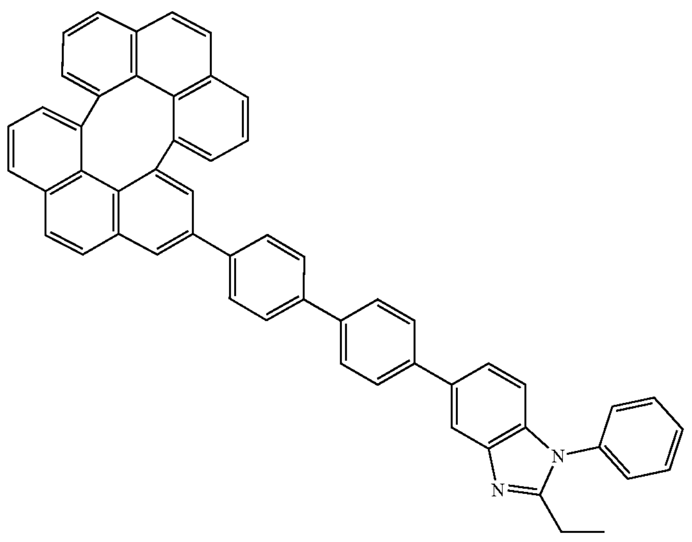
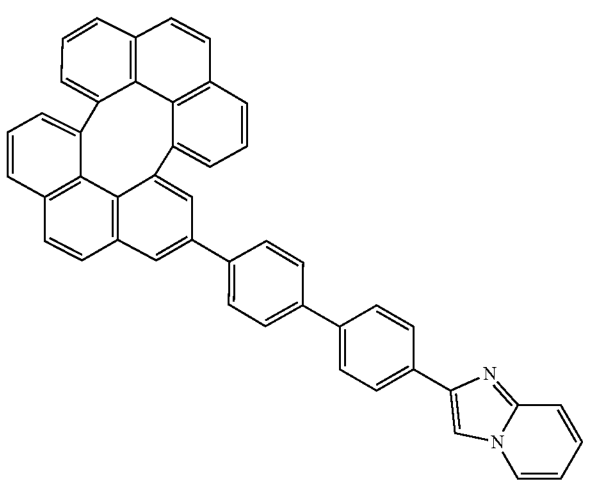
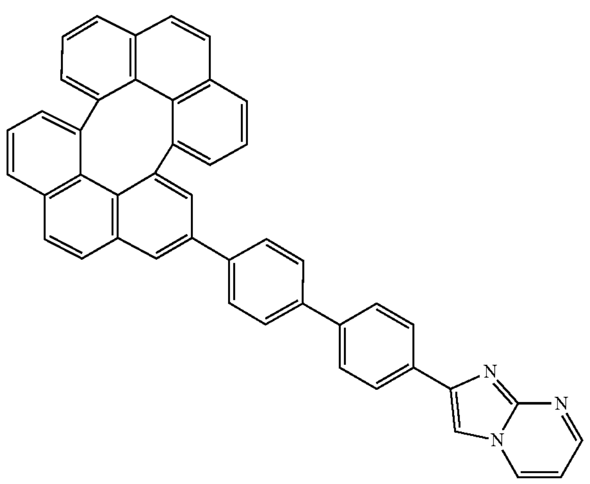

-continued
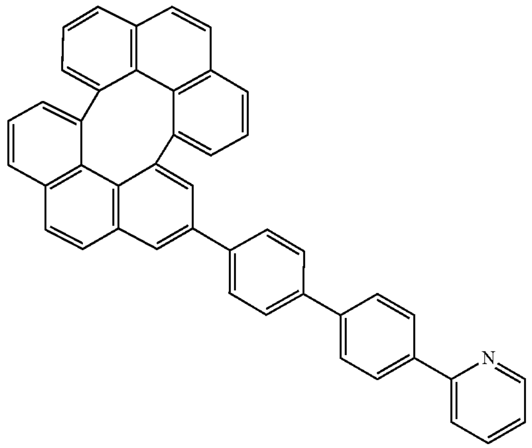
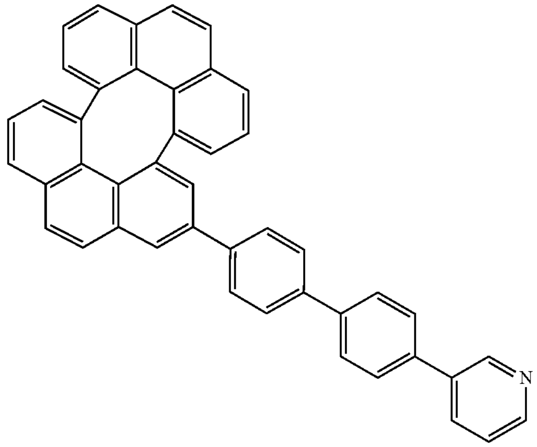
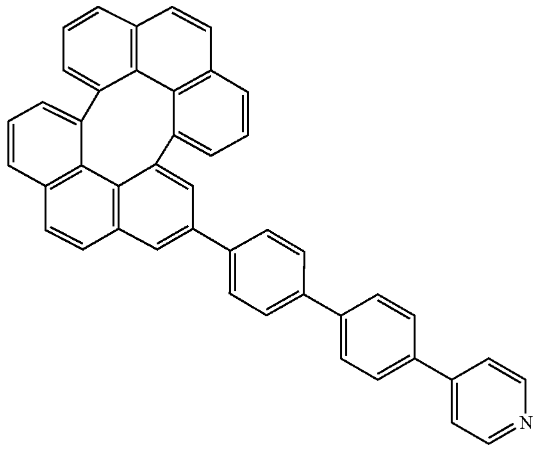
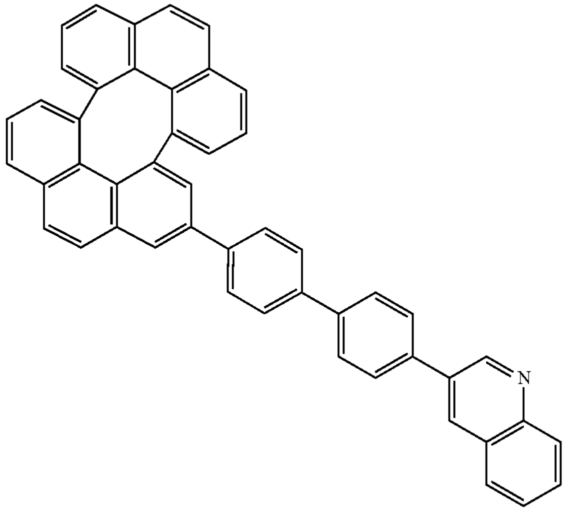
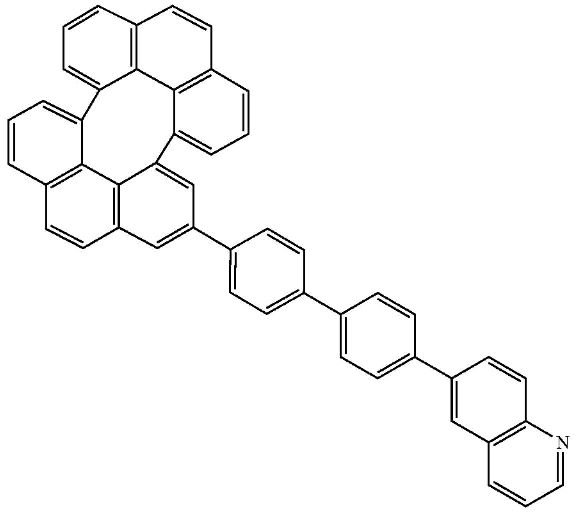
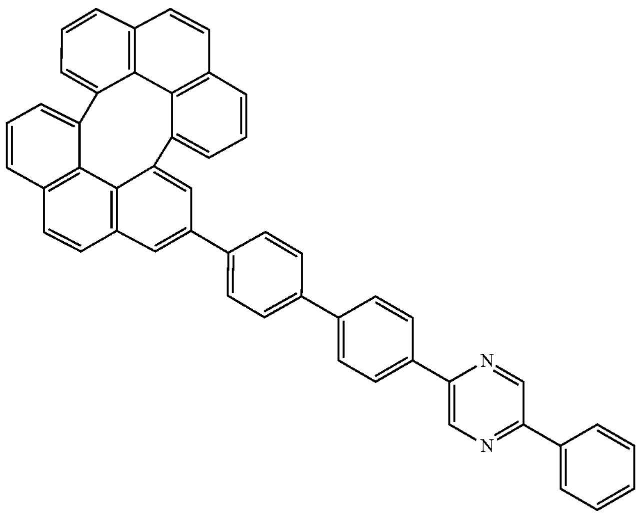

-continued
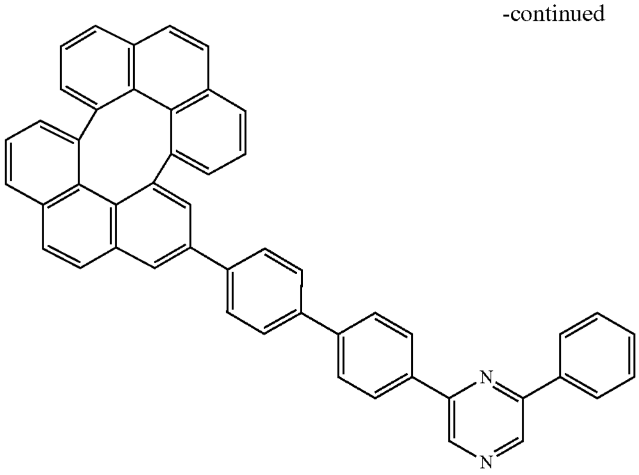
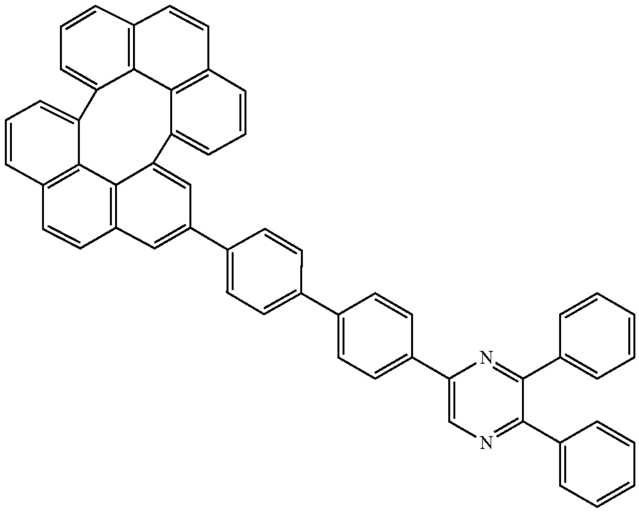
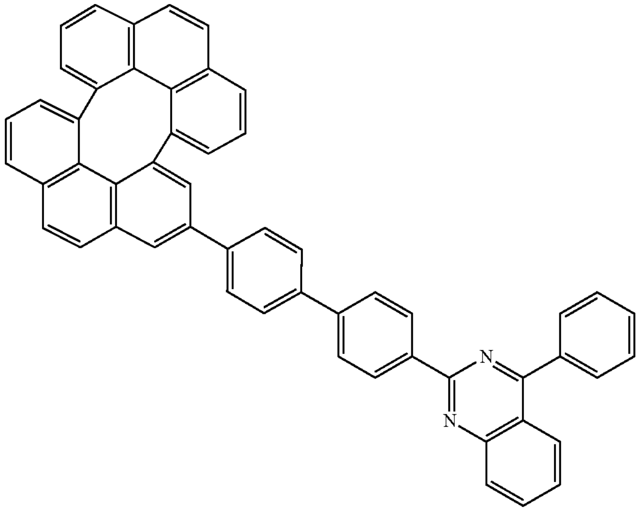

-continued
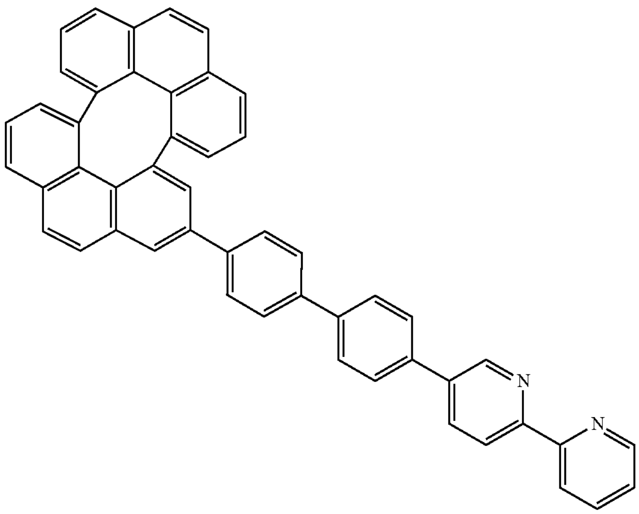
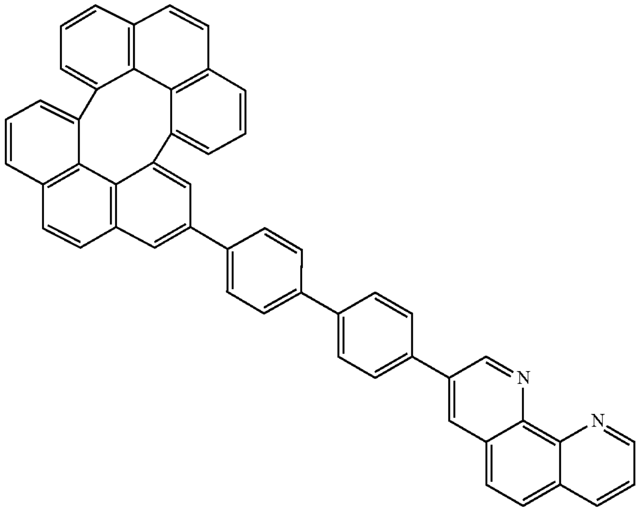
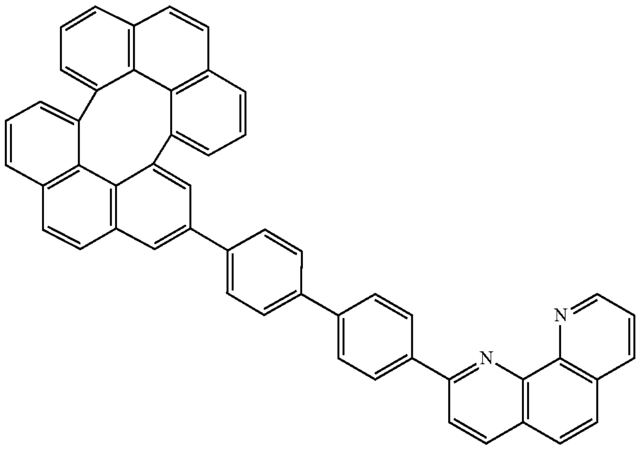

-continued
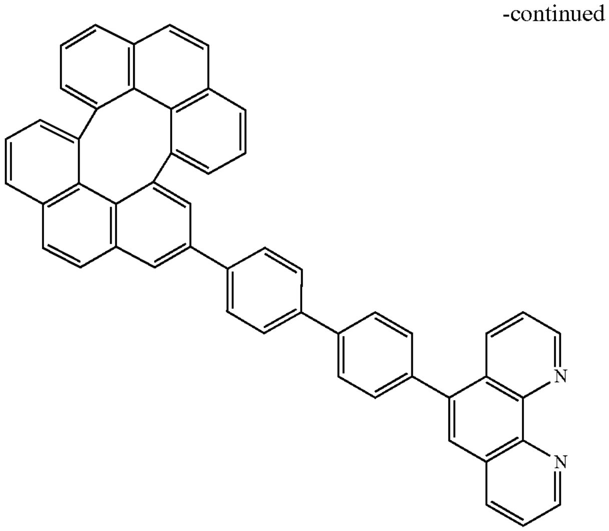
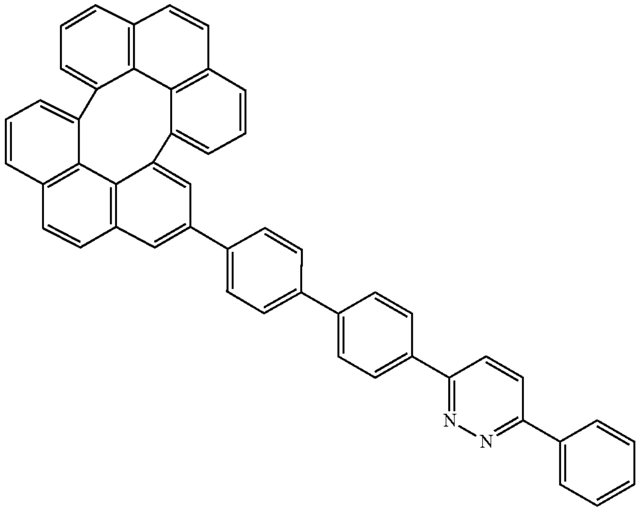
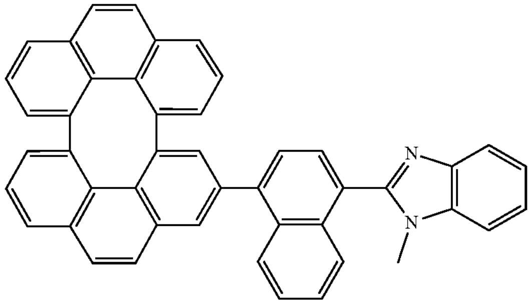
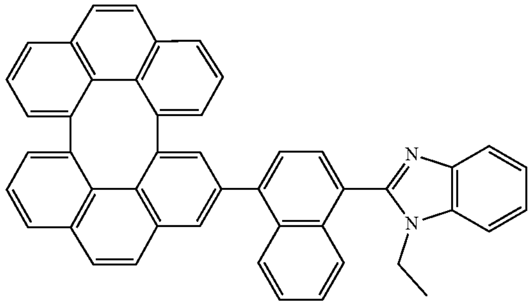
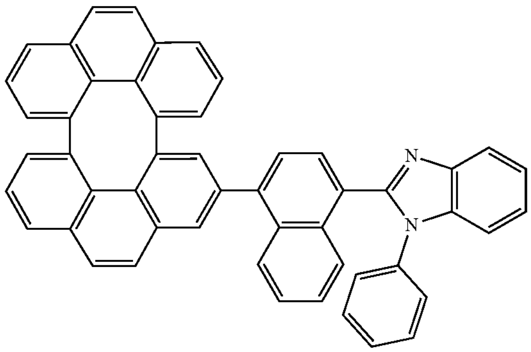
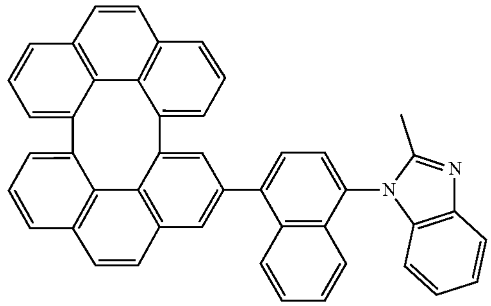

-continued
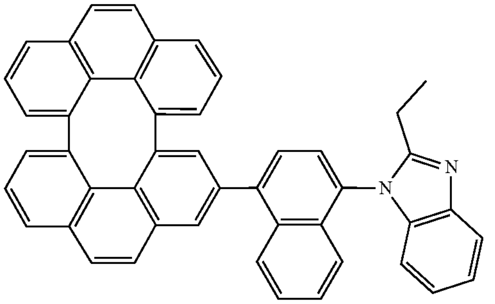
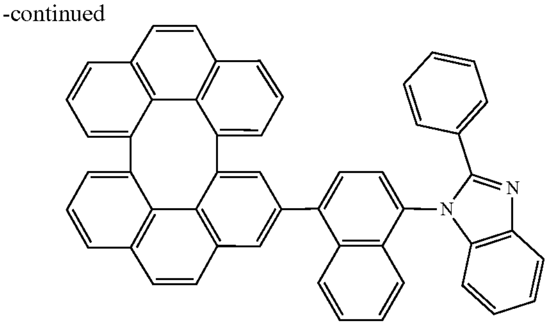
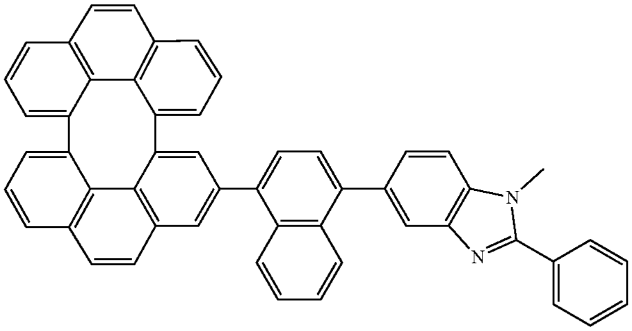
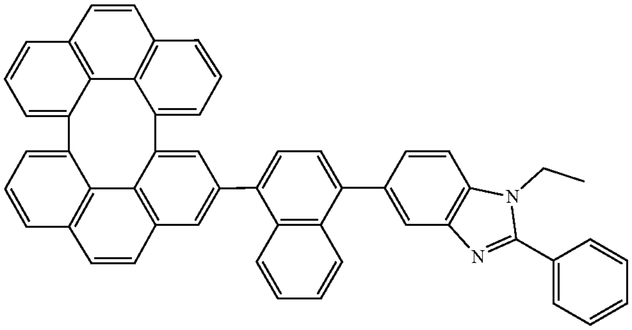
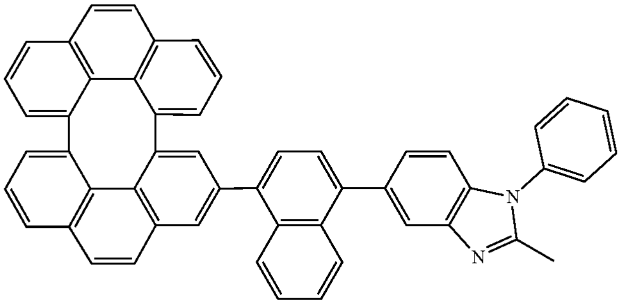
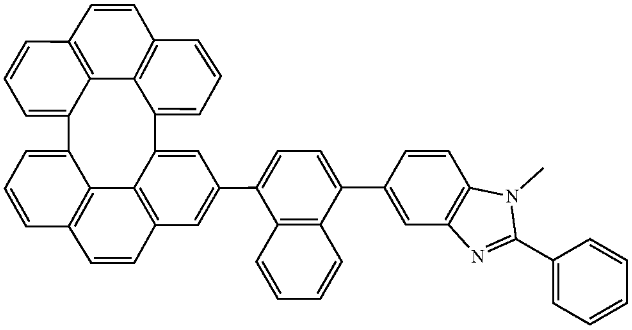

-continued
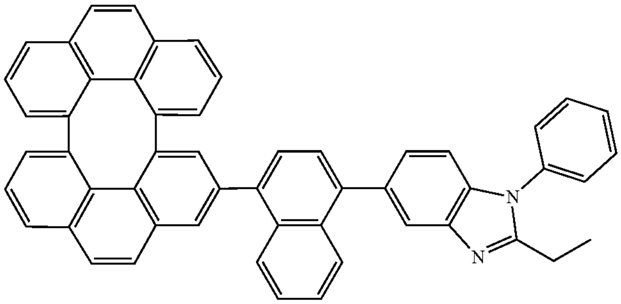
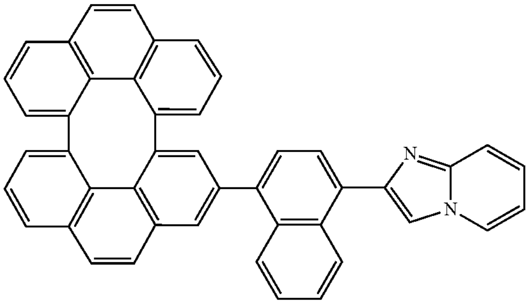
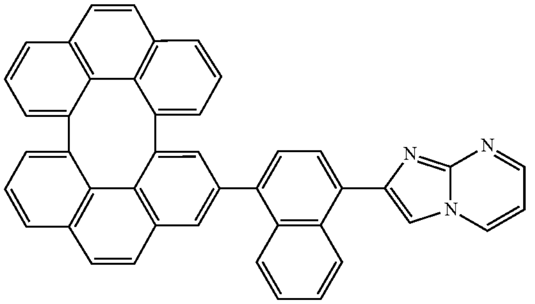
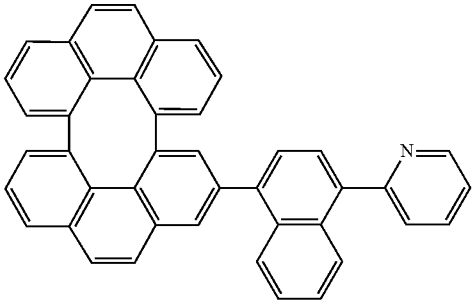
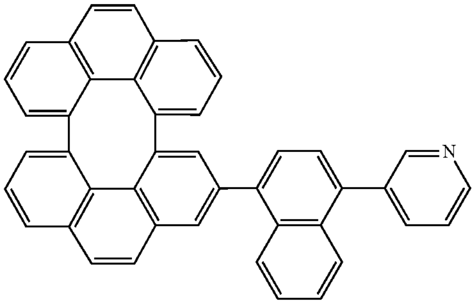
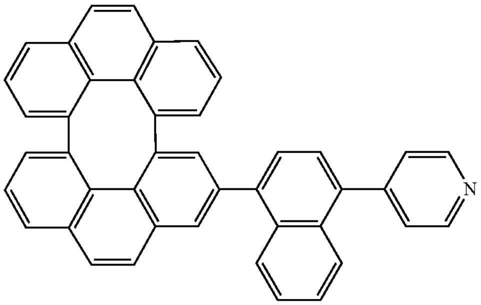
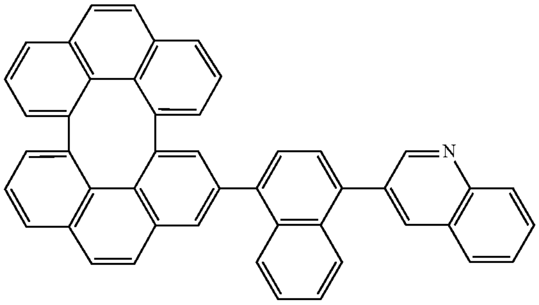
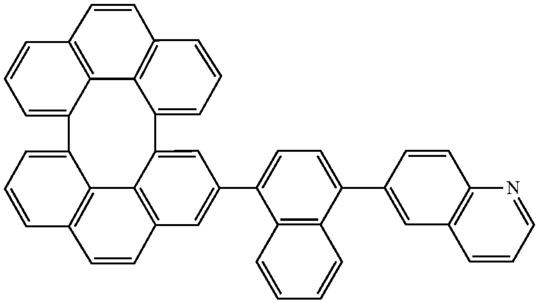
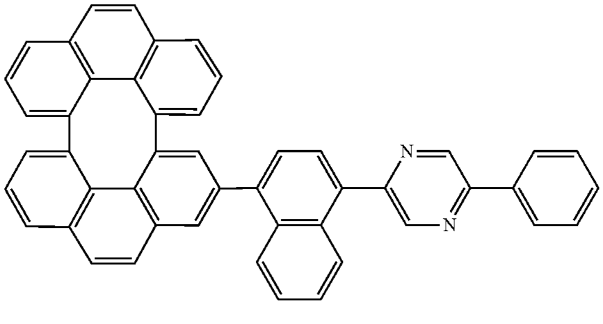
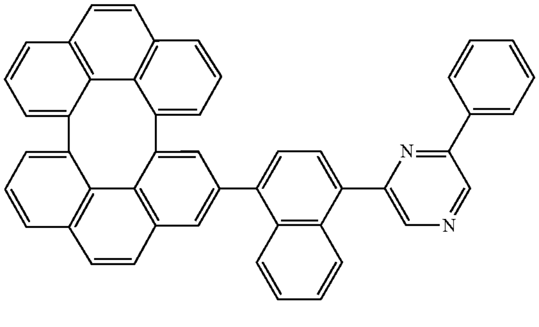

-continued
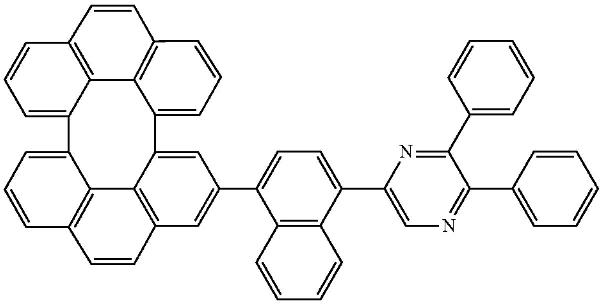
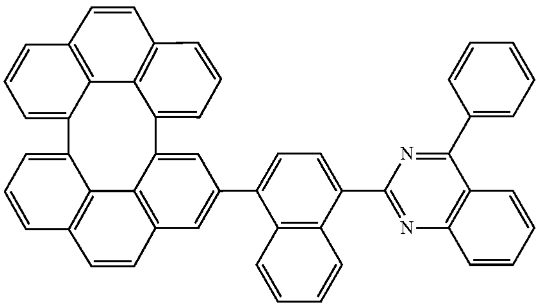
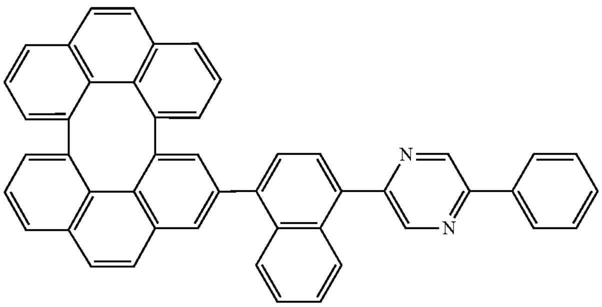
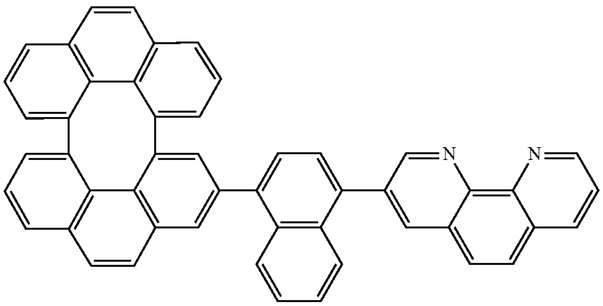
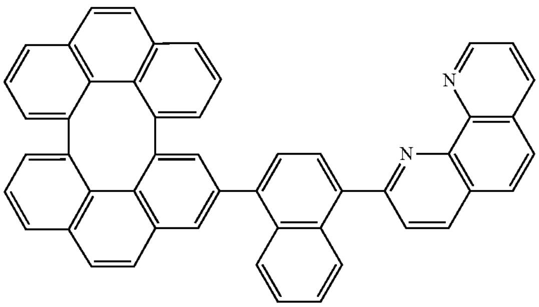
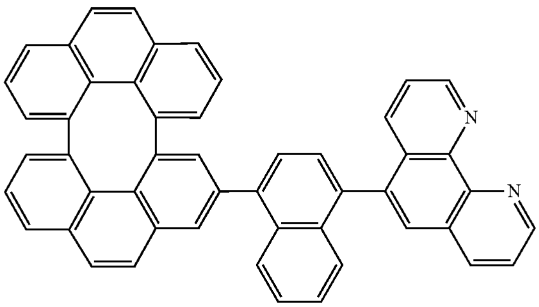
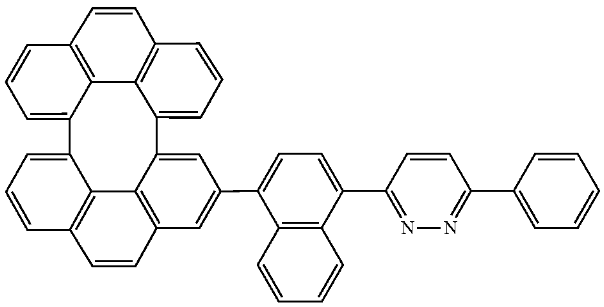

-continued
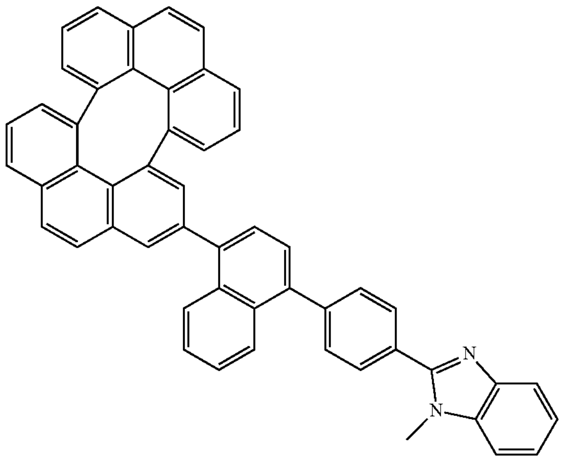
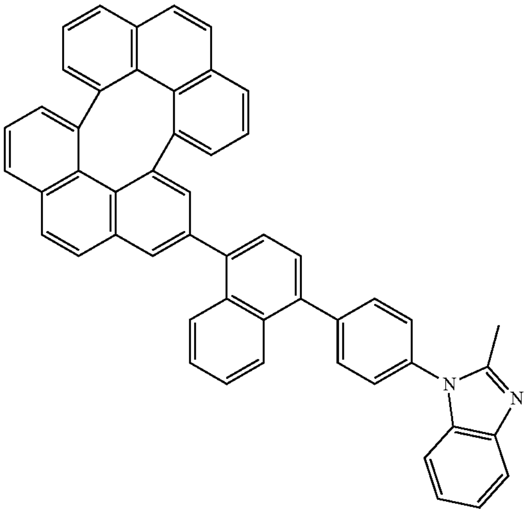
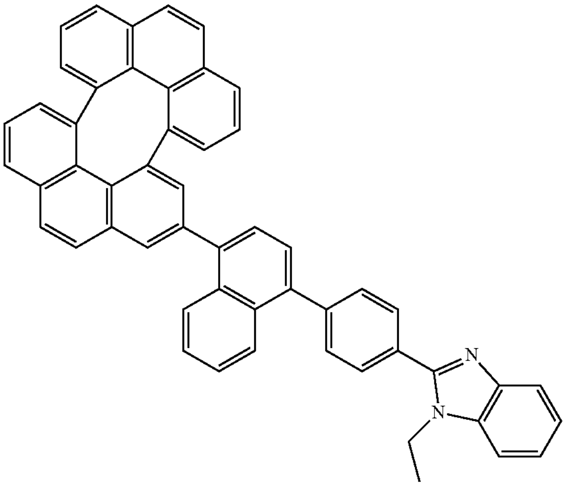
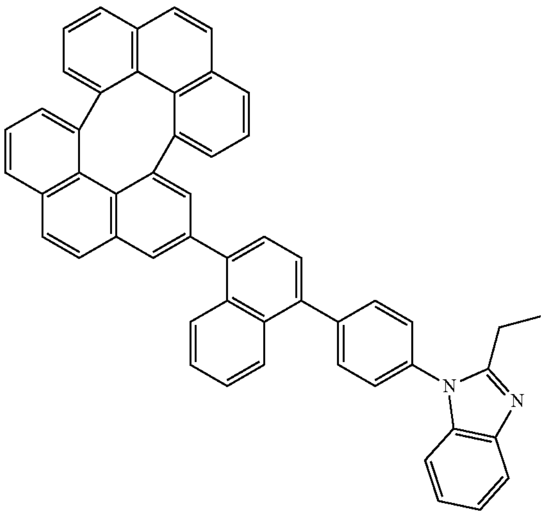
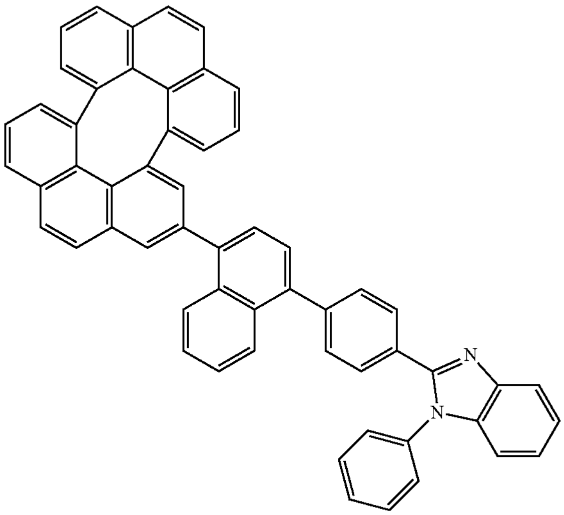
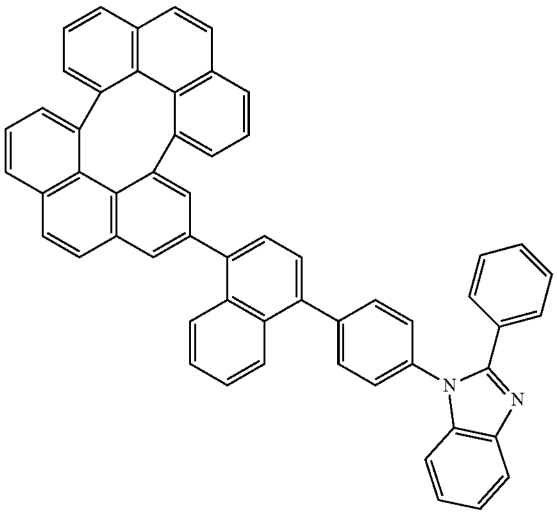

-continued
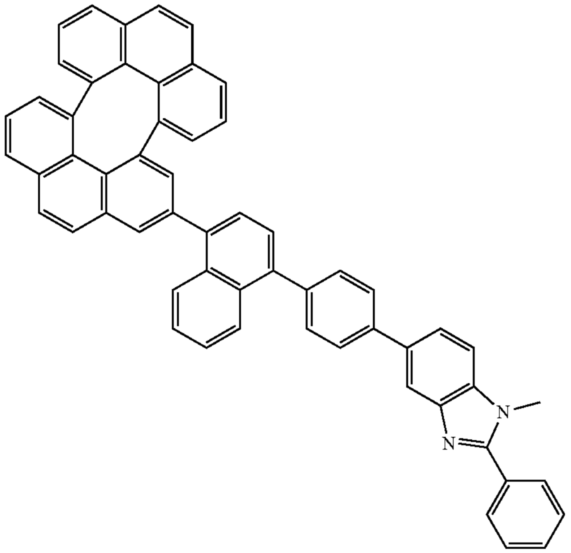
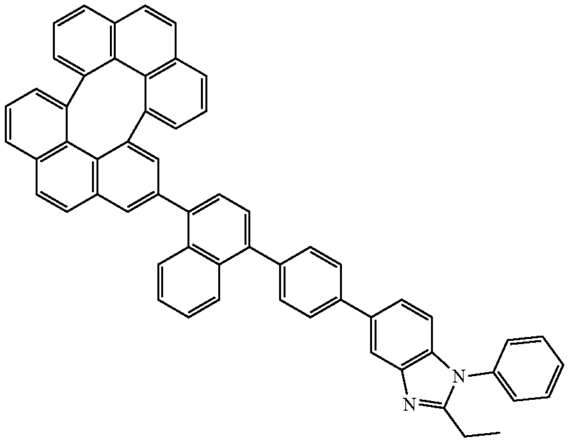
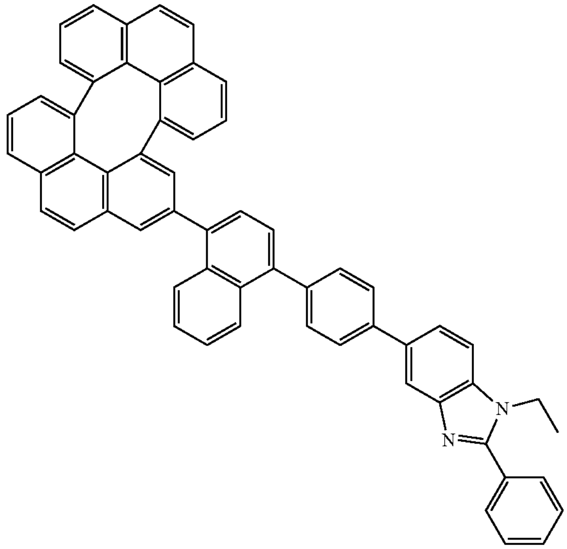
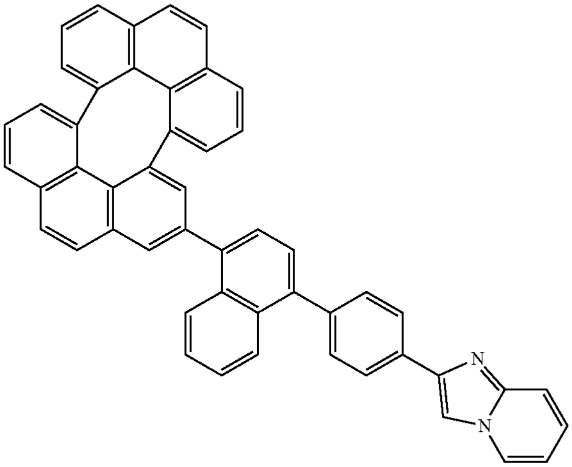
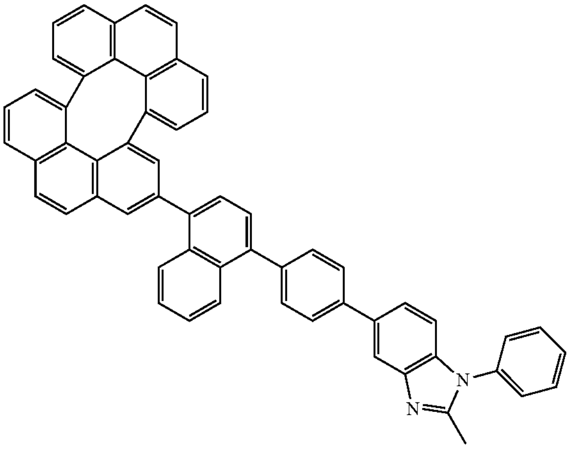
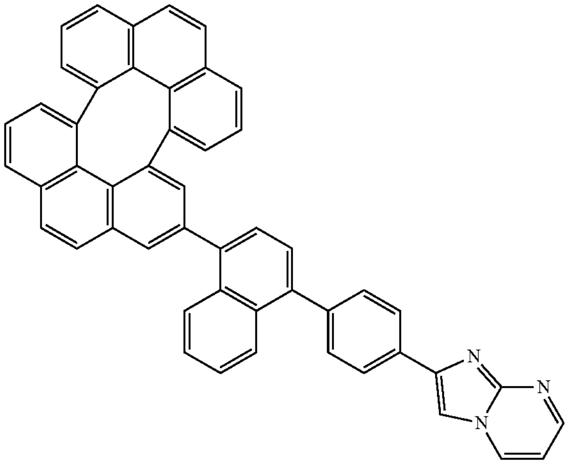
-continued -continued
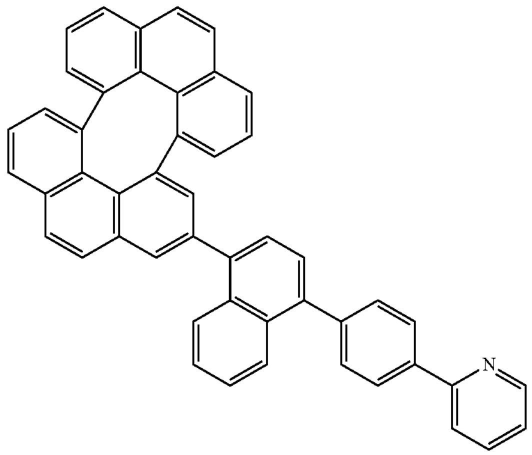
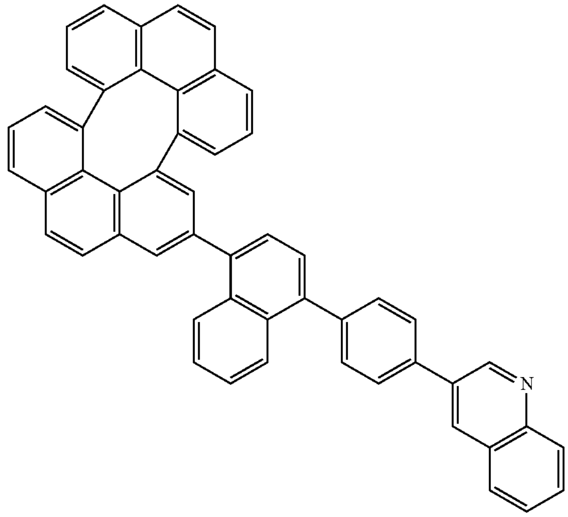
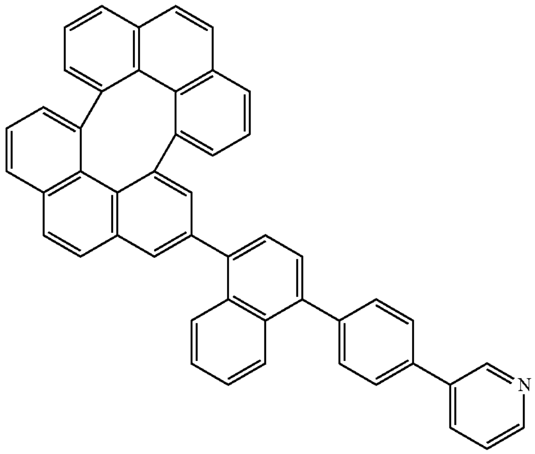
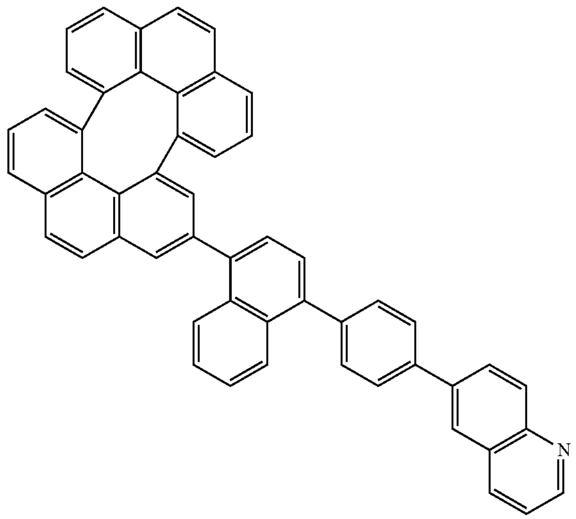
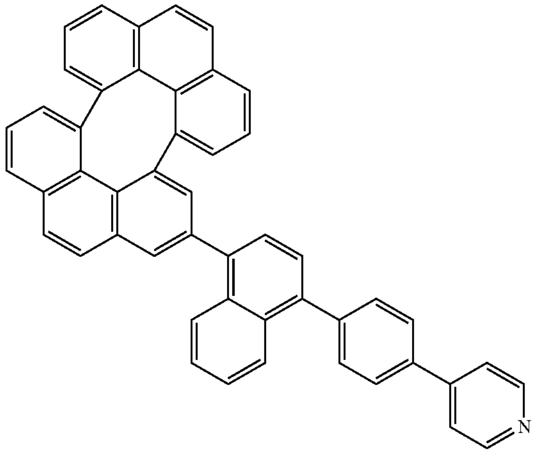
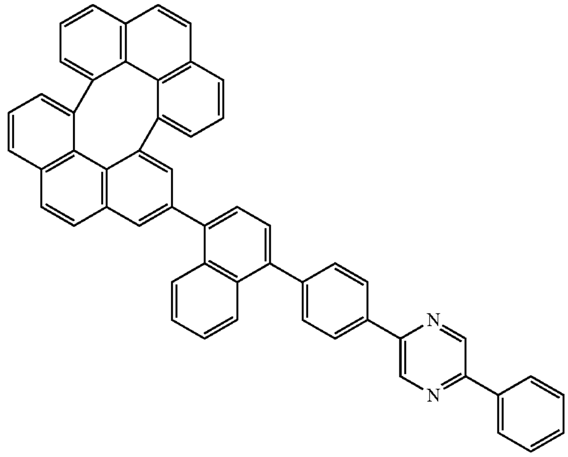

-continued
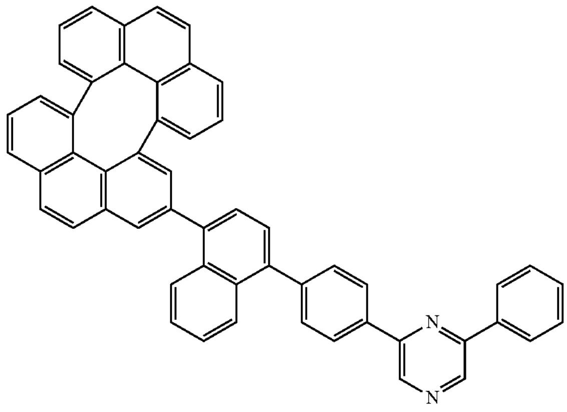
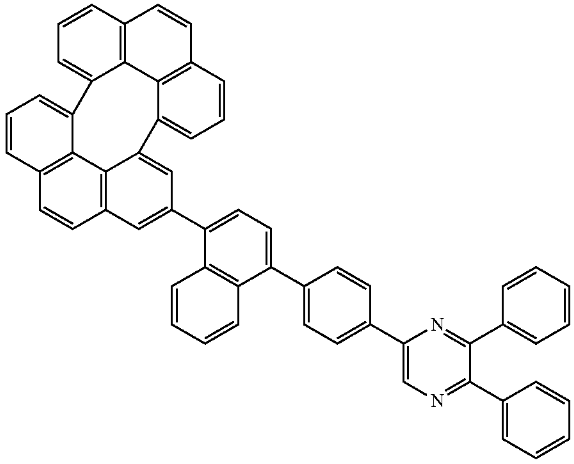
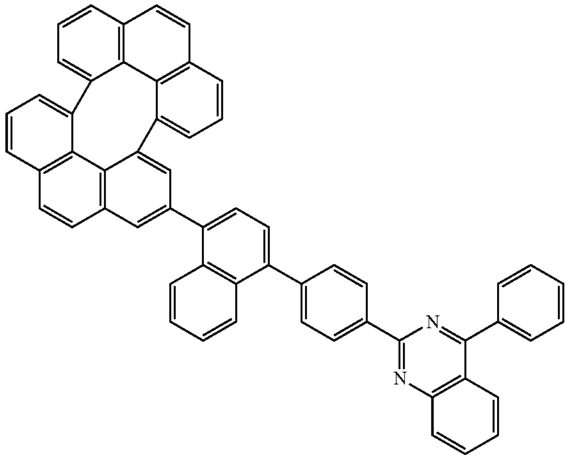
-continued
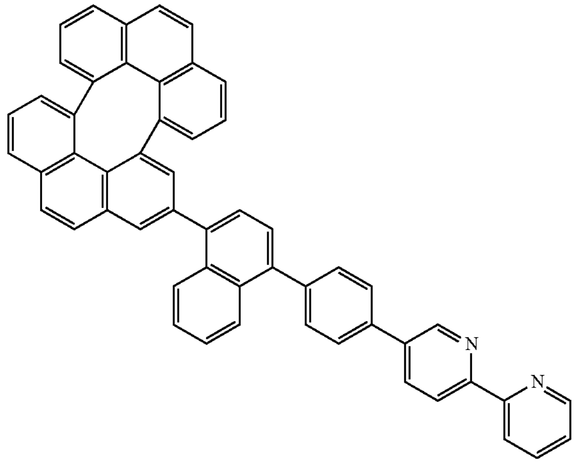
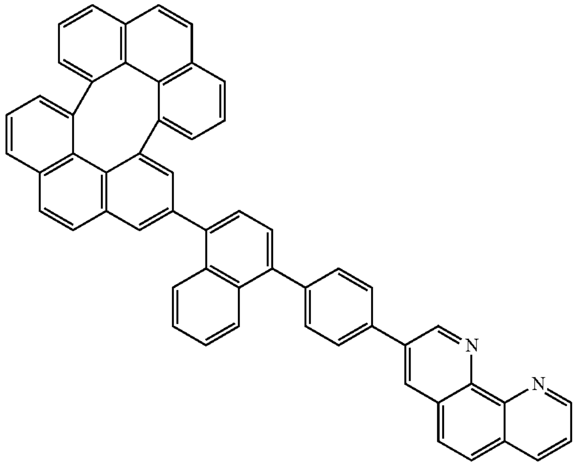
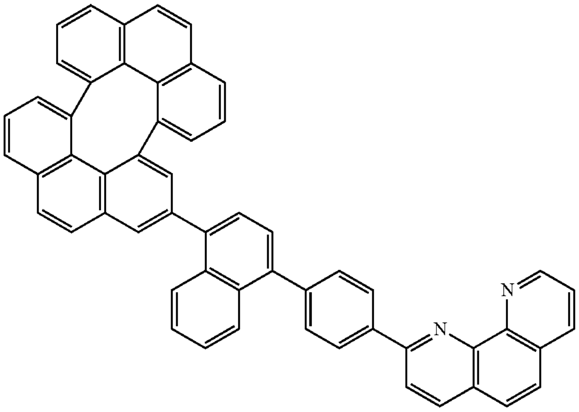

-continued
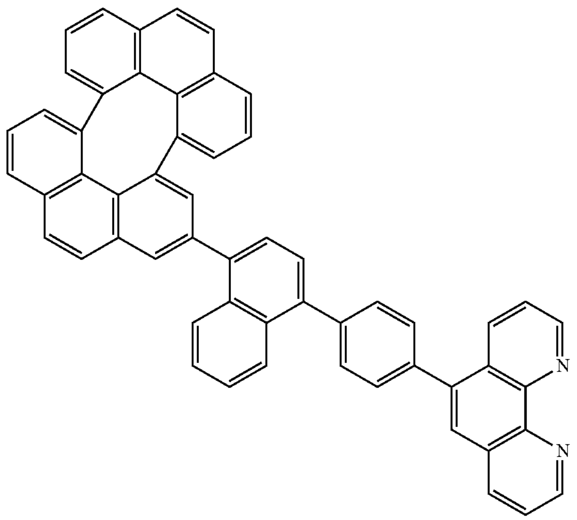
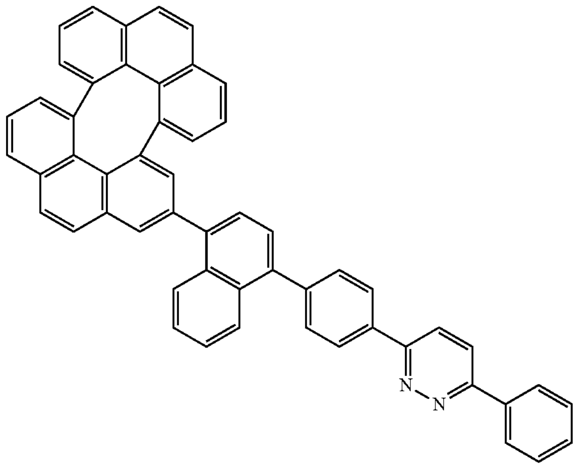
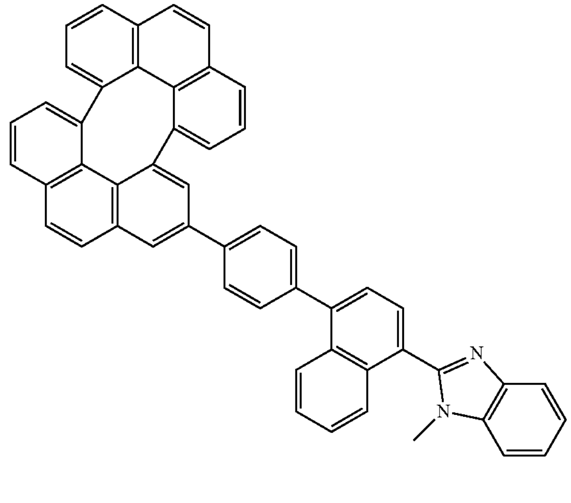
-continued
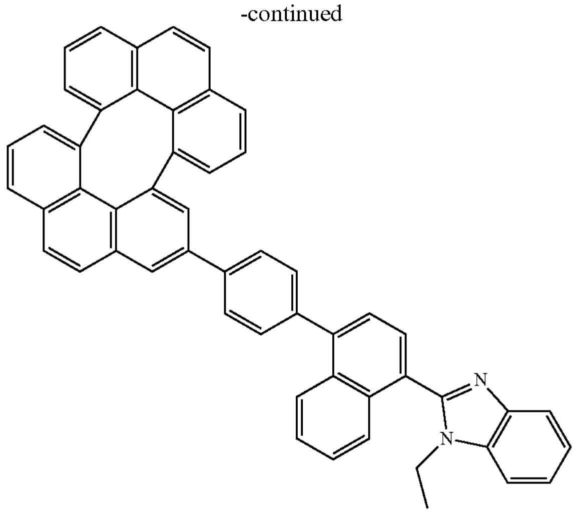
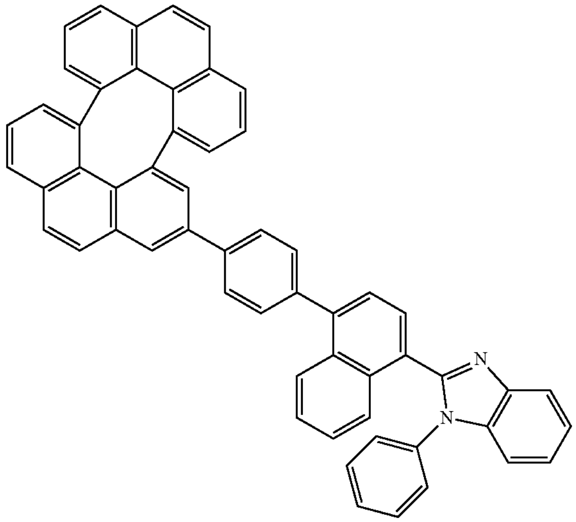
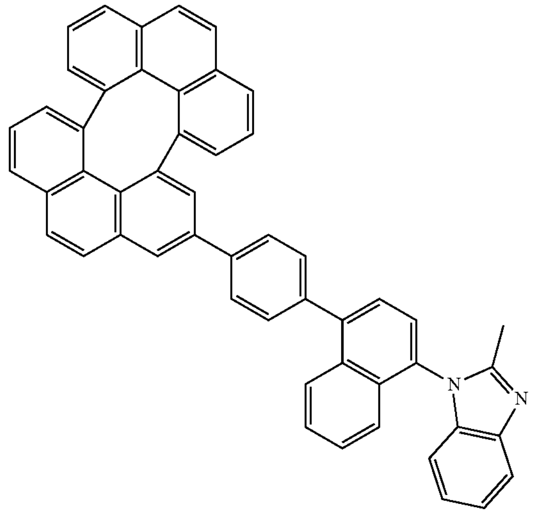

-continued
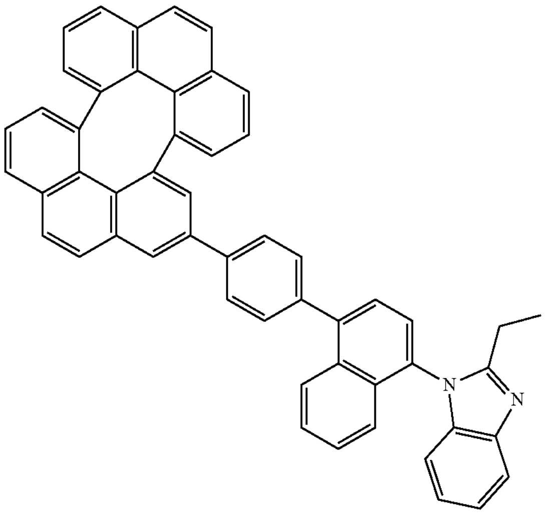
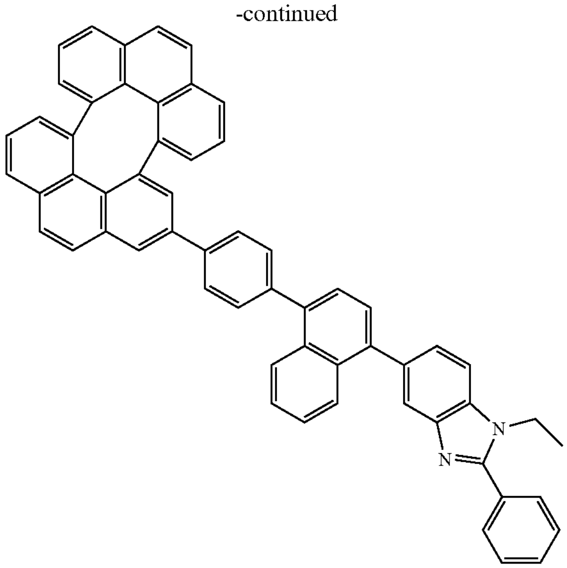
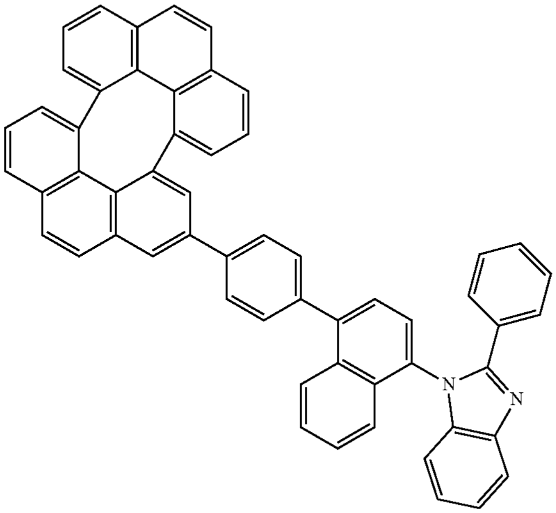
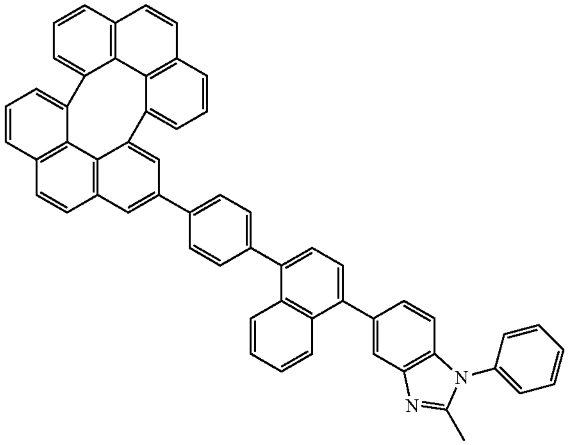
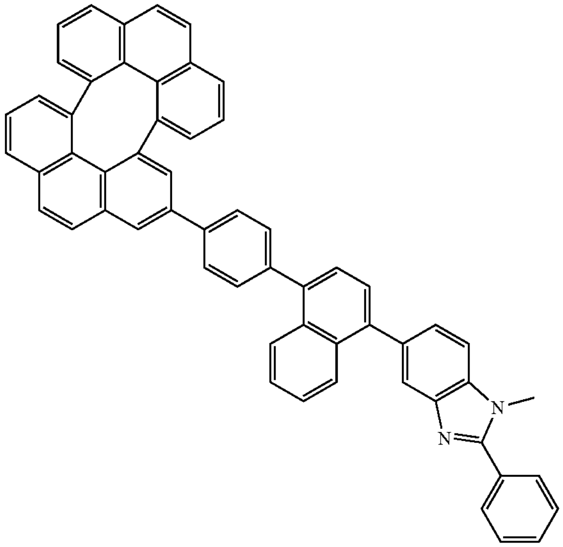
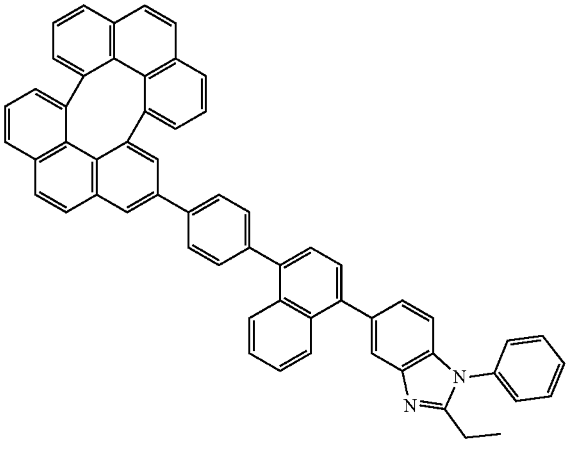

-continued
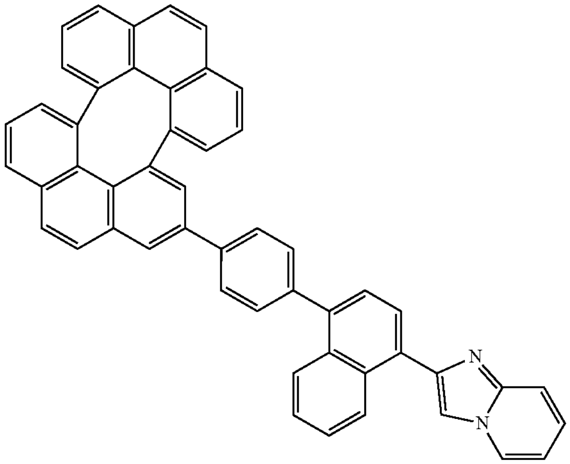
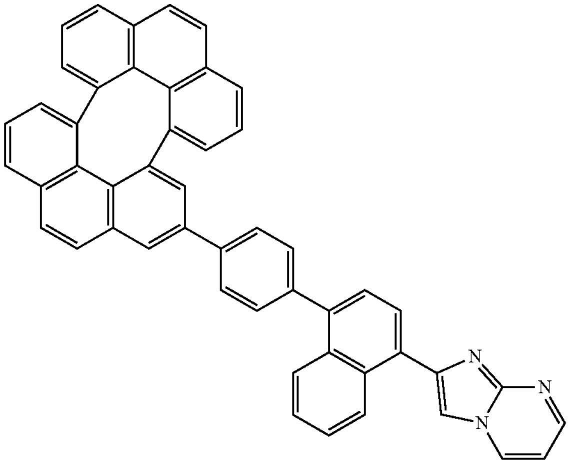
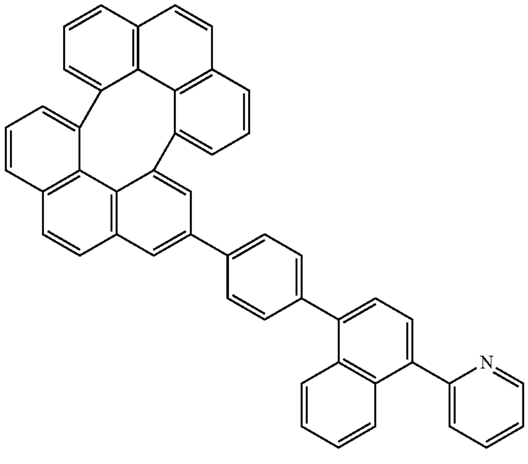
-continued
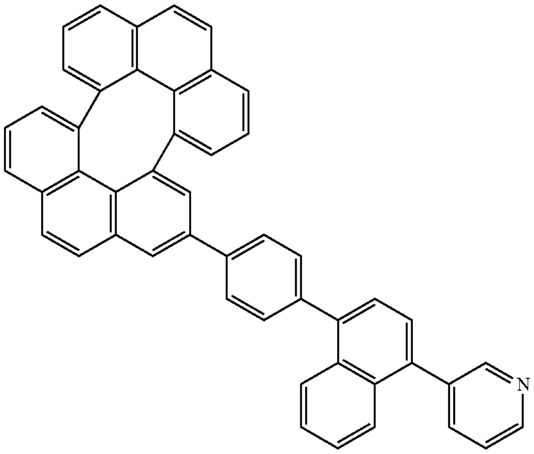
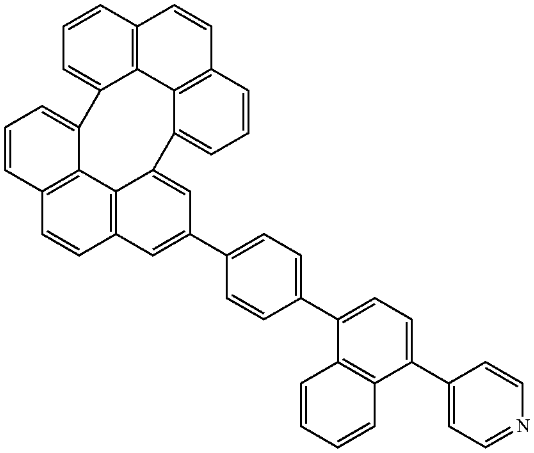
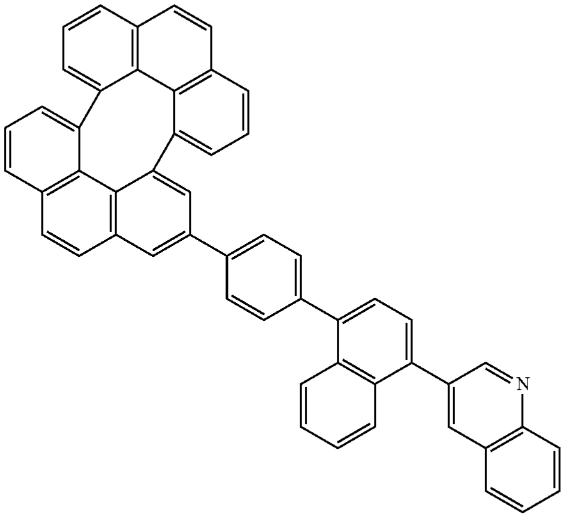

-continued
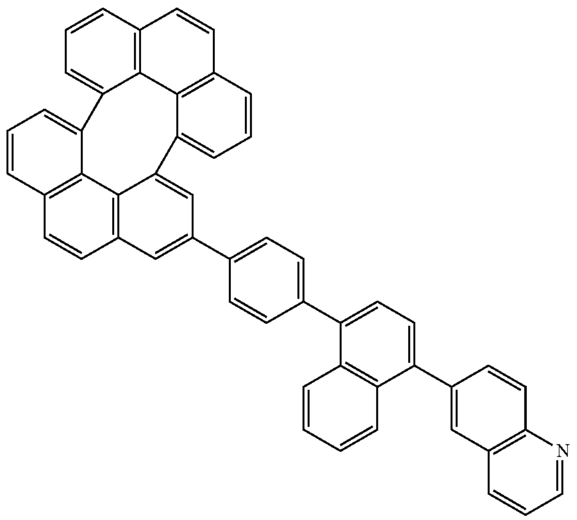
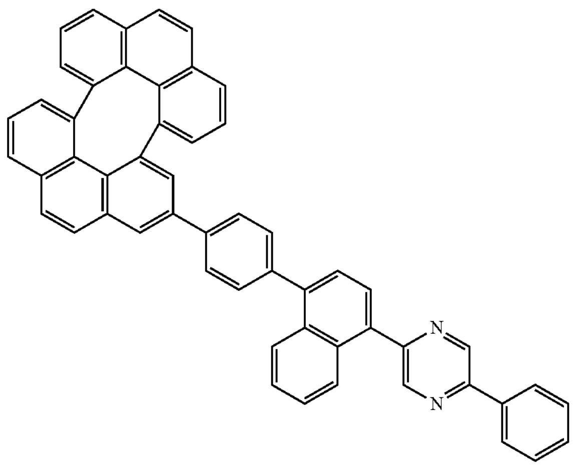
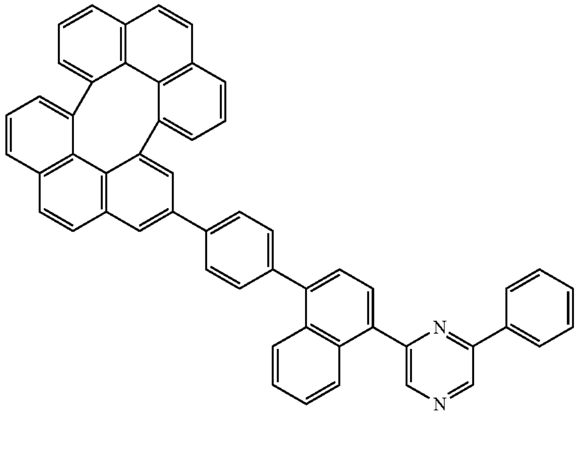
-continued
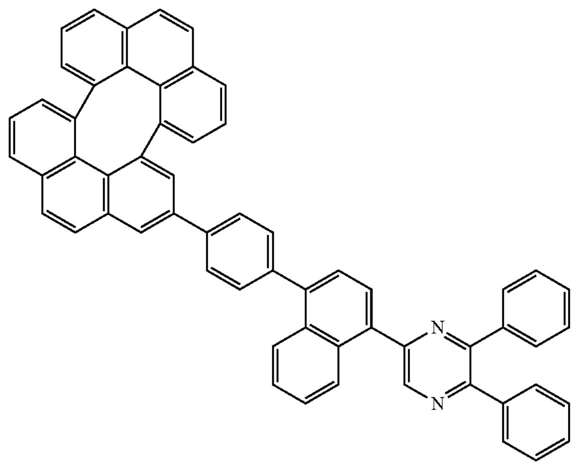
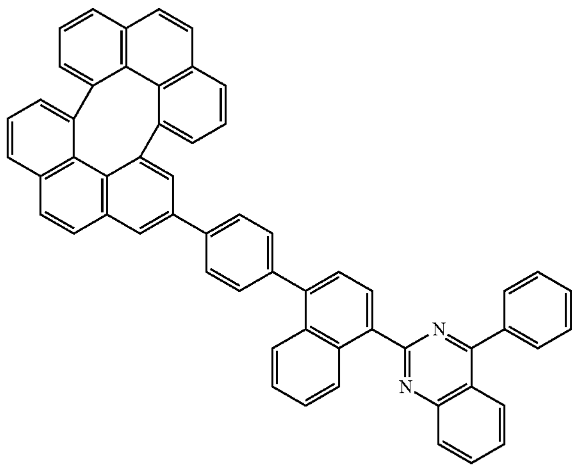
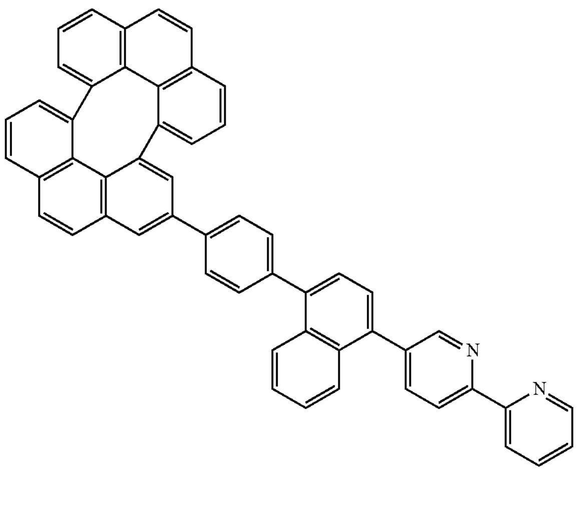

-continued
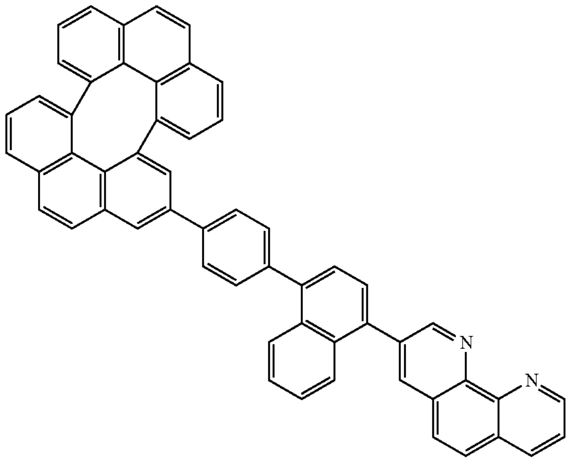
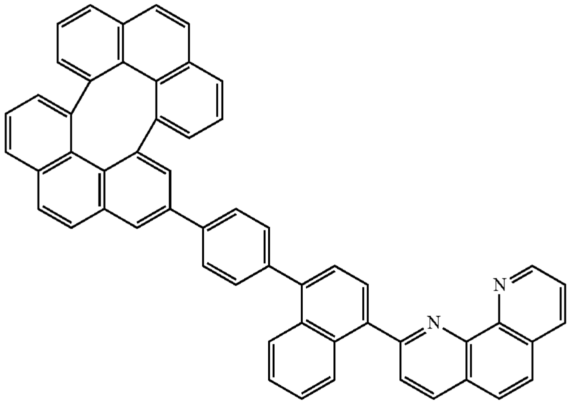
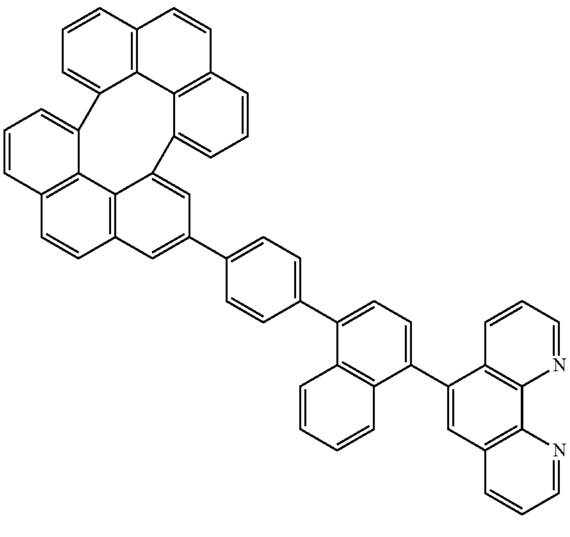
-continued
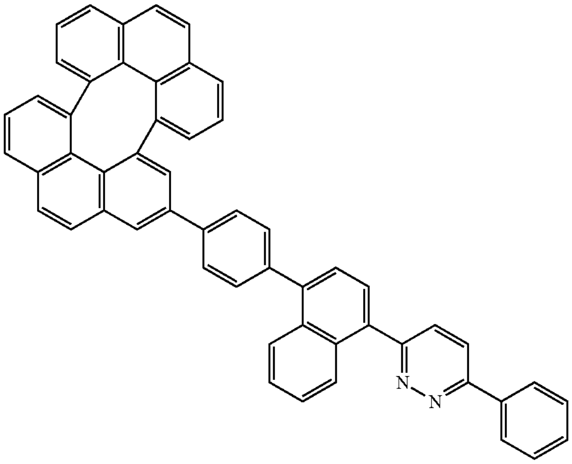
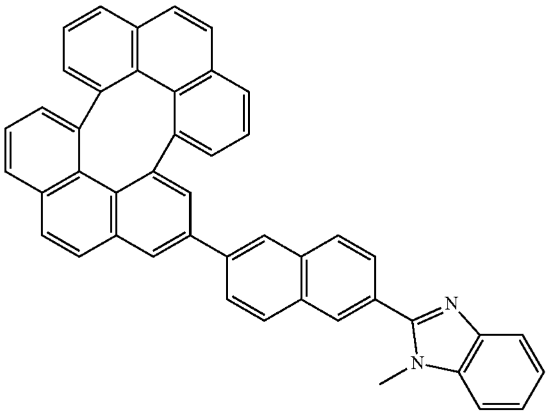
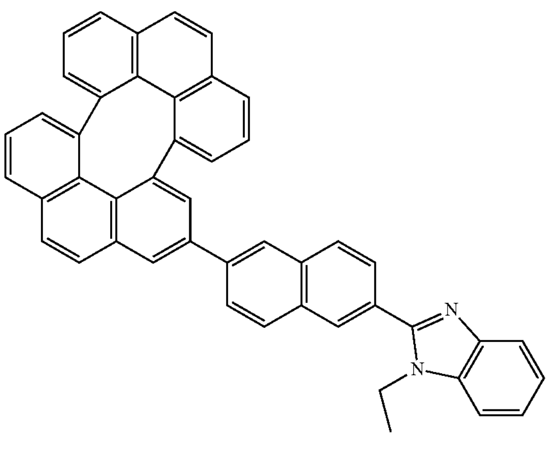

-continued
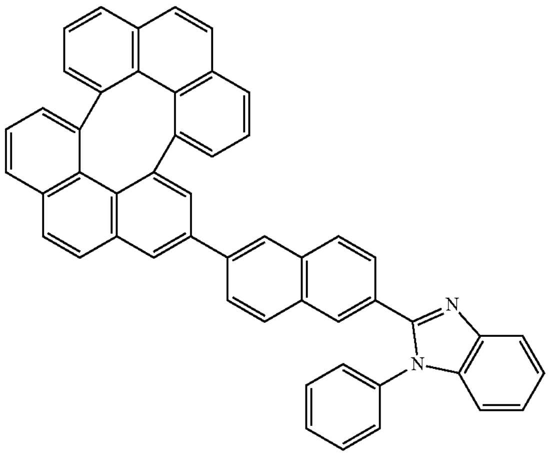
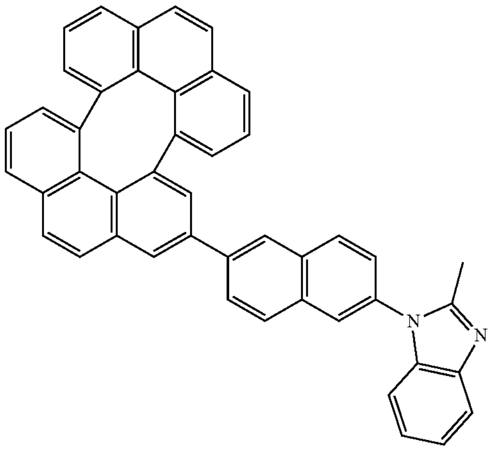
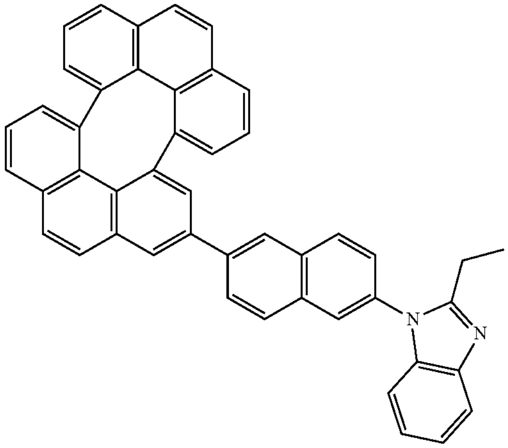
-continued
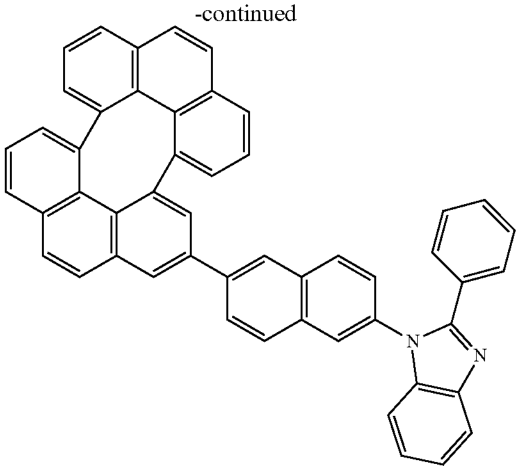
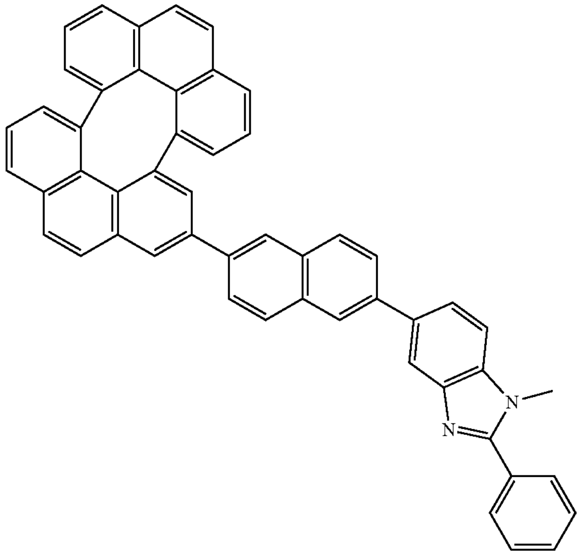
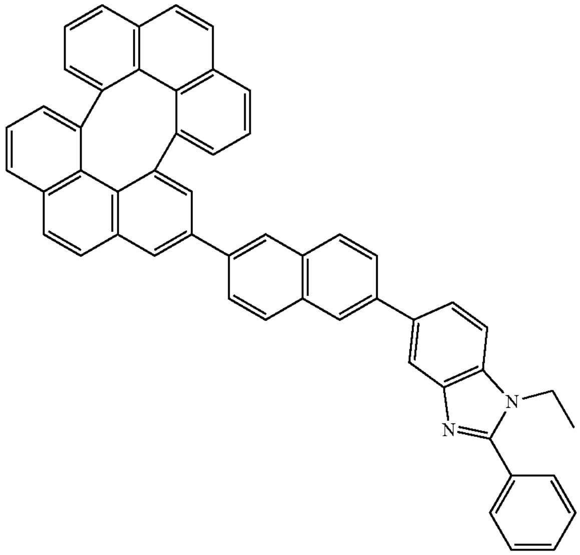

-continued
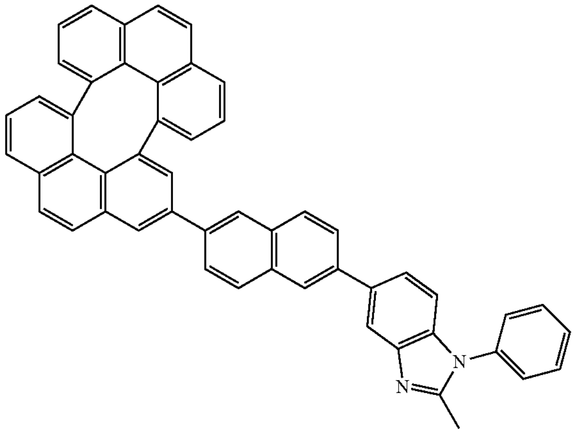
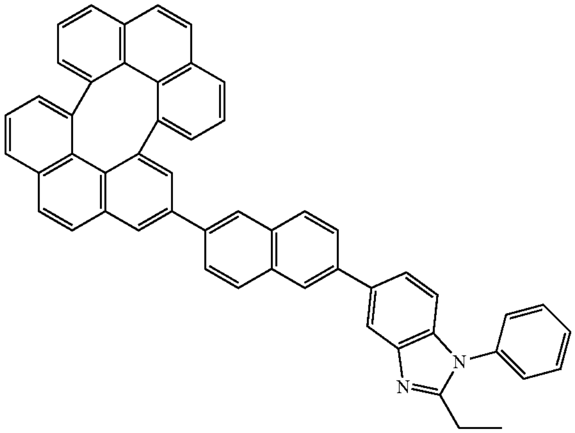
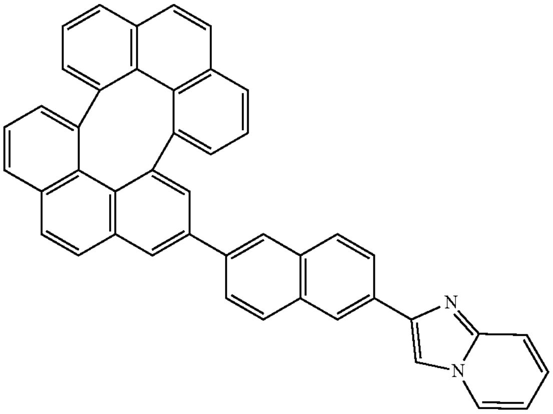
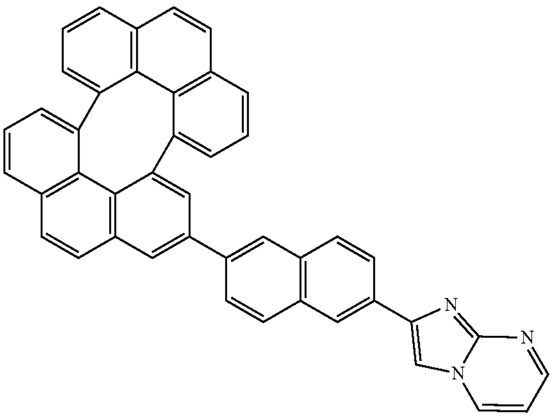
-continued
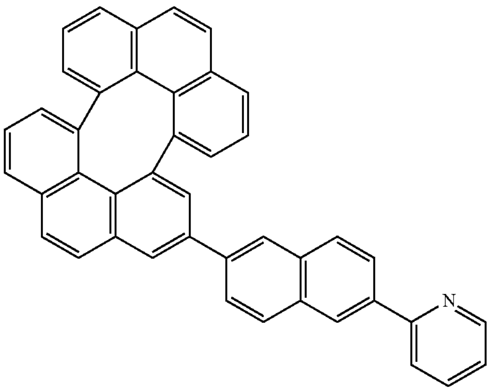
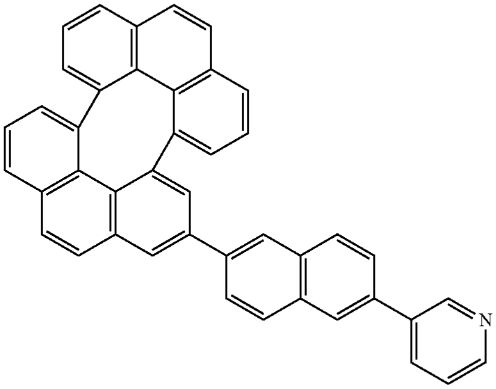
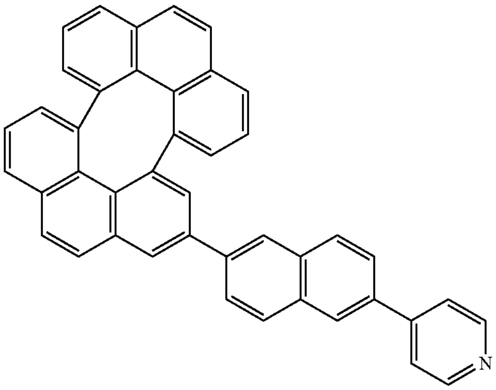
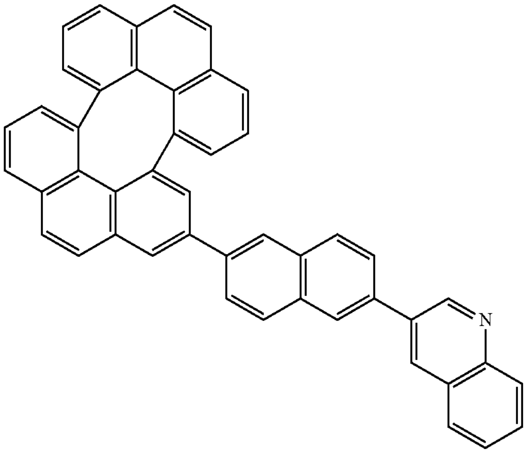

-continued
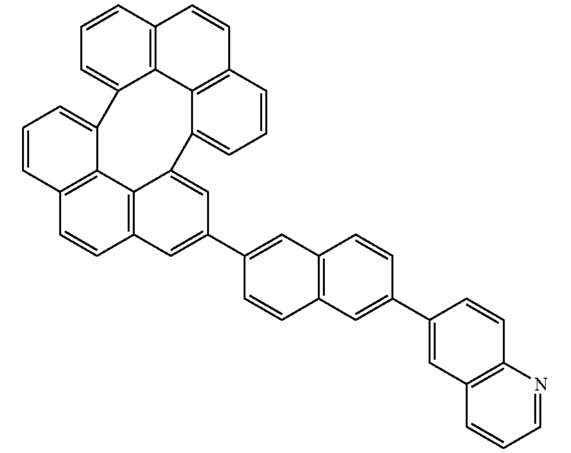
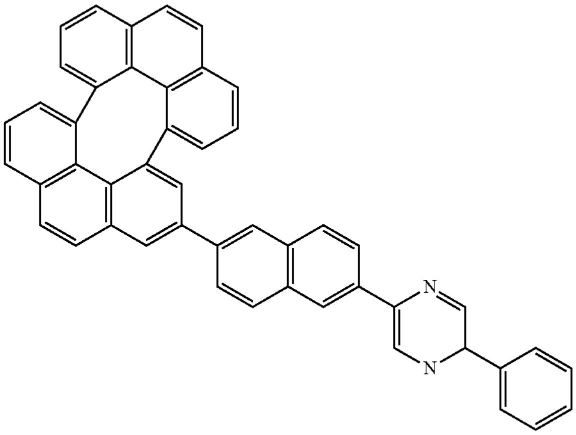
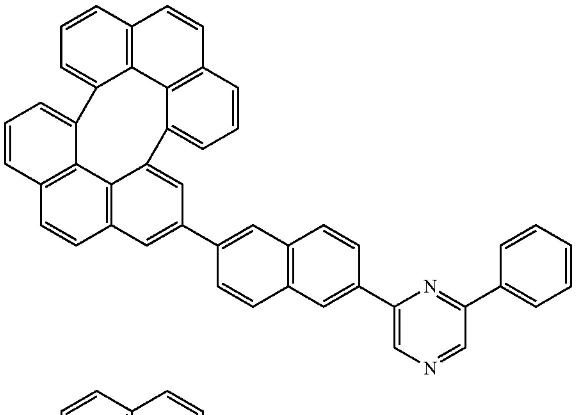
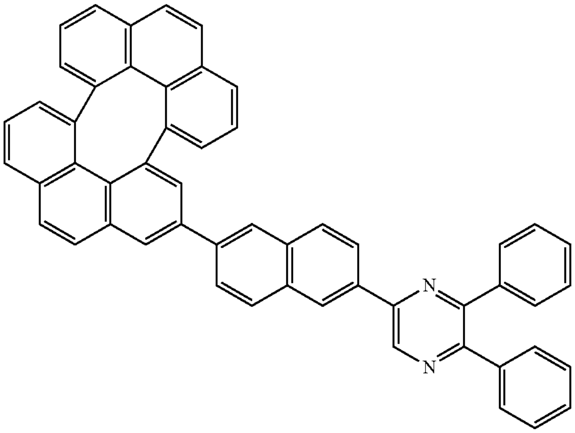
-continued
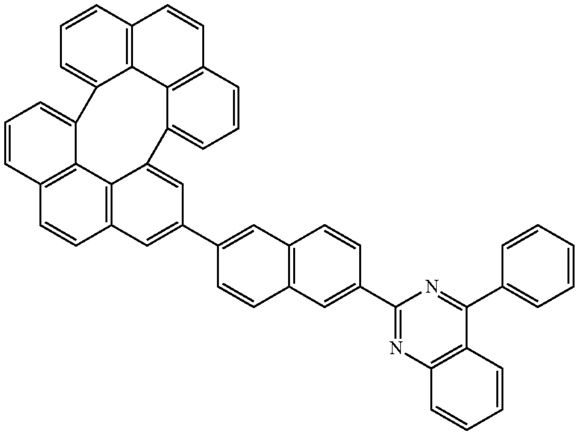
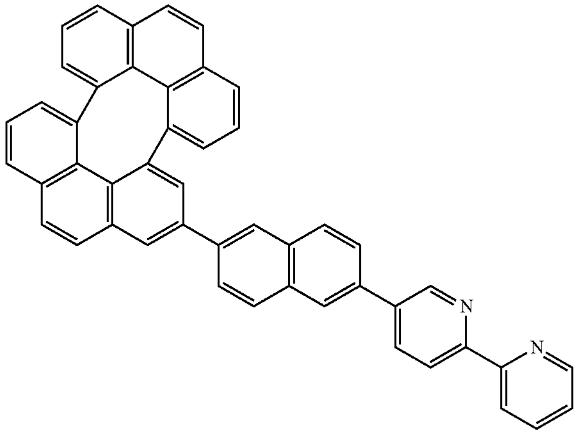
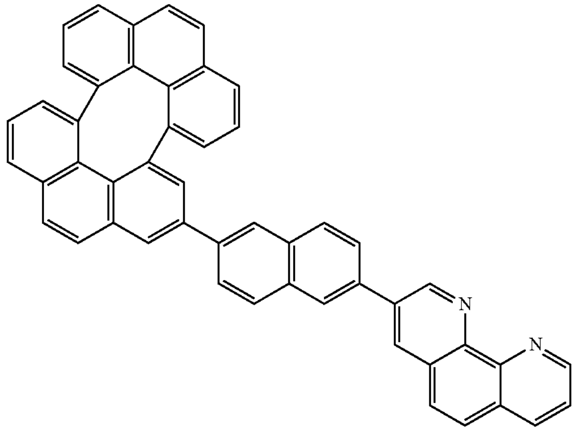
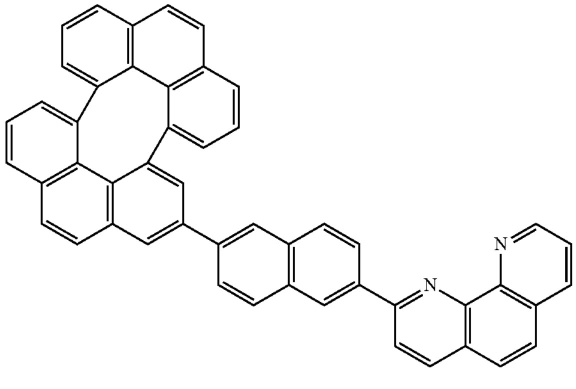

-continued
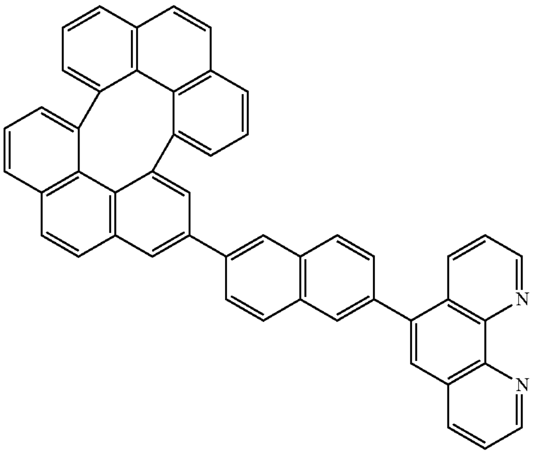
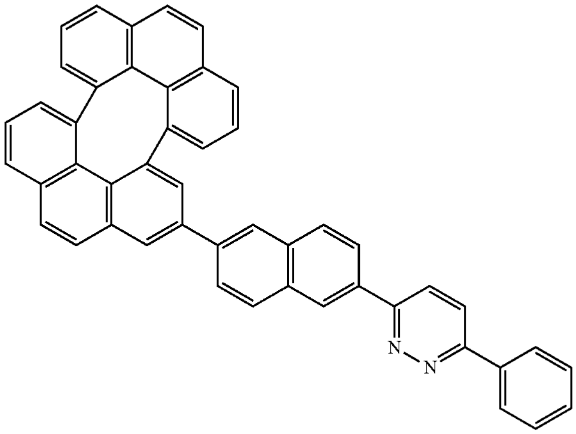
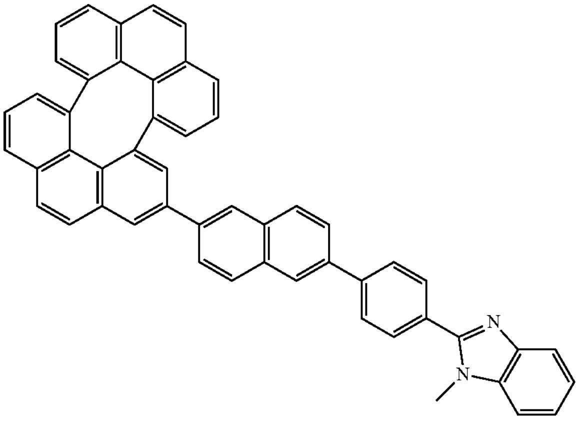
-continued
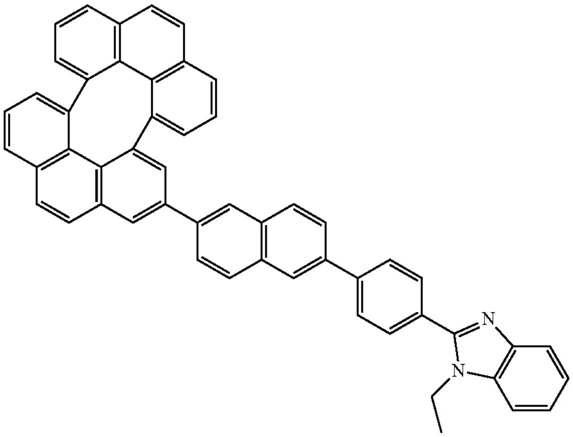
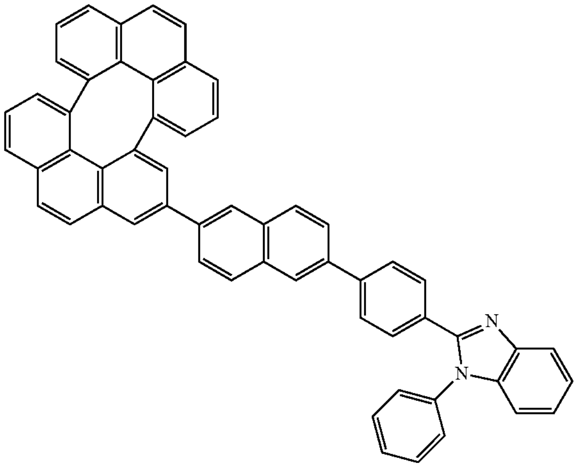
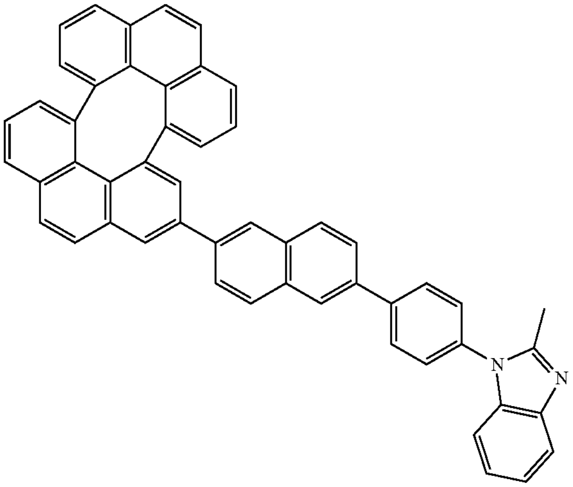

-continued
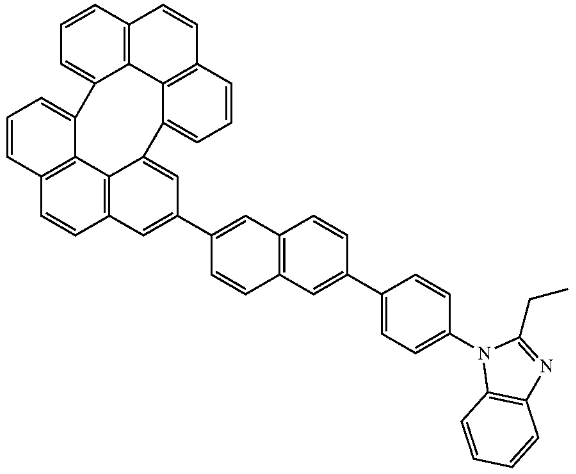
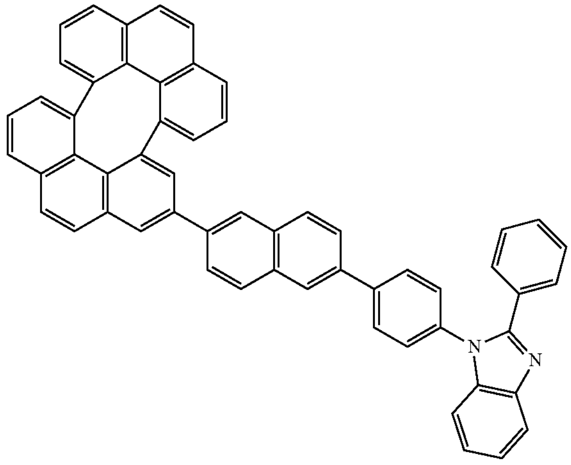
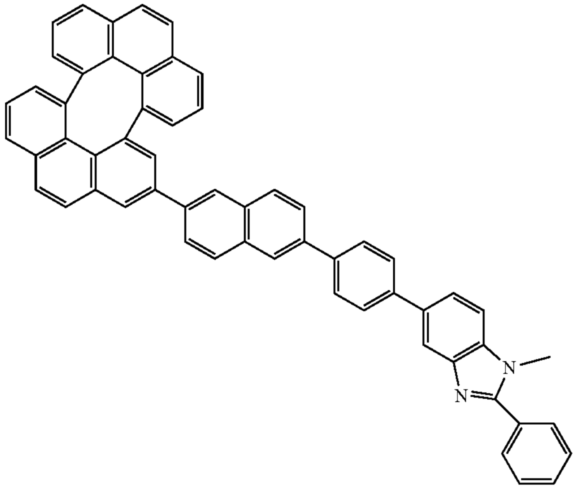
-continued
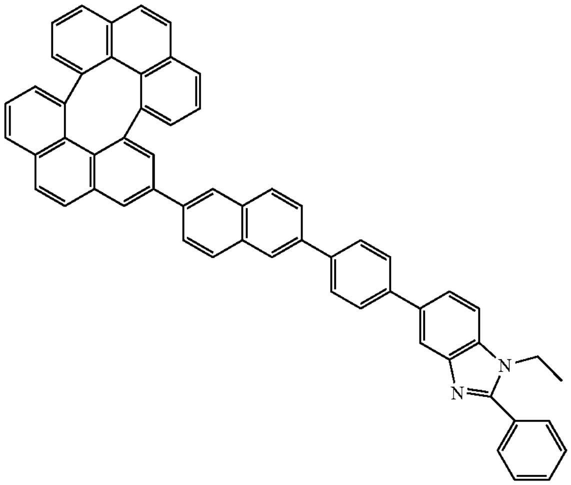
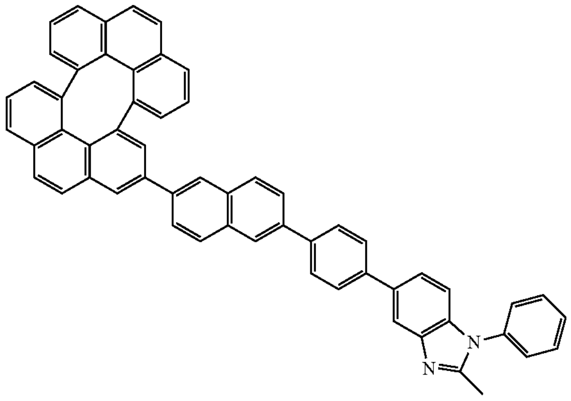
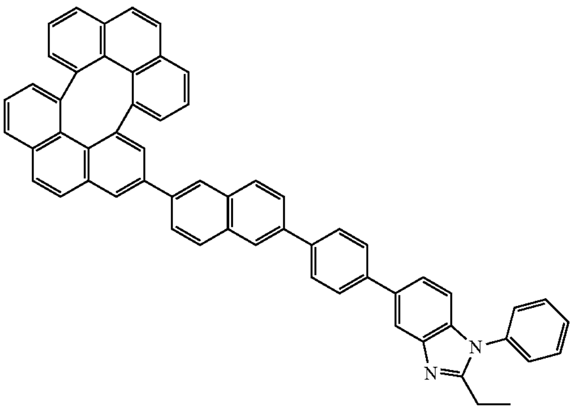
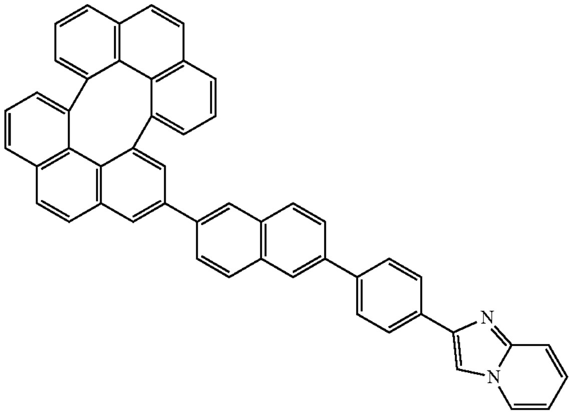

-continued
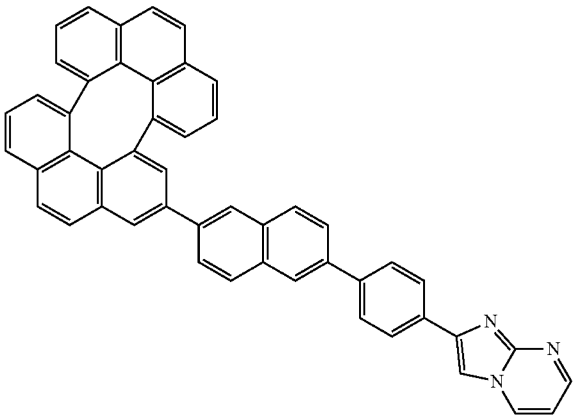
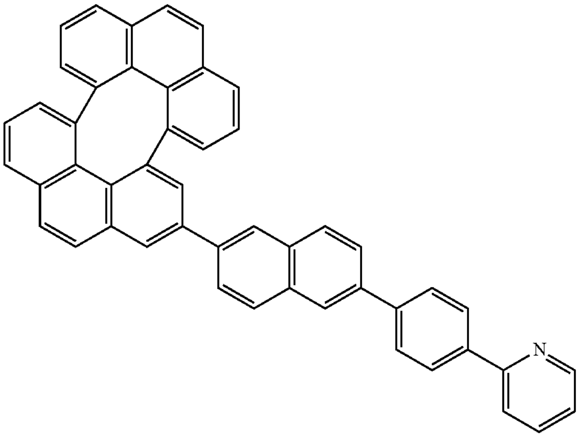
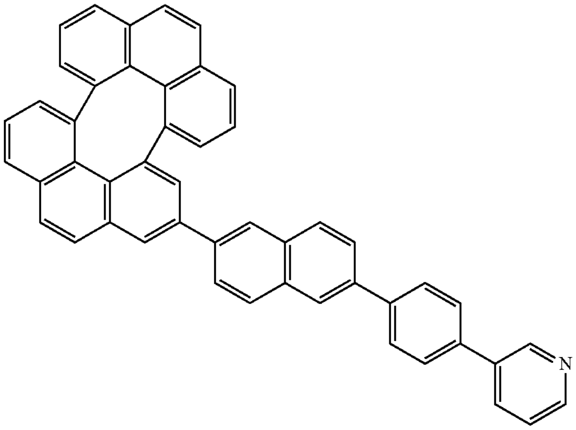
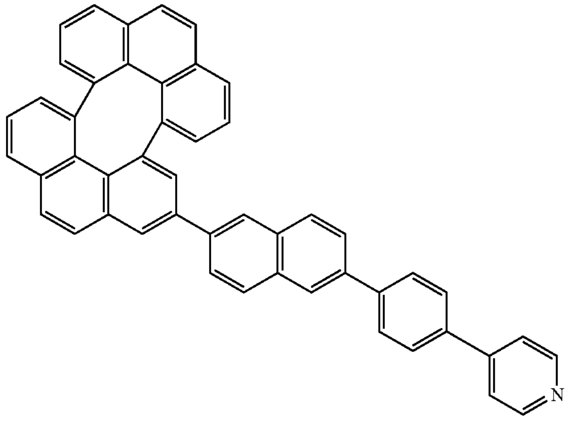
-continued
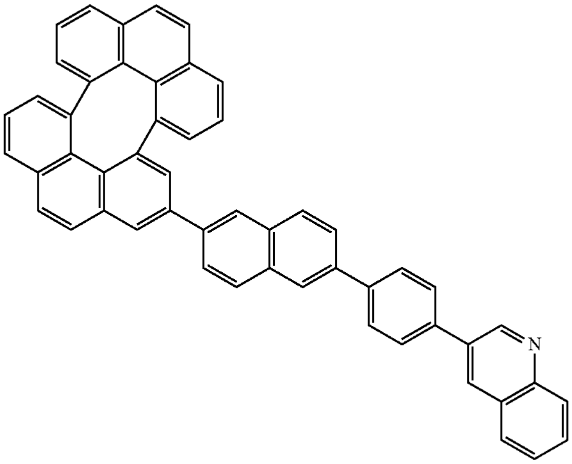
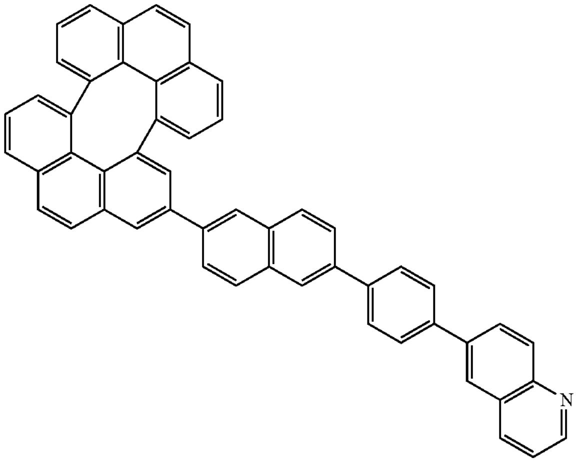
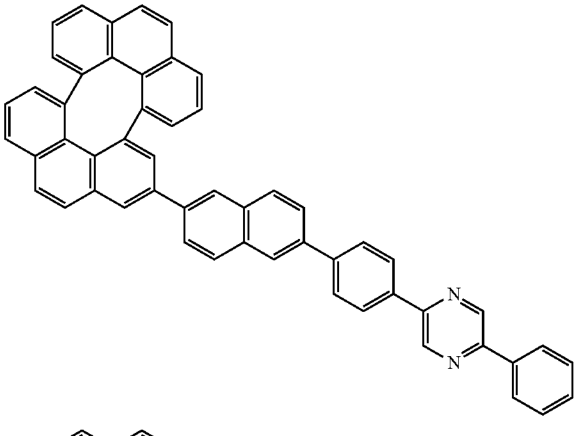
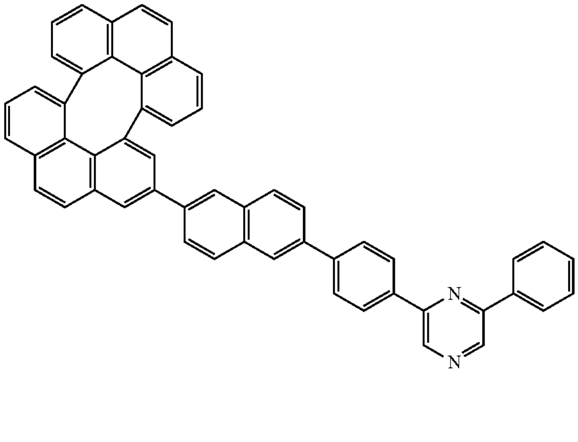

-continued
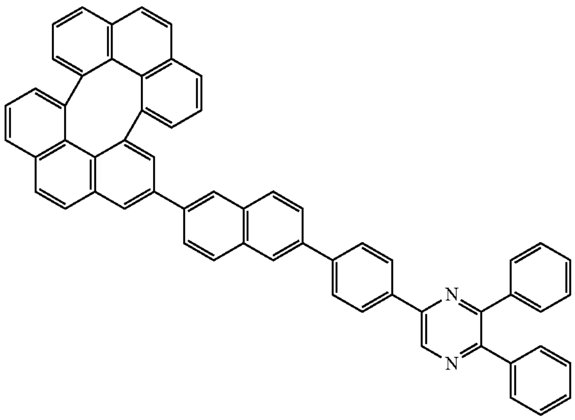
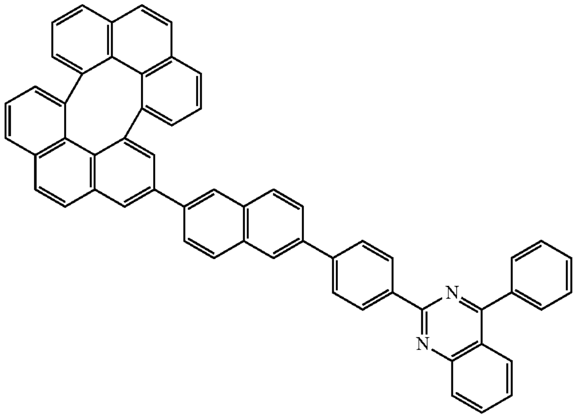
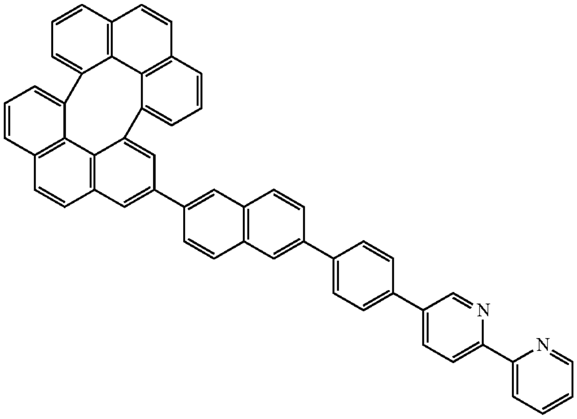
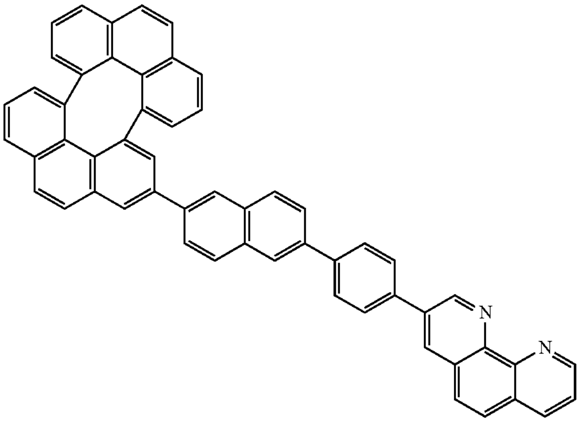
-continued
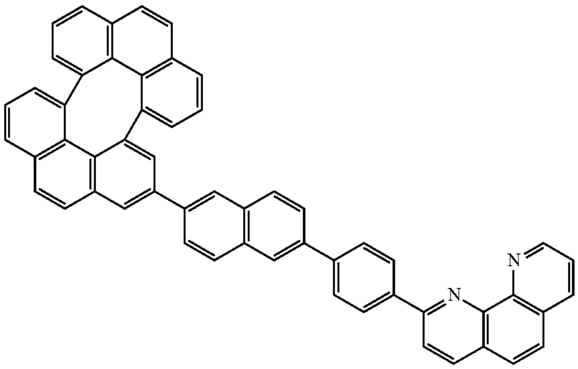
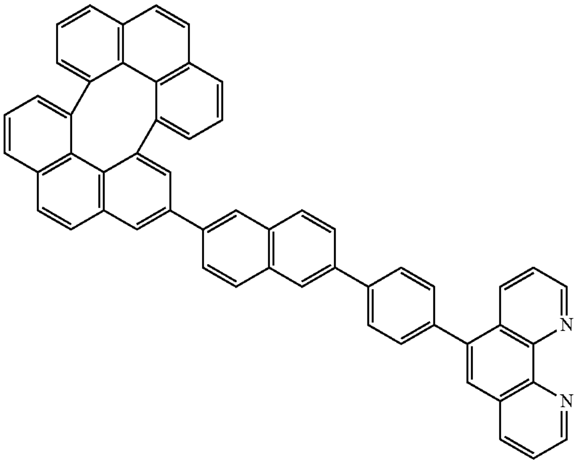
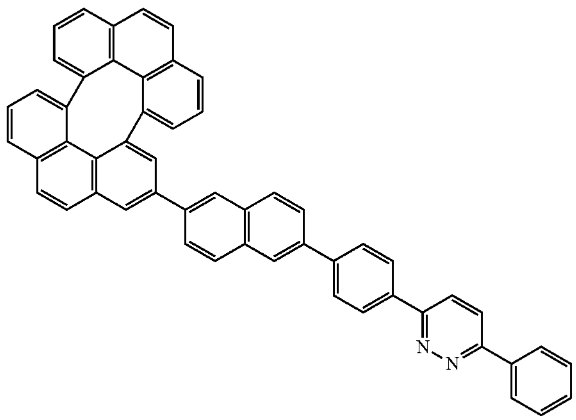
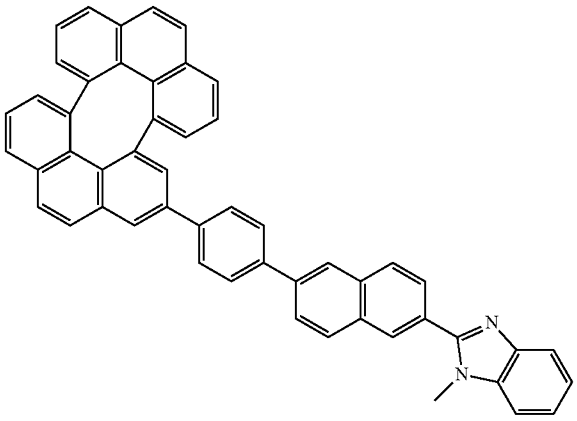

-continued
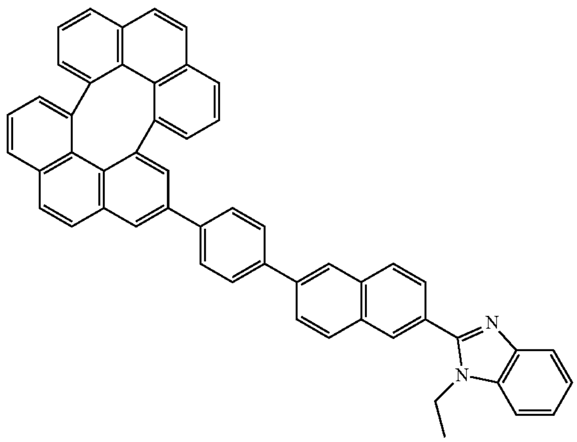
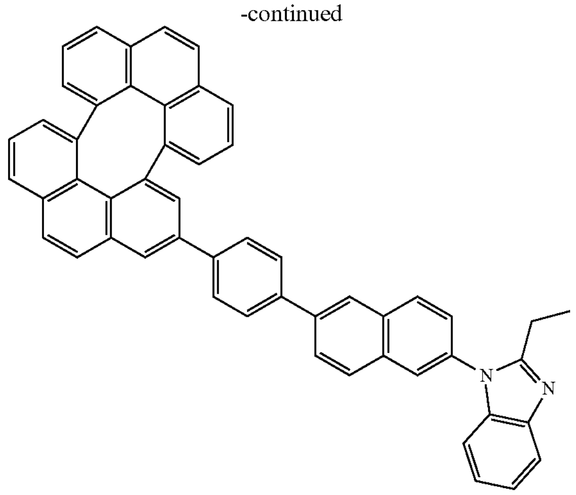
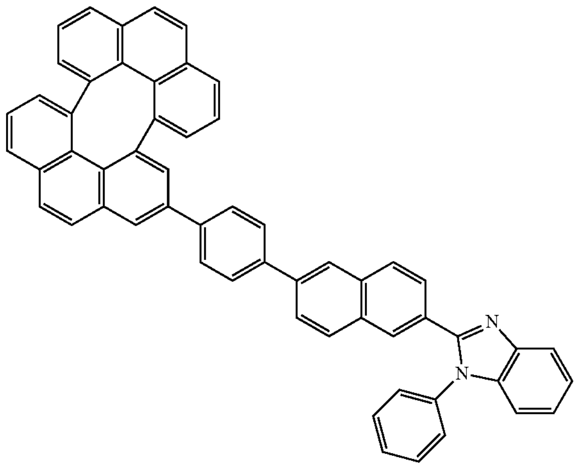
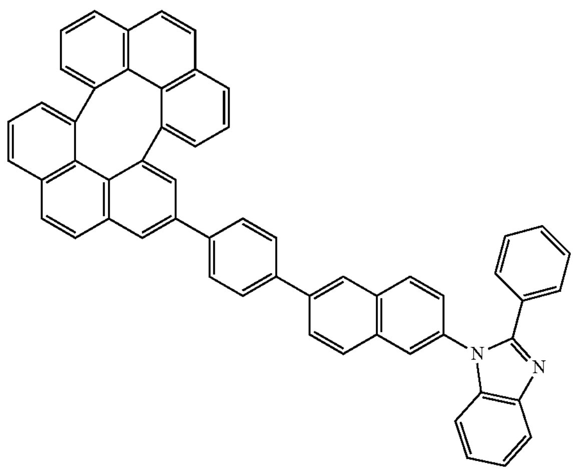
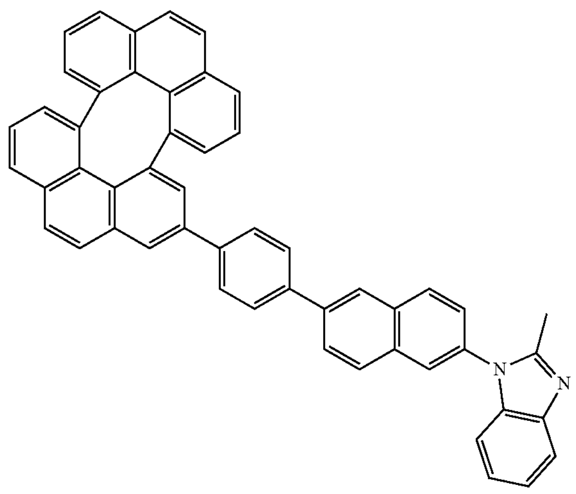
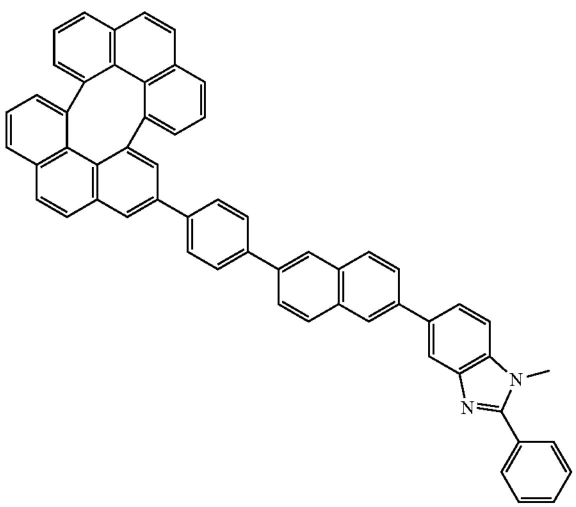

-continued
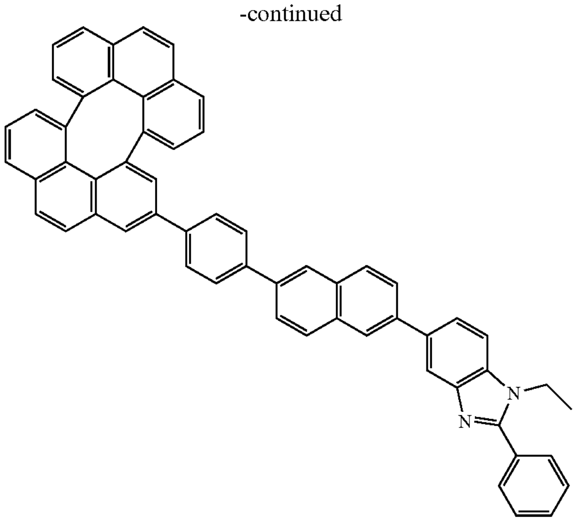
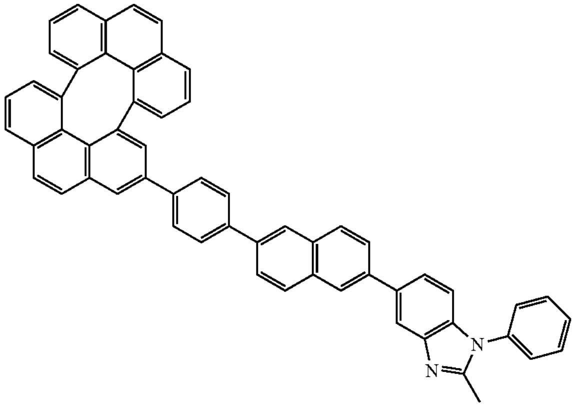
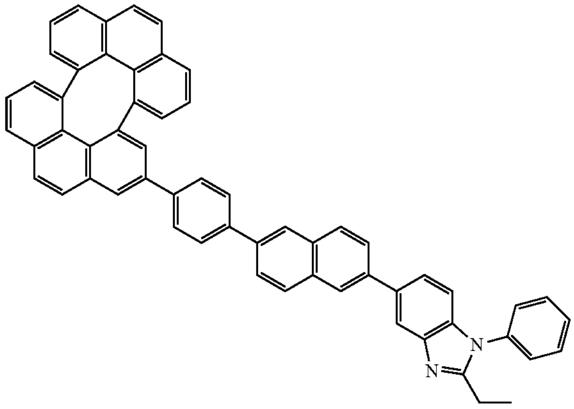
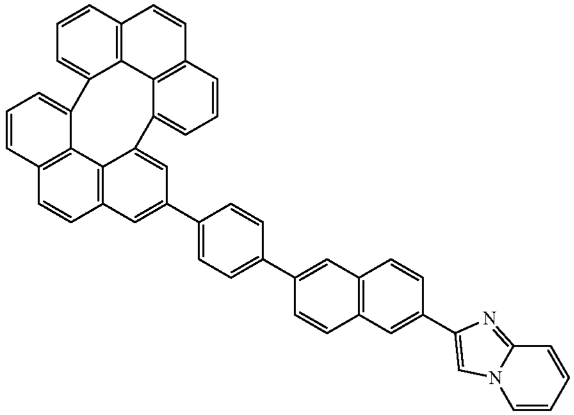
-continued
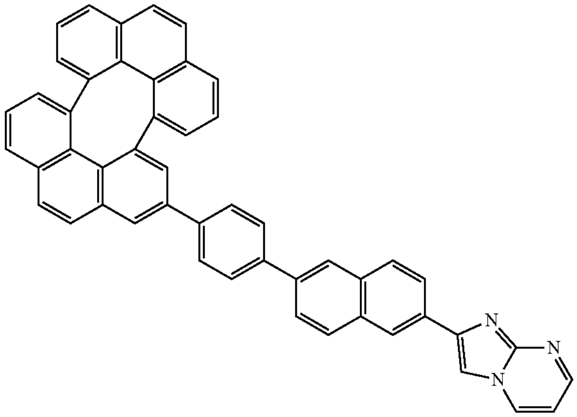
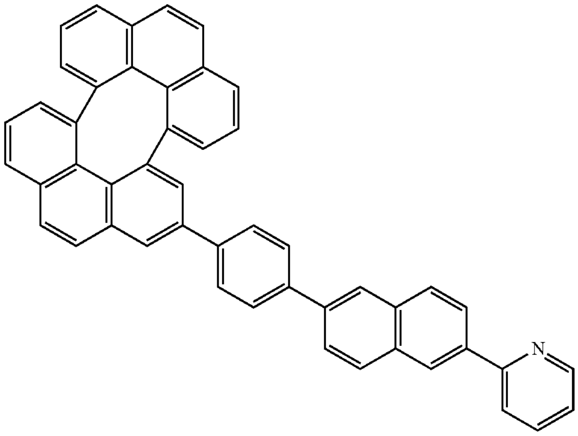
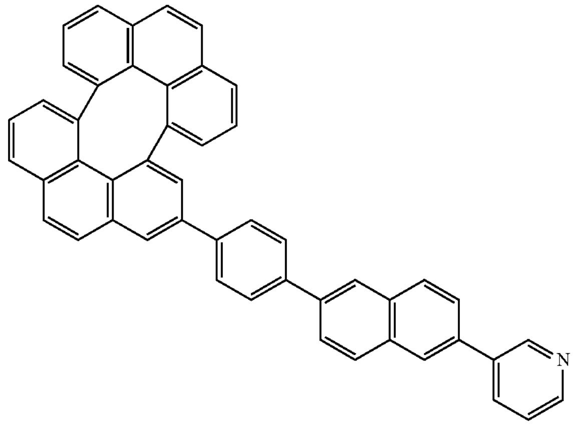
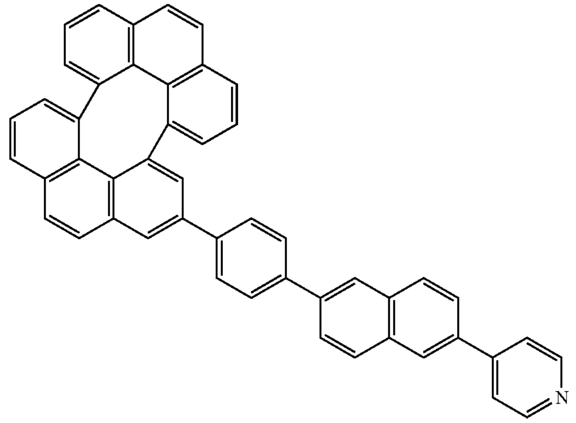

-continued
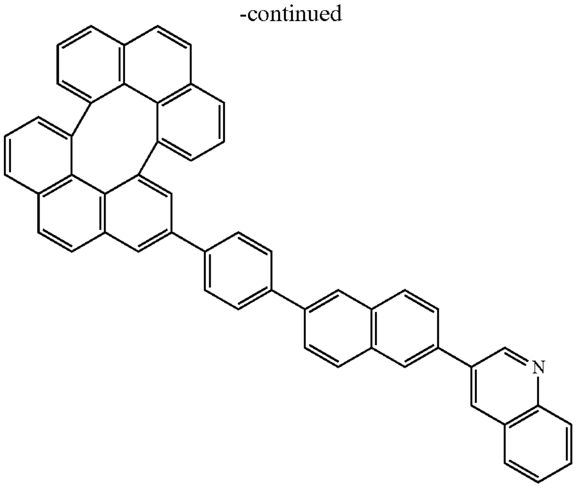
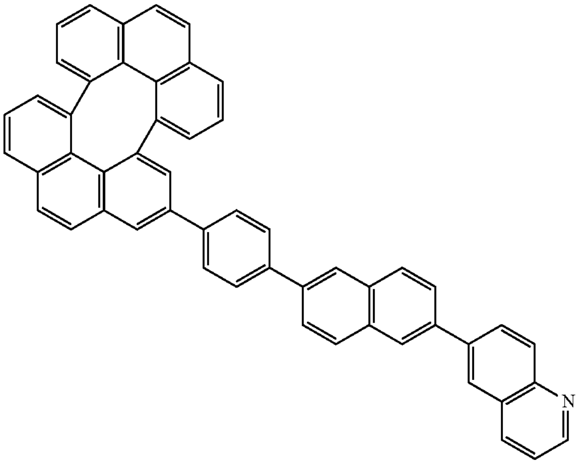
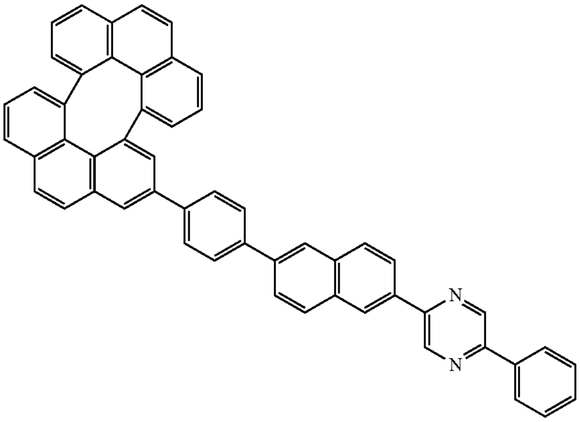
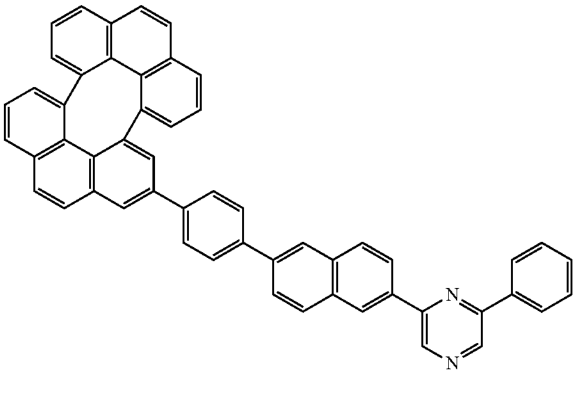
-continued
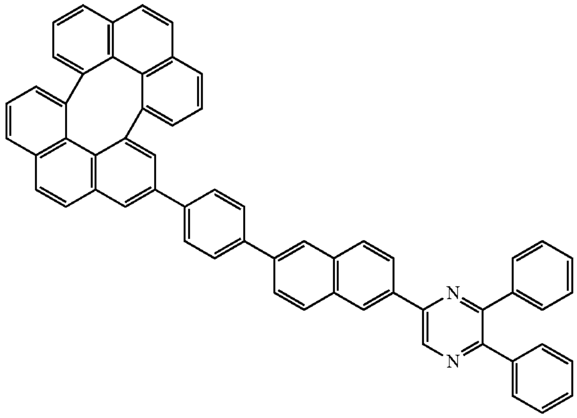
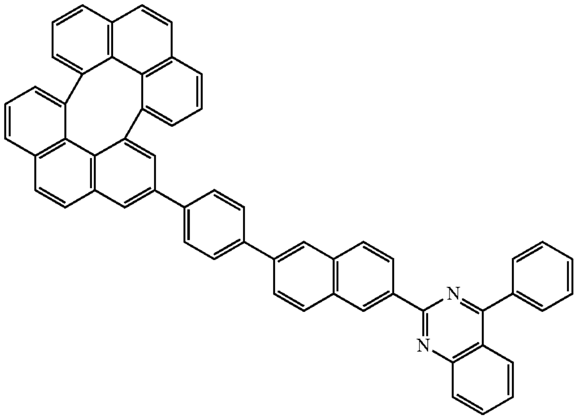
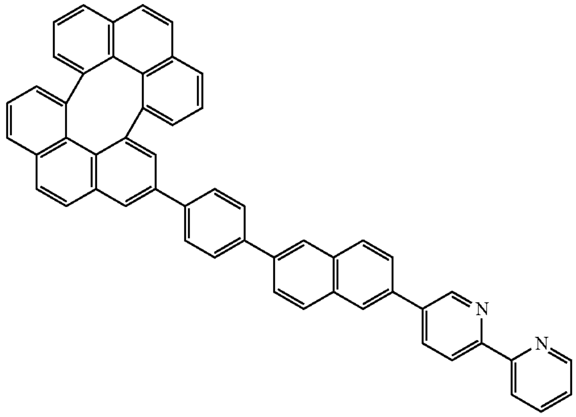
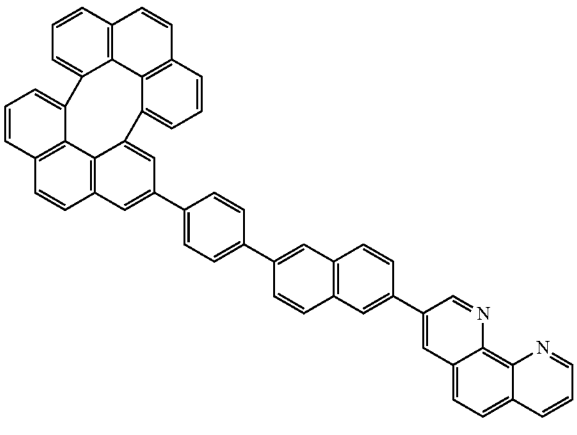

-continued
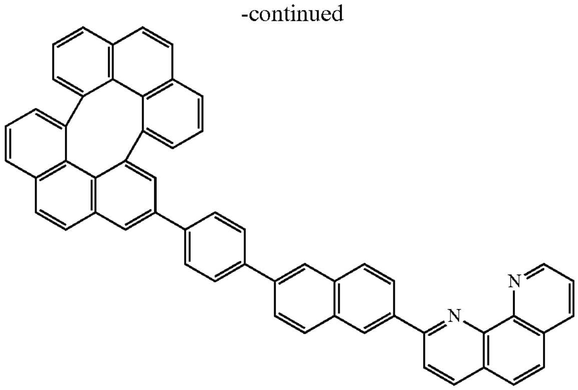
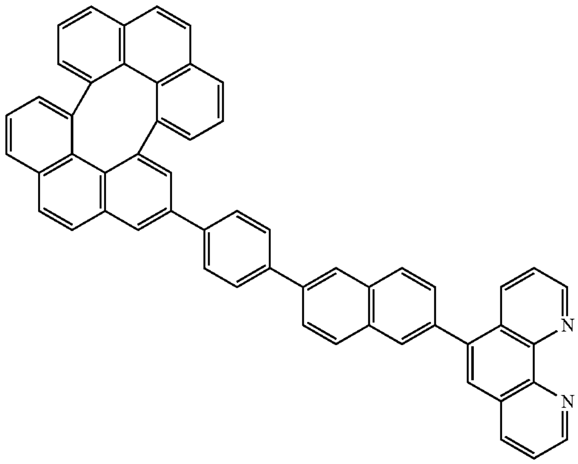
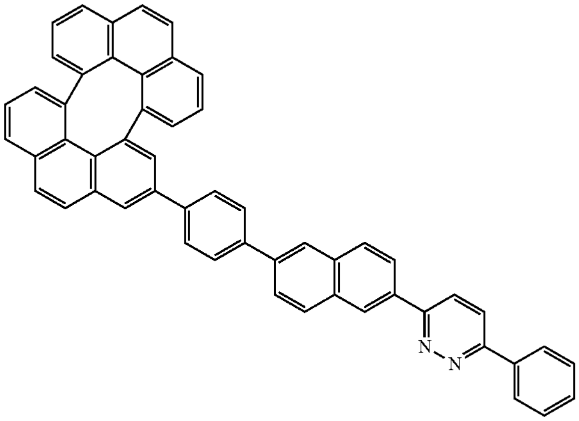
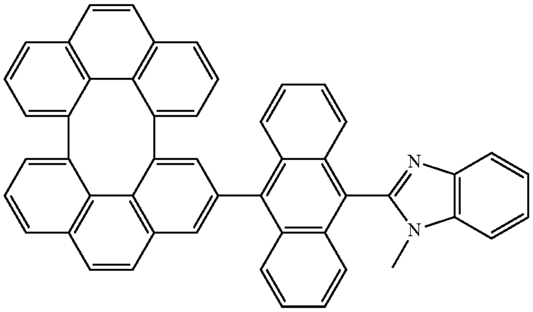
-continued
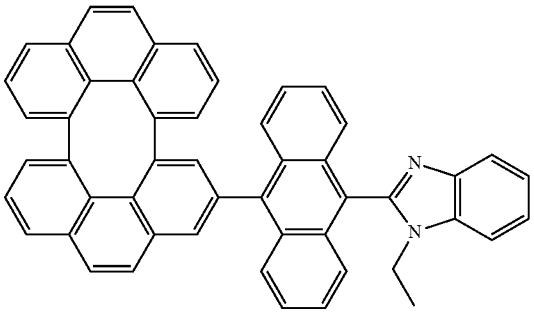
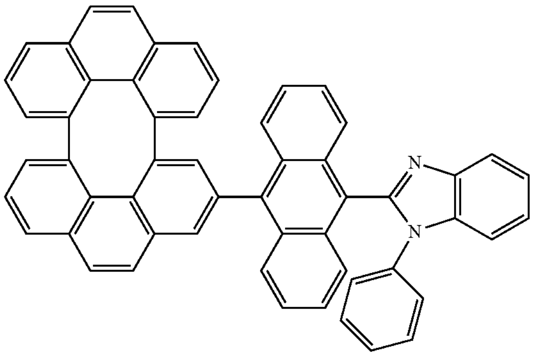
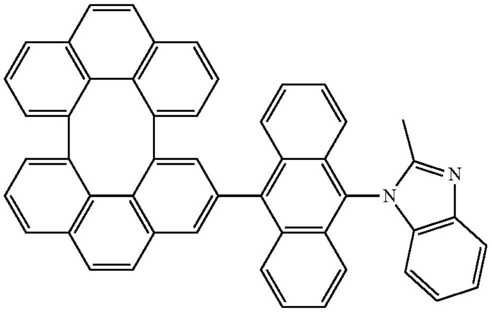
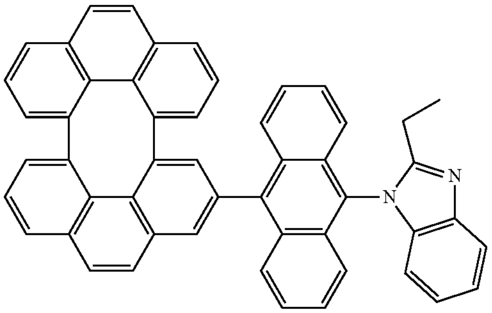
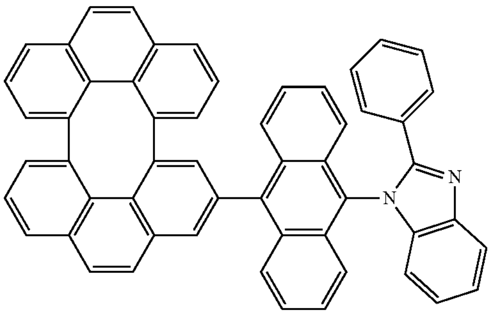

-continued
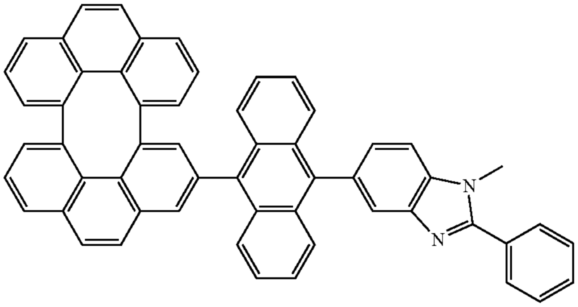
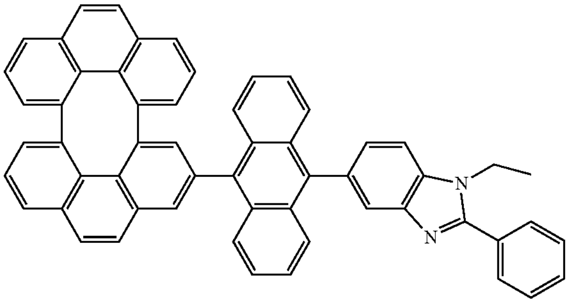
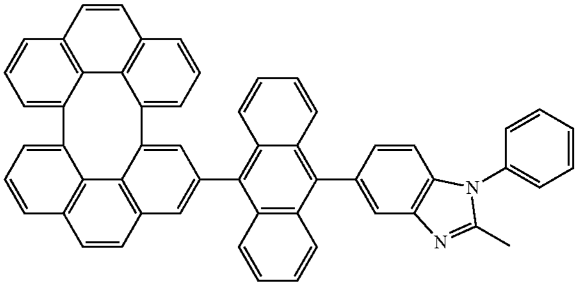
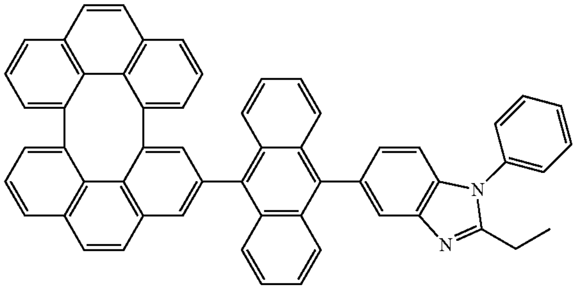
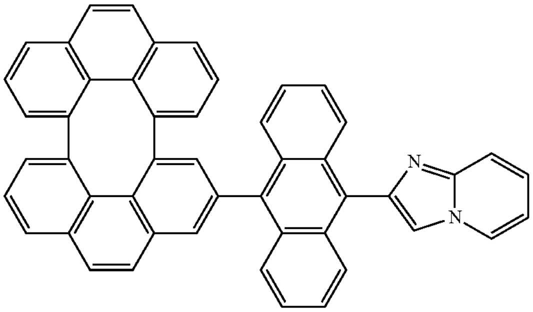
-continued
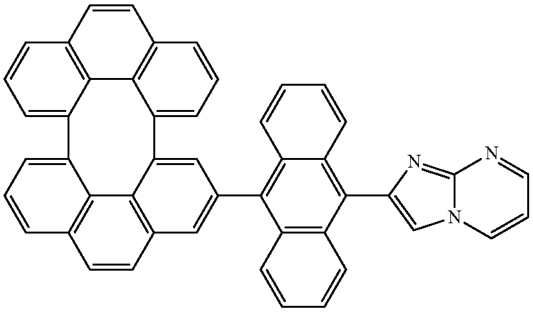
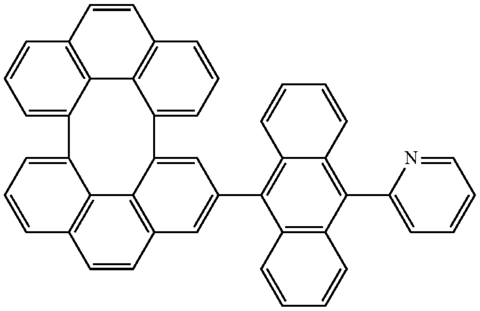
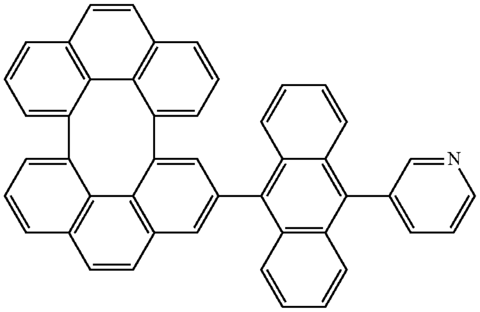
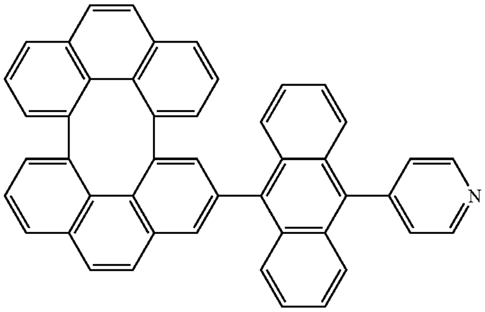
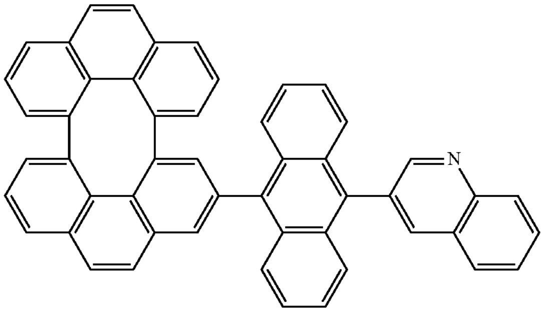

-continued
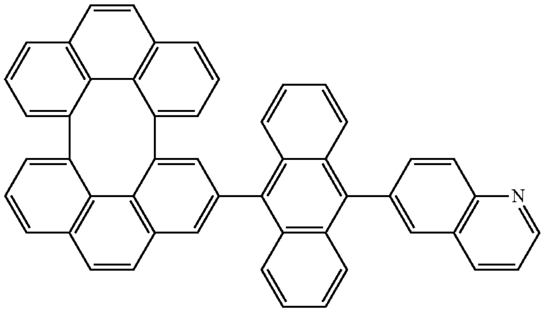
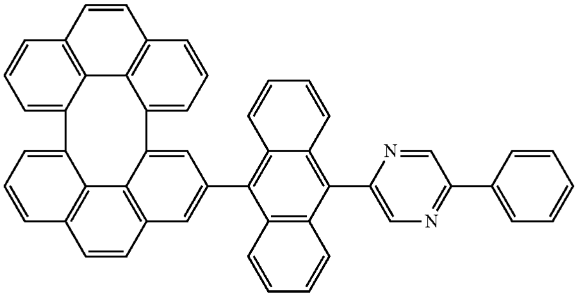
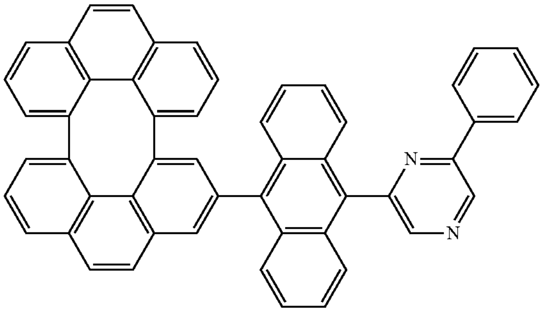
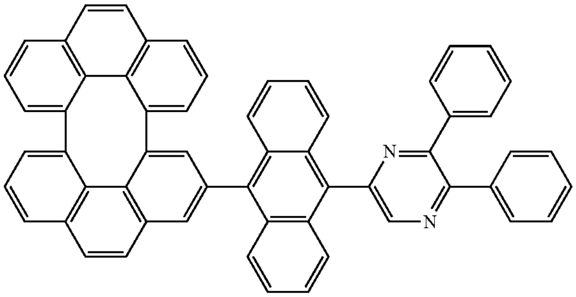
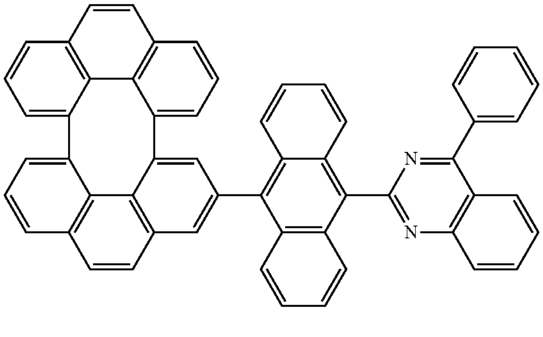
-continued
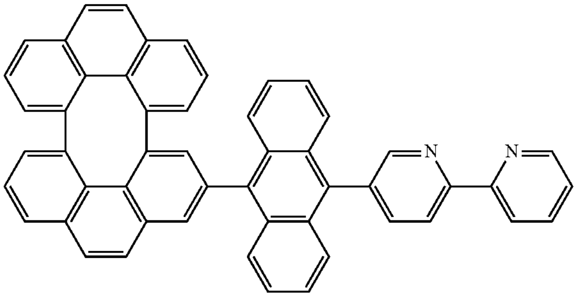
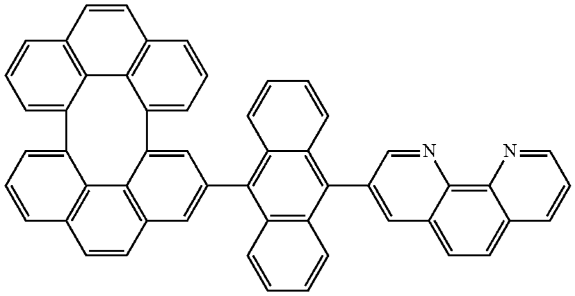
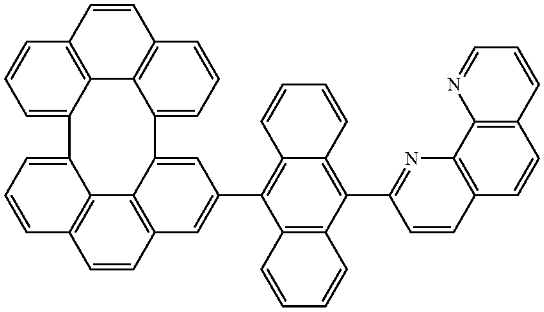
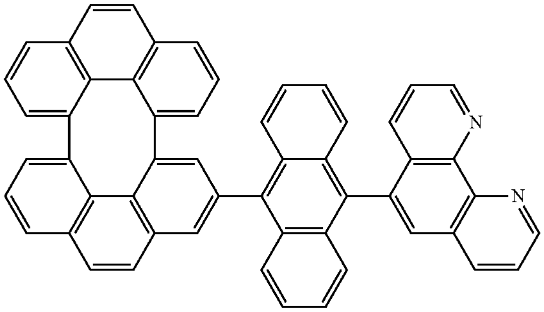
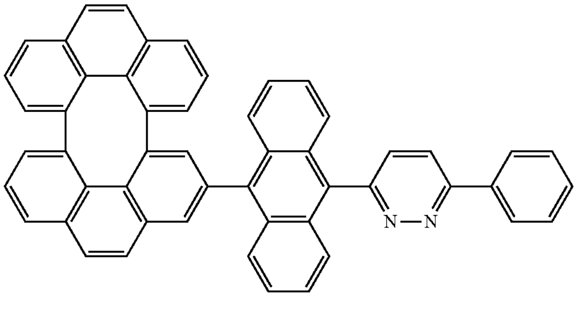

-continued
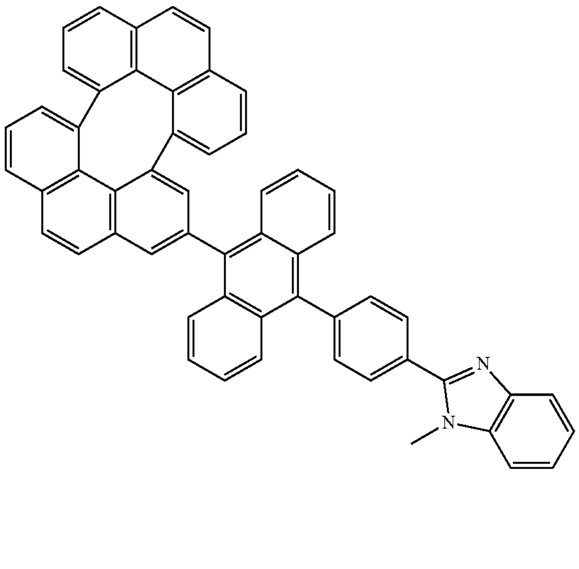
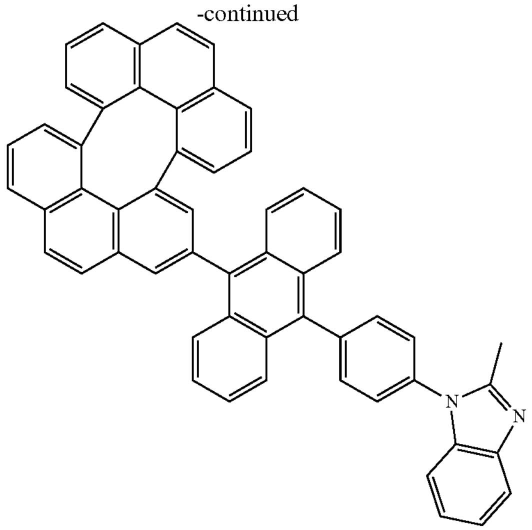
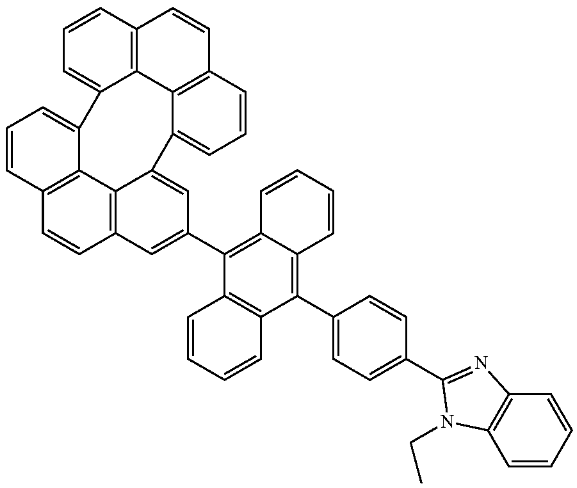
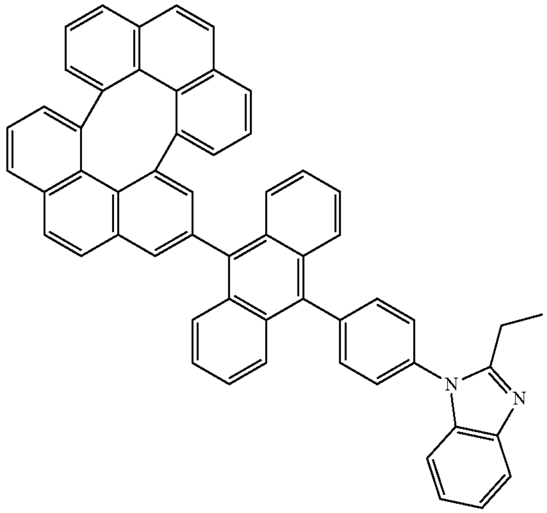
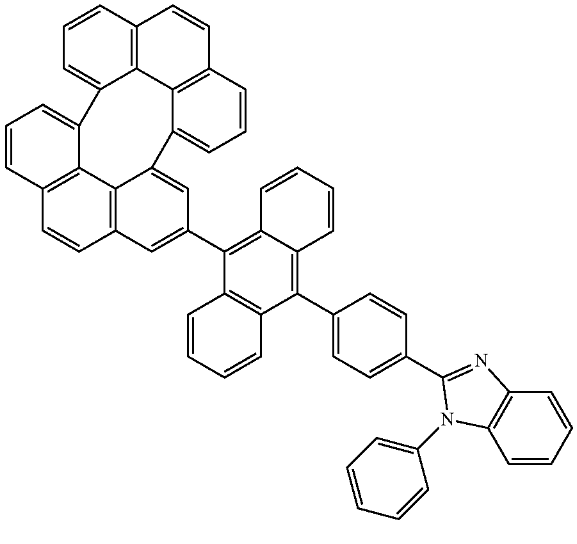
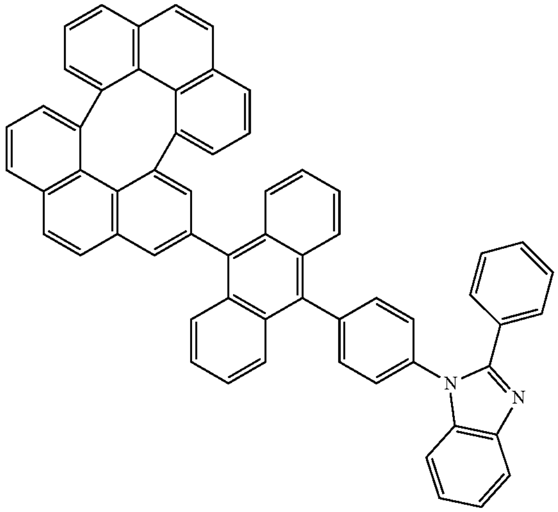

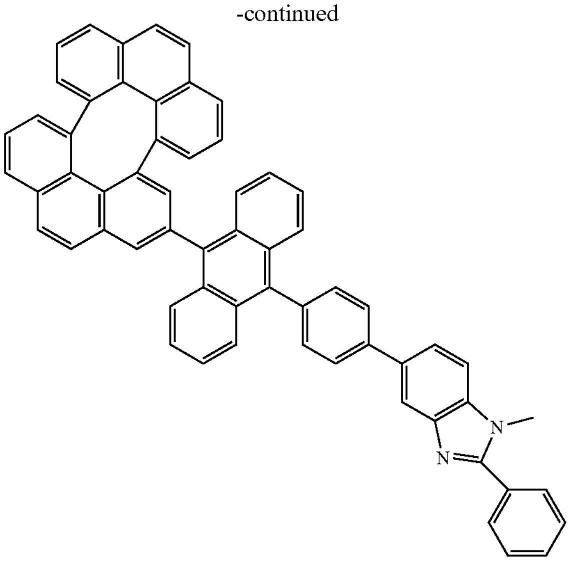
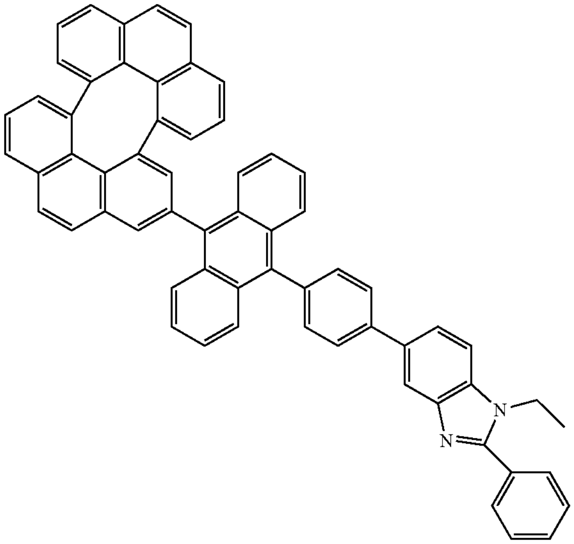
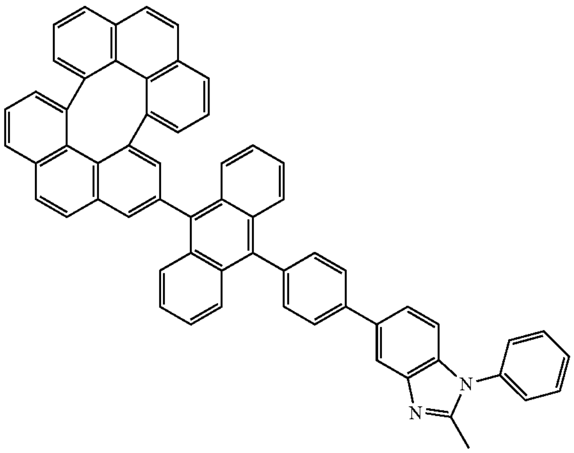
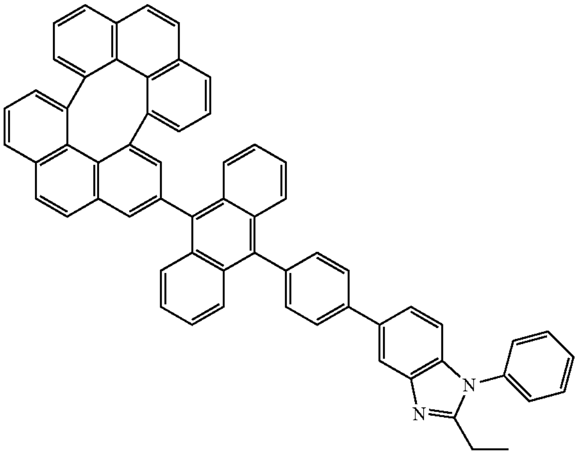
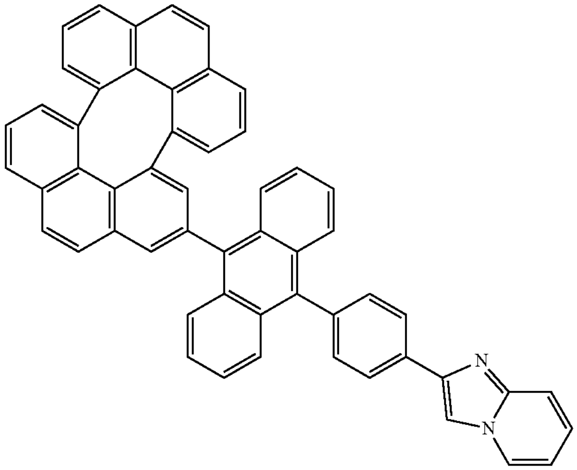
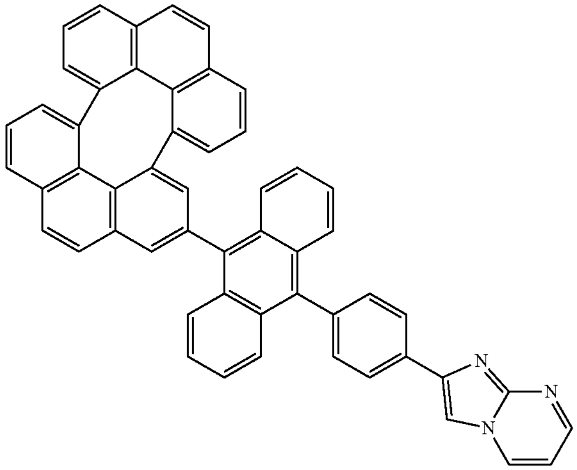

-continued
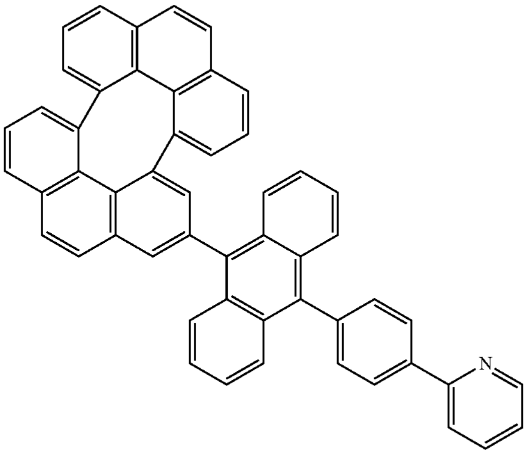
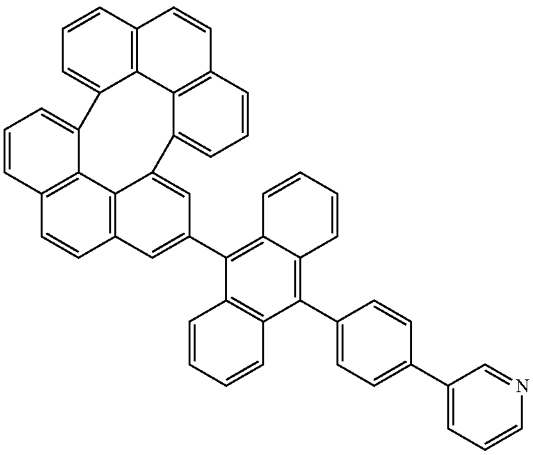
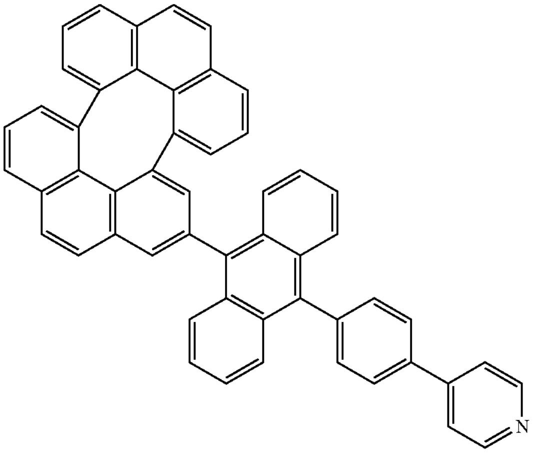
-continued
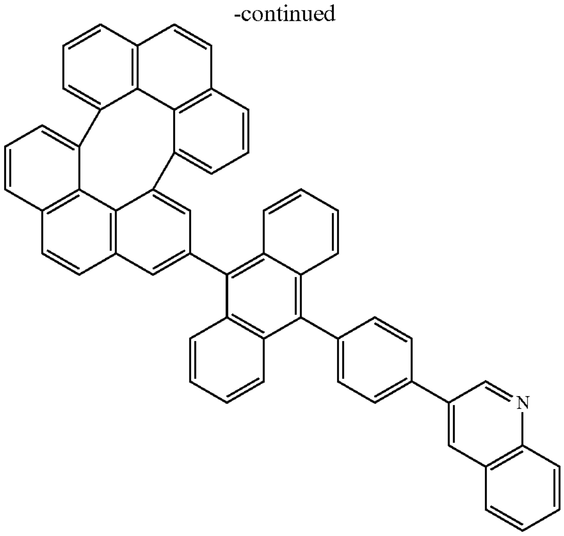
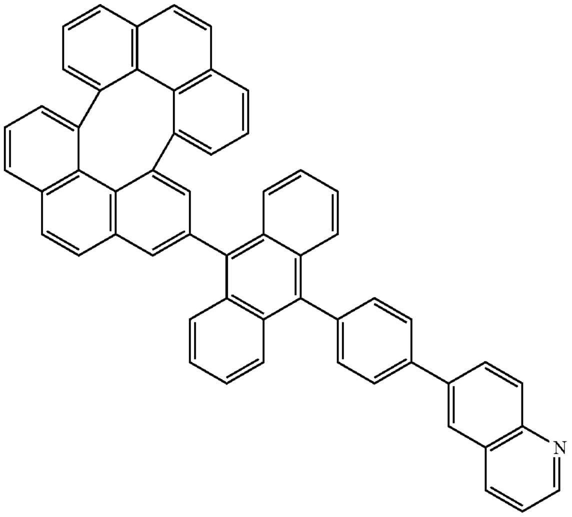
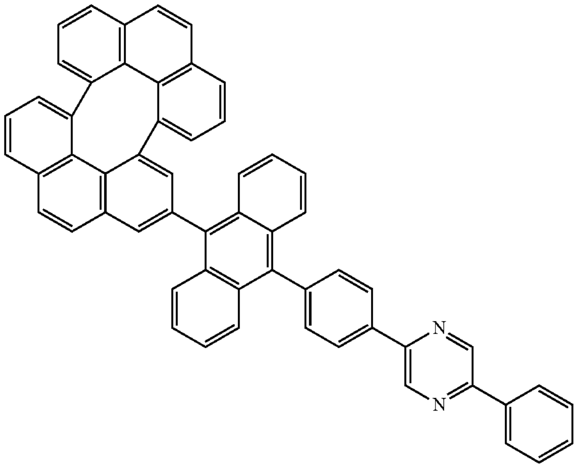

-continued
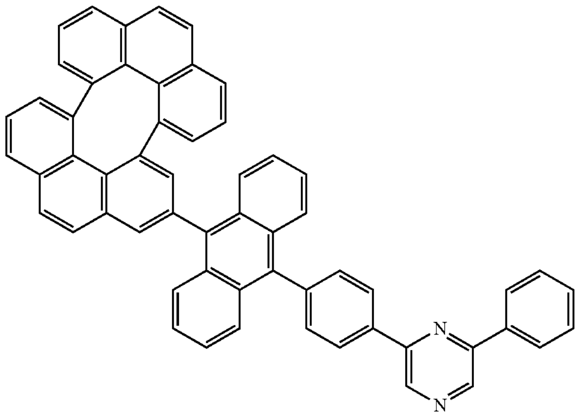
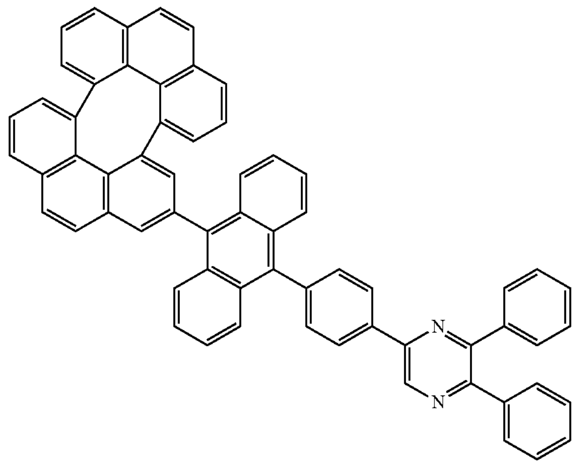
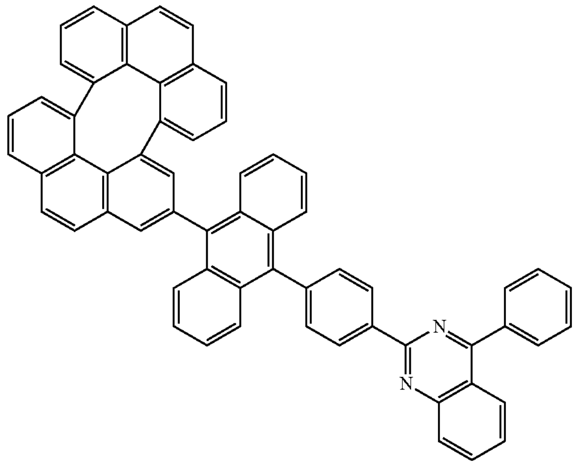
-continued
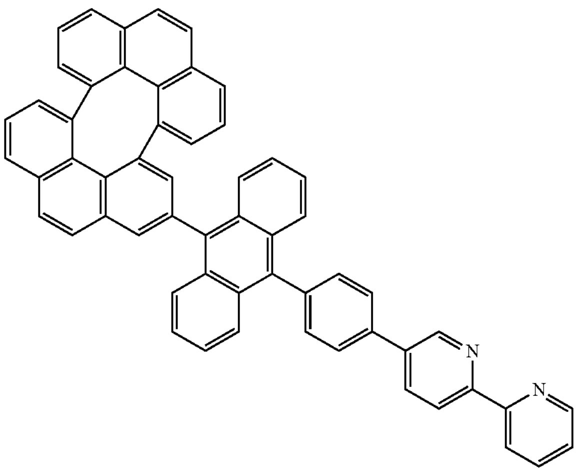
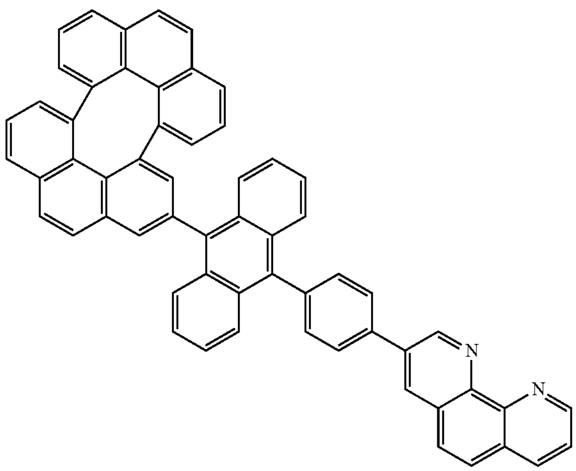
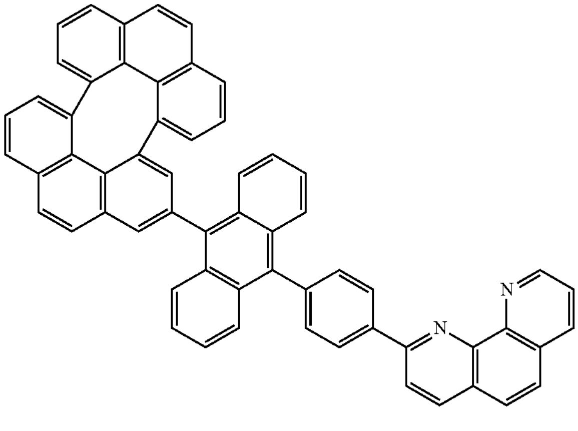

-continued
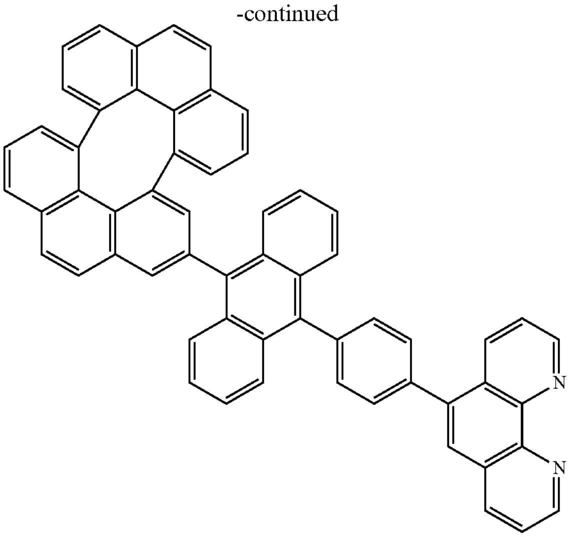
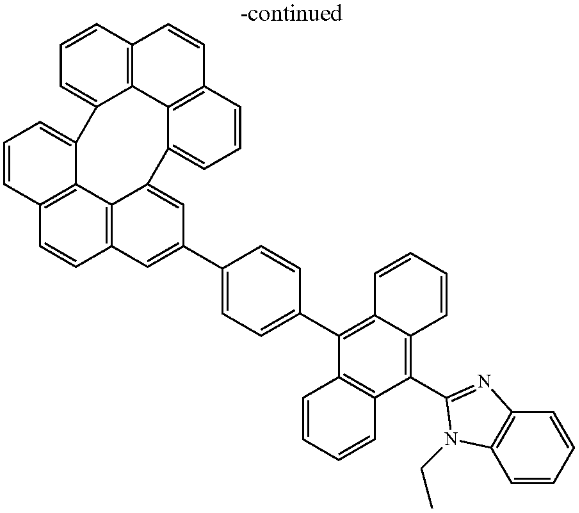
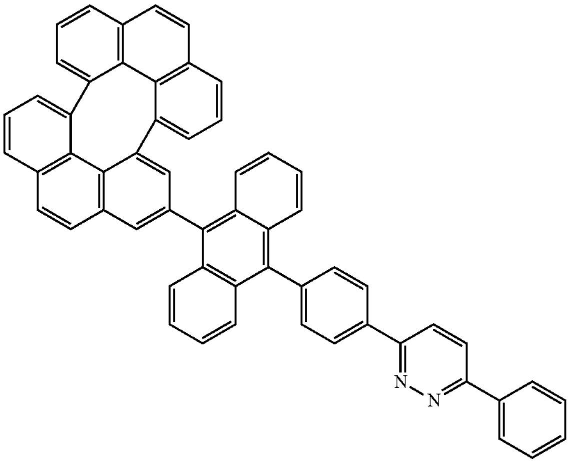
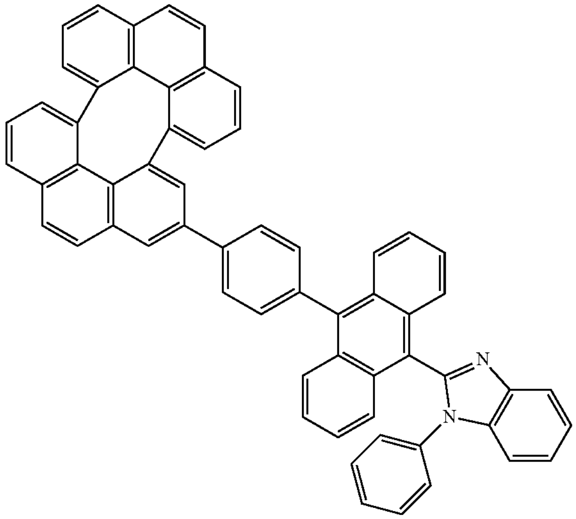
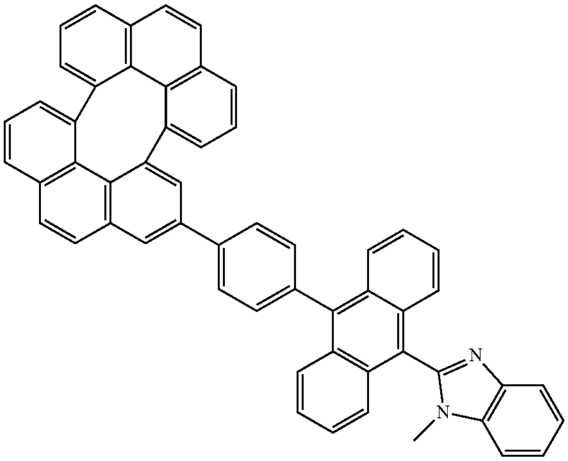
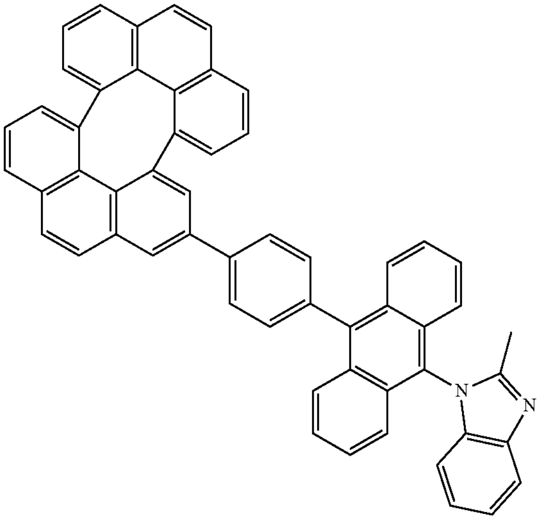

-continued
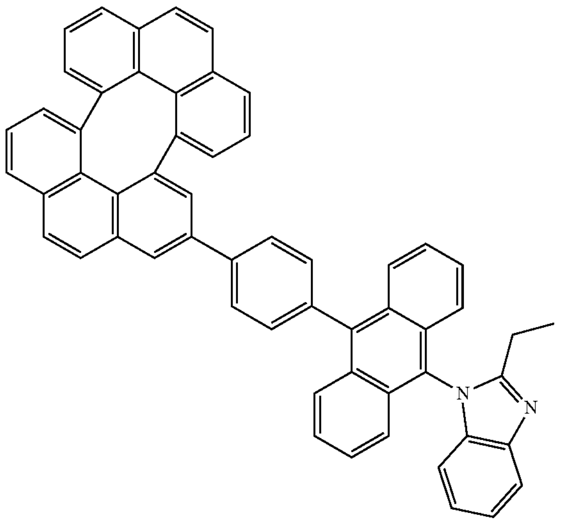
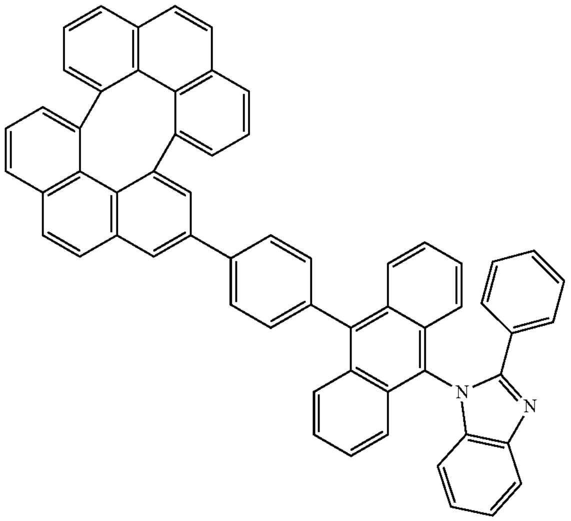
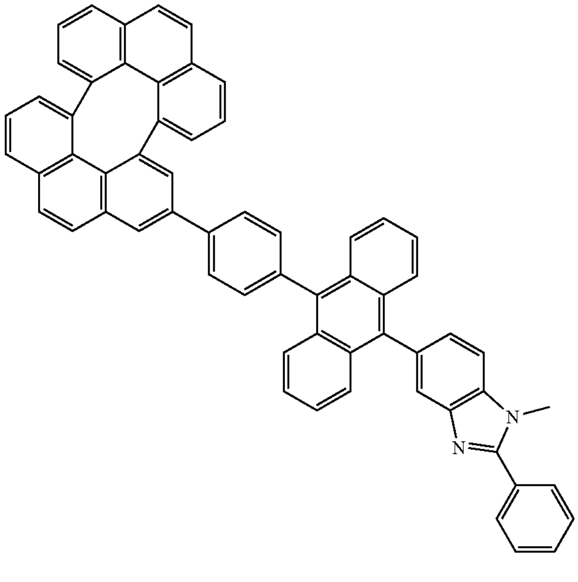
-continued
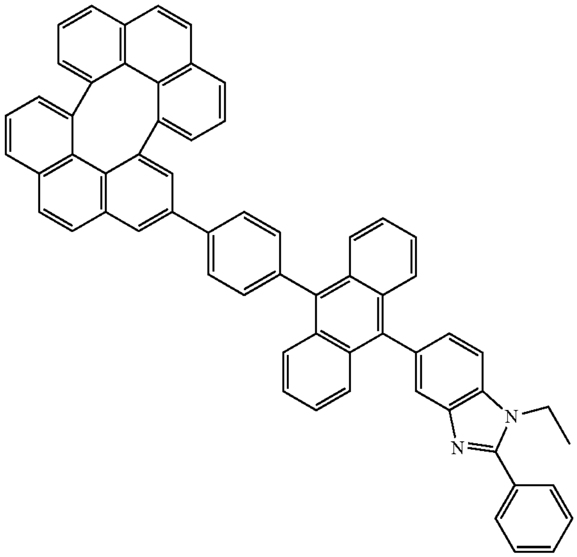
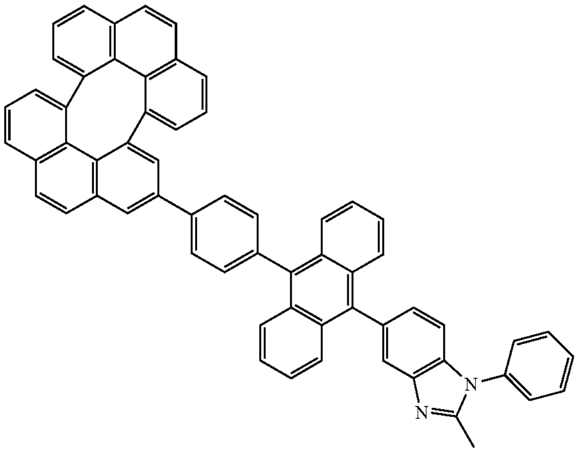
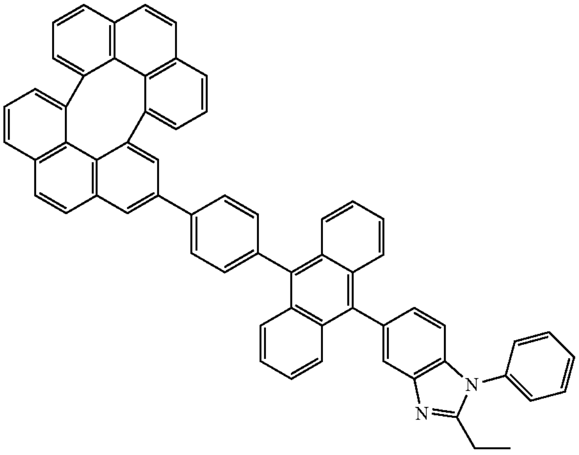

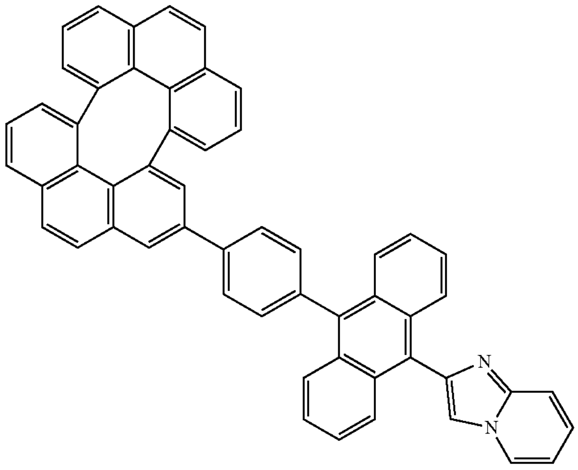
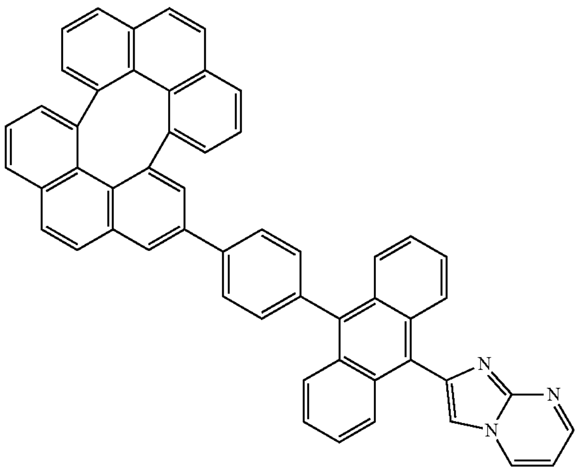
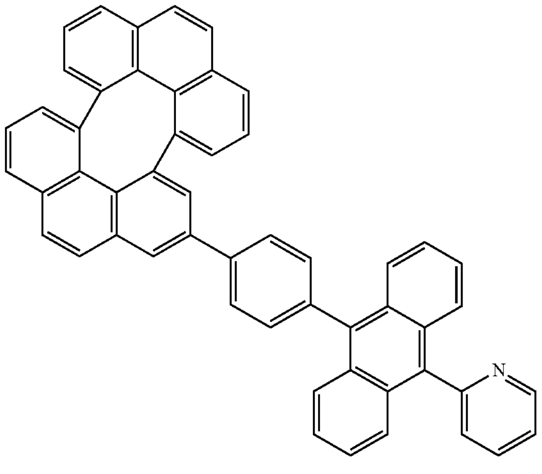
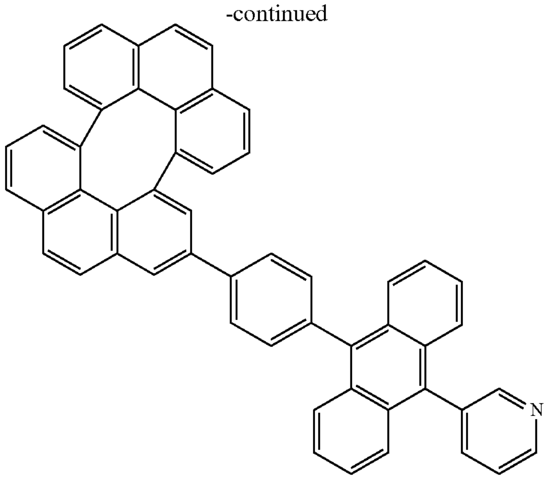
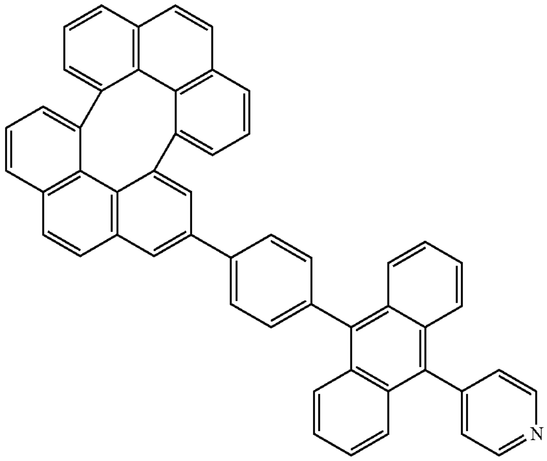
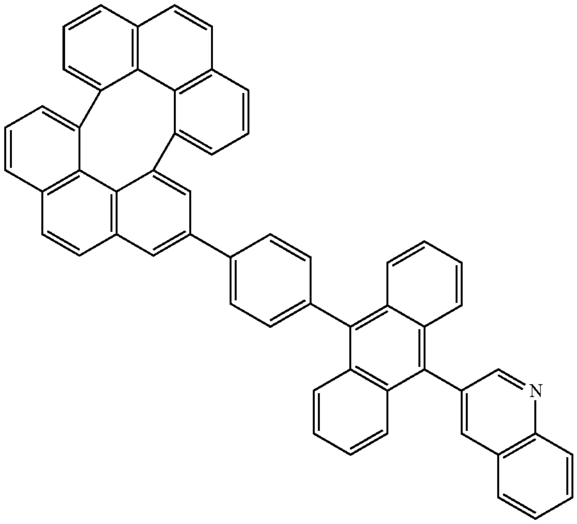

-continued
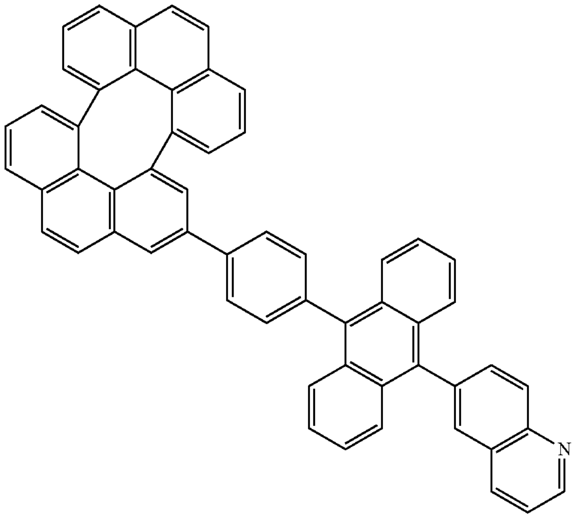
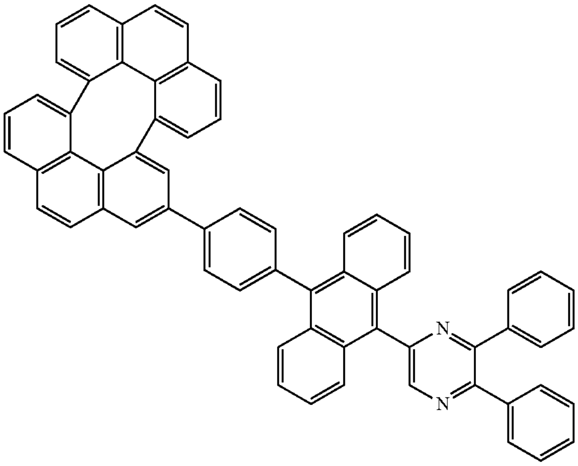
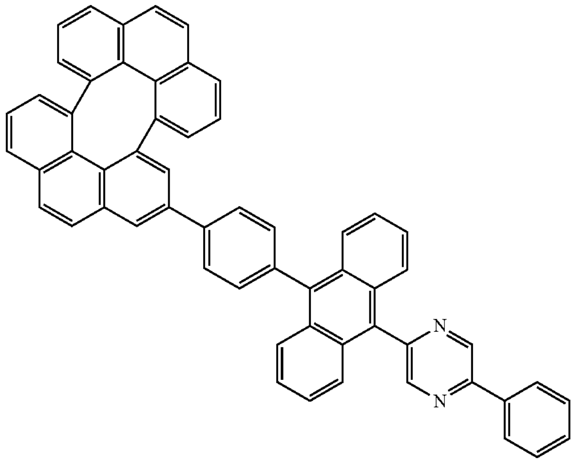
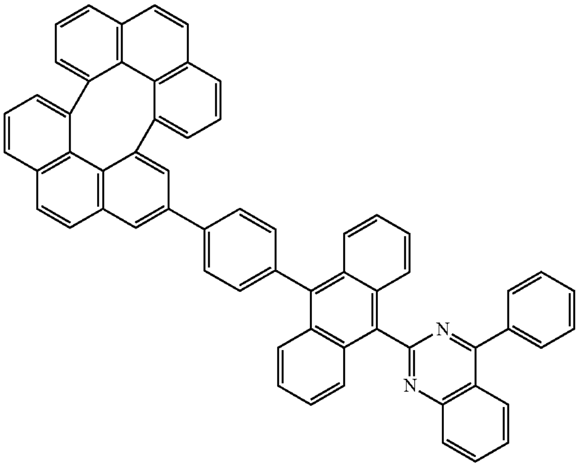
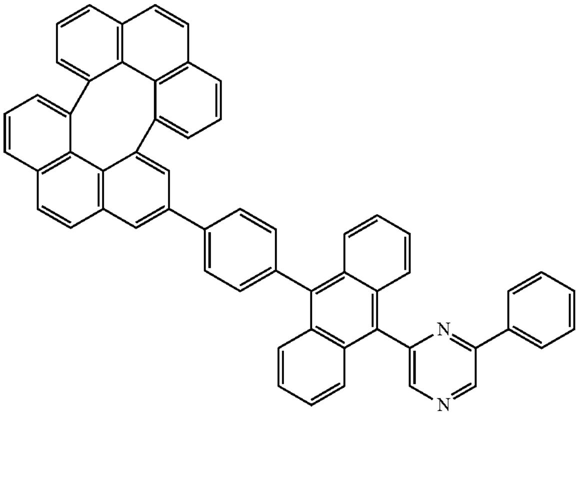
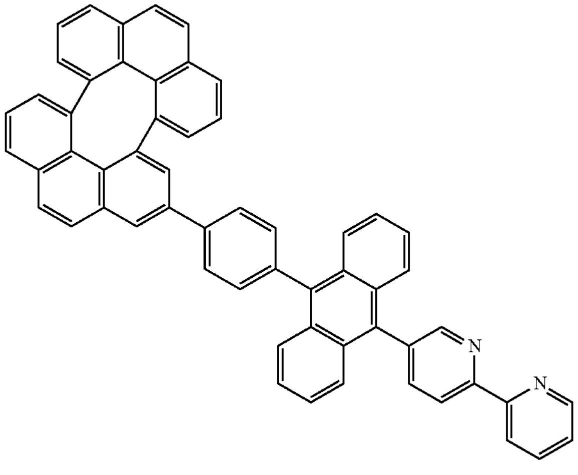
-continued -continued
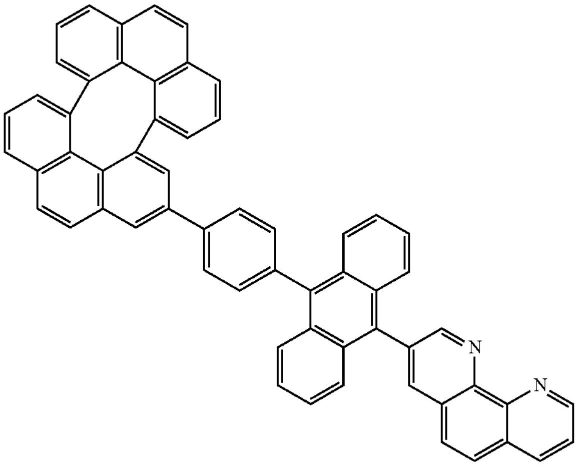
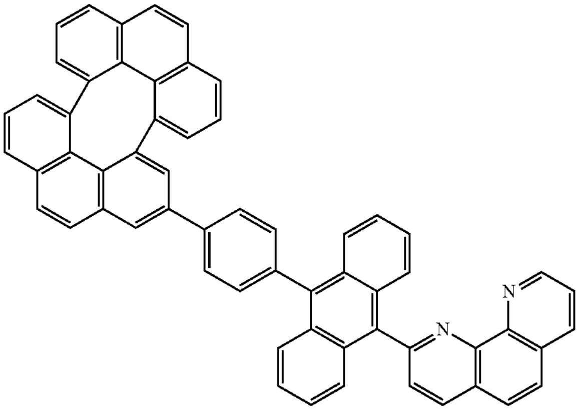
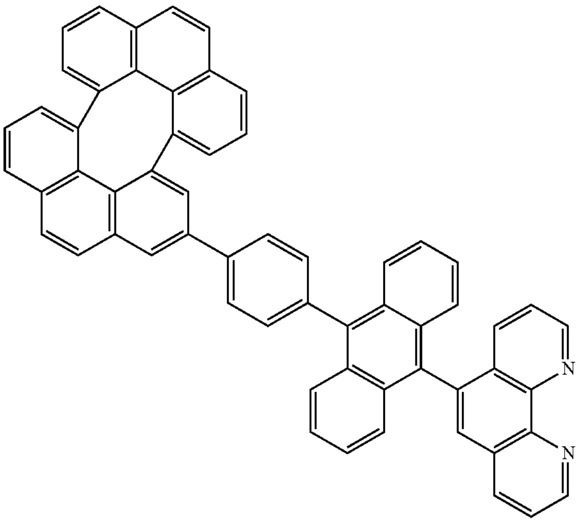
-continued
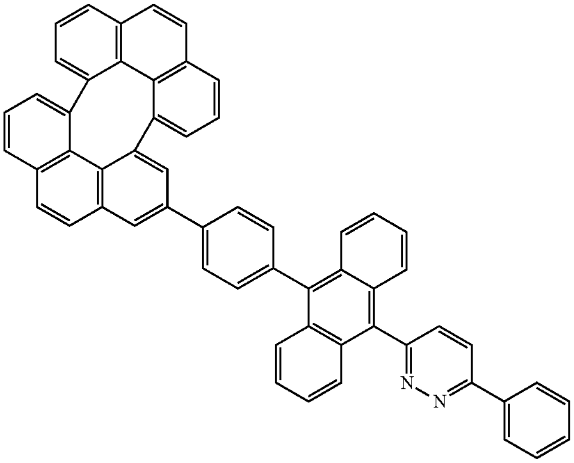
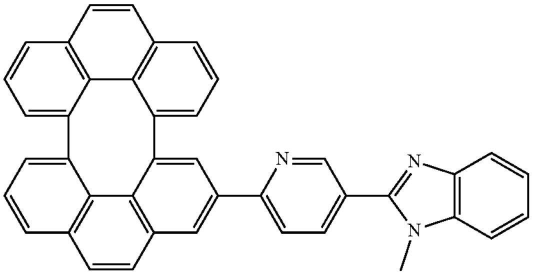
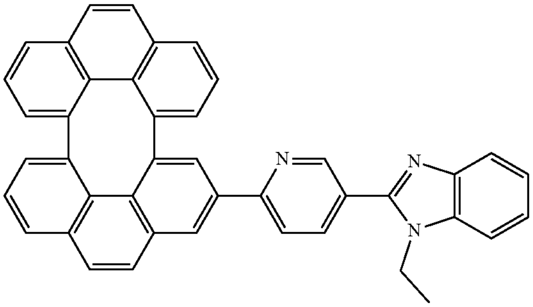
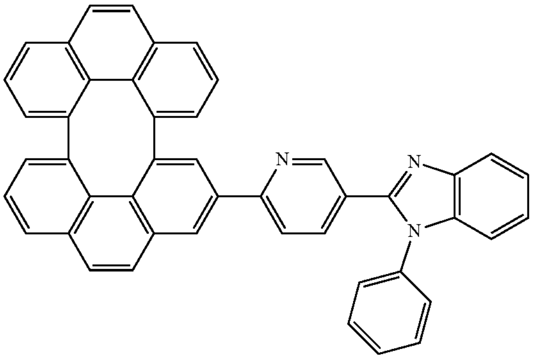

-continued
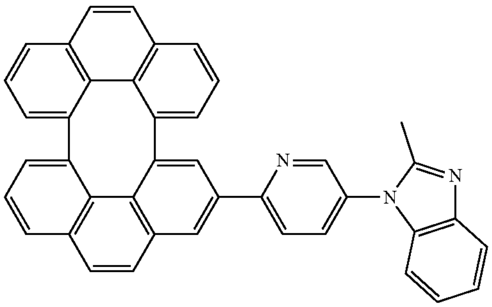
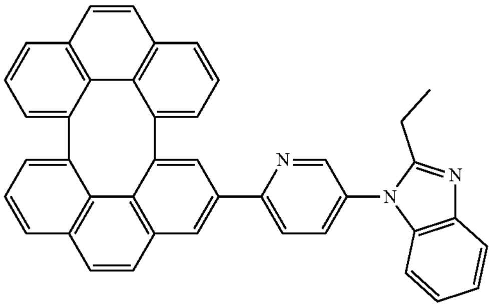
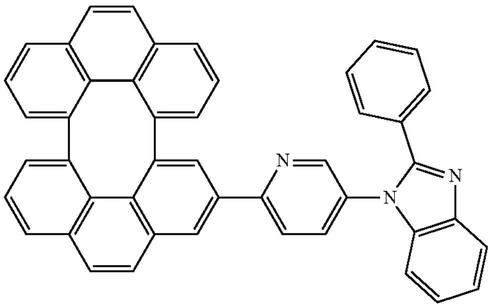
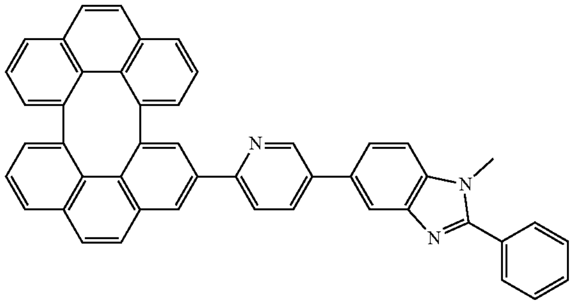
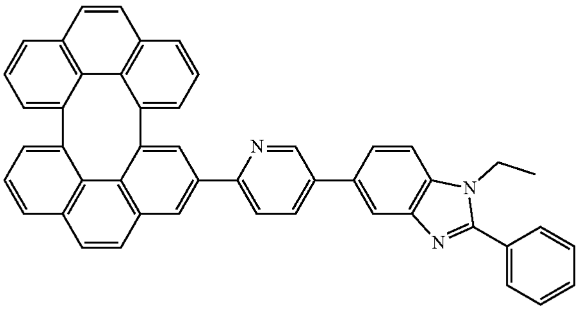
-continued
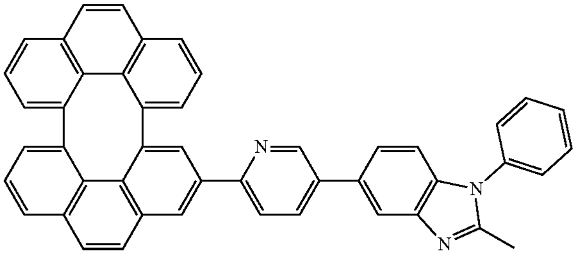
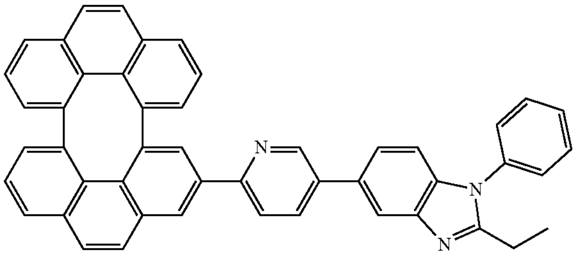
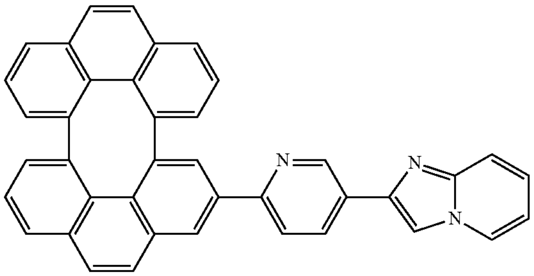
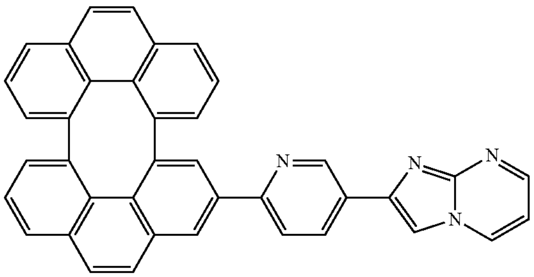
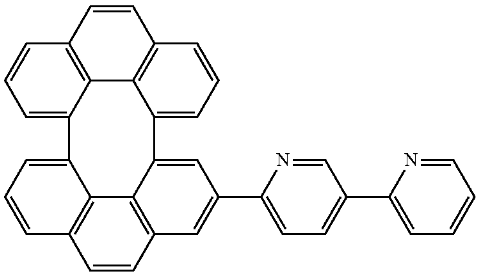
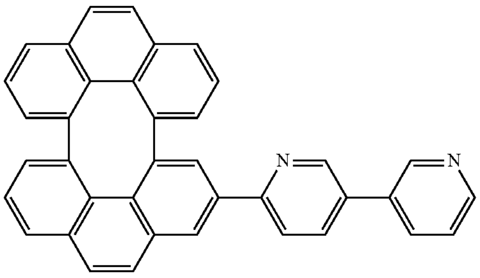

-continued
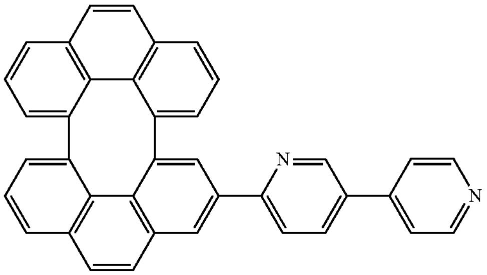
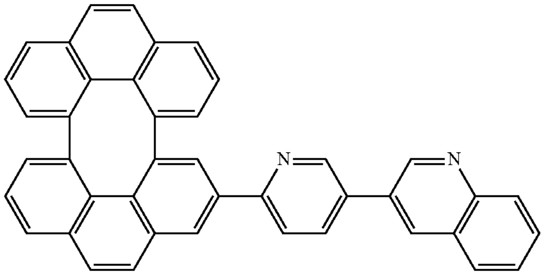
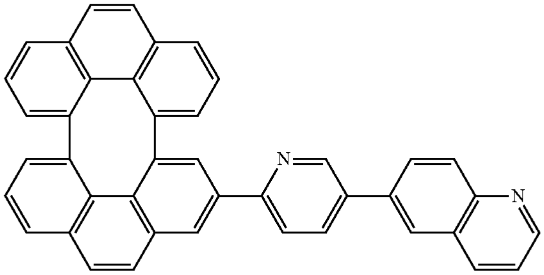
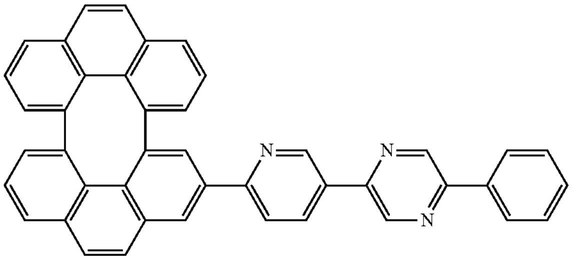
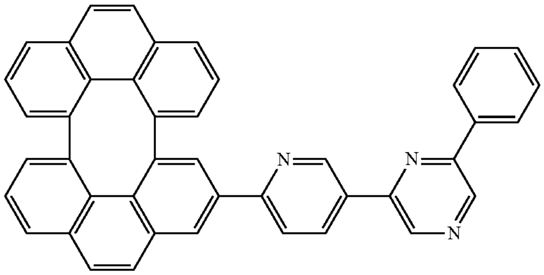
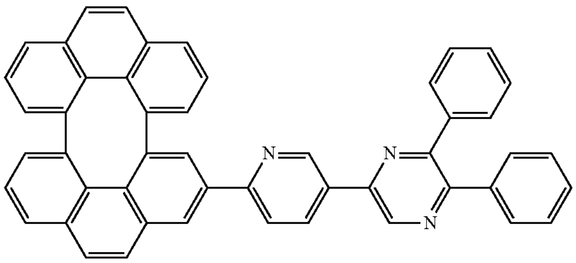
-continued
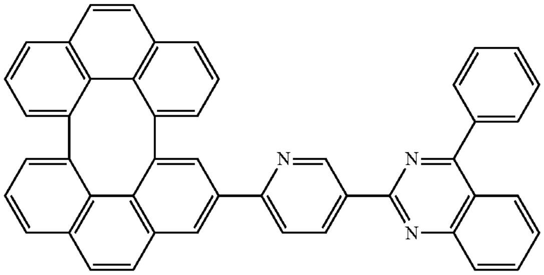
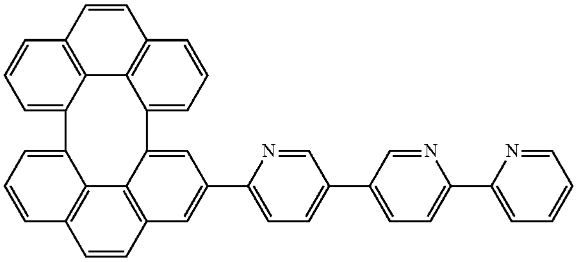
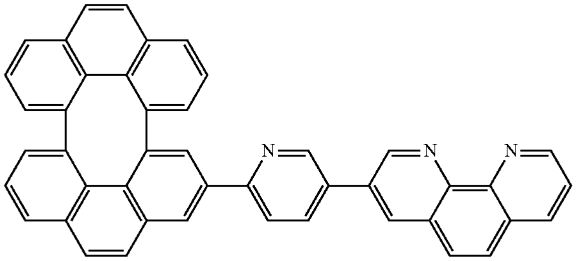
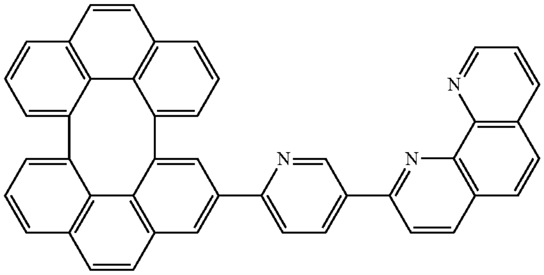
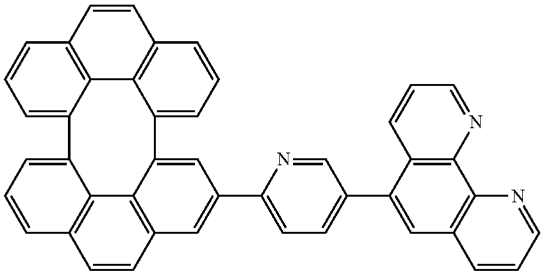
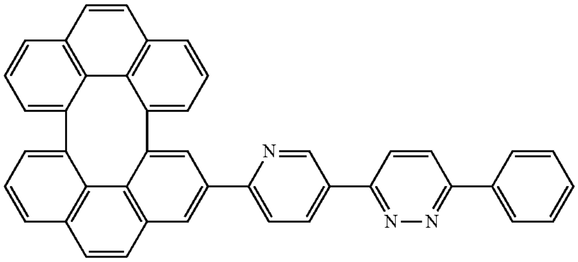

-continued
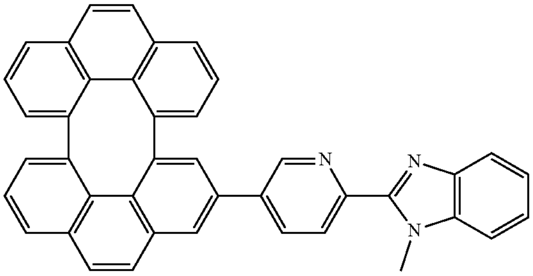
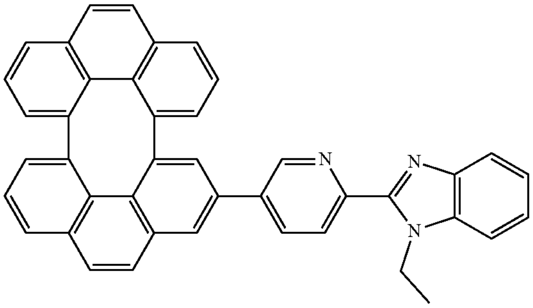
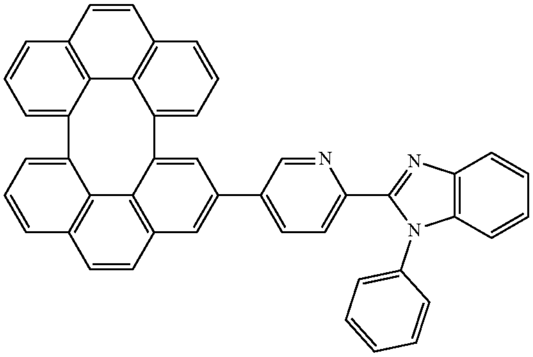
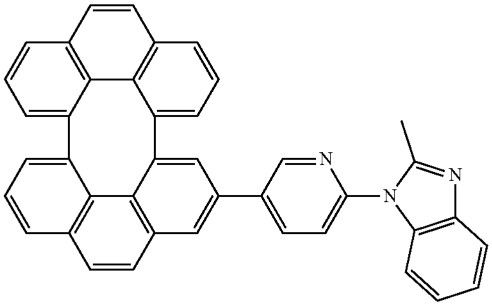
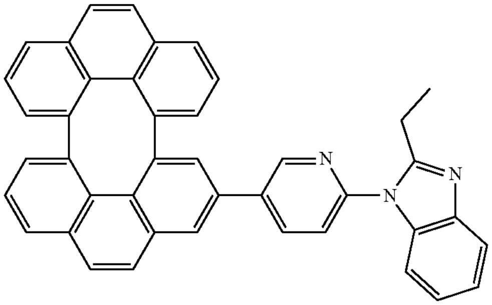
-continued
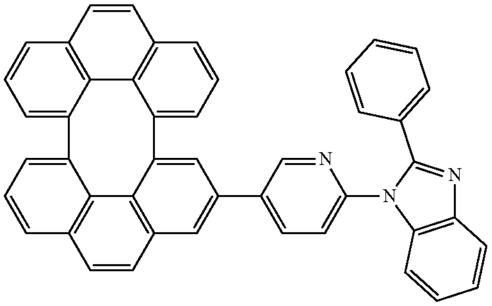
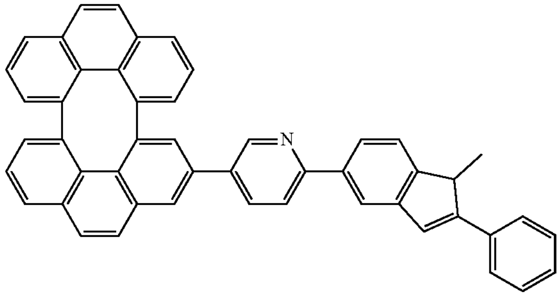
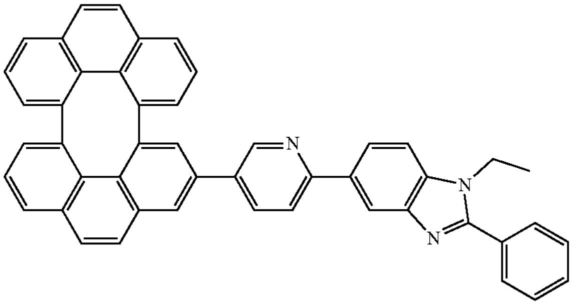
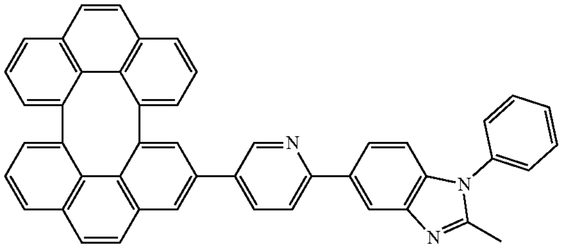
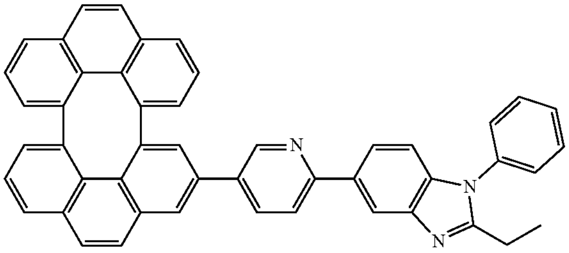
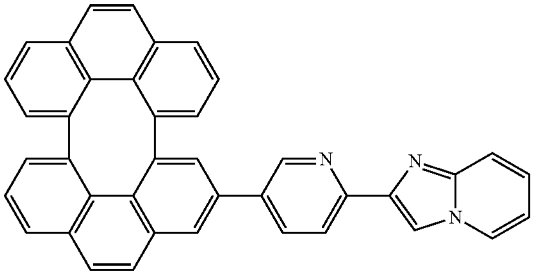

-continued
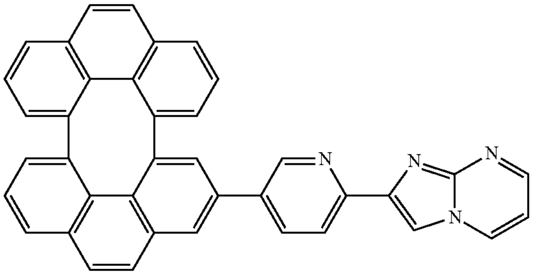
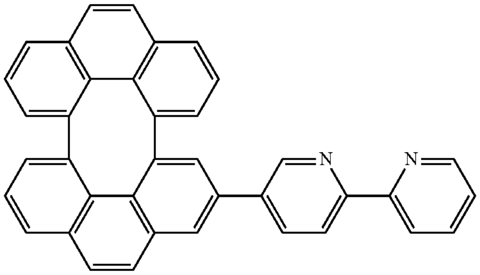
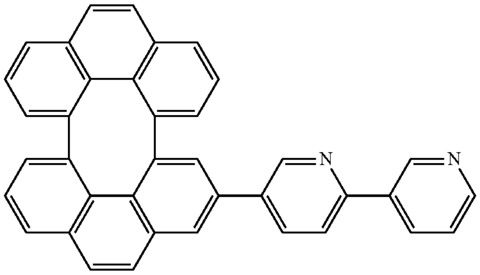
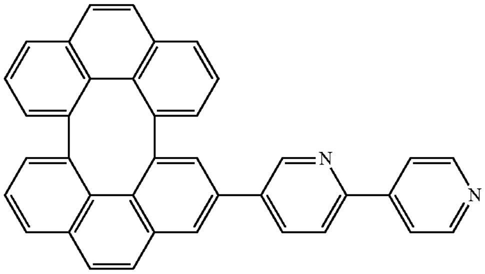
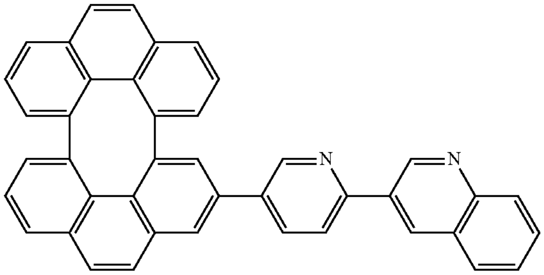
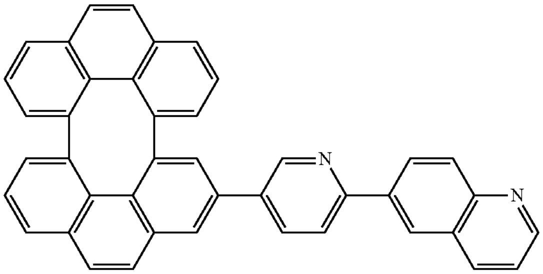
-continued
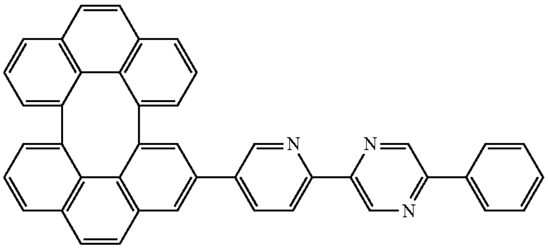
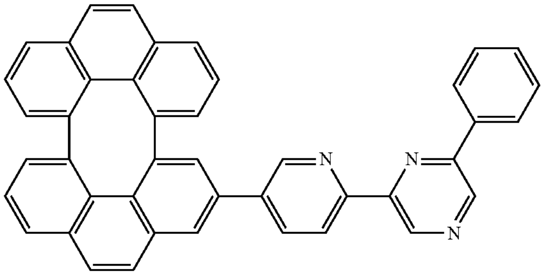
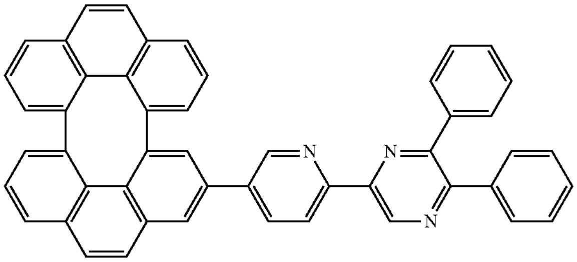
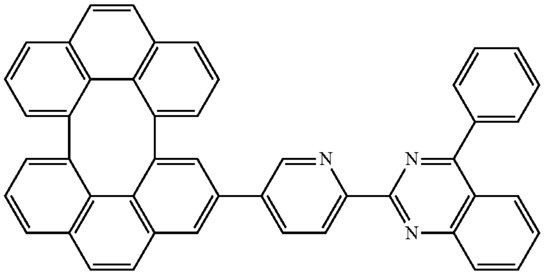
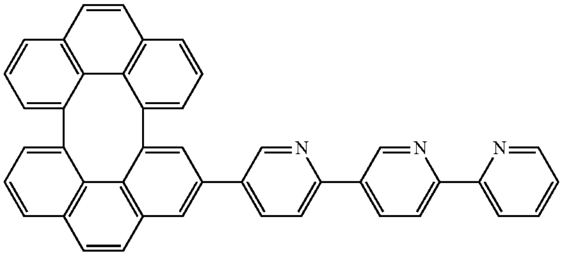
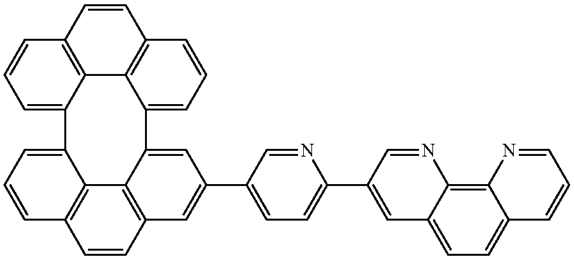

-continued
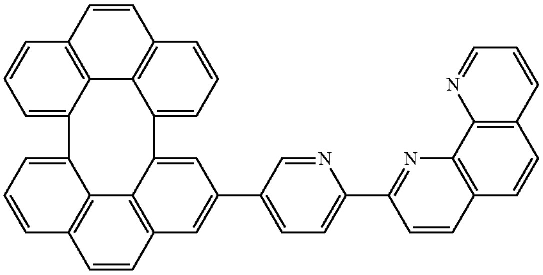
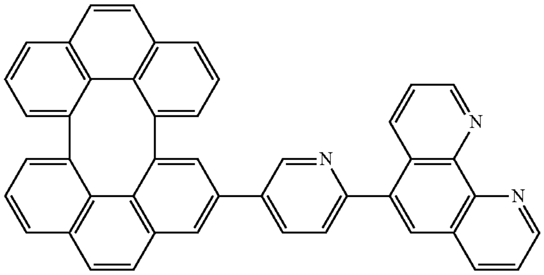
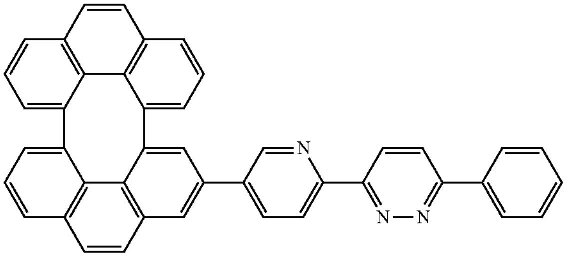
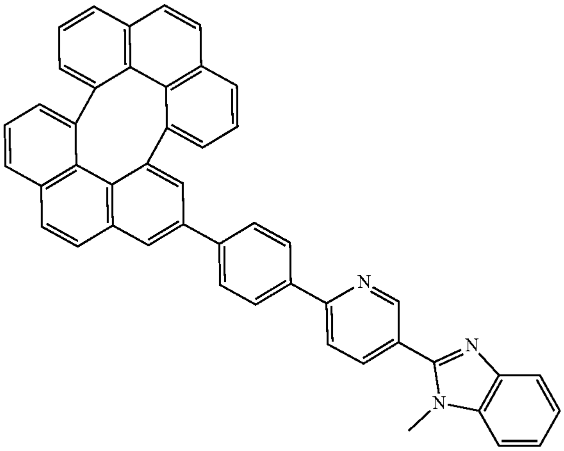
-continued
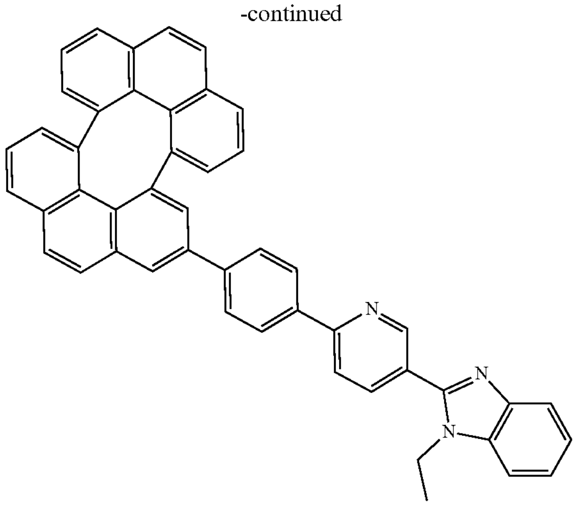
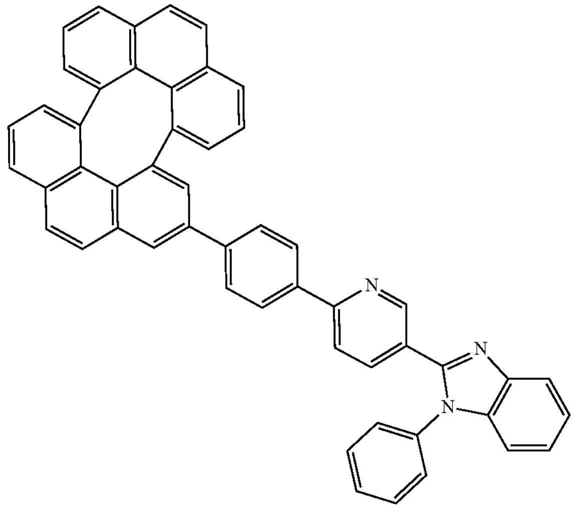
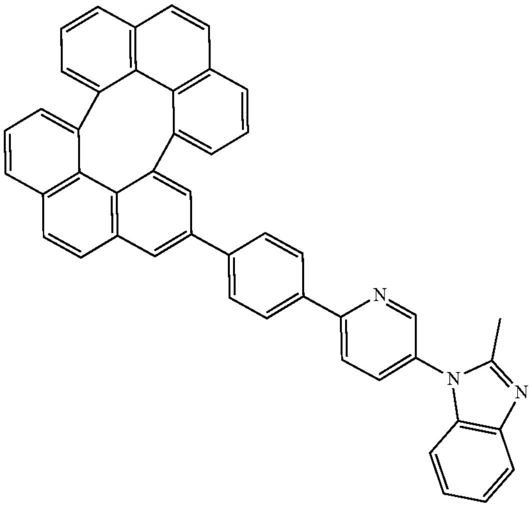

-continued
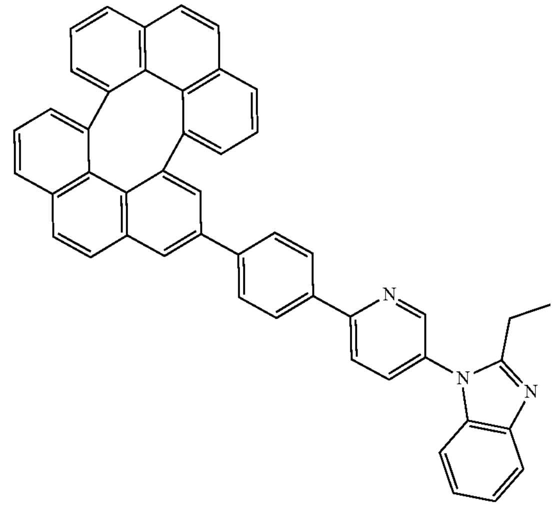
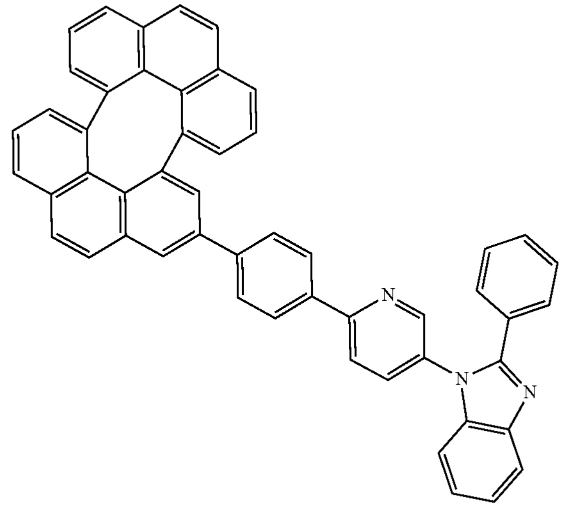
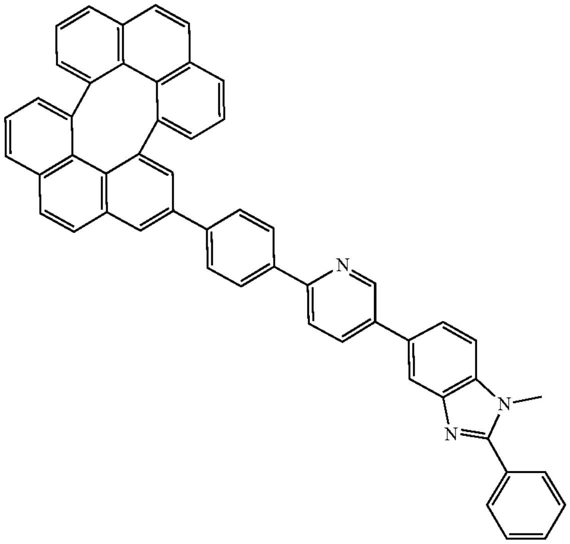
-continued
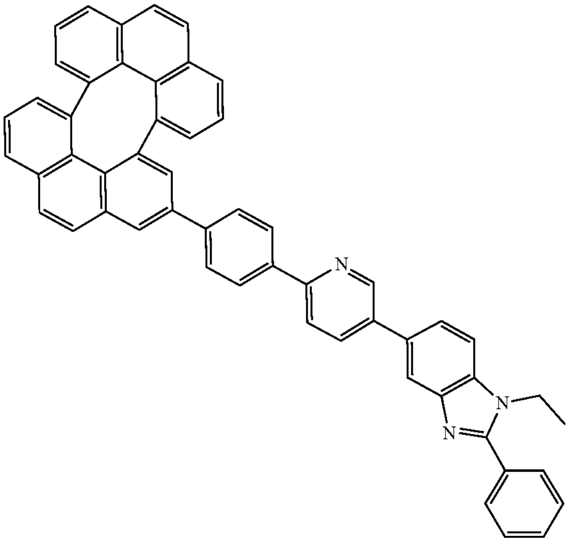
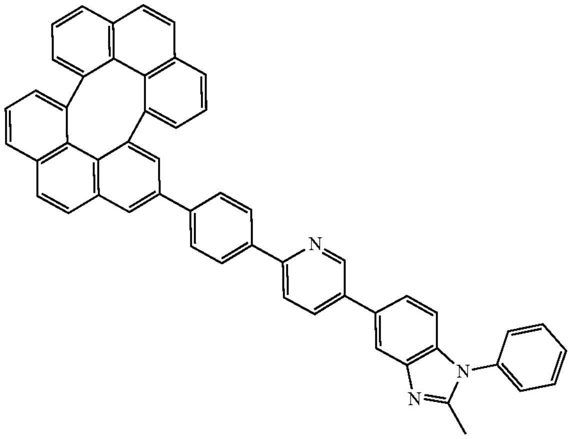
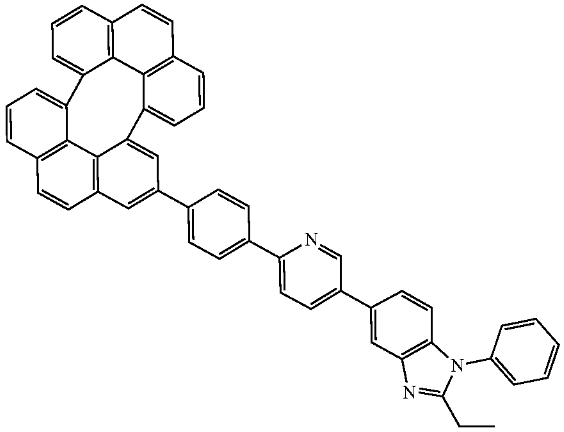

-continued
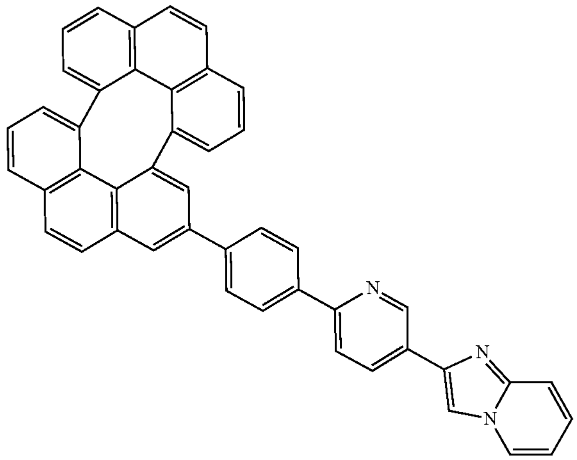
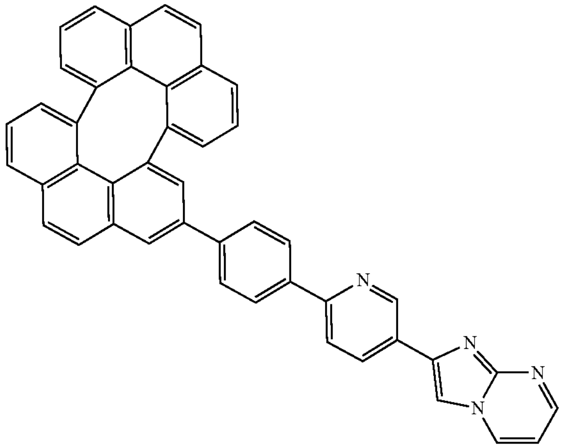
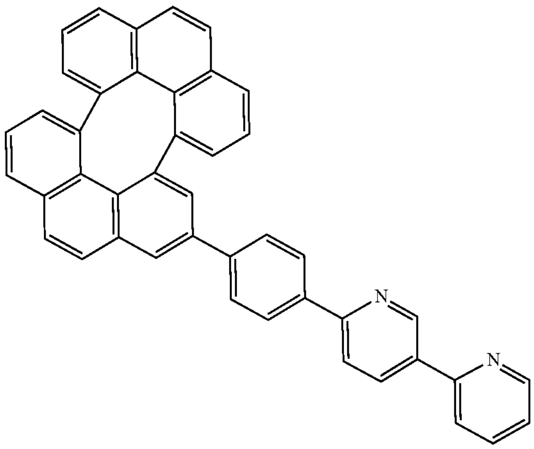
-continued
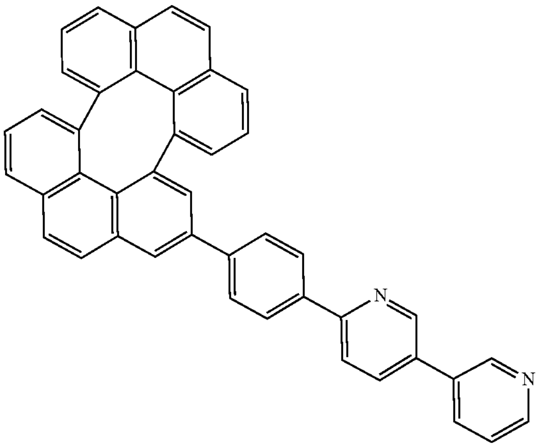
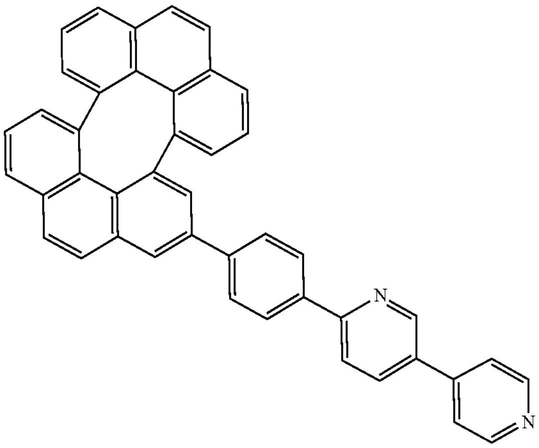
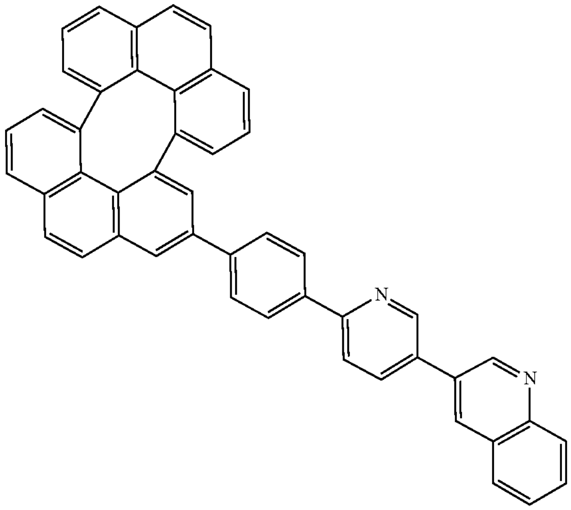

-continued
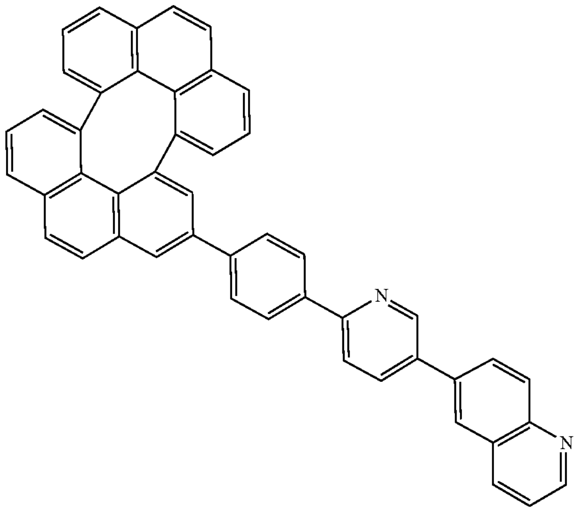
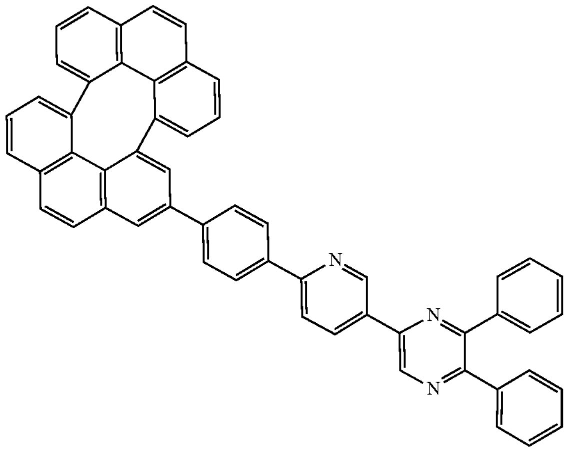
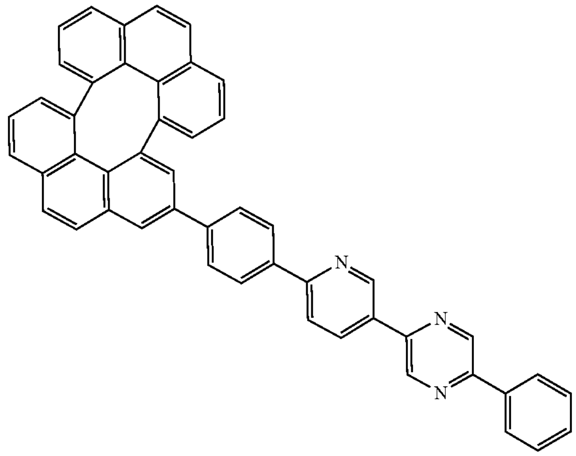
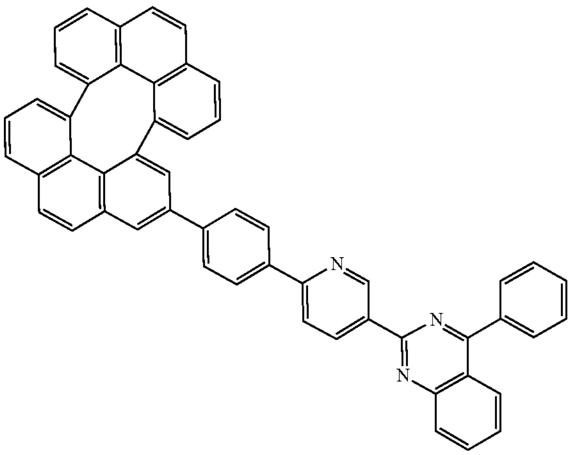
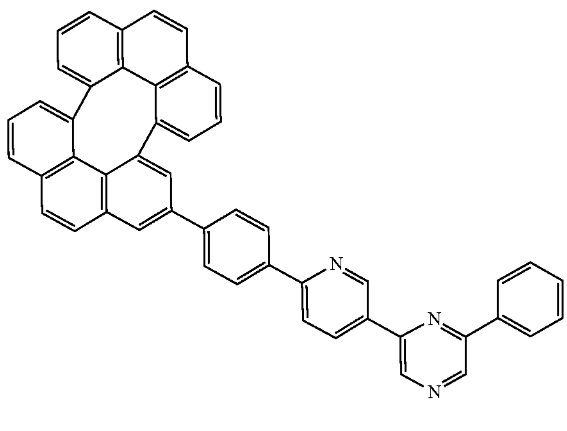
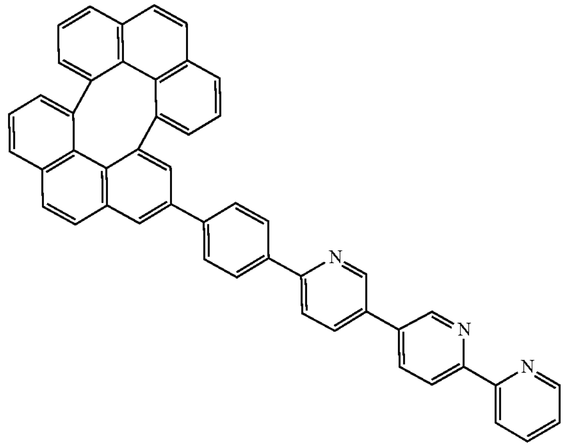
-continued -continued
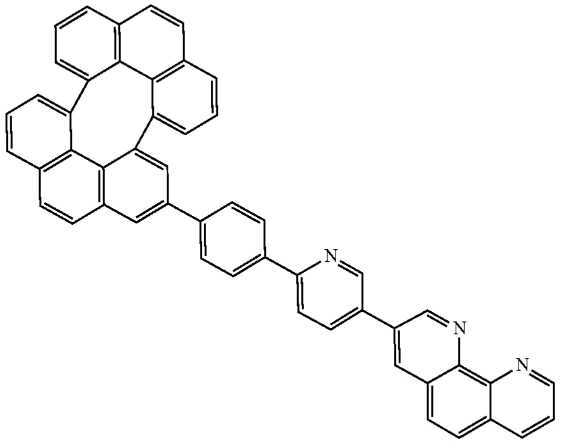
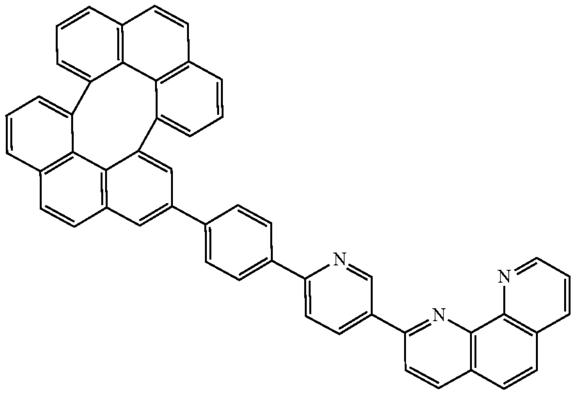
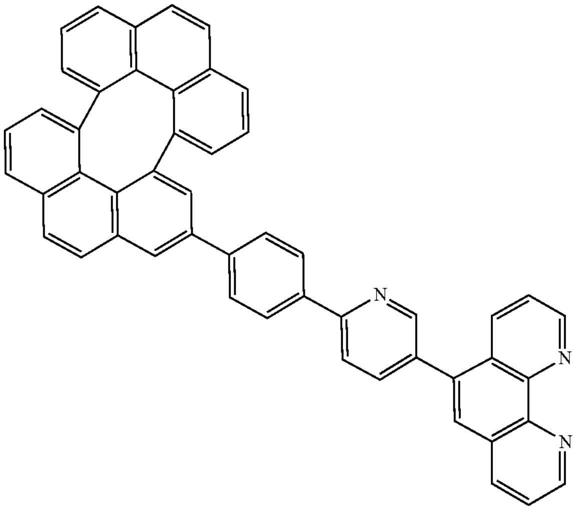
-continued
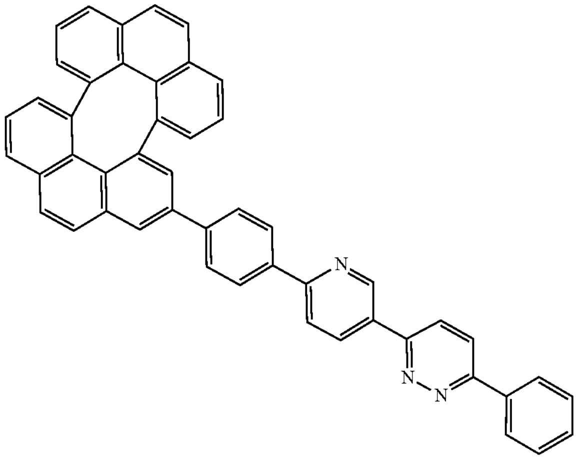
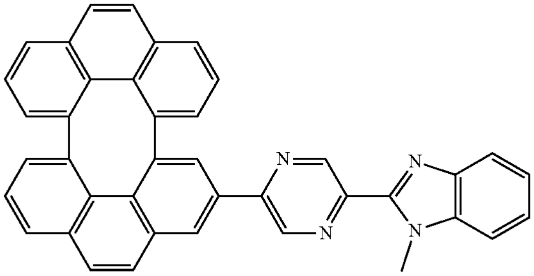
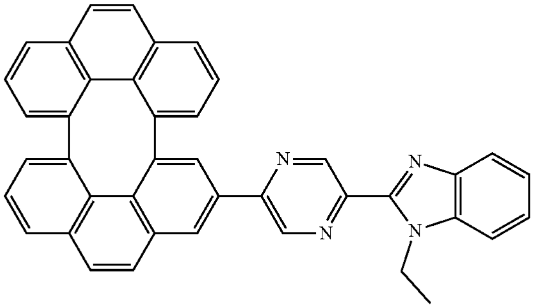
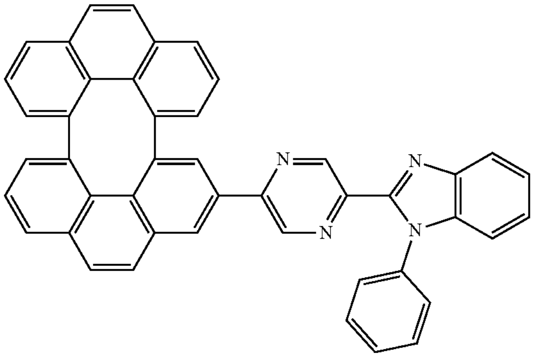
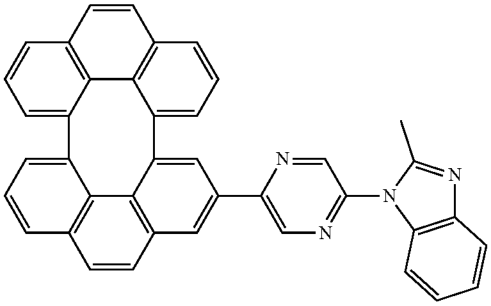

-continued
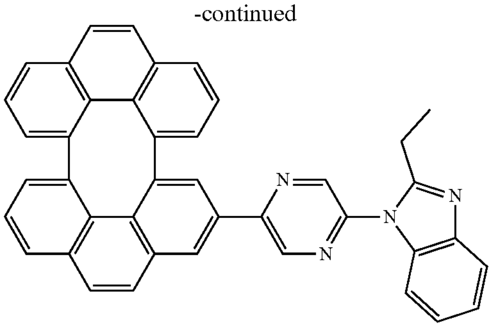
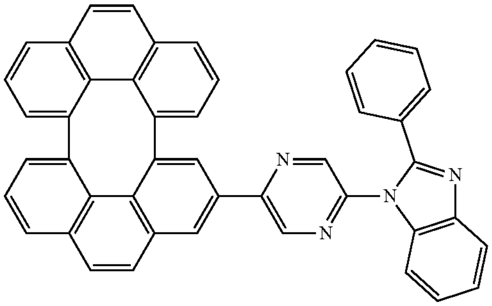
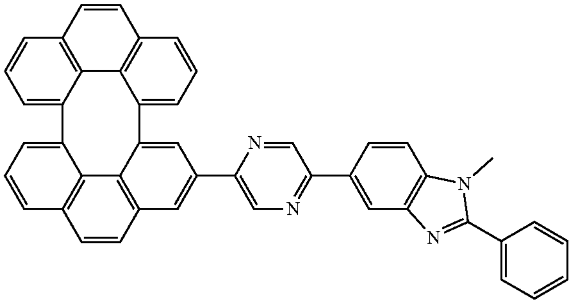
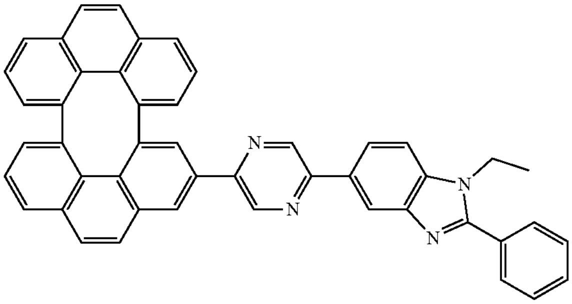
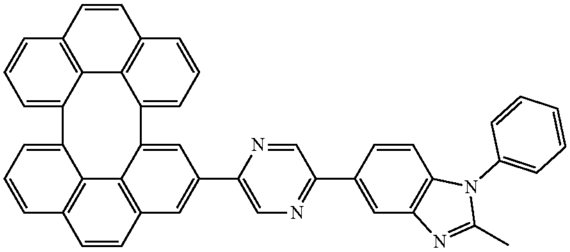
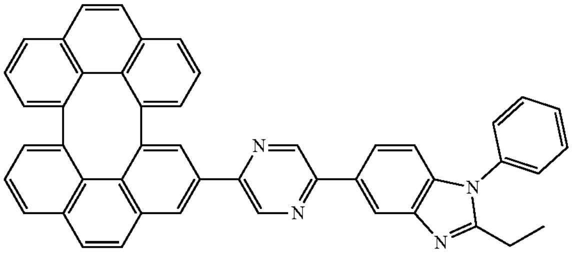
-continued
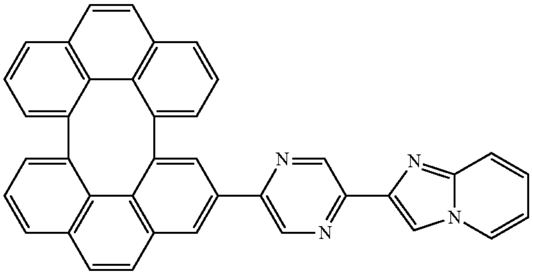
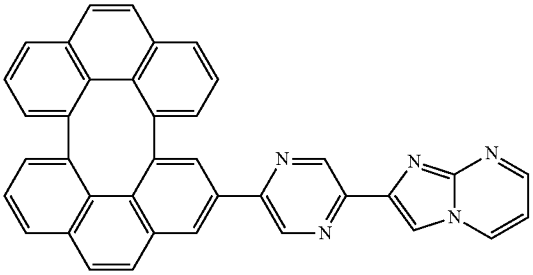
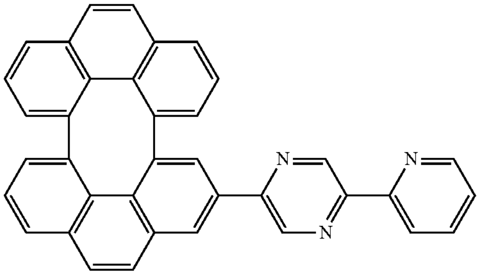
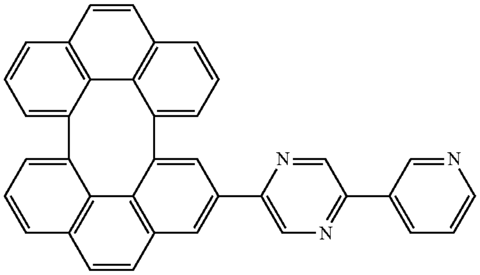
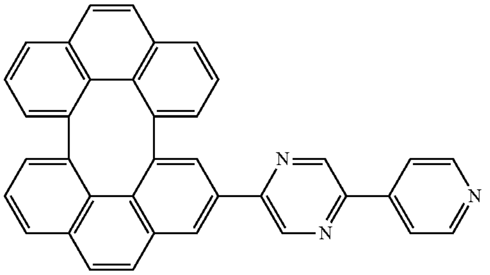
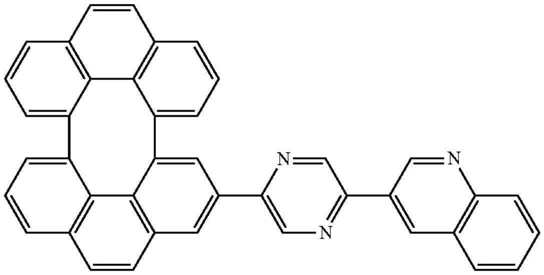

-continued
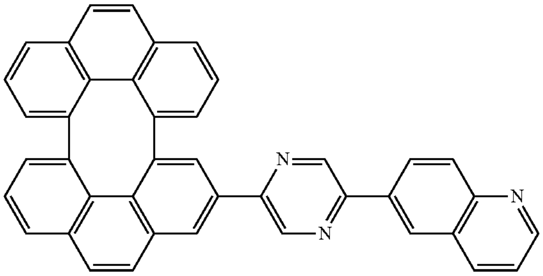
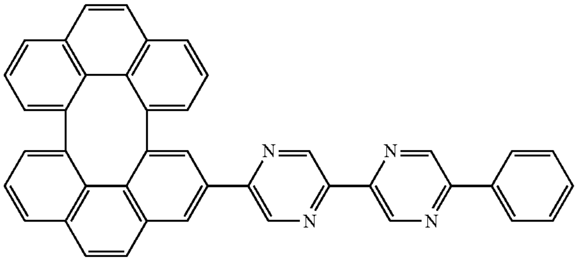
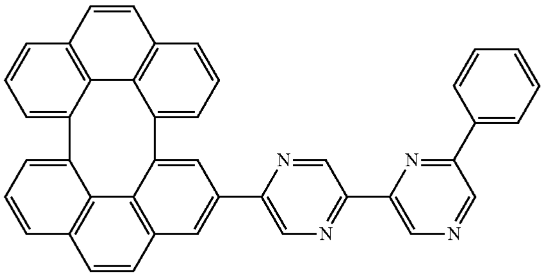
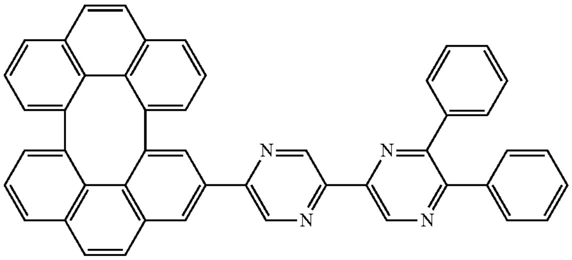
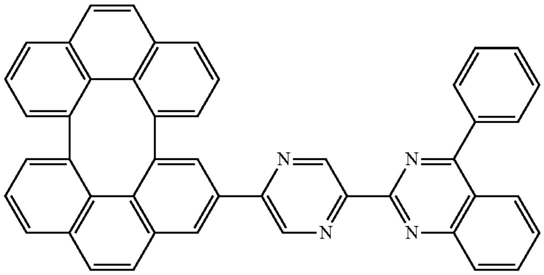
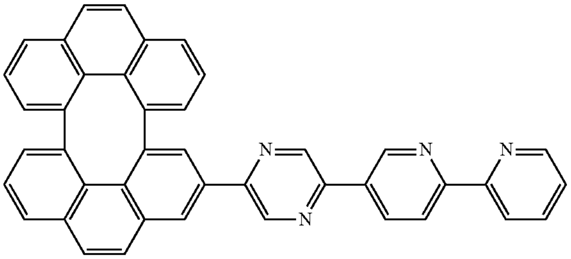
-continued
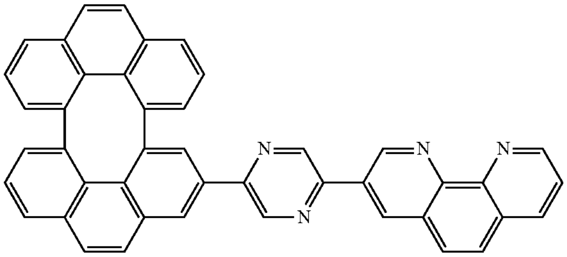
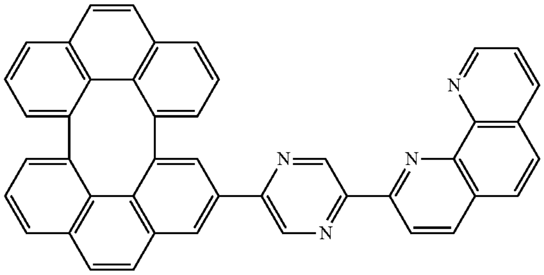
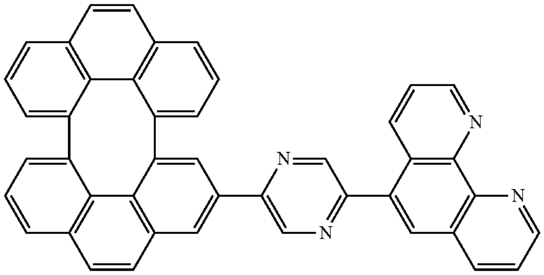
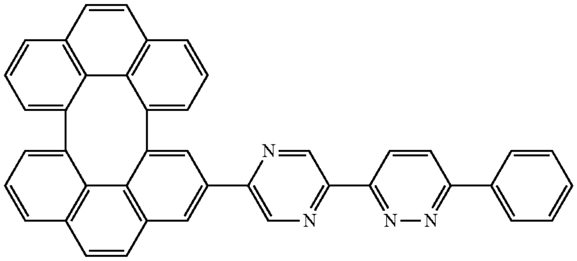
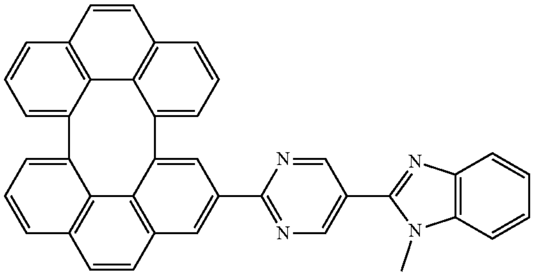
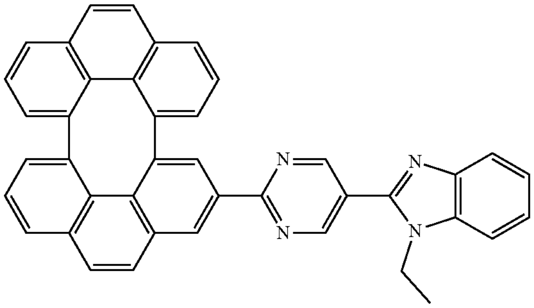

-continued
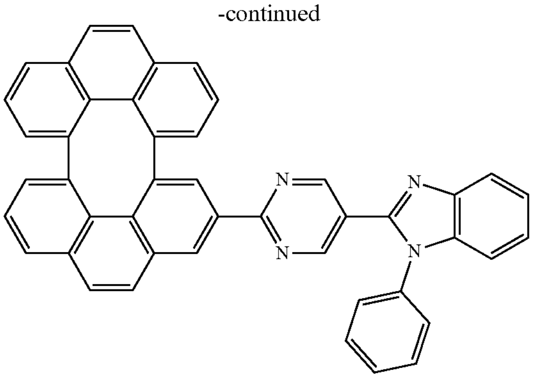
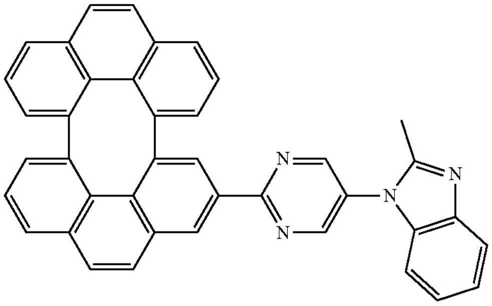
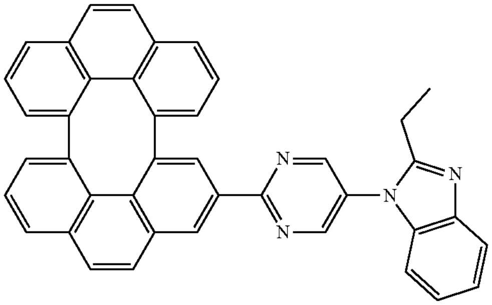
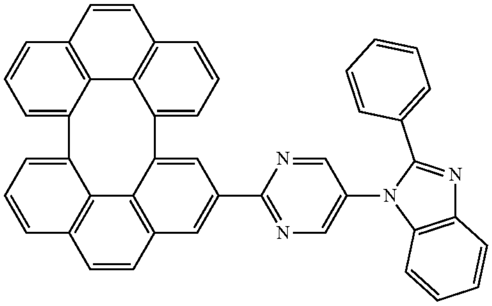
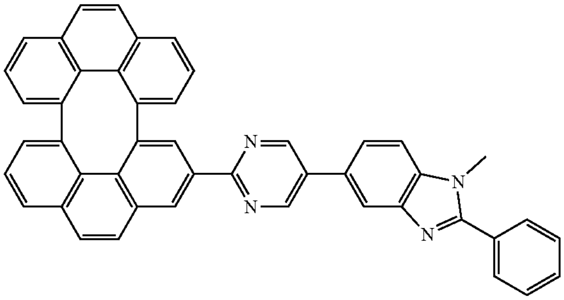
-continued
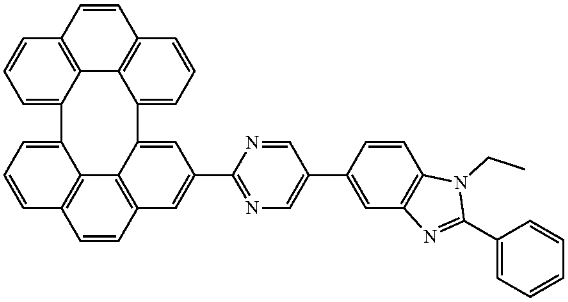
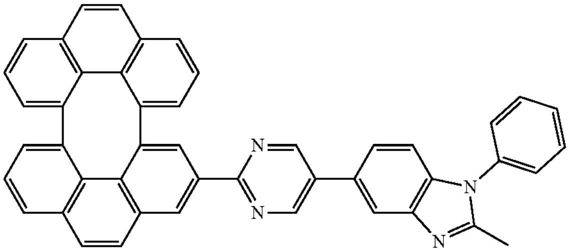
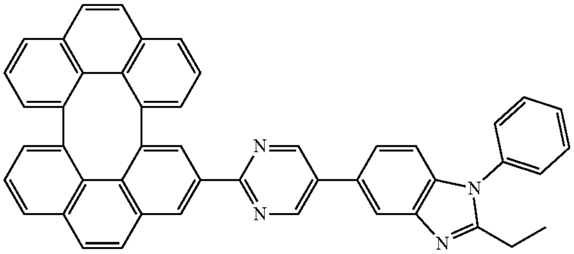
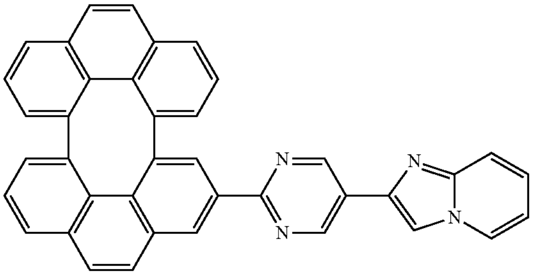
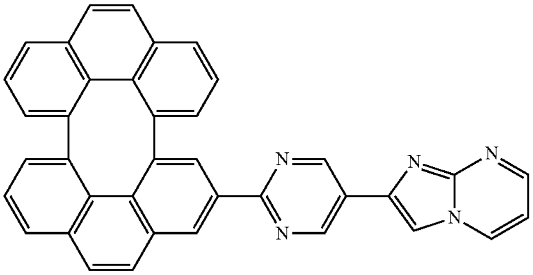
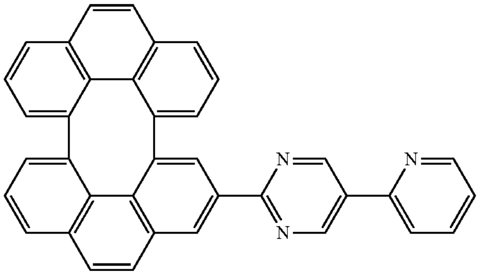

-continued
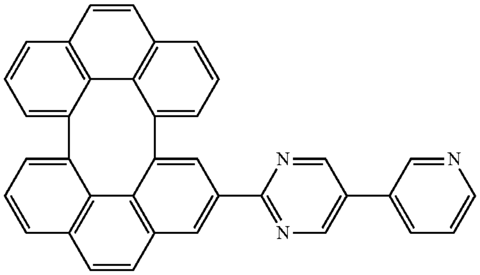
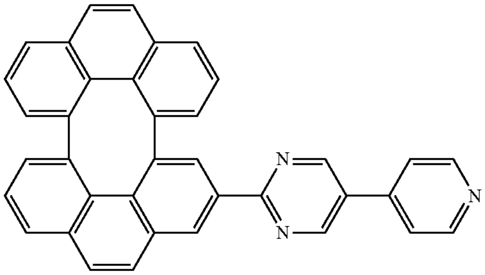
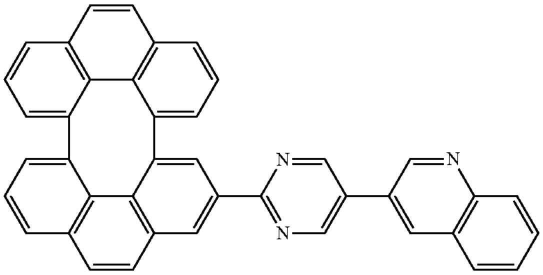
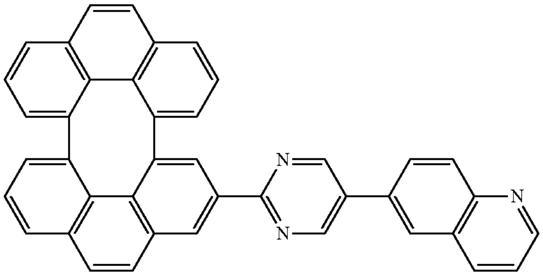
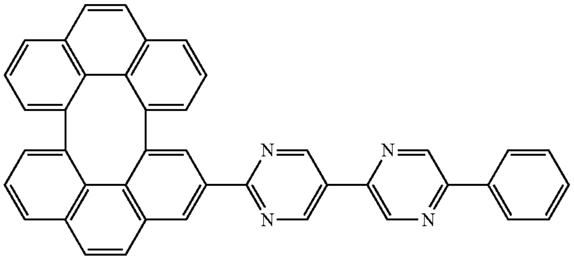
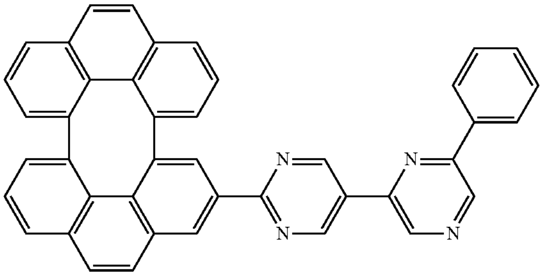
-continued
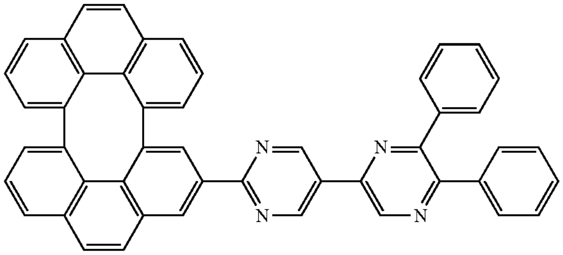
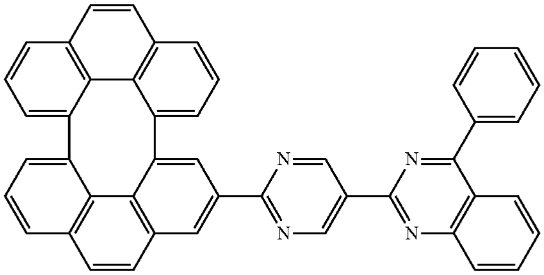
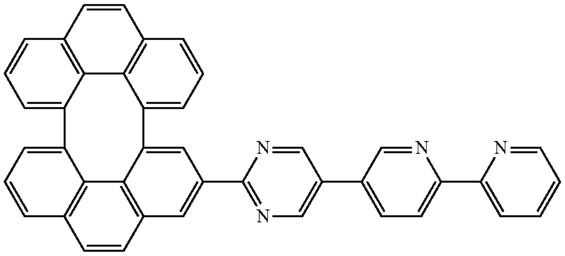
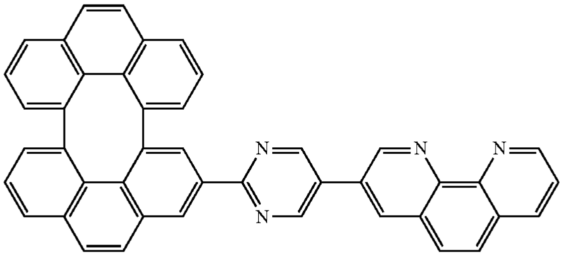
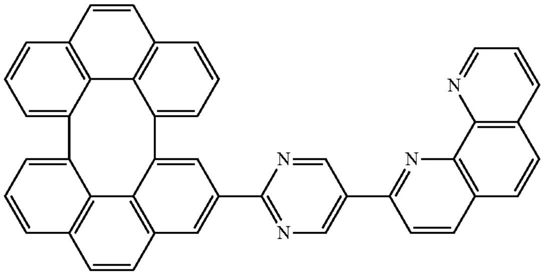
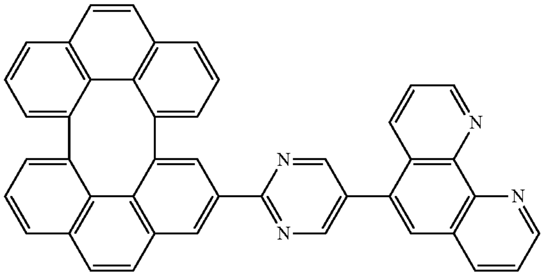

-continued
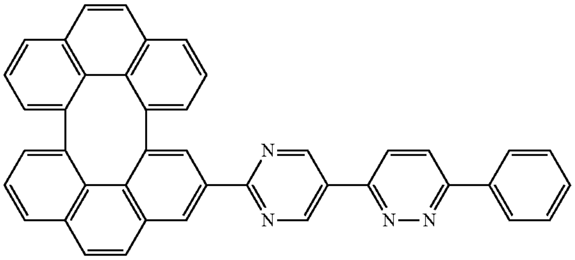
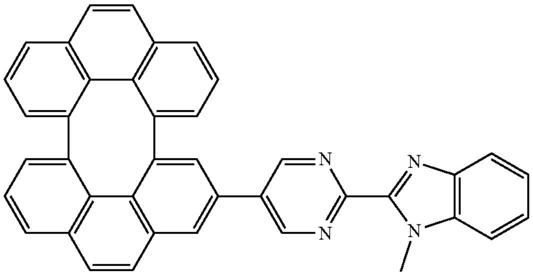
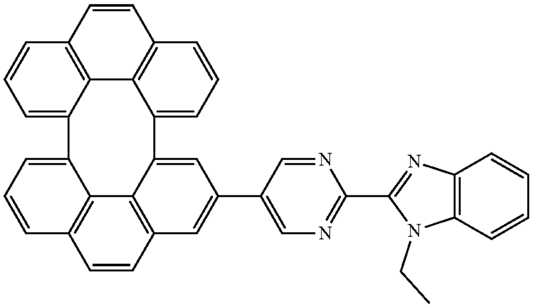
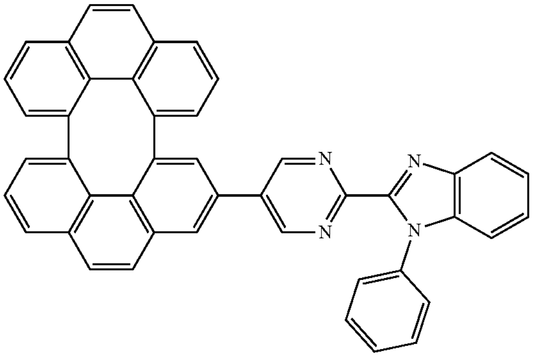
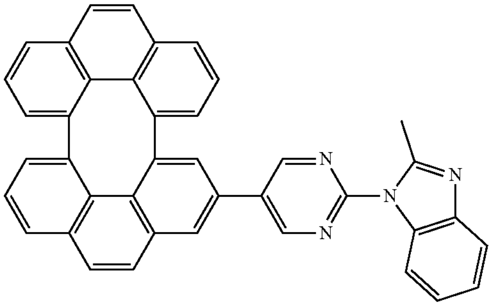
-continued
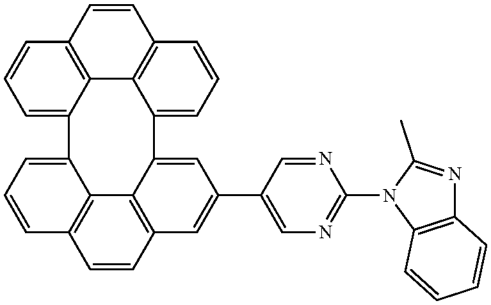
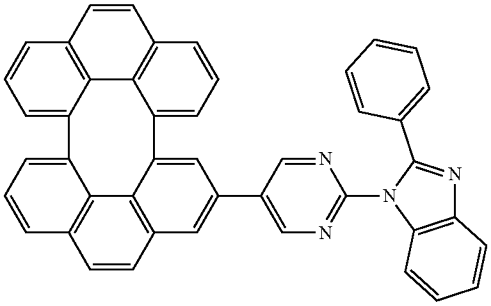
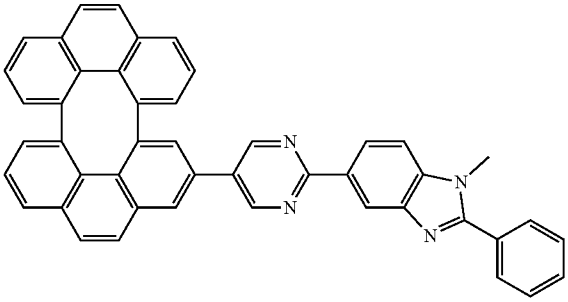
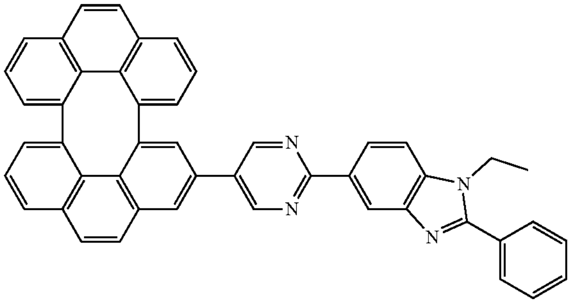
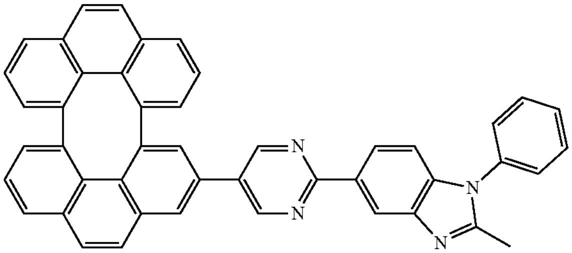
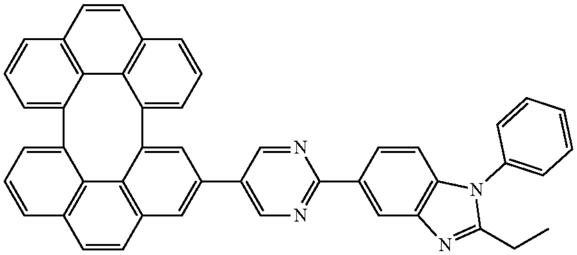

-continued
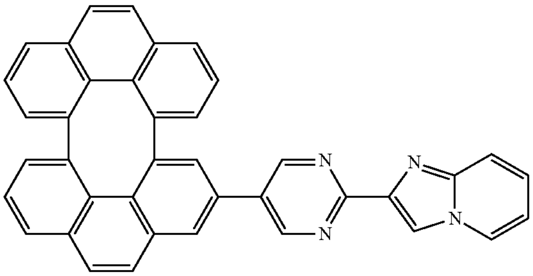
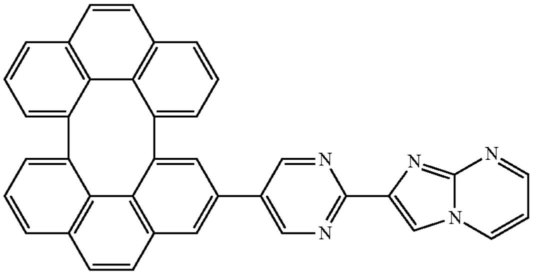
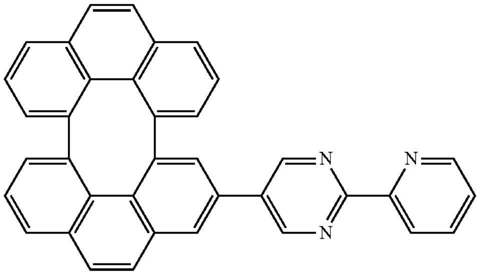
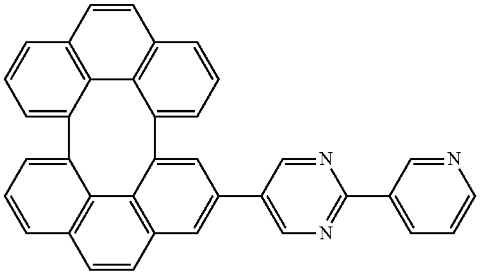
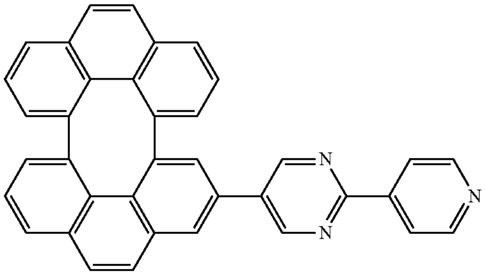
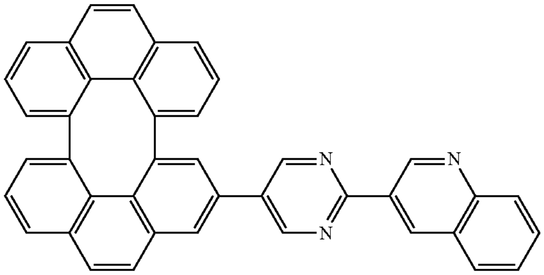
-continued
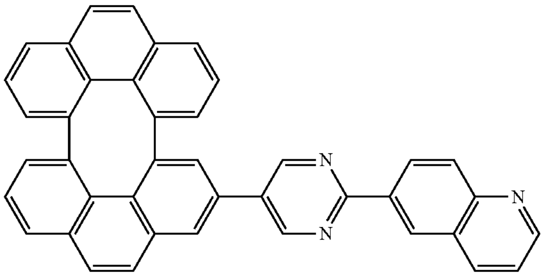
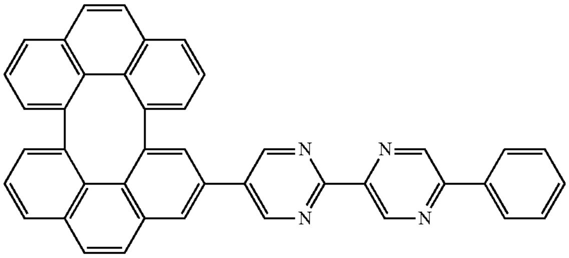
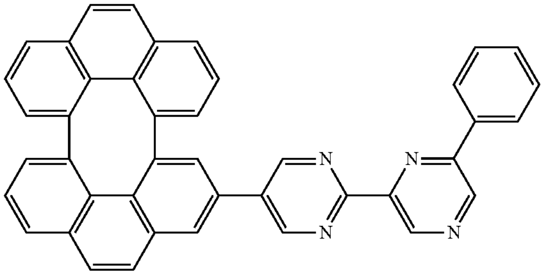
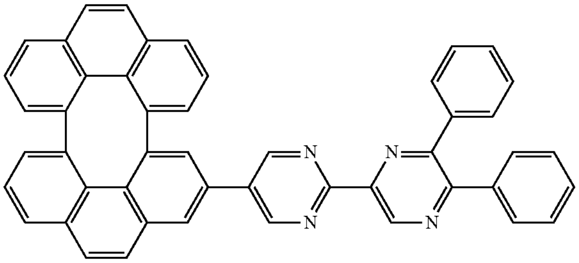
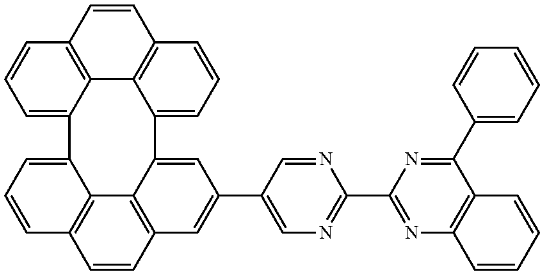
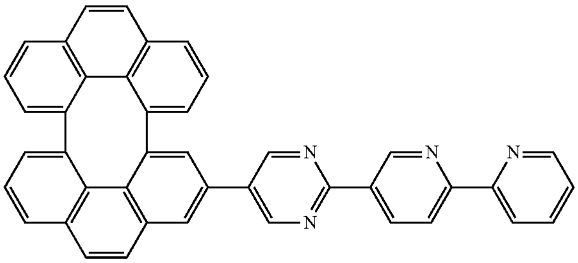

-continued
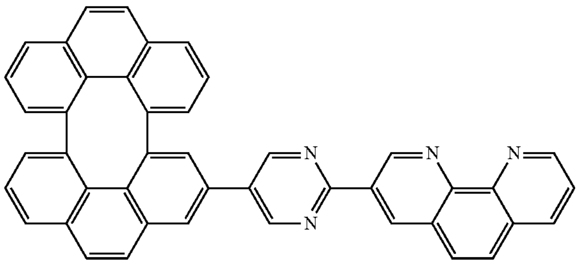
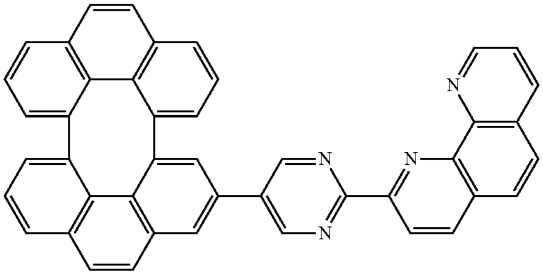
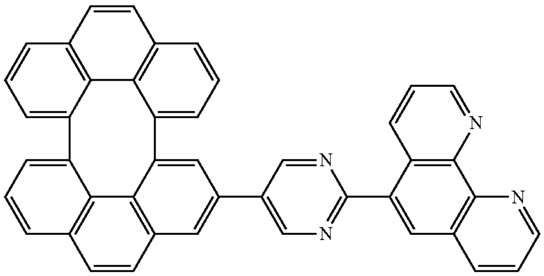
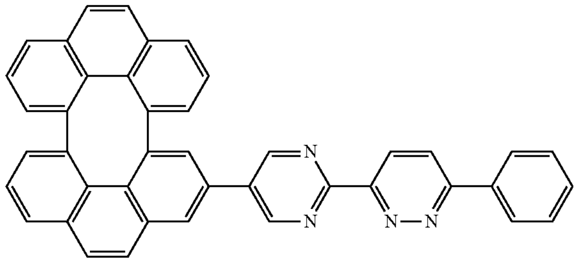
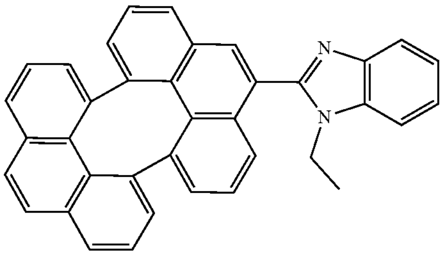
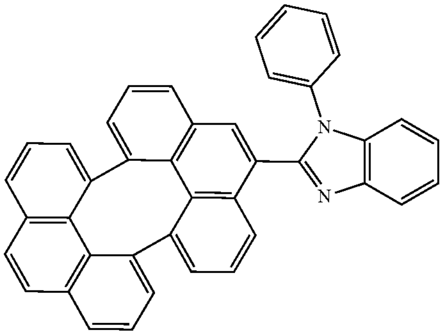
-continued
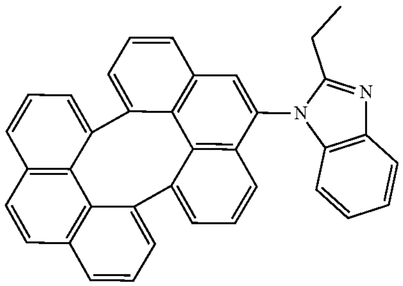
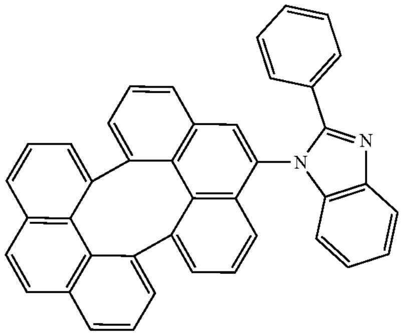
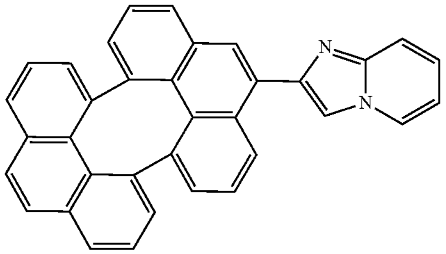
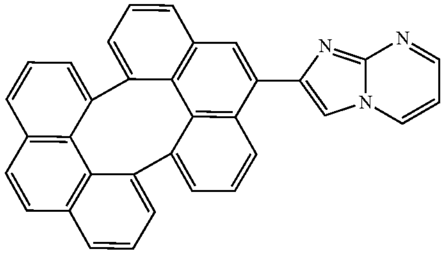
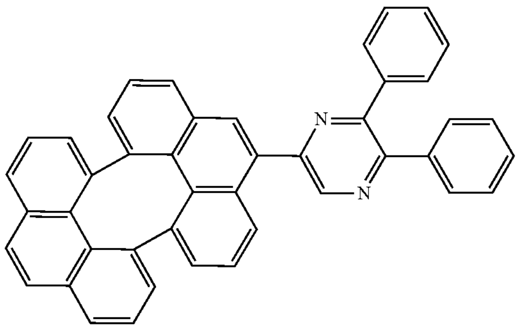

-continued
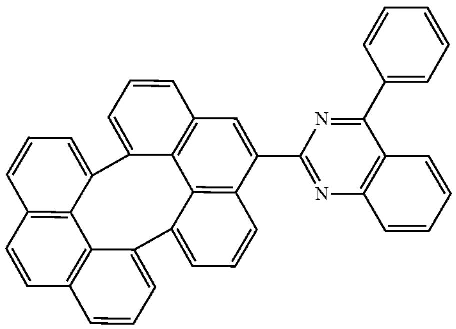
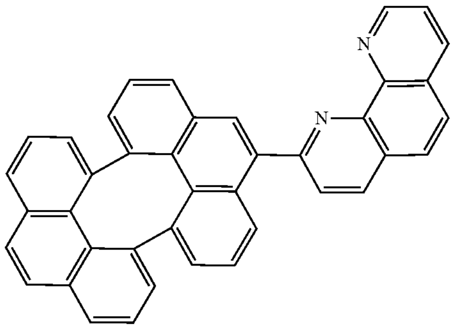
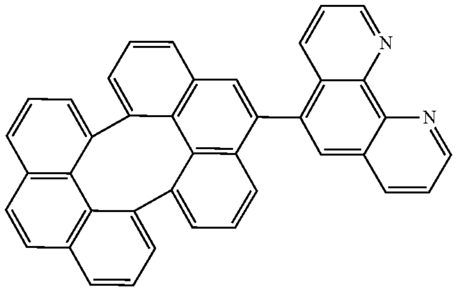
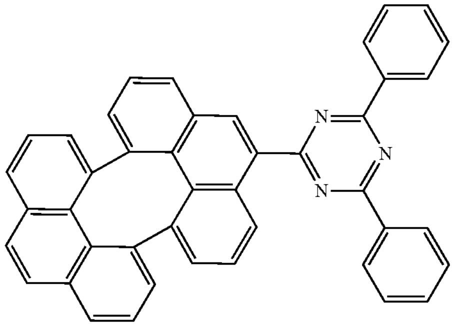
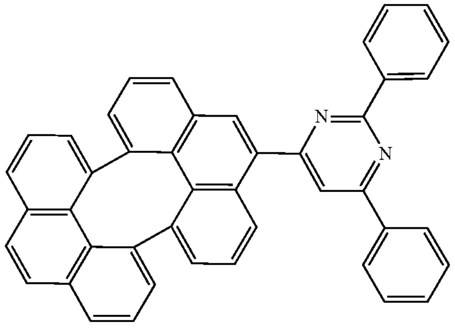
-continued
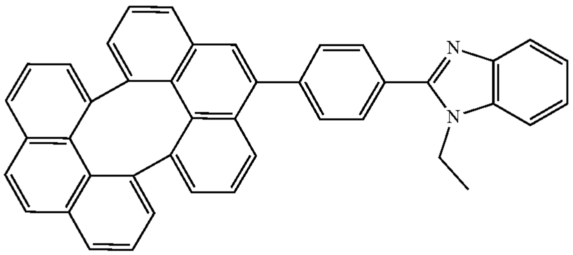
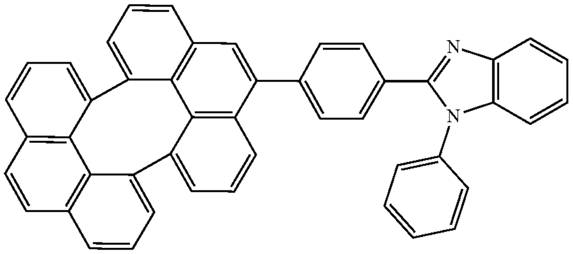
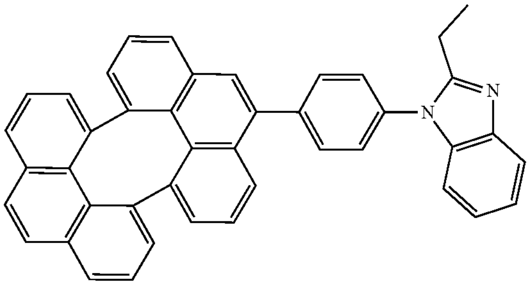
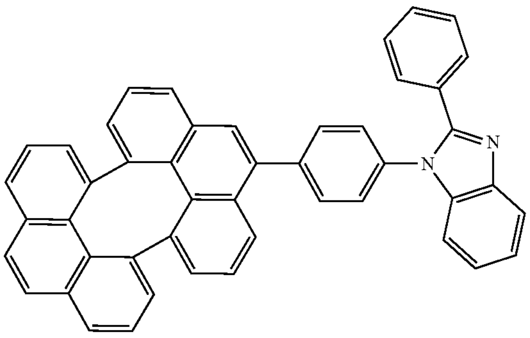
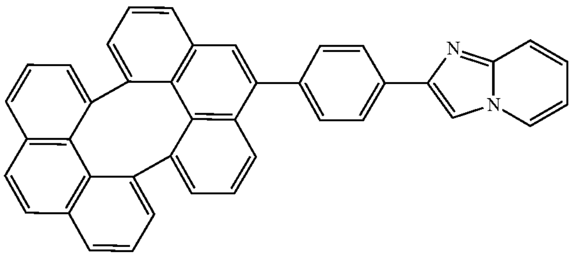
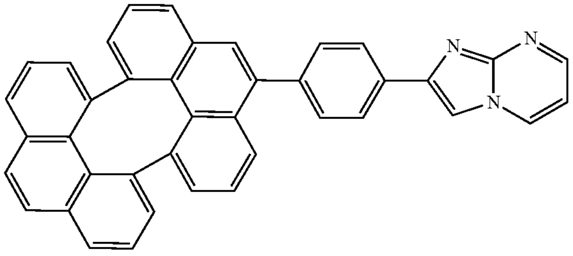

-continued
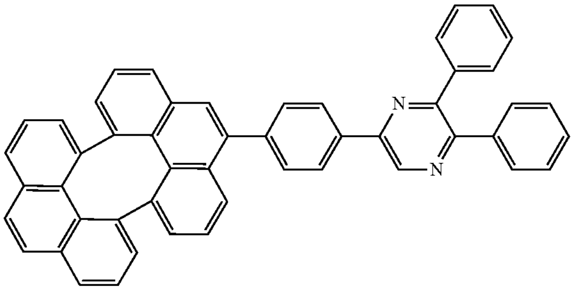
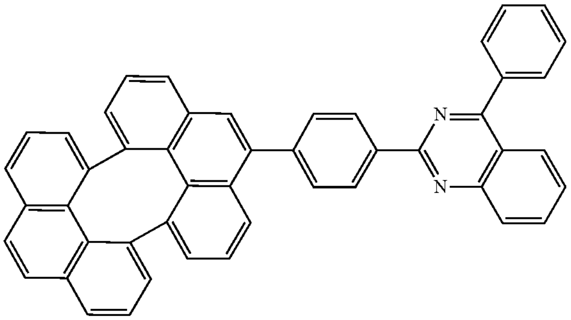
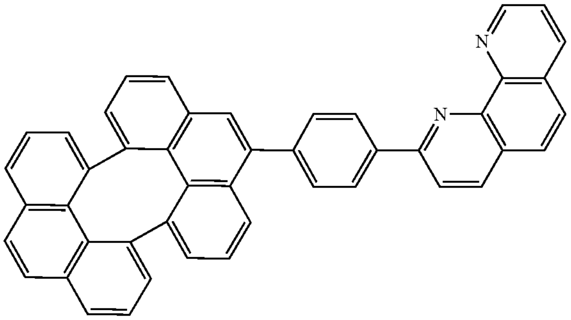
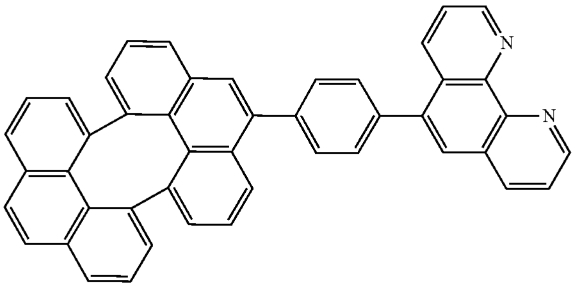
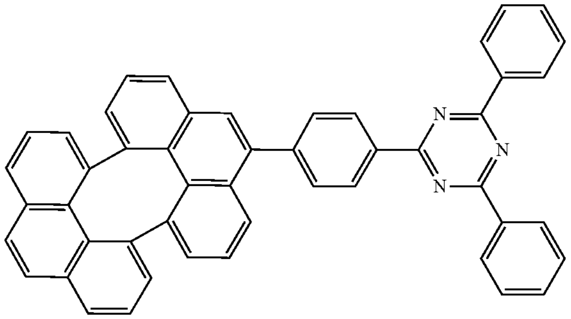
-continued
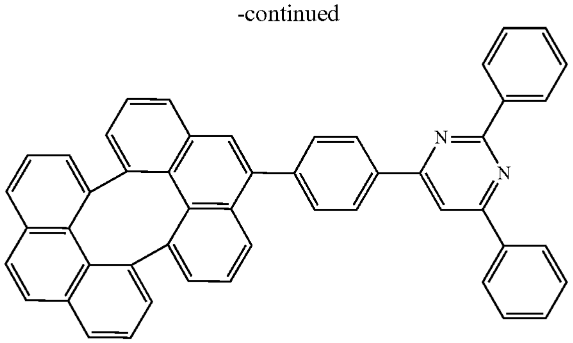
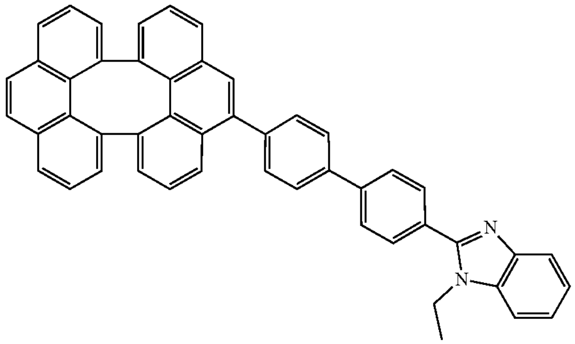
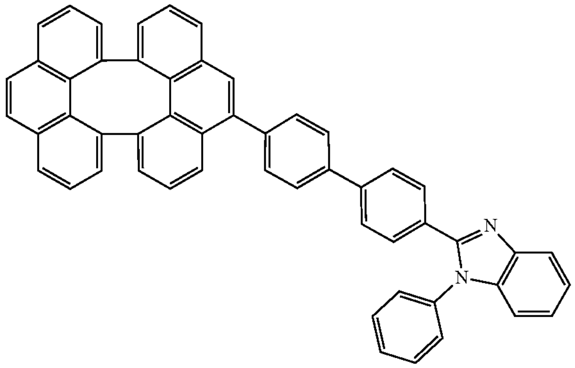
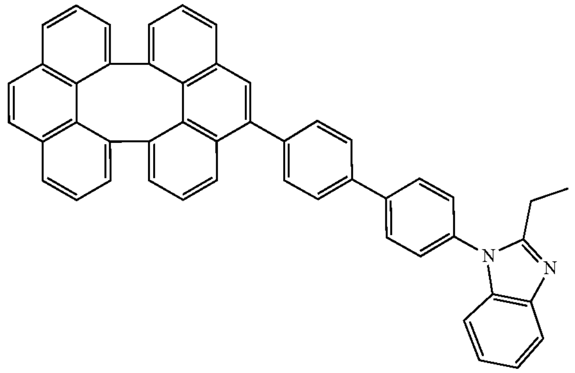

-continued
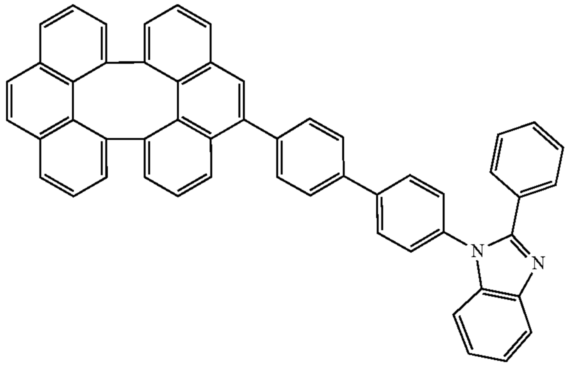
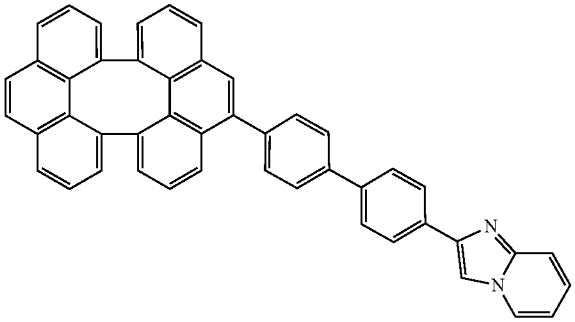
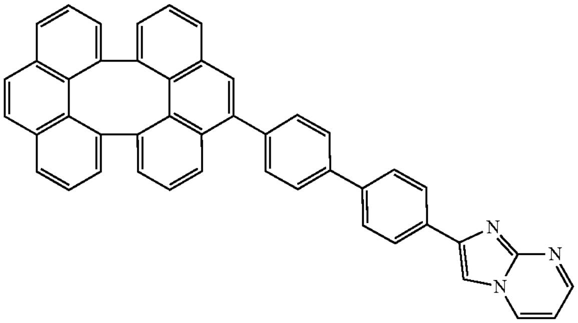
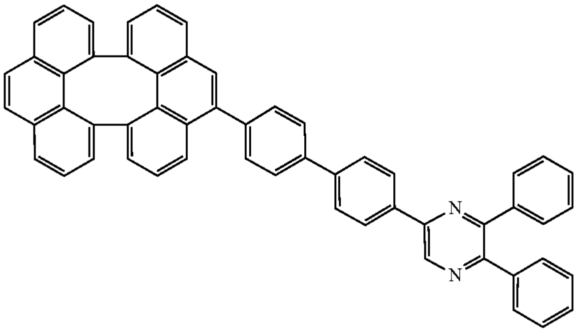
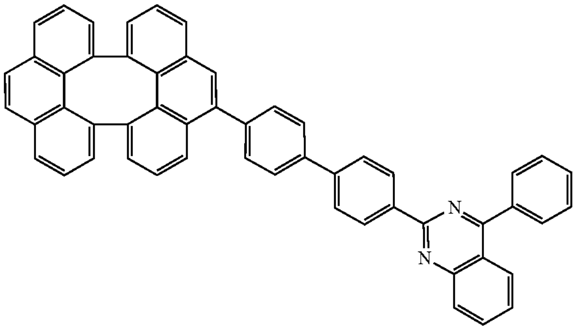
-continued
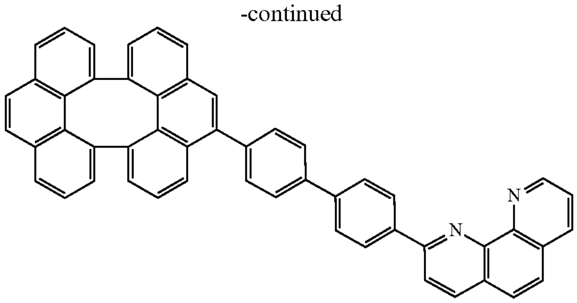
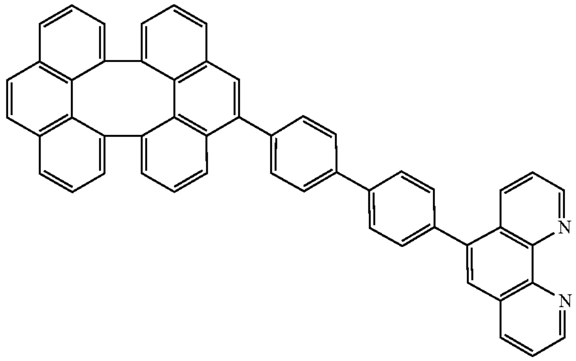
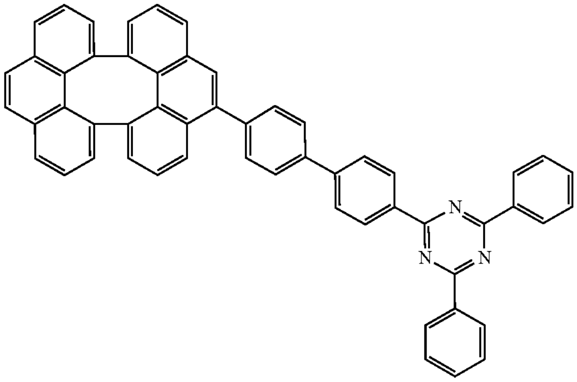
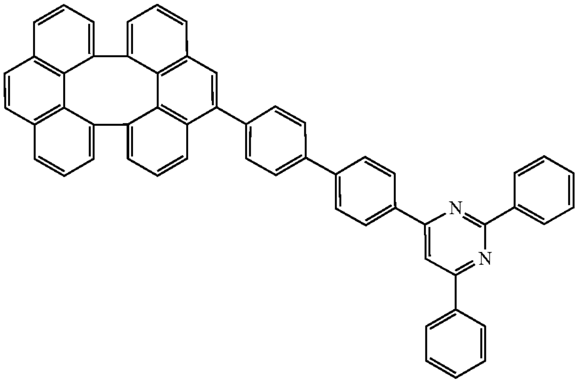
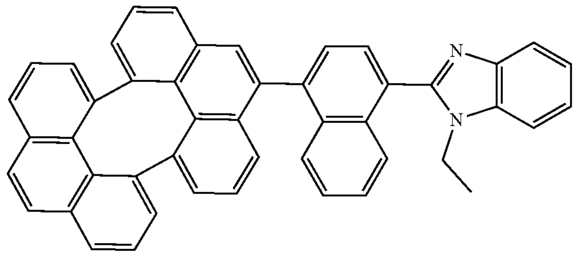

-continued
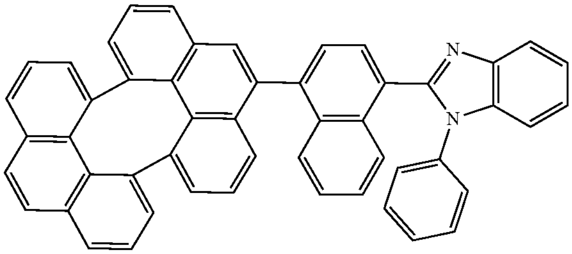
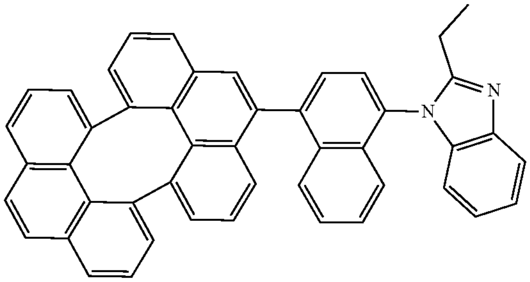
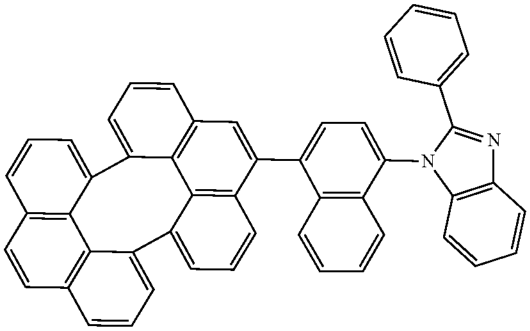
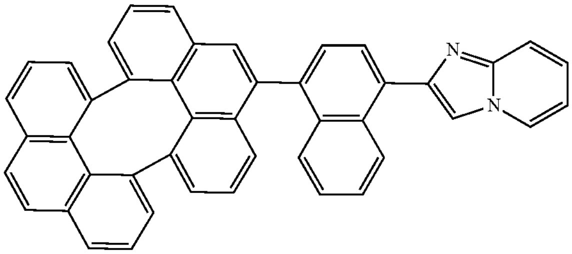
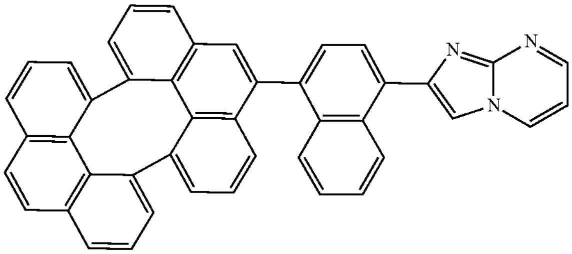
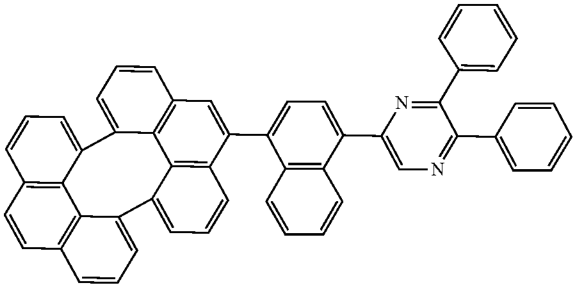
-continued
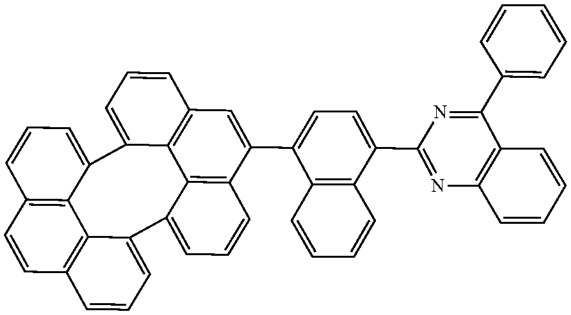
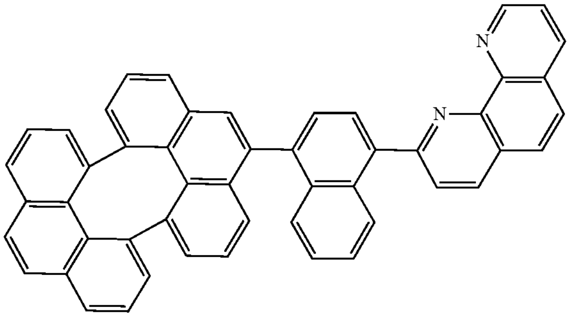
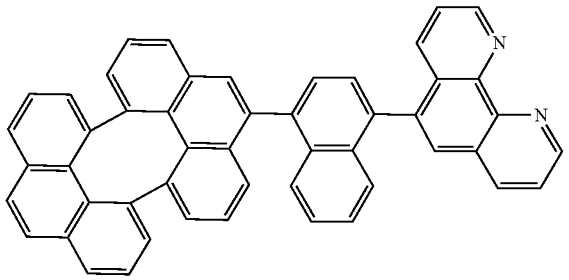
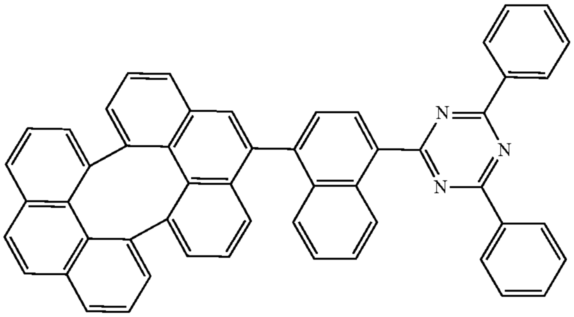
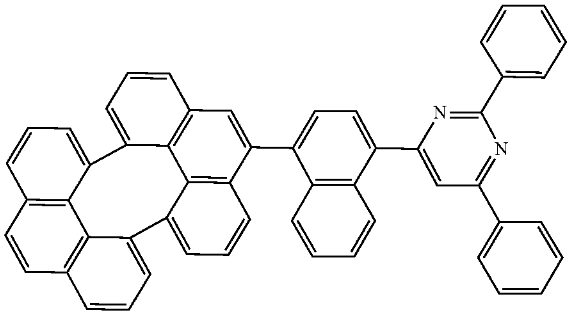

-continued
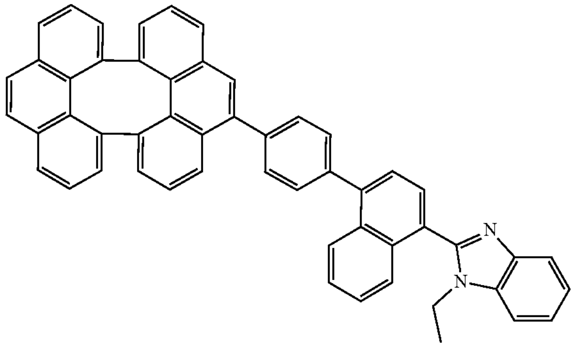
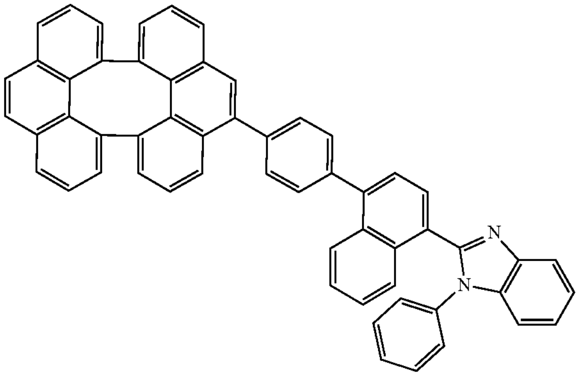
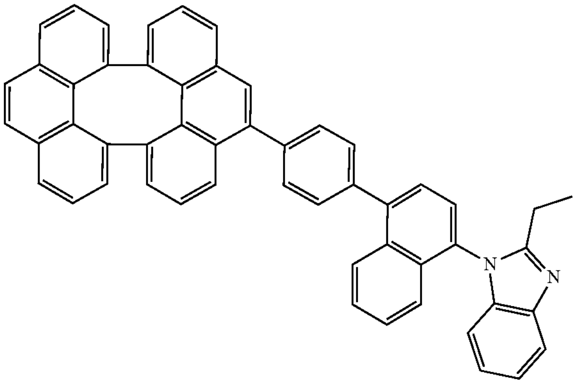
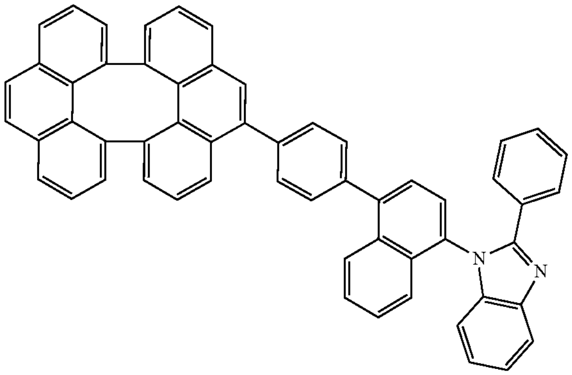
-continued
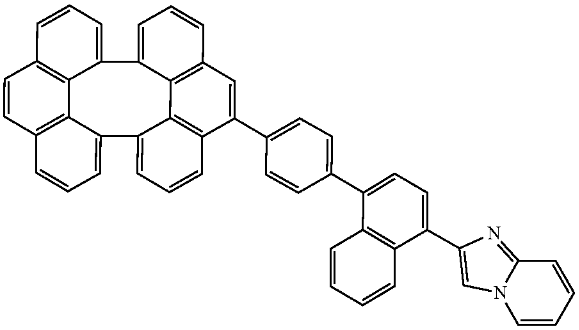
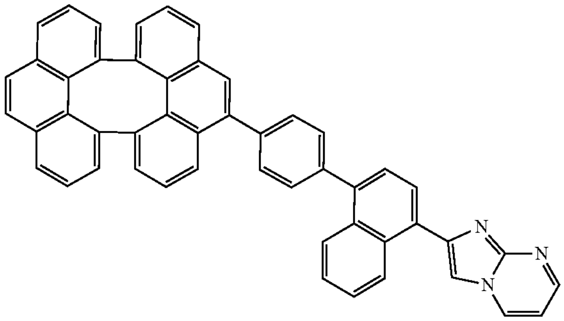
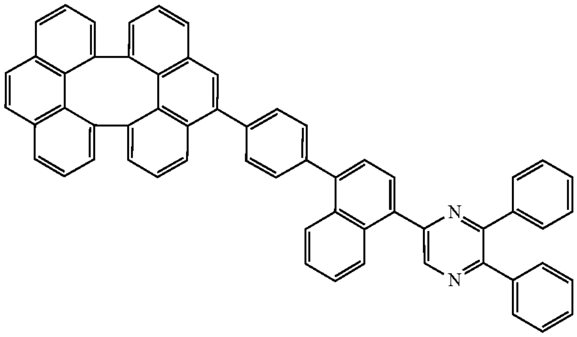
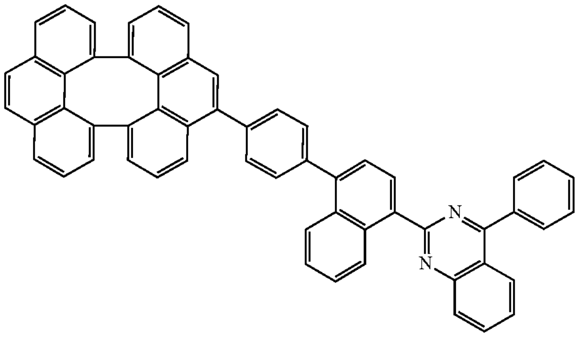
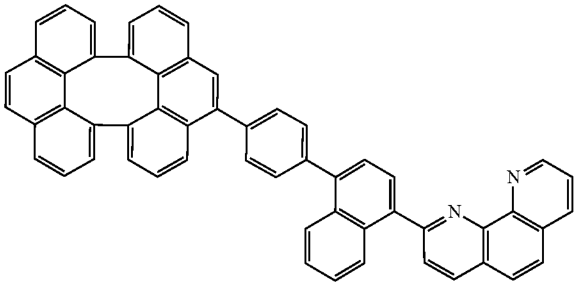

-continued
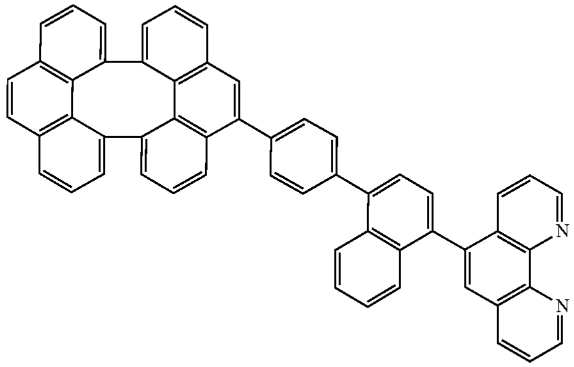
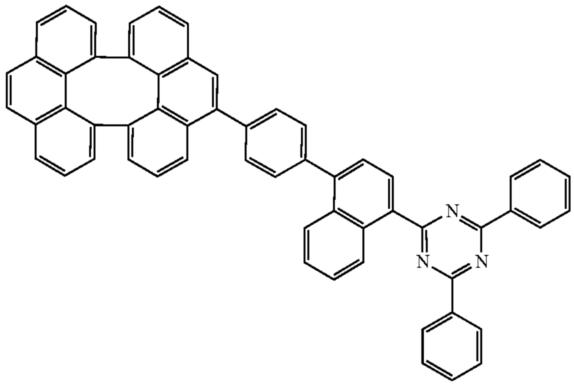
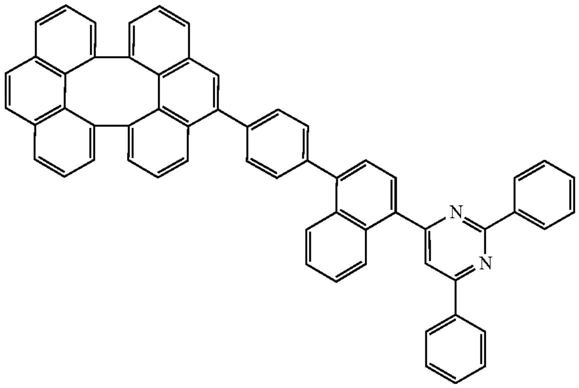
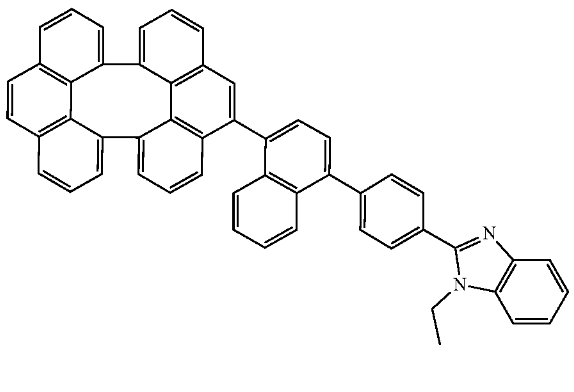
-continued
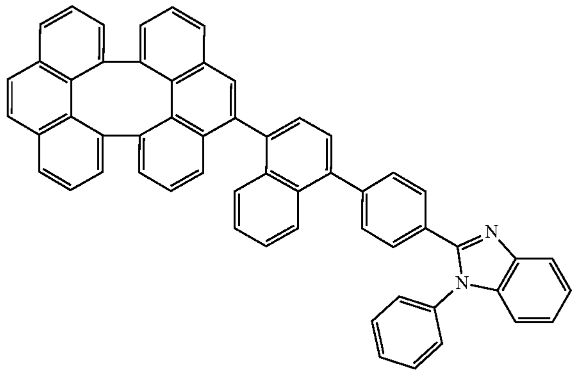
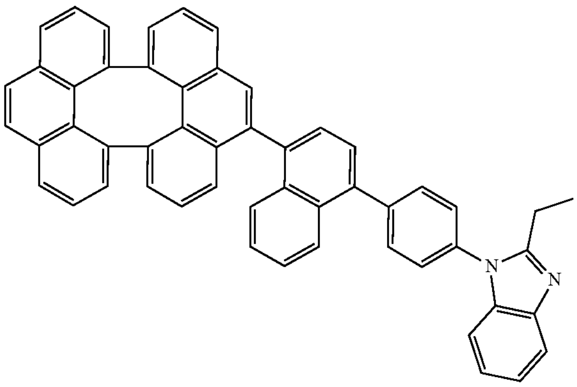
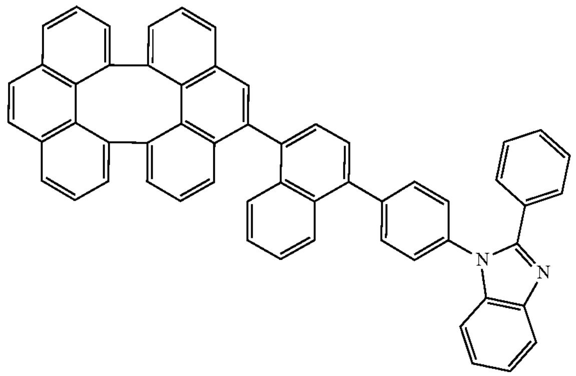
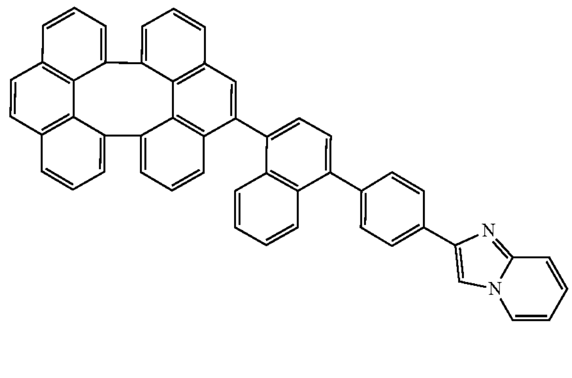

-continued
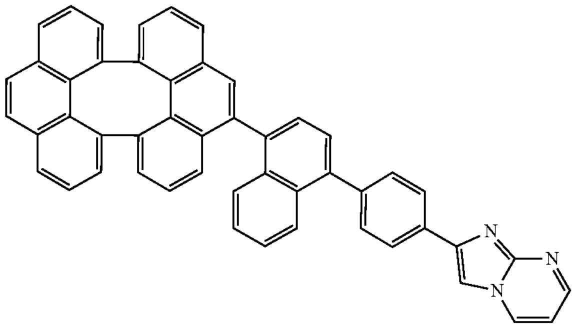
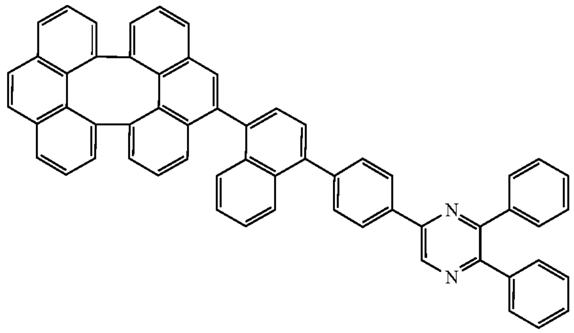
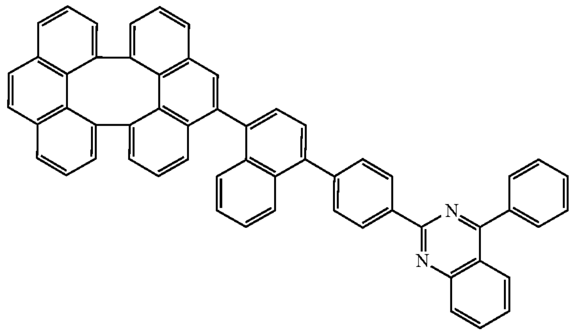
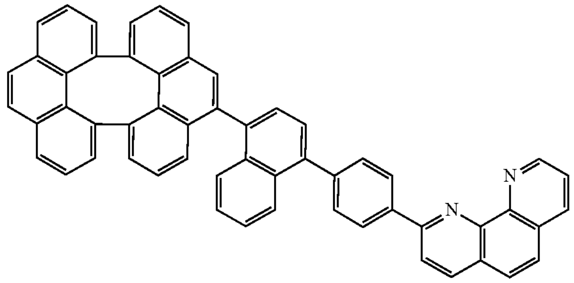
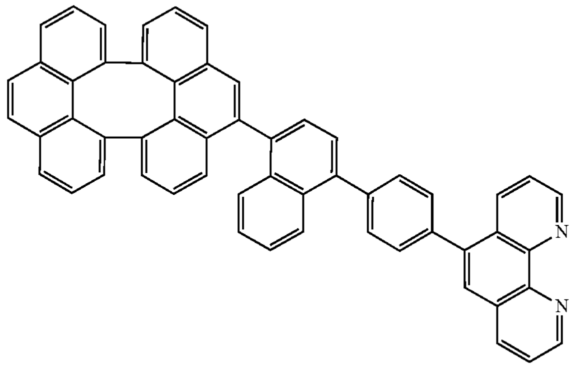
-continued
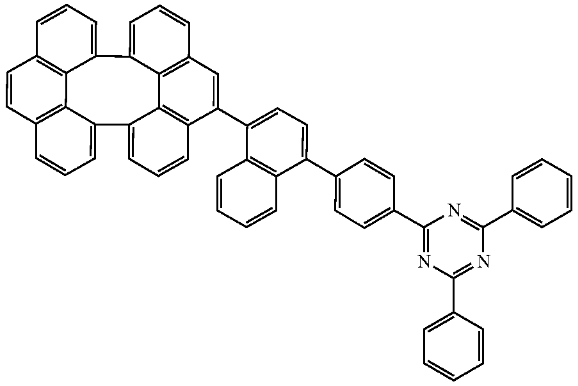
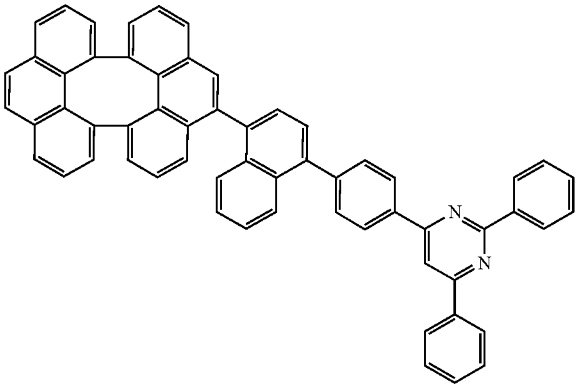
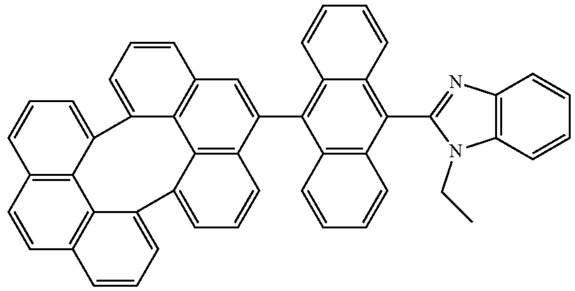
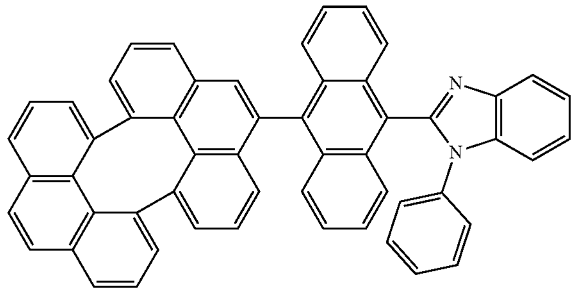

-continued
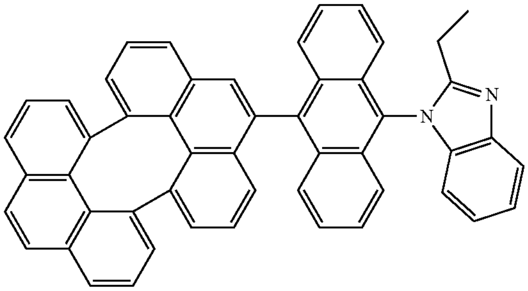
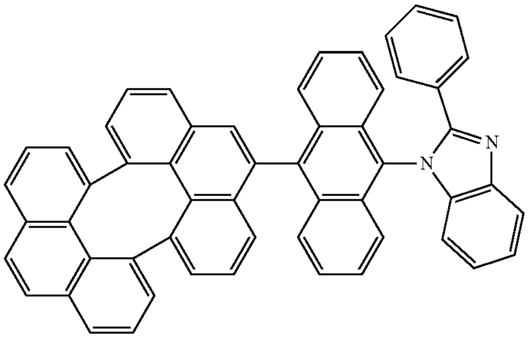
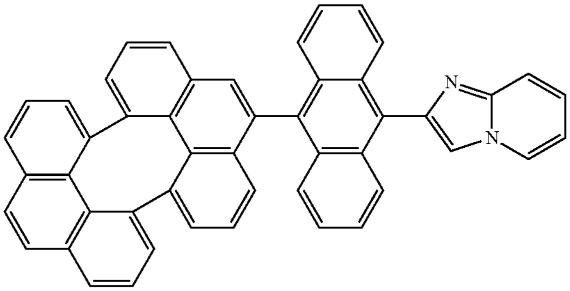
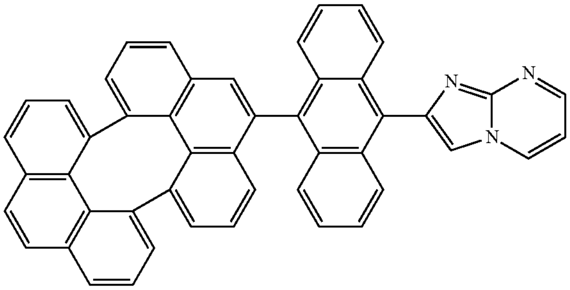
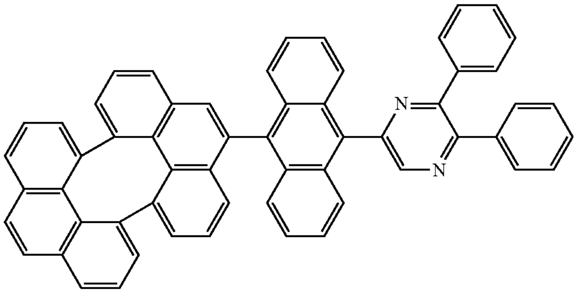
-continued
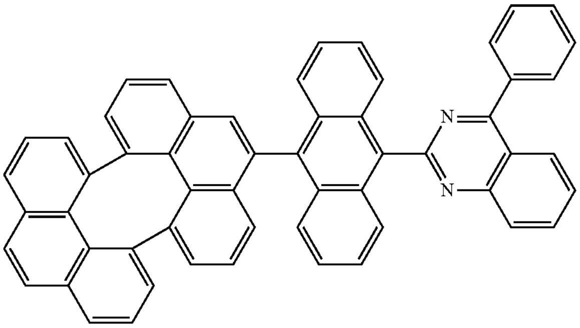
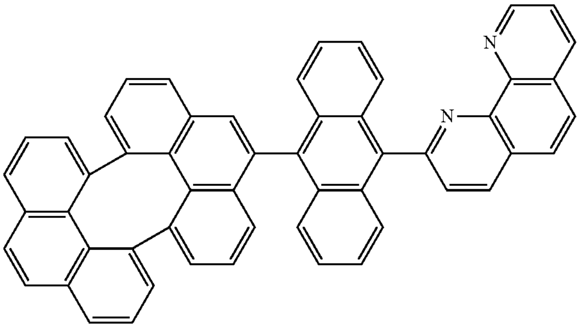
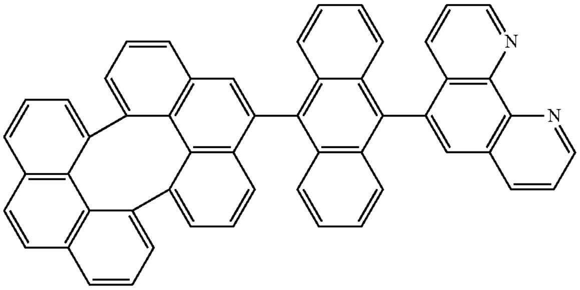
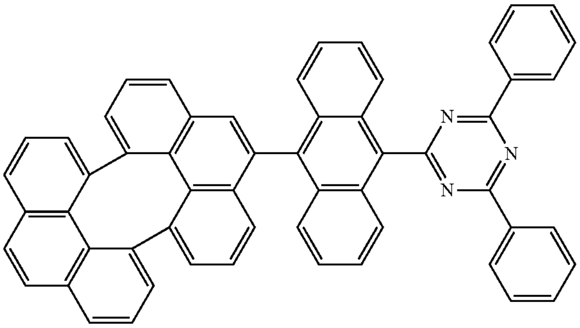
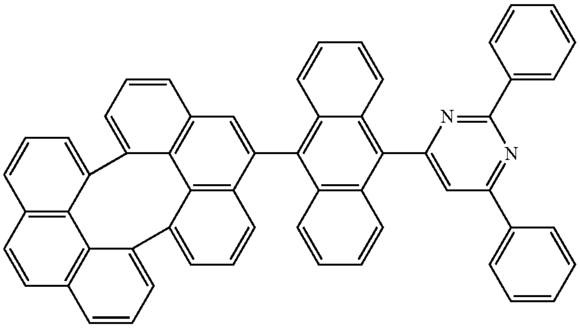

-continued
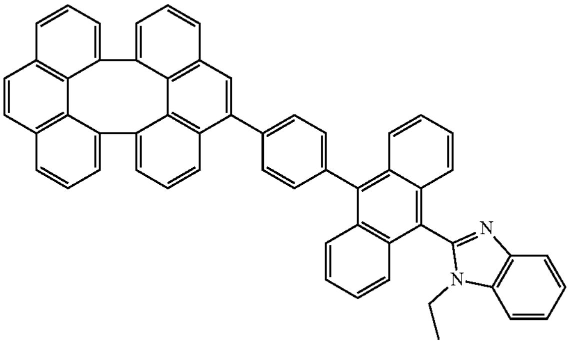
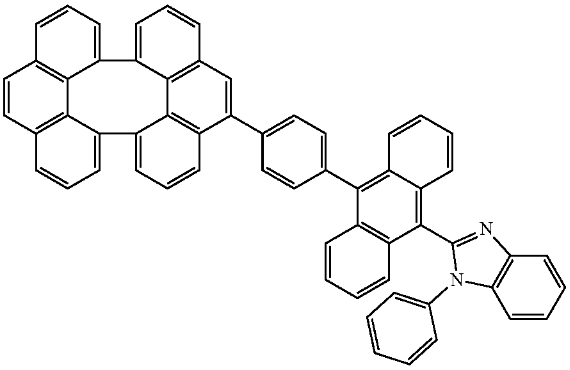
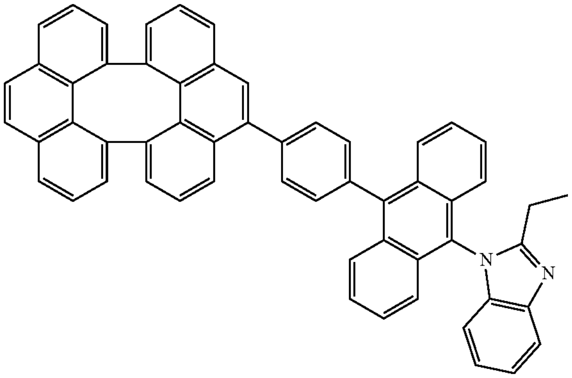
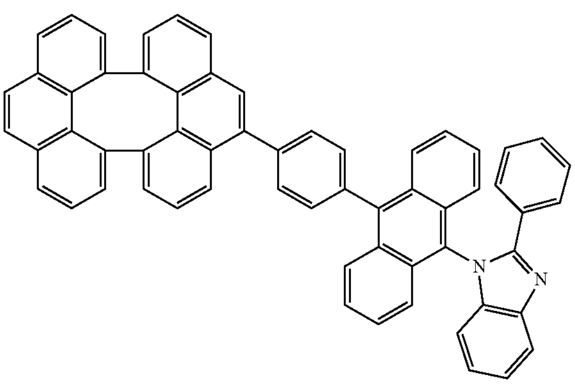
-continued
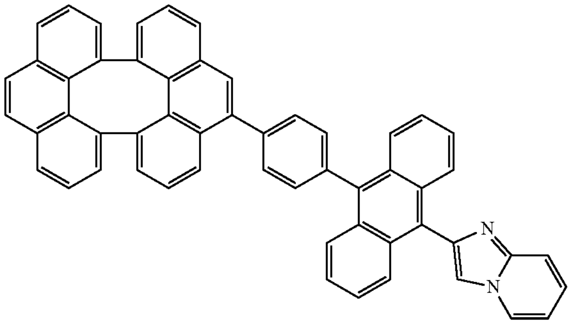
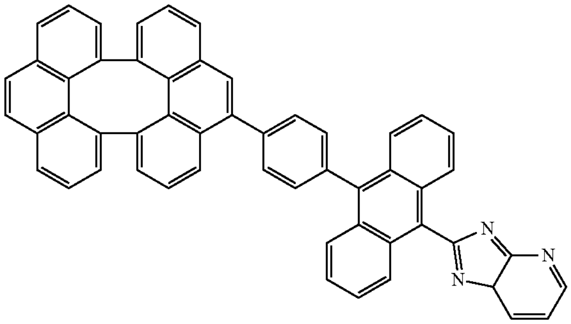
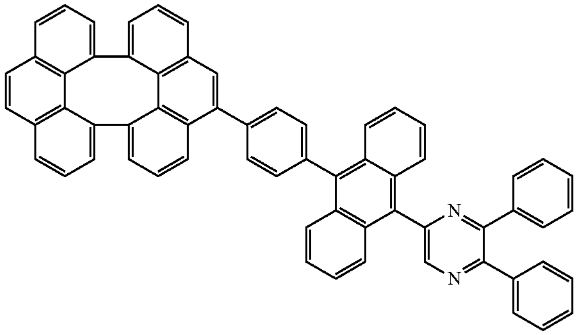
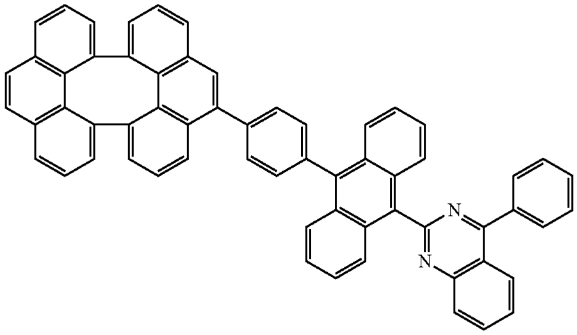
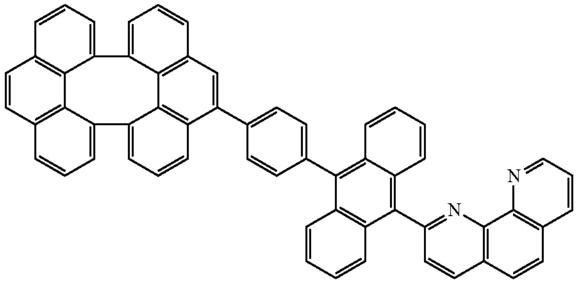

-continued
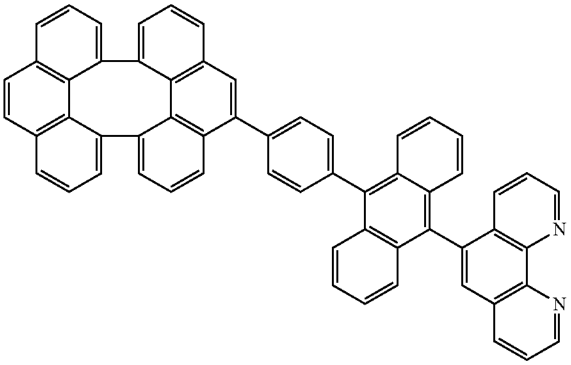
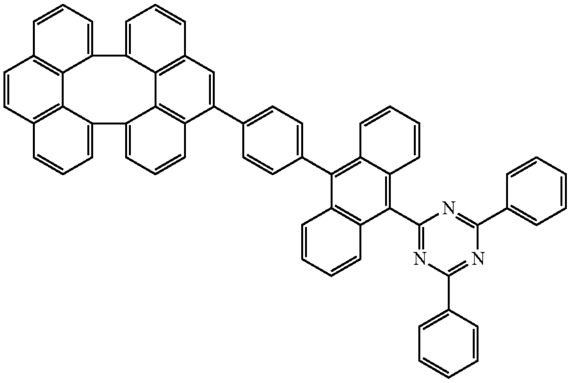
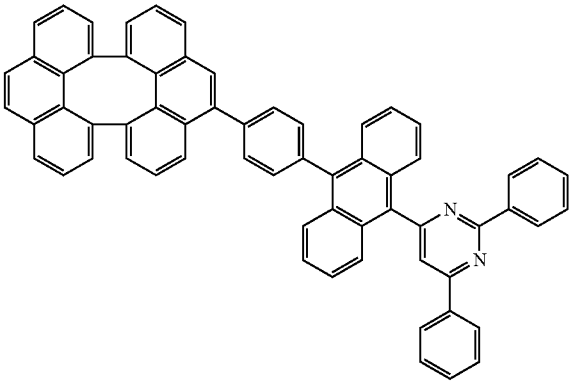
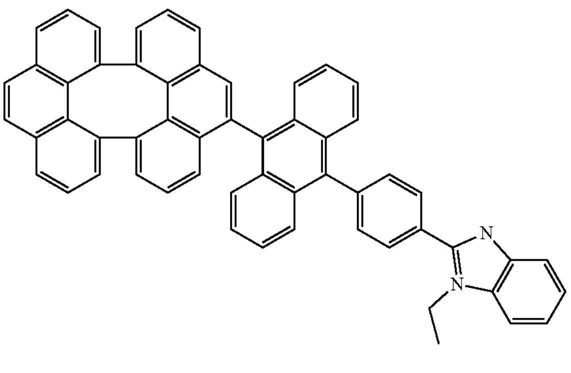
-continued
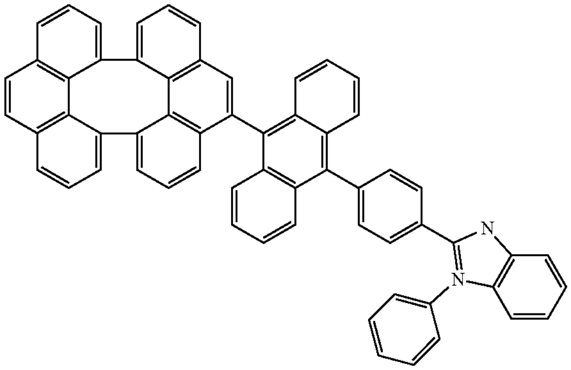
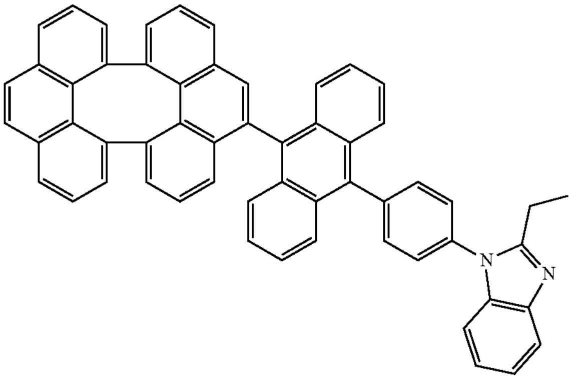
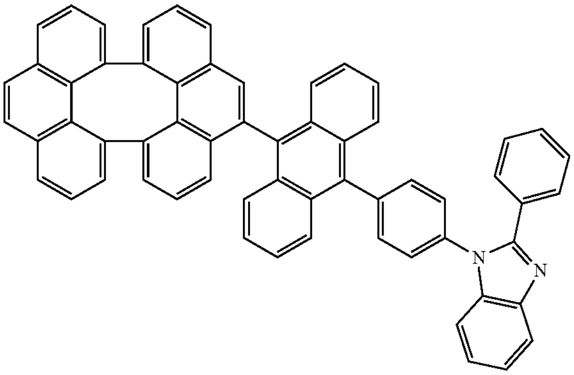
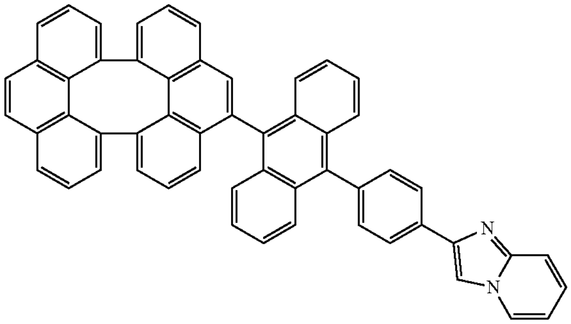

-continued
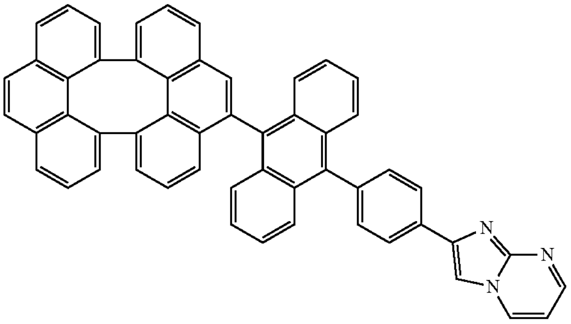
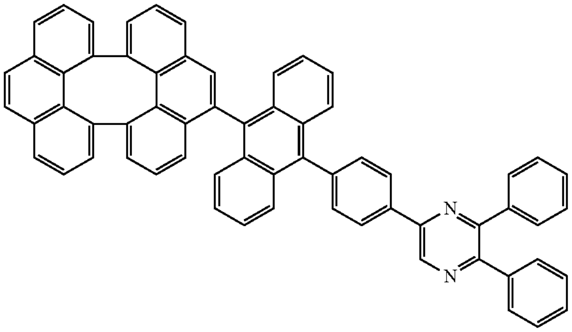
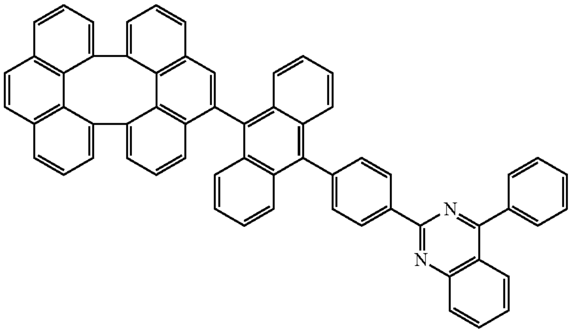
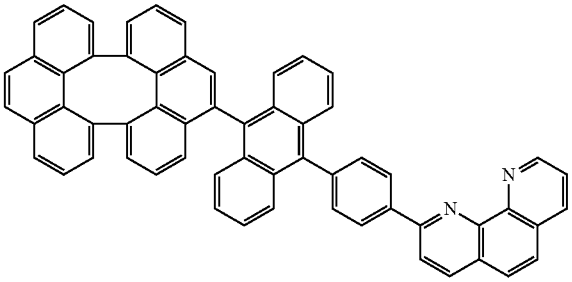
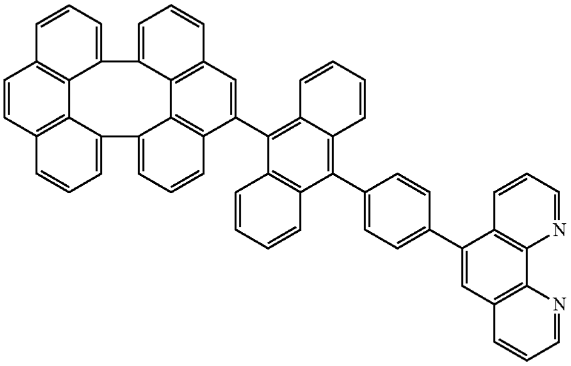
-continued
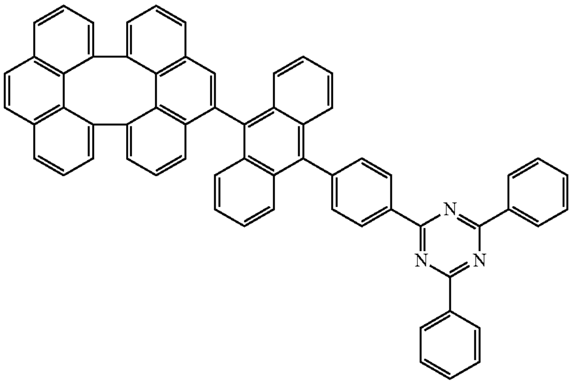
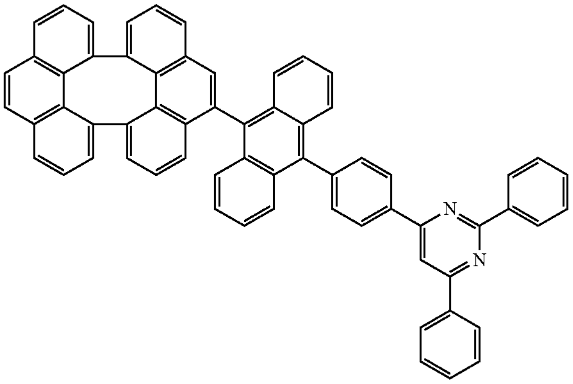
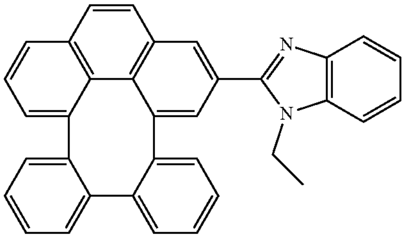
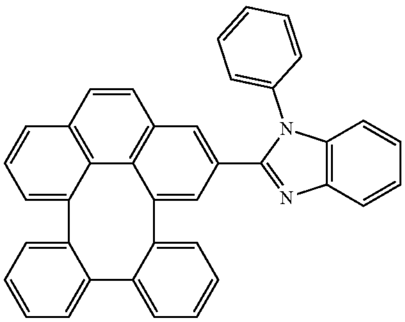
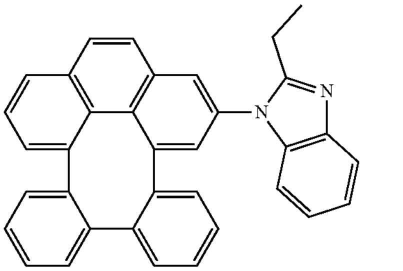

-continued
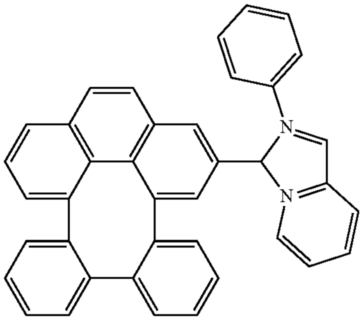
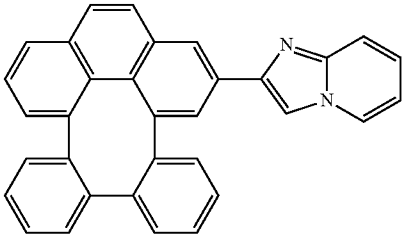
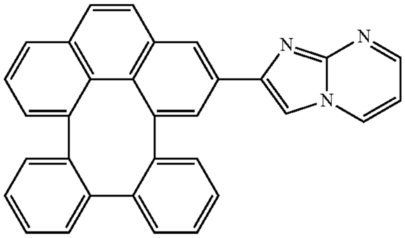
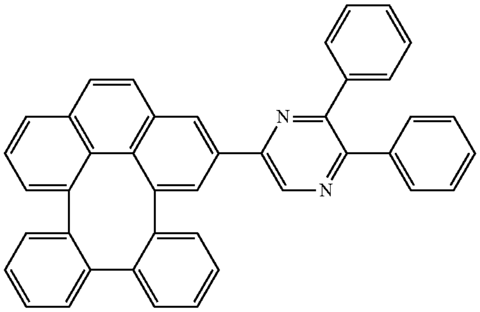
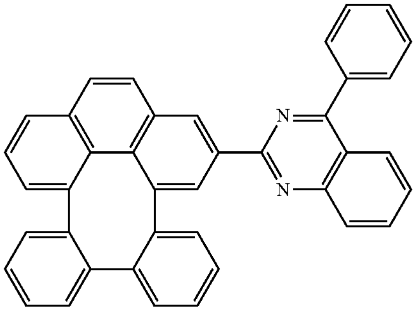
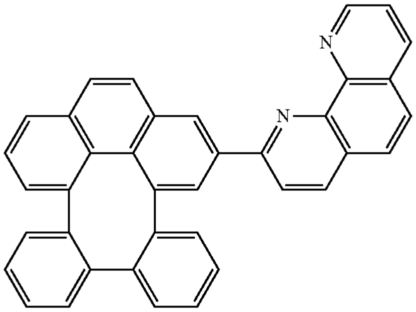
-continued
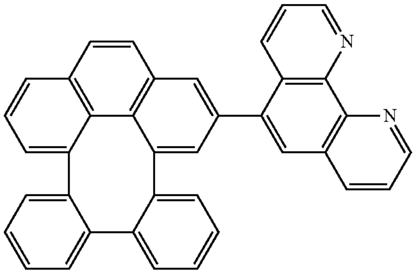
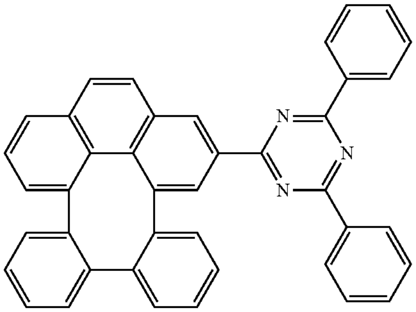
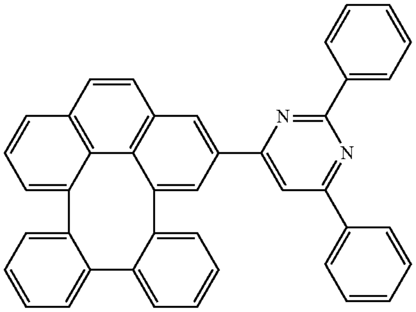
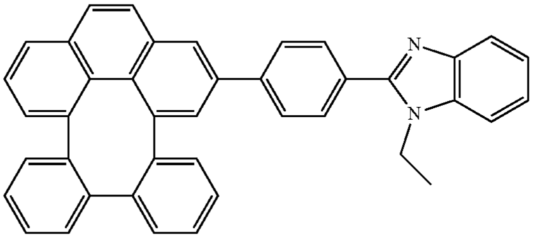
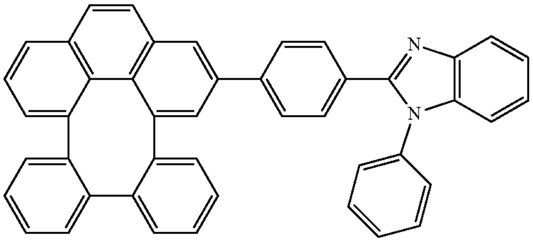
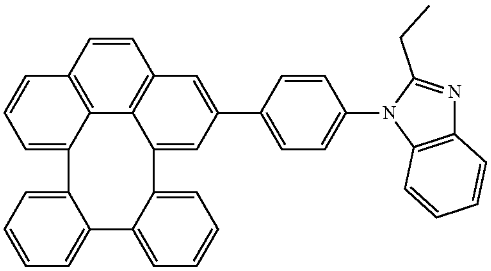

-continued
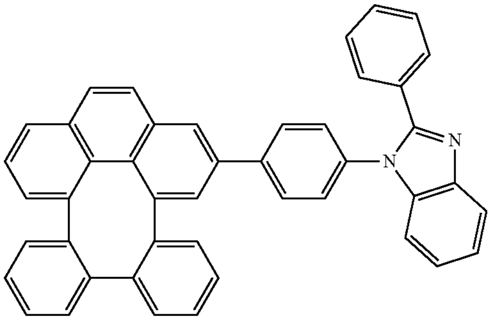
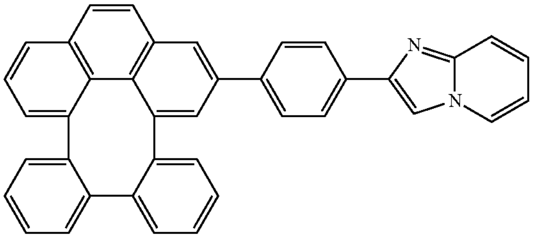
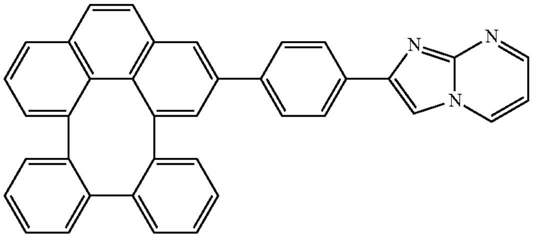
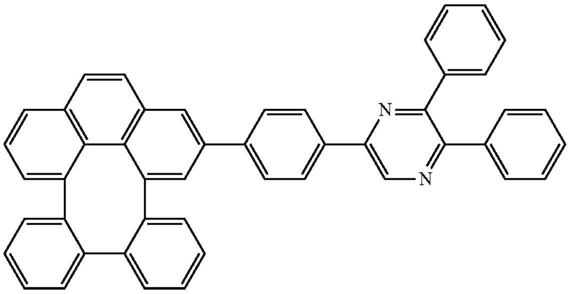
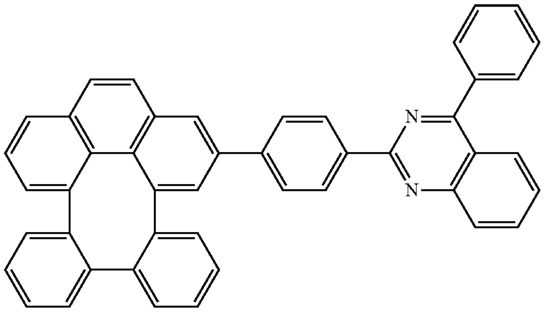
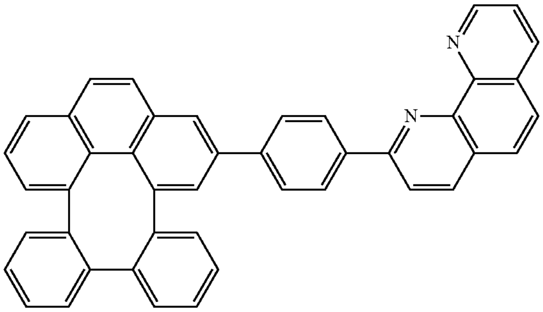
-continued
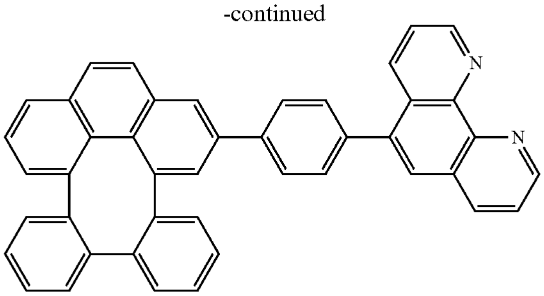
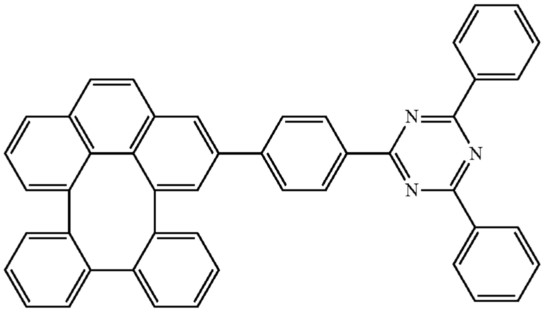
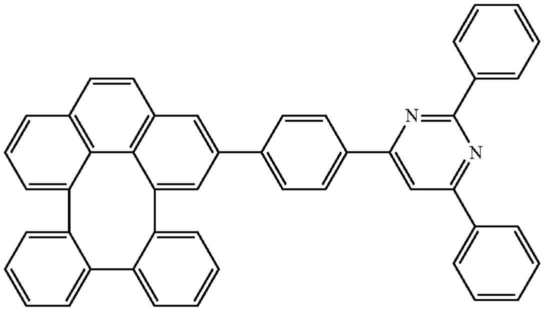
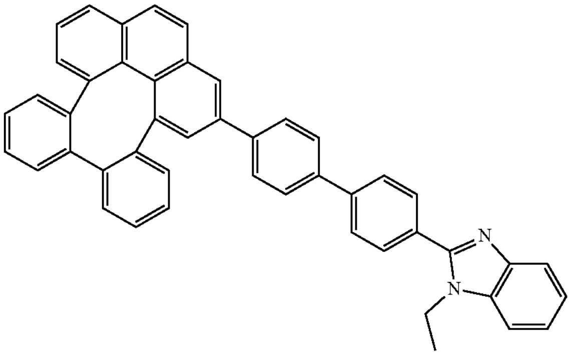
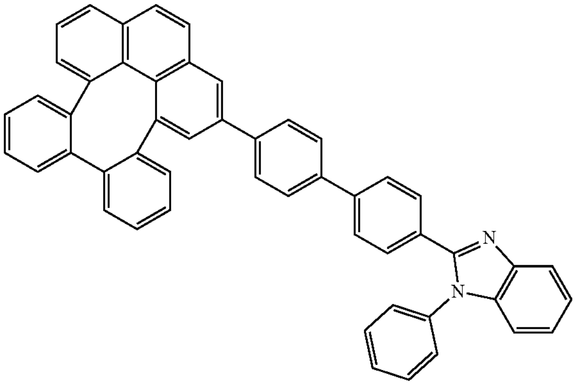

-continued
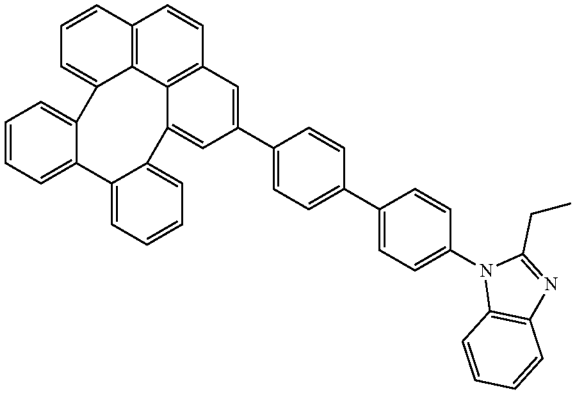
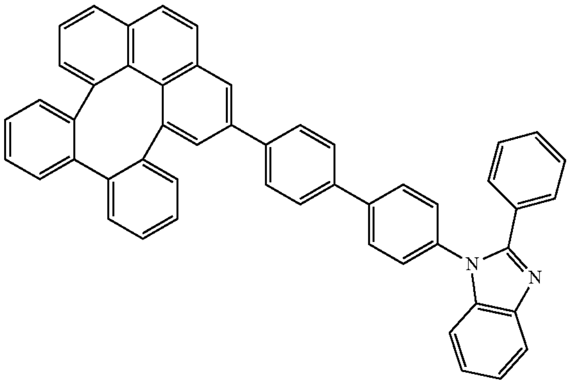
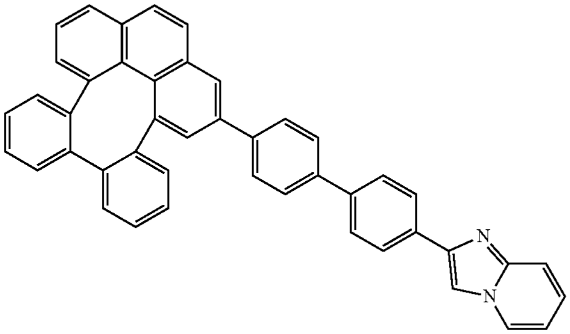
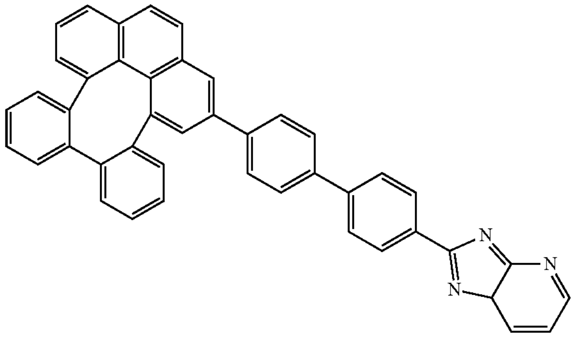
-continued
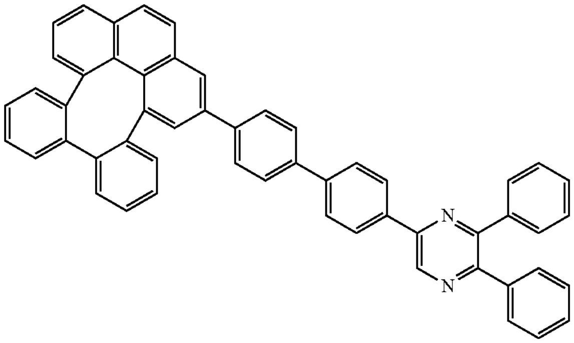
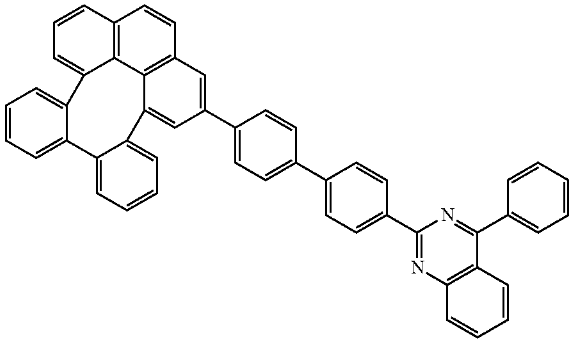
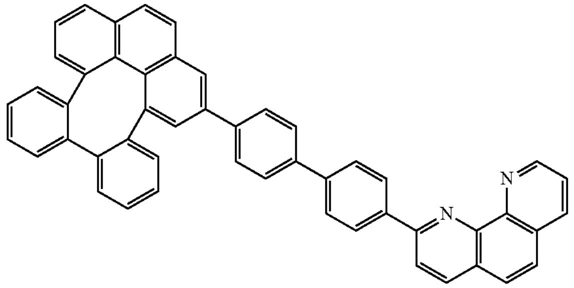
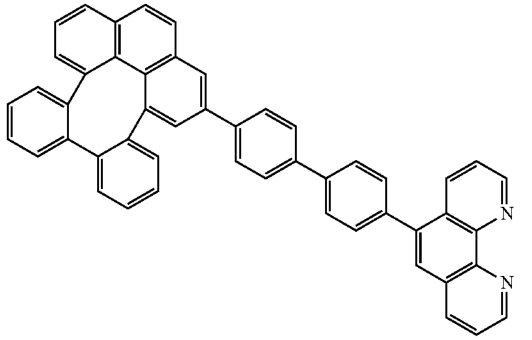
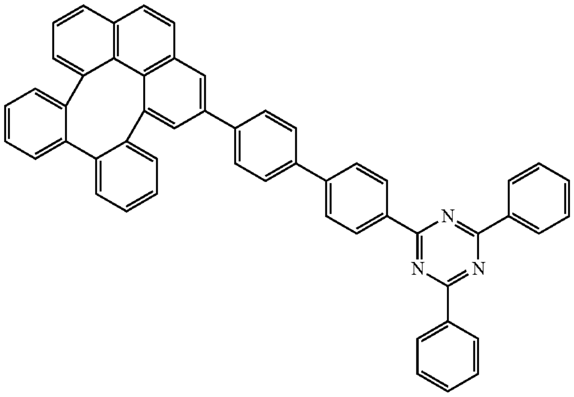

-continued
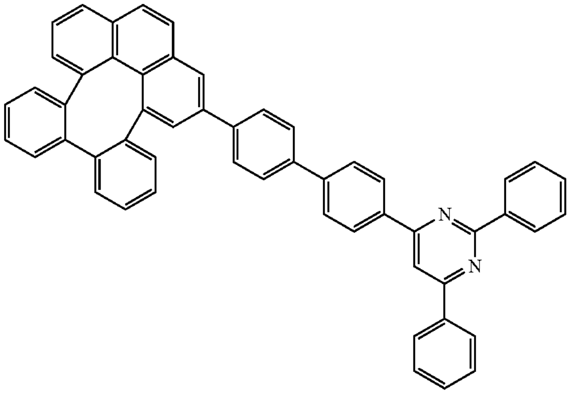
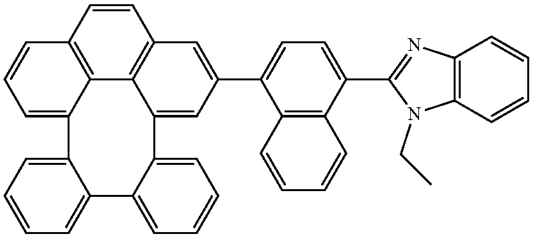
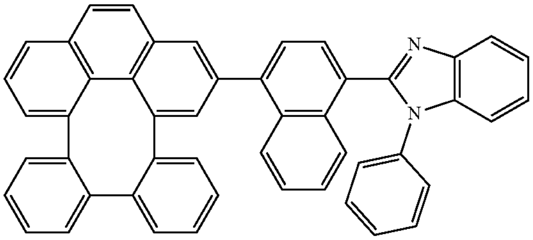
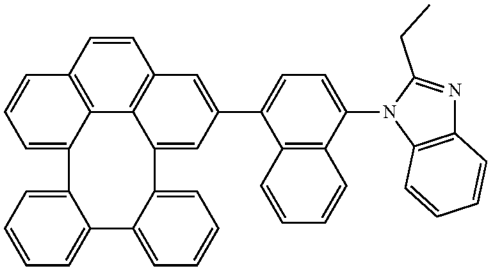
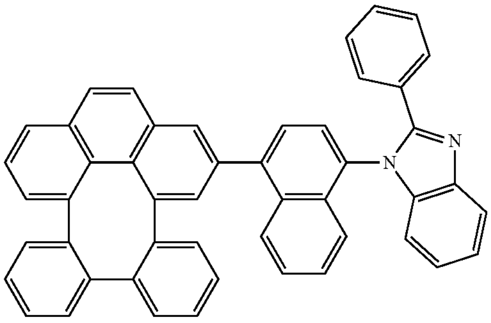
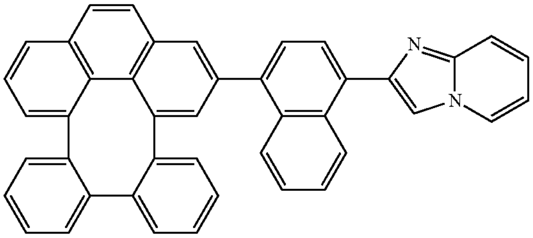
-continued
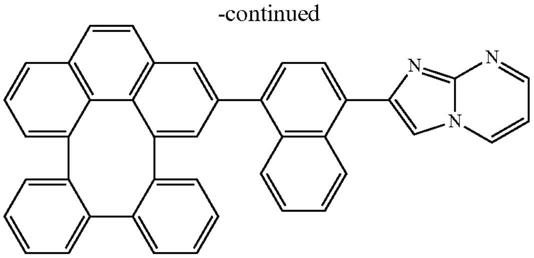
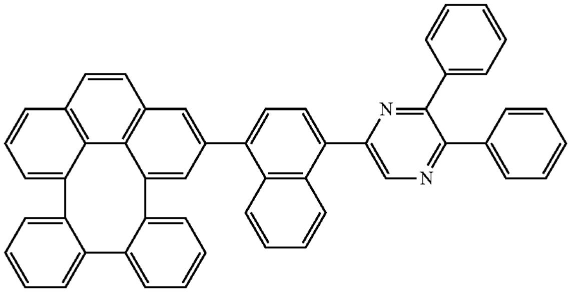
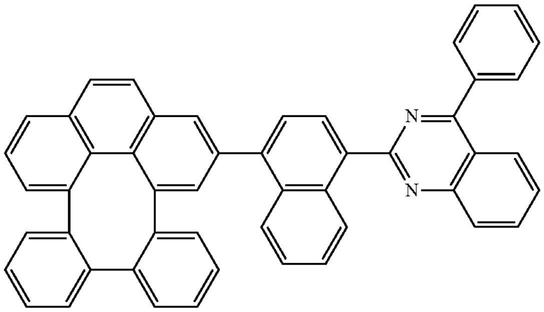
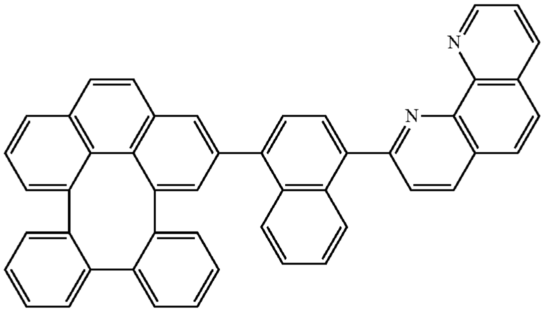
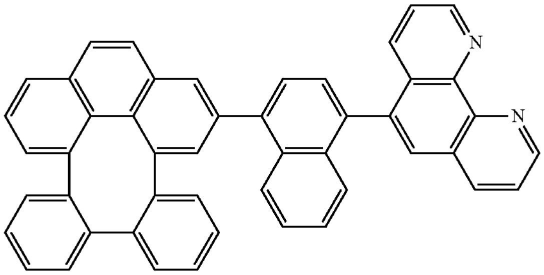
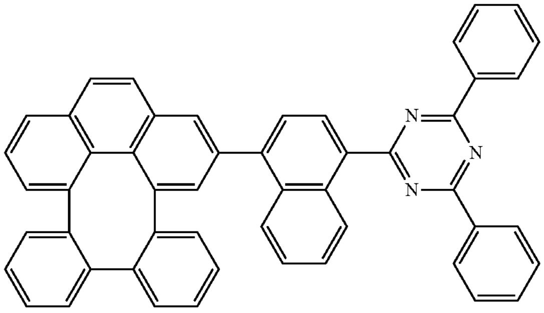

-continued
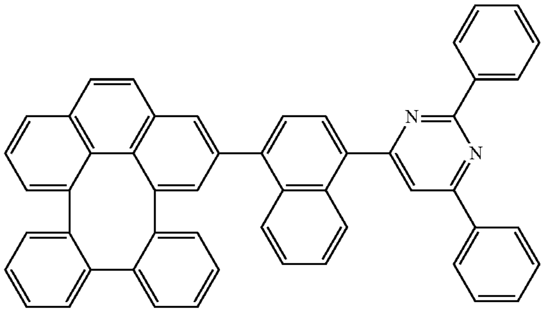
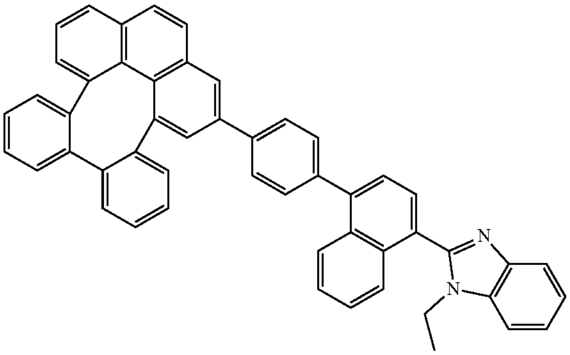
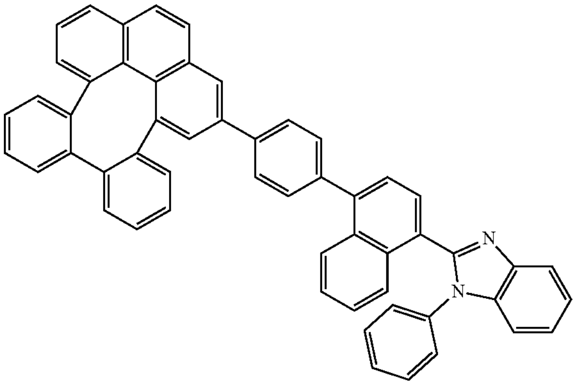
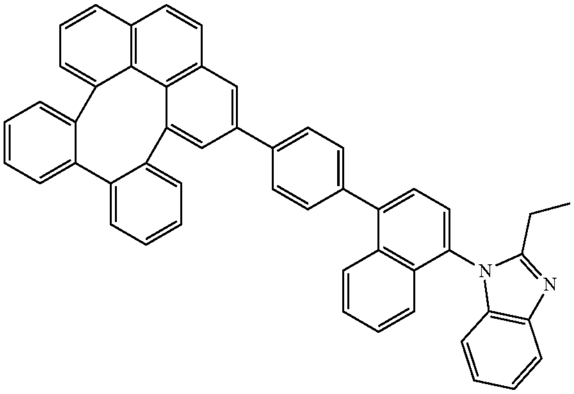
-continued
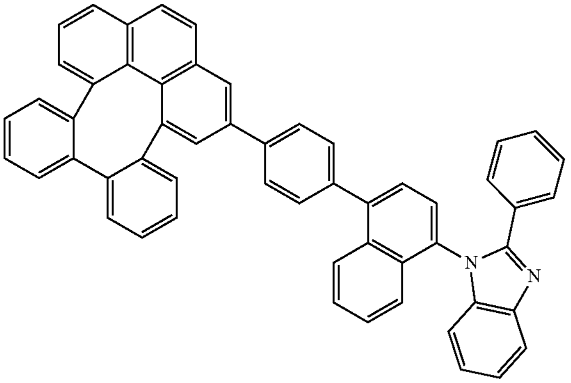
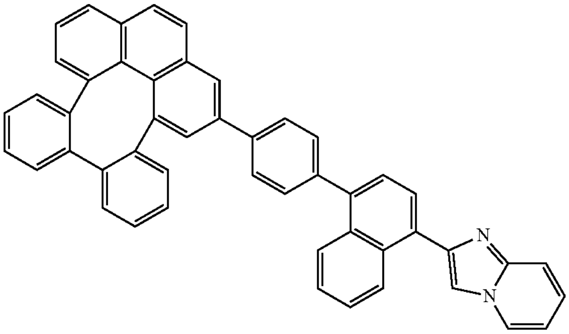
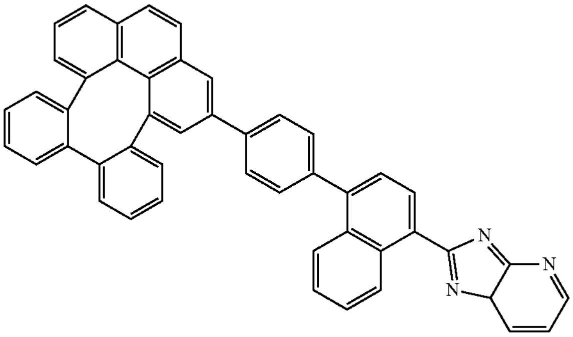
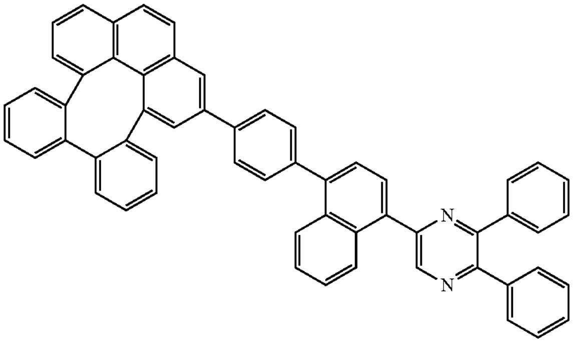

-continued
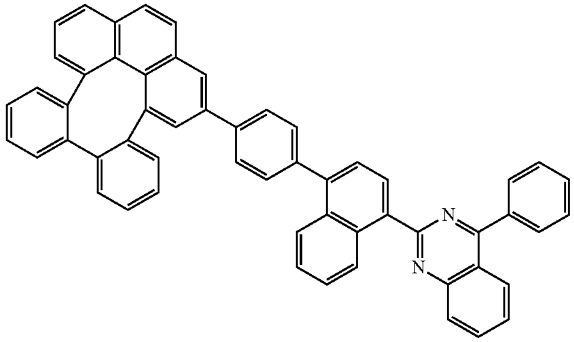
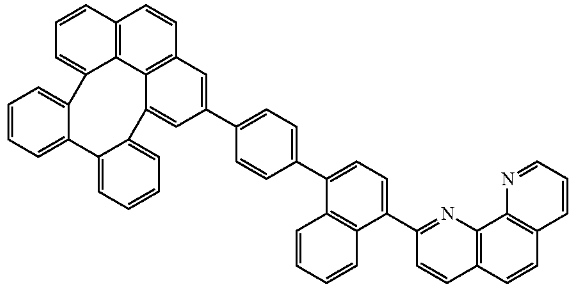
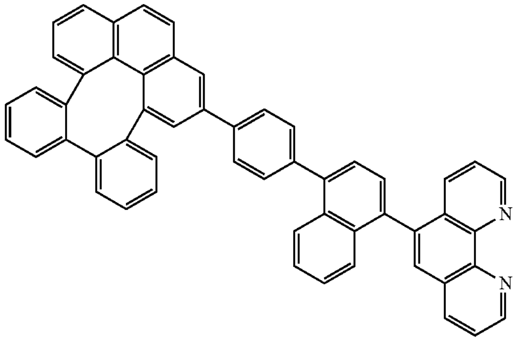
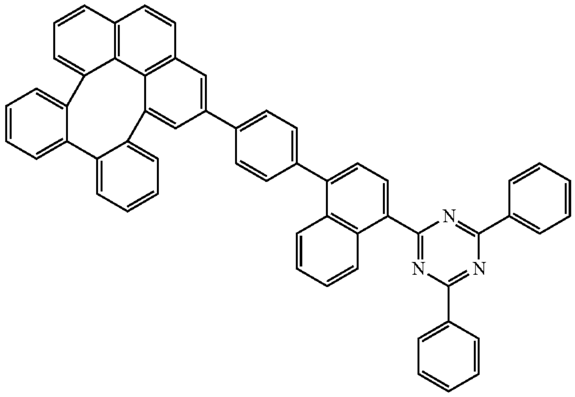
-continued
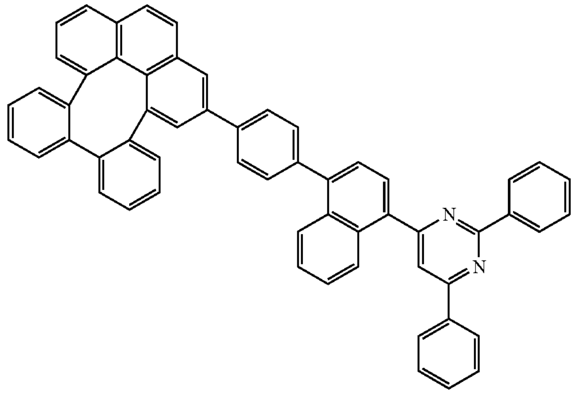
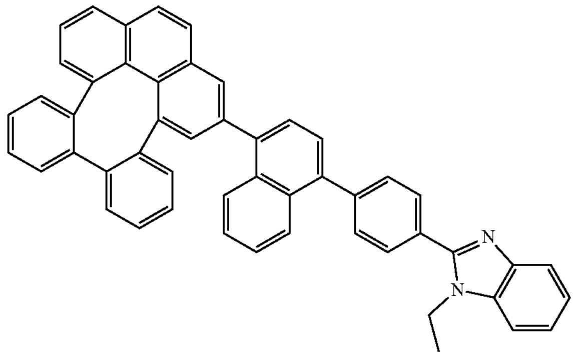
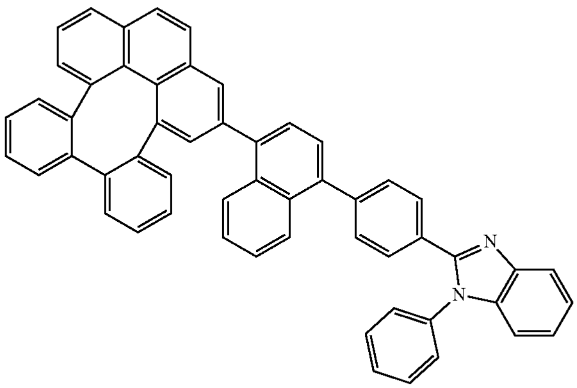
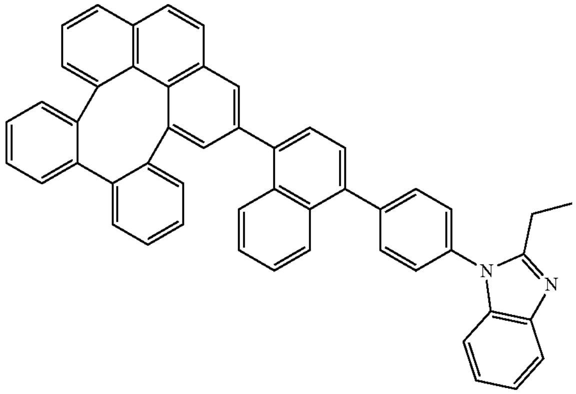

-continued
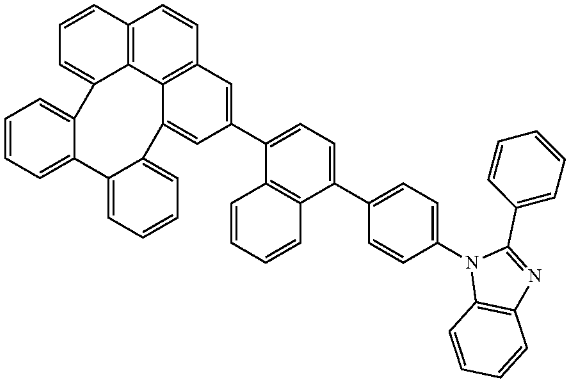
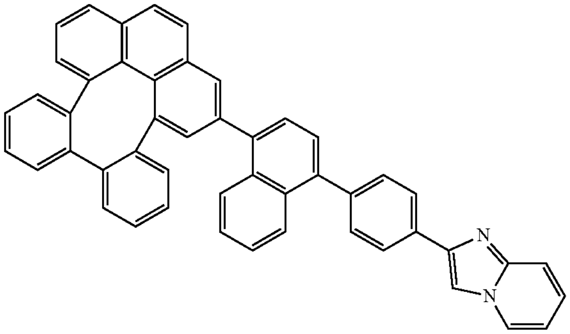
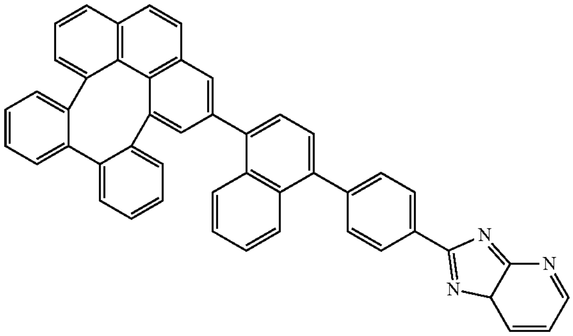
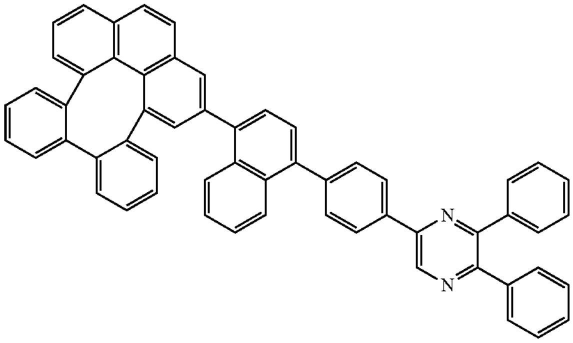
-continued
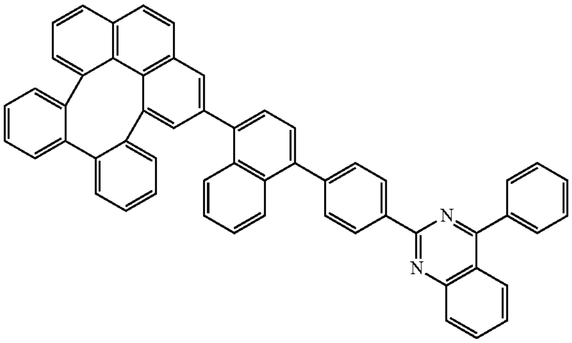
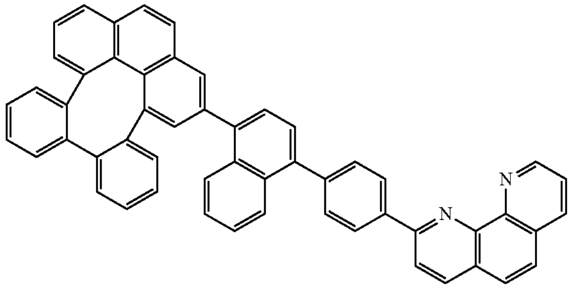
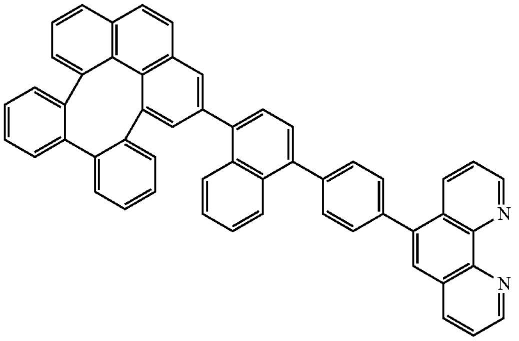
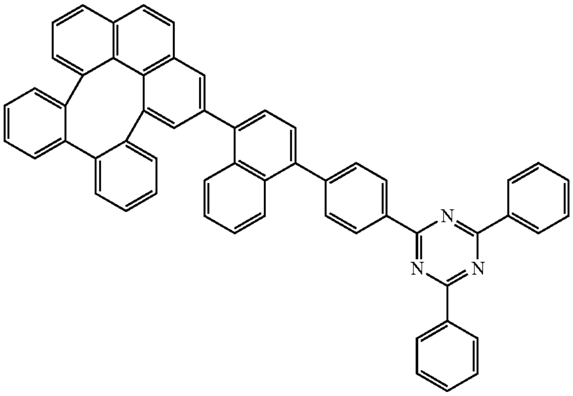

-continued
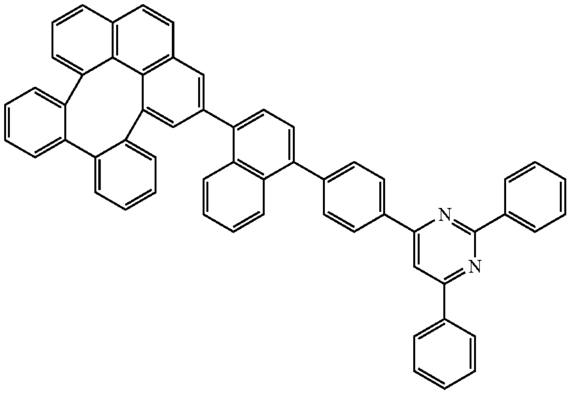
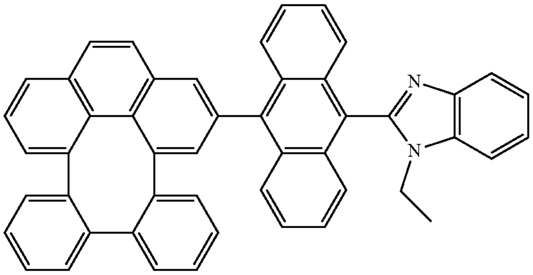
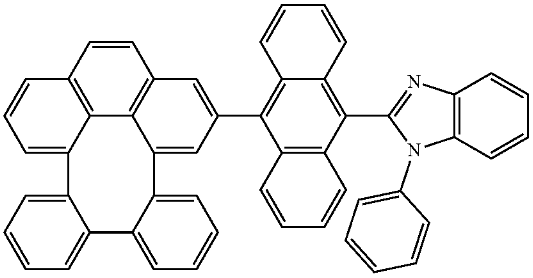
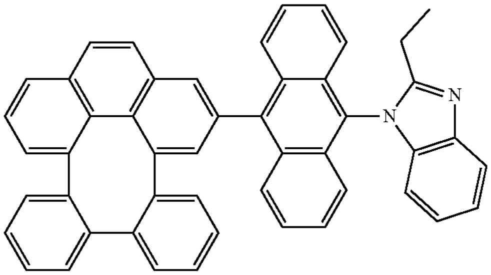
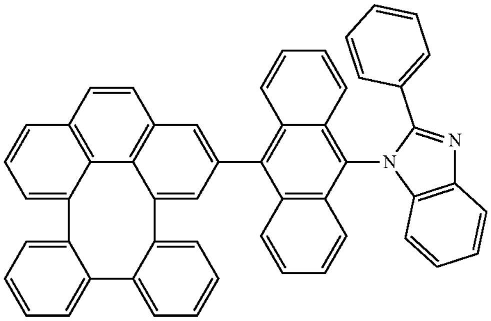
-continued
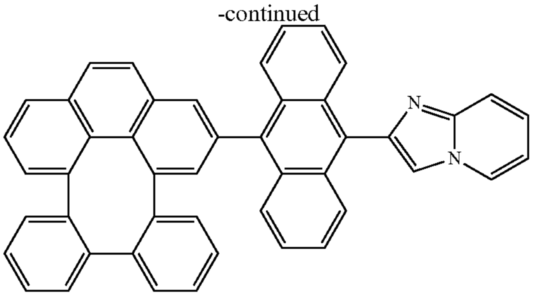
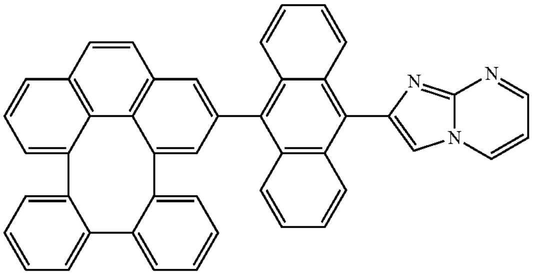
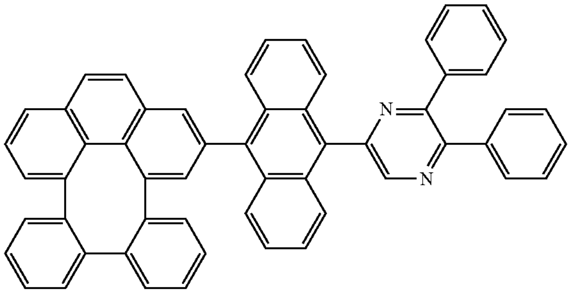
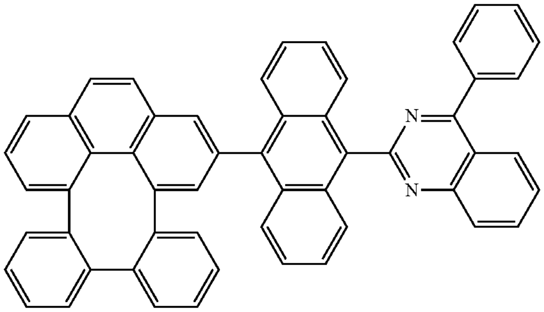
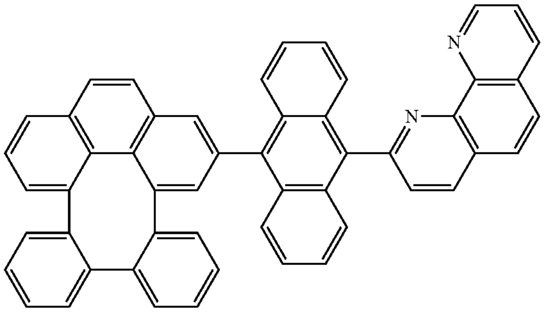
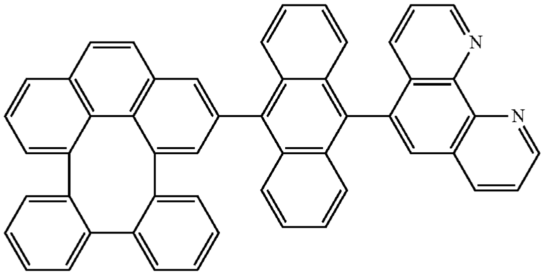

-continued
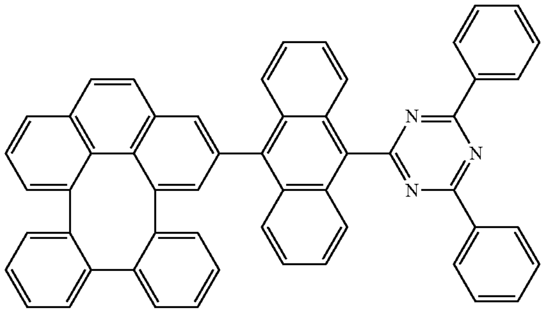
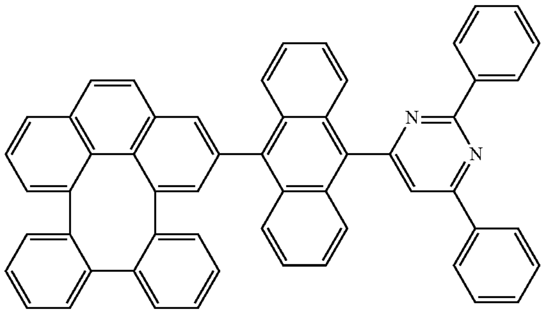
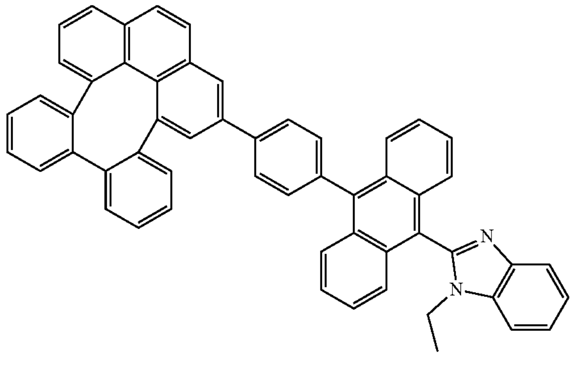
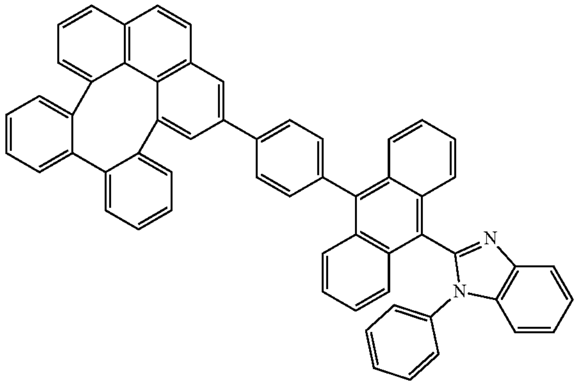
-continued
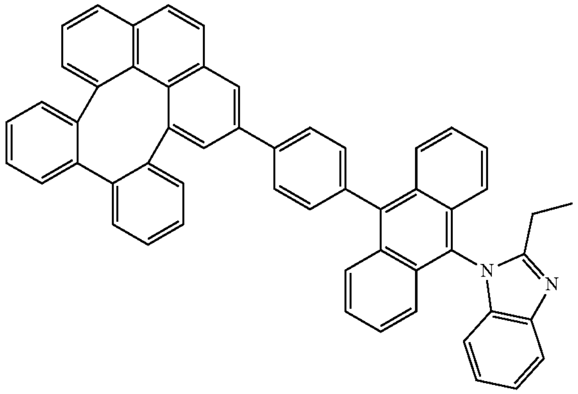
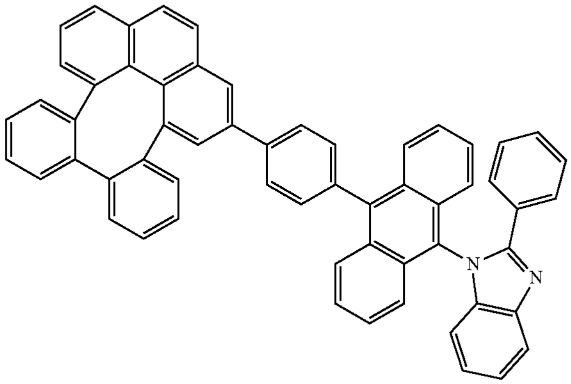
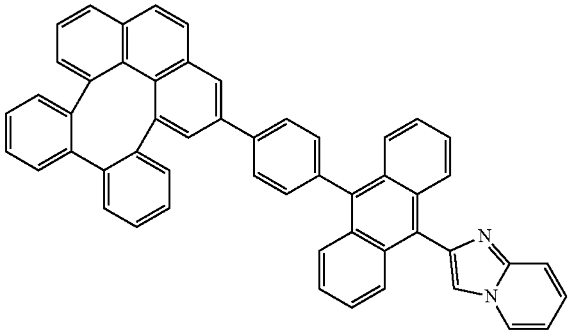
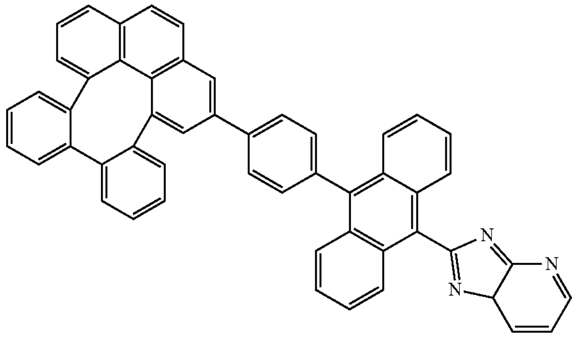

-continued
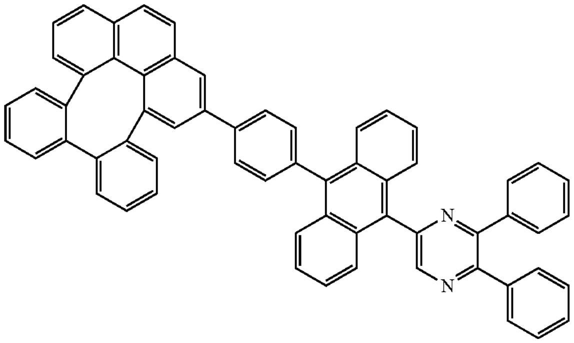
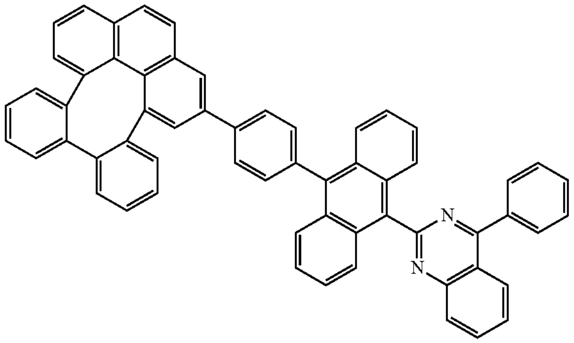
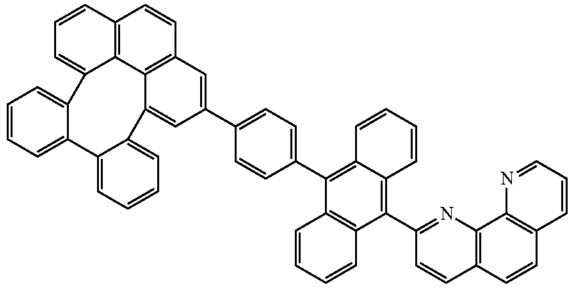
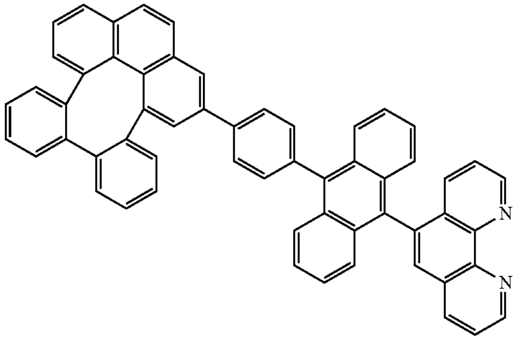
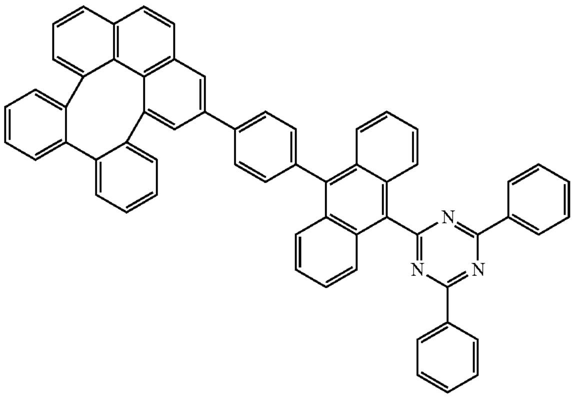
-continued
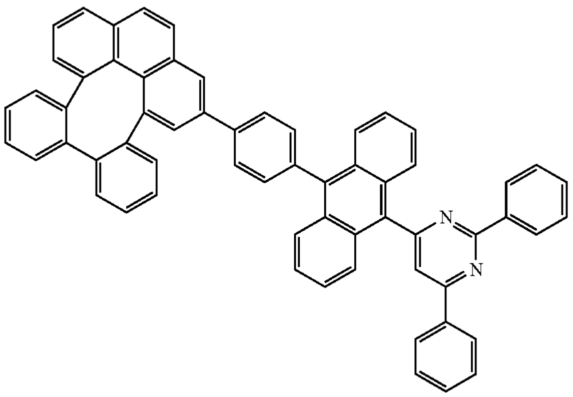
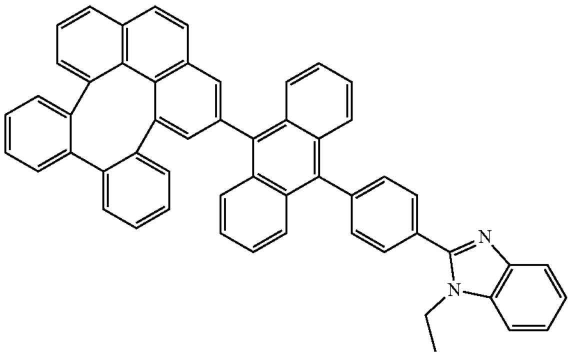
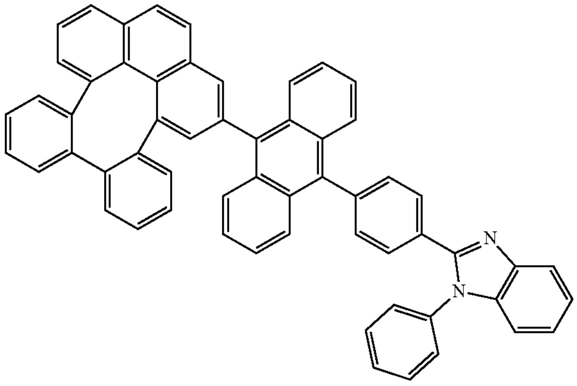
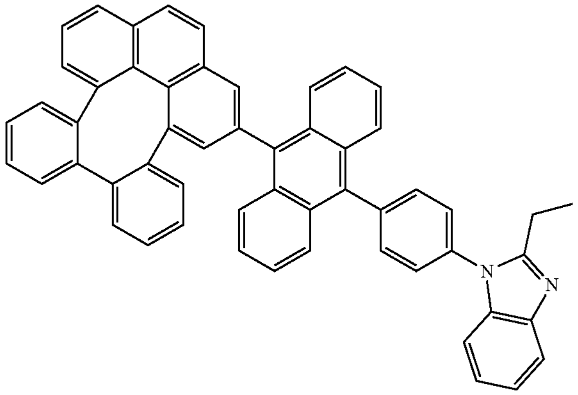

-continued
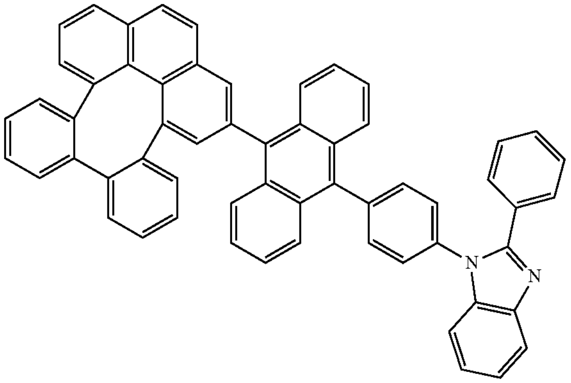
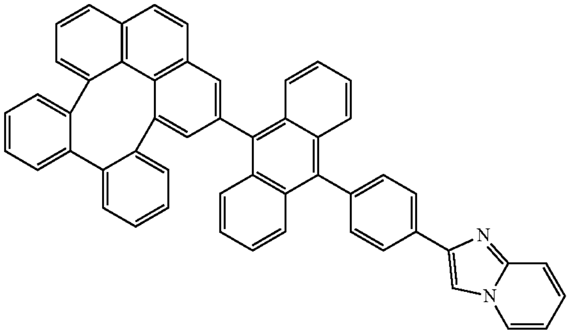
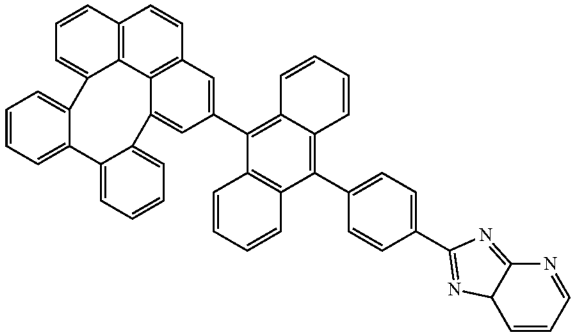
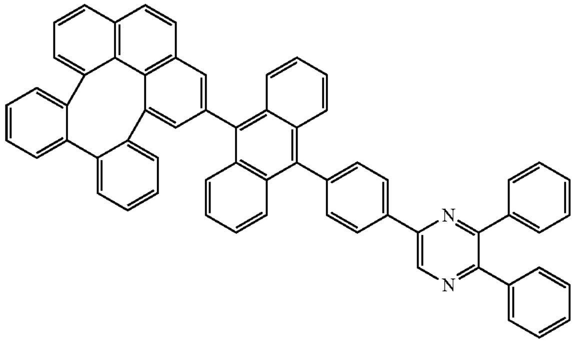
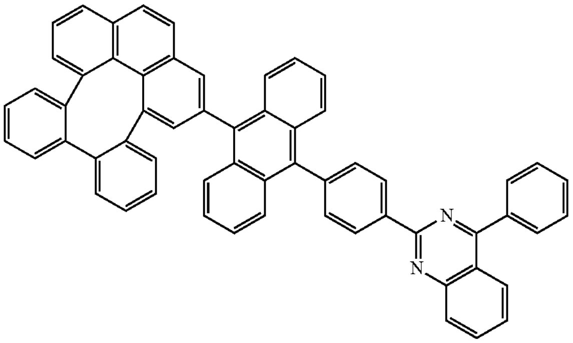
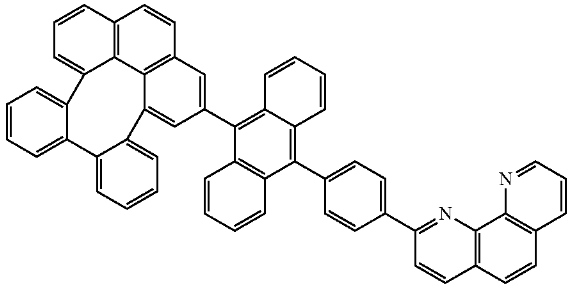
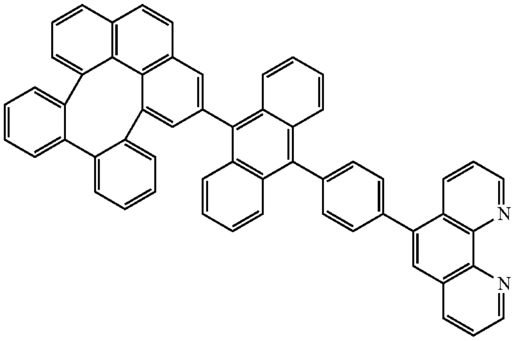
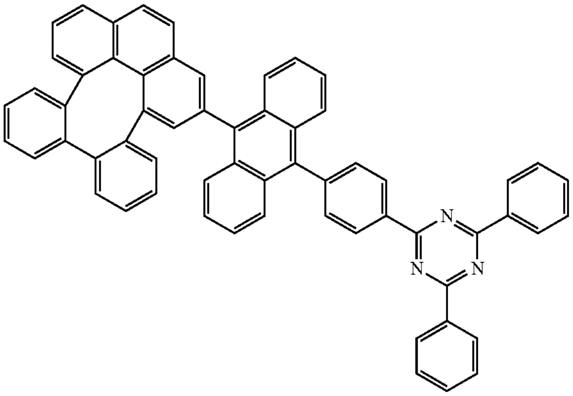
-continued -continued
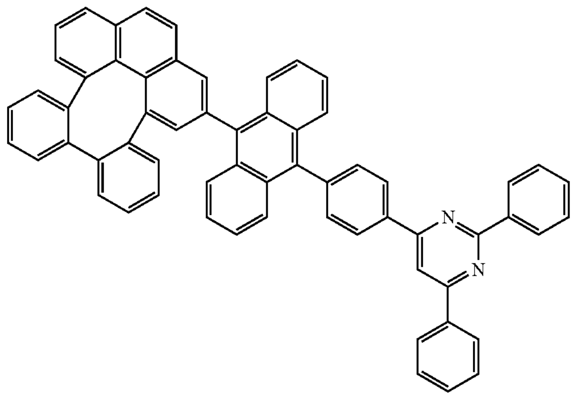
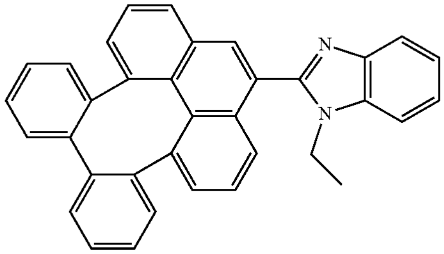
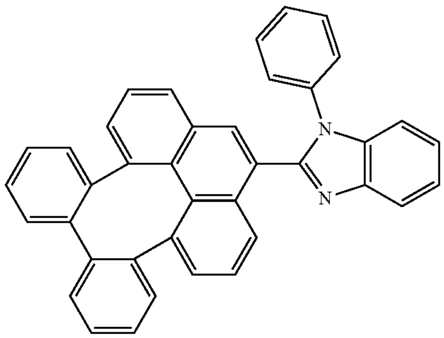
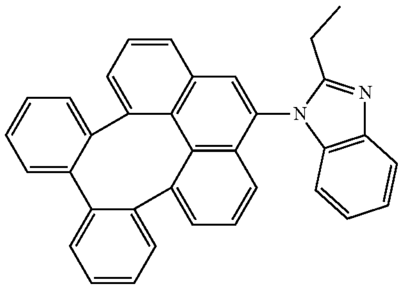
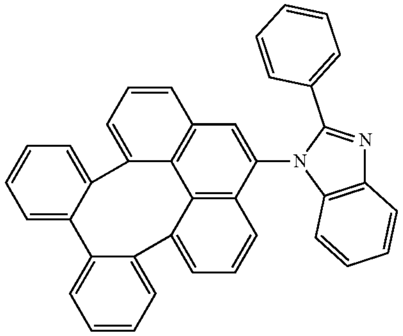
-continued
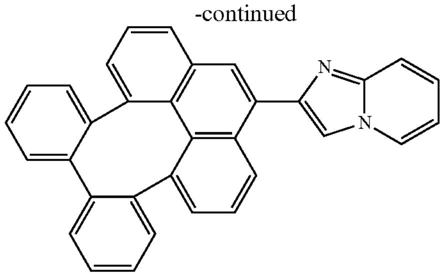
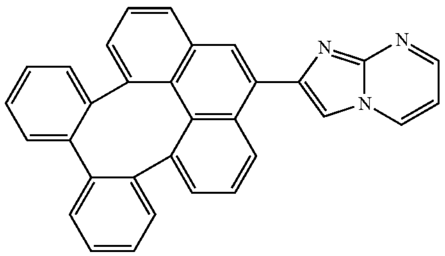
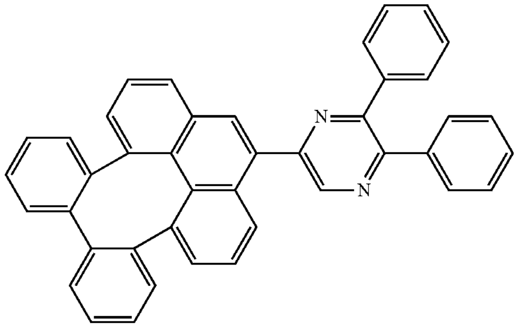
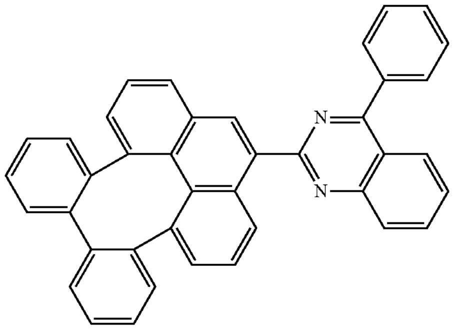
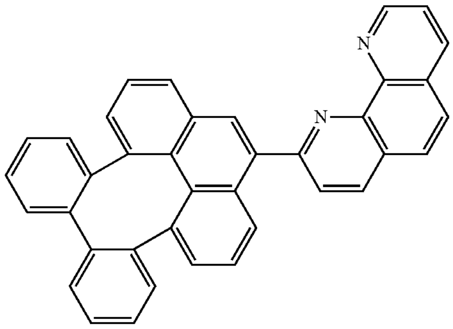

-continued
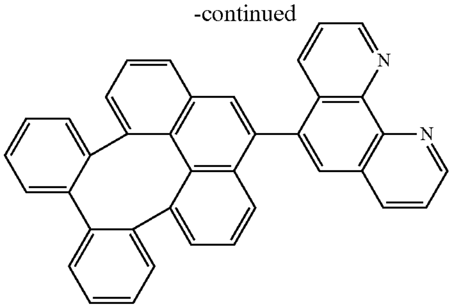
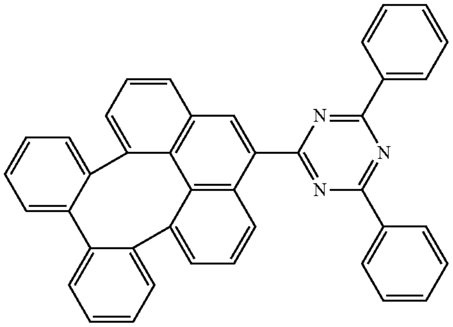
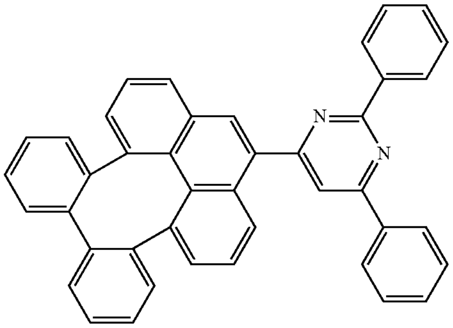
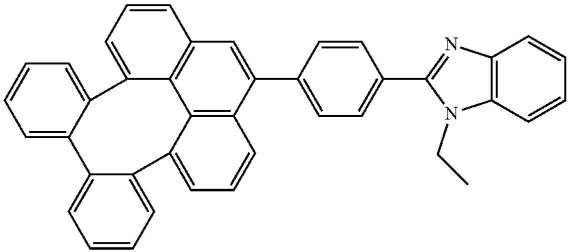
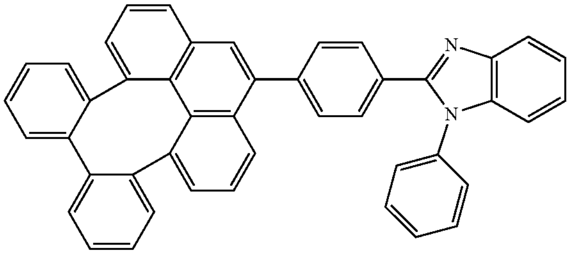
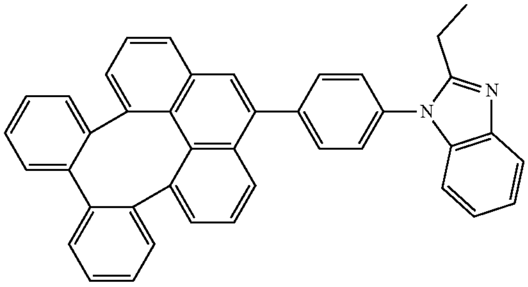
-continued
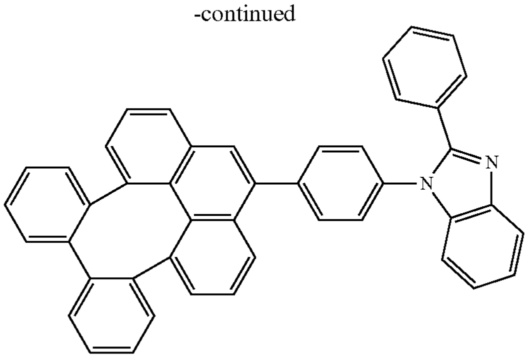
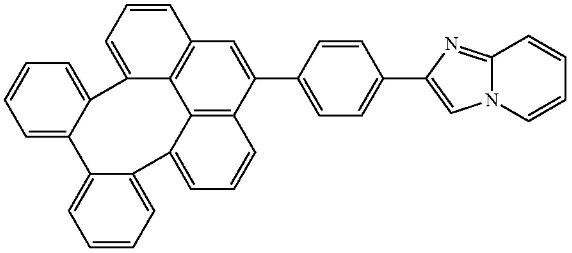
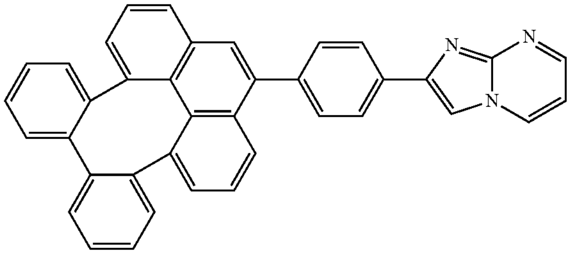
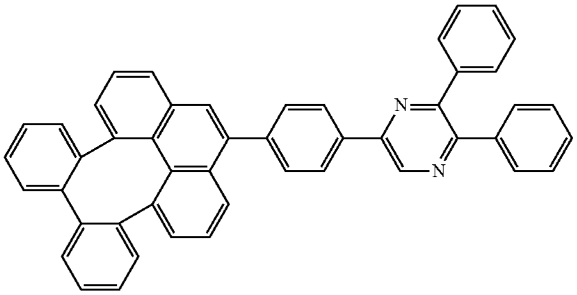
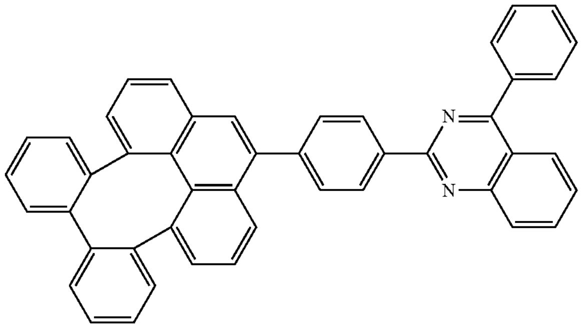

-continued
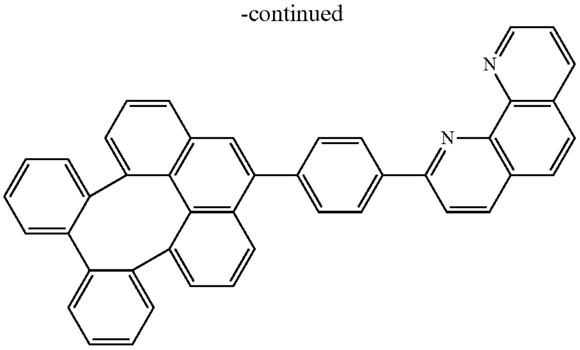
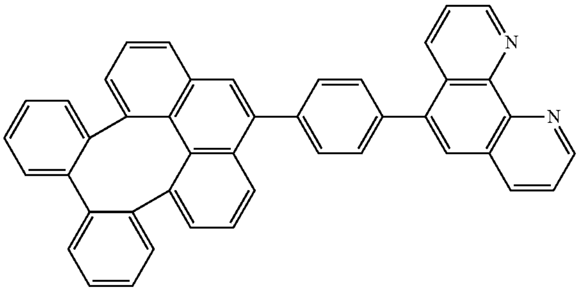
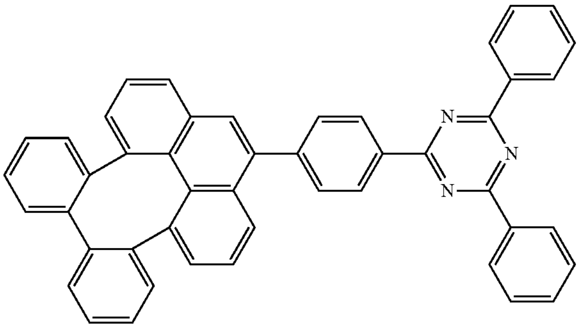
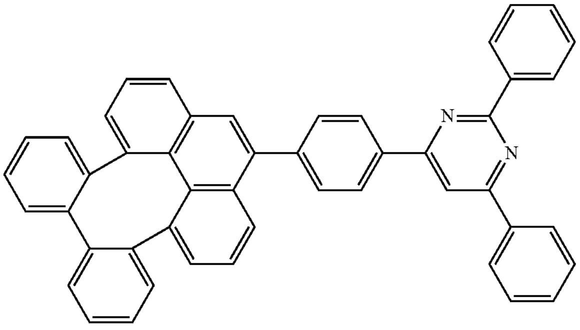
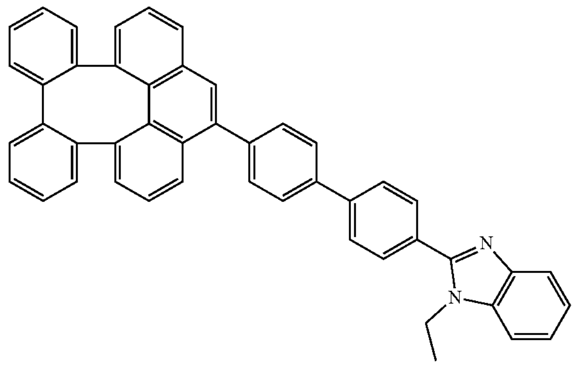
-continued
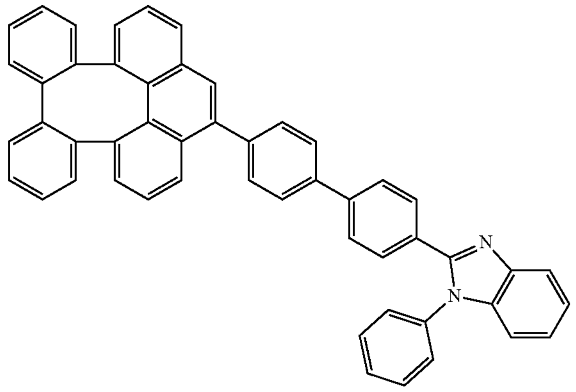
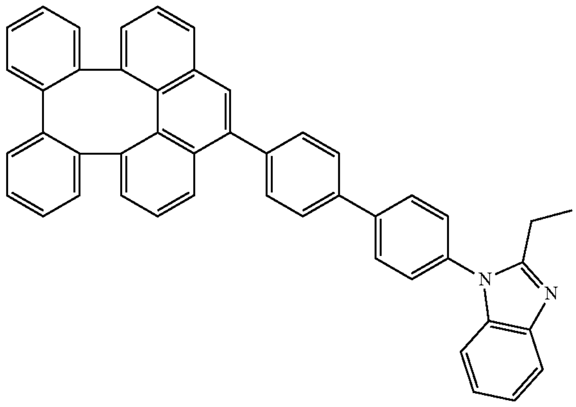
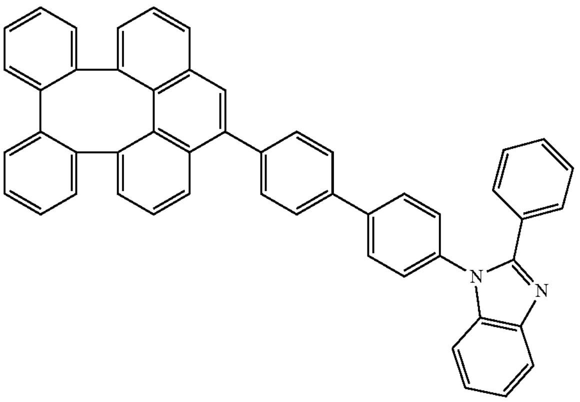
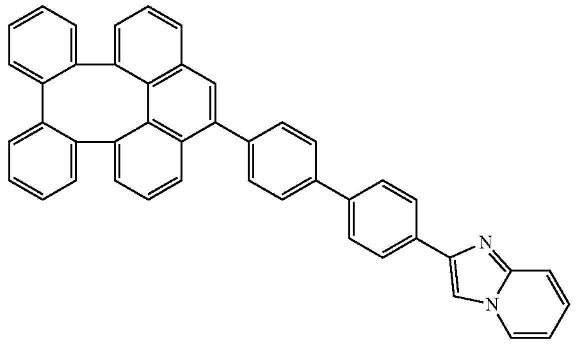

-continued
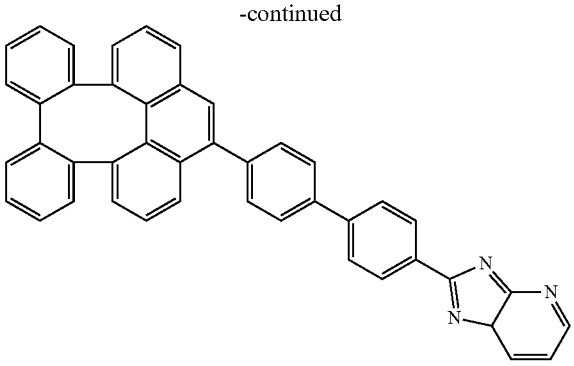
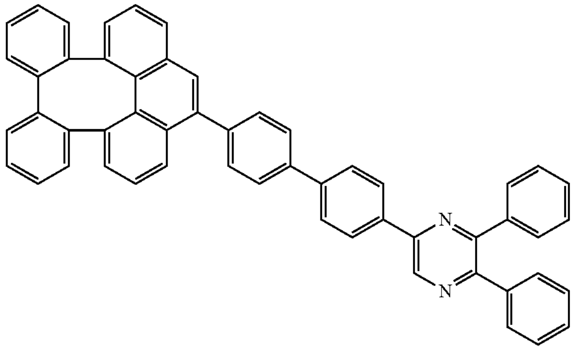
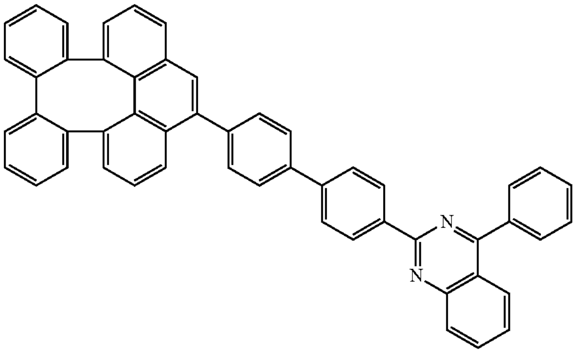
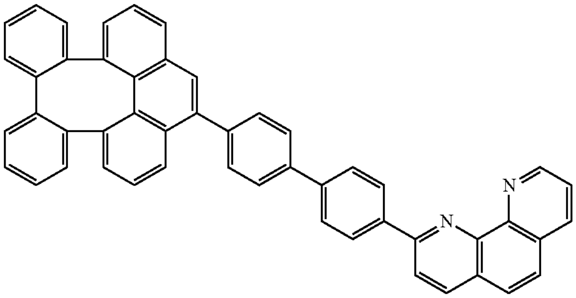
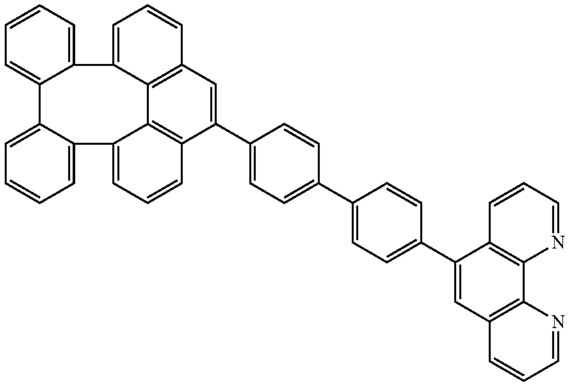
-continued
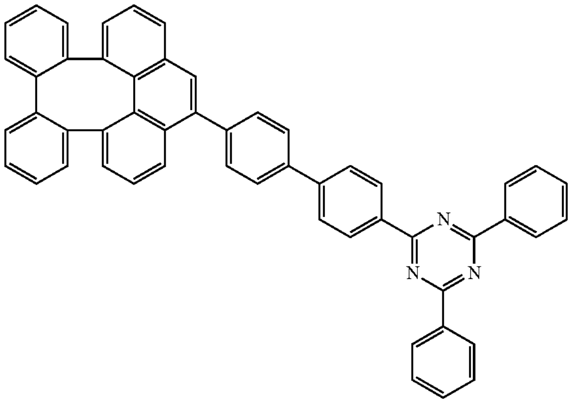
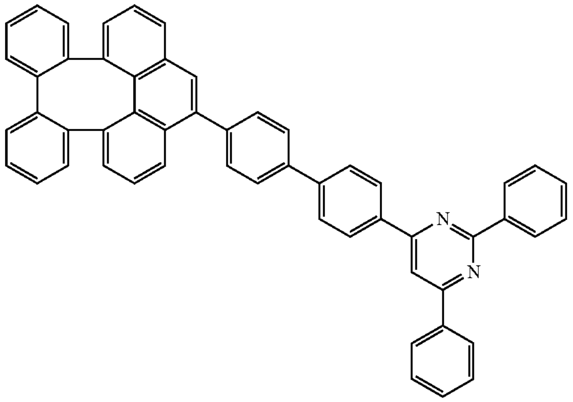
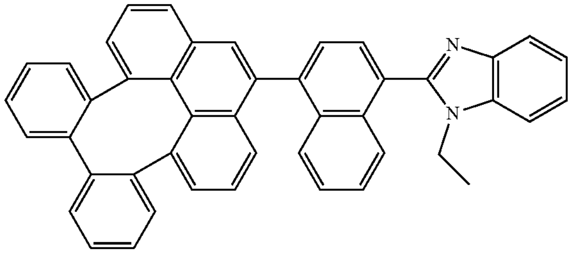
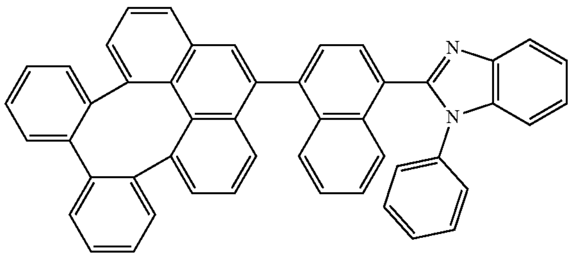
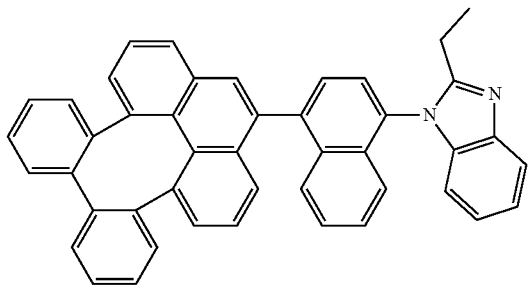

-continued
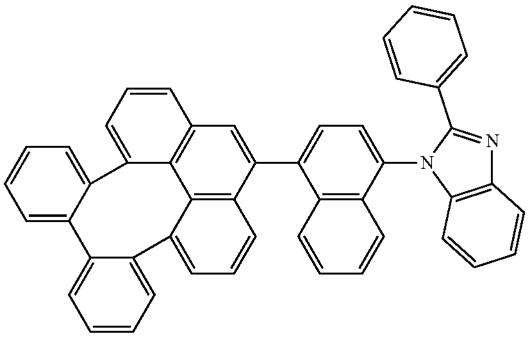
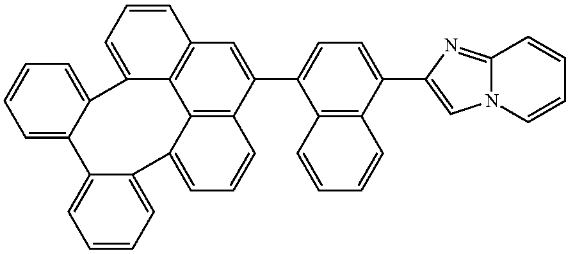
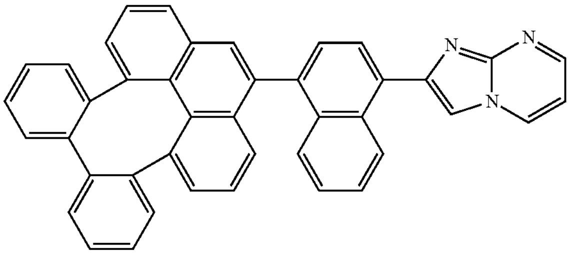
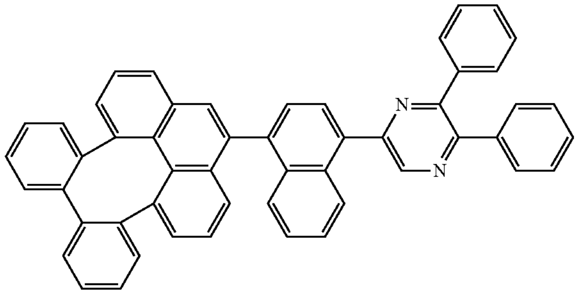
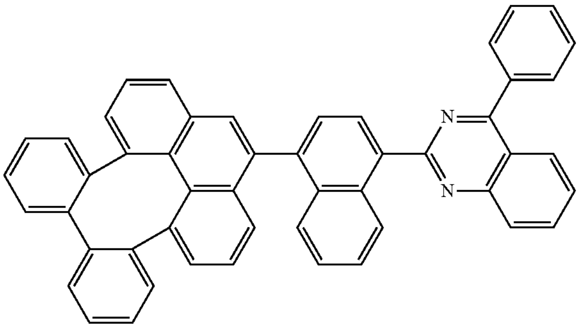
-continued
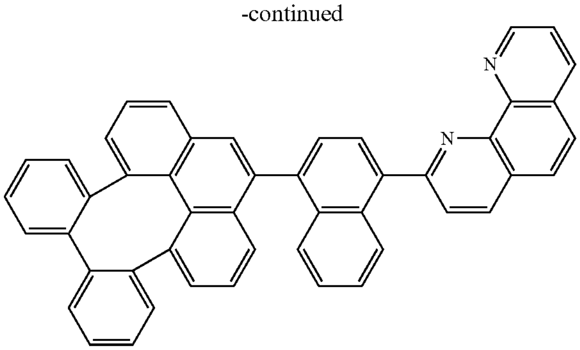
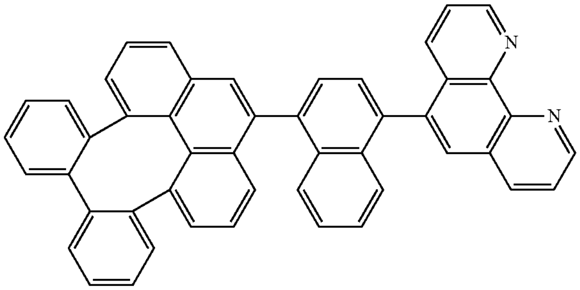
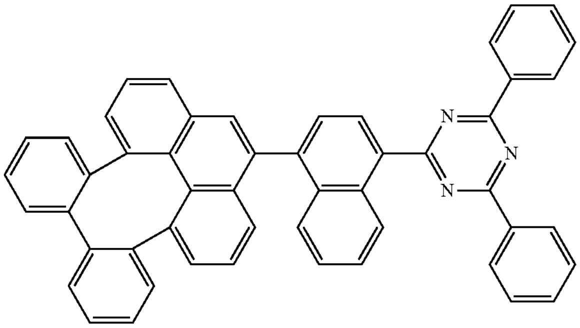
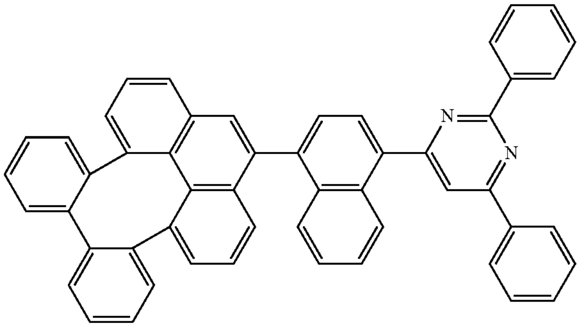
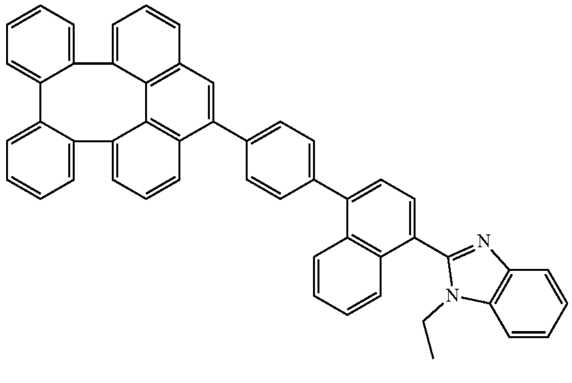

-continued
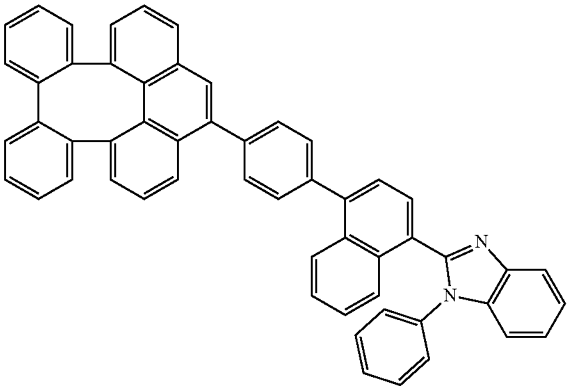
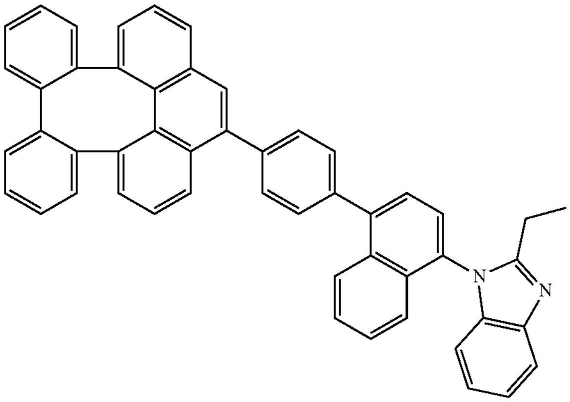
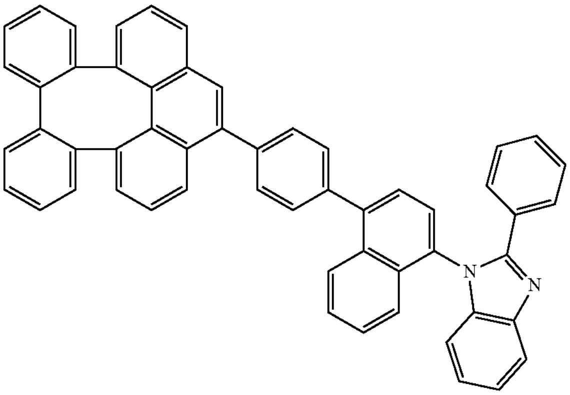
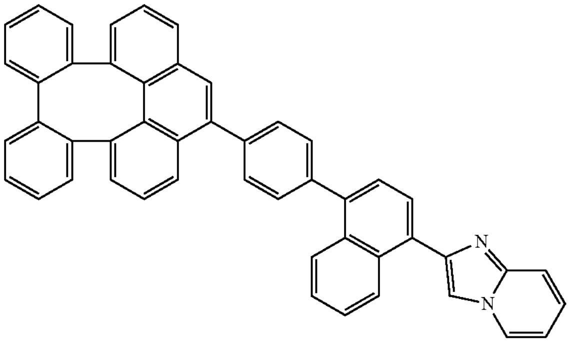
-continued
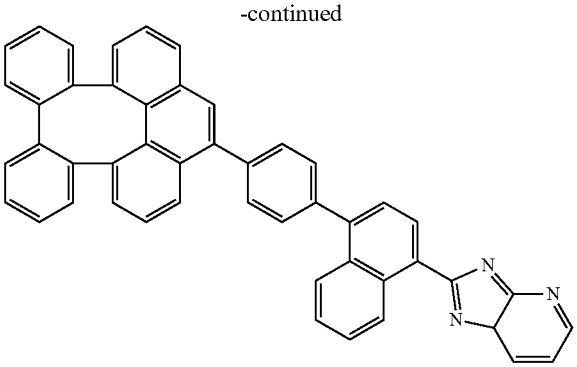
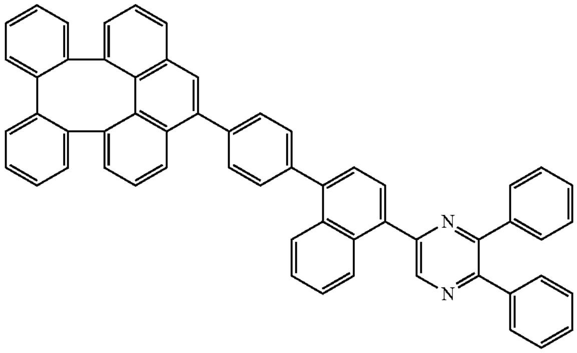
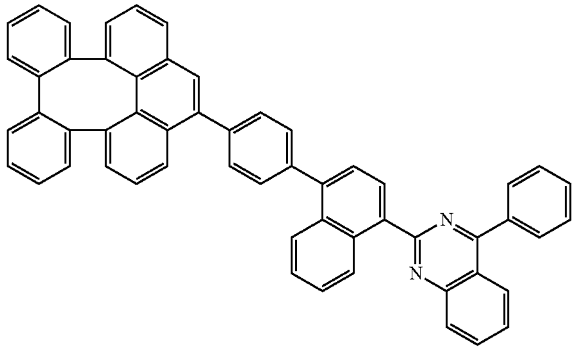
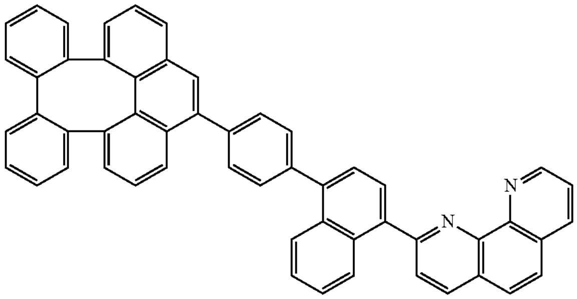
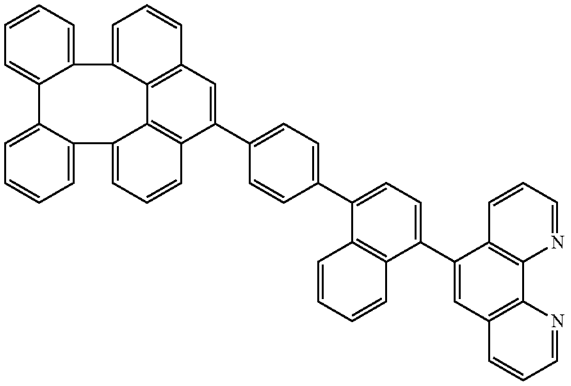

-continued
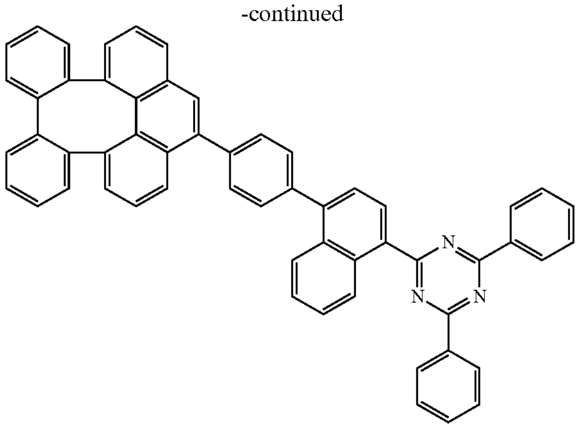
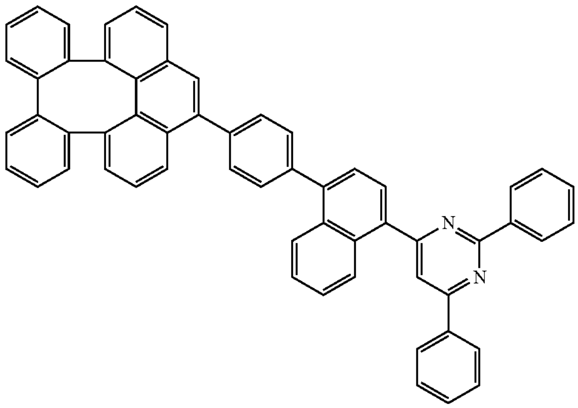
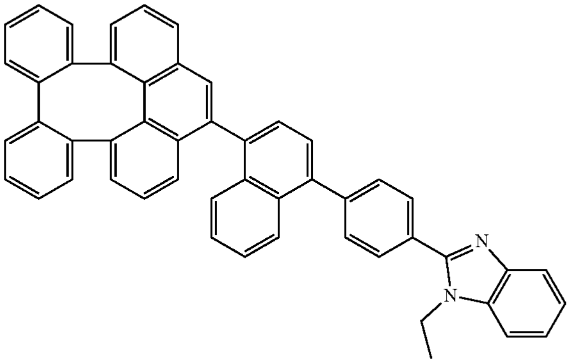
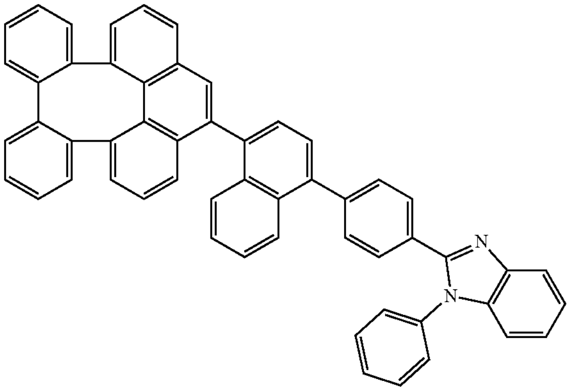
-continued
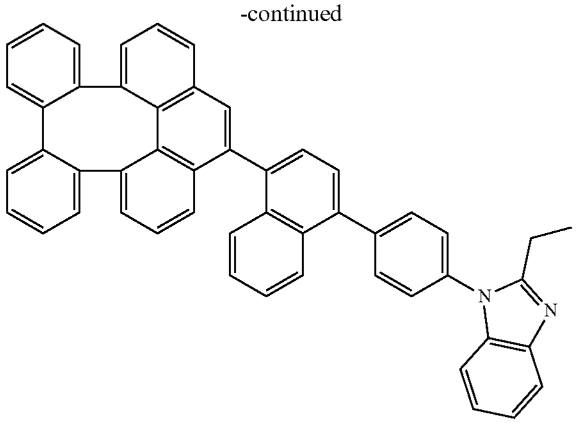
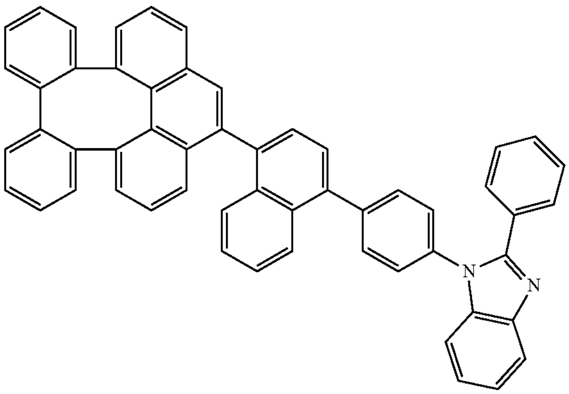
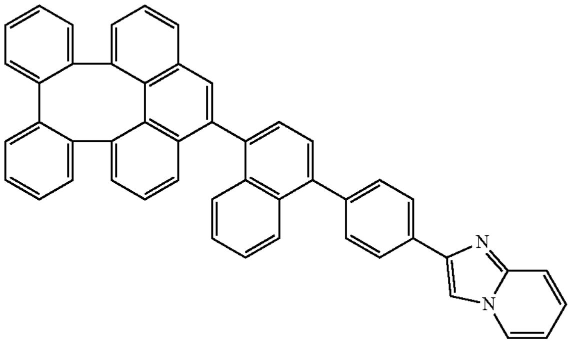
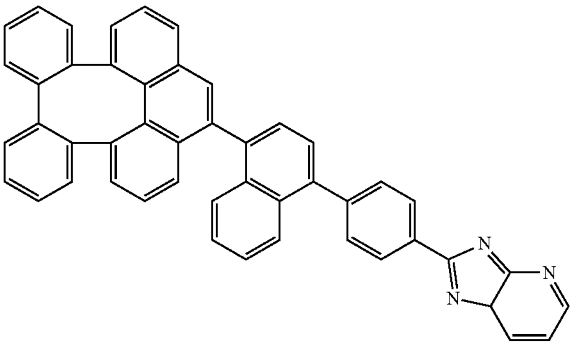

-continued
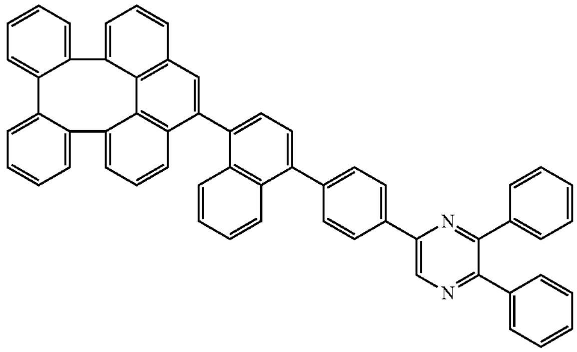
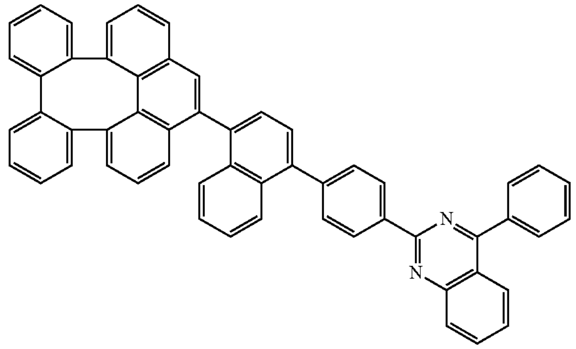
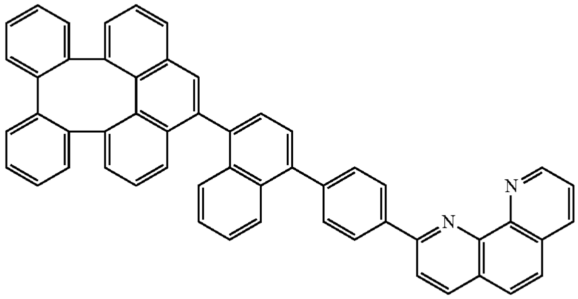
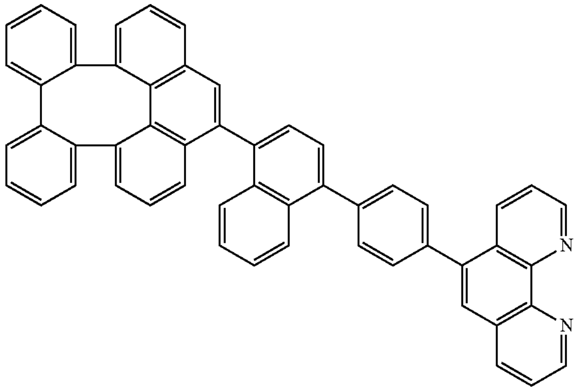
-continued
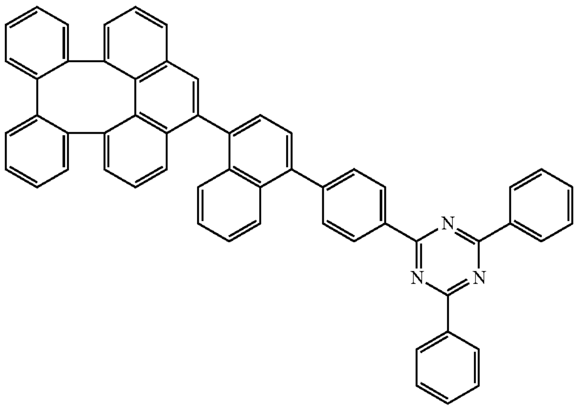
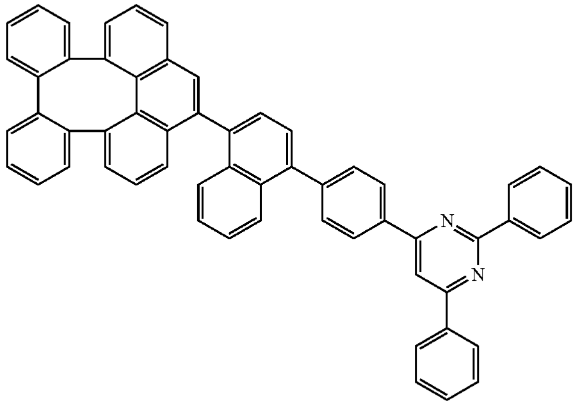
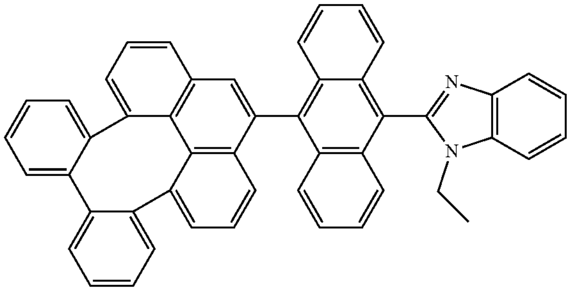
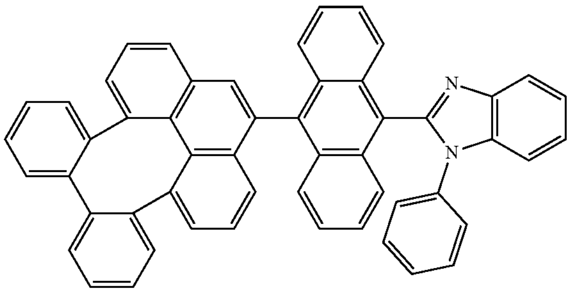
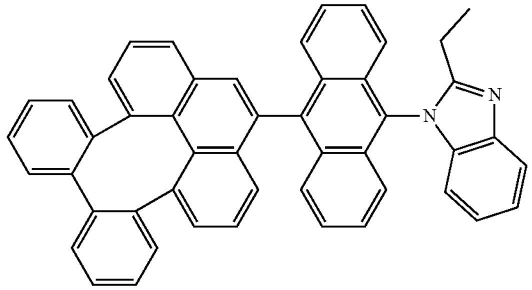

-continued
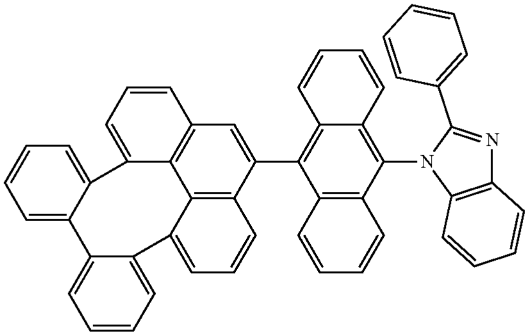
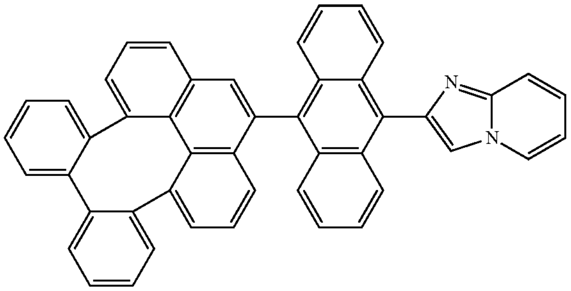
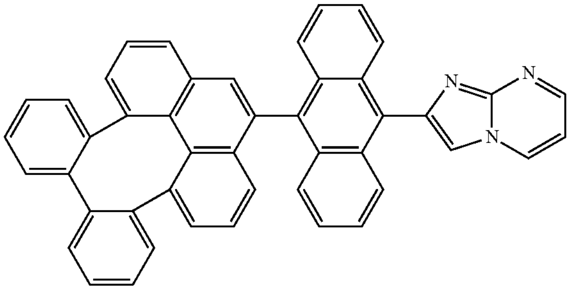
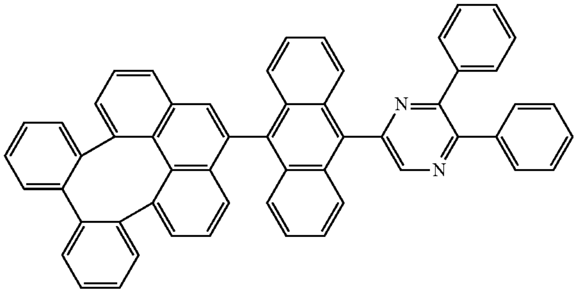
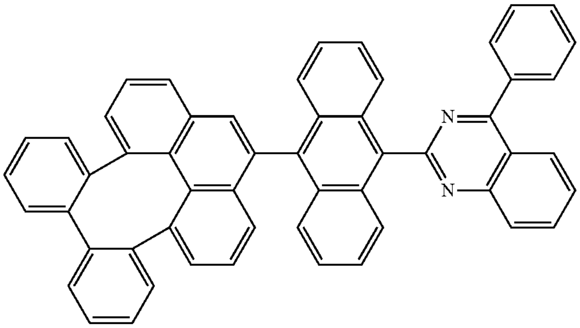
-continued
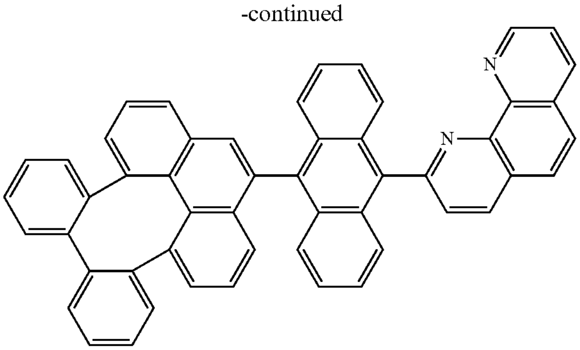
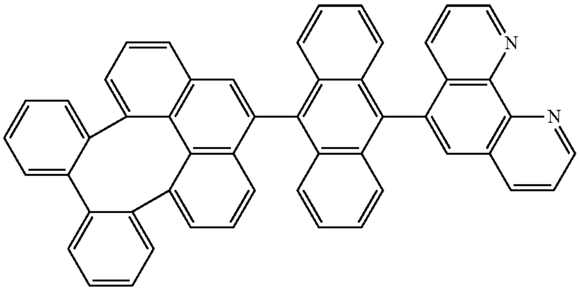
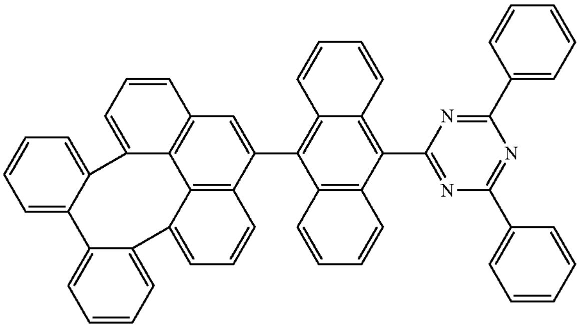
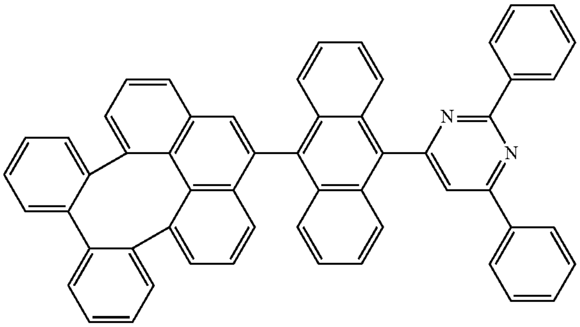
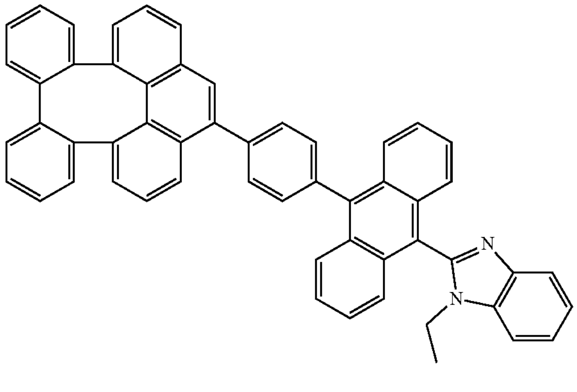

-continued
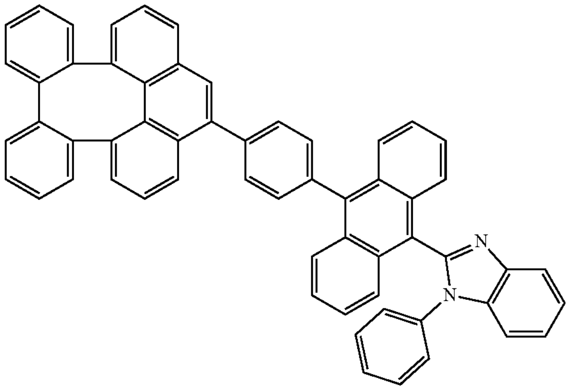
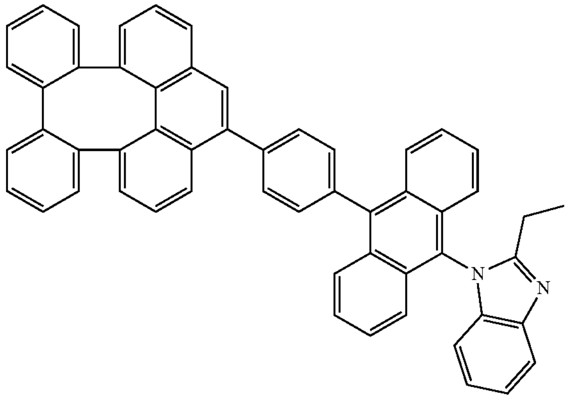
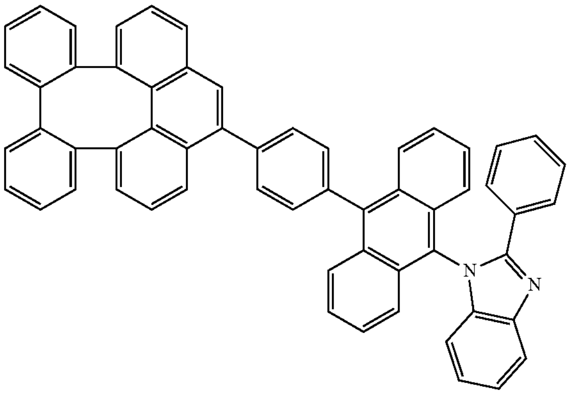
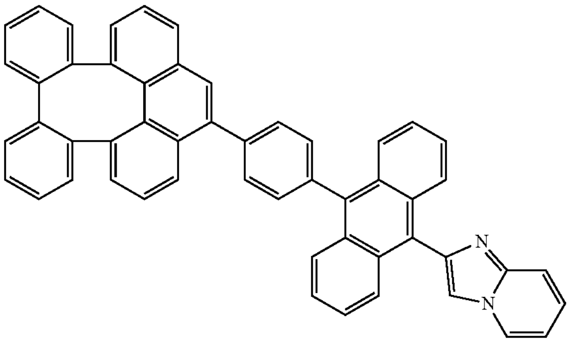
-continued
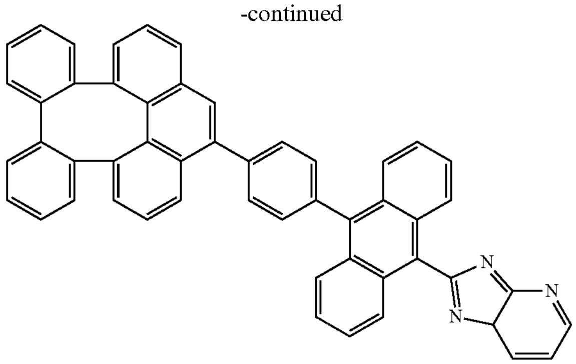
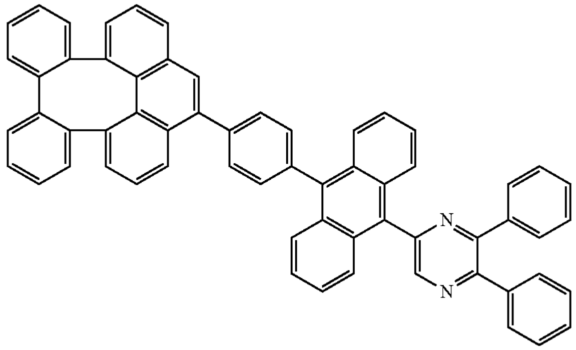
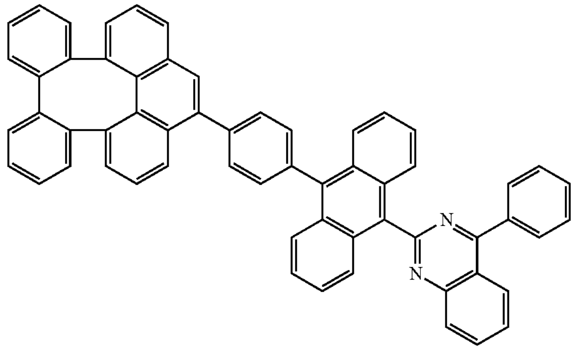
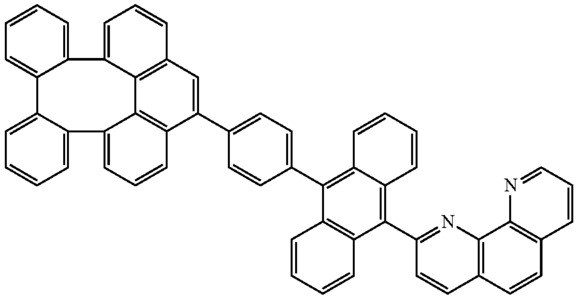
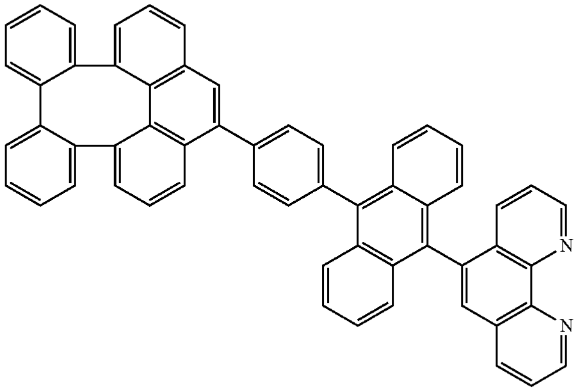

-continued
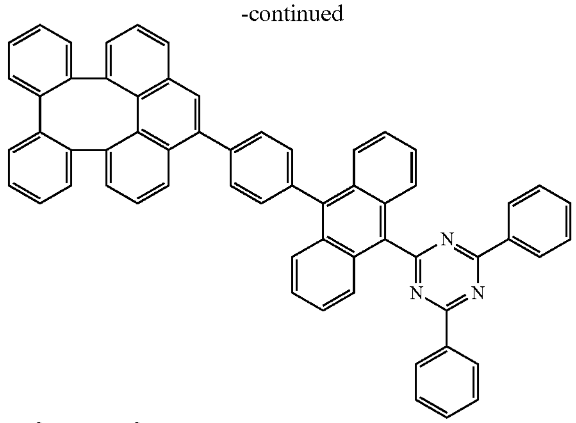
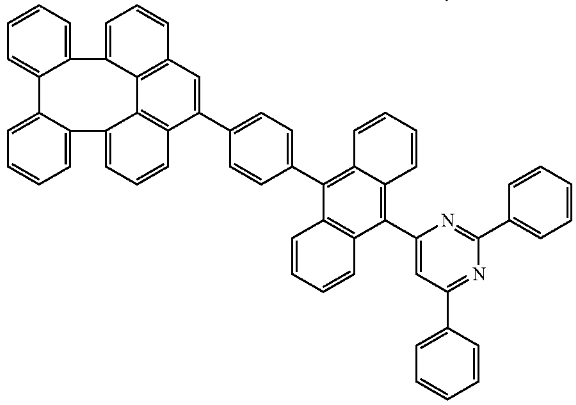
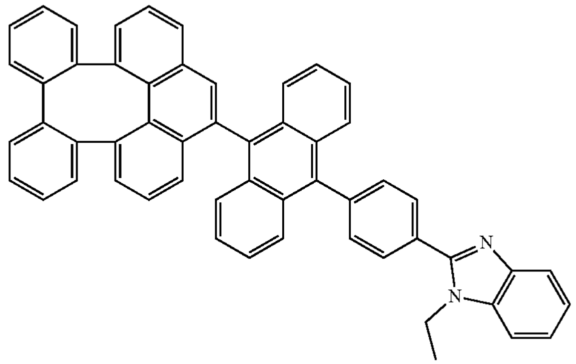
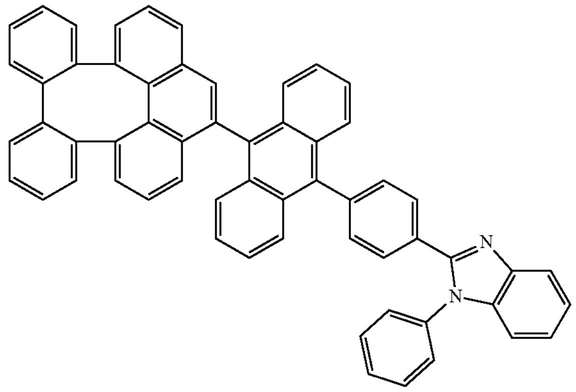
-continued
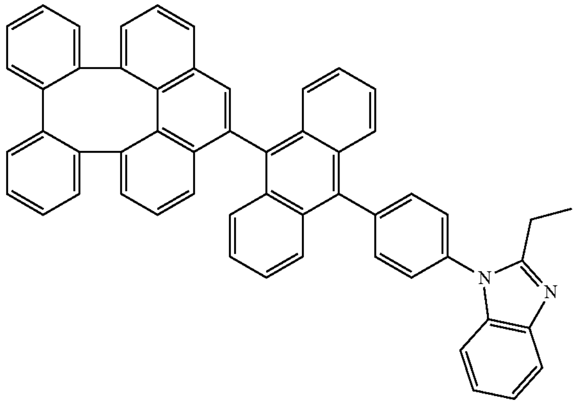
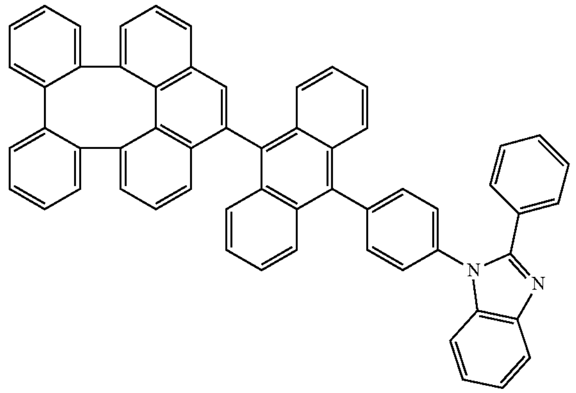
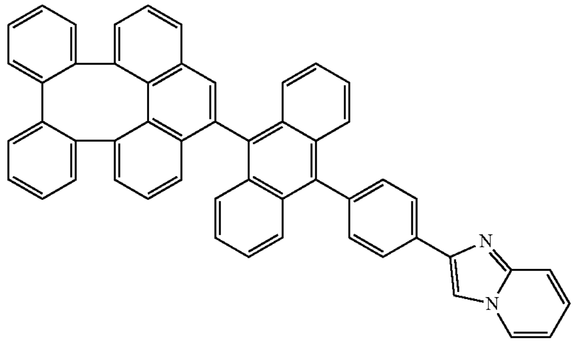
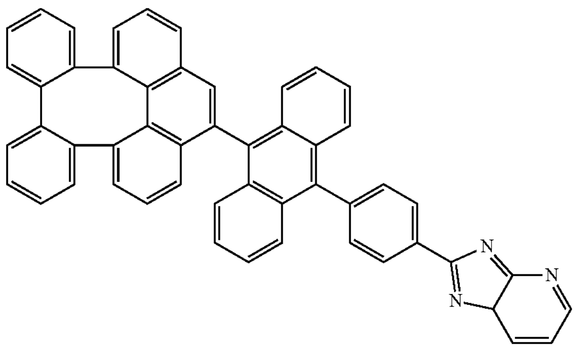

-continued
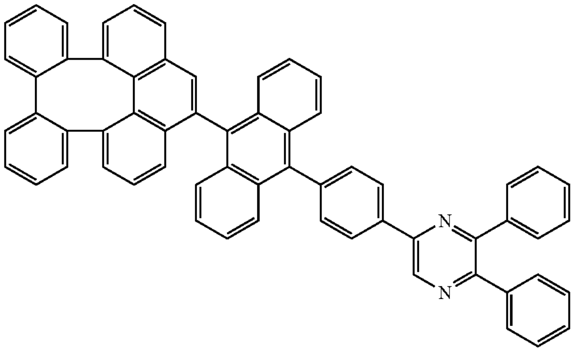
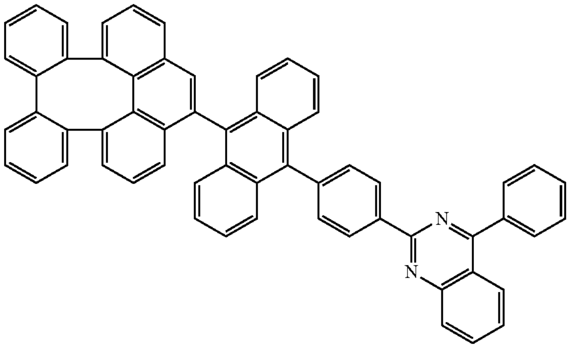
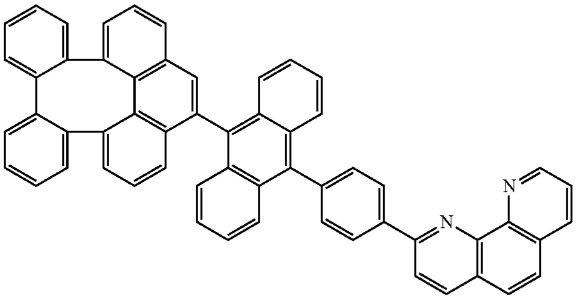
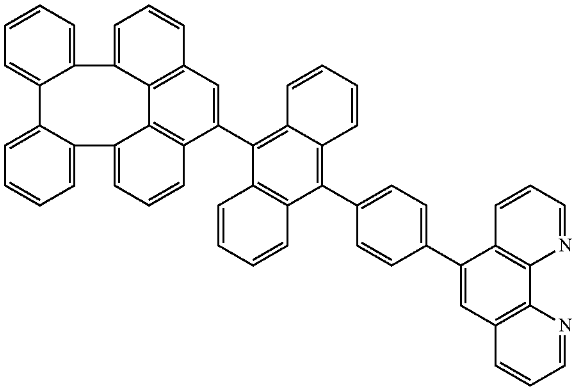
-continued
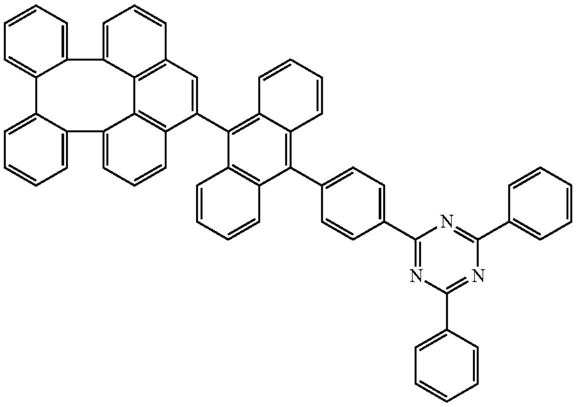
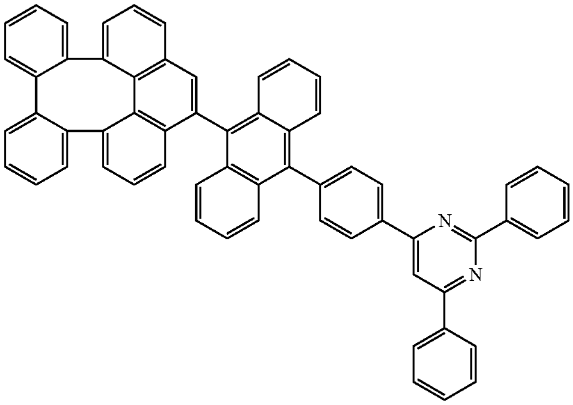
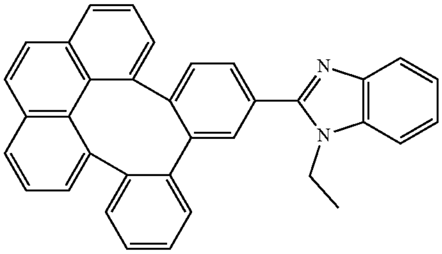
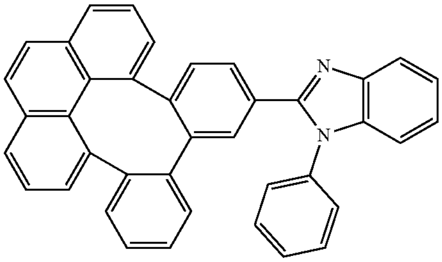
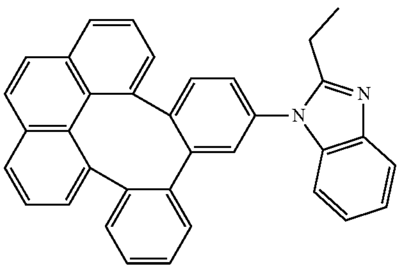

-continued
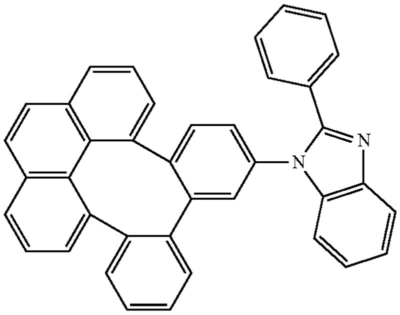
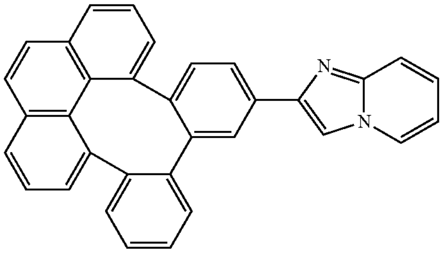
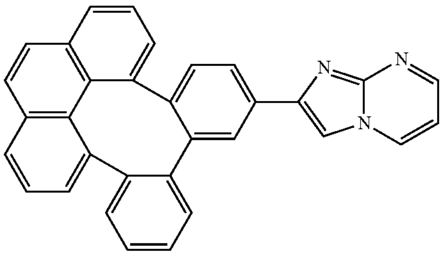
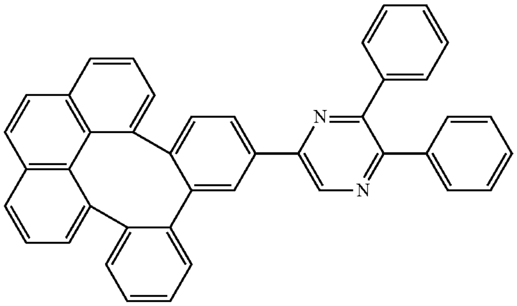
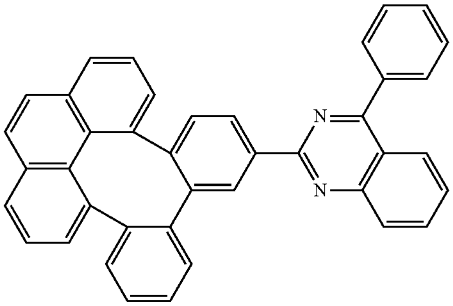
-continued
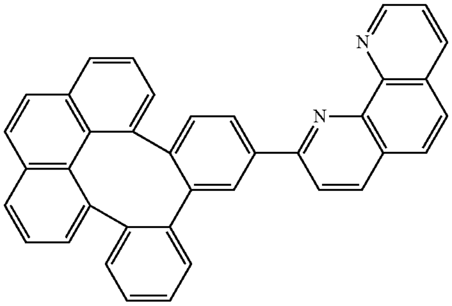
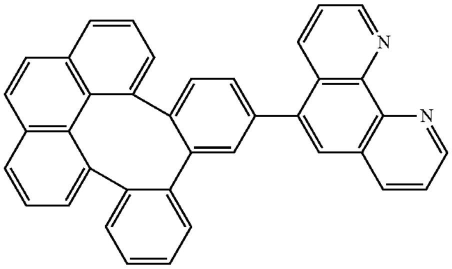
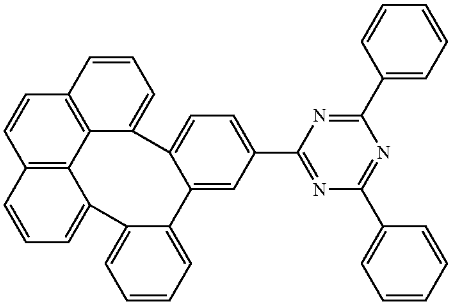
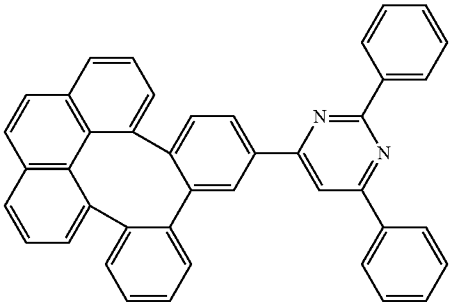
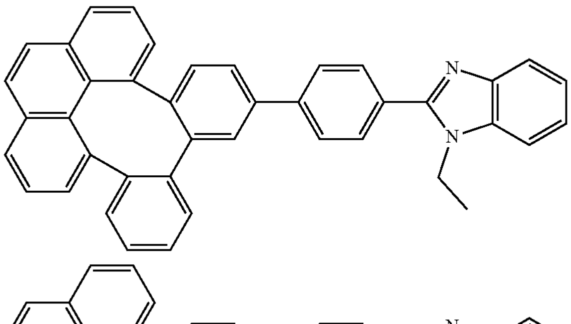
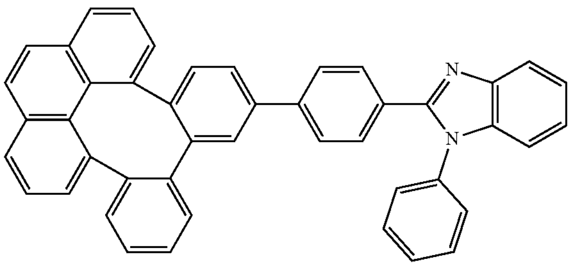

-continued
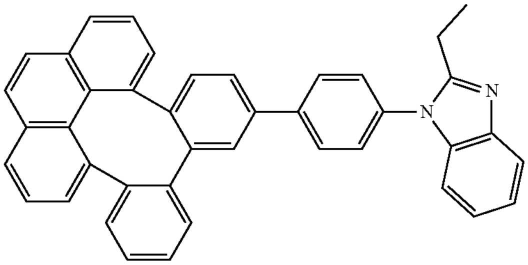
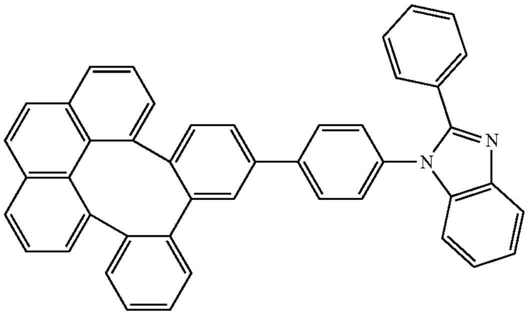
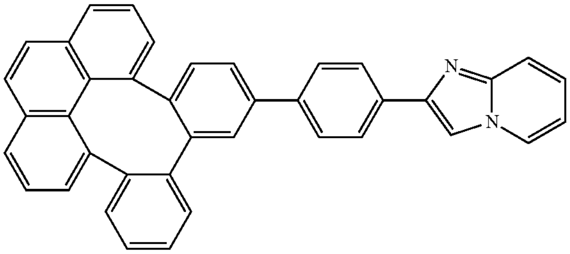
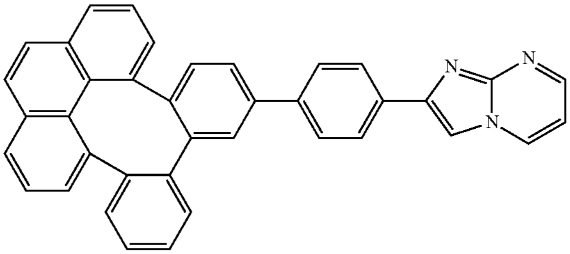
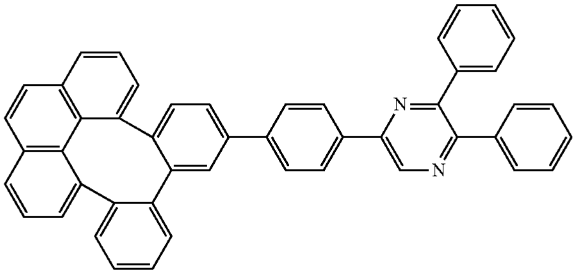
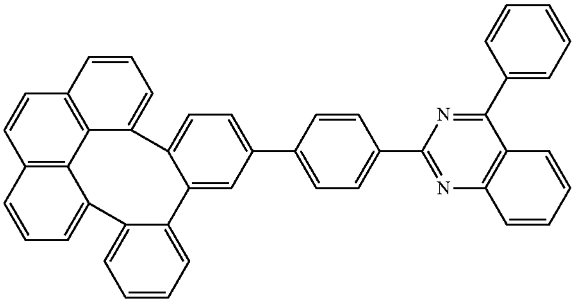
-continued
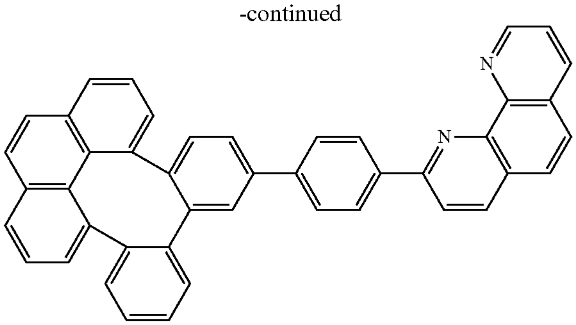
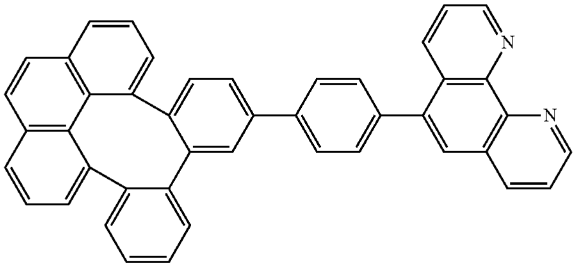
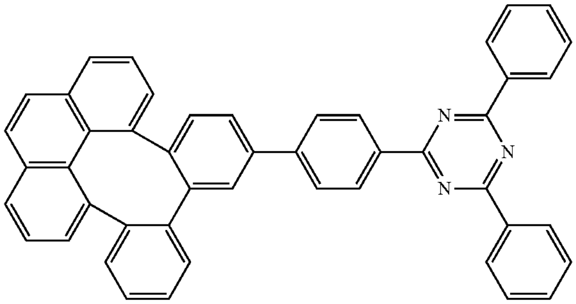
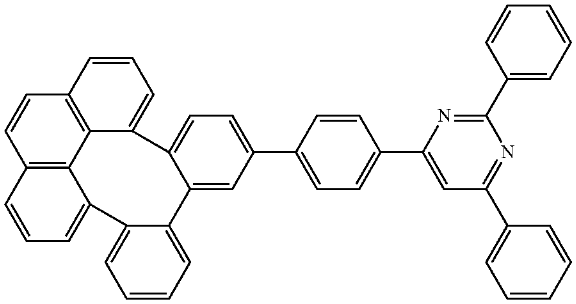
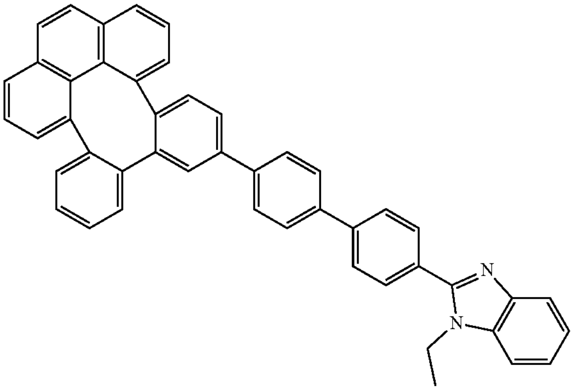

-continued
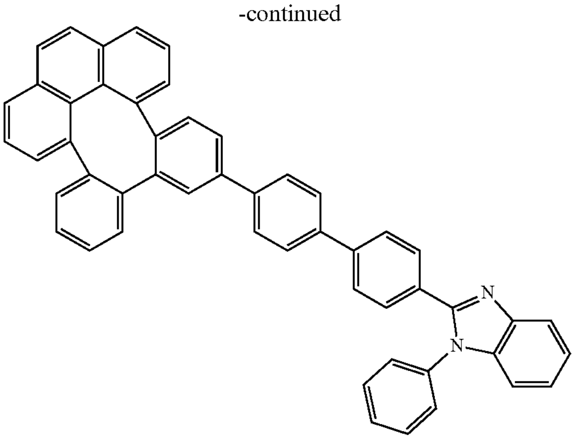
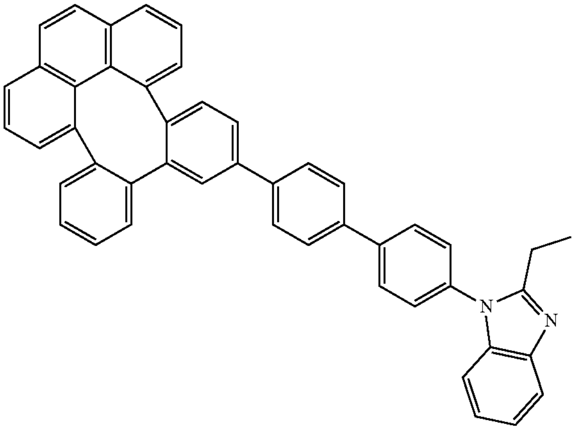
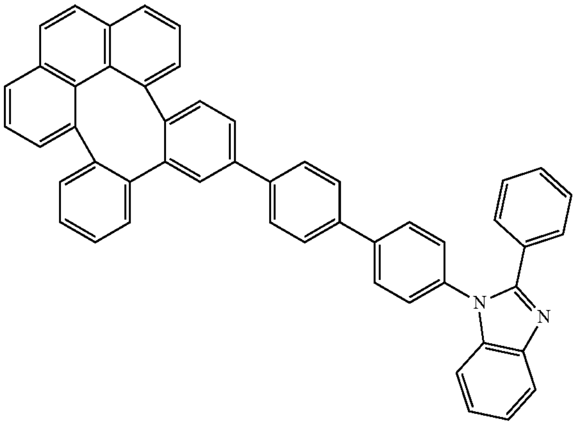
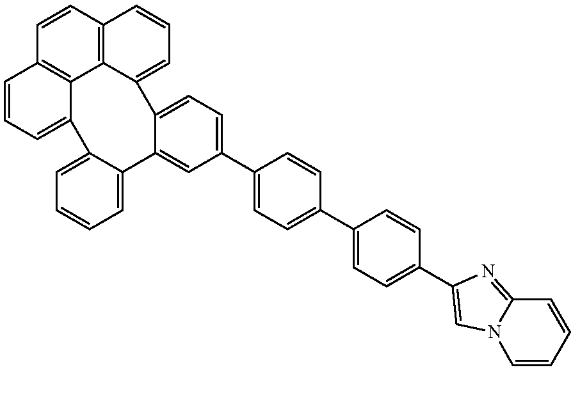
-continued
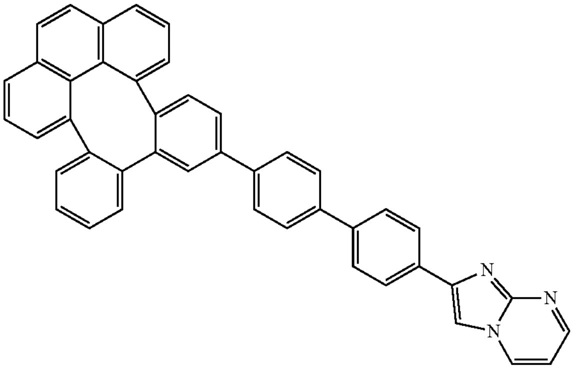
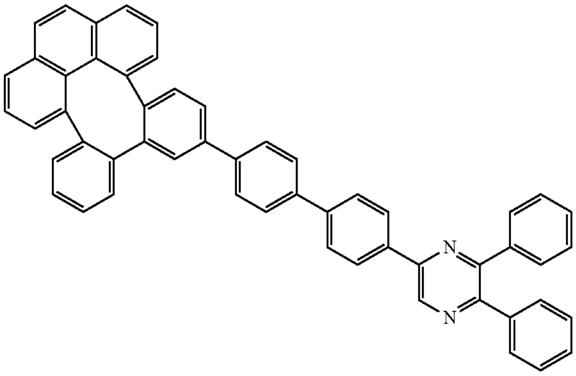
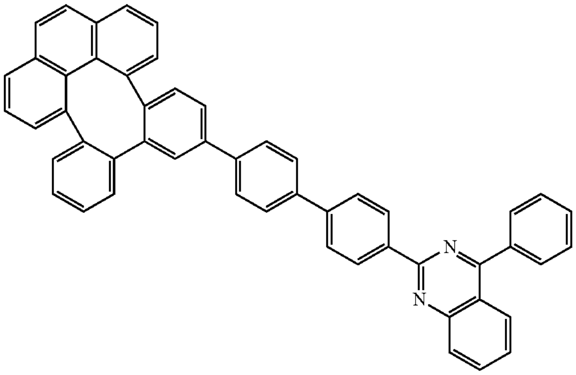
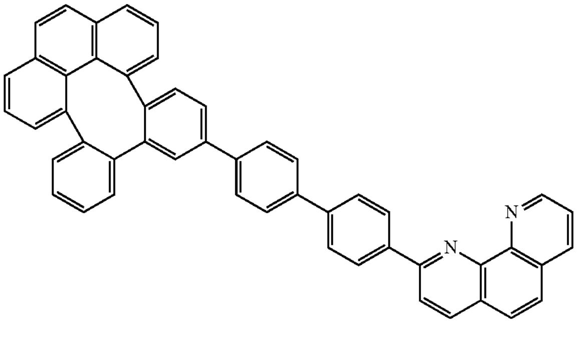

-continued
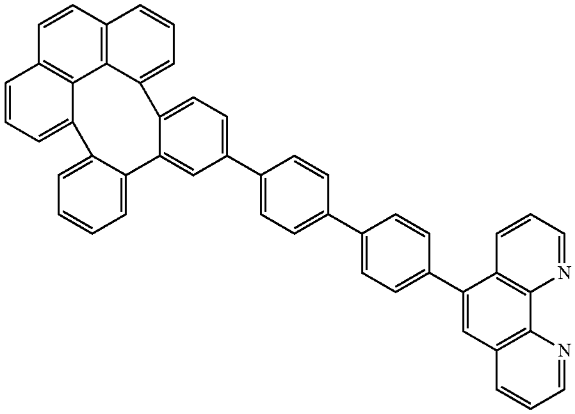
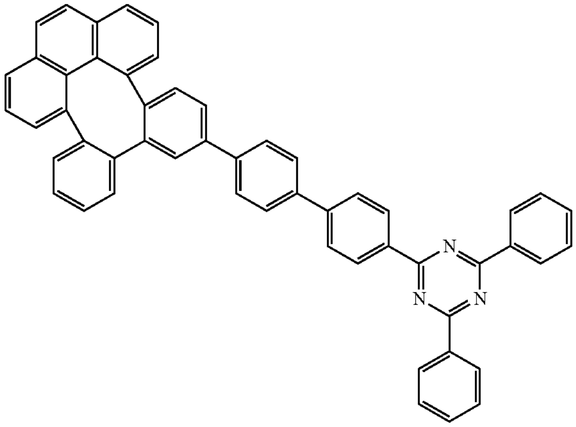
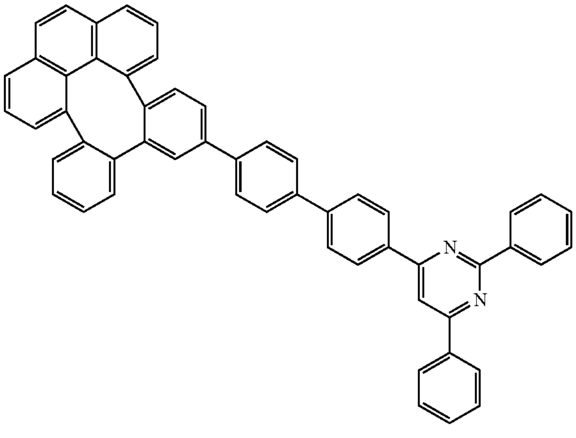
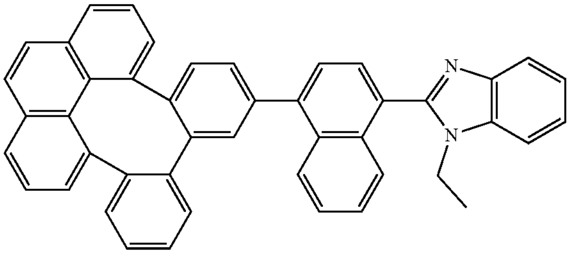
-continued
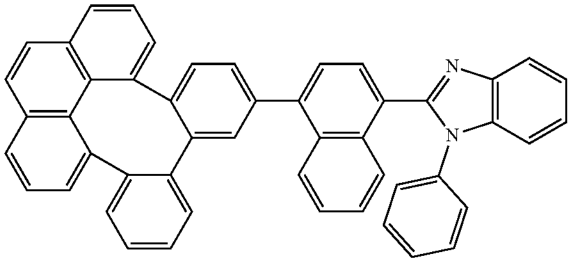
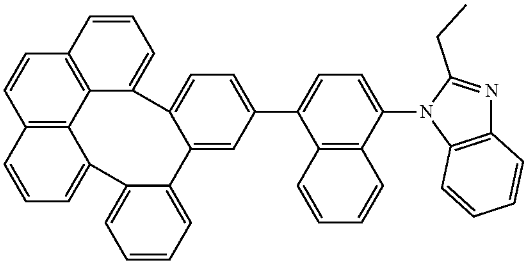
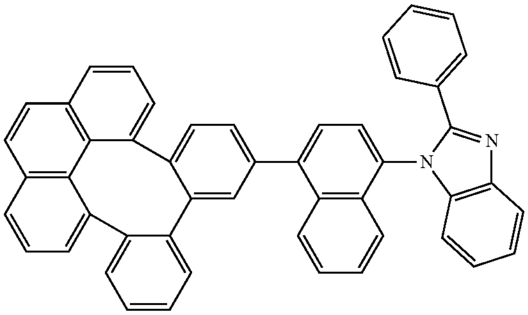
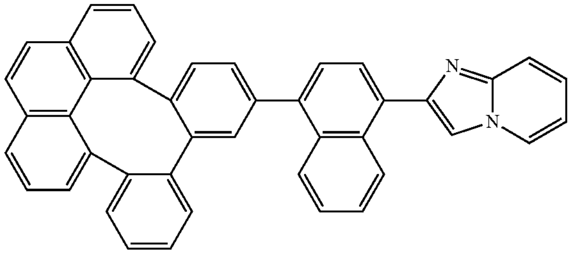
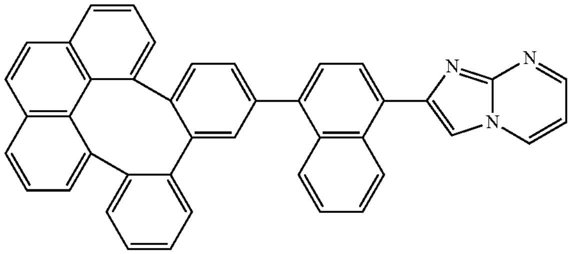
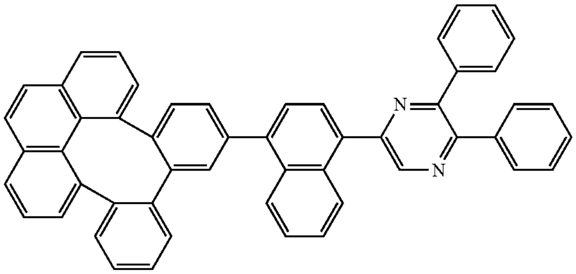

-continued
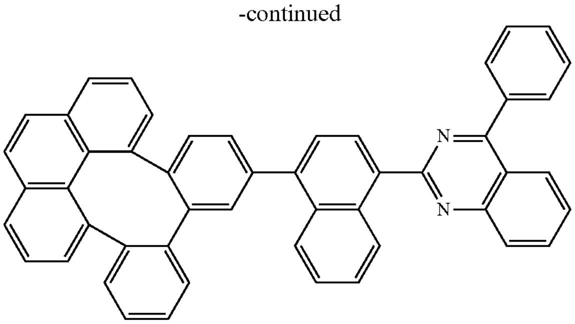
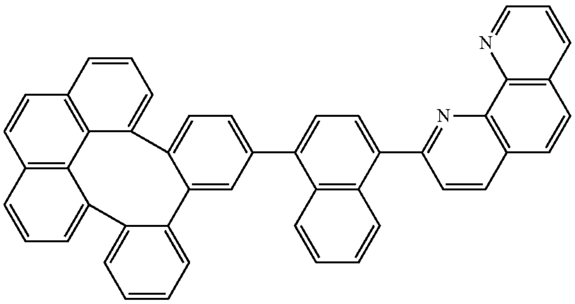
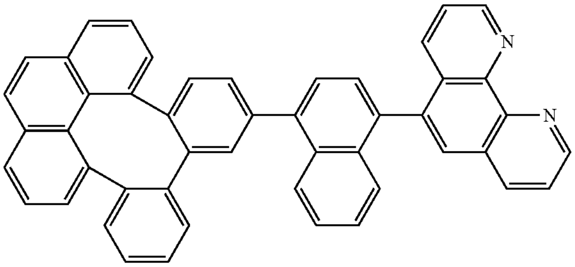
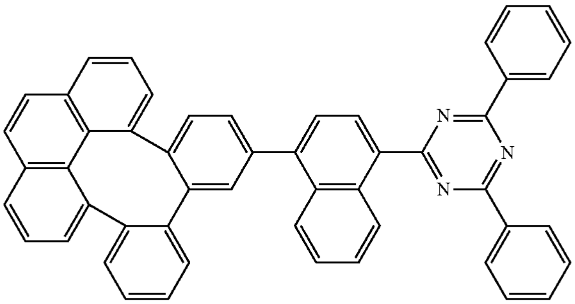
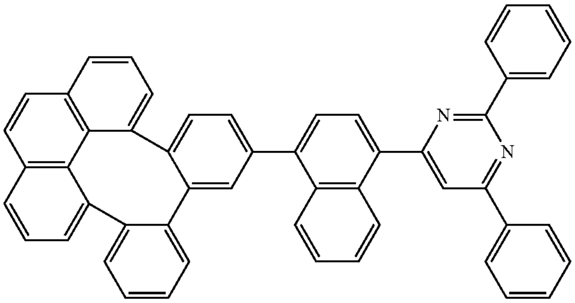
-continued
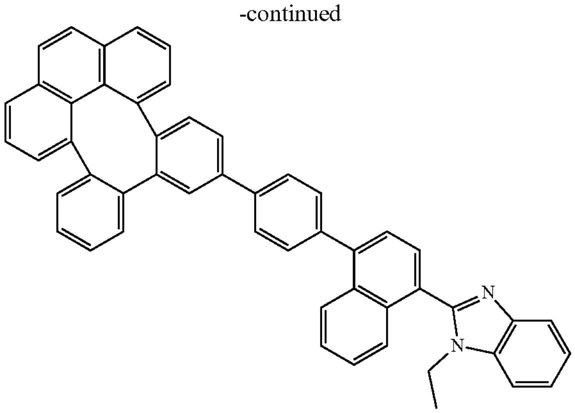
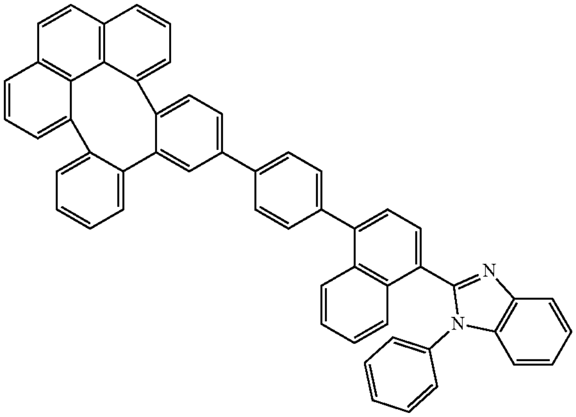
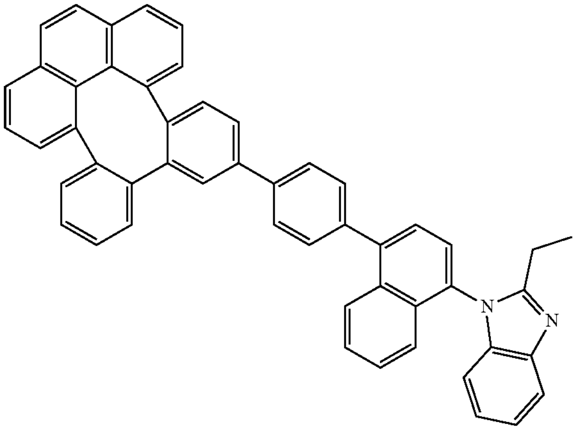
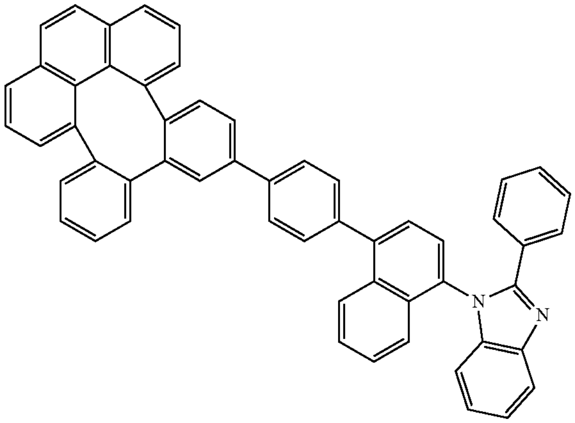

-continued
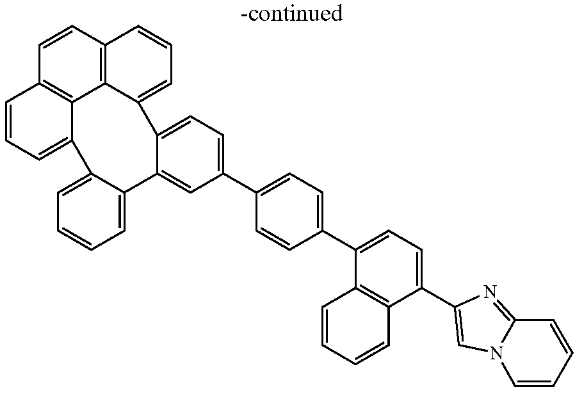
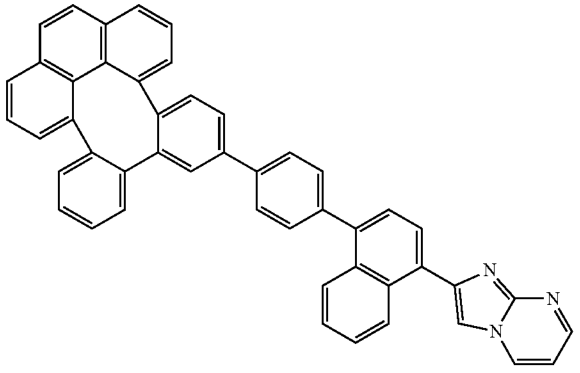
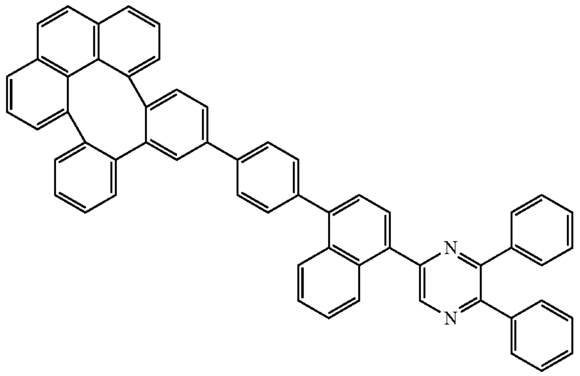
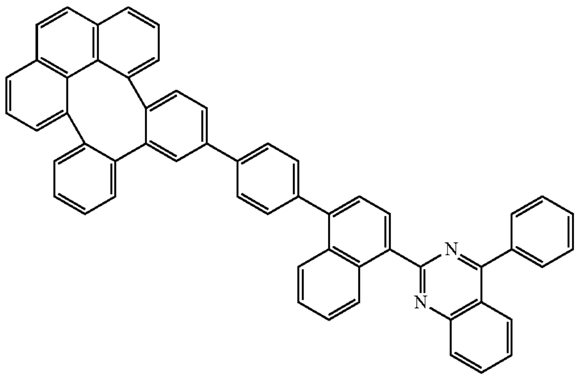
-continued
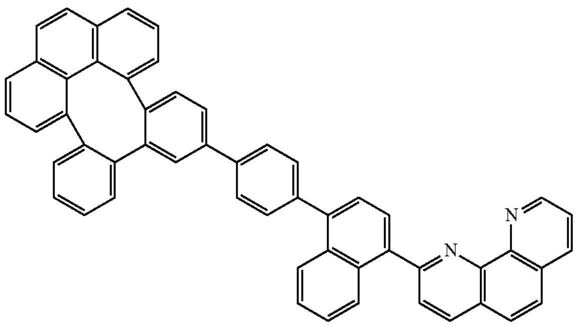
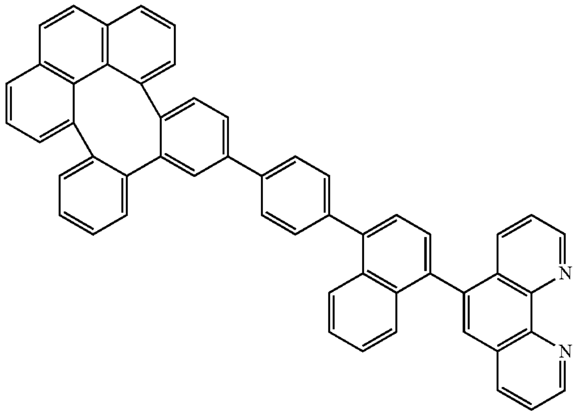
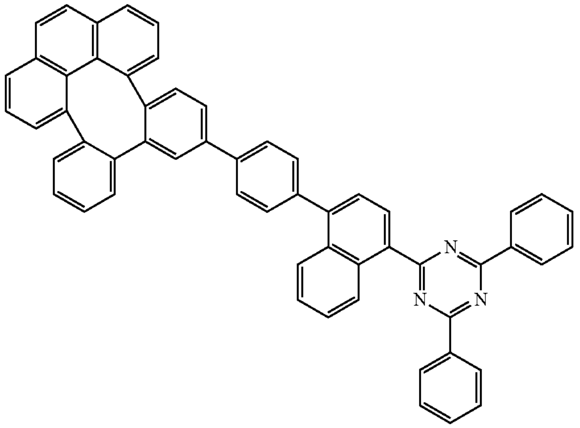
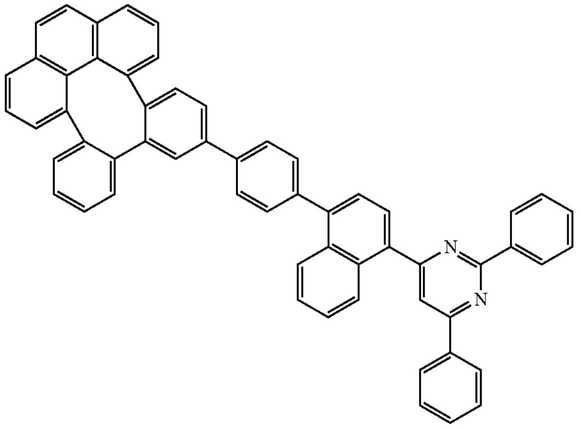

-continued
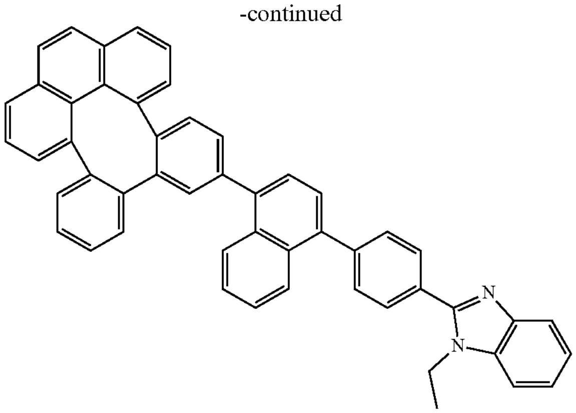
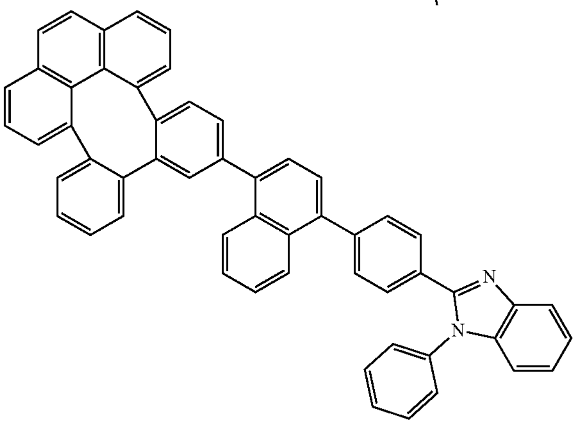
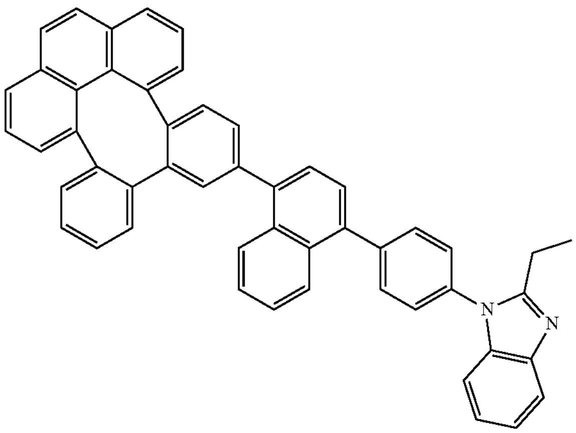
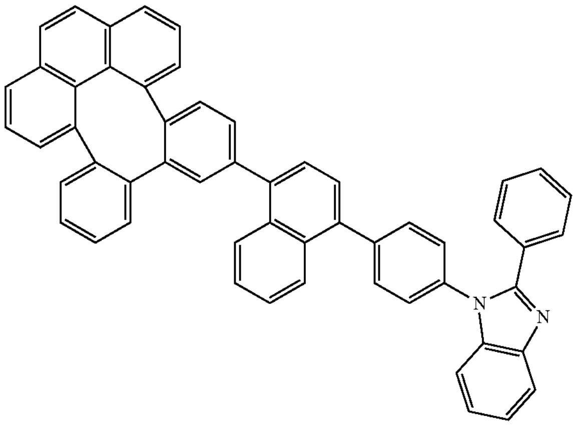
-continued
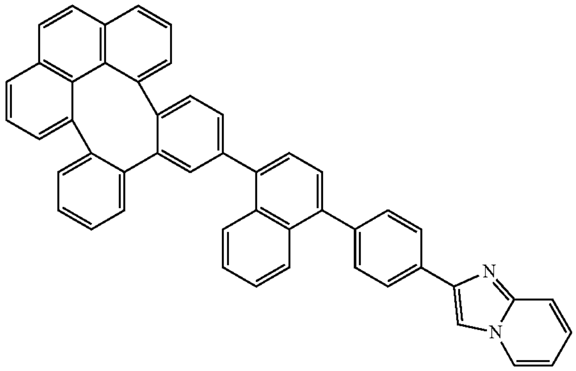
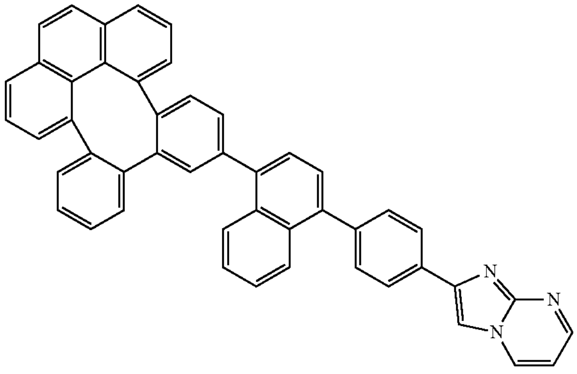
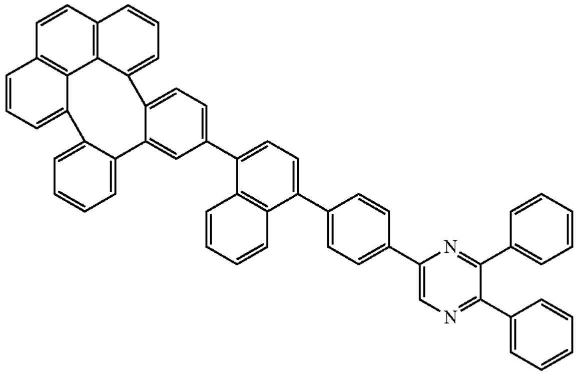
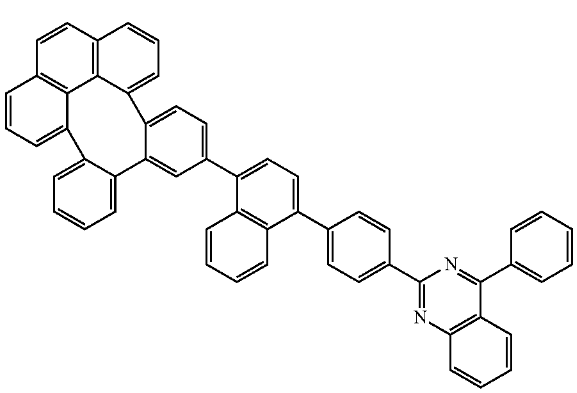

-continued
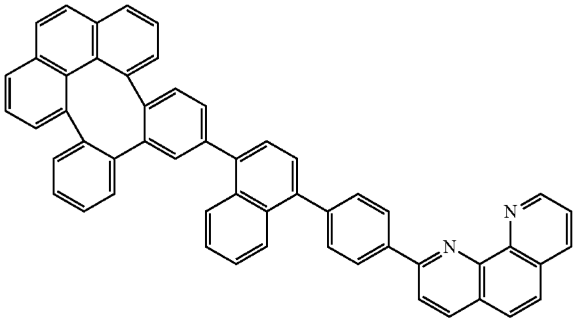
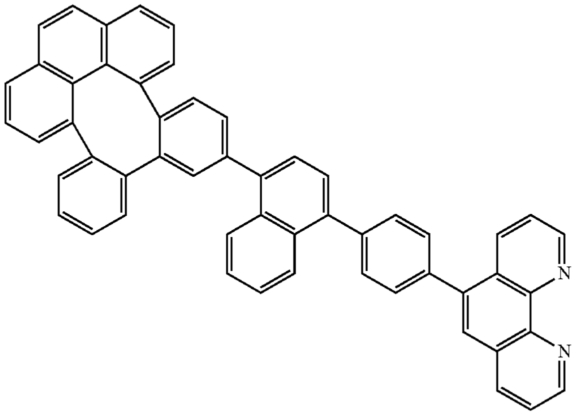
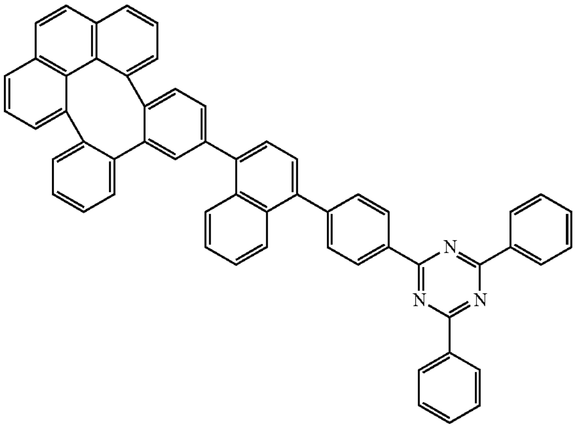
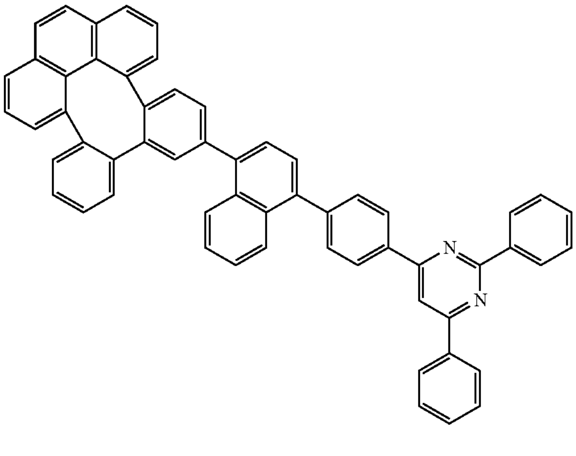
-continued
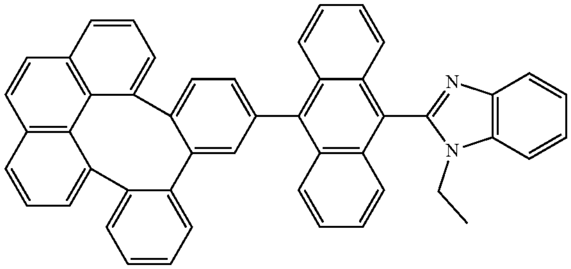
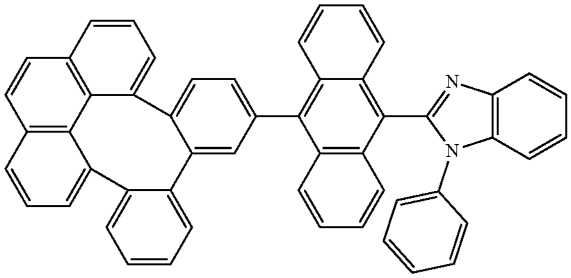
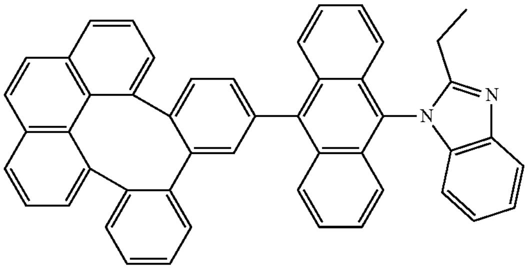
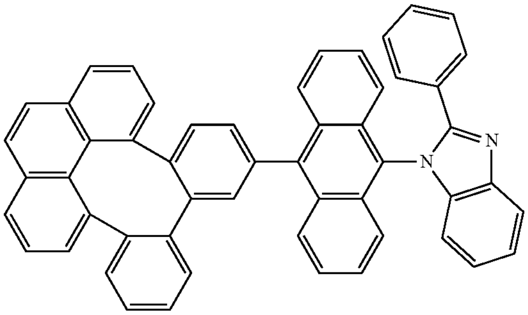
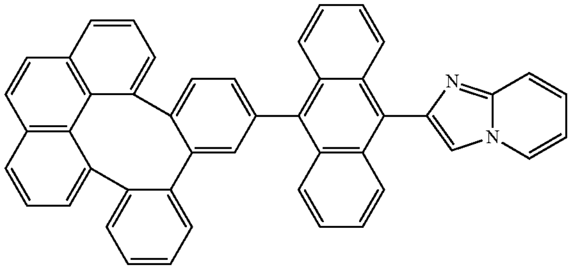
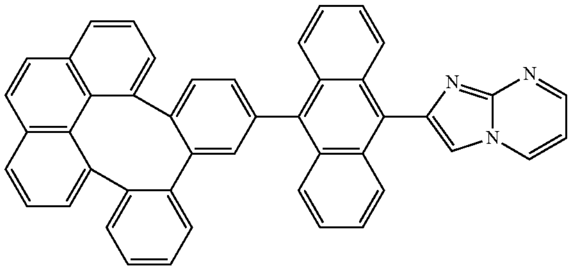

-continued
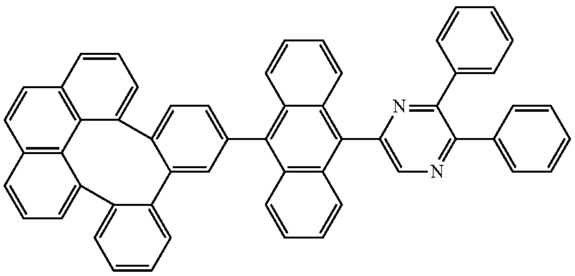
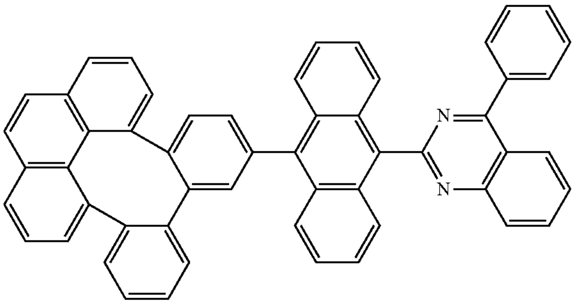
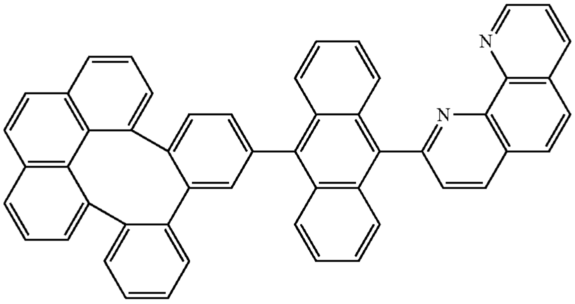
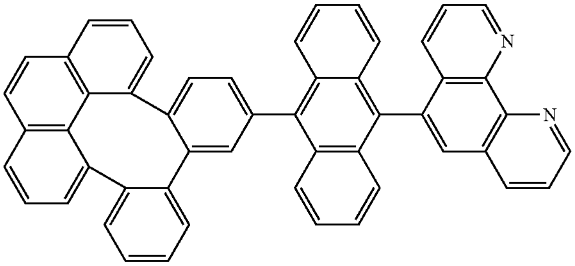
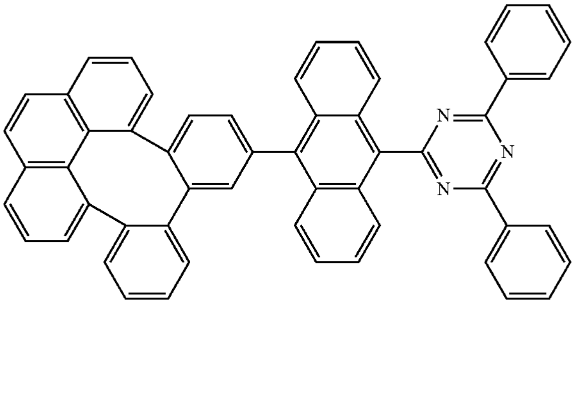
-continued
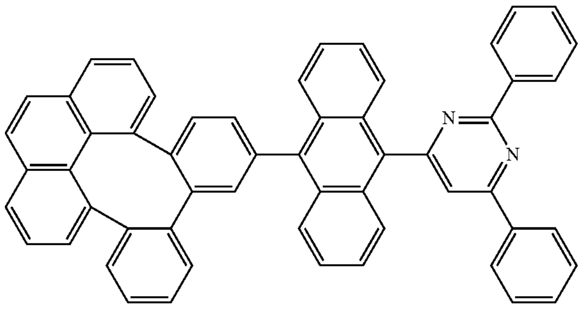
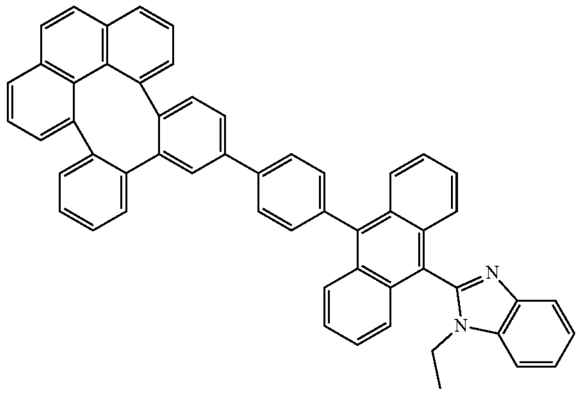
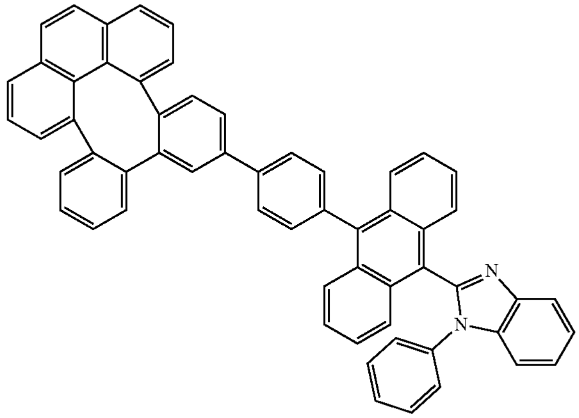
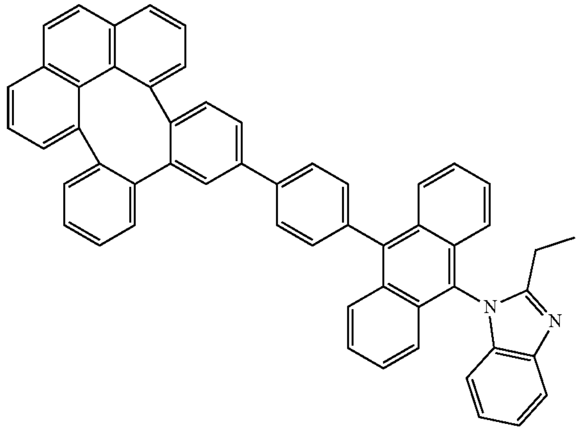

-continued
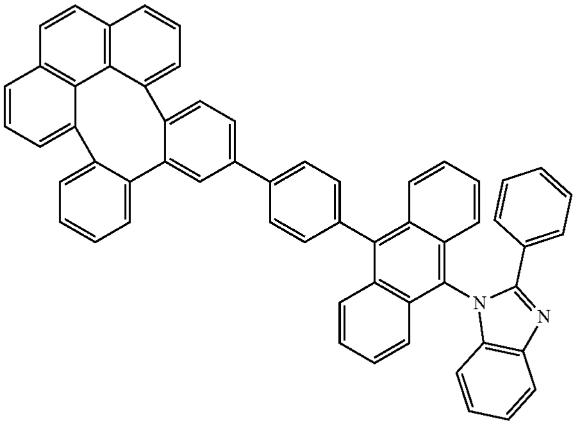
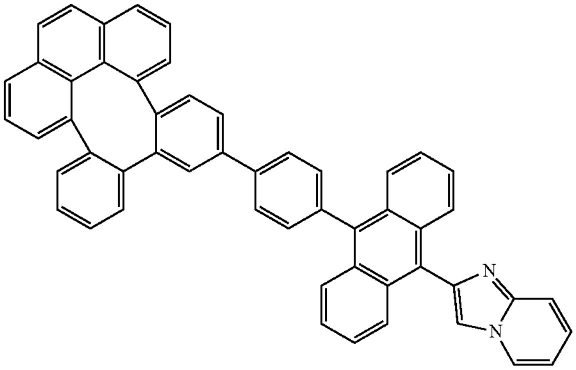
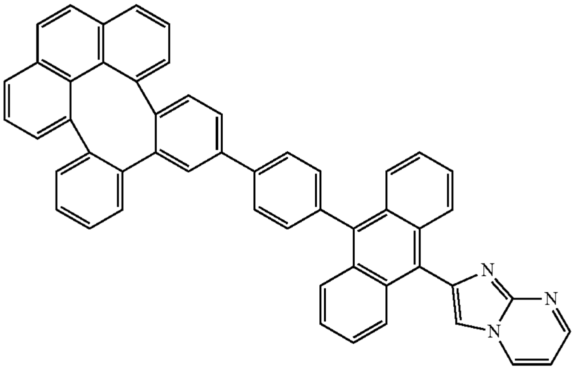
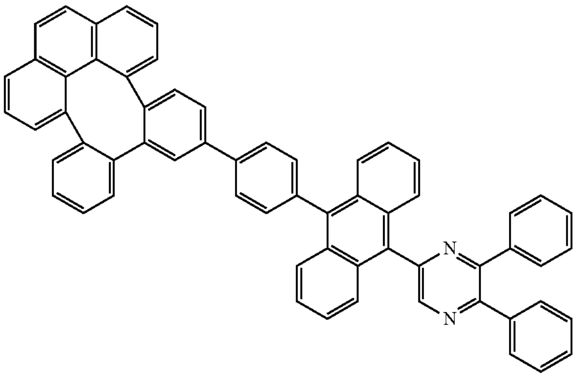
-continued
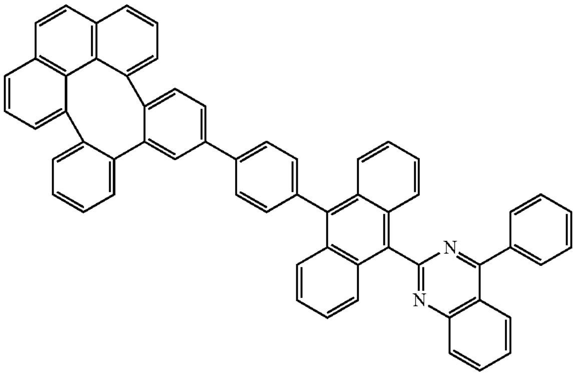
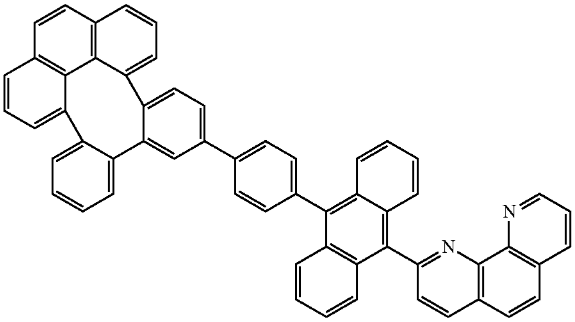
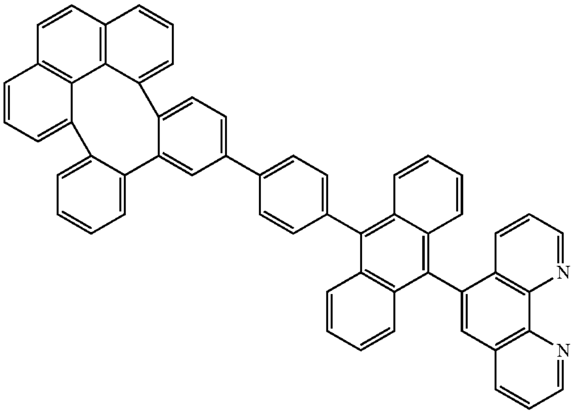
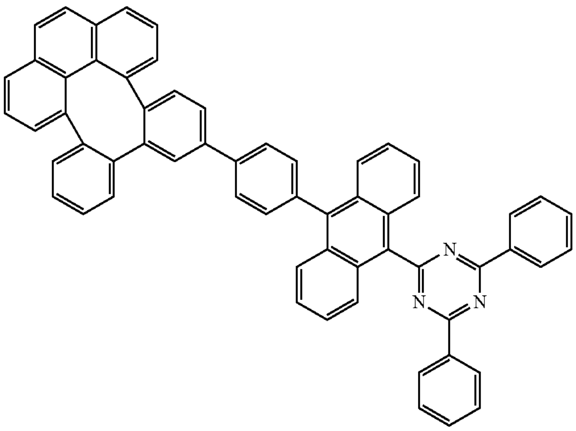

-continued
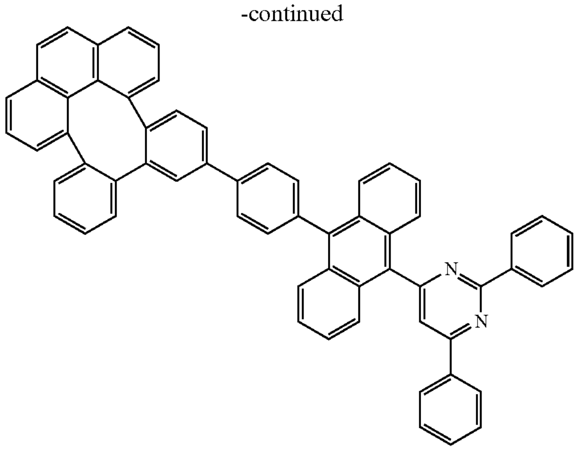
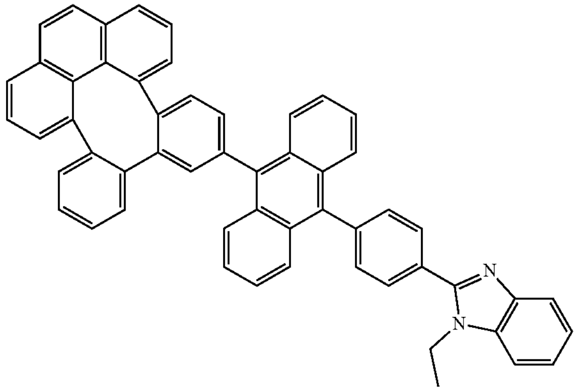
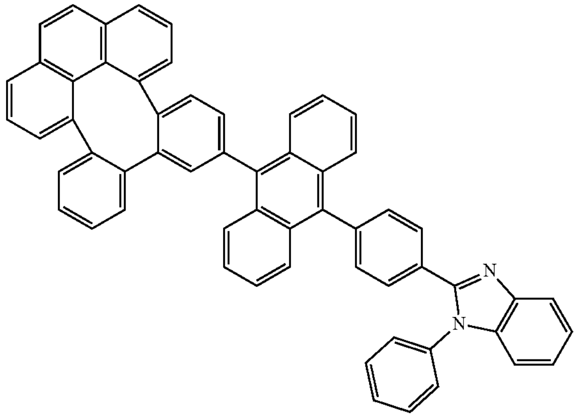
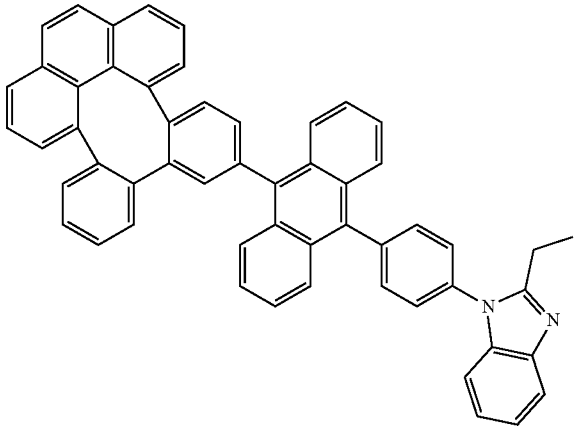
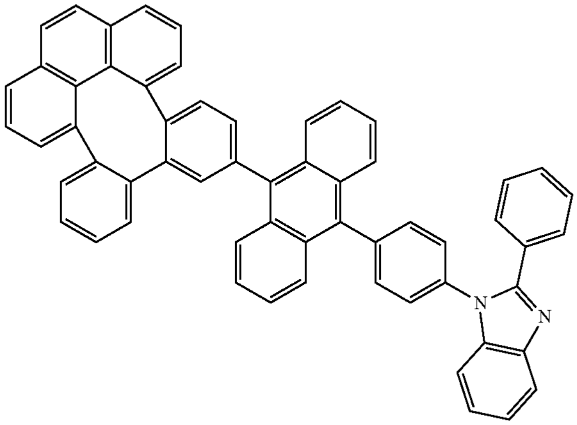
-continued
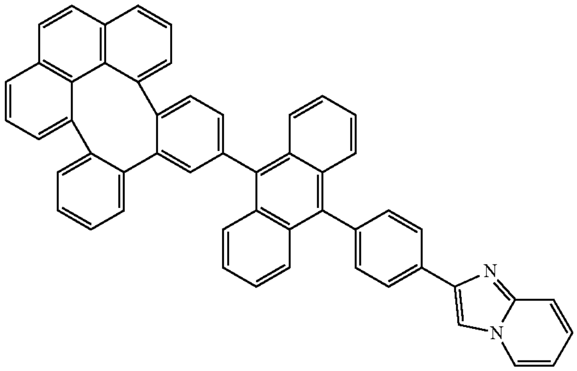
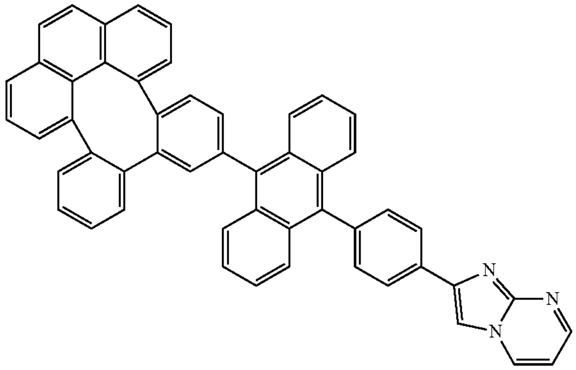
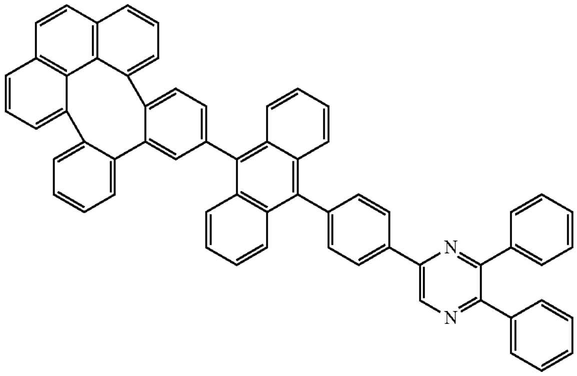

-continued
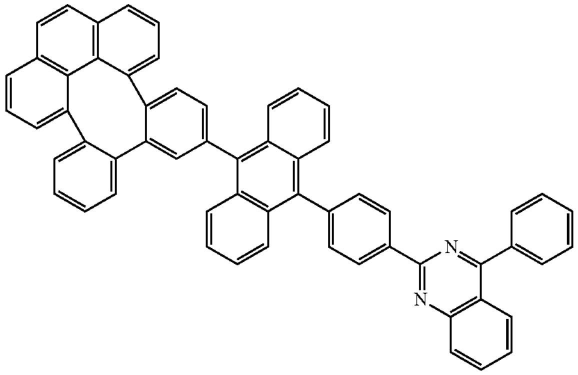
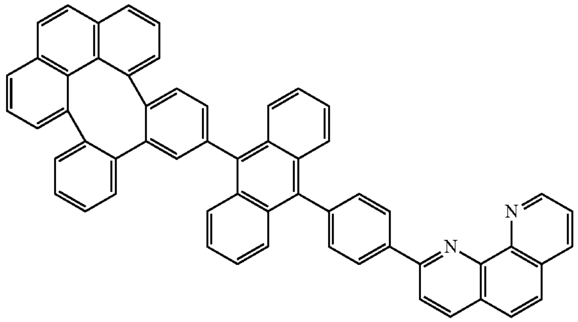
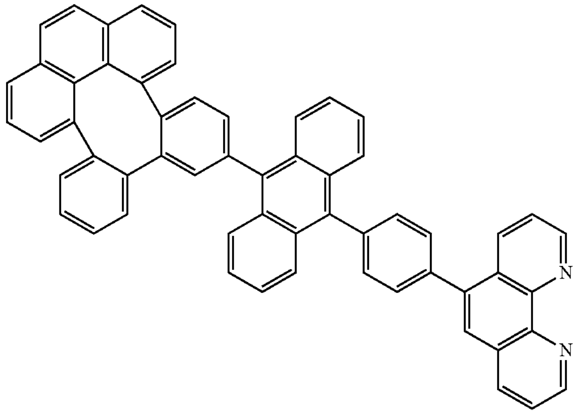
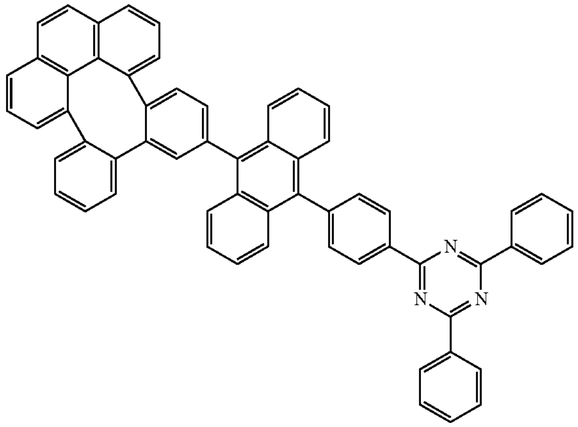
-continued
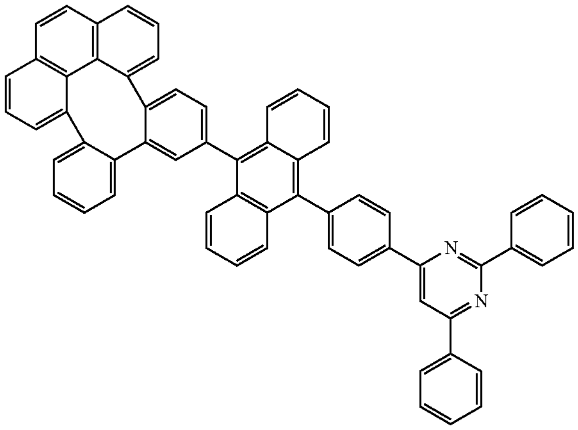
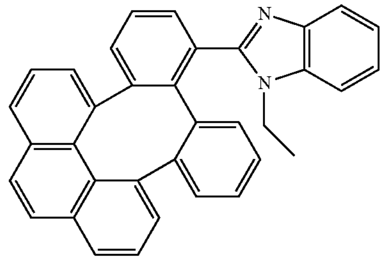
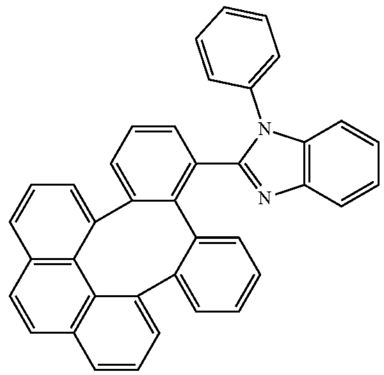
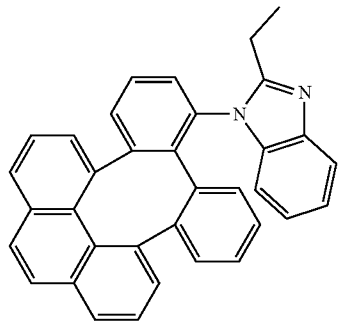

-continued
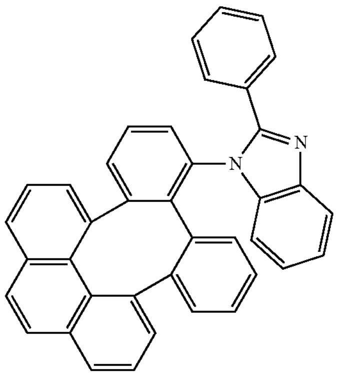
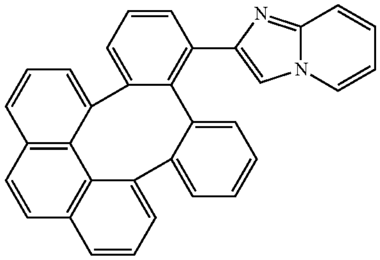
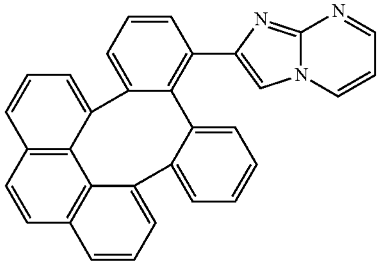
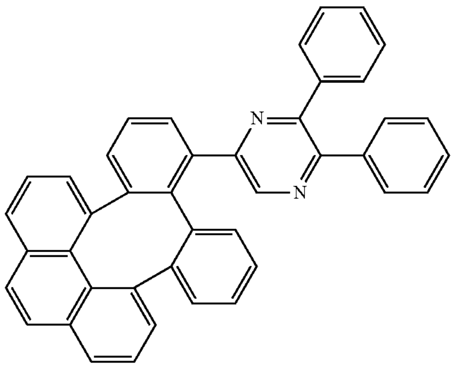
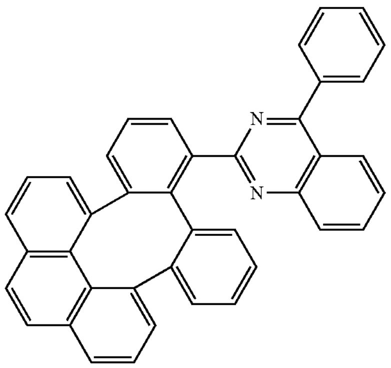
-continued
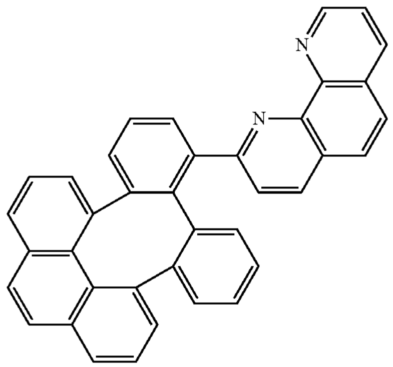
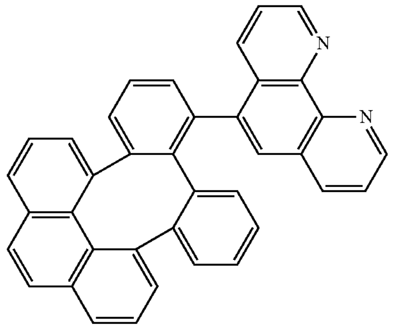
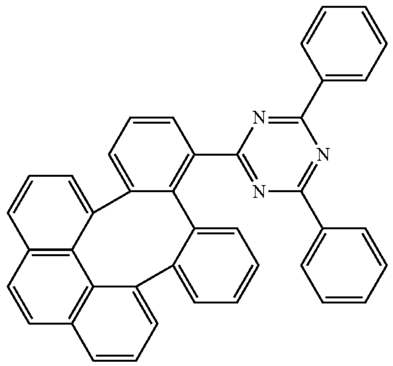
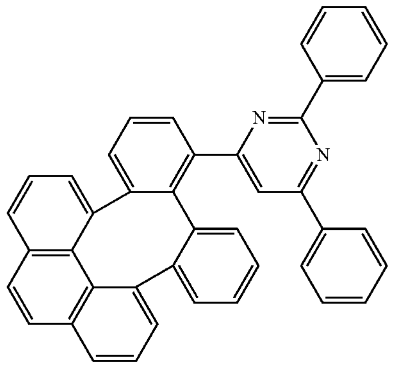
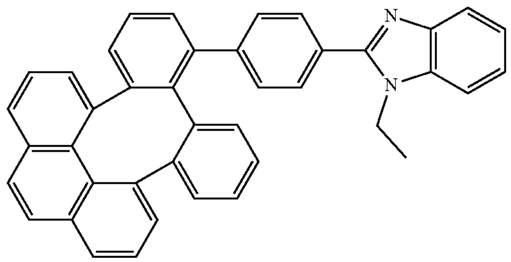

-continued
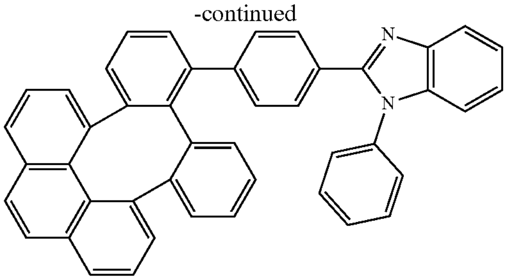
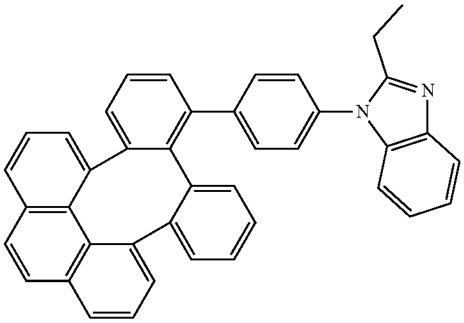
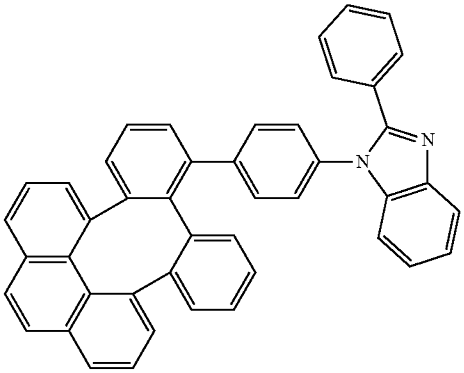
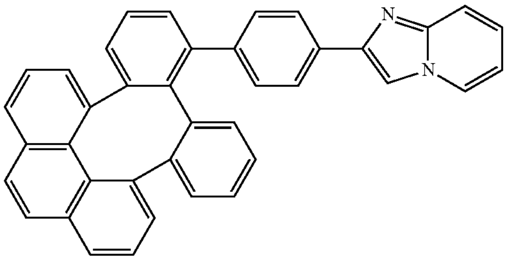
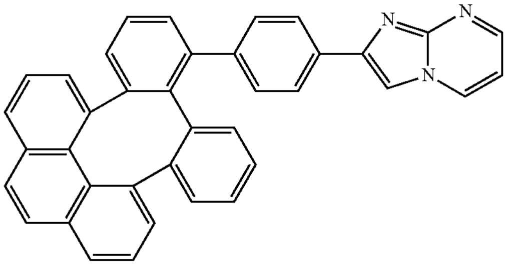
-continued
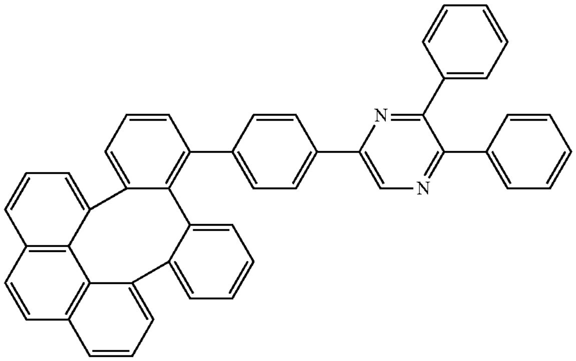
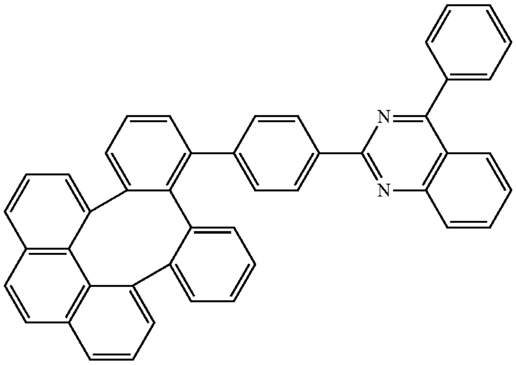
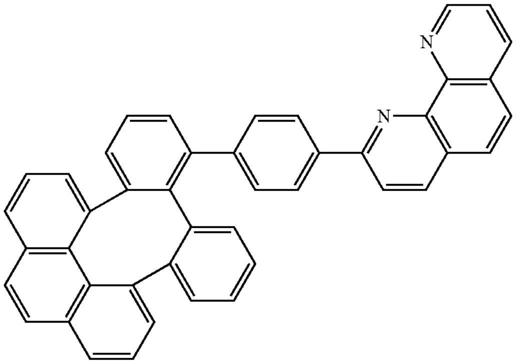
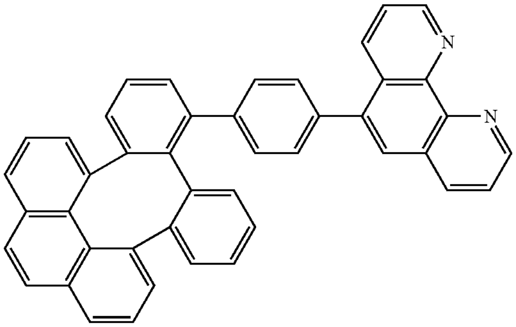

-continued
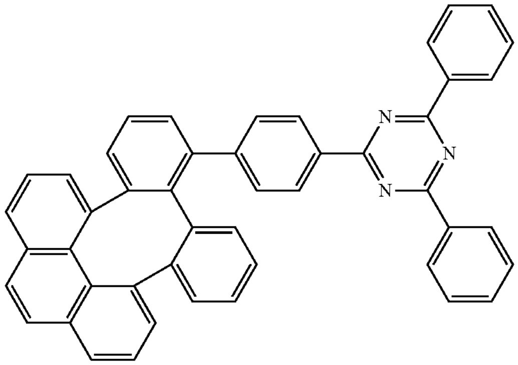
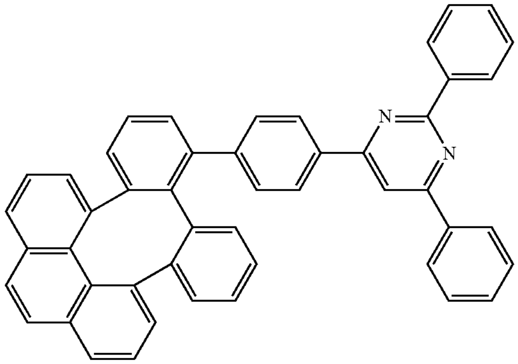
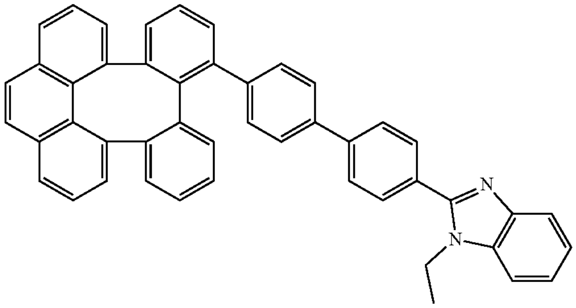
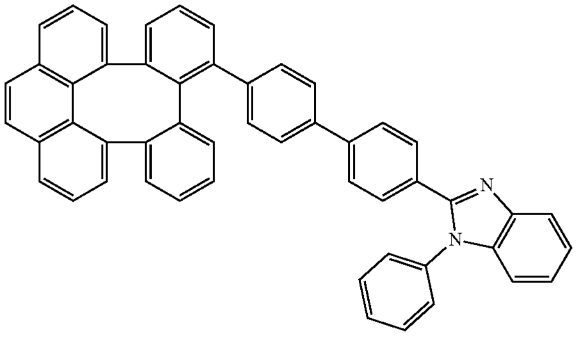
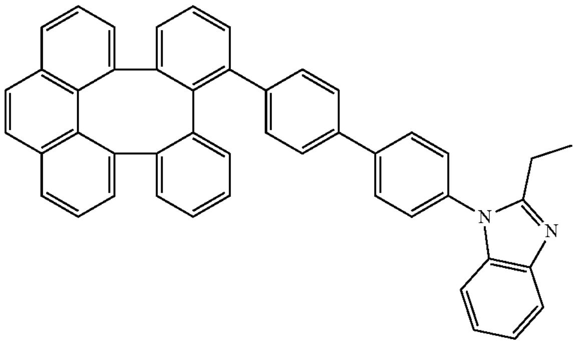
-continued
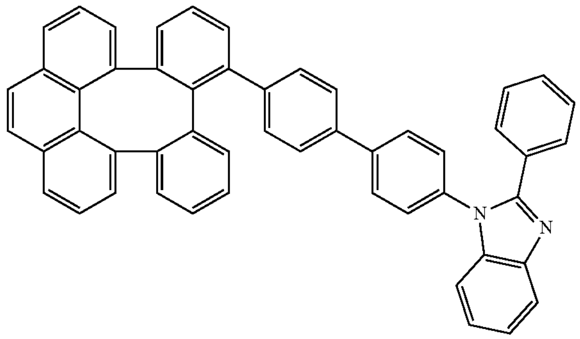
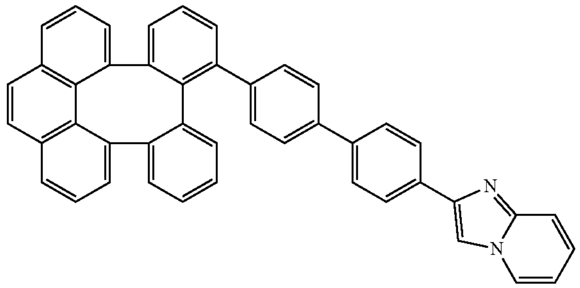
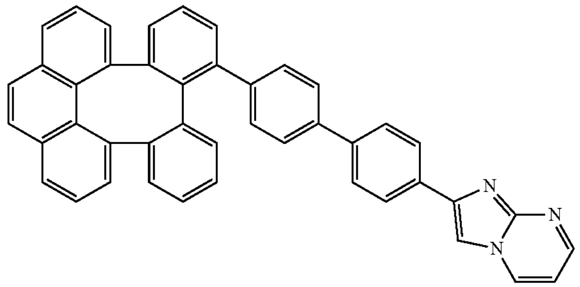
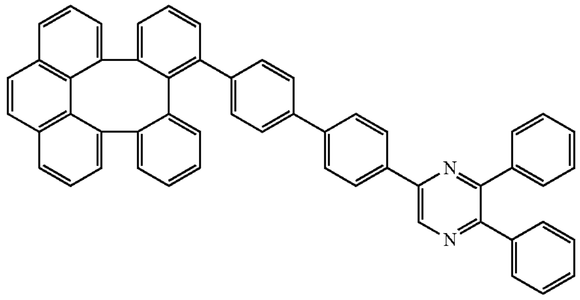
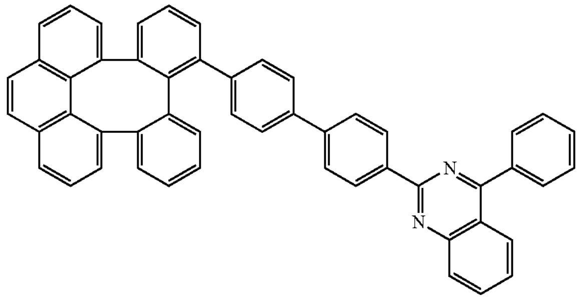

-continued
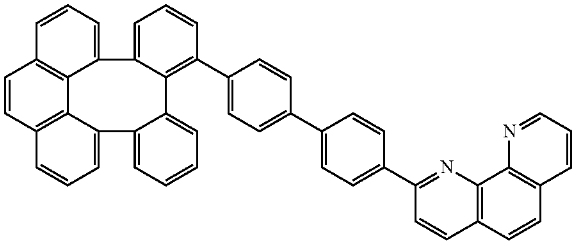
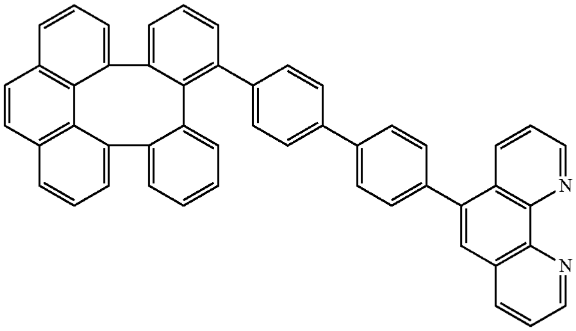
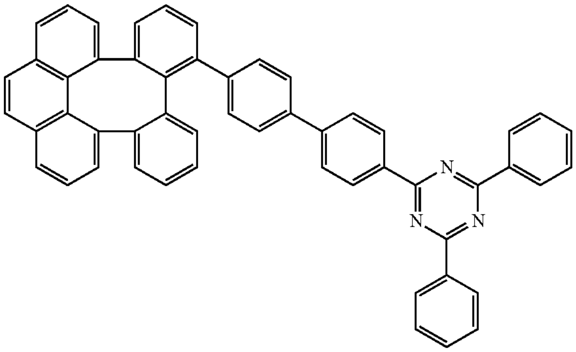
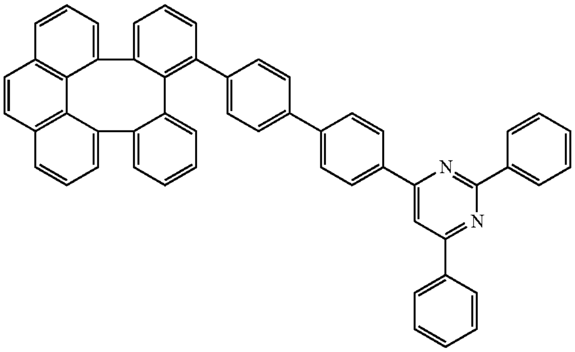
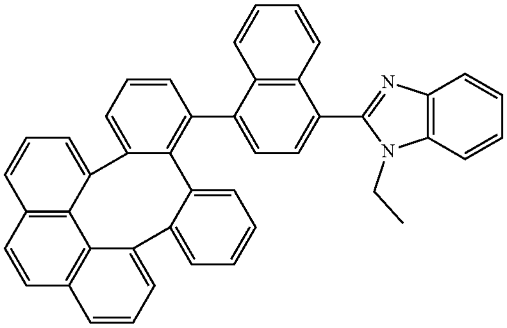
-continued
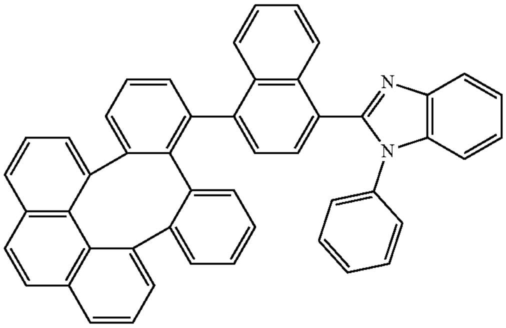
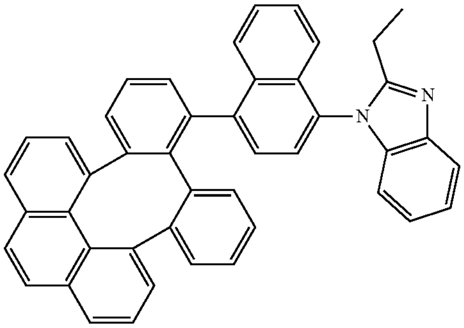
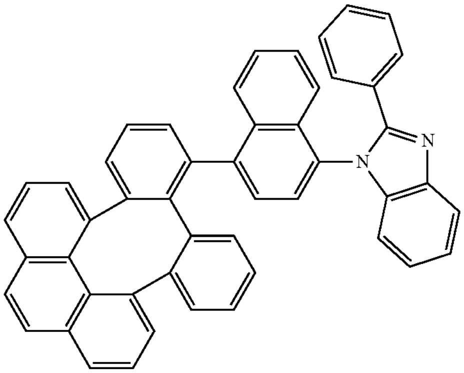
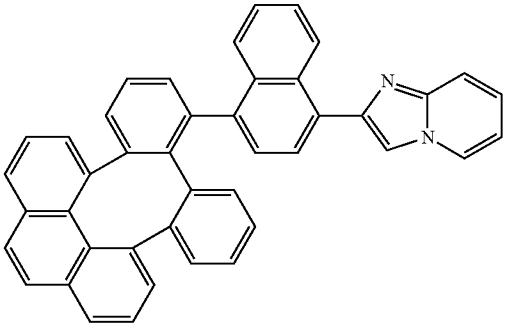
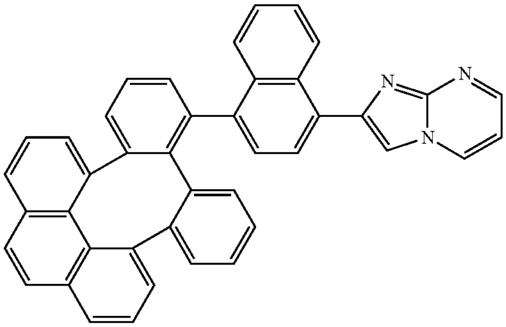

-continued
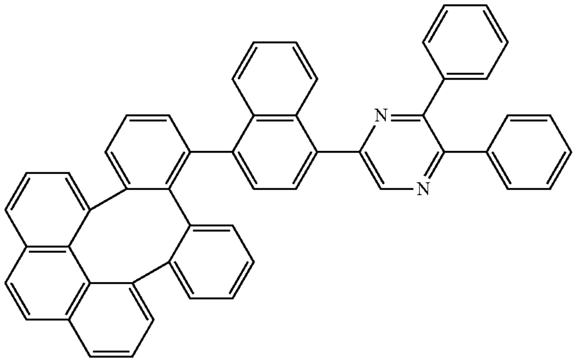
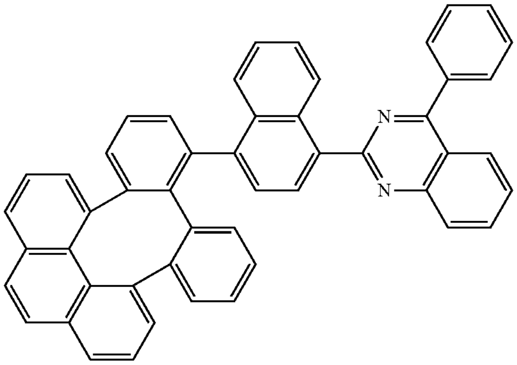
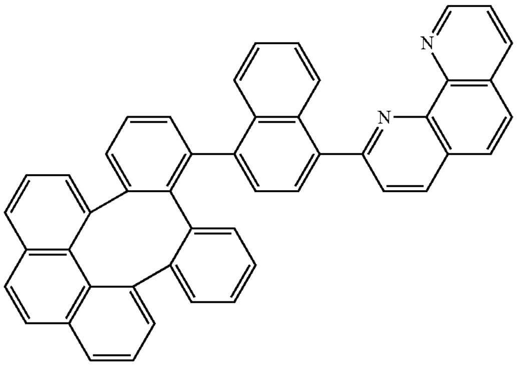
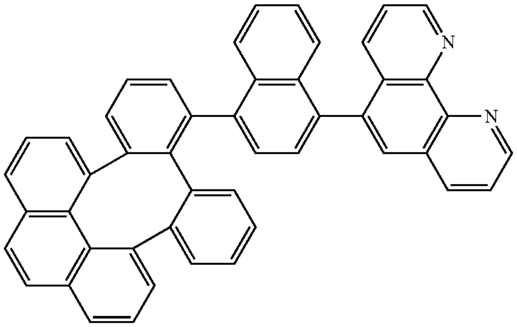
-continued
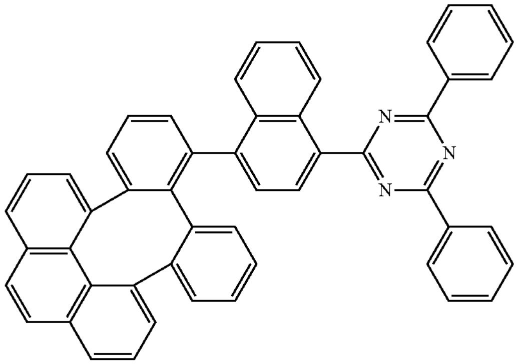
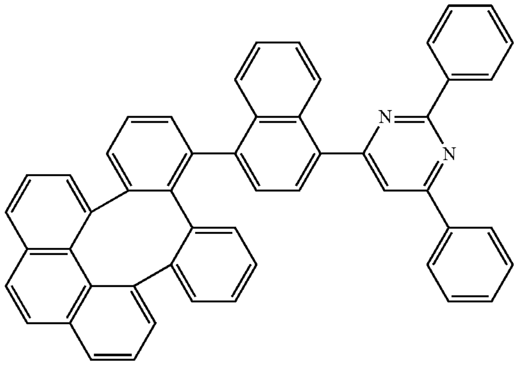
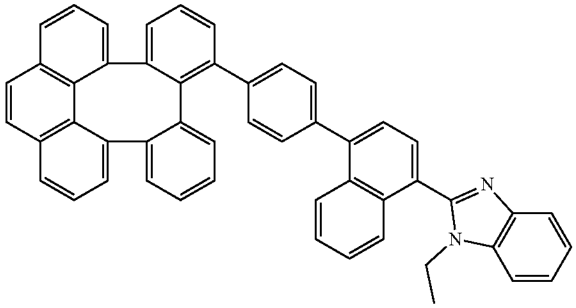
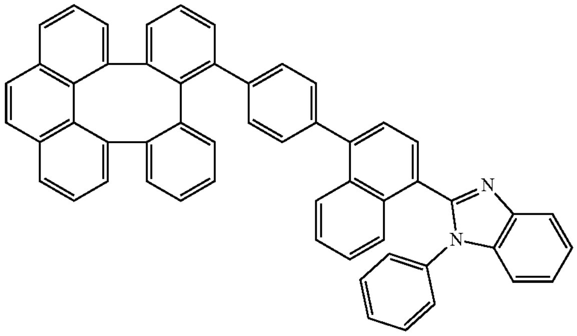
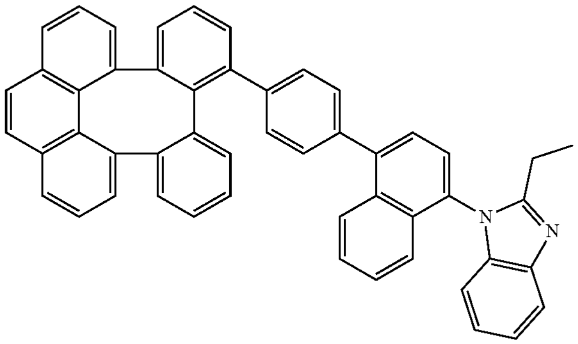

-continued
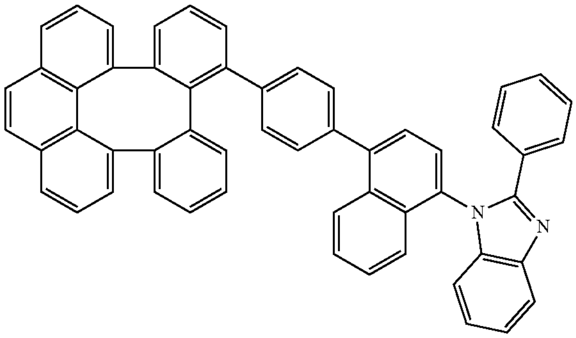
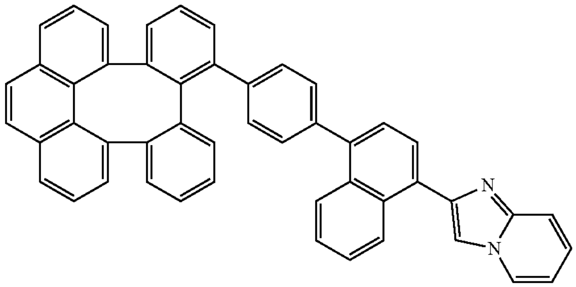
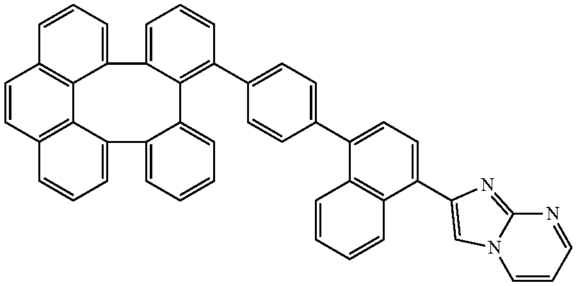
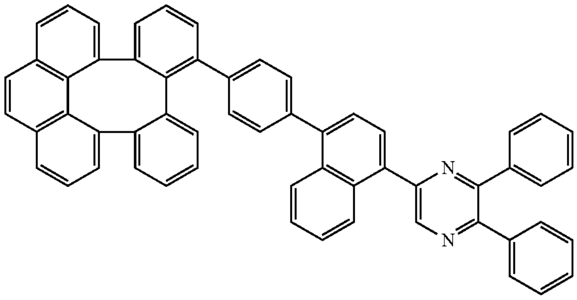
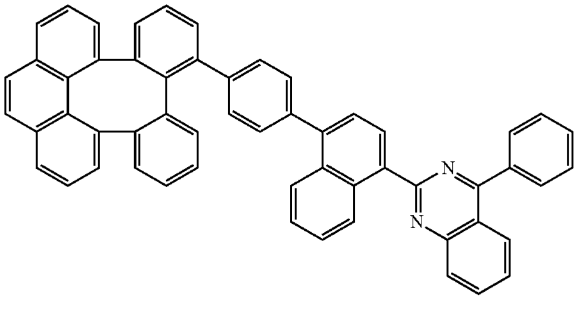
-continued
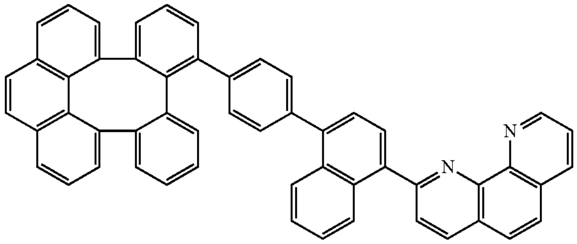
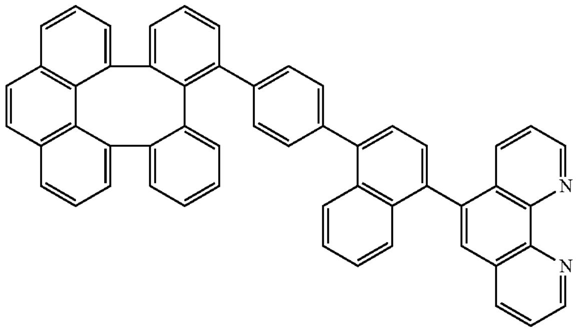
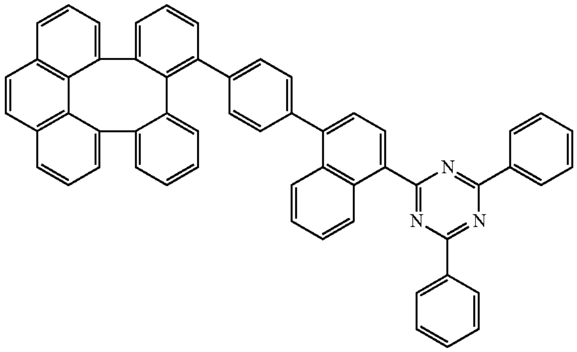
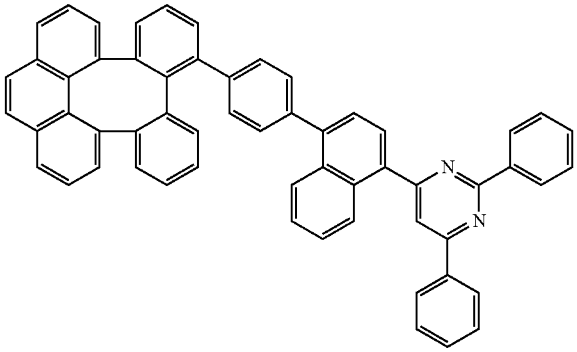
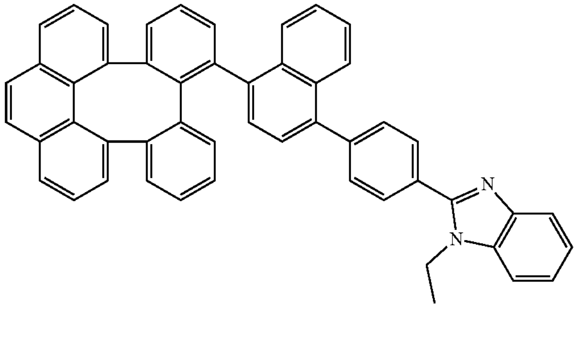

-continued
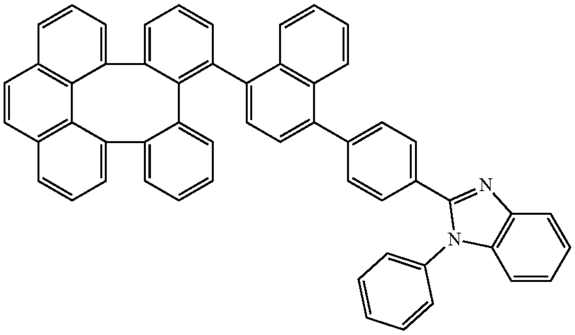
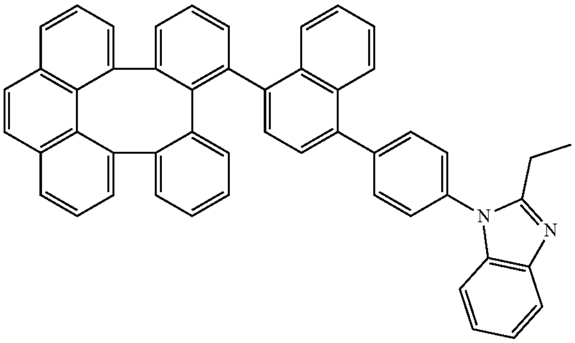
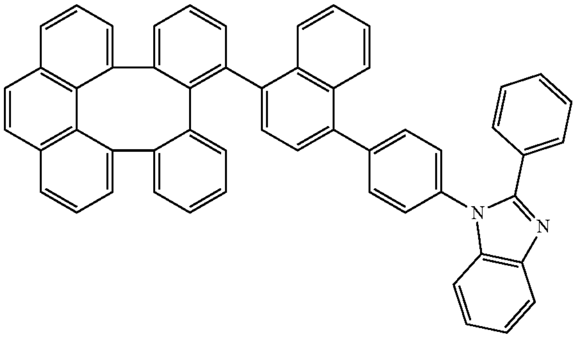
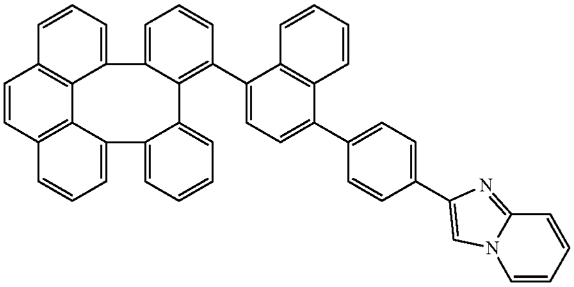
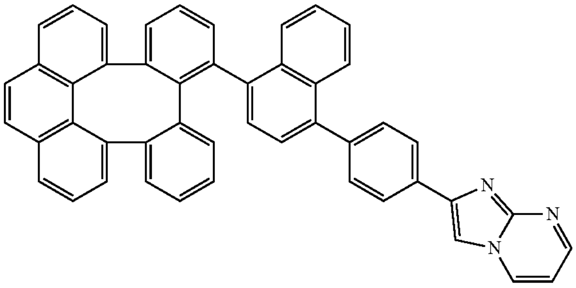
-continued
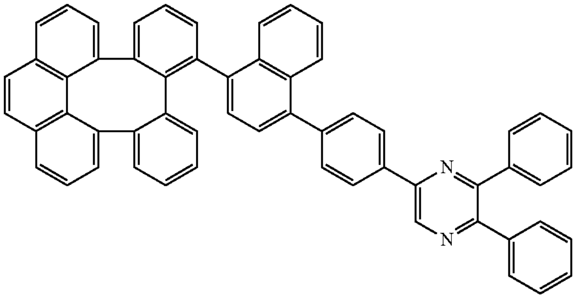
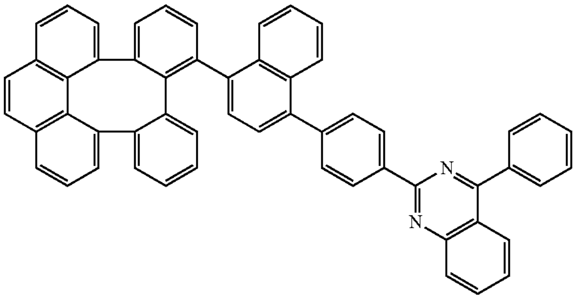
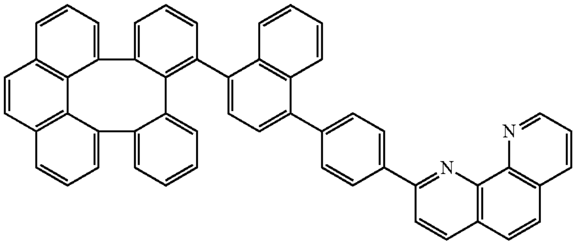
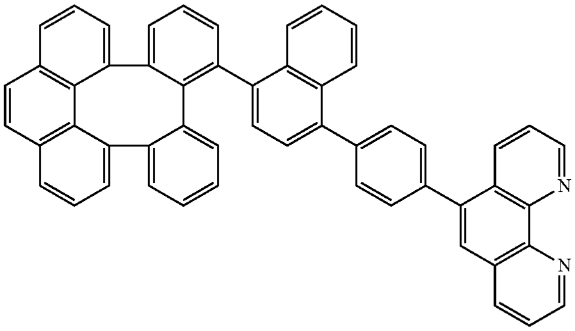
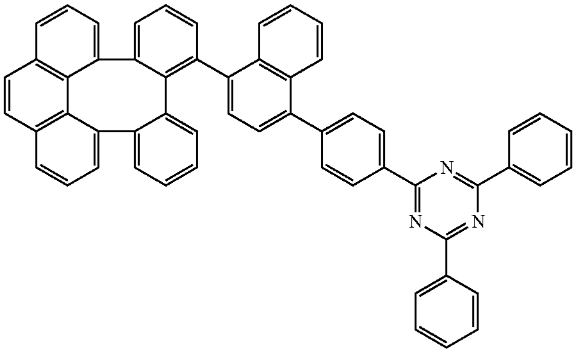

-continued
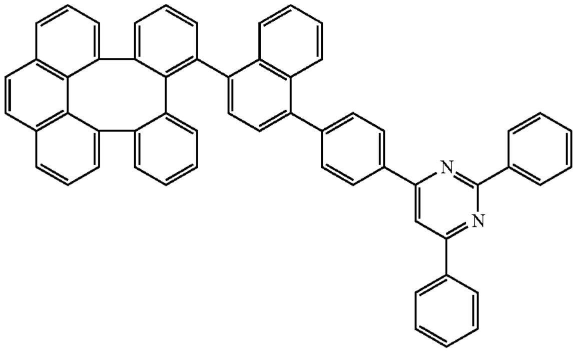
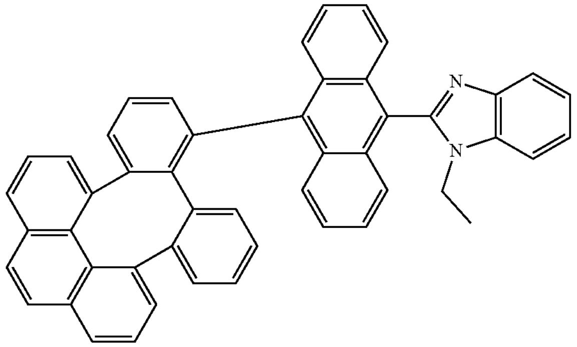
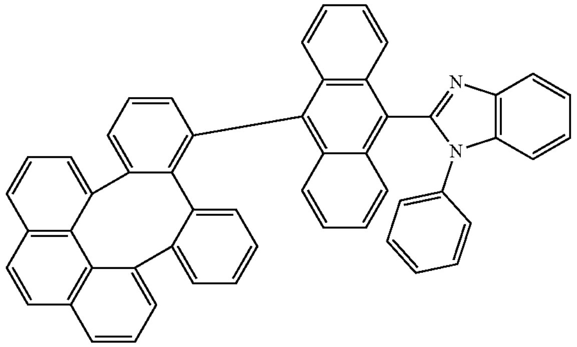
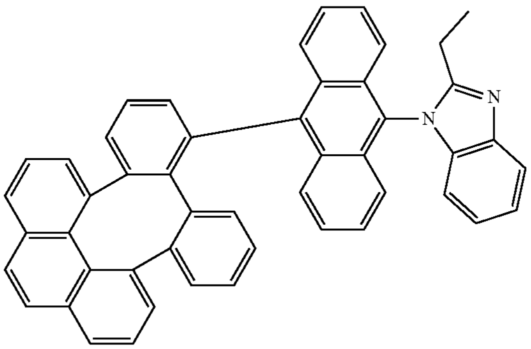
-continued
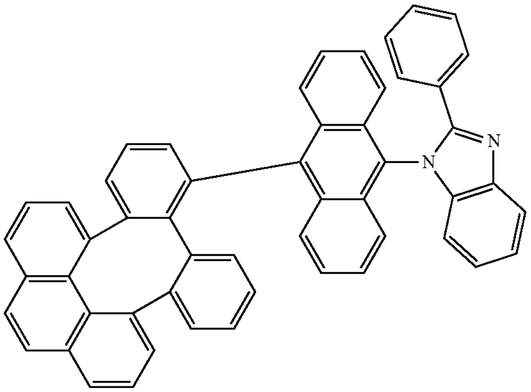
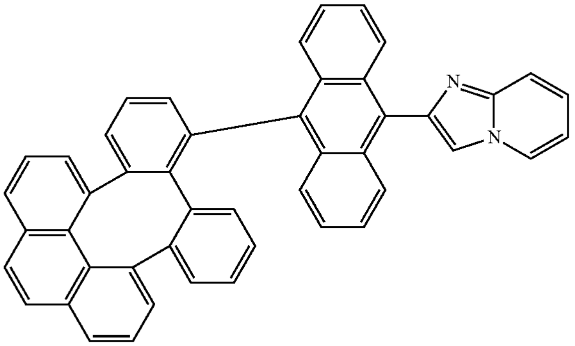
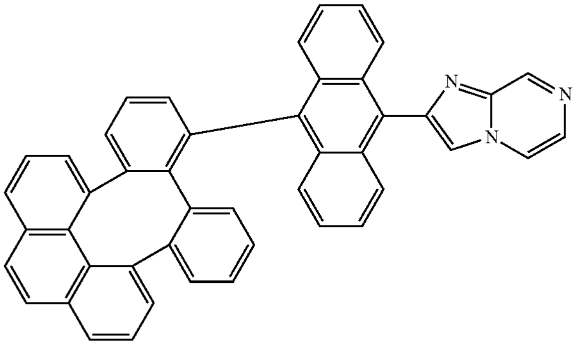
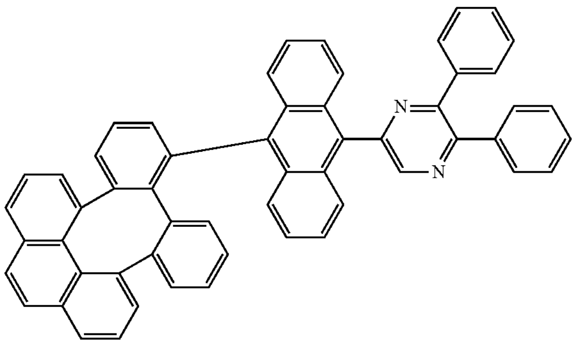

-continued
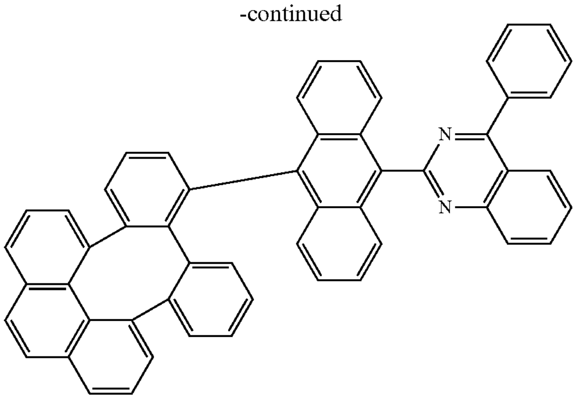
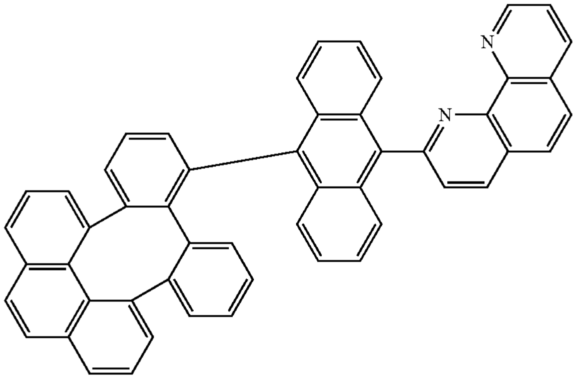
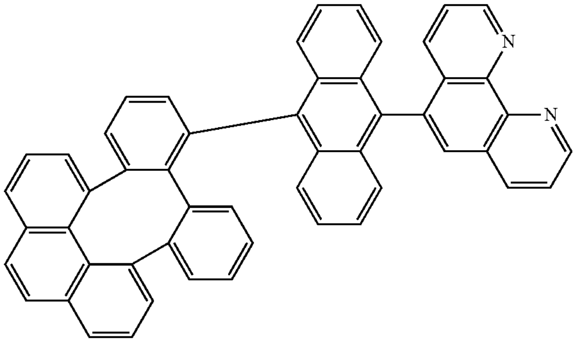
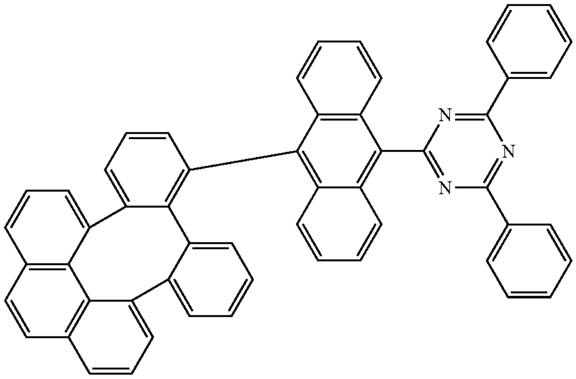
-continued
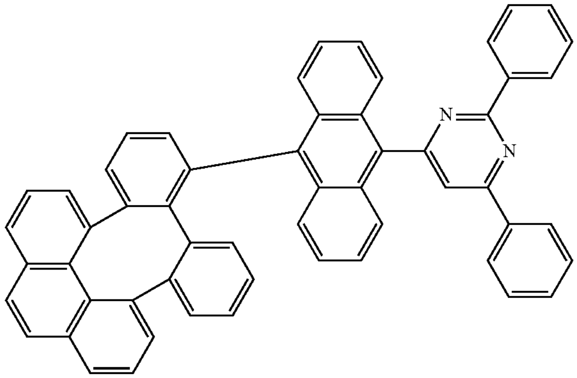
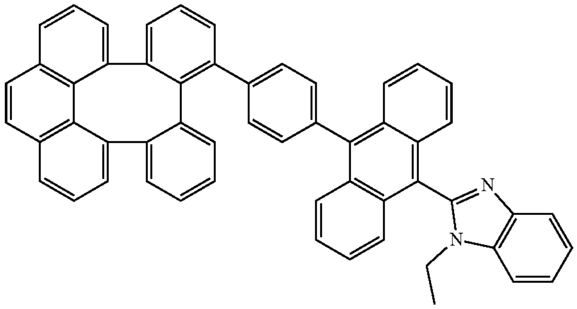
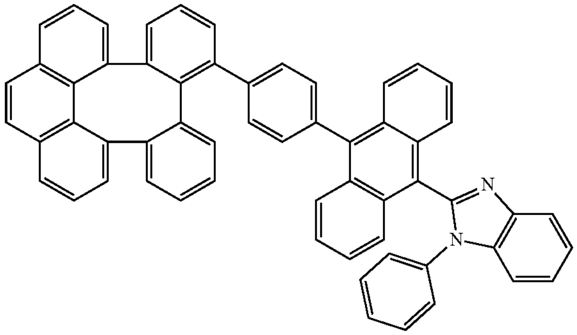
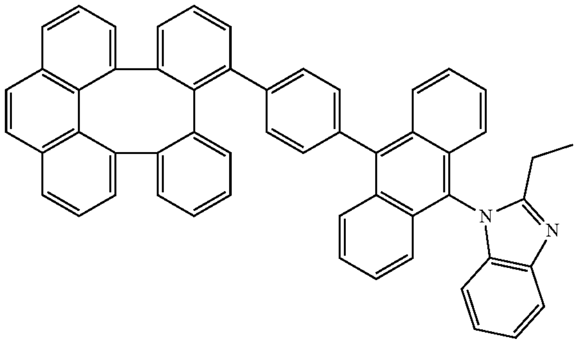
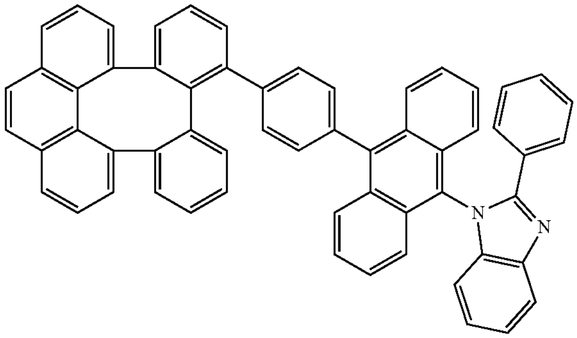

-continued
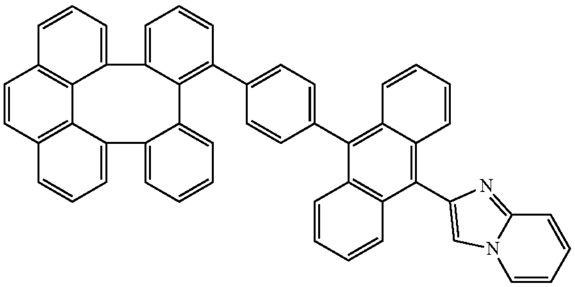
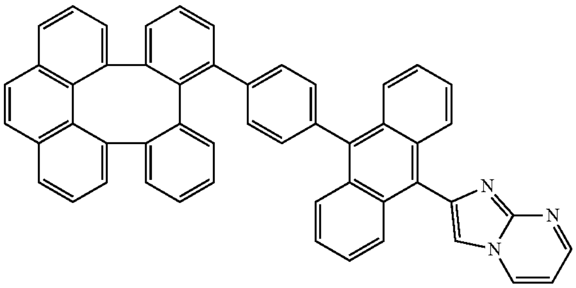
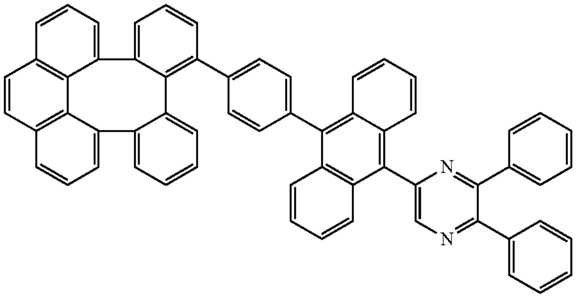
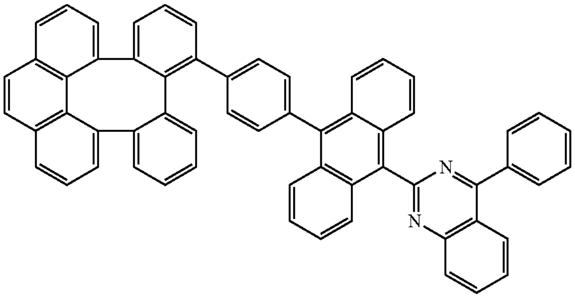
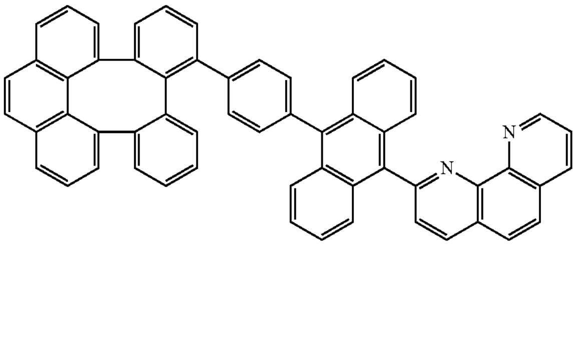
-continued
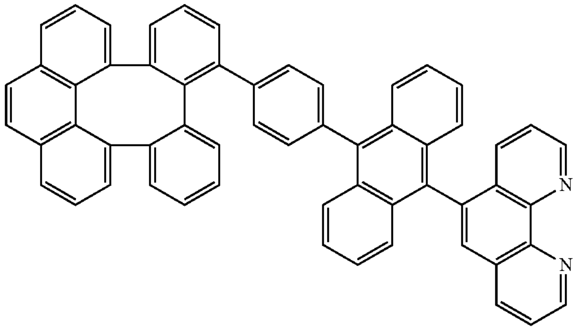
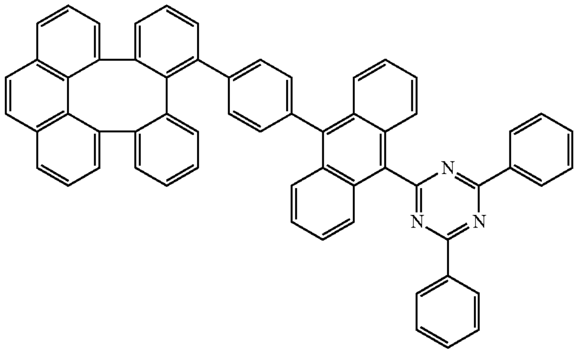
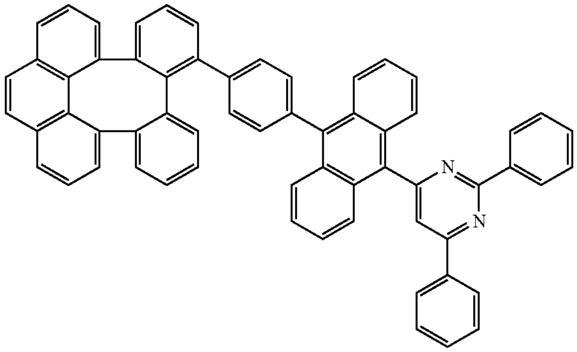
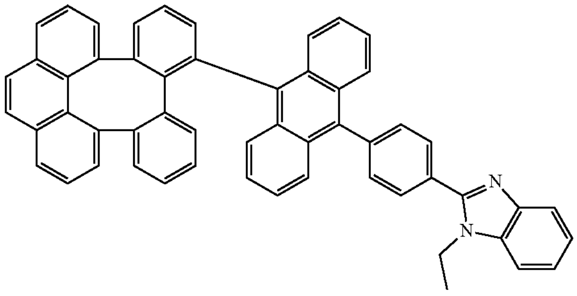
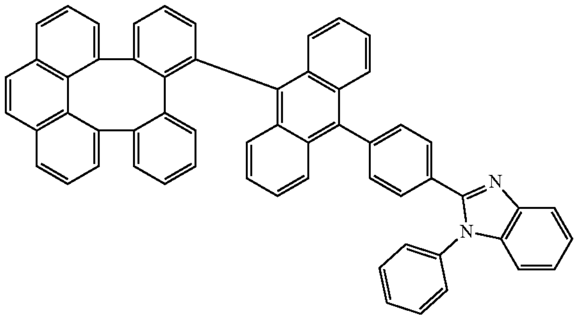

-continued
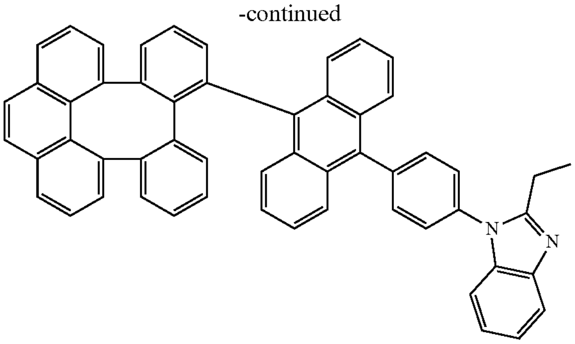
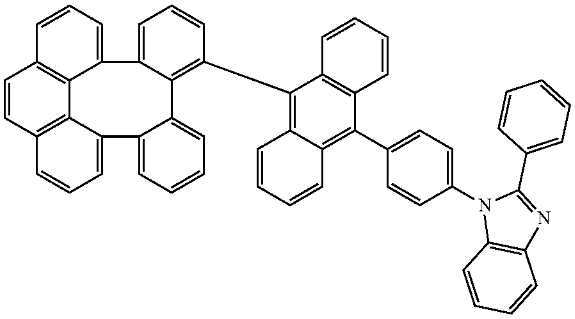
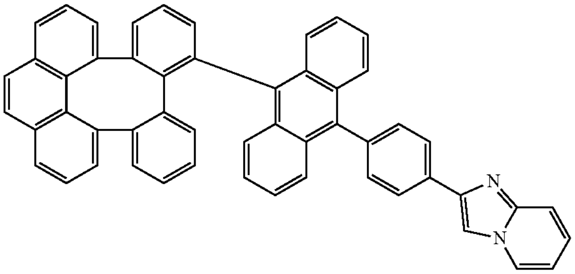
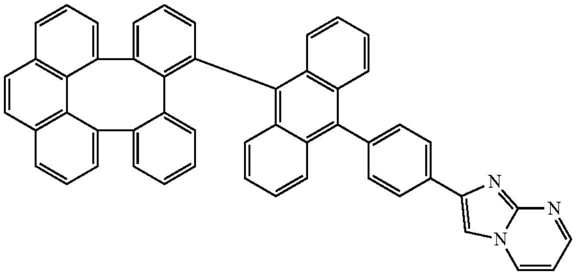
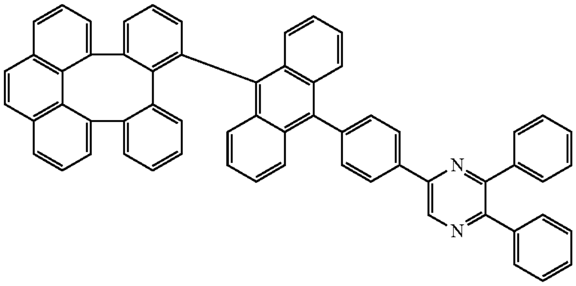
-continued
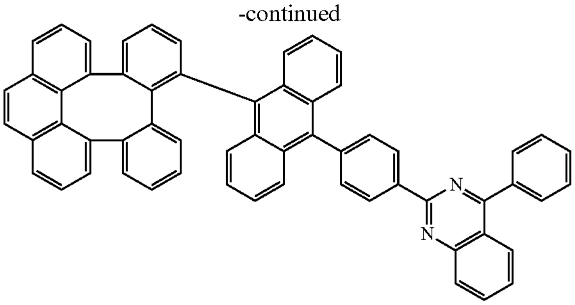
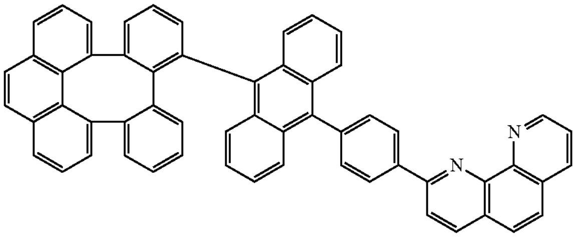
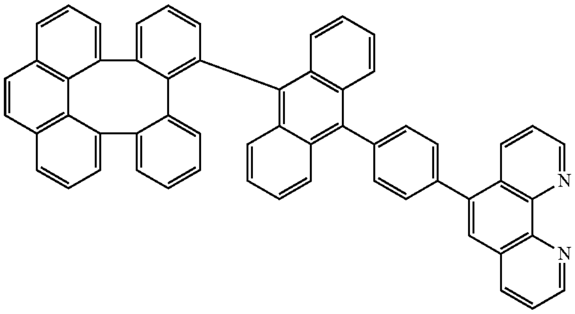
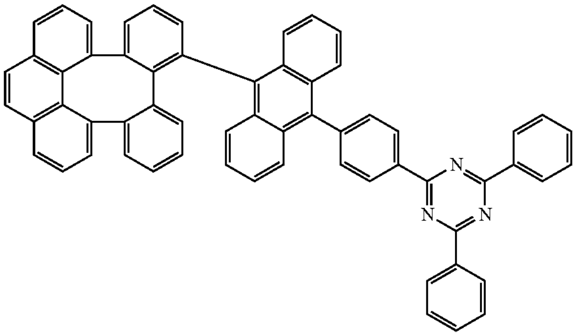
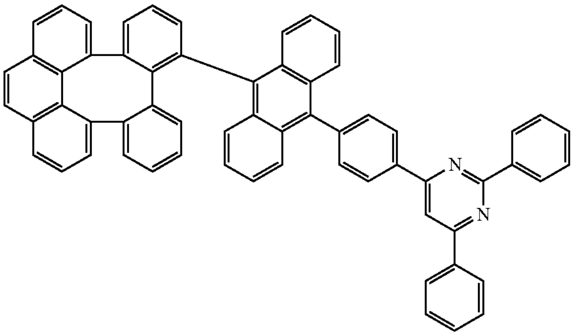

-continued
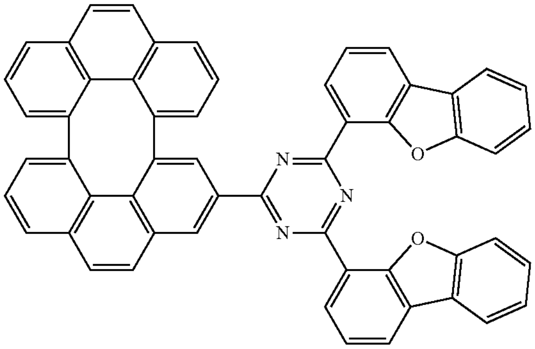
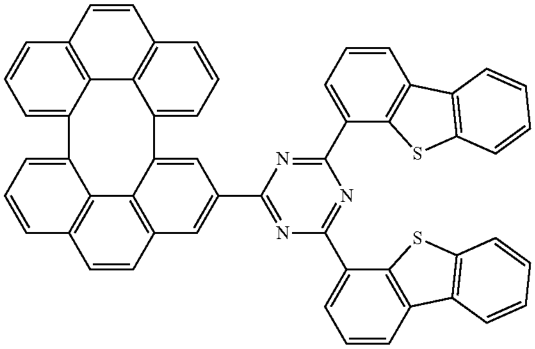
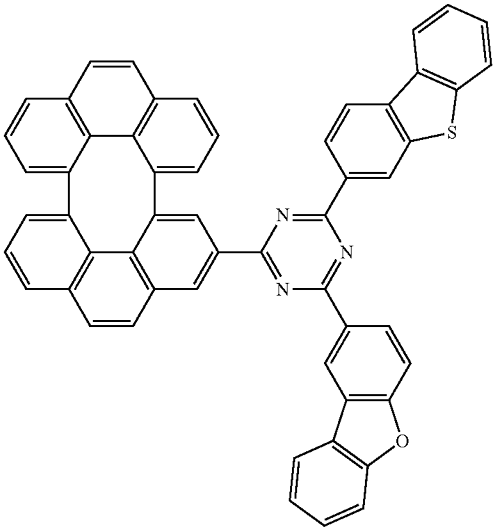
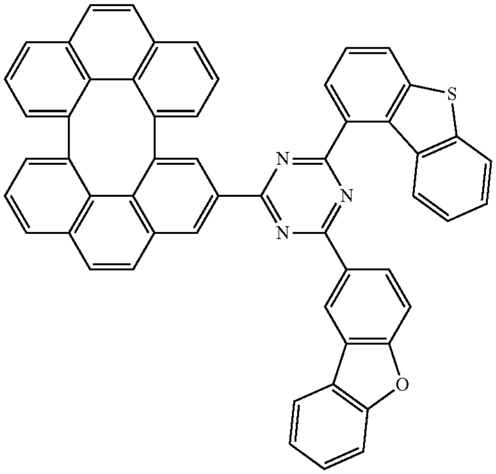
-continued
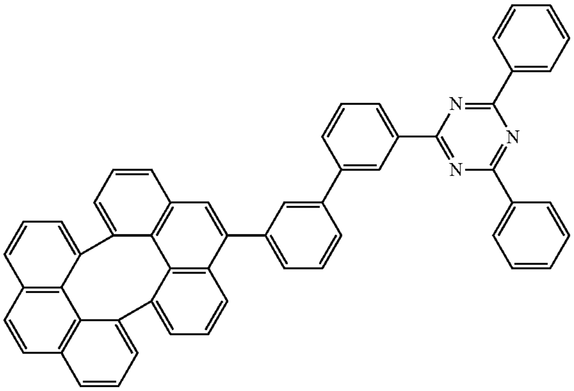
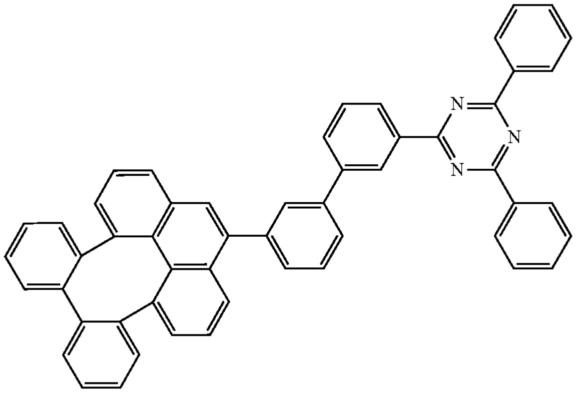
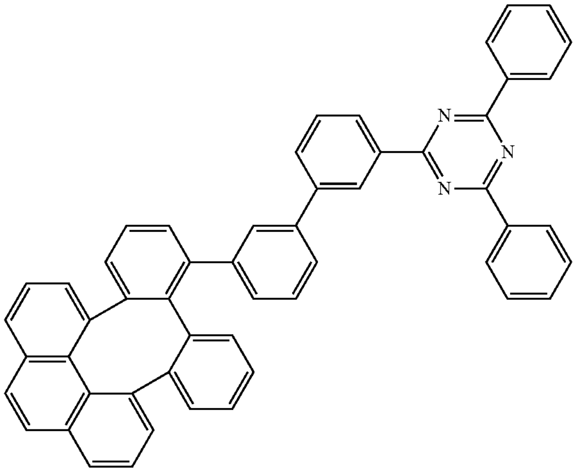
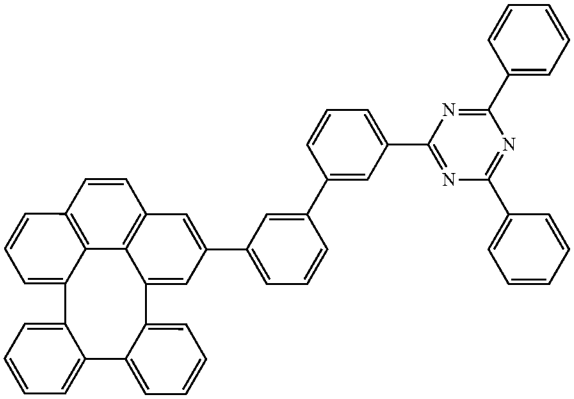

-continued
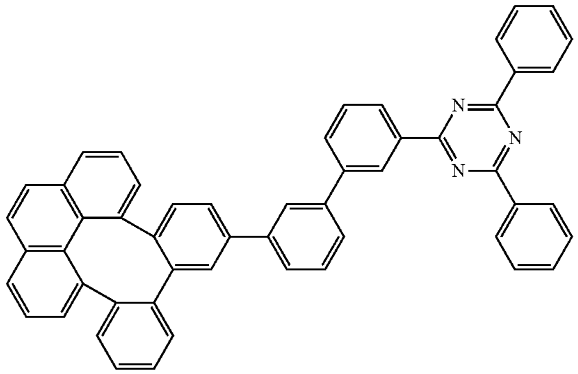
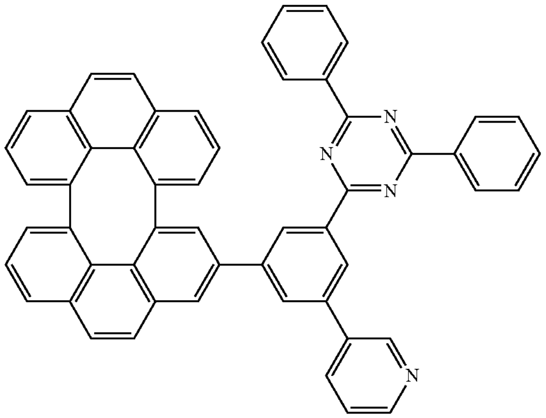
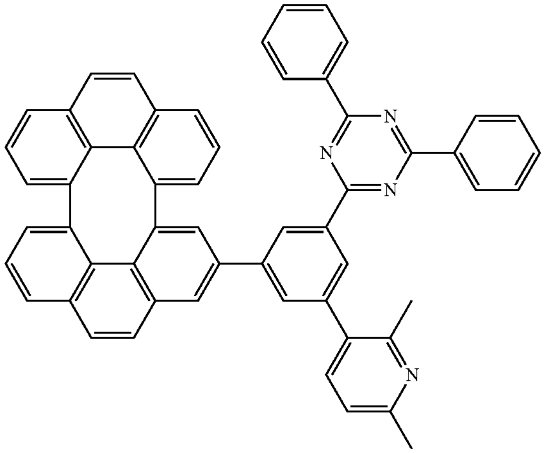
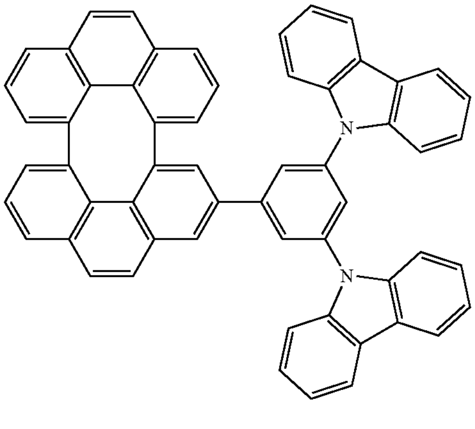
-continued
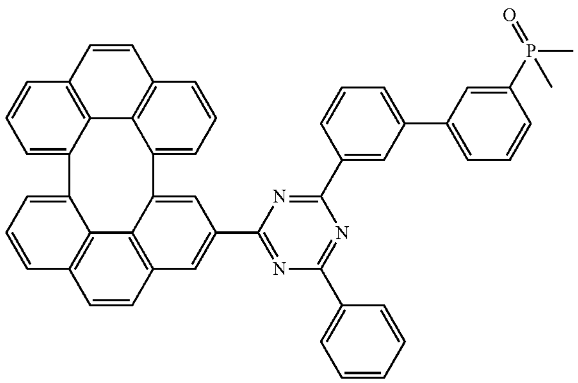
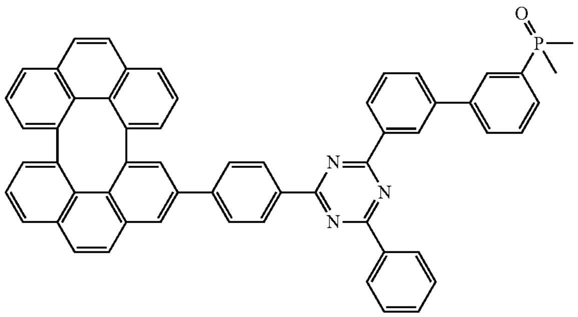
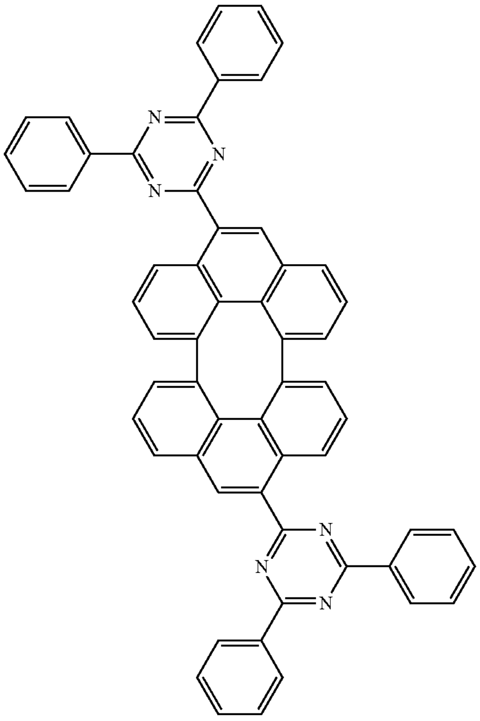

-continued
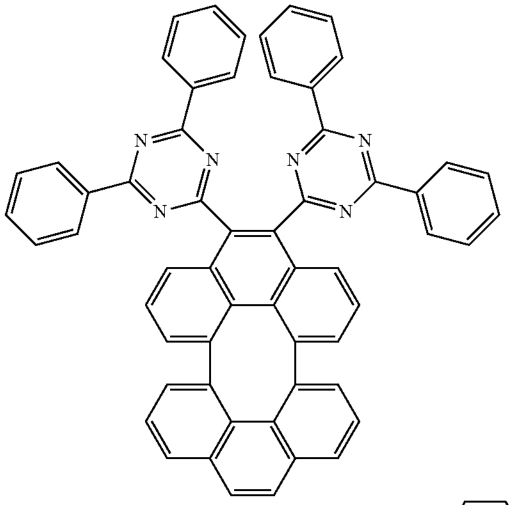
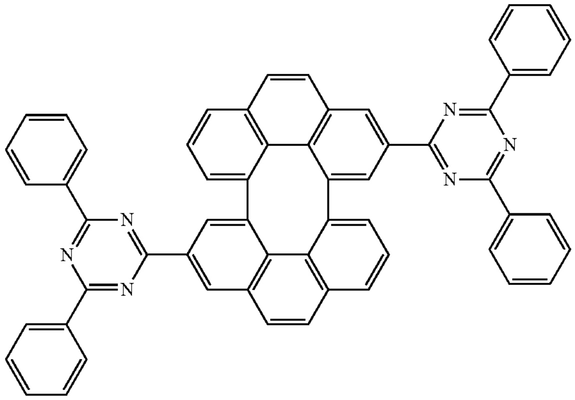
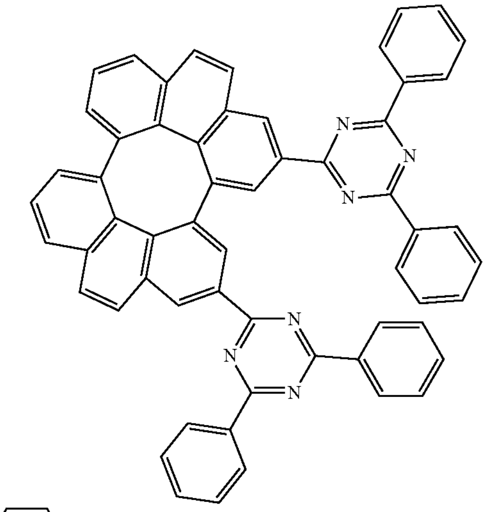
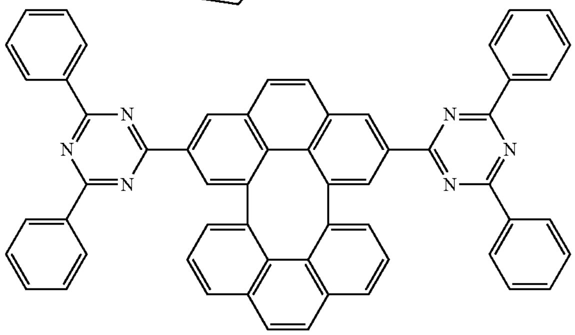
-continued
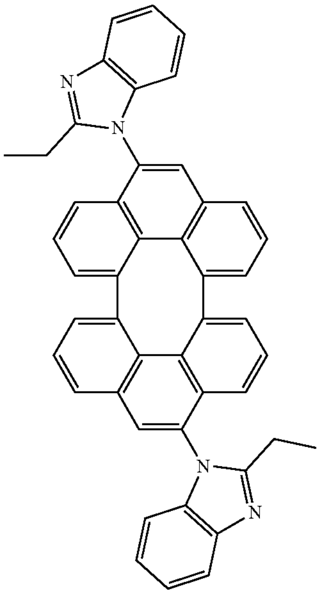
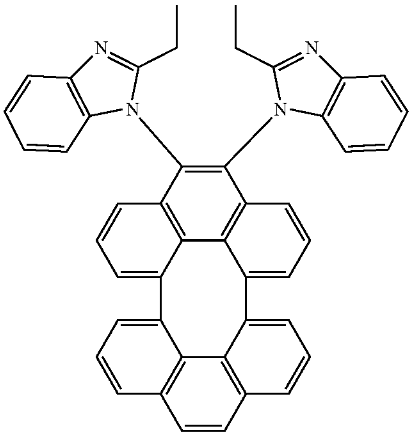
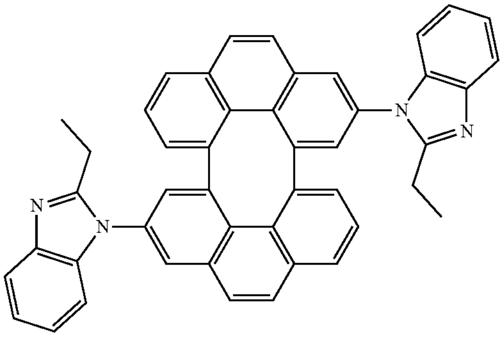

-continued
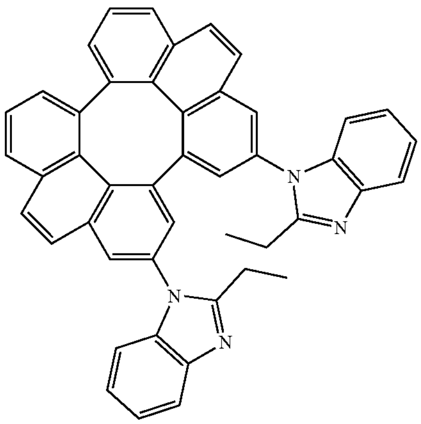
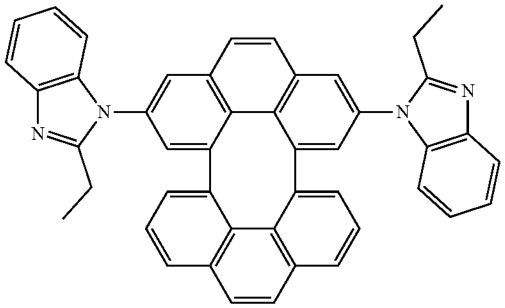
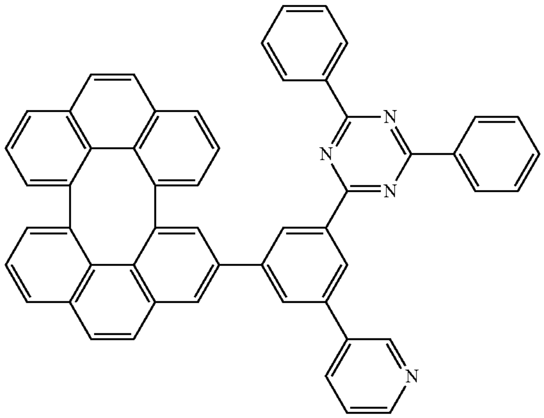
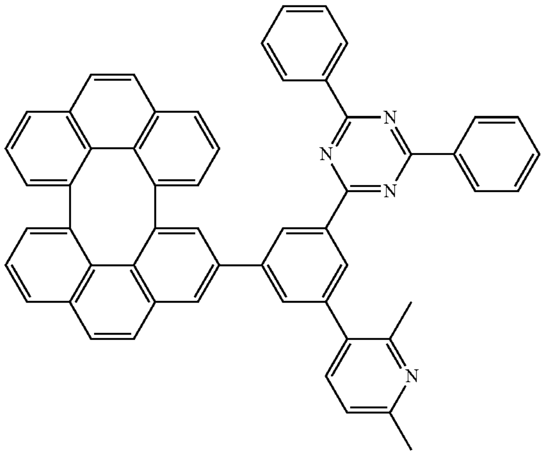
-continued
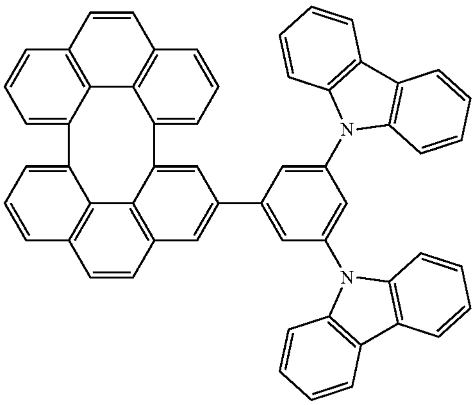
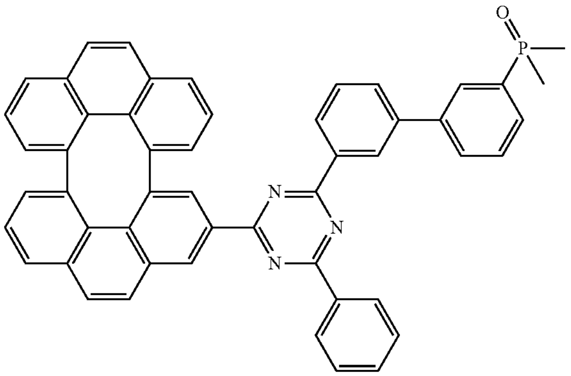
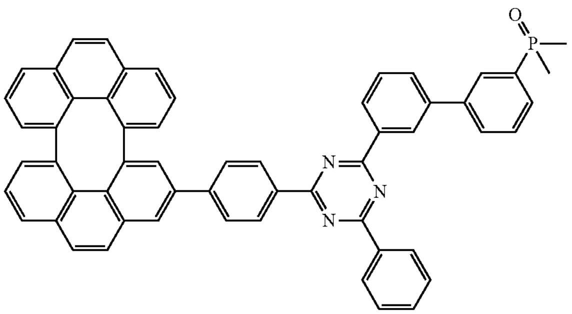

-continued
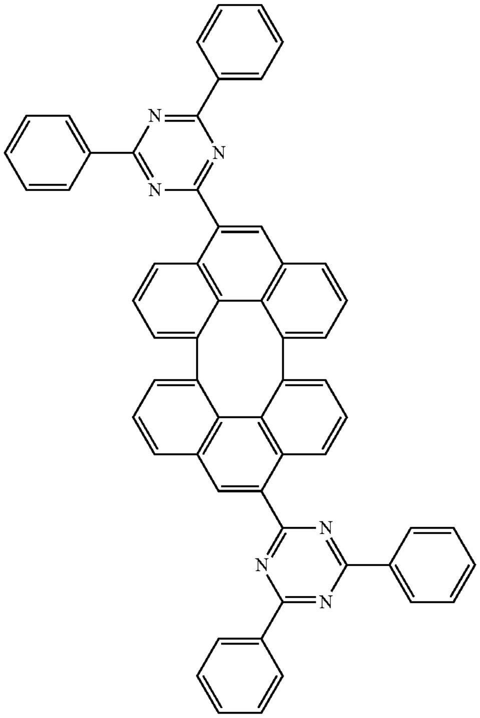
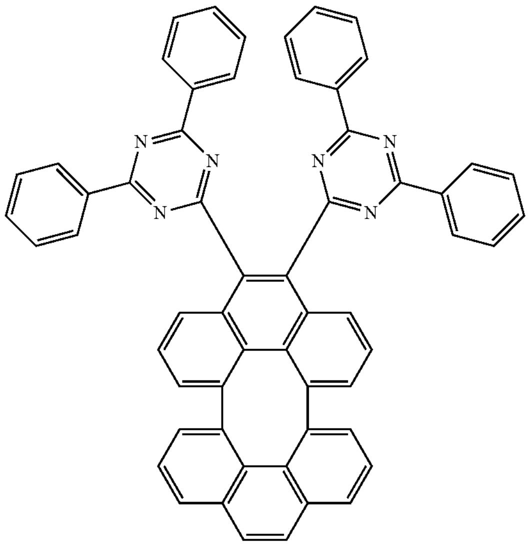
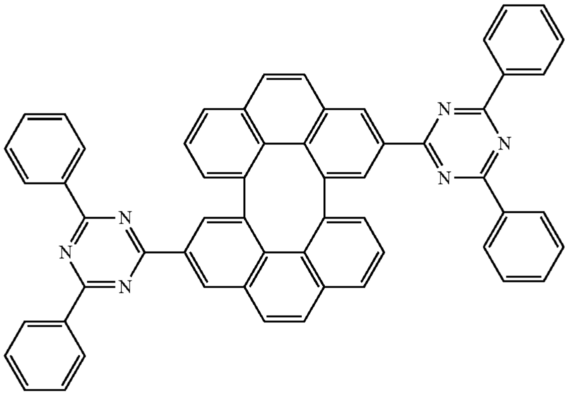
-continued
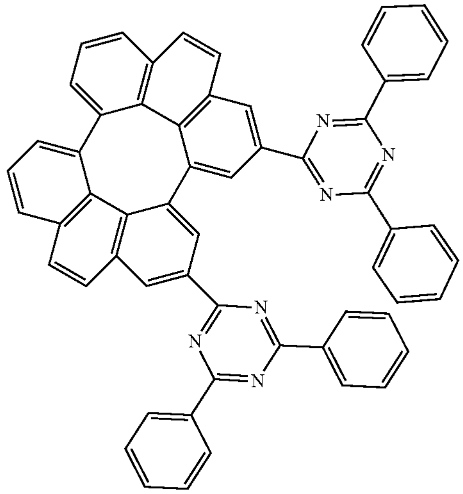
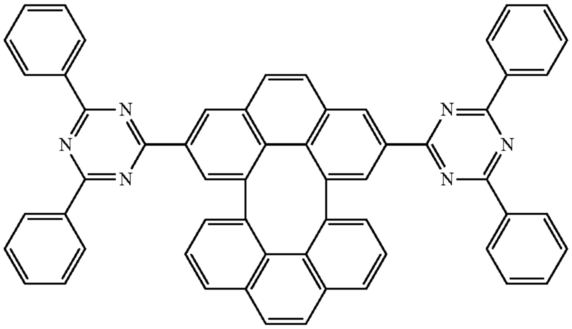
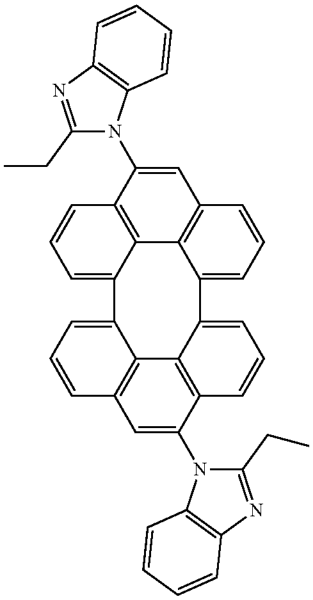

-continued
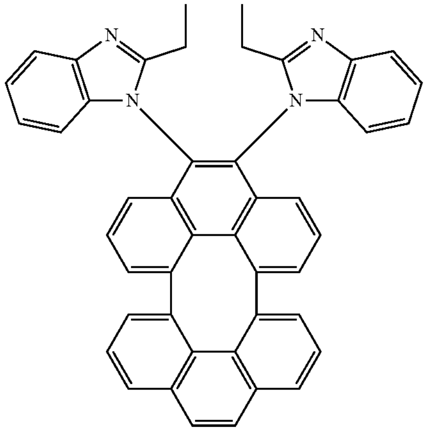
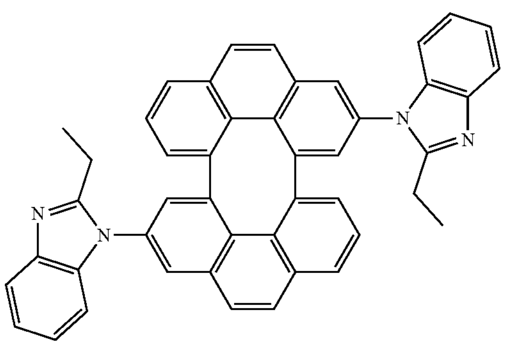
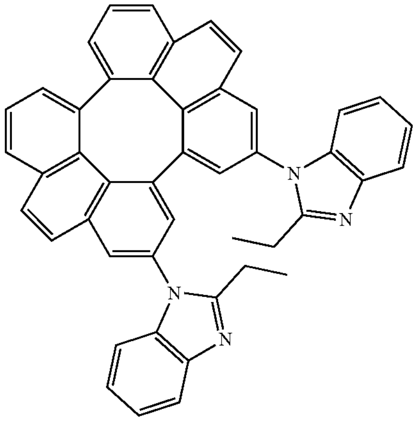
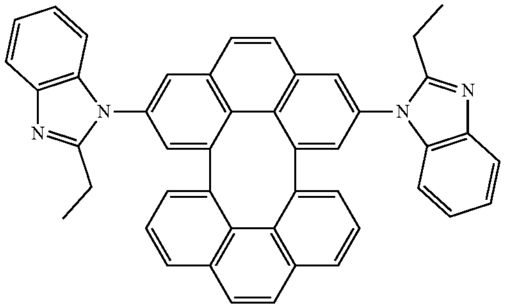 [SMILES: CCc1nc2ccccc2n1-c1cc2ccc3cc(-n4c(CC)nc5ccccc54)cc4c5cccc6ccc7cccc(c(c1)c2c34)c7c65]
-continued
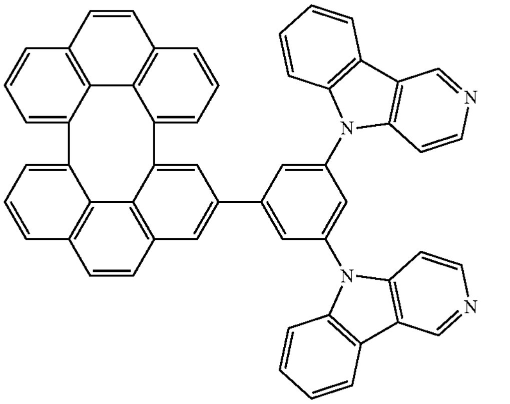
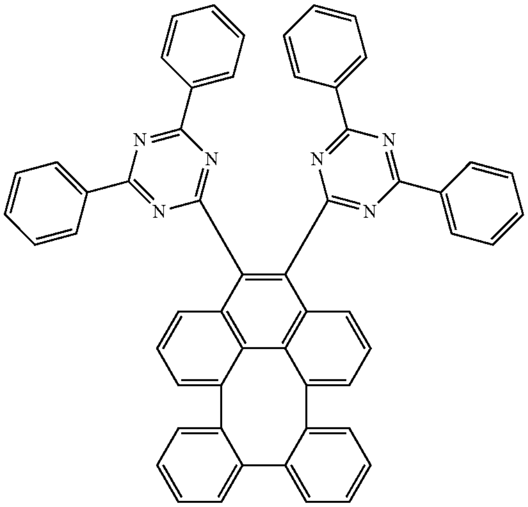
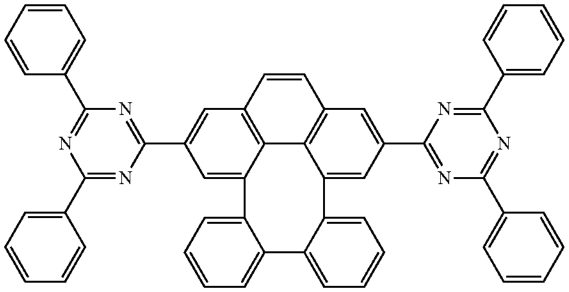
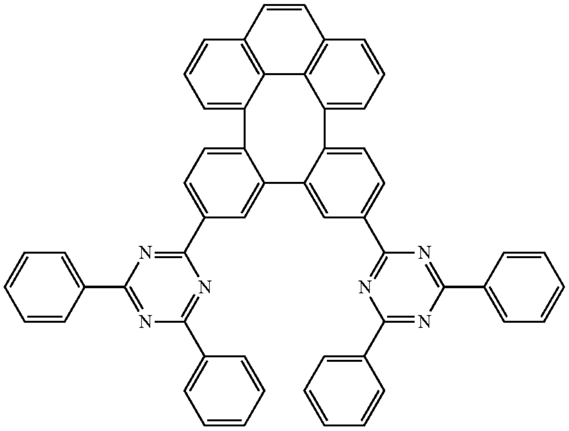

-continued
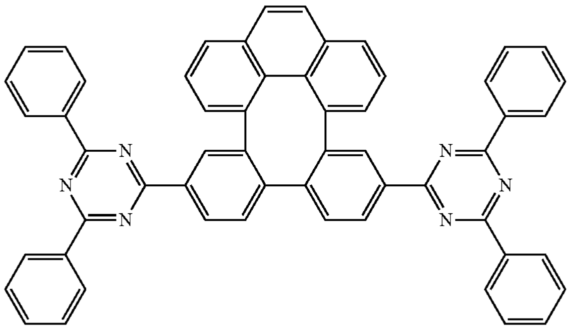
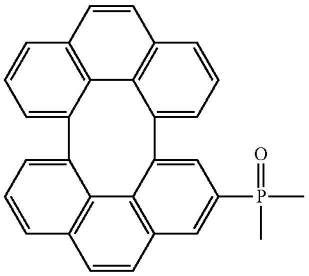
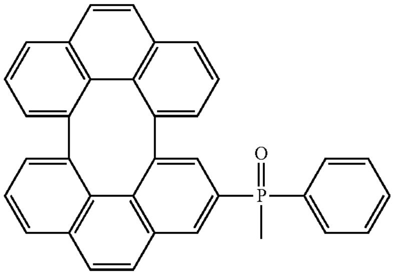
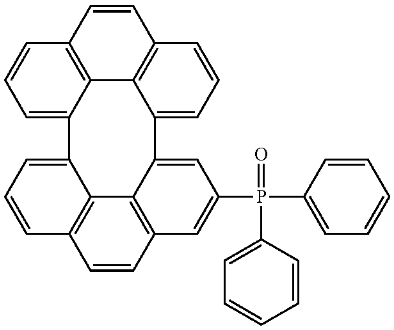
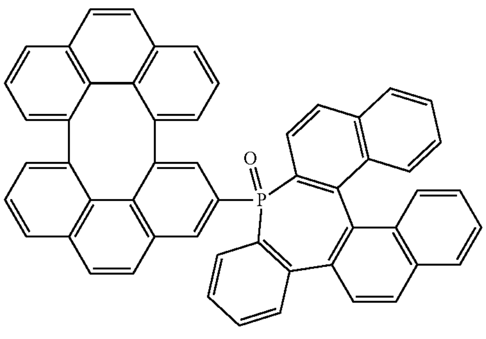
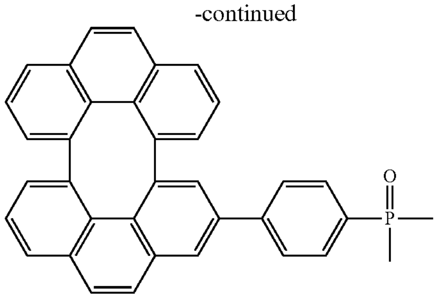
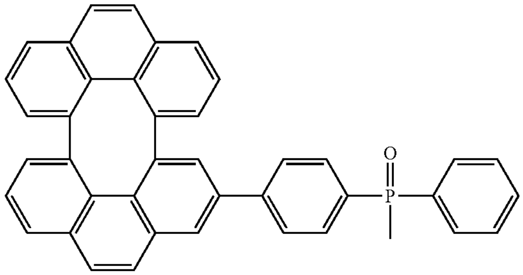
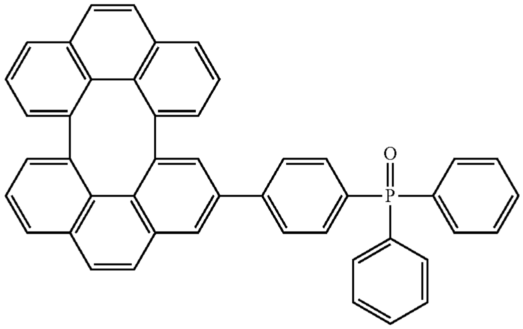
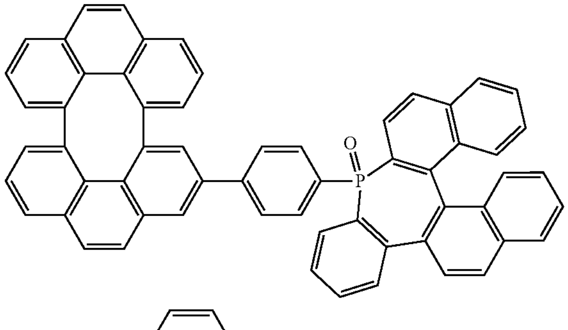
-continued
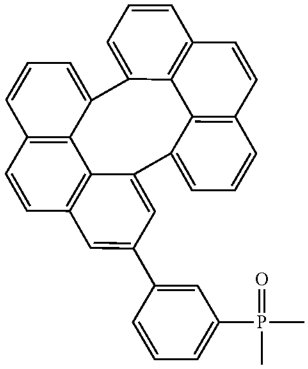

-continued
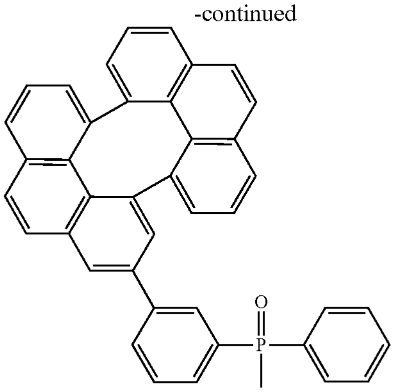
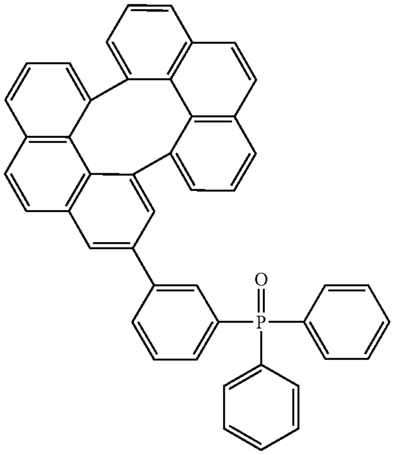
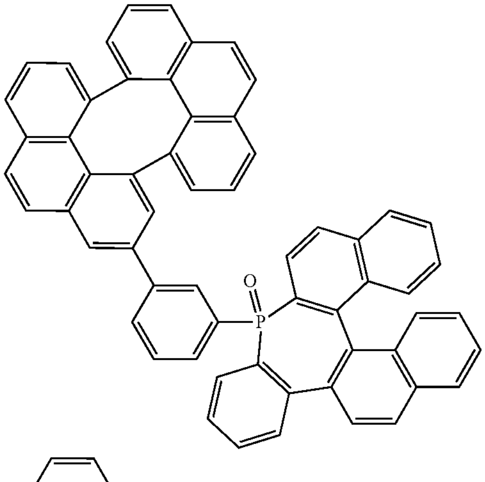
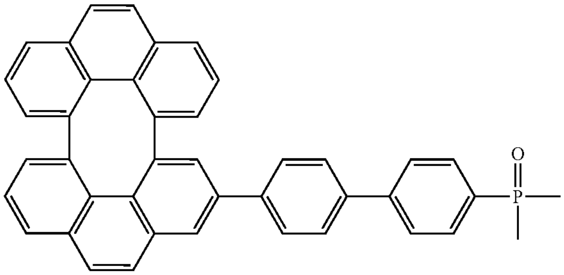
-continued
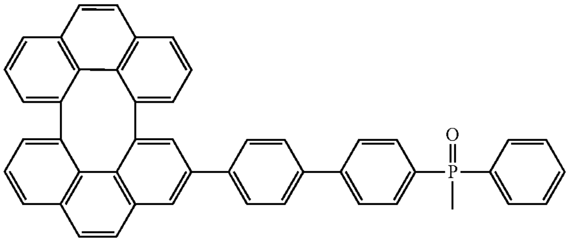
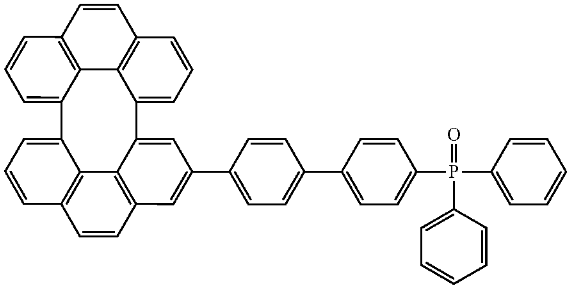
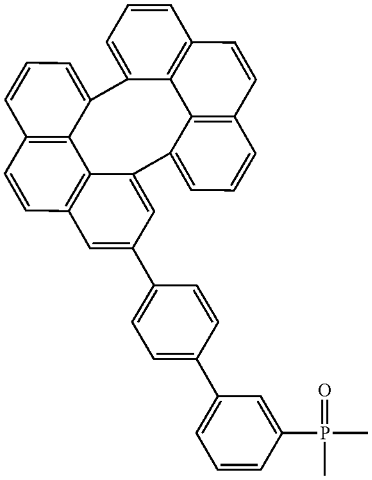
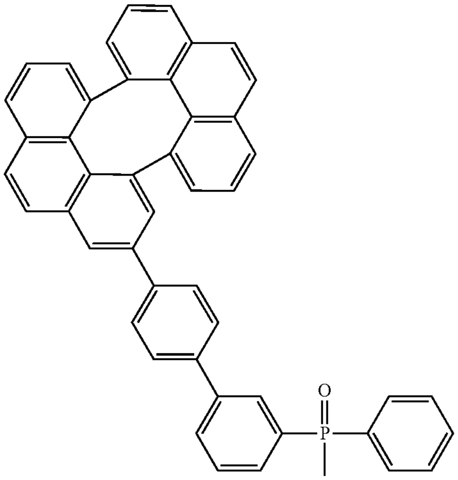

-continued
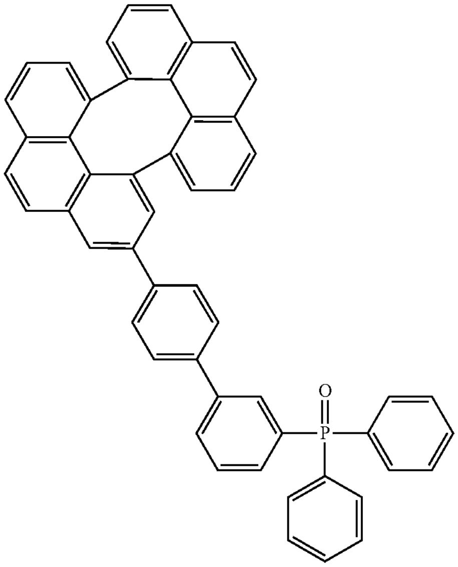
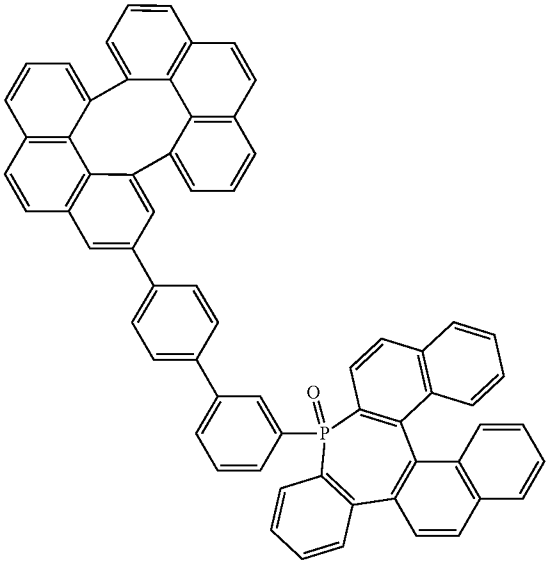
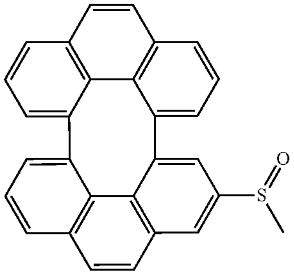
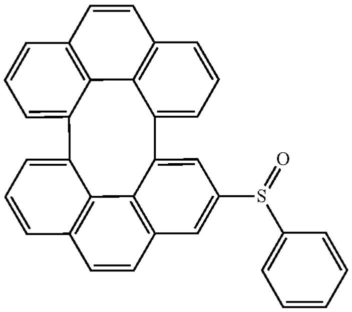
-continued
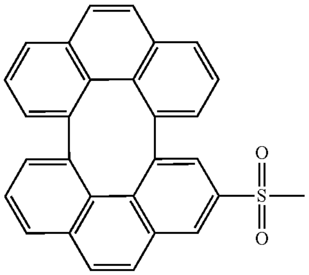
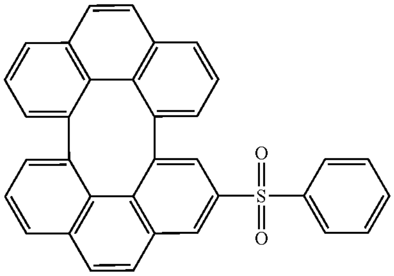
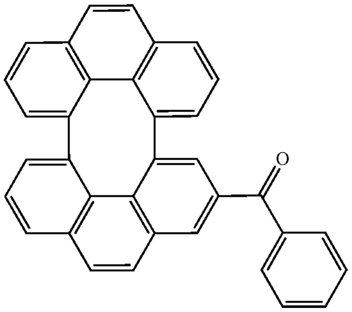
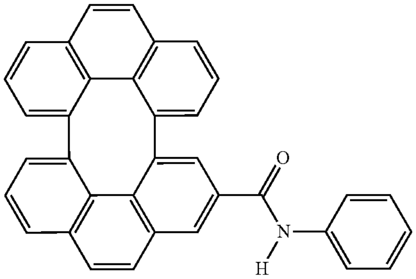
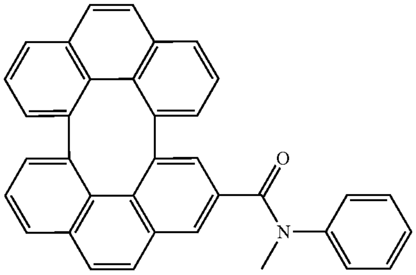

-continued
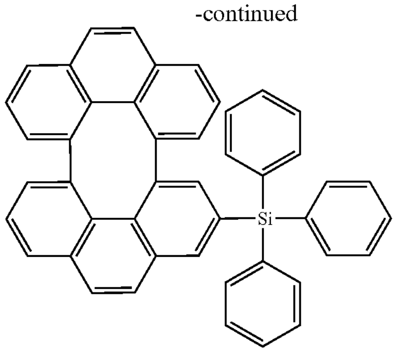
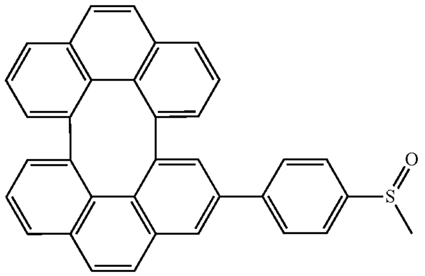
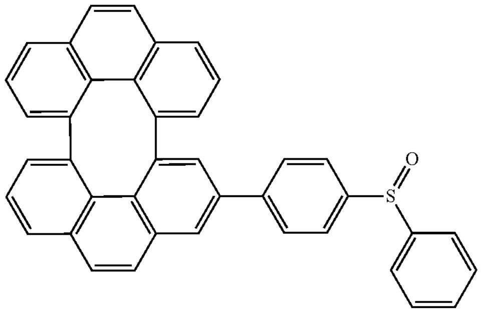
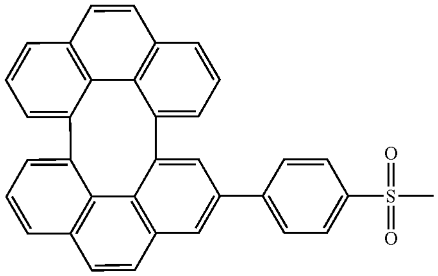
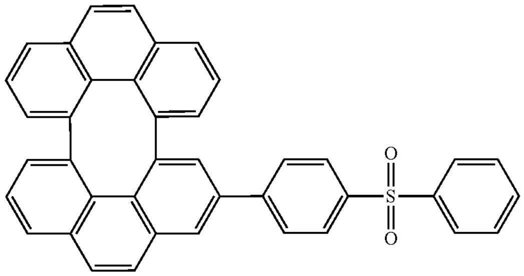
-continued
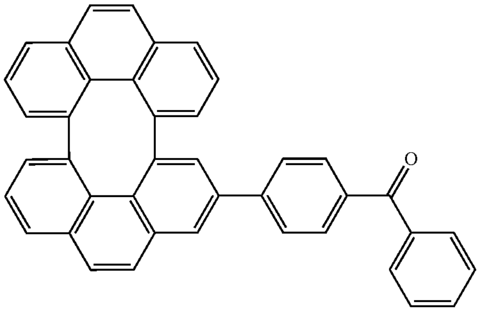
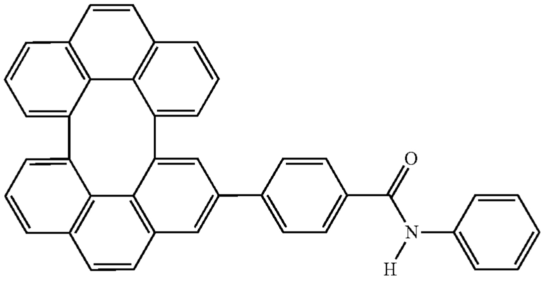
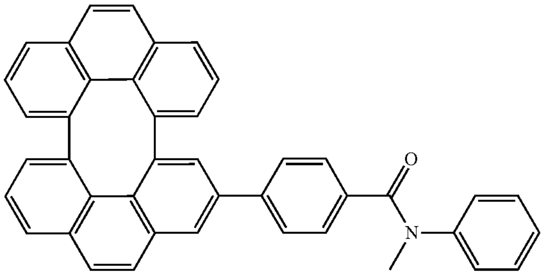
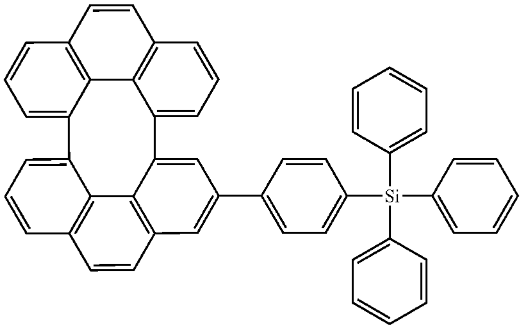
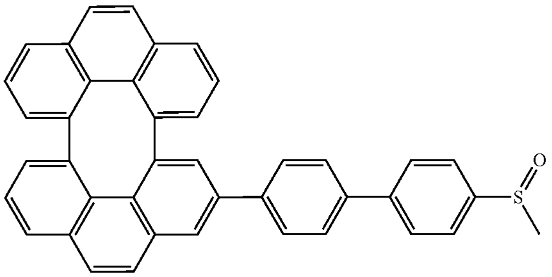

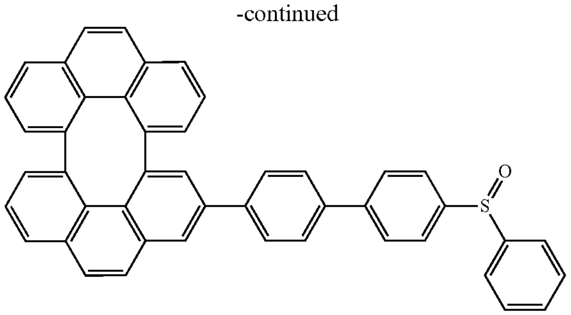
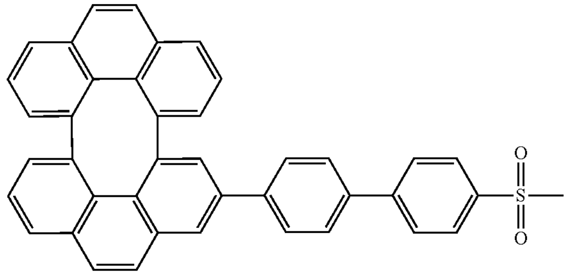
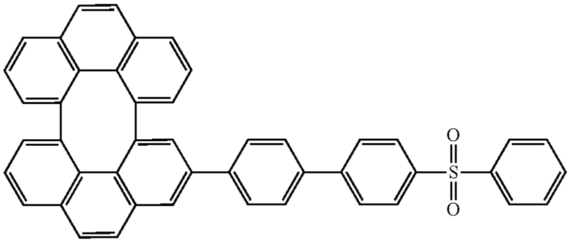
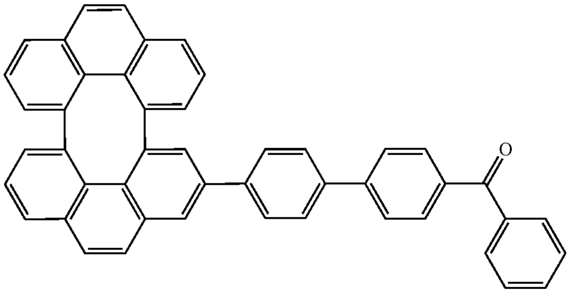
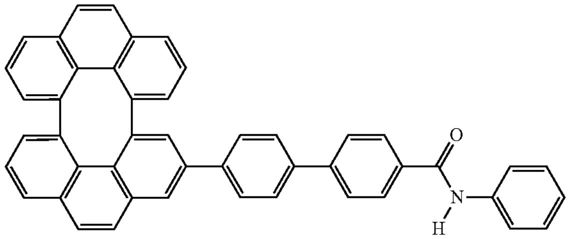
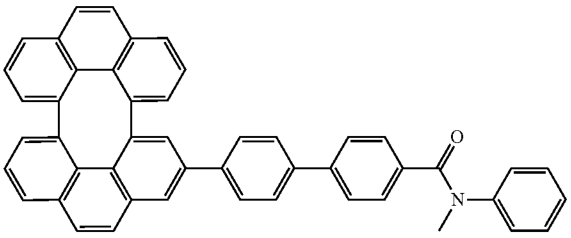
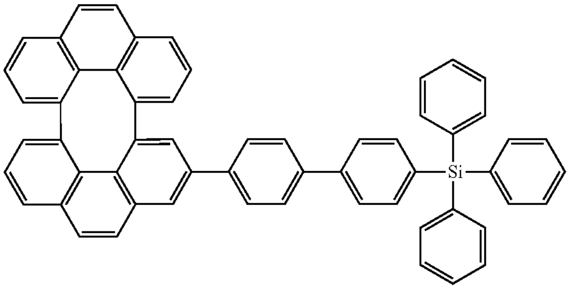
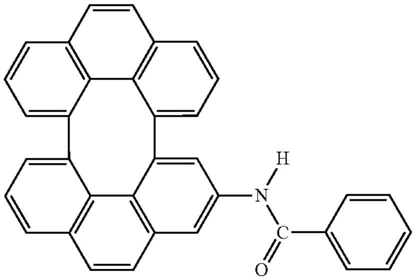
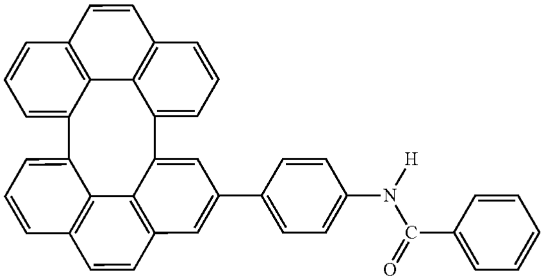
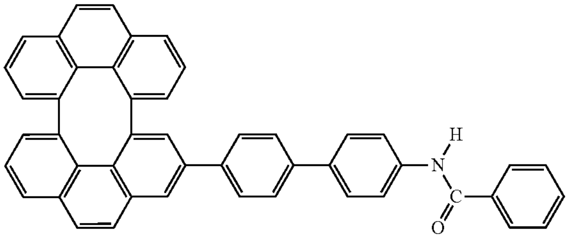
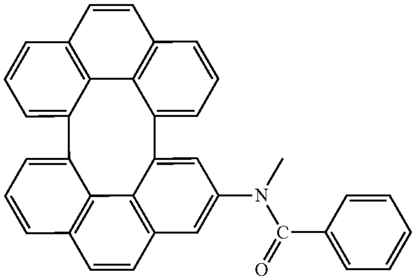
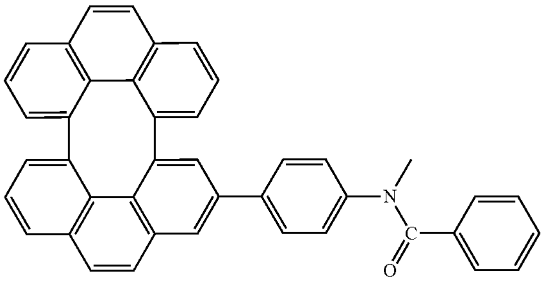

-continued
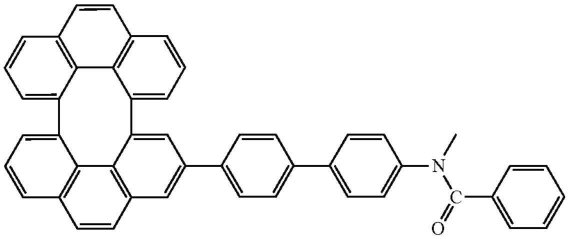
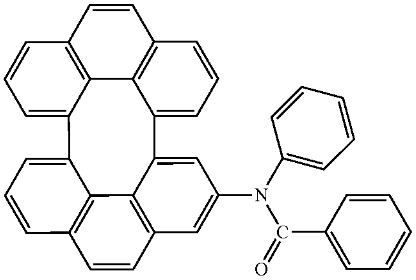
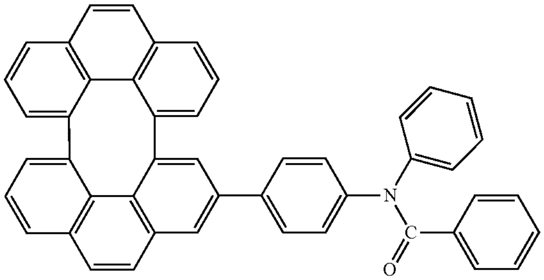
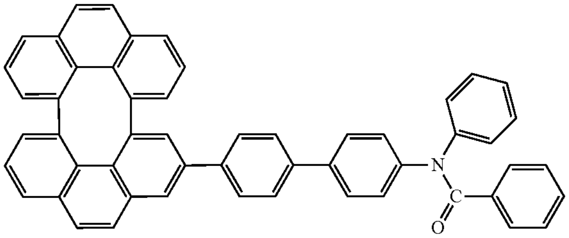
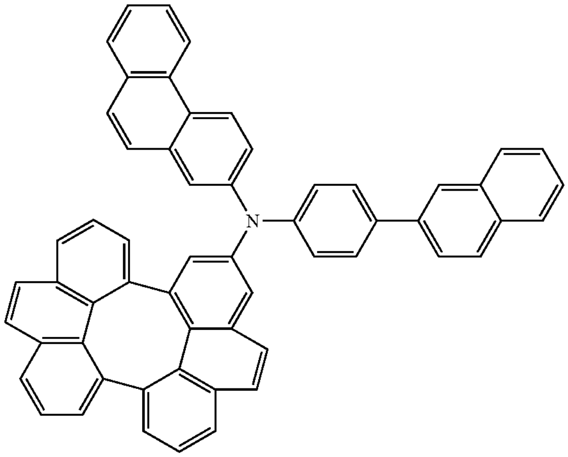
-continued
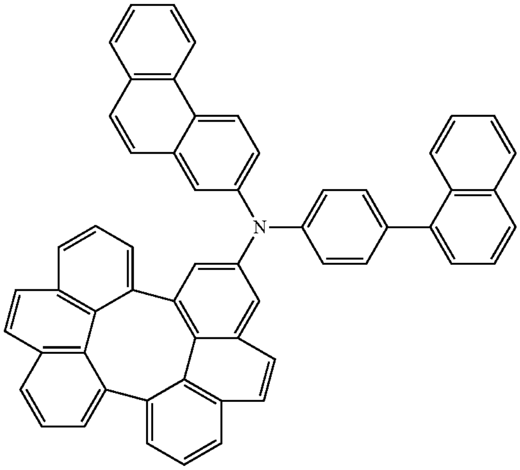
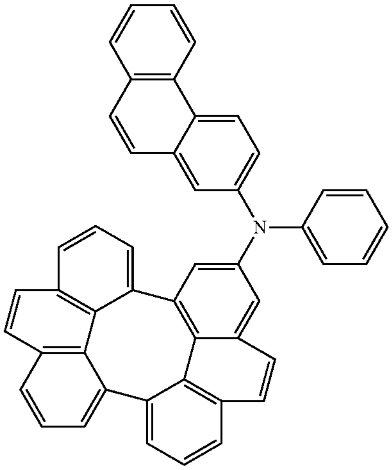
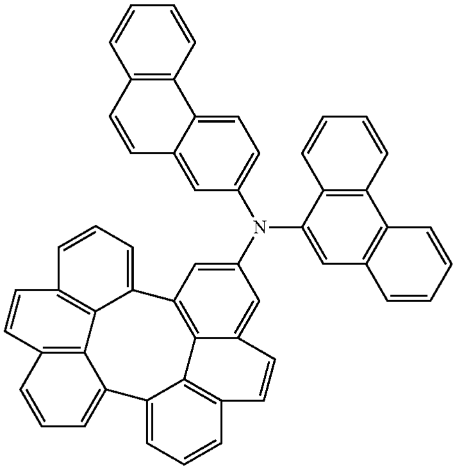

-continued
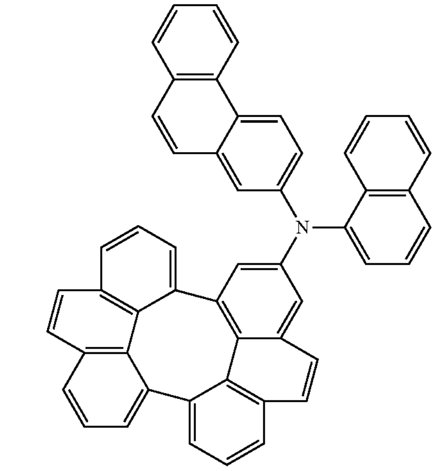
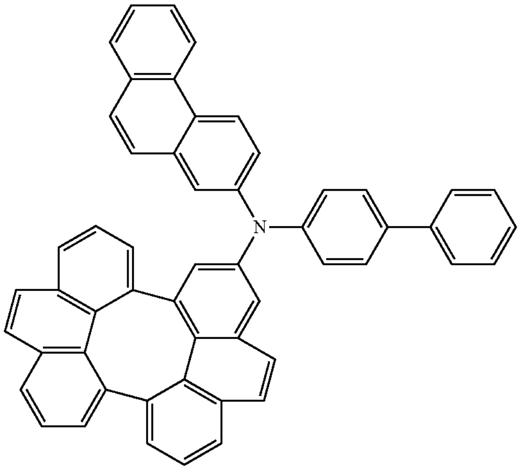
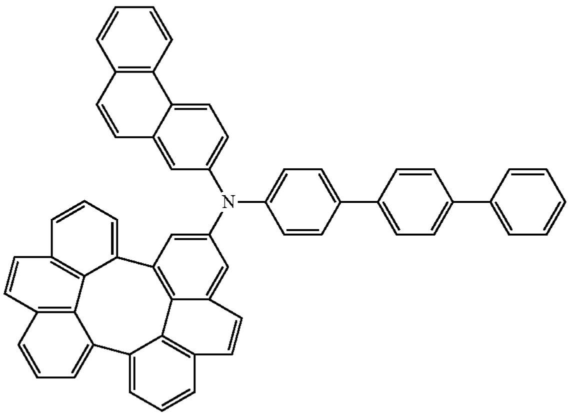
-continued
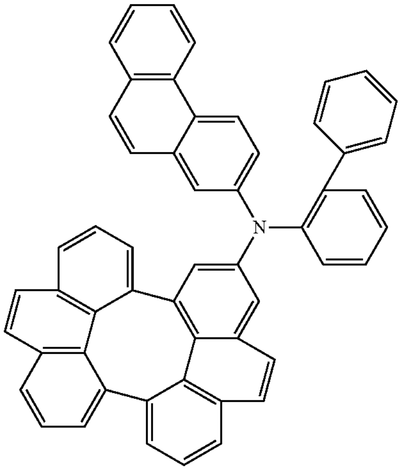
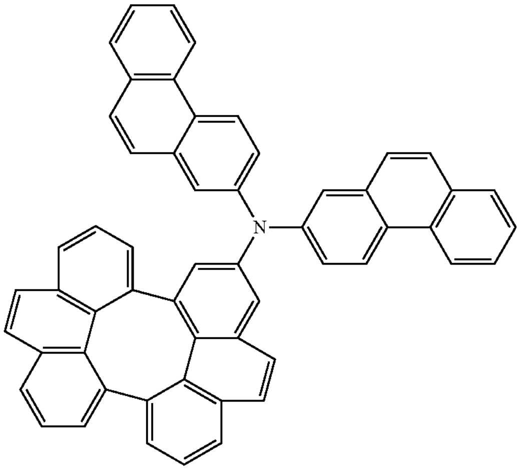
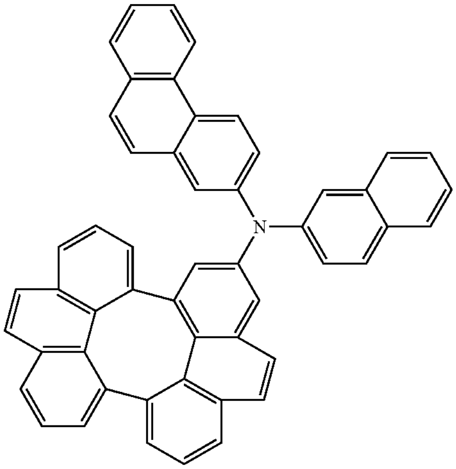

-continued
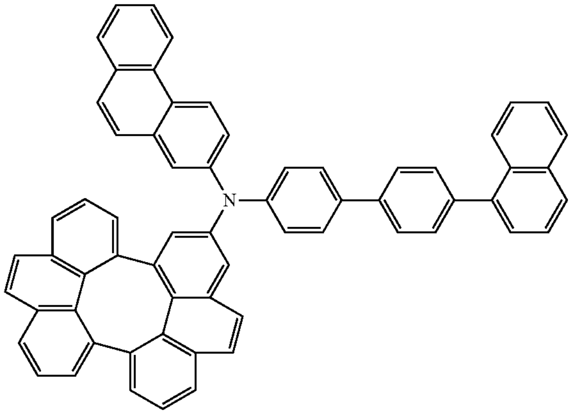
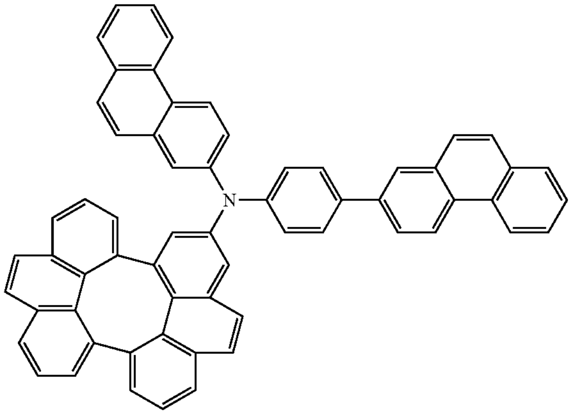
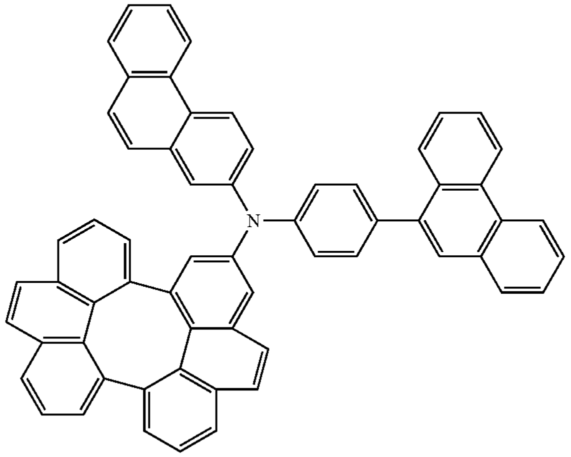
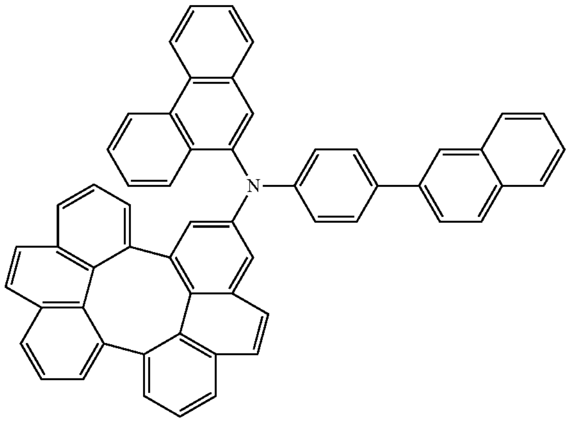
-continued
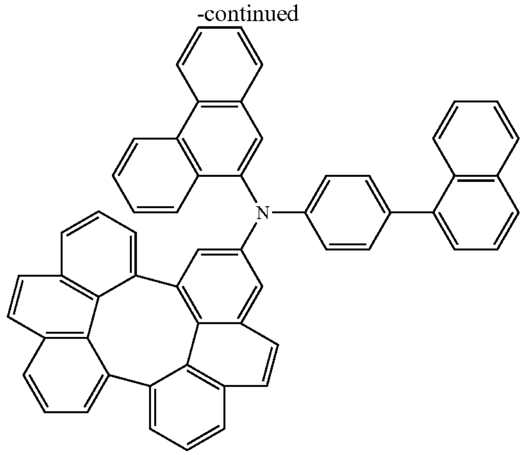
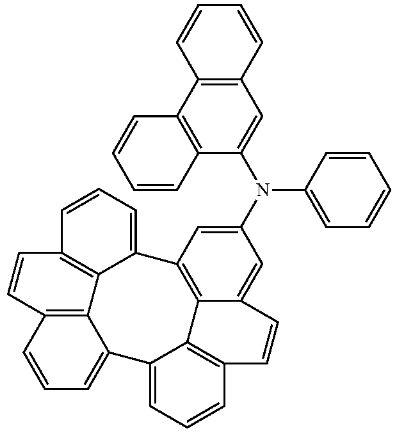
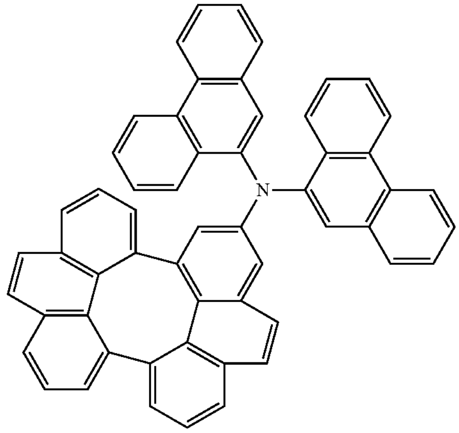
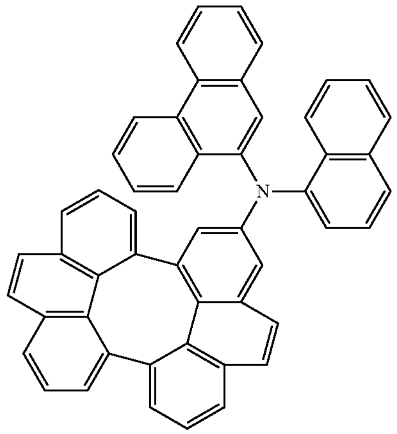

-continued
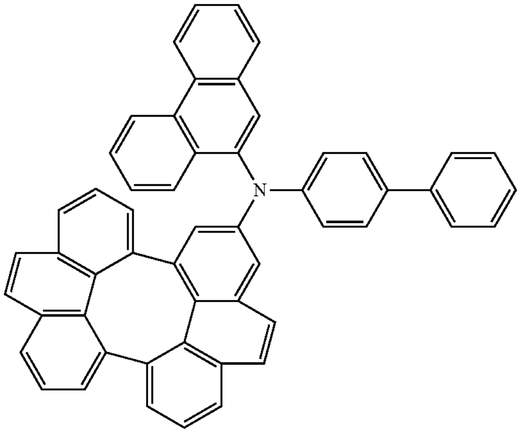
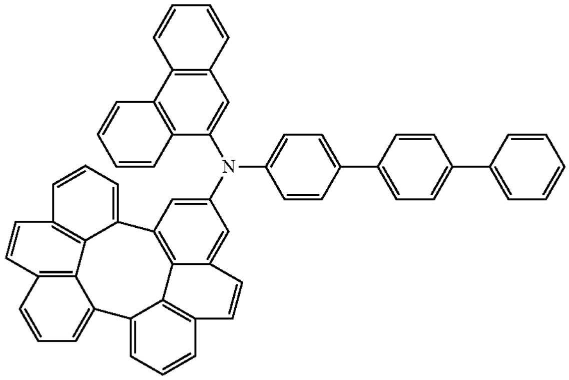
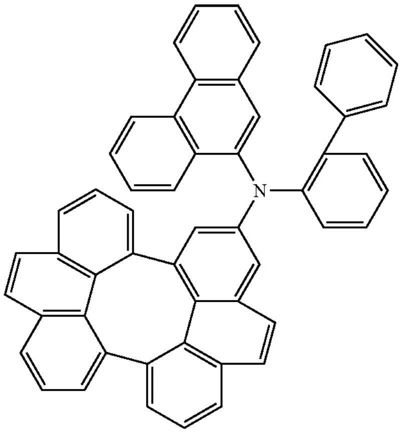
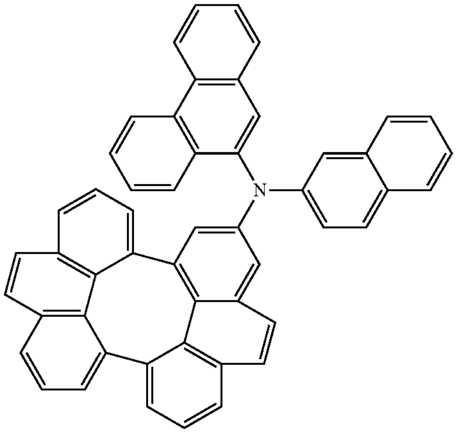
-continued
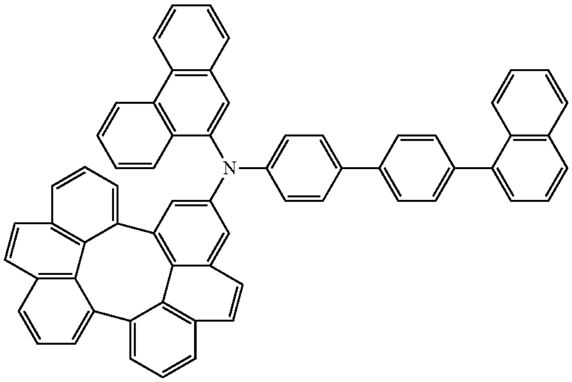
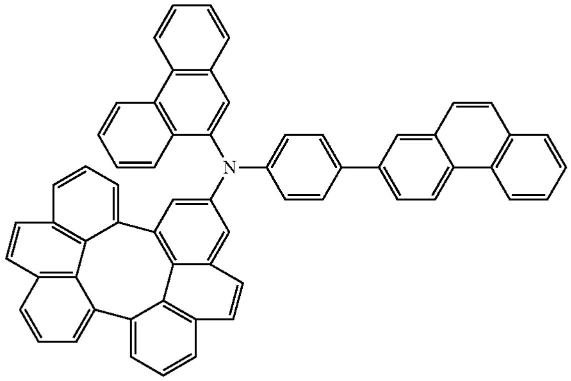
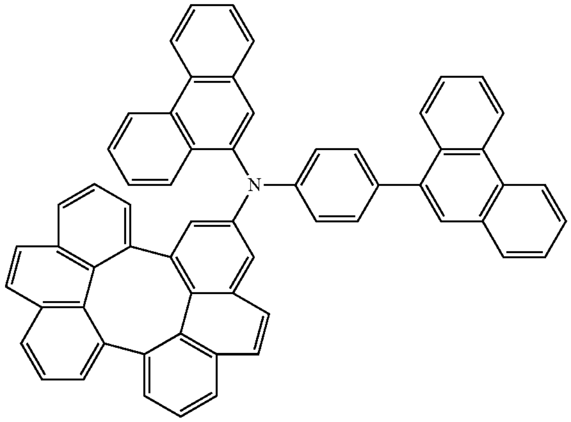
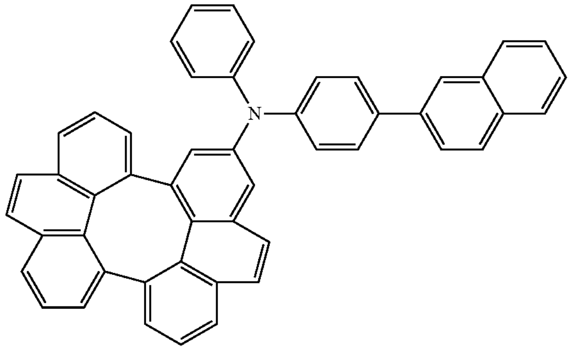

-continued
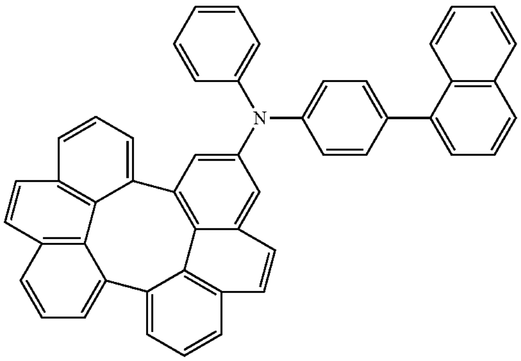
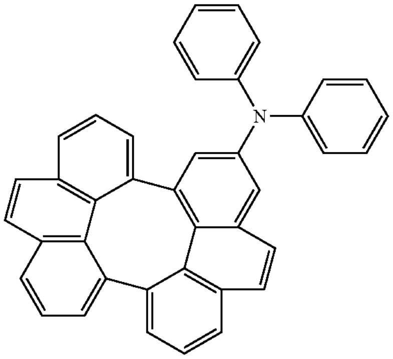
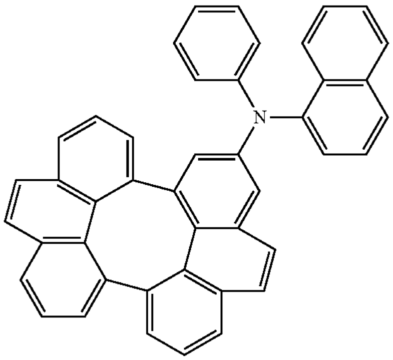
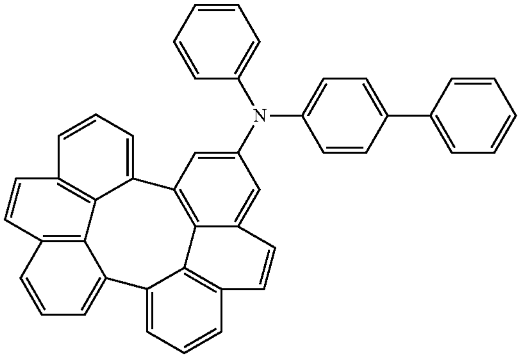
-continued
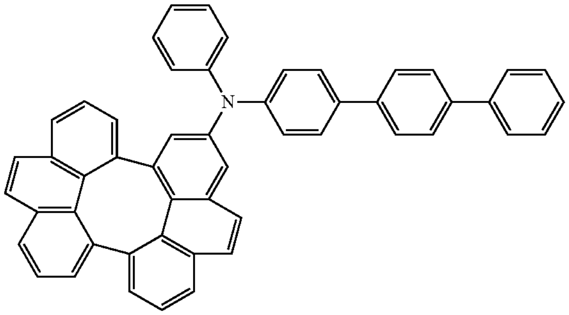
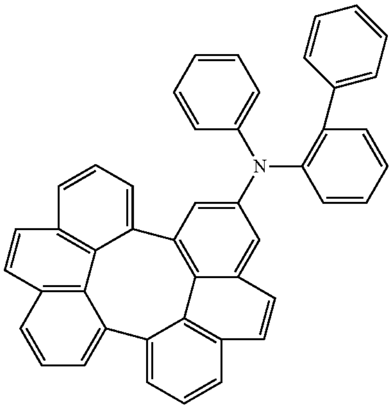
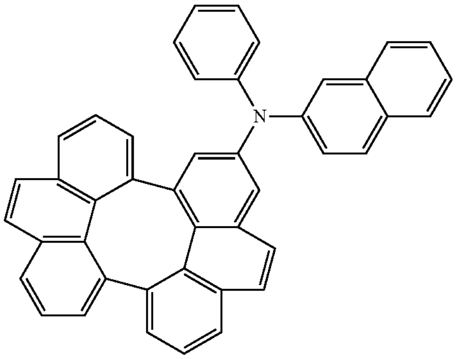
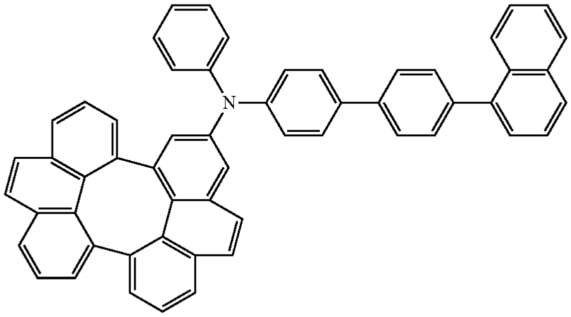
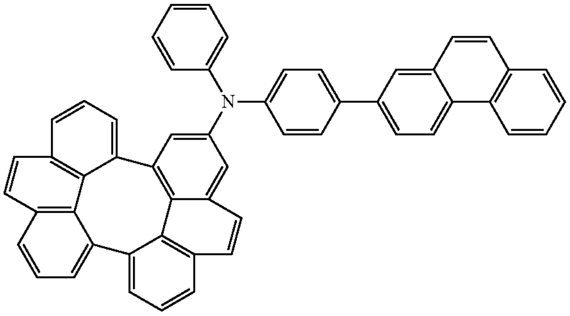

-continued
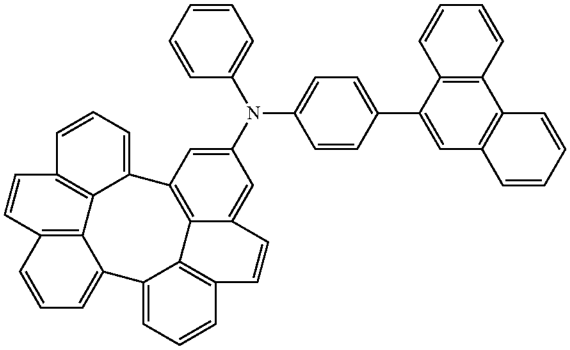
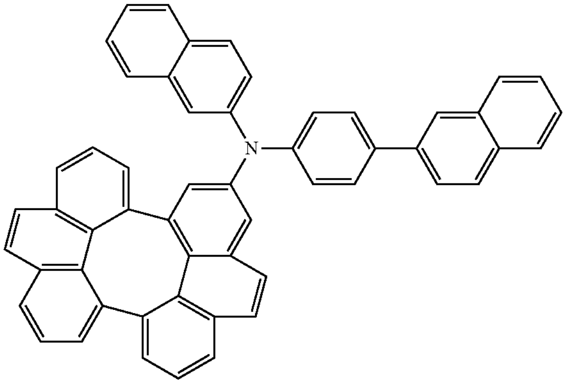
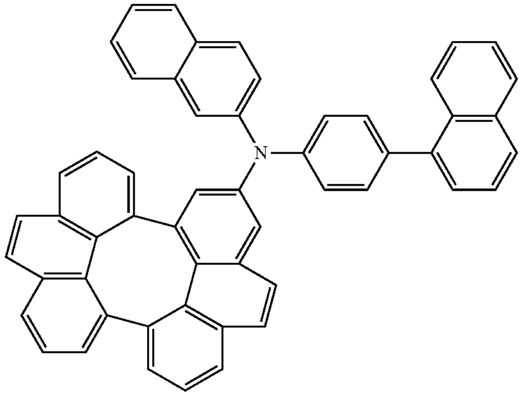
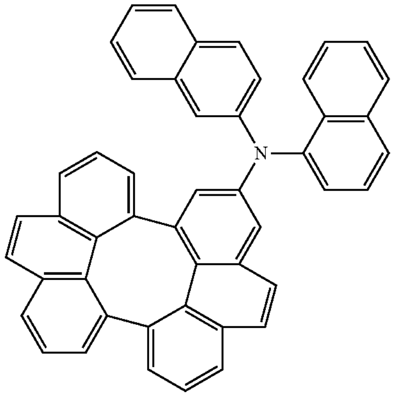
-continued
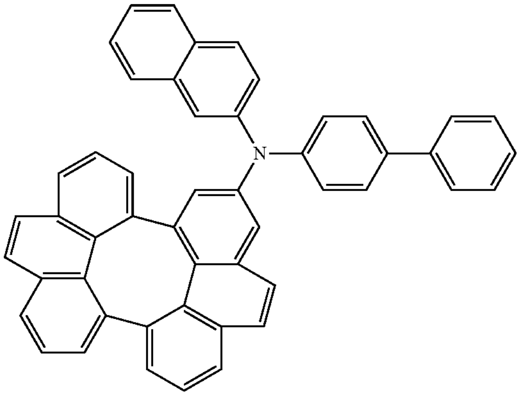
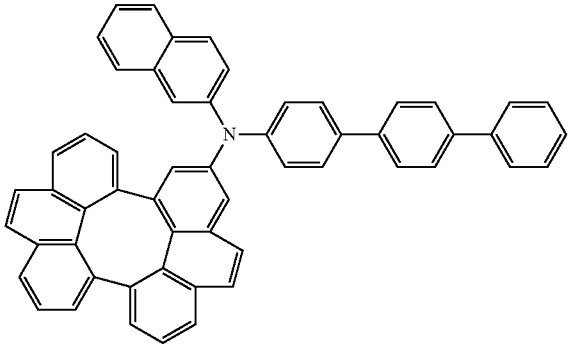
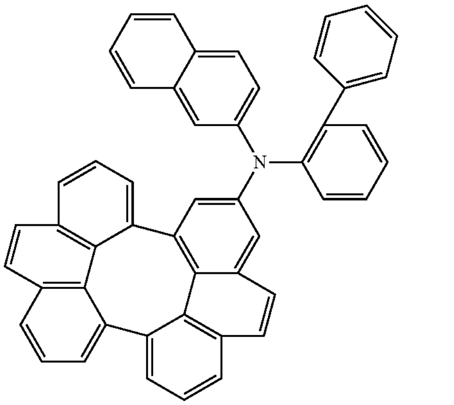
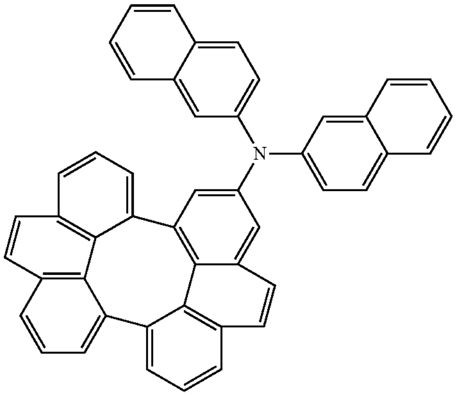

-continued
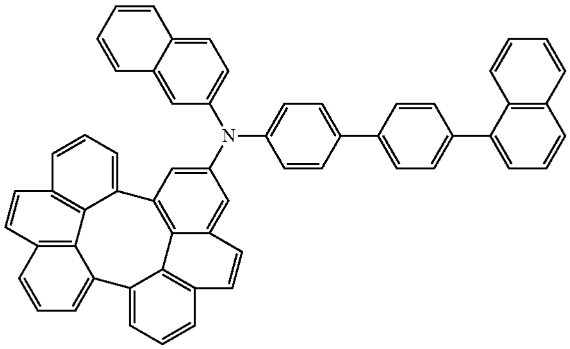
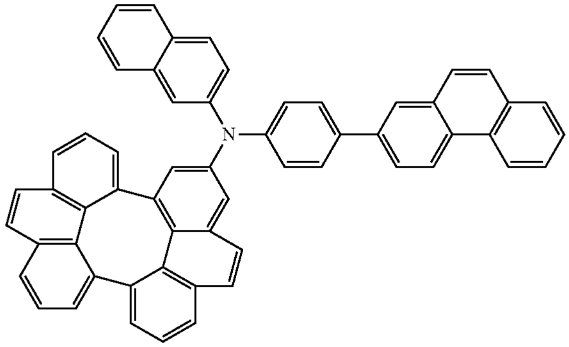
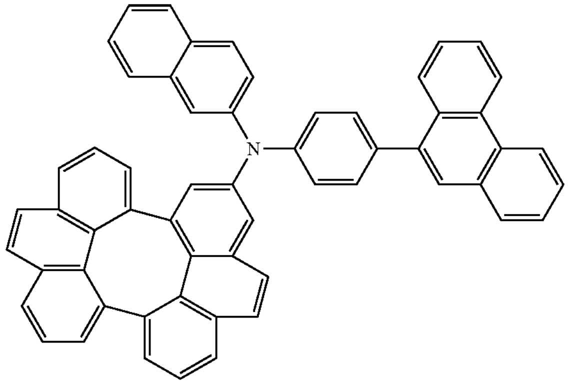
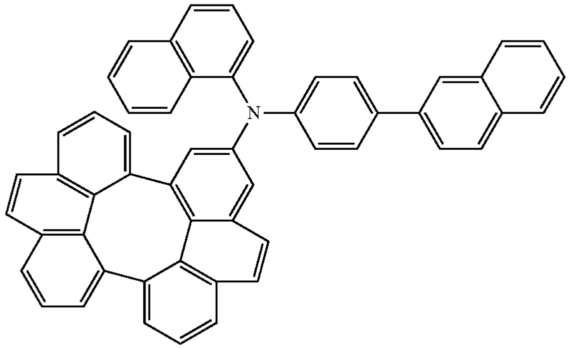
-continued
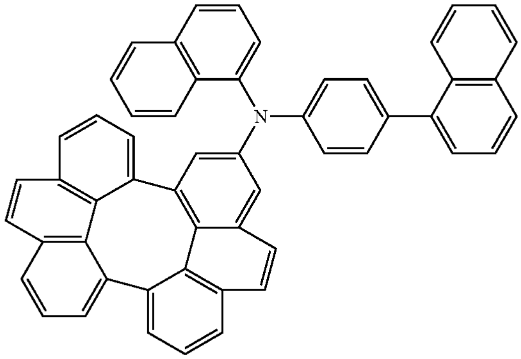
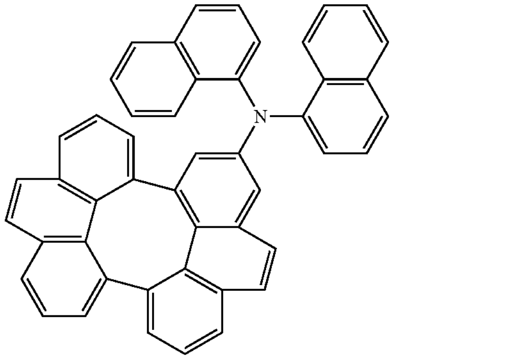
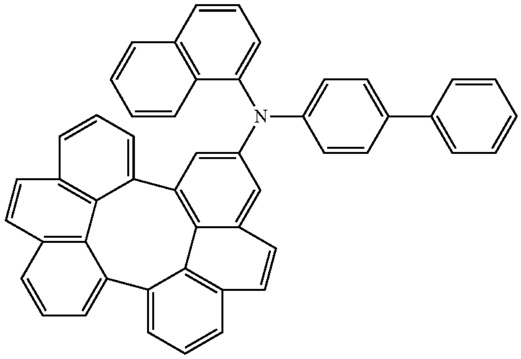
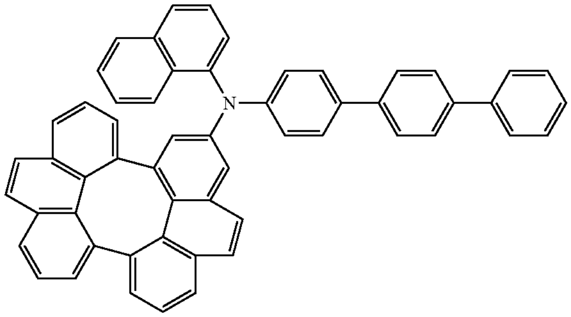

-continued
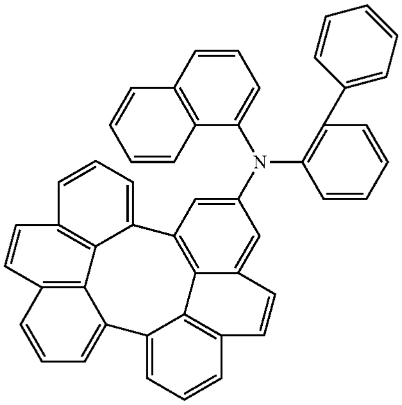
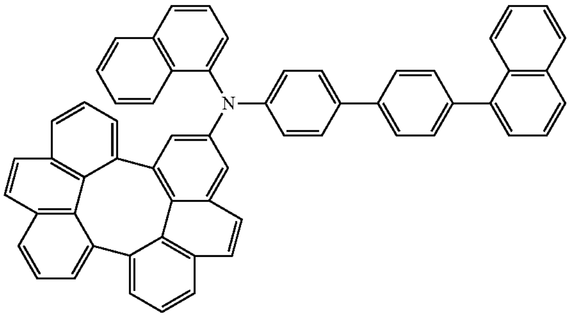
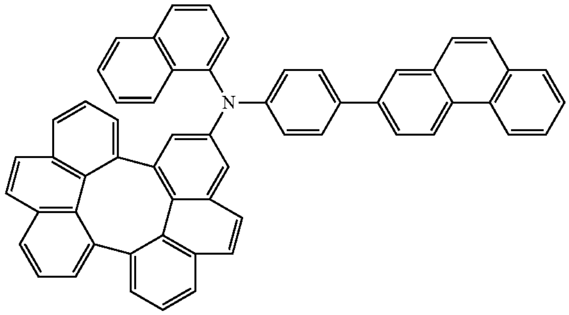
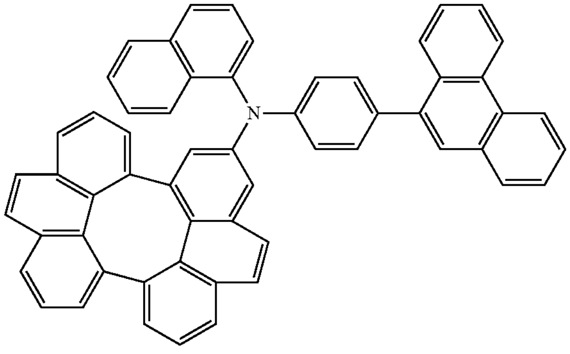
-continued
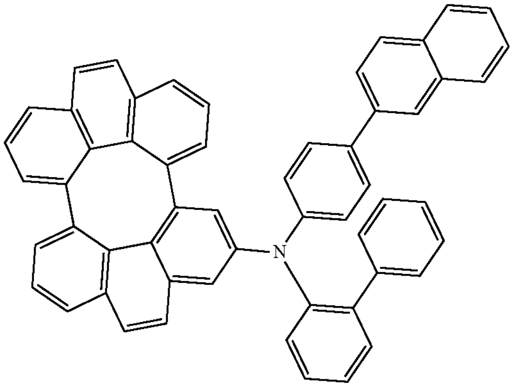
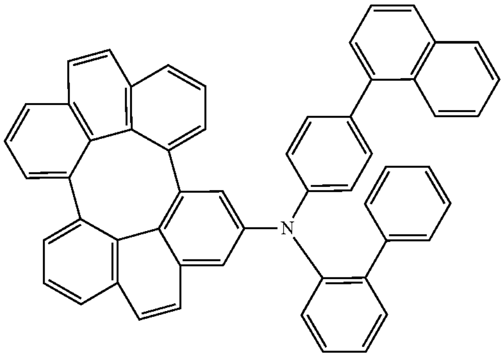
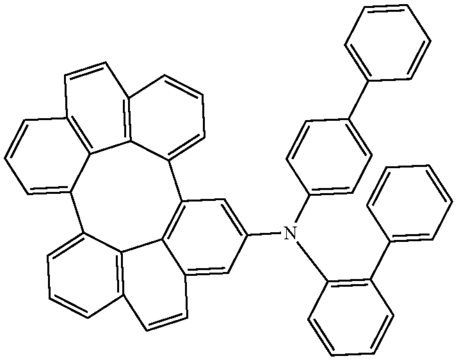
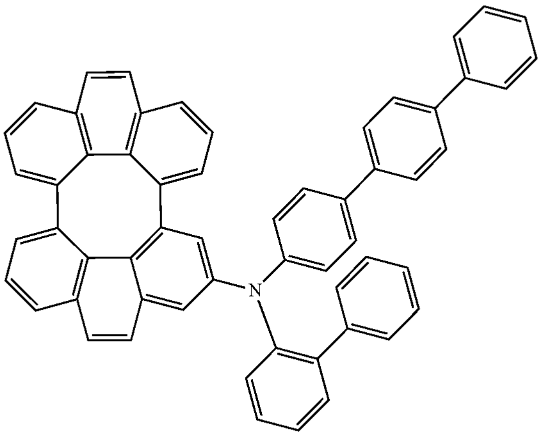

-continued
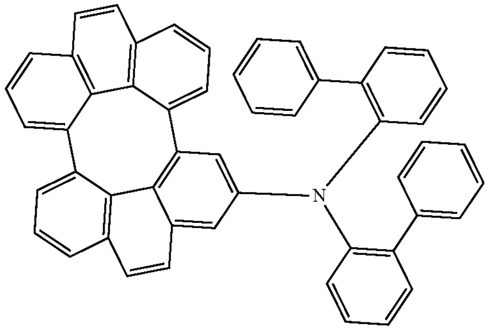
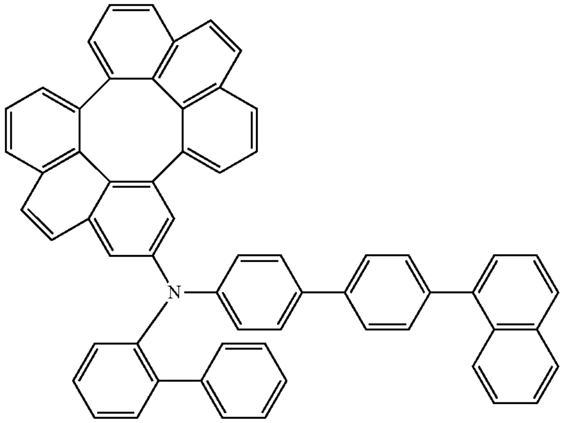
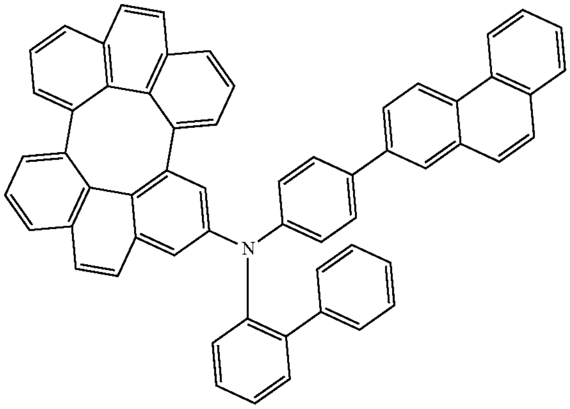
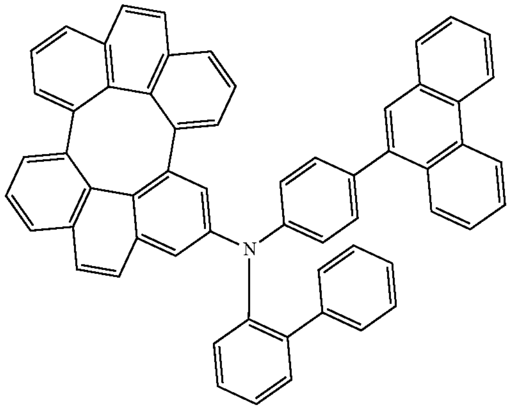
-continued
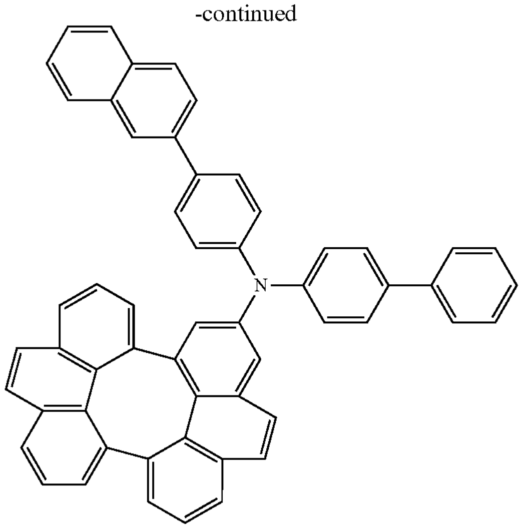
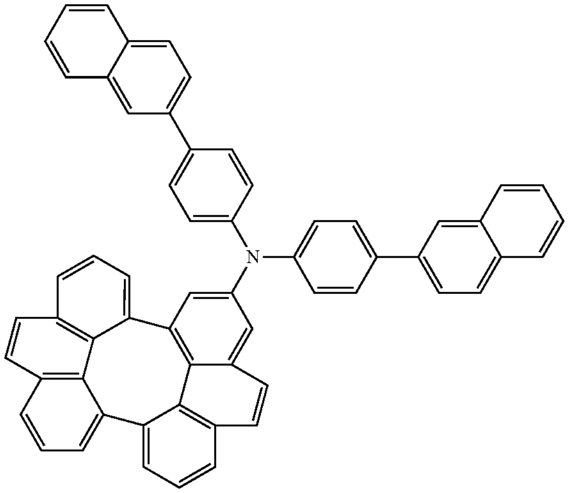
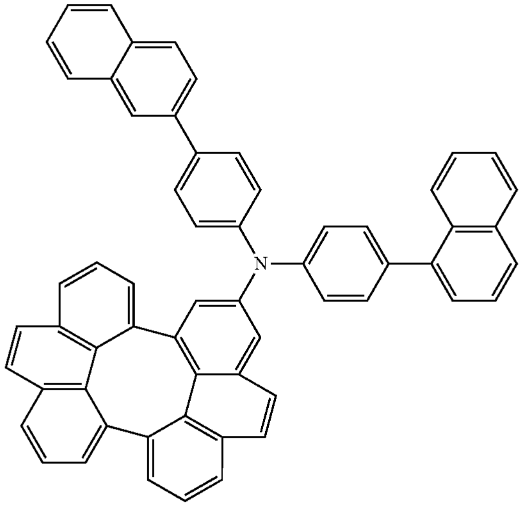

-continued
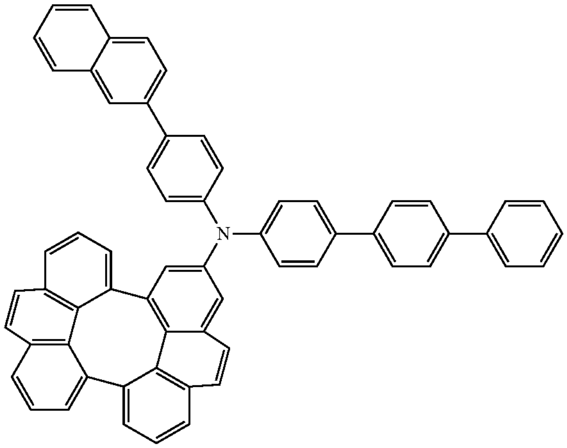
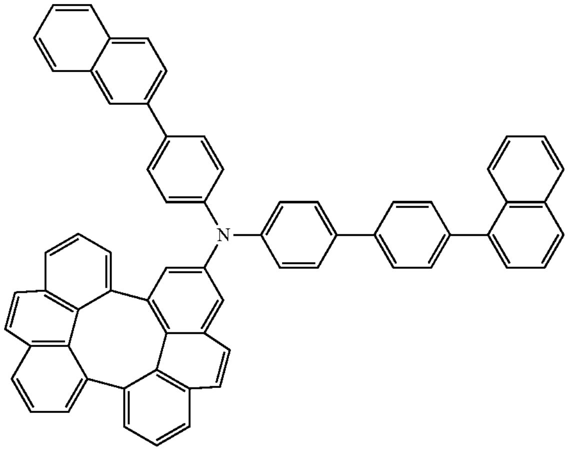
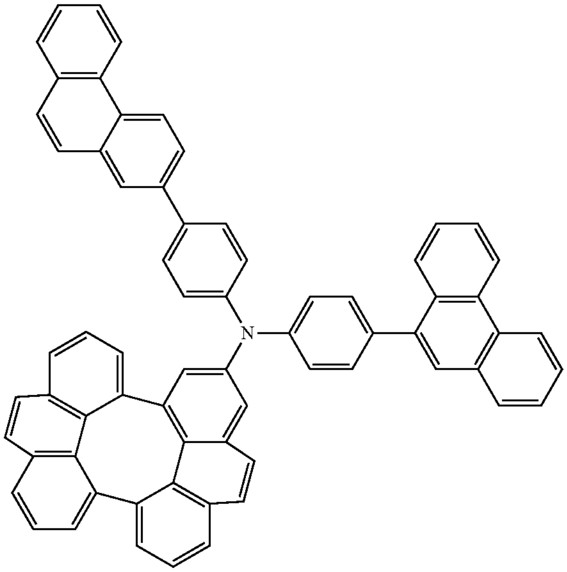
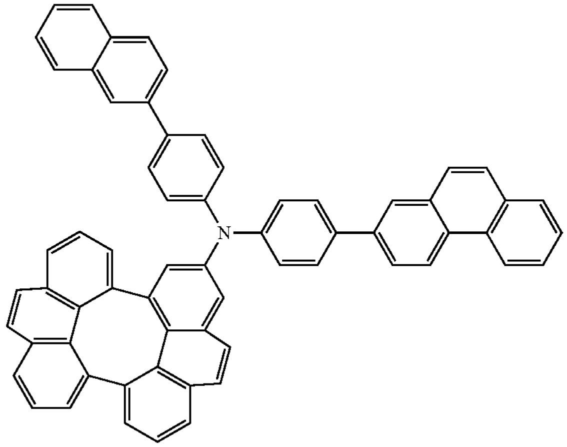
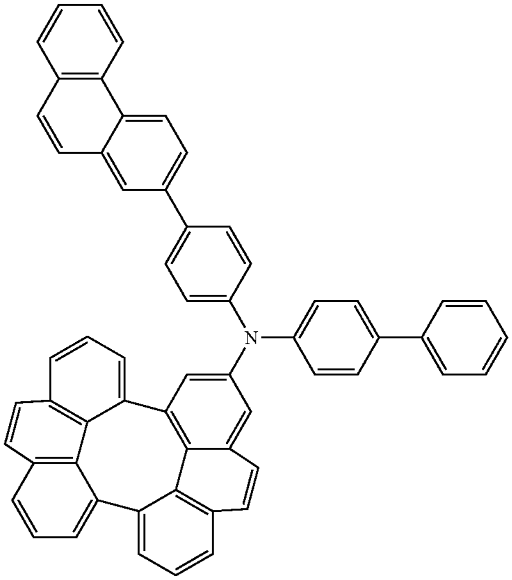
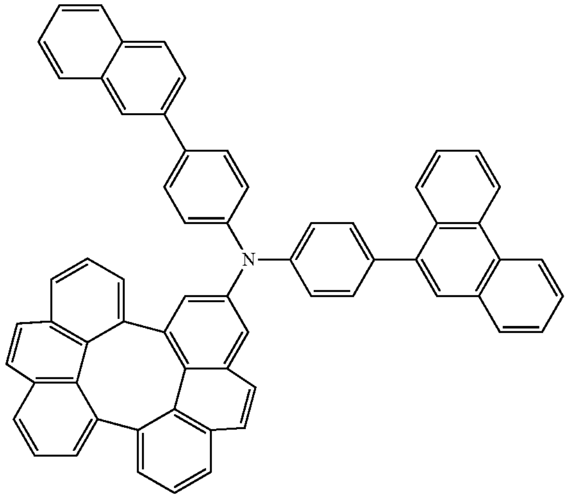

-continued
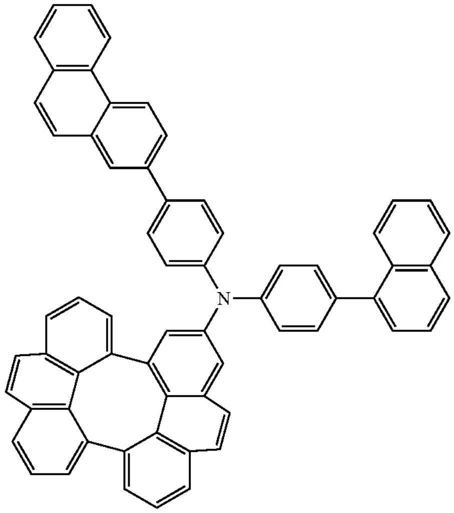
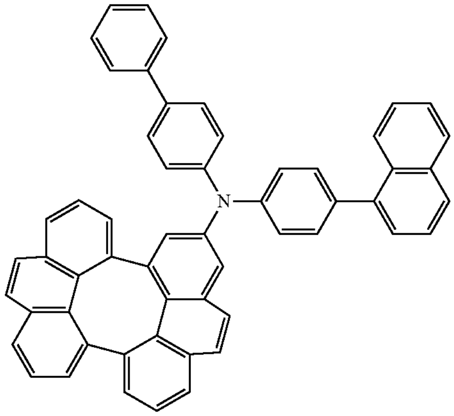
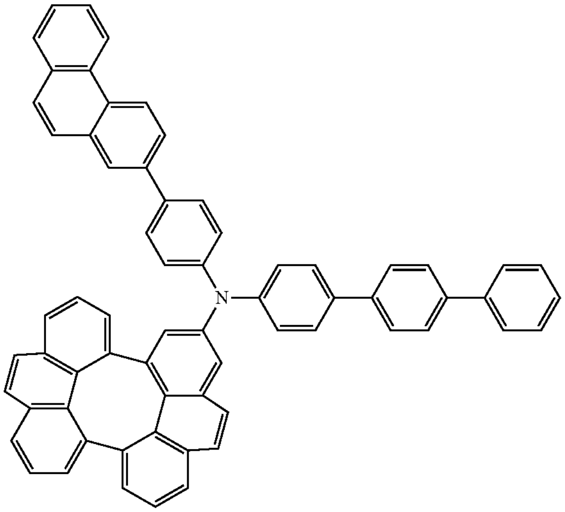
-continued
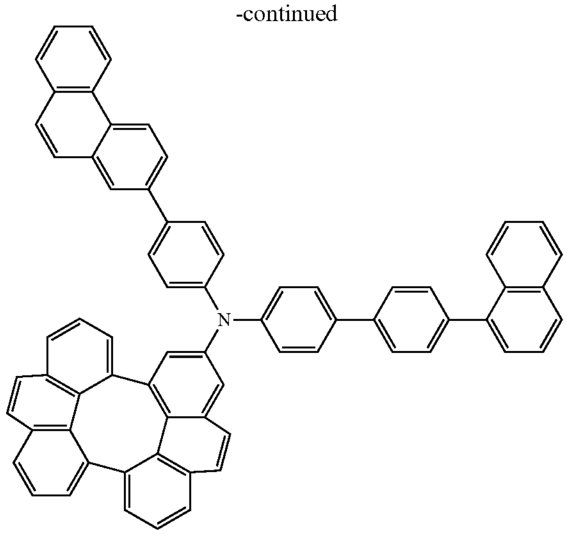
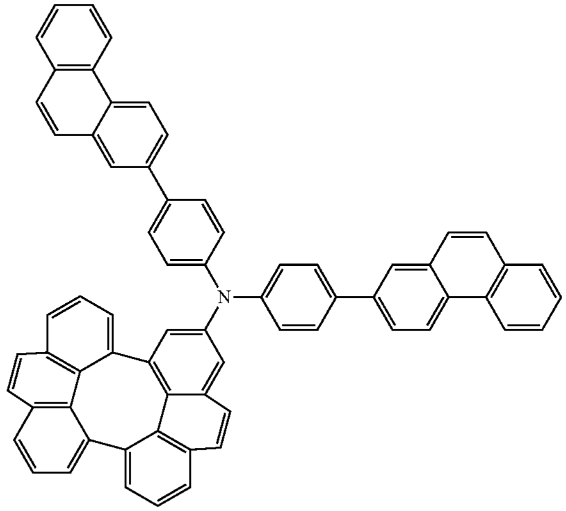
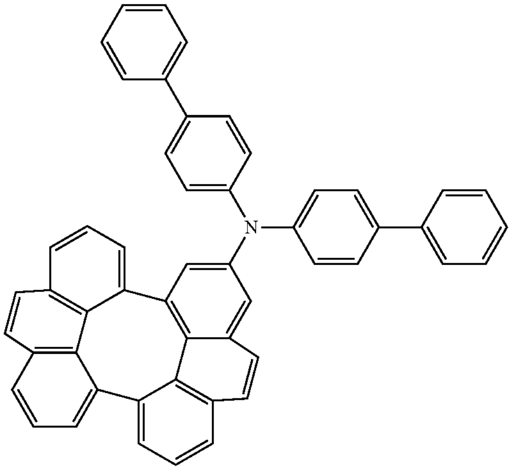

-continued
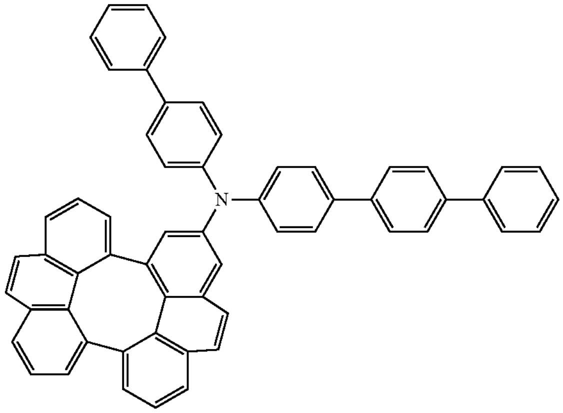
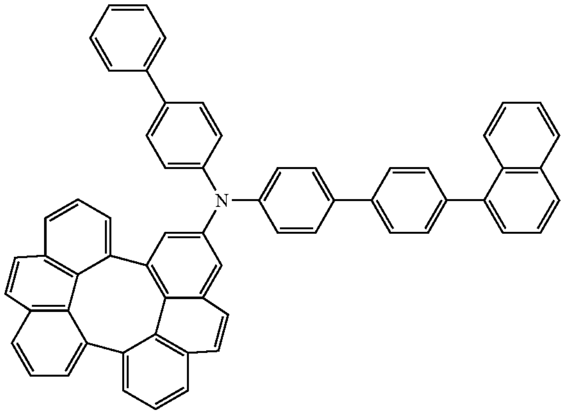
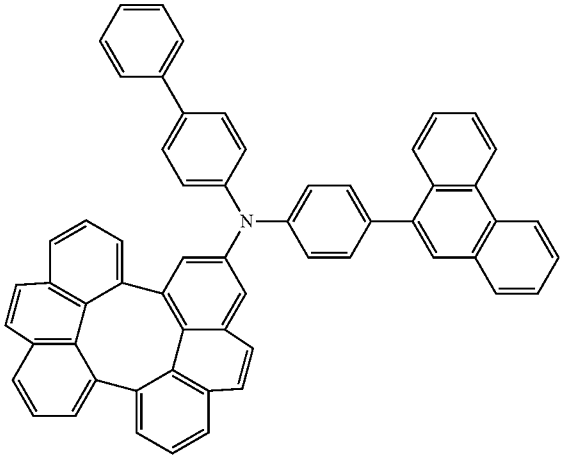
-continued
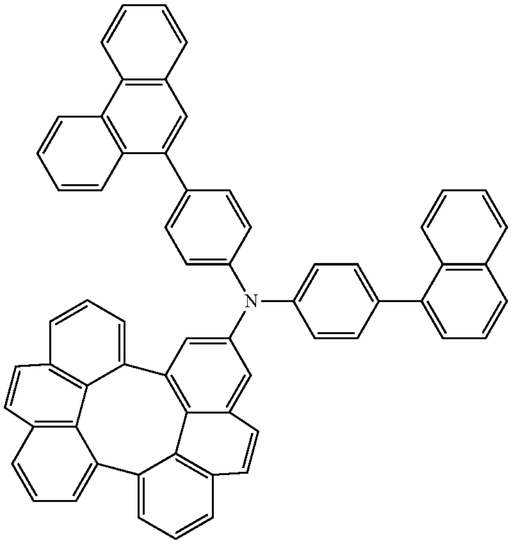
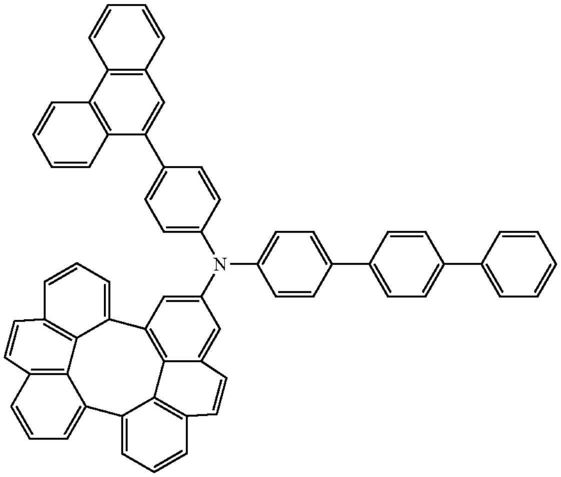
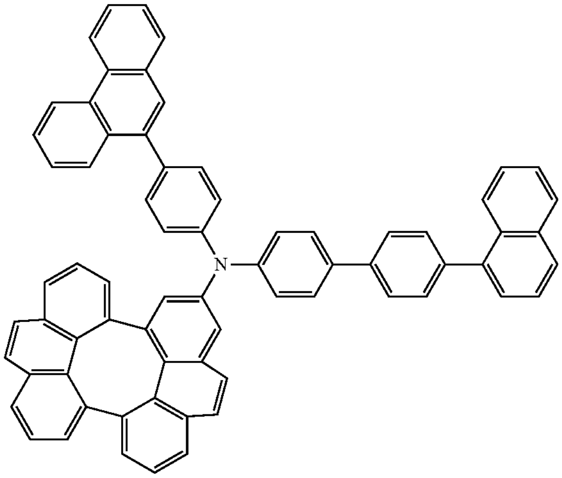

-continued
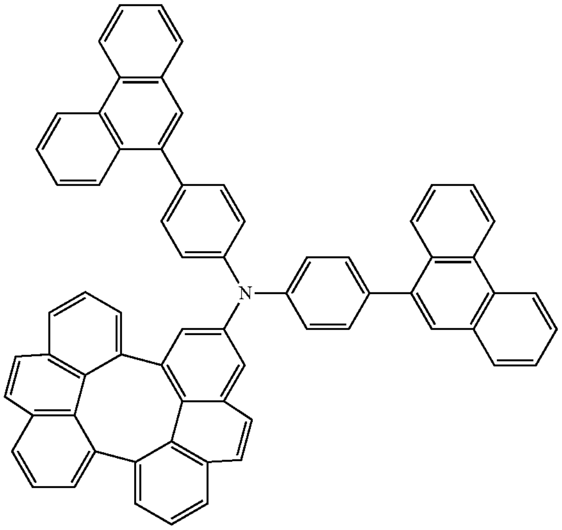
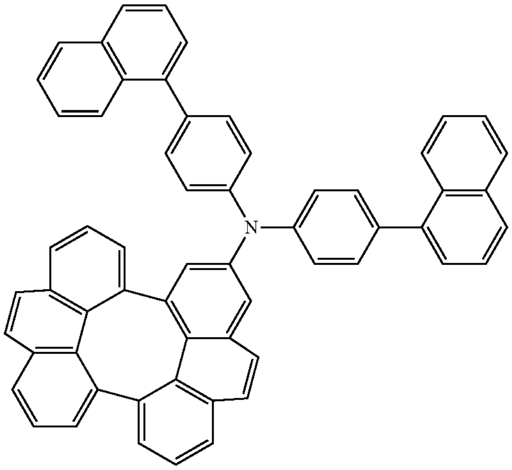
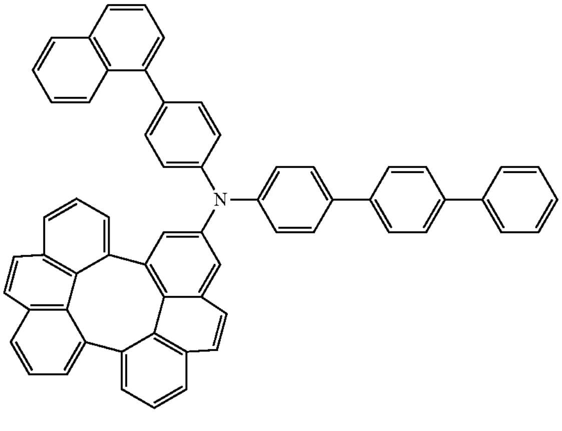
-continued
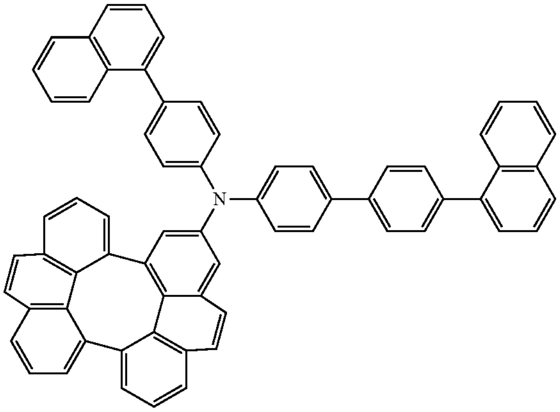
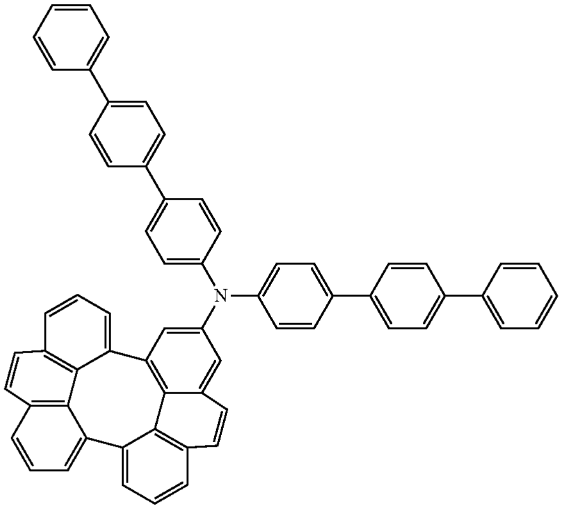
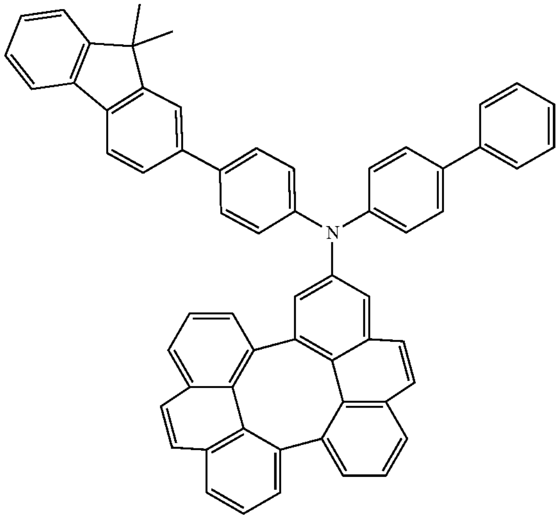

-continued
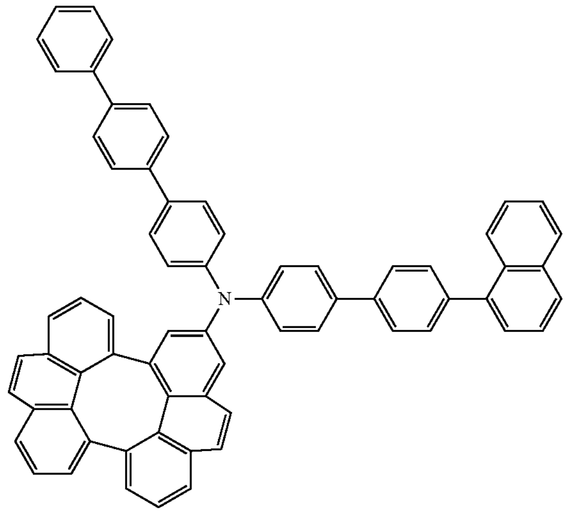
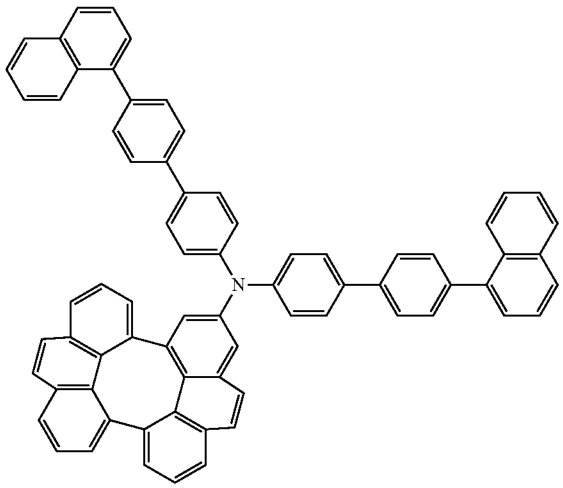
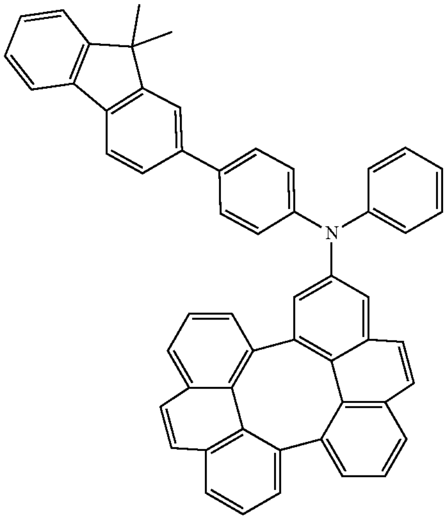
-continued
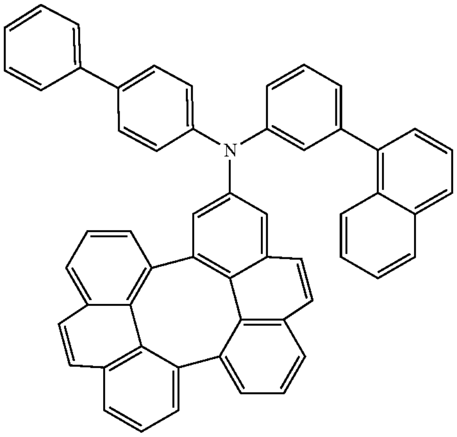
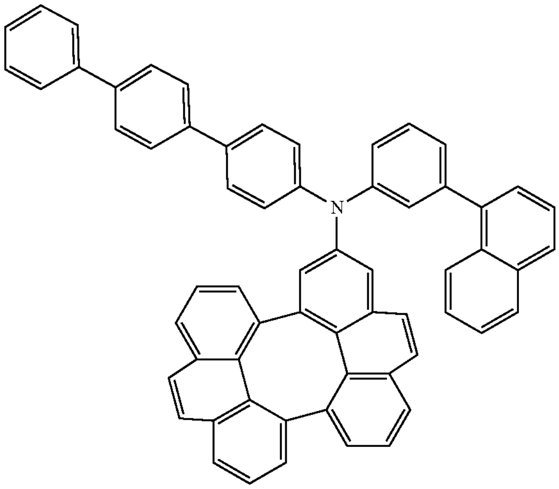
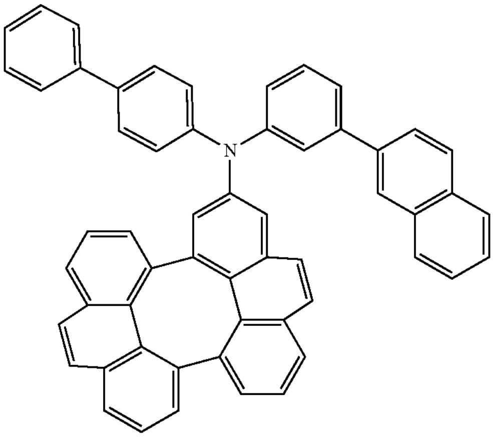

-continued
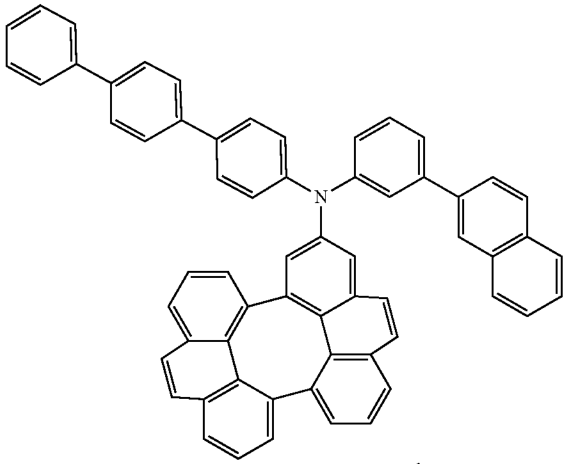
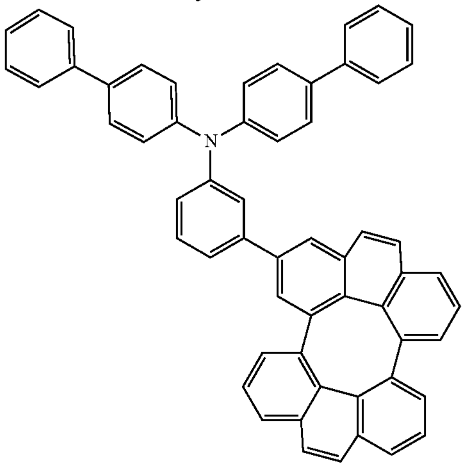
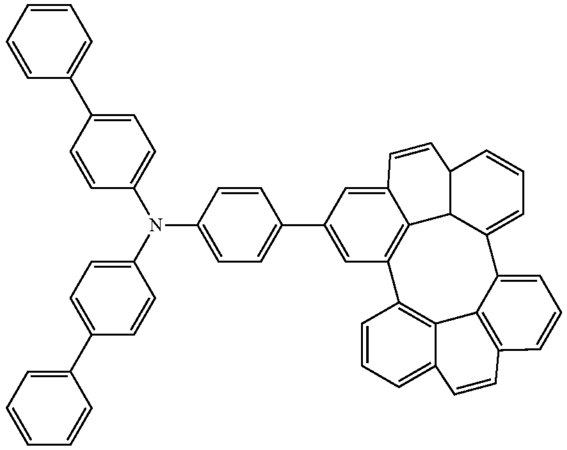
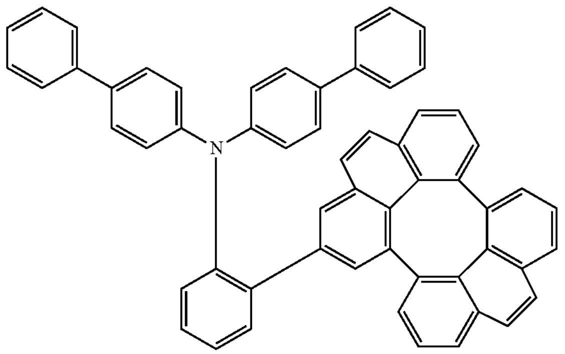
-continued
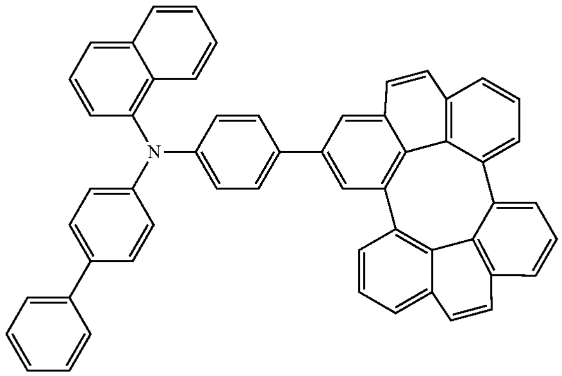
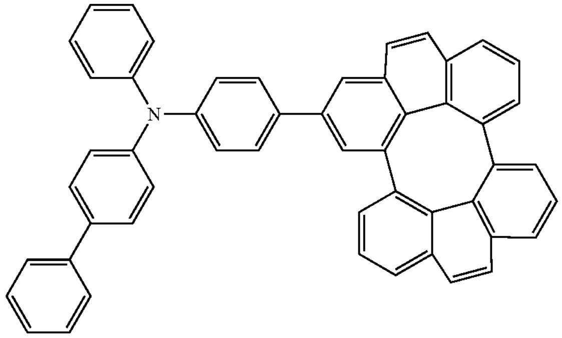
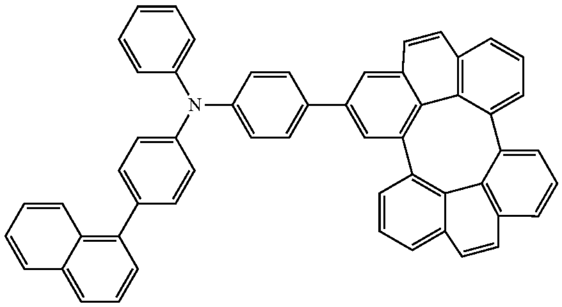
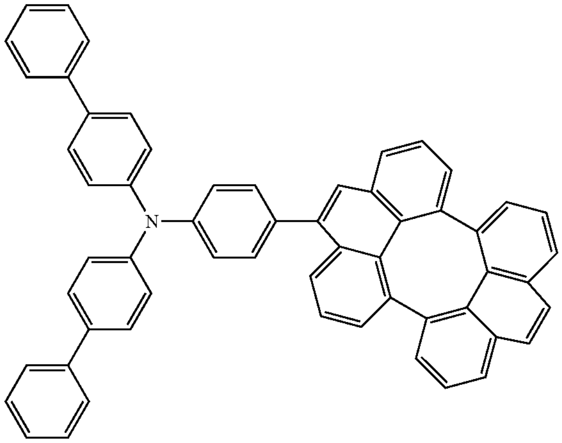

-continued
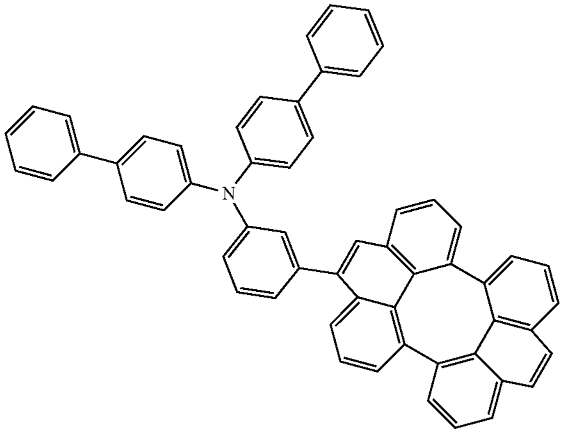
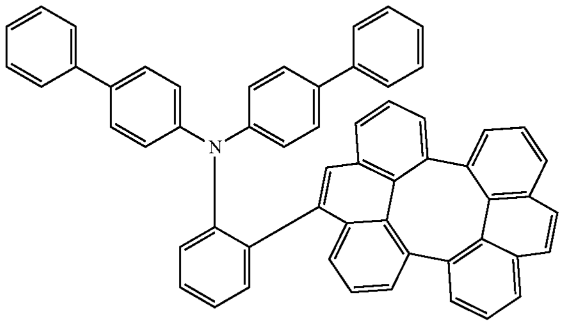
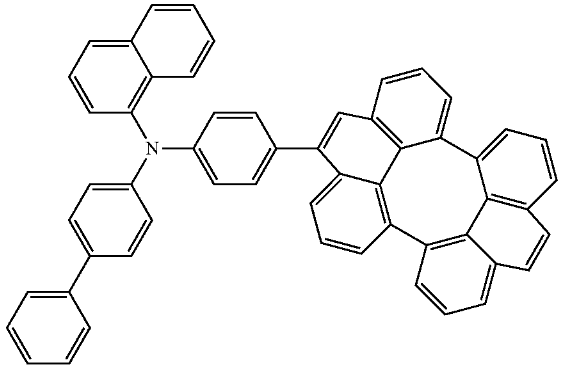
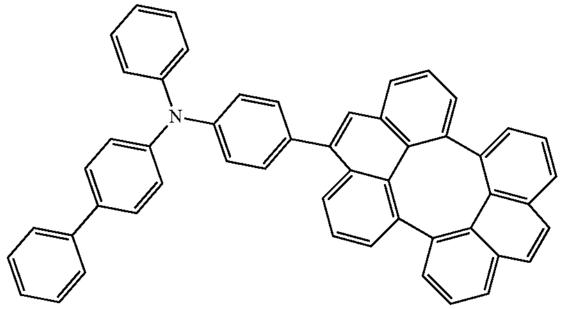
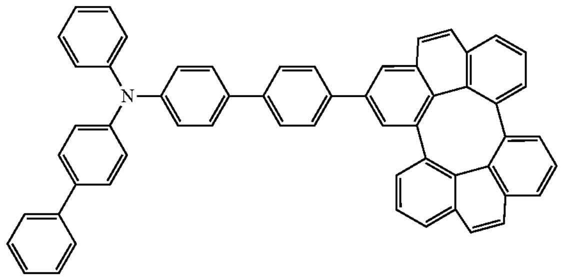
-continued
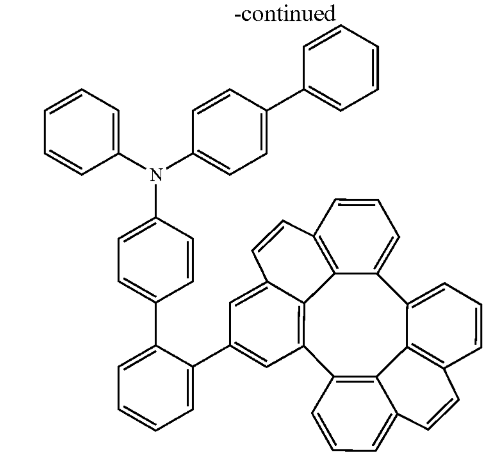
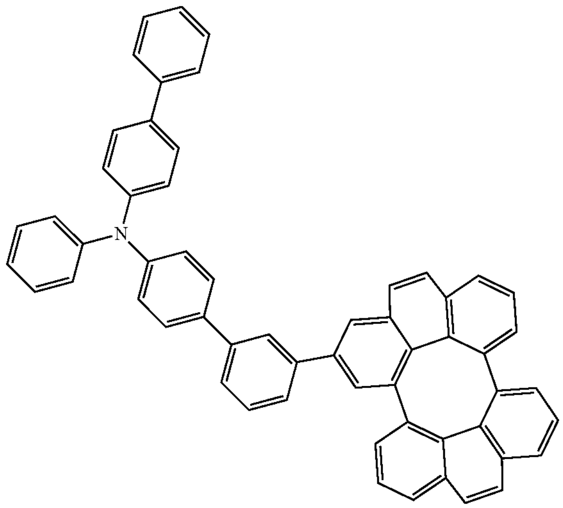
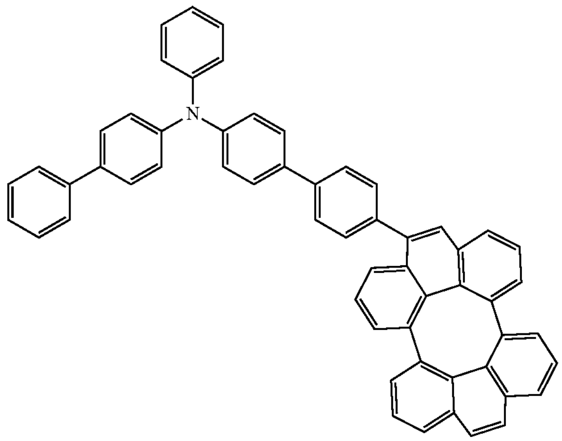

-continued
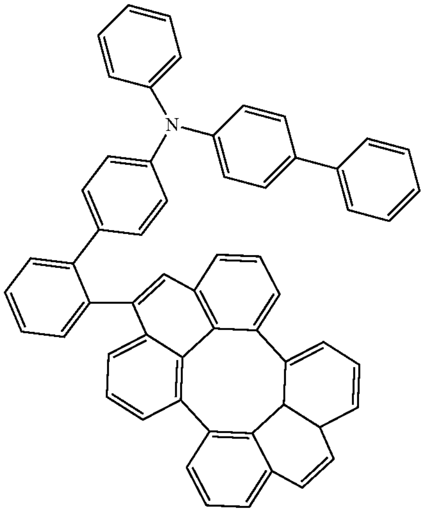
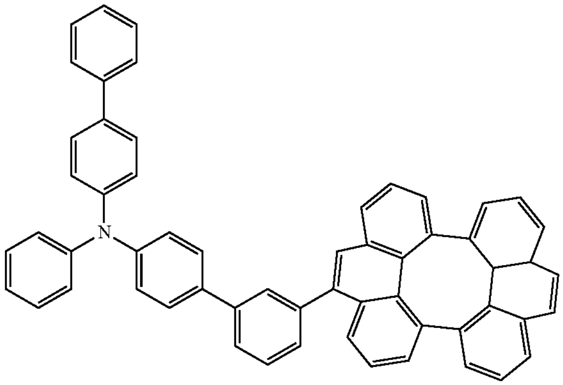
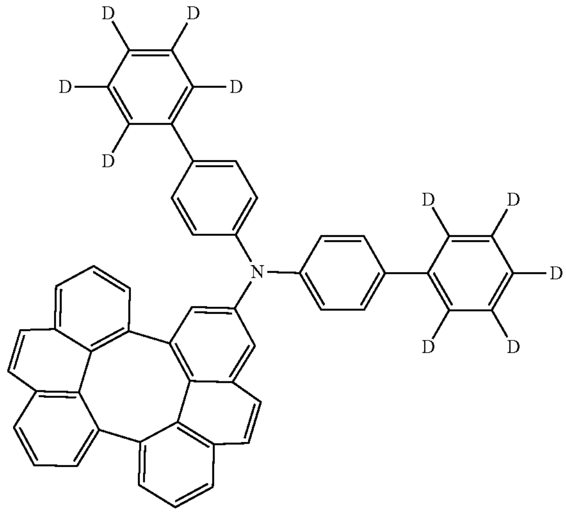
-continued
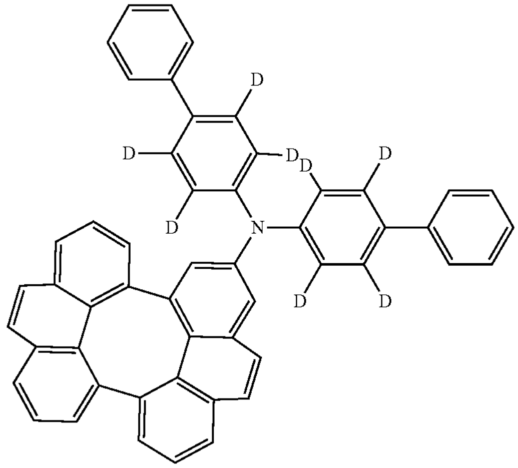
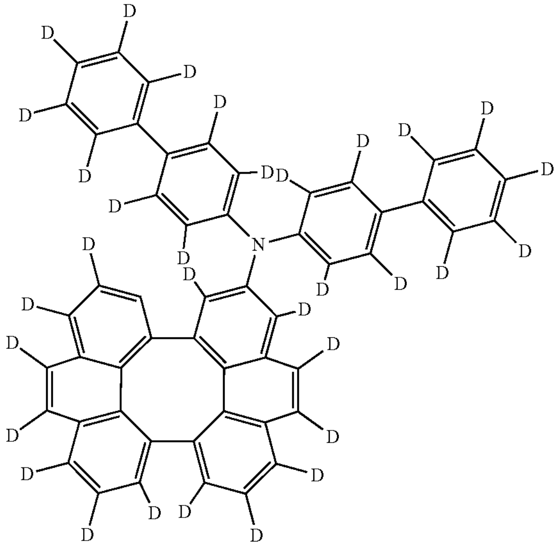
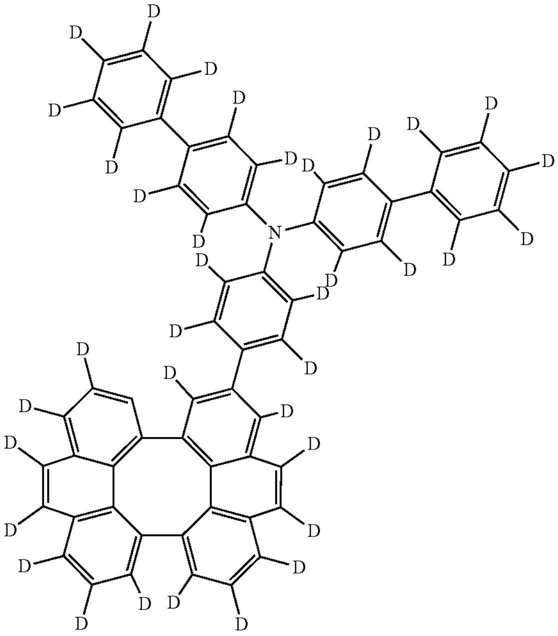

-continued
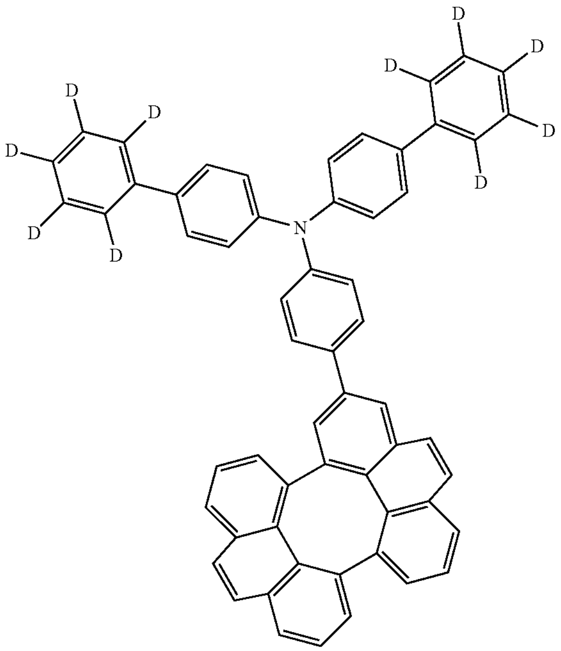
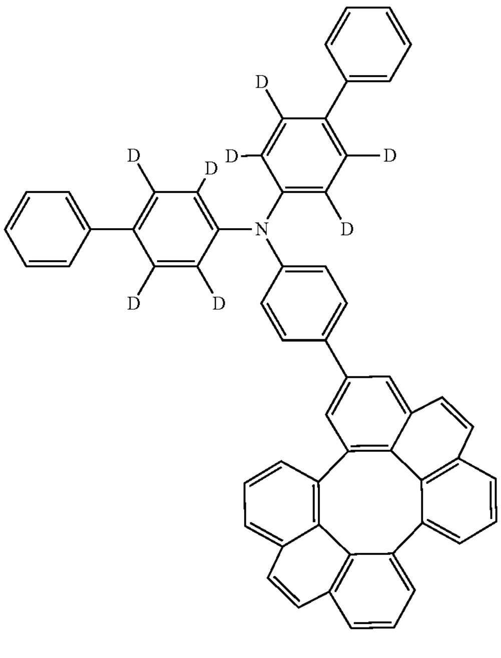
-continued
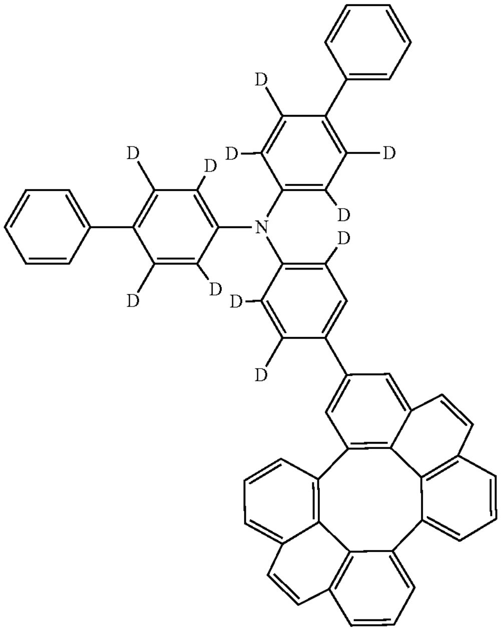
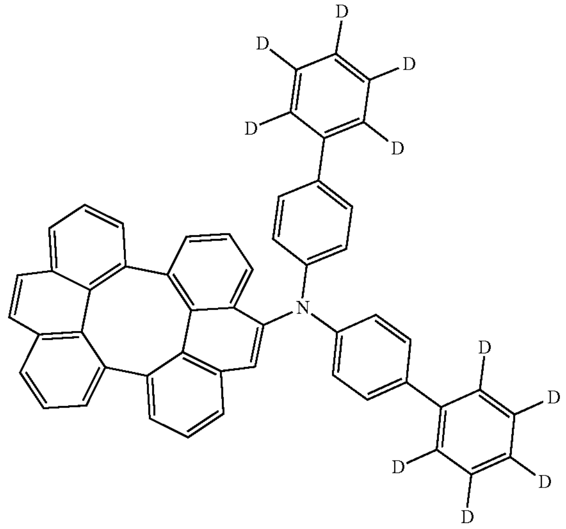
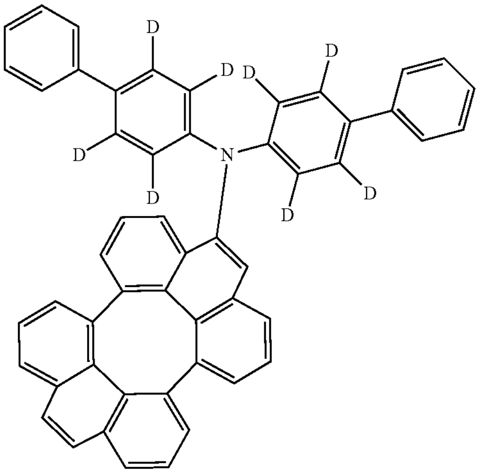

-continued
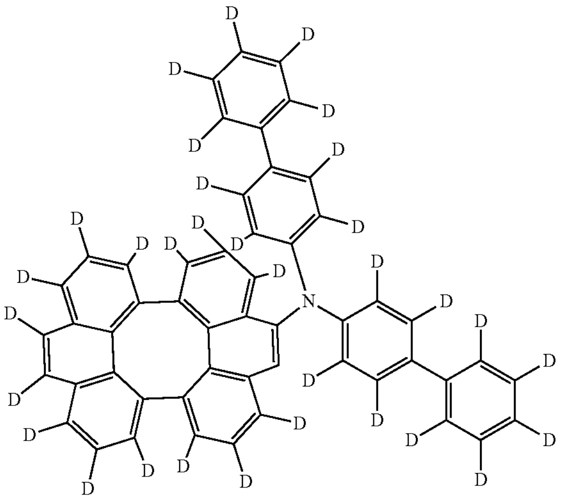
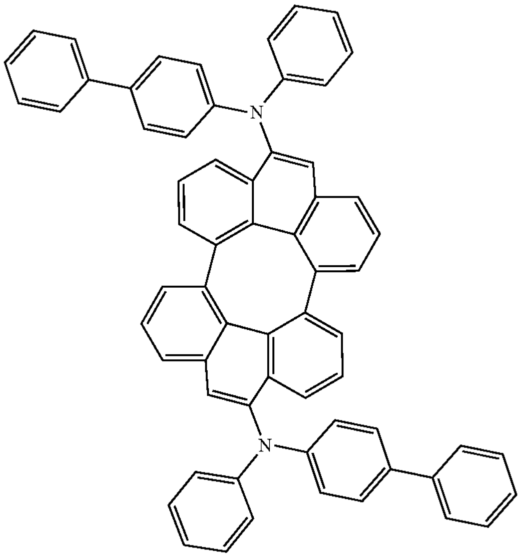
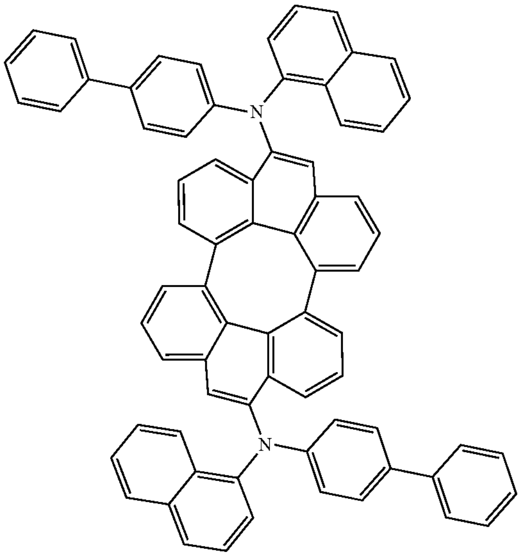
-continued
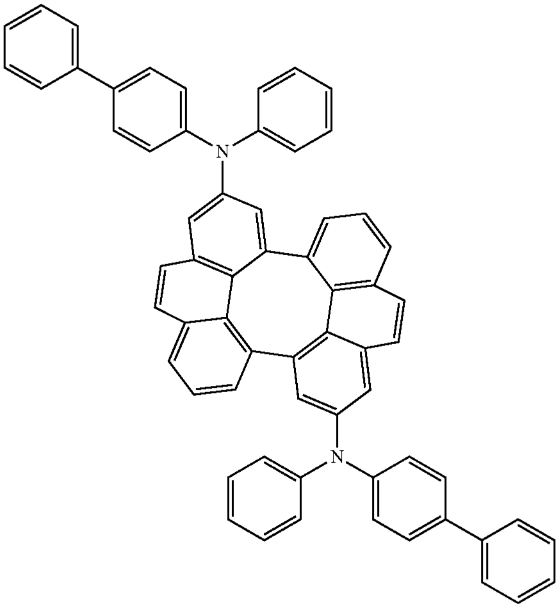
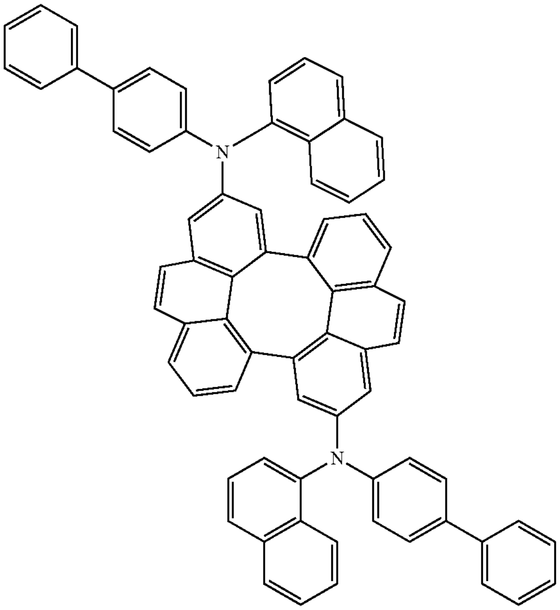

-continued
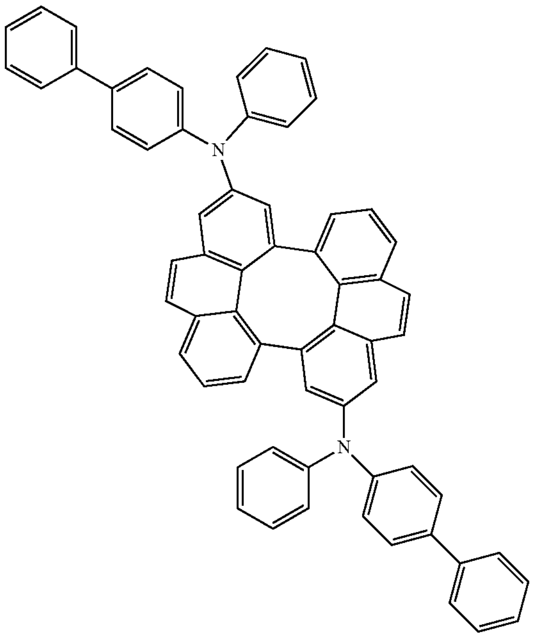
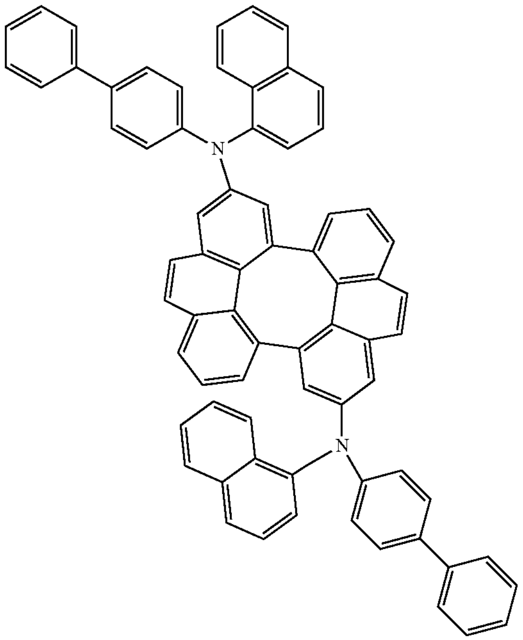
-continued
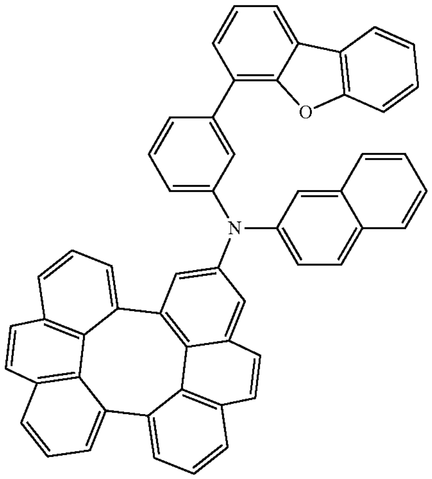
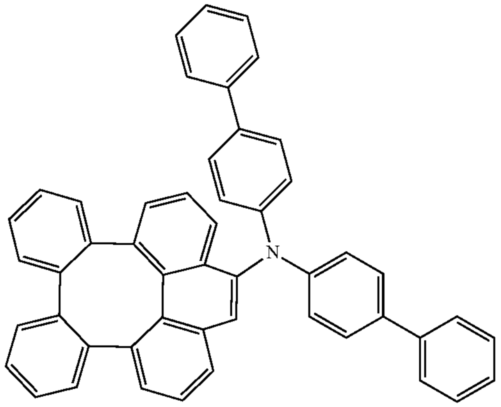
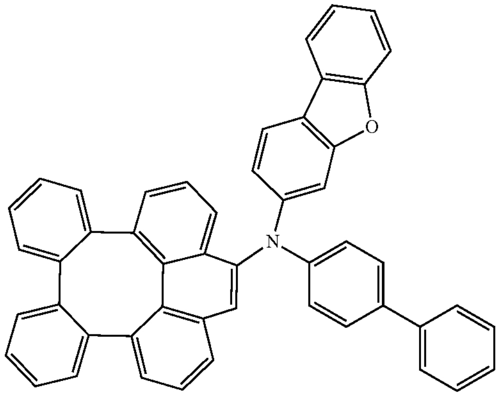
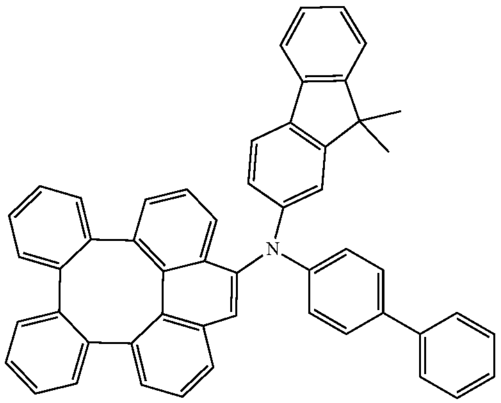

-continued
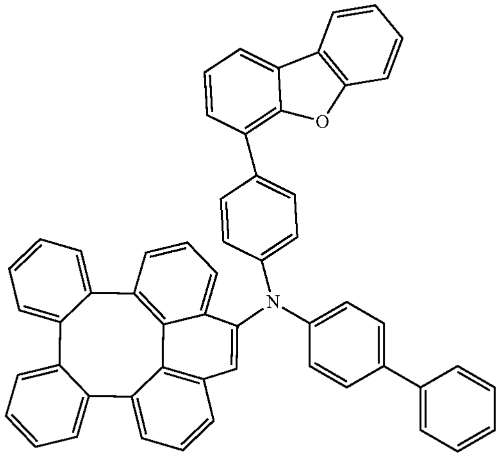
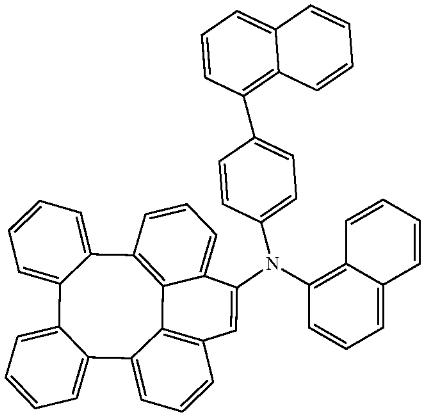
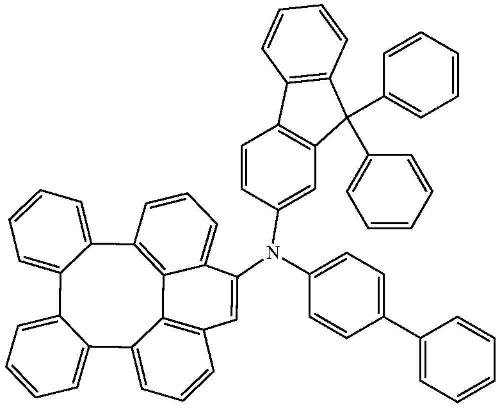
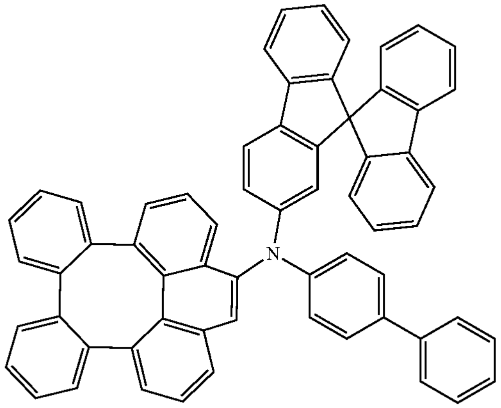
-continued
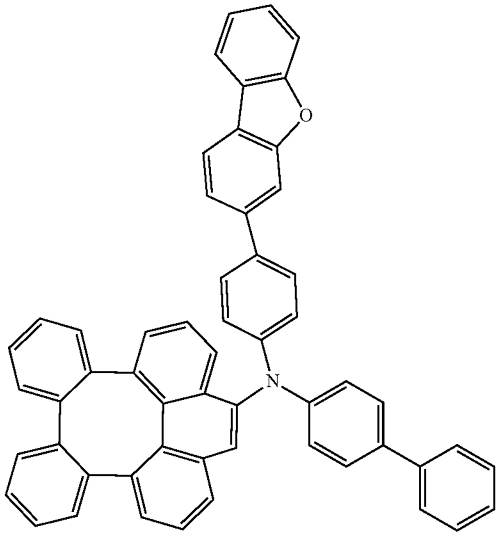
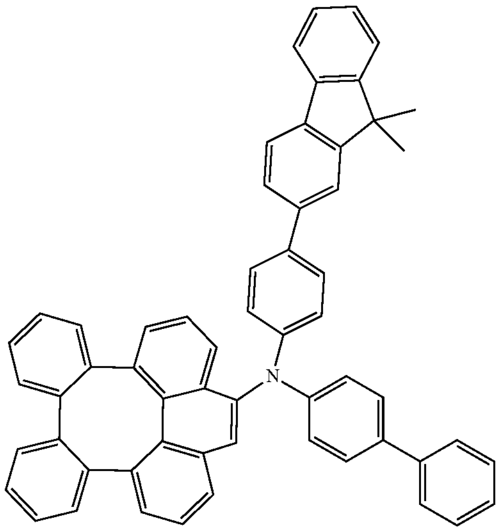
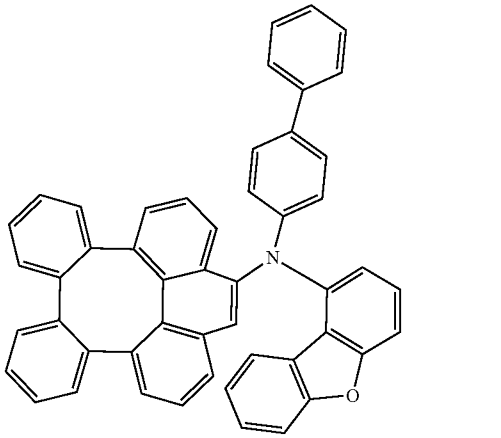

-continued
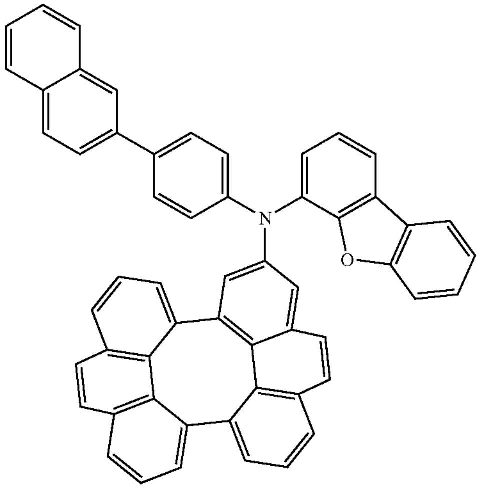
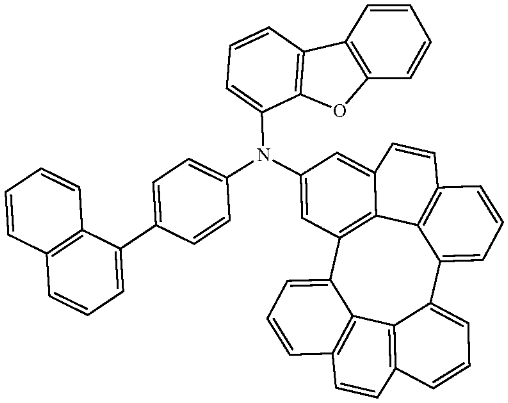
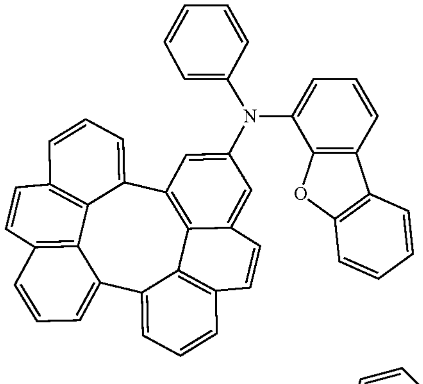
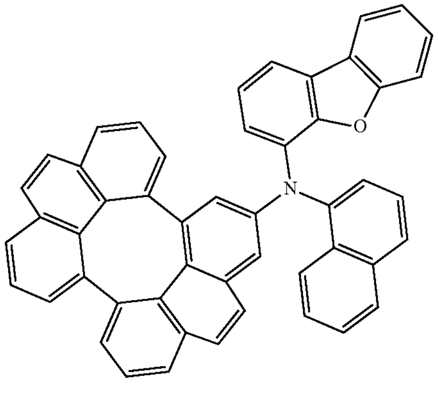
-continued
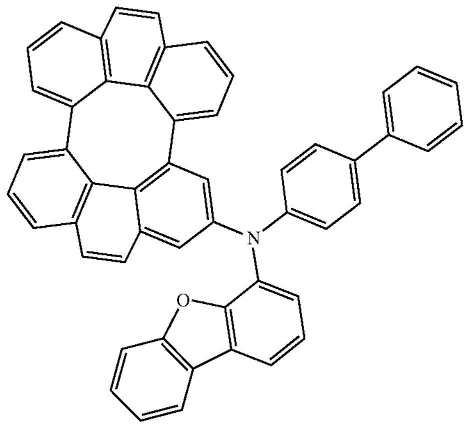
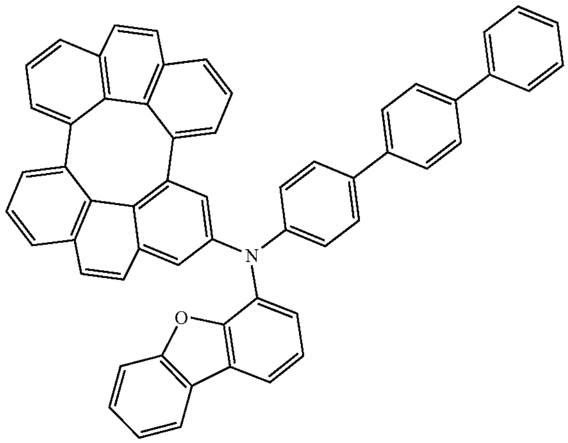
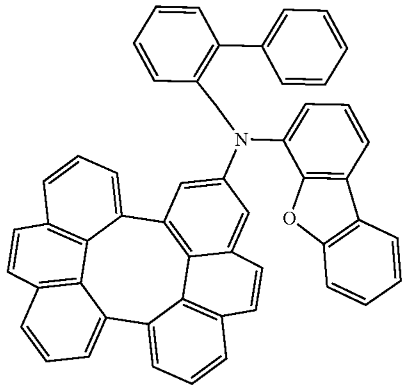
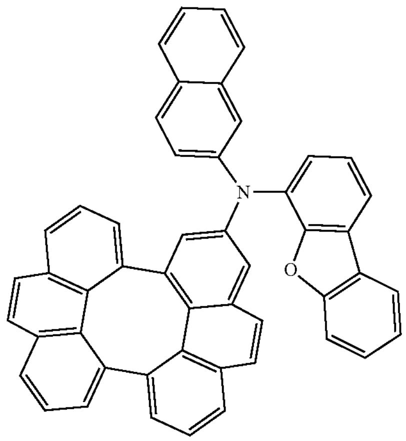

-continued
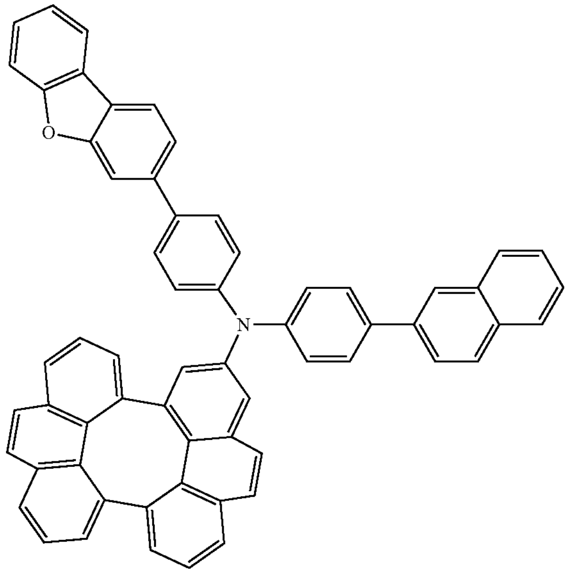
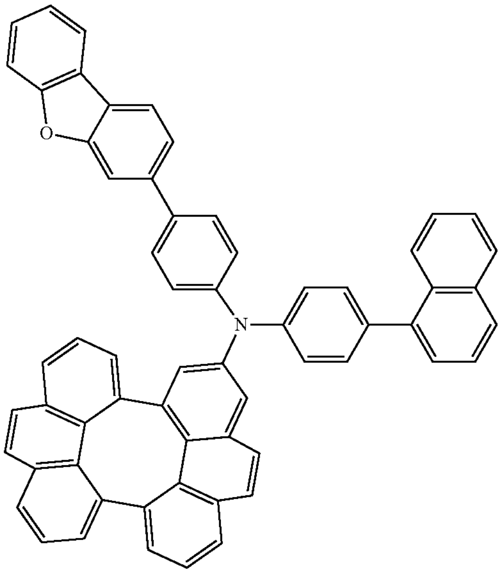
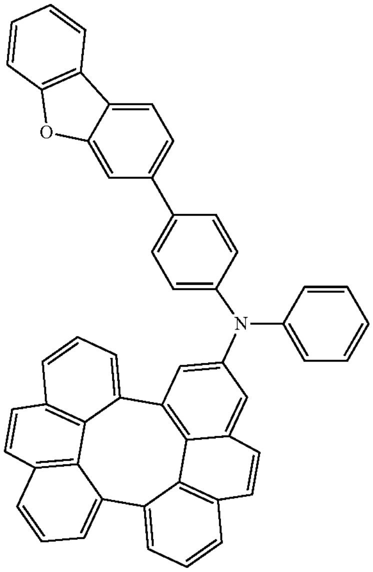
-continued
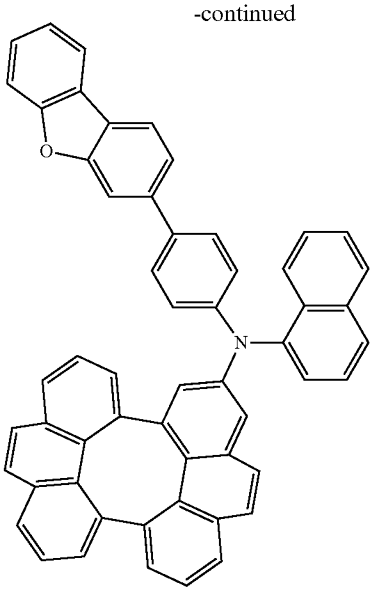
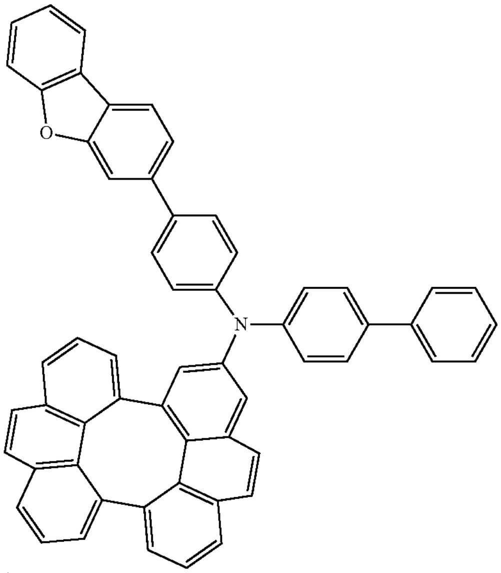
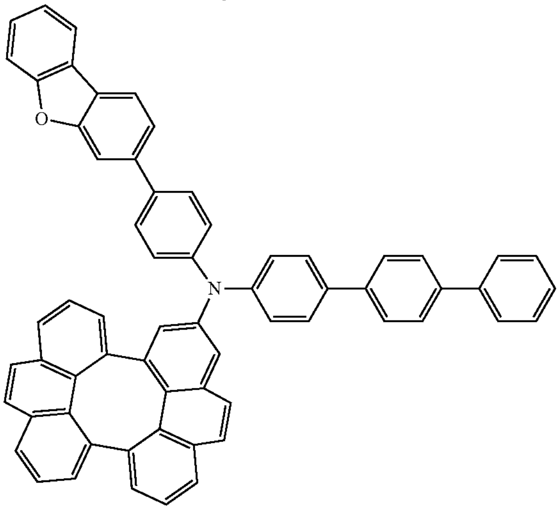

-continued
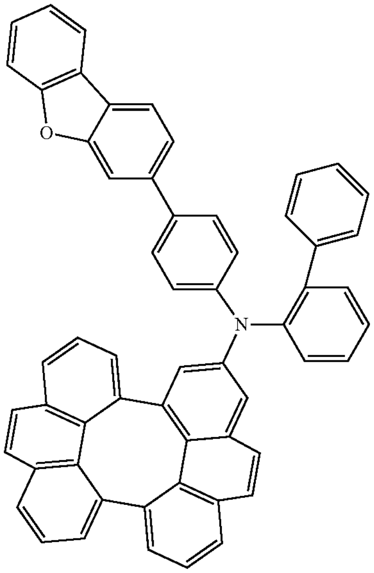
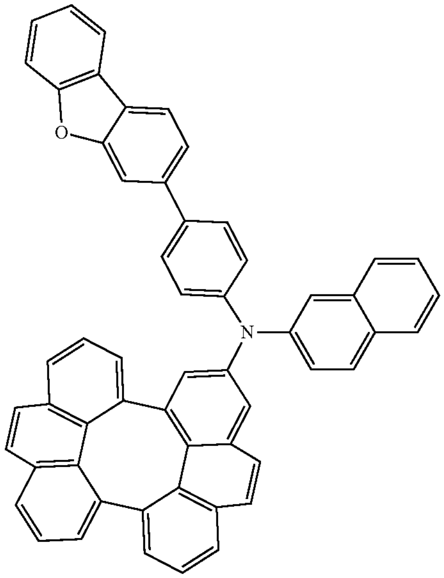
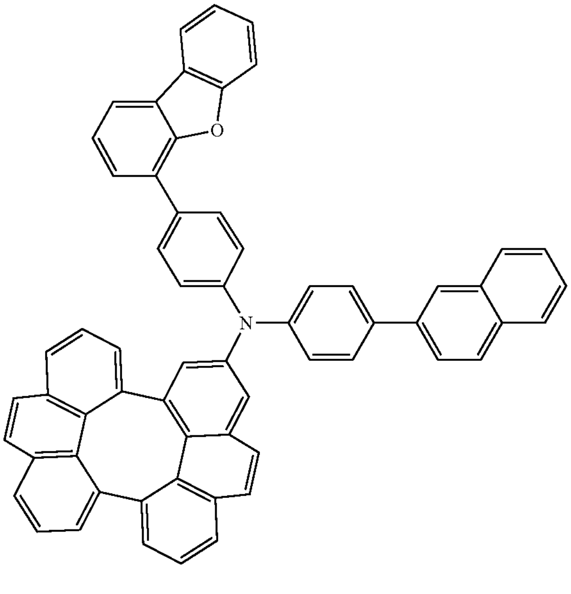
-continued
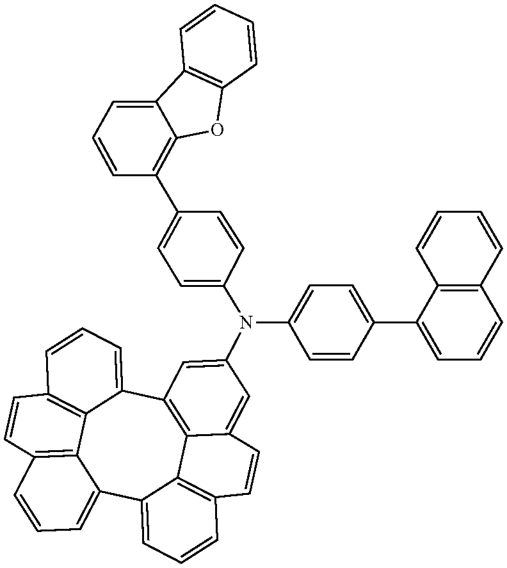
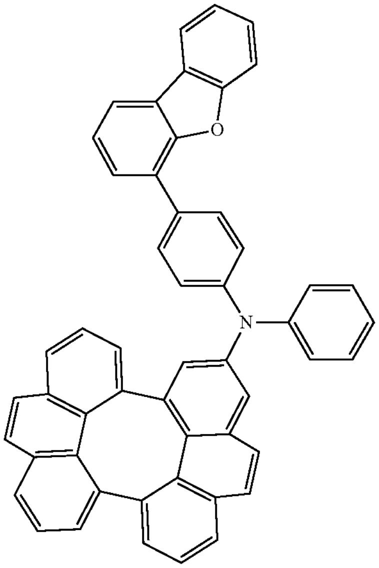
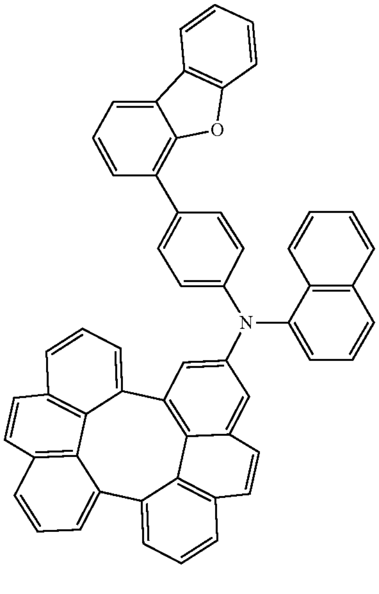

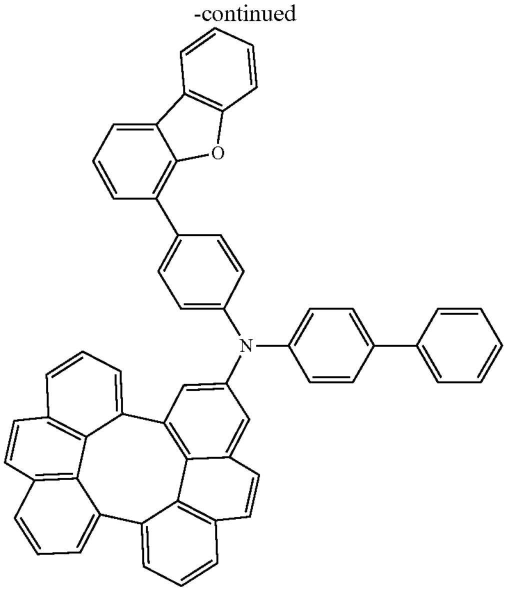
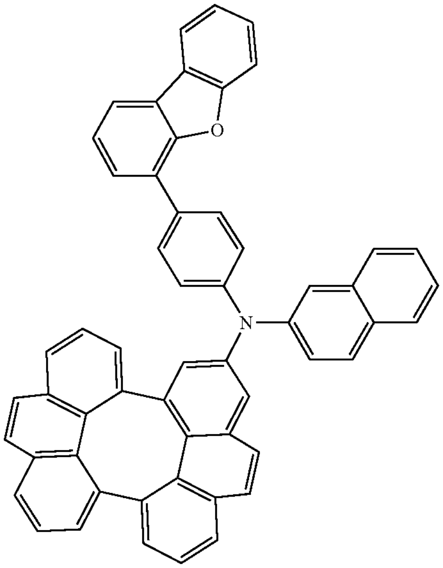
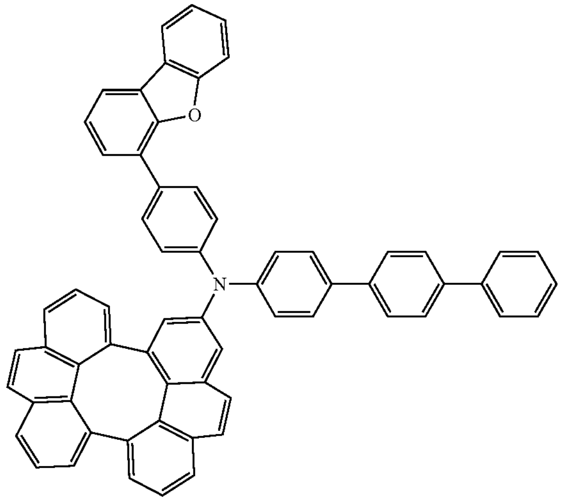
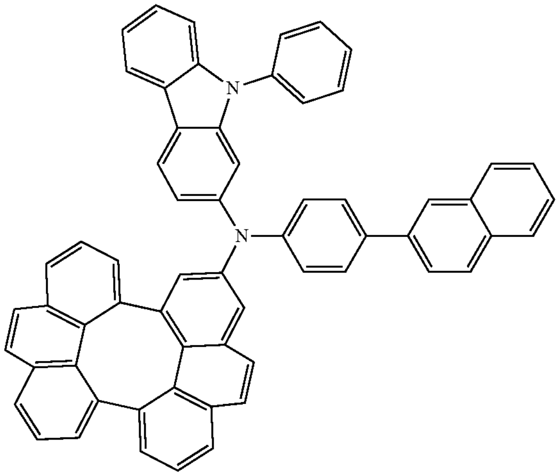
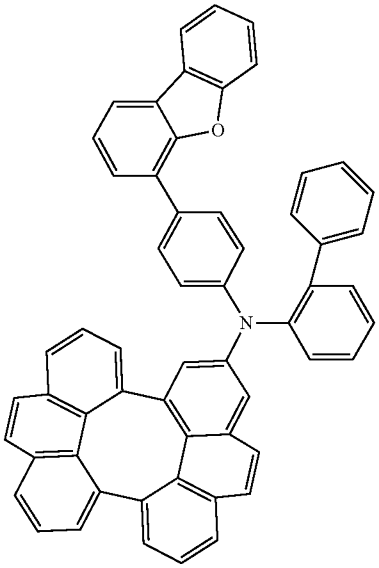
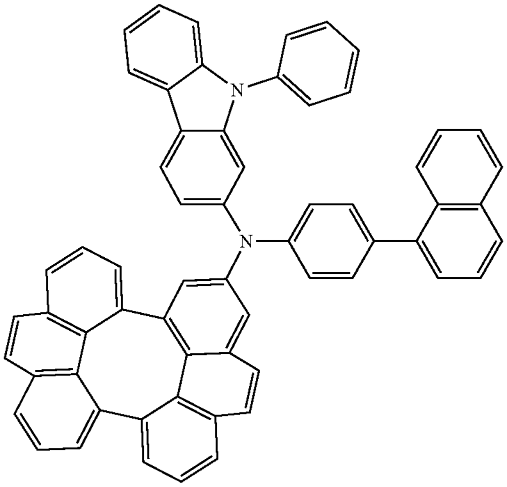

-continued
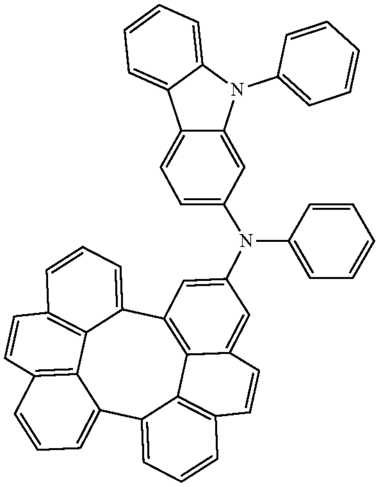
-continued
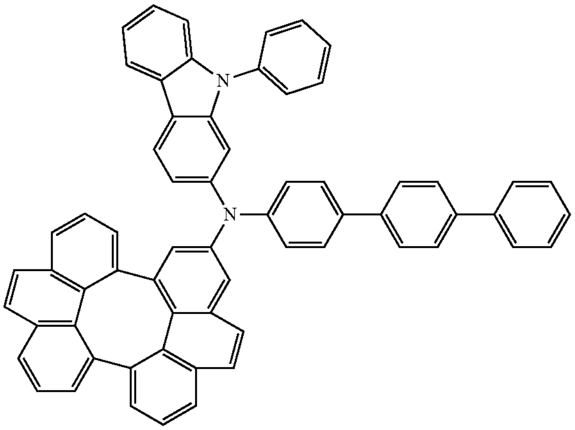
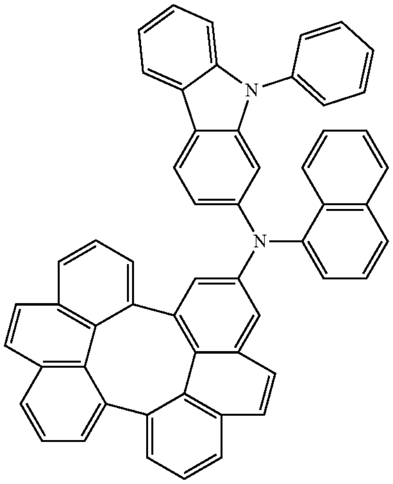
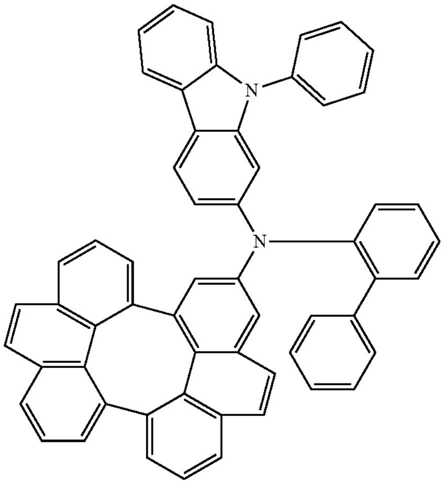
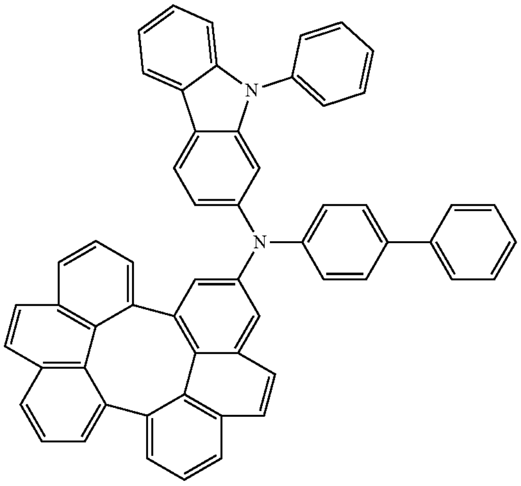
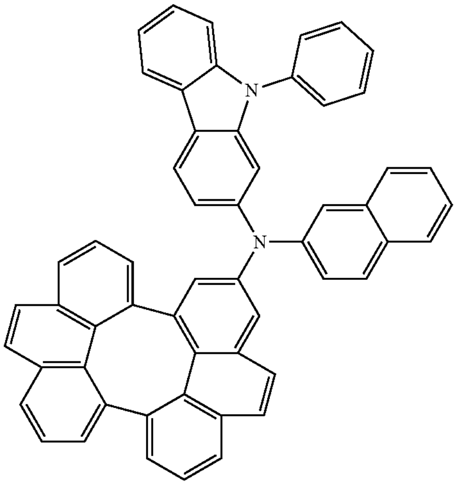

-continued
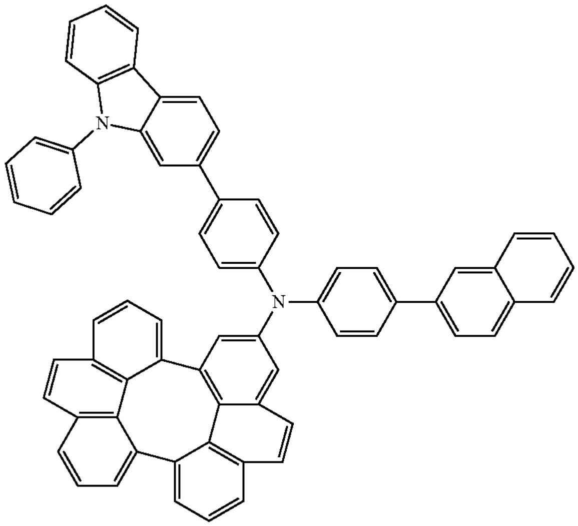
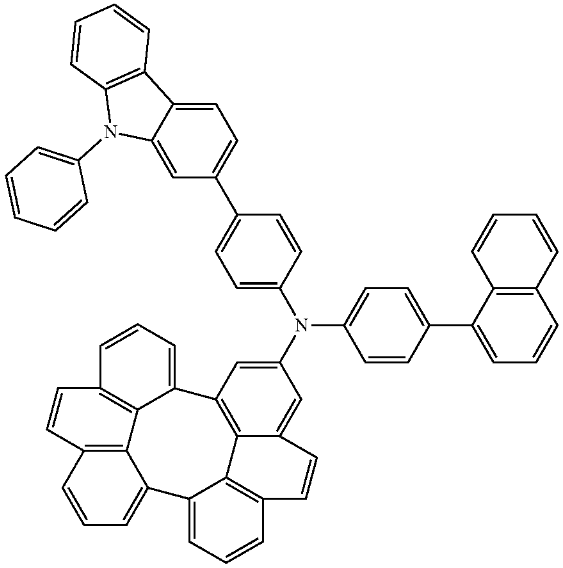
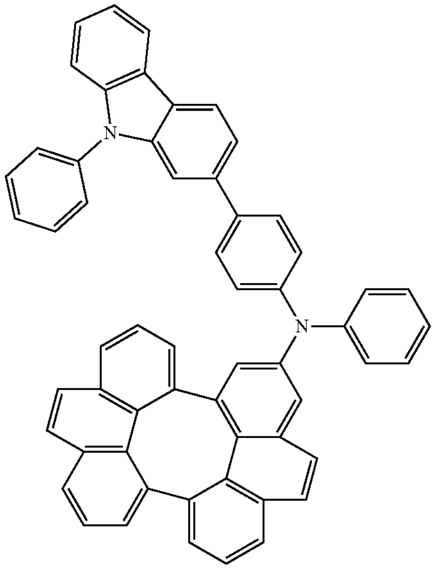
-continued
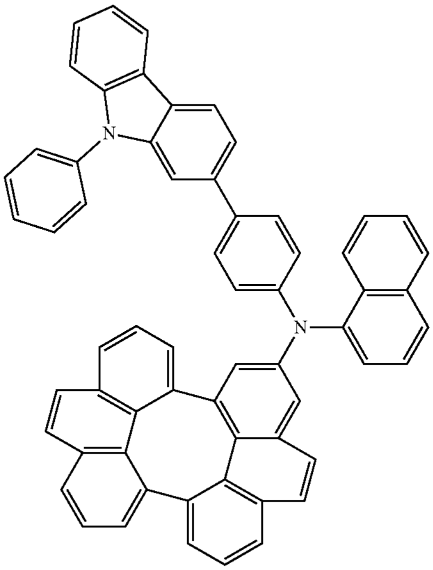
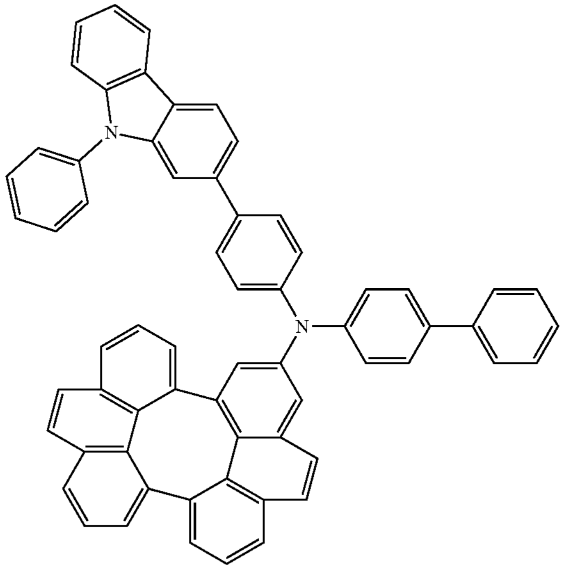
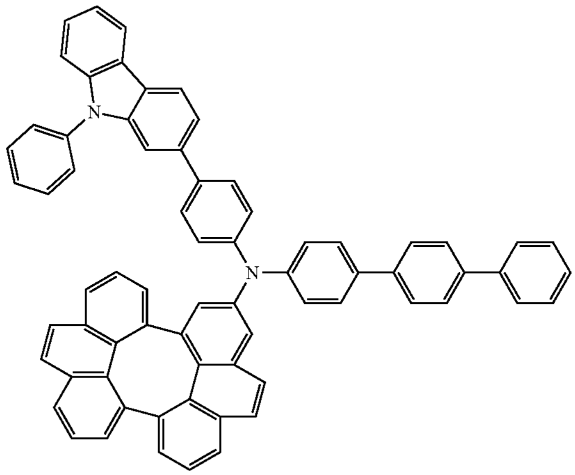

-continued
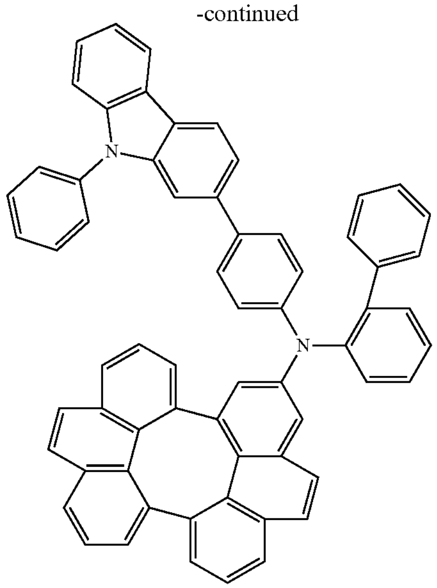
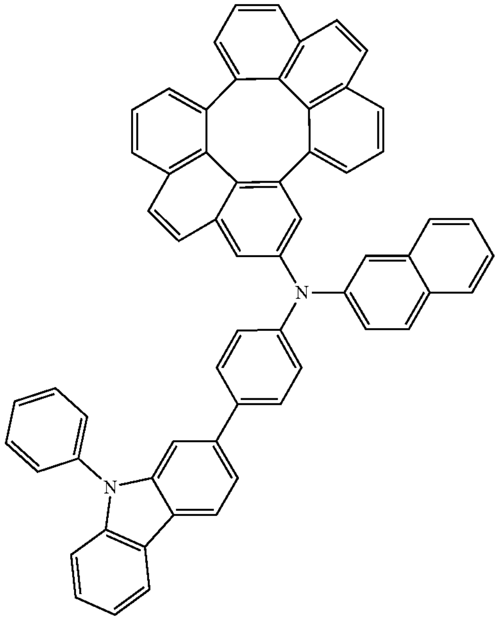
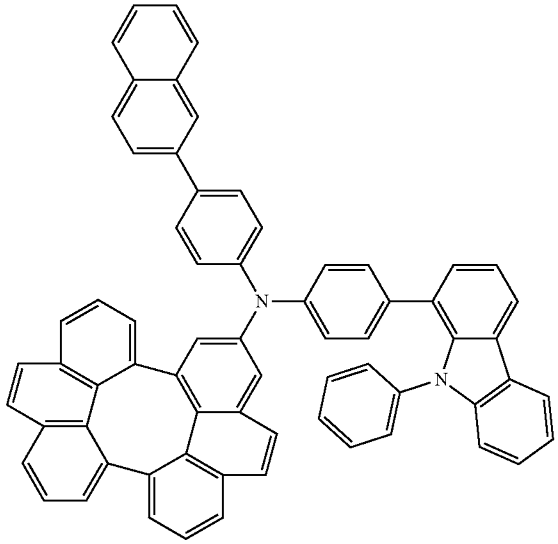
-continued
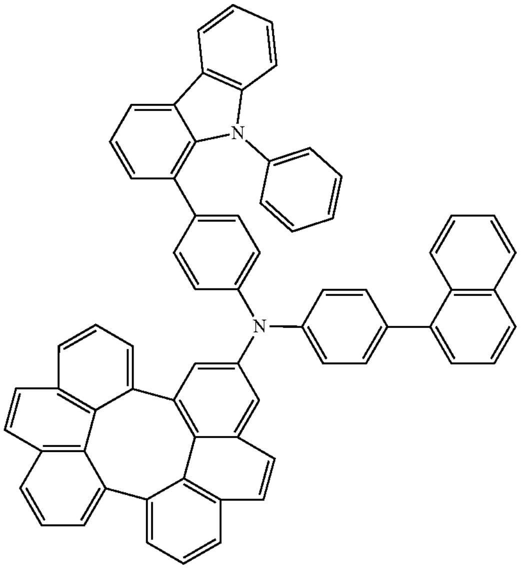
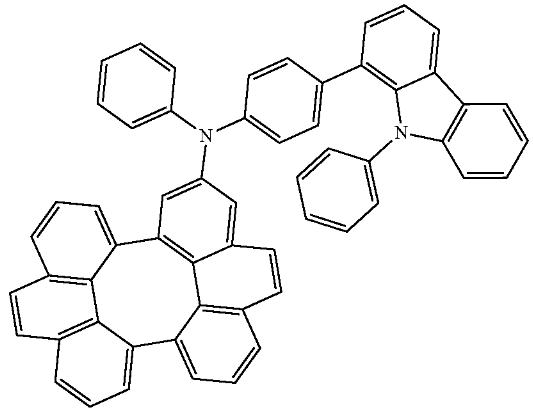
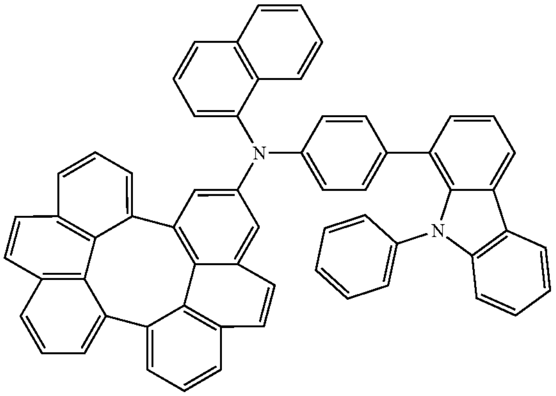

-continued
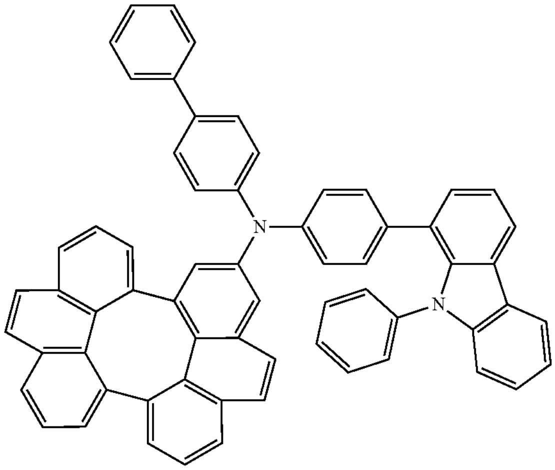
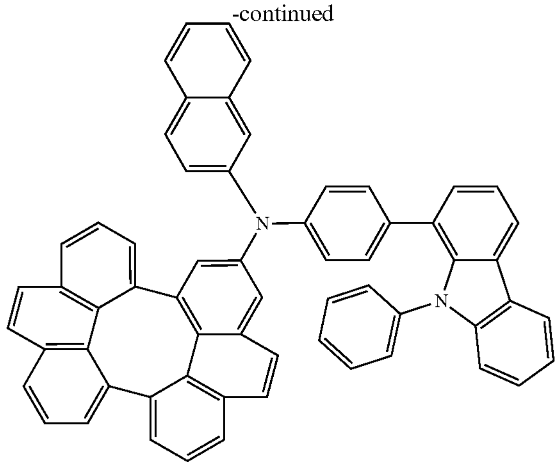
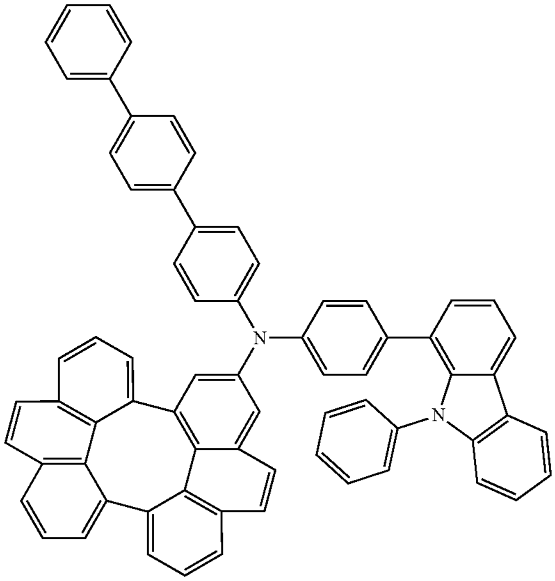
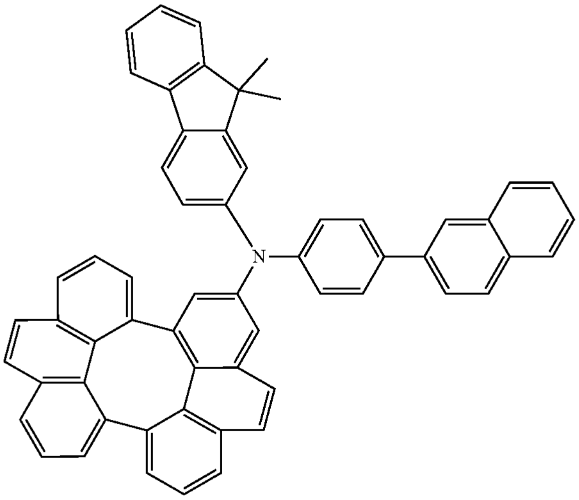
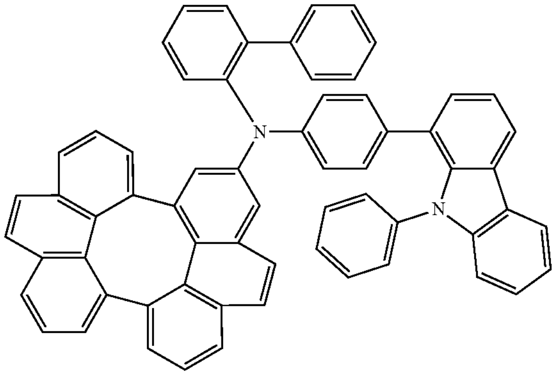
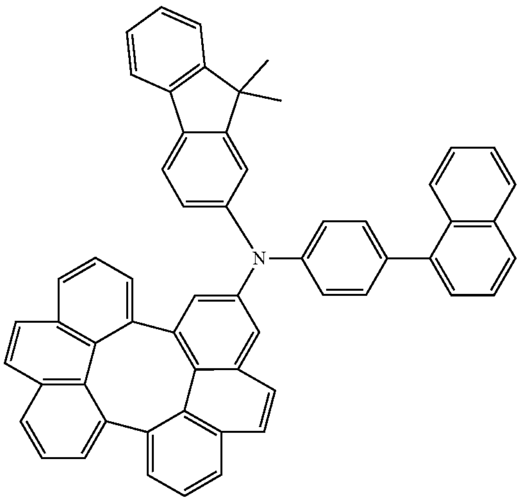
-continued -continued
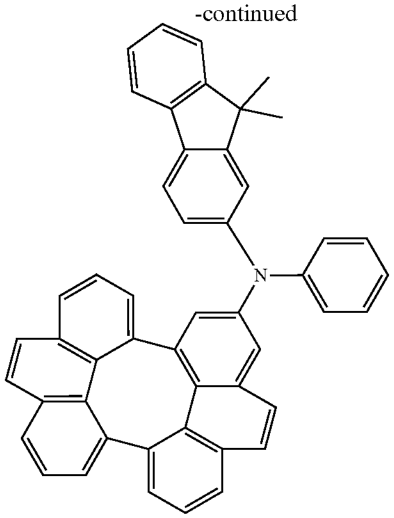
-continued
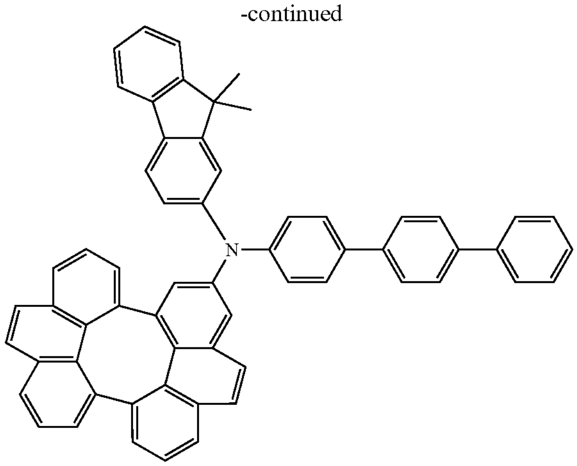
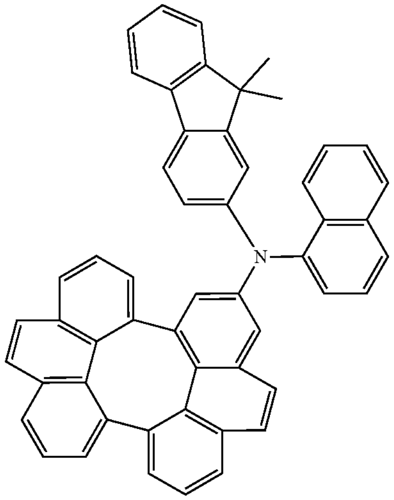
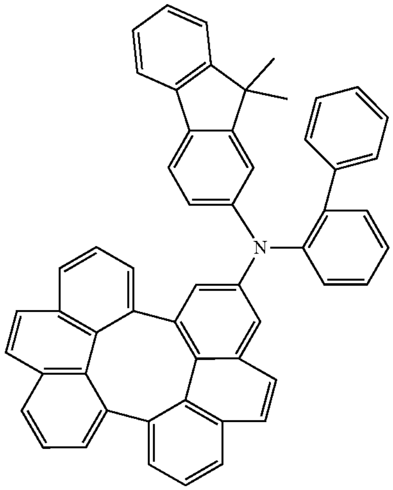
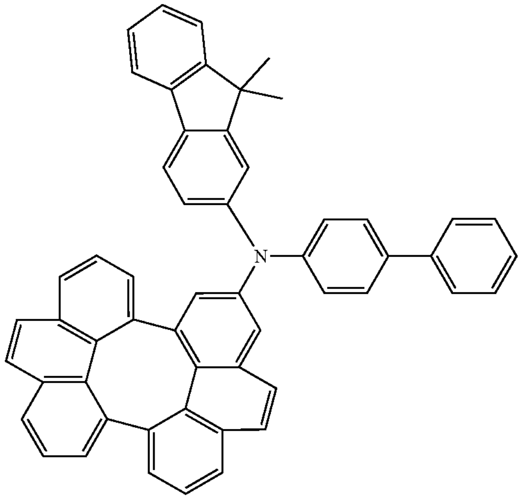
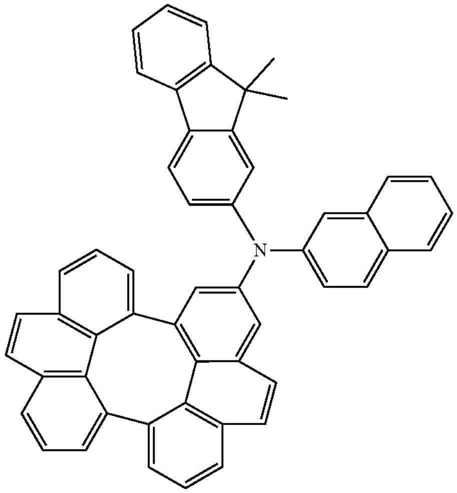

-continued
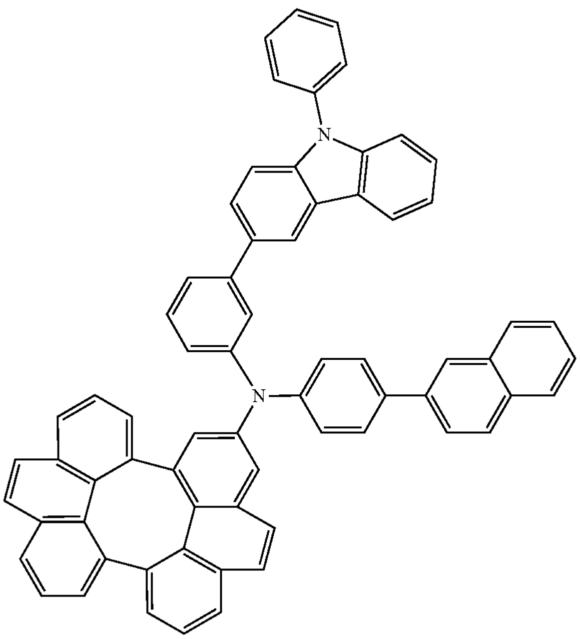
-continued
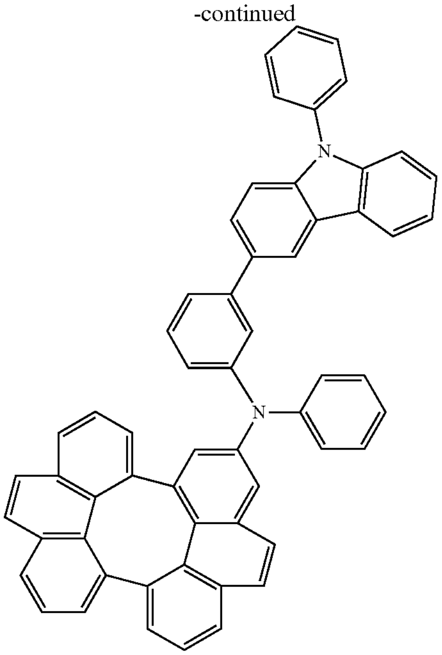
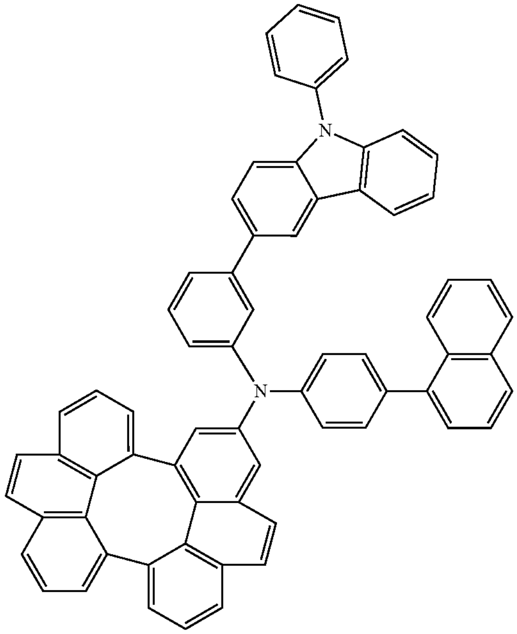
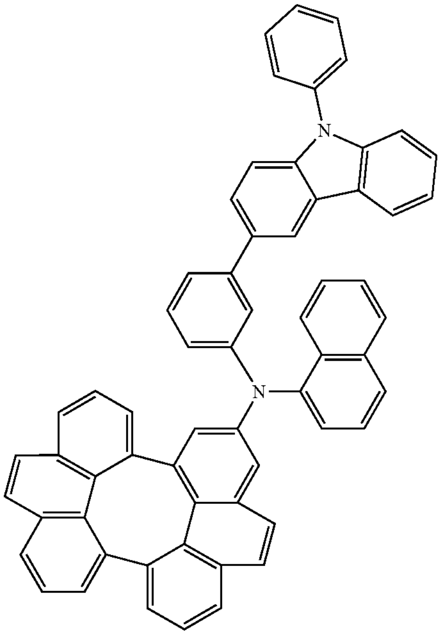

-continued
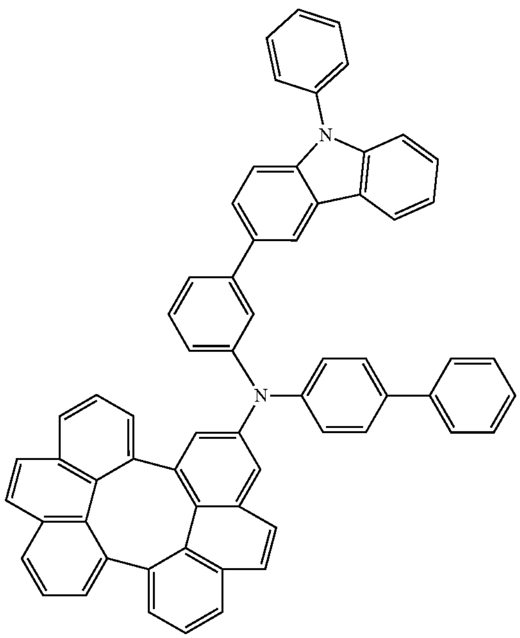
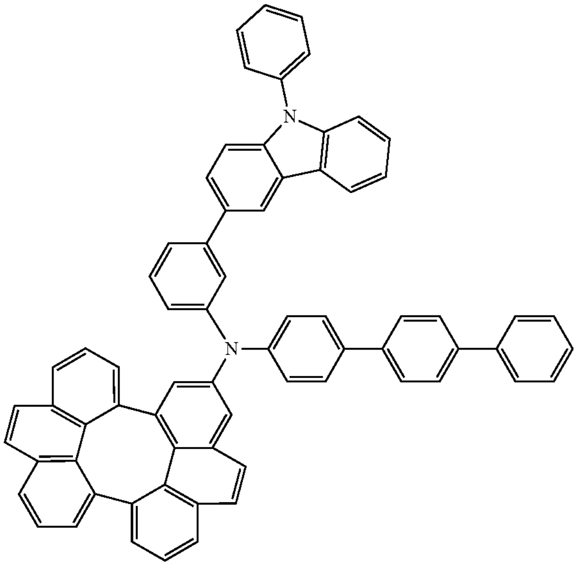
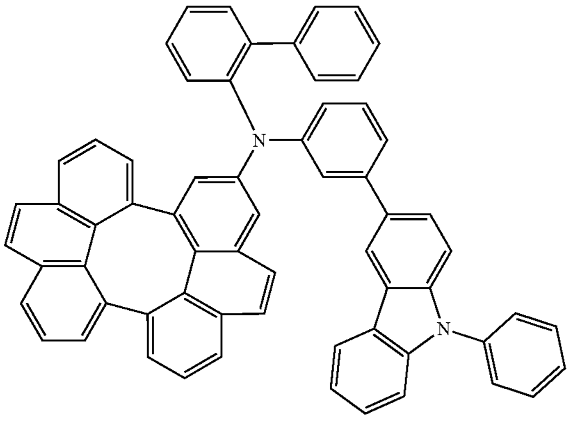
-continued
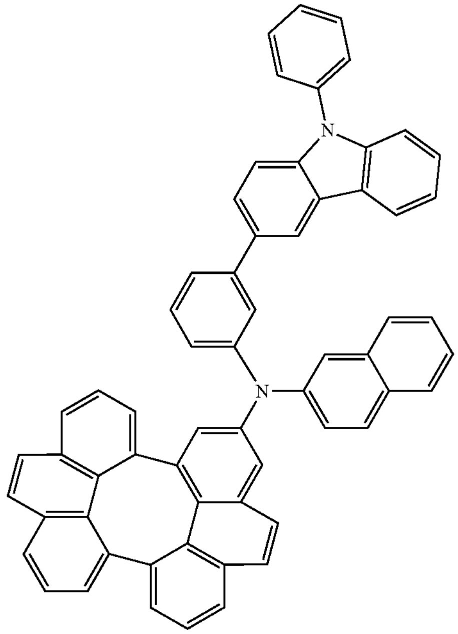
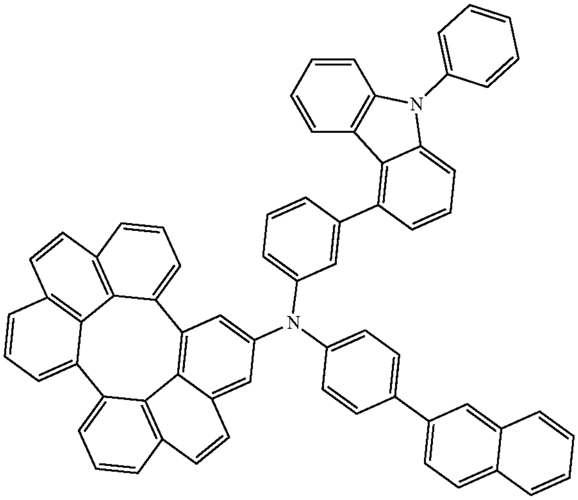
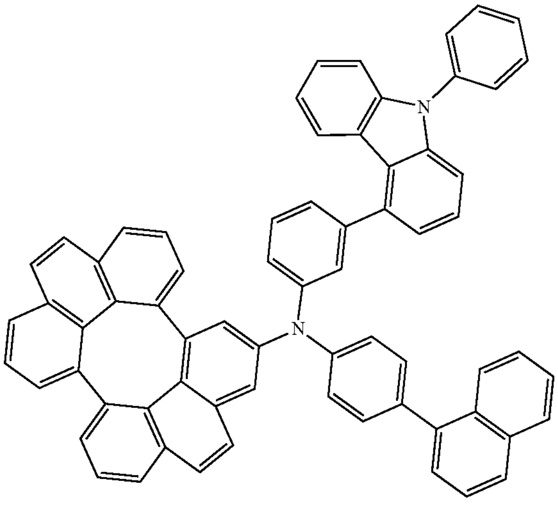

-continued
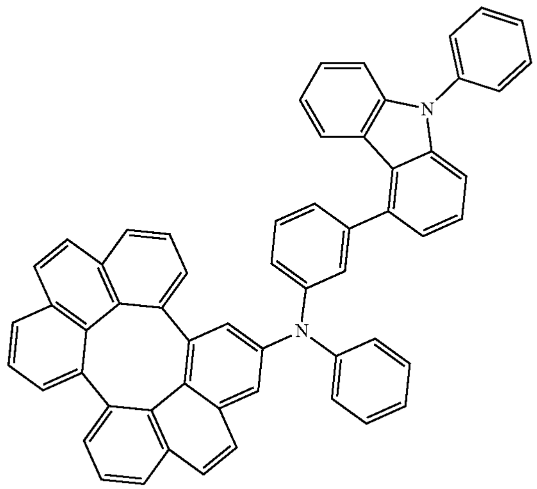
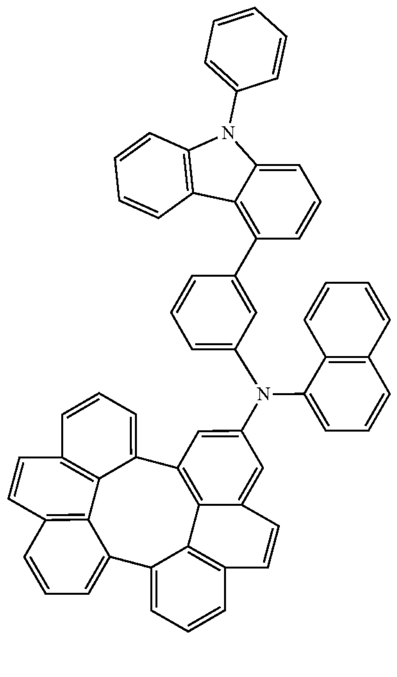
-continued
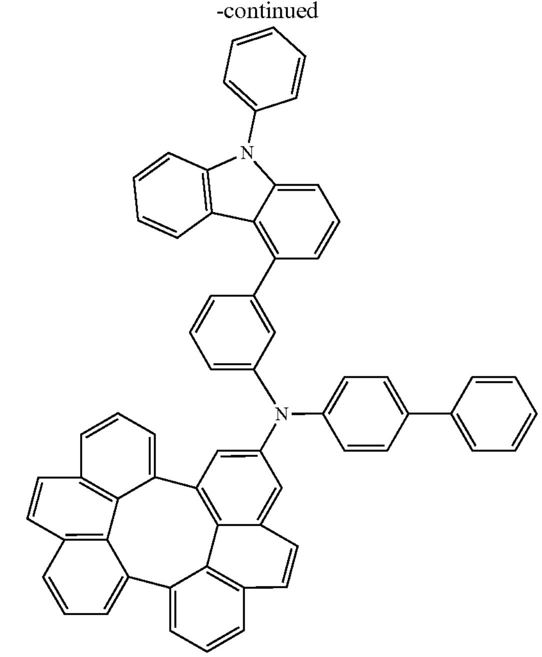
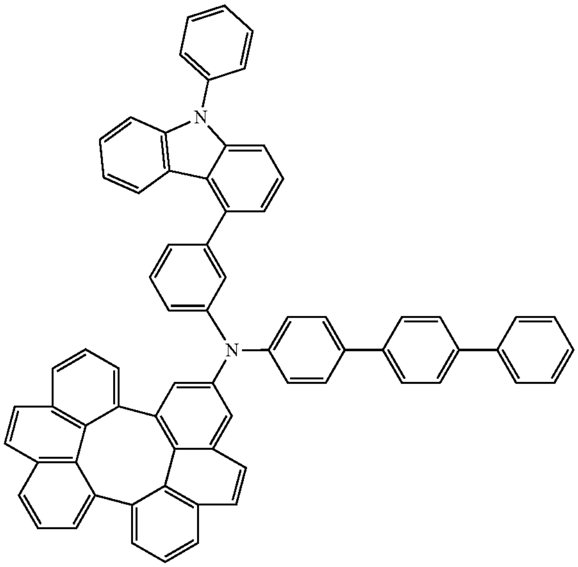
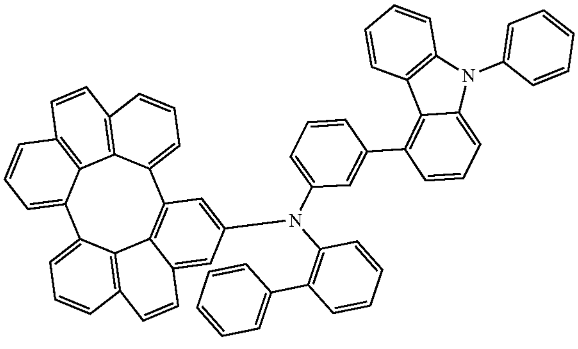

-continued
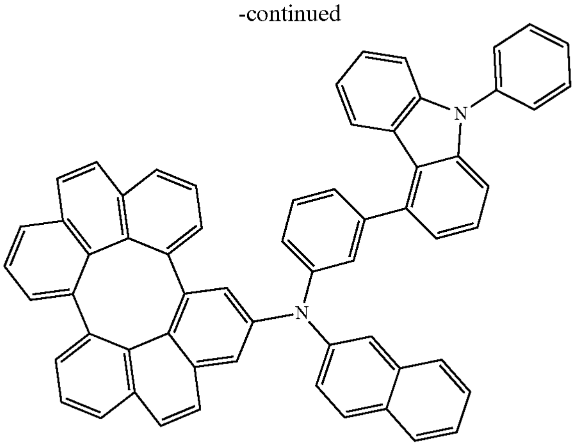
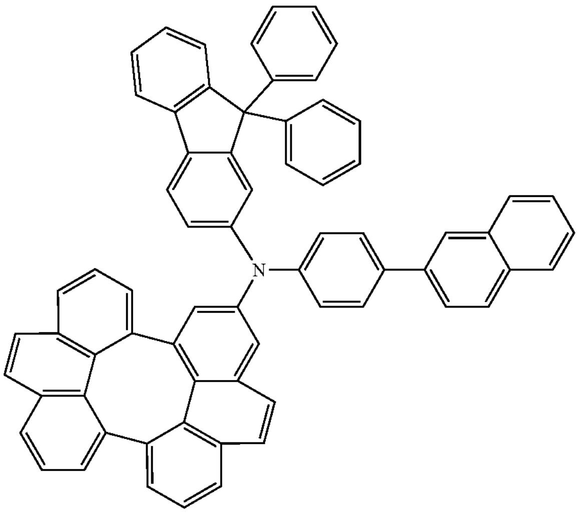
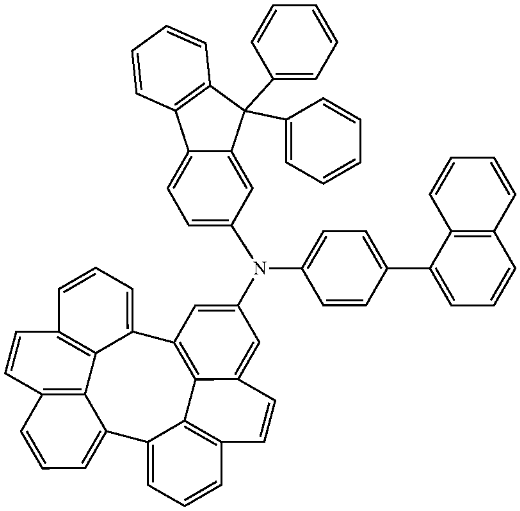
-continued
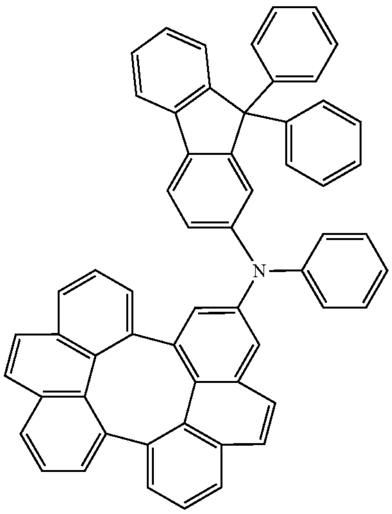
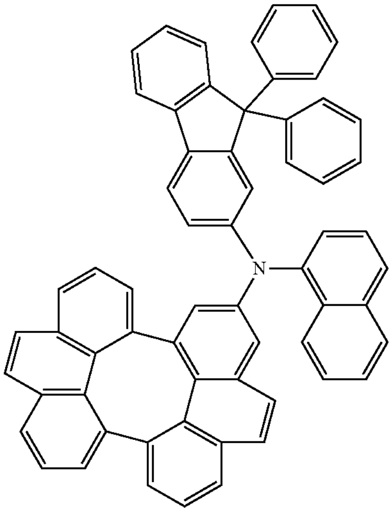
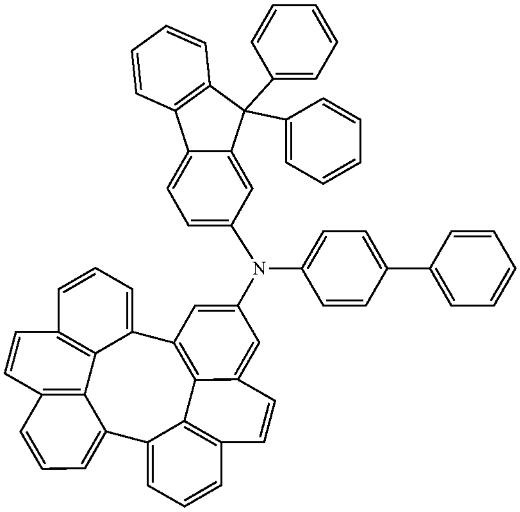

-continued
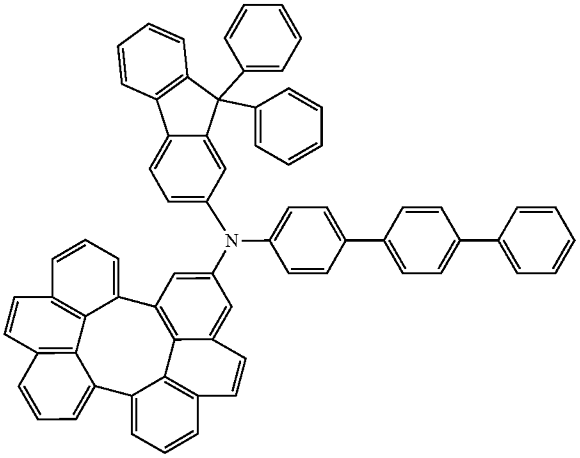
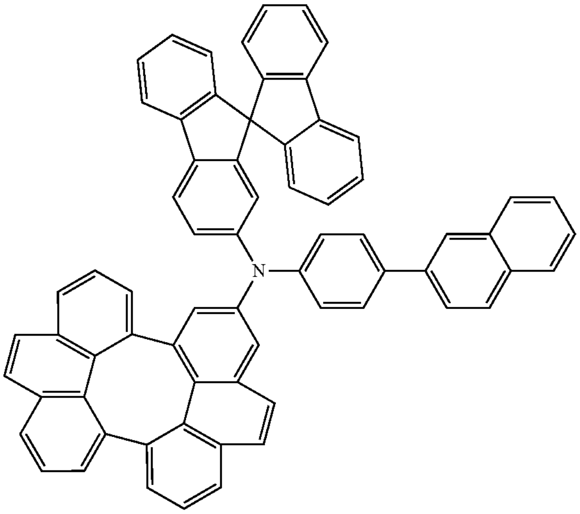
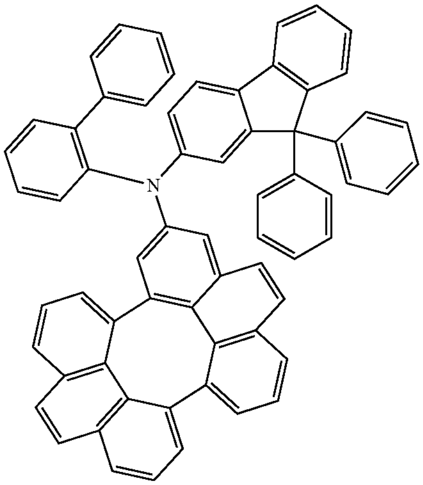
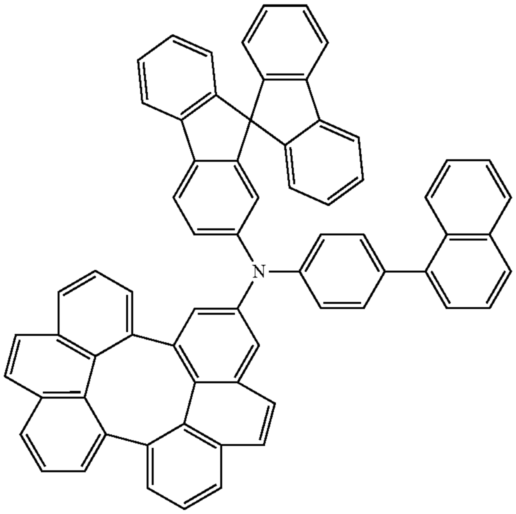
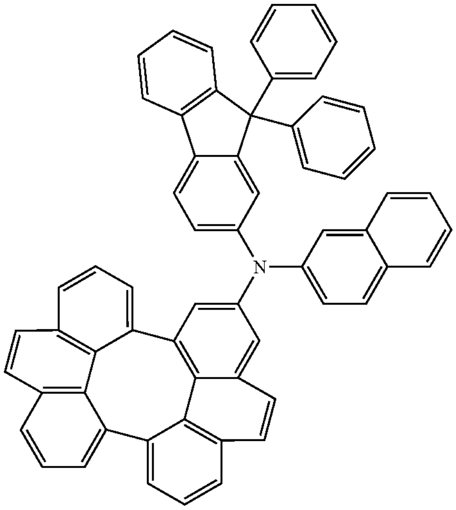
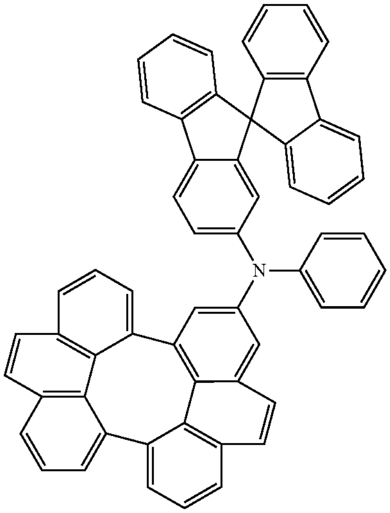

-continued
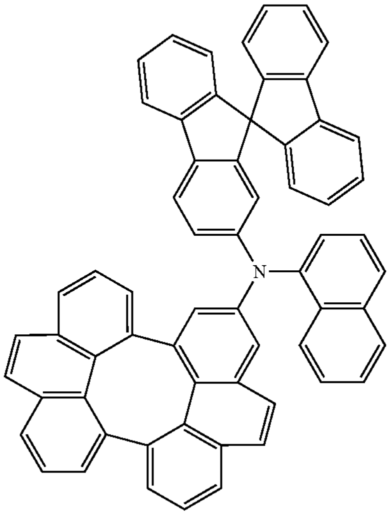
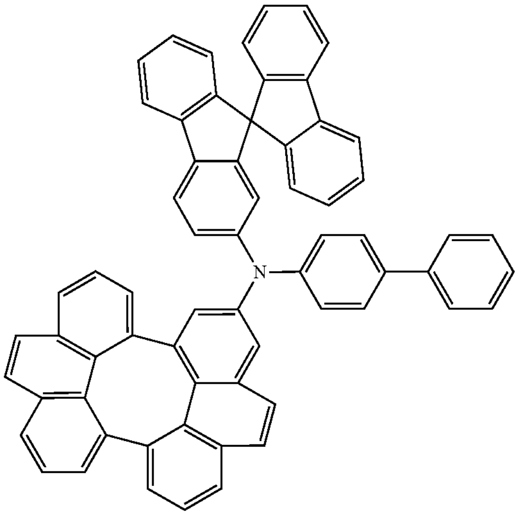
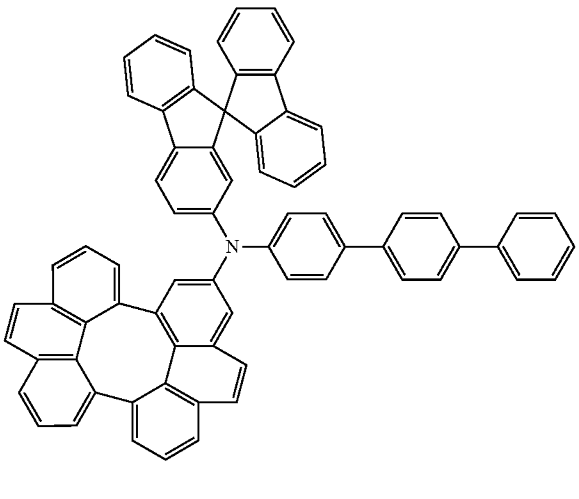
-continued
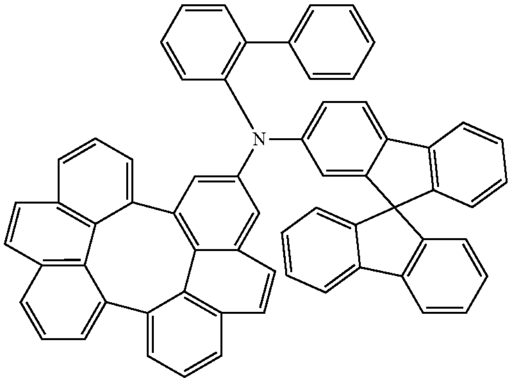
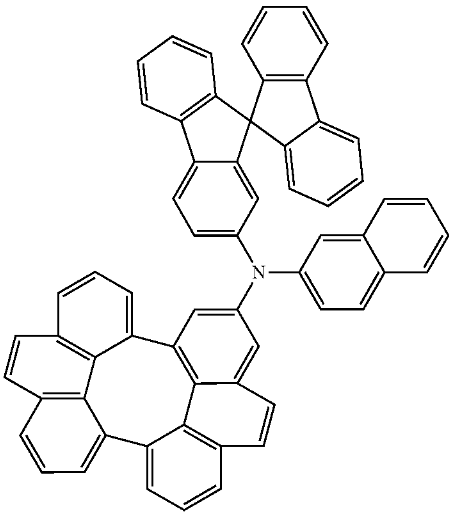
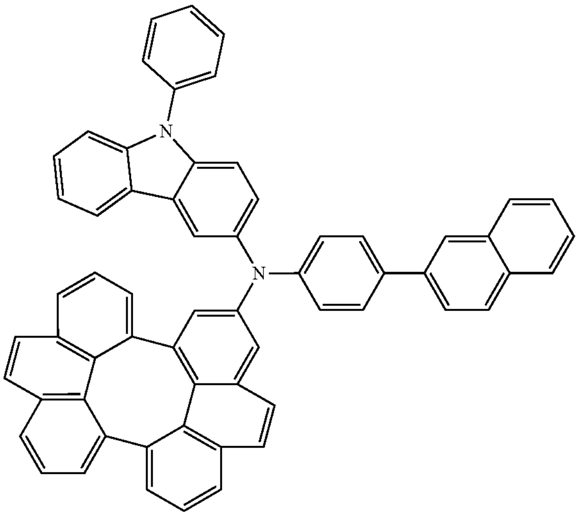

-continued
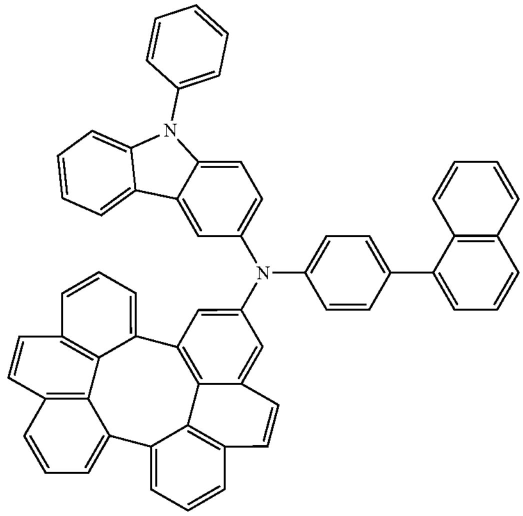
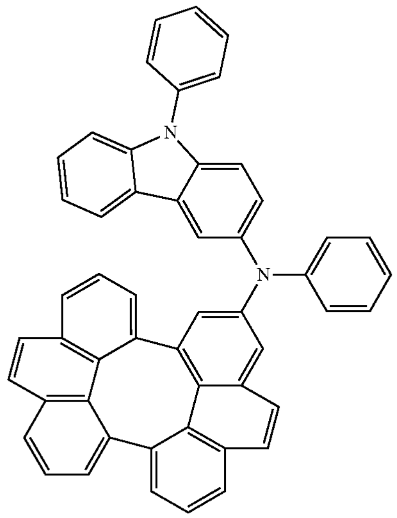
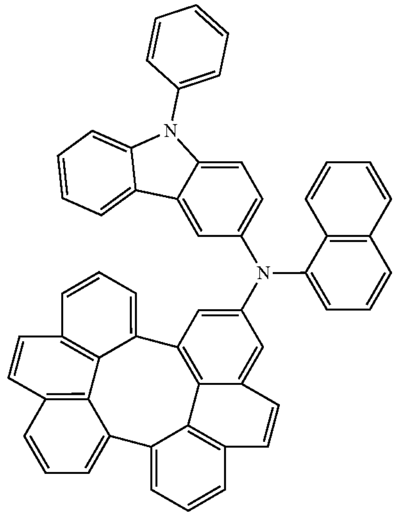
-continued
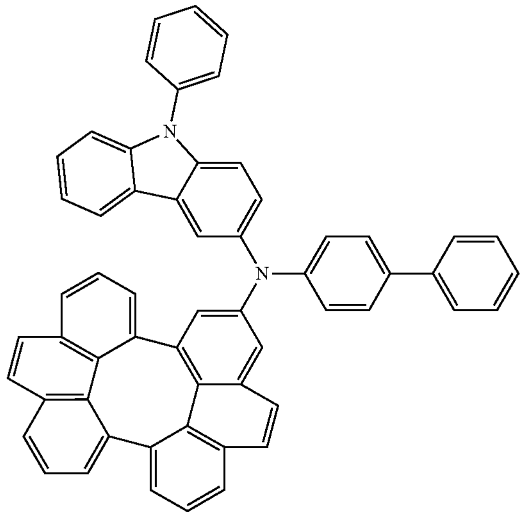
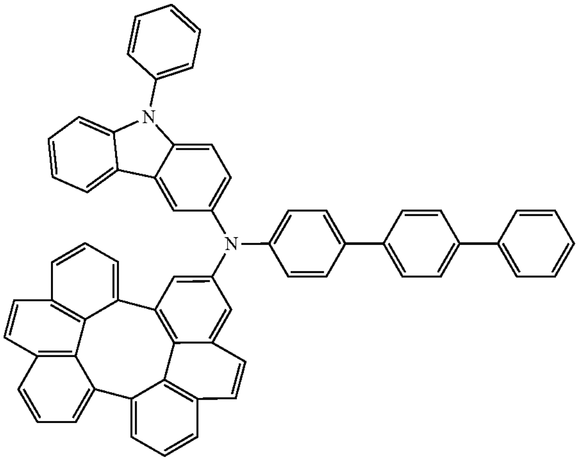
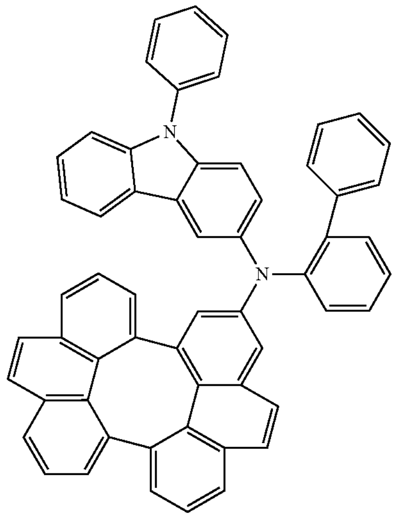

-continued
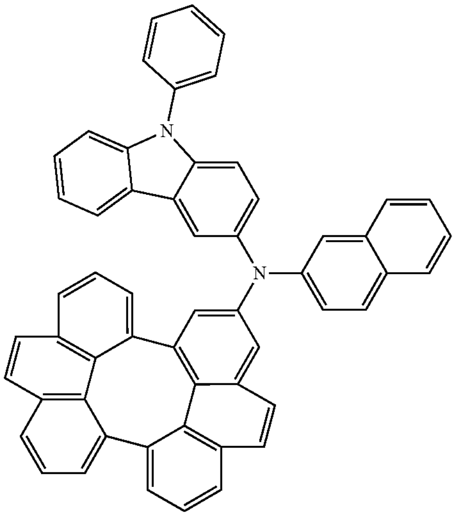
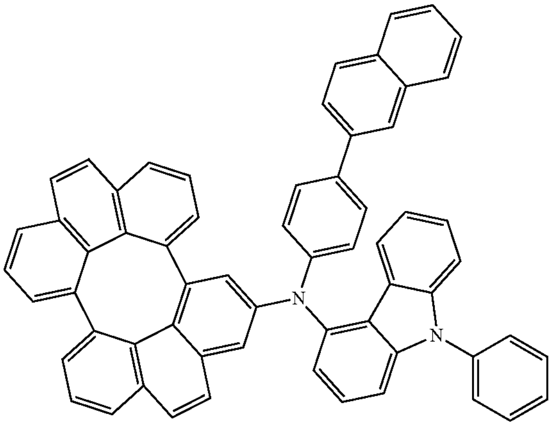
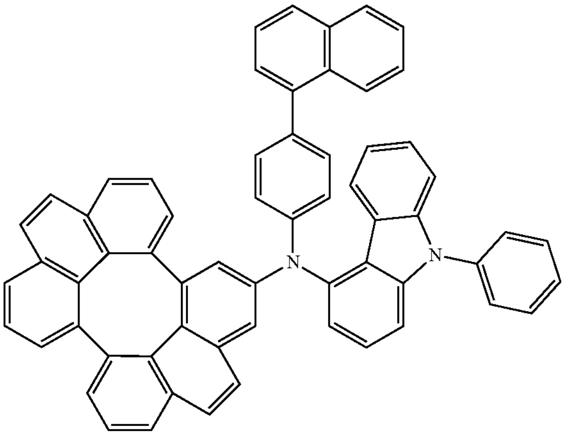
-continued
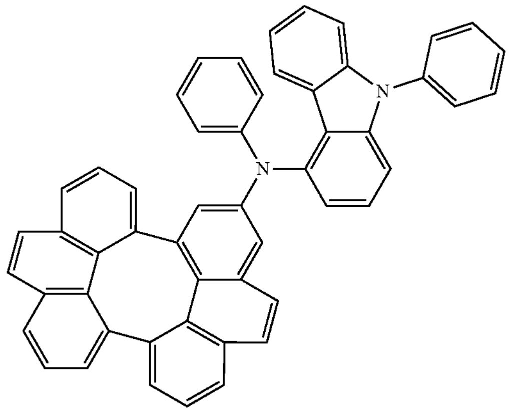
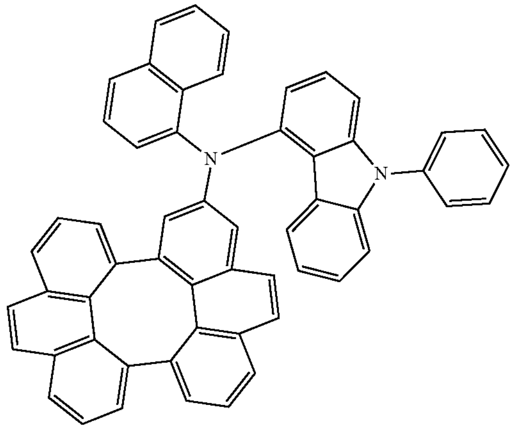
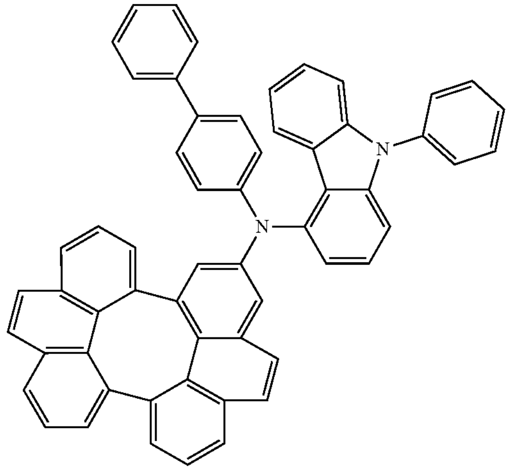

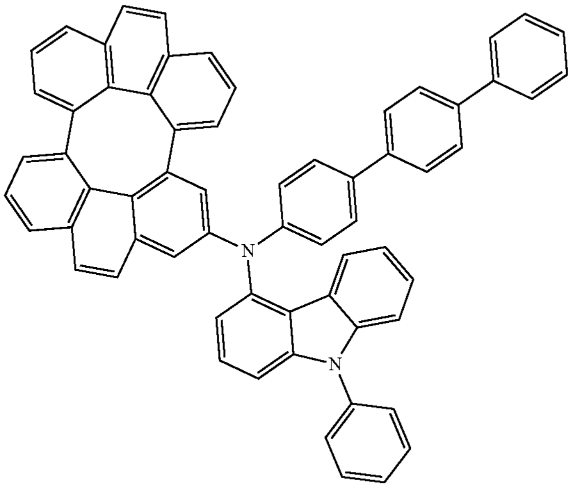
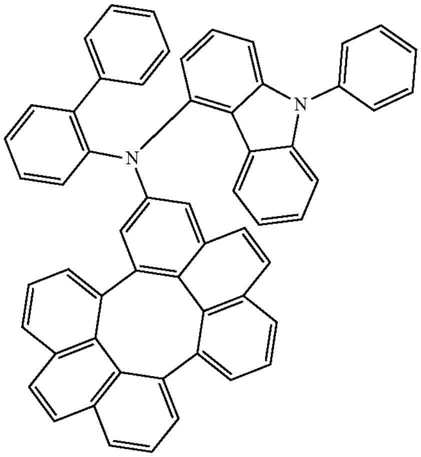
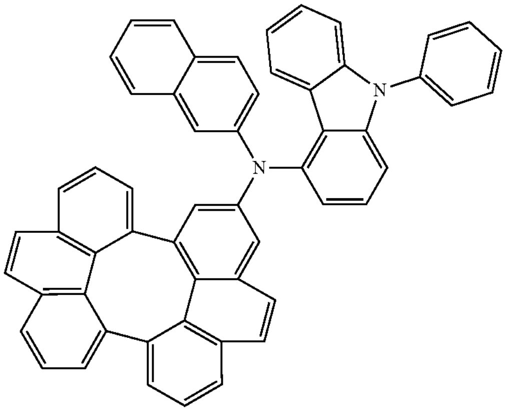
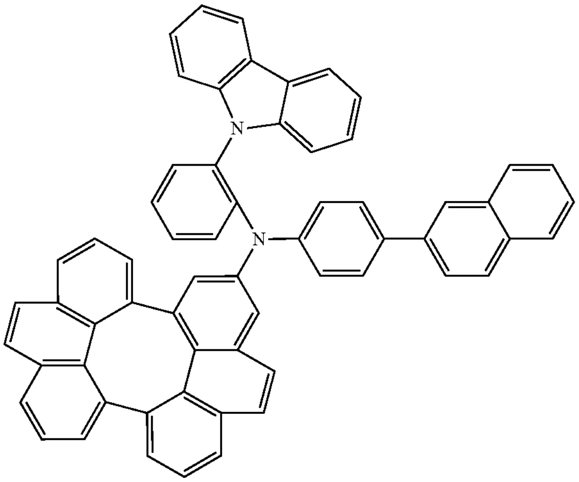
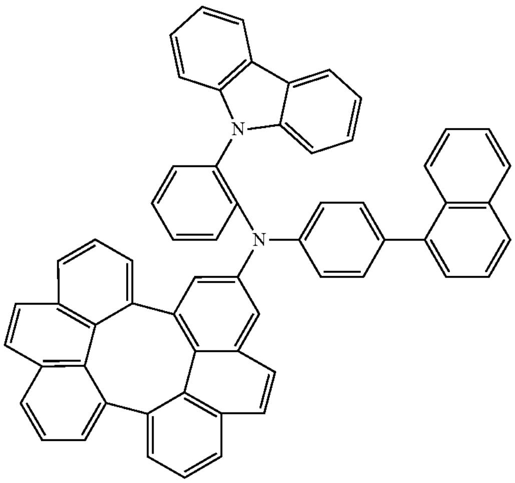
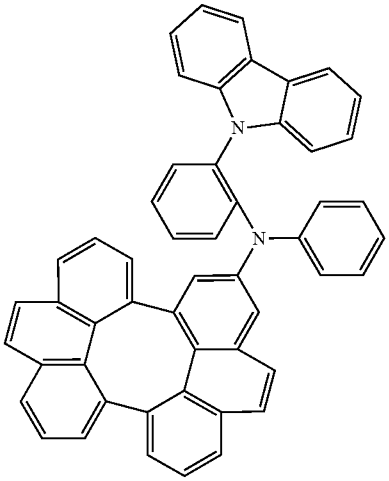

-continued
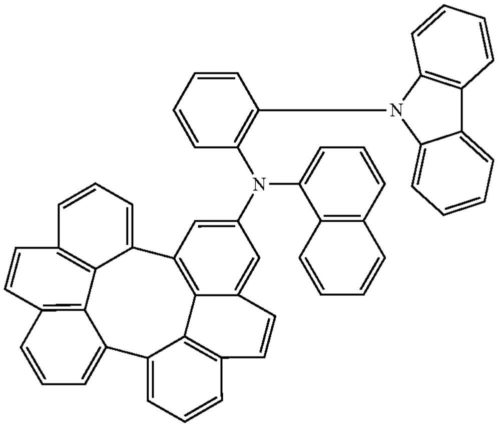
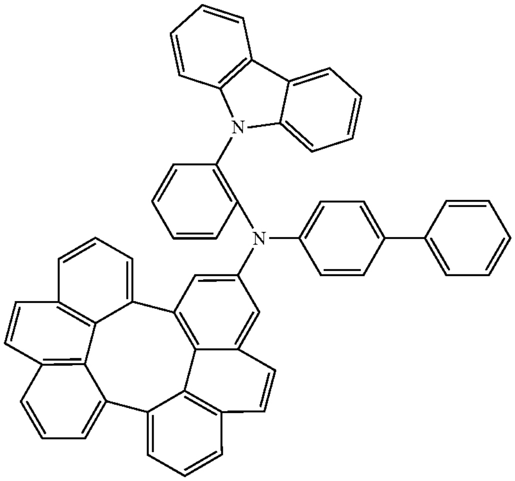
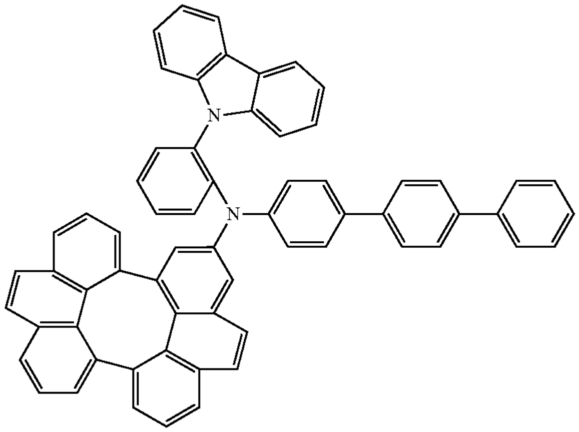
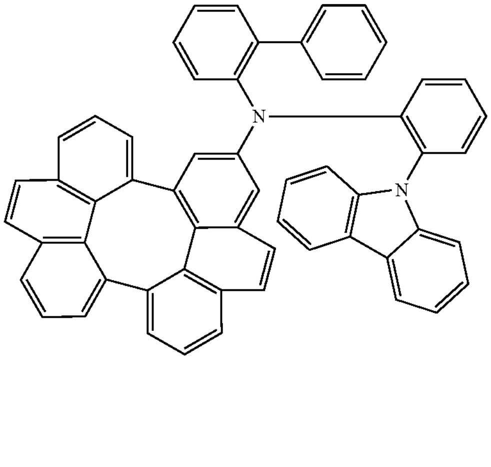
-continued
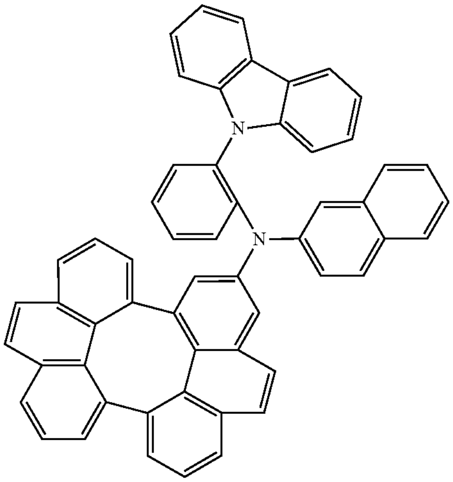
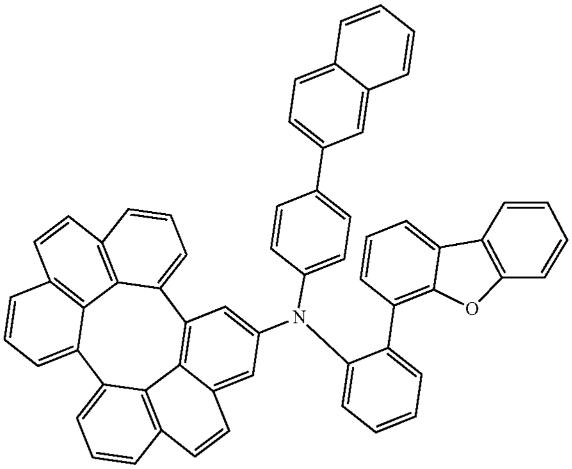
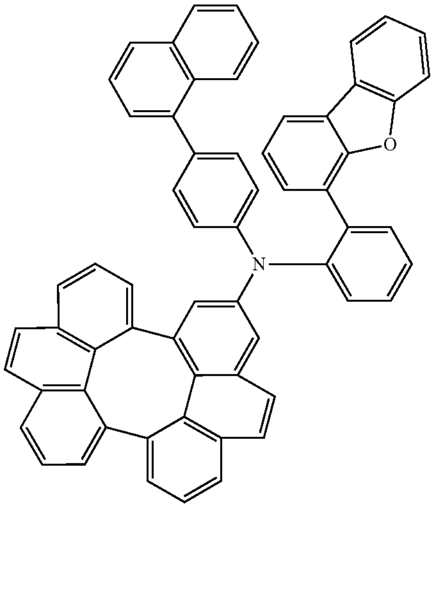

-continued
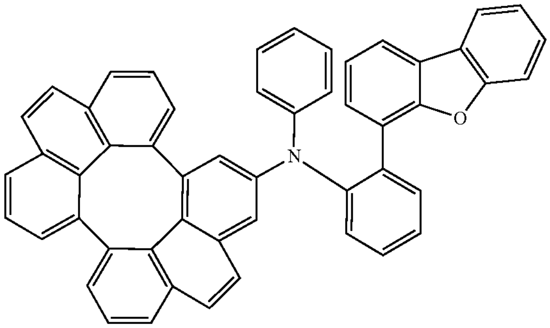
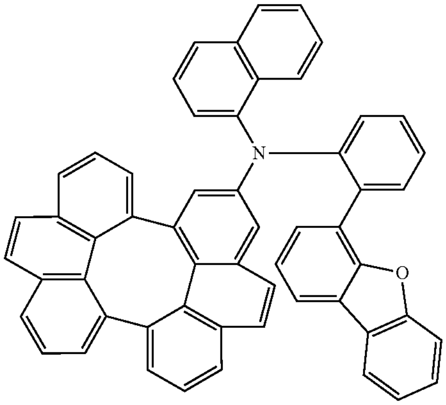
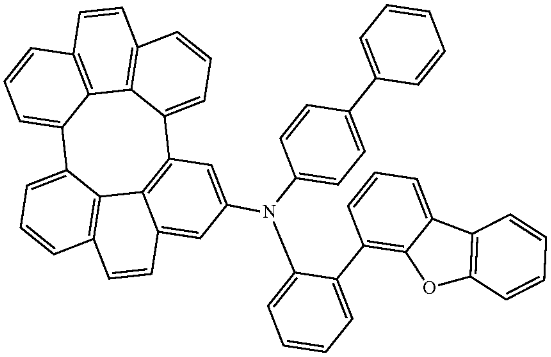
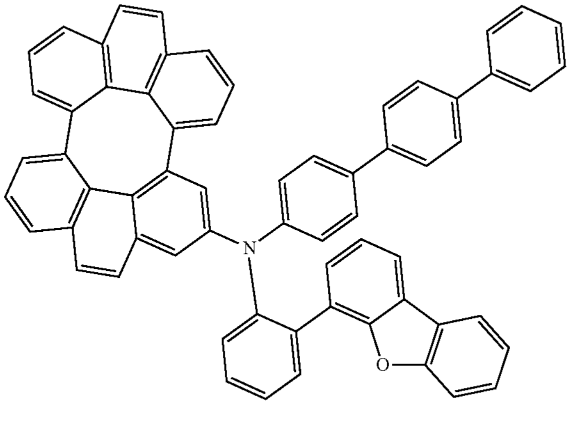
-continued
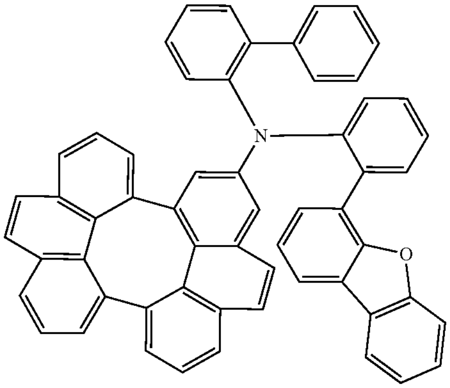
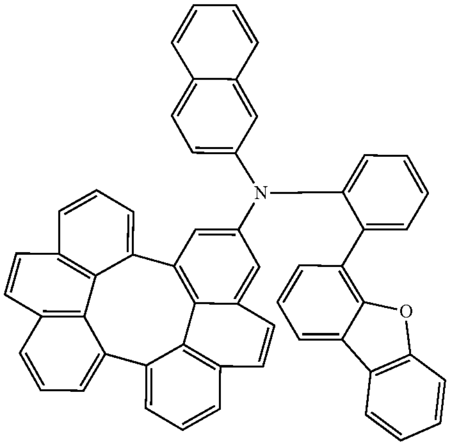
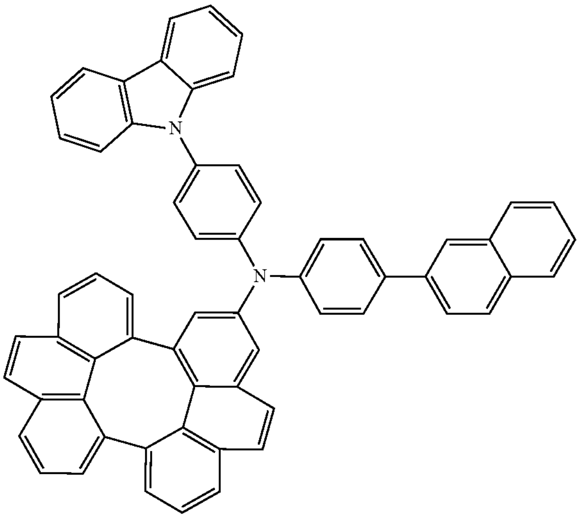

-continued
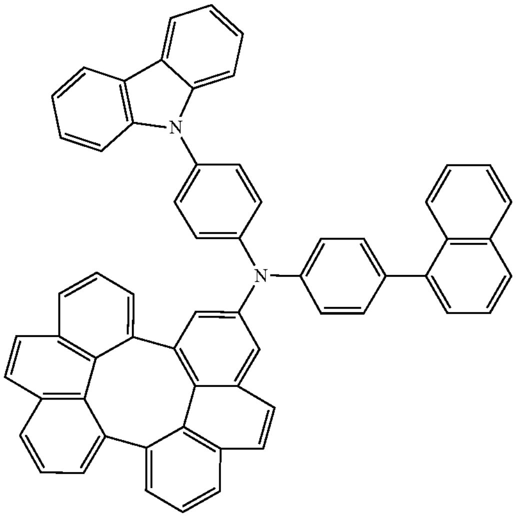
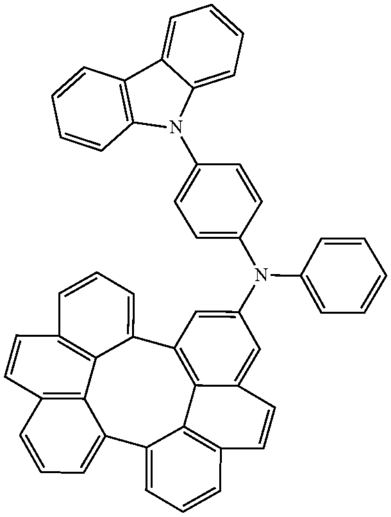
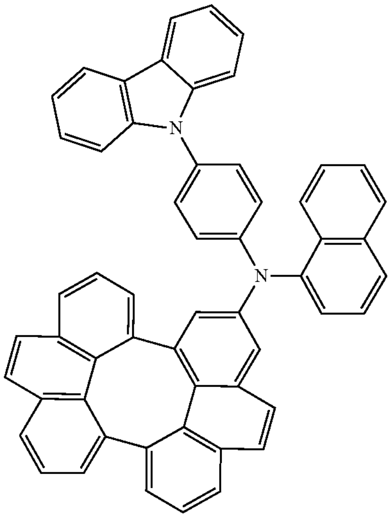
-continued
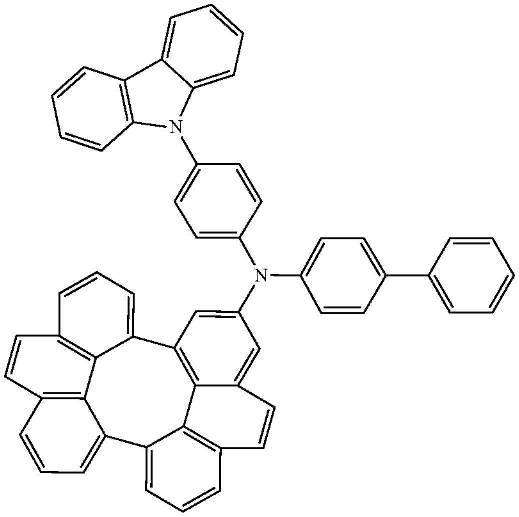
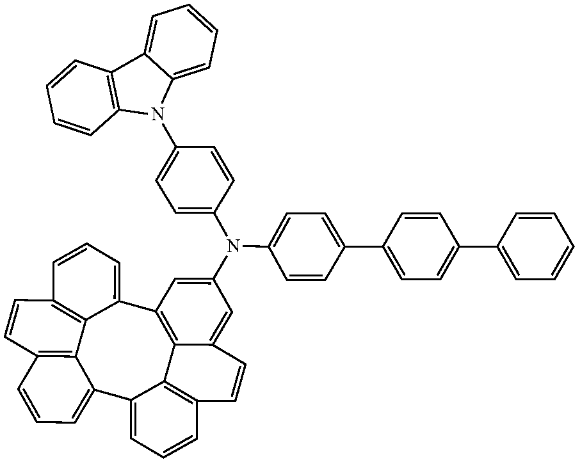
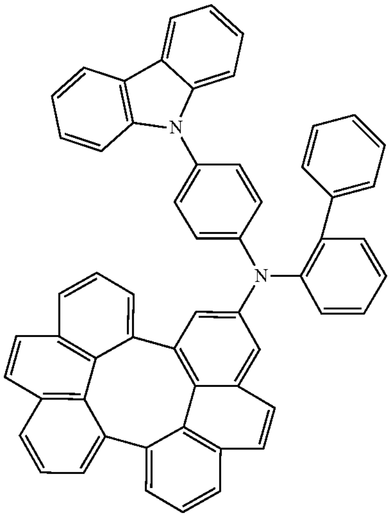

-continued
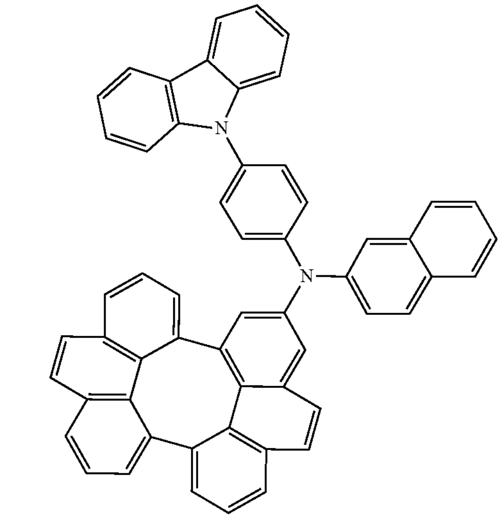
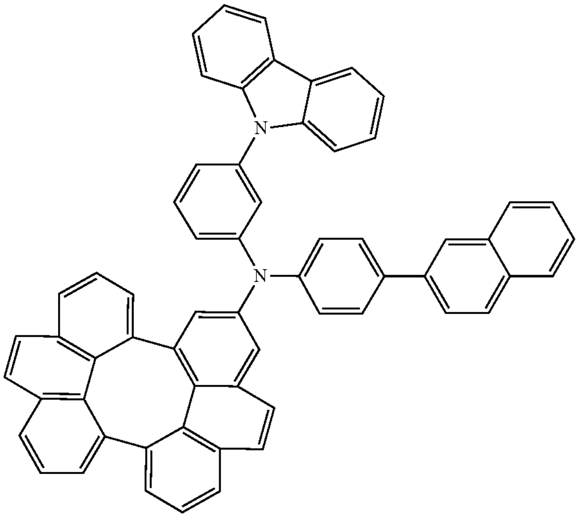
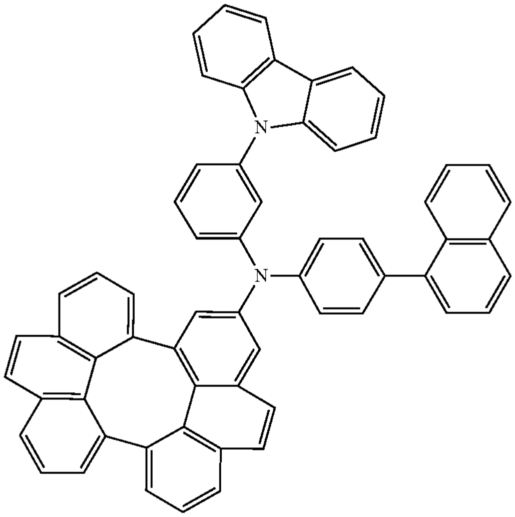
-continued
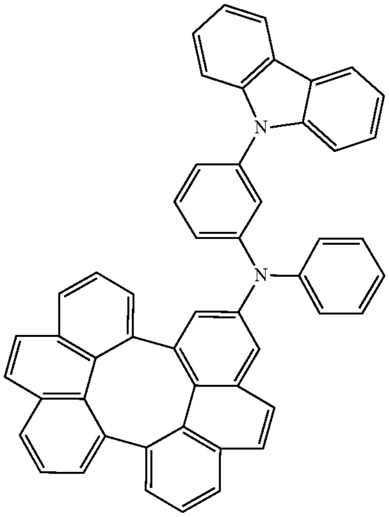
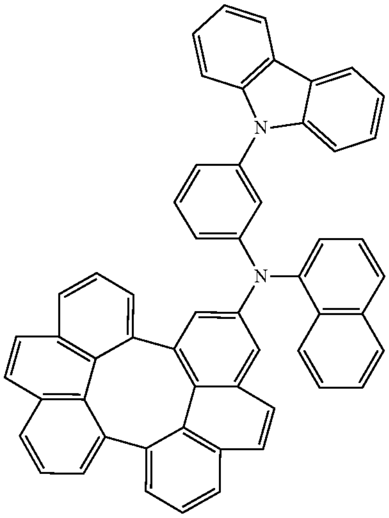
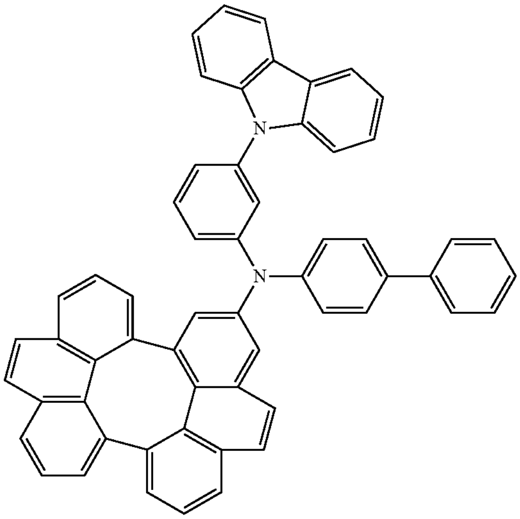

-continued
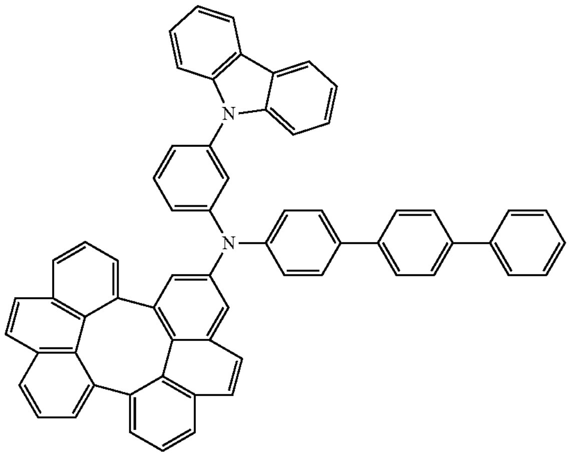
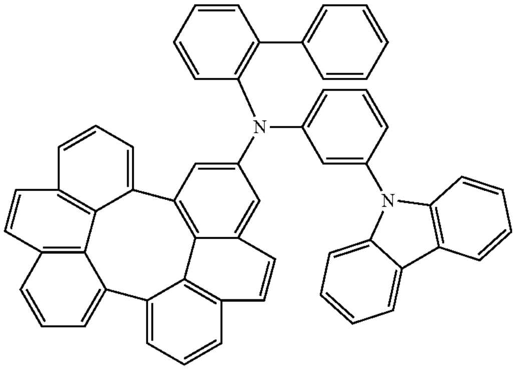
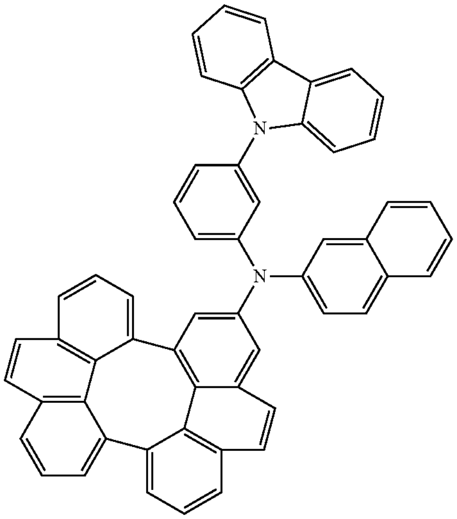
-continued
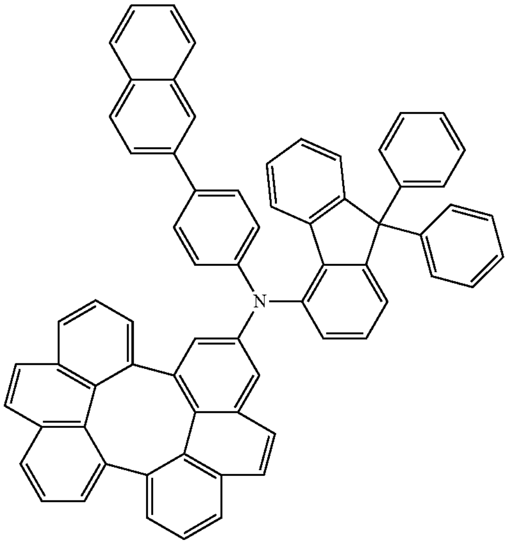
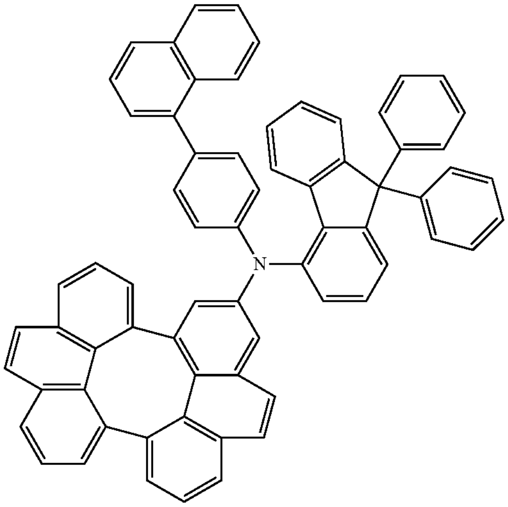
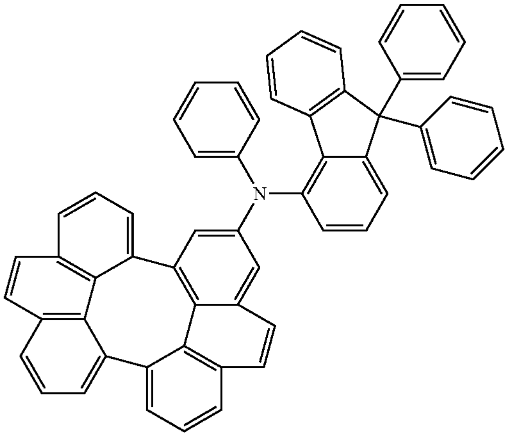

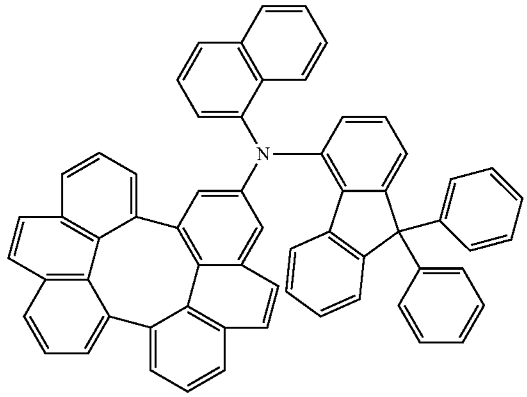
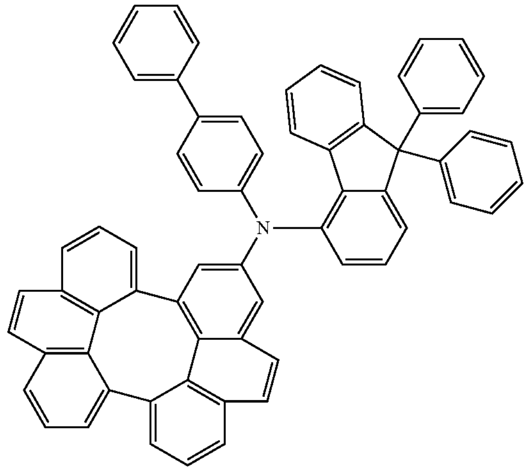
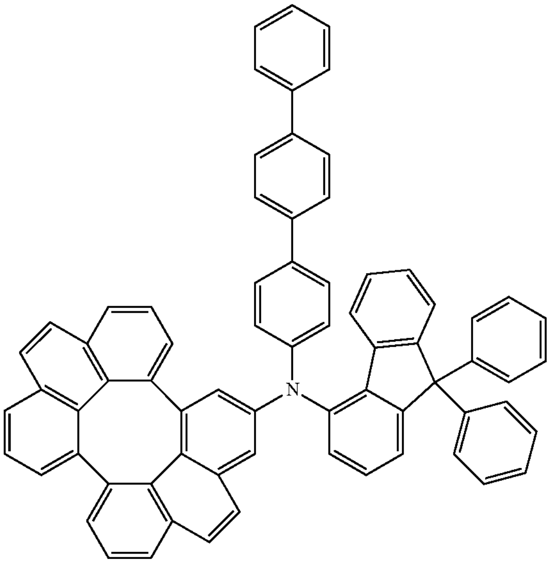
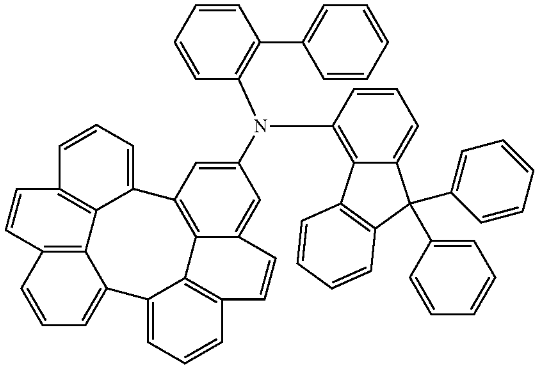
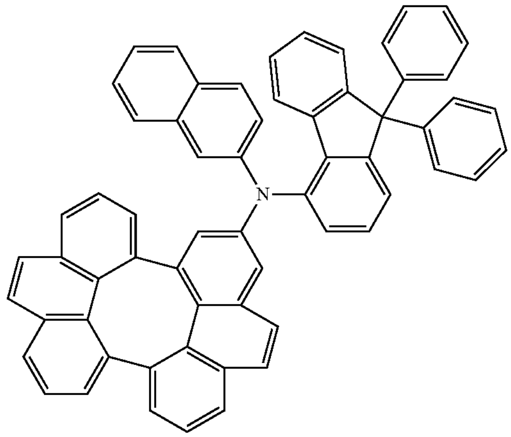
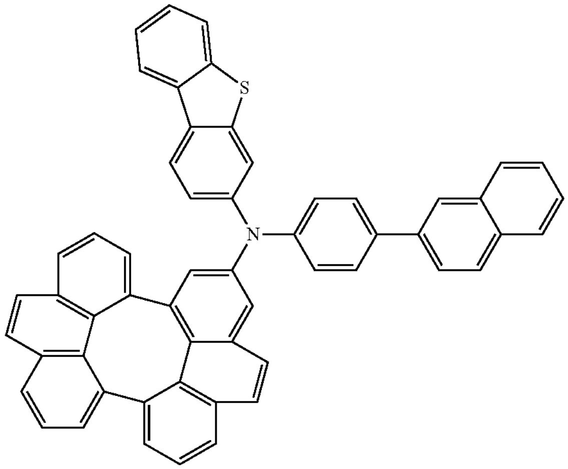

-continued
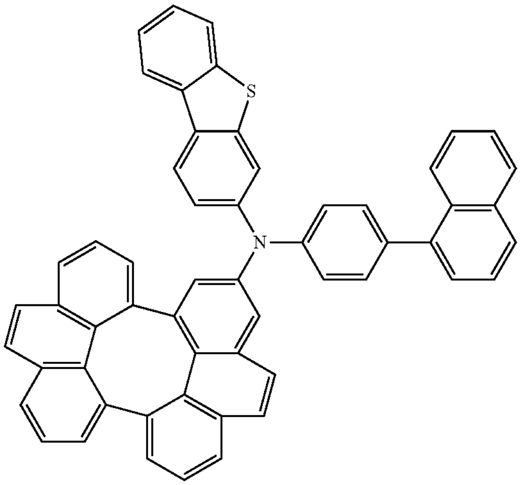
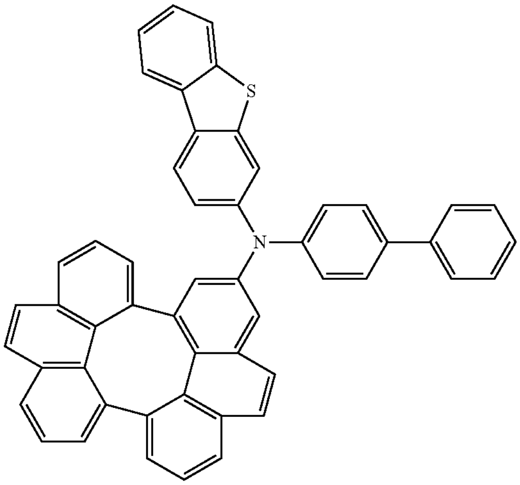
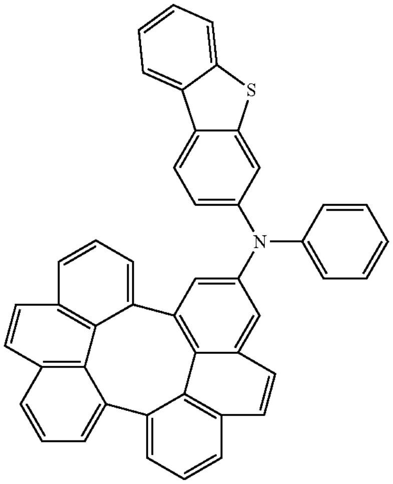
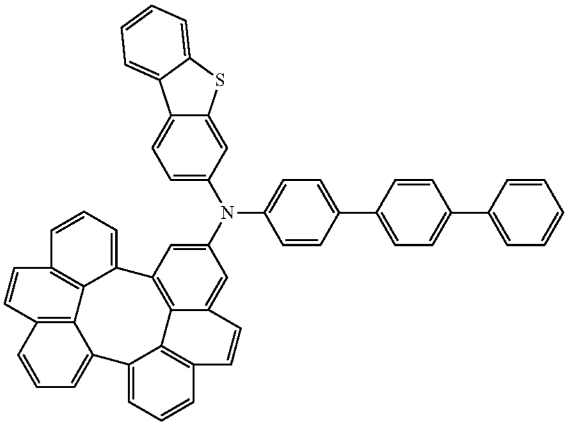
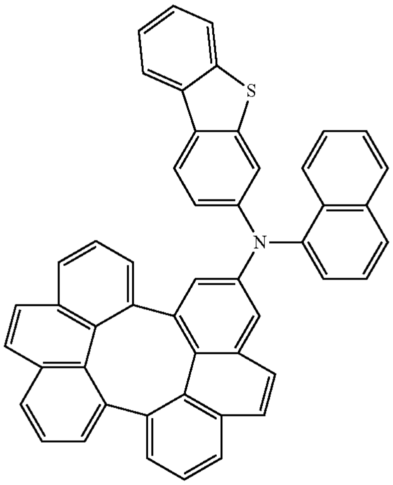
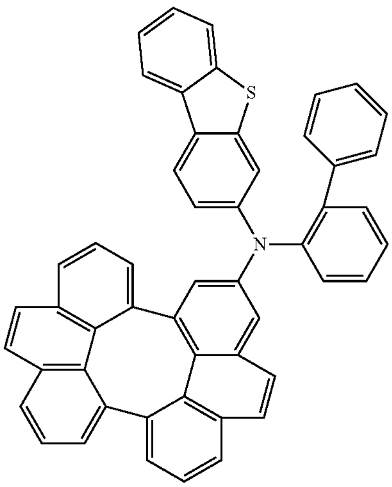
-continued -continued
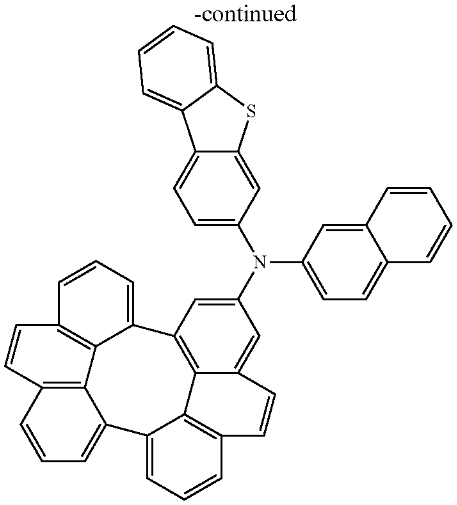
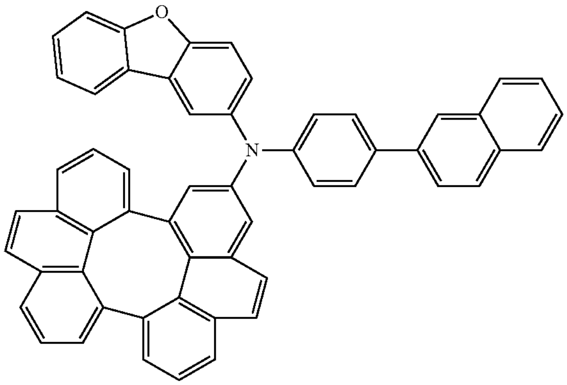
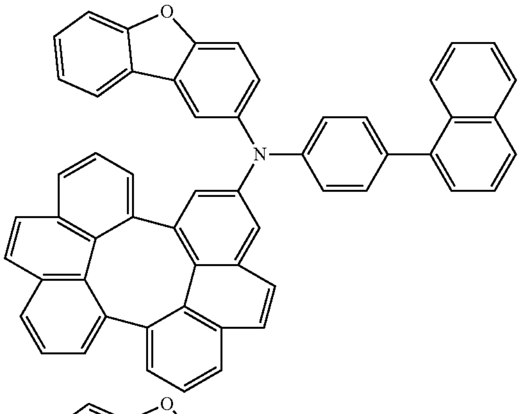
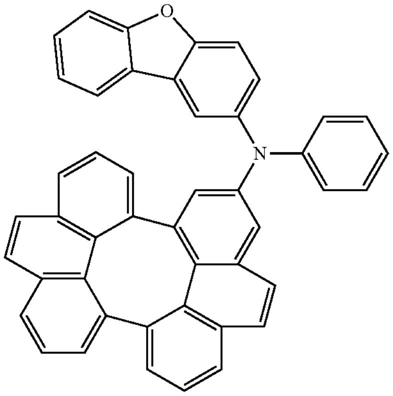
-continued
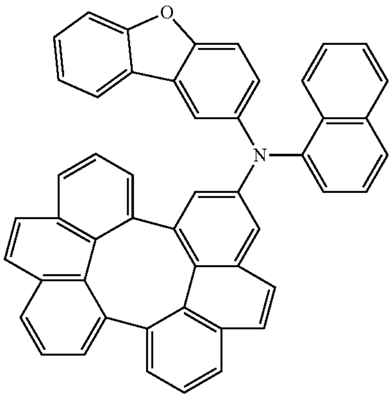
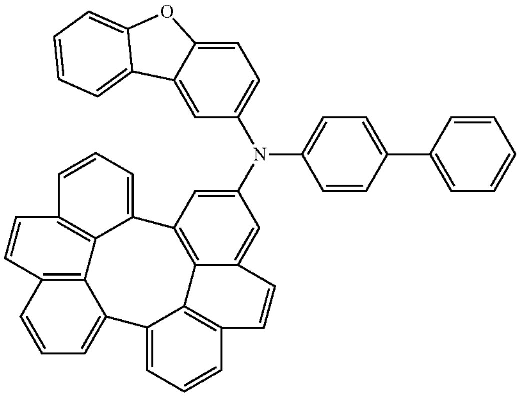
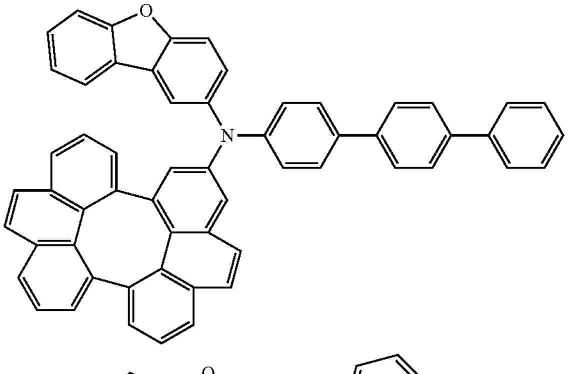
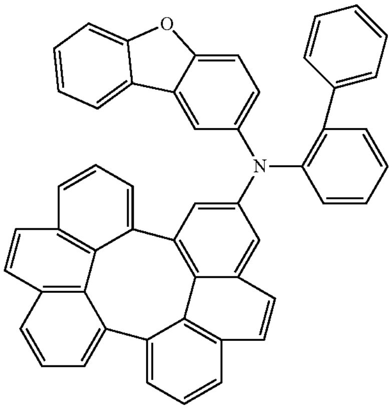

-continued
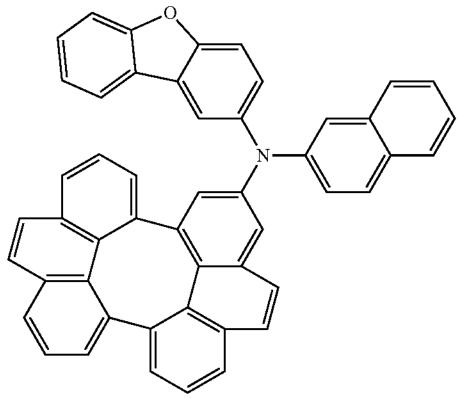
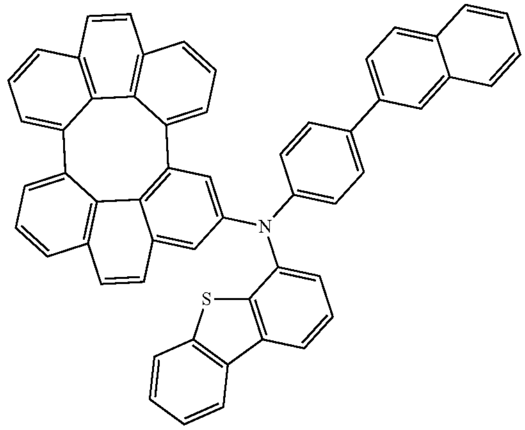
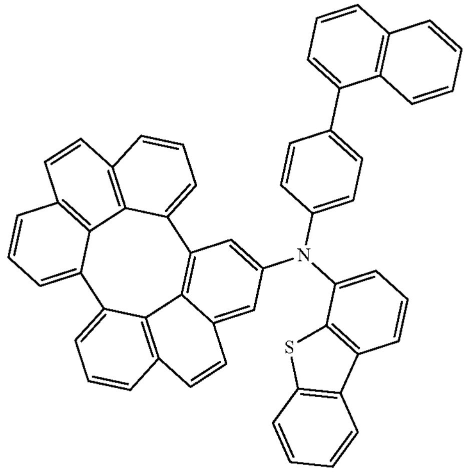
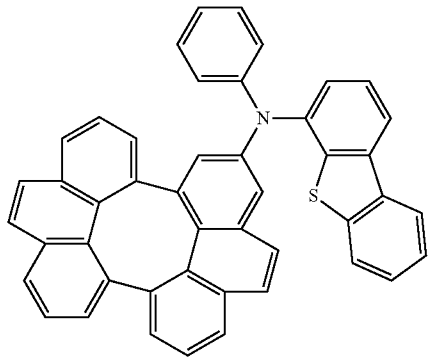
-continued
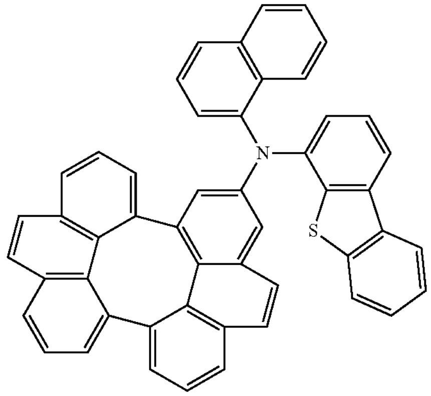
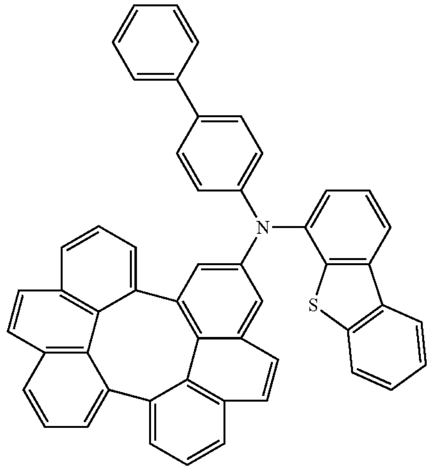
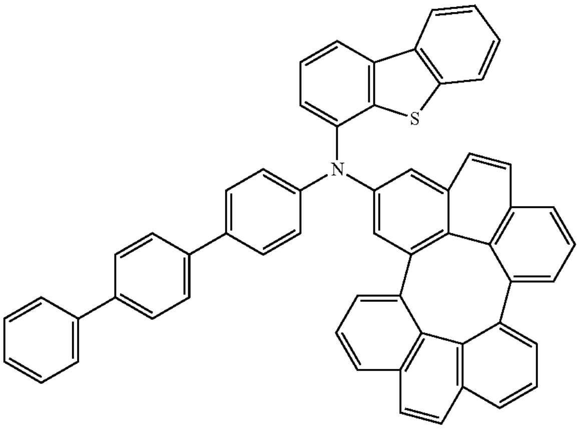
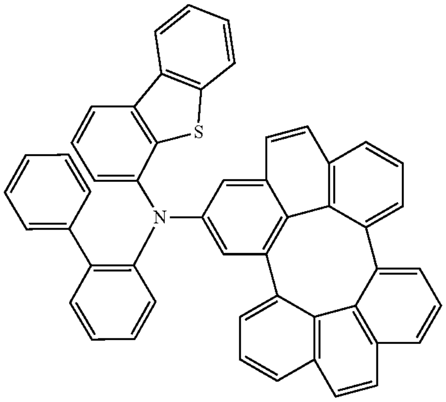

-continued
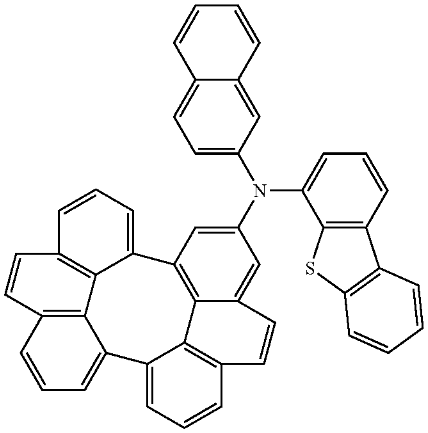
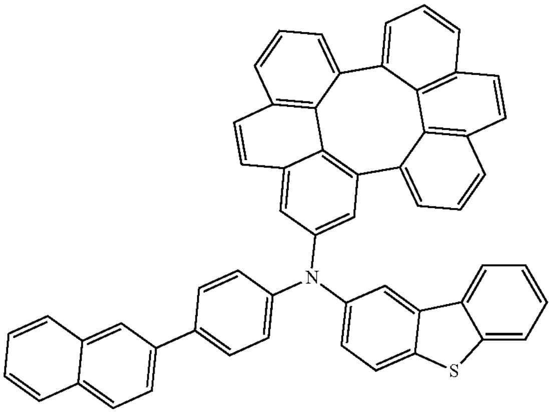
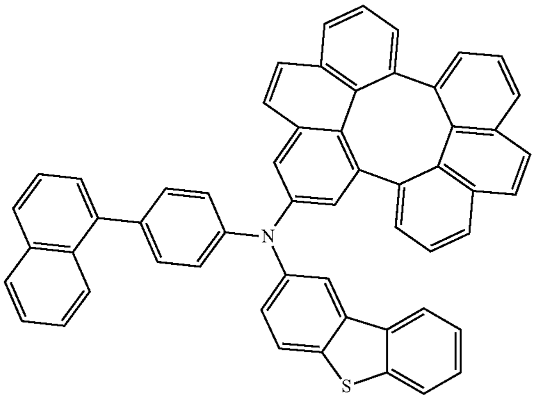
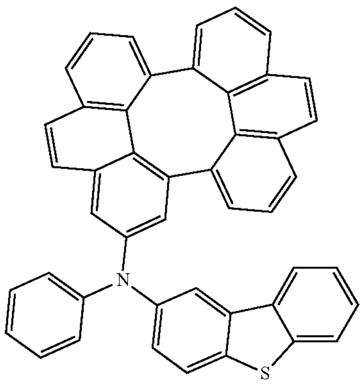
-continued
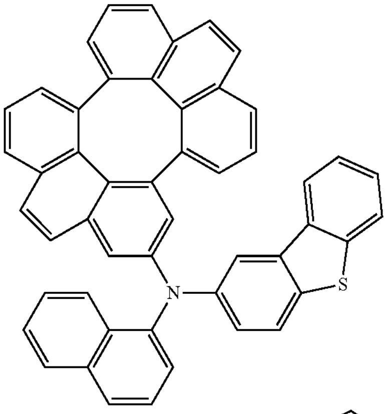
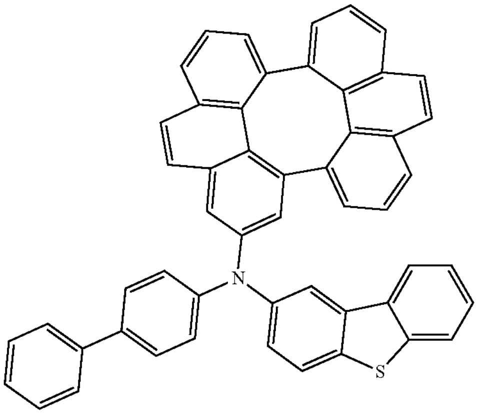
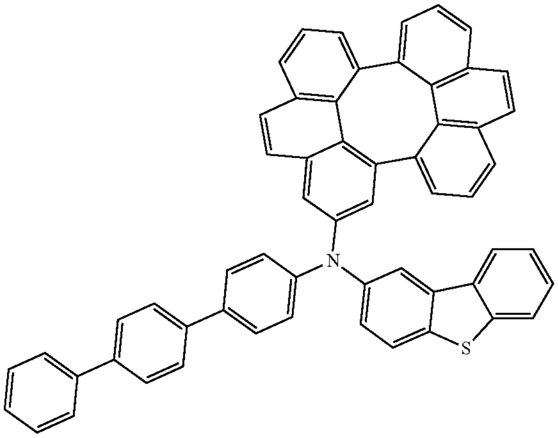
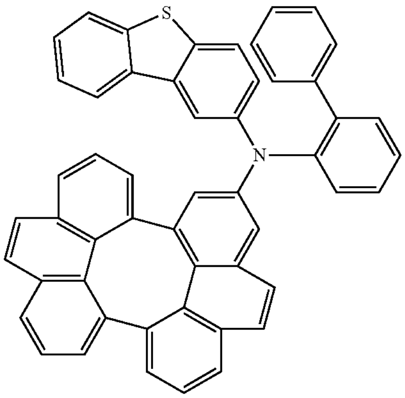

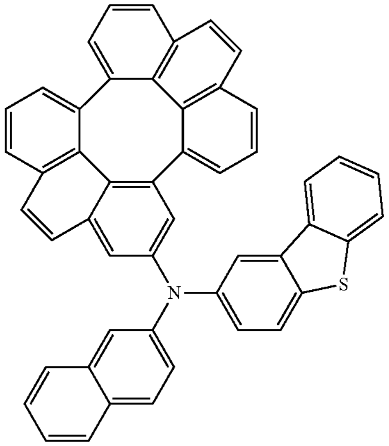
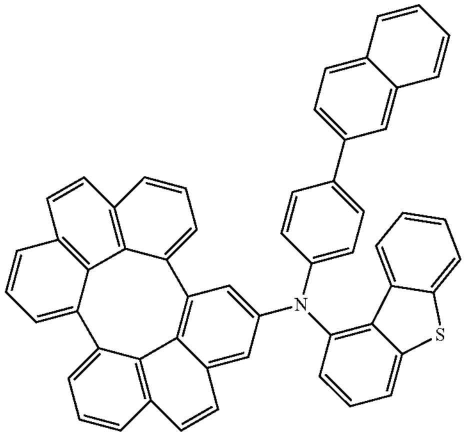
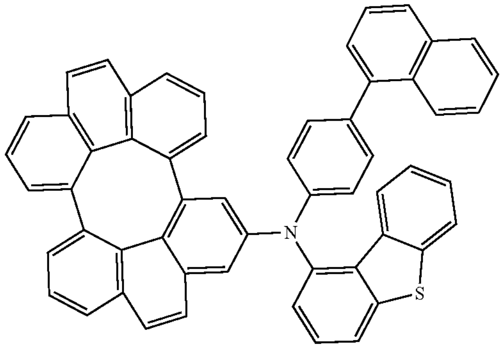
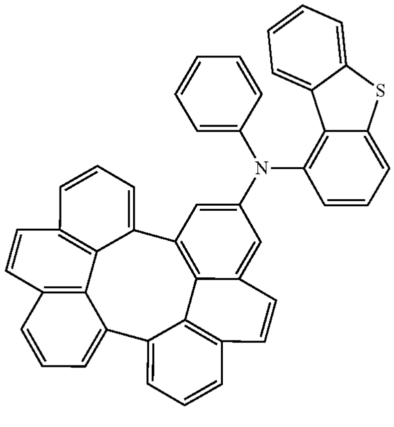
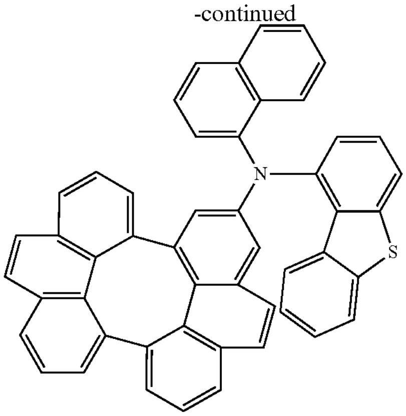
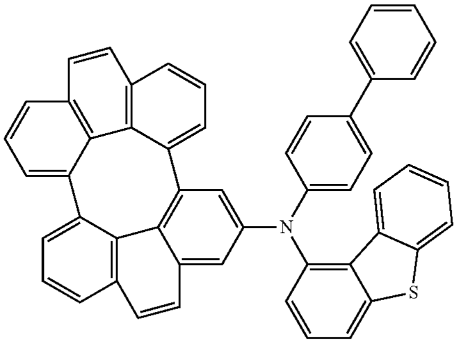
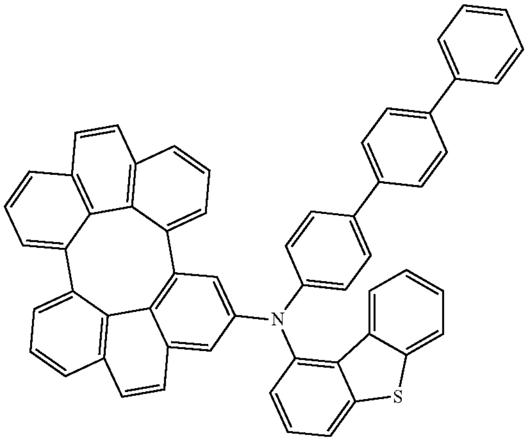
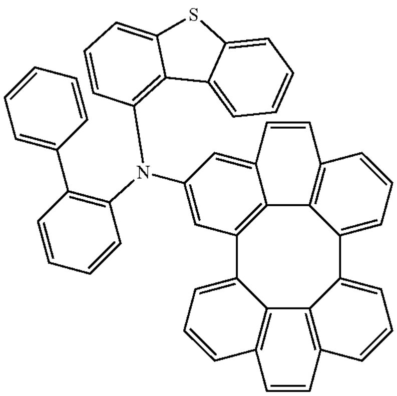

-continued
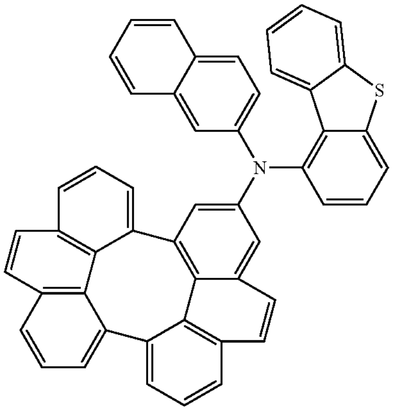
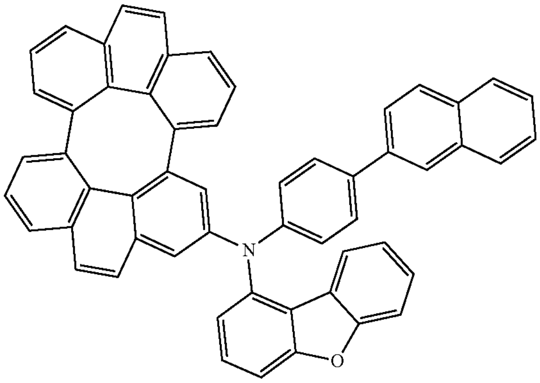
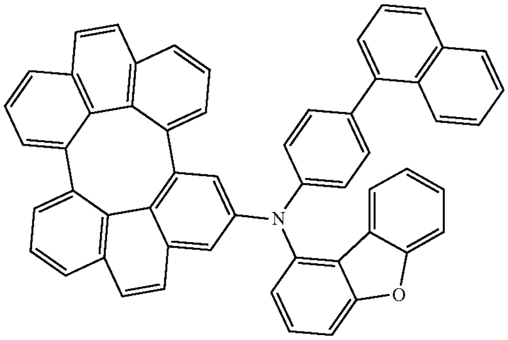
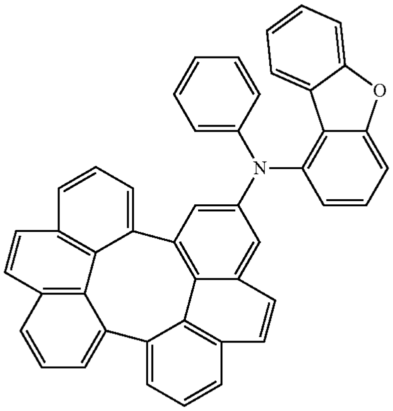
-continued
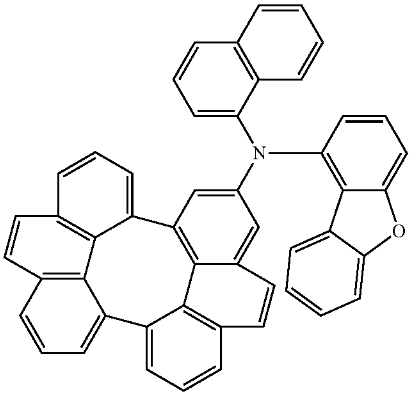
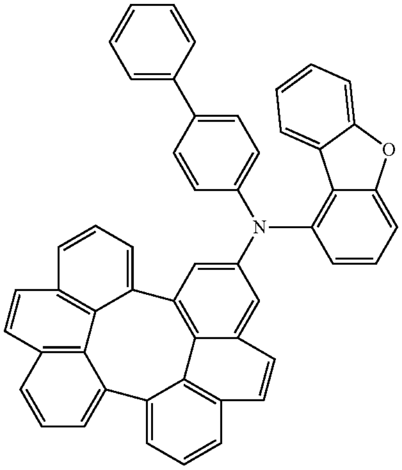
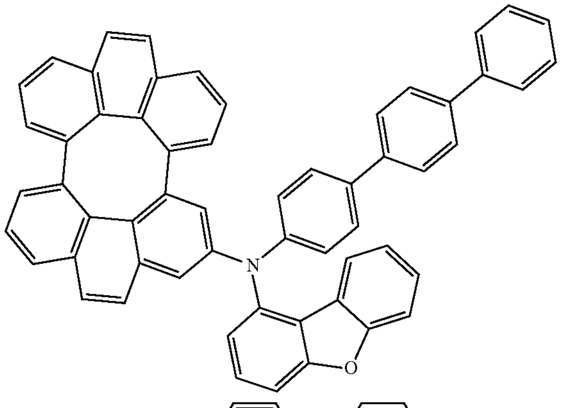
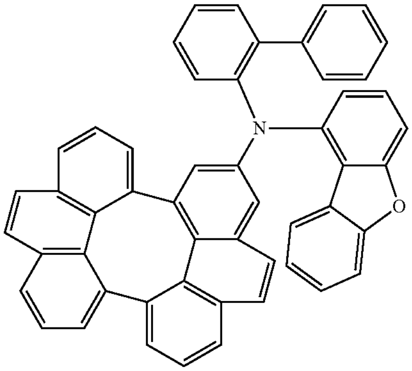

-continued
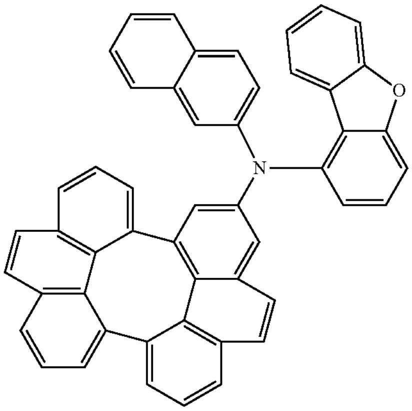
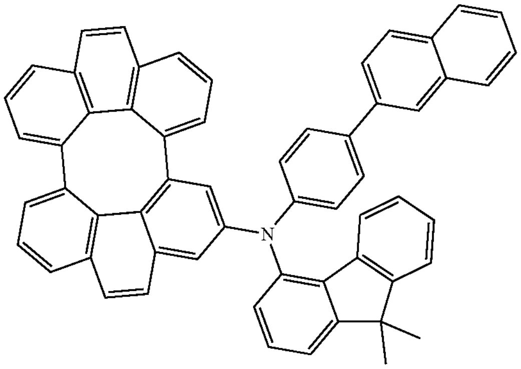
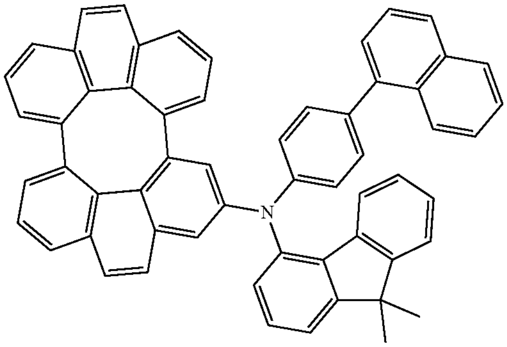
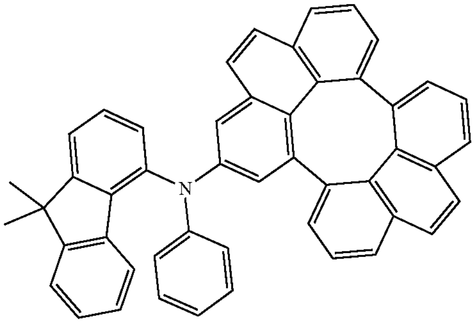
-continued
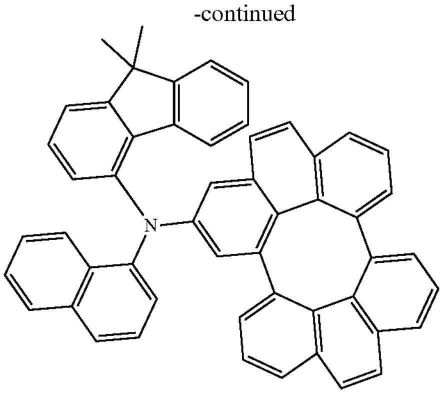
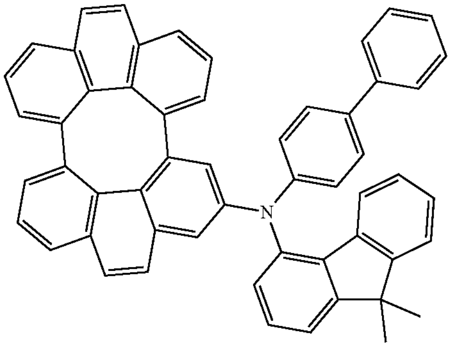
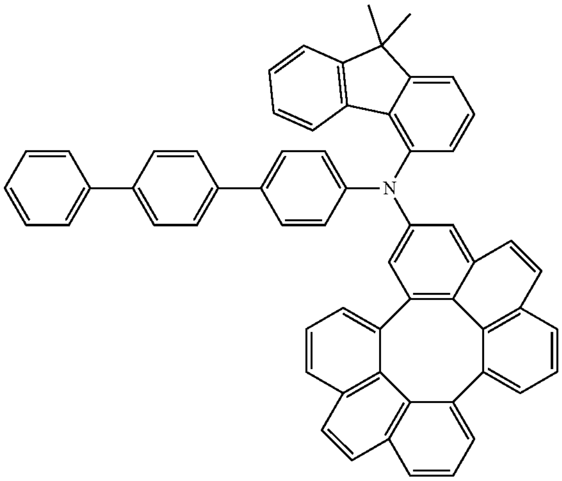
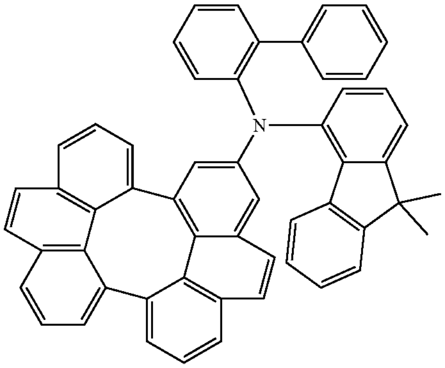

-continued
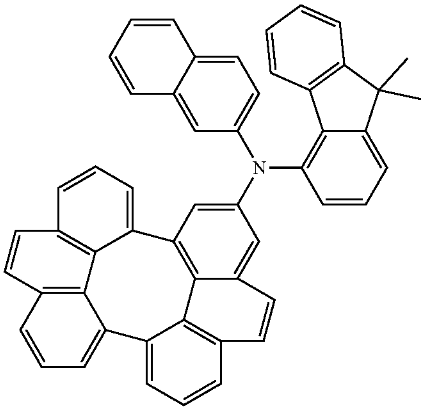
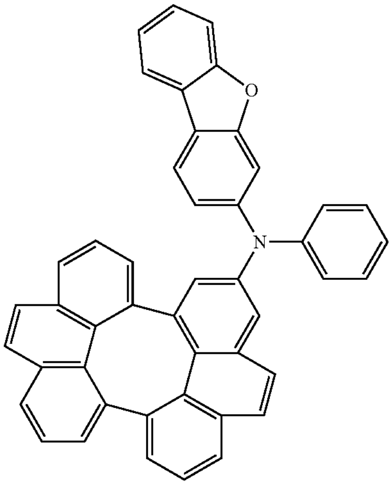
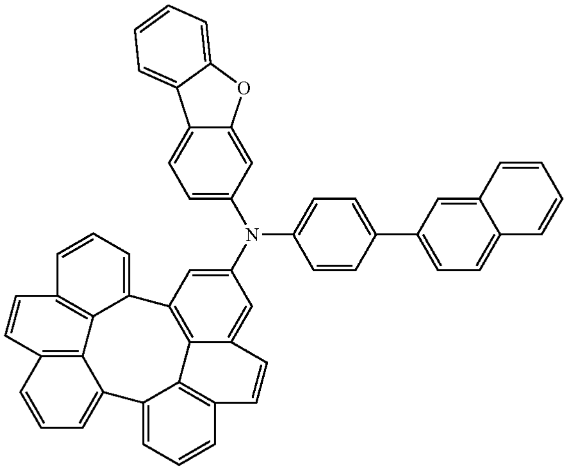
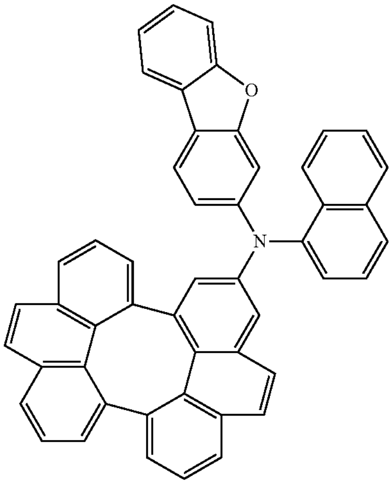
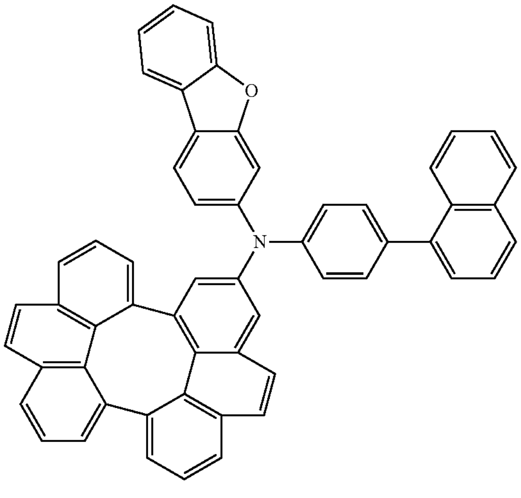
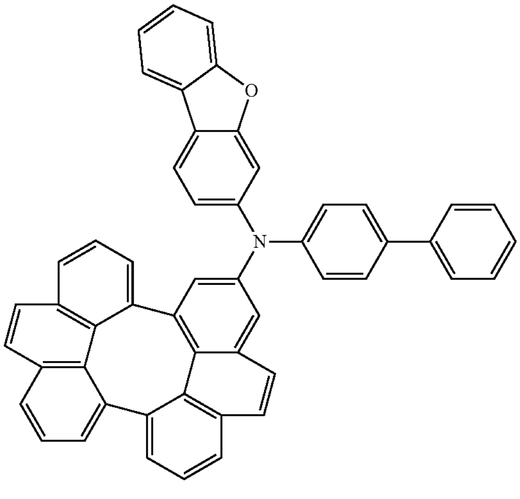
-continued -continued
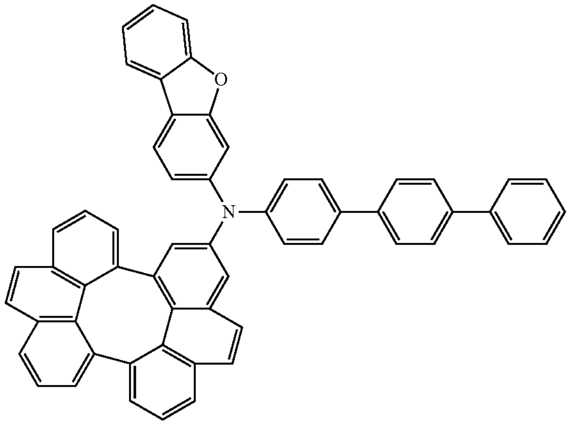
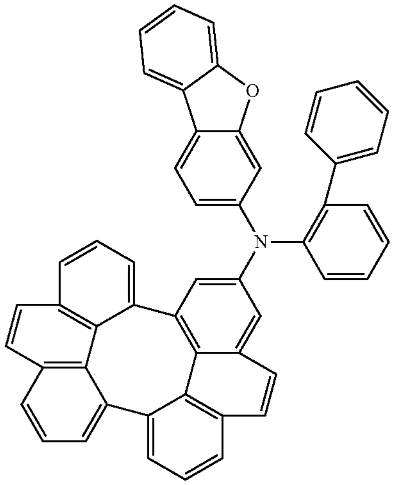
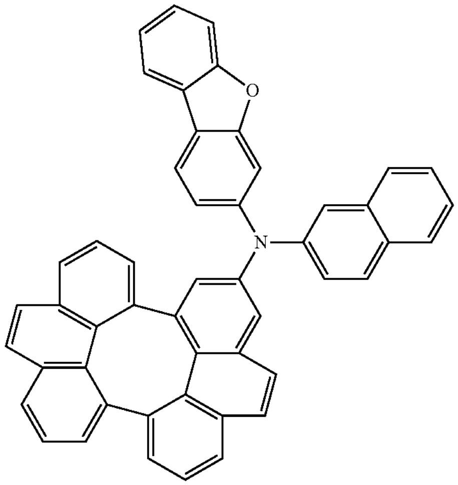
-continued
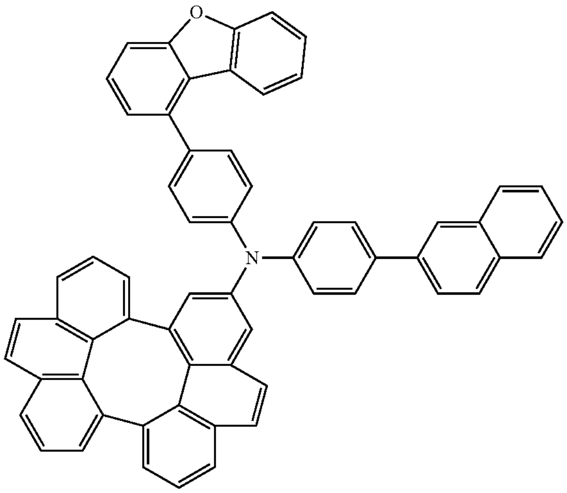
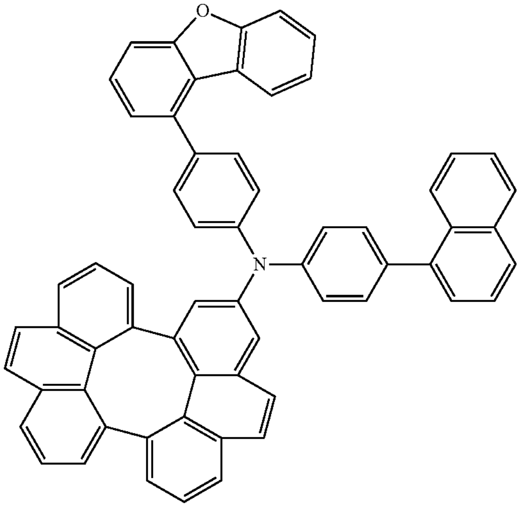
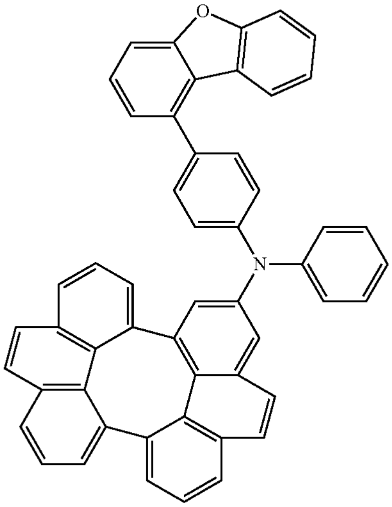

-continued
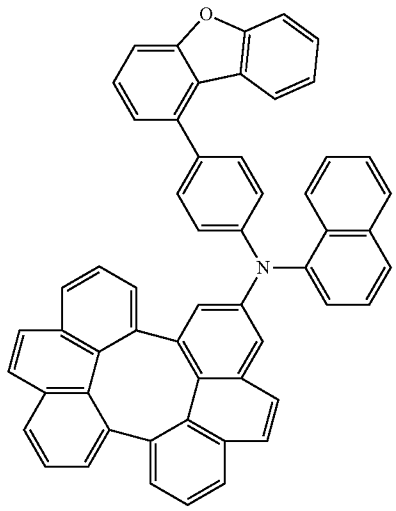
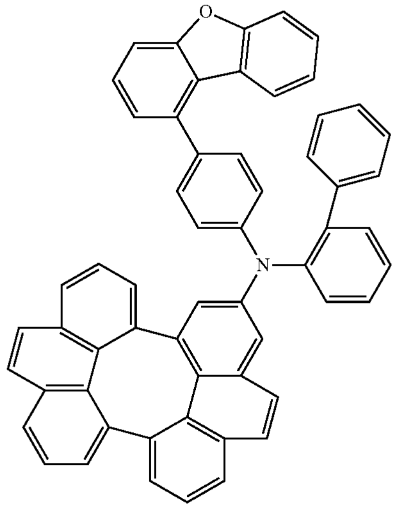
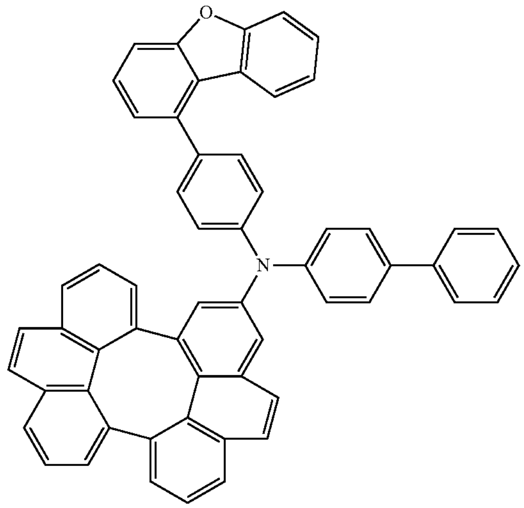
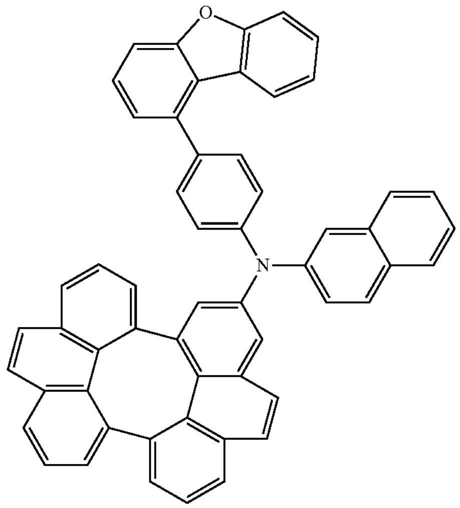
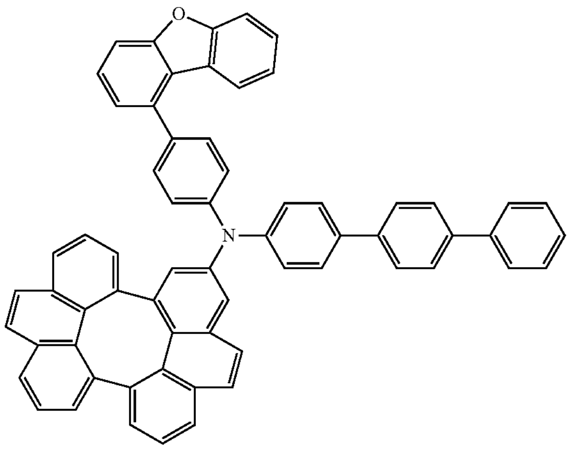
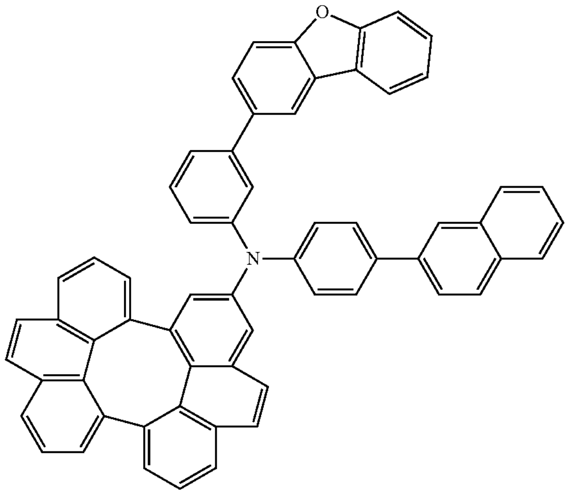

-continued
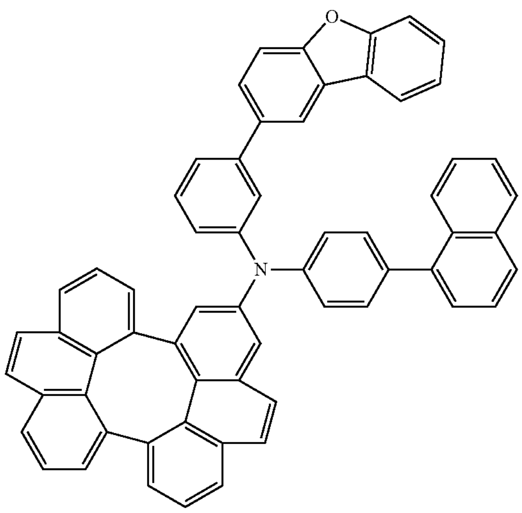
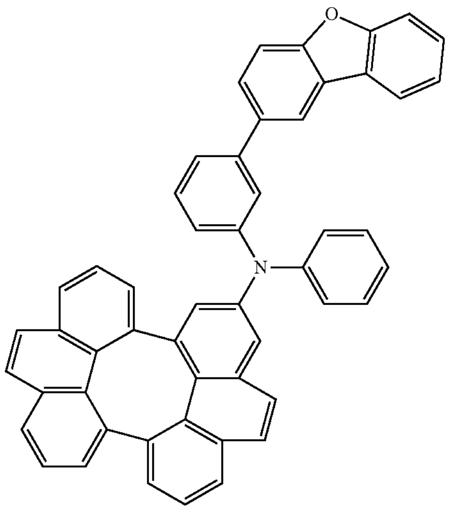
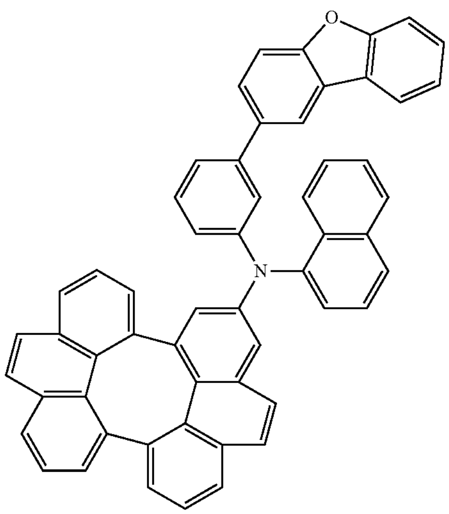
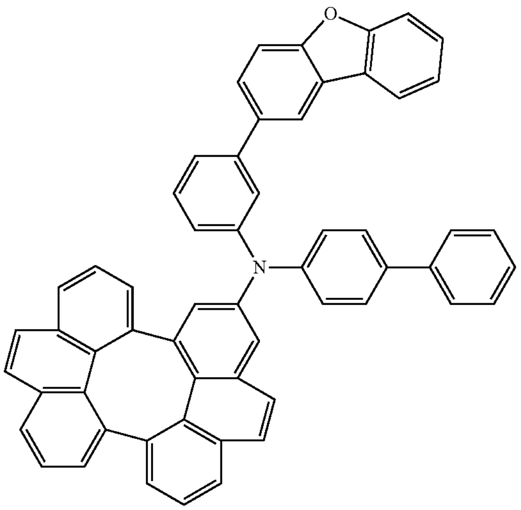
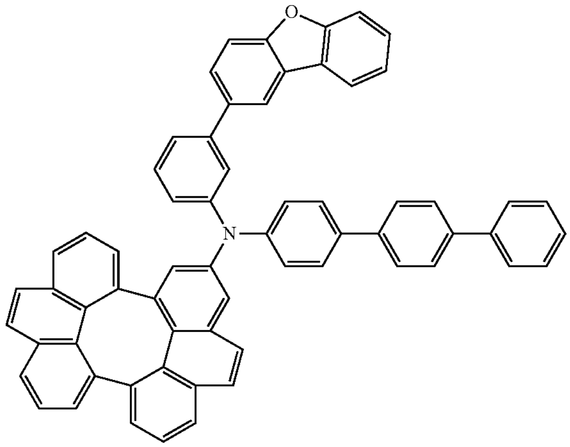
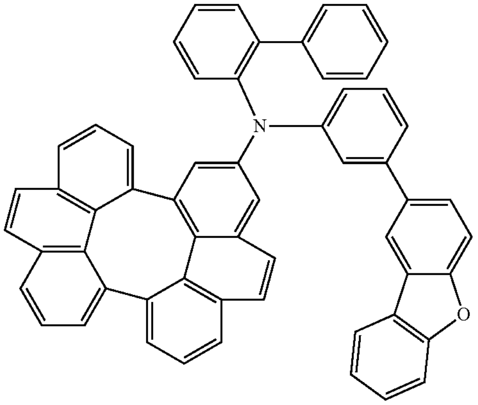

-continued
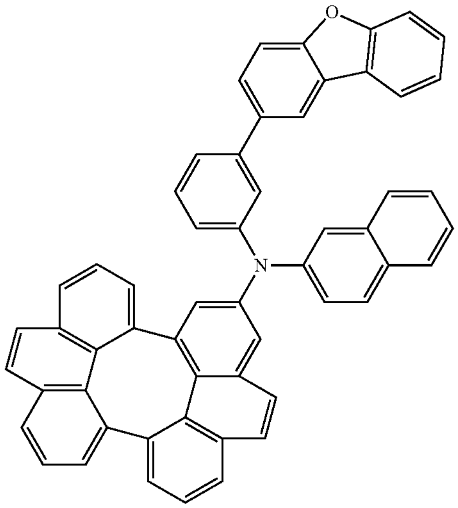
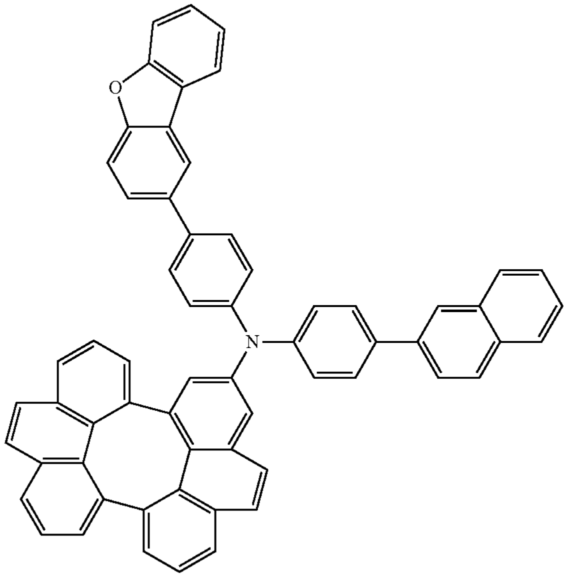
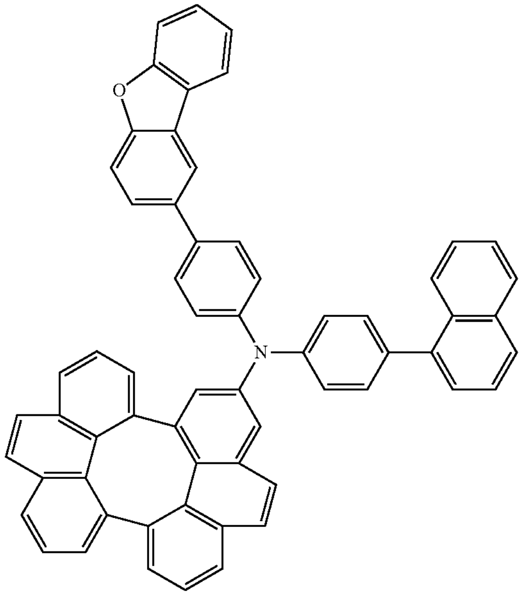
-continued
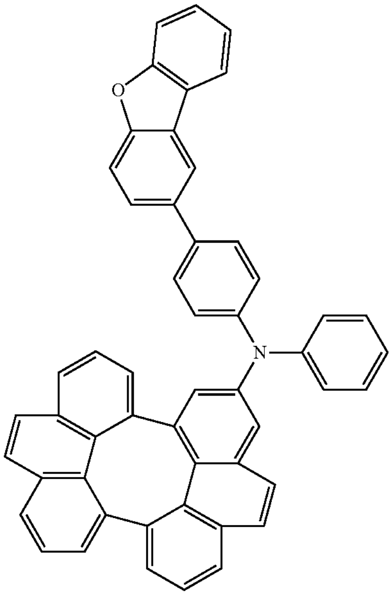
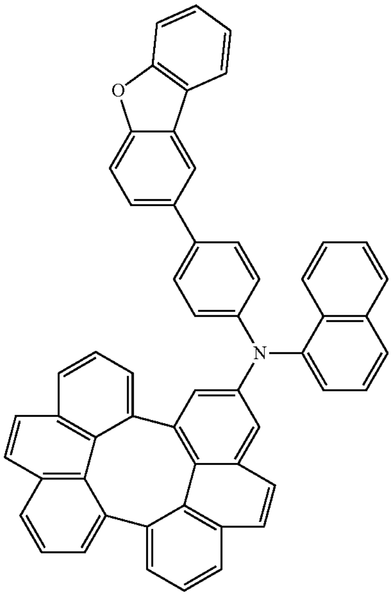

-continued
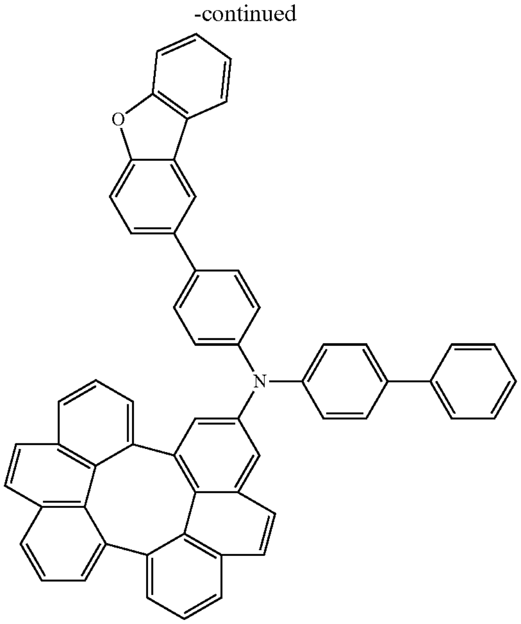
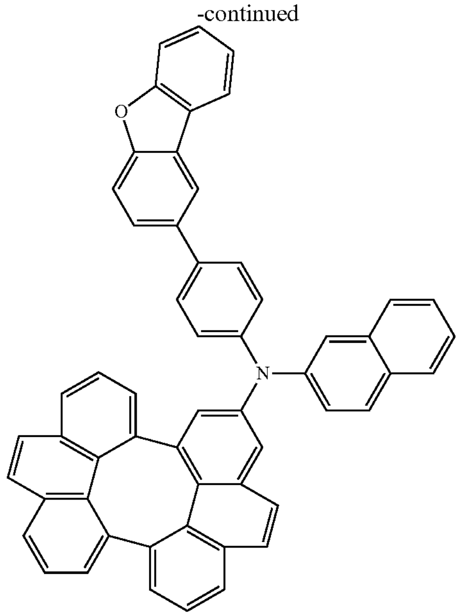
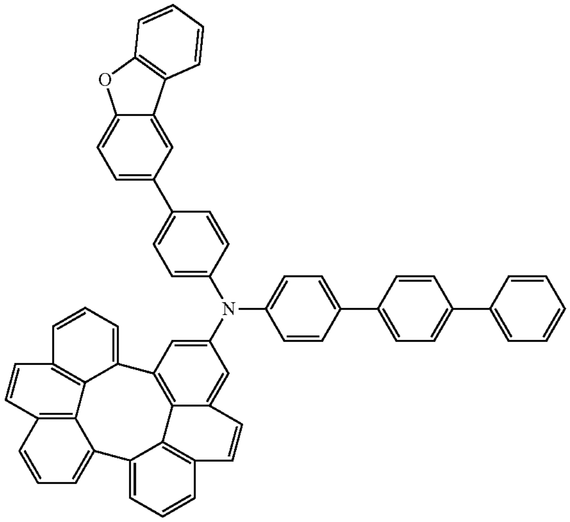
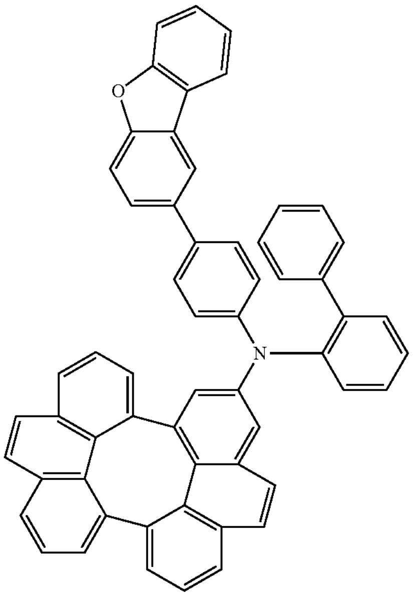
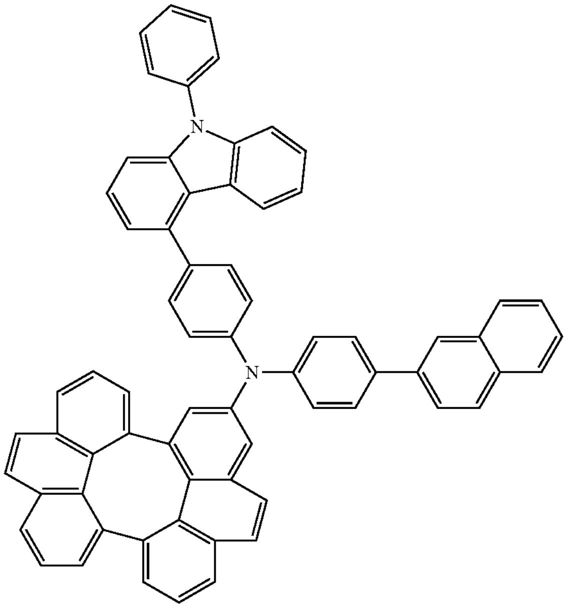
-continued -continued
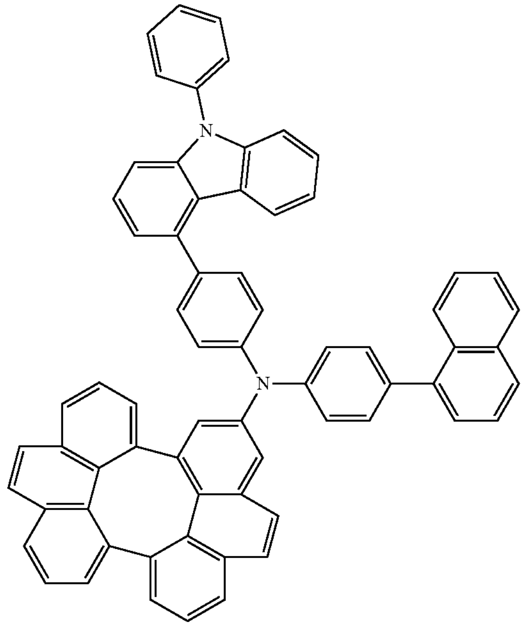
-continued
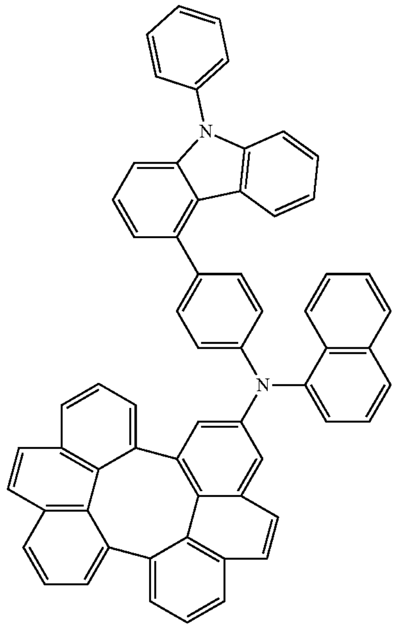
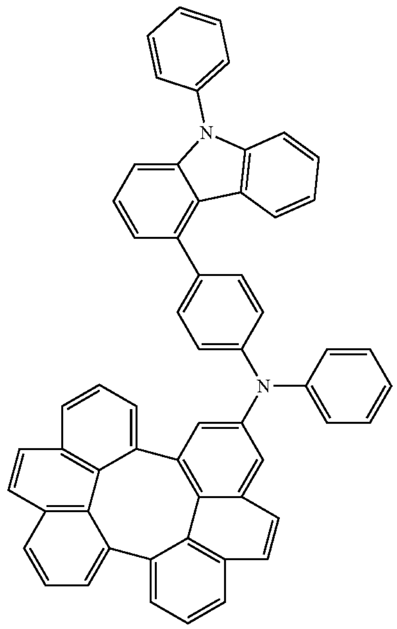
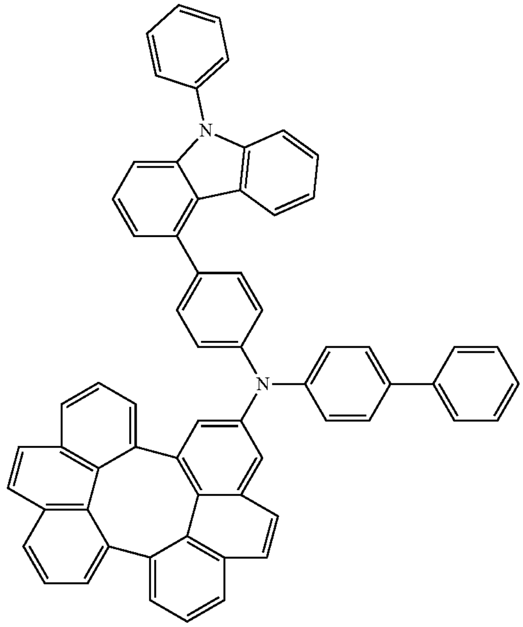

-continued
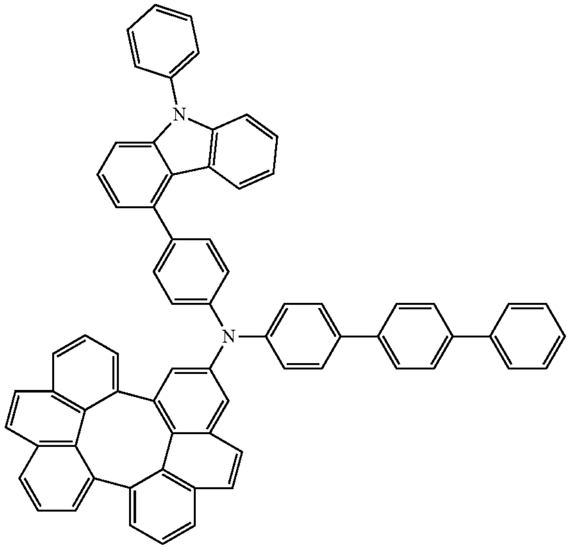
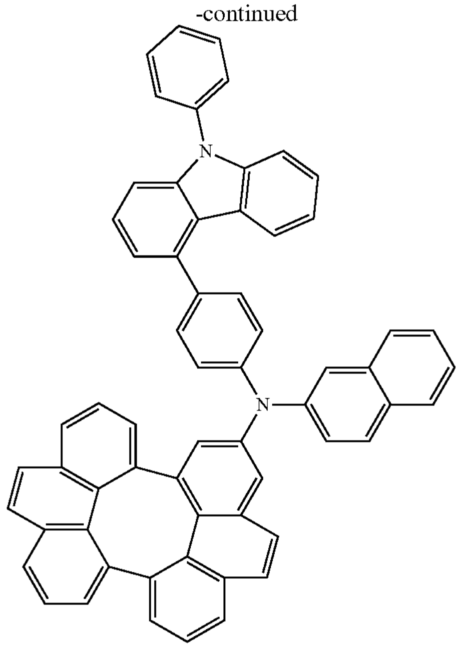
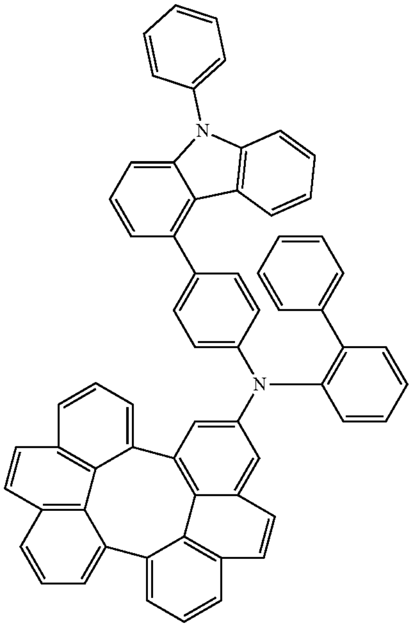
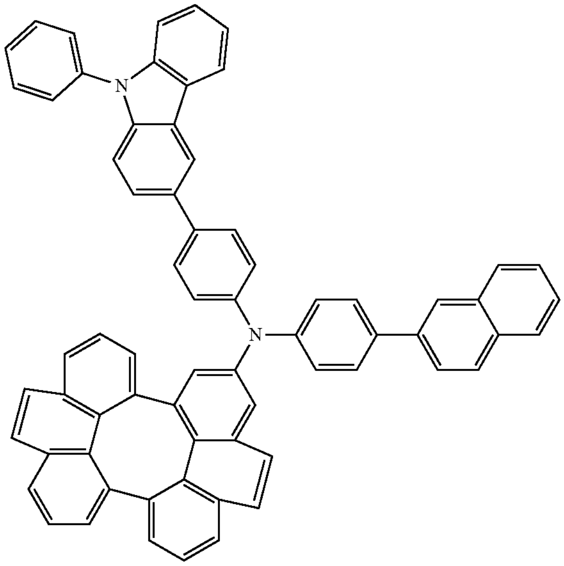

-continued
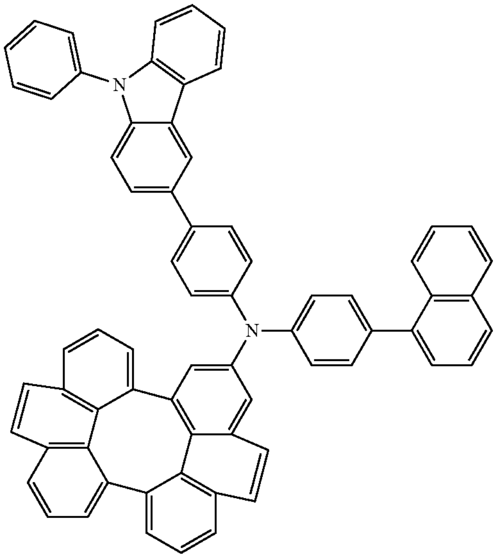
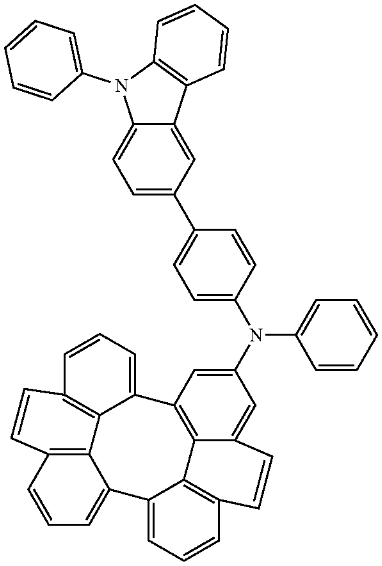
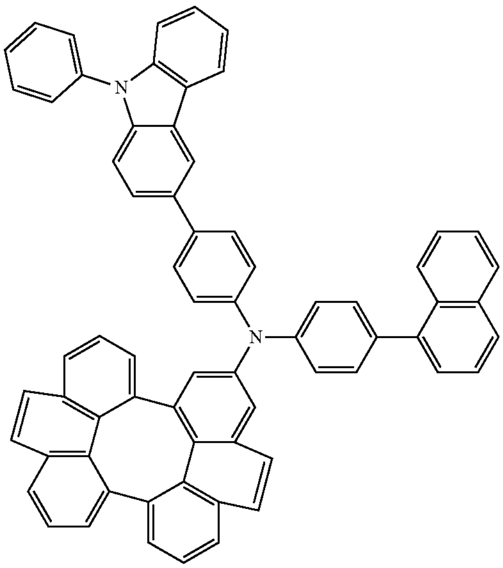
-continued
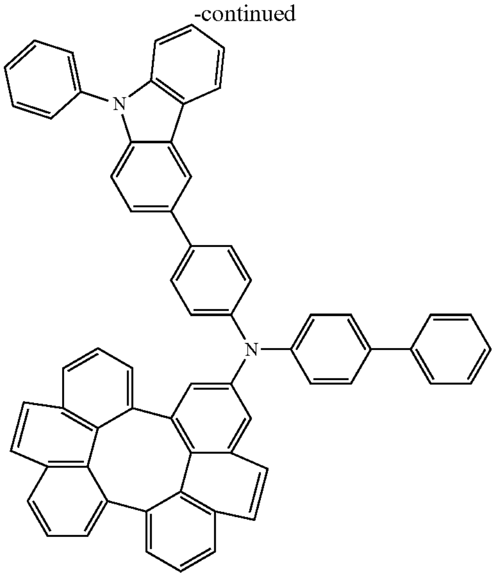
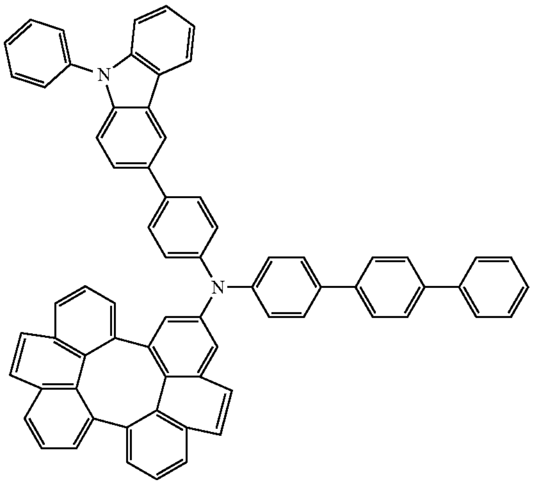
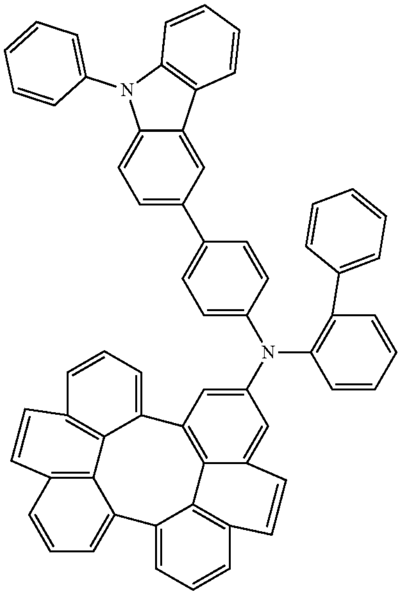

-continued
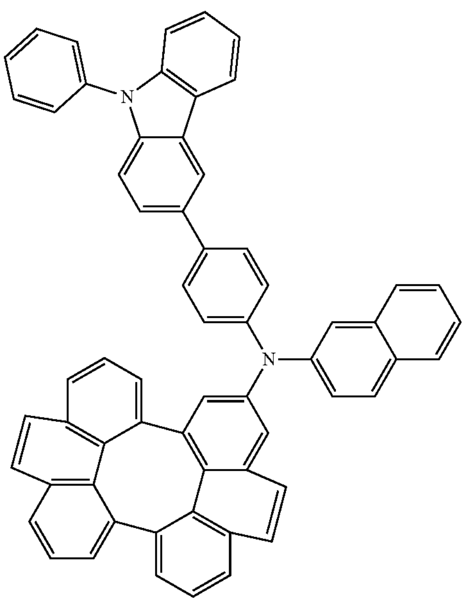
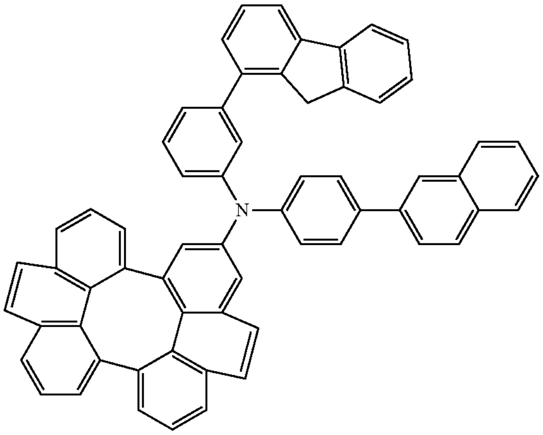
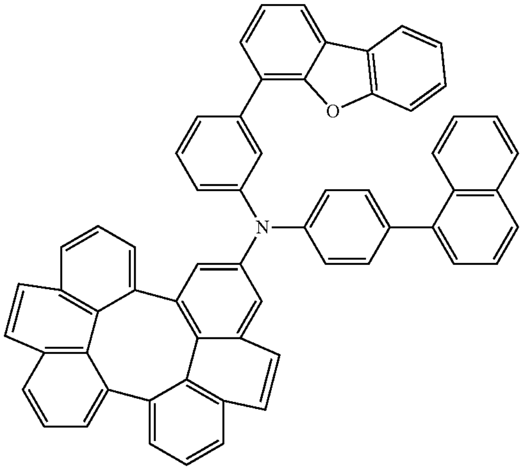
-continued
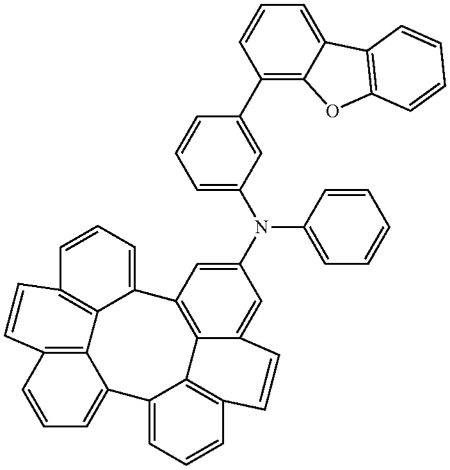
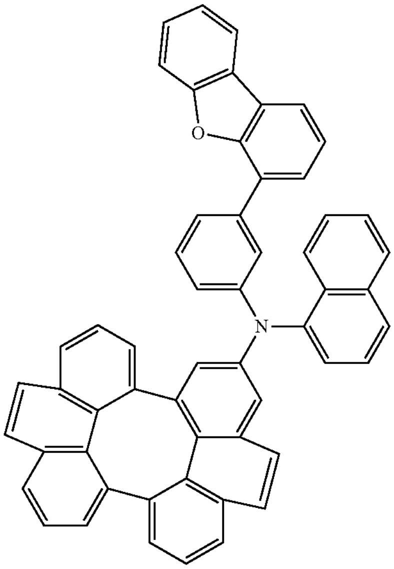
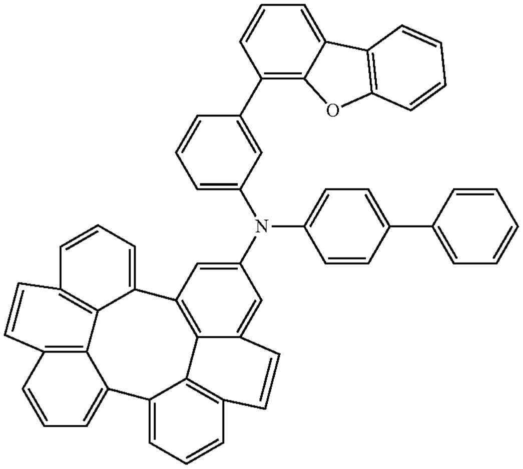

-continued
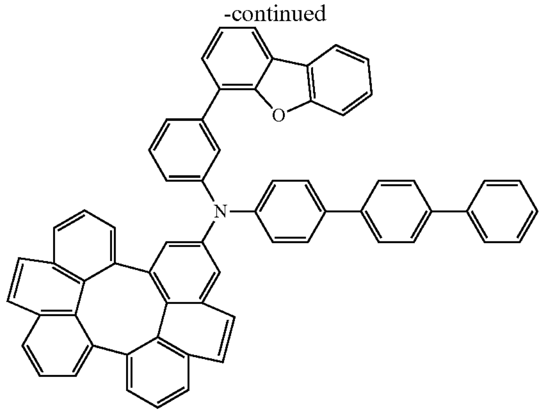
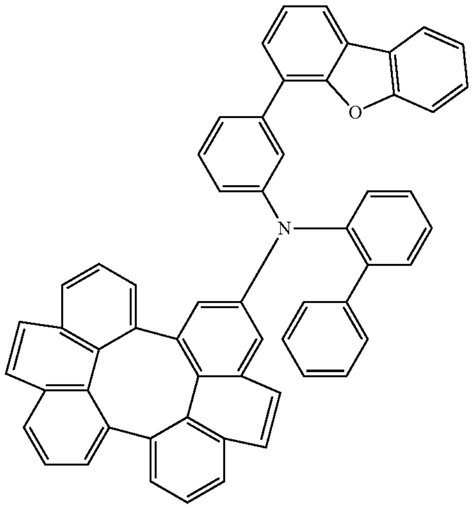
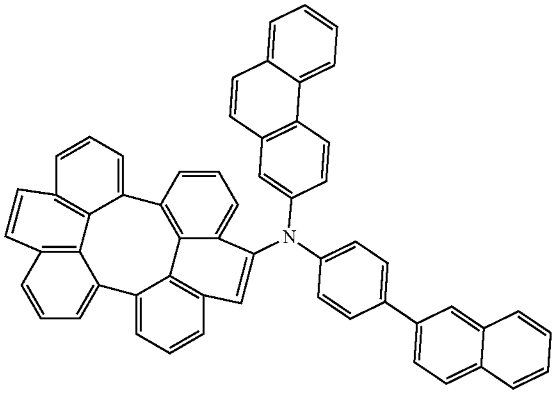
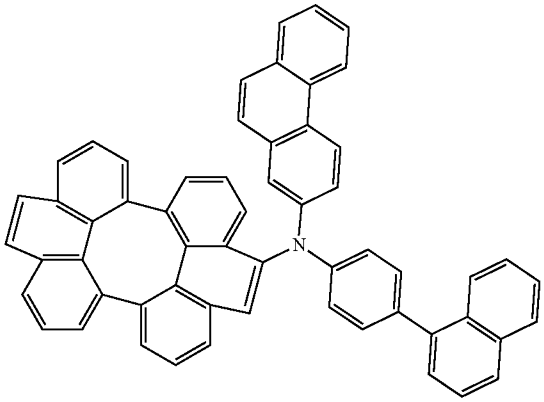
-continued
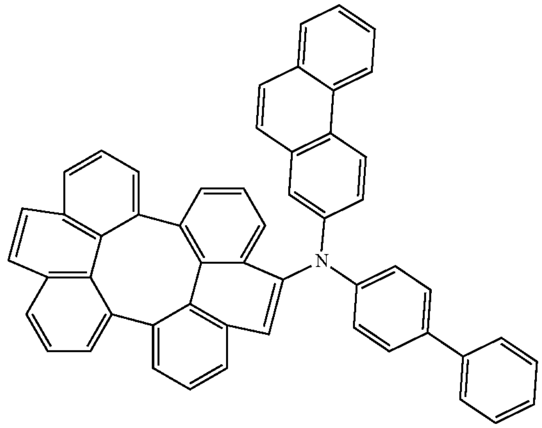
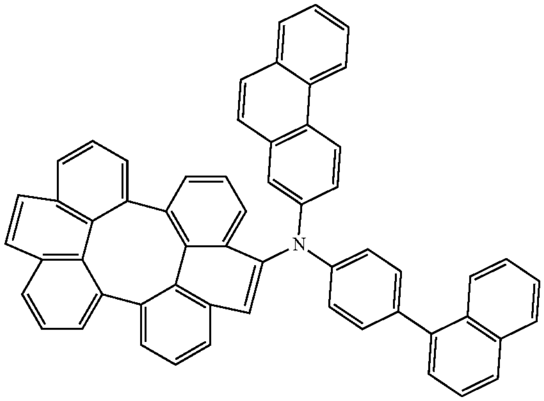
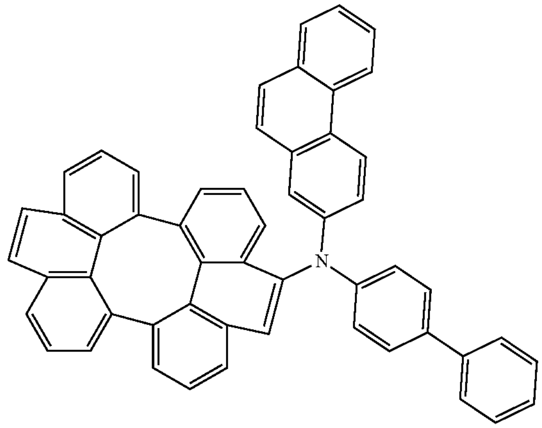
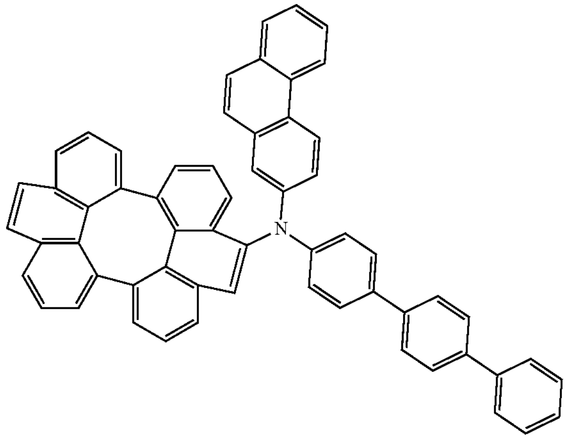

-continued
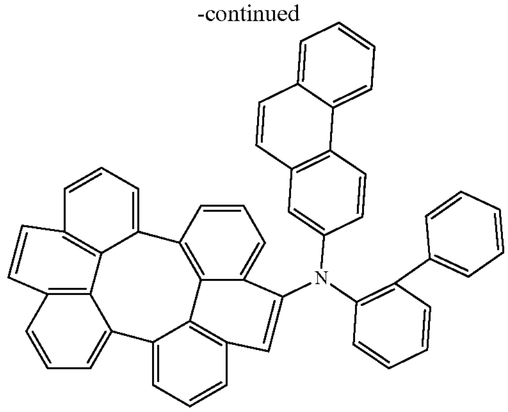
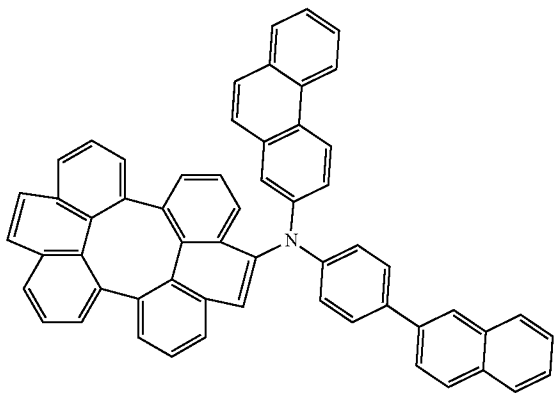
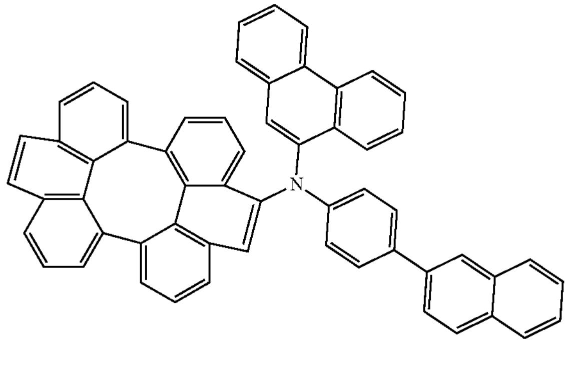
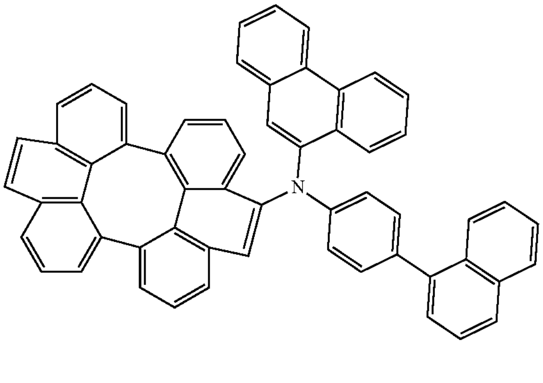
-continued
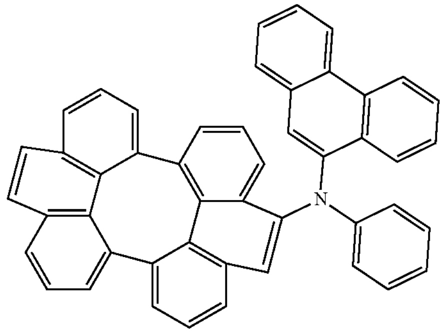
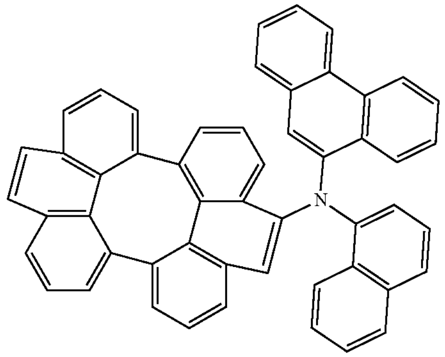
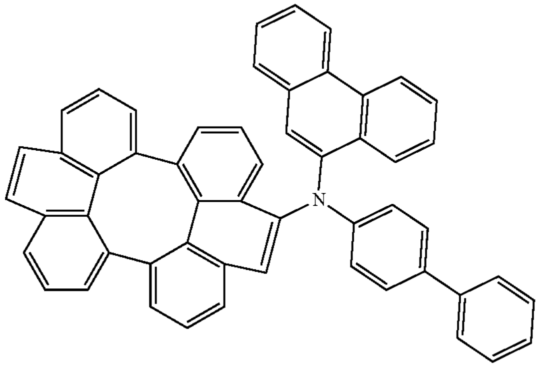
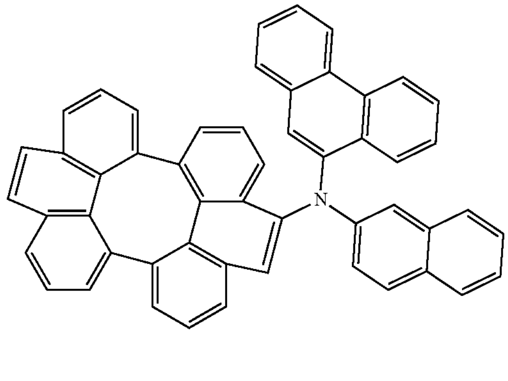

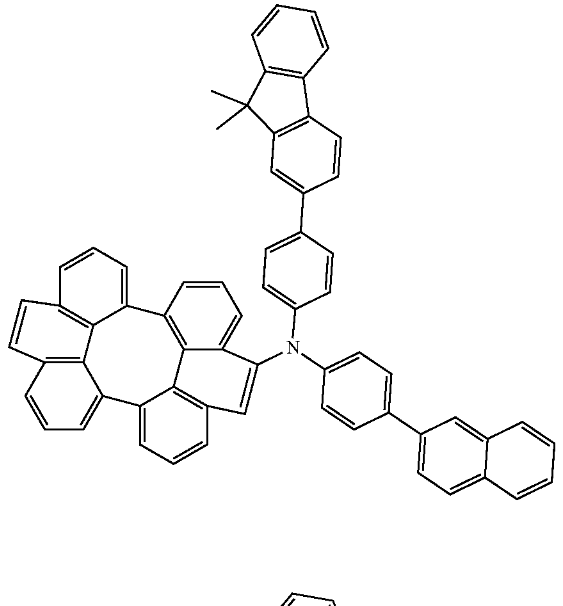
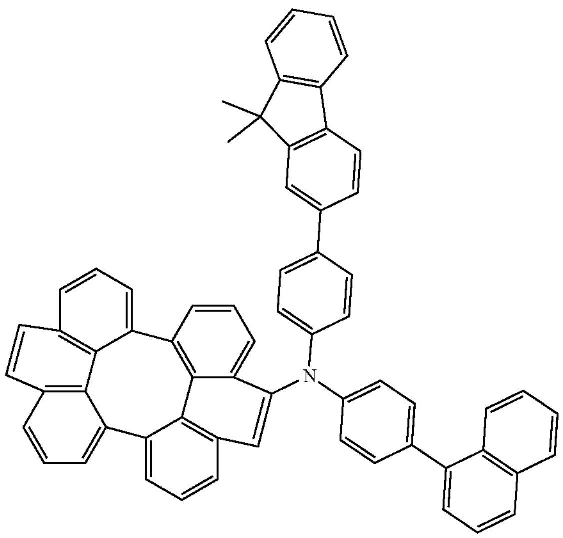
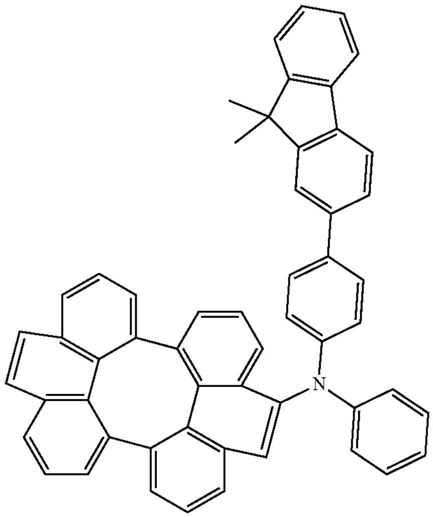
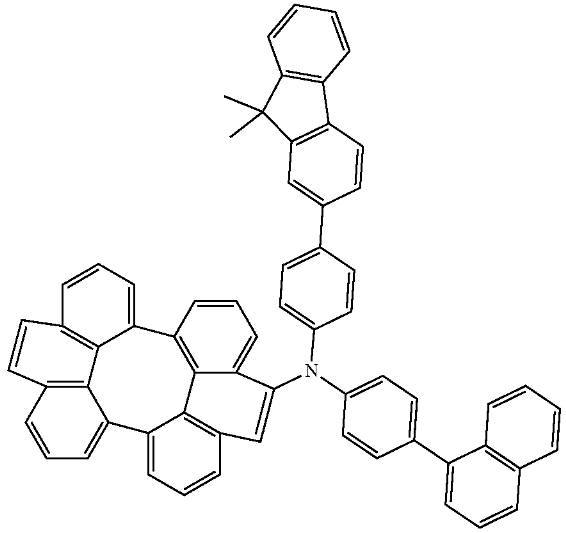
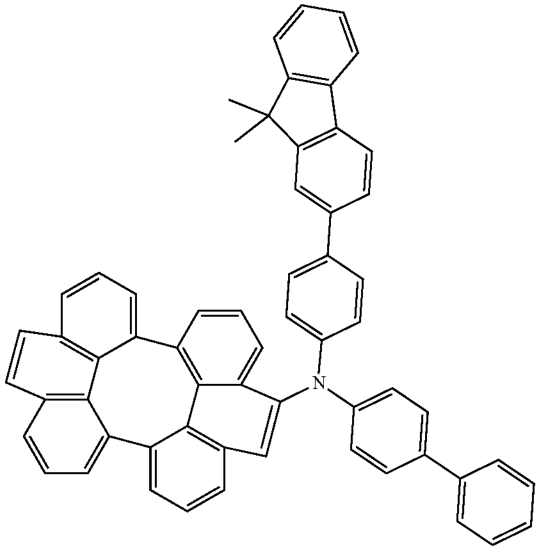
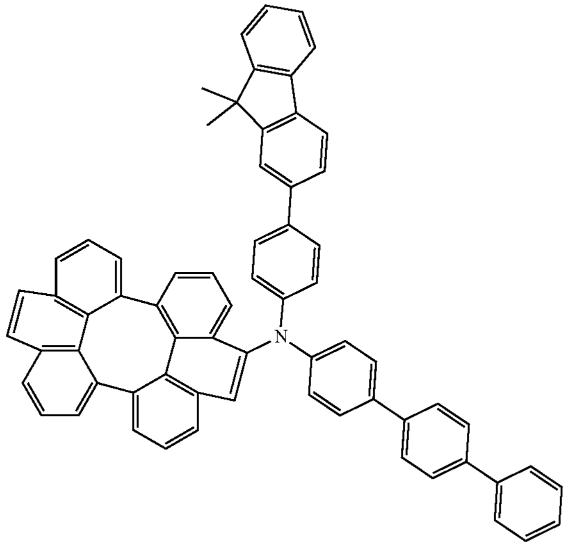

-continued
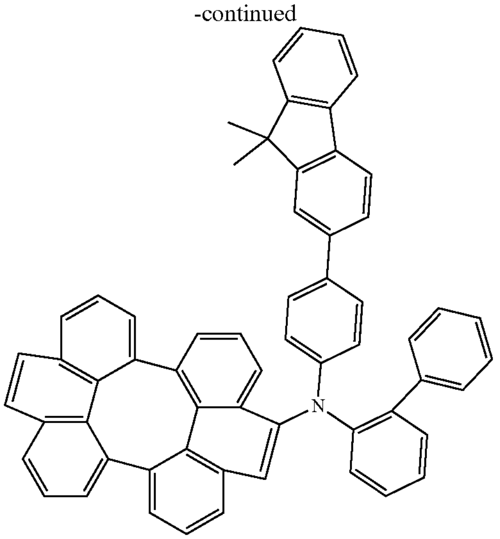
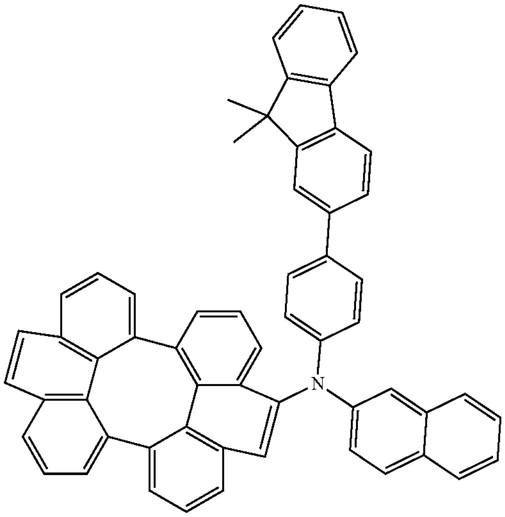
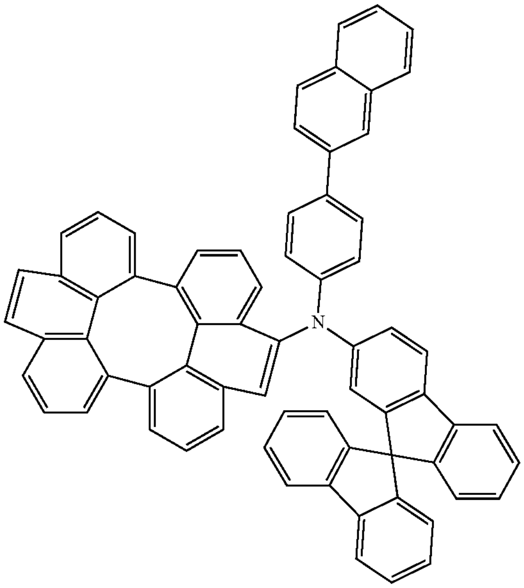
-continued
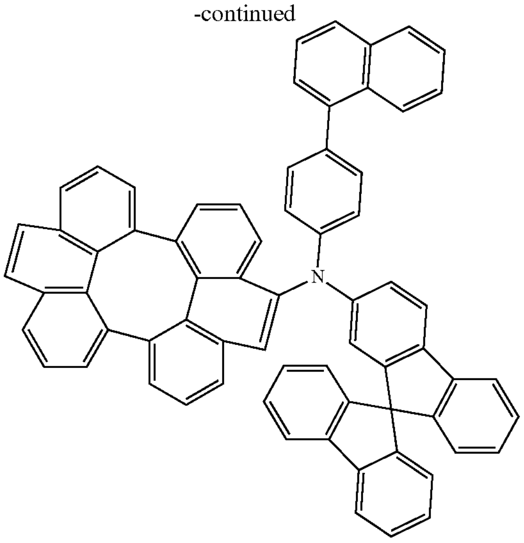
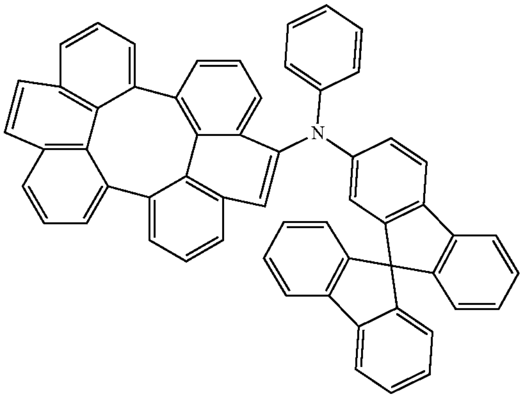
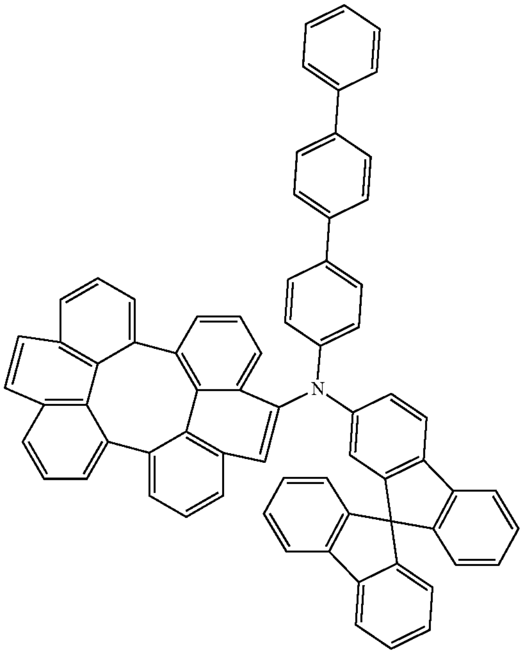

-continued
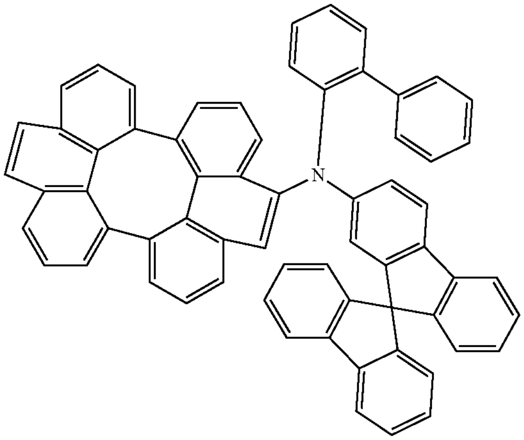
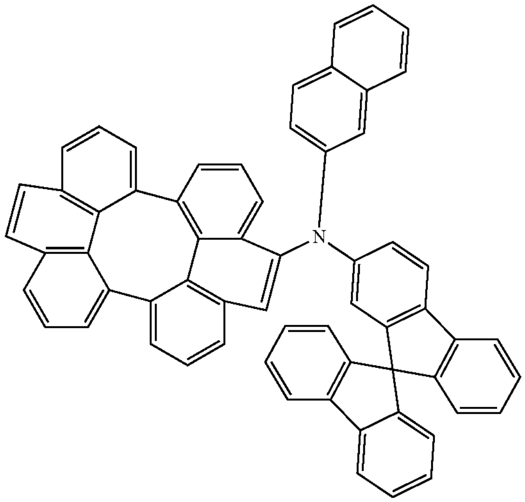
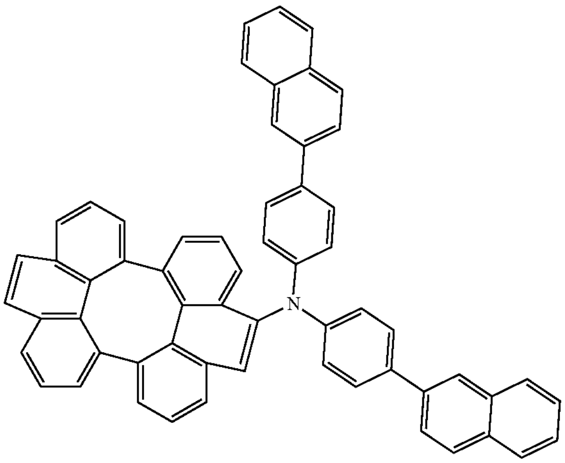
-continued
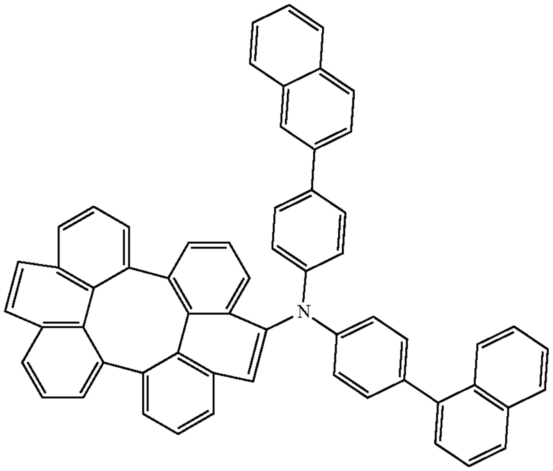
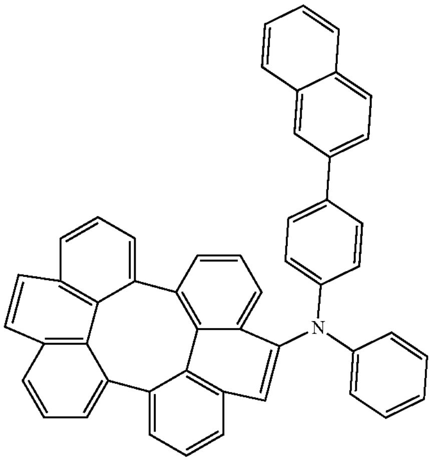
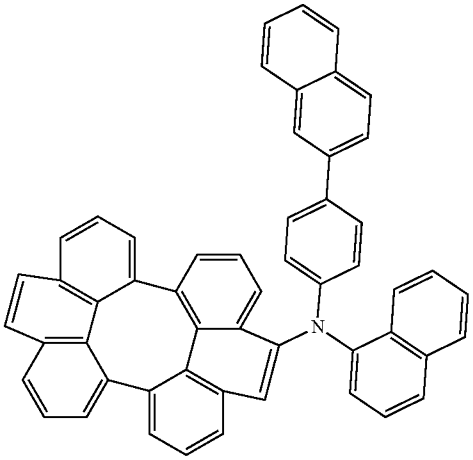

-continued
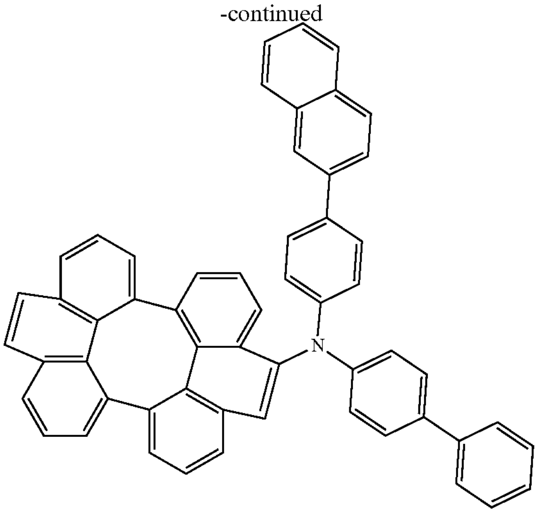
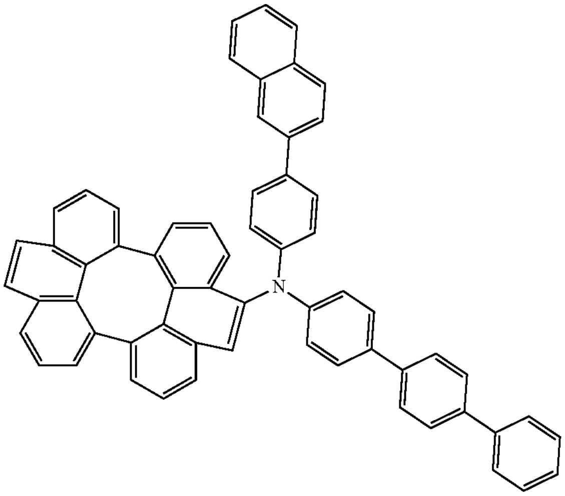
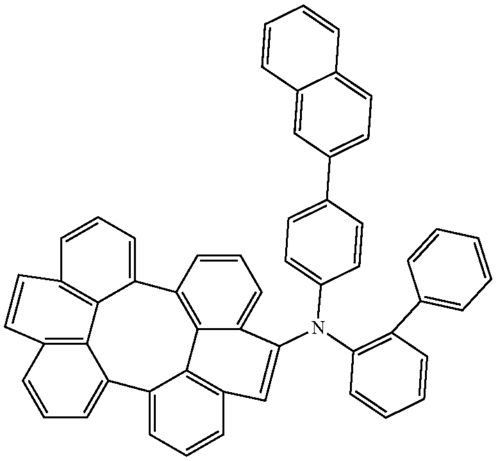
-continued
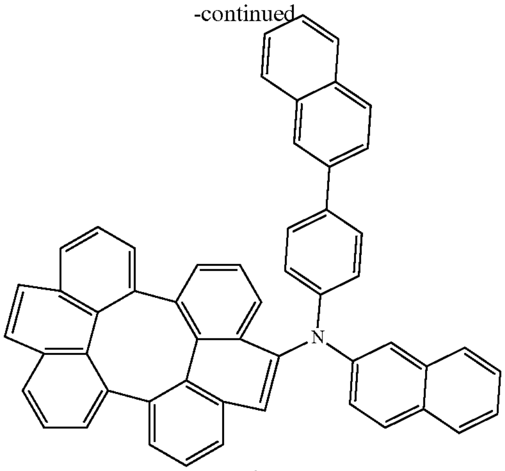
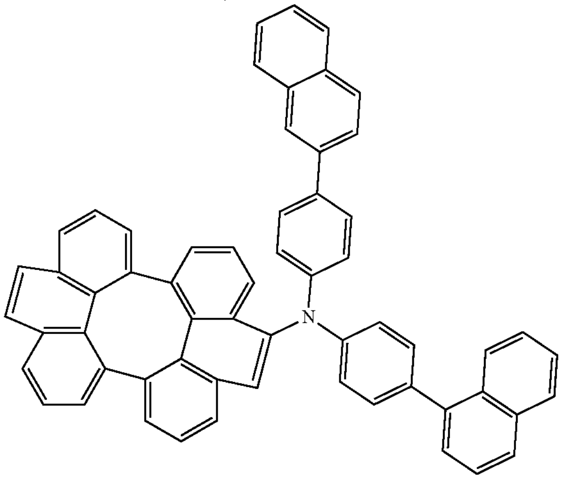
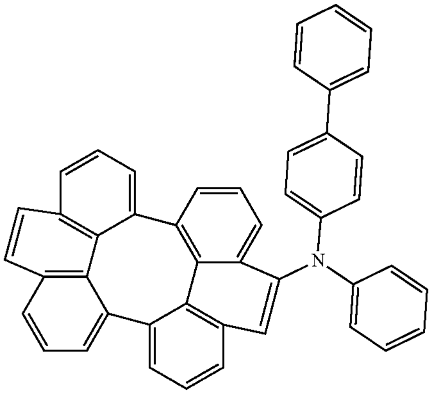
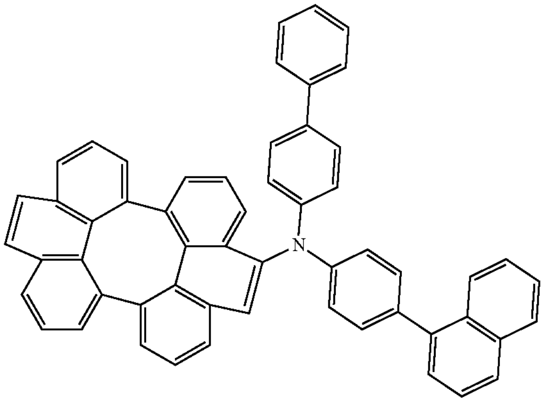

-continued
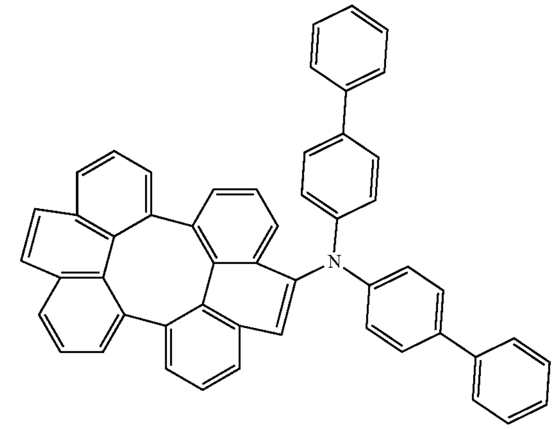
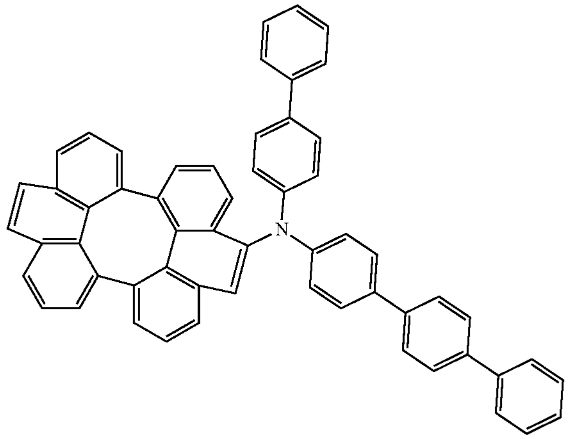
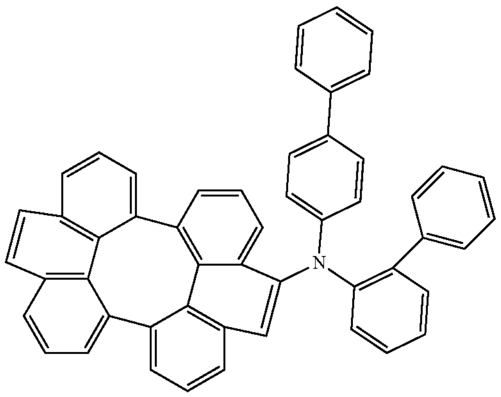
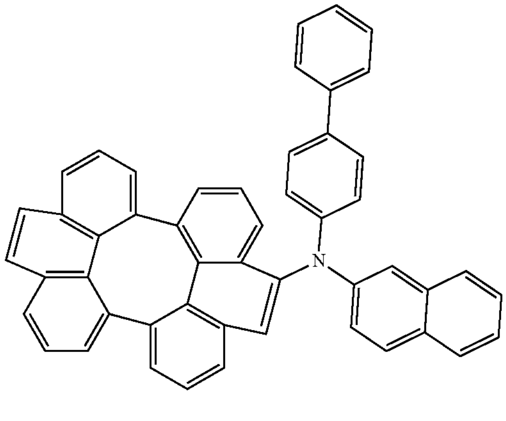
-continued
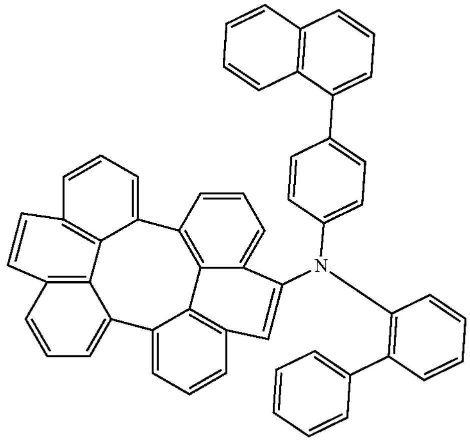
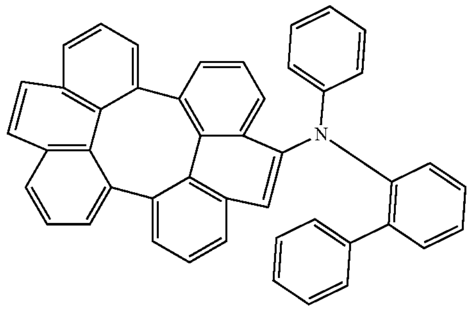
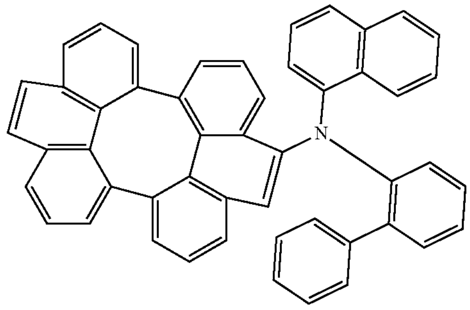
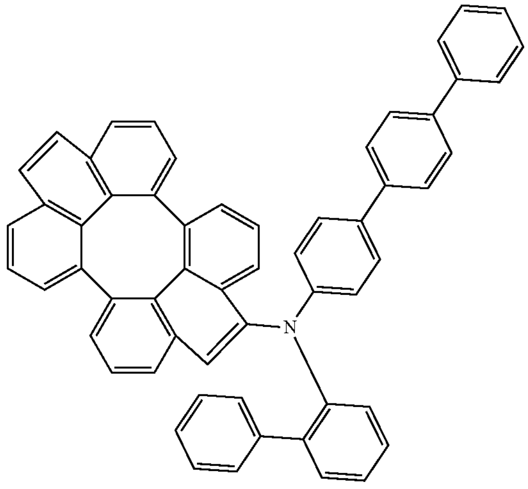

-continued
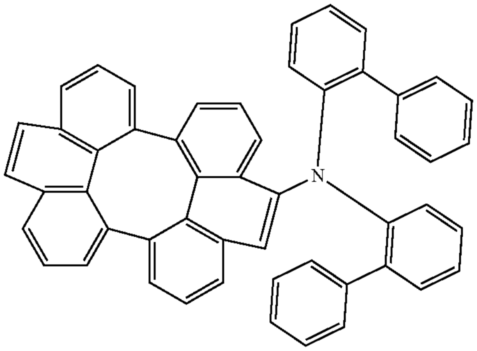
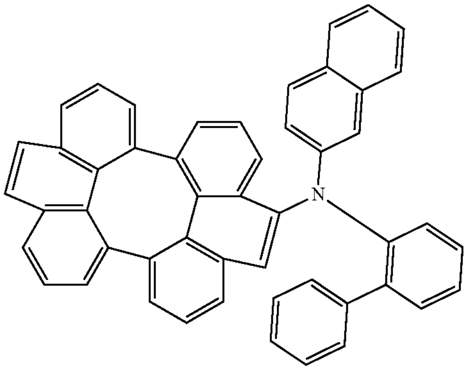
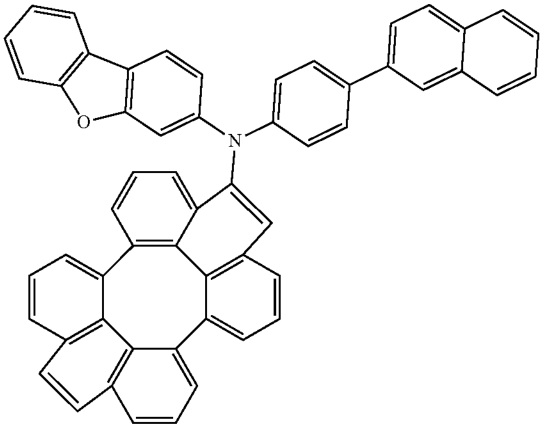
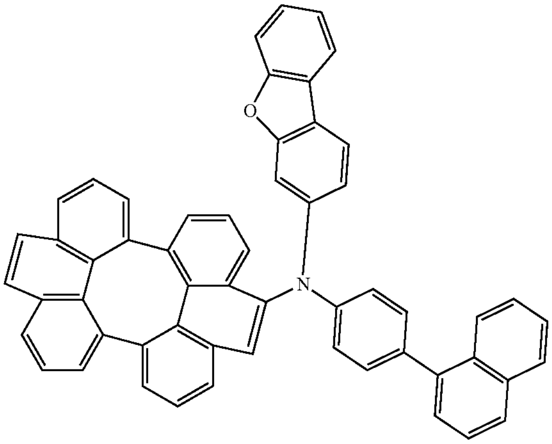
-continued
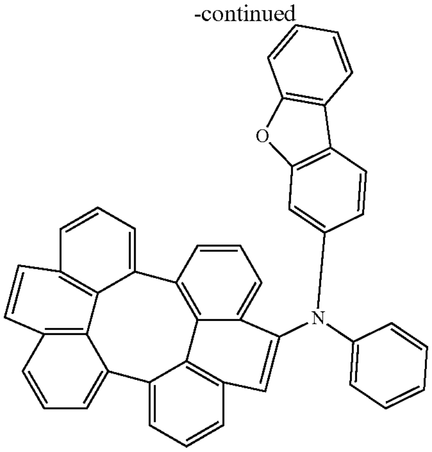
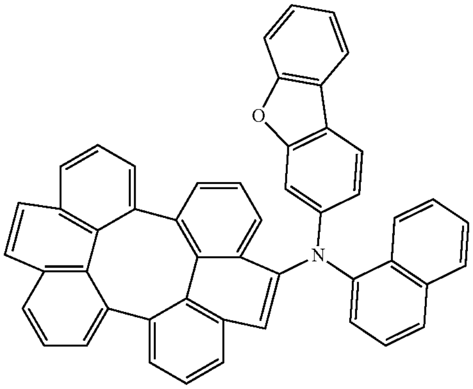
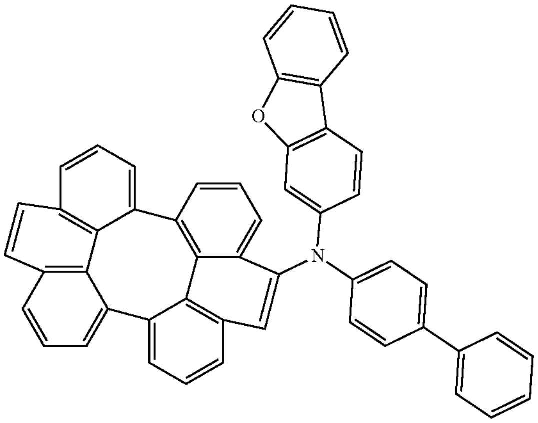
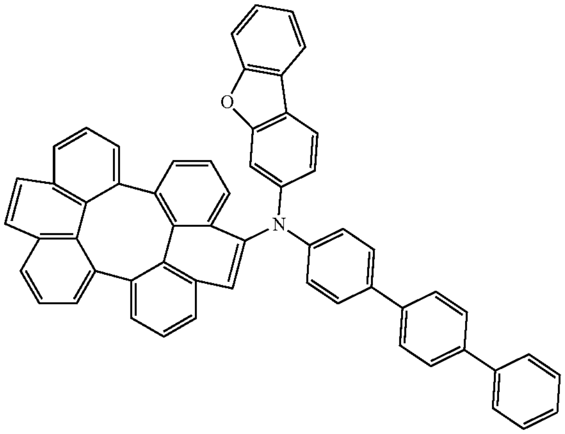

-continued
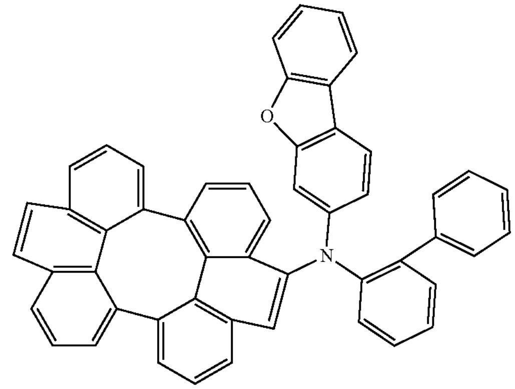
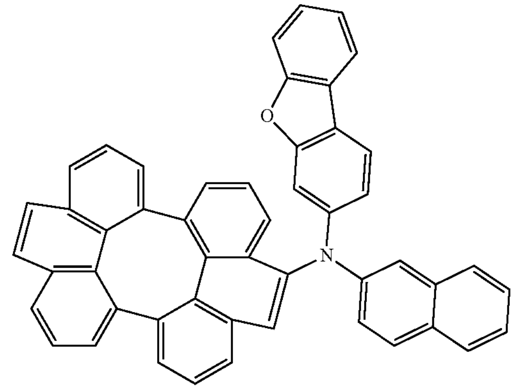
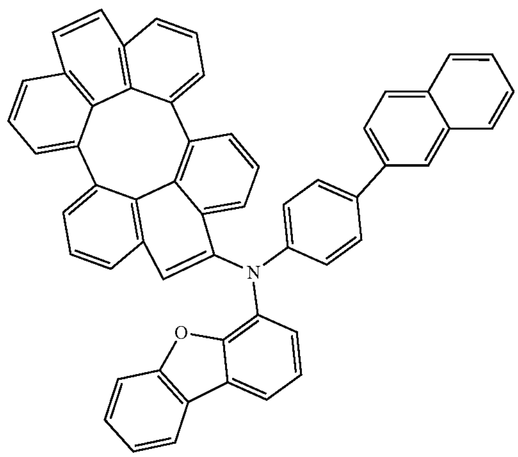
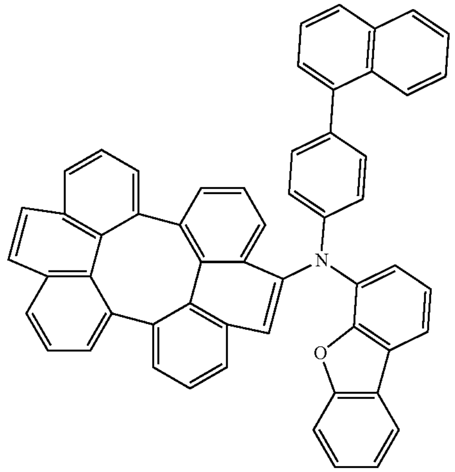
-continued
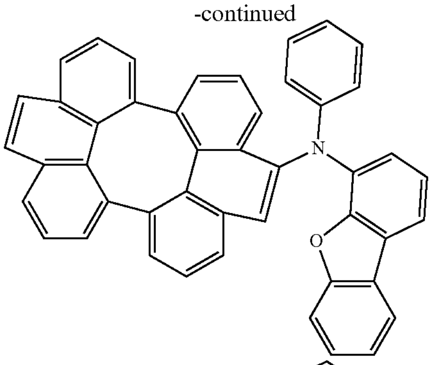
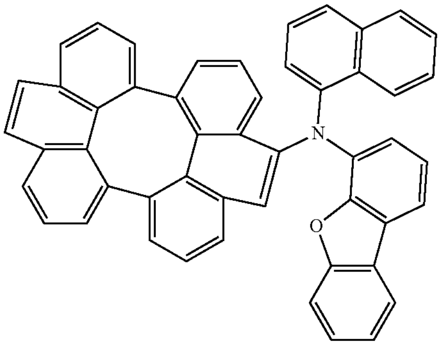
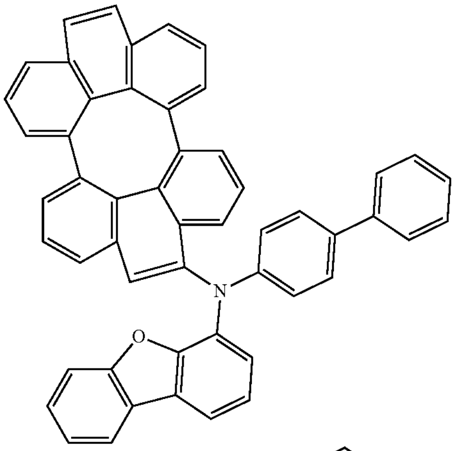
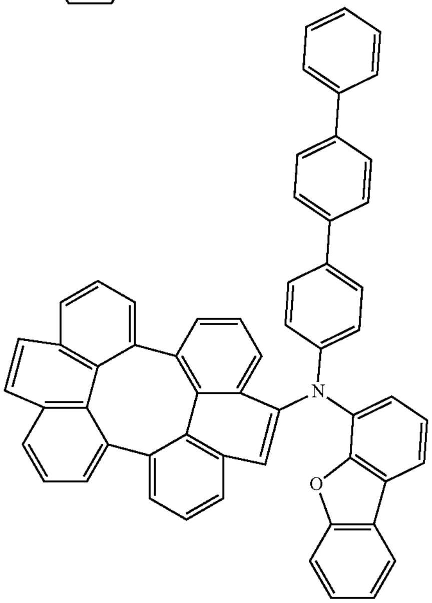

-continued
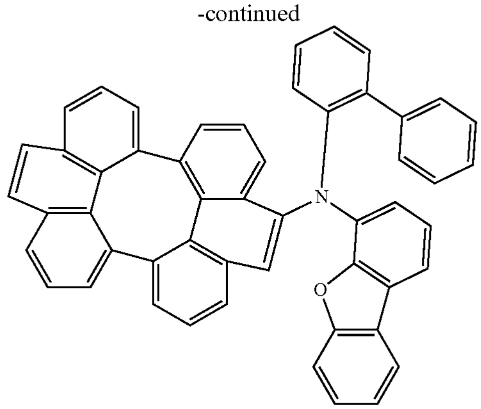
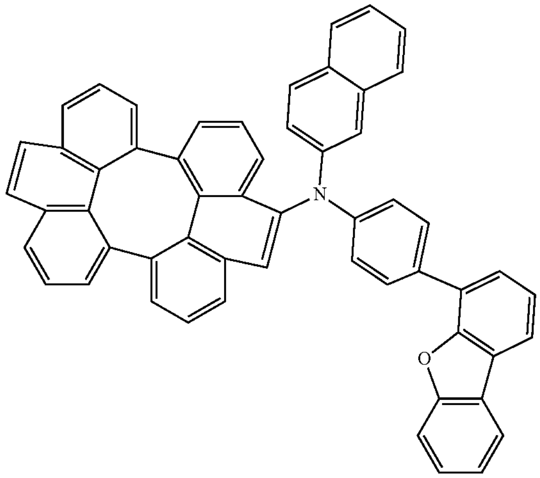
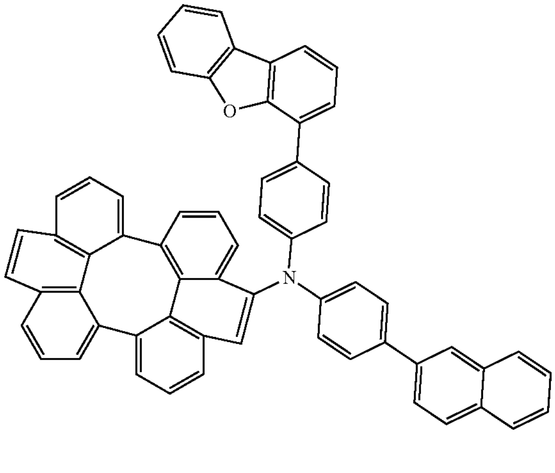
-continued
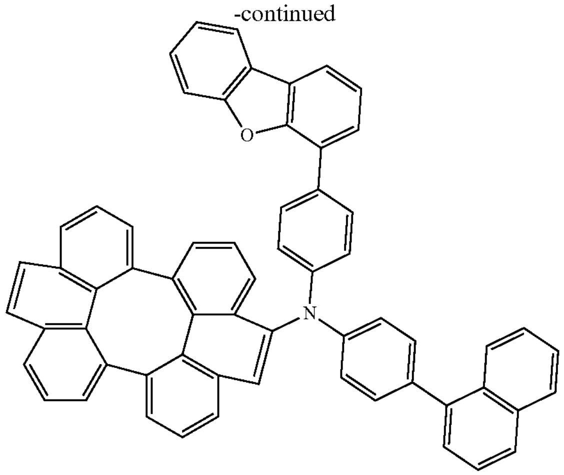
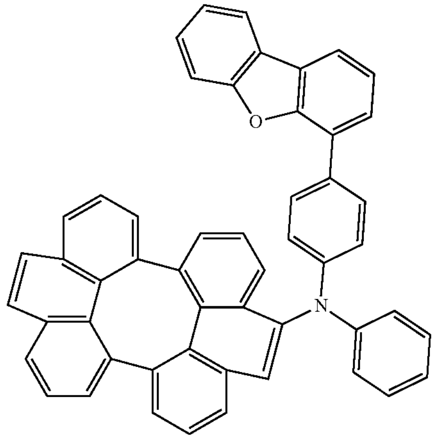
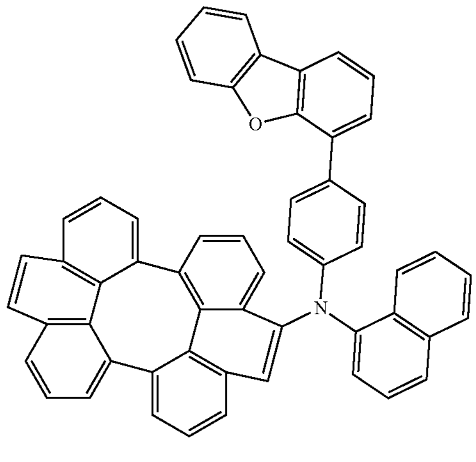

-continued
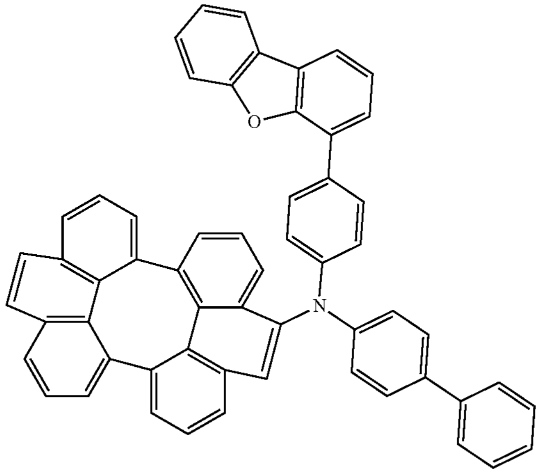
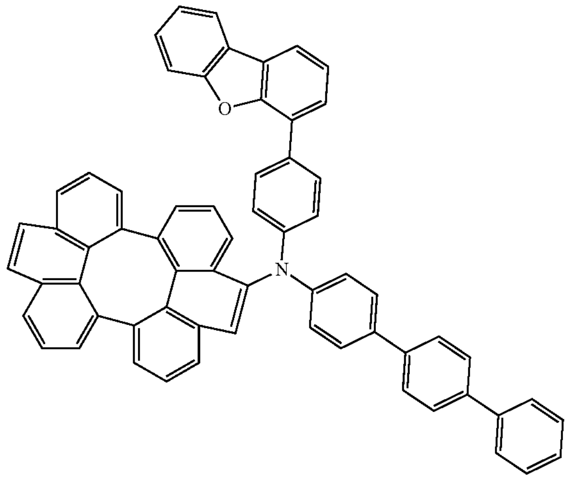
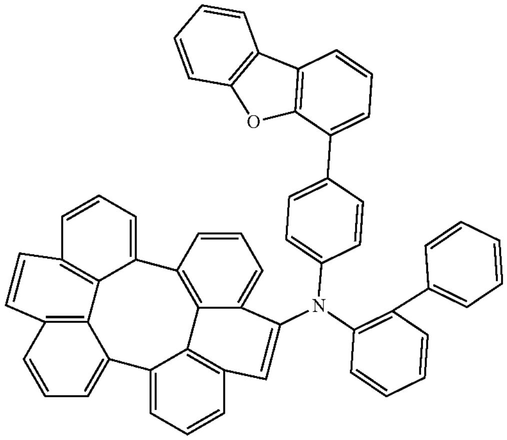
-continued
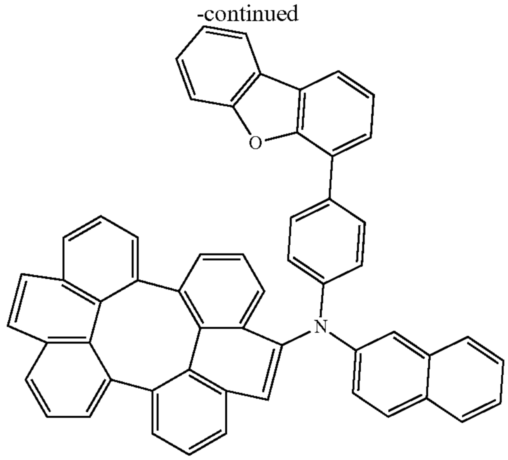
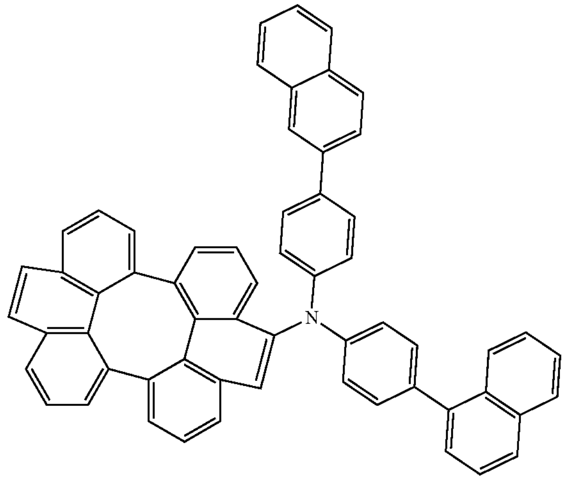
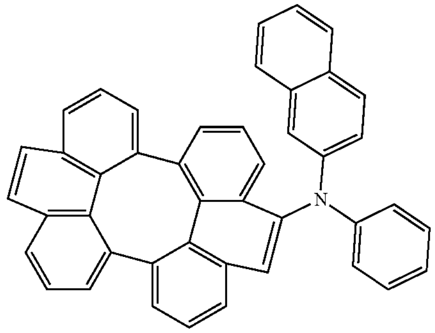
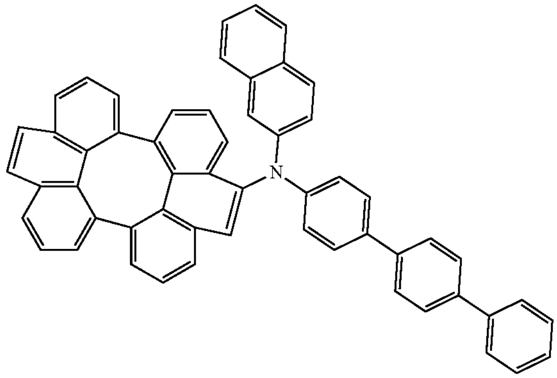

-continued
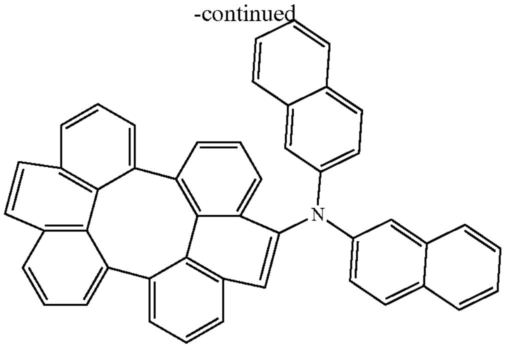
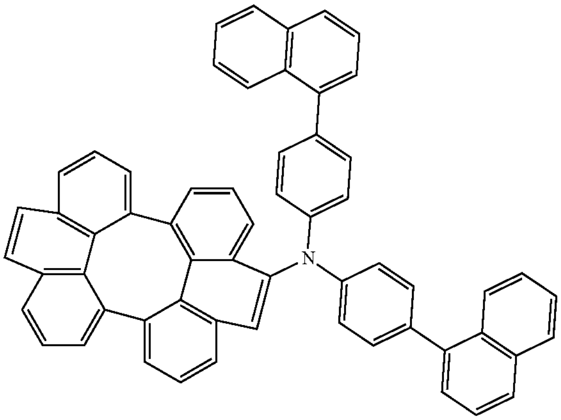
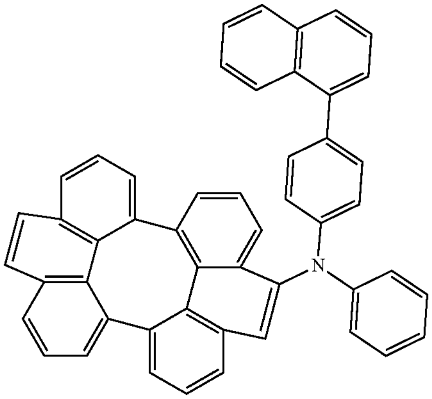
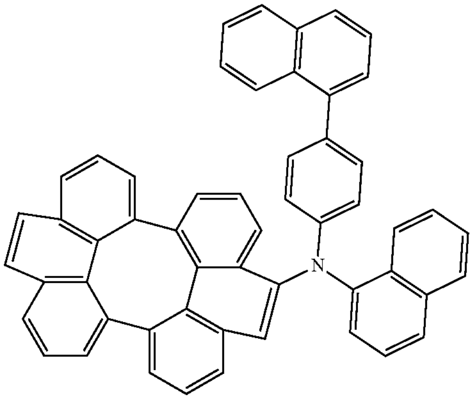
-continued
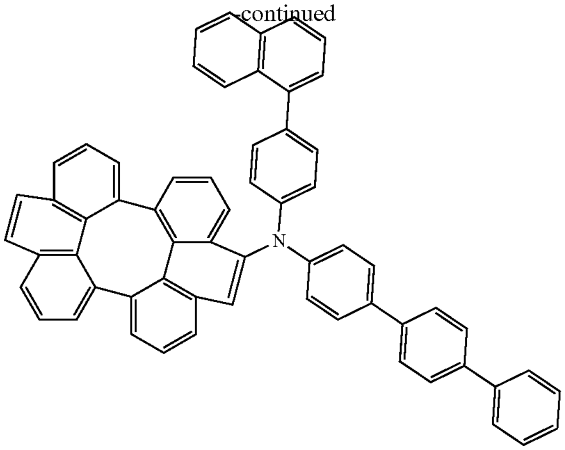
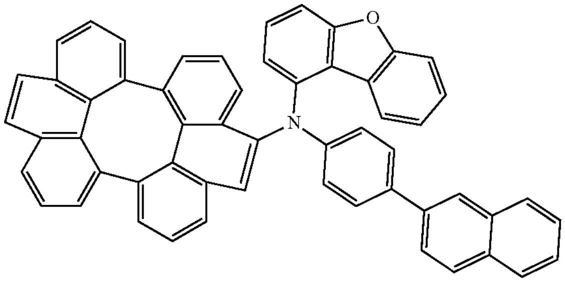
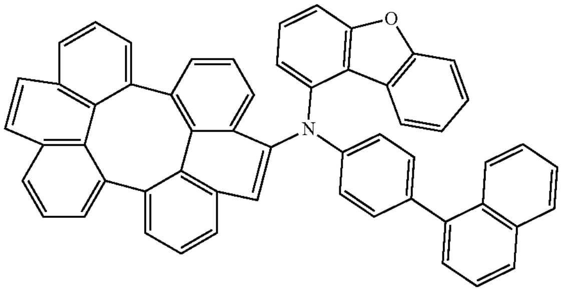
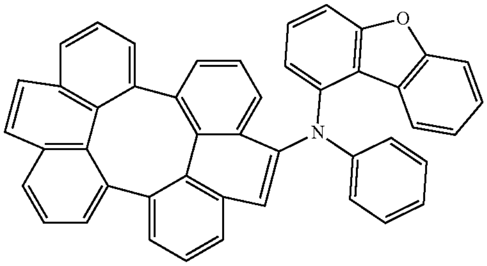
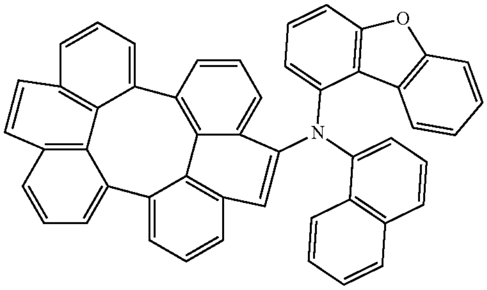

-continued
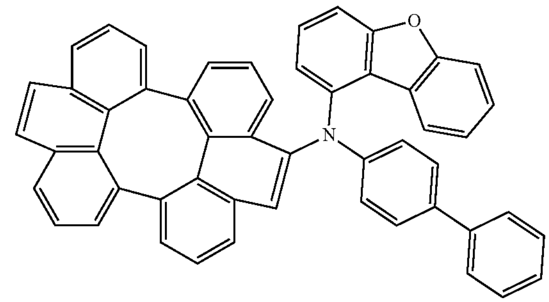
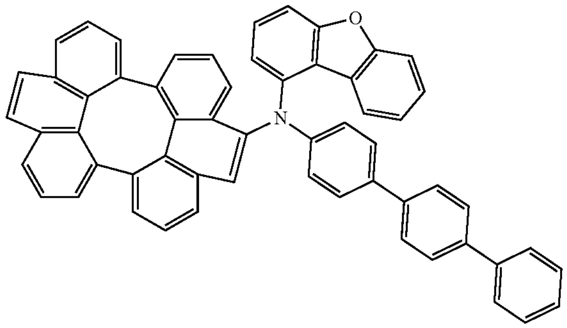
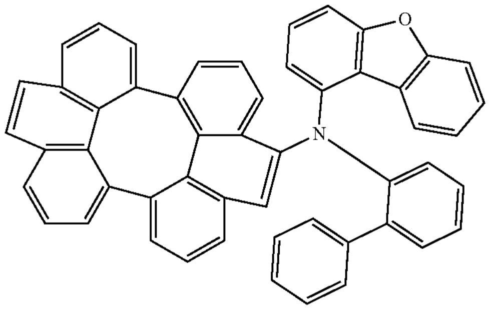
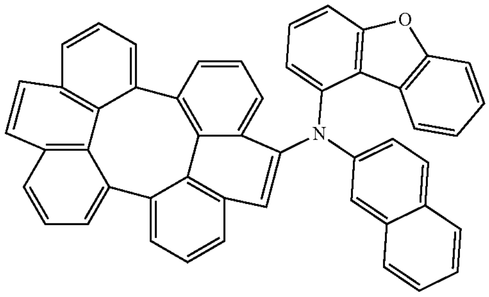
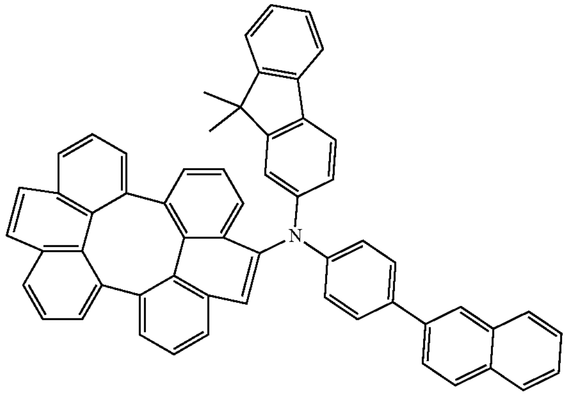
-continued
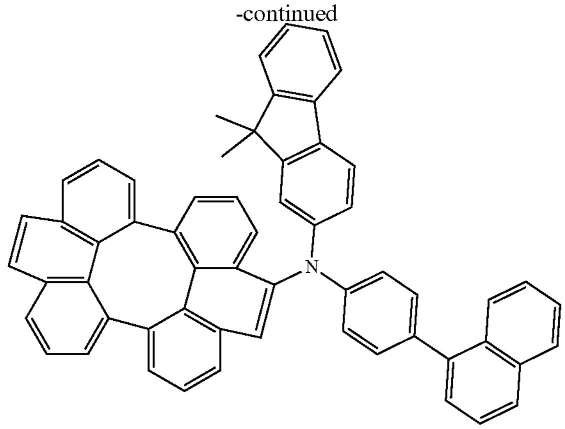
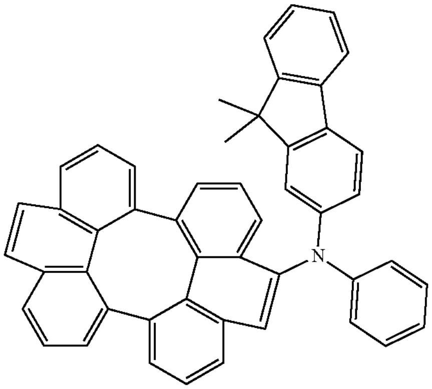
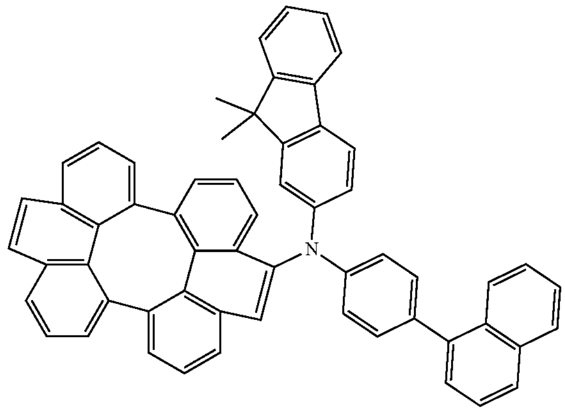
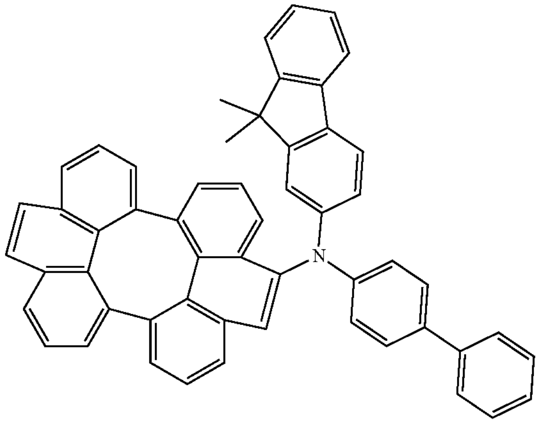

-continued
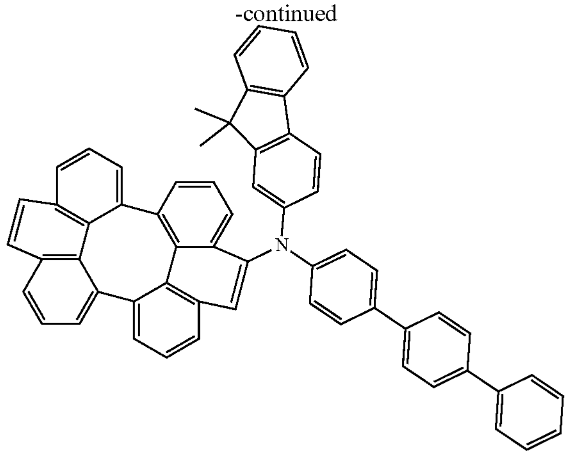
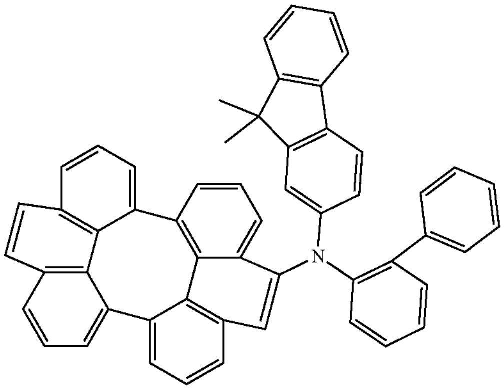
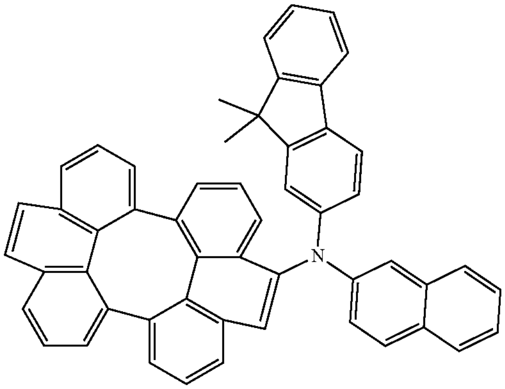
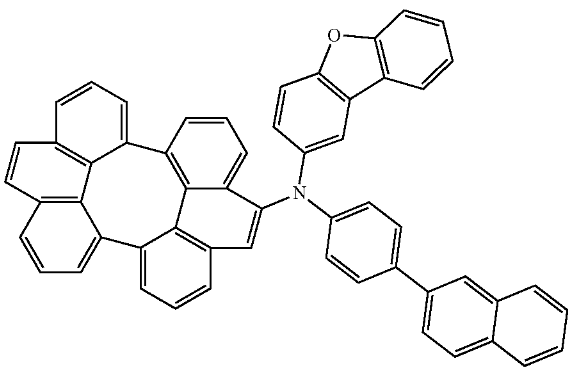
-continued
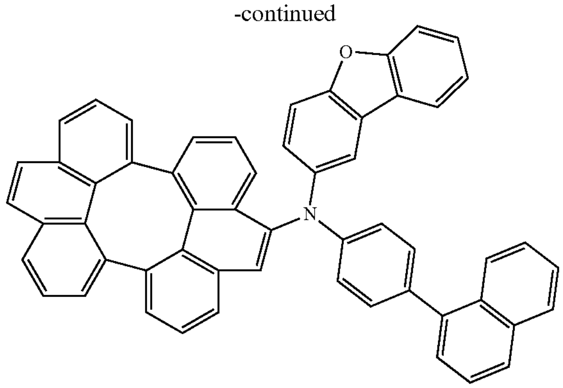
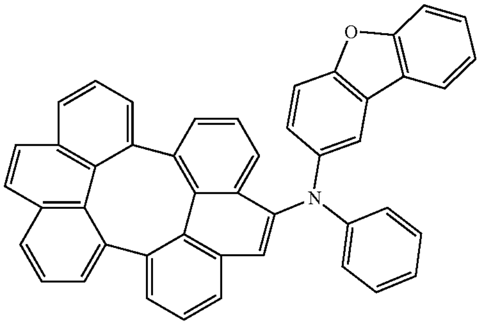
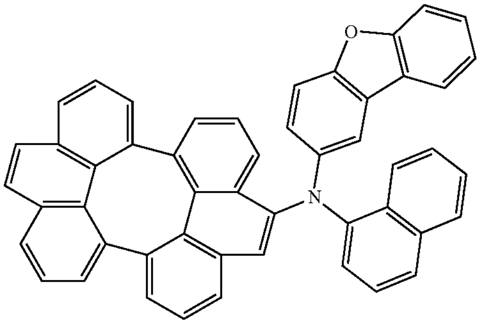
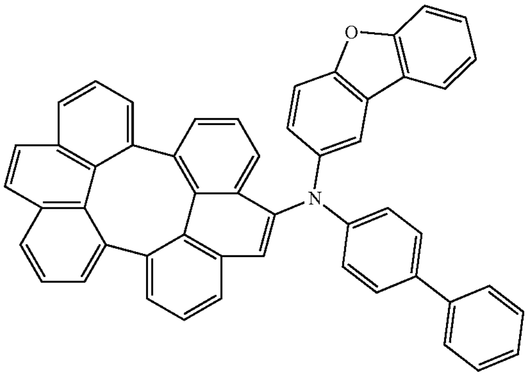

-continued
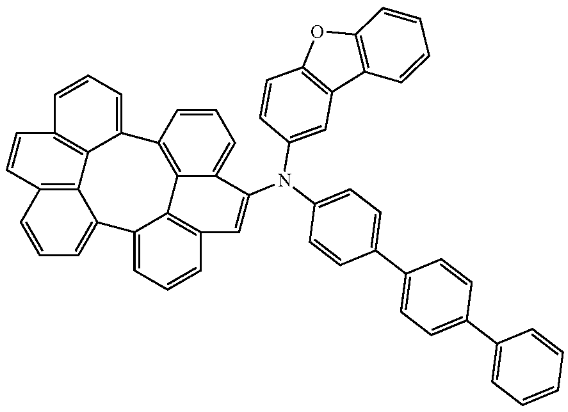
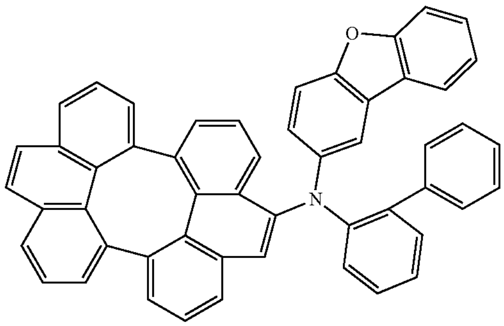
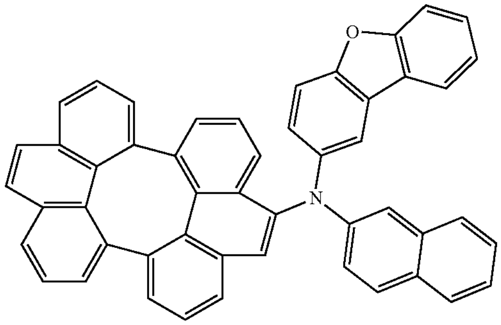
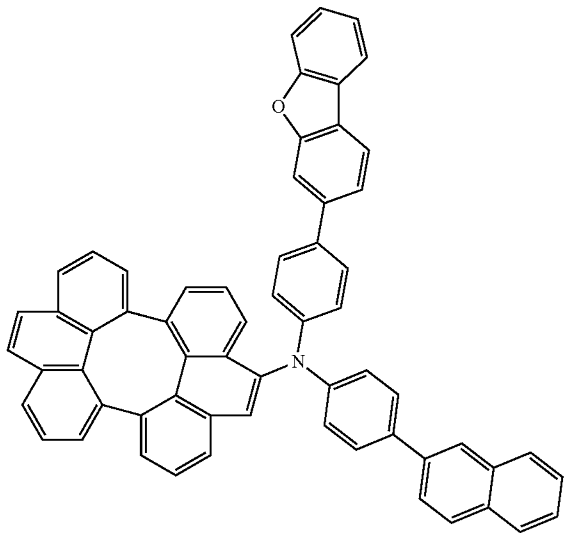
-continued
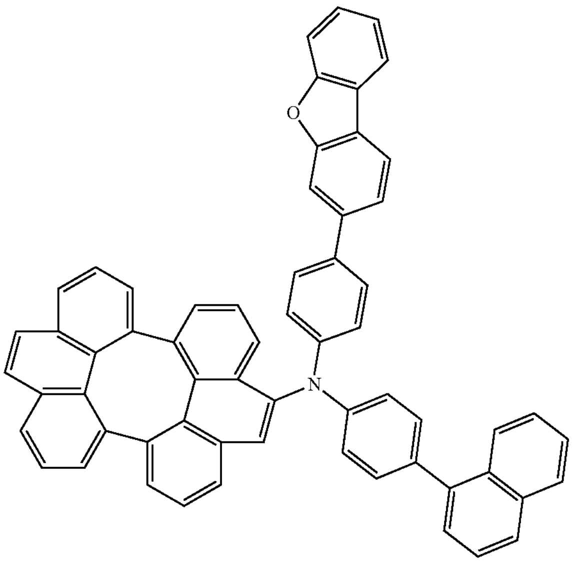
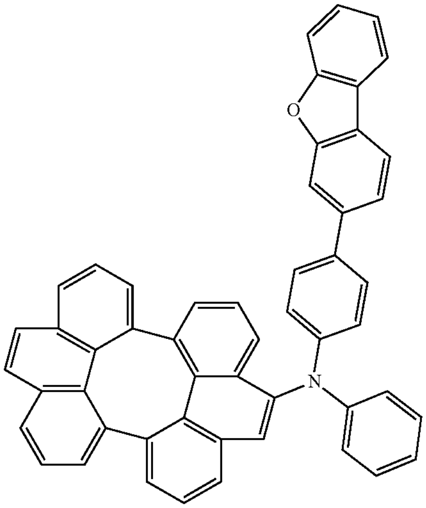
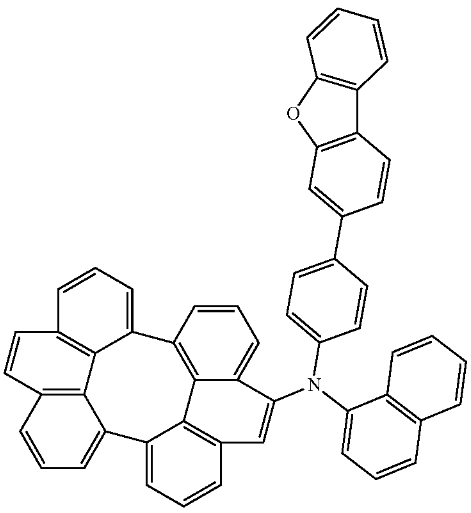

-continued
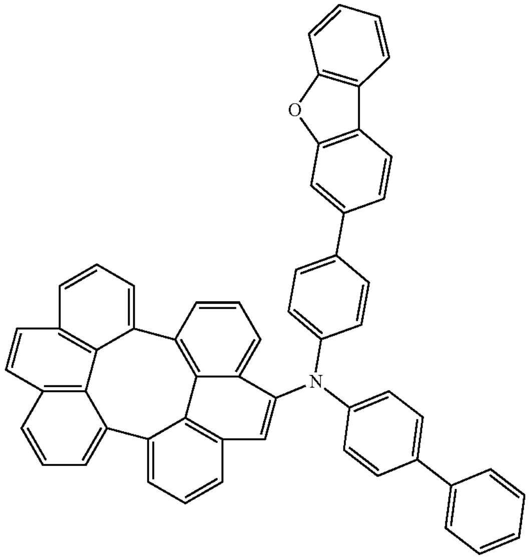
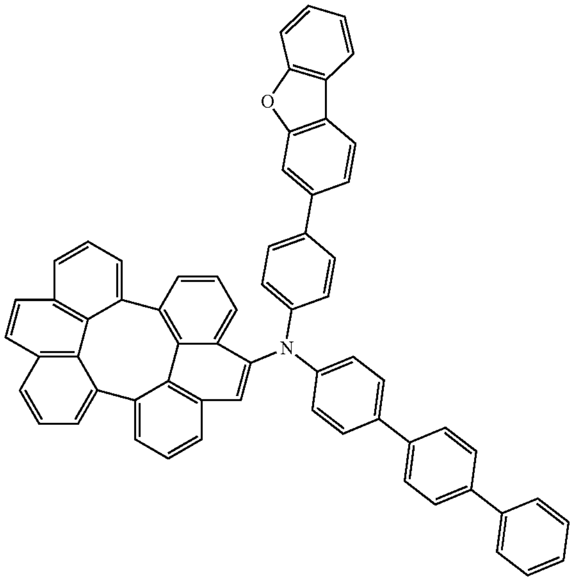
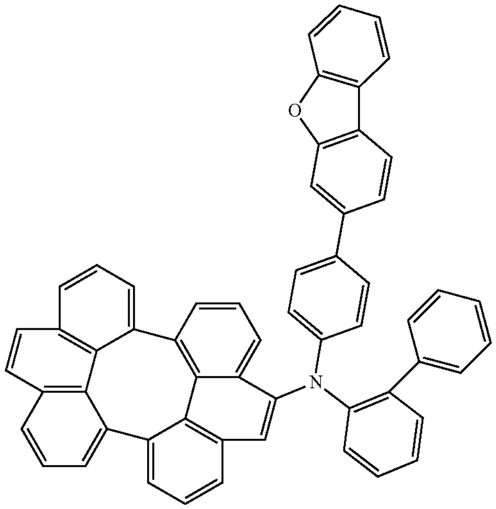
-continued
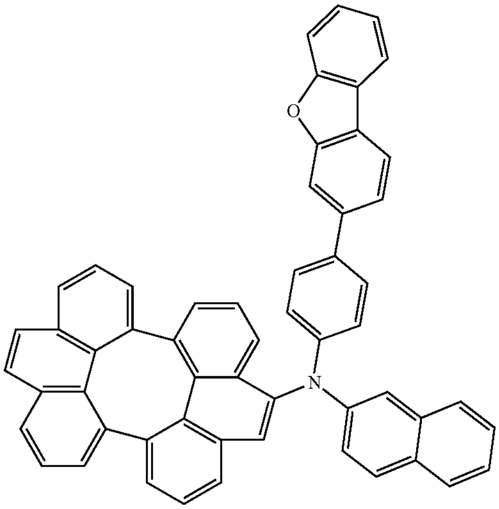
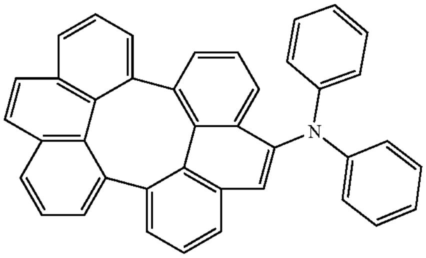
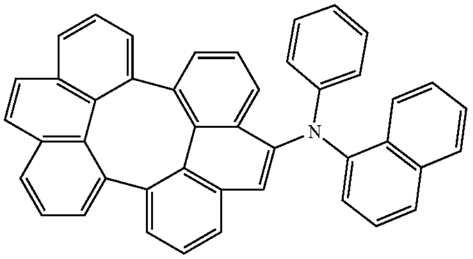
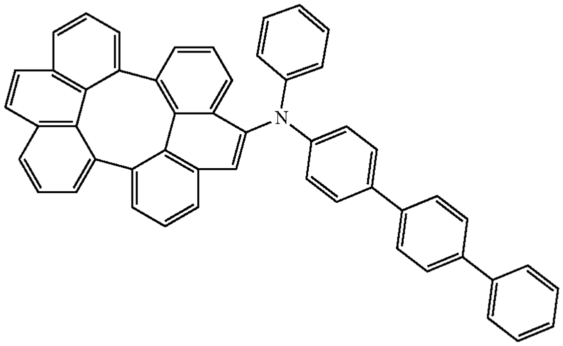

-continued
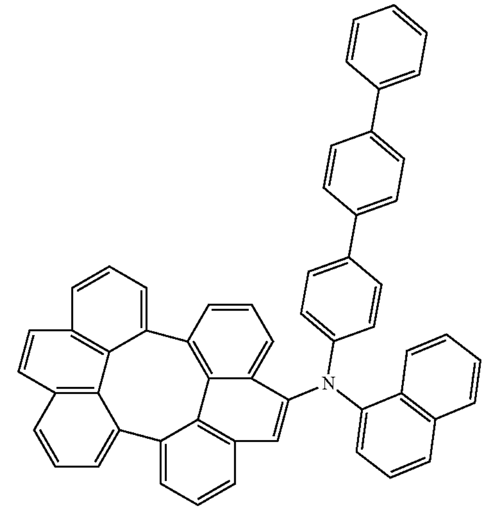
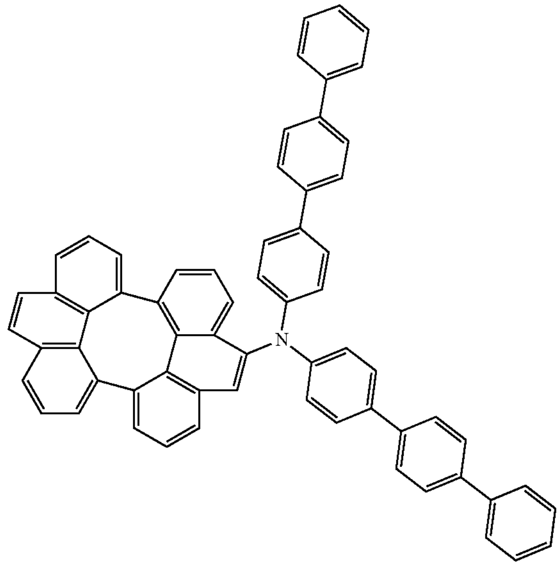
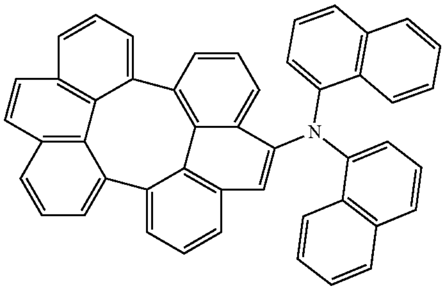
-continued
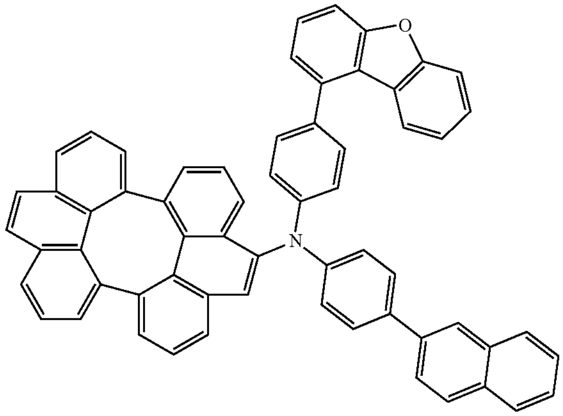
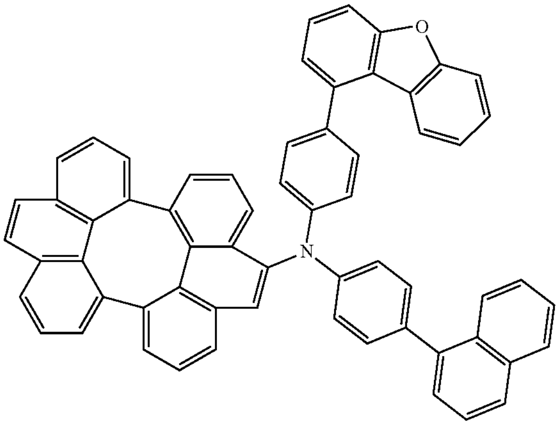
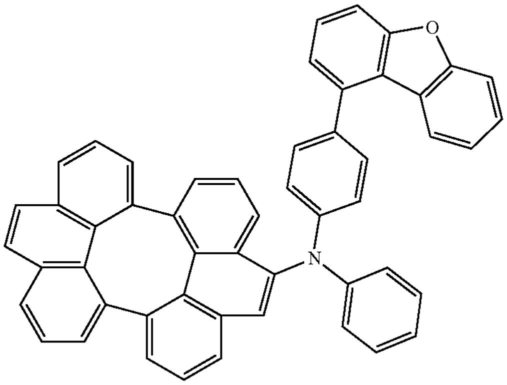
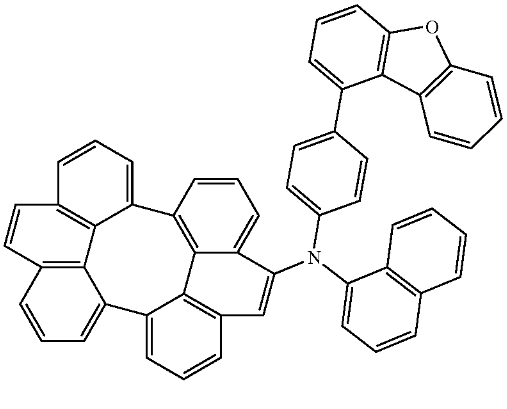

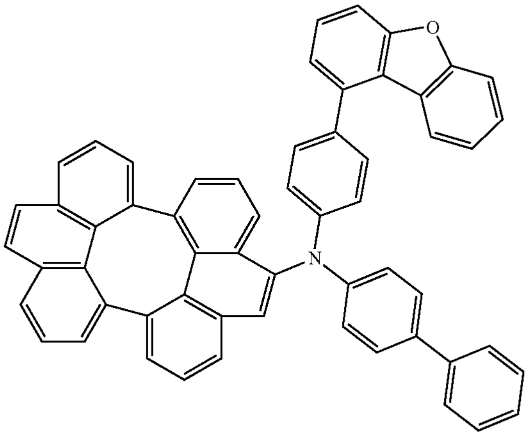
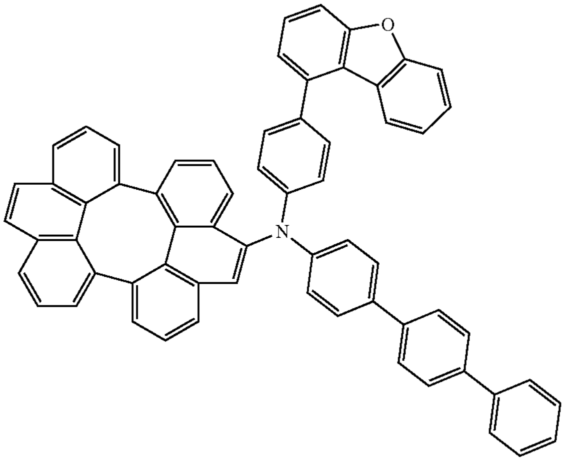
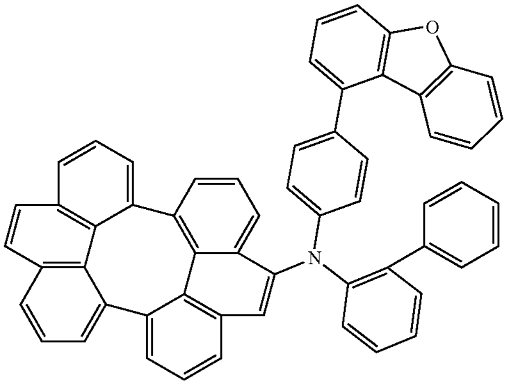
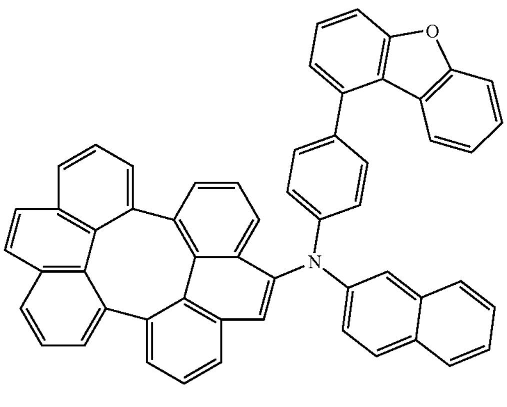
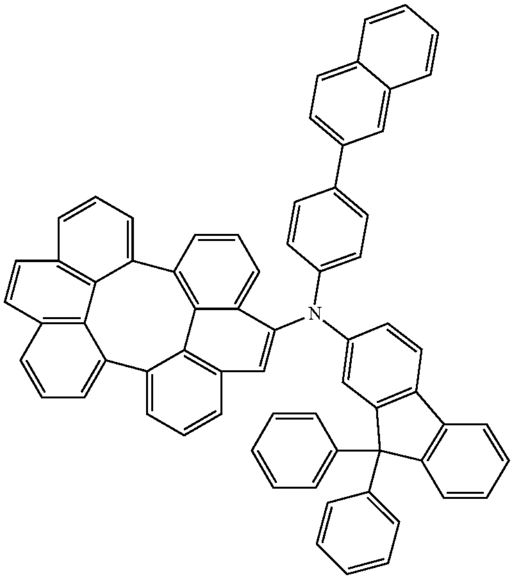
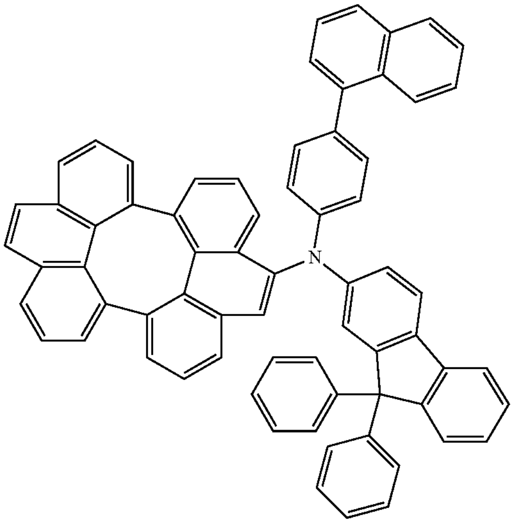
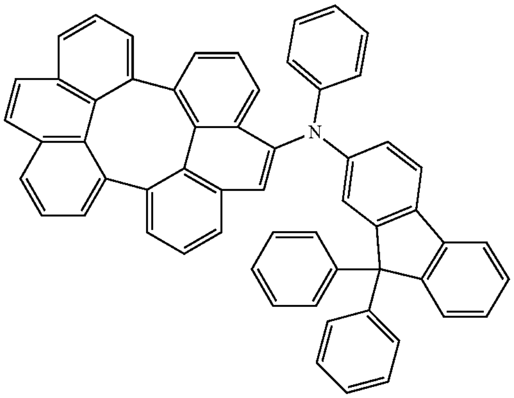

-continued
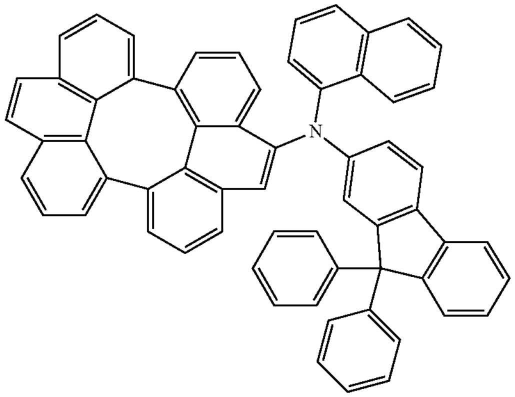
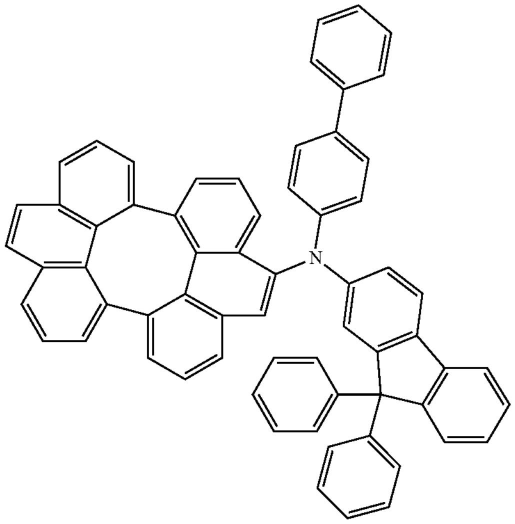
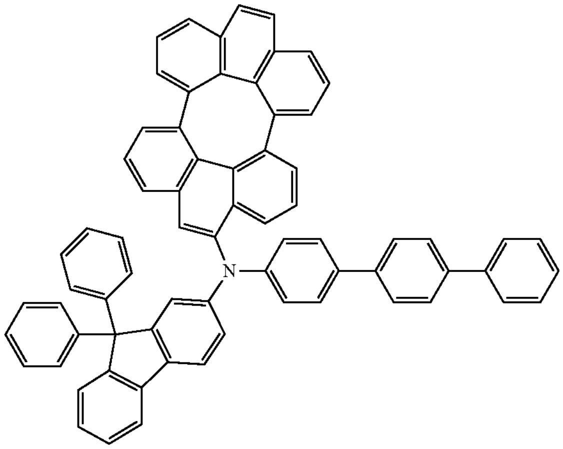
-continued
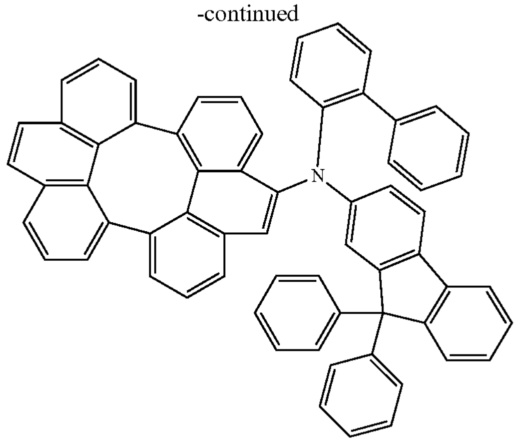
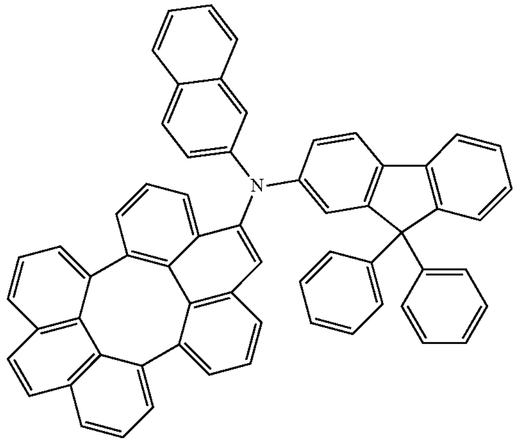
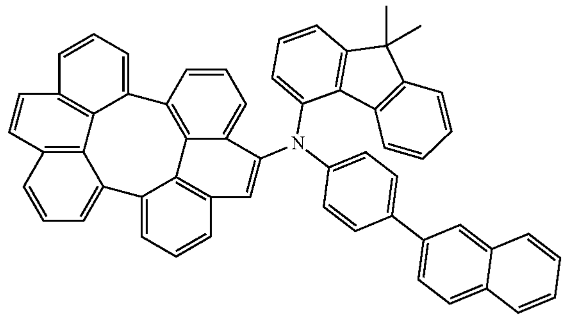
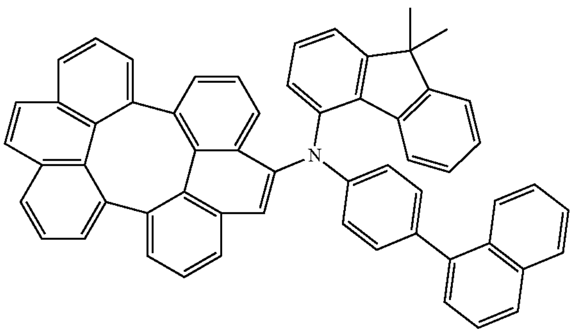

-continued
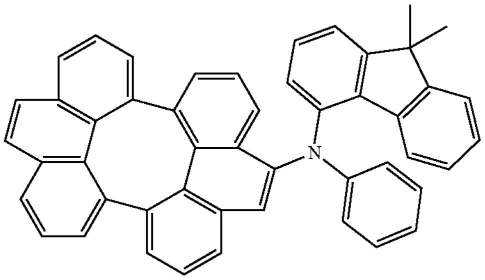
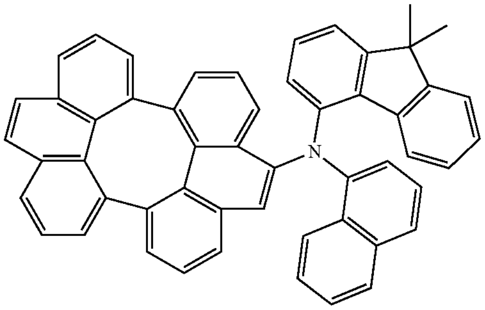
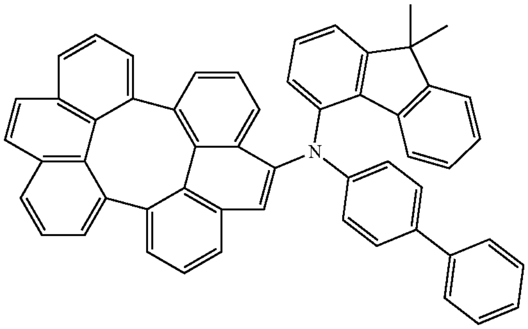
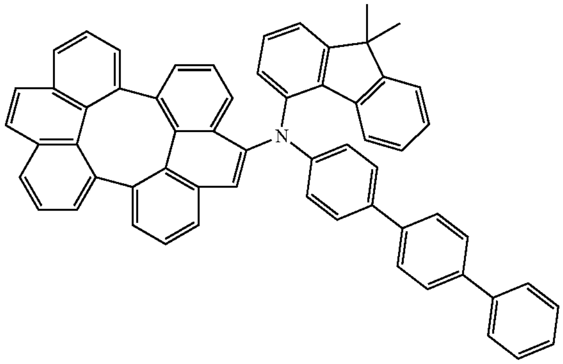
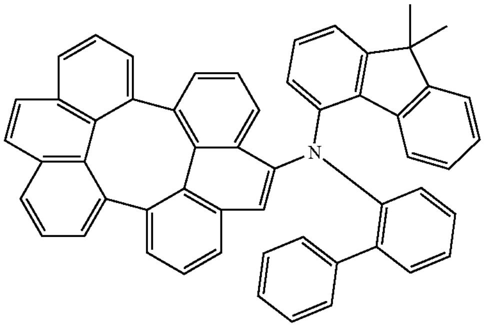
-continued
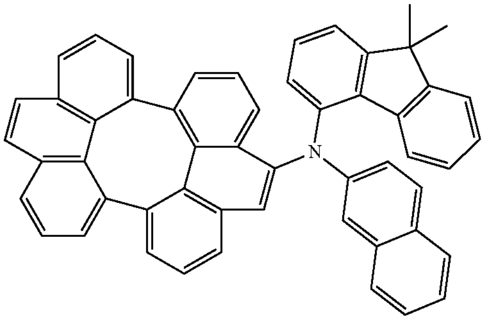
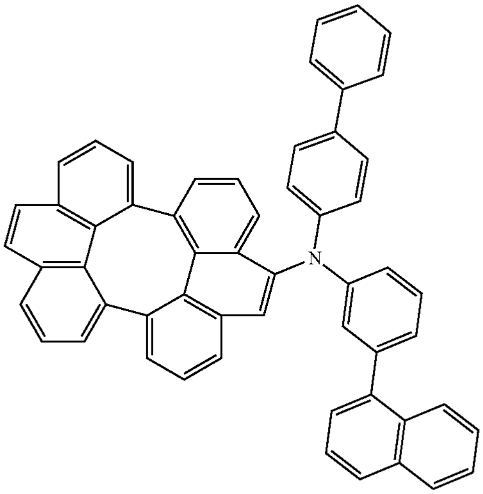
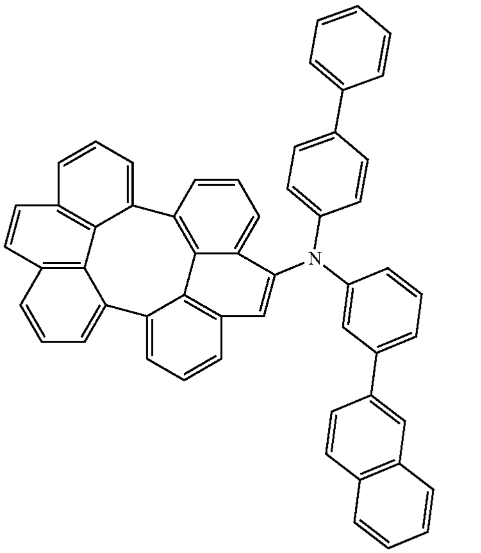
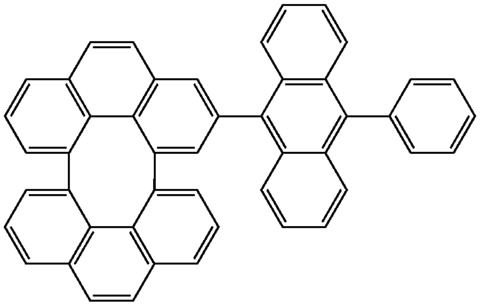

-continued
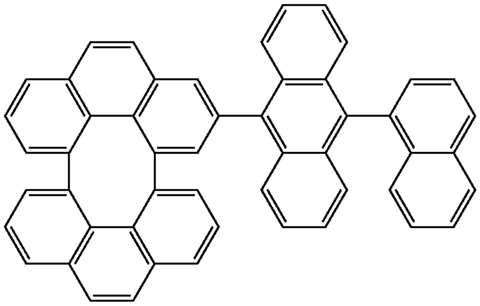
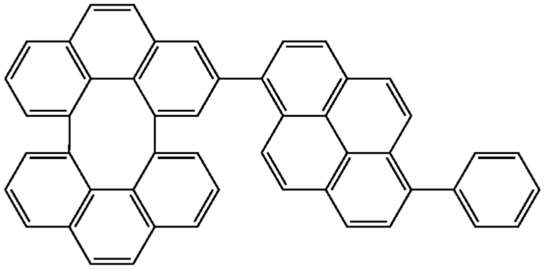
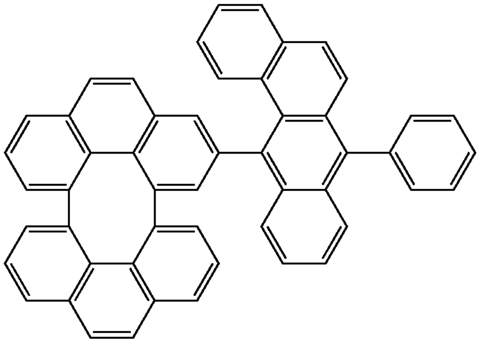
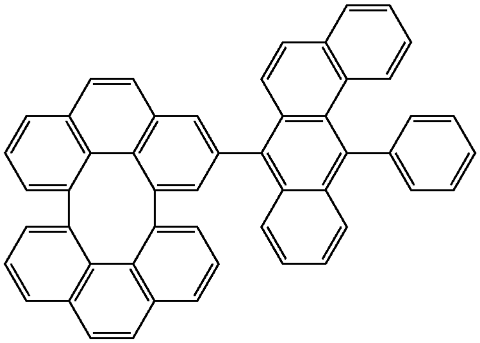
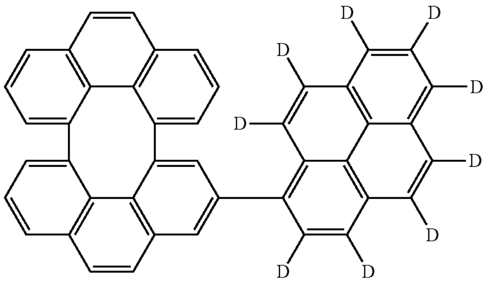
-continued
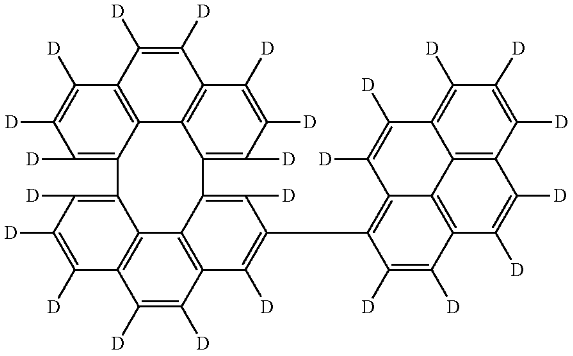
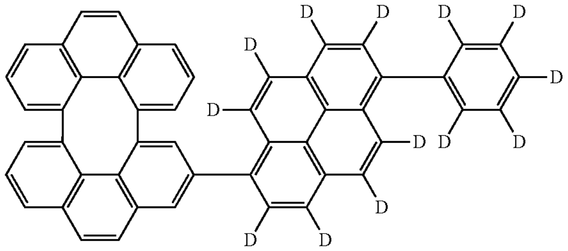
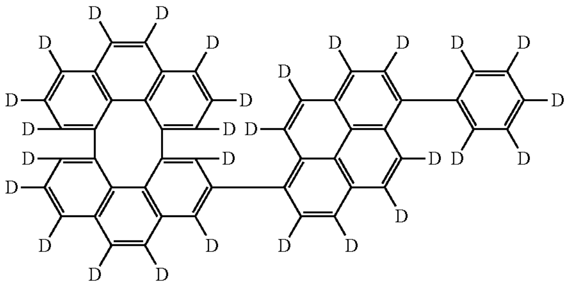
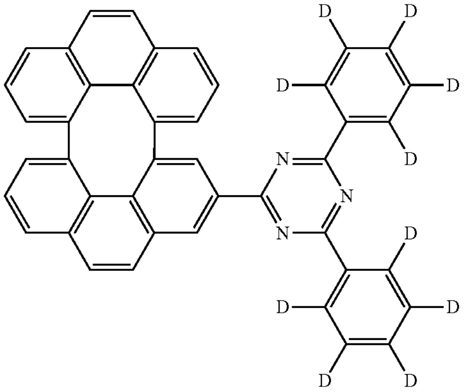
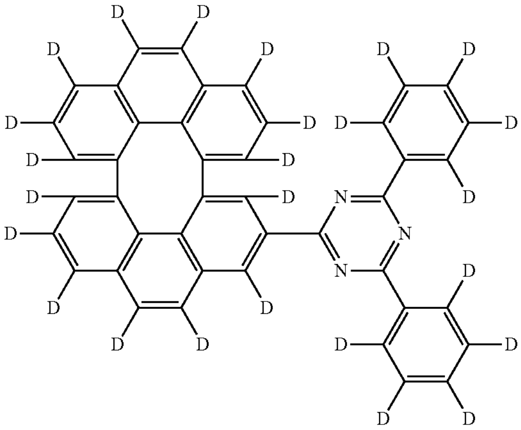

-continued
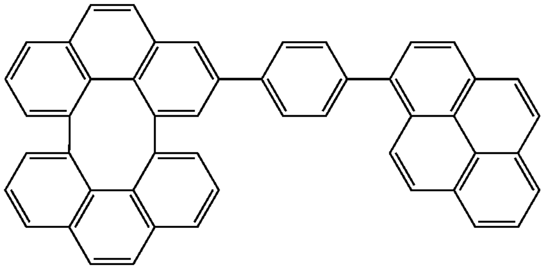
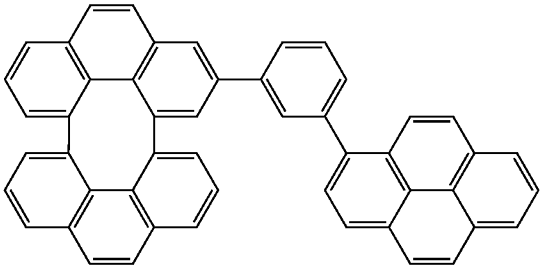
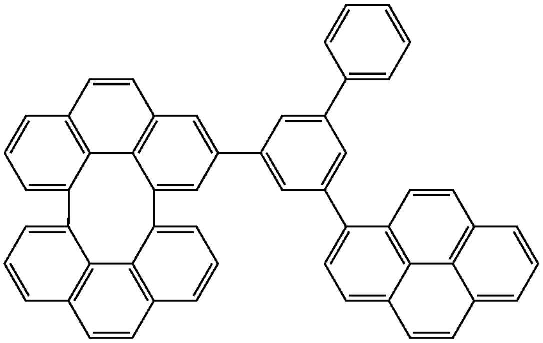
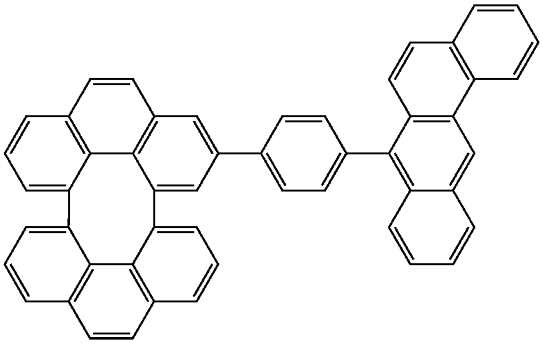
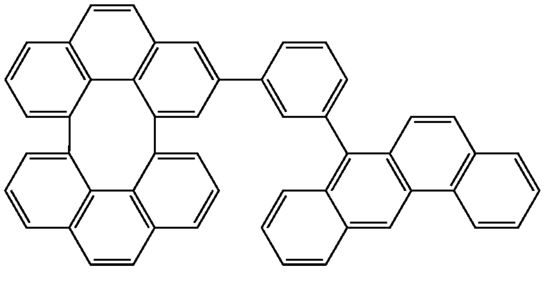
-continued
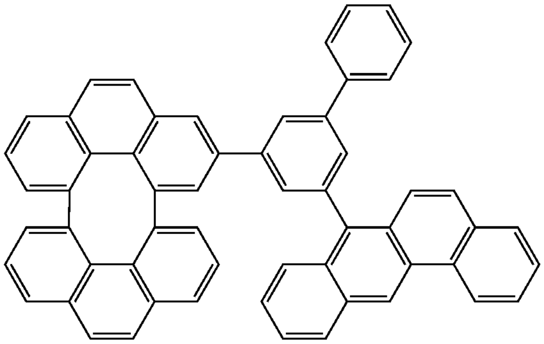
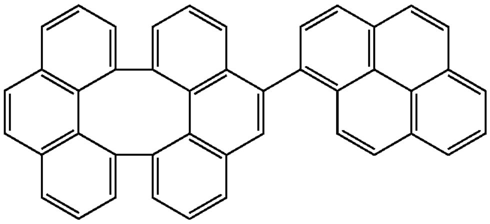
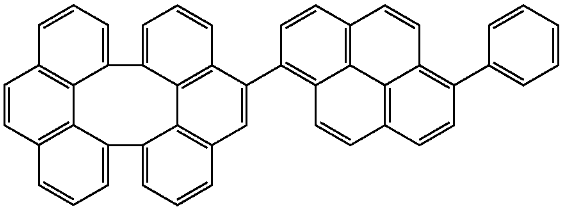
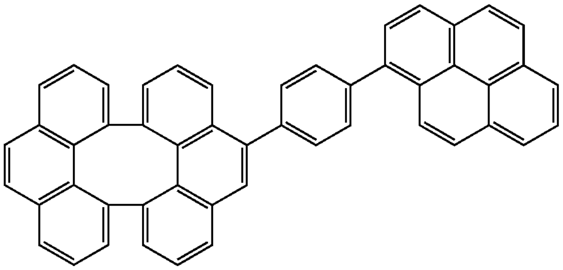
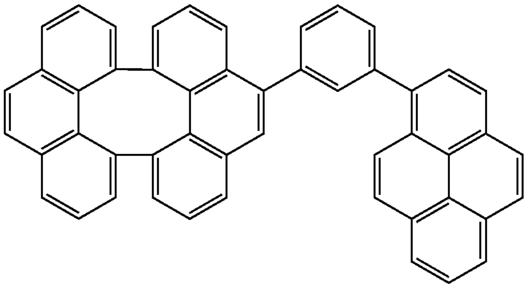

-continued
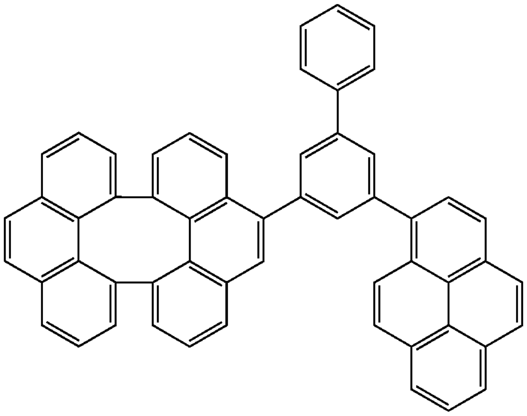
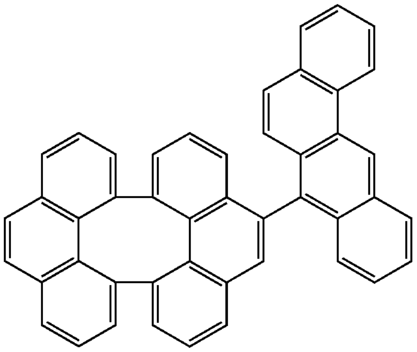
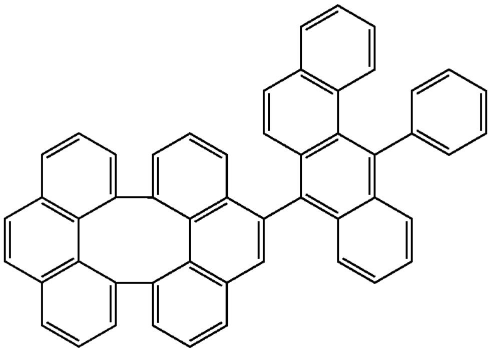
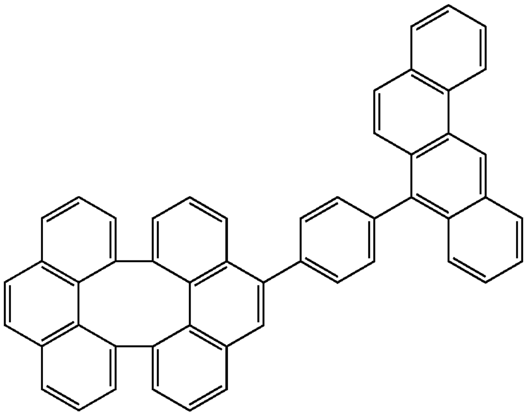
-continued
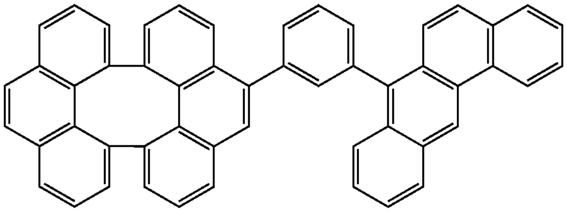
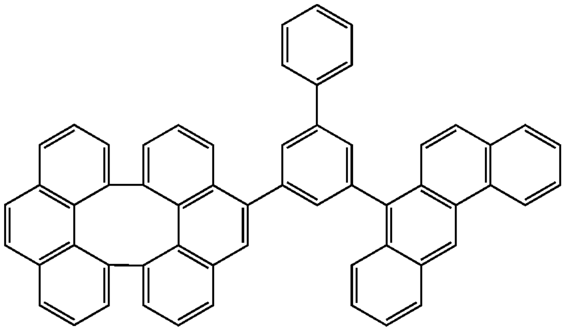
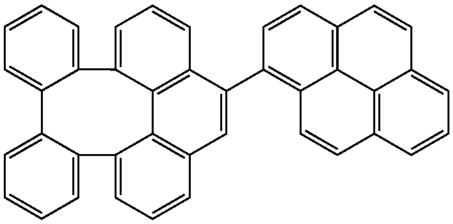
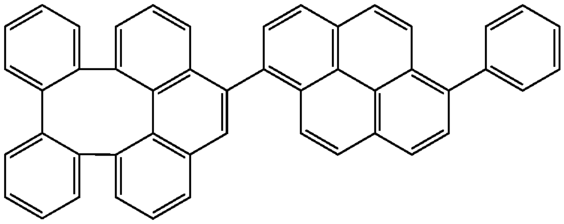
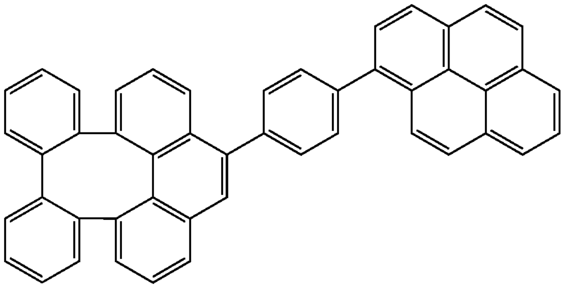
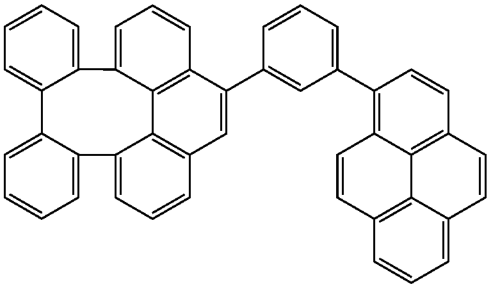

-continued
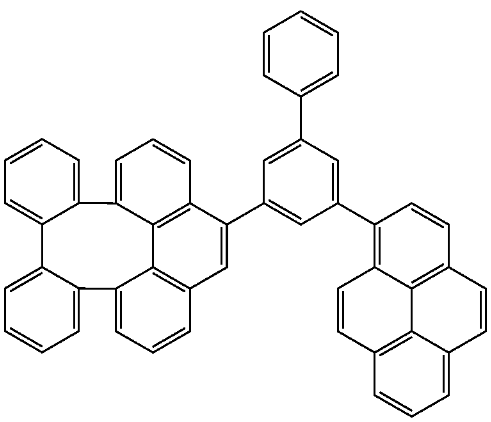
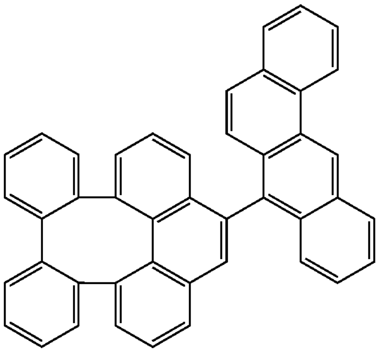
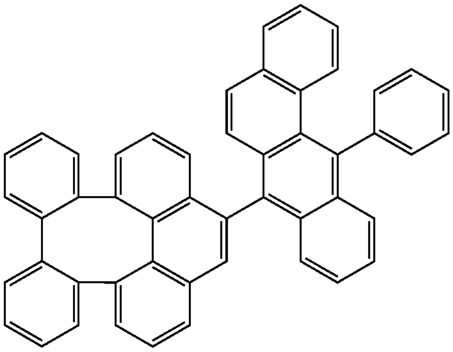
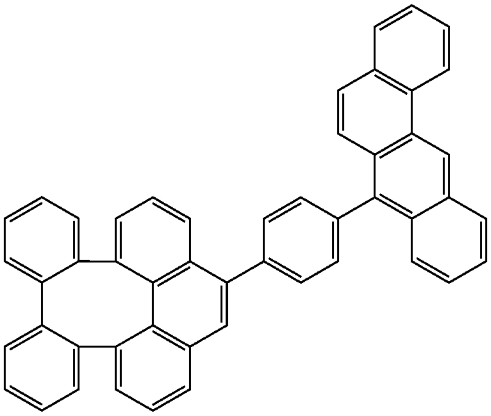
-continued
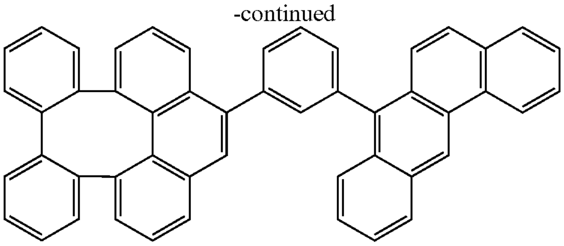
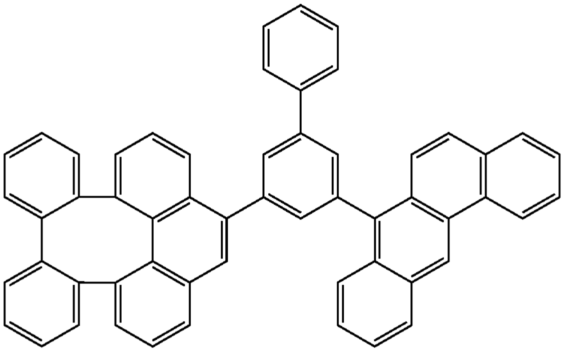
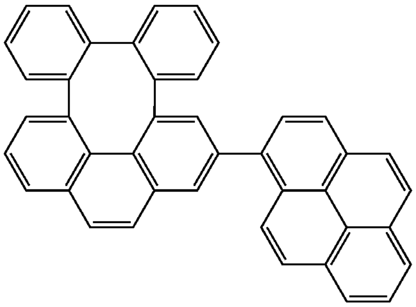
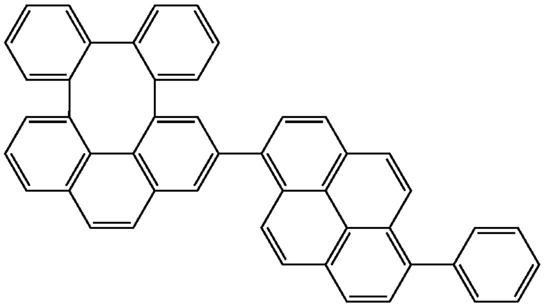
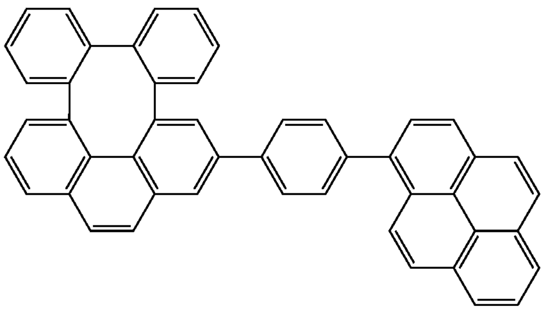

-continued
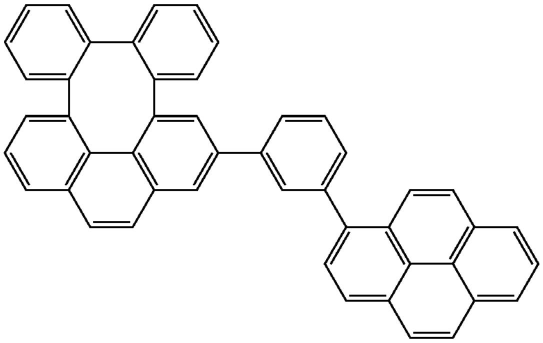
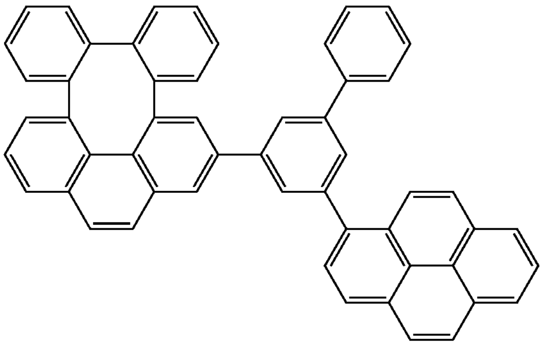
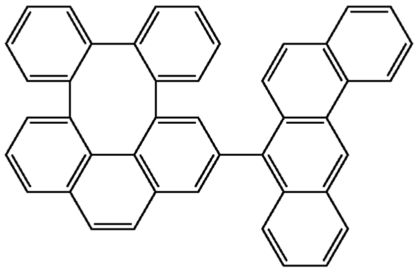
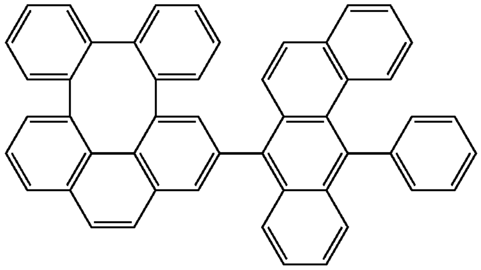
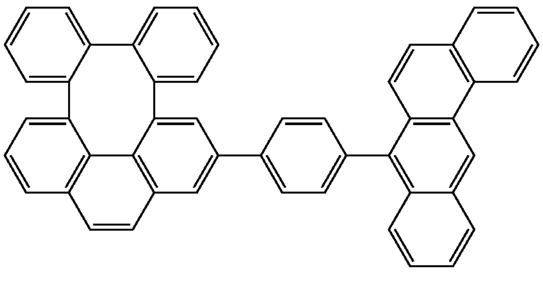
-continued
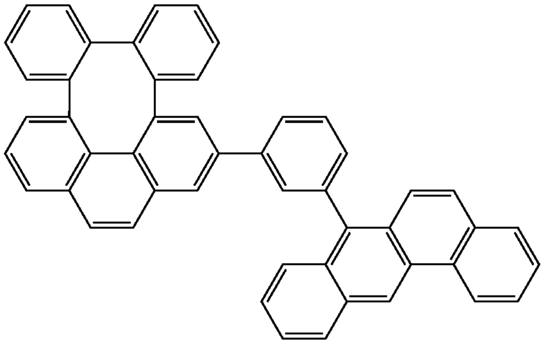
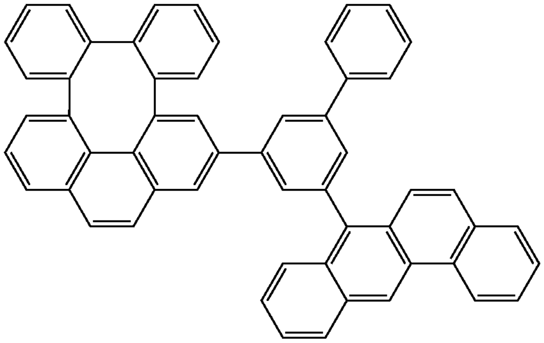
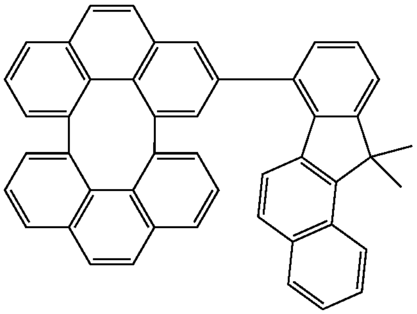
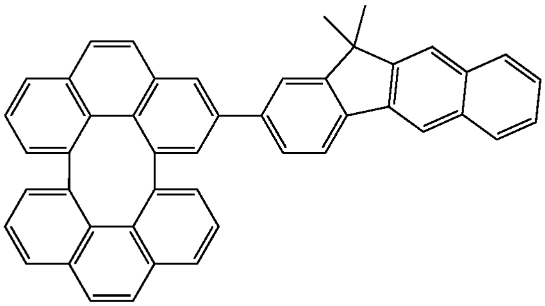
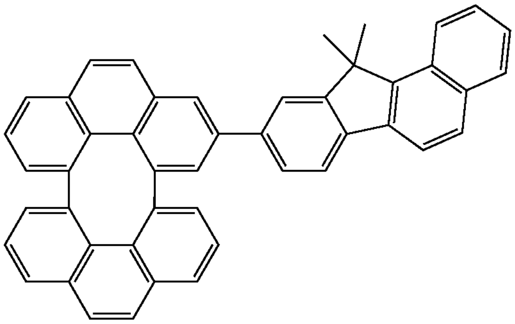

-continued

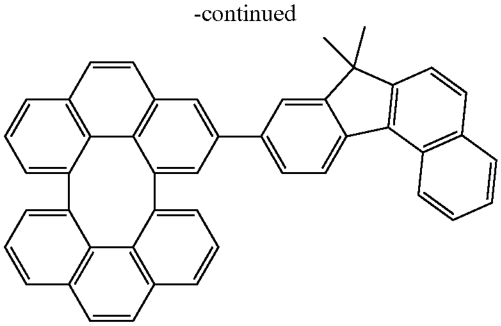

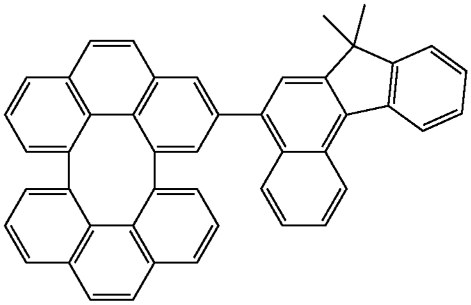

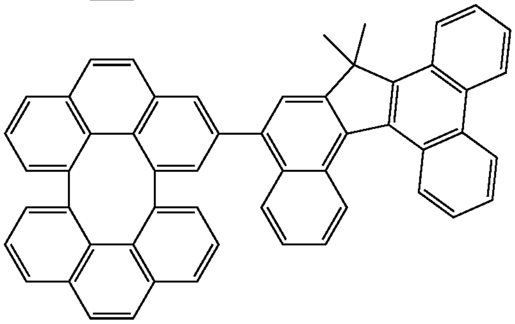

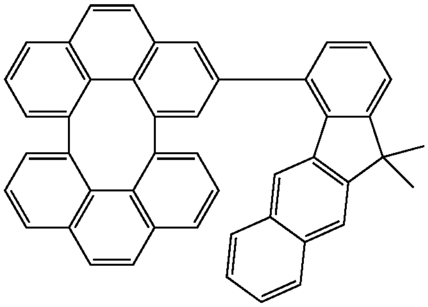

Material for Organic EL Devices

The material for organic EL devices according to one embodiment of the present invention comprises the inventive compound. The content of the inventive compound in the material for organic EL devices may be 1% by mass or more (including 100%), and is preferably 10% by mass or more (including 100%), more preferably 50% by mass or more (including 100%), even more preferably 80% by mass or more (including 100%), and still more preferably 90% by mass or more (including 100%). The material for organic EL devices according to one embodiment of the present invention is useful for the production of an organic EL device.

Organic EL Device

The organic EL device according to one embodiment of the present invention includes an anode, a cathode, and organic layers disposed between the anode and the cathode. The organic layers include a light emitting layer, and at least one layer of the organic layers comprises the inventive compound.

Examples of the organic layer comprising the inventive compound include, and are not limited to, a hole transporting zone (such as a hole injecting layer, a hole transporting layer, an electron blocking layer, and an exciton blocking layer) provided between the anode and the light emitting layer, the light emitting layer, a space layer, and an electron transporting zone (such as an electron injecting layer, an electron transporting layer, and a hole blocking layer) provided between the cathode and the light emitting layer.

In one embodiment of the organic EL device according to the present invention, the organic layers preferably include the electron transporting zone between the cathode and the light emitting layer, the electron transporting zone comprising the inventive compound.

While there is no particular limitation as long as the effect of the present invention is ensured, in one embodiment of the organic EL device according to the present invention, the organic layers more preferably include the electron transporting zone between the cathode and the light emitting layer, the electron transporting zone comprising at least one of the following compounds:

a compound represented by the formula (1A) where at least one selected from $R^1$ to $R^{16}$ is represented by the formula (2A) or (2D), or a compound represented by the formula (1B) where at least one selected from $R^{21}$ to $R^{36}$ is represented by the formula (2A) or (2D);

a compound represented by the formula (1A2A-1), (1A2A-2), (1A2D-1), (1A2D-2), (1B2A-1), (1B2A-2), (1B2A-3), (1B2A-4), (1B2A-5), (1B2D-1), (1B2D-2), (1B2D-3), (1B2D-4), or (1B2D-5); and a compound represented by the formula (1A2A-11), (1A2A-12), (1A2A-13), (1A2A-14), (1A2A-15), (1A2D-11), (1A2D-12), (1A2D-13), (1A2D-14), (1A2D-15), (1B2A-11), (1B2A-12), (1B2A-13), (1B2A-14), (1B2A-15), (1B2A-16), (1B2D-11), (1B2D-12), (1B2D-13), (1B2D-14), (1B2D-15) or (1B2D-16).

Thus, while there is no particular limitation as long as the effect of the present invention is ensured, in one embodiment of the present invention, the inventive compound which can be preferably used as a material for the electron transporting zone is at least one selected from the group consisting of:

a compound represented by the formula (1A) where at least one selected from $R^1$ to $R^{16}$ is represented by the formula (2A) or (2D), and a compound represented by the formula (1B) where at least one selected from $R^{21}$ to $R^{36}$ is represented by the formula (2A) or (2D);

compounds represented by the formulae (1A2A-1), (1A2A-2), (1A2D-1), (1A2D-2), (1B2A-1), (1B2A-2), (1B2A-3), (1B2A-4), (1B2A-5), (1B2D-1), (1B2D-2), (1B2D-3), (1B2D-4), and (1B2D-5); and compounds represented by the formulae (1A2A-11), (1A2A-12), (1A2A-13), (1A2A-14), (1A2A-15), (1A2D-11), (1A2D-12), (1A2D-13), (1A2D-14), (1A2D-15), (1B2A-11), (1B2A-12), (1B2A-13), (1B2A-14), (1B2A-15), (1B2A-16), (1B2D-11), (1B2D-12), (1B2D-13), (1B2D-14), (1B2D-15) and (1B2D-16).

In one embodiment of the organic EL device according to the present invention, the organic layers preferably include the hole transporting zone between the anode and the light emitting layer, the hole transporting zone comprising the inventive compound.

While there is no particular limitation as long as the effect of the present invention is ensured, in one embodiment of the organic EL device according to the present invention, the organic layers preferably include the hole transporting zone between the anode and the light emitting layer, the hole transporting zone comprising at least one of the following compounds:

a compound represented by the formula (1A) where at least one selected from $R^1$ to $R^{16}$ is represented by the formula (2B), or a compound represented by the formula (1B) where at least one selected from $R^{21}$ to $R^{36}$ is represented by the formula (2B);

a compound represented by the formula (1A2B-1), (1A2B-2), (1B2B-1), (1B2B-2), (1B2B-3), (1B2B-4), or (1B2B-5); and a compound represented by the formula (1A2B-11), (1A2B-12), (1A2B-13), (1A2B-14), (1A2B-15), (1B2B-11), (1B2B-12), (1B2B-13), (1B2B-14), (1B2B-15), or (1B2B-16).

Thus, while there is no particular limitation as long as the effect of the present invention is ensured, in one embodiment of the present invention, the inventive compound which can be preferably used as a material for the hole transporting zone is at least one selected from the group consisting of:

a compound represented by the formula (1A) where at least one selected from $R^1$ to $R^{16}$ is represented by the formula (2B), and a compound represented by the formula (1B) where at least one selected from $R^{21}$ to $R^{36}$ is represented by the formula (2B);

compounds represented by the formulae (1A2B-1), (1A2B-2), (1B2B-1), (1B2B-2), (1B2B-3), (1B2B-4), and (1B2B-5); and compounds represented by the formulae (1A2B-11), (1A2B-12), (1A2B-13), (1A2B-14), (1A2B-15), (1B2B-11), (1B2B-12), (1B2B-13), (1B2B-14), (1B2B-15), and (1B2B-16).

In one embodiment of the organic EL device according to the present invention, the light emitting layer preferably comprises the inventive compound as a host material.

While there is no particular limitation as long as the effect of the present invention is ensured, in one embodiment of the organic EL device according to the present invention, the light emitting layer more preferably comprises at least one of the following compounds as a host material:

a compound represented by the formula (1A) where at least one selected from $R^1$ to $R^{16}$ is represented by the formula (2C), or a compound represented by the formula (1B) where at least one selected from $R^{21}$ to $R^{36}$ is represented by the formula (2C);

a compound represented by the formula (1A2C-1), (1A2C-2), (1B2C-1), (1B2C-2), (1B2C-3), (1B2C-4), or (1B2C-5); and a compound represented by the formula (1A2C-11), (1A2C-12), (1A2C-13), (1A2C-14), (1A2C-15), (1B2C-11), (1B2C-12), (1B2C-13), (1B2C-14), (1B2C-15), or (1B2C-16).

Thus, while there is no particular limitation as long as the effect of the present invention is ensured, in one embodiment of the present invention, the inventive compound which can be preferably used as a host material for the light emitting layer is at least one selected from the group consisting of:

a compound represented by the formula (1A) where at least one selected from $R^1$ to $R^{16}$ is represented by the formula (2C), and a compound represented by the formula (1B) where at least one selected from $R^{21}$ to $R^{36}$ is represented by the formula (2C);

compounds represented by the formulae (1A2C-1), (1A2C-2), (1B2C-1), (1B2C-2), (1B2C-3), (1B2C-4), and (1B2C-5); and compounds represented by the formulae (1A2C-11), (1A2C-12), (1A2C-13), (1A2C-14), (1A2C-15), (1B2C-11), (1B2C-12), (1B2C-13), (1B2C-14), (1B2C-15), and (1B2C-16).

The organic EL device according to one embodiment of the present invention may be a fluorescent or phosphorescent light emission-type monochromatic light emitting device or a fluorescent/phosphorescent hybrid-type white light emitting device, and may be a simple type having a single light emitting unit or a tandem type having a plurality of light emitting units. Above all, a fluorescent light emission-type device is preferred. The "light emitting unit" referred to herein refers to a minimum unit that emits light through recombination of injected holes and electrons, which includes organic layers among which at least one layer is a light emitting layer.

For example, as a representative device configuration of the simple type organic EL device, the following device configuration may be exemplified.

(1) Anode/Light Emitting Unit/Cathode

The light emitting unit may be a multilayer type having a plurality of phosphorescent light emitting layers or fluorescent light emitting layers. In this case, a space layer may intervene between the light emitting layers for the purpose of preventing excitons generated in the phosphorescent light emitting layer from diffusing into the fluorescent light emitting layer. Representative layer configurations of the simple type light emitting unit are described below. Layers in parentheses are optional.

(a) (hole injecting layer/) hole transporting layer/fluorescent light emitting layer/electron transporting layer (/electron injecting layer)

(b) (hole injecting layer/) hole transporting layer/phosphorescent light emitting layer/electron transporting layer (/electron injecting layer)

(c) (hole injecting layer/) hole transporting layer/first fluorescent light emitting layer/second fluorescent light emitting layer/electron transporting layer (/electron injecting layer)

(d) (hole injecting layer/) hole transporting layer/first phosphorescent light emitting layer/second phosphorescent light emitting layer/electron transporting layer (/electron injecting layer)

(e) (hole injecting layer/) hole transporting layer/phosphorescent light emitting layer/space layer/fluorescent light emitting layer/electron transporting layer (/electron injecting layer)

(f) (hole injecting layer/) hole transporting layer/first phosphorescent light emitting layer/second phosphorescent light emitting layer/space layer/fluorescent light emitting layer/electron transporting layer (/electron injecting layer)

(g) (hole injecting layer/) hole transporting layer/first phosphorescent light emitting layer/space layer/second phosphorescent light emitting layer/space layer/fluorescent light emitting layer/electron transporting layer (/electron injecting layer)

(h) (hole injecting layer/) hole transporting layer/phosphorescent light emitting layer/space layer/first fluorescent light emitting layer/second fluorescent light emitting layer/electron transporting layer (/electron injecting layer)

(i) (hole injecting layer/) hole transporting layer/electron blocking layer/fluorescent light emitting layer/electron transporting layer (/electron injecting layer)

(j) (hole injecting layer/) hole transporting layer/electron blocking layer/phosphorescent light emitting layer/electron transporting layer (/electron injecting layer)

(k) (hole injecting layer/) hole transporting layer/exciton blocking layer/fluorescent light emitting layer/electron transporting layer (/electron injecting layer)
(l) (hole injecting layer/) hole transporting layer/exciton blocking layer/phosphorescent light emitting layer/ electron transporting layer (/electron injecting layer)
(m) (hole injecting layer/) first hole transporting layer/ second hole transporting layer/fluorescent light emitting layer/electron transporting layer (/electron injecting layer)
(n) (hole injecting layer/) first hole transporting layer/ second hole transporting layer/phosphorescent light emitting layer/electron transporting layer (/electron injecting layer)
(o) (hole injecting layer/) first hole transporting layer/ second hole transporting layer/fluorescent light emitting layer/first electron transporting layer/second electron transporting layer (/electron injecting layer)
(p) (hole injecting layer/) first hole transporting layer/ second hole transporting layer/phosphorescent light emitting layer/first electron transporting layer/second electron transporting layer (/electron injecting layer)
(q) (hole injecting layer/) hole transporting layer/fluorescent light emitting layer/hole blocking layer/electron transporting layer (/electron injecting layer)
(r) (hole injecting layer/) hole transporting layer/phosphorescent light emitting layer/hole blocking layer/electron transporting layer (/electron injecting layer)
(s) (hole injecting layer/) hole transporting layer/fluorescent light emitting layer/exciton blocking layer/electron transporting layer (/electron injecting layer)
(t) (hole injecting layer/) hole transporting layer/phosphorescent light emitting layer/exciton blocking layer/electron transporting layer (/electron injecting layer)

The phosphorescent and fluorescent light emitting layers may emit emission colors different from each other, respectively. Specifically, in the light emitting unit (f), a layer configuration, such as (hole injecting layer/) hole transporting layer/first phosphorescent light emitting layer (red light emission)/second phosphorescent light emitting layer (green light emission)/space layer/fluorescent light emitting layer (blue light emission)/electron transporting layer, may be exemplified.

An electron blocking layer may be properly provided between each light emitting layer and the hole transporting layer or the space layer. A hole blocking layer may be properly provided between each light emitting layer and the electron transporting layer. The employment of the electron blocking layer or the hole blocking layer allows to improve the emission efficiency by trapping electrons or holes within the light emitting layer and increasing the probability of charge recombination in the light emitting layer.

As a representative device configuration of the tandem type organic EL device, the following device configuration may be exemplified.

(2) Anode/First Light Emitting Unit/Intermediate Layer/ Second Light Emitting Unit/Cathode For example, each of the first light emitting unit and the second light emitting unit may be independently selected from the above-described light emitting units.

The intermediate layer is also generally referred to as an intermediate electrode, an intermediate conductive layer, a charge generation layer, an electron withdrawing layer, a connecting layer, or an intermediate insulating layer, and a known material configuration can be used, in which electrons are supplied to the first light emitting unit, and holes are supplied to the second light emitting unit.

FIG. 1 is a schematic illustration showing an example of the configuration of the organic EL device according to one embodiment of the present invention. The organic EL device 1 of this example includes a substrate 2, an anode 3, a cathode 4, and a light emitting unit 10 disposed between the anode 3 and the cathode 4. The light emitting unit 10 includes a light emitting layer 5. A hole transporting zone 6 (such as a hole injecting layer and a hole transporting layer) is provided between the light emitting layer 5 and the anode 3, and an electron transporting zone 7 (such as an electron injecting layer and an electron transporting layer) is provided between the light emitting layer 5 and the cathode 4. In addition, an electron blocking layer (which is not shown in the figure) may be provided on the side of the anode 3 of the light emitting layer 5, and a hole blocking layer (which is not shown in the figure) may be provided on the side of the cathode 4 of the light emitting layer 5. According to the configuration, electrons and holes are trapped in the light emitting layer 5, thereby enabling one to further increase the production efficiency of excitons in the light emitting layer 5.

Figure 2:
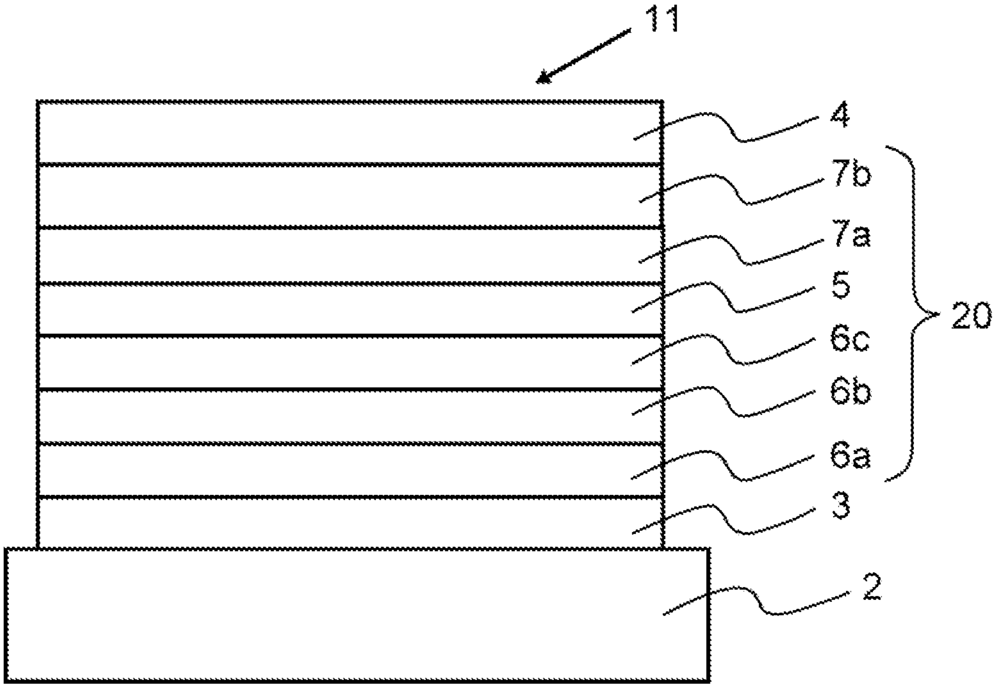
FIG. 2 is a schematic illustration showing another example of the layer configuration of the organic EL device according to one embodiment of the present invention.

FIG. 2 is a schematic illustration showing another configuration of the organic EL device according to one embodiment of the present invention. The organic EL device 11 of this example includes a substrate 2, an anode 3, a cathode 4, and a light emitting unit 20 disposed between the anode 3 and the cathode 4. The light emitting unit 20 includes a light emitting layer 5. The hole transporting zone disposed between the anode 3 and the light emitting layer 5 is formed by a hole injecting layer 6*a*, a first hole transporting layer 6*b* and a second hole transporting layer 6*c*. In addition, the electron transporting zone disposed between the light emitting layer 5 and the cathode 4 consists of a first electron transporting layer 7*a* and a second electron transporting layer 7*b*.

In the present invention, a host combined with a fluorescent dopant material (a fluorescent emitting material) is referred to as a fluorescent host, and a host combined with a phosphorescent dopant material is referred to as a phosphorescent host. The fluorescent host and the phosphorescent host are not distinguished from each other merely by the molecular structures thereof. Specifically, the phosphorescent host means a material that forms a phosphorescent light emitting layer containing a phosphorescent dopant, but does not mean unavailability as a material that forms a fluorescent light emitting layer. The same also applies to the fluorescent host.

Substrate

The substrate is used as a support of the organic EL device. Examples of the substrate include a plate of glass, quartz, and plastic. In addition, a flexible substrate may be used. Examples of the flexible substrate include a plastic substrate made of polyimide, polycarbonate, polyarylate, polyether sulfone, polypropylene, polyester, polyvinyl fluoride, or polyvinyl chloride. In addition, an inorganic vapor deposition film can be used.

Anode

It is preferred that a metal, an alloy, an electrically conductive compound, or a mixture thereof which has a high work function (specifically 4.0 eV or more) is used for the anode formed on the substrate. Specific examples thereof include indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene. Besides, examples there include gold (Au), platinum (Pt), nickel (Ni), tungsten (W), chromium (Cr), molybdenum (Mo), iron (Fe), cobalt (Co), copper (Cu), palladium (Pd), titanium (Ti), or nitrides of the metals (for example, titanium nitride).

These materials are usually deposited by a sputtering method. For example, through a sputtering method, it is possible to form indium oxide-zinc oxide by using a target in which 1 to 10 wt % of zinc oxide is added to indium oxide, and to form indium oxide containing tungsten oxide and zinc oxide by using a target containing 0.5 to 5 wt % of tungsten oxide and 0.1 to 1 wt % of zinc oxide with respect to indium oxide. Besides, the manufacturing may be performed by a vacuum vapor deposition method, a coating method, an inkjet method, a spin coating method, or the like.

The hole injecting layer formed in contact with the anode is formed by using a material that facilitates hole injection regardless of a work function of the anode, and thus, it is possible to use materials generally used as an electrode material (for example, metals, alloys, electrically conductive compounds, or mixtures thereof, elements belonging to Group 1 or 2 of the periodic table of the elements).

It is also possible to use elements belonging to Group 1 or 2 of the periodic table of the elements, which are materials having low work functions, that is, alkali metals, such as lithium (Li) and cesium (Cs), alkaline earth metals, such as magnesium (Mg), calcium (Ca), and strontium (Sr), and alloys containing these (such as MgAg and AlLi), and rare earth metals, such as europium (Eu), and ytterbium (Yb) and alloys containing these. When the anode is formed by using the alkali metals, the alkaline earth metals, and alloys containing these, a vacuum vapor deposition method or a sputtering method can be used. Further, when a silver paste or the like is used, a coating method, an inkjet method, or the like can be used.

Hole Injecting Layer

The hole injecting layer is a layer containing a material having a high hole injection capability (a hole injecting material) and is provided between the anode and the light emitting layer, or between the hole transporting layer, if exists, and the anode.

As the hole injecting material other than the inventive compound, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, and the like can be used.

Examples of the hole injecting layer material also include aromatic amine compounds as low-molecular weight organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

High-molecular weight compounds (such as oligomers, dendrimers, and polymers) may also be used. Examples thereof include high-molecular weight compounds, such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). In addition, high-molecular weight compounds to which an acid is added, such as poly(3,4-ethylenedioxythiophene)/poly (styrene sulfonic acid) (PEDOT/PSS), and polyaniline/poly (styrenesulfonic acid) (PAni/PSS), can also be used.

Furthermore, it is also preferred to use an acceptor material, such as a hexaazatriphenylene (HAT) compound represented by formula (K).

(K)

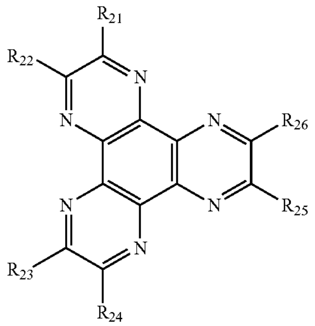

In the above-described formula, $R^{221}$ to $R^{226}$ each independently represent a cyano group, —$CONH_2$, a carboxy group, or —$COOR^{227}$ ($R^{227}$ represents an alkyl group having 1 to 20 carbon atoms or a cycloalkyl group having 3 to 20 carbon atoms). In addition, adjacent two selected from $R^{221}$ and $R^{222}$, $R^{223}$ and $R^{224}$, and $R^{225}$ and $R^{226}$ may be bonded to each other to form a group represented by —CO—O—CO—.

Examples of $R^{227}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer is a layer containing a material having a high hole transporting capability (a hole transporting material) and is provided between the anode and the light emitting layer, or between the hole injecting layer, if exists, and the light emitting layer.

As described above, in one embodiment of the organic EL device according to the present invention, the inventive compound may be used singly or in combination with the following compounds in the hole transporting layer.

The hole transporting layer may have a single layer structure or a multilayer structure including two or more layers. For example, the hole transporting layer may have a two-layer structure including a first hole transporting layer (anode side) and a second hole transporting layer (cathode side). Thus, the hole transporting zone may include the first hole transporting layer on the anode side and the second hole transporting layer on the cathode side. In one embodiment of the organic EL device according to the present invention, the hole transporting layer having a single layer structure is preferably disposed adjacent to the light emitting layer, and the hole transporting layer that is closest to the cathode in the multilayer structure, such as the second hole transporting layer in the two-layer structure, is preferably disposed adjacent to the light emitting layer. In another embodiment of the organic EL device according to the present invention, an electron blocking layer described later and the like may be disposed between the hole transporting layer having a single layer structure and the light emitting layer, or between the hole transporting layer that is closest to the light emitting layer in the multilayer structure and the light emitting layer.

In one embodiment of the organic EL device according to the present invention, at least one of the first hole transporting layer and the second hole transporting layer may comprise the inventive compound. Thus, in the hole transporting layer having a two-layer structure, one or both of the first hole transporting layer and the second hole transporting layer may comprise the inventive compound.

In one embodiment of the organic EL device according to the present invention, it is preferred that only the first hole transporting layer comprise the inventive compound. In another embodiment, it is preferred that only the second hole transporting layer comprise the inventive compound. In yet another embodiment, it is preferred that both the first hole transporting layer and the second hole transporting layer comprise the inventive compound.

An aromatic amine compound, a carbazole derivative, an anthracene derivative, and the like can be used as a hole transporting layer material other than the inventive compound.

Examples of the aromatic amine compound include 4,4'-bis[N-(1-naphthyl)-N-phenylamino]biphenyl (abbreviation: NPB) or N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described compounds have a hole mobility of 10-6 $cm^2$/Vs or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA).

Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

High-molecular weight compounds, such as poly(N-vinylcarbazole) (abbreviation: PVK) and poly(4-vinyltriphenylamine) (abbreviation: PVTPA), can also be used.

Compounds other than those as described above can also be used as long as their hole transporting capability is higher than their electron transporting capability.

Dopant Material of Light Emitting Layer

The light emitting layer is a layer containing a material having a high light emitting property (a dopant material), and various materials can be used. For example, a fluorescent emitting material or a phosphorescent emitting material can be used as the dopant material. The fluorescent emitting material is a compound that emits light from a singlet excited state, and the phosphorescent emitting material is a compound that emits light from a triplet excited state.

Examples of a blue-based fluorescent emitting material that can be used for the light emitting layer include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazole-9-yl)phenyl]-N,N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

Examples of a green-based fluorescent emitting material that can be used for the light emitting layer include an aromatic amine derivative. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthrac ene-2-amine (abbreviation: 2YGABPhA), and N,N,9-triphenylanthracene-9-amine (abbreviation: DPhAPhA).

Examples of a red-based fluorescent emitting material that can be used for the light emitting layer include a tetracene derivative and a diamine derivative. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

In one embodiment of the organic EL device according to the present invention, the light emitting layer preferably contains a fluorescent light emitting material (fluorescent dopant material).

Examples of a blue-based phosphorescent emitting material that can be used for the light emitting layer include a metal complex, such as an iridium complex, an osmium complex, and a platinum complex. Specific examples thereof include bis[2-(4',6'-difluorophenyl)pyridinato-N,C2']iridium(III)tetrakis(1-pyrazolyl)borate (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl)pyridinato-N,C2']iridium(III)acetylacetonate (abbreviation: FIracac).

Examples of a green-based phosphorescent emitting material that can be used for the light emitting layer include an iridium complex. Examples thereof include tris(2-phenylpyridinato-N,C2')iridium(III) (abbreviation: Ir(ppy)3), bis(2-phenylpyridinato-N,C2')iridium(III)acetylacetonate (abbreviation: Ir(ppy)2(acac)), bis(1,2-diphenyl-1H-benzimidazolato)iridium(III)acetylacetonate (abbreviation: Ir(pbi)2(acac)), and bis(benzo[h]quinolinato)iridium(III) acetylacetonate (abbreviation: Ir(bzq)2(acac)).

Examples of a red-based phosphorescent emitting material that can be used for the light emitting layer include a metal complex, such as an iridium complex, a platinum complex, a terbium complex, and a europium complex. Specific examples thereof include organic metal complexes, such as bis[2-(2'-benzo[4,5-a]thienyl)pyridinato-N,C3']iridium(III)acetylacetonate (abbreviation: Ir(btp)2(acac)), bis(1-phenylisoquinolinato-N,C2')iridium(III)acetylacetonate (abbreviation: Ir(piq)2(acac)), (acetylacetonate)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrinplatinum(II) (abbreviation: PtOEP).

Rare earth metal complexes, such as tris(acetylacetonate)(monophenanthroline)terbium(III) (abbreviation: Tb(acac)3(Phen)), tris(1,3-diphenyl-1,3-propanedionate)(monophenanthroline)europium(III) (abbreviation: Eu(DBM)3(Phen)), and tris[1-(2-thenoyl)-3,3,3-trifluoroacetonate](monophenanthroline)europium(III) (abbreviation:

Eu(TTA)3(Phen)), emit light from rare earth metal ions (electron transition between different multiplicities), and thus may be used as the phosphorescent emitting material.

In one embodiment of the organic EL device according to the present invention, the light emitting layer preferably contains a phosphorescent light emitting material (phosphorescent dopant material).

Host Material of Light Emitting Layer

The light emitting layer may have a configuration in which the aforementioned dopant material is dispersed in another material (a host material). It is preferable to use a material having a lowest unoccupied molecular orbital level (LUMO level) higher than that of the dopant material and a highest occupied molecular orbital level (HOMO level) lower than that of the dopant material.

As described above, in one embodiment of the organic EL device according to the present invention, the inventive compound may be used singly or in combination with the following compounds as a host material in the light emitting layer.

Examples of host materials other than the inventive compound include:

(1) a metal complex, such as an aluminum complex, a beryllium complex, and a zinc complex, (2) a heterocyclic compound, such as an oxadiazole derivative, a benzimidazole derivative, and a phenanthroline derivative, (3) a fused aromatic compound, such as a carbazole derivative, an anthracene derivative, a phenanthrene derivative, a pyrene derivative, and a chrysene derivative, and (4) an aromatic amine compound, such as a triarylamine derivative and a fused polycyclic aromatic amine derivative.

For example, metal complexes, such as tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ);

heterocyclic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), and bathophenanthroline (abbreviation: BPhen), bathocuproine (abbreviation: BCP);

fused aromatic compounds, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl(abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene; and aromatic amine compounds, such as N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluorene-2-yl)-N-phenylamino]biphenyl (abbreviation: DFLDPBi), and 4,4'-bis[N-(spiro-9,9'-bifluorene-2-yl)-N-phenylamino]biphenyl (abbreviation: BSPB) can be used. A plurality of host materials may be used.

In particular, in the case of a blue fluorescent device, it is preferred to use the following anthracene compounds as a host material.

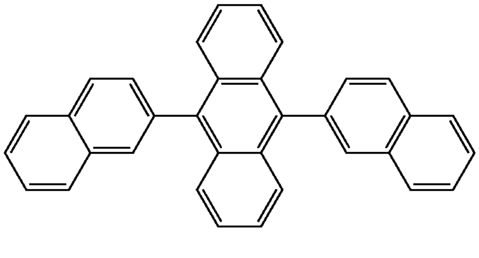

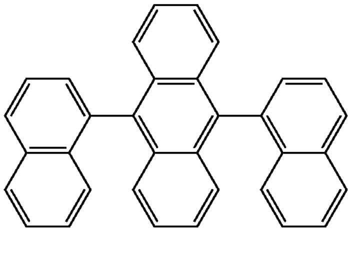

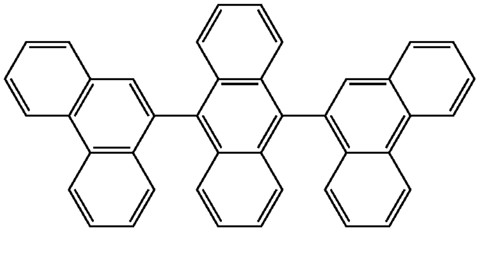

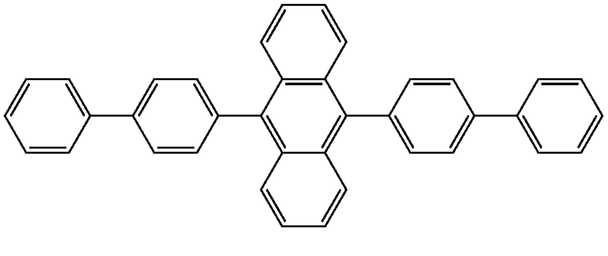

-continued
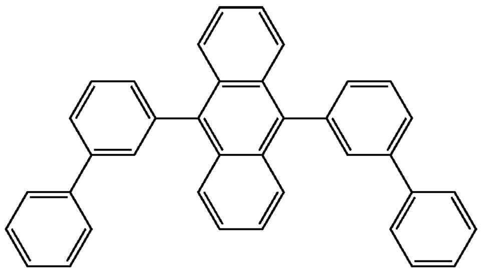
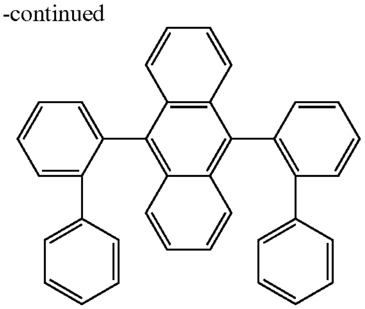
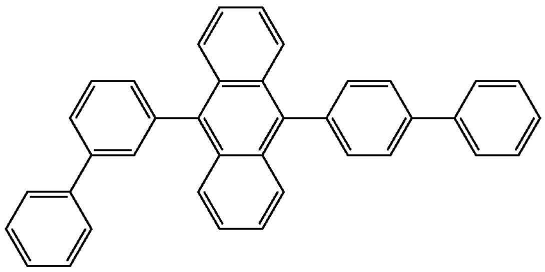
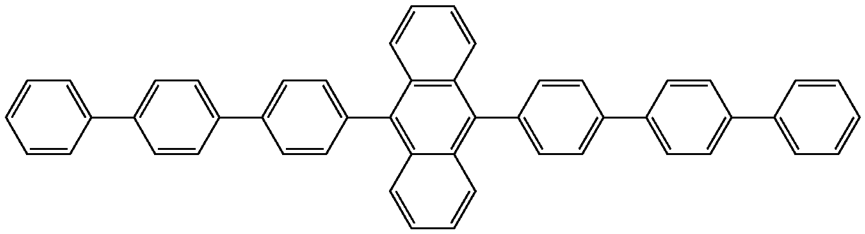
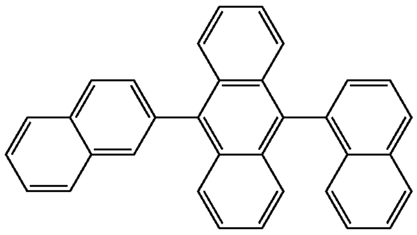
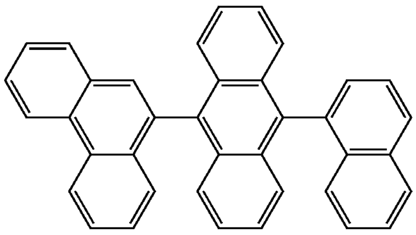
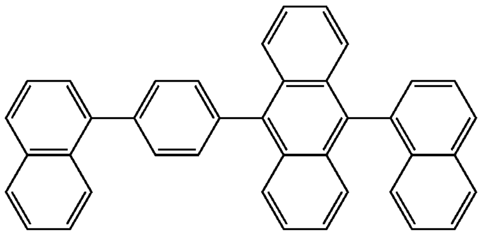
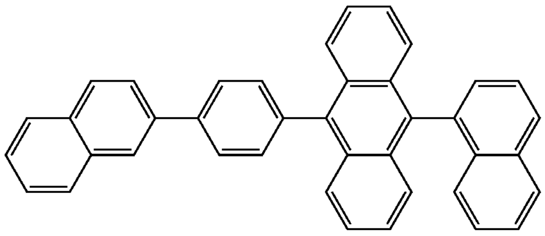
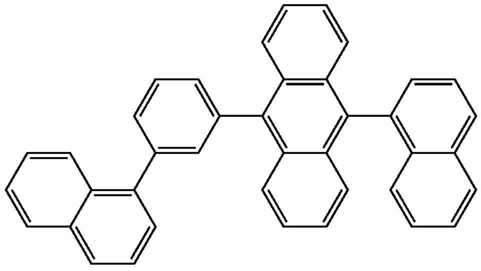
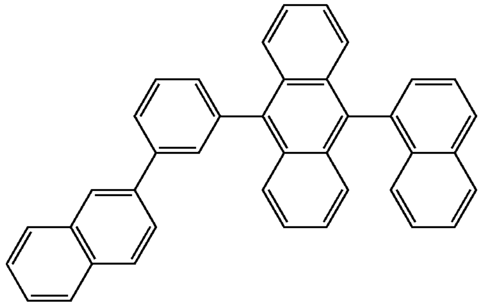

-continued
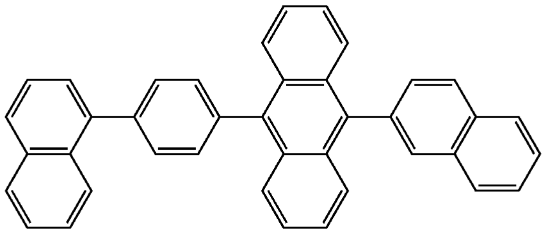
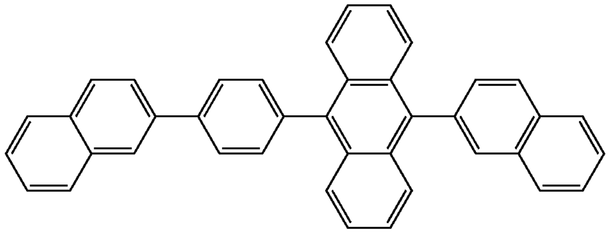
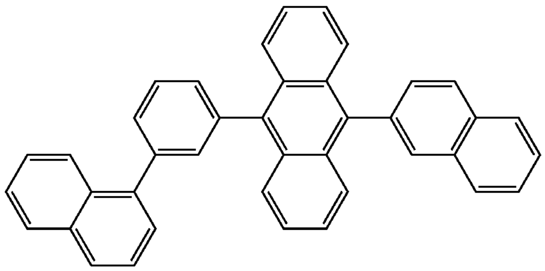
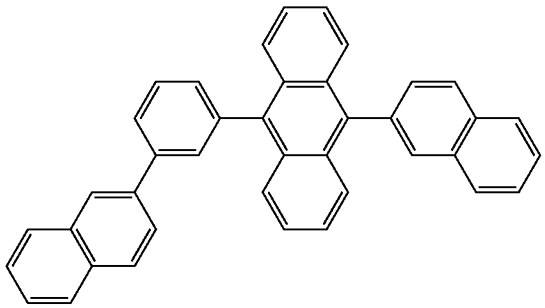
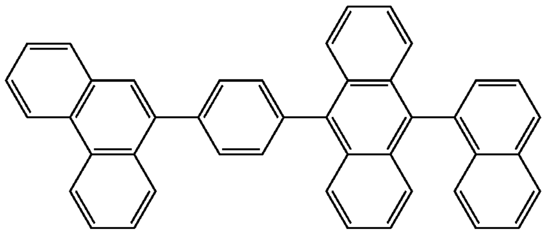
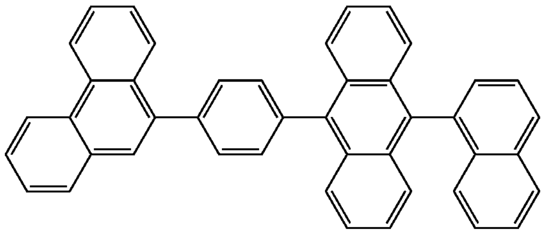
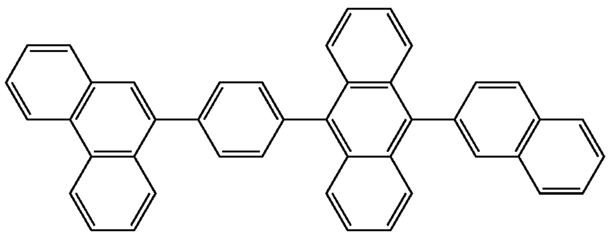
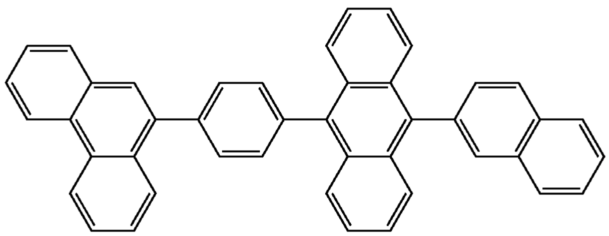
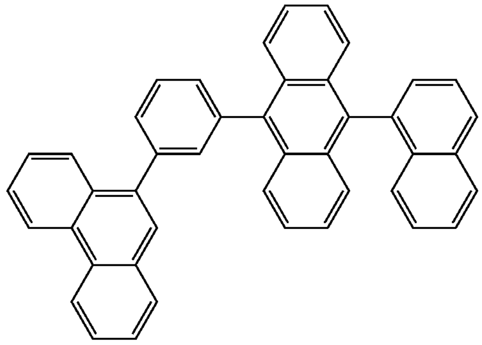

-continued
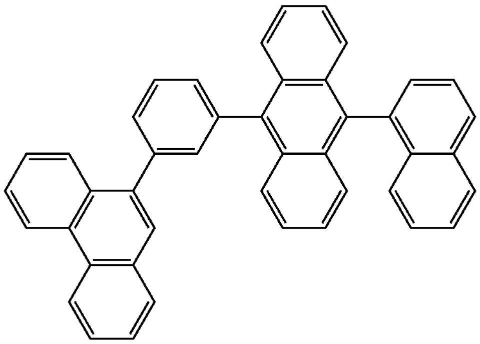
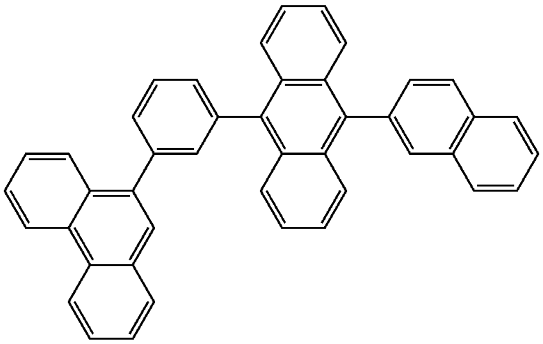
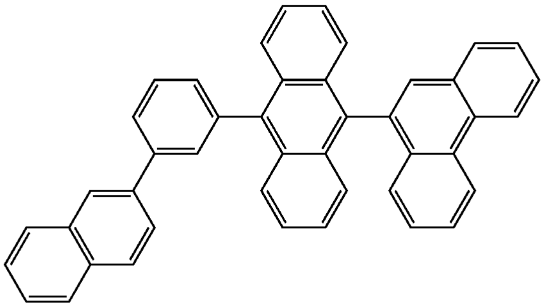
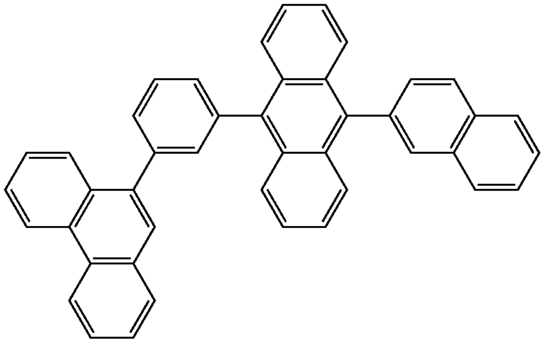
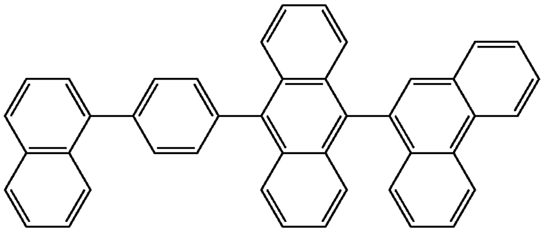
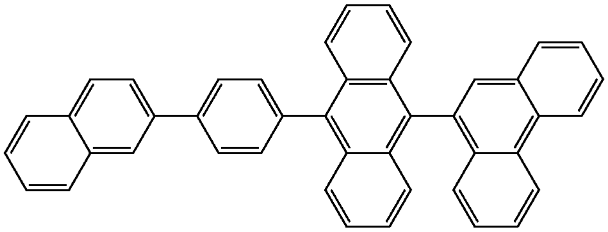
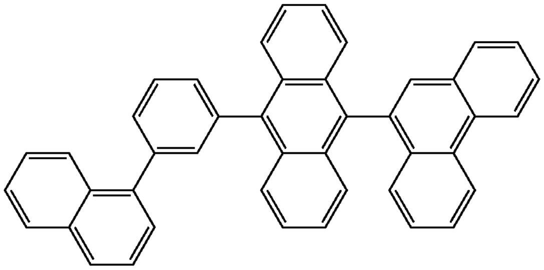
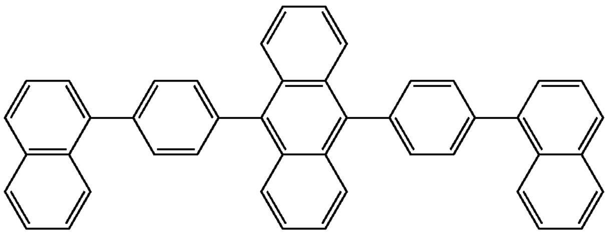

-continued
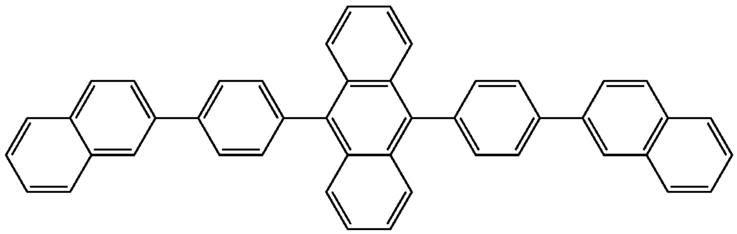
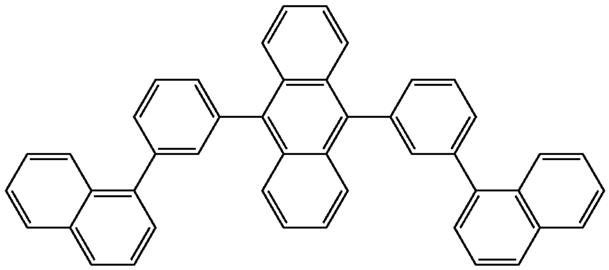
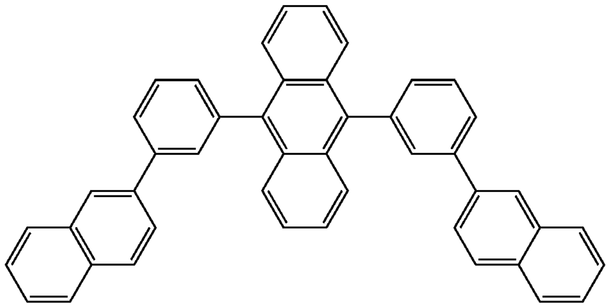
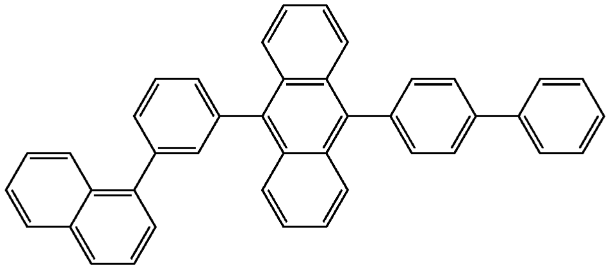
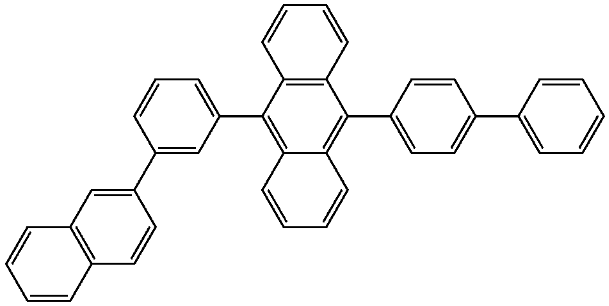
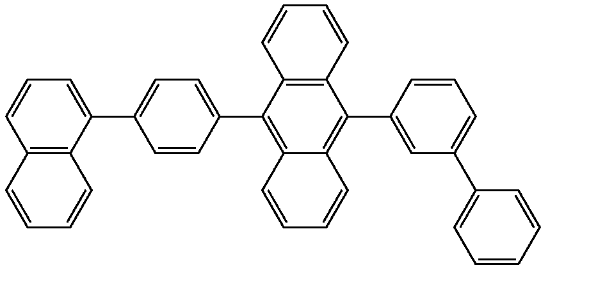

-continued
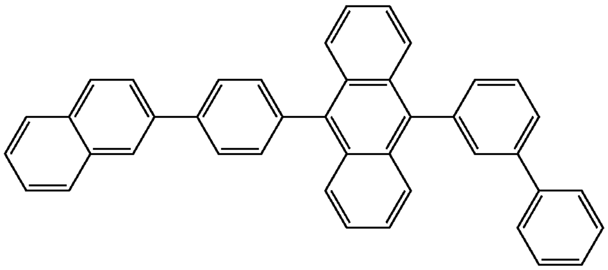
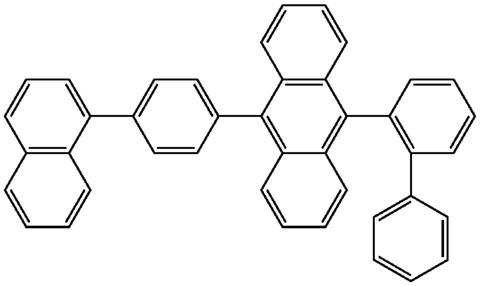
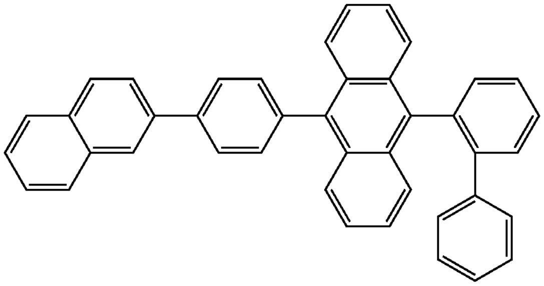
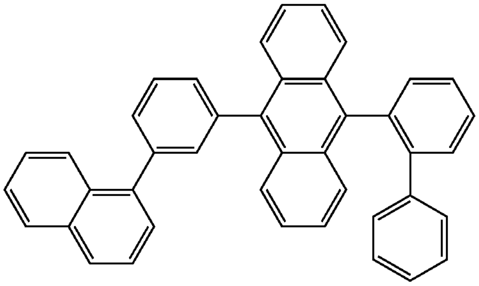
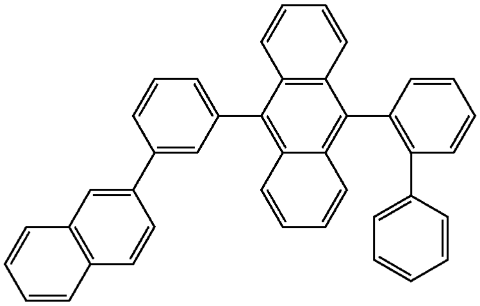
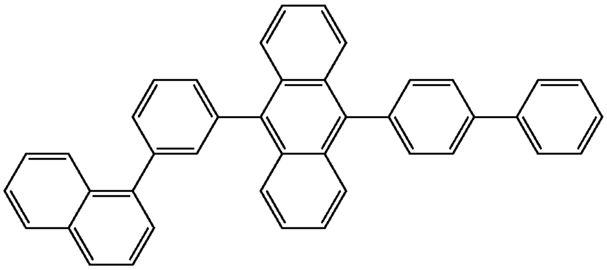
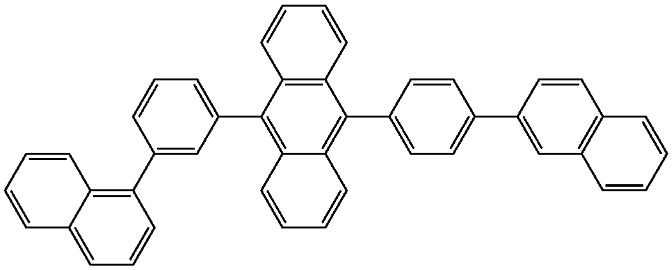
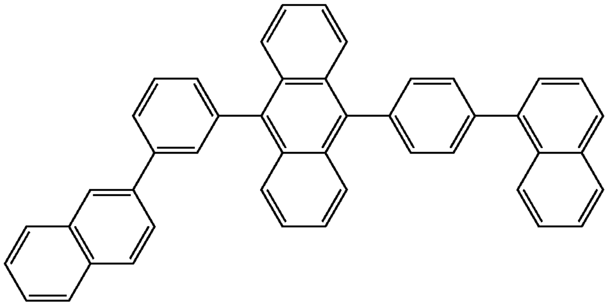

-continued
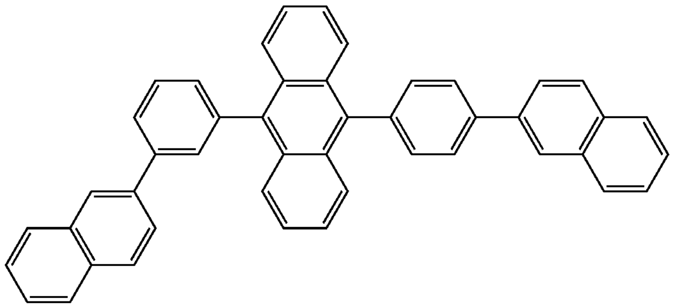
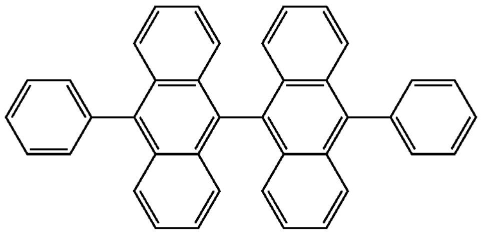
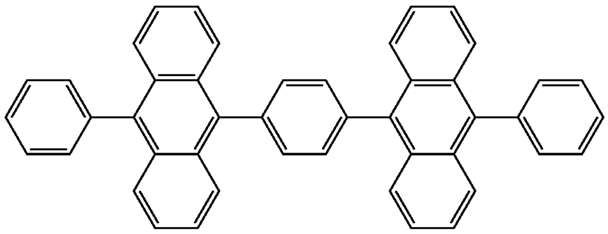
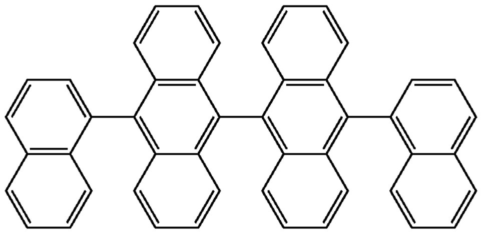
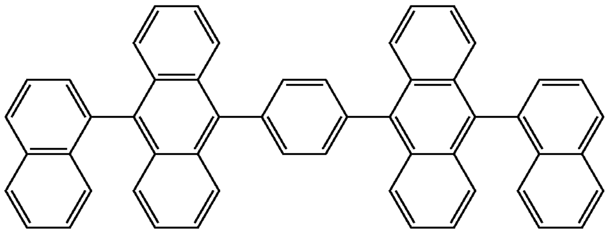
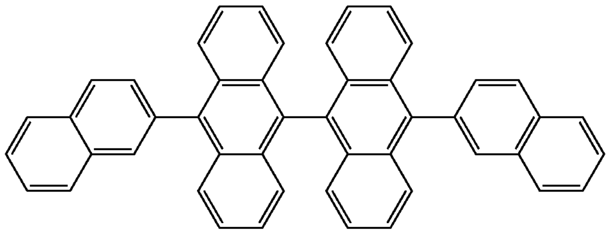
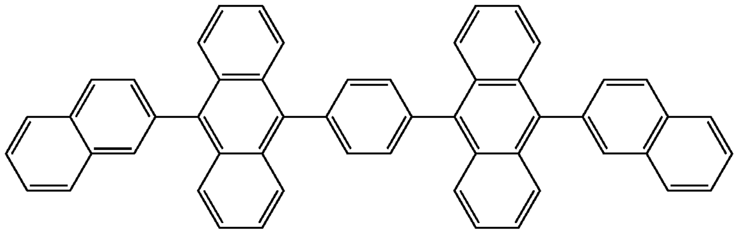
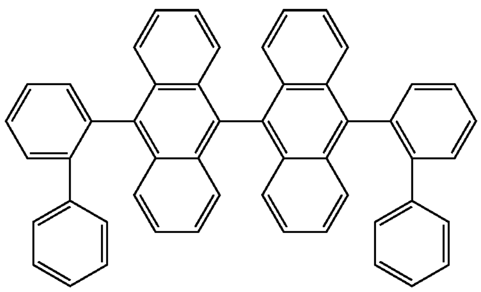
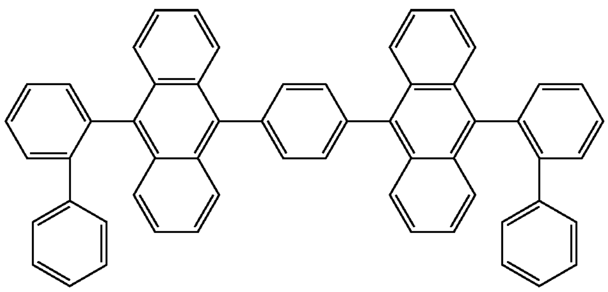

-continued
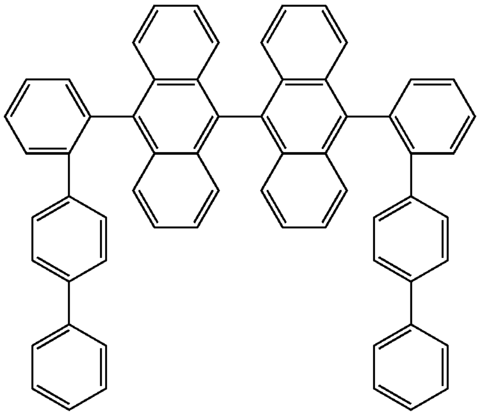
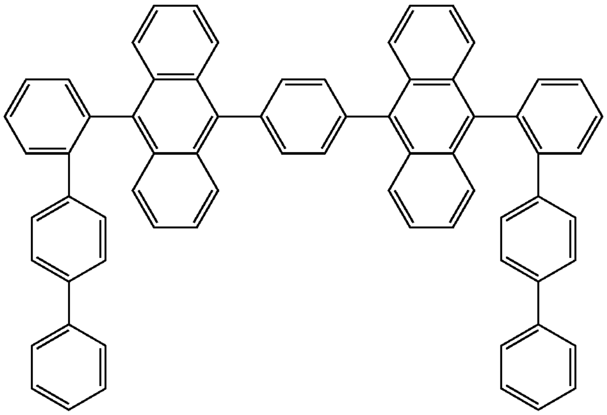
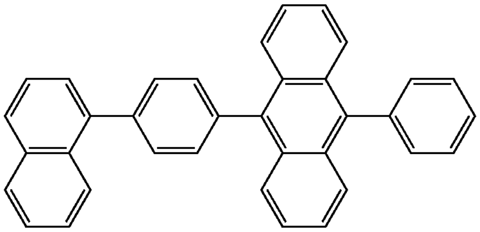
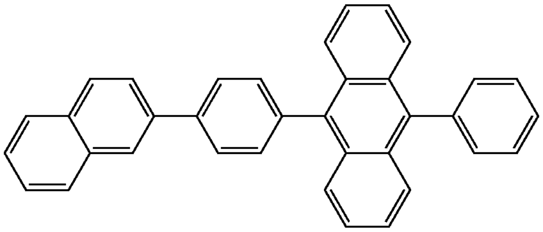
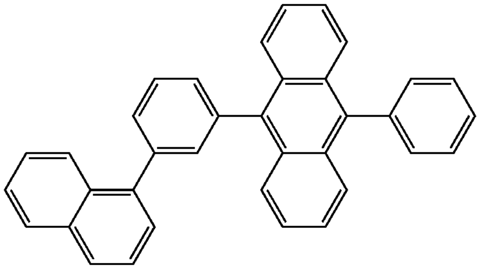
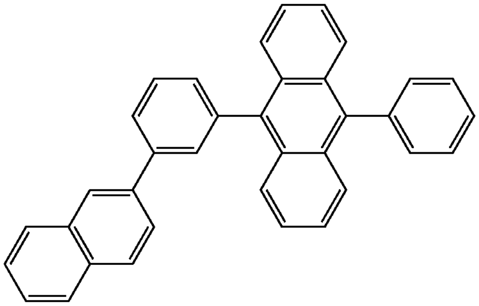
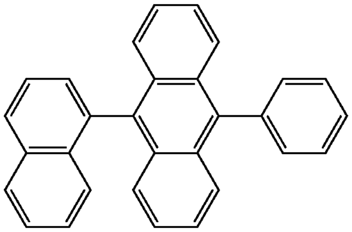
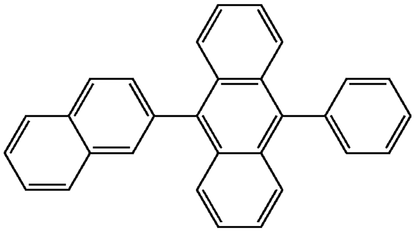
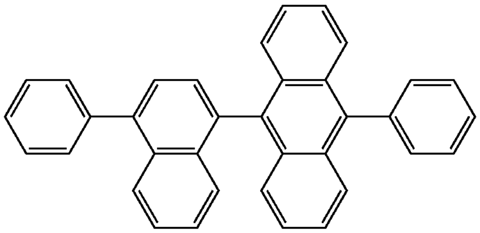
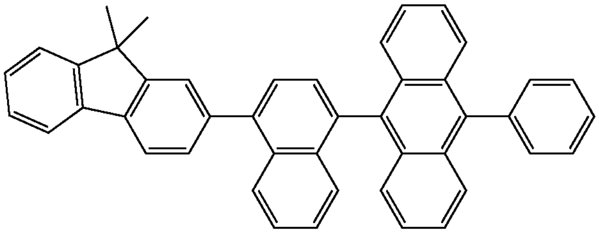
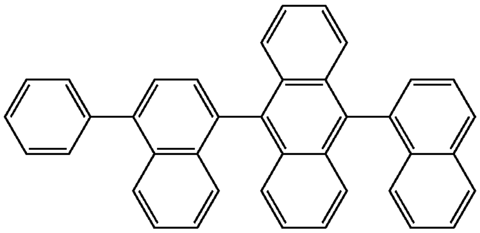
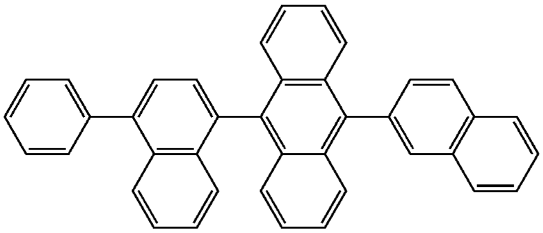

-continued
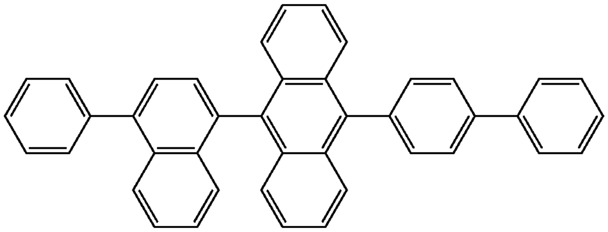
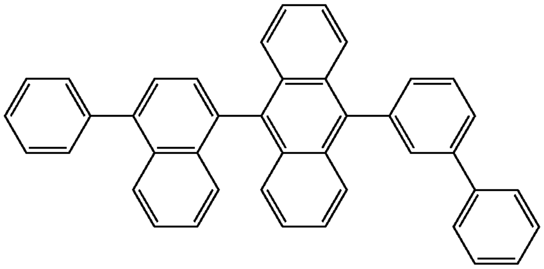
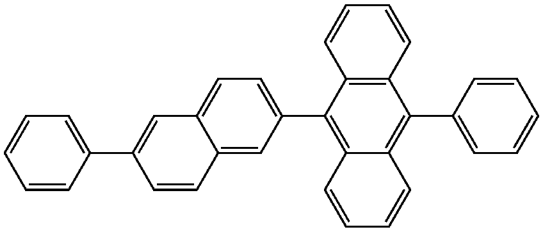
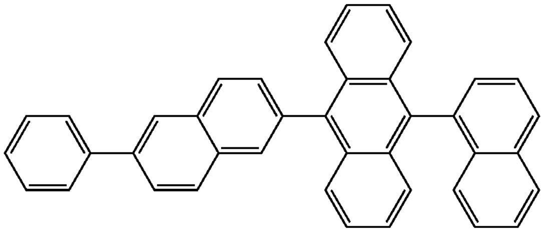
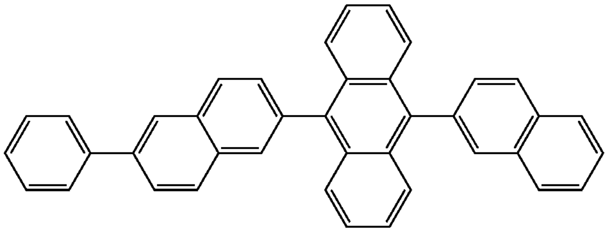
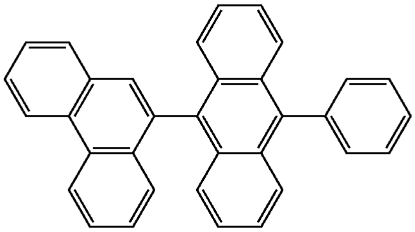
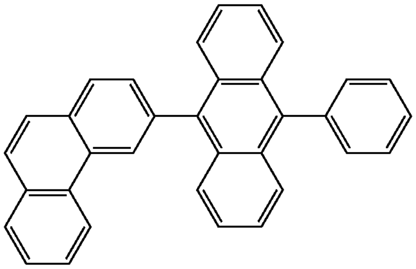
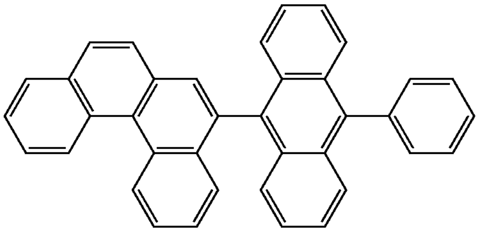
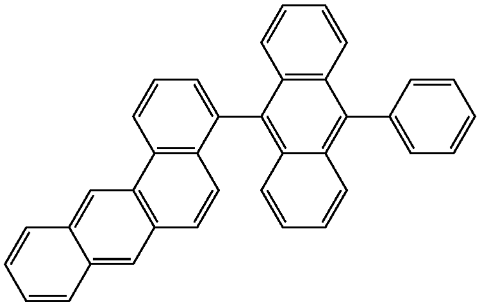
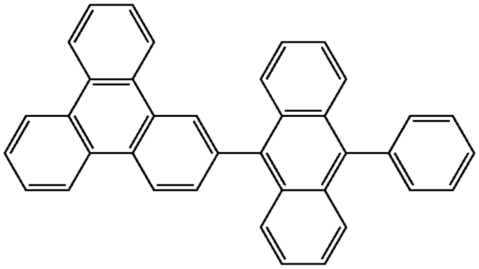

-continued
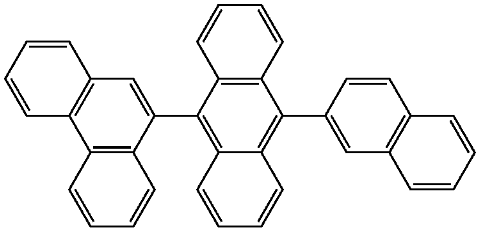
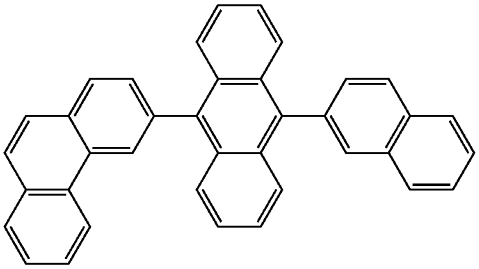
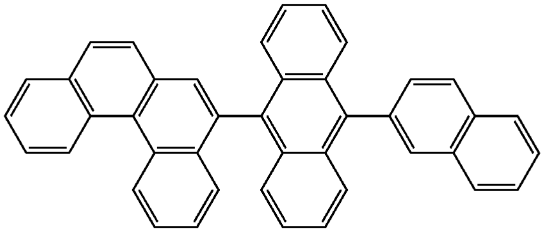
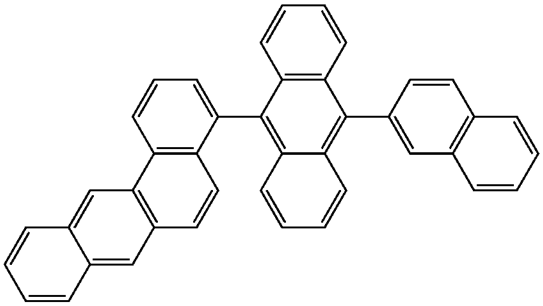
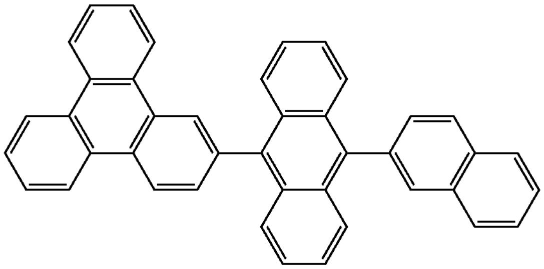
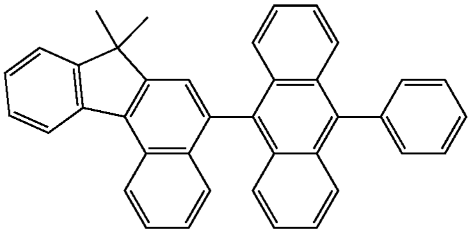
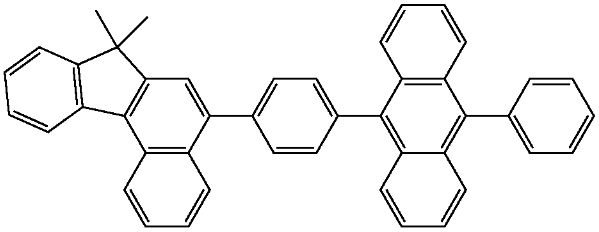
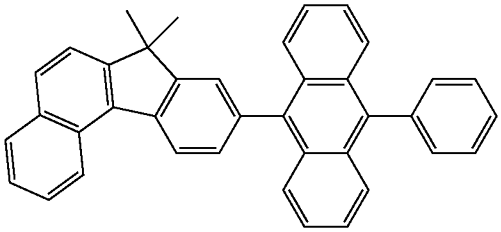
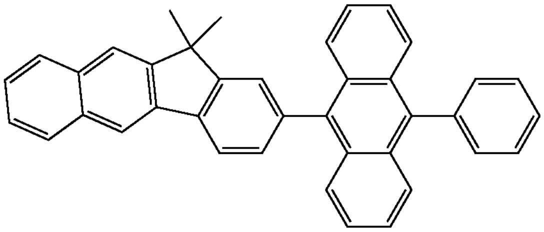
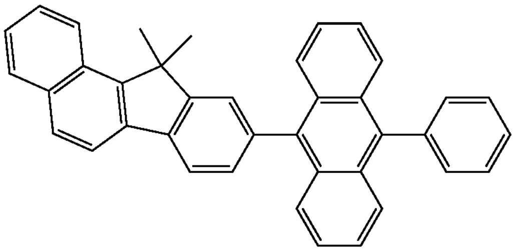
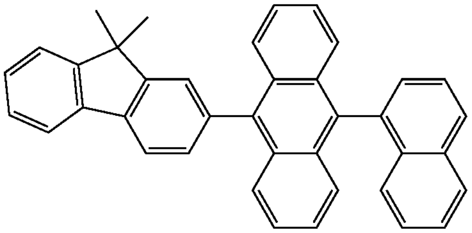
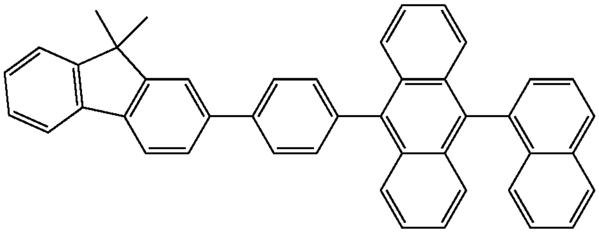

-continued
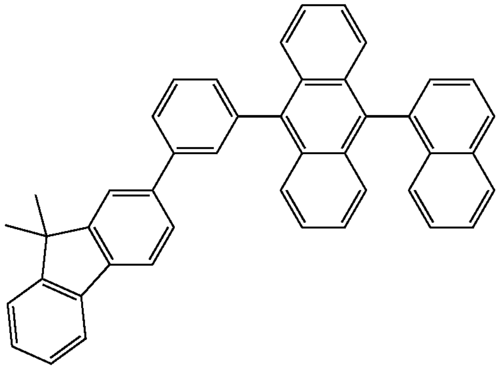
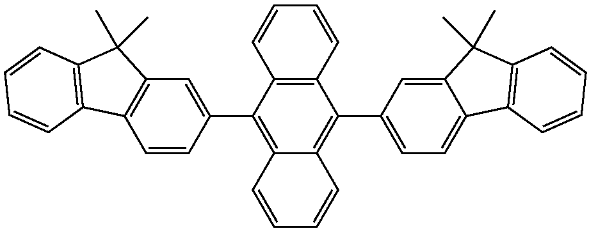
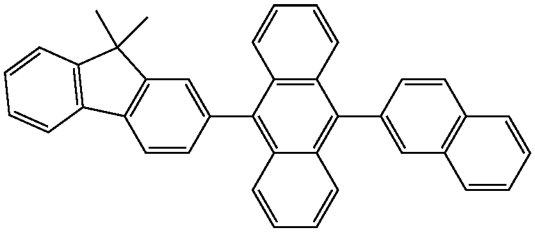
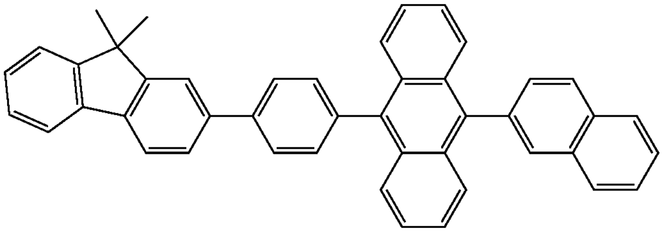
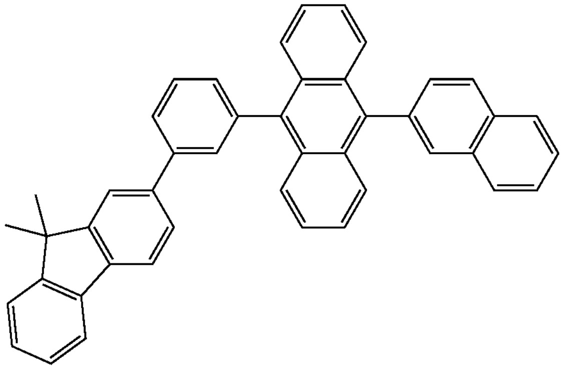
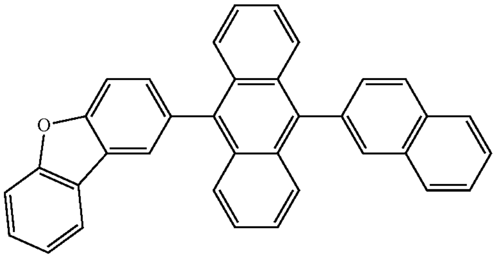
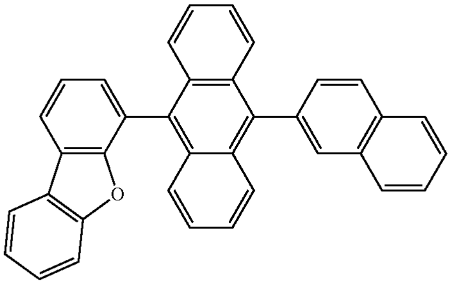
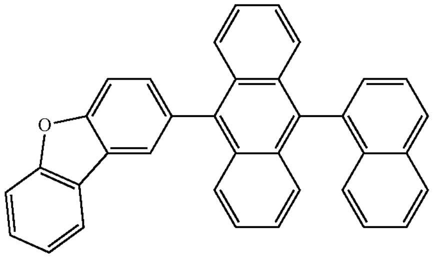

-continued
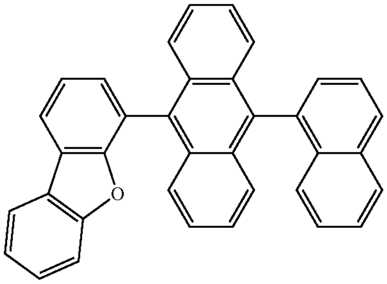
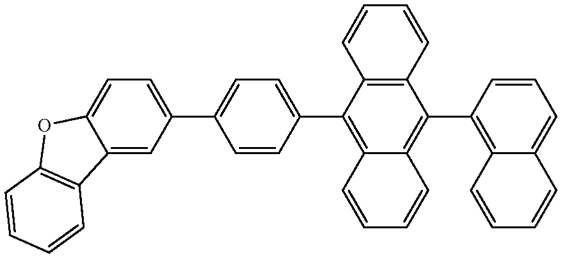
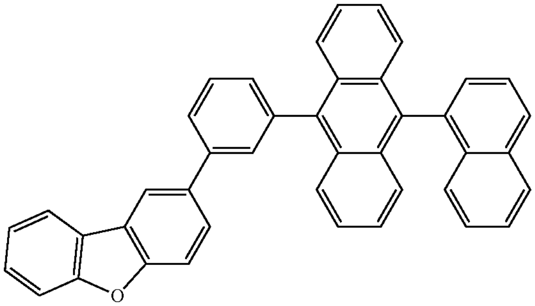
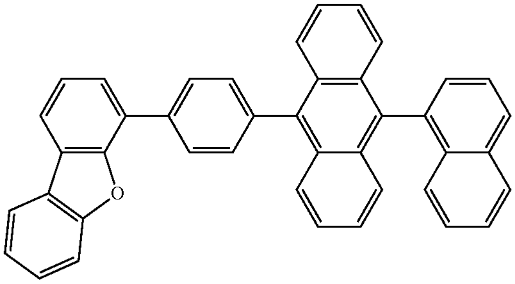
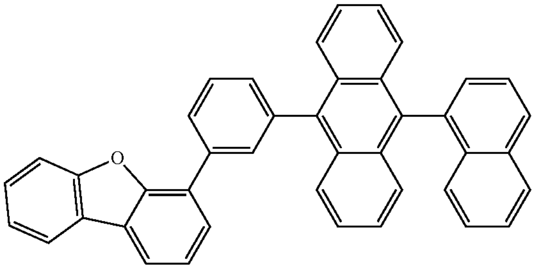
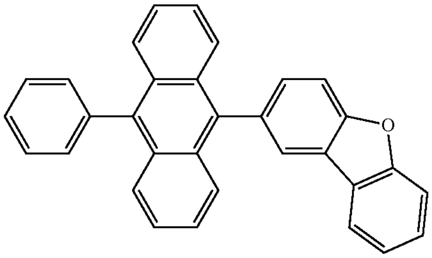
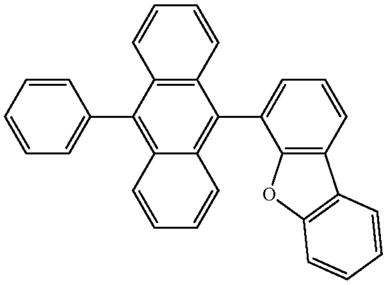
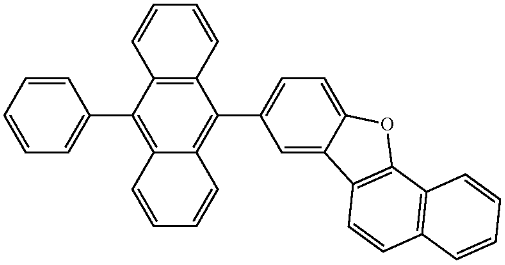
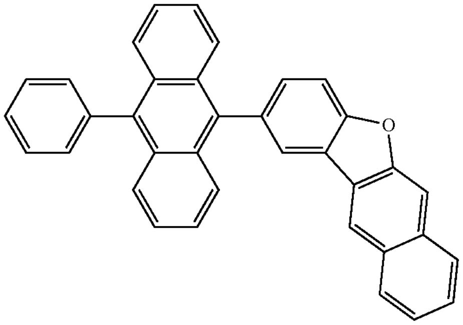
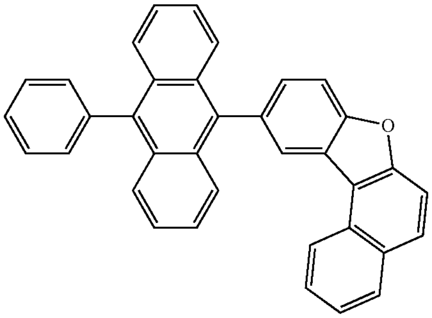

-continued
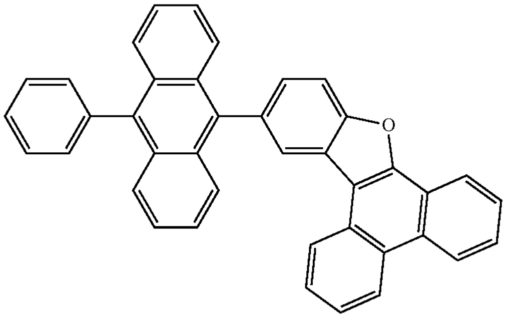
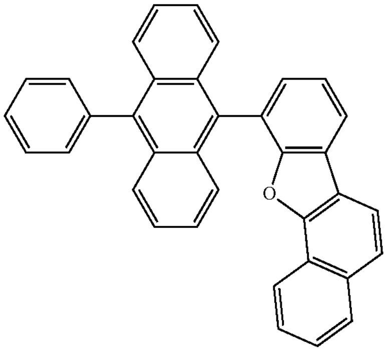
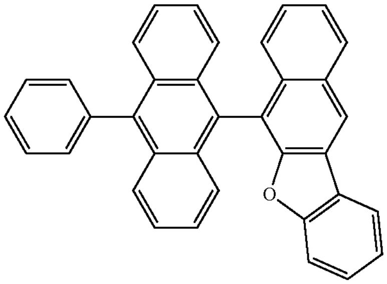
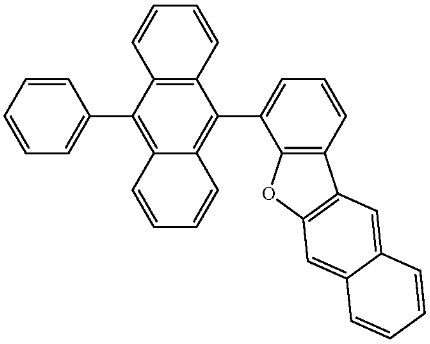
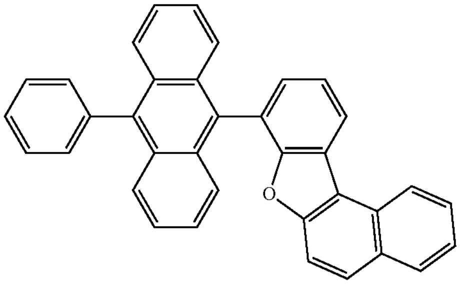
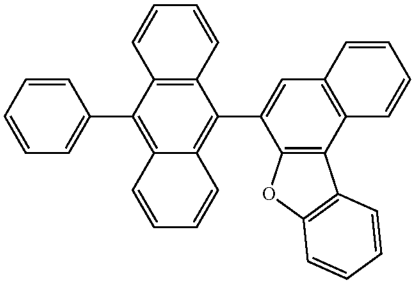
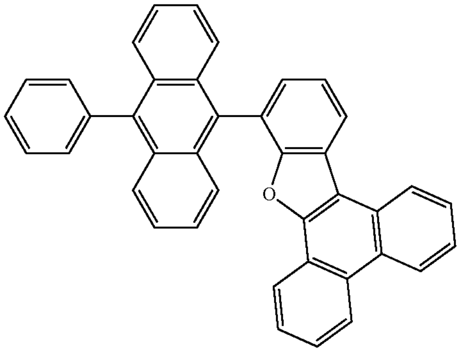
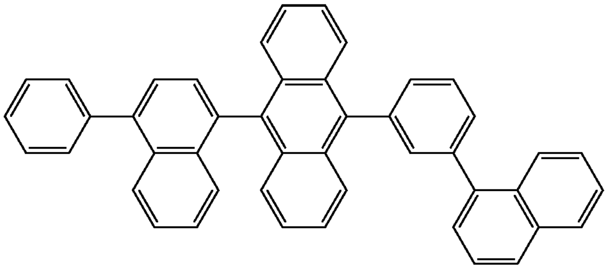
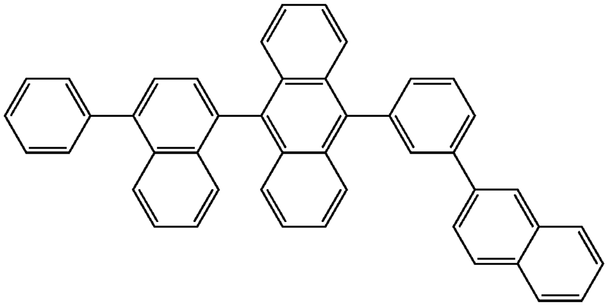

-continued
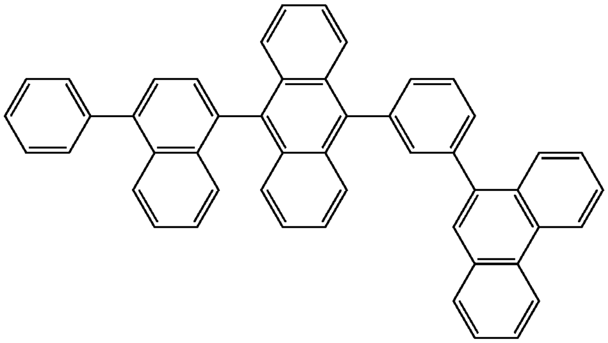
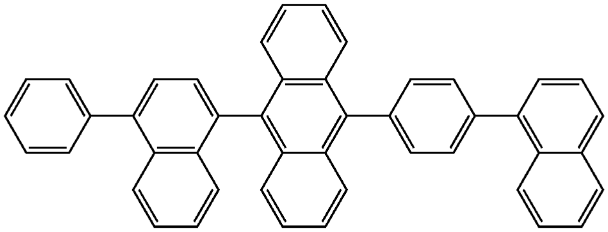
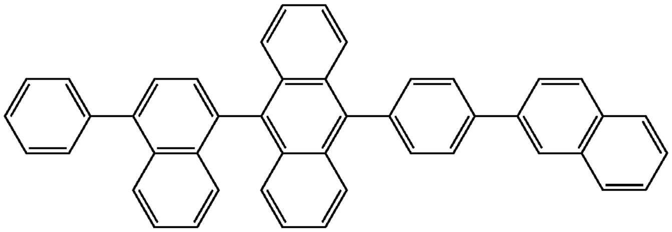
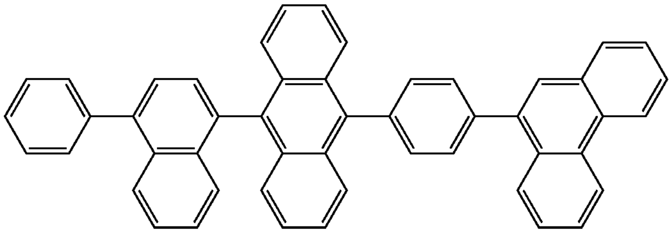
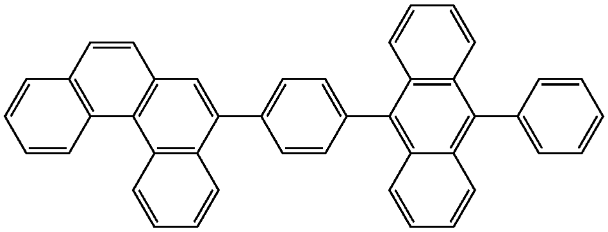
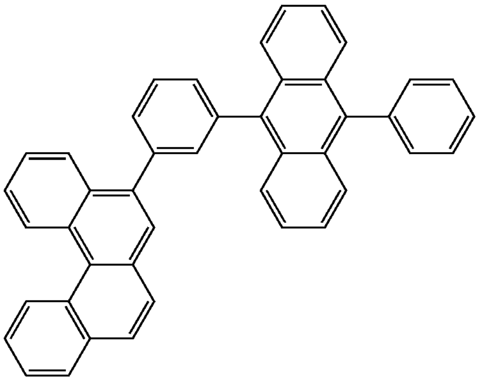

-continued

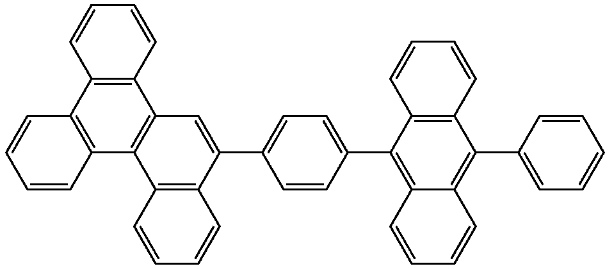

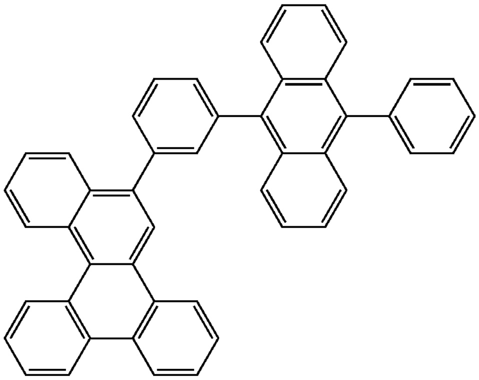

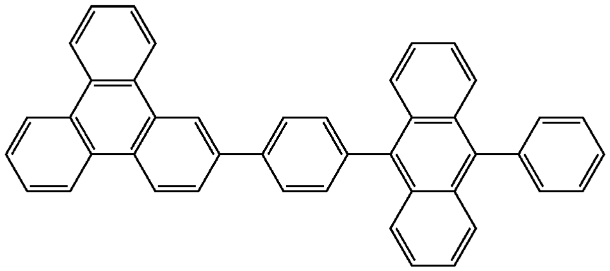

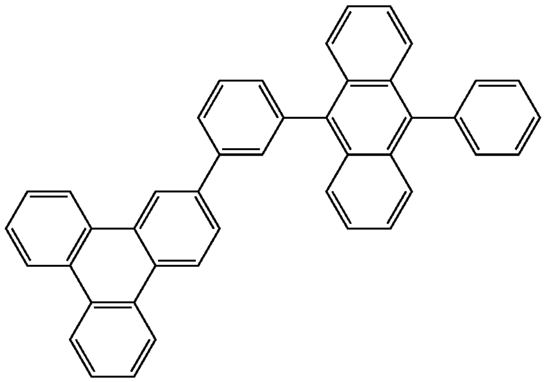

Electron Transporting Layer

The electron transporting layer is a layer containing a material having a high electron transporting capability (an electron transporting material) and is provided between the light emitting layer and the cathode, or between the electron injecting layer, if exists, and the light emitting layer.

As described above, in one embodiment of the organic EL device according to the present invention, the inventive compound may be used singly or in combination with the following compounds in the electron transporting layer.

The electron transporting layer may have a single layer structure or a multilayer structure including two or more layers. For example, the electron transporting layer may have a two-layer structure including a first electron transporting layer (anode side) and a second electron transporting layer (cathode side). Thus, the electron transporting zone may include the first electron transporting layer on the anode side and the second electron transporting layer on the cathode side. In one embodiment of the organic EL device according to the present invention, the electron transporting layer having a single layer structure is preferably disposed adjacent to the light emitting layer, and the electron transporting layer that is closest to the anode in the multilayer structure, such as the first electron transporting layer in the two-layer structure, is preferably disposed adjacent to the light emitting layer. In another embodiment of the organic EL device according to the present invention, a hole blocking layer described later and the like may be disposed between the electron transporting layer having a single layer structure and the light emitting layer, or between the electron transporting layer that is closest to the light emitting layer in the multilayer structure and the light emitting layer.

In one embodiment of the organic EL device according to the present invention, at least one of the first electron transporting layer and the second electron transporting layer may comprise the inventive compound. Thus, in the electron transporting layer having a two-layer structure, one or both of the first electron transporting layer and the second electron transporting layer may comprise the inventive compound.

As described above, the first electron transporting layer is preferably disposed adjacent to the light emitting layer.

In one embodiment of the organic EL device according to the present invention, it is preferred that only the first electron transporting layer comprise the inventive compound. In another embodiment, it is preferred that only the second electron transporting layer comprise the inventive compound. In yet another embodiment, it is preferred that both the first electron transporting layer and the second electron transporting layer comprise the inventive compound.

(1) a metal complex, such as an aluminum complex, a beryllium complex, or a zinc complex, (2) a heteroaromatic compound, such as an imidazole derivative, a benzimidazole derivative, an azine derivative, a carbazole derivative, or a phenanthroline derivative, or (3) a high-molecular weight compound, for example, can be used for the electron transporting layer as a material other than the inventive compound.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: BeBq2), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl)stilbene (abbreviation: BzOs).

Examples of the high-molecular weight compound include poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy).

The above-described materials are materials having an electron mobility of 10-6 $cm^2/Vs$ or more. Materials other than those as described above may also be used in the electron transporting layer as long as they are materials high in the electron transporting capability rather than in the hole transporting capability.

Electron Injecting Layer

The electron injecting layer is a layer containing a material having high electron injection capability. For the electron injecting layer, an alkali metal such as lithium (Li) and cesium (Cs), an alkaline earth metal such as magnesium (Mg), calcium (Ca), and strontium (Sr), a rare earth metal such as europium (Eu) and ytterbium (Yb), or a compound containing any of these metals can be used. Examples of the compounds include an alkali metal oxide, an alkali metal halide, an alkali metal-containing organic complex, an alkaline earth metal oxide, an alkaline earth metal halide, an alkaline earth metal-containing organic complex, a rare earth metal oxide, a rare earth metal halide, and a rare earth metal-containing organic complex. These compounds may be used as a mixture of a plurality thereof.

In addition, a material having an electron transporting capability, in which an alkali metal, an alkaline earth metal, or a compound thereof is contained, specifically Alq in which magnesium (Mg) is contained may be used. In this case, electron injection from the cathode can be more efficiently performed.

Alternatively, in the electron injecting layer, a composite material obtained by mixing an organic compound with an electron donor may be used. Such a composite material is excellent in the electron injection capability and the electron transporting capability because the organic compound receives electrons from the electron donor. In this case, the organic compound is preferably a material excellent in transporting received electrons, and specifically, examples thereof include a material constituting the aforementioned electron transporting layer (such as a metal complex and a heteroaromatic compound). A material having an electron donation property for the organic compound may be used as the electron donor. Specifically, alkali metals, alkaline earth metals, and rare earth metals are preferred, and examples thereof include lithium, cesium, magnesium, calcium, erbium, and ytterbium. In addition, an alkali metal oxide or an alkaline earth metal oxide is preferred, and examples thereof include lithium oxide, calcium oxide, and barium oxide. In addition, a Lewis base, such as magnesium oxide, can also be used. In addition, an organic compound, such as tetrathiafulvalene (abbreviation: TTF), can also be used.

In other words, the electron transporting zone including the electron injecting layer may contain at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex containing an alkali metal, an organic complex containing an alkaline earth metal, and an organic complex containing a rare earth metal.

Cathode

It is preferred that a metal, an alloy, an electrically conductive compound, or a mixture thereof which has a low work function (specifically 3.8 eV or less) is used for the cathode. Specific examples of such a cathode material include elements belonging to group 1 or 2 of the periodic table of the elements, that is, alkali metals, such as lithium (Li) and cesium (Cs), alkaline earth metals, such as magnesium (Mg), calcium (Ca), and strontium (Sr), and alloys containing these (such as MgAg, and AlLi), and rare earth metals, such as europium (Eu), and ytterbium (Yb) and alloys containing these.

When the cathode is formed by using the alkali metals, the alkaline earth metals, and the alloys containing these, a vacuum vapor deposition method or a sputtering method can be adopted. In addition, when a silver paste or the like is used, a coating method, an inkjet method, or the like can be adopted.

By providing the electron injecting layer, the cathode can be formed using various conductive materials, such as Al, Ag, ITO, graphene, and indium oxide-tin oxide containing silicon or silicon oxide regardless of the magnitude of a work function. Such a conductive material can be deposited by using a sputtering method, an inkjet method, a spin coating method, or the like.

Insulating Layer

The organic EL device applies an electric field to an ultrathin film, and thus, pixel defects are likely to occur due to leaks or short-circuiting. In order to prevent this, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate of these may also be used.

Space Layer

The space layer is, for example, a layer provided between a fluorescent light emitting layer and a phosphorescent light emitting layer for the purpose of preventing excitons generated in the phosphorescent light emitting layer from diffusing into the fluorescent light emitting layer, or adjusting a carrier balance, in the case where the fluorescent light emitting layers and the phosphorescent light emitting layers are stacked. The space layer can also be provided among the plurality of phosphorescent light emitting layers.

Since the space layer is provided between the light emitting layers, a material having both an electron transporting capability and a hole transporting capability is preferred. Also, one having a triplet energy of 2.6 eV or more is preferred in order to prevent triplet energy diffusion in the adjacent phosphorescent light emitting layer. Examples of the material used for the space layer include the same as those used for the hole transporting layer as described above.

Blocking Layer

The blocking layer such as the electron blocking layer, the hole blocking layer, or the exciton blocking layer may be provided adjacent to the light emitting layer. The electron blocking layer is a layer that prevents electrons from leaking from the light emitting layer to the hole transporting layer, and the hole blocking layer is a layer that prevents holes from leaking from the light emitting layer to the electron transporting layer. The exciton blocking layer has a function of preventing excitons generated in the light emitting layer from diffusing into the surrounding layers, and trapping the excitons within the light emitting layer.

Each layer of the organic EL device may be formed by a conventionally known vapor deposition method, a coating method, or the like. For example, formation can be performed by a known method using a vapor deposition method such as a vacuum vapor deposition method, or a molecular beam vapor deposition method (MBE method), or a coating method using a solution of a compound for forming a layer, such as a dipping method, a spin-coating method, a casting method, a bar-coating method, and a roll-coating method.

The film thickness of each layer is not particularly limited, but is generally 5 nm to 10 μm, and more preferably 10 nm to 0.2 μm because in general, when the film thickness is too small, defects such as pinholes are likely to occur, and conversely, when the film thickness is too large, a high driving voltage is required and the efficiency decreases.

Electronic Devices

The organic EL device can be used in electronic devices, such as display components of an organic EL panel module and the like, display devices of a television, a mobile phone, a personal computer, and the like, and light emitting devices of lightings and vehicular lamps.

EXAMPLES

The following examples illustrate the present invention in more detail and are not intended to limit the scope of the invention.

Compound Used for Production of Organic EL Device of Example 1

Compound 1

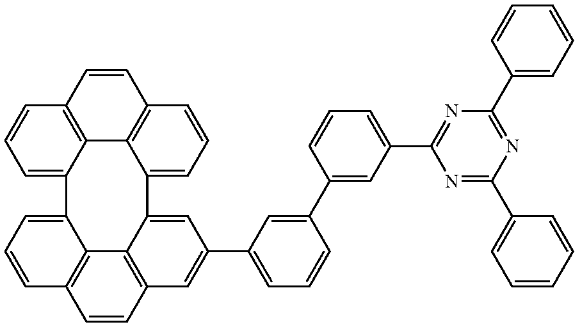

Comparative Compound Used for Production of Organic EL Device of Comparative Example 1

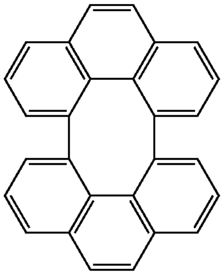 [SMILES: c1cc2ccc3cccc4c5cccc6ccc7cccc(c(c1)c2c34)c7c65]

Comparative Compound 1

Other Compounds Used for Production of Organic EL Devices of Example and Comparative Example

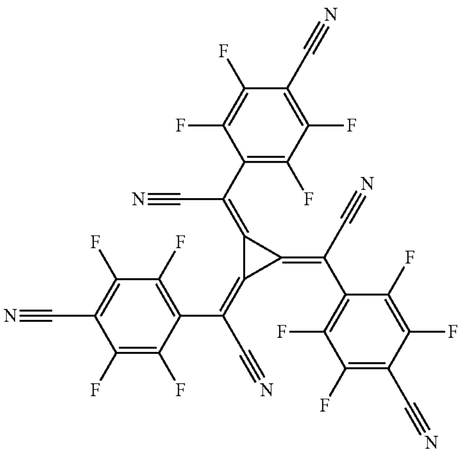

HI-1

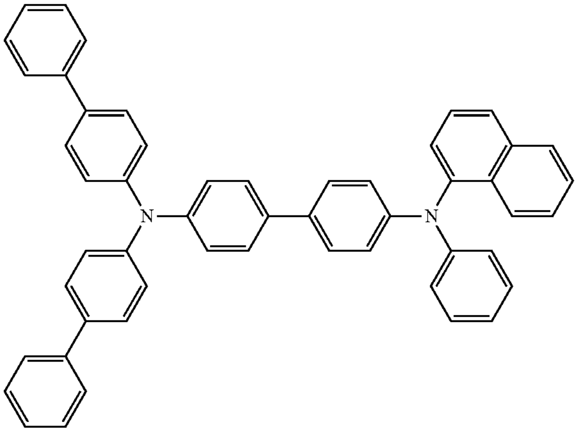

HT-1

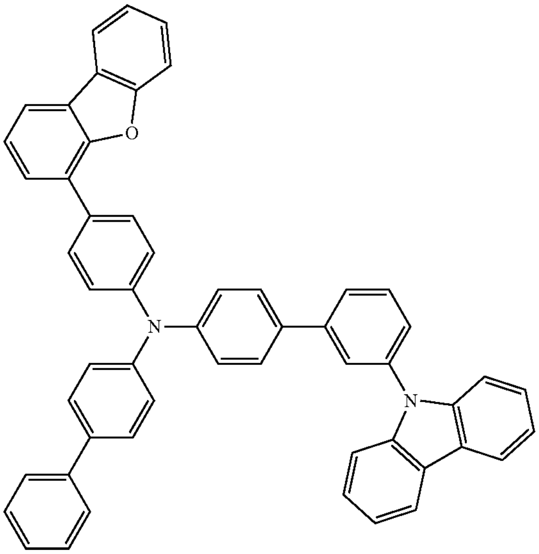

EBL-1

-continued

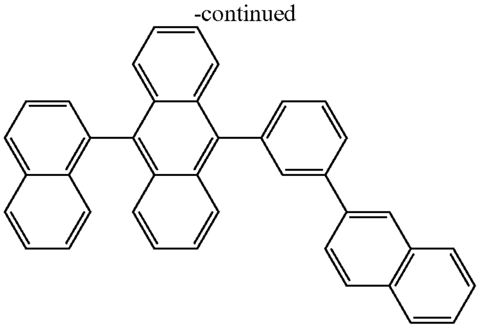

BH-1

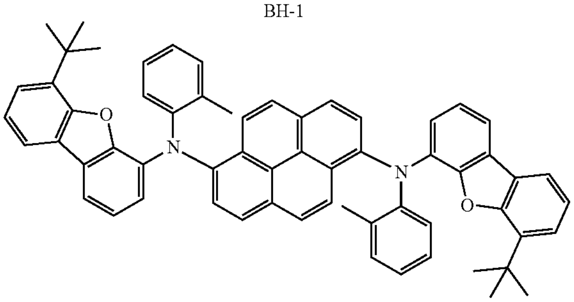

BD-1

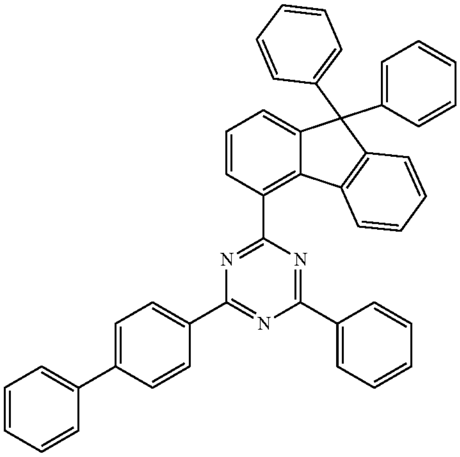

ETL-1

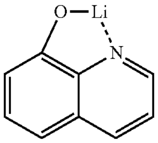

Liq

Production of Organic EL Device

Example 1

A glass substrate having a width of 25 mm, a length of 75 mm and a thickness of 1.1 mm, equipped with an ITO transparent electrode (anode) (manufactured by GEOMATEC Co., Ltd.) was ultrasonically cleaned in isopropyl alcohol for 5 minutes, and then UV ozone-cleaned for 30 minutes. The film thickness of the ITO was 130 nm.

The glass substrate with the ITO transparent electrode after cleaning was mounted on a substrate holder of a vacuum vapor deposition apparatus, and Compound HT-1 and Compound HI-1 were vapor co-deposited on the substrate surface, having the transparent electrode formed thereon, in such a manner as to cover the transparent electrode, thereby forming a hole injecting layer having a thickness of 10 nm. The mass ratio between Compound HT-1 and Compound HI-1 (HT-1: HI-1) was 97:3.

Subsequently, Compound HT-1 was vapor deposited on the hole injecting layer to form a first hole transporting layer having a thickness of 80 nm.

Subsequently, Compound EBL-1 was vapor deposited on this first hole transporting layer to form a second hole transporting layer having a thickness of 5 nm.

Subsequently, Compound BH-1 (host material) and Compound BD-1 (dopant material) were vapor co-deposited on this second hole transporting layer to form a light emitting layer having a thickness of 25 nm. The mass ratio between Compound BH-1 and Compound BD-1 (BH-1: BD-1) was 96:4.

Subsequently, Compound 1 was vapor deposited on the light emitting layer to form a first electron transporting layer having a thickness of 5 nm.

Subsequently, Compound ETL-1 and Liq were vapor co-deposited on the first electron transporting layer to form a second electron transporting layer having a thickness of 20 nm. The mass ratio between Compound ETL-1 and (8-quinolinolato) lithium (abbreviation: Liq) (ETL-1: Liq) was 50:50.

Subsequently, Yb was vapor deposited on the electron transporting layer to form an electron injecting electrode having a thickness of 1 nm.

Subsequently, metal Al was vapor deposited on the electron injecting electrode to form a metal cathode having a thickness of 50 nm.

The layer structure of the organic EL device of Example 1 thus obtained is as follows.

ITO (130)/HT-1: HI-1=97:3 (10)/HT-1 (80)/EBL-1 (5)/BH-1: BD-1=96:4 (25)/Compound 1 (5)/ETL-1: Liq=50:50 (20)/Yb (1)/Al (50)

In the layer structure, each numeral in parentheses indicates a film thickness (nm), and the ratios are by mass.

Comparative Example 1

An organic EL device was produced in the same manner as in Example 1 except that the material for the first electron transporting layer was changed to Comparative Compound 1 as shown in Table 1 below.

Evaluation of Organic EL Device

Measurement of Driving Voltage

A voltage (unit: V) was measured when the organic EL device obtained was driven at a constant direct current by applying the current between the ITO electrode and the metal Al electrode at a current density of 10 mA/$cm^2$ under room temperature.

Measurement of External Quantum Efficiency (EQE)

The organic EL device obtained was driven at a constant direct current at a current density of 10 mA/$cm^2$ under room temperature, and the luminance was measured using a spectroradiometer "CS-1000" (manufactured by Konica Minolta, Inc.). The external quantum efficiency (%) was determined from the measurement results. The results are shown in Table 1.

TABLE 1

(*1)

| | Material for first electron transporting layer | Voltage [V] | EQE [%] |
|---|---|---|---|
| Example 1 | Compound 1 | 3.6 | 9.6 |
| Comparative Example 1 | Comparative Compound 1 | 5.8 | 5.0 |

(*1): Voltage and EQE values at 10 mA/$cm^2$

The results of Table 1 verify that compared to the compound (Comparative Compound 1 of Comparative Example 1) that does not meet the requirement of the present invention, the compound (Compound 1 of Example 1) that meets the requirement of the present invention can be driven at a lower voltage and is significantly improved in the external quantum efficiency.

Compounds 1 to 4 Synthesized in Synthesis Examples 1 to 4

Compound 1

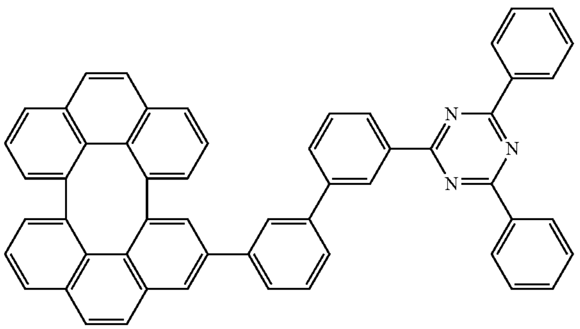

Compound 2

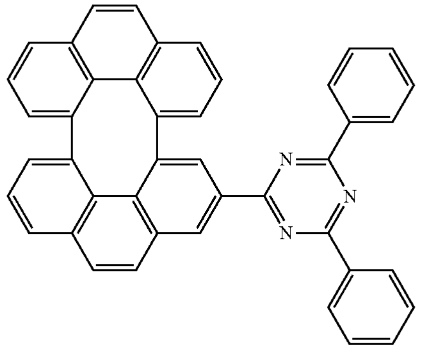

Compound 3

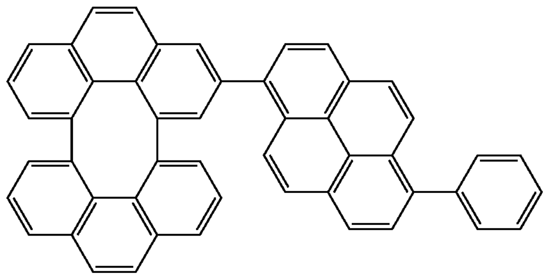

-continued

Compound 4

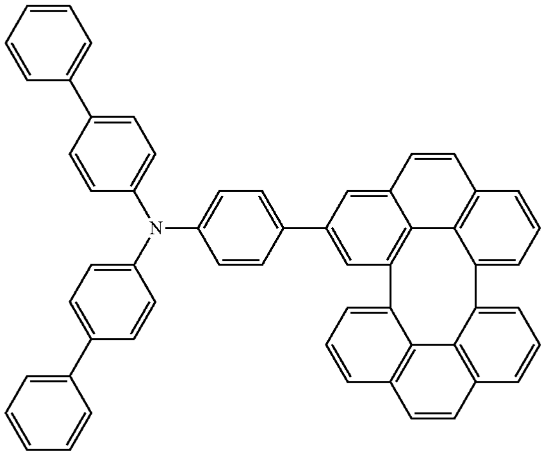

SYNTHESIS OF COMPOUNDS

Synthesis Example 1: Synthesis of Compound M-1

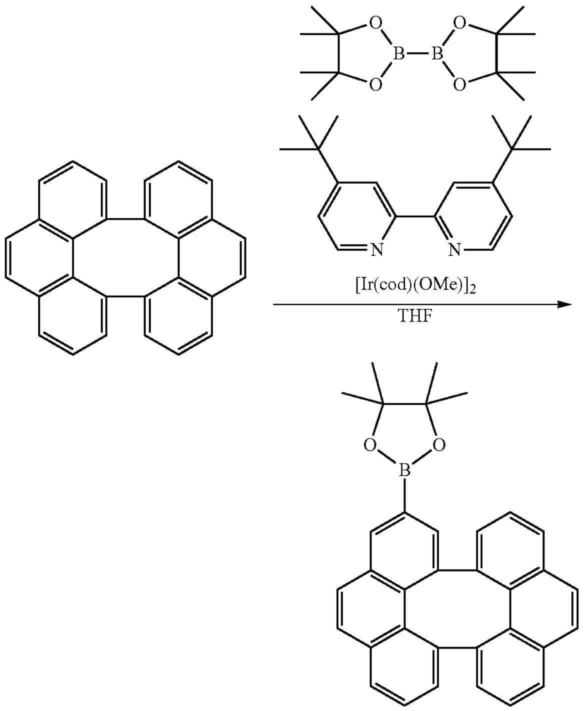

M-1

Dibenzo[def, pqr]tetraphenylene (9.04 g), 4,4,4',4',5,5,5',5'-octamethyl-2,2'-bi-1,3,2-dioxaborolane (3.91 g), 4,4'-di-tert-butyl-2,2'-bipyridyl (0.34 g), and (1,5-cyclooctadiene)(methoxy) iridium (I) dimer (0.43 g) were placed in a flask. After replacing the atmosphere in the flask with argon gas, THF (257 mL) was added to the mixture, and the mixture was heated and stirred for 5 hours under reflux conditions. The solvent was distilled off from the reaction solution, and the resulting solid was purified by silica gel chromatography to obtain Compound M-1 as a white solid (3.62 g, yield 30%).

As a result of mass spectroscopy analysis of the white solid, m/e=479 for the molecular weight of 478.40; the white solid was identified as Compound M-1.

Synthesis Example 1: Synthesis of Compound 1

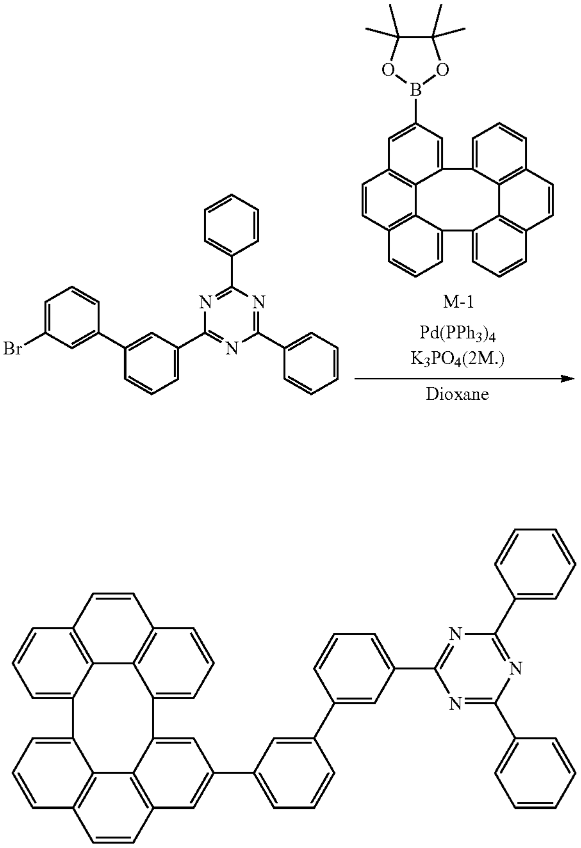

Compound 1

2-(3'-bromobiphenyl-3-yl)-4,6-diphenyl-1,3,5-triazine (2.93 g), Compound M-1 (3.16 g), and tetrakis(triphenylphosphine)palladium(0) (also known as Pd(PPh$_3$)$_4$, 0.36 g) were placed in a flask. After replacing the atmosphere in the flask with argon gas, 1,4-dioxane (63 mL) and an aqueous solution of 2M potassium phosphate (9.5 mL) were added to the mixture, and the mixture was heated and stirred for 8 hours under reflux conditions. The solvent was distilled off from the reaction solution, and the resulting solid was purified by silica gel chromatography to obtain Compound 1 as a white solid (2.90 g, yield 63%). As a result of mass spectroscopy analysis of the white solid, m/e=736 for the molecular weight of 735.89; the white solid was identified as Compound 1.

Synthesis Example 2: Synthesis of Compound 2

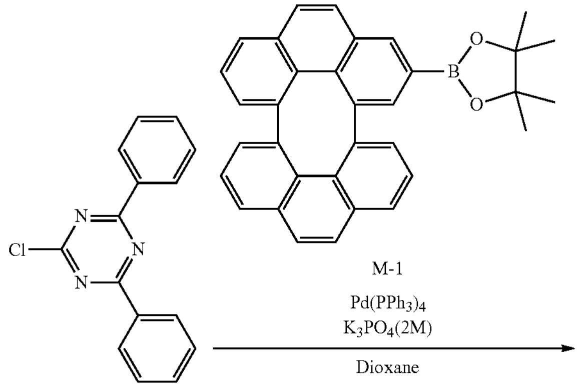

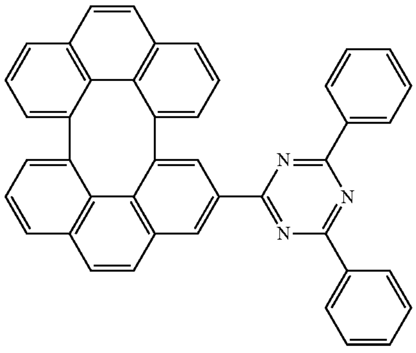

Compound 2

Using 2-chloro-4,6-diphenyl-1,3,5-triazine (2.00 g) and Compound M-1 (3.93 g), Compound 2 was synthesized in the same manner as in Synthesis Example 1. Compound 2 was obtained as a white solid (3.14 g, yield 72%).

As a result of mass spectroscopy analysis of the white solid, m/e=584 for the molecular weight of 583.69; the white solid was identified as Compound 2.

Synthesis Example 3: Synthesis of Compound 3

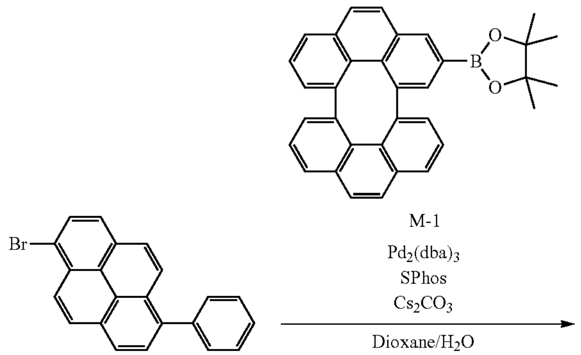

-continued

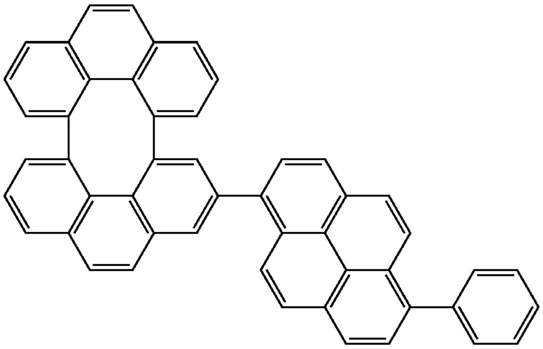

Compound 3

1-bromo-6-phenylpyrene (2.50 g), Compound M-1 (3.35 g), tris(dibenzylideneacetone)dipalladium(0) (also known as $Pd_2(dba)_3$, 0.13 g), 2-dicyclohexylphosphino-2',6'-dimethoxybiphenyl (also known as SPhos, 0.23 g) and cesium carbonate (4.56 g) were placed in a flask. After replacing the atmosphere in the flask with argon gas, 1,4-dioxane (30 mL) and water (5.0 mL) were added to the mixture, and the mixture was heated and stirred for 8 hours under reflux conditions. After cooling the reaction solution, methanol was added to the solution, and the precipitated solid was collected by filtration, followed by cleaning with water and methanol. The resulting crude product was purified by silica gel chromatography and recrystallization using toluene to obtain Compound 3 as a white solid (1.89 g, yield 43%).

As a result of mass spectroscopy analysis of the white solid, m/e=629 for the molecular weight of 628.77; the white solid was identified as Compound 3.

Synthesis Example 4: Synthesis of Compound 4

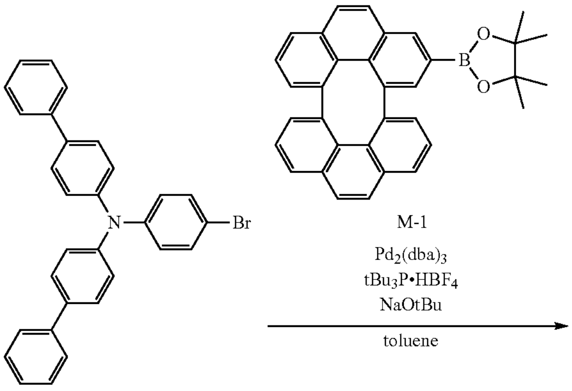

-continued

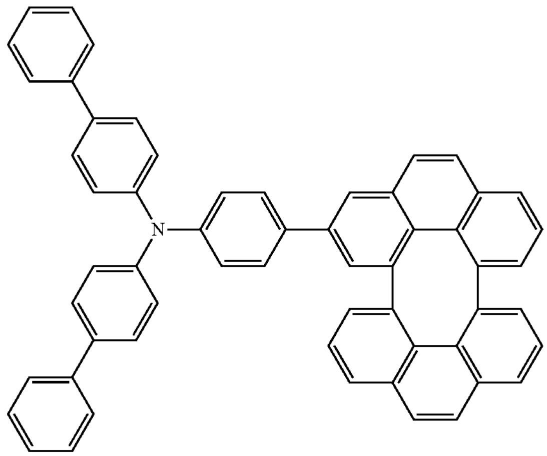

Compound 4

N-([1,1'-biphenyl]-4-yl)-N-(4-bromophenyl)-[1,1'-biphenyl]-4-amine (4.76 g), Compound M-1 (4.78 g), tris(dibenzylideneacetone)dipalladium(0) (also known as $Pd_2(dba)_3$, 0.18 g), tri-tert-butylphosphonium tetrafluoroborate (0.23 g), and sodium tert-butoxide (1.44 g) were placed in a flask. After replacing the atmosphere in the flask with argon gas, toluene (50 mL) was added to the mixture, and the mixture was heated and stirred for 3 hours under reflux conditions. After cooling the reaction solution, the solution was extracted with toluene, followed by vacuum concentration of the extract. The resulting residue was purified by silica gel chromatography and recrystallization using toluene to obtain Compound 4 as a white solid (4.52 g, yield 60%).

As a result of mass spectroscopy analysis of the white solid, m/e=748 for the molecular weight of 747.94; the white solid was identified as Compound 4.

REFERENCE SIGNS LIST

1, 11 organic EL device
2 substrate
3 anode
4 cathode
5 light emitting layer
6 hole transporting zone (hole transporting layer)
6*a* hole injecting layer
6*b* first hole transporting layer
6*c* second hole transporting layer
7 electron transporting zone (electron transporting layer)
7*a* first electron transporting layer
7*b* second electron transporting layer
10, 20 light emitting unit

What is claimed is:

1. A compound represented by the following formula (1A) or (1B):

(1A)

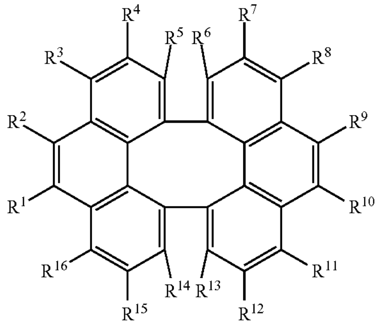

(1B)

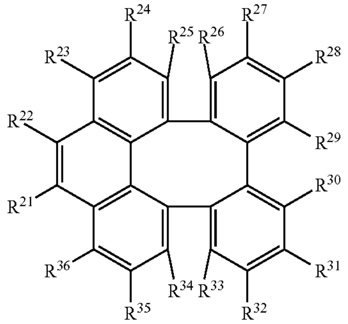

wherein at least one selected from $R^1$ to $R^{16}$ and at least one selected from $R^{21}$ to $R^{36}$ are represented by the following formula (2A), (2B), (2C) or (2D):

(2A)

$$*\text{—}(L^1)_a\text{—HET}$$

(2B)

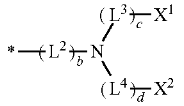

(2C)

$$*\text{—}(L^5)_e\text{—Ar}$$

(2D)

$$*\text{—}(L^6)_f\text{—Y}$$

where * represents a bonding position to a carbon atom in the formula (1A) at which $R^1$ to $R^{16}$ are bonded or a bonding position to a carbon atom in the formula (1B) at which $R^{21}$ to $R^{36}$ are bonded, $L^1$ to $L^6$ each independently represent a substituted or unsubstituted arylene group having 6 to 50 ring carbon atoms, or a substituted or unsubstituted divalent heterocyclic group having 5 to 50 ring atoms, a, b, c, d, e and f each independently represent 0, 1, 2 or 3, and $(L^1)_0$, $(L^2)_0$, $(L^3)_0$, $(L^4)_0$, $(L^5)_0$ and $(L^6)_0$ each independently represent a single bond, when two or more $L^1$s are present, they may be the same or different, when two or more $L^2$s are present, they may be the same or different, when two or more $L^3$s are present, they may be the same or different, when two or more $L^4$s are present, they may be the same or different, when two or more $L^5$s are present, they may be the same or different, and when two or more $L^6$s are present, they may be the same or different, HET represents a substituted or unsubstituted heterocyclic group having 5 to 50 ring atoms, $X^1$ and $X^2$ each independently represent a substituted or unsubstituted aryl group having 6 to 50 ring carbon atoms, or a substituted or unsubstituted heterocyclic group having 5 to 50 ring atoms, Ar represents a substituted or unsubstituted aryl group having 10 to 50 ring carbon atoms, Y represents a group selected from the following formulae (i) to (viii):

(i)

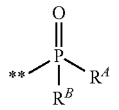

(ii)

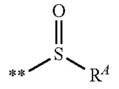

(iii)

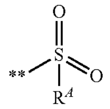

(iv)

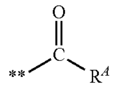

(v)

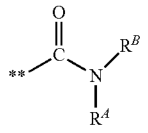

(vi)

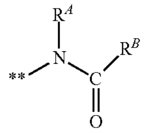

(vii)

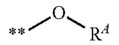

(viii)

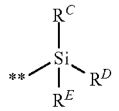

where ** represents a bonding position at which Y is bonded to $L^6$ in the formula (2D), $R^A$ and $R^B$ each independently represent a hydrogen atom or a substituent $Z^1$, $R^C$, $R^D$ and $R^E$ each independently represent a substituted or unsubstituted aryl group having 6 to 50 ring carbon atoms, the substituent $Z^1$ is a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted aralkyl group having 7 to 50 carbon atoms, a substituted or unsubstituted heterocyclic group having 5 to 50 ring atoms, a substituted or unsubstituted haloalkyl group having 1 to 50 carbon atoms, a substituted or unsubstituted haloalkoxy group having 1 to 50 carbon atoms, a group represented by —Si($R_{901}$) ($R_{902}$) ($R_{903}$), a group represented by —O—($R_{904}$), a group represented by —S—($R_{905}$), or a group represented by —N($R_{906}$) ($R_{907}$), $R_{901}$ to $R_{907}$ each independently represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, when two or more $R_{901}$'s are present, the $R_{901}$'s may be the same or different, when two or more $R_{902}$'s are present, the $R_{902}$'s may be the same or different, when two or more $R_{903}$'s are present, the $R_{903}$'s may be the same or different, when two or more $R_{904}$'s are present, the $R_{904}$'s may be the same or different, when two or more $R_{905}$'s are present, the $R_{905}$'s may be the same or different, when two or more $R_{906}$'s are present, the $R_{906}$'s may be the same or different, when two or more $R_{907}$'s are present, the $R_{907}$'s may be the same or different, when $R^1$, $R^2$, $R^9$ and $R^{10}$ in the formula (1A) are all represented by the formula (2A), at least one selected from $R^1$, $R^2$, $R^9$ and $R^{10}$ is the formula (2A) in which HET contains a nitrogen atom, when two or more selected from $R^1$ to $R^{16}$ in the formula (1A) are represented by the formula (2A), they may be the same or different, when two or more selected from $R^1$ to $R^{16}$ are represented by the formula (2B), they may be the same or different, when two or more selected from $R^1$ to $R^{16}$ are represented by the formula (2C), they may be the same or different, and when two or more selected from $R^1$ to $R^{16}$ are represented by the formula (2D), they may be the same or different, and $R^1$ to $R^{16}$ are not bonded to each other, when two or more selected from $R^{21}$ to $R^{36}$ in the formula (1B) are represented by the formula (2A), they may be the same or different, when two or more selected from $R^{21}$ to $R^{36}$ are represented by the formula (2B), they may be the same or different, when two or more selected from $R^{21}$ to $R^{36}$ are represented by the formula (2C), they may be the same or different, and when two or more selected from $R^{21}$ to $R^{36}$ are represented by the formula (2D), they may be the same or different, and $R^{21}$ to $R^{36}$ are not bonded to each other, in the formulae (1A) and (1B), $R^1$ to $R^{16}$ and $R^{21}$ to $R^{36}$ which are not represented by the formula (2A), (2B), (2C) or (2D) each independently represent a hydrogen atom or a substituent $Z^2$, the substituent $Z^2$ is a halogen atom, a nitro group, a cyano group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted phenyl group, a substituted or unsubstituted aralkyl group having 7 to 50 carbon atoms, a substituted or unsubstituted haloalkyl group having 1 to 50 carbon atoms, a substituted or unsubstituted haloalkoxy group having 1 to 50 carbon atoms, a group represented by —$Si(R_{901})(R_{902})(R_{903})$, a group represented by —S—$(R_{905})$, or a group represented by —$N(R_{906})(R_{907})$, $R_{901}$ to $R_{907}$ each independently represent a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, when two or more $R_{901}$'s are present, the $R_{901}$'s may be the same or different, when two or more $R_{902}$'s are present, the $R_{902}$'s may be the same or different, when two or more $R_{903}$'s are present, the $R_{903}$'s may be the same or different, when two or more $R_{905}$'s are present, the $R_{905}$'s may be the same or different, when two or more $R_{906}$'s are present, the $R_{906}$'s may be the same or different, when two or more $R_{907}$'s are present, the $R_{907}$'s may be the same or different, at least one of $R_{901}$ to $R_{903}$ is not a substituted or unsubstituted aryl group having 6 to 50 ring carbon atoms, and at least one of $R_{906}$ and $R_{907}$ is a hydrogen atom, a substituted or unsubstituted alkyl group having 1 to 50 carbon atoms, or a substituted or unsubstituted cycloalkyl group having 3 to 50 ring carbon atoms, and $R_{901}$ to $R_{903}$ are not bonded to each other, and $R_{906}$ and $R_{907}$ are not bonded to each other.

2. The compound according to claim 1, wherein in the formula (1A), at least one selected from $R^1$, $R^2$, $R^4$, $R^7$, $R^9$, $R^{10}$, $R^{12}$, and $R^{15}$ is represented by the formula (2A), (2B), (2C) or (2D) and, in the formula (1B), at least one selected from $R^{21}$, $R^{22}$, $R^{24}$, $R^{27}$, $R^{28}$, $R^{29}$, $R^{30}$, $R^{31}$, $R^{32}$, and $R^{35}$ is represented by the formula (2A), (2B), (2C) or (2D).

3. The compound according to claim 1, wherein the formula (1A) is represented by the following formula (1A2A-1), (1A2A-2), (1A2B-1), (1A2B-2), (1A2C-1), (1A2C-2), (1A2D-1) or (1A2D-2), and the formula (1B) is represented by the following formula (1B2A-1), (1B2A-2), (1B2A-3), (1B2A-4), (1B2A-5), (1B2B-1), (1B2B-2), (1B2B-3), (1B2B-4), (1B2B-5), (1B2C-1), (1B2C-2), (1B2C-3), (1B2C-4), (1B2C-5), (1B2D-1), (1B2D-2), (1B2D-3), (1B2D-4) or (1B2D-5):

(1A2A-1)

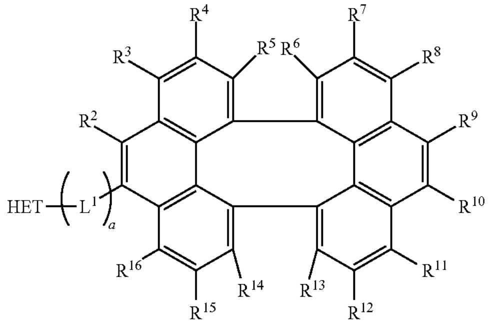

(1A2A-2)

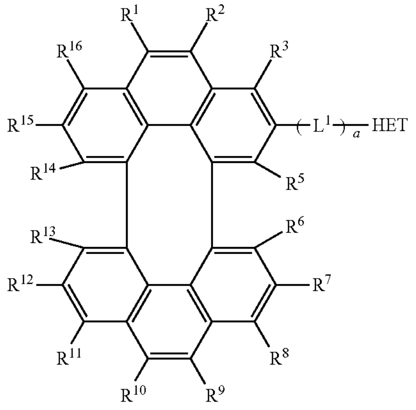

(1A2B-1)

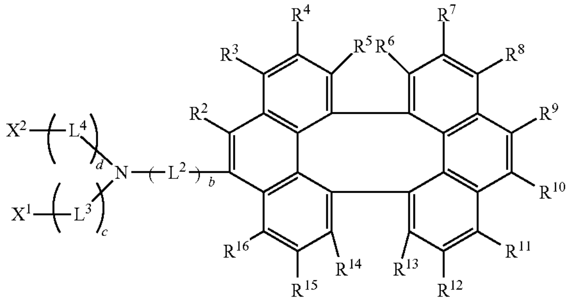

(1A2B-2)

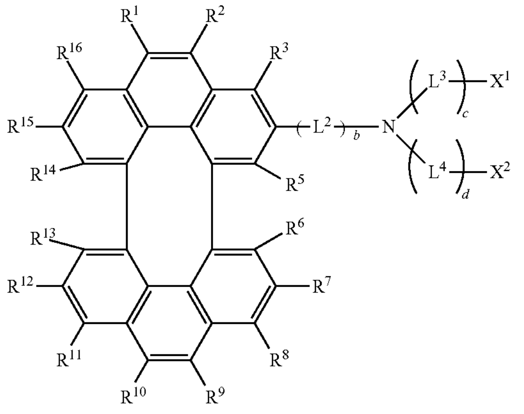

-continued
(1A2C-1)
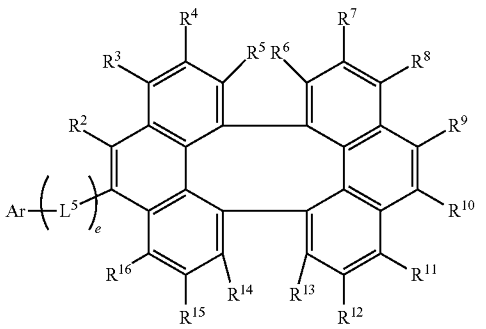
(1A2C-2)
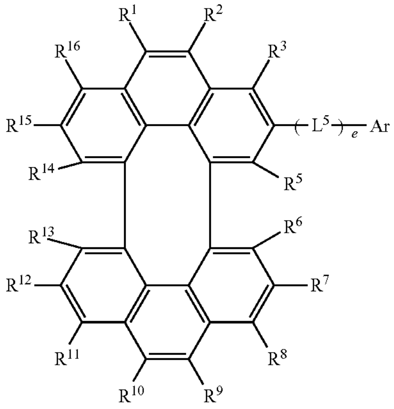
(1A2D-1)
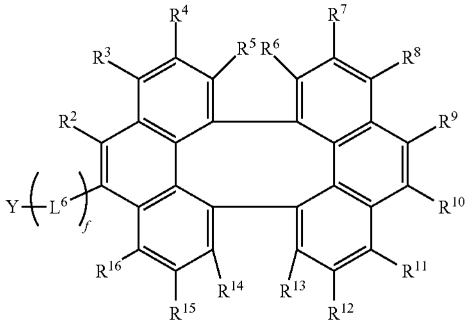
(1A2D-2)
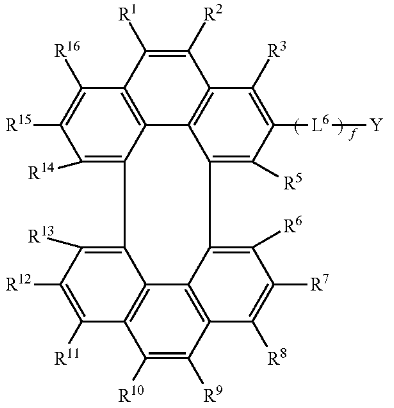
-continued
(1B2A-1)
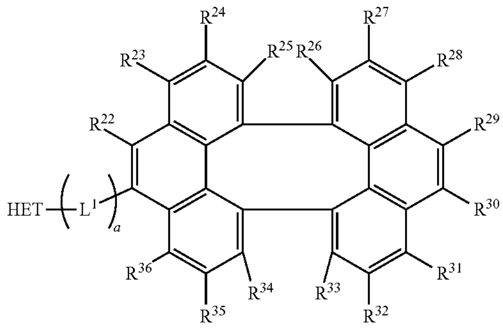
(1B2A-2)
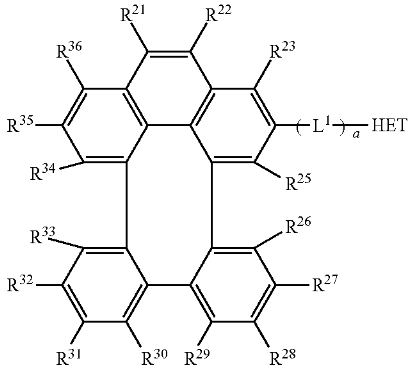
(1B2A-3)
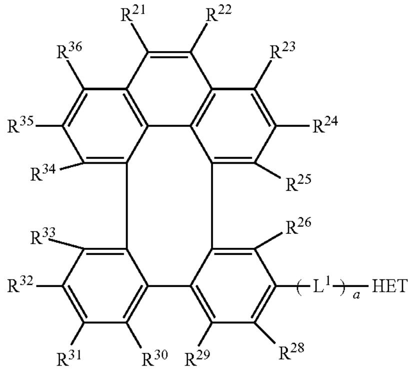
(1B2A-4)
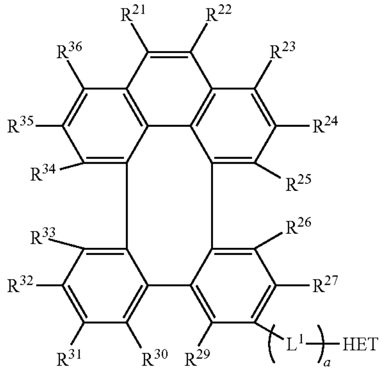

-continued
(1B2A-5)
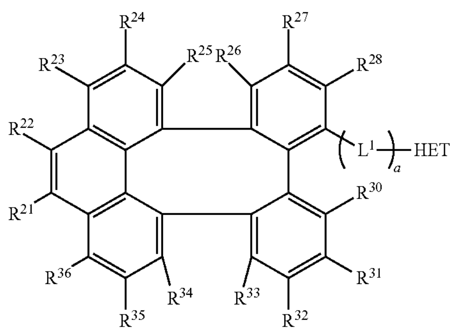
(1B2B-1)
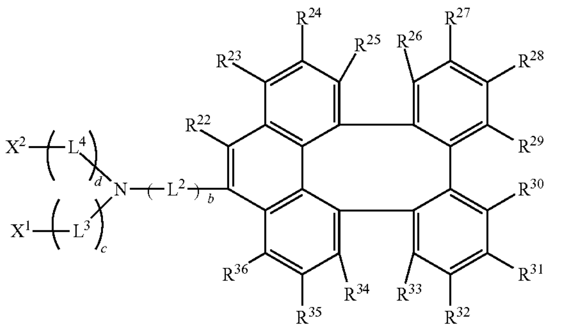
(1B2B-2)
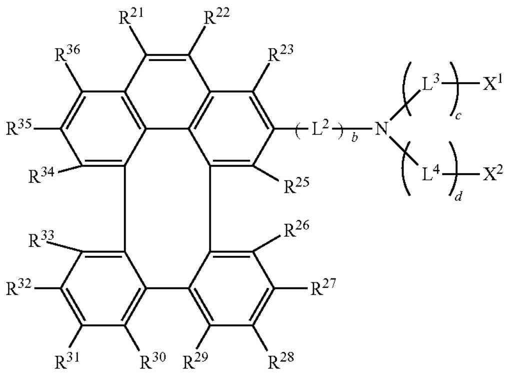
(1B2B-3)
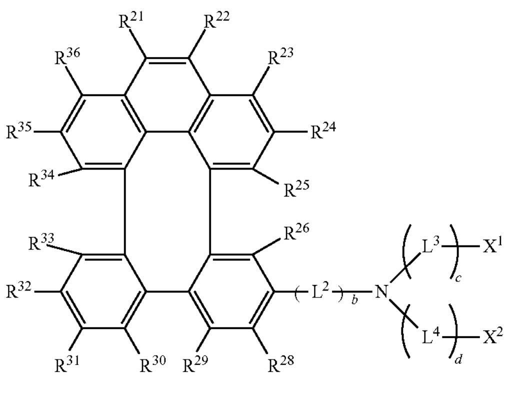
-continued
(1B2B-4)
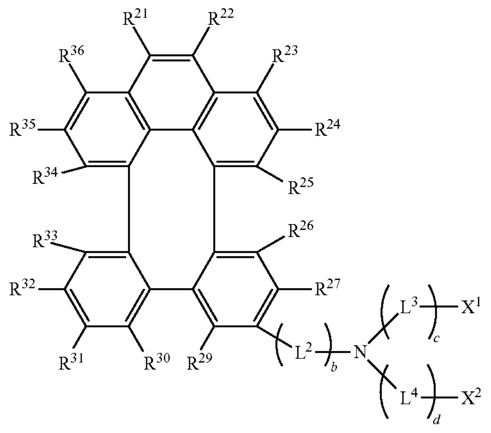
(1B2B-5)
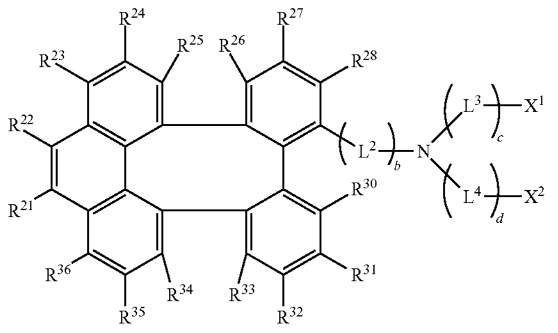
(1B2C-1)
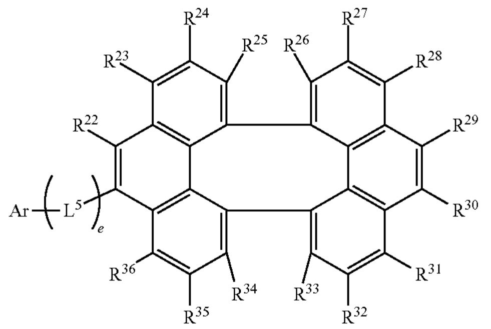
(1B2C-2)
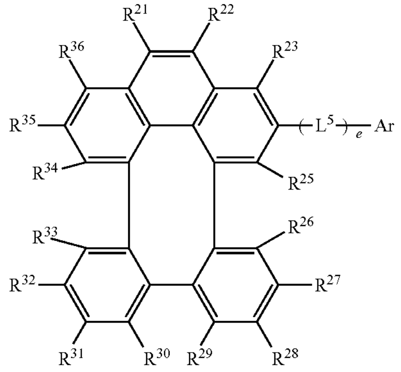

-continued
(1B2C-3)
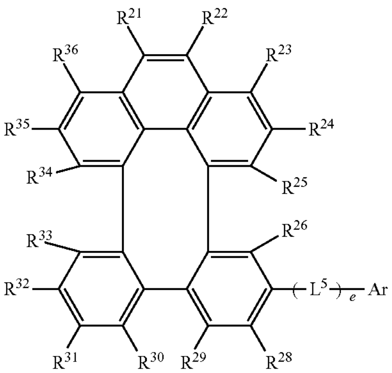
(1B2C-4)
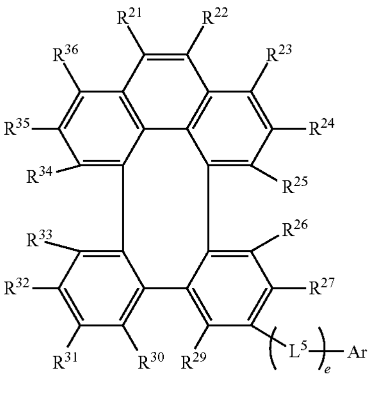
(1B2C-5)
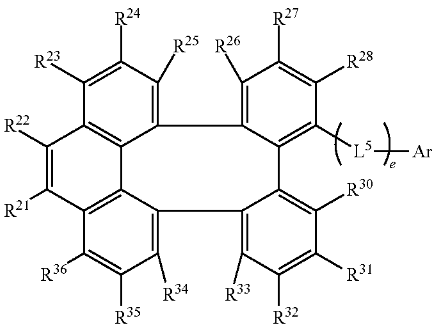
(1B2D-1)
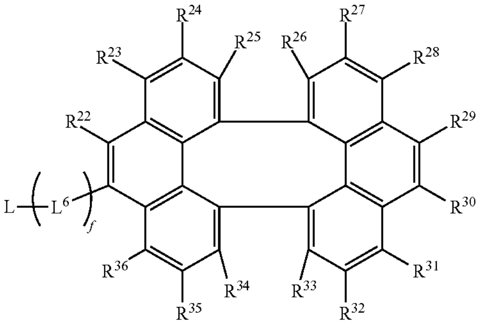
-continued
(1B2D-2)
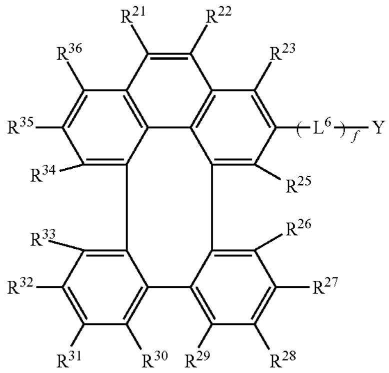
(1B2D-3)
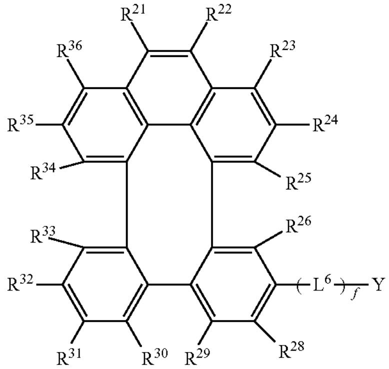
(1B2D-4)
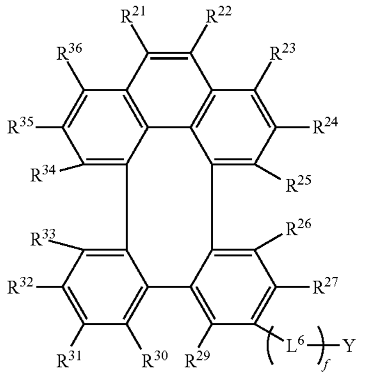
(1B2D-5)
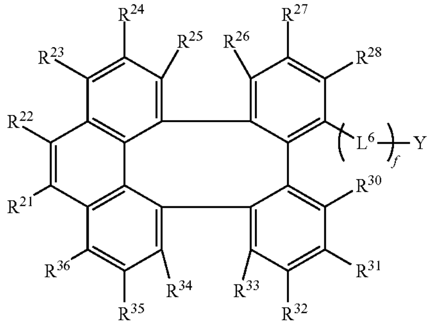
wherein $R^1$ to $R^{16}$, $R^{21}$ to $R^{36}$, $L^1$ to $L^6$, a, b, c, d, e, f, HET, $X^1$, $X^2$, Y and Ar have the same meaning as defined in the formulae (1A) and (1B).
4. The compound according to claim 1, wherein the formula (1A) is represented by the following formula (1A2A-11), (1A2A-12), (1A2A-13), (1A2A-14), (1A2A-

15), (1A2B-11), (1A2B-12), (1A2B-13), (1A2B-14), (1A2B-15), (1A2C-11), (1A2C-12), (1A2C-13), (1A2C-14), (1A2C-15), (1A2D-11), (1A2D-12), (1A2D-13), (1A2D-14) or (1A2D-15), and the formula (1B) is represented by the following formula (1B2A-11), (1B2A-12), (1B2A-13),
(1B2A-14), (1B2A-15), (1B2A-16), (1B2B-11), (1B2B-12), (1B2B-13), (1B2B-14), (1B2B-15), (1B2B-16), (1B2C-11), (1B2C-12), (1B2C-13), (1B2C-14), (1B2C-15), (1B2C-16), (1B2D-11), (1B2D-12), (1B2D-13), (1B2D-14), (1B2D-15) or (1B2D-16):
(1A2A-11)
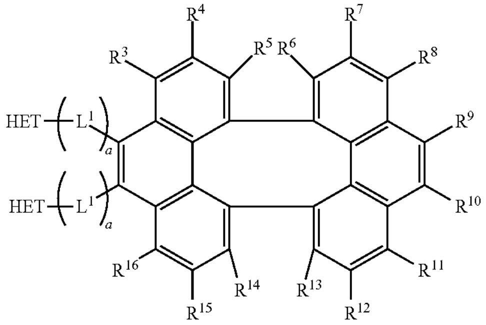
(1A2A-12)
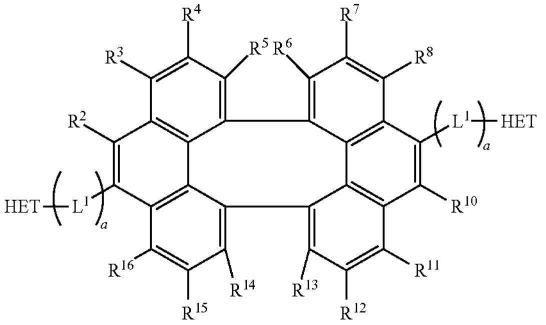
(1A2A-13)
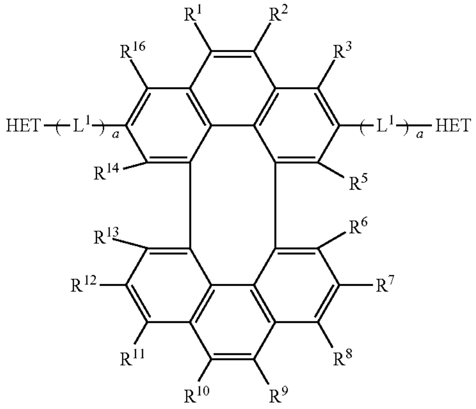
(1A2A-14)
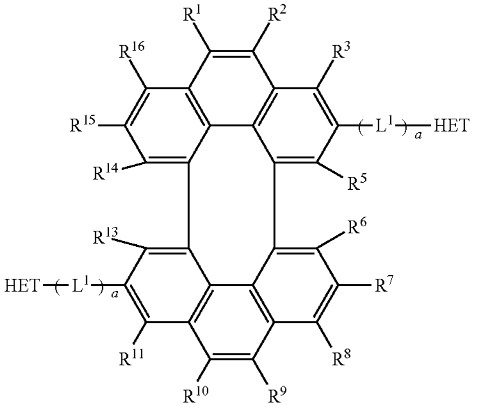
(1A2A-15)
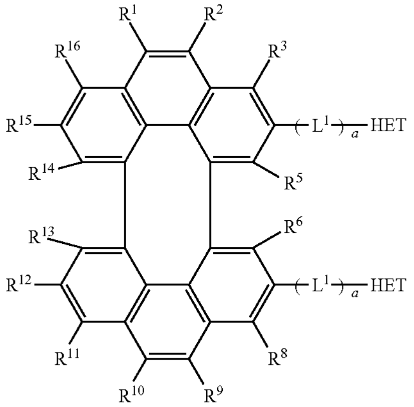
(1A2B-11)
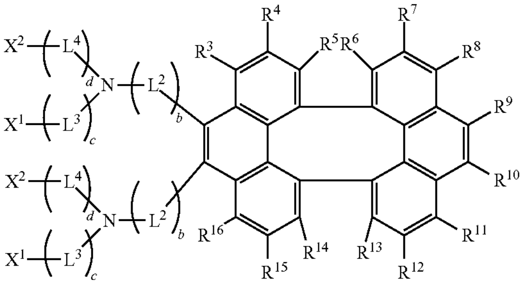

-continued
(1A2B-12)
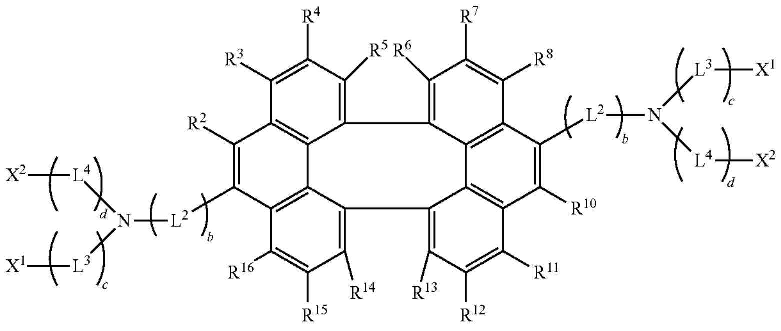
(1A2B-13)
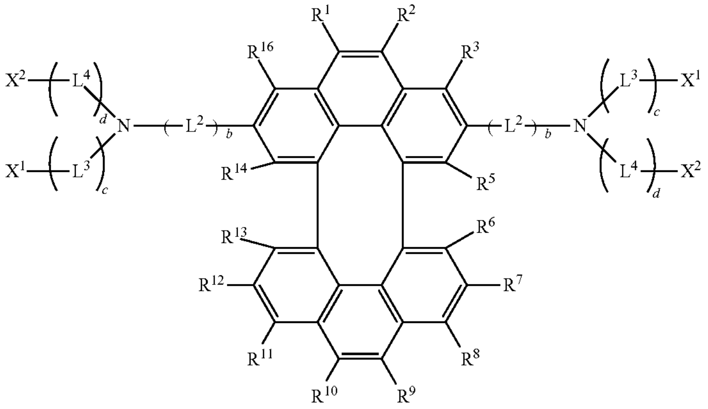
(1A2B-14)
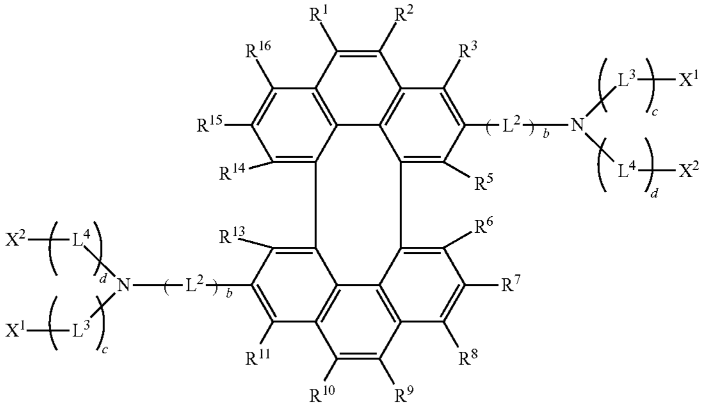
(1A2B-15)
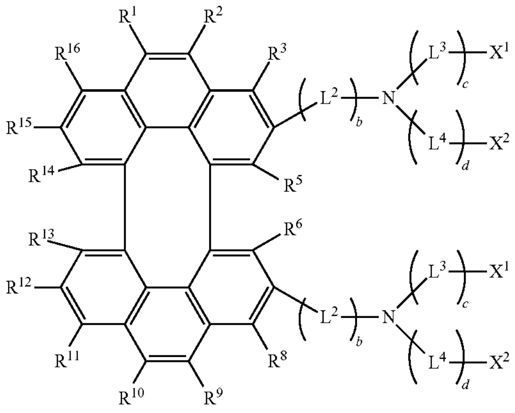
(1A2C-11)
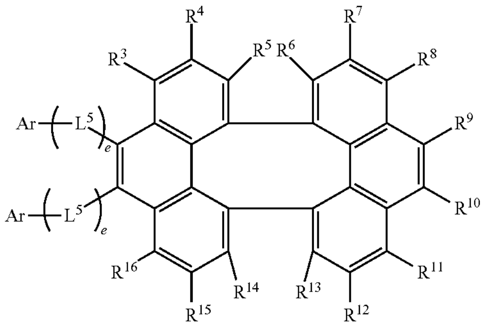

-continued
(1A2C-12)
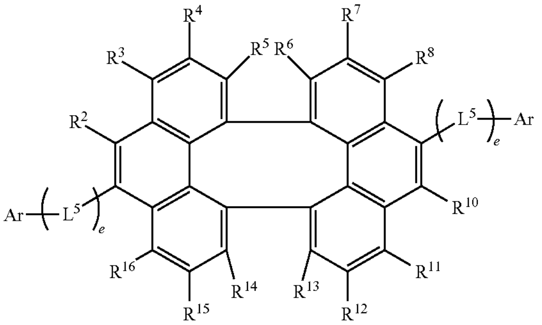
(1A2C-13)
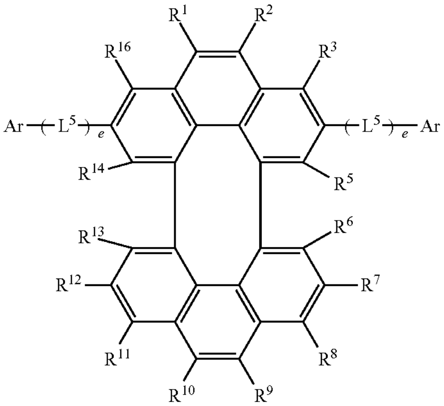
(1A2C-14)
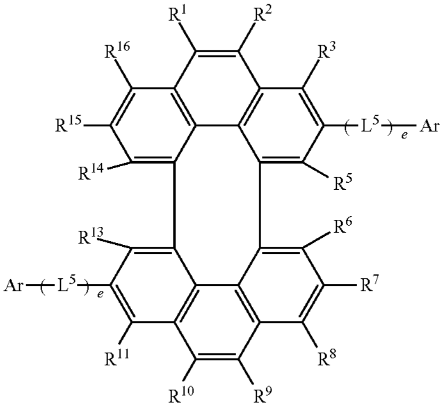
(1A2C-15)
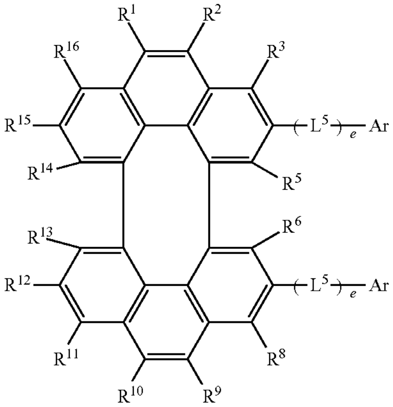
(1A2D-11)
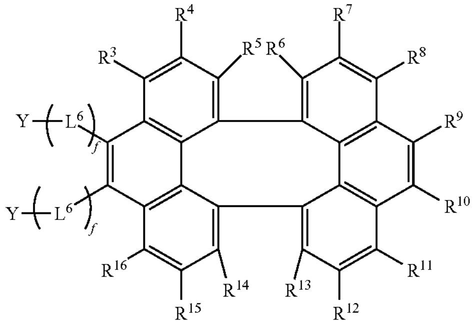
(1A2D-12)
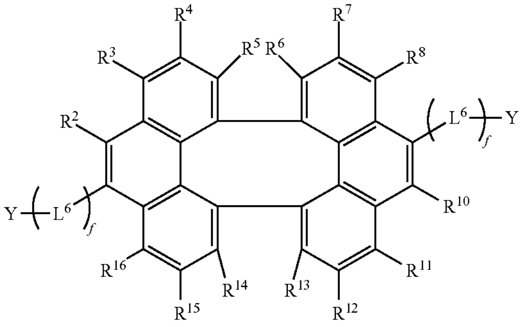
(1A2D-13)
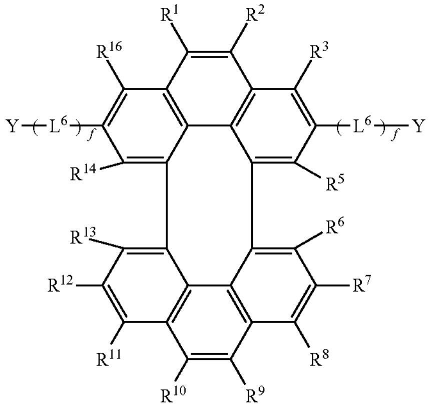
(1A2D-14)
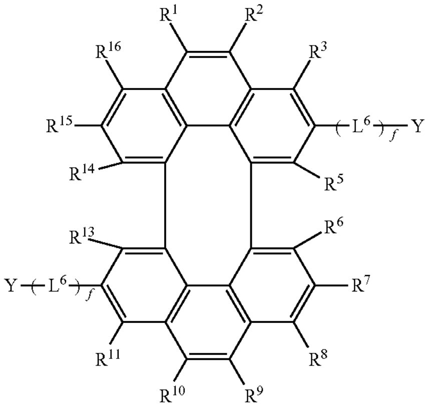

-continued
(1A2D-15)
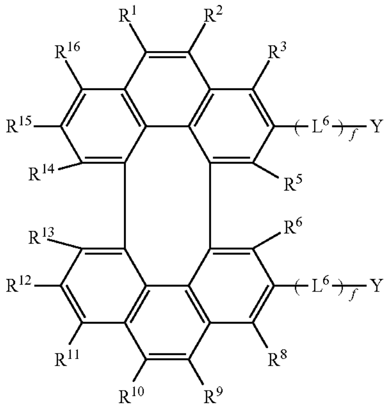
(1B2A-11)
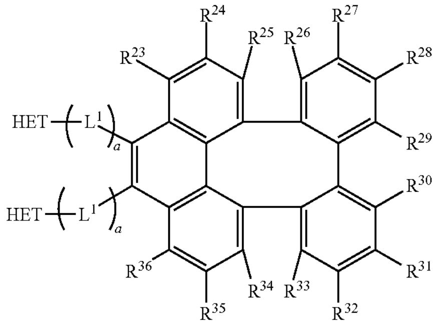
(1B2A-12)
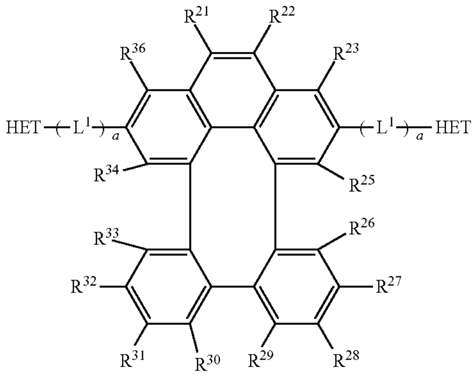
(1B2A-13)
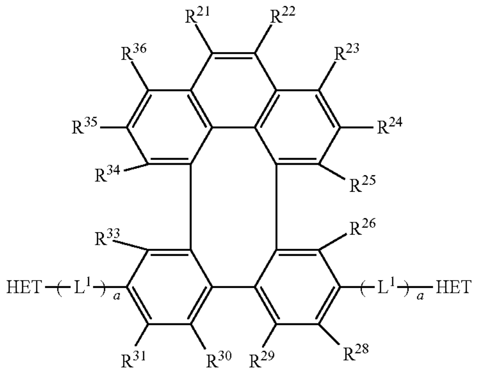
(1B2A-14)
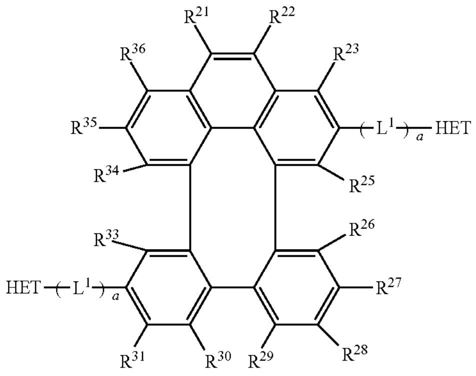
(1B2A-15)
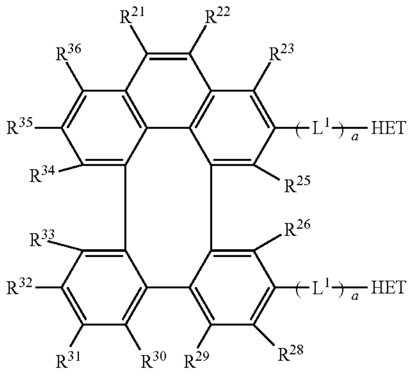
(1B2A-16)
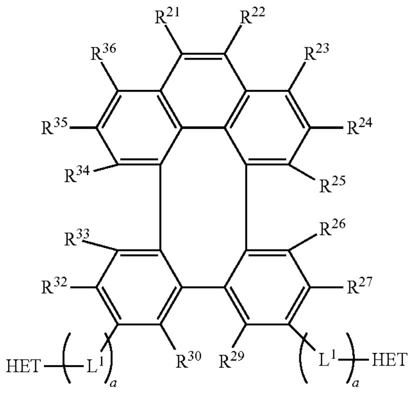
(1B2B-11)
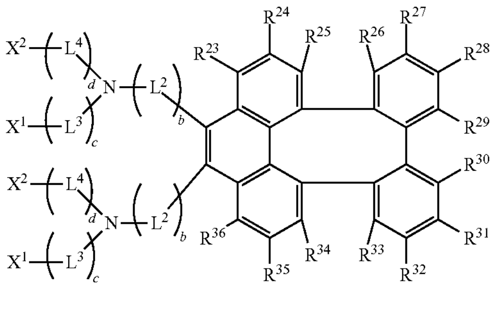

-continued
(1B2B-12)
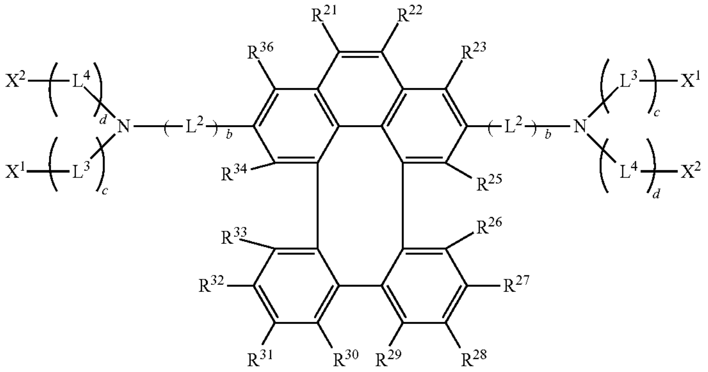
(1B2B-13)
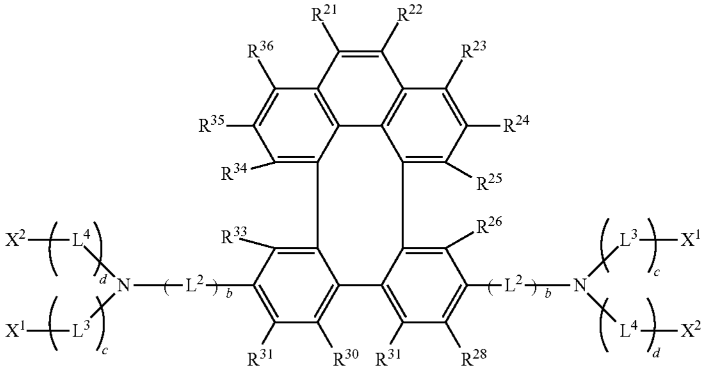
(1B2B-14)
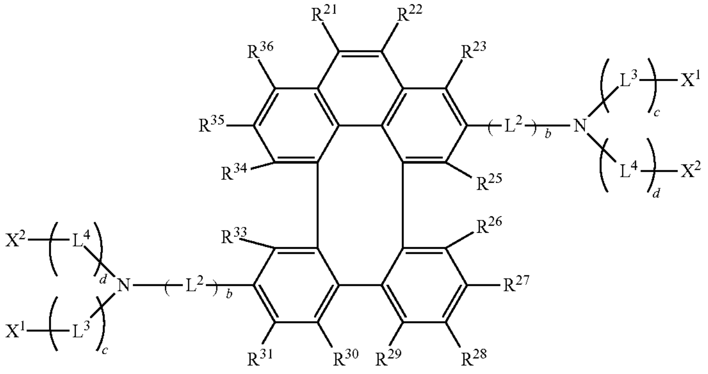
(1B2B-15)
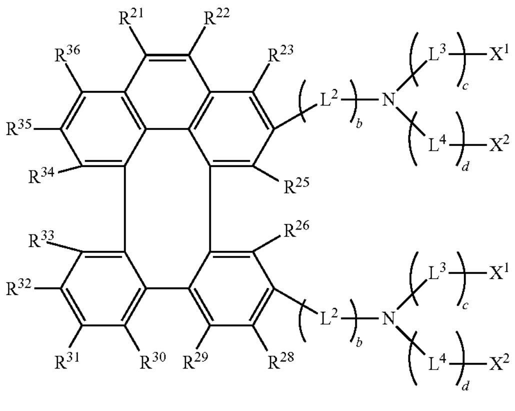
(1B2B-16)
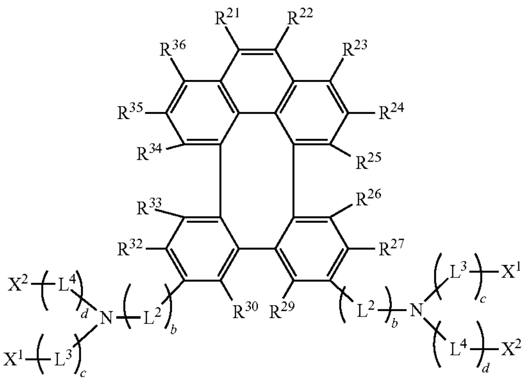

-continued
(1B2C-11)
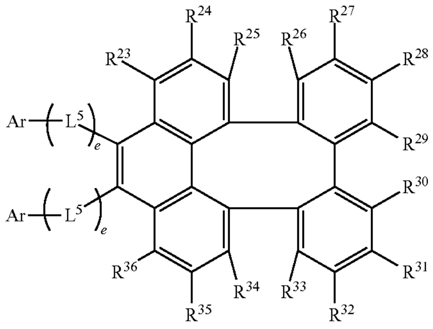
(1B2C-12)
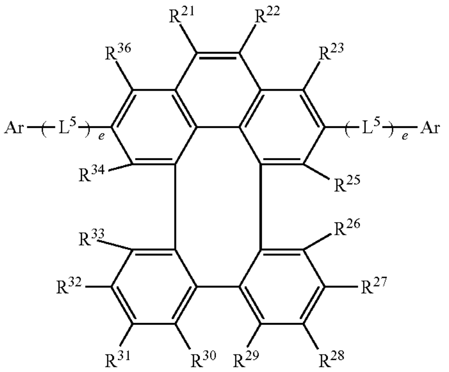
(1B2C-13)
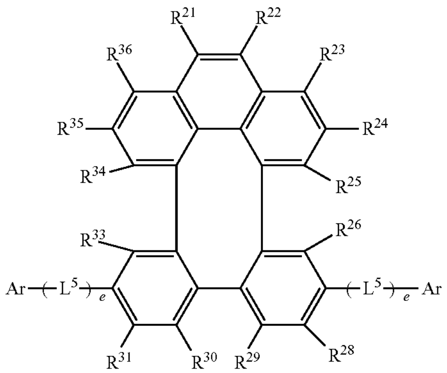
(1B2C-14)
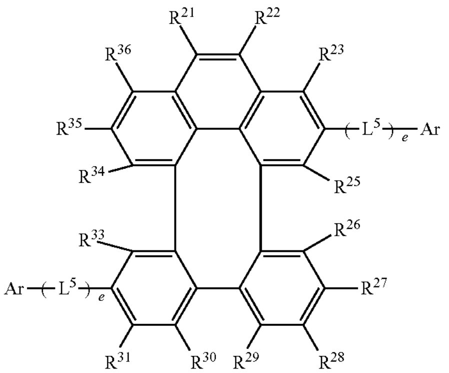
(1B2C-15)
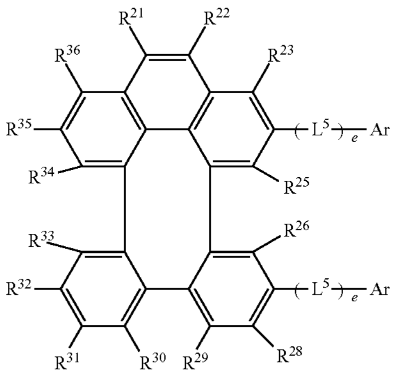
(1B2C-16)
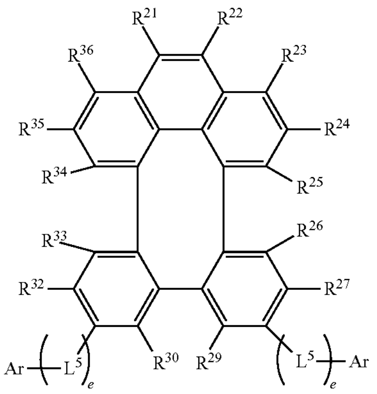
(1B2D-11)
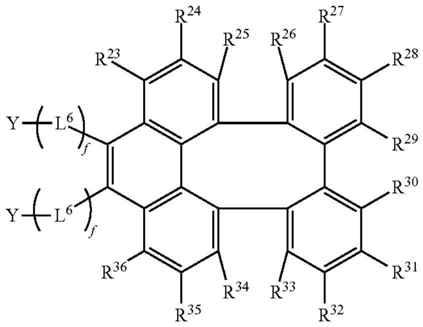
(1B2D-12)
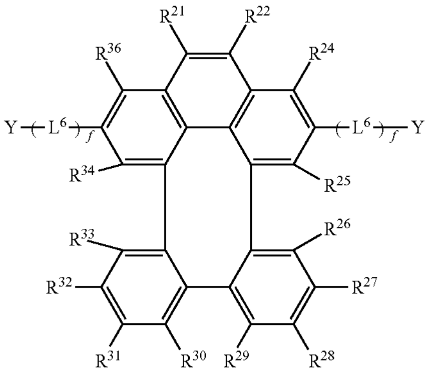

-continued (1B2D-13)

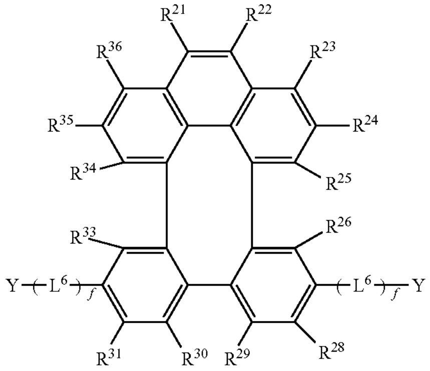

(1B2D-14)

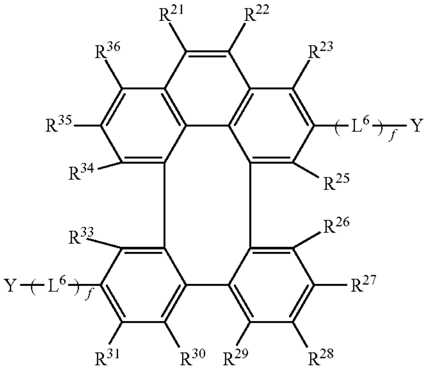

(1B2D-15)

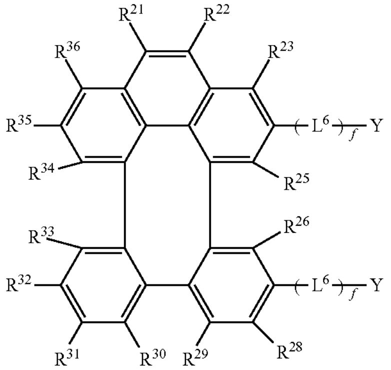

(1B2C-16)

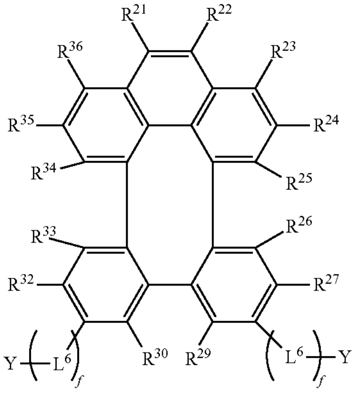

wherein $R^1$ to $R^{16}$, $R^{21}$ to $R^{36}$, $L^1$ to $L^6$, a, b, c, d, e, f, HET, $X^1$, $X^2$, Y and Ar have the same meaning as defined in the formulae (1A) and (1B) and, when there is a plurality of $L^1$ to $L^6$, a, b, c, d, e, f, HET, $X^1$, $X^2$, Y or Ar in each formula, they may be the same or different.

5. The compound according to claim 4, wherein the heterocyclic group having 5 to 50 ring atoms in the substituted or unsubstituted heterocyclic group having 5 to 50 ring atoms, represented by HET, is a pyridyl group, a pyridazinyl group, a pyrimidinyl group, a pyrazinyl group, a bipyridinyl group, a triazinyl group, a quinolizinyl group, a quinolyl group, an isoquinolyl group, a cinnonyl group, a phthalazinyl group, a quinazolinyl group, a quinoxalinyl group, a benzoimidazolyl group, an indazolyl group, an imidazopyridyl group, an imidazopyrimidyl group, a phenanthrolinyl group, a phenanthridinyl group, a carbazolyl group, an azacarbazolyl group or a diazacarbazolyl group.

6. The compound according to claim 1, wherein the heterocyclic group having 5 to 50 ring atoms in the substituted or unsubstituted heterocyclic group having 5 to 50 ring atoms, represented by HET, contains a nitrogen atom as a ring atom.

7. The compound according to claim 1, wherein the heterocyclic groups having 5 to 50 ring atoms in the substituted or unsubstituted heterocyclic groups having 5 to 50 ring atoms, represented by $X^1$ and $X^2$, are each independently a carbazolyl group, a benzocarbazolyl group, a dibenzofuranyl group, a naphthobenzofuranyl group, a dibenzothiophenyl group, or a naphthobenzothiophenyl group.

8. The compound according to claim 1, wherein the aryl groups having 6 to 50 ring carbon atoms in the substituted or unsubstituted aryl groups having 6 to 50 ring carbon atoms, represented by $X^1$ and $X^2$, are each independently a phenyl group, a biphenyl group, a terphenyl group, a naphthyl group, an anthryl group, a benzoantryl group, a phenanthryl group, a benzophenanthril group, a pyrenyl group, a triphenylenyl group, a benzotriphenylenyl group, a fluorenyl group, a fluoranthenyl group, or a benzofluoranthenyl group.

9. The compound according to claim 1, wherein the aryl group having 10 to 50 ring carbon atoms in the substituted or unsubstituted aryl group having 10 to 50 ring carbon atoms, represented by Ar, is a biphenyl group, a terphenyl group, a naphthyl group, an anthryl group, a benzoantryl group, a phenanthryl group, a benzophenanthril group, a pyrenyl group, a triphenylenyl group, a benzotriphenylenyl group, a fluorenyl group, a fluoranthenyl group, or a benzofluoranthenyl group.

10. The compound according to claim 1, wherein Y is represented by the formula (i).

11. The compound according to claim 1, wherein the arylene groups having 6 to 50 ring carbon atoms in the substituted or unsubstituted arylene groups having 6 to 50 ring carbon atoms, represented by $L^1$ to $L^6$, are each independently a phenylene group, a biphenylene group, a naphthylene group, or an anthracenediyl group.

12. The compound according to claim 1, wherein the divalent heterocyclic groups having 5 to 50 ring atoms in the substituted or unsubstituted divalent heterocyclic groups having 5 to 50 ring atoms, represented by $L^1$ to $L^6$, are each independently a divalent group derived by removing a hydrogen atom on a hetero ring from a pyridyl group, a pyridazinyl group, a pyrimidinyl group, a pyrazinyl group, a triazinyl group, a quinoxalinyl group, a quinazolinyl group, a carbazolyl group, a dibenzofuranyl group or a dibenzothiophenyl group.

13. The compound according to claim 1, wherein in the formulae (1A) and (1B), $R^1$ to $R^{16}$ and $R^{21}$ to $R^{36}$ which are not represented by the formula (2A), (2B), (2C) or (2D) are all hydrogen atoms.

14. The compound according to claim 1, wherein the compound represented by the formula (1A) or (1B) contains at least one deuterium atom.

15. A material for organic electroluminescent devices, comprising the compound according to claim 1.

16. An organic electroluminescent device comprising a cathode, an anode, and organic layers disposed between the cathode and the anode, wherein the organic layers include a light emitting layer, and at least one layer of the organic layers comprises the compound according to claim 1.

17. The organic electroluminescent device according to claim 16, wherein the organic layers include an electron transporting zone between the cathode and the light emitting layer, the electron transporting zone comprising the compound.

18. The organic electroluminescent device according to claim 17, wherein the electron transporting zone includes a first electron transporting layer on the anode side and a second electron transporting layer on the cathode side, and wherein one or both of the first electron transporting layer and the second electron transporting layer comprise the compound.

19. The organic electroluminescent device according to claim 18, wherein the first electron transporting layer comprises the compound.

20. The organic electroluminescent device according to claim 18, wherein the first electron transporting layer is disposed adjacent to the light emitting layer.

21. The organic electroluminescent device according to claim 16, wherein the organic layers include a hole transporting zone between the anode and the light emitting layer, the hole transporting zone comprising the compound.

22. The organic electroluminescent device according to claim 21, wherein the hole transporting zone includes a first hole transporting layer on the anode side and a second hole transporting layer on the cathode side, and wherein one or both of the first hole transporting layer and the second hole transporting layer comprise the compound.

23. The organic electroluminescent device according to claim 16, wherein the light emitting layer comprises the compound as a host material.

24. The organic electroluminescent device according to claim 16, wherein the light emitting layer contains a fluorescent dopant material.

25. The organic electroluminescent device according to claim 16, wherein the light emitting layer contains a phosphorescent dopant material.

26. An electronic device comprising the organic electroluminescent device according to claim 16.

* * * * *